US007778779B2

(12) United States Patent
Ratcliffe et al.

(10) Patent No.: US 7,778,779 B2
(45) Date of Patent: Aug. 17, 2010

(54) METHOD OF IDENTIFYING A CHEMICAL ENTITY WHICH IS A HYDROXYLASE MODULATOR

(75) Inventors: Peter John Ratcliffe, Oxford (GB); Christopher William Pugh, Oxford (GB); Christopher Joseph Schofield, Oxford (GB); Kirsty Sarah Hewitson, Oxford (GB); Jonathan Mark Elkins, Oxford (GB)

(73) Assignee: Isis Innovation Limited (GB)

( * ) Notice: Subject to any disclaimer, the term of this patent is extended or adjusted under 35 U.S.C. 154(b) by 203 days.

(21) Appl. No.: 10/531,662

(22) PCT Filed: Oct. 16, 2003

(86) PCT No.: PCT/GB03/04492

§ 371 (c)(1),
(2), (4) Date: Oct. 21, 2005

(87) PCT Pub. No.: WO2004/035812

PCT Pub. Date: Apr. 29, 2004

(65) Prior Publication Data

US 2007/0048728 A1 Mar. 1, 2007

(30) Foreign Application Priority Data

Oct. 16, 2002 (GB) .................................. 0224102
Nov. 14, 2002 (GB) .................................. 0226598

(51) Int. Cl.
*G05D 1/00* (2006.01)
*G01C 22/00* (2006.01)
(52) U.S. Cl. .......................................... 702/11; 702/27
(58) Field of Classification Search ...................... None
See application file for complete search history.

(56) References Cited

FOREIGN PATENT DOCUMENTS

| WO | WO 01/90301 A2 | 11/2001 |
| WO | WO 02/06509 A2 | 1/2002 |
| WO | WO 02/25276 A1 | 3/2002 |
| WO | WO 02/074981 A2 | 9/2002 |
| WO | WO 03/025013 A1 | 3/2003 |

OTHER PUBLICATIONS

Hon et al. (Jun. 5, 2002) Nature, vol. 417, p. 975-978.*
Hewitson et al. (2002) J Biol Chem, vol. 277(29), p. 26351-26355.*
Giege et al. Crystallogenesis of Biological Macromolecules: Facts and Perspectives. Acta Cryst., (1994) D50: 339-350.*
Branden et al. (1999) "Introduction to Protein Structure Second Edition", Garland Publishing Inc., New York, p. 375 and 382.*
Drenth et al. (1995) Principles of X-ray Crystallography, Springer, New York.*
Kierzek et al. (2001) Biophys Chem 91: 1-20.*
Wiencek (1999) Ann Rev Biomed Eng 1:505-534.*
Böohm et al., The computer program LUDI: A new method for the de nove design of enzyme inhibitors, J. Of Comp.-Aided Molec. Design, 1992, 6:61-78.*
Goodsell et al., Automated Docking of Flexible Ligands: Applications of AutoDock, J. of Molec. Recog., 1996, 9:1-5.*
Kohn et al.; "Solid-phase Synthesis of Peptide-Heterocycle Hybrids Containing a Tripeptide-Derived '6,6- fused Bicyclic SubUnit"; Tetrahedron Letters 42; pp. 4453-4457; 2001.
Eguchi et al.; "Solid-Phase Synthesis and Solution Structure of Bicyclic β-turn Peptidomimetics: Diversity at the I Position"; Tetrahedron Letters 42; pp. 1237-1239; 2001.
De Borggraeve et al.; "Synthesis of a Conformationally Restricted Dipeptide Analogue and Its Evaluation as a β-turn Mimic"; Tetrahedron Letters 42, pp. 5693-5695; 2001.
Manzoni et al.; "Synthesis of Spiroazabicycloalkane Amino. Acid Scaffolds as Reverse-Turn Inducer Dipeptide Mimics"; Tetrahedron 57, pp. 249-255; 2001.
Lerner et al.; "X-ray Crystal Stucture of a Bisubstrate Inhibitor Bound to the Enzyme Catechol-O- methyltransferase: A Dramatic Effect of Inhibitor Preorganization on Binding Affinity"; Angew. Chem. Int. Ed., 40, No. 21; pp. 4040-4042; 2001.
Wang et al.; "Structures of Aquifex Aeolicus KDO8P Synthase in Complex with R5P and PEP, and with a Bisubstrate Inhibitor: Role of Active Site Water in Catalysis"; Biochemistry, 40; pp. 15676-15683; 2001.
Jiang et al.; "Combination Biomimetic Chemistry: Parallel Synthesis of a Small Library of β-Hairpin Mimetics Based on Loop III from Human Platelet-Derived Growth Factor B"; Helvetica Chimica Acta, vol. 83, pp. 3097-3112; 2000.
Claridge et al.; "Synthesis and Analysis of Leu-Enkephalin Analogues Containing Reverse Turn Peptidomimetics"; Bioorganic & Medicinal Chemistry Letters, vol. 6, No. 4, pp. 485-490, 1996.
Masimirembwa et al.; "In Vitro High Throughout Screening of Compounds for Favorable Metabolic Properties in Drug Discovery"; Combinatorial Chemistry & High Throughput Screening, vol. 4, pp. 245-263; 2001.
Maier et al.; "Dicyanocarbene and Its Isomers: A Matrix Spectroscopic Study"; Eur. J. Org. Chem. pp2695-2701; 2003.
Belvisi et al.; "Conformational Analysis of Azabicycloalkane Amino Acid Scaffolds as Reverse-Turn Inducer Dipeptide Mimics"; Eur. J. Org. Chem., pp. 2563-2569; 2000.
Wykoff et al.; "Hypoxia-Inducible Expression of Tumor-Associated Carbonic Anhydrases"; Cancer Research 60, pp. 7075-7083; Dec. 15, 2000.

(Continued)

*Primary Examiner*—David J Steadman
*Assistant Examiner*—Alexander D Kim
(74) *Attorney, Agent, or Firm*—Finnegan, Henderson, Farabow, Garrett & Dunner LLP

(57) ABSTRACT

A method of identifying, screening, characterising or designing a chemical entity, which mimics or binds to FIH, is described. The method comprises comparing a structural model of FIH with a structural model for said chemical entity, wherein said structural model of FIH is derived from structural factors or structural coordinates determined by subjecting to X-ray diffraction measurements a crystal comprising FIH. Such chemical entities may be used in the treatment of a condition associated with increased or decreased HIF levels or activity.

8 Claims, 6 Drawing Sheets

OTHER PUBLICATIONS

Burgess; "Solid-Phase Syntheses of β-Turn Analogues to Mimic or Disrupt Protein-Protein Interactions"; Accounts of Chemical Research, vol. 34, No. 10; pp. 826-835; 2001.

Hanessian et al.; "Design and Synthesis of Conformationally Constrained Amino Acids as Versatile Scaffolds and Peptide Mimetics"; Tetrahedron Report No. 426, vol. 53, No. 38; pp. 12789-12854, 1997.

Brünger et al.; "Crystallography & NMR System: A New Software Suite for Macromelcular Structure Determination"; Acta Crystallagraphica, Section D54, pp. 905-921; 1998.

Jones et al.; "Improved Methods for Building Protein Models in Electron Density Maps and the Location of Errors is these Models"; Acta Crystallagraphica, Section A47, pp. 110-119; 1991.

Terwilliger; "Maximum-likelihood Density Modification"; Acta Crystallographica, Section D56; pp. 965-972; 2000.

Terwilliger; "Automated MAD and MIR Structure Solution"; Acta Crystallographica; Section D55; pp. 849-861; 1999.

Collaborative Computational Project, No. 4; "The CCP4 Suite: Programs for Protein Crystallography"; Acta Crystallographica; Section D50, pp. 760-763; 1994.

Krafft et al.; "Synthetic Approaches to Continuous Assays of Retroviral Proteases"; Methods in Enzymology, vol. 241; pp. 70-86; 1994.

Owicki; "Fluorescence Polarization and Anisotrophy in High Throughput Screening: Perspectives and Primer"; Journal of Biomolecular Screening; vol. 5, No. 5, pp. 297-306; 2000. .

Derrer et al.; "Synthesis and Conformational Analysis of a Type VIb β-turn Mimetic Based on an Eight-Membered Lactam"; J. Chemical Society, Perking Trans. I, pp. 2957-2967; 2000.

Mahadevan et al.; "Molecular Dynamics Simulations of Conformational Behavior of Linear RGD Peptidomimetics and Cyclic Prodrugs in Aqueous and Octane Solutions"; Journal of Biomolecular Structure & Dynamics; vol. 19, No. 5, pp. 775-788; 2002.

Gillespie at al.; "Conformational Analysis of Dipeptide Mimetics"; Biopolymers 43; pp. 191-217; 1997.

Gregg L. Semenza; "HIF-1 and Human Disease: One Highly Involved Factor", Genes & Development 14; Cold Spring Laboratory Press; 2000; pp. 1983-1991.

Andrew C.R. Epstein, et al.; C. Elegans EGL-9 and Mammalian Homologs Define a Family of Dioxygenases that Regulate HIF by Prolyl Hydroxylation; Cell, vol. 107; Oct. 5, 2001; pp. 43-54.

Richard K. Bruick, et al.; A Conserved Family of Prolyl-4-Hydroxylases That Modify HIF; Science; vol. 294; Nov. 9, 2001; pp. 1337-1340.

Panu Jaakkola. et al.; "Targeting of HIF-α to the Von Hippel-Lindau Ubiquitylation Complex by $O_2$. Regulated Prolyl Hydroxylation"; Science; vol. 292; Apr. 20, 2001; pp. 468-472.

David Lando et al.; Asparagine Hydroxylation of the HIF Trasactivation Domain: A Hypoxic Switch; Science; vol. 295; Feb. 1, 2002; pp. 858-861.

Steven J. Freedman, et al.; "Structural Basis for Recruitment of CBP/p300 by Hypoxia-Inducible Factor-1α"; PNAS; vol. 99, No. 8; Apr. 16, 2002; pp. 5367-5372.

Sonja A. Dames, et al.; Structural Basis for HIF-1α/CBP Recognition in the Cellular Hypoxic Response; PNAS/vol. 99; No. 8; Apr. 16, 2002; pp. 5271-5276.

Barbara Roth; "Design of Dihydrofolate Reductase Inhibitors from X-Ray Crystal Structures"; Federation Proceedings; vol. 45, No. 12; Nov. 1986; 2765-2772.

Jonathan M. Elkins et al.; "Structure of Factor-inhibiting Hypoxia-inducible Factor (HIF) Reveals Mechanism of Oxidative Modification of HIF-1α"; The Journal of Biological Chemistry; vol. 278, No. 3; Jan. 17, 2003; pp. 1802-1806.

David Lando at al.; FIH-1 is an Asparaginyl Hydroxylase Enzyme that Regulates the Transcriptional Activity of Hypoxia-Inducible Factor; Genes & Development; 16; 2002; pp. 1466-1471.

Kirsty S. Hewiton et al.; "Hypoxia-Inducible Factor (HIF) Asparagine Hydroxylase Is Identical to Factor Inhibiting HIF (FIH) and Is Related to the Cupin Structural Family"; The Journal of Biological Chemistry; vol. 277, No. 29, Jul. 19, 2002; pp. 26351-26355.

Carsten William et al.; "Peptide Blockade of HIFα Degradation Modulates Cellular Metabolism and Angiogenesis"; PANS; vol. 99; No. 16; Aug. 6, 2002; pp. 10423-10428.

Mircea Ivan, et al.; "HIFα Targeted for VHL—Mediated Destruction by Proline Hydroxylation: Implications for $O_2$ Sensing"; Science; vol. 292, Apr. 20, 2001; pp. 464-468.

Panu Jaakkola. et al.; "Targeting of HIF-α to the Von Hippel-Lindau Ubiquitylation Complex by $O_2$. Regulated Prolyl Hydroxylation"; Science; vol. 292; Apr. 20, 2001; pp. 468-472.

Barbara Roth; "Design of Dihydrofolate Reductase Inhibitors from X-Ray Crystal Structures"; Federation Proceedings; vol. 45, No. 12; Nov. 1986; 2765-2772.

David Lando et al.; FIH-1 is an Asparaginyl Hydroxylase Enzyme that Regulates the Transcriptional Activity of Hypoxia-Inducible Factor; Genes & Development; 16; 2002; pp. 1466-1471.

Mircea Ivan, et al.; "HIFα Targeted for VHL-Mediated Destruction by Proline Hydroxylation: Implications for $O_2$ Sensing"; Science; vol. 292, Apr. 20, 2001; pp. 464-468.

U.K. Patent Office Search Report for Application No. GB 0224102.4 Mar. 14, 2003.

* cited by examiner

METHOD OF IDENTIFYING A CHEMICAL ENTITY WHICH IS A HYDROXYLASE MODULATOR

This is a national stage application of International Application No. PCT/GB2003/004492, filed Oct. 16, 2003, which claims benefit of priority to GB 0224102.4, filed Oct. 16, 2002 and GB 0226598.1, filed Nov. 14, 2002, the disclosures of which are incorporated by reference.

FIELD OF INVENTION

The present invention relates to methods of designing inhibitors of FIH using the crystal structure of FIH, and to inhibitors of FIH and their use in the treatment of ischaemia

BACKGROUND OF THE INVENTION

In cells of many organisms exposure to an environment in which oxygen is depleted relative to optimal levels induces a hypoxic response. In these hypoxic cells, activation of a transcriptional cascade involving hypoxia inducible factor (HIF) directs a series of adaptive responses that enhance oxygen delivery or limit oxygen demand. Activation of HIF in cancer and ischaemic hypoxic vascular diseases has revealed its important role in human pathology and demonstrated that manipulation of HIF activity has important therapeutic potential.

The HIF transcriptional complex comprises an αβ heterodimer, HIF-β being a constitutive nuclear protein that dimerises with oxygen regulated HIF-α subunits (Semenza, G. L. (2000) *Genes Dev.* 14, 19831991). The activity of HIF-α, is suppressed by oxygen-dependent modification catalysed by a series of $Fe^{(II)}$ and 2OG dependent dioxygenases that hydroxylate specific HIF-α residues. In the presence of oxygen in human HIF-1α, 4-hydroxylation of Pro402 or Pro564 by a set of HIF prolyl hydroxylase isozymes (PHD1-3) (Epstein et al. (2001) *Cell* 107, 4354; Bruick, R. K., and McKnight, S. L. (2001) *Science* 294, 13371340) mediates its recognition by the von Hippel-Lindau (VHL) ubiquitin ligase complex and consequent targeting for proteasomal destruction (Ivan et al, (2001) *Science* 292, 464468; Jaakkola et al (2001) *Science* 292, 468472, WO 02/074981). In a complementary mechanism FIH catalyses β-hydroxylation of HIF-1α Asn803 (Lando et al, (2002) *Science* 295, 858861) blocking interaction with the transcriptional co-activator p300 (Dames et al., (2002) *Proc. Natl. Acad. Sci. U.S.A.* 99, 52715276; Freedman et al, (2002) *Proc. Natl. Acad. Sci. U.S.A.* 99, 53675372). In hypoxia, limitation of enzymatic activity allows HIF-α to escape destruction and become transcriptionally active.

Inhibition of HIF hydroxylases strongly activates the HIF transcriptional cascade even in the presence of oxygen (Epstein et al. (2001) *Cell* 107, 4354). Thus, inhibition of the HIF hydroxylases results in a pro-angiogenetic response that may be used in the treatment of cardiovascular diseases/ischaemic hypoxic vascular diseases including myocardial infarction and anaemia. A problem with this approach is that the human cells contain other enzymes belonging to the same family as the HIF hydroxylases, i.e. utilising dioxygen (a cosubstrate), 2-oxoglutarate (2OG) (a cosubstrate) and Fe(II) (a cofactor). Such enzymes are exemplified by phytanoyl coenzyme A hydroxylase, procollagen prolyl-4-hydroxylase, procollagen prolyl-3-hydroxylase, gamma-butyrobetaine hydroxylase, Alk B (a DNA repair enzyme) and others including predicted 2OG oxygenases identified on the basis of sequence analyses including a sub-family related to FIH (Hewitson et al., *J BIOL CHEM* 277 (29): 26351-26355, 2002). It is generally agreed that it is desirable that enzyme inhibitors used as pharmaceuticals are selective for their intended target or the targets involved in producing the desired effect. A lack of selectivity can lead to toxic side effects that render particular compounds unsuitable for use in human or animal therapy. One approach to identifying compounds that are selective for the intended target is to undertake structural, mechanistic and other analyses on the intended agents and to use the information gained to aid in the preparation of selective compounds, or more selective compounds (relative to those previously known), for use as pharmaceuticals for use in humans or animals. Here we describe structural and other studies on the HIF hydroxylases that enable the design of selective inhibitors of FIH and related enzymes.

SUMMARY OF THE INVENTION

The present inventors have now identified the site of hydroxylation of asparagine 803 of HIF-1α by FIH. In addition, the inventors have obtained the crystal structure for FIH including identification of the binding site and residues involved in the interaction of FIH with HIF.

Accordingly, the present invention provides a method of identifying, screening, characterising or designing a chemical entity which mimics or binds to FIH, which method comprises comparing a structural model of FIH with a structural model for said chemical entity, wherein said structural model of FIH is derived from structural factors or structural coordinates determined by subjecting to X-ray diffraction measurements a crystal comprising FIH.

The invention also provides for:
the use of the structural co-ordinates obtainable by subjecting a crystal comprising FIH to X-ray diffraction measurements and deducing the structural co-ordinates from the diffraction measurements, to identify, screen, characterise, design or modify a chemical entity;
a chemical entity identified by a method of the invention, wherein said chemical entity inhibits the asparaginyl hydroxylase activity of FIH; and
a chemical entity of the invention for use in a method of treatment.

DETAILED DESCRIPTION OF THE INVENTION

Figure 1:
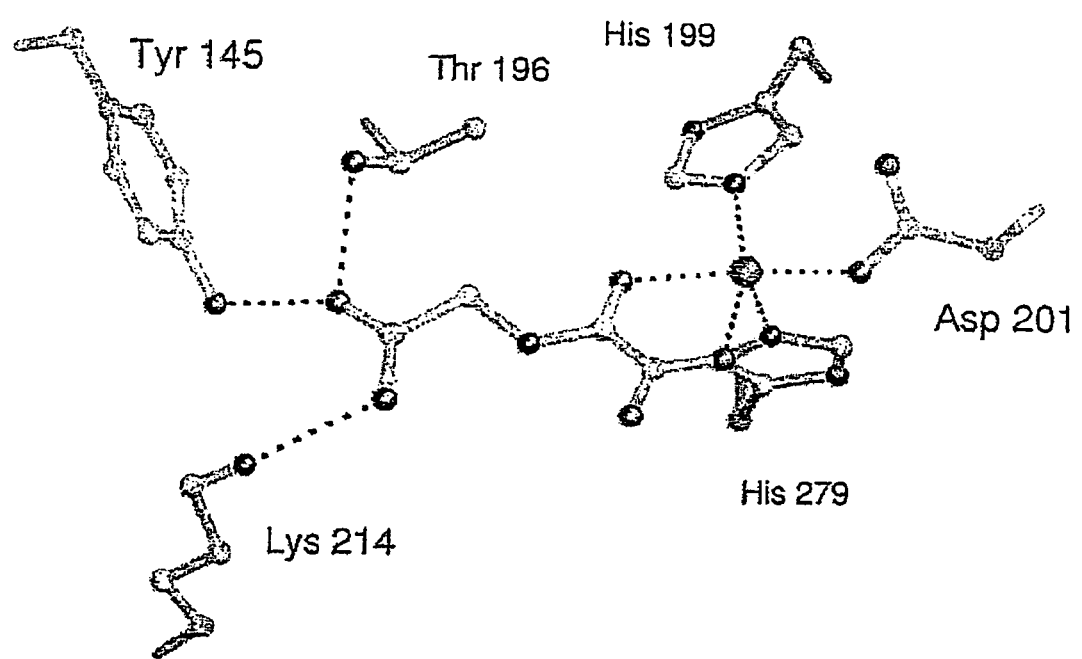
FIG. 1: 2OG binding site.
Figure 2:
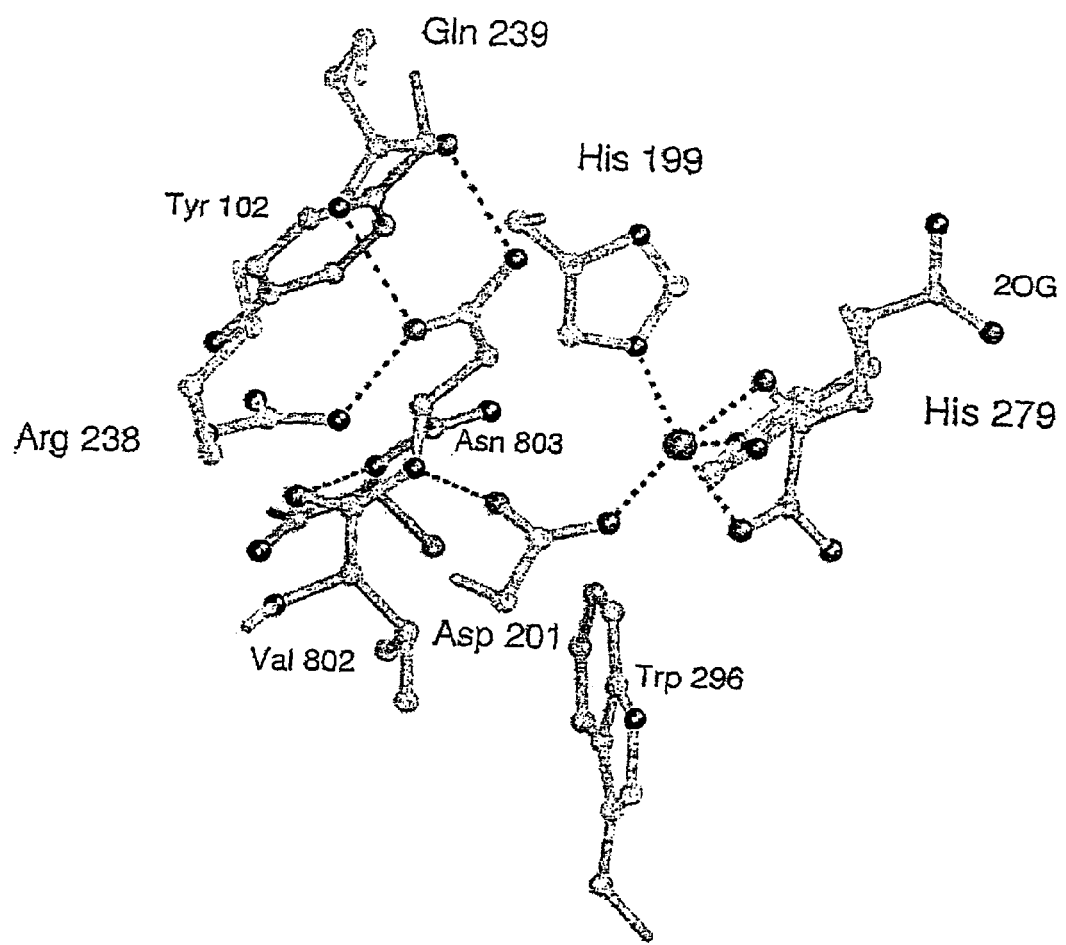
FIG. 2: binding of Asn-803.
Figure 3:
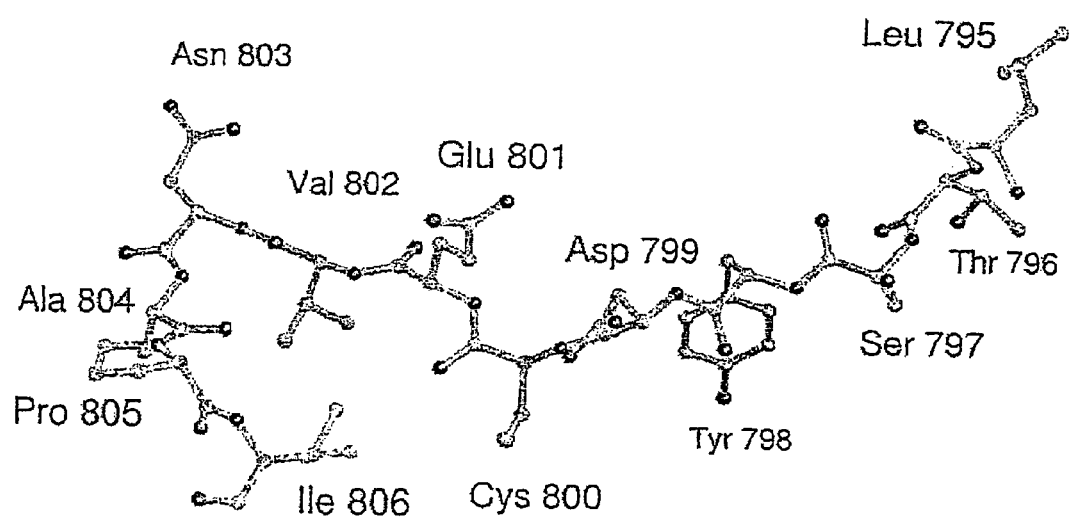
FIG. 3: conformation of CAD at site 1 (SEQ ID NO: 33).
Figure 4:
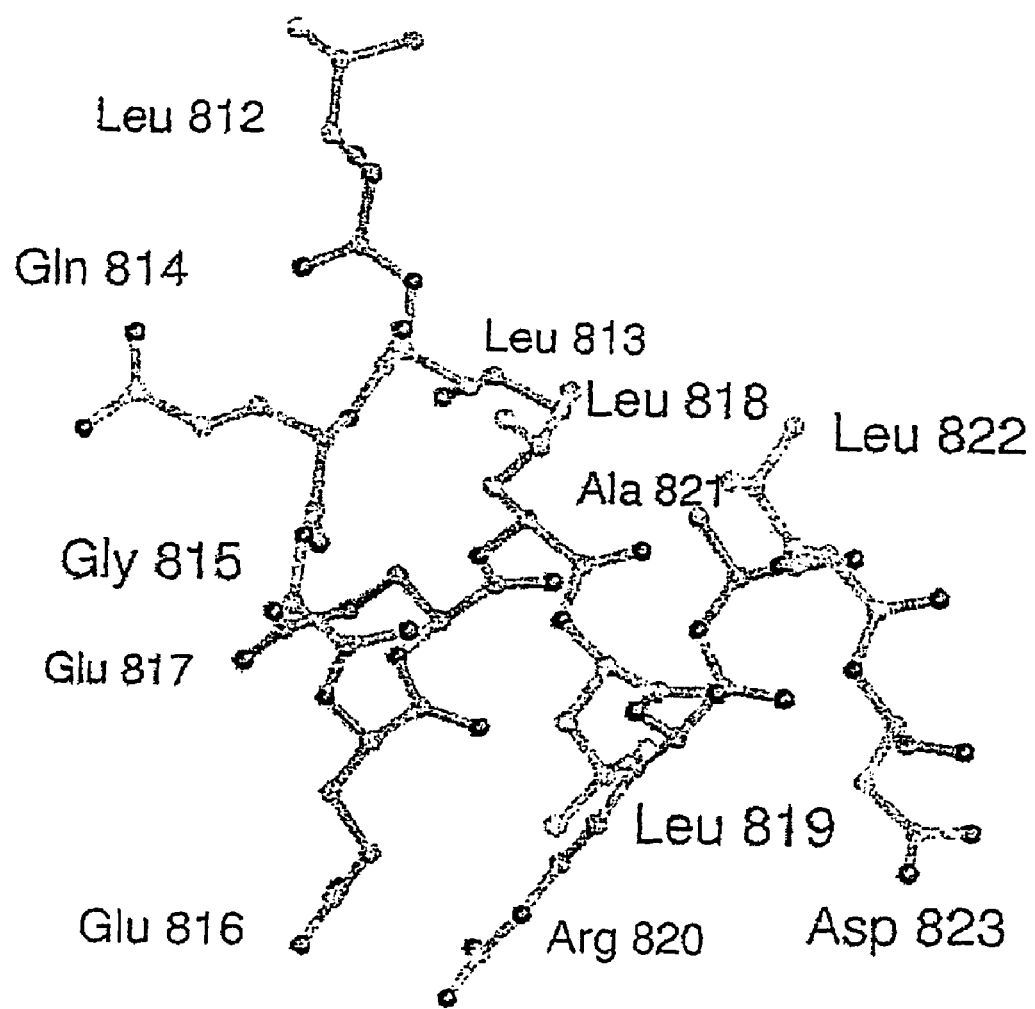
FIG. 4: conformation of CAD at site 2 (SEQ ID NO: 34).
Figure 5:
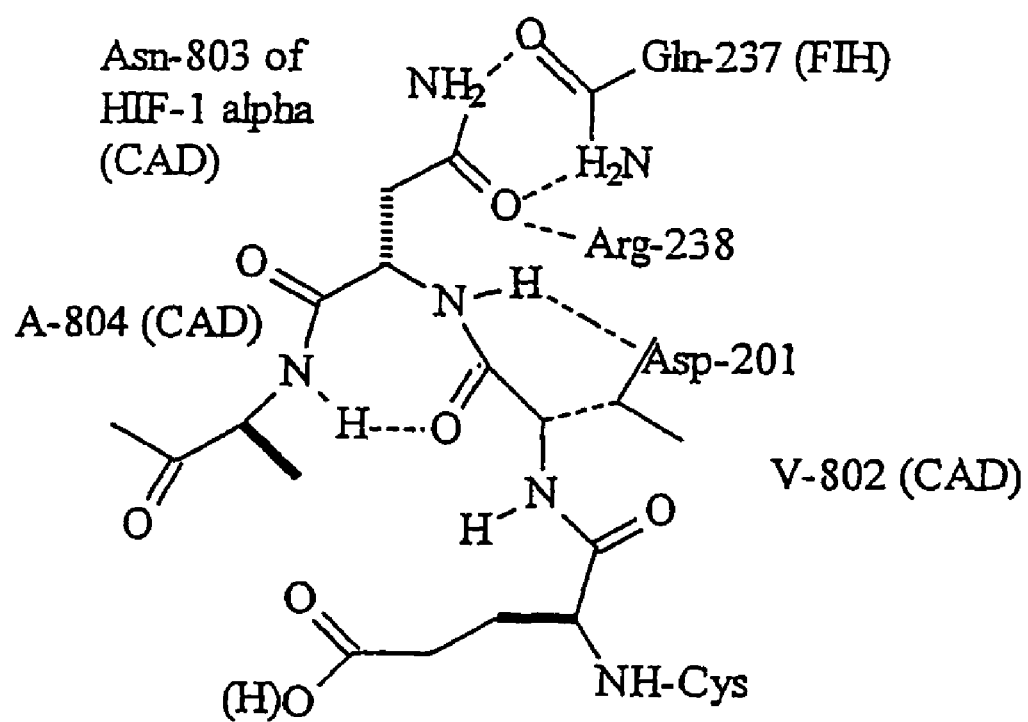
FIG. 5: figure indicating the turn formed by 802-804 of HIF-CAD at the active site of FIH.
Figure 6:
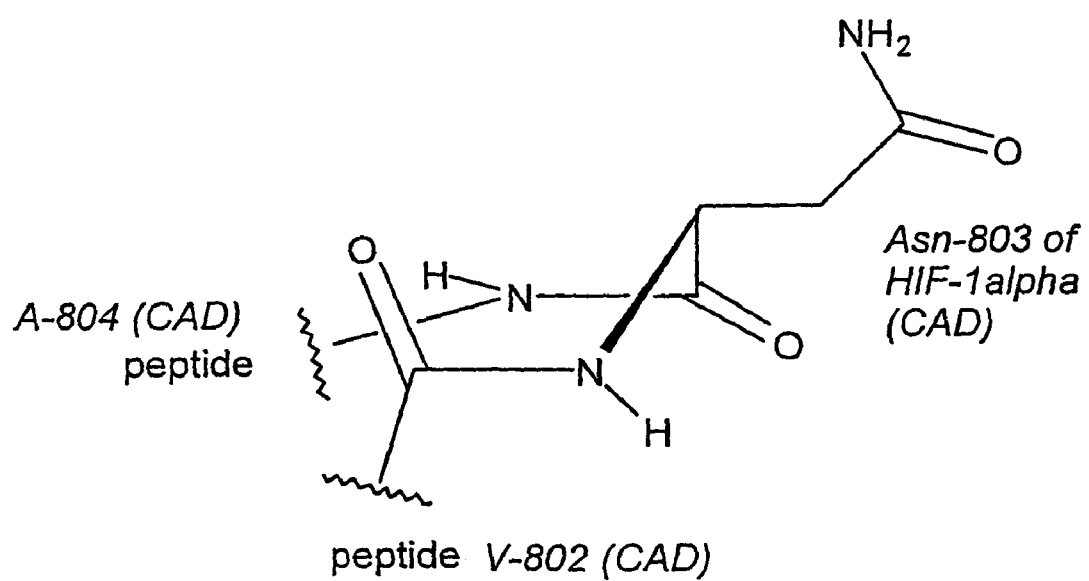
FIG. 6: conformation of the turn formed by residues 802-804 of HIF-CAD at the active site of FIH.

The present inventors have identified the position of asparagine 803 that is hydroxylated by FIH. In addition, the inventors have identified the crystal structure of FIH. This structure therefore allows for identification of the amino acid residues involved in binding of FIH to HIF.

The identification of the interaction and the structures allows for the characterisation or identification of chemical entities which can bind and in particular which can inhibit FIH. A number of different types of inhibitors can be identified as discussed in more detail below.

The inventors have successfully crystallised human FIH. This the first crystallisation of FIH and has enabled determination of the crystal structure. Coordinates from the crystal analysis are set out in Table 3 below. The studies have allowed analysis of the binding of asparagine-803 of HIF and analysis of the conformation of the c-terminal activation domain (CAD) of HIF at the binding sites to FIH. The present invention provides the use of the structural co-ordinates of FIH to identify, characterise, design or screen chemical entities. The chemical entities of interest are those which bind to FIH and in particular which inhibit the asparaginyl hydroxylase activity of FIH. In addition, chemical entities may be identified, characterised or designed which are modified asparagine hydroxylases.

Typically, the structural co-ordinates used are obtainable by subjecting a crystal comprising FIH or a fragment thereof to X-ray diffraction measurements and deducing the structural co-ordinates from the diffraction measurements, to identify, screen, characterise, design or modify a chemical entity. The structural co-ordinates indicate the positions of individual atoms within the crystal and give an indication of the space available for adjusting the position of individual atoms when designing a chemical entity.

The crystal subjected to X-ray diffraction methods comprises FIH or a fragment thereof. The FIH may be from any source but is preferably human FIH. The FIH may be a modified form. For example, the FIH may be modified by insertion, deletion, n-terminal or C-terminal addition, or substitution of amino acid by another amino acid. Amino acid substitutions may be conservative substitutions. Typically, when crystallised, a FIH mutant will adopt a similar 3-dimensional structure to that adopted by the corresponding FIH. A mutant may be an inactive FIH.

References to FIH herein refer to FIH and homologues thereof. Amino acid residues are defined with reference to the position in FIH (see e.g. Hewitson et al). The relevant amino acid residues of homologues of FIH are the equivalent amino acid residues, based on for example the best alignment of homologue to FIH.

A FIH may be isolated by any suitable means for use in crystallisation studies. For example, a FIH may be purified using biochemical means from a suitable source. Typically, however, it will convenient to over express FIH in cells and purify FIH from those cells. Thus, a polynucleotide encoding a FIH may be used in the construction of a vector. The FIH may be crystallised according to any method known to those skilled in the art. X-ray diffraction may be carried according to any suitable method. The data collected from X-ray diffraction experiments may be processed to deduce the structural co-ordinates of FIH using any suitable method.

The invention provides the use of structural co-ordinates to identify, characterise, design or screen a chemical entity. The chemical entity may be one which binds to FIH, or which acts as an inhibitor of asparaginyl hydroxylase activity. Alternatively, the chemical entity may be a modified FIH to alter the activity of a FIH.

A chemical entity which binds to or inhibits FIH is any chemical entity capable of forming an association with the FIH. The binding or inhibition may be non-specific, for example, such an entity may also bind to or inhibit other 2OG oxygenases. Alternatively, an agent may be designed or identified which specifically binds to or inhibits asparaginyl hydroxylases. An agent may be designed or identified which is a specific inhibitor of FIH, but not other asparaginyl hydroxylases.

The structural co-ordinates of FIH allows a skilled person to predict which amino acids are important in active site formation and which amino acids are important in contacting the substrate. The substrate binding site may be shown as a 2 dimensional representation or a 3 dimensional representation produced by physical models or displayed on a computer screen. Such representations can be used to design, identify or screen chemical entities which bind to or inhibit or are predicted to bind to or inhibit FIH. Such representations can also be used to identify modifications of FIH to alter its activity characteristics.

Examples of modifications to FIH include modifications to increase the binding of FIH for its substrate, or to alter the substrate the specificity. Alternative modifications include those which alter the activity of FIH, for example, to remove asparaginyl hydroxylase activity.

The representations of the structures may be used in other ways. For example, the representations of the FIH active site may be used to model constraints by the putative introduction of covalent bonds between the atoms which come close together when FIH binds to a substrate. Representation of the active site may be used to predict which residues of FIH are likely to be involved in steric hindrance. Such residues may be modified, replaced or deleted to decrease esoteric hindrance in order to increase avidity of the peptide for its substrates.

In general, it will be necessary to process the structural co-ordinates obtainable according to the invention in computer-based methods in order to identify or design chemical entities with the desired molecular structure or to identify chemical entities whose structure is complementary to all or part of another chemical entity of interest Thus, chemical entities which have a structure similar to FIH may be identified or designed. Chemical entities which bind to FIH may be identified or designed. Preferably, such chemical entities bind at the active site of FIH and in general may act as inhibitors of asparaginyl hydroxylase activity.

Such computer-based methods fall into two broad classes: database methods and de novo designed methods. In database methods, the chemical entity of interest is compared to all chemical entities present in a database of chemical structures and chemical identities whose structure is in some way similar to the compound of interest identified. The structures in the database are based either on experimental data, generated by NMR or X-ray crystallography, or models of 3 dimensional structures based on 2 dimensional data In de novo design methods, models of chemical entities, for example such are those which might bind to FIH are generated by a computer program using information derived from known structures and/or theoretical rules.

Similarly, the FIH structural coordinates may be used to screen for the expected activity of chemical entities selected, designed or shown to be modulators such as inhibitors of other hydroxylases, for example prolyl hydroxylases. For example the compounds may be screened to assess the likelihood of a prolyl hydroxylase inhibitor additionally inhibiting FIH hydroxylase. Such screening methods may be useful in identifying agents which selectively inhibit HIF prolyl hydroxylase, but not HIF asparaginyl hydroxylase.

Chemical entities designed or selected according to the methods of the invention may be tested and optimised using computational or experimental evaluation. Experimental methods to assay for the activity of asparaginyl hydroxylase are described in more detail below.

Based on the structure of FIH, a number of different types of inhibitors can be identified. These inhibitors are discussed in more detail below.

Dimerisation Inhibitors

The crystallographic asymmetric unit contains one FIH molecule. However, analysis of crystallographic symmetry revealed a dimeric form of FIH, consistent with native gel-electrophoresis analysis. The dimer interface involves the two C-terminal helices of each molecule in an interlocking arrangement predominantly involving hydrophobic interactions. This unusual interface buries a surface area of 3210 Å$^2$, large on average by comparison to other dimeric proteins of this size. Inhibitors of dimerisation include those that bind to residues that form the dimerisation interface including residues selected from 330-346, such as Leu-340 and Ile-344. Inhibitors include peptides or peptide mimetics that correspond to all or part of the FIH residues involved in the dimerisation interface.

For example, such inhibitors may comprise a fragment of FIH, for example, including the residues from 340 to 344, preferably, including residues 330 to 346. Such a fragment may typically have 6 or 10 amino acids in length, preferably, up to 15 or 20 amino acids in length. Alternatively, peptide homologues may be used, for example, which comprise a homologue to the residues of 340 to 344 or 330 to 336, including 1, 2 or more substitutions. Additional agents include peptides or peptide mimetics which can be designed based on the crystal structure to interfere with dimerisation.

Inhibitors Exploiting Metal Binding in FIH:

The structural work defines the presence of Fe(II) at the active site of FIH and by implication related HIF hydroxylases. The iron is bound in an almost octahedral manner by the side chains of His199, Asp201 and His279, the 2-oxo and 1-carboxylate groups of 2OG. In the enzyme-substrate complexes there is a vacant position opposite His279 revealing that the enzyme is primed for dioxygen binding. Accommodation of a ligand opposite His279 may require disruption of the hydrogen bond between Asp201 and CAD Asn803 (the iron and Asn803 β-carbon are only ~4.9 Å apart). Subsequent decarboxylation of 2OG presumably yields an iron-oxo species [Fe$^{(IV)}$=O<->Fe$^{(III)}$—O.] that effects oxidation at the carbon of Asn-803 in the C-terminal transactivation domain (CAD) of HIF.

Compounds that contain functional groups that bind to iron are useful as inhibitors of FIH. Examples of such compounds include thiols, alcohols, phenols including flavonoids such as quercitin and derivatives thereof, carbohydrates, hydroxamates, imidazoles and other heterocycles for example nitrogen containing heterocycles.

Zn$^{(II)}$ binds to FIH in an identical manner to Fe$^{(II)}$ (structure 3), consistent with the metal-mediated hypoxic effect being due to displacement of Fe$^{(II)}$ from the active site of HIF hydroxylases. Since neither Zn(II) nor other metal inhibitors of FIH can replace Fe(II) as a cofactor in catalysis, compounds that preferentially promote the binding of a metal other than iron [such as Zn(II)] at the active site of FIH act as inhibitors.

A further class of inhibitor are non-metallic inhibitors that operate via competing with Fe(II) for binding at the active site. Such inhibitors may bind to any or all of the triad of residues (His-199, Asp-201, His-279), that bind the Fe(II) at the active site of catalytically active FIH.

Inhibitors Exploiting the 2OG Binding Sites

The FIH:CAD structures with NOG reveal that like 2OG it is ligated to iron in a bidentate manner and imply it is an inhibitor due to decreased susceptibility to attack by an iron bound (su)peroxide intermediate or by hindering binding of dioxygen to the metal.

The structural studies on FIH reveal the binding interactions for the 2OG and NOG (see for example FIG. 1). The 5-carboxylate of 2OG (and the equivalent carboxylate of NOG) forms hydrogen bonds with the side-chains of Lys214, Thr196 and Tyr145; such interactions are unprecedented in other structures of 2OG oxygenases. FIH is further unusual in that Lys214 is on the fourth DSBH (double stranded beta-helix) β-strand whereas previously assigned basic 2OG-5-carboxylate binding residues are at the beginning of the eighth DSBH strand.

The structural studies reveal the FIH residues that form the pocket into which 2OG and NOG bind. In addition to the aforementioned these include the side-chains of Ile-281, Leu-186, Leu-188, Phe-207, Thr-196. Knowledge of these interactions enables the design of improved (as measured by binding parameters) and selective inhibitors. Thus, for example an inhibitor binding in the 2OG binding pocket may form hydrophobic interactions with any or all of the side chains of Ile-281, Leu-186 Leu-188, Phe-207, Thr-196. Further it may form electrostatic or hydrogen bonding interactions with the residues involved in binding the 5-carboxylate of 2OG (Lys214, Thr196 and Tyr145).

Selective inhibition of FIH via inhibitors interacting with the 2OG binding residues is exemplified as follows: kinetic analyses of a series of inhibitors based upon N-oxaloyl amino acids revealed the R-enantiomer (IC$_{50}$ 0.4 mM) of N-oxaloylalanine was significantly more potent than the S-enantiomer (IC$_{50}$ 2.5 mM). Analysis of the 2OG binding pocket in FIH reveals that the binding of the S-enantiomer is hindered by interactions between its methyl group and the side chain of Thr-196 and, Ile-281 in the 2OG binding pocket. A reversed selectivity (i.e. the S-enantiomer was more potent) was observed both for procollagen prolyl-hydroxylase and the PHD isozymes, demonstrating it should be possible to develop selective inhibitors for individual types of HIF hydroxylase. Such inhibitors may or may not chelate to an active site metal.

Compounds include those of general formula

(I)

wherein each of R' and R", which may be the same or different, is H, F or C$_1$ to C$_3$ alkyl or substituted alkyl, CH$_2$OH, CH$_2$CO$_2$H or CONH$_2$, X is COOH, SOOH, or CONHH or an ester thereof, or heterocyclic or other group which forms a favourable interaction with one or more of the side chains of Lys-214, Thr-196 and Tyr-145, i.e. those residues involved in binding the 5-carboxylate of 2OG as revealed in the crystallographic analyses, Y is —(CR'''R''')$_n$Z, where Z is —NR'''COCOOH, —NR'''CSCOOH, —NR'''COCOSH, —CHSR'''CONR'''R'''', —CHOR'''CONR'''OR''', —CHSR'''—CONR'''OR''' or —CHOR'''CONR'''NR'''OR''', wherein each R''', which may be the same or different, is H, alkyl, OH or O-alkyl, n is 0 to 3 and preferably 0, or

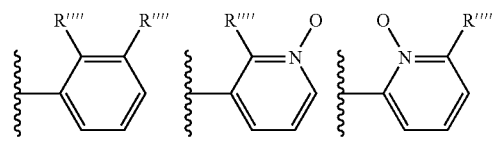

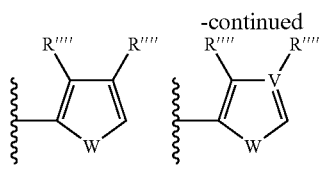

wherein R'''' is OH, OR''' or NHCOR''', and W is S, NH, or O.

Thus X is a group that forms favourable interactions with one or more of the side chains of interactions one or more of the side chains of Lys-214, Thr-196 and Tyr-145, i.e. those residues involved in binding the 5-carboxylate of 2OG. X may be functionalised as a pro-drug such that is delivered to the desired site of action or has desirable pharmokinetic properties. As indicated above, X can be an ester such a methyl or ethyl ester or amide derivative of carboxylic acid versions of X.

If n is 0, Y is typically CONHOH, CONHNH$_2$, NR'''COCOOH, NR'''CSCOOH or NR'''COCOSH. Y is preferentially of a size such that it can chelate to the active site metal whilst maintaining all or some of the favourable binding interactions found in the 2OG binding pocket as defined by crystallographic analyses. As with X, Y may be functionalised as a pro-drug.

When Y contains an aromatic ring as indicated above it can comprise other ring systems including aryl or functionalised aryl rings as well as heterocyclic and functionalised heterocyclic rings. The above rings may be further functionalised to optimise binding at the FIH active site.

Inhibitors Exploiting the Peptide Substrate Binding Site

There are Two Binding Sites

The ES complex structures unexpectedly reveal two separate binding sites involving CAD$_{795-806}$ (i.e residues 795-806 of the C-terminal transactivation domain of HIF) (Site 1) and CAD$_{813}$-822 of HIF (Site 2) with contact surface areas of 1640 Å$^2$ and 1080 Å$^2$, respectively (see for example the figures). CAD residues in these regions are conserved in all known HIF-1α and HIF-2α sequences. The electron density for site 1 was of good quality, with only the side-chain of Tyr798 poorly defined, while that for site 2 was at a lower level and quality, probably reflecting weaker binding at this site. CAD$_{804-806}$ and presumably also CAD$_{807-811}$, for which density was not observed, do not form direct interactions with FIH. Kinetic analyses employed to investigate the relative importance of Sites 1 and 2, revealed that fragments containing site 1 only are hydroxylated by FIH but less efficiently than those containing both sites demonstrating that both are important in binding and that both may be exploited in inhibition studies.

At Site 1 CAD$_{795-803}$ are bound in a groove and adopt a largely extended conformation linked to FIH by ten hydrogen bonds. Asn803 of CAD is strikingly buried at the active and directly adjacent to the Fe$^{(II)}$. CAD Asn803 and Ala804 form a tight turn, stabilised by a hydrogen bond between the backbone carbonyl of Val802 and NH of Ala804, which projects the side chain of Asn803 towards the Few. The side chain of CAD Asn803 is precisely orientated by three hydrogen bonds to enable hydroxylation at the pro-S position of the β-carbon consistent with the NMR assignments (see above) The primary amide of CAD Asn803 is sandwiched between FIH residue Tyr102 and the Fe$^{(II)}$, and forms hydrogen bonds with the side chains of FIH residues Gln239 and Arg238, residues located on the insert to the DSBH motif. Significantly, the substrate and Fear binding sites are directly linked since the backbone nitrogen of CAD Asn803 also forms a hydrogen bond (~3 Å) with the carboxylate oxygen of Asp201 that is not complexed to the iron. Six additional hydrogen bonds stabilise the binding of FIH to CAD$_{795-801}$.

In contrast with Site 1, Site 2 is located on the FIH surface and involves only two hydrogen bonds. CAD$_{816-823}$ of Site 2 form an α-helix, in exact agreement with the structure of this region in complex with CBP/p300 (Dames et al., (2002) Proc. Natl. Acad. Sci. U.S.A. 99, 52715276; Freedman et al, (2002) Proc. Natl. Acad. Sci. U.S.A. 99, 53675372). As in that complex, the highly conserved Leu818, Leu819 and Leu822 sit in a hydrophobic pocket on the surface of FIH and form the basis of the binding interaction and so it is not possible for these residues to bind simultaneously to CBP/p300 and FIH.

The extended loop conformation adopted by the CAD residues at Site 1, contrasts with the α-helical conformation adopted by the same residues when complexed with the 1st transcriptional adaptor zinc-binding domain (TAZ1) of CBP/p300 (Dames et al., (2002) Proc. Natl. Acad. Sci. U.S.A. 99, 52715276; Freedman et al, (2002) Proc. Natl. Acad. Sci. U.S.A. 99, 53675372). The disordered structure observed for the CAD, and other HIF-α residues, when free in solution may thus reflect a requirement to adopt more than one conformation for complex formation with different proteins.

The changes in the conformation of CAD on binding are complemented by changes in FIH revealing an induced fit binding process; Trp296 of FIH undergoes a 50° rotation about $C_{beta}$-$C_{alpha}$ to accommodate CAD Val802, while both Tyr102 and Tyr103 become more ordered. Further evidence of induced fit comes from the significant differences in resolution between the structures obtained with and without CAD fragments bound reflecting ordering of FIH that occurs on binding (structure 4, for comparison, represents FIH complexed with Fe$^{(II)}$ and 2OG alone). Interference in the conformational changes involved in the hypoxic response, in particular those involving the CAD region, e.g. by use of small molecules or by gene or protein therapy, may allow manipulation of the hypoxic response to enable pro or anti-angiogenetic responses.

Thus, the structural studies define the (i) FIH residues involved in binding the CAD of HIF (ii) conformation of FIH when CAD is bound and (iii) conformation of CAD when bound to FIH. These results are useful in the design of selective inhibitors of FIH and related enzymes. Features of the FIH binding sites may be used to mediate tighter binding of inhibitors to FIH or to obtain inhibitors that do not bind tightly to FIH, i.e. avoid inhibition of FIH.

Inhibitors binding at or close to the Site 1 may exploit electrostatic, hydrogen binding and/or hydrophobic interactions with Tyr-102, Asp-104, Lys-106, Asp-201, Glu-202, Gln-147, Gln-239, residues 299-303, His-313, Ala-317, Ile-318, Asn-321, Lys-324, Arg-238, Trp-296, Asn-321-Lys-324. Inhibitors binding at Site 1 may mimic or partially mimic the turn conformation adopted by CAD when bound at Site 1.

Inhibitors binding at or close to Site 2 may exploit electrostatic, hydrogen binding and/or hydrophobic interactions with residues Thr-149, Leu-150, Asn-151, Asp-152 and residues Val-159, Phe-162, Leu-163, Trp-167, Gln-181, Leu-182, Thr-183, Ser-184, Asn-185. Inhibitors binding at Site 2 may mimic or partially mimic the helical conformation adopted by CAD when bound at Site 2.

It is recognised that inhibitors need not bind to both Sites 1 and 2, although that they may, and that Site 1 is preferred over Site 2.

Residues 801-805 of CAD that bind at Site 1, and in particular residues 802-805 form a turn conformation in which the distance of the backbone C=O of 802 to the backbone NH of 804 is ca. 2.8 Å. Including the H-bond formed between the NH of Ala-804 and the carbonyl O of Val-802 of the HIF-1 alpha CAD, the turn contains 7 atoms in a pseudo-ring.

Turns are especially amenable to mimicry by analogues useful for enzyme inhibition or receptor binding. The medicinal chemistry literature is replete with examples of such turn mimics. These can be modified by known methods to bind to specific targets, in particular given the knowledge of the target structure.

Examples of turn mimics and their modifications can be found in the following reviews: Hanessian et al, TETRAHEDRON 53: 12789-12854 Sep. 22 1997; Gillespie et al, BIOPOLYMERS 43: 191-217 1997; and Burgess et al., ACCOUNTS CHEM RES 34: 826-835 2001). Recent examples of primary reports on turns include the following (and references therein) Maier et al, EUR J ORG CHEM: 2686-2689, 2002; Reid et al, J AM CHEM SOC 124: 5673-5683, 2002; Mahadevan et al, J BIOMOL STRUCT DYN 19: 775-788 2002; Eguchi et al, J MED CHEM 45:1395-1398 2002; De Borggraeve et al, TETRAHEDRON LETTERS 42: 5693-5695 2001; Kohn et al, TETRAHEDRON LETT 42: 4453-4457 2001; Eguchi et al, TETRAHEDRON LETT 42: 1237-1239 2001; Manzoni et al, TETRAHEDRON 57: 249-2552001; Jiang et al., HELV CHIM ACTA 83: 3097-3112 2000; Derrer et al, J CHEM SOC PERK T 1: 2957-2967 2000; Belvisi et al, EUR J ORG CHEM: 2563-2569 2000; Claridge et al, BIOORG MED CHEM LETT 6: 485-490 1996.

These include compounds of the general formula:

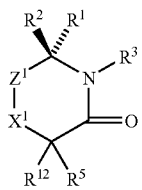

II wherein $R^1$ is such that it can form an electrostatic or H-bonding interaction with Gln-237 and or Arg-238, preferably $CR^8R^9CONH_2$ or an analogue thereof where $R^1$ is hydrogen or a peptide or peptide mimetic (such as those composed of β-amino acids or peptide isosteres), and $R^9$ is hydrogen, optionally functionalised alkyl, optionally functionalised aryl, heteroaryl or any combination thereof such as $CH_2CONH_2$, $R^2$ is hydrogen or a group that will interact favourably with Tyr-102 of FIH, $R^3$ is H or a group which can form a H-bond with Asp-201, $Z^1$ is >C=O or $>CR_5R^9$ where $R^5$ is hydrogen, optionally functionalised alky, aryl, or heteroaryl or any combination thereof, $R^{12}$ is as defined for $R^5$ or is $NHR^6$ where $R^6$ is $COR^5$ or $SO_2R^5$ and $X^1$ is $NR^1$, $NR^4C(R^5)_2$, $C(R^5)_2NR^4$, or O or NH where $R^4$ is $COR^5$ or $SO_2R^5$. In this and in the other formulae each $R^1$, $R^2$, $R^3$, $R^4$, $R^5$, $R^6$, $R^7$, $R^8$, $R^9$, $R^{10}$, $R^1$ and $R^{12}$ can be the same or different. In particular, these compounds may have one of the formulae

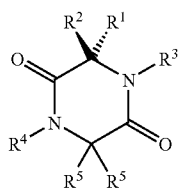 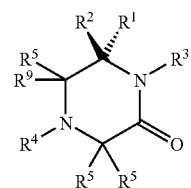

-continued

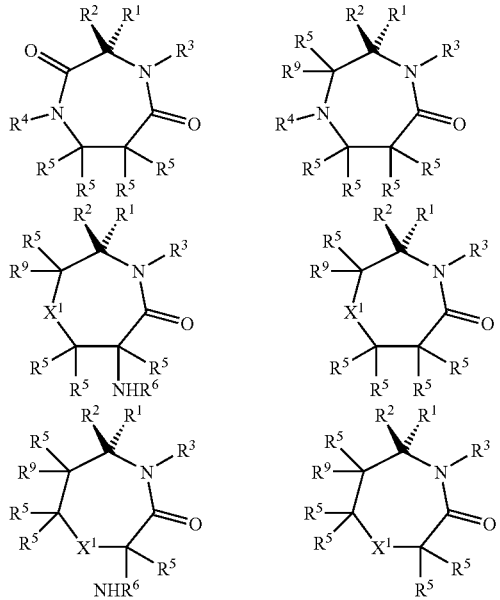

wherein the radicals are as defined above, and $R^7$ and $R^8$ are independently peptides or peptides mimetics or part peptide mimetics, such as those containing or consisting of beta-amino acid residues, urethane, sulphonamide or phosphonamide links.

Other compounds which can be used are those possessing the formula

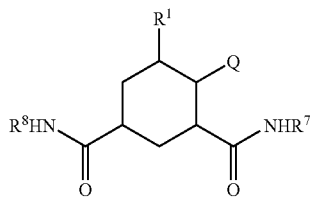

III where Q represents H or OH and $R^7$ and $R^8$ are as defined above.

Further compounds which can be used possess the formula

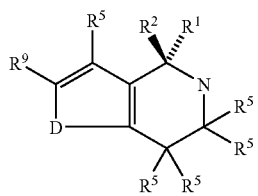

IV wherein $R^1$, $R^2$, $R^5$ and $R^9$ are as defined above and D is S, O, NH or $CHR^9$=$CHR^9$. Thus the ring attached to the six-membered ring is either a five-membered heterocyclic ring or an aryl ring.

In these formulae $R^8$ and $R^9$ can be optimised to bind in the channel linking the 2OG and peptide substrate binding sites and to the 2OG binding site itself.

Cyclic peptides acting as mimics of the turn adopted by CAD in site 1. The cyclo may be formed via peptide links, disulphide bonds or C—C bonds.

Inhibitors Employing a Combination of Binding Sites

It is well known that enzyme inhibitors competing for binding at more than one substrate or cosubstrate binding site, sometimes termed bisubstrate inhibitors, can be useful. Examples can be found in Wang et al, BIOCHEMISTRY-US: 15676-15683 2001; and Lerner et al, ANGEW CHEM INT EDIT 40, 4040-4041, 2001.

In the case of FIH and other 2OG oxygenases bisubtrate inhibitors may be useful since features of 2OG binding may be present in more than one enzyme whereas the CAD substrate is unique. Thus, inhibitors that bind to both binding sites may show improved selectivity over those that bind to the 2OG binding site only. The structural analyses enable the identification of such bisubtrate inhibitors. The 2OG and CAD binding sites are linked to each other via a 'channel' extending from the 2-oxo group of 2OG (or NOG) to the beta-carbon Asn-803 in the FIH.Fe.2OG/NOG.HIF(CAD) complexes. In the structures this 'channel' either appears empty but may be occupied by water molecules. The distance from the C of the 2-oxo group of 2OG to the beta-C of Asn-803 is ca. 6 Å. The distance from the 3-C of 2OG to the beta-C of Asn-803 is ca. 6.6 Å. The information from the structural analyses enables the identification of bisubstrate inhibitors, including the following:

These are compounds of formulae (II) to (IV) as defined above except that they are modified such that they can also bind into the 2OG binding pocket as defined by the crystallographic information. Thus, either $R^2$ or $R^1$ is modified such that they can bind into the 2OG binding pocket. The modification takes the form such that the general formula of $R^1$ or $R^2$ is A-X where X is as defined above and A links X to (II). A is of appropriate length such that X can bind to formula 1 the residues of the 5-carboxylate of 2OG as discussed above under the heading Inhibitors Exploiting the 2OG binding sites.

More generally bi-substrate inhibitors of FIH can have the formula:

where X is as defined above, B is a linker group and C is an entity binding to part of the CAD binding site of FIH, in general $CONH_2$.

B is typically a polymethylene group, generally having 6 to 8 carbon atoms or an equivalent group where one or more of the carbon atoms is replaced by a heteroatom, notably O, S or N and can be functionalised, for example with thiol, alcohol, carboxylate, hydroxamic acid or oxalate to mediate Fe binding. It is preferably 6 to 8 carbon atoms long or its equivalent. Alternatively, B is a linking group which possesses a ring, preferably of 5 to 7 members to which C is attached.

Inhibitors that Bind to the 2OG Binding Site or Part Thereof and the Peptide Substrate Another class of inhibitors bind to the enzyme-substrate complex, i.e. to FIH.Fe(II).HIF(CAD). The structural analyses enable the identification of such inhibitors. As described above 2OG and CAD binding sites are linked to each other via a 'channel' extending from the 2-oxo group of 2OG (or NOG) to the beta-carbon of Asn-803 in the FIH.Fe.2OG/NOG.HIF (CAD) complexes.

Inhibitors of this type may be defined as X–[B]–[E] where X is as defined above, B is a linker group such as defined above and E is an entity binding to part of the CAD when bound to HIF. E may bind to the backbone carbonyl oxygen of Asn-803 of CAD and to the $NH_2$ group of the primary amide of Asn-803.

Mechanism Based Inhibitors

Another class of inhibitors is based upon substrate analogues that can undergo part of the catalytic cycle but either stall at an intermediate stage or cause an aberrant reaction resulting in damage or inhibition. The observation that FIH catalyses hydroxylation of Asn-803 at the beta-position together with the structural analyses enables the design of such inhibitors. Such compounds include analogues of the substrates (inhibitors) in which Asn-803 is replaced with an analogue which does not undergo oxidation such as beta-fluoro-asparagine, beta-di-fluoro-asparagine, beta-methyl-asparagine, beta-dimethyl-asparagine derivatives. Alternatively derivatives that undergo oxidation to give an agent that can be oxidised to give an inactivating group such as an epoxide or metal chelating group may prepared (such mechanism based inhibitors are sometimes referred to as suicide inhibitors). In the case of FIH they include alpha-beta-dehydroasparagine and beta-methylene asparagine.

These include a compound having the formula

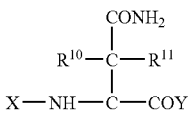

wherein X represents a valine residue or an analogue thereof and Y represents an alanine residue or an analogue thereof, $R^{10}$ is fluorine or $C_1$-$C_3$ alkyl, especially methyl, and $R^{11}$ is fluorine, $C_1$-$C_3$ alkyl or hydrogen i.e. the specified residue is 3-mono- or di-fluoroasparagine or β-mono- or di-methylasparagine.

Alternatively, the compound above may be desaturated, i.e. is an alpha/beta dehydroamino acid ($R^{11}$ not present) or $R^{10}$ and $R^{11}$ may be replaced by a methylene group, i.e. the residue is α, β-dehydro-asparagine or β-methylene asparagine.

If desired the valine residue is connected to one or more units of the peptide DESGLPQLTSYDCE-(SEQ ID NO: 1) in the order given e.g. to glutamic acid (E) alone or to, for aspartic acid (D)-cysteine (C)-glutamic acid (E)-, or a longer chain such as PQLTSYDCE-(residues 6-14 of SEQ ID NO: 1).

For the compounds of this invention suitable aryl rings include phenyl and napthalenyl, which may be further functionalised or fused to other ring systems. Suitable heterocyclic rings include thiophene, pyridine, quinoline, isoquinoline, pyrimidine, pyrazine, pyrone, chromone, coumarin, indole, isoindole, indolizine, benzofuran, pyridazine, purine, oxazole, pyrazole, isothiazole, pyrrolidine, piperidine, indoline, benzothiaphen, morpholine, benzimidazole, azepine, azacine, azoine, oxepine, oxocine, oxoine, piperazine, oxazine, thiazine, thiepine, thiocine, thioine, furan, imidazole, azole, diazole, triazole and tetrazole Ting systems that may be functionalised or fused to other ring systems.

The said alkyl and aryl groups and chains are typically functionalised by alcohol, fluorine, thiol, a carboxylic acid, phosphonic or phosphinic acid, sulphonic acid or other chelating group, in the case of the chains typically via an alkyl group. In the formulae described herein, a branched or straight $C_1$ to $C_6$ alkyl chain may be a methyl, ethyl, propyl, butyl, iso-butyl, tert-butyl, pentyl, neopentyl, tert-pentyl or a primary, secondary or tertiary hexyl group. Preferably the alkyl groups are methyl, the preferred heterocyclic rings are pyrolidine and tetrahydropyran and the preferred aromatic rings are benzene, naphthalene and pyridine.

The compounds which are acids can be present in the form of salts, such as sodium salts.

The crystal structure of FIH also allows identification of those residues involved in asparaginyl hydroxylase activity of FIH. The crystal structures may therefore be used to design modified FIH, for example, which has reduced or no asparaginyl hydroxylase activity, for example, by mutation of critical residue within the active site. In the alternative, those residues involved in substrate binding can be identified and modified, for example, to allow the asparaginyl hydroxylase to accept other substrates than HIF. For example, by enlarging or decreasing the asparagine binding pocket. Such modified asparaginyl hydroxylases can then be produced using standard techniques. The expected activity can then be assayed as described in more detail below, for example, to identify whether the hydroxylase activity with respect to HIF has been reduced or removed, or alternatively, to assess the asparaginyl activity or binding in respect to other substrates.

Compounds which have been identified in accordance with the present invention can be further analysed in assays to monitor for activity of the asparagine hydroxylase enzyme directly. Agents which inhibit or reduce HIF asparagine hydroxylase activity reduce hydroxylation of HIF-α and lead to an increase in the interaction with P300 and in particular the CH1 domain and thus transcriptional activation. This in turn will lead to the activation of systemic local defences against hypoxia or ischaemia that may include the promotion of angiogenesis, erythropoesis, energy metabolism, inflammation, vasomotor function and will also affect apoptotic/proliferative responses.

We describe below in more detail a number of different assays that may be carried out to assay the activity of modulators of HIF hydroxylase activity or of FIH identified in accordance with the present invention and in particular of asparagine hydroxylase activity, or which affect regulation of HIF-α interaction with p300 in a cell and hence which affect HIF mediated activity. Some of these assays utilise HIF polypeptides, and HIF asparagine hydroxylases. Typically, the assays may utilise a human HIF asparagine hydroxylase such as FIH or a fragment or variant of a human HIF asparagine hydroxylase. These components are described in more detail below. Each of these components, where required, may be provided either in purified or unpurified form, for example, as cellular extracts or by purification of the relevant component from such extracts. Alternatively, the relevant component can be expressed using recombinant expression techniques and purified for use in the assay. Alternatively, the components may be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail herein with reference to the HIF hydroxylases. Promoter sequences may be inducible or constitutive promoters depending on the selected assay format. The promoter may be tissue specific. Examples of promoters and other flanking sequences for use in the expression vectors are described in more detail herein with reference to the HIF hydroxylases of the invention and in particular to the human HIF hydroxylases.

HIF Polypeptides and Peptide Analogues

The assays of the present invention may use a substrate of a HIF asparagine hydroxylase and in particular an asparagine containing substrate of the enzyme. In particular, such substrates may be used in assays to monitor for the activity of a modulator of HIF asparagine hydroxylase activity. The substrate may be a HIF polypeptide or peptide analogue thereof. Typically, a HIF polypeptide will be used as the substrate.

Any suitable substrate in which an asparagine residue is hydroxylated by a FIH may be used. In preferred embodiments of the invention, such a substrate is a HIF polypeptide such as a HIF-1α or HIF-2α subunit protein or fragment of either or peptide analogue of the subunit or fragment. Preferably, the HIF-α peptide conveys an oxygen regulated response. Preferably, the HIF-α peptide has a CAD domain and is capable of oxygen regulated interaction with p300 and downstream transcriptional activation. Preferably, such HIF-α peptides are capable of interacting with the p300 CH1 domain. Preferably, such HIF polypeptides, fragments or peptide analogues incorporate an asparagine residue equivalent to Asn 803 defined with reference to HIF-1α. The asparagine equivalent to Asn 803 of HIF-1α may be determined by aligning the HIF variant, fragment or analogue to the sequence of HIF-1α to obtain the best sequence alignment and identifying thereby the asparagine equivalent to Asn 803 of HIF-1α.

A HIF polypeptide may be of eukaryotic origin, in particular a human or other mammalian, HIF-α subunit protein or fragment thereof. Alternatively, the polypeptide may be of *C. elegans* origin. In those assays which monitor for hydroxylation of HIF-α through its interaction with p300, the HIF polypeptide has the ability to bind to a wild type full length p300 protein or a fragment thereof comprising the CH1 domain. Preferably, such binding is able, in a hypoxic cellular environment, to activate transcription.

A number of HIFα subunit proteins have been cloned. These include HIF-1α, the sequence of which is available as Genbank accession number U22431, HIF-2α, available as Genbank accession number U81984 and HIF-3α, available as Genbank accession numbers AC007193 and AC079154. These are all-human HIF α subunit proteins and all may be used in the invention. HIF-α subunit proteins from other species, including murine HIF-1α (accession numbers AF003695, U59496 and X95580), rat HIF-1α (accession number Y09507), murine HIF-2α (accession numbers U81983 and D89787) and murine HIF-3α (accession number AF060194) may also be used in the invention.

One HIF-α protein of particular interest is the *C. elegans* HIFα subunit protein. The *C. elegans* system may be used in assays of the present invention.

There are a number of common structural features found in the two HIF-α subunit proteins identified to date. Some of these features are identified in O'Rourke et al (1999, J. Biol. Chem., 274; 2060-2071) and may be involved in the transactivation functions of the HIF-α subunit proteins. One or more of these common structural features are preferred features of the HIF polypeptides.

Variants of the above HIF-α subunits may be used, such as synthetic variants which have at least 45% amino acid identity to a naturally occurring HIF-α subunit particularly to a human HIF-α subunit such as, for example HIF-1α), preferably at least 50%, 60%, 70%, 80%, 90%, 95% or 98% identity. Such variants may include substitutions or modifications as described above with respect to HIF hydroxylases. Amino acid activity may also be calculated as described above with reference to HIF hydroxylases.

HIF fragments may also include non-peptidyl functionalities and may be optimised for assay purposes such that the level of identity is lowered. Such functionalities may be covalently bound such as sugars or non-covalently bound such as metal ions.

HIFα polypeptides as described herein may be fragments of the HIF-αsubunit protein or variants as described above, provided that said fragments retain the ability to interact with a wild-type p300 CH1 domain. When using proteinogenic amino acid residues, such fragments are desirably at least 20, preferably at least 40, 50, 75, 100, 200, 250 or 400 amino acids in size. Desirably, such fragments include asparagine 803.

Cell based assays of the present invention may involve upregulation of an endogenous HIF-α or expression of a HIF-α by recombinant techniques and in particular of HIF-1α.

Assay Methods

The present invention provides an assay method for an agent identified as a modulator of asparagine hydroxylation of hypoxia inducible factor. The method comprises contacting a HIF asparagine hydroxylase and a test substance in the presence of a substrate of the hydroxylase under conditions in which asparagine hydroxylation occurs in the absence of the test substrate and determining asparagine hydroxylation of the substrate. In an alternative assay, HIF asparagine hydroxylase and the test substance are contacted in the presence of the substrate of the hydroxylase under conditions in which hydroxylation does not occur in the absence of the test substrate. Determination of any asparagine hydroxylation is monitored to identify whether the agent actively acts as a promoter of asparagine hydroxylase.

FIH has been found to hydroxylate HIF-α at an asparagine residue within the CAD domain. This hydroxylation mediates p300 binding and in particular, reduces p300 binding. Such binding leads to transcriptional activation. This interaction and activation may also be used as the basis for an assay of the invention.

Such assays of the present invention may be used to assay the activity of inhibitors of HIF asparagine hydroxylase activity and are thus preferably carried out under conditions under which asparagine hydroxylation would take place in the absence of the test substance. The assays of the invention may also be used to assay the activity of inhibitors which are specific for HIF asparagine hydroxylases and which do not have activity or are less active with other hydroxylases, for example, such as HIF prolyl hydroxylases or other asparagine/aspartamic acid hydroxylases. The assays of the invention may also be used to assay the activity of hydroxylase modulators, such as HIF prolyl hydroxylase inhibitors which are not expected to have activity on FIH based on structural modelling studies, and hence may be used to identify inhibitors which are specific for prolyl hydroxylase.

Methods for Monitoring Modulation

The precise format of any of the screening or assay methods of the present invention may be varied by those of skill in the art using routine skill and knowledge. The skilled person is well aware of the need to additionally employ appropriate controlled experiments. The assays of the present invention may involve monitoring for asparagine hydroxylation of a suitable substrate, monitoring for the utilisation of substrates and co-substrates, monitoring for the production of the expected products between the enzyme and its substrate.

Assay methods of the present invention may also involve screening for the direct interaction between components in the system. Alternatively, assays may be carried out which monitor for downstream effects such as binding of HIF by p300 and downstream effects mediated by HIF such as HIF mediated transcription using suitable reporter constructs or by monitoring for the upregulation of genes or alterations in the expression patterns of genes know to be regulated directly or indirectly by HIF.

Various methods for determining hydroxylation are known in the art and are described and exemplified herein. Any suitable method may be used for determining activity of the HIF hydroxylase such as by substrate or co-substrate utilization, product appearance such as peptide hydroxylation or down-stream effects mediated by hydroxylated or non-hydroxylated products.

Assays may be carried out to monitor directly for hydroxylation of the relevant asparagine residue or another position. Alternatively, assays may be carried out to monitor for depletion of co-factors and co-substrates. Alternatively, such assays may monitor the downstream effects of hydroxylation of HIF or indeed inhibition of hydroxylation of HIF, for example, by monitoring the interaction between HIF and p300 or HIF mediated transcription. Alternatively, reporter gene constructs driven by HIF regulated promoters may be used. Assays are also provided for the identification of enhancers of the activity of the HIF asparagine hydroxylase. Such enhancers may be used to reduce HIFα activity.

In one embodiment, a suitable substrate of the HIF asparagine hydroxylase is provided. This may be HIF-α or a fragment thereof which includes a CAD domain or which includes a residue equivalent to Asn 803 of HIF-1α. The substrate may not be initially hydroxylated at the Asn 803 position. This may be achieved by providing synthetic polypeptide substrates, or by producing HIFα polypeptides in bacterial cells, insect cells or mammalian cells or in in vitro transcription and translation systems. Alternatively, assays may be carried out over a selected time course such that the substrate is produced during the course of the assay, initially in unhydroxylated form.

The substrate, enzyme and potential inhibitor compound may be incubated together under conditions which, in the absence of inhibitor provide for hydroxylation of Asn 803, and the effect of the inhibitor may be determined by determining hydroxylation of the substrate. This may be accomplished by any suitable means. Small polypeptide substrates may be recovered and subject to physical analysis, such as mass spectrometry or chromatography, or to functional analysis, such as the ability to bind to p300 (or displace a reporter molecule from p300). Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

Inhibitor compounds which are identified in this manner may be recovered and formulated as pharmaceutical compositions.

Assays in accordance with the present invention may involve monitoring for the interaction between p300 and HIF. The interaction between HIF and p300 is mediated by hydroxylation of HIF. Transcription and expression of genes known to be upregulated or down regulated by the presence of HIF could be monitored. In particular, upregulation of HIF regulated genes would demonstrate inhibition of asparagine hydroxylation whereas down regulation would suggest enhancement or promotion of asparagine hydroxylation.

In alternative embodiments, reporter constructs may be provided in which promoters mediated by HIF are provided operably linked to a reporter gene. Any suitable reporter gene could be used, such as for example enzymes which may then be used in colorometric, fluorometric, fluorescence resonance or spectrometric assays.

HIF asparagine hydroxlase is a 2OG dependent oxygenase. In the assay methods described herein, typically the HIF asparagine hydroxylase and the substrate of the hydroxylase are contacted in the presence of a co-substrate, such as 2-oxo-glutarate (2OG). The hydroxylase activity of the HIF hydroxylase may be determined by determining the turnover of the co-substrate. This may be achieved by determining the presence and/or amount of reaction products, such as hydroxylated substrate or succinic acid. The amount of product may be determined relative to the amount of substrate. Typically, in such embodiments the substrate may be an HIFα polypeptide and, for example, the product measured may be hydroxylated HIF-α polypeptide.

Alternatively, the end-point determination may be based on conversion of HIFα or peptide fragments (including synthetic and recombinant peptides) derived from HIFα into detectable products. Peptides may be modified to facilitate the assays so that they can be rapidly carried out and may be suitable for high throughput screening.

For example, reverse phase HPLC (C-18 octadecylsilane column), may be used to separate starting synthetic peptide substrates for HIF hydroxylase from the asparagine hydroxylated products, as the latter have a shorter retention time in the column. Modifications of this assay or alternative assays for HIF hydroxylase activity may employ, for example, mass spectrometric, spectroscopic, and/or fluorescence techniques as are well known in the art (Masimirembwa C. et al Combinatorial Chemistry & High Throughput Screening (2001) 4 (3) 245-263, Owicki J. (2000) J. Biomol. Screen. 5 (5) 297-305, Gershkovich A et al (1996) J. Biochem. & Biophys. Meths. 33 (3) 135-162, Kraaft G. et al (1994) Meths. Enzymol. 241 70-86). Fluorescent techniques may employ versions of the substrate modified in such as way as to carry out or optimise spectroscopic or fluorescence assays.

For example, HIFα polypeptide may be immobilised e.g. on a bead or plate, and hydroxylation of the appropriate residue detected using an antibody or other binding molecule which binds the CAD binding domain of HIFα with a different affinity when an asparagine 803 is hydroxylated from when the residue is not hydroxylated. Such antibodies may be obtained by means of standard techniques which are well known in the art, e.g. using a hydroxylated HIFα peptide.

Binding of a molecule which discriminates between the hydroxylated and non-hydroxylated form of a HIFα polypeptide may be assessed using any technique available to those skilled in the art, which may involve determination of the presence of a suitable label.

Assay methods of the present invention may also take the form of an in vivo assay. The in vivo assay may be performed in a cell line such as a yeast strain in which the relevant polypeptides or peptides are expressed from one or more vectors introduced into the cell.

In Vivo Assays

The assays may be carried out using cell based, organ based or whole animal assays conducted in vivo. Such assays may utilize the endogenous expression of the HIF hydroxylase nucleotides and/or polypeptides. In other forms of the invention, upregulation of specific endogenous HIF hydroxylases may be achieved by stimulators of the expression thereof. Such stimulators may be growth factors or chemicals that upregulate specific HIF asparagine hydroxylases. In another form of the assay, nucleotide constructs may be introduced into cells or transgenic animals to increase production of one or more specific HIF asparagine hydroxylases.

HIF complexed with p300 activate hypoxia response elements that are found in the promoters and/or enhancers of endogenous genes that are regulated by the said HIF complexes. Such hypoxia response elements may also be isolated and operationally linked to reporter genes so as to assay the activity of the HIF complex through detection and/or quantitation of the reporter gene or its product Therefore in a further form of the invention the activity of a HIF-α polypeptide that is regulated by HIF asparagine hydroxylase will be assayed by measuring the effects of the HIF complex on the expression of an endogenous gene or reporter gene that is functionally linked to a HIF binding hypoxia response element. Examples of endogenous genes that are regulated in this way are to be found in the role of the aryl hydrocarbon nuclear translocator (ARNT) in hypoxic induction of gene expression, see for example, Studies in ARNT-deficient cells. S. M. Wood, J. M. Gleadle, C. W. Pugh, O. Hankinson, P. J. Ratcliffe. Journal of Biological Chemistry 271 (1996) 15117-15123, and Hypoxia inducible expression of tumor-associated carbonic anyhydrases, C. C. Wykoff, N. J. P. Beasley, K. J. Turner, J. Pastorek, A. Sibtain. G. D. Wilson, H. Turley, K. Talks, P. H. Maxwell, C. W. Pugh, P. J. Ratcliffe, A. L. Harris. Cancer Research 60 (2000) 7075-7083. Examples include but are not limited to glucose transporter isoform 1, phosphoglycerate kinase-1, carbon anhydrase isoform 9, vascular endothelial growth factor. Each of said genes contains one or hypoxia response elements that may be isolated and operationally linked as single or multiple copies to a reporter gene for the measurement of activity of a HIF-α polypeptide that varies in accordance with the activity of a HIF hydroxylase.

The activity of genes or gene products that are regulated by a HIF-α polypeptide in accordance with the activity of a HIF hydroxylase affects cellular, organ, and animal physiology. Assays that utilise a specific functional response that is regulated in accordance with the activity of a HIF-α polypeptide in accordance with the activity of a HIF hydroxylase may be used. Such responses include the uptake rate of glucose or glucose analogues that are not metabolized, the growth of blood vessels by angiogenesis, the activity of a carbonic anhydrase enzyme. It is recognised that many other responses that operate at a cellular or systemic level are controlled by the activity of a HIF-α polypeptide in accordance with the activity of a HIF hydroxylase and may be utilized as assays of the said HIF hydroxylase activity in further aspects of the invention.

A HIF-α polypeptide that is a substrate for a HIF hydroxylase may be fused to a further polypeptide so as to cause the activity of the said HIF hydroxylase to regulate the activity of the fusion peptide. Accordingly a further form of the invention provides for the assay of the activity of a fusion polypeptide. In the preferred form such a fusion polypeptide may contain the whole of part of a HIF-polypeptide, particularly including Asn 803, or the CAD domain. The Gal4 DNA binding domain including the amino acids 1-143 together with the Gal binding upstream activating sequence (UAS) is an example of such a transcription factor and cognate DNA response element whose operation can be assayed by those skilled in the art.

Selectivity

It may also be advantageous to modulate HIF asparagine hydroxylase selectively, as a single target, or in selected hydroxylase groups as well as an entire family. Agents which modulate HIF asparagine hydroxylase activity are therefore preferably specific i.e. they have an increased or enhanced effect on a HIF asparagine hydroxylase relative to other 2OG dependent oxygenases.

Assay methods as described herein may therefore further comprise contacting the test compound with one or more 2OG dependent oxygenases under conditions in which said 2OG dependent oxygenases are normally active and determining activity of said oxygenases. A difference in activity in the presence relative to the absence of test compound is indicative of the test compound modulating the activity of the one or more 2OG dependent oxygenases.

A test compound which provides increased or enhanced modulation of a HIF asparagine hydroxylase, relative to the one or more 2OG dependent oxygenases shows selectivity or specificity for the HIF hydroxylase.

2OG dependent oxygenases may include for example, clavaminte synthase, Alk B deacetoxycephalosporin C synthase, collagen-prolyl-4-hydroxylase, collagen prolyl-3-hydroxylase, lysyl hydroxylase, aspartyl hydroxylase, phytanoyl coenzyme A hydroxylase or gamma-butyrobetaine hydroxylase. 2OG dependent oxygenases may be mammalian, preferably human polypeptides.

The invention provides for the use of such selective inhibitors of HIF asparagine hydroxylases in the manufacture of a medicament for the treatment of a condition associated with reduced HIF activity.

Therapeutic Applications

A compound, substance or agent which is found to have the ability to affect the hydroxylase activity of a HIF asparagine hydroxylase, or the compounds referred to herein as FIH inhibitors has therapeutic and other potential in a number of contexts. For therapeutic treatment, such a compound may be used in combination with any other active substance, e.g. for anti-tumour therapy another anti-tumour compound or therapy, such as radiotherapy or chemotherapy.

An agent identified using one or more primary screens (e.g. in a cell-free system) as having ability to modulate the HIFα asparagine hydroxylation activity of a HIF hydroxylase may be assessed further using one or more secondary screens. A secondary screen may involve testing for an increase or decrease in the amount of HIFα or HIF activity, for example as manifest by the level of a HIF target gene or process present in a cell in the presence of the agent relative to the absence of the agent.

A HIF hydroxylase or a HIF polypeptide may be used in therapies which include treatment with full length polypeptides or fragments thereof, or otherwise modified polypeptides (e.g. to enhance stability or ensure targeting, including in conjunction with other active agents such as antibodies. For example, mutation of HIF-1α to replace Asn 803 with another amino acid residue may prevent hydroxylation and thus promote interaction of HIF-α with p300 and stimulate transcriptional activation.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. Typically, the concentration in such compositions is 0.1 to 50%, generally 0.5 to 20%, especially 1 to 10% by weight based on the weight of the composition. As noted below, a composition according to the present invention may include in addition to an modulator compound as disclosed, one or more other molecules of therapeutic use, such as an anti-tumour agent.

Products Obtained by Assays of the Invention

The invention further provides compounds obtained or identified by methods of the present invention, and compositions comprising said compounds, such as pharmaceutical compositions wherein the compound is in a mixture with a pharmaceutically acceptable carrier or diluent. The carrier may be liquid, e.g. saline, ethanol, glycerol and mixtures thereof, or solid, e.g. in the form of a tablet, or in a semi-solid form such as a gel formulated as a depot formulation or in a transdermally administerable vehicle, such as a transdermal patch.

The invention further provides a method of treatment which includes administering to a patient an agent which interferes with the hydroxylation of the asparagine target residue of an HIFα polypeptide by a HIF hydroxylase. Such agents may include inhibitors of asparagine hydroxylase activity. The invention also provides a method of treatment which includes administering to a patient a compound as defined above.

The therapeutic/prophylactic purpose may be related to the treatment of a condition associated with reduced or suboptimal or increased HIF levels or activity, or conditions in which have normal HIF levels, but where an modulation in HIF activity such as an increase or decrease in HIF activity is desirable such as:

(i) ischaemic conditions, for example organ ischaemia, including coronary, cerebrovascular and peripheral vascular insufficiency. The therapy may be applied in two ways; following declared tissue damage, e.g. myocardial infarction (in order to limit tissue damage), or prophylactically to prevent ischaemia, e.g. promotion of coronary collaterals in the treatment of angina.
(ii) wound healing and organ regeneration
(iv) auto-, allo-, and xeno-transplantation.
(iv) systemic blood pressure
(v) cancer; HIFα is commonly up-regulated in tumour cells and has major effects on tumour growth and angiogenesis.
(vi) inflammatory disorders.
(vii) pulmonary arterial blood pressure, neurodegenerative disease.

Modulating HIF prolyl hydroxylase activity in a person, an organ, or a group of cells may be exploited in different ways to obtain a therapeutic benefit:

(a) Non cell autonomous: The HIF system is used by cells to influence the production of substances which signal to other cells. These signals may then have effects at (i) a distant site (for example erythropoietin acts on the bone marrow) or (ii) locally (angiogenic growth factors increase the local formation of blood vessels). Manipulating non cell autonomous behaviour via altering hydroxylase activity is therefore useful in the treatment of anaemia, and local ischaemia, for example in the eye, brain, heart and limbs. Many other signals that are involved in aspects of physiological homeostasis may be, or are known to be, adjusted by HIF activation. Consequently altering HIF prolyl hydroxylase activity may be used to potentiate or initiate a helpful response for a therapeutic benefit, or to prevent or ameliorate a harmful response. For example, this approach can be used to alter appetite, or blood pressure in the systemic or pulmonary beds.

(b) Cell autonomous: the HIF system is also used by cells to regulate cellular metabolism, and decisions concerning differentiation, proliferation and apoptosis. Therefore manipulating the HIF system can be used to alter the viability and behaviour of cells. An increase in cell viability can be achieved by increasing HIF activation, for example in an ischaemic tissue. This approach can also be used in improving pancreatic beta cell viability as a way of ameliorating diabetes, or of improving the viability or function of a group or groups of neurons in Parkinson's disease, motorneurone disease or forms of dementia. In a different approach, the HIF signal can be manipulated to prevent a group of cells proliferating, or to promote its death or differentiation. For example transient activation of the HIF system in a malignant tumour can be used to provoke death of a substantial number of tumour cells.

Pharmaceutical Compositions

In various further aspects, the present invention thus provides a pharmaceutical composition, medicament, drug or other composition for such a purpose, the composition comprising one or more agents, compounds or substances as described herein, including HIF asparagine hydroxylase inhibitors, or one or more compounds of formula (A) to (F) or derivatives thereof, the use of such a composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:

(a) identifying an agent in accordance with the invention; and (b) formulating the agent thus identified with a pharmaceutically acceptable excipient.

The agent may be used as sole active agent or in combination with one another or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual: The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient The precise nature of the carrier or other material will depend on the route of administration, which may be oral, or by injection, e.g. cutaneous, subcutaneous or intravenous. The compositions will typically be sterile.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased HIF levels or activity. The condition may, for example, be selected from the group consisting of ischaemia, wound healing, auto-, allo-, and xeno-transplantation, systemic high blood pressure, cancer, and inflammatory disorders.

EXAMPLES

Example 1

The position on Asn803 of human HIF-1α that is hydroxylated was identified as described in the following. cDNA sequences encoding FIH-1 were cloned into the pET28a(+) vector (from Novagen) to yield FIH-1 protein with an N-terminal His6 tag to facilitate purification. Purification of crude material by nickel affinity chromatography, followed by thrombin cleavage of the His6 tag, and size exclusion chromatography (Superdex S75) yielded >95% pure protein by SDS-PAGE analysis. Mass spectrometry confirmed the identity of the isolated species. The 19-residue peptide comprising amino acids 788-806 of human HIF-1α was modified by aerobic incubation with FIH-1 FIH (Hewitson et al., J BIOL CHEM 277 (29): 26351-26355, 2002) in the presence of ascorbate, DTT, catalase, 2-oxoglutarate, and iron(II) for 30 minutes at 37° C. The reaction was quenched by cooling to 4° C. and addition of an equal volume of methanol. Precipitate was removed by centrifigation and the supernatant purified by HPLC using a Jupiter C4 column (15 cm×4.6 mm). Peptide was eluted using a gradient of acetonitrile in 0.1% trifluoroacetic acid, freeze-dried from the HPLC solvent for amino acid and mass spectrometric analyses. The sample was freeze-dried a second time from $D_2O$ in preparation for NMR analysis.

Catalytic FIH-1 mediated hydroxylation of a synthetic 19 residue peptide corresponding to residues 788-806 of HIF-1α a was confirmed by mass spectrometric analysis of HPLC purified material: Native peptide 19mer $[M+2H]^{2+}$=1026.67Da, modified peptide 19mer $[M+2H]^{2+}$=1034.61Da, a mass difference of +8Da of the doubly charged ions, corresponding to +16Da in the peptide (oxygen). N-Terminal Edman degradation of the product peptide gave the following sequence: DESGLPQLTSYDCEVxA (SEQ ID NO: 3), where x was not asparagine. The peak from this (16th) cycle of Edman degradation ran to a similar position as the β-hydroxyasparagine standard. Acid hydrolysis of the modified peptide followed by amino acid analysis showed the presence of β-hydroxyaspartic acid only.

Both $^1H$ and $^{13}C$ chemical shift changes between the 19mer peptide substrate and the HPLC purified incubation product were assessed by 2D $^1H$-$^{13}C$ HSQC experiments. In the substrate a grouping of four β-$CH_2$ resonances were assigned as belonging to Asp-1, Tyr-11, Asp-12 and Asn-16 according to their $^1H$ and $^{13}C$ shifts (Evans, J. N. S. (1995) Biomolecular NMR Spectroscopy, Oxford University Press, Oxford, UK). In the product it was clear from both the 2D HSQC and the 1D proton spectra that only three of these four resonances are present. Comparison of the two spectra indicates that the signal assigned to the Asn-16 β-carbon (at δH 2.813 and 2.695 ppm and δC 37.40 ppm in the substrate) has disappeared, consistent with hydroxylation of the asparagine residue at its β-carbon. The resonances due to the two aspartic acid residues had shifted slightly, presumably due to changes in the protonation state, and now occur at a similar $^1H$ chemical shift as the β-protons of the asparagine in the substrate. A difference in the oxidation state of the cysteine between the two samples in unlikely given the near identical chemical shifts for the cysteinyl β-carbon and hydrogens. The change from a double doublet to a single doublet for the β-hydrogen of the hydroxylated residue also rules out any possibility the observed alterations in the NMR spectrum are due to aggregation. Two new resonances have appeared in the product spectrum at δH 4.913 ppm and δC 56.26 ppm and at δH 4.654 ppm and δC 72.22 ppm. These resonances correlate with one another in the 2D COSY spectrum and share a $^1H$-$^1H$ coupling constant of 2.4 Hz and are therefore assigned as the $CH^α$-$CH^β$ of the hydroxylated asparagine. The appearance of these resonances also coincides with the disappearance of the δH 4.706 ppm and δC 51.43 ppm resonances observed in the substrate spectra, which is therefore assigned as the $CH^α$ of the parent asparagine prior to modification. Comparison of the $CH^α$-$CH^β$ coupling constant of 2.4 Hz observed for the hydroxylated Asn-803, with literature values implied the threo isomer is produced.

In summary of the above $^1$NMR experiments: The HSQC experiments gave direct evidence for hydroxylation occurring at the β-carbon of the target asparagine, with the hydroxylated β-carbon appearing significantly deshielded (at 72.22 ppm) and the adjacent α-carbon deshielded to a lesser extent (at 56.26 ppm) relative to the parent asparagine. Changes of these magnitudes in the $^{13}C$ chemical shifts are inconsistent with hydroxylation of the side-chain nitrogen, but consistent with hydroxylation at the β-carbon Further, the $^{13}C$ spectrum of free DL-threo-β-hydroxyasparagine (this study), has resonances at 58.63 ppm and 73.85 ppm corresponding to α- and β-carbons. The product assignment is also consistent with $^1$H-NMR chemical shifts of the α- and β-hydrogens in the β-hydroxyaspartyl residues in EGF-like domains which are 4.48 ppm and 4.36 ppm respectively (with respect to water at 4.75 ppm) when calcium is absent (Selander et al, Biochemistry 29, 8111-8118). The analysis of the coupling constant reported here suggests that the threo-isomer is the one formed on hydroxylation of Asn-803 by FIH-1.

Two reports (Dames et al., (2002) Proc. Natl. Acad. Sci. U.S.A. 99, 52715276; Freedman et al, (2002) Proc. Natl. Acad. Sci. U.S.A. 99, 53675372) reveal how β-hydroxylation of Asn-803 of HIF-1α would be damaging to complex formation with p300. Although the position of hydroxylation was not identified in either report, both imply that hydroxylation at the pro-S position of the β-carbon, i.e. to give the threo (2S, 3S)-isomer, would interfere with the hydrogen bonding that maintains the α-helical conformation adopted by this part of HIF-1α, and also create a need for the energetically unfavourable desolvation of the hydroxyl group. A steric clash between the inserted pro-S hydroxyl group and Ile-353 (numbering from Dames et al (2002) Proc. Natl. Acad. Sci. U.S.A. 99, 52715276) of p300 would disrupt the interaction of the two proteins. Presumably the same mechanism is also used to abrogate the interaction of HIF-2α and p300. The discovery that it is the beta-position of Asn-803 that is modified and the associated mechanistic implications may be used in the design of compounds that bind to p300 thereby displacing HIF-alpha and/in the design of inhibitors of FIH (see below); in both cases to enable pro-angiogenetic pharmaceutical agents.

Example 2

To obtain an FIH:CAD complex suitable for X-ray analysis without oxidation of the CAD or the $Fe^{(II)}$, FIH and various CAD fragments from seven to fifty-two residues were co-crystallised with Fear and 2OG under anaerobic conditions. Structures were also obtained for FIH complexed with $Fe^{(II)}$ and N-oxaloylglycine (NOG, an FIH inhibitor), (anaerobically) and $Zn^{(II)}$ and NOG (aerobically). These structures were solved by molecular replacement using a model obtained by multiple anomalous dispersion on selenomethionine-substituted apo-FIH. Crystalline FIH:CAD complexes were obtained with $CAD_{786-826}$, $Fe^{(II)}$ and NOG or 2OG (structures 1 and 2, Table 1), $CAD_{775}$-826 with $Zn^{(II)}$ and NOG (structure 3). Crystallisation attempts with $CAD_{787-806}$, $CAD_{850-862}$ (HIF-2α, equivalent to HIF-1αC-ADS$_{802-814}$) and $CAD_{800-806}$ did not result in FIH:CAD complexes; solution analyses indicated that CAD fragments shorter than twenty resides are not efficient in vitro substrates.

TABLE 1

Summary of FIH: CAD-fragment complex structures*

| Structure No. | Resolution (Å) | Metal | Co-substrate | Co-crystallisation CAD peptide | Site 1 CAD residues resolved | Site 2 CAD residue resolved | $R_{free}$ (%) | R.m.s.d. from Struct. 1 (Å) | PDB ID. |
|---|---|---|---|---|---|---|---|---|---|
| 1 | 2.15 | Fe | NOG | HIF-1α 786-826 | 795-806 | 812-823 | 21.3 | — | 1H2K |
| 2 | 2.25 | Fe | 2OG | HIF-1α 786-826 | 795-806 | 813-822 | 21.7 | 0.149 | 1H2L |
| 3 | 2.50 | Zn | NOG | HIF-1α 775-826 | 795-806 | 813-822 | 22.5 | 0.136 | 1H2M |
| 4 | 2.84 | Fe | 2OG | HIF-2α 850-862 | — | — | 25.7 | 0.226 | 1H2N |

*Crystalline FIH: CAD complexes were also obtained with Fe$^{(II)}$, HIF-1α 775-786 and 2OG or NOG.

Methods Employed in Structural Work

Protein Expression, Purification and Crystallisation

FIH, CAD$_{775}$-826 and CAD$_{786}$-826 were prepared as described (Hewitson et al., J BIOL CHEM 277 (29): 26351-26355, 2002). Selenomethionine (SeMet) substituted FIH was produced using a metabolic inhibition protocol and LeMaster media supplemented with 50 mg/l L-selenomethionine. SeMet incorporation was >95% by ESI-MS. Aerobic crystallisation of SeMet FIH (at 11 mg ml$^{-1}$) was accomplished by hanging-drop vapour diffusion at 17° C. The mother liquor consisted of 1.2 M ammonium sulphate, 4% PEG 400 and 0.1 M Hepes pH 7.5. Crystallisation of FIH:Fe: CAD fragment complexes was accomplished under an anaerobic atmosphere of argon in a Belle Technology glove box (0.3-0.4 ppm O$_2$) using the same mother liquor and a solution containing FIH (at 11 mg ml$^{-1}$), Fe$^{2+}$ (1 mM), 2OG/NOG (2 mM) and CAD fragment (1 mM). Crystallisation of FIH:Zn:CAD fragment was accomplished aerobically under similar conditions. Peptides were either synthesised by solid phase peptide synthesis or purchased from Biopeptide Co. (San Diego, USA).

Crystallographic Data Collection and Structure Refinement

Crystals were cryocooled by plunging into liquid nitrogen and X-ray data were collected at 100 K using a nitrogen stream. Cryoprotection was accomplished by sequential transfer into a solution containing 1.2 M ammonium sulphate, 3% PEG 400, 0.1 M Hepes pH 7.5 and 10% followed by 24% glycerol. A three-wavelength multiple anomalous dispersion (MAD) dataset was collected to 2.9 Å resolution on beamline 14.2 of the Synchrotron Radiation Source, Daresbury, U.K. Data from crystals of FIH:CAD complexes were collected on beamlines 14.2, 9.6 or 9.5 using ADSC Quantum 4 (14.2 and 9.6) or MarCCD detectors (9.5). All data was processed with the program MOSFLM and the CCP4 suite [Collaborative Computational Project Number 4 Acta Crystallogr. D50, 760-763 (1994)]. The crystals belonged to space group P4$_1$2$_1$2. Six selenium positions were located and phases calculated using the program SOLVE (Terwilliger et al. D55, 849-861, 1999). Density modification, which increased the figure of merit from 0.56 to 0.66, was performed using RESOLVE (Terwilliger Acta Crystallogr. D56, 965-972 2000).

An initial model was built using the program O (Jones et al, Acta Crystallogr. A47, 110-119, 1991), and refined against the SeMet data (remote wavelength) using the program CNS (Brunger Acta Crystallogr. D54, 905-921, 1998). One cycle of simulated annealing followed by grouped B-factor refinement brought the R$_{free}$ to 36.2%. Following further rebuilding and refinement, which brought the R$_{free}$ to 32.3%, the model was transferred to the 2.15 Å dataset. Rebuilding and refinement using REFMAC5 including addition of Fe, substrate and solvent molecules, and refinement of TLS parameters brought the conventional R-factor to 17.8% and the R$_{free}$ to 21.3%. The following residues are missing in the current model: 1-15 and 304-306 of FIH, 786-794, 807-811 and 824-826 of the CAD fragment. According to PROCHECK there are no Ramachandran outliers and 90.7% of residues have most favourable backbone conformations. For the CAD peptide, 77.8% of residues are in the most favourable region with the remaining 22.2% in additionally allowed regions.

Other structures were solved by molecular replacement using the coordinates from the 2.15 Å data and refinement using REFMAC5. In all structures electron density for the Fe and 2OG/NOG was visible throughout refinement. Significant positive difference electron density was observed between the iron and the CAD Asn803 β-carbon. Since B-factor differences between FIH and CAD imply that the CAD is not at 100% occupancy, this may represent an alternative binding-mode for the 1 carboxylate 2OG in the absence of substrate although it could also be due to a ligating water molecule, again in the absence of substrate.

Overview of FIH Structure

The core of FIH comprises a double-stranded beta-helix (DSBH or jellyroll) motif formed from eight β-strands, β8-β11 and β14-β17. Residues 220-259 form an insert between strands 4 and 5 of the DSBH. The bottom face of the DSBH is flanked by an additional four β-strands from the N-terminal region to form an eight-membered antiparallel, β-sheet. The N-terminal strand β1 bisects the face of the DSBH opposite to the active site. The β1 strand has a 360° twist located at a PXXP sequence, in between its interactions with β14 and β2. A similarly positioned β-strand is found in most 2OG oxygenases, though not always from the same region of the protein. The sheet-helix-sheet motif formed by β1, α1 and β2 is conserved in all enzymes of this class except proline 3-hydroxylase and a similar fold in this region is found in the related Cu$^{(II)}$ utilising quercetin 2,3-dioxygenase (QD) (Fusetti et al, STRUCTURE 10 (2): 259-268 2002). The topology of FIH unequivocally defines it as an iron-binding member of the cupin structural family which already includes QD and Mn$^{(II)}$ utilising Type II phosphomannose isomerase (Clissold, P. M., and Ponting, C. P. (2001) Trends Biochem. Sci. 26, 79).

Related Enzymes to FIH

FIH has significant sequence similarity with the JmjC homology region of the jumonji transcription factors (Clissold, P. M., and Ponting, C. P. (2001) *Trends Biochem. Sci.* 26, 79; Hewitson et al., J BIOL CHEM 277 (29): 26351-26355, 2002). These proteins are members of the cupin structural superfamily and have been implicated in cell growth and heart development. The 2OG oxygenase iron binding residues had been identified in some JmjC domains but not assigned as an iron binding motif. Sequence searches in the light of the FIH structure reveal many JmjC proteins with conserved residues that include both this motif and others, including FIH residues Lys214 and Thr196 that are unusually involved in binding the 5-carboxylate of 2OG. The structure thus reveals that FIH is a one of a large family of iron and 2OG dependent oxygenases involved in the regulation of transcription. Since some of the assigned JmjC domains other than FIH are associated with diseases and particular phenotypes their (e.g.) inhibition may be of therapeutic value. (See e.g. Hu et al, ONCOGENE 20 (47): 6946-6954 Oct. 18 2001 and Clissold, P. M., and Ponting, C. P. (2001) *Trends Biochem. Sci.* 26, 79 and references therein).

Table 2. Partial sequence alignment of FIH with a selection of JmjC domain containing proteins (SEQ ID NOS 4-14, 16, 17 and 19-29, respectively, in order of appearance, with sequences containing gaps, denoted by "(#)", presented as with separate sequence identifiers). FIH secondary structure is indicated above the alignment. Selected 2OG binding residues found in FIH are indicated by dark triangles under the alignment and the two iron binding residues by light triangles. SWALL accession numbers are indicated on the left of the alignment.

Table 3. Coordinates for crystal structures 1, code 1H2K (SEQ ID NOS 30-31), 2, code 1H2L (SEQ ID NOS 30-31), 3, code 1H2M (SEQ ID NOS 30 and 32) and 4, code 1H2N (SEQ ID NO 30).

TABLE 2

```
                              α7              β8          β9           β10         β11
Hs  Q969Q7  FIH    FNWNWINKQQ----GKRGWGQ------LTSNLLLIGMEGNVTPAHYDEQ----QNFFAQIKGY---KRCILFPPD
Dm  Q9VU77         ---ELAADLR---VSDLDFAQQ(4)-PPDAVNFWLGDERAVTSMHKDPY----ENVYCVISGH---KDFVLIPPH
Dm  Q9W0M3         ---ALKEDIS-----IPDYCTI(5)PGAVDIKAWLGPAGTVSPMHYDPK----HNLLCQVFGS---KRIILAAPA
Hs  Q9UPP1         ---KIVRKLS---WVENLWPEEC(4)PNVQKYCLMSVRDSYTDFHIDFGGT--SVWYHVLKGE---KIFYLIRPT
Ce  Q9BI67         ---RFVQEIS---MVNRLWPDV(20)PKVEQFCLAGMAGSYTDFHVDFGGS--SVYYHILKGE---KIFYIAAPT
Ce  Q20367         ---RFVQDIS---MAKRLWSDV(11)PKIEQICAAAMANSYTDFHVDFGGT--SVYFHVFKGE(0)KIFYIAAPT
Dm  Q9VHH9         ---EIVRQID---WVDVVWPKQ(17)PKVQKYVLMSVKNCYTDFHLDFGGT--SVWYHILRGS(0)KVFWLIPPT
Sc  P40034         -QNDLVDKIW---SFNGHLEKV(11)PKVTKYILMSVKDAYTDFHLDFAGT--SVYYNVISGQ---KKFLLFPPT
Rn  Q9R153  PASS1  -KTDVFQEVM-WSDFGFP_RNGQE------STLWIGSLGAHTPCHLDSYG---CNLVFQVQGR---KRWHLFPPE
Ce  Q9GYI4         FEDDLFHYAD----DKKRPPH---------RWFVMGPARSGTAIHIDPLGTSAWNSLLQGH----KRWVLIPPI
Dm  Q9V6L0         ---TILDYCNKDYNIQIDGVNT--------AYLYFGMWKTTFAWHTEDMDLYSINYLHFGAP---KTWYVVPPE
Hs  O94877         ---TVLDVVEEECGISIEGVNT--------PYLYFGMWKTTFAWHTEDMDLYSINYLHFGEP----RSWYAIPPE
Ce  Q9U297         ---TILEDTNYE----IKGVNT--------VYLYFGMYKTTFPWHAEDMDLYSINFLHFGAP---KYWFAISSE
Dm  Q9V333         ---TILNLVNTDYNIIIDGVNT--------AYLYFGMWKSSFAWHTEDMDLYSINYLHFGAP---KTWYAIPPA
Hs  O75164         ---TILDLVEKESGITIEGVNT--------PYLYFGMWKTSFAWHTEDMDLYSINYLHFGEP---KSWYSVPPE
Dm  Q9VJ97         FASDWLNEQL-----IQQGKDDY-------RFVYMGPKNSWISYHADVFGSFSWSTNIVGL----KKWLIMPPG
Sp  O13977         FADDWLNAYV-----IDCESDDF-------RFAYLGSHLTTIGLHTDVYASHSFSVNLCGV----KCWLFIDPK
                                                                    ▲                      ▲
```

| | | | | |
|---|---|---|---|---|
| Hs | = | Homo Sapiens | FIH = | Factor Inhibition HIF |
| Dm | = | Drosophila melanogaster | Pass1 = | Protein associating with small stress protein |
| Ce | = | Caenorhabditits elegans | | |
| Sc | = | Saccharomyces cereviseiae | | |
| Rn | = | Rattus norvegicus | | |
| Sp | = | Schizosaccharomyces pombe | | |

TABLE 3

| Coordinates for structures 1 to 4 |
|---|

Structure 1
Below are the coordinates for structure 1 (the 2.15 Å structure of FIH:Fe(II):NOG:CAD):

| | | |
|---|---|---|
| HEADER | TRANSCRIPTION ACTIVATOR/INHIBITOR  12-AUG-02  1H2K | |
| TITLE | FACTOR INHIBITING HIF-1 ALPHA IN COMPLEX WITH HIF-1 ALPHA | |
| TITLE | 2 FRAGMENT PEPTIDE | |
| COMPND | MOL_ID: 1; | |
| COMPND | 2 MOLECULE: FACTOR INHIBITING HIF1; | |
| COMPND | 3 CHAIN: A; | |
| COMPND | 4 ENGINEERED: YES; | |
| COMPND | 5 MOL_ID: 2; | |
| COMPND | 6 MOLECULE: HYPOXIA-INDUCIBLE FACTOR 1 ALPHA; | |
| COMPND | 7 SYNONYM: HIF-1 ALPHA, ARNT INTERACTING PROTEIN, | |
| COMPND | 8 MEMBER OF PAS PROTEIN 1; | |
| COMPND | 9 CHAIN: S; | |
| COMPND | 10 FRAGMENT: C-TERMINAL TRANSACTIVATION DOMAIN FRAGMENT | |
| COMPND | 11 RESIDUES 786-826 | |
| SOURCE | MOL_ID: 1; | |
| SOURCE | 2 ORGANISM_SCIENTIFIC: *HOMO SAPIENS;* | |
| SOURCE | 3 ORGANISM_COMMON: HUMAN; | |
| SOURCE | 4 EXPRESSION_SYSTEM: *ESCHERICHIA COLI;* | |
| SOURCE | 5 EXPRESSION_SYSTEM_STRAIN: BL21(DE3); | |
| SOURCE | 6 EXPRESSION_SYSTEM_PLASMID: PET28A(+); | |
| SOURCE | 7 MOL_ID: 2; | |
| SOURCE | 8 ORGANISM_SCIENTIFIC: *HOMO SAPIENS;* | |
| SOURCE | 9 ORGANISM_COMMON: HUMAN; | |
| SOURCE | 10 EXPRESSION_SYSTEM: *ESCHERICHIA COLI;* | |
| SOURCE | 11 EXPRESSION_SYSTEM_STRAIN: BL21(DE3); | |
| SOURCE | 12 EXPRESSION_SYSTEM_PLASMID: PGEX-GP-1 | |
| KEYWDS | FIH, HIF, DSBH, OXYGENASE, TRANSCRIPTION, HYPOXIA, | |
| KEYWDS | 2 2-OXOGLUTARATE, ASPARAGINYL HYDROXYLASE, PHOSPHORYLATION | |
| EXPDTA | X-RAY DIFFRACTION | |
| AUTHOR | J. M. ELKINS, K. S. HEWITSON, L. A. MCNEILL, I. SCHLEMMINGER, | |
| AUTHOR | 2 J. F. SEIBEL, C. J. SCHOFIELD | |
| REVDAT | 1 03-SEP-02 1H2K    0 | |
| JRNL | AUTH    J. M. ELKINS, K. S. HEWITSON, L. A. MCNEILL, | |
| JRNL | AUTH 2 I. SCHLEMMINGER, J. F. SEIBEL, C. J. SCHOFIELD | |
| JRNL | TITL FIH:HIF-FRAGMENT COMPLEXES | |
| JRNL | REF    TO BE PUBLISHED | |
| JRNL | REFN | |
| REMARK | 2 | |
| REMARK | 2 RESOLUTION. 2.15 ANGSTROMS. | |
| REMARK | 3 | |
| REMARK | 3 REFINEMENT. | |
| REMARK | 3 PROGRAM: REFMAC 5.0 | |
| REMARK | 3 AUTHORS: MURSHUDOV,VAGIN,DODSON | |
| REMARK | 3 | |
| REMARK | 3 REFINEMENT TARGET: MAXIMUM LIKELIHOOD | |
| REMARK | 3 | |
| REMARK | 3 DATA USED IN REFINEMENT. | |
| REMARK | 3 RESOLUTION RANGE HIGH (ANGSTROMS): | 2.15 |
| REMARK | 3 RESOLUTION RANGE LOW (ANGSTROMS): | 18.50 |
| REMARK | 3 DATA CUTOFF (SIGMA(F)): | NONE |
| REMARK | 3 COMPLETENESS FOR RANGE (%): | 99.28 |
| REMARK | 3 NUMBER OF REFLECTIONS: | 28171 |
| REMARK | 3 | |
| REMARK | 3 FIT TO DATA USED IN REFINEMENT. | |
| REMARK | 3 CROSS-VALIDATION METHOD: | THROUGHOUT |
| REMARK | 3 FREE R VALUE TEST SET SELECTION: | RANDOM |
| REMARK | 3 R VALUE (WORKING + TEST SET): | 0.18026 |
| REMARK | 3 R VALUE (WORKING SET): | 0.17761 |
| REMARK | 3 FREE R VALUE: | 0.21305 |
| REMARK | 3 FREE R VALUE TEST SET SIZE (%): | 7.7 |
| REMARK | 3 FREE R VALUE TEST SET COUNT: | 2340 |
| REMARK | 3 | |
| REMARK | 3 FIT IN THE HIGHEST RESOLUTION BIN. | |
| REMARK | 3 TOTAL NUMBER OF BINS USED: | 20 |
| REMARK | 3 BIN RESOLUTION RANGE HIGH: | 2.150 |
| REMARK | 3 BIN RESOLUTION RANGE LOW: | 2.205 |
| REMARK | 3 REFLECTION IN BIN (WORKING SET): | 1906 |
| REMARK | 3 BIN R VALUE (WORKING SET): | 0.222 |
| REMARK | 3 BIN FREE R VALUE SET COUNT: | 152 |
| REMARK | 3 BIN FREE R VALUE: | 0.257 |
| REMARK | 3 | |
| REMARK | 3 NUMBER OF NON-HYDROGEN ATOMS USED IN REFINEMENT. | |
| REMARK | 3 PROTEIN ATOMS: | 2875 |

TABLE 3-continued

Coordinates for structures 1 to 4

| | | | | | | | |
|---|---|---|---|---|---|---|---|
| REMARK | 3 NUCLEIC ACID ATOMS: | 0 | | | | | |
| REMARK | 3 HETEROGEN ATOMS: | 21 | | | | | |
| REMARK | 3 SOLVENT ATOMS: | 194 | | | | | |
| REMARK | 3 | | | | | | |
| REMARK | 3 B VALUES. | | | | | | |
| REMARK | 3 FROM WILSON PLOT (A**2): | NULL | | | | | |
| REMARK | 3 MEAN B VALUE (OVERALL, A**2): | 25.725 | | | | | |
| REMARK | 3 OVERALL ANISOTROPIC B VALUE. | | | | | | |
| REMARK | 3 B11 (A**2): | −0.27 | | | | | |
| REMARK | 3 B22 (A**2): | −0.27 | | | | | |
| REMARK | 3 B33 (A**2): | 0.55 | | | | | |
| REMARK | 3 B12 (A**2): | 0.00 | | | | | |
| REMARK | 3 B13 (A**2): | 0.00 | | | | | |
| REMARK | 3 B23 (A**2): | 0.00 | | | | | |
| REMARK | 3 | | | | | | |
| REMARK | 3 ESTIMATED OVERALL COORDINATE ERROR. | | | | | | |
| REMARK | 3 ESU BASED ON R VALUE (A): | | | 0.174 | | | |
| REMARK | 3 ESU BASED ON FREE R VALUE (A): | | | 0.156 | | | |
| REMARK | 3 ESU BASED ON MAXIMUM LIKELIHOOD (A): | | | 0.147 | | | |
| REMARK | 3 ESU FOR B VALUES BASED ON MAXIMUM LIKELIHOOD (A**2): | | | 5.588 | | | |
| REMARK | 3 | | | | | | |
| REMARK | 3 CORRELATION COEFFICIENTS. | | | | | | |
| REMARK | 3 CORRELATION COEFFICIENT FO-FC: | 0.961 | | | | | |
| REMARK | 3 CORRELATION COEFFICIENT FO-FC FREE: | 0.947 | | | | | |
| REMARK | 3 | | | | | | |
| REMARK | 3 RMS DEVIATIONS FROM IDEAL VALUES | | COUNT | RMS | WEIGHT | | |
| REMARK | 3 BOND LENGTHS REFINED (A): | | 2973; | 0.012; | 0.021 | | |
| REMARK | 3 BOND LENGTHS OTHERS (A): | | 2561; | 0.001; | 0.020 | | |
| REMARK | 3 BOND ANGLES REFINED (DEGREES): | | 4044; | 1.374; | 1.949 | | |
| REMARK | 3 BOND ANGLES OTHERS (DEGREES): | | 5979; | 0.722; | 3.000 | | |
| REMARK | 3 TORSION ANGLES, PERIOD 1 (DEGREES): | | 352; | 4.018; | 3.000 | | |
| REMARK | 3 TORSION ANGLES, PERIOD 3 (DEGREES): | | 515; | 17.698; | 15.000 | | |
| REMARK | 3 CHIRAL-CENTER RESTRAINTS (A**3): | | 416; | 0.086; | 0.200 | | |
| REMARK | 3 GENERAL PLANES REFINED (A): | | 3333; | 0.005; | 0.020 | | |
| REMARK | 3 GENERAL PLANES OTHERS (A): | | 604; | 0.002; | 0.020 | | |
| REMARK | 3 NONBONDED CONTACTS REFINED (A): | | 714; | 0.218; | 0.300 | | |
| REMARK | 3 NON-BONDED CONTACTS OTHERS (A): | | 2499; | 0.204; | 0.300 | | |
| REMARK | 3 H-BOND (X...Y) REFINED (A): | | 259; | 0.152; | 0.500 | | |
| REMARK | 3 H-BOND (X...Y) OTHERS (A): | | 4; | 0.087; | 0.500 | | |
| REMARK | 3 SYMMETRY VDW REFINED (A): | | 18; | 0.245; | 0.300 | | |
| REMARK | 3 SYMMETRY VDW OTHERS (A): | | 72; | 0.248; | 0.300 | | |
| REMARK | 3 SYMMETRY H-BOND REFINED (A): | | 13; | 0.255; | 0.500 | | |
| REMARK | 3 SYMMETRY H-BOND OTHERS (A): | | 1; | 0.052; | 0.500 | | |
| REMARK | 3 | | | | | | |
| REMARK | 3 ISOTROPIC THERMAL FACTOR RESTRAINTS | | COUNT | RMS | WEIGHT | | |
| REMARK | 3 MAIN-CHAIN BOND REFINED (A**2): | | 1777; | 0.618; | 1.500 | | |
| REMARK | 3 MAIN-CHAIN ANGLE REFINED (A**2): | | 2862; | 1.177; | 2.000 | | |
| REMARK | 3 SIDECHAIN BOND REFINED (A**2): | | 1196; | 1.812; | 3.000 | | |
| REMARK | 3 SIDECHAIN ANGLE REFINED (A**2): | | 1182; | 3.002; | 4.500 | | |
| REMARK | 3 | | | | | | |
| REMARK | 3 NCS RESTRAINTS STATISTICS | | | | | | |
| REMARK | 3 NUMBER OF NCS GROUPS: NULL | | | | | | |
| REMARK | 3 | | | | | | |
| REMARK | 3 TLS DETAILS | | | | | | |
| REMARK | 3 NUMBER OF TLS GROUPS: 1 | | | | | | |
| REMARK | 3 | | | | | | |
| REMARK | 3 TLS GROUP: 1 | | | | | | |
| REMARK | 3 NUMBER OF COMPONENTS GROUP: 2 | | | | | | |
| REMARK | 3 COMPONENTS    C    SSSEQI    TO    2 C    SSSEQI | | | | | | |
| REMARK | 3 RESIDUE RANGE:    A    15    A    451 | | | | | | |
| REMARK | 3 RESIDUE RANGE:    S    795    S    823 | | | | | | |
| REMARK | 3 ORIGIN FOR THE GROUP (A): 21.6620 27.4620 28.2370 | | | | | | |
| REMARK | 3 T TENSOR | | | | | | |
| REMARK | 3   T11:    0.1474    T22:    0.0149 | | | | | | |
| REMARK | 3   T33:    0.0919    T12:    −0.0099 | | | | | | |
| REMARK | 3   T13:    −0.0455    T23:    0.0363 | | | | | | |
| REMARK | 3 L TENSOR | | | | | | |
| REMARK | 3   L11:    1.0098    L22:    2.2577 | | | | | | |
| REMARK | 3   L33:    1.2037    L12:    0.6963 | | | | | | |
| REMARK | 3   L13:    0.4840    L23:    1.0420 | | | | | | |
| REMARK | 3 S TENSOR | | | | | | |
| REMARK | 3   S11:    0.0288    S12:    −0.1525    S13:    −0.0400 | | | | | | |
| REMARK | 3   S21:    0.1459    S22:    0.0002    S23:    0.1021 | | | | | | |
| REMARK | 3   S31:    0.1876    S32:    −0.0468    S33:    −0.0290 | | | | | | |
| REMARK | 3 | | | | | | |
| REMARK | 3 BULK SOLVENT MODELLING. | | | | | | |
| REMARK | 3 METHOD USED: BABINET MODEL WITH MASK | | | | | | |

TABLE 3-continued

Coordinates for structures 1 to 4

```
REMARK     3 PARAMETERS FOR MASK CALCULATION
REMARK     3 VDW PROBE RADIUS:    1.40
REMARK     3 ION PROBE RADIUS:    0.80
REMARK     3 SHRINKAGE RADIUS:    0.80
REMARK     3
REMARK     3 OTHER REFINEMENT REMARKS: HYDROGENS HAVE BEEN ADDED IN THE
REMARK     3 RIDING POSITIONS
REMARK     4
REMARK     4 1H2K COMPLIES WITH FORMAT V. 2.3, 09-JULY-1998
REMARK   100
REMARK   100 THIS ENTRY HAS BEEN PROCESSED BY EBI    ON 12-AUG-2002.
REMARK   100 THE EBI ID CODE IS EBI-11170.
REMARK   200
REMARK   200 EXPERIMENTAL DETAILS
REMARK   200 EXPERIMENT TYPE:               X-RAY DIFFRACTION
REMARK   200 DATE OF DATA COLLECTION:       15-MAY-2002
REMARK   200 TEMPERATURE (KELVIN):          100
REMARK   200 PH:                            7.5
REMARK   200 NUMBER OF CRYSTALS USED:       1
REMARK   200
REMARK   200 SYNCHROTRON (Y/N):             Y
REMARK   200 RADIATION SOURCE:              SRS BEAMLINE PX9.6
REMARK   200 BEAMLINE:                      PX9.6
REMARK   200 X-RAY GENERATOR MODEL:         NULL
REMARK   200 MONOCHROMATIC OR LAUE (M/L):   M
REMARK   200 WAVELENGTH OR RANGE (A):       0.87
REMARK   200 MONOCHROMATOR:                 NULL
REMARK   200 OPTICS:                        NULL
REMARK   200
REMARK   200 DETECTOR TYPE:                 CCD
REMARK   200 DETECTOR MANUFACTURER:         ADSC
REMARK   200 INTENSITY-INTEGRATION SOFTWARE:   MOSFLM
REMARK   200 DATA SCALING SOFTWARE:         SCALA
REMARK   200
REMARK   200 NUMBER OF UNIQUE REFLECTIONS:  30574
REMARK   200 RESOLUTION RANGE HIGH (A):     2.15
REMARK   200 RESOLUTION RANGE LOW (A):      18.17
REMARK   200 REJECTION CRITERIA    (SIGMA(I)):    NONE
REMARK   200
REMARK   200 OVERALL.
REMARK   200 COMPLETENESS FOR RANGE (%):    99.2
REMARK   200 DATA REDUNDANCY:               6.3
REMARK   200 R MERGE (I):                   0.052
REMARK   200 R SYM (I):                     NULL
REMARK   200 <I/SIGMA(I)> FOR THE DATA SET: 9.9
REMARK   200
REMARK   200 IN THE HIGHEST RESOLUTION SHELL.
REMARK   200 HIGHEST RESOLUTION SHELL, RANGE HIGH (A):     2.15
REMARK   200 HIGHEST RESOLUTION SHELL, RANGE LOW (A):      2.27
REMARK   200 COMPLETENESS FOR SHELL (%):    96.0
REMARK   200 DATA REDUNDANCY IN SHELL:      3.4
REMARK   200 R MERGE FOR SHELL (I):         0.331
REMARK   200 R SYM FOR SHELL (I):           NULL
REMARK   200 <I/SIGMA(I)> FOR SHELL:        1.5
REMARK   200
REMARK   200 DIFFRACTION PROTOCOL: SINGLE WAVELENGTH
REMARK   200 METHOD USED TO DETERMINE THE STRUCTURE: MAD
REMARK   200 SOFTWARE USED: SOLVE
REMARK   200 STARTING MODEL: NULL
REMARK   200
REMARK   200 REMARK: NULL
REMARK   280
REMARK   280 CRYSTAL
REMARK   280 SOLVENT CONTENT, VS (%): 63
REMARK   280 MATTHEWS COEFFICIENT, VM (ANGSTROMS**3/DA): 3.4
REMARK   280
REMARK   280 CRYSTALLIZATION CONDITIONS: 1.2M AMMONIUM SULPHATE, 4% PEG400,
REMARK   280 0.1M HEPES PH7.5, ARGON ATMOSPHERE, 11MG/ML PROTEIN WITH
REMARK   280 1MM FE(II), 2.5MM NOG AND 2.5MM PEPTIDE
REMARK   290
REMARK   290 CRYSTALLOGRAPHIC SYMMETRY
REMARK   290 SYMMETRY OPERATORS FOR SPACE GROUP: P 41 21 2
REMARK   290
REMARK   290 SYMOP      SYMMETRY
REMARK   290 NNNMMM     OPERATOR
REMARK   290 1555       X,Y,Z
REMARK   290 2555       −X,−Y,1/2+Z
```

TABLE 3-continued

Coordinates for structures 1 to 4

| | | | | | | | |
|---|---|---|---|---|---|---|---|
| REMARK | 290 | 3555 | | 1/2−Y,1/2+X,1/4+Z | | | |
| REMARK | 290 | 4555 | | 1/2+Y,1/2−X,3/4+Z | | | |
| REMARK | 290 | 5555 | | 1/2−X,1/2+Y,1/4−Z | | | |
| REMARK | 290 | 6555 | | 1/2+X,1/2−Y,3/4−Z | | | |
| REMARK | 290 | 7555 | | Y,X,−Z | | | |
| REMARK | 290 | 8555 | | −Y,−X,1/2−Z | | | |
| REMARK | 290 | | | | | | |
| REMARK | 290 | | WHERE NNN −>OPERATOR NUMBER | | | | |
| REMARK | 290 | | MMM −>TRANSLATION VECTOR | | | | |
| REMARK | 290 | | | | | | |
| REMARK | 290 | CRYSTALLOGRAPHIC SYMMETRY TRANSFORMATIONS | | | | | |
| REMARK | 290 | THE FOLLOWING TRANSFORMATIONS OPERATE ON THE ATOM/HETATM | | | | | |
| REMARK | 290 | RECORDS IN THIS ENTRY TO PRODUCE CRYSTALLOGRAPHICAILLY | | | | | |
| REMARK | 290 | RELATED MOLECULES. | | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | 1.000000 | 0.000000 | 0.00000 |
| REMARK | 290 | SMTRY3 | 2 | 0.000000 | 0.000000 | 1.000000 | 73.32800 |
| REMARK | 290 | SMTRY1 | 3 | 0.000000 | −1.000000 | 0.000000 | 43.08050 |
| REMARK | 290 | SMTRY2 | 3 | 1.000000 | 0.000000 | 0.000000 | 43.08050 |
| REMARK | 290 | SMTRY3 | 3 | 0.000000 | −0.000000 | 1.000000 | 36.66400 |
| REMARK | 290 | SMTRY1 | 4 | 0.000000 | 1.000000 | 0.000000 | 43.08050 |
| REMARK | 290 | SMTRY2 | 4 | −1.000000 | 0.000000 | 0.000000 | 43.08050 |
| REMARK | 290 | SMTRY3 | 4 | 0.000000 | 0.000000 | 1.000000 | 109.99200 |
| REMARK | 290 | SMTRY1 | 5 | −1.000000 | 0.000000 | 0.000000 | 43.08050 |
| REMARK | 290 | SMTRY2 | 5 | 0.000000 | 1.000000 | 0.000000 | 43.08050 |
| REMARK | 290 | SMTRY3 | 5 | 0.000000 | 0.000000 | −1.000000 | 36. 66400 |
| REMARK | 290 | SMTRY1 | 6 | 1.000000 | 0.000000 | 0.000000 | 43.08050 |
| REMARK | 290 | SMTRY2 | 6 | 0.000000 | −1.000000 | 0.000000 | 43.08050 |
| REMARK | 290 | SMTRY3 | 6 | 0.000000 | 0.000000 | −1.000000 | 109.99200 |
| REMARK | 290 | SMTRY1 | 7 | 0.000000 | 1.000000 | 0.000000 | 0.00000 |
| REMARK | 290 | SMTRY2 | 7 | 1.000000 | 0.000000 | 0.000000 | 0.00000 |
| REMARK | 290 | SMTRY3 | 7 | 0.000000 | 0.000000 | −1.000000 | 0.00000 |
| REMARK | 290 | SMTRY1 | 8 | 0.000000 | −1.000000 | 0.000000 | 0.00000 |
| REMARK | 290 | SMTRY2 | 8 | −1.000000 | 0.000000 | 0.000000 | 0.00000 |
| REMARK | 290 | SMTRY3 | 8 | 0.000000 | 0.000000 | −1.000000 | 73.32800 |
| REMARK | 290 | | | | | | |
| REMARK | 290 | REMARK: NULL | | | | | |
| REMARK | 300 | | | | | | |
| REMARK | 300 | BIOMOLECULE: 1 | | | | | |
| REMARK | 300 | THIS ENTRY CONTAINS THE CRYSTALLOGRAPHIC ASYMMETRIC UNIT | | | | | |
| REMARK | 300 | WHICH CONSISTS OF 2 CHAIN(S). SEE REMARK 350 FOR | | | | | |
| REMARK | 300 | INFORMATION ON GENERATING THE BIOLOGICAL MOLECULE (5). | | | | | |
| REMARK | 300 | | | | | | |
| REMARK | 300 | QUATERNARY STRUCTURE FOR THIS ENTRY: TETRAMERIC | | | | | |
| REMARK | 300 | | | | | | |
| REMARK | 300 | THE PROTEIN IS A HOMODIMER FORMED BY CHAIN A. | | | | | |
| REMARK | 300 | A HETERODIMERIC ASSOCIATION OF CHAIN A WITH CHAIN S | | | | | |
| REMARK | 300 | PRODUCES A TETRAMER. | | | | | |
| REMARK | 300 | | | | | | |
| REMARK | 300 | THE BURIED SURFACE AREA SHOWN BELOW IS AN AVERAGE | | | | | |
| REMARK | 300 | CALCULATED FOR THE HETEROTETRAMER AND DOES NOT | | | | | |
| REMARK | 300 | CORRESPOND TO THE BURIED SURFACE AREA FOR THE | | | | | |
| REMARK | 300 | HOMODIMER OF CHAIN A | | | | | |
| REMARK | 300 | | | | | | |
| REMARK | 300 | THE HETERO-ASSEMBLY DESCRIBED BY REMARK 350 APPEARS | | | | | |
| REMARK | 300 | TO BE A CASE OF STRONG CRYSTAL PACKING WITH | | | | | |
| REMARK | 300 | THE MEAN DIFFERENCE IN ACCESSIBLE SURFACE AREA PER | | | | | |
| REMARK | 300 | CHAIN BETWEEN THE ISOLATED CHAIN AND THAT FOR | | | | | |
| REMARK | 300 | THE CHAIN IN THE COMPLEX IS 2203.4 ANGSTROM**2 | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE: 1 | | | | | |
| REMARK | 350 | APPLY THE FOLLOWING TO CHAINS: A, S | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | 0.000000 | −1.000000 | 0.000000 | 86.16100 |
| REMARK | 350 | BIOMT2 | 2 | −1.000000 | 0.000000 | 0.000000 | 86.16100 |

TABLE 3-continued

Coordinates for structures 1 to 4

| | | | | | | | | | |
|---|---|---|---|---|---|---|---|---|---|
| REMARK | 350 | BIOMT3 | | 2 | 0.000000 | 0.000000 | −1.000000 | 73.32800 | |
| REMARK | 465 | | | | | | | | |
| REMARK | 465 | MISSING RESIDUES | | | | | | | |
| REMARK | 465 | THE FOLLOWING RESIDUES WERE NOT LOCATED IN THE | | | | | | | |
| REMARK | 465 | EXPERIMENT. (M=MODEL NUMBER; RES=RESIDUE NAME; C=CHAIN | | | | | | | |
| REMARK | 465 | IDENTIFIER; SSSEQ=SEQUENCE NUMBER; I=INSERTION CODE.) | | | | | | | |
| REMARK | 465 | | | | | | | | |
| REMARK | 465 | M | RES | C | SSSEQI | | | | |
| REMARK | 465 | | MET | A | 1 | | | | |
| REMARK | 465 | | ALA | A | 2 | | | | |
| REMARK | 465 | | ALA | A | 3 | | | | |
| REMARK | 465 | | THR | A | 4 | | | | |
| REMARK | 465 | | ALA | A | 5 | | | | |
| REMARK | 465 | | ALA | A | 6 | | | | |
| REMARK | 465 | | GLU | A | 7 | | | | |
| REMARK | 465 | | ALA | A | 8 | | | | |
| REMARK | 465 | | VAL | A | 9 | | | | |
| REMARK | 465 | | ALA | A | 10 | | | | |
| REMARK | 465 | | SER | A | 11 | | | | |
| REMARK | 465 | | GLY | A | 12 | | | | |
| REMARK | 465 | | SER | A | 13 | | | | |
| REMARK | 465 | | GLY | A | 14 | | | | |
| REMARK | 465 | | LYS | A | 304 | | | | |
| REMARK | 465 | | ARG | A | 305 | | | | |
| REMARK | 465 | | ILE | A | 306 | | | | |
| REMARK | 465 | | SER | S | 786 | | | | |
| REMARK | 465 | | MET | S | 787 | | | | |
| REMARK | 465 | | ASP | S | 788 | | | | |
| REMARK | 465 | | GLU | S | 789 | | | | |
| REMARK | 465 | | SER | S | 790 | | | | |
| REMARK | 465 | | GLY | S | 791 | | | | |
| REMARK | 465 | | LEU | S | 792 | | | | |
| REMARK | 465 | | PRO | S | 793 | | | | |
| REMARK | 465 | | GLN | S | 794 | | | | |
| REMARK | 465 | | GLN | S | 807 | | | | |
| REMARK | 465 | | GLY | S | 808 | | | | |
| REMARK | 465 | | SER | S | 809 | | | | |
| REMARK | 465 | | ARG | S | 810 | | | | |
| REMARK | 465 | | ASN | S | 811 | | | | |
| REMARK | 465 | | GLN | S | 824 | | | | |
| REMARK | 465 | | VAL | S | 825 | | | | |
| REMARK | 465 | | ASN | S | 826 | | | | |
| REMARK | 470 | | | | | | | | |
| REMARK | 470 | MISSING ATOM | | | | | | | |
| REMARK | 470 | THE FOLLOWING RESIDUES HAVE MISSING ATOMS (M=MODEL NUMBER; | | | | | | | |
| REMARK | 470 | RES=RESIDUE NAME; C=CHAIN IDENTIFIER; SSEQ=SEQUENCE NUMBER; | | | | | | | |
| REMARK | 470 | I=INSERTION CODE): | | | | | | | |
| REMARK | 470 | M | RES | CSSEQI | | ATOMS | | | |
| REMARK | 470 | | GLU | A | 15 | CG | CD | OE1 | OE2 |
| REMARK | 470 | | GLU | A | 29 | CG | CD | OE1 | OE2 |
| REMARK | 470 | | ASN | A | 87 | CG | OD1 | ND2 | |
| REMARK | 470 | | LYS | A | 106 | CD | CE | NZ | |
| REMARK | 470 | | LYS | A | 115 | CG | CD | CE | NZ |
| REMARK | 470 | | ARG | A | 117 | CG | CD | NE | CZ | NH1 | NH2 |
| REMARK | 470 | | GLN | A | 133 | CG | CD | OE1 | NE2 |
| REMARK | 470 | | GLN | A | 136 | CG | CD | OE1 | NE2 |
| REMARK | 470 | | GLN | A | 137 | CG | CD | OE1 | NE2 |
| REMARK | 470 | | ARG | A | 156 | CG | CD | NE | CZ | NR1 | NH2 |
| REMARK | 470 | | LYS | A | 157 | CD | CE | NZ | |
| REMARK | 470 | | LYS | A | 311 | CG | CD | CE | NZ |
| REMARK | 500 | | | | | | | | |
| REMARK | 500 | GEOMETRY AND STEREOCHEMISTRY | | | | | | | |
| REMARK | 500 | SUBTOPIC: COVALENT BOND ANGLES | | | | | | | |
| REMARK | 500 | | | | | | | | |
| REMARK | 500 | THE STEREOCHEMICAL PARAMETERS OF THE FOLLOWING RESIDUES | | | | | | | |
| REMARK | 500 | HAVE VALUES WHICH DEVIATE FROM EXPECTED VALUES BY MORE | | | | | | | |
| REMARK | 500 | THAN 6*RMSD (M=MODEL NUMBER; RES=RESIDUE NAME; C=CHAIN | | | | | | | |
| REMARK | 500 | IDENTIFIER; SSEQ=SEQUENCE NUMBER; I=INSERTION CODE). | | | | | | | |
| REMARK | 500 | | | | | | | | |
| REMARK | 500 | STANDARD TABLE: | | | | | | | |
| REMARK | 500 | FORMAT: (10X,I3,1X,A3,1X,A1,I4,A1,3(1X,A4,2X),12X,F5.1) | | | | | | | |
| REMARK | 500 | | | | | | | | |
| REMARK | 500 | EXPECTED VALUES: ENGH AND HUBER, 1991 | | | | | | | |
| REMARK | 500 | | | | | | | | |
| REMARK | 500 | M | RES | CSSEQI | | ATM1 | ATM2 | ATM3 | |
| REMARK | 500 | | ASN | A | 84 | N | -  CA  - | C | ANGL. DEV. = 9.3 DEGREES |
| REMARK | 500 | | | | | | | | |

TABLE 3-continued

Coordinates for structures 1 to 4

```
REMARK    500  REMARK: NULL
REMARK    500
REMARK    500  GEOMETRY AND STEREOCHEMISTRY
REMARK    500  SUBTOPIC: COVALENT BOND LENGTHS
REMARK    500
REMARK    500  THE STEREOCHEMICAL PARAMETERS OF THE FOLLOWING RESIDUES
REMARK    500  HAVE VALUES WHICH DEVIATE FROM EXPECTED VALUES BY MORE
REMARK    500  THAN 6*RMSD AND BY MORE THAN 0.150 ANGSTROMS (M=MODEL
REMARK    500  NUMBER; RES=RESIDUE NAME; C=CHAIN IDENTIFIER; SSEQ=SEQUENCE
REMARK    500  NUMBER; I=INSERTION CODE).
REMARK    500
REMARK    500  STANDARD TABLE:
REMARK    500  FORMAT: (10X,I3,1X,A3,1X,A1,I4,A1,1X,2(A4,A1,3X),12X,F5.3)
REMARK    500
REMARK    500  EXPECTED VALUESS: ENGH AND HUBER, 1991
REMARK    500
REMARK    500  M      RES    CSSEQI     ATM1    RES    CSSEQI     ATM2    DEVIATION
REMARK    500         MET    A 343      SD      MET    A 343      CE      −0.249
REMARK    500
REMARK    500  REMARK: NULL
REMARK    500
REMARK    500  GEOMETRY AND STEREOCHEMISTRY
REMARK    500  SUBTOPIC: CLOSE CONTACTS IN SAME ASYMMETRIC UNIT
REMARK    500
REMARK    500  THE FOLLOWING ATOMS ARE IN CLOSE CONTACT.
REMARK    500
REMARK    500  ATM1    RES    C    SSEQI    ATM2    RES    C    SSEQI     DISTANCE
REMARK    500
REMARK    500  O       GLN    A    209      O       HOH    Z    108       2.20
REMARK    525
REMARK    525  SOLVENT
REMARK    525
REMARK    525  THE SOLVENT MOLECULES ARE GIVEN CHAIN IDENTIFIERS TO
REMARK    525  INDICATE THE PROTEIN CHAIN TO WHICH THEY ARE MOST CLOSELY
REMARK    525  ASSOCIATED WITH:
REMARK    525    PROTEIN CHAIN       SOLVENT CHAIN
REMARK    525    A                   Z
REMARK    525    S                   H
REMARK    525
REMARK    525  THE FOLLOWING SOLVENT MOLECULES LIE FARTHER THAN EXPECTED
REMARK    525  FROM THE PROTEIN OR NUCLEIC ACID MOLECULE AND MAY BE
REMARK    525  ASSOCIATED WITH A SYMMETRY RELATED MOLECULE (M=MODEL
REMARK    525  NUMBER; RES=RESIDUE NAME; C=CHAIN IDENTIFIER; SSEQ=SEQUENCE
REMARK    525  NUMBER; I=INSERTION CODE):
REMARK    525
REMARK    525  THESE MOLECULES CAN BE PLACED WITHIN 5.00 ANGSTROM OF THE
REMARK    525  OBSERVED OLIGOMER BY APPLYING THE SYMMETRY TRANSFORMATION
REMARK    525  INDICATED.
REMARK    525
REMARK    525  ORIGINAL COORDINATES
REMARK    525  M    RES    CSSEQI     X         Y         Z         SYMMETRY    TRANS.    DIST.
REMARK    525  1    HOH    W 531      12.359    41.757    15.368    005         545       2.38
REMARK    525  1    HON    W 609      10.971    45.216    18.991    005         545       3.25
REMARK    525  1    HON    W 576      42.075    52.163    47.994    008         665       2.28
REMARK    525  1    HOH    W 687      28.879    5.577     12.106    005         555       2.82
REMARK    525  1    HOH    W 674      24.396    12.792    8.360     005         555       3.20
REMARK    525  1    HOH    W 543      27.797    7.178     14.664    005         555       2.83
REMARK    525  1    HOH    W 607      26.874    53.406    28.524    008         665       2.97
REMARK    600
REMARK    600  HETEROGEN
REMARK    600
REMARK    600  FOR METAL ATOM FE     FE2 A1350 THE COORDINATION ANGLES ARE:
REMARK    600  1 HIS      199A    NE2
REMARK    600  2 ASP      201A    OD2       104.0
REMARK    600  3 HIS      279A    NE2       85.8      88.0
REMARK    600  4 OGA      1351A   O2        163.5     92.4      96.8
REMARK    600  5 OGA      1351A   O2'       86.4      168.8     97.0      77.1
REMARK    600                               1         2         3         4
REMARK    700
REMARK    700  SHEET
REMARK    700  THE SHEET STRUCTURE OF THIS MOLECULE IS BIFURCATED. IN
REMARK    700  ORDER TO REPRESENT THIS FEATURE IN THE SHEET RECORDS BELOW,
REMARK    700  TWO SHEETS ARE DEFINED.
REMARK    800
REMARK    800  SITE
REMARK    800  SITE_IDENTIFIER: FE1
REMARK    800  SITE_DESCRIPTION: FE BINDING SITE FOR CHAIN A
```

TABLE 3-continued

Coordinates for structures 1 to 4

| REMARK | 800 | | | | | | | | | | | | | | |
|---|---|---|---|---|---|---|---|---|---|---|---|---|---|---|---|
| REMARK | 800 SITE_IDENTIFIER: OGA | | | | | | | | | | | | | | |
| REMARK | 800 SITE_DESCRIPTION: OGA BINDING SITE FOR CHAIN A | | | | | | | | | | | | | | |
| REMARK | 800 | | | | | | | | | | | | | | |
| REMARK | 800 SITE_IDENTIFIER: SO1 | | | | | | | | | | | | | | |
| REMARK | 800 SITE_DESCRIPTION: SO4 BINDING SITE FOR CHAIN A | | | | | | | | | | | | | | |
| REMARK | 800 | | | | | | | | | | | | | | |
| REMARK | 800 SITE_IDENTIFIER: SO2 | | | | | | | | | | | | | | |
| REMARK | 800 SITE DESCRIPTION: SO4 BINDING SITE FOR CHAIN A | | | | | | | | | | | | | | |
| REMARK | 900 | | | | | | | | | | | | | | |
| REMARK | 900 RELATED ENTRIES | | | | | | | | | | | | | | |
| REMARK | 900 RELATED ID: 1D7G RELATED DB: PDB | | | | | | | | | | | | | | |
| REMARK | 900 A MODEL FOR THE COMPLEX BETWEEN THE | | | | | | | | | | | | | | |
| REMARK | 900 HYPOXIAINDUCIBLE FACTOR-1 (HIF-1) AND ITS | | | | | | | | | | | | | | |
| REMARK | 900 CONSENSUS DEOXYRIBONUCLEIC ACID SEQUENCE | | | | | | | | | | | | | | |
| REMARK | 900 RELATED ID: 1H2L RELATED DE: PDB | | | | | | | | | | | | | | |
| REMARK | 900 FACTOR INHIBITING HIF-1 ALPHA IN COMPLEX | | | | | | | | | | | | | | |
| REMARK | 900 WITH HIF-1 ALPHA FRAGMENT PEPTIDE | | | | | | | | | | | | | | |
| REMARK | 900 RELATED ID: IH2M RELATED DB: PDB | | | | | | | | | | | | | | |
| REMARK | 900 FACTOR INHIBITING HIF-1 ALPHA IN COMPLEX | | | | | | | | | | | | | | |
| REMARK | 900 WITH HIF-1 ALPHA FRAGMENT PEPTIDE | | | | | | | | | | | | | | |
| REMARK | 900 RELATED ID: 1H2N RELATED OB: PDB | | | | | | | | | | | | | | |
| REMARK | 900 FACTOR INHIBITING HIF-1 ALPHA IN COMPLEX | | | | | | | | | | | | | | |
| REMARK | 900 WITH HIF-1 ALPHA FRAGMENT PEPTIDE | | | | | | | | | | | | | | |
| REMARK | 900 RELATED ID: 1L8C RELATED DB: PDB | | | | | | | | | | | | | | |
| REMARK | 900 STRUCTURAL BASIS FOR HIF-1ALPHA/CBP | | | | | | | | | | | | | | |
| REMARK | 900 RECOGNITION IN THECELLULAR HYPOXIC RESPONSE | | | | | | | | | | | | | | |
| REMARK | 900 RELATED ID: 1LMB RELATED DB: PDB | | | | | | | | | | | | | | |
| REMARK | 900 STRUCTURE OF A HIF-1A-PVHL-ELONGIHB- | | | | | | | | | | | | | | |
| REMARK | 900 ELONGIHC COMPLEX | | | | | | | | | | | | | | |
| REMARK | 900 RELATED ID: 1LQB RELATED DB: PDB | | | | | | | | | | | | | | |
| REMARK | 900 CRYSTAL STRUCTURE OF A HYDROXYLATED HIF-1 | | | | | | | | | | | | | | |
| REMARK | 900 ALPHA PEPTIDEBOUND TO THE PVHL/ELONGIN-C/ | | | | | | | | | | | | | | |
| REMARK | 900 ELONGIN-B COMPLEX | | | | | | | | | | | | | | |
| DBREF | 1H2K A | 1 | 349 | SWS | Q969Q7 | | Q969Q7 | 1 | 349 | | | | | | |
| DBREF | 1H2K S | 786 | 826 | SWS | Q16665 | | HIFA_HUMAN | 786 | 826 | | | | | | |
| SEQRES | 1 A | 349 | MET | ALA | ALA | THR | ALA | ALA | GLU | ALA | VAL | ALA | SER | GLY | SER |
| SEQRES | 2 A | 349 | GLY | GLU | PRO | ARG | GLU | GLU | ALA | GLY | ALA | LEU | GLY | PRO | ALA |
| SEQRES | 3 A | 349 | TRP | ASP | GLU | SER | GLN | LEU | ARG | SER | TYR | SER | PHE | PRO | THR |
| SEQRES | 4 A | 349 | ARG | PRO | ILE | PRO | ARG | LEU | SER | GLN | SER | ASP | PRO | ARG | ALA |
| SEQRES | 5 A | 349 | GLU | GLU | LEU | ILE | GLU | ASN | GLU | GLU | PRO | VAL | VAL | LEU | THR |
| SEQRES | 6 A | 349 | ASP | THR | ASN | LEU | VAL | TYR | PRO | ALA | LEU | LYS | TRP | ASP | LEU |
| SEQRES | 7 A | 349 | GLU | TYR | LEU | GLN | GLU | ASN | ILE | GLY | ASN | GLY | ASP | PHE | SER |
| SEQRES | 8 A | 349 | VAL | TYR | SER | ALA | SER | THR | HIS | LYS | PHE | LEU | TYR | TYR | ASP |
| SEQRES | 9 A | 349 | GLU | LYS | LYS | MET | ALA | ASN | PHE | GLN | ASN | PHE | LYS | PRO | ARG |
| SEQRES | 10 A | 349 | SER | ASN | ARG | GLU | GLU | MET | LYS | PHE | HIS | GLN | PHE | VAL | GLU |
| SEQRES | 11 A | 349 | LYS | LEU | GLN | ASP | ILE | GLN | GLN | ARG | GLY | GLY | GLU | GLU | ARG |
| SEQRES | 12 A | 349 | LEU | TYR | LEU | GLN | GLN | THR | LED | ASN | ASP | THR | VAL | GLY | ARG |
| SEQRES | 13 A | 349 | LYS | ILE | VAL | MET | ASP | PHE | LEU | GLY | PHE | ASN | TRP | ASN | TRP |
| SEQRES | 14 A | 349 | ILE | ASN | LYS | GLN | GLN | GLY | LYS | ARG | GLY | TRP | GLY | GLN | LEU |
| SEQRES | 15 A | 349 | THR | SER | ASN | LEU | LEU | LEU | ILE | GLY | MET | GLU | GLY | ASN | VAL |
| SEQRES | 16 A | 349 | THR | PRO | ALA | HIS | TYR | ASP | GLU | GLN | GLN | ASN | PHE | PHE | ALA |
| SEQRES | 17 A | 349 | GLN | ILE | LYS | GLY | TYR | LYS | ARG | CYS | ILE | LEU | PHE | PRO | PRO |
| SEQRES | 18 A | 349 | ASP | GLN | PHE | GLU | CYS | LEU | TYR | PRO | TYR | PRO | VAL | HIS | HIS |
| SEQRES | 19 A | 349 | PRO | CYS | ASP | ARG | GLN | SER | GLN | VAL | ASP | PHE | ASP | ASN | PRO |
| SEQRES | 20 A | 349 | ASP | TYR | GLU | ARG | PHE | PRO | ASN | PHE | GLN | ASN | VAL | VAL | GLY |
| SEQRES | 21 A | 349 | TYR | GLU | THR | VAL | VAL | GLY | PRO | GLY | ASP | VAL | LEU | TYR | ILE |
| SEQRES | 22 A | 349 | PRO | MET | TYR | TRP | TRP | HIS | HIS | ILE | GLU | SER | LEU | LEU | ASN |
| SEQRES | 23 A | 349 | GLY | GLY | ILE | THR | ILE | THR | VAL | ASN | PHE | TRP | TYR | LYS | GLY |
| SEQRES | 24 A | 349 | ALA | PRO | THR | PRO | LYS | ARG | ILE | GLU | TYR | PRO | LEU | LYS | ALA |
| SEQRES | 25 A | 349 | HIS | GLN | LYS | VAL | ALA | ILE | MET | ARG | ASN | ILE | GLU | LYS | MET |
| SEQRES | 26 A | 349 | LEU | GLY | GLU | ALA | LEU | GLY | ASN | PRO | GLN | GLU | VAL | GLY | PRO |
| SEQRES | 27 A | 349 | LEU | LEU | ASN | THR | MET | ILE | LYS | GLY | ARG | TYR | ASN | | |
| SEQRES | 1 S | 41 | SER | MET | ASP | GLU | SER | GLY | LEU | PRO | GLN | LEU | THR | SER | TYR |
| SEQRES | 2 S | 41 | ASP | CYS | GLU | VAL | ASN | ALA | PRO | ILE | GLN | GLY | SER | ARG | ASN |
| SEQRES | 3 S | 41 | LEU | LEU | GLN | GLY | GLU | GLU | LEU | LEU | ARG | ALA | LEU | ASP | GLN |
| SEQRES | 4 S | 41 | VAL | ASN | | | | | | | | | | | | |
| HET | FE2 A1350 | 1 | | | | | | | | | | | | | |
| HET | OGA A1351 | 10 | | | | | | | | | | | | | |
| HET | SO4 A1352 | 5 | | | | | | | | | | | | | |
| HET | SO4 A1353 | 5 | | | | | | | | | | | | | |
| HETNAM | FE2 FE (II) ION | | | | | | | | | | | | | | |
| HETNAM | OGA N-OXALYOLGLYCINE | | | | | | | | | | | | | | |
| HETNAM | SO4 SULFATE ION | | | | | | | | | | | | | | |
| FORMUL | 3 FE2 | FE1 2+ | | | | | | | | | | | | | |
| FORMUL | 4 OGA | C4 H5 N1 O5 | | | | | | | | | | | | | |

TABLE 3-continued

Coordinates for structures 1 to 4

| | | | | | | | | | | | | | | | | |
|---|---|---|---|---|---|---|---|---|---|---|---|---|---|---|---|---|
| FORMUL | 5 | SO4 | 2(O4 S1 2−) | | | | | | | | | | | | | |
| FORMUL | 6 | HOH | *194(H2 O1) | | | | | | | | | | | | | |
| HELIX | 1 | 1 ASP A | 28 | LEU A | 32 | 5 | | | | | | | | | | 5 |
| HELIX | 2 | 2 ASP A | 49 | ASN A | 58 | 1 | | | | | | | | | | 10 |
| HELIX | 3 | 3 VAL A | 70 | TRP A | 76 | 5 | | | | | | | | | | 7 |
| HELIX | 4 | 4 ASP A | 77 | ILE A | 85 | 1 | | | | | | | | | | 9 |
| HELIX | 5 | 5 ASP A | 104 | GLN A | 112 | 5 | | | | | | | | | | 9 |
| HELIX | 6 | 6 LYS A | 124 | ARG A | 138 | 1 | | | | | | | | | | 15 |
| HELIX | 7 | 7 GLY A | 155 | GLY A | 164 | 1 | | | | | | | | | | 10 |
| HELIX | 8 | 8 ASN A | 166 | GLY A | 178 | 1 | | | | | | | | | | 13 |
| HELIX | 9 | 9 PRO A | 220 | ASP A | 222 | 5 | | | | | | | | | | 3 |
| HELIX | 10 | 10 GLN A | 223 | TYR A | 228 | 1 | | | | | | | | | | 6 |
| HELIX | 11 | 11 PHE A | 252 | VAL A | 258 | 5 | | | | | | | | | | 7 |
| HELIX | 12 | 12 LYS A | 311 | GLY A | 331 | 1 | | | | | | | | | | 21 |
| HELIX | 13 | 13 ASN A | 332 | GLN A | 334 | 5 | | | | | | | | | | 3 |
| HELIX | 14 | 14 GLU A | 335 | LYS A | 345 | 1 | | | | | | | | | | 11 |
| HELIX | 15 | 15 GLN S | 814 | ASP S | 823 | 1 | | | | | | | | | | 10 |
| SHEET | 1 AA | 5 | THR A | 39 | PRO A | 41 | 0 | | | | | | | | | |
| SHEET | 2 AA | 5 | GLY A | 260 | VAL A | 265 | 1 O | GLYA | 260 | N | ARGA | 40 | | | | |
| SHEET | 3 AA | 5 | LYS A | 214 | PHE A | 219 | −1 O | LYS A | 214 | N | VALA | 265 | | | | |
| SHEET | 4 AA | 5 | TRP A | 278 | SER A | 283 | 1 O | TRP A | 278 | N | PHEA | 219 | | | | |
| SHEET | 5 AA | 5 | VAL A | 195 | HIS A | 199 | −1 O | THRA | 196 | N | ILE A | 281 | | | | |
| SHEET | 1 AB | 6 | ARG A | 44 | LEU A | 45 | 0 | | | | | | | | | |
| SHEET | 2 AB | 6 | VAL A | 62 | LEU A | 64 | 1 O | VALA | 63 | N | LEUA | 45 | | | | |
| SHEET | 3 AB | 6 | VAL A | 270 | LEA | 2 | 73 | −1 O | VALA | 270 | N | LEUA | 64 | | | |
| SHEET | 4 AB | 6 | GLN A | 203 | LYS A | 211 | −1 O | ASNA | 205 | N | ILE A | 273 | | | | |
| SHEET | 5 AS | 6 | THR A | 290 | LYS A | 298 | −1 O | ILE A | 291 | N | ILE A | 210 | | | | |
| SHEET | 6 AS | 6 | LEU A | 182 | SER A | 184 | −1 N | THRA | 183 | O | TRP A | 296 | | | | |
| SHEET | 1 AC | 9 | ARG A | 44 | LEU A | 45 | 0 | | | | | | | | | |
| SHEET | 2 AC | 9 | VAL A | 62 | LEU A | 64 | 1 O | VALA | 63 | N | LEUA | 45 | | | | |
| SHEET | 3 AC | 9 | VAL A | 270 | ILE A | 273 | −1 O | VALA | 270 | N | LEUA | 64 | | | | |
| SHEET | 4 AC | 9 | GLN A | 203 | LYS A | 211 | −1 O | ASNA | 205 | N | ILE A | 273 | | | | |
| SHEET | 5 AC | 9 | THR A | 290 | LYS A | 298 | −1 O | ILE A | 291 | N | ILE A | 210 | | | | |
| SHEET | 6 AC | 9 | LED A | 186 | GLY A | 190 | −1 O | LEUA | 186 | N | ASNA | 294 | | | | |
| SHEET | 7 AC | 9 | ARG A | 143 | THR A | 149 | −1 O | THRA | 146 | N | ILE A | 189 | | | | |
| SHEET | 8 AC | 9 | PHE A | 90 | ALA A | 95 | −1 O | SERA | 91 | N | GLNA | 147 | | | | |
| SHEET | 9 AC | 9 | SER A | 118 | MET A | 123 | −1 O | ASNA | 119 | N | SERA | 94 | | | | |
| LINK | | FE | FE2 A1350 | | | | | | NE2 | HIS | A | 199 | 1555 | 15552.12 | | |
| LINK | | FE | FE2 A1350 | | | | | | OD2 | ASP | A | 201 | 1555 | 15552.05 | | |
| LINK | | FE | FE2 A1350 | | | | | | NE2 | HIS | A | 279 | 1555 | 15552.08 | | |
| LINK | | FE | FE2 A1350 | | | | | | O2 | OGA | A | 1351 | 1555 | 15552.13 | | |
| LINK | | FE | FE2 A1350 | | | | | | O2' | OGA | A | 1351 | 1555 | 15552.17 | | |
| CISPEP | 1 | TYR A | 308 | PRO A | 309 | | | | | 0 | −1.09 | | | | | |
| SITE | 1 FE1 | 3 | HIS A 199 | ASP A | 201 | HIS A | 279 | | | | | | | | | |
| SITE | 1 OGA | 11 | TYR A 145 | THR A | 196 | HIS A | 199 | ASP A | 201 | | | | | | | |
| SITE | 2 OGA | 11 | ASN A 205 | PHE A | 207 | LYS A | 214 | HIS A | 279 | | | | | | | |
| SITE | 3 OGA | 11 | ILE A 281 | ASN A | 294 | TRP A | 296 | | | | | | | | | |
| SITE | 1 SO1 | 4 | ARG A 138 | GLY A | 140 | GLU A | 141 | GLU A | 142 | | | | | | | |
| SITE | 1 SO2 | 5 | ARG A 143 | GLU A | 192 | GLY A | 193 | LEU A | 285 | | | | | | | |
| SITE | 2 SO2 | 5 | ASN A 286 | | | | | | | | | | | | | |
| CRYST1 | 86.161 | 86.161 | 146.656 | 90.00 | 90.00 | 90.00 | P 41 21 2 | 8 | | | | | | | | |
| ORIGX1 | 1.000000 | 0.000000 | 0.000000 | 0.00000 | | | | | | | | | | | | |
| ORIGX2 | 0.000000 | 1.000000 | 0.000000 | 0.00000 | | | | | | | | | | | | |
| ORIGX3 | 0.000000 | 0.000000 | 1.000000 | 0.00000 | | | | | | | | | | | | |
| SCALE1 | 0.011606 | 0.000000 | 0.000000 | 0.00000 | | | | | | | | | | | | |
| SCALE2 | 0.000000 | 0.011606 | 0.000000 | 0.00000 | | | | | | | | | | | | |
| SCALE3 | 0.000000 | 0.000000 | 0.006819 | 0.00000 | | | | | | | | | | | | |
| ATOM | 1 | N | GLU | A | 15 | 8.429 | 32.653 | 9.844 | 1.00 | 50.99 | N | | | | | |
| ATOM | 2 | CA | GLU | A | 15 | 7.077 | 32.034 | 9.723 | 1.00 | 51.05 | C | | | | | |
| ATOM | 3 | C | GLU | A | 15 | 7.166 | 30.582 | 10.163 | 1.00 | 50.79 | C | | | | | |
| ATOM | 4 | O | GLU | A | 15 | 8.052 | 29.857 | 9.730 | 1.00 | 51.18 | O | | | | | |
| ATOM | 5 | CB | GLU | A | 15 | 6.570 | 32.124 | 8.296 | 1.00 | 51.20 | C | | | | | |
| ATOM | 6 | N | PRO | A | 16 | 6.254 | 30.150 | 11.022 | 1.00 | 50.50 | N | | | | | |
| ATOM | 7 | CA | PRO | A | 16 | 6.301 | 28.781 | 11.549 | 1.00 | 50.12 | C | | | | | |
| ATOM | 8 | C | PRO | A | 16 | 6.265 | 27.737 | 10.438 | 1.00 | 49.56 | C | | | | | |
| ATOM | 9 | O | PRO | A | 16 | 5.471 | 27.827 | 9.503 | 1.00 | 49.32 | O | | | | | |
| ATOM | 10 | CB | PRO | A | 16 | 5.049 | 28.701 | 12.429 | 1.00 | 50.27 | C | | | | | |
| ATOM | 11 | CG | PRO | A | 16 | 4.734 | 30.135 | 12.770 | 1.00 | 50.58 | C | | | | | |
| ATOM | 12 | CD | PRO | A | 16 | 5.108 | 30.911 | 11.548 | 1.00 | 50.56 | C | | | | | |
| ATOM | 13 | N | ARG | A | 17 | 7.133 | 26.746 | 10.550 | 1.00 | 48.83 | N | | | | | |
| ATOM | 14 | CA | ARG | A | 17 | 7.219 | 25.695 | 9.550 | 1.00 | 48.33 | C | | | | | |
| ATOM | 15 | C | ARG | A | 17 | 5.967 | 24.832 | 9.561 | 1.00 | 47.48 | C | | | | | |
| ATOM | 16 | O | ARG | A | 17 | 5.245 | 24.782 | 10.557 | 1.00 | 47.64 | O | | | | | |
| ATOM | 17 | CE | ARG | A | 17 | 8.421 | 24.798 | 9.835 | 1.00 | 48.61 | C | | | | | |
| ATOM | 18 | CG | ARG | A | 17 | 9.776 | 25.511 | 9.835 | 1.00 | 49.21 | C | | | | | |
| ATOM | 19 | CD | ARG | A | 17 | 10.944 | 24.577 | 10.196 | 1.00 | 49.84 | C | | | | | |
| ATOM | 20 | NE | ARG | A | 17 | 10.918 | 24.137 | 11.596 | 1.00 | 50.12 | N | | | | | |

TABLE 3-continued

Coordinates for structures 1 to 4

| ATOM | 21 | CZ | ARG | A | 17 | 11.455 | 24.809 | 12.623 | 1.00 | 50.99 | C |
|------|----|-----|-----|---|----|--------|--------|--------|------|-------|---|
| ATOM | 22 | NH1 | ARG | A | 17 | 12.065 | 25.979 | 12.431 | 1.00 | 50.40 | N |
| ATOM | 23 | NH2 | ARG | A | 17 | 11.381 | 24.310 | 13.857 | 1.00 | 50.81 | N |
| ATOM | 24 | N | GLU | A | 18 | 5.723 | 24.153 | 8.446 | 1.00 | 46.05 | N |
| ATOM | 25 | CA | GLU | A | 18 | 4.603 | 23.246 | 8.329 | 1.00 | 45.06 | C |
| ATOM | 26 | C | GLU | A | 18 | 5.096 | 21.830 | 8.607 | 1.00 | 44.00 | C |
| ATOM | 27 | O | GLU | A | 18 | 6.101 | 21.405 | 8.044 | 1.00 | 43.89 | O |
| ATOM | 28 | CB | GLU | A | 18 | 4.013 | 23.324 | 6.923 | 1.00 | 45.21 | C |
| ATOM | 29 | CG | GLU | A | 18 | 3.323 | 24.648 | 6.621 | 1.00 | 45.56 | C |
| ATOM | 30 | CD | GLU | A | 18 | 1.951 | 24.780 | 7.265 | 1.00 | 45.64 | C |
| ATOM | 31 | OE1 | GLU | A | 18 | 1.342 | 23.749 | 7.641 | 1.00 | 44.14 | O |
| ATOM | 32 | OE2 | GLU | A | 18 | 1.480 | 25.932 | 7.388 | 1.00 | 45.83 | O |
| ATOM | 33 | N | GLU | A | 19 | 4.396 | 21.113 | 9.484 | 1.00 | 42.49 | N |
| ATOM | 34 | CA | GLU | A | 19 | 4.734 | 19.728 | 9.795 | 1.00 | 41.55 | C |
| ATOM | 35 | C | GLU | A | 19 | 4.357 | 18.817 | 8.635 | 1.00 | 39.79 | C |
| ATOM | 36 | O | GLU | A | 19 | 3.266 | 18.933 | 8.066 | 1.00 | 39.13 | O |
| ATOM | 37 | CB | GLU | A | 19 | 4.010 | 19.256 | 11.052 | 1.00 | 41.88 | C |
| ATOM | 38 | CG | GLU | A | 19 | 4.420 | 19.997 | 12.311 | 1.00 | 44.80 | C |
| ATOM | 39 | CD | GLU | A | 19 | 4.276 | 19.155 | 13.574 | 1.00 | 49.28 | C |
| ATOM | 40 | OE1 | GLU | A | 19 | 3.759 | 18.008 | 13.497 | 1.00 | 51.52 | O |
| ATOM | 41 | OE2 | GLU | A | 19 | 4.695 | 19.643 | 14.656 | 1.00 | 52.76 | O |
| ATOM | 42 | N | ALA | A | 20 | 5.270 | 17.910 | 8.311 | 1.00 | 38.00 | N |
| ATOM | 43 | CA | ALA | A | 20 | 5.099 | 16.952 | 7.227 | 1.00 | 36.77 | C |
| ATOM | 44 | C | ALA | A | 20 | 3.803 | 16.168 | 7.373 | 1.00 | 35.56 | C |
| ATOM | 45 | O | ALA | A | 20 | 3.445 | 15.734 | 8.460 | 1.00 | 35.74 | O |
| ATOM | 46 | CB | ALA | A | 20 | 6.283 | 15.999 | 7.180 | 1.00 | 36.63 | C |
| ATOM | 47 | N | GLY | A | 21 | 3.082 | 16.020 | 6.279 | 1.00 | 34.05 | N |
| ATOM | 48 | CA | GLY | A | 21 | 1.860 | 15.242 | 6.307 | 1.00 | 33.24 | C |
| ATOM | 49 | C | GLY | A | 21 | 0.666 | 16.137 | 6.551 | 1.00 | 32.36 | C |
| ATOM | 50 | O | GLY | A | 21 | 0.393 | 15.673 | 6.951 | 1.00 | 30.93 | O |
| ATOM | 51 | N | ALA | A | 22 | 0.867 | 17.432 | 6.323 | 1.00 | 32.41 | N |
| ATOM | 52 | CA | ALA | A | 22 | 0.184 | 18.425 | 6.459 | 1.00 | 32.78 | C |
| ATOM | 53 | C | ALA | A | 22 | 0.723 | 18.441 | 7.873 | 1.00 | 33.14 | C |
| ATOM | 54 | O | ALA | A | 22 | 1.915 | 18.605 | 8.088 | 1.00 | 32.74 | O |
| ATOM | 55 | CB | ALA | A | 22 | 1.304 | 18.139 | 5.462 | 1.00 | 32.61 | C |
| ATOM | 56 | N | LEU | A | 23 | 0.151 | 18.253 | 8.849 | 1.00 | 34.01 | N |
| ATOM | 57 | CA | LEU | A | 23 | 0.297 | 18.275 | 10.232 | 1.00 | 34.91 | C |
| ATOM | 58 | C | LEU | A | 23 | 0.342 | 19.694 | 10.757 | 1.00 | 35.27 | C |
| ATOM | 59 | O | LEU | A | 23 | 0.528 | 19.918 | 11.943 | 1.00 | 35.72 | O |
| ATOM | 60 | CE | LEU | A | 23 | 0.565 | 17.366 | 11.097 | 1.00 | 35.27 | C |
| ATOM | 61 | CG | LEU | A | 23 | 0.384 | 15.910 | 10.653 | 1.00 | 36.36 | C |
| ATOM | 62 | CD1 | LEU | A | 23 | 1.211 | 14.947 | 11.491 | 1.00 | 37.75 | C |
| ATOM | 63 | CD2 | LEU | A | 23 | 1.077 | 15.523 | 10.719 | 1.00 | 37.98 | C |
| ATOM | 64 | N | GLY | A | 24 | 0.177 | 20.656 | 9.855 | 1.00 | 35.73 | N |
| ATOM | 65 | CA | GLY | A | 24 | 0.332 | 22.053 | 10.194 | 1.00 | 35.66 | C |
| ATOM | 66 | C | GLY | A | 24 | 0.901 | 22.655 | 10.804 | 1.00 | 36.08 | C |
| ATOM | 67 | O | GLY | A | 24 | 1.945 | 22.001 | 10.913 | 1.00 | 36.05 | O |
| ATOM | 68 | N | PRO | A | 25 | 0.764 | 23.894 | 11.253 | 1.00 | 35.96 | N |
| ATOM | 69 | CA | PRO | A | 25 | 1.896 | 24.628 | 11.804 | 1.00 | 36.12 | C |
| ATOM | 70 | C | PRO | A | 25 | 2.327 | 23.980 | 13.108 | 1.00 | 36.32 | C |
| ATOM | 71 | O | PRO | A | 25 | 1.488 | 23.577 | 13.914 | 1.00 | 36.08 | O |
| ATOM | 72 | CE | PRO | A | 25 | 1.341 | 26.047 | 12.043 | 1.00 | 36.15 | C |
| ATOM | 73 | CG | PRO | A | 25 | 0.162 | 25.942 | 11.982 | 1.00 | 35.84 | C |
| ATOM | 74 | CD | PRO | A | 25 | 0.504 | 24.638 | 11.350 | 1.00 | 36.22 | C |
| ATOM | 75 | N | ALA | A | 26 | 3.632 | 23.848 | 13.285 | 1.00 | 36.64 | N |
| ATOM | 76 | CA | ALA | A | 26 | 4.178 | 23.274 | 14.499 | 1.00 | 37.19 | C |
| ATOM | 77 | C | ALA | A | 26 | 3.860 | 24.172 | 15.706 | 1.00 | 36.77 | C |
| ATOM | 78 | O | ALA | A | 26 | 3.595 | 23.678 | 16.808 | 1.00 | 37.19 | O |
| ATOM | 79 | CE | ALA | A | 26 | 5.672 | 23.099 | 14.347 | 1.00 | 37.52 | C |
| ATOM | 80 | N | TRP | A | 27 | 3.848 | 25.479 | 15.484 | 1.00 | 35.62 | N |
| ATOM | 81 | CA | TRP | A | 27 | 3.520 | 26.420 | 16.543 | 1.00 | 35.04 | C |
| ATOM | 82 | C | TRP | A | 27 | 3.029 | 27.729 | 15.933 | 1.00 | 34.20 | C |
| ATOM | 83 | O | TRP | A | 27 | 2.992 | 27.883 | 14.723 | 1.00 | 33.57 | O |
| ATOM | 84 | CE | TRP | A | 27 | 4.774 | 26.672 | 17.382 | 1.00 | 35.28 | C |
| ATOM | 85 | CG | TRP | A | 27 | 5.951 | 26.889 | 16.511 | 1.00 | 34.67 | C |
| ATOM | 86 | CD1 | TRP | A | 27 | 6.761 | 25.930 | 15.955 | 1.00 | 35.52 | C |
| ATOM | 87 | CD2 | TRP | A | 27 | 6.426 | 28.135 | 16.033 | 1.00 | 34.40 | C |
| ATOM | 88 | NE1 | TRP | A | 27 | 7.723 | 26.522 | 15.172 | 1.00 | 35.09 | N |
| ATOM | 89 | CE2 | TRP | A | 27 | 7.541 | 27.877 | 15.209 | 1.00 | 34.23 | C |
| ATOM | 90 | CE3 | TRP | A | 27 | 6.038 | 29.452 | 16.232 | 1.00 | 34.31 | C |
| ATOM | 91 | CZ2 | TRP | A | 27 | 8.255 | 28.879 | 14.592 | 1.00 | 35.79 | C |
| ATOM | 92 | CZ3 | TRP | A | 27 | 6.750 | 30.442 | 15.629 | 1.00 | 36.35 | C |
| ATOM | 93 | CH2 | TRP | A | 27 | 7.847 | 30.154 | 14.808 | 1.00 | 36.47 | C |
| ATOM | 94 | N | ASP | A | 28 | 2.638 | 28.672 | 16.766 | 1.00 | 33.77 | N |
| ATOM | 95 | CA | ASP | A | 28 | 2.259 | 29.970 | 16.249 | 1.00 | 33.48 | C |
| ATOM | 96 | C | ASP | A | 28 | 2.759 | 31.050 | 17.165 | 1.00 | 32.26 | C |
| ATOM | 97 | O | ASP | A | 28 | 3.210 | 30.791 | 18.276 | 1.00 | 32.05 | O |

TABLE 3-continued

| | | | | | | | | | | | |
|---|---|---|---|---|---|---|---|---|---|---|---|
| ATOM | 98 | CE | ASP | A | 28 | 0.749 | 30.080 | 16.037 | 1.00 | 34.30 | C |
| ATOM | 99 | CG | ASP | A | 28 | 0.026 | 29.986 | 17.317 | 1.00 | 36.29 | C |
| ATOM | 100 | OD1 | ASP | A | 28 | 0.184 | 31.027 | 18.002 | 1.00 | 39.59 | O |
| ATOM | 101 | OD2 | ASP | A | 28 | 0.517 | 28.906 | 17.712 | 1.00 | 39.78 | O |
| ATOM | 102 | N | GLU | A | 29 | 2.691 | 32.268 | 16.654 | 1.00 | 31.30 | N |
| ATOM | 103 | CA | GLU | A | 29 | 3.181 | 33.465 | 17.326 | 1.00 | 30.15 | C |
| ATOM | 104 | C | GLU | A | 29 | 2.674 | 33.625 | 18.752 | 1.00 | 28.85 | C |
| ATOM | 105 | O | GLU | A | 29 | 3.407 | 34.036 | 19.621 | 1.00 | 28.58 | O |
| ATOM | 106 | CB | GLU | A | 29 | 2.791 | 34.682 | 16.503 | 1.00 | 30.32 | C |
| ATOM | 107 | N | SER | A | 30 | 1.414 | 33.313 | 18.992 | 1.00 | 27.95 | N |
| ATOM | 108 | CA | SER | A | 30 | 0.845 | 33.501 | 20.320 | 1.00 | 27.46 | C |
| ATOM | 109 | C | SER | A | 30 | 1.537 | 32.671 | 21.389 | 1.00 | 26.93 | C |
| ATOM | 110 | O | SER | A | 30 | 1.312 | 32.907 | 22.567 | 1.00 | 26.79 | O |
| ATOM | 111 | CB | SER | A | 30 | 0.651 | 33.168 | 20.322 | 1.00 | 27.23 | C |
| ATOM | 112 | OG | SER | A | 30 | 0.857 | 31.764 | 20.306 | 1.00 | 27.69 | O |
| ATOM | 113 | N | GLN | A | 31 | 2.360 | 31.703 | 20.984 | 1.00 | 26.55 | N |
| ATOM | 114 | CA | GLN | A | 31 | 3.071 | 30.837 | 21.926 | 1.00 | 26.63 | C |
| ATOM | 115 | C | GLN | A | 31 | 4.419 | 31.409 | 22.334 | 1.00 | 26.66 | C |
| ATOM | 116 | O | GLN | A | 31 | 5.078 | 30.855 | 23.205 | 1.00 | 26.45 | O |
| ATOM | 117 | CE | GLN | A | 31 | 3.282 | 29.426 | 21.349 | 1.00 | 26.41 | C |
| ATOM | 118 | CG | GLN | A | 31 | 1.998 | 28.637 | 21.131 | 1.00 | 26.28 | C |
| ATOM | 119 | CD | GLN | A | 31 | 2.245 | 27.287 | 20.489 | 1.00 | 26.25 | C |
| ATOM | 120 | OE2 | GLN | A | 31 | 2.258 | 27.183 | 19.271 | 1.00 | 27.92 | O |
| ATOM | 121 | NE2 | GLN | A | 31 | 2.465 | 26.258 | 21.305 | 1.00 | 24.36 | N |
| ATOM | 122 | N | LEU | A | 32 | 4.824 | 32.508 | 21.703 | 1.00 | 26.89 | N |
| ATOM | 123 | CA | LEU | A | 32 | 6.083 | 33.176 | 22.029 | 1.00 | 27.24 | C |
| ATOM | 124 | C | LEU | A | 32 | 5.852 | 34.321 | 23.006 | 1.00 | 26.92 | C |
| ATOM | 125 | O | LEU | A | 32 | 4.888 | 35.047 | 22.868 | 1.00 | 26.42 | O |
| ATOM | 126 | C | LEU | A | 32 | 6.717 | 33.746 | 20.760 | 1.00 | 27.46 | C |
| ATOM | 127 | C | GLU | A | 32 | 6.964 | 32.728 | 19.640 | 1.00 | 28.65 | C |
| ATOM | 128 | CD1 | LEU | A | 32 | 7.630 | 33.391 | 18.452 | 1.00 | 29.44 | C |
| ATOM | 129 | CD2 | LEU | A | 32 | 7.792 | 31.573 | 20.127 | 1.00 | 27.98 | C |
| ATOM | 130 | N | ARG | A | 33 | 6.728 | 34.472 | 23.995 | 1.00 | 26.71 | N |
| ATOM | 131 | CA | ARG | A | 33 | 6.627 | 35.596 | 24.923 | 1.00 | 26.77 | C |
| ATOM | 132 | C | ARG | A | 33 | 7.040 | 36.880 | 24.209 | 1.00 | 26.57 | C |
| ATOM | 133 | O | ARG | A | 33 | 7.719 | 36.844 | 23.203 | 1.00 | 26.30 | O |
| ATOM | 134 | CB | ARG | A | 33 | 7.492 | 35.357 | 26.163 | 1.00 | 26.67 | C |
| ATOM | 135 | CG | ARG | A | 33 | 7.052 | 34.141 | 26.983 | 1.00 | 26.29 | C |
| ATOM | 136 | CD | ARG | A | 33 | 7.937 | 33.837 | 28.181 | 1.00 | 25.85 | C |
| ATOM | 137 | NE | ARG | A | 33 | 7.381 | 32.778 | 29.018 | 1.00 | 25.80 | N |
| ATOM | 138 | CZ | ARG | A | 33 | 6.451 | 32.946 | 29.945 | 1.00 | 24.68 | C |
| ATOM | 139 | NH1 | ARG | A | 33 | 5.937 | 34.140 | 30.189 | 1.00 | 23.50 | N |
| ATOM | 140 | NH2 | ARG | A | 33 | 6.029 | 31.901 | 30.637 | 1.00 | 25.35 | N |
| ATOM | 141 | N | SER | A | 34 | 6.633 | 38.020 | 24.732 | 1.00 | 26.80 | N |
| ATOM | 142 | CA | SER | A | 34 | 6.903 | 39.280 | 24.061 | 1.00 | 27.15 | C |
| ATOM | 143 | C | SER | A | 34 | 7.990 | 40.048 | 24.791 | 1.00 | 26.39 | C |
| ATOM | 144 | O | SER | A | 34 | 7.964 | 40.140 | 26.005 | 1.00 | 25.87 | O |
| ATOM | 145 | GB | SER | A | 34 | 5.628 | 40.104 | 24.030 | 1.00 | 27.68 | C |
| ATOM | 146 | OG | SER | A | 34 | 5.494 | 40.737 | 25.285 | 1.00 | 32.47 | O |
| ATOM | 147 | N | TYR | A | 35 | 8.944 | 40.589 | 24.042 | 1.00 | 25.89 | N |
| ATOM | 148 | CA | TYR | A | 35 | 10.110 | 41.223 | 24.637 | 1.00 | 26.28 | C |
| ATOM | 149 | C | TYR | A | 35 | 10.353 | 42.558 | 23.970 | 1.00 | 26.85 | C |
| ATOM | 150 | O | TYR | A | 35 | 9.722 | 42.856 | 22.967 | 1.00 | 26.92 | O |
| ATOM | 151 | GB | TYR | A | 35 | 11.326 | 40.308 | 24.510 | 1.00 | 25.90 | C |
| ATOM | 152 | CG | TYR | A | 35 | 11.169 | 39.032 | 25.309 | 1.00 | 25.33 | C |
| ATOM | 153 | CD1 | TYR | A | 35 | 10.975 | 39.073 | 26.685 | 1.00 | 24.99 | C |
| ATOM | 154 | CD2 | TYR | A | 35 | 11.198 | 37.787 | 24.692 | 1.00 | 23.82 | C |
| ATOM | 155 | GE1 | TYR | A | 35 | 10.823 | 37.898 | 27.429 | 1.00 | 24.56 | C |
| ATOM | 156 | CE2 | TYR | A | 35 | 11.046 | 36.620 | 25.426 | 1.00 | 24.42 | C |
| ATOM | 157 | CZ | TYR | A | 35 | 10.862 | 36.682 | 26.793 | 1.00 | 23.48 | C |
| ATOM | 158 | OH | TYR | A | 35 | 10.696 | 35.524 | 27.513 | 1.00 | 24.75 | O |
| ATOM | 159 | N | SER | A | 36 | 11.304 | 43.327 | 24.496 | 1.00 | 27.27 | N |
| ATOM | 160 | CA | SER | A | 36 | 11.525 | 44.704 | 24.052 | 1.00 | 27.55 | C |
| ATOM | 161 | C | SER | A | 36 | 12.513 | 44.912 | 22.917 | 1.00 | 27.06 | C |
| ATOM | 162 | O | SER | A | 36 | 12.734 | 46.049 | 22.504 | 1.00 | 27.94 | O |
| ATOM | 163 | GB | SER | A | 36 | 12.082 | 45.498 | 25.226 | 1.00 | 27.88 | C |
| ATOM | 164 | OG | SER | A | 36 | 13.350 | 44.976 | 25.590 | 1.00 | 28.36 | O |
| ATOM | 165 | N | PHE | A | 37 | 13.128 | 43.851 | 22.429 | 1.00 | 25.35 | N |
| ATOM | 166 | CA | PHE | A | 37 | 14.202 | 44.014 | 21.461 | 1.00 | 24.62 | C |
| ATOM | 167 | C | PHE | A | 37 | 13.899 | 43.272 | 20.159 | 1.00 | 24.75 | C |
| ATOM | 168 | O | PHE | A | 37 | 13.130 | 42.335 | 20.135 | 1.00 | 24.25 | O |
| ATOM | 169 | GB | PHE | A | 37 | 15.487 | 43.462 | 22.071 | 1.00 | 23.87 | C |
| ATOM | 170 | CG | PHE | A | 37 | 15.318 | 42.069 | 22.635 | 1.00 | 22.53 | C |
| ATOM | 171 | CD1 | PHE | A | 37 | 15.348 | 40.972 | 21.802 | 1.00 | 21.11 | C |
| ATOM | 172 | CD2 | PHE | A | 37 | 15.069 | 41.872 | 23.988 | 1.00 | 21.63 | C |
| ATOM | 173 | GE1 | PHE | A | 37 | 15.158 | 39.687 | 22.314 | 1.00 | 22.41 | C |
| ATOM | 174 | CE2 | PHE | A | 37 | 14.900 | 40.612 | 24.505 | 1.00 | 22.29 | C |

TABLE 3-continued

| | | | | | | | | | | | |
|---|---|---|---|---|---|---|---|---|---|---|---|
| | Coordinates for structures 1 to 4 |

| | | | | | | | | | | | |
|---|---|---|---|---|---|---|---|---|---|---|---|
| ATOM | 175 | CZ | PHE | A | 37 | 14.936 | 39.509 | 23.675 | 1.00 | 21.45 | C |
| ATOM | 176 | N | PRO | A | 38 | 14.489 | 43.715 | 19.067 | 1.00 | 24.94 | N |
| ATOM | 177 | GA | PRO | A | 38 | 14.322 | 43.017 | 17.793 | 1.00 | 24.67 | C |
| ATOM | 178 | C | PRO | A | 38 | 15.267 | 41.823 | 17.678 | 1.00 | 24.41 | C |
| ATOM | 179 | O | PRO | A | 38 | 16.249 | 41.745 | 18.427 | 1.00 | 23.73 | O |
| ATOM | 180 | CE | PRO | A | 38 | 14.725 | 44.072 | 16.783 | 1.00 | 24.75 | C |
| ATOM | 181 | CG | PRO | A | 38 | 15.791 | 44.872 | 17.530 | 1.00 | 26.09 | C |
| ATOM | 182 | CD | PRO | A | 38 | 15.287 | 44.950 | 18.941 | 1.00 | 25.27 | C |
| ATOM | 183 | N | THR | A | 39 | 14.981 | 40.927 | 16.734 | 1.00 | 23.30 | N |
| ATOM | 184 | CA | THR | A | 39 | 15.859 | 39.816 | 16.444 | 1.00 | 23.42 | C |
| ATOM | 185 | C | THR | A | 39 | 15.857 | 39.534 | 14.955 | 1.00 | 24.29 | C |
| ATOM | 186 | O | THR | A | 39 | 14.958 | 39.964 | 14.239 | 1.00 | 24.61 | O |
| ATOM | 187 | GB | THR | A | 39 | 15.368 | 38.538 | 17.135 | 1.00 | 23.09 | C |
| ATOM | 188 | OG1 | THR | A | 39 | 14.044 | 38.232 | 16.680 | 1.00 | 19.92 | O |
| ATOM | 189 | CG2 | THR | A | 39 | 15.213 | 38.731 | 18.641 | 1.00 | 23.03 | C |
| ATOM | 190 | N | ARG | A | 40 | 16.854 | 38.773 | 14.525 | 1.00 | 24.43 | N |
| ATOM | 191 | CA | ARG | A | 40 | 16.982 | 38.273 | 13.170 | 1.00 | 24.91 | C |
| ATOM | 192 | C | ARG | A | 40 | 17.061 | 36.751 | 13.268 | 1.00 | 24.49 | C |
| ATOM | 193 | O | ARG | A | 40 | 17.434 | 36.225 | 14.301 | 1.00 | 23.58 | O |
| ATOM | 194 | GB | ARG | A | 40 | 18.253 | 38.805 | 12.536 | 1.00 | 25.36 | C |
| ATOM | 195 | CG | ARG | A | 40 | 18.208 | 40.281 | 12.248 | 1.00 | 30.74 | C |
| ATOM | 196 | CD | ARG | A | 40 | 16.823 | 40.775 | 11.890 | 1.00 | 34.86 | C |
| ATOM | 197 | NE | ARG | A | 40 | 16.604 | 40.989 | 10.477 | 1.00 | 39.38 | N |
| ATOM | 198 | CZ | ARG | A | 40 | 15.403 | 41.229 | 9.971 | 1.00 | 43.86 | C |
| ATOM | 199 | NH1 | ARG | A | 40 | 14.345 | 41.254 | 10.782 | 1.00 | 45.88 | N |
| ATOM | 200 | NH2 | ARG | A | 40 | 15.252 | 41.457 | 8.674 | 1.00 | 44.96 | N |
| ATOM | 201 | N | PRO | A | 41 | 16.687 | 36.031 | 12.221 | 1.00 | 25.08 | N |
| ATOM | 202 | CA | PRO | A | 41 | 16.715 | 34.565 | 12.290 | 1.00 | 25.39 | C |
| ATOM | 203 | C | PRO | A | 41 | 18.095 | 33.913 | 12.282 | 1.00 | 25.10 | C |
| ATOM | 204 | O | PRO | A | 41 | 19.007 | 34.370 | 11.636 | 1.00 | 25.16 | O |
| ATOM | 205 | CB | PRO | A | 41 | 15.953 | 34.130 | 11.023 | 1.00 | 25.76 | C |
| ATOM | 206 | CG | PRO | A | 41 | 15.286 | 35.392 | 10.504 | 1.00 | 26.54 | C |
| ATOM | 207 | CD | PRO | A | 41 | 16.151 | 36.524 | 10.939 | 1.00 | 24.85 | C |
| ATOM | 208 | N | ILE | A | 42 | 18.225 | 32.823 | 13.020 | 1.00 | 25.28 | N |
| ATOM | 209 | CA | ILE | A | 42 | 19.388 | 31.974 | 12.919 | 1.00 | 24.31 | C |
| ATOM | 210 | C | ILE | A | 42 | 19.147 | 31.116 | 11.677 | 1.00 | 24.68 | C |
| ATOM | 211 | O | ILE | A | 42 | 18.043 | 30.614 | 11.466 | 1.00 | 24.72 | O |
| ATOM | 212 | CB | ILE | A | 42 | 19.481 | 31.104 | 14.163 | 1.00 | 24.80 | C |
| ATOM | 213 | CG1 | ILE | A | 42 | 19.763 | 31.993 | 15.384 | 1.00 | 24.24 | C |
| ATOM | 214 | CG2 | ILE | A | 42 | 20.530 | 30.004 | 13.961 | 1.00 | 23.81 | C |
| ATOM | 215 | CD1 | ILE | A | 42 | 19.531 | 31.325 | 16.729 | 1.00 | 23.59 | C |
| ATOM | 216 | N | PRO | A | 43 | 20.146 | 30.953 | 10.826 | 1.00 | 24.48 | N |
| ATOM | 217 | CA | PRO | A | 43 | 19.963 | 30.108 | 9.651 | 1.00 | 24.60 | C |
| ATOM | 218 | C | PRO | A | 43 | 19.611 | 28.650 | 10.001 | 1.00 | 24.85 | C |
| ATOM | 219 | O | PRO | A | 43 | 20.148 | 28.130 | 10.989 | 1.00 | 24.38 | O |
| ATOM | 220 | CB | PRO | A | 43 | 21.320 | 30.192 | 8.937 | 1.00 | 24.87 | C |
| ATOM | 221 | CG | PRO | A | 43 | 22.040 | 31.372 | 9.541 | 1.00 | 25.04 | C |
| ATOM | 222 | CD | PRO | A | 43 | 21.475 | 31.583 | 10.886 | 1.00 | 24.37 | C |
| ATOM | 223 | N | ARG | A | 44 | 18.686 | 28.032 | 9.248 | 1.00 | 24.70 | N |
| ATOM | 224 | CA | ARG | A | 44 | 18.367 | 26.608 | 9.391 | 1.00 | 25.53 | C |
| ATOM | 225 | C | ARG | A | 44 | 18.910 | 25.943 | 8.152 | 1.00 | 25.00 | C |
| ATOM | 226 | O | ARG | A | 44 | 18.505 | 26.265 | 7.030 | 1.00 | 24.62 | O |
| ATOM | 227 | CB | ARG | A | 44 | 16.873 | 26.287 | 9.452 | 1.00 | 26.51 | C |
| ATOM | 228 | CG | ARG | A | 44 | 16.044 | 27.133 | 10.378 | 1.00 | 29.49 | C |
| ATOM | 229 | CD | ARG | A | 44 | 14.683 | 26.485 | 10.813 | 1.00 | 31.03 | C |
| ATOM | 230 | NE | ARG | A | 44 | 14.401 | 25.120 | 10.323 | 1.00 | 32.36 | N |
| ATOM | 231 | CZ | ARG | A | 44 | 14.174 | 24.057 | 11.126 | 1.00 | 33.85 | C |
| ATOM | 232 | NH1 | ARG | A | 44 | 14.239 | 24.170 | 12.451 | 1.00 | 30.71 | N |
| ATOM | 233 | NH2 | ARG | A | 44 | 13.898 | 22.863 | 10.613 | 1.00 | 35.56 | N |
| ATOM | 234 | N | LEU | A | 45 | 19.815 | 25.006 | 8.337 | 1.00 | 23.97 | N |
| ATOM | 235 | CA | LEU | A | 45 | 20.500 | 24.444 | 7.202 | 1.00 | 23.40 | C |
| ATOM | 236 | C | LEU | A | 45 | 20.684 | 22.967 | 7.352 | 1.00 | 23.52 | C |
| ATOM | 237 | O | LEU | A | 45 | 20.559 | 22.423 | 8.446 | 1.00 | 22.50 | O |
| ATOM | 238 | CS | LEU | A | 45 | 21.888 | 25.064 | 7.093 | 1.00 | 22.62 | C |
| ATOM | 239 | CG | LEU | A | 45 | 21.911 | 26.563 | 6.819 | 1.00 | 23.96 | C |
| ATOM | 240 | CD1 | LEU | A | 45 | 23.317 | 27.111 | 6.947 | 1.00 | 24.52 | C |
| ATOM | 241 | CD2 | LEU | A | 45 | 21.366 | 26.845 | 5.423 | 1.00 | 24.63 | C |
| ATOM | 242 | N | SER | A | 46 | 21.018 | 22.347 | 6.227 | 1.00 | 23.57 | N |
| ATOM | 243 | CA | SER | A | 46 | 21.382 | 20.975 | 6.221 | 1.00 | 24.12 | C |
| ATOM | 244 | C | SER | A | 46 | 22.820 | 20.888 | 6.668 | 1.00 | 24.81 | C |
| ATOM | 245 | O | SER | A | 46 | 23.640 | 21.757 | 6.398 | 1.00 | 23.76 | O |
| ATOM | 246 | CS | SER | A | 46 | 21.236 | 20.354 | 4.830 | 1.00 | 23.80 | C |
| ATOM | 247 | OG | SER | A | 46 | 21.744 | 19.020 | 4.830 | 1.00 | 24.09 | O |
| ATOM | 248 | N | GLN | A | 47 | 23.089 | 19.804 | 7.366 | 1.00 | 25.92 | N |
| ATOM | 249 | CA | GLN | A | 47 | 24.399 | 19.444 | 7.844 | 1.00 | 27.25 | C |
| ATOM | 250 | C | GLN | A | 47 | 25.379 | 19.326 | 6.674 | 1.00 | 27.54 | C |
| ATOM | 251 | O | GLN | A | 47 | 26.563 | 19.564 | 6.836 | 1.00 | 27.97 | O |

TABLE 3-continued

| | | | | | | | | | | | |
|---|---|---|---|---|---|---|---|---|---|---|---|
| | Coordinates for structures 1 to 4 |
| ATOM | 252 | CB | GLN | A | 47 | 24.245 | 18.088 | 8.554 | 1.00 | 28.46 | C |
| ATOM | 253 | CG | GLN | A | 47 | 25.487 | 17.279 | 8.705 | 1.00 | 31.10 | C |
| ATOM | 254 | CD | GLN | A | 47 | 25.776 | 16.372 | 7.570 | 1.00 | 33.17 | C |
| ATOM | 255 | OE1 | GLN | A | 47 | 24.881 | 15.970 | 6.803 | 1.00 | 36.23 | O |
| ATOM | 256 | NE2 | GLN | A | 47 | 27.041 | 16.000 | 7.458 | 1.00 | 36.17 | N |
| ATOM | 257 | N | SER | A | 48 | 24.884 | 18.951 | 5.498 | 1.00 | 27.72 | N |
| ATOM | 258 | CA | SER | A | 48 | 25.736 | 18.809 | 4.323 | 1.00 | 28.35 | C |
| ATOM | 259 | C | SER | A | 48 | 26.016 | 20.150 | 3.629 | 1.00 | 28.86 | C |
| ATOM | 260 | O | SER | A | 48 | 26.825 | 20.235 | 2.711 | 1.00 | 28.96 | O |
| ATOM | 261 | CB | SER | A | 48 | 25.092 | 17.839 | 3.324 | 1.00 | 28.65 | C |
| ATOM | 262 | OG | SER | A | 48 | 23.798 | 18.276 | 2.918 | 1.00 | 28.51 | O |
| ATOM | 263 | N | ASP | A | 49 | 25.347 | 21.203 | 4.065 | 1.00 | 29.16 | N |
| ATOM | 264 | CA | ASP | A | 49 | 25.515 | 22.496 | 3.442 | 1.00 | 29.28 | C |
| ATOM | 265 | C | ASP | A | 49 | 26.800 | 23.163 | 3.913 | 1.00 | 29.71 | C |
| ATOM | 266 | O | ASP | A | 49 | 26.981 | 23.398 | 5.101 | 1.00 | 29.02 | O |
| ATOM | 267 | CB | ASP | A | 49 | 24.325 | 23.369 | 3.783 | 1.00 | 29.35 | C |
| ATOM | 268 | CG | ASP | A | 49 | 24.316 | 24.667 | 3.010 | 1.00 | 29.93 | C |
| ATOM | 269 | OD1 | ASP | A | 49 | 25.398 | 25.183 | 2.666 | 1.00 | 28.14 | O |
| ATOM | 270 | OD2 | ASP | A | 49 | 23.259 | 25.247 | 2.731 | 1.00 | 30.49 | O |
| ATOM | 271 | N | PRO | A | 50 | 27.693 | 23.483 | 2.976 | 1.00 | 30.34 | N |
| ATOM | 272 | CA | PRO | A | 50 | 28.964 | 24.134 | 3.315 | 1.00 | 30.54 | C |
| ATOM | 273 | C | PRO | A | 50 | 28.783 | 25.354 | 4.186 | 1.00 | 30.38 | C |
| ATOM | 274 | O | PRO | A | 50 | 29.661 | 25.651 | 4.990 | 1.00 | 30.53 | O |
| ATOM | 275 | CB | PRO | A | 50 | 29.520 | 24.573 | 1.952 | 1.00 | 30.39 | C |
| ATOM | 276 | CG | PRO | A | 50 | 28.926 | 23.667 | 0.988 | 1.00 | 30.96 | C |
| ATOM | 277 | CD | PRO | A | 50 | 27.574 | 23.243 | 1.531 | 1.00 | 30.51 | C |
| ATOM | 278 | N | ARG | A | 51 | 27.683 | 26.072 | 4.008 | 1.00 | 30.50 | N |
| ATOM | 279 | CA | ARG | A | 51 | 27.439 | 27.253 | 4.817 | 1.00 | 30.94 | C |
| ATOM | 280 | C | ARG | A | 51 | 27.341 | 26.875 | 6.299 | 1.00 | 30.49 | C |
| ATOM | 281 | O | ARG | A | 51 | 27.744 | 27.646 | 7.161 | 1.00 | 29.74 | O |
| ATOM | 282 | CB | ARG | A | 51 | 26.171 | 27.979 | 4.370 | 1.00 | 30.97 | C |
| ATOM | 283 | CG | ARG | A | 51 | 26.337 | 28.781 | 3.099 | 1.00 | 33.47 | C |
| ATOM | 284 | CD | ARG | A | 51 | 25.029 | 29.321 | 2.521 | 1.00 | 34.80 | C |
| ATOM | 285 | NE | ARG | A | 51 | 24.071 | 28.252 | 2.221 | 1.00 | 36.68 | N |
| ATOM | 286 | CZ | ARG | A | 51 | 22.766 | 28.448 | 2.081 | 1.00 | 37.94 | C |
| ATOM | 287 | NH1 | ARG | A | 51 | 22.260 | 29.677 | 2.208 | 1.00 | 39.10 | N |
| ATOM | 288 | NH2 | ARG | A | 51 | 21.967 | 27.436 | 1.794 | 1.00 | 36.51 | N |
| ATOM | 289 | N | ALA | A | 52 | 26.831 | 25.684 | 6.596 | 1.00 | 30.03 | N |
| ATOM | 290 | CA | ALA | A | 52 | 26.697 | 25.288 | 7.993 | 1.00 | 29.96 | C |
| ATOM | 291 | C | ALA | A | 52 | 28.079 | 25.101 | 8.593 | 1.00 | 30.07 | C |
| ATOM | 292 | O | ALA | A | 52 | 28.345 | 25.518 | 9.710 | 1.00 | 29.00 | O |
| ATOM | 293 | CB | ALA | A | 52 | 25.901 | 24.028 | 8.119 | 1.00 | 29.81 | C |
| ATOM | 294 | N | GLU | A | 53 | 28.958 | 24.455 | 7.845 | 1.00 | 30.12 | N |
| ATOM | 295 | CA | GLU | A | 53 | 30.290 | 24.213 | 8.347 | 1.00 | 31.08 | C |
| ATOM | 296 | C | GLU | A | 53 | 30.999 | 25.550 | 8.579 | 1.00 | 30.37 | C |
| ATOM | 297 | O | GLU | A | 53 | 31.683 | 25.730 | 9.580 | 1.00 | 29.89 | O |
| ATOM | 298 | CB | GLU | A | 53 | 31.086 | 23.362 | 7.379 | 1.00 | 31.41 | C |
| ATOM | 299 | CG | GLU | A | 53 | 32.189 | 22.603 | 8.081 | 1.00 | 35.02 | C |
| ATOM | 300 | CD | GLU | A | 53 | 31.785 | 21.185 | 8.507 | 1.00 | 37.87 | C |
| ATOM | 301 | OE1 | GLU | A | 53 | 30.614 | 20.929 | 8.887 | 1.00 | 39.16 | O |
| ATOM | 302 | OE2 | GLU | A | 53 | 32.674 | 20.313 | 8.463 | 1.00 | 40.43 | O |
| ATOM | 303 | N | GLU | A | 54 | 30.811 | 26.479 | 7.652 | 1.00 | 29.84 | N |
| ATOM | 304 | CA | GLU | A | 54 | 31.413 | 27.796 | 7.757 | 1.00 | 30.22 | C |
| ATOM | 305 | C | GLU | A | 54 | 30.975 | 28.486 | 9.045 | 1.00 | 29.05 | C |
| ATOM | 306 | O | GLU | A | 54 | 31.780 | 29.102 | 9.719 | 1.00 | 28.03 | O |
| ATOM | 307 | CB | GLU | A | 54 | 31.026 | 28.680 | 6.573 | 1.00 | 30.53 | C |
| ATOM | 308 | CG | GLU | A | 54 | 31.635 | 28.276 | 5.243 | 1.00 | 34.66 | C |
| ATOM | 309 | CD | GLU | A | 54 | 30.993 | 29.002 | 4.058 | 1.00 | 38.49 | C |
| ATOM | 310 | OE1 | GLU | A | 54 | 30.651 | 30.208 | 4.214 | 1.00 | 42.20 | O |
| ATOM | 311 | OE2 | GLU | A | 54 | 30.829 | 28.368 | 2.975 | 1.00 | 41.54 | O |
| ATOM | 312 | N | LEU | A | 55 | 29.696 | 28.366 | 9.387 | 1.00 | 28.24 | N |
| ATOM | 313 | CA | LEU | A | 55 | 29.177 | 29.029 | 10.571 | 1.00 | 27.28 | C |
| ATOM | 314 | C | LEU | A | 55 | 29.774 | 28.448 | 11.827 | 1.00 | 26.43 | C |
| ATOM | 315 | O | LEU | A | 55 | 30.212 | 29.199 | 12.695 | 1.00 | 25.20 | O |
| ATOM | 316 | CB | LEU | A | 55 | 27.655 | 28.975 | 10.597 | 1.00 | 27.25 | C |
| ATOM | 317 | CG | LEU | A | 55 | 27.027 | 29.829 | 9.502 | 1.00 | 27.43 | C |
| ATOM | 318 | CD1 | LEU | A | 55 | 25.568 | 29.452 | 9.322 | 1.00 | 28.83 | C |
| ATOM | 319 | CD2 | LEU | A | 55 | 27.173 | 31.318 | 9.821 | 1.00 | 26.98 | C |
| ATOM | 320 | N | ILE | A | 56 | 29.829 | 27.116 | 11.915 | 1.00 | 25.75 | N |
| ATOM | 321 | CA | ILE | A | 56 | 30.382 | 26.473 | 13.107 | 1.00 | 25.50 | C |
| ATOM | 322 | C | ILE | A | 56 | 31.874 | 26.815 | 13.254 | 1.00 | 26.26 | C |
| ATOM | 323 | O | ILE | A | 56 | 32.346 | 27.134 | 14.349 | 1.00 | 25.55 | O |
| ATOM | 324 | GB | ILE | A | 56 | 30.192 | 24.955 | 13.059 | 1.00 | 25.63 | C |
| ATOM | 325 | CG1 | ILE | A | 56 | 28.698 | 24.574 | 13.034 | 1.00 | 24.00 | C |
| ATOM | 326 | CG2 | ILE | A | 56 | 30.848 | 24.321 | 14.263 | 1.00 | 25.48 | C |
| ATOM | 327 | CD1 | ILE | A | 56 | 28.439 | 23.170 | 12.531 | 1.00 | 24.10 | C |
| ATOM | 328 | N | GLU | A | 57 | 32.597 | 26.781 | 12.135 | 1.00 | 27.04 | N |

TABLE 3-continued

| | | | | | | | | | | |
|---|---|---|---|---|---|---|---|---|---|---|
| | | | Coordinates for structures 1 to 4 | | | | | | | |
| ATOM | 329 | CA | GLU | A | 57 | 34.023 | 27.082 | 12.107 | 1.00 | 28.01 | C |
| ATOM | 330 | C | GLU | A | 57 | 34.232 | 28.491 | 12.625 | 1.00 | 28.49 | C |
| ATOM | 331 | O | GLU | A | 57 | 35.183 | 28.770 | 13.344 | 1.00 | 28.92 | O |
| ATOM | 332 | GB | GLU | A | 57 | 34.561 | 26.977 | 10.676 | 1.00 | 28.61 | C |
| ATOM | 333 | CG | GLU | A | 57 | 36.053 | 27.224 | 10.509 | 1.00 | 30.77 | C |
| ATOM | 334 | CD | GLU | A | 57 | 36.902 | 26.322 | 11.394 | 1.00 | 35.15 | C |
| ATOM | 335 | OE1 | GLU | A | 57 | 36.556 | 25.127 | 11.591 | 1.00 | 37.11 | O |
| ATOM | 336 | OE2 | GLU | A | 57 | 37.924 | 26.818 | 11.909 | 1.00 | 40.88 | O |
| ATOM | 337 | N | ASN | A | 58 | 33.321 | 29.378 | 12.270 | 1.00 | 28.34 | N |
| ATOM | 338 | CA | ASN | A | 58 | 33.424 | 30.758 | 12.701 | 1.00 | 28.81 | C |
| ATOM | 339 | C | ASN | A | 58 | 32.770 | 31.079 | 14.025 | 1.00 | 27.23 | C |
| ATOM | 340 | O | ASN | A | 58 | 32.630 | 32.233 | 14.374 | 1.00 | 26.07 | O |
| ATOM | 341 | CD | ASN | A | 58 | 32.792 | 31.641 | 11.656 | 1.00 | 29.66 | C |
| ATOM | 342 | CG | ASN | A | 58 | 33.789 | 32.386 | 10.913 | 1.00 | 33.61 | C |
| ATOM | 343 | OD1 | ASN | A | 58 | 34.280 | 31.901 | 9.893 | 1.00 | 38.81 | O |
| ATOM | 344 | ND2 | ASN | A | 58 | 34.160 | 33.582 | 11.429 | 1.00 | 36.72 | N |
| ATOM | 345 | N | GLU | A | 59 | 32.343 | 30.053 | 14.735 | 1.00 | 26.39 | N |
| ATOM | 346 | CA | GLU | A | 59 | 31.712 | 30.241 | 16.030 | 1.00 | 26.36 | C |
| ATOM | 347 | C | GLU | A | 59 | 30.495 | 31.144 | 15.926 | 1.00 | 25.39 | C |
| ATOM | 348 | O | GLU | A | 59 | 30.325 | 32.100 | 16.668 | 1.00 | 24.14 | O |
| ATOM | 349 | CB | GLU | A | 59 | 32.753 | 30.697 | 17.059 | 1.00 | 26.80 | C |
| ATOM | 350 | CG | GLU | A | 59 | 33.717 | 29.537 | 17.316 | 1.00 | 29.10 | C |
| ATOM | 351 | CD | GLU | A | 59 | 34.722 | 29.791 | 18.407 | 1.00 | 32.85 | C |
| ATOM | 352 | OE1 | GLU | A | 59 | 35.790 | 30.330 | 18.080 | 1.00 | 37.47 | O |
| ATOM | 353 | OE2 | GLU | A | 59 | 34.466 | 29.432 | 19.572 | 1.00 | 34.14 | O |
| ATOM | 354 | N | GLU | A | 60 | 29.641 | 30.799 | 14.970 | 1.00 | 24.88 | N |
| ATOM | 355 | CA | GLU | A | 60 | 28.366 | 31.465 | 14.B01 | 1.00 | 25.20 | C |
| ATOM | 356 | C | GLU | A | 60 | 27.262 | 30.414 | 14.822 | 1.00 | 24.01 | C |
| ATOM | 357 | O | GLU | A | 60 | 27.420 | 29.320 | 14.293 | 1.00 | 22.49 | O |
| ATOM | 358 | GB | GLU | A | 60 | 28.343 | 32.249 | 13.505 | 1.00 | 25.69 | C |
| ATOM | 359 | CG | GLU | A | 60 | 29.354 | 33.363 | 13.536 | 1.00 | 30.40 | C |
| ATOM | 360 | CD | GLU | A | 60 | 28.962 | 34.516 | 12.657 | 1.00 | 37.91 | C |
| ATOM | 361 | OE1 | GLU | A | 60 | 29.009 | 34.377 | 11.414 | 1.00 | 38.24 | O |
| ATOM | 362 | OE2 | GLU | A | 60 | 28.595 | 35.566 | 13.236 | 1.00 | 46.50 | O |
| ATOM | 363 | N | PRO | A | 61 | 26.124 | 30.779 | 15.386 | 1.00 | 22.90 | N |
| ATOM | 364 | CA | PRO | A | 61 | 25.045 | 29.816 | 15.571 | 1.00 | 22.49 | C |
| ATOM | 365 | C | PRO | A | 61 | 24.448 | 29.371 | 14.267 | 1.00 | 21.47 | C |
| ATOM | 366 | O | PRO | A | 61 | 24.419 | 30.104 | 13.266 | 1.00 | 20.48 | O |
| ATOM | 367 | CB | PRO | A | 61 | 23.996 | 30.583 | 16.368 | 1.00 | 22.29 | C |
| ATOM | 368 | CG | PRO | A | 61 | 24.315 | 32.053 | 16.148 | 1.00 | 22.67 | C |
| ATOM | 369 | CD | PRO | A | 61 | 25.764 | 32.140 | 15.798 | 1.00 | 22.92 | C |
| ATOM | 370 | N | VAL | A | 62 | 23.957 | 28.142 | 14.283 | 1.00 | 20.87 | N |
| ATOM | 371 | HCA | VAL | A | 62 | 23.248 | 27.591 | 13.146 | 1.00 | 20.94 | C |
| ATOM | 372 | C | VAL | A | 62 | 22.353 | 26.475 | 13.655 | 1.00 | 21.15 | C |
| ATOM | 373 | O | VAL | A | 62 | 22.714 | 25.761 | 14.605 | 1.00 | 21.21 | O |
| ATOM | 374 | GB | VAL | A | 62 | 24.214 | 27.052 | 12.073 | 1.00 | 21.30 | C |
| ATOM | 375 | CG1 | VAL | A | 62 | 25.061 | 25.912 | 12.608 | 1.00 | 22.10 | C |
| ATOM | 376 | CG2 | VAL | A | 62 | 23.440 | 26.587 | 10.825 | 1.00 | 21.19 | C |
| ATOM | 377 | N | VAL | A | 63 | 21.158 | 26.366 | 13.084 | 1.00 | 21.48 | N |
| ATOM | 378 | CA | VAL | A | 63 | 20.302 | 25.231 | 13.374 | 1.00 | 21.87 | C |
| ATOM | 379 | C | VAL | A | 63 | 20.526 | 24.212 | 12.270 | 1.00 | 22.00 | C |
| ATOM | 380 | O | VAL | A | 63 | 20.366 | 24.528 | 11.109 | 1.00 | 22.54 | O |
| ATOM | 381 | CB | VAL | A | 63 | 18.793 | 25.574 | 13.421 | 1.00 | 22.02 | C |
| ATOM | 382 | CG1 | VAL | A | 63 | 17.955 | 24.277 | 13.612 | 1.00 | 21.90 | C |
| ATOM | 383 | CG2 | VAL | A | 63 | 18.494 | 26.522 | 14.546 | 1.00 | 21.22 | C |
| ATOM | 384 | N | LEU | A | 64 | 20.911 | 23.002 | 12.643 | 1.00 | 22.48 | N |
| ATOM | 385 | CA | LEU | A | 64 | 21.067 | 21.902 | 11.710 | 1.00 | 23.08 | C |
| ATOM | 386 | C | LEU | A | 64 | 19.826 | 21.014 | 11.775 | 1.00 | 22.19 | C |
| ATOM | 387 | O | LEU | A | 64 | 19.423 | 20.558 | 12.843 | 1.00 | 21.85 | O |
| ATOM | 388 | CB | LEU | A | 64 | 22.327 | 21.107 | 12.032 | 1.00 | 24.00 | C |
| ATOM | 389 | CG | LEU | A | 64 | 23.614 | 21.930 | 11.984 | 1.00 | 27.02 | C |
| ATOM | 390 | CD1 | LEU | A | 64 | 24.791 | 21.080 | 12.303 | 1.00 | 31.61 | C |
| ATOM | 391 | CD2 | LEU | A | 64 | 23.827 | 22.540 | 10.640 | 1.00 | 29.86 | C |
| ATOM | 392 | N | THR | A | 65 | 19.222 | 20.757 | 10.628 | 1.00 | 21.50 | N |
| ATOM | 393 | CA | THR | A | 65 | 17.943 | 20.056 | 10.613 | 1.00 | 21.95 | C |
| ATOM | 394 | C | THR | A | 65 | 18.022 | 18.561 | 10.389 | 1.00 | 21.35 | C |
| ATOM | 395 | O | THR | A | 65 | 17.028 | 17.870 | 10.581 | 1.00 | 21.37 | O |
| ATOM | 396 | CB | THR | A | 65 | 17.062 | 20.592 | 9.478 | 1.00 | 22.08 | C |
| ATOM | 397 | OG1 | THR | A | 65 | 17.725 | 20.351 | 8.230 | 1.00 | 22.38 | O |
| ATOM | 398 | CG2 | THR | A | 65 | 16.919 | 22.099 | 9.553 | 1.00 | 24.00 | C |
| ATOM | 399 | N | ASP | A | 66 | 19.168 | 18.062 | 9.961 | 1.00 | 21.50 | N |
| ATOM | 400 | CA | ASP | A | 66 | 19.259 | 16.650 | 9.604 | 1.00 | 21.86 | C |
| ATOM | 401 | C | ASP | A | 66 | 20.513 | 15.899 | 10.069 | 1.00 | 21.61 | C |
| ATOM | 402 | O | ASP | A | 66 | 21.070 | 15.088 | 9.316 | 1.00 | 21.82 | O |
| ATOM | 403 | CB | ASP | A | 66 | 19.152 | 16.553 | 8.084 | 1.00 | 22.20 | C |
| ATOM | 404 | CG | ASP | A | 66 | 20.199 | 17.355 | 7.390 | 1.00 | 21.49 | C |
| ATOM | 405 | OD1 | ASP | A | 66 | 21.065 | 17.936 | 8.070 | 1.00 | 21.14 | O |

TABLE 3-continued

Coordinates for structures 1 to 4

| ATOM | 406 | OD2 | ASP | A | 66 | 20.240 | 17.477 | 6.159 | 1.00 | 25.40 | O |
|---|---|---|---|---|---|---|---|---|---|---|---|
| ATOM | 407 | N | THR | A | 67 | 20.967 | 16.158 | 11.287 | 1.00 | 21.05 | N |
| ATOM | 408 | CA | THR | A | 67 | 22.154 | 15.491 | 11.768 | 1.00 | 20.85 | C |
| ATOM | 409 | C | THR | A | 67 | 21.858 | 14.084 | 12.231 | 1.00 | 20.12 | C |
| ATOM | 410 | O | THR | A | 67 | 22.757 | 13.281 | 12.283 | 1.00 | 20.45 | O |
| ATOM | 411 | CB | THR | A | 67 | 22.747 | 16.207 | 12.977 | 1.00 | 20.77 | C |
| ATOM | 412 | OG1 | THR | A | 67 | 21.782 | 16.210 | 14.039 | 1.00 | 20.61 | O |
| ATOM | 413 | CG2 | THR | A | 67 | 23.054 | 17.671 | 12.682 | 1.00 | 22.44 | C |
| ATOM | 414 | N | ASN | A | 68 | 20.614 | 13.815 | 12.618 | 1.00 | 19.51 | N |
| ATOM | 415 | CA | ASN | A | 68 | 20.269 | 12.555 | 13.267 | 1.00 | 19.09 | C |
| ATOM | 416 | C | ASN | A | 68 | 21.116 | 12.349 | 14.517 | 1.00 | 18.40 | C |
| ATOM | 417 | O | ASN | A | 68 | 21.383 | 11.212 | 14.928 | 1.00 | 17.67 | O |
| ATOM | 418 | CB | ASN | A | 68 | 20.455 | 11.362 | 12.325 | 1.00 | 19.63 | C |
| ATOM | 419 | CG | ASN | A | 68 | 19.453 | 11.344 | 11.209 | 1.00 | 19.93 | C |
| ATOM | 420 | OD1 | ASN | A | 68 | 18.253 | 11.236 | 11.442 | 1.00 | 19.76 | O |
| ATOM | 421 | ND2 | ASN | A | 68 | 19.941 | 11.423 | 9.987 | 1.00 | 19.96 | N |
| ATOM | 422 | N | LEU | A | 69 | 21.532 | 13.448 | 15.134 | 1.00 | 18.28 | N |
| ATOM | 423 | CA | LEU | A | 69 | 22.378 | 13.382 | 16.326 | 1.00 | 17.98 | C |
| ATOM | 424 | C | LEU | A | 69 | 21.773 | 12.542 | 17.447 | 1.00 | 17.59 | C |
| ATOM | 425 | O | LEU | A | 69 | 22.478 | 11.725 | 18.039 | 1.00 | 17.61 | O |
| ATOM | 426 | CB | LEU | A | 69 | 22.693 | 14.772 | 16.844 | 1.00 | 18.38 | C |
| ATOM | 427 | CG | LEU | A | 69 | 23.636 | 14.859 | 18.035 | 1.00 | 18.31 | C |
| ATOM | 428 | CD1 | LEU | A | 69 | 24.936 | 14.144 | 17.744 | 1.00 | 20.68 | C |
| ATOM | 429 | CD2 | LEU | A | 69 | 23.907 | 16.299 | 18.399 | 1.00 | 19.25 | C |
| ATOM | 430 | N | VAL | A | 70 | 20.489 | 12.741 | 17.740 | 1.00 | 17.27 | N |
| ATOM | 431 | CA | VAL | A | 70 | 19.811 | 11.989 | 18.794 | 1.00 | 17.72 | C |
| ATOM | 432 | C | VAL | A | 70 | 18.588 | 11.253 | 18.257 | 1.00 | 18.11 | C |
| ATOM | 433 | O | VAL | A | 70 | 17.557 | 11.148 | 18.927 | 1.00 | 17.23 | O |
| ATOM | 434 | CB | VAL | A | 70 | 19.395 | 12.866 | 19.999 | 1.00 | 17.54 | C |
| ATOM | 435 | CG1 | VAL | A | 70 | 20.624 | 13.402 | 20.704 | 1.00 | 19.07 | C |
| ATOM | 436 | CG2 | VAL | A | 70 | 18.451 | 13.994 | 19.599 | 1.00 | 17.50 | C |
| ATOM | 437 | N | TYR | A | 71 | 18.715 | 10.764 | 17.028 | 1.00 | 19.22 | N |
| ATOM | 438 | CA | TYR | A | 71 | 17.615 | 10.071 | 16.367 | 1.00 | 19.79 | C |
| ATOM | 439 | C | TYR | A | 71 | 16.934 | 9.072 | 17.306 | 1.00 | 19.62 | C |
| ATOM | 440 | O | TYR | A | 71 | 15.726 | 9.120 | 17.457 | 1.00 | 18.64 | O |
| ATOM | 441 | CB | TYR | A | 71 | 18.082 | 9.406 | 15.055 | 1.00 | 20.19 | C |
| ATOM | 442 | CG | TYR | A | 71 | 17.156 | 8.320 | 14.554 | 1.00 | 22.29 | C |
| ATOM | 443 | CD1 | TYR | A | 71 | 15.938 | 8.619 | 13.948 | 1.00 | 25.33 | C |
| ATOM | 444 | CD2 | TYR | A | 71 | 17.503 | 6.986 | 14.691 | 1.00 | 23.31 | C |
| ATOM | 445 | CE1 | TYR | A | 71 | 15.080 | 7.555 | 13.480 | 1.00 | 24.74 | C |
| ATOM | 446 | CE2 | TYR | A | 71 | 16.684 | 5.968 | 14.252 | 1.00 | 23.57 | C |
| ATOM | 447 | CZ | TYR | A | 71 | 15.479 | 6.244 | 13.650 | 1.00 | 24.07 | C |
| ATOM | 448 | OH | TYR | A | 71 | 14.686 | 5.159 | 13.266 | 1.00 | 27.86 | O |
| ATOM | 449 | N | PRO | A | 72 | 17.688 | 8.200 | 17.960 | 1.00 | 20.27 | N |
| ATOM | 450 | CA | PRO | A | 72 | 17.074 | 7.196 | 18.840 | 1.00 | 21.30 | C |
| ATOM | 451 | C | PRO | A | 72 | 16.307 | 7.794 | 20.008 | 1.00 | 21.82 | C |
| ATOM | 452 | O | PRO | A | 72 | 15.463 | 7.120 | 20.535 | 1.00 | 21.13 | O |
| ATOM | 453 | CB | PRO | A | 72 | 18.267 | 6.377 | 19.351 | 1.00 | 21.33 | C |
| ATOM | 454 | CG | PRO | A | 72 | 19.362 | 6.650 | 18.386 | 1.00 | 21.75 | C |
| ATOM | 455 | CD | PRO | A | 72 | 19.151 | 8.065 | 17.905 | 1.00 | 20.71 | C |
| ATOM | 456 | N | ALA | A | 73 | 16.588 | 9.038 | 20.391 | 1.00 | 22.47 | N |
| ATOM | 457 | CA | ALA | A | 73 | 15.892 | 9.658 | 21.522 | 1.00 | 23.20 | C |
| ATOM | 458 | C | ALA | A | 73 | 14.567 | 10.293 | 21.103 | 1.00 | 23.47 | C |
| ATOM | 459 | O | ALA | A | 73 | 13.801 | 10.765 | 21.938 | 1.00 | 23.46 | O |
| ATOM | 460 | CB | ALA | A | 73 | 16.783 | 10.718 | 22.173 | 1.00 | 23.27 | C |
| ATOM | 461 | N | LEU | A | 74 | 14.297 | 10.322 | 19.808 | 1.00 | 23.79 | N |
| ATOM | 462 | CA | LEU | A | 74 | 13.086 | 10.967 | 19.329 | 1.00 | 24.10 | C |
| ATOM | 463 | C | LEU | A | 74 | 11.797 | 10.301 | 19.801 | 1.00 | 24.55 | C |
| ATOM | 464 | O | LEU | A | 74 | 10.732 | 10.903 | 19.746 | 1.00 | 23.83 | O |
| ATOM | 465 | CB | LEU | A | 74 | 13.114 | 11.076 | 17.810 | 1.00 | 24.16 | C |
| ATOM | 466 | CG | LEU | A | 74 | 14.185 | 12.061 | 17.296 | 1.00 | 24.67 | C |
| ATOM | 467 | CD1 | LEU | A | 74 | 13.988 | 12.320 | 15.820 | 1.00 | 26.73 | C |
| ATOM | 468 | CD2 | LEU | A | 74 | 14.225 | 13.371 | 18.077 | 1.00 | 23.39 | C |
| ATOM | 469 | N | LYS | A | 75 | 11.897 | 9.053 | 20.244 | 1.00 | 24.97 | N |
| ATOM | 470 | CA | LYS | A | 75 | 10.741 | 8.317 | 20.738 | 1.00 | 25.16 | C |
| ATOM | 471 | C | LYS | A | 75 | 10.589 | 8.519 | 22.245 | 1.00 | 25.37 | C |
| ATOM | 472 | O | LYS | A | 75 | 9.612 | 8.082 | 22.822 | 1.00 | 25.23 | O |
| ATOM | 473 | CB | LYS | A | 75 | 10.885 | 6.819 | 20.428 | 1.00 | 25.16 | C |
| ATOM | 474 | CG | LYS | A | 75 | 12.079 | 6.163 | 21.097 | 1.00 | 25.17 | C |
| ATOM | 475 | CD | LYS | A | 75 | 12.178 | 4.653 | 20.765 | 1.00 | 27.19 | C |
| ATOM | 476 | CE | LYS | A | 75 | 13.646 | 4.220 | 20.609 | 1.00 | 26.95 | C |
| ATOM | 477 | NZ | LYS | A | 75 | 14.348 | 4.123 | 21.868 | 1.00 | 26.22 | N |
| ATOM | 478 | N | TRP | A | 76 | 11.552 | 9.179 | 22.882 | 1.00 | 25.25 | N |
| ATOM | 479 | CA | TRP | A | 76 | 11.486 | 9.389 | 24.319 | 1.00 | 25.56 | C |
| ATOM | 480 | C | TRP | A | 76 | 10.268 | 10.201 | 24.749 | 1.00 | 26.35 | C |
| ATOM | 481 | O | TRP | A | 76 | 9.920 | 11.198 | 24.130 | 1.00 | 26.71 | O |
| ATOM | 482 | CE | TRP | A | 76 | 12.719 | 10.139 | 24.816 | 1.00 | 25.19 | C |

TABLE 3-continued

| | | | | | Coordinates for structures 1 to 4 | | | | | |
|---|---|---|---|---|---|---|---|---|---|---|
| ATOM | 483 | CG | TRP | A | 76 | 13.975 | 9.338 | 24.816 | 1.00 | 24.32 | C |
| ATOM | 484 | CD1 | TRP | A | 76 | 14.129 | 8.059 | 24.393 | 1.00 | 22.72 | C |
| ATOM | 485 | CD2 | TRP | A | 76 | 15.258 | 9.762 | 25.271 | 1.00 | 22.34 | C |
| ATOM | 486 | NE1 | TRP | A | 76 | 15.431 | 7.658 | 24.552 | 1.00 | 20.61 | N |
| ATOM | 487 | CE2 | TRP | A | 76 | 16.145 | 8.685 | 25.096 | 1.00 | 20.28 | C |
| ATOM | 488 | CE3 | TRP | A | 76 | 15.750 | 10.944 | 25.817 | 1.00 | 22.65 | C |
| ATOM | 489 | CZ2 | TRP | A | 76 | 17.481 | 8.756 | 25.437 | 1.00 | 20.18 | C |
| ATOM | 490 | CZ3 | TRP | A | 76 | 17.088 | 11.012 | 26.163 | 1.00 | 21.43 | C |
| ATOM | 491 | CR2 | TRP | A | 76 | 17.932 | 9.934 | 25.970 | 1.00 | 21.94 | C |
| ATOM | 492 | N | ASP | A | 77 | 9.643 | 9.772 | 25.836 | 1.00 | 26.46 | N |
| ATOM | 493 | CA | ASP | A | 77 | 8.583 | 10.530 | 26.467 | 1.00 | 26.47 | C |
| ATOM | 494 | C | ASP | A | 77 | 8.618 | 10.116 | 27.931 | 1.00 | 26.16 | C |
| ATOM | 495 | O | ASP | A | 77 | 9.405 | 9.264 | 28.291 | 1.00 | 26.44 | O |
| ATOM | 496 | CE | ASP | A | 77 | 7.230 | 10.276 | 25.810 | 1.00 | 26.51 | C |
| ATOM | 497 | CG | ASP | A | 77 | 6.795 | 8.835 | 25.885 | 1.00 | 27.32 | C |
| ATOM | 498 | OD1 | ASP | A | 77 | 7.388 | 8.015 | 26.638 | 1.00 | 26.02 | O |
| ATOM | 499 | OD2 | ASP | A | 77 | 5.832 | 8.439 | 25.211 | 1.00 | 29.97 | O |
| ATOM | 500 | N | LEU | A | 78 | 7.790 | 10.705 | 28.775 | 1.00 | 25.96 | N |
| ATOM | 501 | CA | LEU | A | 78 | 7.893 | 10.441 | 30.201 | 1.00 | 26.27 | C |
| ATOM | 502 | C | LEU | A | 78 | 7.716 | 8.965 | 30.539 | 1.00 | 26.14 | C |
| ATOM | 503 | O | LEU | A | 78 | 8.446 | 8.438 | 31.374 | 1.00 | 25.51 | O |
| ATOM | 504 | CB | LEU | A | 78 | 6.905 | 11.301 | 30.979 | 1.00 | 26.32 | C |
| ATOM | 505 | CG | LEU | A | 78 | 7.155 | 12.802 | 30.860 | 1.00 | 27.35 | C |
| ATOM | 506 | CD1 | LEU | A | 78 | 6.098 | 13.579 | 31.623 | 1.00 | 28.05 | C |
| ATOM | 507 | CD2 | LEU | A | 78 | 8.536 | 13.165 | 31.379 | 1.00 | 28.39 | C |
| ATOM | 508 | N | GLU | A | 79 | 6.775 | 8.297 | 29.874 | 1.00 | 26.56 | N |
| ATOM | 509 | CA | GLU | A | 79 | 6.526 | 6.876 | 30.123 | 1.00 | 27.00 | C |
| ATOM | 510 | C | GLU | A | 79 | 7.754 | 6.029 | 29.780 | 1.00 | 26.63 | C |
| ATOM | 511 | O | GLU | A | 79 | 8.220 | 5.231 | 30.583 | 1.00 | 25.94 | O |
| ATOM | 512 | CB | GLU | A | 79 | 5.302 | 6.371 | 29.333 | 1.00 | 27.39 | C |
| ATOM | 513 | CG | GLU | A | 79 | 4.963 | 4.919 | 29.657 | 1.00 | 29.75 | C |
| ATOM | 514 | CD | GLU | A | 79 | 3.803 | 4.347 | 28.854 | 1.00 | 33.15 | C |
| ATOM | 515 | OE1 | GLU | A | 79 | 3.361 | 4.976 | 27.863 | 1.00 | 35.39 | O |
| ATOM | 516 | OE2 | GLU | A | 79 | 3.338 | 3.245 | 29.224 | 1.00 | 35.44 | O |
| ATOM | 517 | N | TYR | A | 80 | 8.279 | 6.205 | 28.575 | 1.00 | 26.53 | N |
| ATOM | 518 | CA | TYR | A | 80 | 9.466 | 5.465 | 28.169 | 1.00 | 26.29 | C |
| ATOM | 519 | C | TYR | A | 80 | 10.669 | 5.763 | 29.072 | 1.00 | 25.83 | C |
| ATOM | 520 | O | TYR | A | 80 | 11.418 | 4.863 | 29.435 | 1.00 | 25.75 | O |
| ATOM | 521 | GB | TYR | A | 80 | 9.812 | 5.802 | 26.728 | 1.00 | 26.53 | C |
| ATOM | 522 | CG | TYR | A | 80 | 11.047 | 5.106 | 26.210 | 1.00 | 26.94 | C |
| ATOM | 523 | CD1 | TYR | A | 80 | 10.971 | 3.836 | 25.637 | 1.00 | 26.53 | C |
| ATOM | 524 | CD2 | TYR | A | 80 | 12.287 | 5.721 | 26.291 | 1.00 | 25.32 | C |
| ATOM | 525 | GE1 | TYR | A | 80 | 12.113 | 3.208 | 25.142 | 1.00 | 26.28 | C |
| ATOM | 526 | CE2 | TYR | A | 80 | 13.416 | 5.109 | 25.823 | 1.00 | 25.73 | C |
| ATOM | 527 | CZ | TYR | A | 80 | 13.331 | 3.861 | 25.240 | 1.00 | 25.94 | C |
| ATOM | 528 | OH | TYR | A | 80 | 14.478 | 3.294 | 24.758 | 1.00 | 25.55 | O |
| ATOM | 529 | N | LEU | A | 81 | 10.859 | 7.016 | 29.448 | 1.00 | 25.62 | N |
| ATOM | 530 | CA | LEU | A | 81 | 12.000 | 7.350 | 30.309 | 1.00 | 25.87 | C |
| ATOM | 531 | C | LEU | A | 81 | 11.821 | 6.794 | 31.733 | 1.00 | 26.06 | C |
| ATOM | 532 | O | LEU | A | 81 | 12.763 | 6.263 | 32.327 | 1.00 | 26.00 | O |
| ATOM | 533 | GB | LEU | A | 81 | 12.250 | 8.863 | 30.340 | 1.00 | 25.81 | C |
| ATOM | 534 | CG | LEU | A | 81 | 12.748 | 9.501 | 29.030 | 1.00 | 25.65 | C |
| ATOM | 535 | CD1 | LEU | A | 81 | 12.828 | 11.010 | 29.174 | 1.00 | 26.40 | C |
| ATOM | 536 | CD2 | LEU | A | 81 | 14.102 | 8.959 | 28.592 | 1.00 | 25.79 | C |
| ATOM | 537 | N | GLN | A | 82 | 10.617 | 6.913 | 32.274 | 1.00 | 26.27 | N |
| ATOM | 538 | CA | GLN | A | 82 | 10.338 | 6.388 | 33.602 | 1.00 | 26.77 | C |
| ATOM | 539 | C | GLN | A | 82 | 10.640 | 4.897 | 33.623 | 1.00 | 26.51 | C |
| ATOM | 540 | O | GLN | A | 82 | 11.232 | 4.384 | 34.552 | 1.00 | 26.60 | O |
| ATOM | 541 | GB | GLN | A | 82 | 8.877 | 6.611 | 33.974 | 1.00 | 26.90 | C |
| ATOM | 542 | CG | GLN | A | 82 | 8.466 | 5.856 | 35.236 | 1.00 | 28.41 | C |
| ATOM | 543 | CD | GLN | A | 82 | 7.315 | 6.501 | 35.987 | 1.00 | 30.63 | C |
| ATOM | 544 | OE1 | GLN | A | 82 | 6.755 | 7.501 | 35.551 | 1.00 | 32.13 | O |
| ATOM | 545 | NE2 | GLN | A | 82 | 6.944 | 5.907 | 37.116 | 1.00 | 34.12 | N |
| ATOM | 546 | N | GLU | A | 83 | 10.252 | 4.216 | 32.561 | 1.00 | 26.68 | N |
| ATOM | 547 | CA | GLU | A | 83 | 10.429 | 2.773 | 32.456 | 1.00 | 26.90 | C |
| ATOM | 548 | C | GLU | A | 83 | 11.893 | 2.359 | 32.295 | 1.00 | 26.42 | C |
| ATOM | 549 | O | GLU | A | 83 | 12.285 | 1.294 | 32.764 | 1.00 | 25.50 | O |
| ATOM | 550 | GB | GLU | A | 83 | 9.604 | 2.257 | 31.273 | 1.00 | 26.84 | C |
| ATOM | 551 | CG | GLU | A | 83 | 9.607 | 0.753 | 31.080 | 1.00 | 29.20 | C |
| ATOM | 552 | CD | GLU | A | 83 | 8.902 | 0.014 | 32.205 | 1.00 | 31.92 | C |
| ATOM | 553 | OE1 | GLU | A | 83 | 8.258 | 0.666 | 33.060 | 1.00 | 34.06 | O |
| ATOM | 554 | OE2 | GLU | A | 83 | 9.008 | 1.221 | 32.243 | 1.00 | 33.78 | O |
| ATOM | 555 | N | ASN | A | 84 | 12.711 | 3.223 | 31.700 | 1.00 | 25.79 | N |
| ATOM | 556 | CA | ASN | A | 84 | 14.063 | 2.824 | 31.312 | 1.00 | 25.87 | C |
| ATOM | 557 | C | ASN | A | 84 | 15.273 | 3.607 | 31.810 | 1.00 | 26.08 | C |
| ATOM | 558 | O | ASN | A | 84 | 16.392 | 3.138 | 31.628 | 1.00 | 26.05 | O |
| ATOM | 559 | GB | ASN | A | 84 | 14.137 | 2.844 | 29.784 | 1.00 | 25.74 | C |

TABLE 3-continued

Coordinates for structures 1 to 4

| ATOM | 560 | CG | ASN | A | 84 | 13.262 | 1.799 | 29.152 | 1.00 | 25.67 | C |
|---|---|---|---|---|---|---|---|---|---|---|---|
| ATOM | 561 | ND1 | ASN | A | 84 | 13.402 | 0.608 | 29.439 | 1.00 | 24.26 | O |
| ATOM | 562 | ND2 | ASN | A | 84 | 12.354 | 2.231 | 28.288 | 1.00 | 22.66 | N |
| ATOM | 563 | N | ILE | A | 85 | 15.087 | 4.773 | 32.422 | 1.00 | 26.02 | N |
| ATOM | 564 | CA | ILE | A | 85 | 16.240 | 5.599 | 32.763 | 1.00 | 26.74 | C |
| ATOM | 565 | C | ILE | A | 85 | 16.930 | 5.307 | 34.099 | 1.00 | 26.89 | C |
| ATOM | 566 | O | ILE | A | 85 | 17.820 | 6.054 | 34.519 | 1.00 | 26.93 | O |
| ATOM | 567 | CB | ILE | A | 85 | 15.846 | 7.076 | 32.688 | 1.00 | 26.70 | C |
| ATOM | 568 | CG1 | ILE | A | 85 | 17.049 | 7.923 | 32.270 | 1.00 | 27.99 | C |
| ATOM | 569 | CG2 | ILE | A | 85 | 15.232 | 7.535 | 33.988 | 1.00 | 26.50 | C |
| ATOM | 570 | CD1 | ILE | A | 85 | 16.696 | 9.389 | 32.000 | 1.00 | 28.77 | C |
| ATOM | 571 | N | GLY | A | 86 | 16.503 | 4.253 | 34.773 | 1.00 | 27.27 | N |
| ATOM | 572 | CA | GLY | A | 86 | 17.130 | 3.834 | 36.018 | 1.00 | 27.51 | C |
| ATOM | 573 | C | GLY | A | 86 | 16.573 | 4.453 | 37.289 | 1.00 | 27.73 | C |
| ATOM | 574 | O | GLY | A | 86 | 15.563 | 5.163 | 37.268 | 1.00 | 27.80 | O |
| ATOM | 575 | N | ASN | A | 87 | 17.273 | 4.186 | 38.392 | 1.00 | 27.70 | N |
| ATOM | 576 | CA | ASN | A | 87 | 16.864 | 4.603 | 39.726 | 1.00 | 27.53 | C |
| ATOM | 577 | C | ASN | A | 87 | 17.849 | 5.602 | 40.320 | 1.00 | 27.33 | C |
| ATOM | 578 | O | ASN | A | 87 | 17.932 | 5.762 | 41.539 | 1.00 | 26.97 | O |
| ATOM | 579 | CB | ASN | A | 87 | 16.726 | 3.367 | 40.644 | 1.00 | 27.60 | C |
| ATOM | 580 | N | GLY | A | 88 | 18.601 | 6.273 | 39.455 | 1.00 | 27.41 | N |
| ATOM | 581 | CA | GLY | A | 88 | 19.528 | 7.307 | 39.888 | 1.00 | 27.29 | C |
| ATOM | 582 | C | GLY | A | 88 | 18.762 | 8.549 | 40.288 | 1.00 | 27.18 | C |
| ATOM | 583 | O | GLY | A | 88 | 17.570 | 8.654 | 40.001 | 1.00 | 27.43 | O |
| ATOM | 584 | N | ASP | A | 89 | 19.437 | 9.489 | 40.945 | 1.00 | 27.04 | N |
| ATOM | 585 | CA | ASP | A | 89 | 18.808 | 10.739 | 41.366 | 1.00 | 26.88 | C |
| ATOM | 586 | C | ASP | A | 89 | 18.761 | 11.755 | 40.227 | 1.00 | 26.69 | C |
| ATOM | 587 | O | ASP | A | 89 | 19.697 | 11.848 | 39.446 | 1.00 | 26.91 | O |
| ATOM | 588 | CB | ASP | A | 89 | 19.596 | 11.372 | 42.504 | 1.00 | 26.95 | C |
| ATOM | 589 | CG | ASP | A | 89 | 19.375 | 10.688 | 43.834 | 1.00 | 27.28 | C |
| ATOM | 590 | OD1 | ASP | A | 89 | 18.499 | 9.811 | 43.939 | 1.00 | 29.31 | O |
| ATOM | 591 | OD2 | ASP | A | 89 | 20.040 | 10.983 | 44.839 | 1.00 | 27.32 | O |
| ATOM | 592 | N | PHE | A | 90 | 17.687 | 12.531 | 40.152 | 1.00 | 26.24 | N |
| ATOM | 593 | CA | PHE | A | 90 | 17.598 | 13.594 | 39.165 | 1.00 | 26.10 | C |
| ATOM | 594 | C | PHE | A | 90 | 17.407 | 14.931 | 39.866 | 1.00 | 26.23 | C |
| ATOM | 595 | O | PHE | A | 90 | 16.629 | 15.037 | 40.811 | 1.00 | 26.48 | O |
| ATOM | 596 | CB | PHE | A | 90 | 16.460 | 13.322 | 38.184 | 1.00 | 25.91 | C |
| ATOM | 597 | CG | PHE | A | 90 | 16.747 | 12.201 | 37.241 | 1.00 | 25.26 | C |
| ATOM | 598 | CO1 | PHE | A | 90 | 16.601 | 10.886 | 37.640 | 1.00 | 25.32 | C |
| ATOM | 599 | CD2 | PHE | A | 90 | 17.190 | 12.459 | 35.958 | 1.00 | 26.02 | C |
| ATOM | 600 | CE1 | PHE | A | 90 | 16.872 | 9.856 | 36.777 | 1.00 | 24.09 | C |
| ATOM | 601 | CE2 | PHE | A | 90 | 17.460 | 11.427 | 35.091 | 1.00 | 25.07 | C |
| ATOM | 602 | CZ | PHE | A | 90 | 17.308 | 10.117 | 35.512 | 1.00 | 24.67 | C |
| ATOM | 603 | N | SER | A | 91 | 18.149 | 15.941 | 39.430 | 1.00 | 26.33 | N |
| ATOM | 604 | CA | SER | A | 91 | 17.985 | 17.280 | 39.973 | 1.00 | 26.48 | C |
| ATOM | 605 | C | SER | A | 91 | 16.777 | 17.923 | 39.310 | 1.00 | 26.71 | C |
| ATOM | 606 | O | SER | A | 91 | 16.696 | 18.029 | 38.077 | 1.00 | 26.09 | O |
| ATOM | 607 | CB | SER | A | 91 | 19.226 | 18.152 | 39.763 | 1.00 | 26.25 | C |
| ATOM | 608 | OG | SER | A | 91 | 20.364 | 17.543 | 40.326 | 1.00 | 26.61 | O |
| ATOM | 609 | N | VAL | A | 92 | 15.835 | 18.327 | 40.150 | 1.00 | 27.06 | N |
| ATOM | 610 | CA | VAL | A | 92 | 14.629 | 18.971 | 39.695 | 1.00 | 27.44 | C |
| ATOM | 611 | C | VAL | A | 92 | 14.468 | 20.295 | 40.405 | 1.00 | 27.57 | C |
| ATOM | 612 | O | VAL | A | 92 | 14.475 | 20.376 | 41.642 | 1.00 | 26.69 | O |
| ATOM | 613 | CB | VAL | A | 92 | 13.407 | 18.132 | 40.004 | 1.00 | 27.60 | C |
| ATOM | 614 | CG1 | VAL | A | 92 | 12.164 | 18.800 | 39.432 | 1.00 | 28.15 | C |
| ATOM | 615 | CG2 | VAL | A | 92 | 13.584 | 16.731 | 39.457 | 1.00 | 27.84 | C |
| ATOM | 616 | N | TYR | A | 93 | 14.312 | 21.334 | 39.598 | 1.00 | 27.77 | N |
| ATOM | 617 | CA | TYR | A | 93 | 14.120 | 22.661 | 40.108 | 1.00 | 27.91 | C |
| ATOM | 618 | C | TYR | A | 93 | 12.654 | 22.940 | 40.172 | 1.00 | 28.16 | C |
| ATOM | 619 | O | TYR | A | 93 | 11.894 | 22.525 | 39.303 | 1.00 | 28.02 | O |
| ATOM | 620 | CB | TYR | A | 93 | 14.810 | 23.673 | 39.216 | 1.00 | 27.94 | C |
| ATOM | 621 | CG | TYR | A | 93 | 16.291 | 23.593 | 39.368 | 1.00 | 29.53 | C |
| ATOM | 622 | CD1 | TYR | A | 93 | 16.929 | 24.258 | 40.395 | 1.00 | 29.48 | C |
| ATOM | 623 | CD2 | TYR | A | 93 | 17.046 | 22.815 | 38.552 | 1.00 | 30.95 | C |
| ATOM | 624 | GE1 | TYR | A | 93 | 18.266 | 24.169 | 40.553 | 1.00 | 29.93 | C |
| ATOM | 625 | CE2 | TYR | A | 93 | 18.386 | 22.726 | 38.679 | 1.00 | 31.90 | C |
| ATOM | 626 | CZ | TYR | A | 93 | 18.985 | 23.402 | 39.704 | 1.00 | 31.56 | C |
| ATOM | 627 | OH | TYR | A | 93 | 20.327 | 23.306 | 39.878 | 1.00 | 35.47 | O |
| ATOM | 628 | N | SER | A | 94 | 12.282 | 23.669 | 41.208 | 1.00 | 28.70 | N |
| ATOM | 629 | CA | SER | A | 94 | 10.913 | 24.037 | 41.459 | 1.00 | 29.47 | C |
| ATOM | 630 | C | SER | A | 94 | 10.856 | 25.547 | 41.554 | 1.00 | 29.69 | C |
| ATOM | 631 | O | SER | A | 94 | 11.705 | 26.167 | 42.187 | 1.00 | 29.50 | O |
| ATOM | 632 | CB | SER | A | 94 | 10.456 | 23.411 | 42.774 | 1.00 | 29.32 | C |
| ATOM | 633 | OG | SER | A | 94 | 9.093 | 23.701 | 43.009 | 1.00 | 30.85 | O |
| ATOM | 634 | N | ALA | A | 95 | 9.858 | 26.146 | 40.928 | 1.00 | 30.39 | N |
| ATOM | 635 | CA | ALA | A | 95 | 9.760 | 27.591 | 40.929 | 1.00 | 31.04 | C |
| ATOM | 636 | C | ALA | A | 95 | 8.330 | 28.064 | 40.932 | 1.00 | 31.76 | C |

TABLE 3-continued

| | | | | | | | | | | | |
|---|---|---|---|---|---|---|---|---|---|---|---|
| | Coordinates for structures 1 to 4 |
| ATOM | 637 | O | ALA | A | 95 | 7.425 | 27.386 | 40.452 | 1.00 | 31.87 | O |
| ATOM | 638 | CB | ALA | A | 95 | 10.480 | 28.165 | 39.716 | 1.00 | 31.12 | C |
| ATOM | 639 | N | SER | A | 96 | 8.147 | 29.258 | 41.467 | 1.00 | 32.54 | N |
| ATOM | 640 | CA | SER | A | 96 | 6.848 | 29.891 | 41.489 | 1.00 | 33.42 | C |
| ATOM | 641 | C | SER | A | 96 | 6.708 | 30.869 | 40.326 | 1.00 | 33.15 | C |
| ATOM | 642 | O | SER | A | 96 | 5.662 | 31.487 | 40.163 | 1.00 | 34.35 | O |
| ATOM | 643 | CB | SER | A | 96 | 6.673 | 30.661 | 42.787 | 1.00 | 33.88 | C |
| ATOM | 644 | OG | SER | A | 96 | 5.380 | 31.217 | 42.815 | 1.00 | 35.79 | O |
| ATOM | 645 | N | THR | A | 97 | 7.775 | 31.031 | 39.554 | 1.00 | 32.09 | N |
| ATOM | 646 | CA | THR | A | 97 | 7.797 | 31.920 | 38.397 | 1.00 | 31.44 | C |
| ATOM | 647 | C | THR | A | 97 | 8.185 | 31.095 | 37.191 | 1.00 | 30.26 | C |
| ATOM | 648 | O | THR | A | 97 | 8.693 | 30.003 | 37.348 | 1.00 | 29.72 | O |
| ATOM | 649 | CB | THR | A | 97 | 8.857 | 33.031 | 38.582 | 1.00 | 31.64 | C |
| ATOM | 650 | OG1 | THR | A | 97 | 9.147 | 33.656 | 37.323 | 1.00 | 32.17 | O |
| ATOM | 651 | CG2 | THR | A | 97 | 10.227 | 32.455 | 38.978 | 1.00 | 31.73 | C |
| ATOM | 652 | N | HIS | A | 98 | 7.974 | 31.623 | 35.996 | 1.00 | 29.35 | N |
| ATOM | 653 | CA | HIS | A | 98 | 8.379 | 30.915 | 34.780 | 1.00 | 28.83 | C |
| ATOM | 654 | C | HIS | A | 98 | 9.899 | 30.969 | 34.589 | 1.00 | 28.37 | C |
| ATOM | 655 | O | HIS | A | 98 | 10.467 | 30.189 | 33.824 | 1.00 | 27.53 | O |
| ATOM | 656 | CB | HIS | A | 98 | 7.671 | 31.490 | 33.548 | 1.00 | 28.76 | C |
| ATOM | 657 | CG | HIS | A | 98 | 7.936 | 32.942 | 33.309 | 1.00 | 28.53 | C |
| ATOM | 658 | ND1 | HIS | A | 98 | 7.271 | 33.944 | 33.984 | 1.00 | 29.18 | N |
| ATOM | 659 | CD2 | HIS | A | 98 | 8.793 | 33.566 | 32.463 | 1.00 | 29.68 | C |
| ATOM | 660 | CE1 | HIS | A | 98 | 7.708 | 35.120 | 33.568 | 1.00 | 29.42 | C |
| ATOM | 661 | HD2 | HIS | A | 98 | 8.638 | 34.919 | 32.650 | 1.00 | 29.10 | N |
| ATOM | 662 | N | LYS | A | 99 | 10.562 | 31.874 | 35.299 | 1.00 | 27.85 | N |
| ATOM | 663 | CA | LYS | A | 99 | 11.997 | 32.041 | 35.124 | 1.00 | 28.24 | C |
| ATOM | 664 | C | LYS | A | 99 | 12.878 | 31.143 | 35.997 | 1.00 | 27.69 | C |
| ATOM | 665 | O | LYS | A | 99 | 12.892 | 31.278 | 37.216 | 1.00 | 29.10 | O |
| ATOM | 666 | CB | LYS | A | 99 | 12.366 | 33.498 | 35.349 | 1.00 | 28.47 | C |
| ATOM | 667 | CG | LYS | A | 99 | 11.836 | 34.410 | 34.255 | 1.00 | 30.42 | C |
| ATOM | 668 | CD | LYS | A | 99 | 12.431 | 35.791 | 34.347 | 1.00 | 32.66 | C |
| ATOM | 669 | CE | LYS | A | 99 | 11.757 | 36.624 | 35.421 | 1.00 | 34.45 | C |
| ATOM | 670 | NZ | LYS | A | 99 | 10.569 | 37.347 | 34.884 | 1.00 | 35.39 | N |
| ATOM | 671 | N | PHE | A | 100 | 13.621 | 30.237 | 35.376 | 1.00 | 26.40 | N |
| ATOM | 672 | CA | PHE | A | 100 | 14.551 | 29.397 | 36.127 | 1.00 | 25.95 | C |
| ATOM | 673 | C | PHE | A | 100 | 15.978 | 29.920 | 35.995 | 1.00 | 25.87 | C |
| ATOM | 674 | O | PHE | A | 100 | 16.809 | 29.386 | 35.247 | 1.00 | 25.86 | O |
| ATOM | 675 | CB | PHE | A | 100 | 14.469 | 27.945 | 35.686 | 1.00 | 25.48 | C |
| ATOM | 676 | CG | PHE | A | 100 | 13.211 | 27.267 | 36.109 | 1.00 | 25.06 | C |
| ATOM | 677 | CD1 | PHE | A | 100 | 12.047 | 27.436 | 35.388 | 1.00 | 24.80 | C |
| ATOM | 678 | CD2 | PHE | A | 100 | 13.191 | 26.472 | 37.238 | 1.00 | 25.18 | C |
| ATOM | 679 | CE1 | PHE | A | 100 | 10.886 | 26.805 | 35.772 | 1.00 | 25.96 | C |
| ATOM | 680 | CE2 | PHE | A | 100 | 12.030 | 25.835 | 37.631 | 1.00 | 25.79 | C |
| ATOM | 681 | CZ | PHE | A | 100 | 10.878 | 26.004 | 36.898 | 1.00 | 26.05 | C |
| ATOM | 682 | N | LEU | A | 101 | 16.237 | 30.997 | 36.709 | 1.00 | 25.77 | N |
| ATOM | 683 | CA | LEU | A | 101 | 17.549 | 31.589 | 36.747 | 1.00 | 25.85 | C |
| ATOM | 684 | C | LEU | A | 101 | 18.527 | 30.605 | 37.381 | 1.00 | 25.87 | C |
| ATOM | 685 | O | LEU | A | 101 | 18.319 | 30.136 | 38.503 | 1.00 | 24.99 | O |
| ATOM | 686 | CB | LEU | A | 101 | 17.488 | 32.876 | 37.559 | 1.00 | 25.84 | C |
| ATOM | 687 | CG | LEU | A | 101 | 18.795 | 33.656 | 37.708 | 1.00 | 26.07 | C |
| ATOM | 688 | CD1 | LEU | A | 101 | 19.244 | 34.200 | 36.377 | 1.00 | 25.11 | C |
| ATOM | 689 | CD2 | LEU | A | 101 | 18.609 | 34.800 | 38.710 | 1.00 | 27.75 | C |
| ATOM | 690 | N | TYR | A | 102 | 19.582 | 30.274 | 36.644 | 1.00 | 26.56 | N |
| ATOM | 691 | CA | TYR | A | 102 | 20.611 | 29.380 | 37.159 | 1.00 | 26.99 | C |
| ATOM | 692 | C | TYR | A | 102 | 21.430 | 30.072 | 38.260 | 1.00 | 27.10 | C |
| ATOM | 693 | O | TYR | A | 102 | 21.711 | 31.264 | 38.174 | 1.00 | 27.00 | O |
| ATOM | 694 | CB | TYR | A | 102 | 21.562 | 28.939 | 36.053 | 1.00 | 27.26 | C |
| ATOM | 695 | CG | TYR | A | 102 | 22.667 | 28.088 | 36.620 | 1.00 | 28.93 | C |
| ATOM | 696 | CD1 | TYR | A | 102 | 22.457 | 26.750 | 36.914 | 1.00 | 29.52 | C |
| ATOM | 697 | CD2 | TYR | A | 102 | 23.906 | 28.636 | 36.909 | 1.00 | 31.11 | C |
| ATOM | 698 | CE1 | TYR | A | 102 | 23.463 | 25.979 | 37.480 | 1.00 | 32.23 | C |
| ATOM | 699 | CE2 | TYR | A | 102 | 24.913 | 27.872 | 37.470 | 1.00 | 32.52 | C |
| ATOM | 700 | CZ | TYR | A | 102 | 24.693 | 26.549 | 37.750 | 1.00 | 33.88 | C |
| ATOM | 701 | OH | TYR | A | 102 | 25.727 | 25.794 | 38.314 | 1.00 | 38.68 | O |
| ATOM | 702 | N | TYR | A | 103 | 21.793 | 29.322 | 39.296 | 1.00 | 26.83 | N |
| ATOM | 703 | CA | TYR | A | 103 | 22.667 | 29.840 | 40.343 | 1.00 | 27.22 | C |
| ATOM | 704 | C | TYR | A | 103 | 23.613 | 28.750 | 40.834 | 1.00 | 26.77 | C |
| ATOM | 705 | O | TYR | A | 103 | 23.287 | 27.556 | 40.853 | 1.00 | 25.60 | O |
| ATOM | 706 | CB | TYR | A | 103 | 21.880 | 30.440 | 41.517 | 1.00 | 27.38 | C |
| ATOM | 707 | CG | TYR | A | 103 | 20.909 | 29.493 | 42.154 | 1.00 | 29.11 | C |
| ATOM | 708 | CD1 | TYR | A | 103 | 19.639 | 29.340 | 41.639 | 1.00 | 30.58 | C |
| ATOM | 709 | CD2 | TYR | A | 103 | 21.257 | 28.759 | 43.279 | 1.00 | 32.13 | C |
| ATOM | 710 | CE1 | TYR | A | 103 | 18.734 | 28.469 | 42.212 | 1.00 | 32.78 | C |
| ATOM | 711 | CE2 | TYR | A | 103 | 20.357 | 27.887 | 43.877 | 1.00 | 33.15 | C |
| ATOM | 712 | CZ | TYR | A | 103 | 19.096 | 27.745 | 43.329 | 1.00 | 34.41 | C |
| ATOM | 713 | OH | TYR | A | 103 | 18.187 | 26.888 | 43.892 | 1.00 | 37.44 | O |

TABLE 3-continued

| | | | | | Coordinates for structures 1 to 4 | | | | | |
|---|---|---|---|---|---|---|---|---|---|---|
| ATOM | 714 | N | ASP | A | 104 | 24.798 | 29.182 | 41.225 | 1.00 | 26.36 | N |
| ATOM | 715 | CA | ASP | A | 104 | 25.832 | 28.273 | 41.673 | 1.00 | 26.28 | C |
| ATOM | 716 | C | ASP | A | 104 | 25.802 | 28.239 | 43.184 | 1.00 | 26.21 | C |
| ATOM | 717 | O | ASP | A | 104 | 26.163 | 29.212 | 43.845 | 1.00 | 25.45 | O |
| ATOM | 718 | CE | ASP | A | 104 | 27.174 | 28.765 | 41.154 | 1.00 | 25.92 | C |
| ATOM | 719 | CG | ASP | A | 104 | 28.330 | 27.889 | 41.575 | 1.00 | 27.39 | C |
| ATOM | 720 | OD1 | ASP | A | 104 | 28.161 | 26.973 | 42.437 | 1.00 | 27.13 | O |
| ATOM | 721 | OD2 | ASP | A | 104 | 29.459 | 28.068 | 41.075 | 1.00 | 27.68 | O |
| ATOM | 722 | N | GLU | A | 105 | 25.358 | 27.114 | 43.724 | 1.00 | 26.46 | N |
| ATOM | 723 | CA | GLU | A | 105 | 25.218 | 26.962 | 45.162 | 1.00 | 27.02 | C |
| ATOM | 724 | C | GLU | A | 105 | 26.540 | 27.199 | 45.916 | 1.00 | 26.91 | C |
| ATOM | 725 | O | GLU | A | 105 | 26.523 | 27.718 | 47.026 | 1.00 | 26.51 | O |
| ATOM | 726 | CE | GLU | A | 105 | 24.602 | 25.587 | 45.481 | 1.00 | 27.45 | C |
| ATOM | 727 | CG | GLU | A | 105 | 23.088 | 25.556 | 45.254 | 1.00 | 29.46 | C |
| ATOM | 728 | CD | GLU | A | 105 | 22.527 | 24.158 | 45.025 | 1.00 | 32.85 | C |
| ATOM | 729 | OE1 | GLU | A | 105 | 22.908 | 23.234 | 45.765 | 1.00 | 32.90 | O |
| ATOM | 730 | OE2 | GLU | A | 105 | 21.703 | 23.980 | 44.085 | 1.00 | 35.16 | O |
| ATOM | 731 | N | LYS | A | 106 | 27.680 | 26.874 | 45.305 | 1.00 | 27.12 | N |
| ATOM | 732 | CA | LYS | A | 106 | 28.979 | 27.041 | 45.983 | 1.00 | 27.54 | C |
| ATOM | 733 | C | LYS | A | 106 | 29.331 | 28.493 | 46.258 | 1.00 | 27.70 | C |
| ATOM | 734 | O | LYS | A | 106 | 30.164 | 28.769 | 47.099 | 1.00 | 27.61 | O |
| ATOM | 735 | CE | LYS | A | 106 | 30.127 | 26.441 | 45.163 | 1.00 | 27.58 | C |
| ATOM | 736 | CG | LYS | A | 106 | 30.038 | 24.928 | 44.918 | 1.00 | 28.61 | C |
| ATOM | 737 | N | LYS | A | 107 | 28.713 | 29.420 | 45.537 | 1.00 | 27.99 | N |
| ATOM | 738 | CA | LYS | A | 107 | 29.020 | 30.826 | 45.694 | 1.00 | 28.30 | C |
| ATOM | 739 | C | LYS | A | 107 | 28.034 | 31.513 | 46.631 | 1.00 | 29.21 | C |
| ATOM | 740 | O | LYS | A | 107 | 28.175 | 32.701 | 46.917 | 1.00 | 29.08 | O |
| ATOM | 741 | CE | LYS | A | 107 | 29.040 | 31.524 | 44.324 | 1.00 | 28.30 | C |
| ATOM | 742 | CG | LYS | A | 107 | 30.344 | 31.291 | 43.516 | 1.00 | 28.07 | C |
| ATOM | 743 | CD | LYS | A | 107 | 30.242 | 31.737 | 42.034 | 1.00 | 27.29 | C |
| ATOM | 744 | CE | LYS | A | 107 | 31.584 | 31.518 | 41.315 | 1.00 | 26.86 | C |
| ATOM | 745 | NZ | LYZ | A | 107 | 31.642 | 31.889 | 39.870 | 1.00 | 24.80 | N |
| ATOM | 746 | H | MET | A | 108 | 27.041 | 30.781 | 47.125 | 1.00 | 30.08 | N |
| ATOM | 747 | CA | MET | A | 108 | 26.031 | 31.405 | 47.982 | 1.00 | 31.53 | C |
| ATOM | 748 | C | MET | A | 108 | 26.581 | 31.952 | 49.309 | 1.00 | 32.44 | C |
| ATOM | 749 | O | MET | A | 108 | 26.102 | 32.972 | 49.812 | 1.00 | 32.47 | O |
| ATOM | 750 | CB | MET | A | 108 | 24.862 | 30.452 | 48.218 | 1.00 | 31.81 | C |
| ATOM | 751 | CG | MET | A | 108 | 24.072 | 30.193 | 46.932 | 1.00 | 33.07 | C |
| ATOM | 752 | SD | MET | A | 108 | 22.625 | 29.140 | 47.064 | 1.00 | 35.76 | 5 |
| ATOM | 753 | CE | MET | A | 108 | 21.540 | 30.140 | 48.050 | 1.00 | 35.99 | C |
| ATOM | 754 | H | ALA | A | 109 | 27.603 | 31.315 | 49.860 | 1.00 | 33.56 | H |
| ATOM | 755 | CA | ALA | A | 109 | 28.154 | 31.769 | 51.138 | 1.00 | 34.94 | C |
| ATOM | 756 | C | ALA | A | 109 | 28.651 | 33.212 | 51.060 | 1.00 | 35.81 | C |
| ATOM | 757 | O | ALA | A | 109 | 28.483 | 33.989 | 51.991 | 1.00 | 36.23 | O |
| ATOM | 758 | CB | ALA | A | 109 | 29.279 | 30.838 | 51.606 | 1.00 | 34.82 | C |
| ATOM | 759 | H | ASN | A | 110 | 29.236 | 33.575 | 49.929 | 1.00 | 37.05 | N |
| ATOM | 760 | CA | ASN | A | 110 | 29.774 | 34.918 | 49.748 | 1.00 | 37.94 | C |
| ATOM | 761 | C | ASN | A | 110 | 28.731 | 35.992 | 49.413 | 1.00 | 38.13 | C |
| ATOM | 762 | O | ASN | A | 110 | 29.064 | 37.167 | 49.293 | 1.00 | 37.92 | O |
| ATOM | 763 | CB | ASN | A | 110 | 30.855 | 34.878 | 48.669 | 1.00 | 38.16 | C |
| ATOM | 764 | CG | ASN | A | 110 | 32.050 | 34.035 | 49.079 | 1.00 | 39.37 | C |
| ATOM | 765 | OD1 | ASN | A | 110 | 32.407 | 33.964 | 50.265 | 1.00 | 40.12 | O |
| ATOM | 766 | ND2 | ASN | A | 110 | 32.670 | 33.377 | 48.103 | 1.00 | 39.46 | N |
| ATOM | 767 | N | PHE | A | 111 | 27.480 | 35.588 | 49.234 | 1.00 | 38.71 | N |
| ATOM | 768 | CA | PHE | A | 111 | 26.408 | 36.539 | 48.966 | 1.00 | 39.02 | C |
| ATOM | 769 | C | PHE | A | 111 | 25.180 | 36.135 | 49.773 | 1.00 | 39.71 | C |
| ATOM | 770 | O | PHE | A | 111 | 24.143 | 35.747 | 49.232 | 1.00 | 39.45 | O |
| ATOM | 771 | CB | PHE | A | 111 | 26.091 | 36.603 | 47.471 | 1.00 | 38.97 | C |
| ATOM | 772 | CG | PHE | A | 111 | 27.110 | 37.362 | 46.672 | 1.00 | 38.04 | C |
| ATOM | 773 | CD1 | PHE | A | 111 | 28.329 | 36.791 | 46.363 | 1.00 | 37.99 | C |
| ATOM | 774 | CD2 | PHE | A | 111 | 26.851 | 38.642 | 46.235 | 1.00 | 36.83 | C |
| ATOM | 775 | CE1 | PHE | A | 111 | 29.269 | 37.493 | 45.635 | 1.00 | 37.68 | C |
| ATOM | 776 | CE2 | PHE | A | 111 | 27.788 | 39.339 | 45.500 | 1.00 | 36.08 | C |
| ATOM | 777 | CZ | PHE | A | 111 | 28.994 | 38.768 | 45.208 | 1.00 | 35.84 | C |
| ATOM | 778 | N | GLN | A | 112 | 25.315 | 36.267 | 51.085 | 1.00 | 40.62 | H |
| ATOM | 779 | CA | GLN | A | 112 | 24.286 | 35.852 | 52.029 | 1.00 | 41.31 | C |
| ATOM | 780 | C | GLN | A | 112 | 22.915 | 36.430 | 51.721 | 1.00 | 41.10 | C |
| ATOM | 781 | O | GLN | A | 112 | 21.906 | 35.827 | 52.060 | 1.00 | 41.31 | O |
| ATOM | 782 | CB | GLN | A | 112 | 24.701 | 36.236 | 53.451 | 1.00 | 41.65 | C |
| ATOM | 783 | CG | GLN | A | 112 | 26.058 | 35.694 | 53.882 | 1.00 | 43.80 | C |
| ATOM | 784 | CD | GLN | A | 112 | 26.104 | 34.177 | 53.938 | 1.00 | 46.42 | C |
| ATOM | 785 | OE1 | GLN | A | 112 | 25.394 | 33.501 | 53.191 | 1.00 | 48.56 | O |
| ATOM | 786 | NE2 | GLN | A | 112 | 26.951 | 33.637 | 54.816 | 1.00 | 46.94 | N |
| ATOM | 787 | N | ASN | A | 113 | 22.876 | 37.588 | 51.074 | 1.00 | 41.02 | H |
| ATOM | 788 | CA | ASN | A | 113 | 21.606 | 38.229 | 50.749 | 1.00 | 40.98 | C |
| ATOM | 789 | C | ASN | A | 113 | 20.954 | 37.760 | 49.440 | 1.00 | 40.71 | C |
| ATOM | 790 | O | ASN | A | 113 | 19.889 | 38.251 | 49.071 | 1.00 | 40.77 | O |

TABLE 3-continued

| | | | | | Coordinates for structures 1 to 4 | | | | | |
|---|---|---|---|---|---|---|---|---|---|---|
| ATOM | 791 | CB | ASN | A | 113 | 21.778 | 39.753 | 50.737 | 1.00 | 41.09 | C |
| ATOM | 792 | CG | ASN | A | 113 | 22.129 | 40.314 | 52.123 | 1.00 | 41.51 | C |
| ATOM | 793 | OD1 | ASN | A | 113 | 21.717 | 39.772 | 53.158 | 1.00 | 40.60 | O |
| ATOM | 794 | ND2 | ASN | A | 113 | 22.892 | 41.401 | 52.141 | 1.00 | 41.19 | N |
| ATOM | 795 | N | PHE | A | 114 | 21.571 | 36.826 | 48.725 | 1.00 | 40.34 | H |
| ATOM | 796 | CA | PHE | A | 114 | 20.934 | 36.321 | 47.515 | 1.00 | 39.86 | C |
| ATOM | 797 | C | PHE | A | 114 | 19.908 | 35.266 | 47.902 | 1.00 | 39.46 | C |
| ATOM | 798 | O | PHE | A | 114 | 20.235 | 34.299 | 48.584 | 1.00 | 38.82 | O |
| ATOM | 799 | CB | PHE | A | 114 | 21.940 | 35.714 | 46.552 | 1.00 | 39.96 | C |
| ATOM | 800 | CG | PHE | A | 114 | 21.298 | 35.059 | 45.362 | 1.00 | 40.54 | C |
| ATOM | 801 | CO1 | PHE | A | 114 | 20.670 | 35.828 | 44.395 | 1.00 | 40.29 | C |
| ATOM | 802 | CD2 | PHE | A | 114 | 21.295 | 33.679 | 45.224 | 1.00 | 40.62 | C |
| ATOM | 803 | CE1 | PHE | A | 114 | 20.061 | 35.237 | 43.307 | 1.00 | 40.20 | C |
| ATOM | 804 | CE2 | PHE | A | 114 | 20.684 | 33.082 | 44.124 | 1.00 | 40.36 | C |
| ATOM | 805 | CZ | PHE | A | 114 | 20.066 | 33.866 | 43.172 | 1.00 | 40.52 | C |
| ATOM | 806 | N | LYS | A | 115 | 18.669 | 35.457 | 47.461 | 1.00 | 39.11 | N |
| ATOM | 807 | CA | LYS | A | 115 | 17.596 | 34.529 | 47.787 | 1.00 | 39.02 | C |
| ATOM | 808 | C | LYS | A | 115 | 17.042 | 33.938 | 46.497 | 1.00 | 38.71 | C |
| ATOM | 809 | O | LYS | A | 115 | 16.285 | 34.590 | 45.787 | 1.00 | 39.00 | O |
| ATOM | 810 | CB | LYS | A | 115 | 16.498 | 35.251 | 48.578 | 1.00 | 39.14 | C |
| ATOM | 811 | N | PRO | A | 116 | 17.389 | 32.691 | 46.213 | 1.00 | 38.17 | N |
| ATOM | 812 | CA | PRO | A | 116 | 17.027 | 32.060 | 44.938 | 1.00 | 37.95 | C |
| ATOM | 813 | C | PRO | A | 116 | 15.532 | 31.889 | 44.783 | 1.00 | 37.38 | C |
| ATOM | 814 | O | PRO | A | 116 | 14.865 | 31.506 | 45.733 | 1.00 | 37.36 | O |
| ATOM | 815 | CB | PRO | A | 116 | 17.684 | 30.679 | 45.004 | 1.00 | 38.15 | C |
| ATOM | 816 | CG | PRO | A | 116 | 18.416 | 30.604 | 46.297 | 1.00 | 38.40 | C |
| ATOM | 817 | CD | PRO | A | 116 | 18.079 | 31.775 | 47.125 | 1.00 | 38.19 | C |
| ATOM | 818 | N | ARG | A | 117 | 15.027 | 32.161 | 43.590 | 1.00 | 36.84 | N |
| ATOM | 819 | CA | ARG | A | 117 | 13.611 | 32.028 | 43.293 | 1.00 | 36.61. | C |
| ATOM | 820 | C | ARG | A | 117 | 13.259 | 30.581 | 42.984 | 1.00 | 36.38 | C |
| ATOM | 821 | O | ARG | A | 117 | 12.084 | 30.230 | 42.913 | 1.00 | 36.44 | O |
| ATOM | 822 | CB | ARG | A | 117 | 13.235 | 32.913 | 42.122 | 1.00 | 36.62 | C |
| ATOM | 823 | N | SER | A | 118 | 14.271 | 29.745 | 42.777 | 1.00 | 35.79 | N |
| ATOM | 824 | CA | SER | A | 118 | 14.025 | 28.339 | 42.538 | 1.00 | 35.51 | C |
| ATOM | 825 | C | SER | A | 118 | 14.844 | 27.491 | 43.512 | 1.00 | 35.35 | C |
| ATOM | 826 | O | SER | A | 118 | 15.888 | 27.923 | 43.991 | 1.00 | 35.16 | O |
| ATOM | 827 | CB | SER | A | 118 | 14.330 | 27.976 | 41.086 | 1.00 | 35.26 | C |
| ATOM | 828 | OG | SER | A | 118 | 15.689 | 28.164 | 40.795 | 1.00 | 35.14 | O |
| ATOM | 829 | N | ASN | A | 119 | 14.329 | 26.306 | 43.824 | 1.00 | 35.11 | N |
| ATOM | 830 | CA | ASN | A | 119 | 14.997 | 25.373 | 44.715 | 1.00 | 35.21 | C |
| ATOM | 831 | C | ASN | A | 119 | 15.233 | 24.049 | 44.022 | 1.00 | 34.26 | C |
| ATOM | 832 | O | ASN | A | 119 | 14.401 | 23.595 | 43.244 | 1.00 | 34.11 | O |
| ATOM | 833 | CB | ASN | A | 119 | 14.145 | 25.110 | 45.957 | 1.00 | 35.95 | C |
| ATOM | 834 | CG | ASN | A | 119 | 13.636 | 26.382 | 46.592 | 1.00 | 38.47 | C |
| ATOM | 835 | OD1 | ASN | A | 119 | 14.417 | 27.245 | 47.025 | 1.00 | 41.76 | O |
| ATOM | 836 | ND2 | ASN | A | 119 | 12.314 | 26.511 | 46.657 | 1.00 | 42.21 | N |
| ATOM | 837 | N | ARG | A | 120 | 16.368 | 23.434 | 44.326 | 1.00 | 33.75 | N |
| ATOM | 838 | CA | ARG | A | 120 | 16.750 | 22.149 | 43.761 | 1.00 | 33.33 | C |
| ATOM | 839 | C | ARG | A | 120 | 16.327 | 21.045 | 44.699 | 1.00 | 33.26 | C |
| ATOM | 840 | O | ARG | A | 120 | 16.523 | 21.138 | 45.910 | 1.00 | 33.07 | O |
| ATOM | 841 | CB | ARG | A | 120 | 18.270 | 22.075 | 43.592 | 1.00 | 33.37 | C |
| ATOM | 842 | CG | ARG | A | 120 | 18.759 | 20.889 | 42.771 | 1.00 | 32.70 | C |
| ATOM | 843 | CD | ARG | A | 120 | 20.277 | 20.732 | 42.743 | 1.00 | 31.64 | C |
| ATOM | 844 | NE | ARG | A | 120 | 20.892 | 21.165 | 43.992 | 1.00 | 31.16 | N |
| ATOM | 845 | CZ | ARG | A | 120 | 21.233 | 20.357 | 44.993 | 1.00 | 31.33 | C |
| ATOM | 846 | NH1 | ARG | A | 120 | 21.027 | 19.047 | 44.920 | 1.00 | 30.77 | N |
| ATOM | 847 | NH2 | ARG | A | 120 | 21.789 | 20.867 | 46.077 | 1.00 | 31.01 | N |
| ATOM | 848 | N | GLU | A | 121 | 15.735 | 20.001 | 44.137 | 1.00 | 32.98 | N |
| ATOM | 849 | CA | GLU | A | 121 | 15.379 | 18.827 | 44.904 | 1.00 | 32.85 | C |
| ATOM | 850 | C | GLU | A | 121 | 15.846 | 17.630 | 44.095 | 1.00 | 32.17 | C |
| ATOM | 851 | O | GLU | A | 121 | 15.744 | 17.612 | 42.864 | 1.00 | 32.36 | O |
| ATOM | 852 | CB | GLU | A | 121 | 13.874 | 18.767 | 45.179 | 1.00 | 33.21 | C |
| ATOM | 853 | CG | GLU | A | 121 | 13.420 | 17.468 | 45.826 | 1.00 | 35.39 | C |
| ATOM | 854 | CD | GLU | A | 121 | 12.189 | 17.629 | 46.699 | 1.00 | 38.11 | C |
| ATOM | 855 | OE1 | GLU | A | 121 | 12.326 | 18.152 | 47.830 | 1.00 | 41.26 | O |
| ATOM | 856 | OE2 | GLU | A | 121 | 11.091 | 17.221 | 46.270 | 1.00 | 39.55 | O |
| ATOM | 857 | N | GLU | A | 122 | 16.400 | 16.648 | 44.786 | 1.00 | 31.28 | N |
| ATOM | 858 | CA | GLU | A | 122 | 16.886 | 15.448 | 44.150 | 1.00 | 30.61 | C |
| ATOM | 859 | C | GLU | A | 122 | 15.814 | 14.392 | 44.298 | 1.00 | 30.31 | C |
| ATOM | 860 | O | GLU | A | 122 | 15.328 | 14.165 | 45.395 | 1.00 | 30.07 | O |
| ATOM | 861 | CB | GLU | A | 122 | 18.163 | 14.980 | 44.833 | 1.00 | 30.52 | C |
| ATOM | 862 | CG | GLU | A | 122 | 19.293 | 15.983 | 44.771 | 1.00 | 29.67 | C |
| ATOM | 863 | CD | GLU | A | 122 | 19.747 | 16.253 | 43.348 | 1.00 | 29.79 | C |
| ATOM | 864 | OE1 | GLU | A | 122 | 20.120 | 15.280 | 42.667 | 1.00 | 28.28 | O |
| ATOM | 865 | OE2 | GLU | A | 122 | 19.734 | 17.439 | 42.914 | 1.00 | 27.93 | O |
| ATOM | 866 | N | MET | A | 123 | 15.432 | 13.751 | 43.202 | 1.00 | 29.74 | N |
| ATOM | 867 | CA | MET | A | 123 | 14.407 | 12.728 | 43.277 | 1.00 | 29.77 | C |

TABLE 3-continued

| | | | | | | | | | | | |
|---|---|---|---|---|---|---|---|---|---|---|---|
| ATOM | 868 | C | MET | A | 123 | 14.594 | 11.683 | 42.202 | 1.00 | 29.31 | C |
| ATOM | 869 | O | MET | A | 123 | 15.408 | 11.842 | 41.294 | 1.00 | 29.42 | O |
| ATOM | 870 | CB | MET | A | 123 | 13.016 | 13.354 | 43.165 | 1.00 | 29.81 | C |
| ATOM | 871 | CG | MET | A | 123 | 12.749 | 14.057 | 41.865 | 1.00 | 30.27 | C |
| ATOM | 872 | SD | MET | A | 123 | 11.181 | 14.960 | 41.871 | 1.00 | 31.65 | S |
| ATOM | 873 | CE | MET | A | 123 | 11.582 | 16.371 | 42.804 | 1.00 | 31.47 | C |
| ATOM | 874 | N | LYS | A | 124 | 13.835 | 10.604 | 42.332 | 1.00 | 28.82 | N |
| ATOM | 875 | CA | LYS | A | 124 | 13.841 | 9.535 | 41.352 | 1.00 | 28.33 | C |
| ATOM | 876 | C | LYS | A | 124 | 12.959 | 9.976 | 40.191 | 1.00 | 27.51 | C |
| ATOM | 877 | O | LYS | A | 124 | 12.077 | 10.817 | 40.361 | 1.00 | 26.52 | O |
| ATOM | 878 | CE | LYS | A | 124 | 13.330 | 8.242 | 41.984 | 1.00 | 28.45 | C |
| ATOM | 879 | CG | LYS | A | 124 | 14.153 | 7.783 | 43.204 | 1.00 | 29.42 | C |
| ATOM | 880 | CD | LYS | A | 124 | 15.597 | 7.442 | 42.804 | 1.00 | 30.46 | C |
| ATOM | 881 | CE | LYS | A | 124 | 16.479 | 7.067 | 43.992 | 1.00 | 30.52 | C |
| ATOM | 882 | NZ | LYS | A | 124 | 17.928 | 7.324 | 43.699 | 1.00 | 30.05 | N |
| ATOM | 883 | N | PHE | A | 125 | 13.188 | 9.407 | 39.014 | 1.00 | 26.98 | N |
| ATOM | 884 | CA | PHE | A | 125 | 12.477 | 9.871 | 37.826 | 1.00 | 26.83 | C |
| ATOM | 885 | C | PHE | A | 125 | 10.974 | 9.762 | 37.972 | 1.00 | 26.77 | C |
| ATOM | 886 | O | PHE | A | 125 | 10.245 | 10.673 | 37.585 | 1.00 | 26.38 | O |
| ATOM | 887 | CB | PHE | A | 125 | 12.927 | 9.138 | 36.568 | 1.00 | 26.71 | C |
| ATOM | 888 | CG | PHE | A | 125 | 12.613 | 9.891 | 35.316 | 1.00 | 26.32 | C |
| ATOM | 889 | CD1 | PHE | A | 125 | 13.476 | 10.876 | 34.849 | 1.00 | 26.29 | C |
| ATOM | 890 | CD2 | PHE | A | 125 | 11.438 | 9.657 | 34.635 | 1.00 | 26.06 | C |
| ATOM | 891 | CE1 | PHE | A | 125 | 13.183 | 11.594 | 33.715 | 1.00 | 25.70 | C |
| ATOM | 892 | CE2 | PHE | A | 125 | 11.140 | 10.368 | 33.483 | 1.00 | 26.70 | C |
| ATOM | 893 | CZ | PHE | A | 125 | 12.018 | 11.341 | 33.025 | 1.00 | 26.87 | C |
| ATOM | 894 | N | HIS | A | 126 | 10.527 | 8.649 | 38.550 | 1.00 | 26.77 | N |
| ATOM | 895 | CA | HIS | A | 126 | 9.113 | 8.396 | 38.753 | 1.00 | 26.82 | C |
| ATOM | 896 | C | HIS | A | 126 | 8.517 | 9.390 | 39.734 | 1.00 | 26.68 | C |
| ATOM | 897 | O | HIS | A | 126 | 7.326 | 9.670 | 39.687 | 1.00 | 26.03 | O |
| ATOM | 898 | CB | HIS | A | 126 | 8.882 | 6.951 | 39.238 | 1.00 | 27.07 | C |
| ATOM | 899 | CG | HIS | A | 126 | 9.028 | 6.767 | 40.717 | 1.00 | 27.39 | C |
| ATOM | 900 | ND1 | HIS | A | 126 | 7.959 | 6.836 | 41.582 | 1.00 | 28.48 | N |
| ATOM | 901 | CD2 | HIS | A | 126 | 10.115 | 6.505 | 41.484 | 1.00 | 28.33 | C |
| ATOM | 902 | CE1 | HIS | A | 126 | 8.382 | 6.636 | 42.819 | 1.00 | 28.68 | C |
| ATOM | 903 | ND2 | HIS | A | 126 | 9.687 | 6.439 | 42.788 | 1.00 | 27.97 | N |
| ATOM | 904 | N | GLU | A | 127 | 9.342 | 9.918 | 40.630 | 1.00 | 27.00 | N |
| ATOM | 905 | CA | GLU | A | 127 | 8.876 | 10.930 | 41.572 | 1.00 | 27.34 | C |
| ATOM | 906 | C | GLU | A | 127 | 8.683 | 12.259 | 40.838 | 1.00 | 27.36 | C |
| ATOM | 907 | O | GLU | A | 127 | 7.761 | 13.026 | 41.126 | 1.00 | 26.86 | O |
| ATOM | 908 | CE | GLU | A | 127 | 9.862 | 11.084 | 42.728 | 1.00 | 27.31 | C |
| ATOM | 909 | CG | GLU | A | 127 | 10.018 | 9.821 | 43.552 | 1.00 | 28.69 | C |
| ATOM | 910 | CD | GLU | A | 127 | 10.959 | 9.992 | 44.722 | 1.00 | 29.65 | C |
| ATOM | 911 | OE1 | GLU | A | 127 | 12.139 | 10.318 | 44.485 | 1.00 | 29.56 | O |
| ATOM | 912 | OE2 | GLU | A | 127 | 10.509 | 9.787 | 45.876 | 1.00 | 30.92 | O |
| ATOM | 913 | N | PHE | A | 128 | 9.554 | 12.519 | 39.876 | 1.00 | 27.91 | N |
| ATOM | 914 | CA | PHE | A | 128 | 9.453 | 13.736 | 39.068 | 1.00 | 28.21 | C |
| ATOM | 915 | C | PHE | A | 128 | 8.149 | 13.658 | 38.282 | 1.00 | 29.04 | C |
| ATOM | 916 | O | PHE | A | 128 | 7.354 | 14.600 | 38.255 | 1.00 | 29.03 | O |
| ATOM | 917 | CB | PHE | A | 128 | 10.643 | 13.838 | 38.115 | 1.00 | 27.74 | C |
| ATOM | 918 | CG | PHE | A | 128 | 10.427 | 14.792 | 36.959 | 1.00 | 27.06 | C |
| ATOM | 919 | CD1 | PHE | A | 128 | 10.189 | 16.138 | 37.185 | 1.00 | 25.41 | C |
| ATOM | 920 | CD2 | PHE | A | 128 | 10.480 | 14.343 | 35.657 | 1.00 | 25.60 | C |
| ATOM | 921 | CE1 | PHE | A | 128 | 9.985 | 17.000 | 36.144 | 1.00 | 25.41 | C |
| ATOM | 922 | CE2 | PHE | A | 128 | 10.281 | 15.215 | 34.604 | 1.00 | 26.59 | C |
| ATOM | 923 | CZ | PHE | A | 128 | 10.032 | 16.540 | 34.846 | 1.00 | 25.61 | C |
| ATOM | 924 | N | VAL | A | 129 | 7.925 | 12.500 | 37.677 | 1.00 | 29.90 | N |
| ATOM | 925 | CA | VAL | A | 129 | 6.756 | 12.285 | 36.847 | 1.00 | 30.82 | C |
| ATOM | 926 | C | VAL | A | 129 | 5.476 | 12.447 | 37.669 | 1.00 | 31.61 | C |
| ATOM | 927 | O | VAL | A | 129 | 4.515 | 13.091 | 37.234 | 1.00 | 31.39 | O |
| ATOM | 928 | CB | VAL | A | 129 | 6.793 | 10.883 | 36.213 | 1.00 | 30.92 | C |
| ATOM | 929 | CG1 | VAL | A | 129 | 5.479 | 10.582 | 35.503 | 1.00 | 31.15 | C |
| ATOM | 930 | CG2 | VAL | A | 129 | 7.975 | 10.751 | 35.253 | 1.00 | 30.61 | C |
| ATOM | 931 | N | GLU | A | 130 | 5.475 | 11.858 | 38.861 | 1.00 | 32.42 | N |
| ATOM | 932 | CA | GLU | A | 130 | 4.332 | 11.946 | 39.761 | 1.00 | 33.13 | C |
| ATOM | 933 | C | GLU | A | 130 | 4.070 | 13.403 | 40.126 | 1.00 | 33.42 | C |
| ATOM | 934 | O | GLU | A | 130 | 2.930 | 13.867 | 40.081 | 1.00 | 33.01 | O |
| ATOM | 935 | CB | GLU | A | 130 | 4.587 | 11.108 | 41.017 | 1.00 | 33.20 | C |
| ATOM | 936 | CG | GLU | A | 130 | 4.537 | 9.609 | 40.755 | 1.00 | 34.22 | C |
| ATOM | 937 | CD | GLU | A | 130 | 5.294 | 8.792 | 41.789 | 1.00 | 35.55 | C |
| ATOM | 938 | OE1 | GLU | A | 130 | 5.630 | 9.339 | 42.861 | 1.00 | 37.02 | O |
| ATOM | 939 | OE2 | GLU | A | 130 | 5.558 | 7.598 | 41.525 | 1.00 | 35.99 | O |
| ATOM | 940 | N | LYS | A | 131 | 5.128 | 14.120 | 40.486 | 1.00 | 34.00 | N |
| ATOM | 941 | CA | LYS | A | 131 | 4.994 | 15.538 | 40.800 | 1.00 | 34.79 | C |
| ATOM | 942 | C | LYS | A | 131 | 4.354 | 16.286 | 39.637 | 1.00 | 35.25 | C |
| ATOM | 943 | O | LYS | A | 131 | 3.449 | 17.089 | 39.835 | 1.00 | 34.81 | O |
| ATOM | 944 | CE | LYS | A | 131 | 6.345 | 16.171 | 41.100 | 1.00 | 34.89 | C |

TABLE 3-continued

Coordinates for structures 1 to 4

| ATOM | 945 | CG | LYS | A | 131 | 6.597 | 16.477 | 42.554 | 1.00 | 35.57 | C |
|---|---|---|---|---|---|---|---|---|---|---|---|
| ATOM | 946 | CD | LYS | A | 131 | 7.191 | 17.868 | 42.694 | 1.00 | 36.25 | C |
| ATOM | 947 | CE | LYS | A | 131 | 7.862 | 18.072 | 44.034 | 1.00 | 37.30 | C |
| ATOM | 948 | NZ | LYS | A | 131 | 8.108 | 19.526 | 44.332 | 1.00 | 37.49 | N |
| ATOM | 949 | N | LEU | A | 132 | 4.829 | 16.038 | 38.422 | 1.00 | 36.00 | N |
| ATOM | 950 | CA | LEU | A | 132 | 4.243 | 16.701 | 37.268 | 1.00 | 37.05 | C |
| ATOM | 951 | C | LEU | A | 132 | 2.755 | 16.406 | 37.170 | 1.00 | 37.67 | C |
| ATOM | 952 | O | LEU | A | 132 | 1.963 | 17.300 | 36.870 | 1.00 | 37.77 | O |
| ATOM | 953 | CB | LEU | A | 132 | 4.919 | 16.260 | 35.979 | 1.00 | 37.39 | C |
| ATOM | 954 | CG | LEU | A | 132 | 6.310 | 16.803 | 35.710 | 1.00 | 38.29 | C |
| ATOM | 955 | CD1 | LEU | A | 132 | 6.783 | 16.289 | 34.363 | 1.00 | 39.35 | C |
| ATOM | 956 | CD2 | LEU | A | 132 | 6.306 | 18.314 | 35.721 | 1.00 | 39.70 | C |
| ATOM | 957 | N | GLN | A | 133 | 2.386 | 15.151 | 37.417 | 1.00 | 38.34 | N |
| ATOM | 958 | CA | GLN | A | 133 | 0.989 | 14.730 | 37.373 | 1.00 | 39.11 | C |
| ATOM | 959 | C | GLN | A | 133 | 0.132 | 15.434 | 38.427 | 1.00 | 39.73 | C |
| ATOM | 960 | O | GLN | A | 133 | 0.966 | 15.897 | 38.126 | 1.00 | 39.61 | O |
| ATOM | 961 | CE | GLN | A | 133 | 0.886 | 13.213 | 37.538 | 1.00 | 39.05 | C |
| ATOM | 962 | N | ASP | A | 134 | 0.629 | 15.507 | 39.658 | 1.00 | 40.61 | N |
| ATOM | 963 | CA | ASP | A | 134 | 0.108 | 16.149 | 40.747 | 1.00 | 41.70 | C |
| ATOM | 964 | C | ASP | A | 134 | 0.398 | 17.626 | 40.451 | 1.00 | 41.68 | C |
| ATOM | 965 | O | ASP | A | 134 | 1.470 | 18.137 | 40.770 | 1.00 | 41.28 | O |
| ATOM | 966 | CE | ASP | A | 134 | 0.678 | 16.030 | 42.056 | 1.00 | 42.32 | C |
| ATOM | 967 | CG | ASP | A | 134 | 0.165 | 16.351 | 43.286 | 1.00 | 44.92 | C |
| ATOM | 968 | OD1 | ASP | A | 134 | 1.235 | 16.991 | 43.152 | 1.00 | 48.33 | O |
| ATOM | 969 | OD2 | ASP | A | 134 | 0.164 | 15.991 | 44.442 | 1.00 | 48.64 | O |
| ATOM | 970 | N | ILE | A | 135 | 0.563 | 18.312 | 39.842 | 1.00 | 41.92 | N |
| ATOM | 971 | CA | ILE | A | 135 | 0.383 | 19.717 | 39.512 | 1.00 | 42.18 | C |
| ATOM | 972 | C | ILE | A | 135 | 0.715 | 19.862 | 38.471 | 1.00 | 42.41 | C |
| ATOM | 973 | O | ILE | A | 135 | 1.635 | 20.664 | 38.634 | 1.00 | 42.49 | O |
| ATOM | 974 | CE | ILE | A | 135 | 1.696 | 20.324 | 38.997 | 1.00 | 42.17 | C |
| ATOM | 975 | CG1 | ILE | A | 135 | 2.720 | 20.399 | 40.131 | 1.00 | 42.25 | C |
| ATOM | 976 | CG2 | ILE | A | 135 | 1.451 | 21.708 | 38.437 | 1.00 | 42.11 | C |
| ATOM | 977 | CD1 | ILE | A | 135 | 4.151 | 20.438 | 39.653 | 1.00 | 42.91 | C |
| ATOM | 978 | N | GLN | A | 136 | 0.614 | 19.075 | 37.407 | 1.00 | 42.71 | N |
| ATOM | 979 | CA | GLN | A | 136 | 1.593 | 19.114 | 36.333 | 1.00 | 43.09 | C |
| ATOM | 980 | C | GLN | A | 136 | 2.991 | 18.935 | 36.900 | 1.00 | 43.56 | C |
| ATOM | 981 | O | GLN | A | 136 | 3.863 | 19.785 | 36.707 | 1.00 | 43.93 | O |
| ATOM | 982 | CB | GLN | A | 136 | 1.298 | 18.031 | 35.317 | 1.00 | 43.10 | C |
| ATOM | 983 | N | GLN | A | 137 | 3.181 | 17.844 | 37.635 | 1.00 | 43.82 | N |
| ATOM | 984 | CA | GLN | A | 137 | 4.486 | 17.493 | 38.182 | 1.00 | 44.02 | C |
| ATOM | 985 | C | GLN | A | 137 | 5.023 | 18.540 | 39.144 | 1.00 | 44.08 | C |
| ATOM | 986 | O | GLN | A | 137 | 6.202 | 18.891 | 39.080 | 1.00 | 44.46 | O |
| ATOM | 987 | CE | GLN | A | 137 | 4.425 | 16.124 | 38.868 | 1.00 | 44.00 | C |
| ATOM | 988 | N | ARG | A | 138 | 4.169 | 19.043 | 40.031 | 1.00 | 43.93 | N |
| ATOM | 989 | CA | ARG | A | 138 | 4.606 | 20.022 | 41.024 | 1.00 | 43.76 | C |
| ATOM | 990 | C | ARG | A | 138 | 4.578 | 21.445 | 40.463 | 1.00 | 43.34 | C |
| ATOM | 991 | O | ARG | A | 138 | 4.681 | 22.415 | 41.214 | 1.00 | 43.54 | O |
| ATOM | 992 | CE | ARG | A | 138 | 3.751 | 19.919 | 42.299 | 1.00 | 43.84 | C |
| ATOM | 993 | CG | ARG | A | 138 | 2.420 | 20.679 | 42.279 | 1.00 | 44.85 | C |
| ATOM | 994 | CD | ARG | A | 138 | 1.493 | 20.279 | 43.420 | 1.00 | 45.82 | C |
| ATOM | 995 | NE | ARG | A | 138 | 0.372 | 21.197 | 43.620 | 1.00 | 46.44 | N |
| ATOM | 996 | CZ | ARG | A | 138 | 0.914 | 20.863 | 43.499 | 1.00 | 47.95 | C |
| ATOM | 997 | NH1 | ARG | A | 138 | 1.262 | 19.627 | 43.162 | 1.00 | 49.02 | N |
| ATOM | 998 | NH2 | ARG | A | 138 | 1.864 | 21.767 | 43.709 | 1.00 | 47.70 | N |
| ATOM | 999 | N | GLY | A | 139 | 4.450 | 21.569 | 39.143 | 1.00 | 42.62 | N |
| ATOM | 1000 | CA | GLY | A | 139 | 4.371 | 22.871 | 38.504 | 1.00 | 41.93 | C |
| ATOM | 1001 | C | GLY | A | 139 | 3.389 | 23.820 | 39.174 | 1.00 | 41.28 | C |
| ATOM | 1002 | O | GLY | A | 139 | 3.607 | 25.030 | 39.196 | 1.00 | 41.58 | O |
| ATOM | 1003 | N | GLY | A | 140 | 2.291 | 23.292 | 39.703 | 1.00 | 40.31 | N |
| ATOM | 1004 | CA | GLY | A | 140 | 1.329 | 24.119 | 40.410 | 1.00 | 39.43 | C |
| ATOM | 1005 | C | GLY | A | 140 | 0.563 | 25.070 | 39.512 | 1.00 | 38.71 | C |
| ATOM | 1006 | O | GLY | A | 140 | 0.495 | 24.871 | 38.294 | 1.00 | 38.40 | O |
| ATOM | 1007 | N | GLU | A | 141 | 0.003 | 26.117 | 40.110 | 1.00 | 37.82 | N |
| ATOM | 1008 | CA | GLU | A | 141 | 0.829 | 27.066 | 39.363 | 1.00 | 37.20 | C |
| ATOM | 1009 | C | GLU | A | 141 | 2.320 | 26.726 | 39.491 | 1.00 | 35.94 | C |
| ATOM | 1010 | O | GLU | A | 141 | 3.160 | 27.356 | 38.845 | 1.00 | 35.76 | O |
| ATOM | 1011 | CE | GLU | A | 141 | 0.590 | 28.510 | 39.828 | 1.00 | 37.63 | C |
| ATOM | 1012 | CG | GLU | A | 141 | 0.729 | 29.146 | 39.379 | 1.00 | 39.51 | C |
| ATOM | 1013 | CD | GLU | A | 141 | 0.936 | 29.164 | 37.866 | 1.00 | 41.63 | C |
| ATOM | 1014 | OE1 | GLU | A | 141 | 0.056 | 29.147 | 37.102 | 1.00 | 42.42 | O |
| ATOM | 1015 | OE2 | GLU | A | 141 | 2.115 | 29.202 | 37.434 | 1.00 | 43.77 | O |
| ATOM | 1016 | N | GLU | A | 142 | 2.652 | 25.742 | 40.326 | 1.00 | 34.29 | N |
| ATOM | 1017 | CA | GLU | A | 142 | 4.045 | 25.351 | 40.510 | 1.00 | 33.08 | C |
| ATOM | 1018 | C | GLU | A | 142 | 4.655 | 24.938 | 39.170 | 1.00 | 31.87 | C |
| ATOM | 1019 | O | GLU | A | 142 | 3.958 | 24.443 | 38.296 | 1.00 | 31.87 | O |
| ATOM | 1020 | CB | GLU | A | 142 | 4.170 | 24.201 | 41.519 | 1.00 | 32.96 | C |
| ATOM | 1021 | CG | GLU | A | 142 | 5.610 | 23.914 | 41.942 | 1.00 | 32.71 | C |

TABLE 3-continued

| | | | | | | Coordinates for structures 1 to 4 | | | | | |
|---|---|---|---|---|---|---|---|---|---|---|---|
| ATOM | 1022 | CD | GLU | A | 142 | 5.761 | 22.730 | 42.896 | 1.00 | 33.55 | C |
| ATOM | 1023 | OE1 | GLU | A | 142 | 4.778 | 22.001 | 43.146 | 1.00 | 32.41 | O |
| ATOM | 1024 | OE2 | GLU | A | 142 | 6.888 | 22.520 | 43.398 | 1.00 | 34.13 | O |
| ATOM | 1025 | N | ARG | A | 143 | 5.954 | 25.156 | 39.017 | 1.00 | 30.56 | N |
| ATOM | 1026 | CA | ARG | A | 143 | 6.662 | 24.766 | 37.803 | 1.00 | 29.79 | C |
| ATOM | 1027 | C | ARG | A | 143 | 7.878 | 23.939 | 38.142 | 1.00 | 28.70 | C |
| ATOM | 1028 | O | ARG | A | 143 | 8.565 | 24.210 | 39.127 | 1.00 | 28.88 | O |
| ATOM | 1029 | CB | ARG | A | 143 | 7.142 | 25.991 | 37.040 | 1.00 | 29.90 | C |
| ATOM | 1030 | CG | ARG | A | 143 | 6.043 | 26.832 | 36.441 | 1.00 | 30.80 | C |
| ATOM | 1031 | CD | ARG | A | 143 | 6.591 | 27.992 | 35.636 | 1.00 | 30.70 | C |
| ATOM | 1032 | NE | ARG | A | 143 | 5.538 | 28.715 | 34.935 | 1.00 | 30.86 | N |
| ATOM | 1033 | CZ | ARG | A | 143 | 5.168 | 28.487 | 33.682 | 1.00 | 29.53 | C |
| ATOM | 1034 | NH1 | ARG | A | 143 | 5.763 | 27.547 | 32.941 | 1.00 | 27.51 | N |
| ATOM | 1035 | NH2 | ARG | A | 143 | 4.196 | 29.216 | 33.168 | 1.00 | 30.04 | N |
| ATOM | 1036 | N | LEU | A | 144 | 8.156 | 22.943 | 37.315 | 1.00 | 27.27 | N |
| ATOM | 1037 | CA | LEU | A | 144 | 9.319 | 22.102 | 37.518 | 1.00 | 26.47 | C |
| ATOM | 1038 | C | LEU | A | 144 | 10.220 | 22.148 | 36.297 | 1.00 | 25.40 | C |
| ATOM | 1039 | O | LEU | A | 144 | 9.755 | 22.330 | 35.172 | 1.00 | 25.39 | O |
| ATOM | 1040 | CB | LEU | A | 144 | 8.893 | 20.652 | 37.753 | 1.00 | 26.70 | C |
| ATOM | 1041 | CG | LEU | A | 144 | 7.922 | 20.416 | 38.915 | 1.00 | 27.15 | C |
| ATOM | 1042 | CD1 | LEU | A | 144 | 7.575 | 18.921 | 39.059 | 1.00 | 27.40 | C |
| ATOM | 1043 | CD2 | LEU | A | 144 | 8.488 | 20.956 | 40.221 | 1.00 | 27.42 | C |
| ATOM | 1044 | N | TYR | A | 145 | 11.511 | 21.974 | 36.527 | 1.00 | 23.90 | N |
| ATOM | 1045 | CA | TYR | A | 145 | 12.458 | 21.871 | 35.441 | 1.00 | 23.15 | C |
| ATOM | 1046 | C | TYR | A | 145 | 13.516 | 20.857 | 35.868 | 1.00 | 23.04 | C |
| ATOM | 1047 | O | TYR | A | 145 | 14.328 | 21.130 | 36.740 | 1.00 | 22.58 | O |
| ATOM | 1048 | CB | TYR | A | 145 | 13.080 | 23.235 | 35.107 | 1.00 | 23.01 | C |
| ATOM | 1049 | CG | TYR | A | 145 | 13.522 | 23.419 | 33.666 | 1.00 | 21.34 | C |
| ATOM | 1050 | CD1 | TYR | A | 145 | 13.824 | 22.333 | 32.863 | 1.00 | 20.11 | C |
| ATOM | 1051 | CD2 | TYR | A | 145 | 13.662 | 24.691 | 33.119 | 1.00 | 21.14 | C |
| ATOM | 1052 | CE1 | TYR | A | 145 | 14.219 | 22.494 | 31.563 | 1.00 | 20.22 | C |
| ATOM | 1053 | CE2 | TYR | A | 145 | 14.075 | 24.866 | 31.807 | 1.00 | 19.81 | C |
| ATOM | 1054 | CZ | TYR | A | 145 | 14.349 | 23.764 | 31.027 | 1.00 | 19.19 | C |
| ATOM | 1055 | OH | TYR | A | 145 | 14.736 | 23.903 | 29.699 | 1.00 | 18.36 | O |
| ATOM | 1056 | N | LEU | A | 146 | 13.461 | 19.666 | 35.287 | 1.00 | 22.75 | N |
| ATOM | 1057 | CA | LEU | A | 146 | 14.490 | 18.661 | 35.516 | 1.00 | 23.17 | C |
| ATOM | 1058 | C | LEU | A | 146 | 15.720 | 19.005 | 34.679 | 1.00 | 22.99 | C |
| ATOM | 1059 | O | LEU | A | 146 | 15.604 | 19.264 | 33.490 | 1.00 | 22.81 | O |
| ATOM | 1060 | CB | LEU | A | 146 | 13.980 | 17.282 | 35.115 | 1.00 | 23.33 | C |
| ATOM | 1061 | CG | LEU | A | 146 | 14.992 | 16.141 | 35.274 | 1.00 | 24.98 | C |
| ATOM | 1062 | CD1 | LEU | A | 146 | 14.276 | 14.846 | 35.622 | 1.00 | 24.56 | C |
| ATOM | 1063 | CD2 | LEU | A | 146 | 15.849 | 15.946 | 34.016 | 1.00 | 26.13 | C |
| ATOM | 1064 | N | GLN | A | 147 | 16.891 | 18.983 | 35.299 | 1.00 | 23.05 | N |
| ATOM | 1065 | CA | GLN | A | 147 | 18.135 | 19.314 | 34.619 | 1.00 | 23.65 | C |
| ATOM | 1066 | C | GLN | A | 147 | 19.158 | 18.394 | 35.231 | 1.00 | 23.86 | C |
| ATOM | 1067 | O | GLN | A | 147 | 19.573 | 18.597 | 36.364 | 1.00 | 24.61 | O |
| ATOM | 1068 | CB | GLN | A | 147 | 18.516 | 20.793 | 34.821 | 1.00 | 23.53 | C |
| ATOM | 1069 | CG | GLN | A | 147 | 17.386 | 21.770 | 34.461 | 1.00 | 24.34 | C |
| ATOM | 1070 | CD | GLN | A | 147 | 17.800 | 23.238 | 34.482 | 1.00 | 26.20 | C |
| ATOM | 1071 | OE1 | GLN | A | 147 | 17.034 | 24.114 | 34.035 | 1.00 | 29.67 | O |
| ATOM | 1072 | NE2 | GLN | A | 147 | 18.979 | 23.514 | 34.988 | 1.00 | 21.33 | N |
| ATOM | 1073 | N | GLN | A | 148 | 19.542 | 17.369 | 34.485 | 1.00 | 24.35 | N |
| ATOM | 1074 | CA | GLN | A | 148 | 20.393 | 16.314 | 35.006 | 1.00 | 24.70 | C |
| ATOM | 1075 | C | GLN | A | 148 | 21.319 | 15.753 | 33.964 | 1.00 | 25.16 | C |
| ATOM | 1076 | O | GLN | A | 148 | 20.898 | 15.378 | 32.866 | 1.00 | 24.21 | O |
| ATOM | 1077 | CB | GLN | A | 148 | 19.525 | 15.172 | 35.526 | 1.00 | 24.97 | C |
| ATOM | 1078 | CG | GLN | A | 148 | 20.317 | 13.940 | 35.953 | 1.00 | 25.54 | C |
| ATOM | 1079 | CD | GLN | A | 148 | 21.275 | 14.256 | 37.085 | 1.00 | 26.98 | C |
| ATOM | 1080 | OE1 | GLN | A | 148 | 20.892 | 14.941 | 38.042 | 1.00 | 26.73 | O |
| ATOM | 1081 | NE2 | GLN | A | 148 | 22.522 | 13.786 | 36.976 | 1.00 | 26.37 | N |
| ATOM | 1082 | N | THR | A | 149 | 22.592 | 15.704 | 34.321 | 1.00 | 25.94 | N |
| ATOM | 1083 | CA | THR | A | 149 | 23.603 | 15.134 | 33.466 | 1.00 | 27.43 | C |
| ATOM | 1084 | C | THR | A | 149 | 23.369 | 13.632 | 33.324 | 1.00 | 27.29 | C |
| ATOM | 1085 | O | THR | A | 149 | 23.081 | 12.965 | 34.303 | 1.00 | 27.40 | O |
| ATOM | 1086 | CB | THR | A | 149 | 24.990 | 15.430 | 34.075 | 1.00 | 27.91 | C |
| ATOM | 1087 | OG1 | THR | A | 149 | 25.282 | 16.829 | 33.901 | 1.00 | 30.41 | O |
| ATOM | 1088 | CG2 | THR | A | 149 | 26.078 | 14.776 | 33.276 | 1.00 | 30.12 | C |
| ATOM | 1089 | N | LEU | A | 150 | 23.461 | 13.117 | 32.100 | 1.00 | 27.79 | N |
| ATOM | 1090 | CA | LEU | A | 150 | 23.321 | 11.690 | 31.832 | 1.00 | 28.02 | C |
| ATOM | 1091 | C | LEU | A | 150 | 24.549 | 10.935 | 32.364 | 1.00 | 28.42 | C |
| ATOM | 1092 | O | LEU | A | 150 | 25.682 | 11.261 | 32.002 | 1.00 | 28.86 | O |
| ATOM | 1093 | CB | LEU | A | 150 | 23.194 | 11.435 | 30.326 | 1.00 | 28.08 | C |
| ATOM | 1094 | CG | LEU | A | 150 | 21.929 | 11.937 | 29.622 | 1.00 | 28.70 | C |
| ATOM | 1095 | CD1 | LEU | A | 150 | 22.016 | 11.725 | 28.117 | 1.00 | 28.62 | C |
| ATOM | 1096 | CD2 | LEU | A | 150 | 20.697 | 11.260 | 30.175 | 1.00 | 29.47 | C |
| ATOM | 1097 | N | ASN | A | 151 | 24.332 | 9.928 | 33.203 | 1.00 | 28.58 | N |
| ATOM | 1098 | CA | ASN | A | 151 | 25.434 | 9.156 | 33.781 | 1.00 | 28.79 | C |

TABLE 3-continued

| | | | | | | | | | | | |
|---|---|---|---|---|---|---|---|---|---|---|---|
| ATOM | 1099 | C | ASN | A | 151 | 25.194 | 7.636 | 33.782 | 1.00 | 29.24 | C |
| ATOM | 1100 | O | ASN | A | 151 | 24.197 | 7.163 | 33.238 | 1.00 | 29.60 | O |
| ATOM | 1101 | CB | ASN | A | 151 | 25.657 | 9.631 | 35.208 | 1.00 | 28.77 | C |
| ATOM | 1102 | CG | ASN | A | 151 | 24.459 | 9.367 | 36.084 | 1.00 | 28.05 | C |
| ATOM | 1103 | OD1 | ASN | A | 151 | 23.936 | 8.246 | 36.126 | 1.00 | 29.02 | O |
| ATOM | 1104 | ND2 | AEN | A | 151 | 24.000 | 10.396 | 36.772 | 1.00 | 26.99 | N |
| ATOM | 1105 | N | ASP | A | 152 | 26.083 | 6.885 | 34.437 | 1.00 | 29.71 | N |
| ATOM | 1106 | CA | ASP | A | 152 | 26.039 | 5.410 | 34.448 | 1.00 | 30.06 | C |
| ATOM | 1107 | C | ASP | A | 152 | 24.850 | 4.733 | 35.075 | 1.00 | 29.51 | C |
| ATOM | 1108 | O | ASP | A | 152 | 24.771 | 3.503 | 35.026 | 1.00 | 28.98 | O |
| ATOM | 1109 | CS | ASP | A | 152 | 27.199 | 4.829 | 35.250 | 1.00 | 30.99 | C |
| ATOM | 1110 | CG | ASP | A | 152 | 28.447 | 5.561 | 35.048 | 1.00 | 33.80 | C |
| ATOM | 1111 | OD1 | ASP | A | 152 | 28.636 | 6.071 | 33.918 | 1.00 | 40.13 | O |
| ATOM | 1112 | OD2 | ASP | A | 152 | 29.274 | 5.719 | 35.960 | 1.00 | 35.65 | O |
| ATOM | 1113 | N | THR | A | 153 | 23.959 | 5.468 | 35.722 | 1.00 | 28.96 | N |
| ATOM | 1114 | CA | THR | A | 153 | 22.831 | 4.792 | 36.359 | 1.00 | 28.42 | C |
| ATOM | 1115 | C | THR | A | 153 | 21.685 | 4.594 | 35.387 | 1.00 | 27.75 | C |
| ATOM | 1116 | O | THR | A | 153 | 20.730 | 3.909 | 35.712 | 1.00 | 27.68 | O |
| ATOM | 1117 | CB | THR | A | 153 | 22.330 | 5.552 | 37.584 | 1.00 | 28.53 | C |
| ATOM | 1118 | OG1 | THR | A | 153 | 21.833 | 6.836 | 37.193 | 1.00 | 28.91 | O |
| ATOM | 1119 | CG2 | THR | A | 153 | 23.473 | 5.855 | 38.540 | 1.00 | 29.18 | C |
| ATOM | 1120 | N | VAL | A | 154 | 21.766 | 5.171 | 34.194 | 1.00 | 26.76 | N |
| ATOM | 1121 | CA | VAL | A | 154 | 20.671 | 4.996 | 33.246 | 1.00 | 26.61 | C |
| ATOM | 1122 | C | VAL | A | 154 | 20.583 | 3.531 | 32.895 | 1.00 | 26.77 | C |
| ATOM | 1123 | O | VAL | A | 154 | 21.592 | 2.832 | 32.923 | 1.00 | 27.36 | O |
| ATOM | 1124 | CB | VAL | A | 154 | 20.838 | 5.826 | 31.964 | 1.00 | 26.05 | C |
| ATOM | 1125 | CG1 | VAL | A | 154 | 20.914 | 7.279 | 32.312 | 1.00 | 26.14 | C |
| ATOM | 1126 | CG2 | VAL | A | 154 | 22.071 | 5.383 | 31.182 | 1.00 | 25.62 | C |
| ATOM | 1127 | N | GLY | A | 155 | 19.379 | 3.072 | 32.568 | 1.00 | 26.71 | N |
| ATOM | 1128 | CA | GLY | A | 155 | 19.147 | 1.674 | 32.252 | 1.00 | 26.42 | C |
| ATOM | 1129 | C | GLY | A | 155 | 19.531 | 1.266 | 30.840 | 1.00 | 26.67 | C |
| ATOM | 1130 | O | GLY | A | 155 | 19.894 | 2.093 | 29.983 | 1.00 | 26.52 | O |
| ATOM | 1131 | N | ARG | A | 156 | 19.390 | 0.028 | 30.599 | 1.00 | 26.49 | N |
| ATOM | 1132 | CA | ARG | A | 156 | 19.811 | 0.684 | 29.364 | 1.00 | 26.54 | C |
| ATOM | 1133 | C | ARG | A | 156 | 19.305 | 0.053 | 28.068 | 1.00 | 25.95 | C |
| ATOM | 1134 | O | ARG | A | 156 | 20.089 | 0.194 | 27.160 | 1.00 | 26.26- | O |
| ATOM | 1135 | CB | ARG | A | 156 | 19.429 | 2.165 | 29.418 | 1.00 | 26.28 | C |
| ATOM | 1136 | N | LYS | A | 157 | 18.004 | 0.175 | 27.964 | 1.00 | 25.43 | N |
| ATOM | 1137 | CA | LYS | A | 157 | 17.460 | 0.777 | 26.756 | 1.00 | 25.11 | C |
| ATOM | 1138 | C | LYS | A | 157 | 18.026 | 2.198 | 26.517 | 1.00 | 25.50 | C |
| ATOM | 1139 | O | LYS | A | 157 | 18.249 | 2.595 | 25.372 | 1.00 | 25.14 | O |
| ATOM | 1140 | CB | LYS | A | 157 | 15.927 | 0.796 | 26.809 | 1.00 | 24.88 | C |
| ATOM | 1141 | CG | LYS | A | 157 | 15.255 | 0.572 | 26.516 | 1.00 | 24.25 | C |
| ATOM | 1142 | N | ILE | A | 158 | 18.257 | 2.956 | 27.585 | 1.00 | 25.35 | N |
| ATOM | 1143 | CA | ILE | A | 158 | 18.766 | 4.326 | 27.432 | 1.00 | 25.61 | C |
| ATOM | 1144 | C | ILE | A | 158 | 20.205 | 4.250 | 26.971 | 1.00 | 25.76 | C |
| ATOM | 1145 | O | ILE | A | 158 | 20.661 | 5.058 | 26.166 | 1.00 | 25.39 | O |
| ATOM | 1146 | CE | ILE | A | 158 | 18.662 | 5.107 | 28.740 | 1.00 | 25.41 | C |
| ATOM | 1147 | CG1 | ILE | A | 158 | 17.202 | 5.245 | 29.162 | 1.00 | 25.92 | C |
| ATOM | 1148 | CG2 | ILE | A | 158 | 19.297 | 6.475 | 28.601 | 1.00 | 25.61 | C |
| ATOM | 1149 | CD1 | ILE | A | 158 | 16.331 | 5.924 | 28.174 | 1.00 | 27.88 | C |
| ATOM | 1150 | N | VAL | A | 159 | 20.909 | 3.251 | 27.481 | 1.00 | 26.10 | N |
| ATOM | 1151 | CA | VAL | A | 159 | 22.276 | 3.010 | 27.079 | 1.00 | 26.57 | C |
| ATOM | 1152 | C | VAL | A | 159 | 22.279 | 2.703 | 25.585 | 1.00 | 26.40 | C |
| ATOM | 1153 | O | VAL | A | 159 | 23.074 | 3.248 | 24.840 | 1.00 | 26.32 | O |
| ATOM | 1154 | CB | VAL | A | 159 | 22.895 | 1.850 | 27.883 | 1.00 | 26.94 | C |
| ATOM | 1155 | CG1 | VAL | A | 159 | 24.136 | 1.310 | 27.193 | 1.00 | 27.73 | C |
| ATOM | 1156 | CG2 | VAL | A | 159 | 23.223 | 2.308 | 29.298 | 1.00 | 26.73 | C |
| ATOM | 1157 | N | MET | A | 160 | 21.363 | 1.852 | 25.145 | 1.00 | 26.48 | N |
| ATOM | 1158 | CA | MET | A | 160 | 21.270 | 1.518 | 23.721 | 1.00 | 26.52 | C |
| ATOM | 1159 | C | MET | A | 160 | 20.985 | 2.771 | 22.880 | 1.00 | 25.02 | C |
| ATOM | 1160 | O | MET | A | 160 | 21.600 | 2.986 | 21.845 | 1.00 | 24.31 | O |
| ATOM | 1161 | CE | MET | A | 160 | 20.183 | 0.476 | 23.485 | 1.00 | 27.05 | C |
| ATOM | 1162 | CG | MET | A | 160 | 20.540 | 0.900 | 24.001 | 1.00 | 30.45 | C |
| ATOM | 1163 | SD | MET | A | 160 | 21.843 | 1.730 | 23.058 | 1.00 | 34.87 | 5 |
| ATOM | 1164 | CE | MET | A | 160 | 20.957 | 2.028 | 21.496 | 1.00 | 36.94 | C |
| ATOM | 1165 | N | ASP | A | 161 | 20.047 | 3.589 | 23.342 | 1.00 | 23.96 | N |
| ATOM | 1166 | CA | ASP | A | 161 | 19.699 | 4.831 | 22.665 | 1.00 | 23.14 | C |
| ATOM | 1167 | C | ASP | A | 161 | 20.890 | 5.781 | 22.550 | 1.00 | 21.93 | C |
| ATOM | 1168 | O | ASP | A | 161 | 21.167 | 6.323 | 21.480 | 1.00 | 21.41 | O |
| ATOM | 1169 | CB | ASP | A | 161 | 18.549 | 5.528 | 23.402 | 1.00 | 23.13 | C |
| ATOM | 1170 | CG | ASP | A | 161 | 17.250 | 4.762 | 23.293 | 1.00 | 24.08 | C |
| ATOM | 1171 | OD1 | ASP | A | 161 | 17.182 | 3.812 | 22.478 | 1.00 | 21.27 | O |
| ATOM | 1172 | OD2 | ASP | A | 161 | 16.248 | 5.035 | 23.980 | 1.00 | 25.87 | O |
| ATOM | 1173 | N | PHE | A | 162 | 21.575 | 5.973 | 23.671 | 1.00 | 20.59 | N |
| ATOM | 1174 | CA | PHE | A | 162 | 22.712 | 6.859 | 23.765 | 1.00 | 19.97 | C |
| ATOM | 1175 | C | PHE | A | 162 | 23.802 | 6.409 | 22.809 | 1.00 | 19.19 | C |

TABLE 3-continued

| | | | | | | | | | | | |
|---|---|---|---|---|---|---|---|---|---|---|---|
| | | | | | Coordinates for structures 1 to 4 | | | | | | |
| ATOM | 1176 | O | PHE | A | 162 | 24.410 | 7.213 | 22.160 | 1.00 | 18.98 | O |
| ATOM | 1177 | CB | PHE | A | 162 | 23.223 | 6.859 | 25.220 | 1.00 | 20.44 | C |
| ATOM | 1178 | CG | PHE | A | 162 | 24.386 | 7.755 | 25.470 | 1.00 | 20.78 | C |
| ATOM | 1179 | CD1 | PHE | A | 162 | 24.206 | 9.107 | 25.673 | 1.00 | 25.50 | C |
| ATOM | 1180 | CD2 | PHE | A | 162 | 25.662 | 7.245 | 25.542 | 1.00 | 23.71 | C |
| ATOM | 1181 | CE1 | PHE | A | 162 | 25.290 | 9.930 | 25.935 | 1.00 | 25.85 | C |
| ATOM | 1182 | CE2 | PHE | A | 162 | 26.755 | 8.072 | 25.795 | 1.00 | 24.89 | C |
| ATOM | 1183 | CZ | PHE | A | 162 | 26.572 | 9.394 | 26.001 | 1.00 | 23.50 | C |
| ATOM | 1184 | N | LEU | A | 163 | 24.062 | 5.115 | 22.744 | 1.00 | 19.25 | N |
| ATOM | 1185 | CA | LEU | A | 163 | 25.084 | 4.597 | 21.838 | 1.00 | 19.42 | C |
| ATOM | 1186 | C | LEU | A | 163 | 24.715 | 4.804 | 20.361 | 1.00 | 18.63 | C |
| ATOM | 1187 | O | LEU | A | 163 | 25.585 | 4.831 | 19.493 | 1.00 | 18.21 | O |
| ATOM | 1188 | CE | LEU | A | 163 | 25.297 | 3.115 | 22.104 | 1.00 | 19.49 | C |
| ATOM | 1189 | CG | LEU | A | 163 | 25.988 | 2.812 | 23.422 | 1.00 | 20.88 | C |
| ATOM | 1190 | CE1 | LEU | A | 163 | 25.980 | 1.319 | 23.651 | 1.00 | 22.44 | C |
| ATOM | 1191 | CD2 | LEU | A | 163 | 27.407 | 3.368 | 23.396 | 1.00 | 21.73 | C |
| ATOM | 1192 | N | GLY | A | 164 | 23.419 | 4.917 | 20.104 | 1.00 | 18.01 | N |
| ATOM | 1193 | CA | GLY | A | 164 | 22.889 | 5.158 | 18.779 | 1.00 | 18.55 | C |
| ATOM | 1194 | C | GLY | A | 164 | 22.873 | 6.622 | 18.355 | 1.00 | 18.40 | C |
| ATOM | 1195 | O | GLY | A | 164 | 22.406 | 6.921 | 17.256 | 1.00 | 19.24 | O |
| ATOM | 1196 | N | PHE | A | 165 | 23.365 | 7.521 | 19.209 | 1.00 | 17.50 | N |
| ATOM | 1197 | CA | PHE | A | 165 | 23.493 | 8.913 | 18.831 | 1.00 | 17.67 | C |
| ATOM | 1198 | C | PHE | A | 165 | 24.497 | 8.955 | 17.663 | 1.00 | 17.49 | C |
| ATOM | 1199 | O | PHE | A | 165 | 25.293 | 8.028 | 17.497 | 1.00 | 16.10 | O |
| ATOM | 1200 | CE | PHE | A | 165 | 23.984 | 9.753 | 20.018 | 1.00 | 17.47 | C |
| ATOM | 1201 | CG | PHE | A | 165 | 22.932 | 10.004 | 21.098 | 1.00 | 18.51 | C |
| ATOM | 1202 | CD1 | PHE | A | 165 | 21.645 | 9.479 | 21.009 | 1.00 | 19.26 | C |
| ATOM | 1203 | CD2 | PHE | A | 165 | 23.242 | 10.784 | 22.203 | 1.00 | 18.52 | C |
| ATOM | 1204 | CE1 | PHE | A | 165 | 20.697 | 9.730 | 21.996 | 1.00 | 18.44 | C |
| ATOM | 1205 | CE2 | PHE | A | 165 | 22.303 | 11.030 | 23.199 | 1.00 | 18.52 | C |
| ATOM | 1206 | CZ | PHE | A | 165 | 21.032 | 10.500 | 23.100 | 1.00 | 18.90 | C |
| ATOM | 1207 | N | ASN | A | 166 | 24.466 | 10.009 | 16.854 | 1.00 | 17.77 | N |
| ATOM | 1208 | CA | ASN | A | 166 | 25.393 | 10.110 | 15.712 | 1.00 | 18.29 | C |
| ATOM | 1209 | C | ASN | A | 166 | 26.787 | 10.622 | 16.129 | 1.00 | 18.73 | C |
| ATOM | 1210 | O | ASN | A | 166 | 27.156 | 11.795 | 15.897 | 1.00 | 19.54 | O |
| ATOM | 1211 | CB | ASN | A | 166 | 24.793 | 10.972 | 14.598 | 1.00 | 17.92 | C |
| ATOM | 1212 | CG | ASN | A | 166 | 25.571 | 10.861 | 13.293 | 1.00 | 17.28 | C |
| ATOM | 1213 | OD1 | ASN | A | 166 | 26.679 | 10.289 | 13.262 | 1.00 | 16.53 | |
| ATOM | 1214 | ND2 | ASN | A | 166 | 24.994 | 11.395 | 12.204 | 1.00 | 12.92 | N |
| ATOM | 1215 | N | TRP | A | 167 | 27.527 | 9.739 | 16.789 | 1.00 | 19.26 | N |
| ATOM | 1216 | CA | TRP | A | 167 | 28.867 | 10.035 | 17.264 | 1.00 | 19.76 | C |
| ATOM | 1217 | C | TRP | A | 167 | 29.785 | 10.266 | 16.084 | 1.00 | 19.88 | C |
| ATOM | 1218 | O | TRP | A | 167 | 30.731 | 11.031 | 16.169 | 1.00 | 19.35 | O |
| ATOM | 1219 | CE | TRP | A | 167 | 29.384 | 8.864 | 18.130 | 1.00 | 19.92 | C |
| ATOM | 1220 | CG | TRP | A | 167 | 28.556 | 8.728 | 19.351 | 1.00 | 20.39 | C |
| ATOM | 1221 | CD1 | TRP | A | 167 | 27.686 | 7.727 | 19.656 | 1.00 | 20.85 | C |
| ATOM | 1222 | CD2 | TRP | A | 167 | 28.445 | 9.686 | 20.400 | 1.00 | 20.99 | C |
| ATOM | 1223 | NE1 | TRP | A | 167 | 27.059 | 7.995 | 20.851 | 1.00 | 21.18 | |
| ATOM | 1224 | CE2 | TRP | A | 167 | 27.509 | 9.194 | 21.325 | 1.00 | 20.70 | C |
| ATOM | 1225 | CE3 | TRP | A | 167 | 29.065 | 10.916 | 20.664 | 1.00 | 21.55 | C |
| ATOM | 1226 | CZ2 | TRP | A | 167 | 27.183 | 9.871 | 22.488 | 1.00 | 22.63 | C |
| ATOM | 1227 | CZ3 | TRP | A | 167 | 28.731 | 11.589 | 21.804 | 1.00 | 21.78 | C |
| ATOM | 1228 | CR2 | TRP | A | 167 | 27.789 | 11.071 | 22.706 | 1.00 | 22.79 | C |
| ATOM | 1229 | N | ASN | A | 168 | 29.529 | 9.577 | 14.979 | 1.00 | 20.07 | N |
| ATOM | 1230 | CA | ASN | A | 168 | 30.374 | 9.759 | 13.818 | 1.00 | 20.50 | C |
| ATOM | 1231 | C | ASN | A | 168 | 30.396 | 11.237 | 13.421 | 1.00 | 20.67 | C |
| ATOM | 1232 | O | ASN | A | 168 | 31.465 | 11.806 | 13.207 | 1.00 | 19.54 | O |
| ATOM | 1233 | CB | ASN | A | 168 | 29.917 | 8.930 | 12.628 | 1.00 | 20.87 | C |
| ATOM | 1234 | CG | ASN | A | 168 | 30.818 | 9.129 | 11.423 | 1.00 | 22.96 | C |
| ATOM | 1235 | OD1 | ASN | A | 168 | 32.027 | 8.923 | 11.522 | 1.00 | 25.54 | O |
| ATOM | 1236 | ND2 | ASN | A | 168 | 30.247 | 9.578 | 10.295 | 1.00 | 23.09 | N |
| ATOM | 1237 | N | TRP | A | 169 | 29.211 | 11.844 | 13.338 | 1.00 | 20.57 | N |
| ATOM | 1238 | CA | TRP | A | 169 | 29.106 | 13.226 | 12.917 | 1.00 | 20.23 | C |
| ATOM | 1239 | C | TRP | A | 169 | 29.653 | 14.188 | 13.972 | 1.00 | 20.59 | C |
| ATOM | 1240 | O | TRP | A | 169 | 30.367 | 15.118 | 13.634 | 1.00 | 20.09 | O |
| ATOM | 1241 | CB | TRP | A | 169 | 27.662 | 13.618 | 12.570 | 1.00 | 20.35 | C |
| ATOM | 1242 | CG | TRP | A | 169 | 27.542 | 15.101 | 12.238 | 1.00 | 19.49 | C |
| ATOM | 1243 | CD1 | TRP | A | 169 | 27.769 | 15.693 | 11.026 | 1.00 | 19.03 | C |
| ATOM | 1244 | CD2 | TRP | A | 169 | 27.203 | 16.157 | 13.137 | 1.00 | 20.25 | C |
| ATOM | 1245 | NE1 | TRP | A | 169 | 27.578 | 17.052 | 11.117 | 1.00 | 20.36 | N |
| ATOM | 1246 | CE2 | TRP | A | 169 | 27.244 | 17.366 | 12.406 | 1.00 | 19.45 | C |
| ATOM | 1247 | CE3 | TRP | A | 169 | 26.874 | 16.207 | 14.492 | 1.00 | 20.60 | C |
| ATOM | 1248 | CZ2 | TRP | A | 169 | 26.964 | 18.600 | 12.975 | 1.00 | 21.03 | C |
| ATOM | 1249 | CZ3 | TRP | A | 169 | 26.614 | 17.433 | 15.064 | 1.00 | 23.09 | C |
| ATOM | 1250 | CH2 | TRP | A | 169 | 26.649 | 18.621 | 14.297 | 1.00 | 23.61 | C |
| ATOM | 1251 | N | ILE | A | 170 | 29.326 | 13.979 | 15.239 | 1.00 | 20.47 | N |
| ATOM | 1252 | CA | ILE | A | 170 | 29.759 | 14.926 | 16.241 | 1.00 | 20.67 | C |

TABLE 3-continued

Coordinates for structures 1 to 4

| ATOM | 1253 | C | ILE | A | 170 | 31.262 | 14.772 | 16.567 | 1.00 | 21.18 | C |
|---|---|---|---|---|---|---|---|---|---|---|---|
| ATOM | 1254 | O | ILE | A | 170 | 31.943 | 15.758 | 16.836 | 1.00 | 21.20 | O |
| ATOM | 1255 | CB | ILE | A | 170 | 28.842 | 14.892 | 17.483 | 1.00 | 20.61 | C |
| ATOM | 1256 | CG1 | ILE | A | 170 | 28.900 | 16.231 | 18.221 | 1.00 | 20.05 | C |
| ATOM | 1257 | CG2 | ILE | A | 170 | 29.191 | 13.755 | 18.402 | 1.00 | 19.89 | C |
| ATOM | 1258 | CD1 | ILE | A | 170 | 27.865 | 16.353 | 19.329 | 1.00 | 21.00 | C |
| ATOM | 1259 | N | ASN | A | 171 | 31.780 | 13.556 | 16.527 | 1.00 | 20.74 | N |
| ATOM | 1260 | CA | ASN | A | 171 | 33.214 | 13.355 | 16.715 | 1.00 | 21.80 | C |
| ATOM | 1261 | C | ASN | A | 171 | 34.024 | 14.093 | 15.634 | 1.00 | 22.34 | C |
| ATOM | 1262 | O | ASN | A | 171 | 35.093 | 14.652 | 15.916 | 1.00 | 21.98 | O |
| ATOM | 1263 | CB | ASN | A | 171 | 33.581 | 11.857 | 16.718 | 1.00 | 21.55 | C |
| ATOM | 1264 | CG | ASN | A | 171 | 33.111 | 11.124 | 17.981 | 1.00 | 21.20 | C |
| ATOM | 1265 | OD1 | ASN | A | 171 | 32.637 | 11.724 | 18.963 | 1.00 | 21.35 | O |
| ATOM | 1266 | ND2 | ASN | A | 171 | 33.263 | 9.830 | 17.962 | 1.00 | 19.36 | N |
| ATOM | 1267 | N | LYS | A | 172 | 33.529 | 14.097 | 14.400 | 1.00 | 22.97 | N |
| ATOM | 1268 | CA | LYS | A | 172 | 34.218 | 14.847 | 13.353 | 1.00 | 24.09 | C |
| ATOM | 1269 | C | LYS | A | 172 | 34.167 | 16.342 | 13.656 | 1.00 | 23.61 | C |
| ATOM | 1270 | O | LYS | A | 172 | 35.166 | 17.041 | 13.511 | 1.00 | 23.54 | O |
| ATOM | 1271 | CB | LYS | A | 172 | 33.669 | 14.529 | 11.961 | 1.00 | 24.58 | C |
| ATOM | 1272 | CG | LYS | A | 172 | 34.087 | 13.163 | 11.491 | 1.00 | 27.56 | C |
| ATOM | 1273 | CD | LYS | A | 172 | 33.653 | 12.852 | 10.034 | 1.00 | 31.03 | C |
| ATOM | 1274 | CE | LYS | A | 172 | 34.323 | 11.576 | 9.565 | 1.00 | 33.01 | C |
| ATOM | 1275 | NZ | LYS | A | 172 | 34.357 | 11.406 | 8.070 | 1.00 | 36.89 | N |
| ATOM | 1276 | N | GLN | A | 173 | 33.019 | 16.834 | 14.109 | 1.00 | 23.74 | N |
| ATOM | 1277 | CA | GLN | A | 173 | 32.914 | 18.245 | 14.482 | 1.00 | 23.87 | C |
| ATOM | 1278 | C | GLN | A | 173 | 33.960 | 18.578 | 15.547 | 1.00 | 23.86 | C |
| ATOM | 1279 | O | GLN | A | 173 | 34.739 | 19.500 | 15.374 | 1.00 | 24.25 | O |
| ATOM | 1280 | CB | GLN | A | 173 | 31.517 | 18.590 | 14.993 | 1.00 | 23.63 | C |
| ATOM | 1281 | CG | GLN | A | 173 | 30.451 | 18.619 | 13.916 | 1.00 | 24.53 | C |
| ATOM | 1282 | CD | GLN | A | 173 | 30.753 | 19.634 | 12.851 | 1.00 | 25.08 | C |
| ATOM | 1283 | OE1 | GLN | A | 173 | 31.194 | 20.740 | 13.157 | 1.00 | 26.69 | O |
| ATOM | 1284 | NE2 | GLN | A | 173 | 30.512 | 19.273 | 11.601 | 1.00 | 23.36 | N |
| ATOM | 1285 | N | GLN | A | 174 | 33.963 | 17.822 | 16.635 | 1.00 | 23.63 | N |
| ATOM | 1286 | CA | GLN | A | 174 | 34.925 | 17.995 | 17.717 | 1.00 | 23.91 | C |
| ATOM | 1287 | C | GLN | A | 174 | 36.365 | 18.053 | 17.161 | 1.00 | 24.01 | C |
| ATOM | 1288 | O | GLN | A | 174 | 37.133 | 18.962 | 17.480 | 1.00 | 23.39 | O |
| ATOM | 1289 | CB | GLN | A | 174 | 34.783 | 16.840 | 18.717 | 1.00 | 23.67 | C |
| ATOM | 1290 | CG | GLN | A | 174 | 35.688 | 16.913 | 19.934 | 1.00 | 24.07 | C |
| ATOM | 1291 | CD | GLN | A | 174 | 35.595 | 15.668 | 20.799 | 1.00 | 25.12 | C |
| ATOM | 1292 | OE1 | GLN | A | 174 | 35.229 | 14.602 | 20.312 | 1.00 | 25.70 | O |
| ATOM | 1293 | NE2 | GLN | A | 174 | 35.901 | 15.803 | 22.084 | 1.00 | 23.63 | N |
| ATOM | 1294 | N | GLY | A | 175 | 36.706 | 17.080 | 16.334 | 1.00 | 23.75 | N |
| ATOM | 1295 | CA | GLY | A | 175 | 38.005 | 17.028 | 15.696 | 1.00 | 24.73 | C |
| ATOM | 1296 | C | GLY | A | 175 | 38.268 | 18.209 | 14.768 | 1.00 | 25.21 | C |
| ATOM | 1297 | O | GLY | A | 175 | 39.310 | 18.842 | 14.854 | 1.00 | 25.60 | O |
| ATOM | 1298 | N | LYS | A | 176 | 37.327 | 18.518 | 13.888 | 1.00 | 25.81 | N |
| ATOM | 1299 | CA | LYS | A | 176 | 37.491 | 19.634 | 12.961 | 1.00 | 26.88 | C |
| ATOM | 1300 | C | LYS | A | 176 | 37.719 | 20.997 | 13.638 | 1.00 | 26.95 | C |
| ATOM | 1301 | O | LYS | A | 176 | 38.490 | 21.803 | 13.136 | 1.00 | 26.74 | O |
| ATOM | 1302 | CB | LYS | A | 176 | 36.256 | 19.778 | 12.077 | 1.00 | 27.35 | C |
| ATOM | 1303 | CG | LYS | A | 176 | 36.093 | 18.716 | 11.009 | 1.00 | 29.87 | C |
| ATOM | 1304 | CD | LYS | A | 176 | 34.894 | 19.085 | 10.137 | 1.00 | 33.21 | C |
| ATOM | 1305 | CE | LYS | A | 176 | 33.948 | 17.932 | 9.961 | 1.00 | 35.30 | C |
| ATOM | 1306 | NZ | LYZ | A | 176 | 32.558 | 18.388 | 9.643 | 1.00 | 37.22 | N |
| ATOM | 1307 | N | ARG | A | 177 | 37.031 | 21.257 | 14.749 | 1.00 | 26.93 | N |
| ATOM | 1308 | CA | ARG | A | 177 | 37.153 | 22.539 | 15.430 | 1.00 | 27.36 | C |
| ATOM | 1309 | C | ARG | A | 177 | 38.241 | 22.611 | 16.509 | 1.00 | 26.63 | C |
| ATOM | 1310 | O | ARG | A | 177 | 38.402 | 23.650 | 17.135 | 1.00 | 25.85 | O |
| ATOM | 1311 | CB | ARG | A | 177 | 35.832 | 22.902 | 16.114 | 1.00 | 27.86 | C |
| ATOM | 1312 | CG | ARG | A | 177 | 34.625 | 22.712 | 15.267 | 1.00 | 29.88 | C |
| ATOM | 1313 | CD | ARG | A | 177 | 34.653 | 23.460 | 13.973 | 1.00 | 32.39 | C |
| ATOM | 1314 | NE | ARG | A | 177 | 33.683 | 22.854 | 13.084 | 1.00 | 34.54 | N |
| ATOM | 1315 | CZ | ARG | A | 177 | 33.841 | 22.701 | 11.790 | 1.00 | 37.31 | C |
| ATOM | 1316 | NH1 | ARG | A | 177 | 34.952 | 23.110 | 11.189 | 1.00 | 38.34 | N |
| ATOM | 1317 | NH2 | ARG | A | 177 | 32.877 | 22.126 | 11.088 | 1.00 | 38.88 | N |
| ATOM | 1318 | N | GLY | A | 178 | 38.950 | 21.510 | 16.743 | 1.00 | 26.35 | N |
| ATOM | 1319 | CA | GLY | A | 178 | 39.998 | 21.470 | 17.753 | 1.00 | 25.46 | C |
| ATOM | 1320 | C | GLY | A | 178 | 39.473 | 21.514 | 19.176 | 1.00 | 25.27 | C |
| ATOM | 1321 | O | GLY | A | 178 | 40.213 | 21.818 | 20.123 | 1.00 | 25.46 | O |
| ATOM | 1322 | N | TRP | A | 179 | 38.199 | 21.202 | 19.359 | 1.00 | 24.30 | N |
| ATOM | 1323 | CA | TRP | A | 179 | 37.639 | 21.260 | 20.692 | 1.00 | 24.02 | C |
| ATOM | 1324 | C | TRP | A | 179 | 38.290 | 20.266 | 21.638 | 1.00 | 23.85 | C |
| ATOM | 1325 | O | TRP | A | 179 | 38.958 | 19.333 | 21.226 | 1.00 | 22.62 | O |
| ATOM | 1326 | CB | TRP | A | 179 | 36.136 | 21.011 | 20.674 | 1.00 | 23.73 | C |
| ATOM | 1327 | CG | TRP | A | 179 | 35.346 | 22.061 | 19.962 | 1.00 | 23.92 | C |
| ATOM | 1328 | CD1 | TRP | A | 179 | 35.787 | 23.291 | 19.531 | 1.00 | 22.69 | C |
| ATOM | 1329 | CD2 | TRP | A | 179 | 33.968 | 21.981 | 19.594 | 1.00 | 23.74 | C |

TABLE 3-continued

| | | | | | | | | | | | |
|---|---|---|---|---|---|---|---|---|---|---|---|
| | | | | Coordinates for structures 1 to 4 | | | | | | | |
| ATOM | 1330 | NE1 | TRP | A | 179 | 34.765 | 23.968 | 18.912 | 1.00 | 24.45 | N |
| ATOM | 1331 | CE2 | TRP | A | 179 | 33.636 | 23.183 | 18.929 | 1.00 | 24.47 | C |
| ATOM | 1332 | CE3 | TRP | A | 179 | 32.984 | 21.002 | 19.730 | 1.00 | 23.10 | C |
| ATOM | 1333 | CZ2 | TRP | A | 179 | 32.379 | 23.422 | 18.414 | 1.00 | 23.69 | C |
| ATOM | 1334 | CZ3 | TRP | A | 179 | 31.733 | 21.241 | 19.211 | 1.00 | 21.89 | C |
| ATOM | 1335 | CH2 | TRP | A | 179 | 31.435 | 22.445 | 18.573 | 1.00 | 23.90 | C |
| ATOM | 1336 | N | GLY | A | 180 | 38.080 | 20.499 | 22.925 | 1.00 | 24.08 | N |
| ATOM | 1337 | CA | GLY | A | 180 | 38.488 | 19.558 | 23.941 | 1.00 | 24.08 | C |
| ATOM | 1338 | C | GLY | A | 180 | 37.437 | 18.476 | 24.103 | 1.00 | 24.64 | C |
| ATOM | 1339 | O | GLY | A | 180 | 36.618 | 18.234 | 23.202 | 1.00 | 24.66 | O |
| ATOM | 1340 | N | GLN | A | 181 | 37.437 | 17.830 | 25.261 | 1.00 | 24.77 | N |
| ATOM | 1341 | CA | GLN | A | 181 | 36.575 | 16.682 | 25.471 | 1.00 | 25.23 | C |
| ATOM | 1342 | C | GLN | A | 181 | 35.117 | 17.039 | 25.725 | 1.00 | 24.50 | C |
| ATOM | 1343 | O | GLN | A | 181 | 34.779 | 18.151 | 26.149 | 1.00 | 24.42 | O |
| ATOM | 1344 | CB | GLN | A | 181 | 37.094 | 15.847 | 26.646 | 1.00 | 25.76 | C |
| ATOM | 1345 | CG | GLN | A | 181 | 36.720 | 16.409 | 28.025 | 1.00 | 28.85 | C |
| ATOM | 1346 | CD | GLN | A | 181 | 37.046 | 15.434 | 29.156 | 1.00 | 33.38 | C |
| ATOM | 1347 | OE1 | GLN | A | 181 | 38.186 | 15.003 | 29.293 | 1.00 | 36.10 | O |
| ATOM | 1348 | NE2 | GLN | A | 181 | 36.044 | 15.085 | 29.958 | 1.00 | 36.04 | N |
| ATOM | 1349 | N | LEU | A | 182 | 34.262 | 16.078 | 25.423 | 1.00 | 23.71 | N |
| ATOM | 1350 | CA | LEU | A | 182 | 32.857 | 16.110 | 25.792 | 1.00 | 23.70 | C |
| ATOM | 1351 | C | LEU | A | 182 | 32.876 | 16.040 | 27.317 | 1.00 | 22.68 | C |
| ATOM | 1352 | O | LEU | A | 182 | 33.406 | 15.079 | 27.849 | 1.00 | 21.72 | O |
| ATOM | 1353 | CB | LEU | A | 182 | 32.179 | 14.836 | 25.273 | 1.00 | 23.82 | C |
| ATOM | 1354 | CG | LEU | A | 182 | 30.661 | 14.693 | 25.199 | 1.00 | 23.38 | C |
| ATOM | 1355 | CD1 | LEU | A | 182 | 30.243 | 13.231 | 25.368 | 1.00 | 26.04 | C |
| ATOM | 1356 | CD2 | LEU | A | 182 | 29.977 | 15.501 | 26.192 | 1.00 | 29.73 | C |
| ATOM | 1357 | N | THR | A | 183 | 32.323 | 17.031 | 28.021 | 1.00 | 21.93 | N |
| ATOM | 1358 | CA | THR | A | 183 | 32.300 | 16.971 | 29.484 | 1.00 | 21.44 | C |
| ATOM | 1359 | C | THR | A | 183 | 31.004 | 16.388 | 29.984 | 1.00 | 21.27 | C |
| ATOM | 1360 | O | THR | A | 183 | 30.972 | 15.766 | 31.032 | 1.00 | 21.29 | O |
| ATOM | 1361 | CB | THR | A | 183 | 32.490 | 18.362 | 30.150 | 1.00 | 21.73 | C |
| ATOM | 1362 | OG1 | THR | A | 183 | 31.463 | 19.257 | 29.715 | 1.00 | 20.35 | O |
| ATOM | 1363 | CG2 | THR | A | 183 | 33.796 | 19.015 | 29.725 | 1.00 | 20.91 | C |
| ATOM | 1364 | N | SER | A | 184 | 29.918 | 16.590 | 29.251 | 1.00 | 21.42 | N |
| ATOM | 1365 | CA | SER | A | 184 | 28.649 | 16.053 | 29.689 | 1.00 | 21.45 | C |
| ATOM | 1366 | C | SER | A | 184 | 27.537 | 16.272 | 28.714 | 1.00 | 21.46 | C |
| ATOM | 1367 | O | SER | A | 184 | 27.672 | 17.031 | 27.753 | 1.00 | 21.17 | O |
| ATOM | 1368 | CB | SER | A | 184 | 28.243 | 16.687 | 31.006 | 1.00 | 21.74 | C |
| ATOM | 1369 | OG | SER | A | 184 | 27.919 | 18.049 | 30.845 | 1.00 | 23.24 | O |
| ATOM | 1370 | N | ASN | A | 185 | 26.445 | 15.575 | 28.982 | 1.00 | 21.21 | N |
| ATOM | 1371 | CA | ASN | A | 185 | 25.216 | 15.712 | 28.245 | 1.00 | 22.29 | C |
| ATOM | 1372 | C | ASN | A | 185 | 24.154 | 16.005 | 29.273 | 1.00 | 22.08 | C |
| ATOM | 1373 | O | ASN | A | 185 | 23.886 | 15.184 | 30.135 | 1.00 | 22.25 | O |
| ATOM | 1374 | CB | ASN | A | 185 | 24.856 | 14.416 | 27.497 | 1.00 | 22.67 | C |
| ATOM | 1375 | CG | ASN | A | 185 | 25.885 | 14.037 | 26.454 | 1.00 | 23.57 | C |
| ATOM | 1376 | OD1 | ASN | A | 185 | 26.646 | 13.097 | 26.655 | 1.00 | 27.51 | O |
| ATOM | 1377 | ND2 | ASN | A | 185 | 25.905 | 14.754 | 25.329 | 1.00 | 24.27 | N |
| ATOM | 1378 | N | LEU | A | 186 | 23.574 | 17.189 | 29.202 | 1.00 | 22.01 | N |
| ATOM | 1379 | CA | LEU | A | 186 | 22.529 | 17.563 | 30.135 | 1.00 | 22.03 | C |
| ATOM | 1380 | C | LEU | A | 186 | 21.170 | 17.219 | 29.558 | 1.00 | 22.00 | C |
| ATOM | 1381 | O | LEU | A | 186 | 20.844 | 17.592 | 28.435 | 1.00 | 22.34 | O |
| ATOM | 1382 | CB | LEU | A | 186 | 22.578 | 19.065 | 30.423 | 1.00 | 21.68 | C |
| ATOM | 1383 | CG | LEU | A | 186 | 21.707 | 19.538 | 31.588 | 1.00 | 22.25 | C |
| ATOM | 1384 | CD1 | LEU | A | 186 | 22.252 | 18.985 | 32.891 | 1.00 | 22.43 | C |
| ATOM | 1385 | CD2 | LEU | A | 186 | 21.643 | 21.098 | 31.648 | 1.00 | 23.35 | C |
| ATOM | 1386 | N | LEU | A | 187 | 20.377 | 16.518 | 30.344 | 1.00 | 22.19 | N |
| ATOM | 1387 | CA | LEU | A | 187 | 19.009 | 16.198 | 29.979 | 1.00 | 21.95 | C |
| ATOM | 1388 | C | LEU | A | 187 | 18.149 | 17.286 | 30.603 | 1.00 | 21.91 | C |
| ATOM | 1389 | O | LEU | A | 187 | 18.232 | 17.521 | 31.823 | 1.00 | 21.61 | O |
| ATOM | 1390 | CB | LEU | A | 187 | 18.616 | 14.830 | 30.527 | 1.00 | 21.55 | C |
| ATOM | 1391 | CG | LEU | A | 187 | 17.129 | 14.488 | 30.477 | 1.00 | 22.78 | C |
| ATOM | 1392 | CD1 | LEU | A | 187 | 16.616 | 14.429 | 29.054 | 1.00 | 23.66 | C |
| ATOM | 1393 | CD2 | LEU | A | 187 | 16.866 | 13.143 | 31.174 | 1.00 | 22.84 | C |
| ATOM | 1394 | N | LEU | A | 188 | 17.348 | 17.956 | 29.770 | 1.00 | 21.56 | N |
| ATOM | 1395 | CA | LEU | A | 188 | 16.461 | 19.000 | 30.227 | 1.00 | 22.26 | C |
| ATOM | 1396 | C | LEU | A | 188 | 14.993 | 18.662 | 29.920 | 1.00 | 22.55 | C |
| ATOM | 1397 | O | LEU | A | 188 | 14.588 | 18.517 | 28.760 | 1.00 | 23.16 | O |
| ATOM | 1398 | CB | LEU | A | 188 | 16.827 | 20.327 | 29.562 | 1.00 | 22.84 | C |
| ATOM | 1399 | CG | LEU | A | 188 | 18.244 | 20.840 | 29.821 | 1.00 | 22.60 | C |
| ATOM | 1400 | CD1 | LEU | A | 188 | 18.967 | 21.111 | 28.523 | 1.00 | 23.92 | C |
| ATOM | 1401 | CD2 | LEU | A | 188 | 18.177 | 22.088 | 30.655 | 1.00 | 24.56 | C |
| ATOM | 1402 | N | ILE | A | 189 | 14.181 | 18.577 | 30.958 | 1.00 | 22.15 | N |
| ATOM | 1403 | CA | ILE | A | 189 | 12.769 | 18.315 | 30.756 | 1.00 | 22.34 | C |
| ATOM | 1404 | C | ILE | A | 189 | 11.996 | 19.395 | 31.460 | 1.00 | 22.37 | C |
| ATOM | 1405 | O | ILE | A | 189 | 12.072 | 19.528 | 32.692 | 1.00 | 22.77 | O |
| ATOM | 1406 | CB | ILE | A | 189 | 12.377 | 16.953 | 31.281 | 1.00 | 21.60 | C |

TABLE 3-continued

| | | | | | | | | | | | |
|---|---|---|---|---|---|---|---|---|---|---|---|
| | Coordinates for structures 1 to 4 |
| ATOM | 1407 | CG1 | ILE | A | 189 | 13.254 | 15.888 | 30.638 | 1.00 | 21.85 | C |
| ATOM | 1408 | CG2 | ILE | A | 189 | 10.928 | 16.708 | 30.958 | 1.00 | 22.51 | C |
| ATOM | 1409 | CD1 | ILE | A | 189 | 12.918 | 14.425 | 31.075 | 1.00 | 23.06 | C |
| ATOM | 1410 | N | GLY | A | 190 | 11.276 | 20.186 | 30.673 | 1.00 | 22.37 | N |
| ATOM | 1411 | CA | GLY | A | 190 | 10.587 | 21.336 | 31.206 | 1.00 | 22.29 | C |
| ATOM | 1412 | C | GLY | A | 190 | 9.124 | 21.342 | 30.902 | 1.00 | 22.48 | C |
| ATOM | 1413 | O | GLY | A | 190 | 8.652 | 20.633 | 30.007 | 1.00 | 22.39 | O |
| ATOM | 1414 | N | MET | A | 191 | 8.402 | 22.134 | 31.687 | 1.00 | 22.74 | N |
| ATOM | 1415 | CA | MET | A | 191 | 6.991 | 22.339 | 31.467 | 1.00 | 23.16 | C |
| ATOM | 1416 | C | MET | A | 191 | 6.838 | 23.482 | 30.478 | 1.00 | 22.94 | C |
| ATOM | 1417 | O | MET | A | 191 | 7.738 | 24.329 | 30.338 | 1.00 | 23.03 | O |
| ATOM | 1418 | CB | MET | A | 191 | 6.283 | 22.673 | 32.784 | 1.00 | 23.69 | C |
| ATOM | 1419 | CG | MET | A | 191 | 6.224 | 21.513 | 33.741 | 1.00 | 25.02 | C |
| ATOM | 1420 | SD | MET | A | 191 | 5.664 | 21.927 | 35.415 | 1.00 | 28.11 | S |
| ATOM | 1421 | CE | MET | A | 191 | 4.016 | 22.460 | 35.097 | 1.00 | 28.35 | C |
| ATOM | 1422 | N | GLU | A | 192 | 5.712 | 23.492 | 29.773 | 1.00 | 22.60 | N |
| ATOM | 1423 | CA | GLU | A | 192 | 5.410 | 24.544 | 28.810 | 1.00 | 22.83 | C |
| ATOM | 1424 | C | GLU | A | 192 | 5.495 | 25.895 | 29.490 | 1.00 | 22.51 | C |
| ATOM | 1425 | O | GLU | A | 192 | 5.062 | 26.046 | 30.614 | 1.00 | 22.41 | O |
| ATOM | 1426 | CB | GLU | A | 192 | 4.005 | 24.342 | 28.249 | 1.00 | 22.86 | C |
| ATOM | 1427 | CG | GLU | A | 192 | 2.925 | 24.367 | 29.315 | 1.00 | 24.36 | C |
| ATOM | 1428 | CD | GLU | A | 192 | 1.572 | 23.891 | 28.814 | 1.00 | 25.71 | C |
| ATOM | 1429 | OE1 | GLU | A | 192 | 1.503 | 23.294 | 27.718 | 1.00 | 25.51 | O |
| ATOM | 1430 | OE2 | GLU | A | 192 | 0.582 | 24.128 | 29.525 | 1.00 | 26.30 | O |
| ATOM | 1431 | N | GLY | A | 193 | 6.069 | 26.888 | 28.828 | 1.00 | 22.95 | N |
| ATOM | 1432 | CA | GLY | A | 193 | 6.185 | 28.199 | 29.444 | 1.00 | 22.50 | C |
| ATOM | 1433 | C | GLY | A | 193 | 7.465 | 28.414 | 30.254 | 1.00 | 22.36 | C |
| ATOM | 1434 | O | GLY | A | 193 | 7.756 | 29.544 | 30.602 | 1.00 | 23.08 | O |
| ATOM | 1435 | N | ASN | A | 194 | 8.219 | 27.361 | 30.566 | 1.00 | 21.60 | N |
| ATOM | 1436 | CA | ASN | A | 194 | 9.456 | 27.506 | 31.341 | 1.00 | 21.44 | C |
| ATOM | 1437 | C | ASN | A | 194 | 10.489 | 28.320 | 30.581 | 1.00 | 21.19 | C |
| ATOM | 1438 | O | ASN | A | 194 | 10.635 | 28.134 | 29.372 | 1.00 | 22.08 | O |
| ATOM | 1439 | CB | ASN | A | 194 | 10.099 | 26.147 | 31.629 | 1.00 | 21.05 | C |
| ATOM | 1440 | CG | ASN | A | 194 | 9.494 | 25.435 | 32.801 | 1.00 | 20.86 | C |
| ATOM | 1441 | OD1 | ASN | A | 194 | 8.509 | 25.883 | 33.385 | 1.00 | 22.48 | O |
| ATOM | 1442 | ND2 | ASN | A | 194 | 10.092 | 24.312 | 33.167 | 1.00 | 17.74 | N |
| ATOM | 1443 | N | VAL | A | 195 | 11.213 | 29.183 | 31.290 | 1.00 | 20.69 | N |
| ATOM | 1444 | CA | VAL | A | 195 | 12.268 | 29.993 | 30.701 | 1.00 | 20.84 | C |
| ATOM | 1445 | C | VAL | A | 195 | 13.572 | 29.854 | 31.450 | 1.00 | 20.06 | C |
| ATOM | 1446 | O | VAL | A | 195 | 13.601 | 29.874 | 32.681 | 1.00 | 20.75 | O |
| ATOM | 1447 | CB | VAL | A | 195 | 11.903 | 31.502 | 30.686 | 1.00 | 21.41 | C |
| ATOM | 1448 | CG1 | VAL | A | 195 | 13.081 | 32.357 | 30.219 | 1.00 | 22.24 | C |
| ATOM | 1449 | CG2 | VAL | A | 195 | 10.666 | 31.767 | 29.843 | 1.00 | 22.30 | C |
| ATOM | 1450 | N | THR | A | 196 | 14.651 | 29.673 | 30.702 | 1.00 | 19.51 | N |
| ATOM | 1451 | CA | THR | A | 196 | 15.993 | 29.737 | 31.257 | 1.00 | 19.52 | C |
| ATOM | 1452 | C | THR | A | 196 | 16.487 | 31.117 | 30.820 | 1.00 | 19.98 | C |
| ATOM | 1453 | O | THR | A | 196 | 16.653 | 31.352 | 29.620 | 1.00 | 19.56 | O |
| ATOM | 1454 | CB | THR | A | 196 | 16.896 | 28.677 | 30.675 | 1.00 | 19.26 | C |
| ATOM | 1455 | OG1 | THR | A | 196 | 16.526 | 27.366 | 31.162 | 1.00 | 21.13 | O |
| ATOM | 1456 | CG2 | THR | A | 196 | 18.309 | 28.886 | 31.185 | 1.00 | 19.85 | C |
| ATOM | 1457 | N | PRO | A | 197 | 16.627 | 32.043 | 31.767 | 1.00 | 20.27 | N |
| ATOM | 1458 | CA | PRO | A | 197 | 17.046 | 33.412 | 31.463 | 1.00 | 20.52 | C |
| ATOM | 1459 | C | PRO | A | 197 | 18.431 | 33.497 | 30.836 | 1.00 | 20.89 | C |
| ATOM | 1460 | O | PRO | A | 197 | 19.277 | 32.609 | 31.025 | 1.00 | 20.66 | O |
| ATOM | 1461 | CB | PRO | A | 197 | 17.018 | 34.099 | 32.825 | 1.00 | 21.22 | C |
| ATOM | 1462 | CG | PRO | A | 197 | 16.144 | 33.263 | 33.657 | 1.00 | 21.01 | C |
| ATOM | 1463 | CD | PRO | A | 197 | 16.309 | 31.872 | 33.189 | 1.00 | 20.28 | C |
| ATOM | 1464 | N | ALA | A | 198 | 18.633 | 34.577 | 30.089 | 1.00 | 20.28 | N |
| ATOM | 1465 | CA | ALA | A | 198 | 19.841 | 34.817 | 29.341 | 1.00 | 20.22 | C |
| ATOM | 1466 | C | ALA | A | 198 | 21.130 | 34.634 | 30.146 | 1.00 | 20.58 | C |
| ATOM | 1467 | O | ALA | A | 198 | 21.284 | 35.186 | 31.235 | 1.00 | 19.91 | O |
| ATOM | 1468 | CB | ALA | A | 198 | 19.791 | 36.222 | 28.759 | 1.00 | 20.52 | C |
| ATOM | 1469 | N | HIS | A | 199 | 22.062 | 33.891 | 29.563 | 1.00 | 20.87 | N |
| ATOM | 1470 | CA | HIS | A | 199 | 23.371 | 33.646 | 30.158 | 1.00 | 21.41 | C |
| ATOM | 1471 | C | HIS | A | 199 | 24.281 | 33.168 | 29.063 | 1.00 | 21.82 | C |
| ATOM | 1472 | O | HIS | A | 199 | 23.826 | 32.892 | 27.943 | 1.00 | 21.80 | O |
| ATOM | 1473 | CB | HIS | A | 199 | 23.305 | 32.534 | 31.198 | 1.00 | 21.44 | C |
| ATOM | 1474 | CG | HIS | A | 199 | 22.915 | 31.220 | 30.617 | 1.00 | 22.21 | C |
| ATOM | 1475 | ND1 | HIS | A | 199 | 21.619 | 30.940 | 30.253 | 1.00 | 21.93 | N |
| ATOM | 1476 | CD2 | HIS | A | 199 | 23.644 | 30.120 | 30.296 | 1.00 | 22.04 | C |
| ATOM | 1477 | CE1 | HIS | A | 199 | 21.561 | 29.721 | 29.749 | 1.00 | 23.76 | C |
| ATOM | 1478 | ND2 | HIS | A | 199 | 22.777 | 29.214 | 29.737 | 1.00 | 22.57 | N |
| ATOM | 1479 | N | TYR | A | 200 | 25.568 | 33.060 | 29.384 | 1.00 | 22.40 | N |
| ATOM | 1480 | CA | TYR | A | 200 | 26.536 | 32.456 | 28.469 | 1.00 | 22.34 | C |
| ATOM | 1481 | C | TYR | A | 200 | 27.225 | 31.316 | 29.197 | 1.00 | 22.03 | C |
| ATOM | 1482 | O | TYR | A | 200 | 27.328 | 31.330 | 30.425 | 1.00 | 21.90 | O |
| ATOM | 1483 | CB | TYR | A | 200 | 27.544 | 33.458 | 27.924 | 1.00 | 22.22 | C |

TABLE 3-continued

Coordinates for structures 1 to 4

| ATOM | 1484 | CG | TYR | A | 200 | 28.517 | 34.051 | 28.924 | 1.00 | 22.16 | C |
| ATOM | 1485 | CD1 | TYR | A | 200 | 29.746 | 33.454 | 29.171 | 1.00 | 21.36 | C |
| ATOM | 1486 | CD2 | TYR | A | 200 | 28.236 | 35.246 | 29.565 | 1.00 | 22.58 | C |
| ATOM | 1487 | CE1 | TYR | A | 200 | 30.638 | 33.997 | 30.052 | 1.00 | 21.48 | C |
| ATOM | 1488 | CE2 | TYR | A | 200 | 29.128 | 35.806 | 30.462 | 1.00 | 21.46 | C |
| ATOM | 1489 | CZ | TYR | A | 200 | 30.334 | 35.189 | 30.695 | 1.00 | 22.03 | C |
| ATOM | 1490 | OH | TYR | A | 200 | 31.230 | 35.733 | 31.593 | 1.00 | 20.69 | O |
| ATOM | 1491 | N | ASP | A | 201 | 27.681 | 30.310 | 28.444 | 1.00 | 22.42 | N |
| ATOM | 1492 | CA | ASP | A | 201 | 28.381 | 29.152 | 29.048 | 1.00 | 22.10 | C |
| ATOM | 1493 | C | ASP | A | 201 | 29.801 | 29.142 | 28.531 | 1.00 | 21.96 | C |
| ATOM | 1494 | O | ASP | A | 201 | 30.018 | 29.601 | 27.433 | 1.00 | 22.26 | O |
| ATOM | 1495 | CB | ASP | A | 201 | 27.722 | 27.840 | 28.661 | 1.00 | 21.97 | C |
| ATOM | 1496 | CG | ASP | A | 201 | 26.311 | 27.714 | 29.181 | 1.00 | 21.99 | C |
| ATOM | 1497 | OD1 | ASP | A | 201 | 26.126 | 27.649 | 30.421 | 1.00 | 22.61 | O |
| ATOM | 1498 | OD2 | ASP | A | 201 | 25.330 | 27.624 | 28.412 | 1.00 | 19.35 | O |
| ATOM | 1499 | N | GLU | A | 202 | 30.769 | 28.620 | 29.283 | 1.00 | 21.66 | N |
| ATOM | 1500 | CA | GLU | A | 202 | 32.146 | 28.612 | 28.773 | 1.00 | 23.16 | C |
| ATOM | 1501 | C | GLU | A | 202 | 32.515 | 27.334 | 28.035 | 1.00 | 23.38 | C |
| ATOM | 1502 | O | GLU | A | 202 | 33.684 | 26.951 | 28.049 | 1.00 | 25.48 | O |
| ATOM | 1503 | CB | GLU | A | 202 | 33.178 | 28.774 | 29.897 | 1.00 | 23.46 | C |
| ATOM | 1504 | CG | GLU | A | 202 | 33.110 | 30.064 | 30.681 | 1.00 | 26.52 | C |
| ATOM | 1505 | CD | GLU | A | 202 | 34.233 | 30.132 | 31.704 | 1.00 | 28.11 | C |
| ATOM | 1506 | OE1 | GLU | A | 202 | 34.207 | 29.387 | 32.698 | 1.00 | 29.06 | O |
| ATOM | 1507 | OE2 | GLU | A | 202 | 35.148 | 30.920 | 31.490 | 1.00 | 31.04 | O |
| ATOM | 1508 | N | GLN | A | 203 | 31.538 | 26.632 | 27.476 | 1.00 | 22.70 | N |
| ATOM | 1509 | CA | GLN | A | 203 | 31.808 | 25.451 | 26.685 | 1.00 | 22.01 | C |
| ATOM | 1510 | C | GLN | A | 203 | 31.049 | 25.576 | 25.373 | 1.00 | 21.93 | C |
| ATOM | 1511 | O | GLN | A | 203 | 30.113 | 26.378 | 25.253 | 1.00 | 22.49 | O |
| ATOM | 1512 | CB | GLN | A | 203 | 31.409 | 24.169 | 27.427 | 1.00 | 22.02 | C |
| ATOM | 1513 | CG | GLN | A | 203 | 32.287 | 23.822 | 28.657 | 1.00 | 22.33 | C |
| ATOM | 1514 | CD | GLN | A | 203 | 32.103 | 22.379 | 29.165 | 1.00 | 23.14 | C |
| ATOM | 1515 | OE1 | GLN | A | 203 | 31.948 | 21.448 | 28.370 | 1.00 | 21.46 | O |
| ATOM | 1516 | NE2 | GLN | A | 203 | 32.138 | 22.203 | 30.489 | 1.00 | 21.21 | N |
| ATOM | 1517 | N | GLN | A | 204 | 31.486 | 24.807 | 24.380 | 1.00 | 21.81 | N |
| ATOM | 1518 | CA | GLN | A | 204 | 30.806 | 24.720 | 23.092 | 1.00 | 21.45 | C |
| ATOM | 1519 | C | GLN | A | 204 | 29.610 | 23.799 | 23.295 | 1.00 | 21.12 | C |
| ATOM | 1520 | O | GLN | A | 204 | 29.673 | 22.862 | 24.088 | 1.00 | 20.29 | O |
| ATOM | 1521 | CB | GLN | A | 204 | 31.740 | 24.140 | 22.040 | 1.00 | 21.75 | C |
| ATOM | 1522 | CG | GLN | A | 204 | 33.033 | 24.928 | 21.852 | 1.00 | 21.56 | C |
| ATOM | 1523 | CD | GLN | A | 204 | 32.856 | 26.198 | 21.000 | 1.00 | 21.57 | C |
| ATOM | 1524 | OE1 | GLN | A | 204 | 31.741 | 26.609 | 20.692 | 1.00 | 20.30 | O |
| ATOM | 1525 | NE2 | GLN | A | 204 | 33.966 | 26.776 | 20.594 | 1.00 | 18.60 | N |
| ATOM | 1526 | N | ASN | A | 205 | 28.522 | 24.060 | 22.580 | 1.00 | 21.25 | N |
| ATOM | 1527 | CA | ASN | A | 205 | 27.291 | 23.316 | 22.795 | 1.00 | 21.04 | C |
| ATOM | 1528 | C | ASN | A | 205 | 26.529 | 22.977 | 21.526 | 1.00 | 21.25 | C |
| ATOM | 1529 | O | ASN | A | 205 | 26.160 | 23.880 | 20.747 | 1.00 | 20.22 | O |
| ATOM | 1530 | CB | ASN | A | 205 | 26.387 | 24.194 | 23.654 | 1.00 | 21.95 | C |
| ATOM | 1531 | CG | ASN | A | 205 | 25.116 | 23.507 | 24.098 | 1.00 | 21.98 | C |
| ATOM | 1532 | OD1 | ASN | A | 205 | 24.759 | 22.418 | 23.643 | 1.00 | 21.21 | O |
| ATOM | 1533 | ND2 | ASN | A | 205 | 24.400 | 24.178 | 24.979 | 1.00 | 17.72 | N |
| ATOM | 1534 | N | PHE | A | 206 | 26.314 | 21.677 | 21.319 | 1.00 | 19.90 | N |
| ATOM | 1535 | CA | PHE | A | 206 | 25.339 | 21.230 | 20.354 | 1.00 | 19.77 | C |
| ATOM | 1536 | C | PHE | A | 206 | 24.085 | 20.869 | 21.150 | 1.00 | 19.25 | C |
| ATOM | 1537 | O | PHE | A | 206 | 24.094 | 19.939 | 21.959 | 1.00 | 19.15 | O |
| ATOM | 1538 | CB | PHE | A | 206 | 25.849 | 20.049 | 19.545 | 1.00 | 20.09 | C |
| ATOM | 1539 | CG | PHE | A | 206 | 26.786 | 20.442 | 18.454 | 1.00 | 19.77 | C |
| ATOM | 1540 | CD1 | PHE | A | 206 | 26.371 | 21.294 | 17.453 | 1.00 | 22.21 | C |
| ATOM | 1541 | CD2 | PHE | A | 206 | 28.079 | 19.973 | 18.435 | 1.00 | 20.21 | C |
| ATOM | 1542 | CE1 | PHE | A | 206 | 27.213 | 21.643 | 16.434 | 1.00 | 22.06 | C |
| ATOM | 1543 | CE2 | PHE | A | 206 | 28.941 | 20.336 | 17.418 | 1.00 | 20.66 | C |
| ATOM | 1544 | CZ | PHE | A | 206 | 28.504 | 21.190 | 16.427 | 1.00 | 22.18 | C |
| ATOM | 1545 | N | PHE | A | 207 | 23.009 | 21.596 | 20.869 | 1.00 | 18.42 | N |
| ATOM | 1546 | CA | PHE | A | 207 | 21.760 | 21.590 | 21.620 | 1.00 | 18.78 | C |
| ATOM | 1547 | C | PHE | A | 207 | 20.732 | 20.841 | 20.804 | 1.00 | 19.36 | C |
| ATOM | 1548 | O | PHE | A | 207 | 20.241 | 21.359 | 19.818 | 1.00 | 19.26 | O |
| ATOM | 1549 | CE | PHE | A | 207 | 21.366 | 23.063 | 21.836 | 1.00 | 18.70 | C |
| ATOM | 1550 | CG | PHE | A | 207 | 20.120 | 23.301 | 22.635 | 1.00 | 17.94 | C |
| ATOM | 1551 | CD1 | PHE | A | 207 | 18.899 | 23.404 | 22.007 | 1.00 | 17.78 | C |
| ATOM | 1552 | CD2 | PHE | A | 207 | 20.188 | 23.548 | 23.989 | 1.00 | 18.50 | C |
| ATOM | 1553 | CE1 | PHE | A | 207 | 17.772 | 23.684 | 22.713 | 1.00 | 19.52 | C |
| ATOM | 1554 | CE2 | PHE | A | 207 | 19.052 | 23.823 | 24.705 | 1.00 | 20.66 | C |
| ATOM | 1555 | CZ | PHE | A | 207 | 17.836 | 23.909 | 24.053 | 1.00 | 19.44 | C |
| ATOM | 1556 | N | ALA | A | 208 | 20.435 | 19.618 | 21.234 | 1.00 | 19.90 | N |
| ATOM | 1557 | CA | ALA | A | 208 | 19.628 | 18.670 | 20.469 | 1.00 | 20.17 | C |
| ATOM | 1558 | C | ALA | A | 208 | 18.210 | 18.541 | 20.991 | 1.00 | 20.52 | C |
| ATOM | 1559 | O | ALA | A | 208 | 17.971 | 17.946 | 22.047 | 1.00 | 20.61 | O |
| ATOM | 1560 | CB | ALA | A | 208 | 20.294 | 17.308 | 20.494 | 1.00 | 19.33 | C |

TABLE 3-continued

| | | | | | | | | | | | |
|---|---|---|---|---|---|---|---|---|---|---|---|
| | Coordinates for structures 1 to 4 |
| ATOM | 1561 | N | GLN | A | 209 | 17.270 | 19.076 | 20.219 | 1.00 | 20.94 | N |
| ATOM | 1562 | CA | GLN | A | 209 | 15.880 | 19.062 | 20.627 | 1.00 | 20.82 | C |
| ATOM | 1563 | C | GLN | A | 209 | 15.227 | 17.712 | 20.323 | 1.00 | 20.75 | C |
| ATOM | 1564 | O | GLN | A | 209 | 15.401 | 17.129 | 19.224 | 1.00 | 19.59 | O |
| ATOM | 1565 | CE | GLN | A | 209 | 15.141 | 20.216 | 19.961 | 1.00 | 20.91 | C |
| ATOM | 1566 | CG | GLN | A | 209 | 13.735 | 20.431 | 20.463 | 1.00 | 20.52 | C |
| ATOM | 1567 | CD | GLN | A | 209 | 13.673 | 20.840 | 21.928 | 1.00 | 20.69 | C |
| ATOM | 1568 | OE1 | GLN | A | 209 | 14.702 | 21.155 | 22.562 | 1.00 | 19.72 | O |
| ATOM | 1569 | NE2 | GLN | A | 209 | 12.460 | 20.852 | 22.473 | 1.00 | 19.21 | N |
| ATOM | 1570 | N | ILE | A | 210 | 14.442 | 17.248 | 21.296 | 1.00 | 20.72 | N |
| ATOM | 1571 | CA | ILE | A | 210 | 13.853 | 15.922 | 21.252 | 1.00 | 21.43 | C |
| ATOM | 1572 | C | ILE | A | 210 | 12.334 | 15.911 | 21.292 | 1.00 | 21.72 | C |
| ATOM | 1573 | O | ILE | A | 210 | 11.728 | 15.195 | 20.534 | 1.00 | 22.12 | O |
| ATOM | 1574 | CE | ILE | A | 210 | 14.396 | 15.095 | 22.424 | 1.00 | 21.84 | C |
| ATOM | 1575 | CG1 | ILE | A | 210 | 15.859 | 14.733 | 22.156 | 1.00 | 22.48 | C |
| ATOM | 1576 | CG2 | ILE | A | 210 | 13.581 | 13.832 | 22.622 | 1.00 | 21.83 | C |
| ATOM | 1577 | CD1 | ILE | A | 210 | 16.631 | 14.354 | 23.382 | 1.00 | 24.34 | C |
| ATOM | 1578 | N | LYS | A | 211 | 11.728 | 16.677 | 22.188 | 1.00 | 22.08 | N |
| ATOM | 1579 | CA | LYS | A | 211 | 10.279 | 16.715 | 22.319 | 1.00 | 21.72 | C |
| ATOM | 1580 | C | LYS | A | 211 | 9.858 | 18.130 | 22.564 | 1.00 | 21.67 | C |
| ATOM | 1581 | O | LYS | A | 211 | 10.468 | 18.841 | 23.372 | 1.00 | 20.87 | O |
| ATOM | 1582 | CE | LYS | A | 211 | 9.797 | 15.856 | 23.487 | 1.00 | 22.44 | C |
| ATOM | 1583 | CG | LYS | A | 211 | 8.267 | 15.562 | 23.479 | 1.00 | 23.29 | C |
| ATOM | 1584 | CD | LYS | A | 211 | 7.791 | 15.022 | 24.824 | 1.00 | 25.02 | C |
| ATOM | 1585 | CE | LYS | A | 211 | 6.494 | 14.215 | 24.757 | 1.00 | 26.00 | C |
| ATOM | 1586 | NZ | LYS | A | 211 | 5.561 | 14.522 | 23.634 | 1.00 | 26.43 | N |
| ATOM | 1587 | N | GLY | A | 212 | 8.798 | 18.541 | 21.875 | 1.00 | 21.35 | N |
| ATOM | 1588 | CA | GLY | A | 212 | 8.306 | 19.891 | 21.994 | 1.00 | 21.71 | C |
| ATOM | 1589 | C | GLY | A | 212 | 9.195 | 20.906 | 21.297 | 1.00 | 21.63 | C |
| ATOM | 1590 | O | GLY | A | 212 | 10.150 | 20.572 | 20.591 | 1.00 | 21.32 | O |
| ATOM | 1591 | N | TYR | A | 213 | 8.871 | 22.166 | 21.522 | 1.00 | 22.35 | N |
| ATOM | 1592 | CA | TYR | A | 213 | 9.533 | 23.279 | 20.862 | 1.00 | 22.42 | c |
| ATOM | 1593 | C | TYR | A | 213 | 10.028 | 24.293 | 21.868 | 1.00 | 22.33 | C |
| ATOM | 1594 | O | TYR | A | 213 | 9.340 | 24.589 | 22.853 | 1.00 | 21.55 | O |
| ATOM | 1595 | CB | TYR | A | 213 | 8.556 | 23.951 | 19.916 | 1.00 | 23.46 | C |
| ATOM | 1596 | CG | TYR | A | 213 | 8.114 | 23.034 | 18.815 | 1.00 | 24.81 | C |
| ATOM | 1597 | CD1 | TYR | A | 213 | 7.100 | 22.112 | 19.020 | 1.00 | 28.16 | C |
| ATOM | 1598 | CD2 | TYR | A | 213 | 8.751 | 23.051 | 17.589 | 1.00 | 26.74 | C |
| ATOM | 1599 | CE1 | TYR | A | 213 | 6.716 | 21.237 | 18.011 | 1.00 | 28.91 | C |
| ATOM | 1600 | CE2 | TYR | A | 213 | 8.378 | 22.193 | 16.585 | 1.00 | 28.63 | C |
| ATOM | 1601 | CZ | TYR | A | 213 | 7.366 | 21.295 | 16.795 | 1.00 | 29.44 | C |
| ATOM | 1602 | OH | TYR | A | 213 | 7.013 | 20.456 | 15.756 | 1.00 | 33.67 | O |
| ATOM | 1603 | N | LYS | A | 214 | 11.239 | 24.788 | 21.609 | 1.00 | 21.60 | N |
| ATOM | 1604 | CA | LYS | A | 214 | 11.875 | 25.793 | 22.414 | 1.00 | 21.89 | C |
| ATOM | 1605 | C | LYS | A | 214 | 12.312 | 26.947 | 21.528 | 1.00 | 21.62 | C |
| ATOM | 1606 | O | LYS | A | 214 | 12.878 | 26.747 | 20.442 | 1.00 | 22.07 | O |
| ATOM | 1607 | CE | LYS | A | 214 | 13.103 | 25.239 | 23.140 | 1.00 | 22.10 | C |
| ATOM | 1608 | CG | LYS | A | 214 | 12.796 | 24.385 | 24.338 | 1.00 | 22.63 | C |
| ATOM | 1609 | CD | LYS | A | 214 | 14.103 | 23.893 | 24.964 | 1.00 | 24.24 | C |
| ATOM | 1610 | CE | LYS | A | 214 | 13.923 | 23.478 | 26.402 | 1.00 | 23.54 | C |
| ATOM | 1611 | NZ | LYZ | A | 214 | 15.169 | 22.872 | 26.951 | 1.00 | 22.10 | N |
| ATOM | 1612 | N | ARG | A | 215 | 12.007 | 28.156 | 21.974 | 1.00 | 20.97 | N |
| ATOM | 1613 | CA | ARG | A | 215 | 12.447 | 29.347 | 21.277 | 1.00 | 20.73 | C |
| ATOM | 1614 | C | ARG | A | 215 | 13.778 | 29.724 | 21.900 | 1.00 | 20.03 | C |
| ATOM | 1615 | O | ARG | A | 215 | 13.885 | 29.828 | 23.113 | 1.00 | 19.70 | O |
| ATOM | 1616 | CE | ARG | A | 215 | 11.461 | 30.470 | 21.493 | 1.00 | 21.30 | C |
| ATOM | 1617 | CG | ARG | A | 215 | 11.754 | 31.760 | 20.726 | 1.00 | 22.21 | C |
| ATOM | 1618 | CD | ARG | A | 215 | 11.177 | 32.925 | 21.473 | 1.00 | 24.71 | C |
| ATOM | 1619 | NE | ARG | A | 215 | 11.122 | 34.156 | 20.715 | 1.00 | 25.47 | N |
| ATOM | 1620 | CZ | ARG | A | 215 | 10.479 | 35.235 | 21.130 | 1.00 | 26.28 | C |
| ATOM | 1621 | NE1 | ARG | A | 215 | 9.844 | 35.245 | 22.299 | 1.00 | 26.07 | N |
| ATOM | 1622 | NH2 | ARG | A | 215 | 10.483 | 36.314 | 20.384 | 1.00 | 28.83 | N |
| ATOM | 1623 | N | CYS | A | 216 | 14.794 | 29.877 | 21.074 | 1.00 | 19.45 | N |
| ATOM | 1624 | CA | CYS | A | 216 | 16.116 | 30.219 | 21.554 | 1.00 | 19.58 | C |
| ATOM | 1625 | C | CYS | A | 216 | 16.503 | 31.587 | 20.993 | 1.00 | 19.92 | C |
| ATOM | 1626 | O | CYS | A | 216 | 16.503 | 31.774 | 19.789 | 1.00 | 20.16 | O |
| ATOM | 1627 | CE | CYS | A | 216 | 17.110 | 29.186 | 21.073 | 1.00 | 20.01 | C |
| ATOM | 1628 | SG | CYS | A | 216 | 16.693 | 27.450 | 21.462 | 1.00 | 21.39 | S |
| ATOM | 1629 | N | ILE | A | 217 | 16.812 | 32.530 | 21.878 | 1.00 | 19.28 | N |
| ATOM | 1630 | CA | ILE | A | 217 | 17.286 | 33.845 | 21.504 | 1.00 | 19.58 | C |
| ATOM | 1631 | C | ILE | A | 217 | 18.742 | 33.961 | 21.937 | 1.00 | 19.21 | C |
| ATOM | 1632 | O | ILE | A | 217 | 19.055 | 33.849 | 23.126 | 1.00 | 19.05 | O |
| ATOM | 1633 | CB | ILE | A | 217 | 16.424 | 34.943 | 22.168 | 1.00 | 19.88 | C |
| ATOM | 1634 | CG1 | ILE | A | 217 | 14.926 | 34.687 | 21.878 | 1.00 | 20.56 | O |
| ATOM | 1635 | CG2 | ILE | A | 217 | 16.803 | 36.312 | 21.627 | 1.00 | 20.25 | C |
| ATOM | 1636 | CD1 | ILE | A | 217 | 13.984 | 35.692 | 22.488 | 1.00 | 20.99 | C |
| ATOM | 1637 | N | LEU | A | 218 | 19.620 | 34.176 | 20.965 | 1.00 | 19.01 | N |

TABLE 3-continued

| | | | | | | | | | | | |
|---|---|---|---|---|---|---|---|---|---|---|---|
| | Coordinates for structures 1 to 4 |
| ATOM | 1638 | CA | LEU | A | 218 | 21.048 | 34.271 | 21.222 | 1.00 | 19.61 | C |
| ATOM | 1639 | C | LEU | A | 218 | 21.568 | 35.682 | 20.970 | 1.00 | 20.43 | C |
| ATOM | 1640 | O | LEU | A | 218 | 21.018 | 36.414 | 20.136 | 1.00 | 19.76 | O |
| ATOM | 1641 | CD | LEU | A | 218 | 21.816 | 33.329 | 20.308 | 1.00 | 19.66 | C |
| ATOM | 1642 | CG | LEU | A | 218 | 21.906 | 31.881 | 20.778 | 1.00 | 19.74 | C |
| ATOM | 1643 | CD1 | LEU | A | 218 | 20.549 | 31.237 | 20.905 | 1.00 | 20.56 | C |
| ATOM | 1644 | CD2 | LEU | A | 218 | 22.733 | 31.099 | 19.798 | 1.00 | 21.32 | C |
| ATOM | 1645 | N | PHE | A | 219 | 22.626 | 36.046 | 21.700 | 1.00 | 20.11 | N |
| ATOM | 1646 | CA | PHE | A | 219 | 23.282 | 37.324 | 21.524 | 1.00 | 20.96 | C |
| ATOM | 1647 | C | PHE | A | 219 | 24.805 | 37.078 | 21.453 | 1.00 | 21.19 | C |
| ATOM | 1648 | O | PHE | A | 219 | 25.351 | 36.313 | 22.257 | 1.00 | 21.20 | O |
| ATOM | 1649 | CE | PHE | A | 219 | 22.942 | 38.304 | 22.678 | 1.00 | 20.97 | C |
| ATOM | 1650 | CG | PHE | A | 219 | 21.463 | 38.456 | 22.954 | 1.00 | 20.44 | C |
| ATOM | 1651 | CO1 | PHE | A | 219 | 20.821 | 37.637 | 23.846 | 1.00 | 21.46 | C |
| ATOM | 1652 | CD2 | PHE | A | 219 | 20.724 | 39.447 | 22.334 | 1.00 | 22.49 | C |
| ATOM | 1653 | CE1 | PHE | A | 219 | 19.472 | 37.790 | 24.108 | 1.00 | 22.33 | C |
| ATOM | 1654 | CE2 | PHE | A | 219 | 19.387 | 39.605 | 22.605 | 1.00 | 21.32 | C |
| ATOM | 1655 | CS | PHE | A | 219 | 18.760 | 38.773 | 23.480 | 1.00 | 21.50 | C |
| ATOM | 1656 | N | PRO | A | 220 | 25.485 | 37.705 | 20.498 | 1.00 | 21.20 | N |
| ATOM | 1657 | CA | PRO | A | 220 | 26.936 | 37.541 | 20.368 | 1.00 | 21.72 | C |
| ATOM | 1658 | C | PRO | A | 220 | 27.683 | 38.108 | 21.569 | 1.00 | 21.31 | C |
| ATOM | 1659 | O | PRO | A | 220 | 27.165 | 38.972 | 22.280 | 1.00 | 20.90 | O |
| ATOM | 1660 | CB | PRO | A | 220 | 27.302 | 38.341 | 19.120 | 1.00 | 21..41 | C |
| ATOM | 1661 | CG | PRO | A | 220 | 26.020 | 38.781 | 18.510 | 1.00 | 23.12 | C |
| ATOM | 1662 | CD | PRO | A | 220 | 24.938 | 38.637 | 19.508 | 1.00 | 22.22 | C |
| ATOM | 1663 | N | PRO | A | 221 | 28.884 | 37.594 | 21.806 | 1.00 | 21.46 | N |
| ATOM | 1664 | CA | PRO | A | 221 | 29.721 | 38.053 | 22.918 | 1.00 | 21.33 | C |
| ATOM | 1665 | C | PRO | A | 221 | 29.961 | 39.556 | 22.940 | 1.00 | 21.04 | C |
| ATOM | 1666 | O | PRO | A | 221 | 30.220 | 40.096 | 24.009 | 1.00 | 20.68 | O |
| ATOM | 1667 | CB | PRO | A | 221 | 31.032 | 37.325 | 22.681 | 1.00 | 21.42 | C |
| ATOM | 1668 | CG | PRO | A | 221 | 30.656 | 36.134 | 21.939 | 1.00 | 22.42 | C |
| ATOM | 1669 | CD | PRO | A | 221 | 29.522 | 36.510 | 21.041 | 1.00 | 21.53 | C |
| ATOM | 1670 | N | ASP | A | 222 | 29.877 | 40.225 | 21.792 | 1.00 | 21.47 | N |
| ATOM | 1671 | CA | ASP | A | 222 | 30.128 | 41.669 | 21.749 | 1.00 | 21.80 | C |
| ATOM | 1672 | C | ASP | A | 222 | 28.946 | 42.464 | 22.271 | 1.00 | 21.74 | C |
| ATOM | 1673 | O | ASP | A | 222 | 28.970 | 43.685 | 22.261 | 1.00 | 22.16 | O |
| ATOM | 1674 | CB | ASP | A | 222 | 30.568 | 42.148 | 20.355 | 1.00 | 21.85 | C |
| ATOM | 1675 | CG | ASP | A | 222 | 29.433 | 42.151 | 19.325 | 1.00 | 24.83 | C |
| ATOM | 1676 | OD1 | ASP | A | 222 | 28.311 | 41.668 | 19.585 | 1.00 | 25.32 | O |
| ATOM | 1677 | OD2 | ASP | A | 222 | 29.595 | 42.607 | 18.186 | 1.00 | 29.30 | O |
| ATOM | 1678 | N | GLN | A | 223 | 27.916 | 41.775 | 22.748 | 1.00 | 21.94 | N |
| ATOM | 1679 | CA | GLN | A | 223 | 26.794 | 42.453 | 23.388 | 1.00 | 22.17 | C |
| ATOM | 1680 | C | GLN | A | 223 | 26.897 | 42.388 | 24.928 | 1.00 | 21.93 | C |
| ATOM | 1681 | O | GLN | A | 223 | 25.926 | 42.681 | 25.660 | 1.00 | 21.70 | O |
| ATOM | 1682 | CB | GLN | A | 223 | 25.456 | 41.911 | 22.832 | 1.00 | 22.84 | C |
| ATOM | 1683 | CG | GLN | A | 223 | 25.149 | 42.508 | 21.412 | 1.00 | 25.34 | C |
| ATOM | 1684 | CD | GLN | A | 223 | 23.728 | 42.283 | 20.965 | 1.00 | 27.81 | C |
| ATOM | 1685 | OE1 | GLN | A | 223 | 22.801 | 42.473 | 21.750 | 1.00 | 30.00 | O |
| ATOM | 1686 | NE2 | GLN | A | 223 | 23.543 | 41.850 | 19.709 | 1.00 | 29.69 | N |
| ATOM | 1687 | N | PHE | A | 224 | 28.079 | 42.027 | 25.417 | 1.00 | 21.04 | N |
| ATOM | 1688 | CA | PHE | A | 224 | 28.363 | 42.035 | 26.860 | 1.00 | 21.41 | C |
| ATOM | 1689 | C | PHE | A | 224 | 27.886 | 43.350 | 27.527 | 1.00 | 21.57 | C |
| ATOM | 1690 | O | PHE | A | 224 | 27.240 | 43.315 | 28.561 | 1.00 | 21.34 | O |
| ATOM | 1691 | CB | PHE | A | 224 | 29.883 | 41.874 | 27.076 | 1.00 | 20.95 | C |
| ATOM | 1692 | CG | PHE | A | 224 | 30.304 | 41.773 | 28.529 | 1.00 | 21.82 | C |
| ATOM | 1693 | CD1 | PHE | A | 224 | 30.452 | 42.912 | 29.319 | 1.00 | 19.33 | C |
| ATOM | 1694 | CD2 | PHE | A | 224 | 30.595 | 40.552 | 29.089 | 1.00 | 20.01 | C |
| ATOM | 1695 | CE1 | PHE | A | 224 | 30.870 | 42.807 | 30.630 | 1.00 | 20.89 | C |
| ATOM | 1696 | CE2 | PHE | A | 224 | 31.025 | 40.449 | 30.397 | 1.00 | 20.59 | C |
| ATOM | 1697 | CZ | PHE | A | 224 | 31.151 | 41.579 | 31.171 | 1.00 | 20.99 | C |
| ATOM | 1698 | N | GLU | A | 225 | 28.195 | 44.495 | 26.916 | 1.00 | 22.10 | N |
| ATOM | 1699 | CA | GLU | A | 225 | 27.823 | 45.800 | 27.466 | 1.00 | 23.01 | C |
| ATOM | 1700 | C | GLU | A | 225 | 26.337 | 46.042 | 27.574 | 1.00 | 22.26 | C |
| ATOM | 1701 | O | GLU | A | 225 | 25.928 | 46.946 | 28.311 | 1.00 | 21.91 | O |
| ATOM | 1702 | CB | GLU | A | 225 | 28.401 | 46.935 | 26.624 | 1.00 | 24.27 | C |
| ATOM | 1703 | CG | GLU | A | 225 | 29.886 | 47.133 | 26.857 | 1.00 | 29.26 | C |
| ATOM | 1704 | CD | GLU | A | 225 | 30.312 | 48.579 | 27.062 | 1.00 | 35.91 | C |
| ATOM | 1705 | OE1 | GLU | A | 225 | 29.745 | 49.317 | 27.942 | 1.00 | 39.92 | O |
| ATOM | 1706 | OE2 | GLU | A | 225 | 31.281 | 48.958 | 26.368 | 1.00 | 40.78 | O |
| ATOM | 1707 | N | CYS | A | 226 | 25.539 | 45.258 | 26.836 | 1.00 | 21.15 | N |
| ATOM | 1708 | CA | CYS | A | 226 | 24.081 | 45.396 | 26.851 | 1.00 | 21.01 | C |
| ATOM | 1709 | C | CYS | A | 226 | 23.359 | 44.417 | 27.768 | 1.00 | 20.67 | C |
| ATOM | 1710 | O | CYS | A | 226 | 22.159 | 44.601 | 28.043 | 1.00 | 18.85 | O |
| ATOM | 1711 | CB | CYS | A | 226 | 23.520 | 45.190 | 25.447 | 1.00 | 20.88 | C |
| ATOM | 1712 | SG | CYS | A | 226 | 24.194 | 46.296 | 24.190 | 1.00 | 22.39 | S |
| ATOM | 1713 | N | LEU | A | 227 | 24.085 | 43.399 | 28.256 | 1.00 | 20.56 | N |
| ATOM | 1714 | CA | LEU | A | 227 | 23.461 | 42.304 | 28.985 | 1.00 | 20.48 | C |

TABLE 3-continued

Coordinates for structures 1 to 4

| ATOM | 1715 | C | LEU | A | 227 | 23.795 | 42.185 | 30.466 | 1.00 | 20.42 | C |
|---|---|---|---|---|---|---|---|---|---|---|---|
| ATOM | 1716 | O | LEU | A | 227 | 23.180 | 41.398 | 31.187 | 1.00 | 20.78 | O |
| ATOM | 1717 | CB | LEU | A | 227 | 23.737 | 41.003 | 28.232 | 1.00 | 21.20 | C |
| ATOM | 1718 | CG | LEU | A | 227 | 22.865 | 40.993 | 26.963 | 1.00 | 22.96 | C |
| ATOM | 1719 | CD1 | LEU | A | 227 | 23.373 | 40.023 | 25.929 | 1.00 | 24.99 | C |
| ATOM | 1720 | CD2 | LEU | A | 227 | 21.420 | 40.655 | 27.323 | 1.00 | 24.79 | C |
| ATOM | 1721 | N | TYR | A | 228 | 24.793 | 42.939 | 30.901 | 1.00 | 20.08 | N |
| ATOM | 1722 | CA | TYR | A | 228 | 25.060 | 43.127 | 32.303 | 1.00 | 19.66 | C |
| ATOM | 1723 | C | TYR | A | 228 | 25.061 | 41.858 | 33.165 | 1.00 | 19.95 | C |
| ATOM | 1724 | O | TYR | A | 228 | 24.229 | 41.697 | 34.058 | 1.00 | 19.69 | O |
| ATOM | 1725 | CS | TYR | A | 228 | 24.050 | 44.137 | 32.857 | 1.00 | 19.77 | C |
| ATOM | 1726 | CG | TYR | A | 228 | 24.028 | 45.481 | 32.119 | 1.00 | 19.37 | C |
| ATOM | 1727 | CD1 | TYR | A | 228 | 24.836 | 46.513 | 32.515 | 1.00 | 18.65 | C |
| ATOM | 1728 | CD2 | TYR | A | 228 | 23.180 | 45.697 | 31.036 | 1.00 | 19.82 | C |
| ATOM | 1729 | CE1 | TYR | A | 228 | 24.819 | 47.759 | 31.862 | 1.00 | 20.56 | C |
| ATOM | 1730 | CE2 | TYR | A | 228 | 23.143 | 46.920 | 30.380 | 1.00 | 20.78 | C |
| ATOM | 1731 | CZ | TYR | A | 228 | 23.962 | 47.956 | 30.801 | 1.00 | 20.88 | C |
| ATOM | 1732 | OH | TYR | A | 228 | 23.944 | 49.174 | 30.152 | 1.00 | 19.73 | O |
| ATOM | 1733 | N | PRO | A | 229 | 26.028 | 40.981 | 32.941 | 1.00 | 19.99 | N |
| ATOM | 1734 | CA | PRO | A | 229 | 26.140 | 39.781 | 33.768 | 1.00 | 20.44 | C |
| ATOM | 1735 | C | PRO | A | 229 | 26.481 | 40.141 | 35.196 | 1.00 | 19.99 | C |
| ATOM | 1736 | O | PRO | A | 229 | 27.130 | 41.166 | 35.451 | 1.00 | 20.03 | O |
| ATOM | 1737 | CB | PRO | A | 229 | 27.334 | 39.043 | 33.157 | 1.00 | 20.11 | C |
| ATOM | 1738 | CG | PRO | A | 229 | 28.125 | 40.130 | 32.541 | 1.00 | 21.04 | C |
| ATOM | 1739 | CD | PRO | A | 229 | 27.099 | 41.050 | 31.935 | 1.00 | 19.79 | C |
| ATOM | 1740 | N | TYR | A | 230 | 26.044 | 39.294 | 36.115 | 1.00 | 19.50 | N |
| ATOM | 1741 | CA | TYR | A | 230 | 26.348 | 39.458 | 37.511 | 1.00 | 19.17 | C |
| ATOM | 1742 | C | TYR | A | 230 | 27.860 | 39.464 | 37.704 | 1.00 | 19.14 | C |
| ATOM | 1743 | O | TYR | A | 230 | 28.598 | 39.060 | 36.832 | 1.00 | 18.83 | O |
| ATOM | 1744 | CB | TYR | A | 230 | 25.746 | 38.313 | 38.320 | 1.00 | 18.51 | C |
| ATOM | 1745 | CG | TYR | A | 230 | 24.253 | 38.411 | 38.531 | 1.00 | 18.95 | C |
| ATOM | 1746 | CD1 | TYR | A | 230 | 23.368 | 37.949 | 37.560 | 1.00 | 18.39 | C |
| ATOM | 1747 | CD2 | TYR | A | 230 | 23.719 | 38.969 | 39.707 | 1.00 | 18.65 | C |
| ATOM | 1748 | CE1 | TYR | A | 230 | 22.001 | 38.006 | 37.751 | 1.00 | 17.34 | C |
| ATOM | 1749 | CE2 | TYR | A | 230 | 22.337 | 39.043 | 39.903 | 1.00 | 17.05 | C |
| ATOM | 1750 | CZ | TYR | A | 230 | 21.492 | 38.550 | 38.909 | 1.00 | 17.79 | C |
| ATOM | 1751 | OH | TYR | A | 230 | 20.127 | 38.601 | 39.051 | 1.00 | 19.77 | O |
| ATOM | 1752 | N | PRO | A | 231 | 28.316 | 39.963 | 38.843 | 1.00 | 19.95 | N |
| ATOM | 1753 | CA | PRO | A | 231 | 29.722 | 39.829 | 39.213 | 1.00 | 20.42 | C |
| ATOM | 1754 | C | PRO | A | 231 | 30.157 | 38.339 | 39.187 | 1.00 | 20.93 | C |
| ATOM | 1755 | O | PRO | A | 231 | 29.345 | 37.463 | 39.506 | 1.00 | 20.71 | O |
| ATOM | 1756 | CB | PRO | A | 231 | 29.755 | 40.369 | 40.642 | 1.00 | 20.70 | C |
| ATOM | 1757 | CG | PRO | A | 231 | 28.588 | 41.341 | 40.716 | 1.00 | 20.76 | C |
| ATOM | 1758 | CD | PRO | A | 231 | 27.528 | 40.701 | 39.845 | 1.00 | 19.53 | C |
| ATOM | 1759 | N | VAL | A | 232 | 31.413 | 38.067 | 38.831 | 1.00 | 20.93 | N |
| ATOM | 1760 | CA | VAL | A | 232 | 31.906 | 36.685 | 38.742 | 1.00 | 21.31 | C |
| ATOM | 1761 | C | VAL | A | 232 | 31.722 | 35.843 | 40.014 | 1.00 | 20.95 | C |
| ATOM | 1762 | O | VAL | A | 232 | 31.431 | 34.650 | 39.934 | 1.00 | 20.50 | O |
| ATOM | 1763 | CS | VAL | A | 232 | 33.398 | 36.655 | 38.304 | 1.00 | 21.35 | C |
| ATOM | 1764 | CG1 | VAL | A | 232 | 34.029 | 35.280 | 38.552 | 1.00 | 22.23 | C |
| ATOM | 1765 | CG2 | VAL | A | 232 | 33.533 | 37.031 | 36.850 | 1.00 | 21.71 | C |
| ATOM | 1766 | N | HIS | A | 233 | 31.872 | 36.455 | 41.181 | 1.00 | 21.10 | N |
| ATOM | 1767 | CA | HIS | A | 233 | 31.742 | 35.721 | 42.438 | 1.00 | 21.01 | C |
| ATOM | 1768 | C | HIS | A | 233 | 30.302 | 35.571 | 42.944 | 1.00 | 20.95 | C |
| ATOM | 1769 | O | HIS | A | 233 | 30.045 | 34.864 | 43.914 | 1.00 | 19.92 | O |
| ATOM | 1770 | CB | HIS | A | 233 | 32.606 | 36.363 | 43.501 | 1.00 | 21.12 | C |
| ATOM | 1771 | CG | HIS | A | 233 | 34.063 | 36.342 | 43.174 | 1.00 | 21.52 | C |
| ATOM | 1772 | ND1 | HIS | A | 233 | 34.720 | 37.424 | 42.625 | 1.00 | 22.78 | N |
| ATOM | 1773 | CD2 | HIS | A | 233 | 34.993 | 35.368 | 43.318 | 1.00 | 22.27 | C |
| ATOM | 1774 | CE1 | HIS | A | 233 | 35.994 | 37.114 | 42.446 | 1.00 | 24.00 | C |
| ATOM | 1775 | ND2 | HIS | A | 233 | 36.186 | 35.870 | 42.857 | 1.00 | 23.34 | N |
| ATOM | 1776 | N | HIS | A | 234 | 29.364 | 36.236 | 42.288 | 1.00 | 20.94 | N |
| ATOM | 1777 | CA | HIS | A | 234 | 27.959 | 36.081 | 42.630 | 1.00 | 21.27 | C |
| ATOM | 1778 | C | HIS | A | 234 | 27.493 | 34.722 | 42.103 | 1.00 | 21.28 | C |
| ATOM | 1779 | O | HIS | A | 234 | 28.022 | 34.233 | 41.107 | 1.00 | 21.02 | O |
| ATOM | 1780 | CB | HIS | A | 234 | 27.169 | 37.203 | 41.989 | 1.00 | 21.52 | C |
| ATOM | 1781 | CG | HIS | A | 234 | 25.730 | 37.253 | 42.374 | 1.00 | 21.54 | C |
| ATOM | 1782 | ND1 | HIS | A | 234 | 24.769 | 36.498 | 41.740 | 1.00 | 21.95 | N |
| ATOM | 1783 | CD2 | HIS | A | 234 | 25.073 | 38.028 | 43.269 | 1.00 | 22.67 | C |
| ATOM | 1784 | CE1 | HIS | A | 234 | 23.585 | 36.779 | 42.254 | 1.00 | 22.38 | C |
| ATOM | 1785 | ND2 | HIS | A | 234 | 23.743 | 37.700 | 43.187 | 1.00 | 21.91 | N |
| ATOM | 1786 | N | PRO | A | 235 | 26.551 | 34.087 | 42.792 | 1.00 | 21.11 | N |
| ATOM | 1787 | CA | PRO | A | 235 | 25.999 | 32.809 | 42.338 | 1.00 | 21.46 | C |
| ATOM | 1788 | C | PRO | A | 235 | 25.461 | 32.835 | 40.916 | 1.00 | 21.10 | C |
| ATOM | 1789 | O | PRO | A | 235 | 25.517 | 31.802 | 40.244 | 1.00 | 20.37 | O |
| ATOM | 1790 | CE | PRO | A | 235 | 24.860 | 32.551 | 43.325 | 1.00 | 21.90 | C |
| ATOM | 1791 | CG | PRO | A | 235 | 25.316 | 33.240 | 44.574 | 1.00 | 22.00 | C |

TABLE 3-continued

| | | | | | | Coordinates for structures 1 to 4 | | | | |
|---|---|---|---|---|---|---|---|---|---|---|
| ATOM | 1792 | CD | PRO | A | 235 | 26.007 | 34.485 | 44.100 | 1.00 | 21.41 | C |
| ATOM | 1793 | N | CYS | A | 236 | 24.997 | 33.989 | 40.452 | 1.00 | 20.41 | N |
| ATOM | 1794 | CA | CYS | A | 236 | 24.456 | 34.077 | 39.110 | 1.00 | 20.17 | C |
| ATOM | 1795 | C | CYS | A | 236 | 25.503 | 34.554 | 38.107 | 1.00 | 20.00 | C |
| ATOM | 1796 | O | CYS | A | 236 | 25.180 | 35.111 | 37.061 | 1.00 | 20.30 | O |
| ATOM | 1797 | CE | CYS | A | 236 | 23.195 | 34.924 | 39.090 | 1.00 | 19.66 | C |
| ATOM | 1798 | SG | CYS | A | 236 | 21.914 | 34.209 | 40.133 | 1.00 | 20.71 | S |
| ATOM | 1799 | N | ASP | A | 237 | 26.768 | 34.311 | 38.433 | 1.00 | 19.87 | N |
| ATOM | 1800 | CA | ASP | A | 237 | 27.857 | 34.498 | 37.485 | 1.00 | 19.60 | C |
| ATOM | 1801 | C | ASP | A | 237 | 27.459 | 33.915 | 36.105 | 1.00 | 19.48 | C |
| ATOM | 1802 | O | ASP | A | 237 | 26.883 | 32.834 | 36.020 | 1.00 | 18.94 | O |
| ATOM | 1803 | CB | ASP | A | 237 | 29.075 | 33.789 | 38.031 | 1.00 | 19.20 | C |
| ATOM | 1804 | CG | ASP | A | 237 | 30.268 | 33.842 | 37.107 | 1.00 | 20.58 | C |
| ATOM | 1805 | OD1 | ASP | A | 237 | 30.477 | 34.871 | 36.373 | 1.00 | 18.56 | O |
| ATOM | 1806 | OD2 | ASP | A | 237 | 31.070 | 32.868 | 37.077 | 1.00 | 19.51 | O |
| ATOM | 1807 | N | ARG | A | 238 | 27.749 | 34.675 | 35.056 | 1.00 | 19.85 | N |
| ATOM | 1808 | CA | ARG | A | 238 | 27.459 | 34.332 | 33.664 | 1.00 | 20.90 | C |
| ATOM | 1809 | C | ARG | A | 238 | 26.002 | 34.572 | 33.247 | 1.00 | 20.67 | C |
| ATOM | 1810 | O | ARG | A | 238 | 25.709 | 34.491 | 32.059 | 1.00 | 21.20 | O |
| ATOM | 1811 | CE | ARG | A | 238 | 27.854 | 32.876 | 33.319 | 1.00 | 21.44 | C |
| ATOM | 1812 | CG | ARG | A | 238 | 29.330 | 32.585 | 33.482 | 1.00 | 21.04 | C |
| ATOM | 1813 | CD | ARG | A | 238 | 29.710 | 31.150 | 33.145 | 1.00 | 22.38 | C |
| ATOM | 1814 | NE | ARG | A | 238 | 29.080 | 30.243 | 34.085 | 1.00 | 23.86 | N |
| ATOM | 1815 | CZ | ARG | A | 238 | 27.937 | 29.584 | 33.874 | 1.00 | 25.81 | C |
| ATOM | 1816 | NH1 | ARG | A | 238 | 27.262 | 29.686 | 32.712 | 1.00 | 24.18 | N |
| ATOM | 1817 | NH2 | ARG | A | 238 | 27.471 | 28.810 | 34.849 | 1.00 | 27.18 | N |
| ATOM | 1818 | N | GLN | A | 239 | 25.105 | 34.845 | 34.190 | 1.00 | 19.94 | N |
| ATOM | 1819 | CA | GLN | A | 239 | 23.722 | 35.141 | 33.833 | 1.00 | 20.58 | C |
| ATOM | 1820 | C | GLN | A | 239 | 23.535 | 36.661 | 33.740 | 1.00 | 20.50 | C |
| ATOM | 1821 | O | GLN | A | 239 | 24.219 | 37.402 | 34.446 | 1.00 | 20.63 | O |
| ATOM | 1822 | CE | GLN | A | 239 | 22.735 | 34.591 | 34.863 | 1.00 | 20.32 | C |
| ATOM | 1823 | CG | GLN | A | 239 | 23.159 | 33.314 | 35.594 | 1.00 | 20.84 | C |
| ATOM | 1824 | CD | GLN | A | 239 | 23.367 | 32.137 | 34.673 | 1.00 | 21.23 | C |
| ATOM | 1825 | OE2 | GLN | A | 239 | 22.434 | 31.675 | 34.014 | 1.00 | 21.22 | O |
| ATOM | 1826 | NE2 | GLN | A | 239 | 24.591 | 31.655 | 34.616 | 1.00 | 20.93 | N |
| ATOM | 1827 | N | SER | A | 240 | 22.600 | 37.112 | 32.900 | 1.00 | 20.07 | N |
| ATOM | 1828 | CA | SER | A | 240 | 22.282 | 38.533 | 32.768 | 1.00 | 20.18 | C |
| ATOM | 1829 | C | SER | A | 240 | 21.498 | 39.027 | 33.969 | 1.00 | 20.71 | C |
| ATOM | 1830 | O | SER | A | 240 | 20.619 | 38.316 | 34.467 | 1.00 | 20.85 | O |
| ATOM | 1831 | CE | SER | A | 240 | 21.405 | 38.776 | 31.539 | 1.00 | 20.29 | C |
| ATOM | 1832 | OG | SER | A | 240 | 21.007 | 40.137 | 31.454 | 1.00 | 21.43 | O |
| ATOM | 1833 | N | GLN | A | 241 | 21.793 | 40.246 | 34.426 | 1.00 | 20.46 | N |
| ATOM | 1834 | CA | GLN | A | 241 | 21.013 | 40.839 | 35.496 | 1.00 | 20.42 | C |
| ATOM | 1835 | C | GLN | A | 241 | 19.711 | 41.433 | 34.965 | 1.00 | 20.26 | C |
| ATOM | 1836 | O | GLN | A | 241 | 18.839 | 41.767 | 35.726 | 1.00 | 19.62 | O |
| ATOM | 1837 | CE | GLN | A | 241 | 21.770 | 41.949 | 36.201 | 1.00 | 20.32 | C |
| ATOM | 1838 | CG | GLN | A | 241 | 23.019 | 41.544 | 36.912 | 1.00 | 20.58 | C |
| ATOM | 1839 | CD | GLN | A | 241 | 23.771 | 42.767 | 37.423 | 1.00 | 21.94 | C |
| ATOM | 1840 | OE1 | GLN | A | 241 | 23.524 | 43.210 | 38.514 | 1.00 | 23.52 | O |
| ATOM | 1841 | NE2 | GLN | A | 241 | 24.670 | 43.304 | 36.624 | 1.00 | 20.84 | N |
| ATOM | 1842 | N | VAL | A | 242 | 19.557 | 41.563 | 33.659 | 1.00 | 20.57 | N |
| ATOM | 1843 | CA | VAL | A | 242 | 18.361 | 42.229 | 33.182 | 1.00 | 20.73 | C |
| ATOM | 1844 | C | VAL | A | 242 | 17.173 | 41.309 | 33.246 | 1.00 | 20.69 | C |
| ATOM | 1845 | O | VAL | A | 242 | 17.244 | 40.190 | 32.757 | 1.00 | 21.13 | O |
| ATOM | 1846 | CE | VAL | A | 242 | 18.498 | 42.667 | 31.712 | 1.00 | 21.03 | C |
| ATOM | 1847 | CG1 | VAL | A | 242 | 17.204 | 43.377 | 31.250 | 1.00 | 20.85 | C |
| ATOM | 1848 | CG2 | VAL | A | 242 | 19.723 | 43.527 | 31.498 | 1.00 | 20.71 | C |
| ATOM | 1849 | N | ASP | A | 243 | 16.071 | 41.786 | 33.813 | 1.00 | 20.62 | N |
| ATOM | 1850 | CA | ASP | A | 243 | 14.807 | 41.042 | 33.788 | 1.00 | 20.64 | C |
| ATOM | 1851 | C | ASP | A | 243 | 14.148 | 41.348 | 32.448 | 1.00 | 20.94 | C |
| ATOM | 1852 | O | ASP | A | 243 | 13.591 | 42.438 | 32.230 | 1.00 | 19.75 | O |
| ATOM | 1853 | CE | ASP | A | 243 | 13.916 | 41.471 | 34.963 | 1.00 | 20.88 | C |
| ATOM | 1854 | CC | ASP | A | 243 | 12.526 | 40.894 | 34.898 | 1.00 | 21.39 | C |
| ATOM | 1855 | OD1 | ASP | A | 243 | 12.209 | 40.153 | 33.941 | 1.00 | 23.25 | O |
| ATOM | 1856 | OD2 | ASP | A | 243 | 11.672 | 41.130 | 35.784 | 1.00 | 23.49 | O |
| ATOM | 1857 | N | PHE | A | 244 | 14.238 | 40.385 | 31.541 | 1.00 | 21.19 | N |
| ATOM | 1858 | CA | PHE | A | 244 | 13.717 | 40.549 | 30.197 | 1.00 | 21.56 | C |
| ATOM | 1859 | C | PHE | A | 244 | 12.225 | 40.916 | 30.204 | 1.00 | 22.49 | C |
| ATOM | 1860 | O | PHE | A | 244 | 11.734 | 41.521 | 29.260 | 1.00 | 21.85 | O |
| ATOM | 1861 | CE | PHE | A | 244 | 13.940 | 39.275 | 29.378 | 1.00 | 21.85 | C |
| ATOM | 1862 | CC | PHE | A | 244 | 15.316 | 39.152 | 28.743 | 1.00 | 20.87 | C |
| ATOM | 1863 | CO1 | PHE | A | 244 | 16.457 | 39.540 | 29.399 | 1.00 | 20.74 | C |
| ATOM | 1864 | CD2 | PHE | A | 244 | 15.446 | 38.617 | 27.483 | 1.00 | 21.00 | C |
| ATOM | 1865 | CE1 | PHE | A | 244 | 17.691 | 39.407 | 28.810 | 1.00 | 19.77 | C |
| ATOM | 1866 | CE2 | PHE | A | 244 | 16.687 | 38.470 | 26.890 | 1.00 | 20.94 | C |
| ATOM | 1867 | CZ | PHE | A | 244 | 17.805 | 38.881 | 27.551 | 1.00 | 20.34 | C |
| ATOM | 1868 | N | ASP | A | 245 | 11.500 | 40.554 | 31.259 | 1.00 | 23.56 | N |

TABLE 3-continued

| | | | | | | | | | | |
|---|---|---|---|---|---|---|---|---|---|---|
| | | | | | Coordinates for structures 1 to 4 | | | | | |
| ATOM | 1869 | CA | ASP | A | 245 | 10.072 | 40.831 | 31.311 | 1.00 | 24.26 | C |
| ATOM | 1870 | C | ASP | A | 245 | 9.794 | 42.256 | 31.814 | 1.00 | 24.66 | C |
| ATOM | 1871 | O | ASP | A | 245 | 8.711 | 42.762 | 31.607 | 1.00 | 24.21 | O |
| ATOM | 1872 | CE | ASP | A | 245 | 9.353 | 39.841 | 32.222 | 1.00 | 24.74 | C |
| ATOM | 1873 | CG | ASP | A | 245 | 9.408 | 38.427 | 31.721 | 1.00 | 26.56 | C |
| ATOM | 1874 | OD1 | ASP | A | 245 | 9.368 | 38.210 | 30.493 | 1.00 | 28.81 | O |
| ATOM | 1875 | OD2 | ASP | A | 245 | 9.489 | 37.455 | 32.498 | 1.00 | 28.39 | O |
| ATOM | 1876 | N | ASN | A | 246 | 10.758 | 42.876 | 32.492 | 1.00 | 24.80 | N |
| ATOM | 1877 | CA | ASN | A | 246 | 10.605 | 44.244 | 32.989 | 1.00 | 25.56 | C |
| ATOM | 1878 | C | ASN | A | 246 | 11.960 | 44.902 | 33.106 | 1.00 | 25.31 | C |
| ATOM | 1879 | O | ASN | A | 246 | 12.500 | 45.064 | 34.205 | 1.00 | 25.43 | O |
| ATOM | 1880 | CE | ASN | A | 246 | 9.912 | 44.285 | 34.345 | 1.00 | 26.09 | C |
| ATOM | 1881 | CC | ASN | A | 246 | 9.555 | 45.716 | 34.765 | 1.00 | 29.59 | C |
| ATOM | 1882 | OD1 | ASN | A | 246 | 9.366 | 46.598 | 33.912 | 1.00 | 32.67 | O |
| ATOM | 1883 | ND2 | ASN | A | 246 | 9.468 | 45.954 | 36.075 | 1.00 | 33.42 | N |
| ATOM | 1884 | N | PRO | A | 247 | 12.525 | 45.257 | 31.96.1 | 1.00 | 25.08 | N |
| ATOM | 1885 | CA | PRO | A | 247 | 13.885 | 45.782 | 31.911 | 1.00 | 24.89 | C |
| ATOM | 1886 | C | PRO | A | 247 | 13.992 | 47.144 | 32.579 | 1.00 | 24.95 | C |
| ATOM | 1887 | O | PRO | A | 247 | 13.217 | 48.049 | 32.297 | 1.00 | 24.55 | O |
| ATOM | 1888 | CE | PRO | A | 247 | 14.182 | 45.899 | 30.413 | 1.00 | 25.05 | C |
| ATOM | 1889 | CC | PRO | A | 247 | 13.016 | 45.325 | 29.702 | 1.00 | 25.39 | C |
| ATOM | 1890 | CD | PRO | A | 247 | 11.890 | 45.184 | 30.640 | 1.00 | 25.02 | C |
| ATOM | 1891 | N | ASP | A | 248 | 14.976 | 47.267 | 33.460 | 1.00 | 24.53 | N |
| ATOM | 1892 | CA | ASP | A | 248 | 15.216 | 48.489 | 34.167 | 1.00 | 24.65 | C |
| ATOM | 1893 | C | ASP | A | 248 | 16.271 | 49.284 | 33.389 | 1.00 | 24.54 | C |
| ATOM | 1894 | O | ASP | A | 248 | 17.472 | 49.077 | 33.552 | 1.00 | 23.15 | O |
| ATOM | 1895 | CE | ASP | A | 248 | 15.706 | 48.144 | 35.564 | 1.00 | 24.64 | C |
| ATOM | 1896 | CC | ASP | A | 248 | 15.787 | 49.343 | 36.454 | 1.00 | 26.02 | C |
| ATOM | 1897 | OD1 | ASP | A | 248 | 16.035 | 50.466 | 35.944 | 1.00 | 26.95 | O |
| ATOM | 1898 | OD2 | ASP | A | 248 | 15.609 | 49.249 | 37.684 | 1.00 | 27.69 | O |
| ATOM | 1899 | N | TYR | A | 249 | 15.812 | 50.181 | 32.525 | 1.00 | 24.81 | N |
| ATOM | 1900 | CA | TYR | A | 249 | 16.720 | 50.936 | 31.673 | 1.00 | 25.45 | C |
| ATOM | 1901 | C | TYR | A | 249 | 17.573 | 51.954 | 32.426 | 1.00 | 25.90 | C |
| ATOM | 1902 | O | TYR | A | 249 | 18.585 | 52.421 | 31.897 | 1.00 | 25.80 | O |
| ATOM | 1903 | CB | TYR | A | 249 | 15.948 | 51.615 | 30.544 | 1.00 | 25.57 | C |
| ATOM | 1904 | CG | TYR | A | 249 | 15.244 | 50.651 | 29.630 | 1.00 | 24.58 | C |
| ATOM | 1905 | CD1 | TYR | A | 249 | 15.930 | 49.624 | 29.003 | 1.00 | 25.44 | C |
| ATOM | 1906 | CD2 | TYR | A | 249 | 13.890 | 50.764 | 29.404 | 1.00 | 24.48 | C |
| ATOM | 1907 | CE1 | TYR | A | 249 | 15.276 | 48.731 | 28.173 | 1.00 | 25.01 | C |
| ATOM | 1908 | CE2 | TYR | A | 249 | 13.234 | 49.892 | 28.583 | 1.00 | 24.43 | C |
| ATOM | 1909 | CZ | TYR | A | 249 | 13.927 | 48.883 | 27.969 | 1.00 | 24.47 | C |
| ATOM | 1910 | OH | TYR | A | 249 | 13.252 | 48.043 | 27.142 | 1.00 | 25.97 | O |
| ATOM | 1911 | N | GLU | A | 250 | 17.195 | 52.278 | 33.660 | 1.00 | 26.10 | N |
| ATOM | 1912 | CA | GLU | A | 250 | 17.999 | 53.190 | 34.458 | 1.00 | 26.93 | C |
| ATOM | 1913 | C | GLU | A | 250 | 19.259 | 52.492 | 34.929 | 1.00 | 25.85 | C |
| ATOM | 1914 | O | GLU | A | 250 | 20.329 | 53.086 | 34.964 | 1.00 | 25.90 | O |
| ATOM | 1915 | CB | GLU | A | 250 | 17.219 | 53.740 | 35.661 | 1.00 | 27.56 | C |
| ATOM | 1916 | CG | GLU | A | 250 | 16.021 | 54.576 | 35.246 | 1.00 | 32.34 | C |
| ATOM | 1917 | CD | GLU | A | 250 | 15.420 | 55.366 | 36.385 | 1.00 | 36.85 | C |
| ATOM | 1918 | OE1 | GLU | A | 250 | 15.945 | 55.309 | 37.516 | 1.00 | 42.35 | O |
| ATOM | 1919 | OE2 | GLU | A | 250 | 14.422 | 56.057 | 36.142 | 1.00 | 40.82 | O |
| ATOM | 1920 | N | ARG | A | 251 | 19.136 | 51.233 | 35.315 | 1.00 | 24.58 | N |
| ATOM | 1921 | CA | ARG | A | 251 | 20.297 | 50.502 | 35.756 | 1.00 | 23.76 | C |
| ATOM | 1922 | C | ARG | A | 251 | 21.030 | 49.909 | 34.568 | 1.00 | 22.91 | C |
| ATOM | 1923 | O | ARG | A | 251 | 22.242 | 49.773 | 34.602 | 1.00 | 22.42 | O |
| ATOM | 1924 | CB | ARG | A | 251 | 19.896 | 49.374 | 36.696 | 1.00 | 24.55 | C |
| ATOM | 1925 | CG | ARG | A | 251 | 19.421 | 49.802 | 38.077 | 1.00 | 25.88 | C |
| ATOM | 1926 | CD | ARG | A | 251 | 18.894 | 48.629 | 38.921 | 1.00 | 29.50 | C |
| ATOM | 1927 | NE | ARG | A | 251 | 19.993 | 47.764 | 39.349 | 1.00 | 31.63 | N |
| ATOM | 1928 | CZ | ARG | A | 251 | 19.894 | 46.467 | 39.623 | 1.00 | 33.13 | C |
| ATOM | 1929 | NH1 | ARG | A | 251 | 18.736 | 45.826 | 39.521 | 1.00 | 33.12 | N |
| ATOM | 1930 | NH2 | ARG | A | 251 | 20.978 | 45.805 | 39.998 | 1.00 | 33.93 | N |
| ATOM | 1931 | N | PHE | A | 252 | 20.300 | 49.560 | 33.515 | 1.00 | 21.47 | N |
| ATOM | 1932 | CA | PHE | A | 252 | 20.898 | 48.863 | 32.379 | 1.00 | 21.32 | C |
| ATOM | 1933 | C | PHE | A | 252 | 20.576 | 49.552 | 31.056 | 1.00 | 20.68 | C |
| ATOM | 1934 | O | PHE | A | 252 | 19.934 | 48.984 | 30.187 | 1.00 | 20.79 | O |
| ATOM | 1935 | CB | PHE | A | 252 | 20.355 | 47.434 | 32.344 | 1.00 | 21.09 | C |
| ATOM | 1936 | CG | PHE | A | 252 | 20.373 | 46.738 | 33.690 | 1.00 | 20.96 | C |
| ATOM | 1937 | CD1 | PHE | A | 252 | 21.555 | 46.560 | 34.376 | 1.00 | 19.28 | C |
| ATOM | 1938 | CD2 | PHE | A | 252 | 19.207 | 46.238 | 34.247 | 1.00 | 21.43 | C |
| ATOM | 1939 | CE1 | PHE | A | 252 | 21.571 | 45.891 | 35.609 | 1.00 | 20.54 | C |
| ATOM | 1940 | CE2 | PHE | A | 252 | 19.217 | 45.588 | 35.488 | 1.00 | 22.13 | C |
| ATOM | 1941 | CZ | PHE | A | 252 | 20.403 | 45.414 | 36.156 | 1.00 | 20.96 | C |
| ATOM | 1942 | N | PRO | A | 253 | 21.057 | 50.767 | 30.884 | 1.00 | 20.56 | N |
| ATOM | 1943 | CA | PRO | A | 253 | 20.658 | 51.566 | 29.714 | 1.00 | 20.38 | C |
| ATOM | 1944 | C | PRO | A | 253 | 20.984 | 50.916 | 28.361 | 1.00 | 20.20 | C |
| ATOM | 1945 | O | PRO | A | 253 | 20.191 | 51.053 | 27.428 | 1.00 | 19.48 | O |

TABLE 3-continued

Coordinates for structures 1 to 4

| ATOM | 1946 | CB | PRO | A | 253 | 21.383 | 52.903 | 29.928 | 1.00 | 19.77 | C |
|---|---|---|---|---|---|---|---|---|---|---|---|
| ATOM | 1947 | CG | PRO | A | 253 | 22.562 | 52.555 | 30.895 | 1.00 | 20.60 | C |
| ATOM | 1948 | CD | PRO | A | 253 | 21.986 | 51.484 | 31.782 | 1.00 | 20.69 | C |
| ATOM | 1949 | N | ASN | A | 254 | 22.091 | 50.187 | 28.240 | 1.00 | 20.32 | N |
| ATOM | 1950 | CA | ASN | A | 254 | 22.409 | 49.613 | 26.938 | 1.00 | 20.12 | C |
| ATOM | 1951 | C | ASN | A | 254 | 21.572 | 48.393 | 26.554 | 1.00 | 19.96 | C |
| ATOM | 1952 | O | ASN | A | 254 | 21.675 | 47.892 | 25.441 | 1.00 | 19.16 | O |
| ATOM | 1953 | CB | ASN | A | 254 | 23.893 | 49.336 | 26.784 | 1.00 | 20.06 | C |
| ATOM | 1954 | CG | ASN | A | 254 | 24.706 | 50.601 | 26.697 | 1.00 | 21.51 | C |
| ATOM | 1955 | OD1 | ASN | A | 254 | 25.502 | 50.896 | 27.598 | 1.00 | 23.96 | O |
| ATOM | 1956 | ND2 | ASN | A | 254 | 24.514 | 51.373 | 25.614 | 1.00 | 20.38 | N |
| ATOM | 1957 | N | PHE | A | 255 | 20.724 | 47.922 | 27.455 | 1.00 | 19.81 | N |
| ATOM | 1958 | CA | PHE | A | 255 | 19.807 | 46.858 | 27.063 | 1.00 | 19.54 | C |
| ATOM | 1959 | C | PHE | A | 255 | 18.855 | 47.384 | 25.977 | 1.00 | 19.69 | C |
| ATOM | 1960 | O | PHE | A | 255 | 18.194 | 46.606 | 25.274 | 1.00 | 19.77 | O |
| ATOM | 1961 | CB | PHE | A | 255 | 19.023 | 46.330 | 28.252 | 1.00 | 19.22 | C |
| ATOM | 1962 | CG | PHE | A | 255 | 18.269 | 45.105 | 27.940 | 1.00 | 20.47 | C |
| ATOM | 1963 | CD1 | PHE | A | 255 | 18.928 | 43.922 | 27.736 | 1.00 | 20.23 | C |
| ATOM | 1964 | CD2 | PHE | A | 255 | 16.909 | 45.148 | 27.758 | 1.00 | 20.13 | C |
| ATOM | 1965 | CE1 | PHE | A | 255 | 18.243 | 42.786 | 27.416 | 1.00 | 21.65 | C |
| ATOM | 1966 | CE2 | PHE | A | 255 | 16.227 | 44.023 | 27.432 | 1.00 | 20.73 | C |
| ATOM | 1967 | CZ | PHE | A | 255 | 16.886 | 42.842 | 27.257 | 1.00 | 22.63 | C |
| ATOM | 1968 | N | GLN | A | 256 | 18.790 | 48.707 | 25.841 | 1.00 | 19.89 | N |
| ATOM | 1969 | CA | GLN | A | 256 | 17.969 | 49.345 | 24.794 | 1.00 | 20.24 | C |
| ATOM | 1970 | C | GLN | A | 256 | 18.595 | 49.160 | 23.403 | 1.00 | 19.74 | C |
| ATOM | 1971 | O | GLN | A | 256 | 17.969 | 49.443 | 22.384 | 1.00 | 19.92 | O |
| ATOM | 1972 | CB | GLN | A | 256 | 17.778 | 50.849 | 25.095 | 1.00 | 20.01 | C |
| ATOM | 1973 | CG | GLN | A | 256 | 16.736 | 51.095 | 26.197 | 1.00 | 21.20 | C |
| ATOM | 1974 | CD | GLN | A | 256 | 16.741 | 52.513 | 26.764 | 1.00 | 22.14 | C |
| ATOM | 1975 | OE1 | GLN | A | 256 | 15.711 | 53.195 | 26.741 | 1.00 | 23.01 | O |
| ATOM | 1976 | NE2 | GLN | A | 256 | 17.874 | 52.943 | 27.298 | 1.00 | 21.42 | N |
| ATOM | 1977 | N | ASN | A | 257 | 19.845 | 48.716 | 23.385 | 1.00 | 19.66 | N |
| ATOM | 1978 | CA | ASN | A | 257 | 20.580 | 48.485 | 22.155 | 1.00 | 20.07 | C |
| ATOM | 1979 | C | ASN | A | 257 | 20.757 | 47.005 | 21.811 | 1.00 | 20.73 | C |
| ATOM | 1980 | O | ASN | A | 257 | 21.416 | 46.694 | 20.823 | 1.00 | 20.96 | O |
| ATOM | 1981 | CB | ASN | A | 257 | 21.969 | 49.100 | 22.232 | 1.00 | 19.17 | C |
| ATOM | 1982 | CG | ASN | A | 257 | 21.941 | 50.550 | 22.635 | 1.00 | 20.82 | C |
| ATOM | 1983 | OD1 | ASN | A | 257 | 22.413 | 50.902 | 23.722 | 1.00 | 21.51 | O |
| ATOM | 1984 | ND2 | ASN | A | 257 | 21.396 | 51.407 | 21.763 | 1.00 | 16.92 | N |
| ATOM | 1985 | N | VAL | A | 258 | 20.190 | 46.098 | 22.596 | 1.00 | 21.59 | N |
| ATOM | 1986 | CA | VAL | A | 258 | 20.410 | 44.660 | 22.347 | 1.00 | 23.34 | C |
| ATOM | 1987 | C | VAL | A | 258 | 19.671 | 44.172 | 21.112 | 1.00 | 23.85 | C |
| ATOM | 1988 | O | VAL | A | 258 | 18.549 | 44.611 | 20.818 | 1.00 | 24.10 | O |
| ATOM | 1989 | CB | VAL | A | 258 | 20.015 | 43.806 | 23.573 | 1.00 | 23.68 | C |
| ATOM | 1990 | CG1 | VAL | A | 258 | 18.507 | 43.720 | 23.685 | 1.00 | 24.12 | C |
| ATOM | 1991 | CG2 | VAL | A | 258 | 20.570 | 42.436 | 23.445 | 1.00 | 28.30 | C |
| ATOM | 1992 | N | VAL | A | 259 | 20.314 | 43.286 | 20.360 | 1.00 | 24.47 | N |
| ATOM | 1993 | CA | VAL | A | 259 | 19.705 | 42.721 | 19.154 | 1.00 | 24.91 | C |
| ATOM | 1994 | C | VAL | A | 259 | 20.004 | 41.215 | 19.140 | 1.00 | 24.93 | C |
| ATOM | 1995 | O | VAL | A | 259 | 21.152 | 40.829 | 19.119 | 1.00 | 25.32 | O |
| ATOM | 1996 | CB | VAL | A | 259 | 20.281 | 43.362 | 17.895 | 1.00 | 24.88 | C |
| ATOM | 1997 | CG1 | VAL | A | 259 | 19.667 | 42.738 | 16.670 | 1.00 | 26.38 | C |
| ATOM | 1998 | CG2 | VAL | A | 259 | 20.051 | 44.869 | 17.909 | 1.00 | 24.83 | C |
| ATOM | 1999 | N | GLY | A | 260 | 18.974 | 40.381 | 19.186 | 1.00 | 25.06 | N |
| ATOM | 2000 | CA | GLY | A | 260 | 19.166 | 38.944 | 19.232 | 1.00 | 25.64 | C |
| ATOM | 20P1 | C | GLY | A | 260 | 19.076 | 38.221 | 17.887 | 1.00 | 25.42 | C |
| ATOM | 2002 | O | GLY | A | 260 | 18.679 | 38.796 | 16.869 | 1.00 | 25.77 | O |
| ATOM | 2003 | N | TYR | A | 261 | 19.497 | 36.965 | 17.907 | 1.00 | 25.04 | N |
| ATOM | 2004 | CA | TYR | A | 261 | 19.380 | 36.049 | 16.792 | 1.00 | 25.30 | C |
| ATOM | 2005 | C | TYR | A | 261 | 18.428 | 34.973 | 17.328 | 1.00 | 24.63 | C |
| ATOM | 2006 | O | TYR | A | 261 | 18.676 | 34.417 | 18.392 | 1.00 | 24.77 | O |
| ATOM | 2007 | CB | TYR | A | 261 | 20.729 | 35.414 | 16.482 | 1.00 | 25.84 | C |
| ATOM | 2008 | CG | TYR | A | 261 | 21.750 | 36.315 | 15.825 | 1.00 | 28.57 | C |
| ATOM | 2009 | CD1 | TYR | A | 261 | 21.821 | 36.423 | 14.447 | 1.00 | 34.41 | C |
| ATOM | 2010 | CD2 | TYR | A | 261 | 22.631 | 37.049 | 16.574 | 1.00 | 29.87 | C |
| ATOM | 2011 | CE1 | TYR | A | 261 | 22.752 | 37.255 | 13.838 | 1.00 | 35.64 | C |
| ATOM | 2012 | CE2 | TYR | A | 261 | 23.576 | 37.852 | 15.986 | 1.00 | 32.26 | C |
| ATOM | 2013 | CZ | TYR | A | 261 | 23.644 | 37.949 | 14.623 | 1.00 | 34.92 | C |
| ATOM | 2014 | OH | TYR | A | 261 | 24.582 | 38.772 | 14.047 | 1.00 | 38.39 | O |
| ATOM | 2015 | N | GLU | A | 262 | 17.325 | 34.698 | 16.658 | 1.00 | 23.64 | N |
| ATOM | 2016 | CA | GLU | A | 262 | 16.376 | 33.758 | 17.244 | 1.00 | 24.03 | C |
| ATOM | 2017 | C | GLU | A | 262 | 15.933 | 32.660 | 16.306 | 1.00 | 23.15 | C |
| ATOM | 2018 | O | GLU | A | 262 | 16.063 | 32.766 | 15.078 | 1.00 | 22.51 | O |
| ATOM | 2019 | CB | GLU | A | 262 | 15.172 | 34.482 | 17.861 | 1.00 | 24.11 | C |
| ATOM | 2020 | CG | GLU | A | 262 | 13.899 | 34.502 | 17.057 | 1.00 | 26.35 | C |
| ATOM | 2021 | CD | GLU | A | 262 | 12.744 | 35.177 | 17.785 | 1.00 | 27.98 | C |
| ATOM | 2022 | OE1 | GLU | A | 262 | 12.743 | 36.415 | 17.872 | 1.00 | 27.19 | O |

TABLE 3-continued

| | | | | | | | | | | | |
|---|---|---|---|---|---|---|---|---|---|---|---|
| ATOM | 2023 | OE2 | GLU | A | 262 | 11.818 | 34.476 | 18.254 | 1.00 | 29.21 | O |
| ATOM | 2024 | N | THR | A | 263 | 15.455 | 31.587 | 16.917 | 1.00 | 22.58 | N |
| ATOM | 2025 | CA | THR | A | 263 | 14.939 | 30.458 | 16.170 | 1.00 | 22.52 | C |
| ATOM | 2026 | C | THR | A | 263 | 14.047 | 29.617 | 17.076 | 1.00 | 22.48 | C |
| ATOM | 2027 | O | THR | A | 263 | 14.107 | 29.712 | 18.313 | 1.00 | 22.14 | O |
| ATOM | 2028 | CE | THR | A | 263 | 16.117 | 29.607 | 15.659 | 1.00 | 22.55 | C |
| ATOM | 2029 | OG1 | THR | A | 263 | 15.665 | 28.666 | 14.675 | 1.00 | 22.25 | O |
| ATOM | 2030 | CG2 | THR | A | 263 | 16.693 | 28.743 | 16.770 | 1.00 | 22.79 | C |
| ATOM | 2031 | N | VAL | A | 264 | 13.208 | 28.797 | 16.472 | 1.00 | 21.62 | N |
| ATOM | 2032 | CA | VAL | A | 264 | 12.453 | 27.860 | 17.263 | 1.00 | 22.45 | C |
| ATOM | 2033 | C | VAL | A | 264 | 12.871 | 26.474 | 16.837 | 1.00 | 22.76 | C |
| ATOM | 2034 | O | VAL | A | 264 | 12.779 | 26.134 | 15.673 | 1.00 | 22.77 | O |
| ATOM | 2035 | CB | VAL | A | 264 | 10.964 | 28.027 | 17.087 | 1.00 | 23.08 | C |
| ATOM | 2036 | CG1 | VAL | A | 264 | 10.234 | 26.805 | 17.643 | 1.00 | 23.67 | C |
| ATOM | 2037 | CG2 | VAL | A | 264 | 10.499 | 29.344 | 17.767 | 1.00 | 22.75 | C |
| ATOM | 2038 | N | VAL | A | 265 | 13.389 | 25.695 | 17.777 | 1.00 | 22.93 | N |
| ATOM | 2039 | CA | VAL | A | 265 | 13.779 | 24.329 | 17.458 | 1.00 | 23.08 | C |
| ATOM | 2040 | C | VAL | A | 265 | 12.738 | 23.317 | 17.886 | 1.00 | 22.86 | C |
| ATOM | 2041 | O | VAL | A | 265 | 12.105 | 23.473 | 18.932 | 1.00 | 23.06 | O |
| ATOM | 2042 | CB | VAL | A | 265 | 15.143 | 23.937 | 18.075 | 1.00 | 22.94 | C |
| ATOM | 2043 | CG1 | VAL | A | 265 | 16.243 | 24.745 | 17.404 | 1.00 | 23.66 | C |
| ATOM | 2044 | CG2 | VAL | A | 265 | 15.169 | 24.122 | 19.592 | 1.00 | 22.99 | C |
| ATOM | 2045 | N | GLY | A | 266 | 12.574 | 22.290 | 17.056 | 1.00 | 21.77 | N |
| ATOM | 2046 | CA | GLY | A | 266 | 11.683 | 21.178 | 17.355 | 1.00 | 21.98 | C |
| ATOM | 2047 | C | GLY | A | 266 | 12.376 | 19.826 | 17.263 | 1.00 | 20.97 | C |
| ATOM | 2048 | O | GLY | A | 266 | 13.562 | 19.757 | 16.999 | 1.00 | 20.63 | O |
| ATOM | 2049 | N | PRO | A | 267 | 11.643 | 18.737 | 17.461 | 1.00 | 21.23 | N |
| ATOM | 2050 | CA | PRO | A | 267 | 12.253 | 17.403 | 17.427 | 1.00 | 20.68 | C |
| ATOM | 2051 | C | PRO | A | 267 | 13.126 | 17.183 | 16.203 | 1.00 | 20.04 | C |
| ATOM | 2052 | O | PRO | A | 267 | 12.666 | 17.371 | 15.081 | 1.00 | 19.35 | O |
| ATOM | 2053 | CE | PRO | A | 267 | 11.039 | 16.463 | 17.379 | 1.00 | 21.29 | C |
| ATOM | 2054 | CG | PRO | A | 267 | 9.970 | 17.202 | 18.037 | 1.00 | 22.85 | C |
| ATOM | 2055 | CD | PRO | A | 267 | 10.188 | 18.676 | 17.710 | 1.00 | 21.61 | C |
| ATOM | 2056 | N | GLY | A | 268 | 14.376 | 16.787 | 16.411 | 1.00 | 20.31 | N |
| ATOM | 2057 | CA | GLY | A | 268 | 15.278 | 16.518 | 15.305 | 1.00 | 19.95 | C |
| ATOM | 2058 | C | GLY | A | 268 | 16.256 | 17.627 | 14.993 | 1.00 | 20.50 | C |
| ATOM | 2059 | O | GLY | A | 268 | 17.277 | 17.400 | 14.311 | 1.00 | 21.62 | O |
| ATOM | 2060 | N | ASP | A | 269 | 15.965 | 18.831 | 15.477 | 1.00 | 19.81 | N |
| ATOM | 2061 | CA | ASP | A | 269 | 16.818 | 19.977 | 15.217 | 1.00 | 19.75 | C |
| ATOM | 2062 | C | ASP | A | 269 | 17.970 | 20.003 | 16.215 | 1.00 | 19.67 | C |
| ATOM | 2063 | O | ASP | A | 269 | 17.811 | 19.625 | 17.377 | 1.00 | 18.76 | O |
| ATOM | 2064 | CE | ASP | A | 269 | 16.032 | 21.288 | 15.386 | 1.00 | 19.99 | C |
| ATOM | 2065 | CG | ASP | A | 269 | 14.916 | 21.464 | 14.374 | 1.00 | 20.91 | C |
| ATOM | 2066 | OD1 | ASP | A | 269 | 14.935 | 20.842 | 13.287 | 1.00 | 22.13 | O |
| ATOM | 2067 | OD2 | ASP | A | 269 | 13.987 | 22.259 | 14.576 | 1.00 | 23.27 | O |
| ATOM | 2068 | N | VAL | A | 270 | 19.116 | 20.481 | 15.746 | 1.00 | 19.56 | N |
| ATOM | 2069 | CA | VAL | A | 270 | 20.276 | 20.700 | 16.595 | 1.00 | 19.57 | C |
| ATOM | 2070 | C | VAL | A | 270 | 20.747 | 22.137 | 16.444 | 1.00 | 19.33 | C |
| ATOM | 2071 | O | VAL | A | 270 | 21.033 | 22.594 | 15.352 | 1.00 | 19.78 | O |
| ATOM | 2072 | CB | VAL | A | 270 | 21.404 | 19.776 | 16.215 | 1.00 | 19.55 | C |
| ATOM | 2073 | CG1 | VAL | A | 270 | 22.646 | 20.154 | 16.966 | 1.00 | 20.05 | C |
| ATOM | 2074 | CG2 | VAL | A | 270 | 21.001 | 18.342 | 16.535 | 1.00 | 19.44 | C |
| ATOM | 2075 | N | LEU | A | 271 | 20.786 | 22.870 | 17.539 | 1.00 | 19.33 | N |
| ATOM | 2076 | CA | LEU | A | 271 | 21.263 | 24.229 | 17.501 | 1.00 | 19.02 | C |
| ATOM | 2077 | C | LEU | A | 271 | 22.677 | 24.272 | 18.036 | 1.00 | 19.15 | C |
| ATOM | 2078 | O | LEU | A | 271 | 22.961 | 23.787 | 19.130 | 1.00 | 18.74 | O |
| ATOM | 2079 | CE | LEU | A | 271 | 20.376 | 25.120 | 18.331 | 1.00 | 19.93 | C |
| ATOM | 2080 | CG | LEU | A | 271 | 20.892 | 26.549 | 18.573 | 1.00 | 20.11 | C |
| ATOM | 2081 | CD1 | LEU | A | 271 | 21.011 | 27.358 | 17.296 | 1.00 | 19.41 | C |
| ATOM | 2082 | CD2 | LEU | A | 271 | 19.979 | 27.245 | 19.555 | 1.00 | 20.25 | C |
| ATOM | 2083 | N | TYR | A | 272 | 23.582 | 24.818 | 17.244 | 1.00 | 19.15 | N |
| ATOM | 2084 | CA | TYR | A | 272 | 24.924 | 25.051 | 17.718 | 1.00 | 19.70 | C |
| ATOM | 2085 | C | TYR | A | 272 | 24.914 | 26.360 | 18.483 | 1.00 | 19.63 | C |
| ATOM | 2086 | O | TYR | A | 272 | 24.646 | 27.395 | 17.897 | 1.00 | 20.44 | O |
| ATOM | 2087 | CE | TYR | A | 272 | 25.908 | 25.172 | 16.547 | 1.00 | 19.86 | C |
| ATOM | 2088 | CG | TYR | A | 272 | 27.293 | 25.654 | 16.962 | 1.00 | 21.59 | C |
| ATOM | 2089 | CD1 | TYR | A | 272 | 27.952 | 25.093 | 18.048 | 1.00 | 22.02 | C |
| ATOM | 2090 | CD2 | TYR | A | 272 | 27.936 | 26.668 | 16.278 | 1.00 | 20.87 | C |
| ATOM | 2091 | CE1 | TYR | A | 272 | 29.214 | 25.522 | 18.421 | 1.00 | 19.87 | C |
| ATOM | 2092 | CE2 | TYR | A | 272 | 29.200 | 27.098 | 16.649 | 1.00 | 20.88 | C |
| ATOM | 2093 | CZ | TYR | A | 272 | 29.834 | 26.517 | 17.721 | 1.00 | 21.07 | C |
| ATOM | 2094 | OH | TYR | A | 272 | 31.091 | 26.937 | 18.104 | 1.00 | 18.93 | O |
| ATOM | 2095 | N | ILE | A | 273 | 25.210 | 26.308 | 19.776 | 1.00 | 19.80 | N |
| ATOM | 2096 | CA | ILE | A | 273 | 25.342 | 27.500 | 20.598 | 1.00 | 20.12 | C |
| ATOM | 2097 | C | ILE | A | 273 | 26.837 | 27.683 | 20.883 | 1.00 | 20.39 | C |
| ATOM | 2098 | O | ILE | A | 273 | 27.393 | 27.000 | 21.760 | 1.00 | 19.88 | O |
| ATOM | 2099 | CE | ILE | A | 273 | 24.576 | 27.366 | 21.901 | 1.00 | 19.72 | C |

TABLE 3-continued

Coordinates for structures 1 to 4

| ATOM | 2100 | CG1 | ILE | A | 273 | 23.111 | 27.045 | 21.624 | 1.00 | 20.57 | C |
|---|---|---|---|---|---|---|---|---|---|---|---|
| ATOM | 2101 | CG2 | ILE | A | 273 | 24.661 | 28.695 | 22.696 | 1.00 | 20.99 | C |
| ATOM | 2102 | CD1 | ILE | A | 273 | 22.296 | 26.797 | 22.876 | 1.00 | 20.93 | C |
| ATOM | 2103 | N | PRO | A | 274 | 27.487 | 28.611 | 20.182 | 1.00 | 20.23 | N |
| ATOM | 2104 | CA | PRO | A | 274 | 28.938 | 28.743 | 20.326 | 1.00 | 21.16 | C |
| ATOM | 2105 | C | PRO | A | 274 | 29.289 | 29.264 | 21.704 | 1.00 | 21.39 | C |
| ATOM | 2106 | O | PRO | A | 274 | 28.520 | 30.027 | 22.317 | 1.00 | 20.89 | O |
| ATOM | 2107 | CB | PRO | A | 274 | 29.353 | 29.757 | 19.230 | 1.00 | 21.62 | C |
| ATOM | 2108 | CG | PRO | A | 274 | 28.089 | 30.056 | 18.410 | 1.00 | 21.22 | C |
| ATOM | 2109 | CD | PRO | A | 274 | 26.919 | 29.621 | 19.282 | 1.00 | 20.51 | C |
| ATOM | 2110 | N | MET | A | 275 | 30.450 | 28.831 | 22.180 | 1.00 | 21.53 | N |
| ATOM | 2111 | CA | MET | A | 275 | 30.953 | 29.207 | 23.479 | 1.00 | 22.30 | C |
| ATOM | 2112 | C | MET | A | 275 | 30.920 | 30.734 | 23.636 | 1.00 | 21.94 | C |
| ATOM | 2113 | O | MET | A | 275 | 31.160 | 31.442 | 22.675 | 1.00 | 20.78 | O |
| ATOM | 2114 | CB | MET | A | 275 | 32.367 | 28.695 | 23.589 | 1.00 | 23.06 | C |
| ATOM | 2115 | CG | MET | A | 275 | 32.937 | 28.734 | 24.966 | 1.00 | 27.00 | C |
| ATOM | 2116 | SD | MET | A | 275 | 34.545 | 27.926 | 24.991 | 1.00 | 33.74 | S |
| ATOM | 2117 | CE | MET | A | 275 | 35.263 | 28.479 | 23.499 | 1.00 | 32.50 | C |
| ATOM | 2118 | N | TYR | A | 276 | 30.583 | 31.211 | 24.832 | 1.00 | 21.96 | N |
| ATOM | 2119 | CA | TYR | A | 276 | 30.485 | 32.656 | 25.138 | 1.00 | 23.15 | C |
| ATOM | 2120 | C | TYR | A | 276 | 29.256 | 33.365 | 24.546 | 1.00 | 22.39 | C |
| ATOM | 2121 | O | TYR | A | 276 | 28.989 | 34.496 | 24.899 | 1.00 | 22.58 | O |
| ATOM | 2122 | CB | TYR | A | 276 | 31.776 | 33.409 | 24.760 | 1.00 | 23.80 | C |
| ATOM | 2123 | CG | TYR | A | 276 | 32.904 | 33.136 | 25.729 | 1.00 | 28.82 | C |
| ATOM | 2124 | CD1 | TYR | A | 276 | 32.940 | 33.756 | 26.951 | 1.00 | 32.73 | C |
| ATOM | 2125 | CD2 | TYR | A | 276 | 33.935 | 32.246 | 25.415 | 1.00 | 35.83 | C |
| ATOM | 2126 | CE1 | TYR | A | 276 | 33.956 | 33.507 | 27.864 | 1.00 | 35.96 | C |
| ATOM | 2127 | CE2 | TYR | A | 276 | 34.975 | 31.992 | 26.336 | 1.00 | 38.59 | C |
| ATOM | 2128 | CZ | TYR | A | 276 | 34.958 | 32.628 | 27.562 | 1.00 | 38.60 | C |
| ATOM | 2129 | OH | TYR | A | 276 | 35.951 | 32.421 | 28.513 | 1.00 | 45.18 | O |
| ATOM | 2130 | N | TRP | A | 277 | 28.488 | 32.709 | 23.684 | 1.00 | 21.71 | N |
| ATOM | 2131 | CA | TRP | A | 277 | 27.281 | 33.350 | 23.149 | 1.00 | 21.24 | C |
| ATOM | 2132 | C | TRP | A | 277 | 26.184 | 33.278 | 24.152 | 1.00 | 20.90 | C |
| ATOM | 2133 | O | TRP | A | 277 | 25.914 | 32.217 | 24.708 | 1.00 | 21.96 | O |
| ATOM | 2134 | CB | TRP | A | 277 | 26.790 | 32.711 | 21.856 | 1.00 | 21.01 | C |
| ATOM | 2135 | CG | TRP | A | 277 | 27.547 | 33.166 | 20.670 | 1.00 | 19.98 | C |
| ATOM | 2136 | CD1 | TRP | A | 277 | 28.875 | 33.013 | 20.462 | 1.00 | 17.90 | C |
| ATOM | 2137 | CD2 | TRP | A | 277 | 27.030 | 33.832 | 19.519 | 1.00 | 19.76 | C |
| ATOM | 2138 | NE1 | TRP | A | 277 | 29.218 | 33.533 | 19.247 | 1.00 | 18.64 | N |
| ATOM | 2139 | CE2 | TRP | A | 277 | 28.106 | 34.071 | 18.662 | 1.00 | 18.29 | C |
| ATOM | 2140 | CE3 | TRP | A | 277 | 25.764 | 34.305 | 19.151 | 1.00 | 20.56 | C |
| ATOM | 2141 | CZ2 | TRP | A | 277 | 27.963 | 34.716 | 17.442 | 1.00 | 19.63 | C |
| ATOM | 2142 | CZ3 | TRP | A | 277 | 25.624 | 34.950 | 17.943 | 1.00 | 21.16 | C |
| ATOM | 2143 | CH2 | TRP | A | 277 | 26.720 | 35.137 | 17.095 | 1.00 | 19.92 | C |
| ATOM | 2144 | N | TRP | A | 278 | 25.574 | 34.426 | 24.405 | 1.00 | 20.32 | N |
| ATOM | 2145 | CA | TRP | A | 278 | 24.452 | 34.533 | 25.316 | 1.00 | 20.13 | C |
| ATOM | 2146 | C | TRP | A | 278 | 23.268 | 33.787 | 24.741 | 1.00 | 19.99 | C |
| ATOM | 2147 | O | TRP | A | 278 | 23.083 | 33.758 | 23.538 | 1.00 | 20.42 | O |
| ATOM | 2148 | CB | TRP | A | 278 | 24.025 | 35.999 | 25.441 | 1.00 | 20.65 | C |
| ATOM | 2149 | CG | TRP | A | 278 | 25.031 | 36.864 | 26.107 | 1.00 | 20.56 | C |
| ATOM | 2150 | CD1 | TRP | A | 278 | 26.078 | 37.526 | 25.519 | 1.00 | 19.63 | C |
| ATOM | 2151 | CD2 | TRP | A | 278 | 25.096 | 37.160 | 27.501 | 1.00 | 19.59 | C |
| ATOM | 2152 | NE1 | TRP | A | 278 | 26.772 | 38.233 | 26.469 | 1.00 | 20.70 | N |
| ATOM | 2153 | CE2 | TRP | A | 278 | 26.191 | 38.012 | 27.699 | 1.00 | 20.10 | C |
| ATOM | 2154 | CE3 | TRP | A | 278 | 24.318 | 36.811 | 28.601 | 1.00 | 20.98 | C |
| ATOM | 2155 | CZ2 | TRP | A | 278 | 26.527 | 38.515 | 28.951 | 1.00 | 20.24 | C |
| ATOM | 2156 | CZ3 | TRP | A | 278 | 24.668 | 37.299 | 29.849 | 1.00 | 23.26 | C |
| ATOM | 2157 | CH2 | TRP | A | 278 | 25.759 | 38.146 | 30.011 | 1.00 | 20.41 | C |
| ATOM | 2158 | N | HIS | A | 279 | 22.463 | 33.194 | 25.591 | 1.00 | 19.84 | N |
| ATOM | 2159 | CA | HIS | A | 279 | 21.269 | 32.530 | 25.122 | 1.00 | 20.78 | C |
| ATOM | 2160 | C | HIS | A | 279 | 20.202 | 32.495 | 26.192 | 1.00 | 20.37 | C |
| ATOM | 2161 | O | HIS | A | 279 | 20.479 | 32.275 | 27.370 | 1.00 | 20.66 | O |
| ATOM | 2162 | CB | HIS | A | 279 | 21.540 | 31.098 | 24.604 | 1.00 | 20.86 | C |
| ATOM | 2163 | CG | HIS | A | 279 | 22.349 | 30.238 | 25.528 | 1.00 | 21.83 | C |
| ATOM | 2164 | ND1 | HIS | A | 279 | 23.720 | 30.324 | 25.608 | 1.00 | 23.19 | N |
| ATOM | 2165 | CD2 | HIS | A | 279 | 21.988 | 29.240 | 26.371 | 1.00 | 23.96 | C |
| ATOM | 2166 | CE1 | HIS | A | 279 | 24.175 | 29.411 | 26.449 | 1.00 | 22.20 | C |
| ATOM | 2167 | ND2 | HIS | A | 279 | 23.144 | 28.747 | 26.940 | 1.00 | 23.84 | N |
| ATOM | 2168 | N | HIS | A | 280 | 18.994 | 32.718 | 25.711 | 1.00 | 20.90 | N |
| ATOM | 2169 | CA | HIS | A | 280 | 17.742 | 32.758 | 26.441 | 1.00 | 21.22 | C |
| ATOM | 2170 | C | HIS | A | 280 | 16.910 | 31.676 | 25.793 | 1.00 | 21.42 | C |
| ATOM | 2171 | O | HIS | A | 280 | 16.749 | 31.685 | 24.580 | 1.00 | 21.70 | O |
| ATOM | 2172 | CB | HIS | A | 280 | 17.099 | 34.124 | 26.224 | 1.00 | 21.04 | C |
| ATOM | 2173 | CG | HIS | A | 280 | 15.632 | 34.168 | 26.489 | 1.00 | 21.54 | C |
| ATOM | 2174 | ND1 | HIS | A | 280 | 15.096 | 34.836 | 27.571 | 1.00 | 22.76 | N |
| ATOM | 2175 | CD2 | HIS | A | 280 | 14.581 | 33.660 | 25.802 | 1.00 | 22.74 | C |
| ATOM | 2176 | CE1 | HIS | A | 280 | 13.779 | 34.721 | 27.546 | 1.00 | 23.23 | C |

TABLE 3-continued

| | | | | | | | | | | | |
|---|---|---|---|---|---|---|---|---|---|---|---|
| \multicolumn{12}{l}{Coordinates for structures 1 to 4} |
| ATOM | 2177 | ND2 | HIS | A | 280 | 13.441 | 34.014 | 26.482 | 1.00 | 23.05 | N |
| ATOM | 2178 | N | ILE | A | 281 | 16.367 | 30.755 | 26.584 | 1.00 | 22.31 | N |
| ATOM | 2179 | CA | ILE | A | 281 | 15.649 | 29.599 | 26.040 | 1.00 | 22.39 | C |
| ATOM | 2180 | C | ILE | A | 281 | 14.304 | 29.443 | 26.722 | 1.00 | 22.72 | C |
| ATOM | 2181 | O | ILE | A | 281 | 14.216 | 29.419 | 27.945 | 1.00 | 22.70 | O |
| ATOM | 2182 | CE | ILE | A | 281 | 16.527 | 28.336 | 26.189 | 1.00 | 22.98 | C |
| ATOM | 2183 | CG1 | ILE | A | 281 | 17.771 | 28.504 | 25.305 | 1.00 | 24.90 | C |
| ATOM | 2184 | CG2 | ILE | A | 281 | 15.770 | 27.059 | 25.771 | 1.00 | 21.60 | C |
| ATOM | 2185 | CD1 | ILE | A | 281 | 18.795 | 27.556 | 25.554 | 1.00 | 27.31 | C |
| ATOM | 2186 | N | GLU | A | 282 | 13.252 | 29.350 | 25.920 | 1.00 | 22.93 | N |
| ATOM | 2187 | CA | GLU | A | 282 | 11.903 | 29.205 | 26.458 | 1.00 | 23.35 | C |
| ATOM | 2188 | C | GLU | A | 282 | 11.101 | 28.105 | 25.769 | 1.00 | 22.59 | C |
| ATOM | 2189 | O | GLU | A | 282 | 11.092 | 27.982 | 24.549 | 1.00 | 21.77 | O |
| ATOM | 2190 | CE | GLU | A | 282 | 11.144 | 30.538 | 26.393 | 1.00 | 23.47 | C |
| ATOM | 2191 | CG | GLU | A | 282 | 10.830 | 31.055 | 25.009 | 1.00 | 25.70 | C |
| ATOM | 2192 | CD | GLU | A | 282 | 10.281 | 32.483 | 25.023 | 1.00 | 25.79 | C |
| ATOM | 2193 | OE1 | GLU | A | 282 | 10.898 | 33.356 | 25.665 | 1.00 | 27.49 | O |
| ATOM | 2194 | OE2 | GLU | A | 282 | 9.241 | 32.740 | 24.391 | 1.00 | 26.03 | O |
| ATOM | 2195 | N | SER | A | 283 | 10.456 | 27.293 | 26.588 | 1.00 | 22.44 | N |
| ATOM | 2196 | CA | SER | A | 283 | 9.570 | 26.246 | 26.103 | 1.00 | 23.00 | C |
| ATOM | 2197 | C | SER | A | 283 | 8.256 | 26.916 | 25.753 | 1.00 | 23.56 | C |
| ATOM | 2198 | O | SER | A | 283 | 7.685 | 27.615 | 26.584 | 1.00 | 24.14 | O |
| ATOM | 2199 | CB | SER | A | 283 | 9.346 | 25.204 | 27.188 | 1.00 | 22.59 | C |
| ATOM | 2200 | OG | SER | A | 283 | 10.496 | 24.400 | 27.345 | 1.00 | 22.67 | O |
| ATOM | 2201 | N | LEU | A | 284 | 7.763 | 26.694 | 24.541 | 1.00 | 24.07 | O |
| ATOM | 2202 | CA | LEU | A | 284 | 6.581 | 27.412 | 24.070 | 1.00 | 24.80 | C |
| ATOM | 2203 | C | LEU | A | 284 | 5.386 | 27.324 | 25.004 | 1.00 | 24.51 | C |
| ATOM | 2204 | O | LEU | A | 284 | 5.098 | 26.271 | 25.602 | 1.00 | 23.93 | O |
| ATOM | 2205 | CE | LEU | A | 284 | 6.161 | 26.947 | 22.682 | 1.00 | 25.09 | C |
| ATOM | 2206 | CG | LEU | A | 284 | 7.185 | 27.083 | 21.555 | 1.00 | 26.46 | C |
| ATOM | 2207 | CD1 | LEU | A | 284 | 6.475 | 27.236 | 20.215 | 1.00 | 28.29 | C |
| ATOM | 2208 | CD2 | LEU | A | 284 | 8.123 | 28.188 | 21.775 | 1.00 | 26.10 | C |
| ATOM | 2209 | N | LEU | A | 285 | 4.718 | 28.463 | 25.136 | 1.00 | 24.41 | N |
| ATOM | 2210 | CA | LEU | A | 285 | 3.506 | 28.554 | 25.930 | 1.00 | 24.83 | C |
| ATOM | 2211 | C | LEU | A | 285 | 2.526 | 27.583 | 25.323 | 1.00 | 24.68 | C |
| ATOM | 2212 | O | LEU | A | 285 | 2.393 | 27.516 | 24.110 | 1.00 | 24.08 | O |
| ATOM | 2213 | CB | LEU | A | 285 | 2.927 | 29.961 | 25.872 | 1.00 | 24.79 | C |
| ATOM | 2214 | CG | LEU | A | 285 | 3.825 | 31.078 | 26.397 | 1.00 | 25.19 | C |
| ATOM | 2215 | CD1 | LEU | A | 285 | 3.298 | 32.434 | 25.954 | 1.00 | 26.02 | C |
| ATOM | 2216 | CD2 | LEU | A | 285 | 3.925 | 30.999 | 27.898 | 1.00 | 26.27 | C |
| ATOM | 2217 | N | ASN | A | 286 | 1.867 | 26.815 | 26.173 | 1.00 | 25.20 | N |
| ATOM | 2218 | CA | ASN | A | 286 | 0.867 | 25.848 | 25.730 | 1.00 | 25.85 | C |
| ATOM | 2219 | C | ASN | A | 286 | 1.371 | 24.791 | 24.742 | 1.00 | 25.23 | C |
| ATOM | 2220 | O | ASN | A | 286 | 0.594 | 24.267 | 23.965 | 1.00 | 24.38 | O |
| ATOM | 2221 | CE | ASN | A | 286 | 0.319 | 26.599 | 25.124 | 1.00 | 26.54 | C |
| ATOM | 2222 | CG | ASN | A | 286 | 0.957 | 27.546 | 26.109 | 1.00 | 29.40 | C |
| ATOM | 2223 | OD1 | ASN | A | 286 | 1.478 | 27.118 | 27.140 | 1.00 | 33.49 | O |
| ATOM | 2224 | ND2 | ASN | A | 286 | 0.893 | 28.843 | 25.821 | 1.00 | 33.58 | N |
| ATOM | 2225 | N | GLY | A | 287 | 2.669 | 24.487 | 24.774 | 1.00 | 24.55 | N |
| ATOM | 2226 | CA | GLY | A | 287 | 3.243 | 23.518 | 23.863 | 1.00 | 24.10 | C |
| ATOM | 2227 | C | GLY | A | 287 | 3.524 | 22.167 | 24.487 | 1.00 | 23.80 | C |
| ATOM | 2228 | O | GLY | A | 287 | 4.110 | 21.301 | 23.838 | 1.00 | 24.10 | O |
| ATOM | 2229 | N | GLY | A | 288 | 3.100 | 21.971 | 25.734 | 1.00 | 23.32 | N |
| ATOM | 2230 | CA | GLY | A | 288 | 3.360 | 20.730 | 26.439 | 1.00 | 23.24 | C |
| ATOM | 2231 | C | GLY | A | 288 | 4.808 | 20.673 | 26.903 | 1.00 | 23.49 | C |
| ATOM | 2232 | O | GLY | A | 288 | 5.548 | 21.646 | 26.741 | 1.00 | 22.86 | O |
| ATOM | 2233 | N | ILE | A | 289 | 5.220 | 19.539 | 27.462 | 1.00 | 23.36 | N |
| ATOM | 2234 | CA | ILE | A | 289 | 6.571 | 19.406 | 27.983 | 1.00 | 23.99 | C |
| ATOM | 2235 | C | ILE | A | 289 | 7.601 | 19.374 | 26.874 | 1.00 | 23.28 | C |
| ATOM | 2236 | O | ILE | A | 289 | 7.324 | 18.958 | 25.755 | 1.00 | 23.68 | O |
| ATOM | 2237 | CE | ILE | A | 289 | 6.750 | 18.123 | 28.817 | 1.00 | 24.68 | C |
| ATOM | 2238 | CG1 | ILE | A | 289 | 6.819 | 16.912 | 27.901 | 1.00 | 26.90 | C |
| ATOM | 2239 | CG2 | ILE | A | 289 | 5.648 | 17.983 | 29.885 | 1.00 | 25.75 | C |
| ATOM | 2240 | CD1 | ILE | A | 289 | 7.294 | 15.640 | 28.613 | 1.00 | 29.37 | C |
| ATOM | 2241 | N | THR | A | 290 | 8.811 | 19.790 | 27.210 | 1.00 | 22.42 | N |
| ATOM | 2242 | CA | THR | A | 290 | 9.904 | 19.768 | 26.264 | 1.00 | 21.38 | C |
| ATOM | 2243 | C | THR | A | 290 | 11.030 | 18.880 | 26.774 | 1.00 | 20.56 | C |
| ATOM | 2244 | O | THR | A | 290 | 11.243 | 18.743 | 27.986 | 1.00 | 19.81 | O |
| ATOM | 2245 | CE | THR | A | 290 | 10.461 | 21.175 | 26.053 | 1.00 | 21.70 | C |
| ATOM | 2246 | OG1 | THR | A | 290 | 10.823 | 21.761 | 27.308 | 1.00 | 20.15 | O |
| ATOM | 2247 | CG2 | THR | A | 290 | 9.405 | 22.108 | 25.460 | 1.00 | 21.76 | C |
| ATOM | 2248 | N | ILE | A | 291 | 11.757 | 18.296 | 25.841 | 1.00 | 19.36 | N |
| ATOM | 2249 | CA | ILE | A | 291 | 12.903 | 17.503 | 26.190 | 1.00 | 19.73 | C |
| ATOM | 2250 | C | ILE | A | 291 | 14.044 | 17.865 | 25.286 | 1.00 | 19.29 | C |
| ATOM | 2251 | O | ILE | A | 291 | 13.862 | 17.976 | 24.083 | 1.00 | 19.81 | O |
| ATOM | 2252 | CB | ILE | A | 291 | 12.598 | 15.992 | 26.085 | 1.00 | 20.08 | C |
| ATOM | 2253 | CG1 | ILE | A | 291 | 11.467 | 15.609 | 27.044 | 1.00 | 20.06 | C |

TABLE 3-continued

| | | | | | | | | | | | |
|---|---|---|---|---|---|---|---|---|---|---|---|
| | | | | | Coordinates for structures 1 to 4 | | | | | | |
| ATOM | 2254 | CG2 | ILE | A | 291 | 13.873 | 15.214 | 26.378 | 1.00 | 20.21 | C |
| ATOM | 2255 | CD1 | ILE | A | 291 | 11.028 | 14.131 | 26.931 | 1.00 | 21.77 | C |
| ATOM | 2256 | N | THR | A | 292 | 15.215 | 18.070 | 25.882 | 1.00 | 18.95 | N |
| ATOM | 2257 | CA | THR | A | 292 | 16.406 | 18.407 | 25.156 | 1.00 | 19.17 | C |
| ATOM | 2258 | C | THR | A | 292 | 17.589 | 17.691 | 25.753 | 1.00 | 19.18 | C |
| ATOM | 2259 | O | THR | A | 292 | 17.671 | 17.497 | 26.965 | 1.00 | 19.21 | O |
| ATOM | 2260 | CE | THR | A | 292 | 16.703 | 19.937 | 25.259 | 1.00 | 19.83 | C |
| ATOM | 2261 | OG1 | THR | A | 292 | 15.559 | 20.724 | 24.879 | 1.00 | 20.23 | O |
| ATOM | 2262 | CG2 | THR | A | 292 | 17.787 | 20.350 | 24.270 | 1.00 | 20.15 | C |
| ATOM | 2263 | N | VAL | A | 293 | 18.530 | 17.314 | 24.903 | 1.00 | 19.25 | N |
| ATOM | 2264 | CA | VAL | A | 293 | 19.809 | 16.824 | 25.387 | 1.00 | 19.51 | C |
| ATOM | 2265 | C | VAL | A | 293 | 20.912 | 17.667 | 24.749 | 1.00 | 19.58 | C |
| ATOM | 2266 | O | VAL | A | 293 | 20.962 | 17.792 | 23.535 | 1.00 | 18.47 | O |
| ATOM | 2267 | CE | VAL | A | 293 | 20.024 | 15.345 | 25.063 | 1.00 | 19.73 | C |
| ATOM | 2268 | CG1 | VAL | A | 293 | 21.490 | 14.951 | 25.250 | 1.00 | 20.24 | C |
| ATOM | 2269 | CG2 | VAL | A | 293 | 19.146 | 14.478 | 25.968 | 1.00 | 20.65 | C |
| ATOM | 2270 | N | ASN | A | 294 | 21.766 | 18.277 | 25.569 | 1.00 | 19.85 | N |
| ATOM | 2271 | CA | ASN | A | 294 | 22.882 | 19.057 | 25.039 | 1.00 | 20.26 | C |
| ATOM | 2272 | C | ASN | A | 294 | 24.179 | 18.232 | 25.052 | 1.00 | 20.35 | C |
| ATOM | 2273 | O | ASII | A | 294 | 24.233 | 17.131 | 25.634 | 1.00 | 21.82 | O |
| ATOM | 2274 | CB | ASN | A | 294 | 23.008 | 20.443 | 25.727 | 1.00 | 20.82 | C |
| ATOM | 2275 | CG | ASN | A | 294 | 23.676 | 20.388 | 27.102 | 1.00 | 21.84 | C |
| ATOM | 2276 | OD3 | ASN | A | 294 | 24.209 | 19.354 | 27.495 | 1.00 | 21.66 | O |
| ATOM | 2277 | ND2 | ASN | A | 294 | 23.630 | 21.519 | 27.849 | 1.00 | 21.23 | N |
| ATOM | 2278 | N | PHE | A | 295 | 25.186 | 18.729 | 24.346 | 1.00 | 20.69 | N |
| ATOM | 2279 | CA | PHE | A | 295 | 26.490 | 18.095 | 24.233 | 1.00 | 20.46 | C |
| ATOM | 2280 | C | PHE | A | 295 | 27.452 | 19.240 | 24.494 | 1.00 | 21.42 | C |
| ATOM | 2281 | O | PHE | A | 295 | 27.573 | 20.167 | 23.653 | 1.00 | 20.85 | O |
| ATOM | 2282 | CB | PHE | A | 295 | 26.728 | 17.569 | 22.814 | 1.00 | 20.62 | C |
| ATOM | 2283 | CG | PHE | A | 295 | 25.898 | 16.366 | 22.440 | 1.00 | 21.15 | C |
| ATOM | 2284 | CD1 | PHE | A | 295 | 24.526 | 16.468 | 22.247 | 1.00 | 21.98 | C |
| ATOM | 2285 | CD2 | PHE | A | 295 | 26.498 | 15.130 | 22.256 | 1.00 | 19.31 | C |
| ATOM | 2286 | CE1 | PHE | A | 295 | 23.791 | 15.343 | 21.902 | 1.00 | 19.77 | C |
| ATOM | 2287 | CE2 | PHE | A | 295 | 25.762 | 14.037 | 21.885 | 1.00 | 17.96 | C |
| ATOM | 2288 | CZ | PHE | A | 295 | 24.424 | 14.138 | 21.720 | 1.00 | 17.87 | C |
| ATOM | 2289 | N | TRP | A | 296 | 28.123 | 19.196 | 25.645 | 1.00 | 21.19 | N |
| ATOM | 2290 | CA | TRP | A | 296 | 29.023 | 20.275 | 26.050 | 1.00 | 21.46 | C |
| ATOM | 2291 | C | TRP | A | 296 | 30.481 | 19.834 | 25.873 | 1.00 | 21.42 | C |
| ATOM | 2292 | O | TRP | A | 296 | 30.898 | 18.795 | 26.387 | 1.00 | 21.96 | O |
| ATOM | 2293 | CB | TRP | A | 296 | 28.760 | 20.669 | 27.498 | 1.00 | 21.13 | C |
| ATOM | 2294 | CG | TRP | A | 296 | 27.853 | 21.859 | 27.710 | 1.00 | 21.95 | C |
| ATOM | 2295 | CD1 | TRP | A | 296 | 27.797 | 22.987 | 26.955 | 1.00 | 23.23 | C |
| ATOM | 2296 | CD2 | TRP | A | 296 | 26.935 | 22.067 | 28.797 | 1.00 | 22.27 | C |
| ATOM | 2297 | NE1 | TRP | A | 296 | 26.882 | 23.869 | 27.478 | 1.00 | 22.26 | N |
| ATOM | 2298 | CE2 | TRP | A | 296 | 26.336 | 23.329 | 28.607 | 1.00 | 22.53 | C |
| ATOM | 2299 | CE3 | TRP | A | 296 | 26.531 | 21.298 | 29.894 | 1.00 | 24.83 | C |
| ATOM | 2300 | CZ2 | TRP | A | 296 | 25.362 | 23.840 | 29.463 | 1.00 | 22.34 | C |
| ATOM | 2301 | CZ3 | TRP | A | 296 | 25.557 | 21.810 | 30.754 | 1.00 | 24.59 | C |
| ATOM | 2302 | CH2 | TRP | A | 296 | 24.993 | 23.075 | 30.531 | 1.00 | 23.75 | C |
| ATOM | 2303 | N | TYR | A | 297 | 31.235 | 20.632 | 25.126 | 1.00 | 21.64 | N |
| ATOM | 2304 | CA | TYR | A | 297 | 32.633 | 20.361 | 24.845 | 1.00 | 21.81 | C |
| ATOM | 2305 | C | TYR | A | 297 | 33.482 | 21.523 | 25.320 | 1.00 | 22.41 | C |
| ATOM | 2306 | O | TYR | A | 297 | 33.110 | 22.682 | 25.146 | 1.00 | 21.78 | O |
| ATOM | 2307 | CB | TYR | A | 297 | 32.862 | 20.198 | 23.344 | 1.00 | 21.49 | C |
| ATOM | 2308 | CG | TYR | A | 297 | 32.287 | 18.943 | 22.761 | 1.00 | 21.77 | C |
| ATOM | 2309 | CD1 | TYR | A | 297 | 30.934 | 18.870 | 22.415 | 1.00 | 21.68 | C |
| ATOM | 2310 | CD2 | TYR | A | 297 | 33.083 | 17.841 | 22.526 | 1.00 | 19.80 | C |
| ATOM | 2311 | CE1 | TYR | A | 297 | 30.405 | 17.734 | 21.890 | 1.00 | 22.16 | C |
| ATOM | 2312 | CE2 | TYR | A | 297 | 32.555 | 16.690 | 21.993 | 1.00 | 20.99 | C |
| ATOM | 2313 | CZ | TYR | A | 297 | 31.215 | 16.637 | 21.686 | 1.00 | 21.46 | C |
| ATOM | 2314 | OH | TYR | A | 297 | 30.673 | 15.494 | 21.159 | 1.00 | 22.11 | O |
| ATOM | 2315 | N | LYS | A | 298 | 34.632 | 21.220 | 25.899 | 1.00 | 23.17 | N |
| ATOM | 2316 | CA | LYS | A | 298 | 35.566 | 22.273 | 26.288 | 1.00 | 24.45 | C |
| ATOM | 2317 | C | LYS | A | 298 | 36.074 | 22.912 | 25.021 | 1.00 | 24.21 | C |
| ATOM | 2318 | O | LYS | A | 298 | 36.264 | 22.228 | 24.025 | 1.00 | 23.35 | O |
| ATOM | 2319 | CE | LYS | A | 298 | 36.748 | 21.699 | 27.085 | 1.00 | 24.85 | C |
| ATOM | 2320 | CG | LYS | A | 298 | 36.436 | 21.416 | 28.552 | 1.00 | 28.00 | C |
| ATOM | 2321 | CD | LYS | A | 298 | 37.657 | 20.865 | 29.298 | 1.00 | 31.59 | C |
| ATOM | 2322 | CE | LYS | A | 298 | 37.309 | 20.447 | 30.730 | 1.00 | 33.77 | C |
| ATOM | 2323 | NZ | LYS | A | 298 | 38.406 | 19.627 | 31.367 | 1.00 | 36.02 | N |
| ATOM | 2324 | N | GLY | A | 299 | 36.317 | 24.216 | 25.056 | 1.00 | 25.28 | |
| ATOM | 2325 | CA | GLY | A | 299 | 36.818 | 24.909 | 23.886 | 1.00 | 26.38 | C |
| ATOM | 2326 | C | GLY | A | 299 | 38.254 | 24.542 | 23.547 | 1.00 | 27.78 | C |
| ATOM | 2327 | O | GLY | A | 299 | 38.935 | 23.895 | 24.315 | 1.00 | 27.16 | O |
| ATOM | 2328 | N | ALA | A | 300 | 38.690 | 24.949 | 22.366 | 1.00 | 30.42 | N |
| ATOM | 2329 | CA | ALA | A | 300 | 40.062 | 24.762 | 21.918 | 1.00 | 32.93 | C |
| ATOM | 2330 | C | ALA | A | 300 | 41.021 | 25.544 | 22.819 | 1.00 | 35.12 | C |

TABLE 3-continued

| | | | | | | | | | | | |
|---|---|---|---|---|---|---|---|---|---|---|---|
| ATOM | 2331 | O | ALA | A | 300 | 40.597 | 26.337 | 23.646 | 1.00 | 34.87 | O |
| ATOM | 2332 | CE | ALA | A | 300 | 40.199 | 25.249 | 20.472 | 1.00 | 32.98 | C |
| ATOM | 2333 | H | PRO | A | 301 | 42.318 | 25.355 | 22.615 | 1.00 | 38.54 | N |
| ATOM | 2334 | CA | PRO | A | 301 | 43.347 | 26.012 | 23.440 | 1.00 | 40.37 | C |
| ATOM | 2335 | C | PRO | A | 301 | 43.548 | 27.484 | 23.102 | 1.00 | 41.99 | C |
| ATOM | 2336 | O | PRO | A | 301 | 43.379 | 27.853 | 21.950 | 1.00 | 42.88 | O |
| ATOM | 2337 | CB | PRO | A | 301 | 44.615 | 25.246 | 23.061 | 1.00 | 40.42 | C |
| ATOM | 2338 | CG | PRO | A | 301 | 44.397 | 24.879 | 21.638 | 1.00 | 39.87 | C |
| ATOM | 2339 | CD | PRO | A | 301 | 42.919 | 24.544 | 21.535 | 1.00 | 38.98 | C |
| ATOM | 2340 | N | THR | A | 302 | 43.915 | 28.293 | 24.090 | 1.00 | 44.60 | H |
| ATOM | 2341 | CA | THR | A | 302 | 44.209 | 29.725 | 23.912 | 1.00 | 46.30 | C |
| ATOM | 2342 | C | THR | A | 302 | 45.593 | 29.790 | 23.315 | 1.00 | 47.41 | C |
| ATOM | 2343 | O | THR | A | 302 | 46.534 | 29.388 | 23.992 | 1.00 | 47.96 | O |
| ATOM | 2344 | CB | THR | A | 302 | 44.242 | 30.391 | 25.294 | 1.00 | 46.57 | C |
| ATOM | 2345 | OG1 | THR | A | 302 | 42.941 | 30.320 | 25.895 | 1.00 | 48.00 | O |
| ATOM | 2346 | CG2 | THR | A | 302 | 44.526 | 31.869 | 25.199 | 1.00 | 47.24 | C |
| ATOM | 2347 | N | PRO | A | 303 | 45.782 | 30.336 | 22.112 | 1.00 | 48.55 | H |
| ATOM | 2348 | CA | PRO | A | 303 | 47.090 | 30.170 | 21.473 | 1.00 | 48.80 | C |
| ATOM | 2349 | C | PRO | A | 303 | 48.210 | 30.717 | 22.341 | 1.00 | 48.76 | C |
| ATOM | 2350 | O | PRO | A | 303 | 47.874 | 31.450 | 23.269 | 1.00 | 49.07 | O |
| ATOM | 2351 | CB | PRO | A | 303 | 46.967 | 30.980 | 20.185 | 1.00 | 49.07 | C |
| ATOM | 2352 | CG | PRO | A | 303 | 45.504 | 31.101 | 19.952 | 1.00 | 48.93 | C |
| ATOM | 2353 | CD | PRO | A | 303 | 44.916 | 31.243 | 21.330 | 1.00 | 48.62 | C |
| ATOM | 2354 | N | GLU | A | 307 | 46.795 | 36.776 | 18.436 | 1.00 | 52.62 | H |
| ATOM | 2355 | CA | GLU | A | 307 | 46.885 | 37.814 | 17.415 | 1.00 | 52.76 | C |
| ATOM | 2356 | C | GLU | A | 307 | 45.865 | 38.906 | 17.636 | 1.00 | 52.00 | C |
| ATOM | 2357 | O | GLU | A | 307 | 44.757 | 38.658 | 18.096 | 1.00 | 52.48 | O |
| ATOM | 2358 | CB | GLU | A | 307 | 46.686 | 37.246 | 15.996 | 1.00 | 53.32 | C |
| ATOM | 2359 | CG | GLU | A | 307 | 46.893 | 38.307 | 14.908 | 1.00 | 54.63 | C |
| ATOM | 2360 | CD | GLU | A | 307 | 46.862 | 37.764 | 13.487 | 1.00 | 56.43 | C |
| ATOM | 2361 | OE1 | GLU | A | 307 | 46.527 | 36.574 | 13.290 | 1.00 | 57.49 | O |
| ATOM | 2362 | OE2 | GLU | A | 307 | 47.173 | 38.543 | 12.558 | 1.00 | 57.89 | O |
| ATOM | 2363 | N | TYR | A | 308 | 46.255 | 40.125 | 17.303 | 1.00 | 51.19 | N |
| ATOM | 2364 | CA | TYR | A | 308 | 45.367 | 41.267 | 17.405 | 1.00 | 50.55 | C |
| ATOM | 2365 | C | TYR | A | 308 | 44.747 | 41.494 | 16.039 | 1.00 | 49.51 | C |
| ATOM | 2366 | O | TYR | A | 308 | 45.300 | 41.053 | 15.028 | 1.00 | 49.70 | O |
| ATOM | 2367 | CE | TYR | A | 308 | 46.151 | 42.485 | 17.867 | 1.00 | 50.82 | C |
| ATOM | 2368 | CG | TYR | A | 308 | 46.702 | 42.286 | 19.259 | 1.00 | 52.47 | C |
| ATOM | 2369 | CD1 | TYR | A | 308 | 45.949 | 42.632 | 20.373 | 1.00 | 53.15 | C |
| ATOM | 2370 | CD2 | TYR | A | 308 | 47.948 | 41.696 | 19.462 | 1.00 | 53.79 | C |
| ATOM | 2371 | CE1 | TYR | A | 308 | 46.426 | 42.426 | 21.643 | 1.00 | 54.22 | C |
| ATOM | 2372 | CE2 | TYR | A | 308 | 48.437 | 41.487 | 20.736 | 1.00 | 54.76 | C |
| ATOM | 2373 | CZ | TYR | A | 308 | 47.670 | 41.857 | 21.824 | 1.00 | 55.10 | C |
| ATOM | 2374 | OH | TYR | A | 308 | 48.146 | 41.659 | 23.101 | 1.00 | 56.68 | O |
| ATOM | 2375 | N | PRO | A | 309 | 43.584 | 42.135 | 15.981 | 1.00 | 47.88 | N |
| ATOM | 2376 | CA | PRO | A | 309 | 42.843 | 42.621 | 17.169 | 1.00 | 46.21 | C |
| ATOM | 2377 | C | PRO | A | 309 | 42.139 | 41.503 | 17.952 | 1.00 | 43.75 | C |
| ATOM | 2378 | O | PRO | A | 309 | 41.768 | 40.503 | 17.369 | 1.00 | 44.10 | O |
| ATOM | 2379 | CB | PRO | A | 309 | 41.804 | 43.566 | 16.562 | 1.00 | 46.39 | C |
| ATOM | 2380 | CG | PRO | A | 309 | 41.610 | 43.069 | 15.128 | 1.00 | 47.65 | C |
| ATOM | 2381 | CD | PRO | A | 309 | 42.899 | 42.431 | 14.716 | 1.00 | 48.06 | C |
| ATOM | 2382 | N | LEU | A | 310 | 41.973 | 41.672 | 19.256 | 1.00 | 40.94 | H |
| ATOM | 2383 | CA | LEU | A | 310 | 41.349 | 40.650 | 20.093 | 1.00 | 38.75 | C |
| ATOM | 2384 | C | LEU | A | 310 | 39.863 | 40.491 | 19.817 | 1.00 | 36.87 | C |
| ATOM | 2385 | O | LEU | A | 310 | 39.148 | 41.474 | 19.610 | 1.00 | 37.02 | O |
| ATOM | 2386 | CE | LEU | A | 310 | 41.499 | 41.017 | 21.566 | 1.00 | 38.63 | C |
| ATOM | 2387 | CG | LEU | A | 310 | 42.571 | 40.351 | 22.435 | 1.00 | 37.97 | C |
| ATOM | 2388 | CD1 | LEU | A | 310 | 43.840 | 40.049 | 21.711 | 1.00 | 37.27 | C |
| ATOM | 2389 | CD2 | LEU | A | 310 | 42.836 | 41.234 | 23.637 | 1.00 | 37.27 | C |
| ATOM | 2390 | N | LYS | A | 311 | 39.392 | 39.254 | 19.847 | 1.00 | 34.04 | N |
| ATOM | 2391 | CA | LYS | A | 311 | 37.972 | 38.998 | 19.702 | 1.00 | 32.20 | C |
| ATOM | 2392 | C | LYS | A | 311 | 37.208 | 39.376 | 20.968 | 1.00 | 30.33 | C |
| ATOM | 2393 | O | LYS | A | 311 | 37.760 | 39.421 | 22.072 | 1.00 | 29.17 | O |
| ATOM | 2394 | CB | LYS | A | 311 | 37.733 | 37.504 | 19.371 | 1.00 | 32.59 | C |
| ATOM | 2395 | N | ALA | A | 312 | 35.924 | 39.641 | 20.788 | 1.00 | 28.23 | N |
| ATOM | 2396 | CA | ALA | A | 312 | 35.074 | 40.011 | 21.895 | 1.00 | 27.38 | C |
| ATOM | 2397 | C | ALA | A | 312 | 35.148 | 38.973 | 23.005 | 1.00 | 26.28 | C |
| ATOM | 2398 | O | ALA | A | 312 | 35.271 | 39.334 | 24.172 | 1.00 | 24.54 | O |
| ATOM | 2399 | CB | ALA | A | 312 | 33.641 | 40.205 | 21.421 | 1.00 | 27.09 | C |
| ATOM | 2400 | N | HIS | A | 313 | 35.101 | 37.689 | 22.649 | 1.00 | 25.72 | N |
| ATOM | 2401 | CA | HIS | A | 313 | 35.086 | 36.669 | 23.674 | 1.00 | 25.82 | C |
| ATOM | 2402 | C | HIS | A | 313 | 36.399 | 36.609 | 24.428 | 1.00 | 24.79 | C |
| ATOM | 2403 | O | HIS | A | 313 | 36.428 | 36.183 | 25.557 | 1.00 | 24.19 | O |
| ATOM | 2404 | CB | HIS | A | 313 | 34.688 | 35.293 | 23.129 | 1.00 | 26.92 | C |
| ATOM | 2405 | CG | HIS | A | 313 | 35.741 | 34.641 | 22.303 | 1.00 | 29.84 | C |
| ATOM | 2406 | ND1 | HIS | A | 313 | 35.896 | 34.903 | 20.954 | 1.00 | 35.52 | N |
| ATOM | 2407 | CD2 | HIS | A | 313 | 36.702 | 33.746 | 22.627 | 1.00 | 33.54 | C |

TABLE 3-continued

| | | | | | | | | | | | |
|---|---|---|---|---|---|---|---|---|---|---|---|
| ATOM | 2408 | CE1 | HIS | A | 313 | 36.921 | 34.208 | 20.489 | 1.00 | 35.03 | C |
| ATOM | 2409 | ND2 | HIS | A | 313 | 37.424 | 33.491 | 21.481 | 1.00 | 35.78 | N |
| ATOM | 2410 | N | GLN | A | 314 | 37.479 | 37.042 | 23.803 | 1.00 | 24.43 | N |
| ATOM | 2411 | CA | GLN | A | 314 | 38.762 | 37.092 | 24.465 | 1.00 | 24.34 | C |
| ATOM | 2412 | C | GLN | A | 314 | 38.762 | 38.226 | 25.510 | 1.00 | 24.39 | C |
| ATOM | 2413 | O | GLN | A | 314 | 39.327 | 38.081 | 26.590 | 1.00 | 24.82 | O |
| ATOM | 2414 | CB | GLN | A | 314 | 39.882 | 37.290 | 23.439 | 1.00 | 24.47 | C |
| ATOM | 2415 | CG | GLN | A | 314 | 40.032 | 36.106 | 22.472 | 1.00 | 25.49 | C |
| ATOM | 2416 | CD | GLN | A | 314 | 41.036 | 36.362 | 21.366 | 1.00 | 25.52 | C |
| ATOM | 2417 | OE1 | GLN | A | 314 | 40.878 | 37.287 | 20.563 | 1.00 | 27.59 | O |
| ATOM | 2418 | NE2 | GLN | A | 314 | 42.078 | 35.553 | 21.330 | 1.00 | 28.22 | N |
| ATOM | 2419 | N | LYS | A | 315 | 38.113 | 39.337 | 25.196 | 1.00 | 23.51 | N |
| ATOM | 2420 | CA | LYS | A | 315 | 38.000 | 40.423 | 26.154 | 1.00 | 23.79 | C |
| ATOM | 2421 | C | LYS | A | 315 | 37.125 | 39.979 | 27.325 | 1.00 | 23.05 | C |
| ATOM | 2422 | O | LYS | A | 315 | 37.373 | 40.347 | 28.465 | 1.00 | 21.38 | O |
| ATOM | 2423 | CB | LYS | A | 315 | 37.421 | 41.667 | 25.504 | 1.00 | 24.09 | C |
| ATOM | 2424 | CG | LYS | A | 315 | 38.382 | 42.286 | 24.533 | 1.00 | 26.96 | C |
| ATOM | 2425 | CD | LYS | A | 315 | 37.849 | 43.552 | 23.947 | 1.00 | 31.28 | C |
| ATOM | 2426 | CE | LYS | A | 315 | 38.856 | 44.156 | 22.977 | 1.00 | 34.34 | C |
| ATOM | 2427 | NZ | LYZ | A | 315 | 38.207 | 45.098 | 22.005 | 1.00 | 36.25 | N |
| ATOM | 2428 | N | VAL | A | 316 | 36.109 | 39.177 | 27.041 | 1.00 | 22.30 | N |
| ATOM | 2429 | CA | VAL | A | 316 | 35.276 | 38.673 | 28.113 | 1.00 | 22.39 | C |
| ATOM | 2430 | C | VAL | A | 316 | 36.124 | 37.800 | 29.063 | 1.00 | 22.29 | C |
| ATOM | 2431 | O | VAL | A | 316 | 36.040 | 37.932 | 30.274 | 1.00 | 21.27 | O |
| ATOM | 2432 | CB | VAL | A | 316 | 34.065 | 37.887 | 27.595 | 1.00 | 22.03 | C |
| ATOM | 2433 | CG1 | VAL | A | 316 | 33.309 | 37.282 | 28.750 | 1.00 | 21.64 | C |
| ATOM | 2434 | CG2 | VAL | A | 316 | 33.123 | 38.796 | 26.802 | 1.00 | 22.46 | C |
| ATOM | 2435 | N | ALA | A | 317 | 36.964 | 36.941 | 28.499 | 1.00 | 22.09 | O |
| ATOM | 2436 | CA | ALA | A | 317 | 37.848 | 36.086 | 29.295 | 1.00 | 21.98 | C |
| ATOM | 2437 | C | ALA | A | 317 | 38.783 | 36.916 | 30.164 | 1.00 | 21.61 | C |
| ATOM | 2438 | O | ALA | A | 317 | 39.042 | 36.573 | 31.300 | 1.00 | 21.05 | O |
| ATOM | 2439 | CB | ALA | A | 317 | 38.668 | 35.147 | 28.380 | 1.00 | 22.01 | C |
| ATOM | 2440 | N | ILE | A | 318 | 39.273 | 38.016 | 29.606 | 1.00 | 21.45 | O |
| ATOM | 2441 | CA | ILE | A | 318 | 40.162 | 38.917 | 30.318 | 1.00 | 21.24 | C |
| ATOM | 2442 | C | ILE | A | 318 | 39.431 | 39.511 | 31.524 | 1.00 | 21.38 | C |
| ATOM | 2443 | O | ILE | A | 318 | 39.937 | 39.462 | 32.646 | 1.00 | 20.76 | O |
| ATOM | 2444 | CB | ILE | A | 318 | 40.709 | 40.023 | 29.377 | 1.00 | 20.58 | C |
| ATOM | 2445 | CG1 | ILE | A | 318 | 41.715 | 39.434 | 28.400 | 1.00 | 21.19 | C |
| ATOM | 2446 | CG2 | ILE | A | 318 | 41.354 | 41.167 | 30.185 | 1.00 | 20.20 | C |
| ATOM | 2447 | CD1 | ILE | A | 318 | 42.223 | 40.419 | 27.353 | 1.00 | 21.35 | C |
| ATOM | 2448 | N | MET | A | 319 | 38.234 | 40.030 | 31.287 | 1.00 | 20.83 | N |
| ATOM | 2449 | CA | MET | A | 319 | 37.446 | 40.622 | 32.355 | 1.00 | 21.31 | C |
| ATOM | 2450 | C | MET | A | 319 | 37.154 | 39.617 | 33.454 | 1.00 | 21.52 | C |
| ATOM | 2451 | O | MET | A | 319 | 37.326 | 39.911 | 34.651 | 1.00 | 21.13 | O |
| ATOM | 2452 | CB | MET | A | 319 | 36.177 | 41.260 | 31.818 | 1.00 | 21.01 | C |
| ATOM | 2453 | CG | MET | A | 319 | 36.423 | 42.519 | 30.971 | 1.00 | 21.17 | C |
| ATOM | 2454 | SD | MET | A | 319 | 34.860 | 43.346 | 30.459 | 1.00 | 22.71 | S |
| ATOM | 2455 | CE | MET | A | 319 | 34.204 | 42.152 | 29.206 | 1.00 | 22.13 | C |
| ATOM | 2456 | N | ARG | A | 320 | 36.767 | 38.408 | 33.068 | 1.00 | 21.34 | N |
| ATOM | 2457 | CA | ARG | A | 320 | 36.532 | 37.399 | 34.075 | 1.00 | 21.12 | C |
| ATOM | 2458 | C | ARG | A | 320 | 37.801 | 37.186 | 34.898 | 1.00 | 21.25 | C |
| ATOM | 2459 | O | ARG | A | 320 | 37.747 | 37.064 | 36.122 | 1.00 | 21.48 | O |
| ATOM | 2460 | CB | ARG | A | 320 | 36.102 | 36.095 | 33.427 | 1.00 | 21.01 | C |
| ATOM | 2461 | CG | ARG | A | 320 | 34.723 | 36.145 | 32.741 | 1.00 | 20.63 | C |
| ATOM | 2462 | CD | ARG | A | 320 | 34.324 | 34.795 | 32.142 | 1.00 | 18.73 | C |
| ATOM | 2463 | NE | ARG | A | 320 | 34.225 | 33.824 | 33.225 | 1.00 | 19.25 | N |
| ATOM | 2464 | CZ | ARG | A | 320 | 33.247 | 33.809 | 34.115 | 1.00 | 19.86 | C |
| ATOM | 2465 | NH1 | ARG | A | 320 | 32.259 | 34.689 | 34.062 | 1.00 | 21.08 | N |
| ATOM | 2466 | NH2 | ARG | A | 320 | 33.263 | 32.923 | 35.081 | 1.00 | 23.29 | O |
| ATOM | 2467 | N | ASN | A | 321 | 38.947 | 37.123 | 34.231 | 1.00 | 20.94 | N |
| ATOM | 2468 | CA | ASN | A | 321 | 40.184 | 36.855 | 34.939 | 1.00 | 20.88 | C |
| ATOM | 2469 | C | ASN | A | 321 | 40.535 | 37.981 | 35.916 | 1.00 | 20.93 | C |
| ATOM | 2470 | O | ASN | A | 321 | 40.962 | 37.716 | 37.047 | 1.00 | 21.77 | O |
| ATOM | 2471 | CB | ASN | A | 321 | 41.324 | 36.552 | 33.958 | 1.00 | 21.04 | C |
| ATOM | 2472 | CG | ASN | A | 321 | 41.288 | 35.099 | 33.447 | 1.00 | 22.80 | C |
| ATOM | 2473 | OD1 | ASN | A | 321 | 40.924 | 34.193 | 34.185 | 1.00 | 23.97 | O |
| ATOM | 2474 | ND2 | ASN | A | 321 | 41.666 | 34.887 | 32.193 | 1.00 | 21.35 | N |
| ATOM | 2475 | N | ILE | A | 322 | 40.355 | 39.233 | 35.505 | 1.00 | 20.14 | N |
| ATOM | 2476 | CA | ILE | A | 322 | 40.633 | 40.336 | 36.408 | 1.00 | 20.06 | C |
| ATOM | 2477 | C | ILE | A | 322 | 39.742 | 40.196 | 37.650 | 1.00 | 19.42 | C |
| ATOM | 2478 | O | ILE | A | 322 | 40.207 | 40.345 | 38.767 | 1.00 | 18.73 | O |
| ATOM | 2479 | CB | ILE | A | 322 | 40.372 | 41.690 | 35.715 | 1.00 | 20.21 | C |
| ATOM | 2480 | CG1 | ILE | A | 322 | 41.320 | 41.894 | 34.535 | 1.00 | 21.54 | C |
| ATOM | 2481 | CG2 | ILE | A | 322 | 40.504 | 42.823 | 36.699 | 1.00 | 20.53 | C |
| ATOM | 2482 | CD1 | ILE | A | 322 | 42.806 | 41.798 | 34.868 | 1.00 | 24.56 | C |
| ATOM | 2483 | N | GLU | A | 323 | 38.458 | 39.904 | 37.454 | 1.00 | 18.94 | N |
| ATOM | 2484 | CA | GLU | A | 323 | 37.553 | 39.757 | 38.576 | 1.00 | 18.98 | C |

TABLE 3-continued

| | | | | | | | | | | | |
|---|---|---|---|---|---|---|---|---|---|---|---|
| \multicolumn{12}{|c|}{Coordinates for structures 1 to 4} |
| ATOM | 2485 | C | GLU | A | 323 | 38.027 | 38.651 | 39.492 | 1.00 | 19.33 | C |
| ATOM | 2486 | O | GLU | A | 323 | 38.084 | 38.832 | 40.707 | 1.00 | 19.05 | O |
| ATOM | 2487 | CB | GLU | A | 323 | 36.113 | 39.538 | 38.106 | 1.00 | 19.25 | C |
| ATOM | 2488 | CG | GLU | A | 323 | 35.518 | 40.803 | 37.484 | 1.00 | 19.34 | C |
| ATOM | 2489 | CD | GLU | A | 323 | 34.143 | 40.616 | 36.855 | 1.00 | 18.71 | C |
| ATOM | 2490 | OE1 | GLU | A | 323 | 33.183 | 40.332 | 37.573 | 1.00 | 19.19 | O |
| ATOM | 2491 | OE2 | GLU | A | 323 | 34.024 | 40.805 | 35.636 | 1.00 | 19.56 | O |
| ATOM | 2492 | N | LYS | A | 324 | 38.425 | 37.528 | 38.908 | 1.00 | 19.55 | N |
| ATOM | 2493 | CA | LYS | A | 324 | 38.874 | 36.379 | 39.693 | 1.00 | 20.24 | C |
| ATOM | 2494 | C | LYS | A | 324 | 40.115 | 36.707 | 40.513 | 1.00 | 20.68 | C |
| ATOM | 2495 | O | LYS | A | 324 | 40.157 | 36.405 | 41.699 | 1.00 | 20.83 | O |
| ATOM | 2496 | CB | LYS | A | 324 | 39.175 | 35.175 | 38.789 | 1.00 | 20.07 | C |
| ATOM | 2497 | CG | LYS | A | 324 | 37.924 | 34.507 | 38.212 | 1.00 | 20.57 | C |
| ATOM | 2498 | CD | LYS | A | 324 | 38.331 | 33.318 | 37.350 | 1.00 | 20.28 | C |
| ATOM | 2499 | CE | LYS | A | 324 | 37.137 | 32.689 | 36.621 | 1.00 | 19.29 | C |
| ATOM | 2500 | NZ | LYS | A | 324 | 37.596 | 31.460 | 35.876 | 1.00 | 17.17 | N |
| ATOM | 2501 | N | MET | A | 325 | 41.112 | 37.320 | 39.885 | 1.00 | 21.21 | N |
| ATOM | 2502 | CA | MET | A | 325 | 42.366 | 37.657 | 40.568 | 1.00 | 22.87 | C |
| ATOM | 2503 | C | MET | A | 325 | 42.162 | 38.665 | 41.699 | 1.00 | 22.44 | C |
| ATOM | 2504 | O | MET | A | 325 | 42.763 | 38.560 | 42.771 | 1.00 | 22.08 | O |
| ATOM | 2505 | CB | MET | A | 325 | 43.380 | 38.232 | 39.572 | 1.00 | 23.32 | C |
| ATOM | 2506 | CG | MET | A | 325 | 43.993 | 37.195 | 38.671 | 1.00 | 27.47 | C |
| ATOM | 2507 | SD | MET | A | 325 | 44.795 | 37.924 | 37.197 | 1.00 | 35.56 | s |
| ATOM | 2508 | CE | MET | A | 325 | 45.664 | 39.189 | 38.009 | 1.00 | 34.71 | C |
| ATOM | 2509 | N | LEU | A | 326 | 41.309 | 39.641 | 41.452 | 1.00 | 22.71 | N |
| ATOM | 2510 | CA | LEU | A | 326 | 41.043 | 40.670 | 42.449 | 1.00 | 23.24 | C |
| ATOM | 2511 | C | LEU | A | 326 | 40.385 | 40.073 | 43.679 | 1.00 | 23.15 | C |
| ATOM | 2512 | O | LEU | A | 326 | 40.735 | 40.417 | 44.795 | 1.00 | 22.40 | O |
| ATOM | 2513 | GB | LEU | A | 326 | 40.151 | 41.735 | 41.865 | 1.00 | 23.01 | C |
| ATOM | 2514 | CG | LEU | A | 326 | 40.677 | 43.139 | 41.625 | 1.00 | 25.86 | C |
| ATOM | 2515 | CD1 | LEU | A | 326 | 42.187 | 43.277 | 41.529 | 1.00 | 26.53 | C |
| ATOM | 2516 | CD2 | LEU | A | 326 | 39.986 | 43.672 | 40.377 | 1.00 | 25.54 | C |
| ATOM | 2517 | N | GLY | A | 327 | 39.441 | 39.164 | 43.460 | 1.00 | 23.29 | N |
| ATOM | 2518 | CA | GLY | A | 327 | 38.760 | 38.489 | 44.547 | 1.00 | 23.97 | C |
| ATOM | 2519 | C | GLY | A | 327 | 39.728 | 37.723 | 45.418 | 1.00 | 24.63 | C |
| ATOM | 2520 | O | GLY | A | 327 | 39.659 | 37.783 | 46.649 | 1.00 | 24.75 | O |
| ATOM | 2521 | N | GLU | A | 328 | 40.644 | 37.002 | 44.778 | 1.00 | 25.03 | N |
| ATOM | 2522 | CA | GLU | A | 328 | 41.671 | 36.265 | 45.506 | 1.00 | 26.08 | C |
| ATOM | 2523 | C | GLU | A | 328 | 42.661 | 37.180 | 46.223 | 1.00 | 25.43 | C |
| ATOM | 2524 | O | GLU | A | 328 | 43.029 | 36.926 | 47.367 | 1.00 | 25.16 | O |
| ATOM | 2525 | CB | GLU | A | 328 | 42.442 | 35.368 | 44.546 | 1.00 | 26.76 | C |
| ATOM | 2526 | CG | GLU | A | 328 | 41.576 | 34.278 | 43.947 | 1.00 | 30.36 | C |
| ATOM | 2527 | CD | GLU | A | 328 | 41.719 | 32.957 | 44.676 | 1.00 | 35.76 | C |
| ATOM | 2528 | OE1 | GLU | A | 328 | 42.091 | 32.986 | 45.878 | 1.00 | 38.79 | O |
| ATOM | 2529 | OE2 | GLU | A | 328 | 41.483 | 31.896 | 44.034 | 1.00 | 38.82 | O |
| ATOM | 2530 | N | ALA | A | 329 | 43.094 | 38.240 | 45.552 | 1.00 | 24.91 | N |
| ATOM | 2531 | CA | ALA | A | 329 | 44.102 | 39.119 | 46.134 | 1.00 | 24.95 | C |
| ATOM | 2532 | C | ALA | A | 329 | 43.535 | 39.929 | 47.285 | 1.00 | 24.94 | C |
| ATOM | 2533 | O | ALA | A | 329 | 44.197 | 40.147 | 48.276 | 1.00 | 24.57 | O |
| ATOM | 2534 | CE | ALA | A | 329 | 44.682 | 40.022 | 45.088 | 1.00 | 24.88 | C |
| ATOM | 2535 | N | LEU | A | 330 | 42.290 | 40.354 | 47.161 | 1.00 | 25.47 | N |
| ATOM | 2536 | CA | LEU | A | 330 | 41.672 | 41.133 | 48.219 | 1.00 | 26.16 | C |
| ATOM | 2537 | C | LEU | A | 330 | 41.212 | 40.265 | 49.379 | 1.00 | 26.80 | C |
| ATOM | 2538 | O | LEU | A | 330 | 40.994 | 40.761 | 50.471 | 1.00 | 27.00 | O |
| ATOM | 2539 | CE | LEU | A | 330 | 40.504 | 41.930 | 47.669 | 1.00 | 26.08 | C |
| ATOM | 2540 | CG | LEU | A | 330 | 40.954 | 42.981 | 46.653 | 1.00 | 26.04 | C |
| ATOM | 2541 | CD1 | LEU | A | 330 | 39.760 | 43.489 | 45.888 | 1.00 | 26.16 | C |
| ATOM | 2542 | CD2 | LEU | A | 330 | 41.688 | 44.134 | 47.353 | 1.00 | 26.65 | C |
| ATOM | 2543 | N | GLY | A | 331 | 41.037 | 38.977 | 49.126 | 1.00 | 27.87 | N |
| ATOM | 2544 | CA | GLY | A | 331 | 40.645 | 38.039 | 50.158 | 1.00 | 28.89 | C |
| ATOM | 2545 | C | GLY | A | 331 | 39.176 | 38.086 | 50.526 | 1.00 | 29.43 | C |
| ATOM | 2546 | O | GLY | A | 331 | 38.763 | 37.435 | 51.478 | 1.00 | 30.62 | O |
| ATOM | 2547 | N | ASN | A | 332 | 38.400 | 38.887 | 49.808 | 1.00 | 29.59 | N |
| ATOM | 2548 | CA | ASN | A | 332 | 36.963 | 38.995 | 50.023 | 1.00 | 29.64 | C |
| ATOM | 2549 | C | ASN | A | 332 | 36.367 | 39.500 | 48.718 | 1.00 | 29.00 | C |
| ATOM | 2550 | O | ASN | A | 332 | 36.649 | 40.605 | 48.303 | 1.00 | 28.70 | O |
| ATOM | 2551 | CE | ASN | A | 332 | 36.656 | 39.973 | 51.156 | 1.00 | 30.15 | C |
| ATOM | 2552 | CG | ASN | A | 332 | 35.162 | 40.094 | 51.441 | 1.00 | 31.82 | C |
| ATOM | 2553 | OD1 | ASN | A | 332 | 34.335 | 39.531 | 50.734 | 1.00 | 34.71 | O |
| ATOM | 2554 | ND2 | ASN | A | 332 | 34.818 | 40.818 | 52.504 | 1.00 | 35.11 | N |
| ATOM | 2555 | N | PRO | A | 333 | 35.528 | 38.706 | 48.081 | 1.00 | 28.53 | N |
| ATOM | 2556 | CA | PRO | A | 333 | 35.001 | 39.075 | 46.771 | 1.00 | 28.25 | C |
| ATOM | 2557 | C | PRO | A | 333 | 34.176 | 40.343 | 46.807 | 1.00 | 27.91 | C |
| ATOM | 2558 | O | PRO | A | 333 | 34.033 | 40.984 | 45.776 | 1.00 | 26.99 | O |
| ATOM | 2559 | CE | PRO | A | 333 | 34.120 | 37.893 | 46.368 | 1.00 | 28.16 | C |
| ATOM | 2560 | CG | PRO | A | 333 | 34.137 | 36.938 | 47.468 | 1.00 | 28.91 | C |
| ATOM | 2561 | CD | PRO | A | 333 | 35.022 | 37.415 | 48.561 | 1.00 | 28.96 | C |

TABLE 3-continued

| | | | | | Coordinates for structures 1 to 4 | | | | | |
|---|---|---|---|---|---|---|---|---|---|---|
| ATOM | 2562 | N   | GLN | A | 334 | 33.638 | 40.701 | 47.965 | 1.00 | 27.80 | N |
| ATOM | 2563 | CA  | GLN | A | 334 | 32.814 | 41.896 | 48.039 | 1.00 | 27.97 | C |
| ATOM | 2564 | C   | GLN | A | 334 | 33.665 | 43.155 | 47.975 | 1.00 | 26.77 | C |
| ATOM | 2565 | O   | GLN | A | 334 | 33.144 | 44.245 | 47.764 | 1.00 | 26.51 | O |
| ATOM | 2566 | CB  | GLN | A | 334 | 31.906 | 41.867 | 49.278 | 1.00 | 28.98 | C |
| ATOM | 2567 | CG  | GLN | A | 334 | 30.675 | 40.969 | 49.038 | 1.00 | 32.17 | C |
| ATOM | 2568 | CD  | GLN | A | 334 | 29.661 | 40.962 | 50.175 | 1.00 | 35.54 | C |
| ATOM | 2569 | OE1 | GLN | A | 334 | 29.682 | 41.840 | 51.048 | 1.00 | 37.92 | O |
| ATOM | 2570 | NE2 | GLN | A | 334 | 28.760 | 39.961 | 50.163 | 1.00 | 36.72 | N |
| ATOM | 2571 | N   | GLU | A | 335 | 34.974 | 43.007 | 48.132 | 1.00 | 25.19 | N |
| ATOM | 2572 | CA  | GLU | A | 335 | 35.860 | 44.151 | 48.018 | 1.00 | 24.41 | C |
| ATOM | 2573 | C   | GLU | A | 335 | 36.170 | 44.466 | 46.537 | 1.00 | 22.68 | C |
| ATOM | 2574 | O   | GLU | A | 335 | 36.700 | 45.521 | 46.228 | 1.00 | 21.42 | O |
| ATOM | 2575 | CB  | GLU | A | 335 | 37.150 | 43.928 | 48.835 | 1.00 | 24.98 | C |
| ATOM | 2576 | CG  | GLU | A | 335 | 36.974 | 44.148 | 50.343 | 1.00 | 27.94 | C |
| ATOM | 2577 | CD  | GLU | A | 335 | 38.264 | 44.055 | 51.139 | 1.00 | 31.85 | C |
| ATOM | 2578 | OE1 | GLU | A | 335 | 39.248 | 44.736 | 50.777 | 1.00 | 34.79 | O |
| ATOM | 2579 | OE2 | GLU | A | 335 | 38.298 | 43.312 | 52.158 | 1.00 | 36.87 | O |
| ATOM | 2580 | N   | VAL | A | 336 | 35.809 | 43.566 | 45.625 | 1.00 | 21.32 | N |
| ATOM | 2581 | CA  | VAL | A | 336 | 36.113 | 43.751 | 44.201 | 1.00 | 20.37 | C |
| ATOM | 2582 | C   | VAL | A | 336 | 35.541 | 45.034 | 43.603 | 1.00 | 20.01 | C |
| ATOM | 2583 | O   | VAL | A | 336 | 36.247 | 45.798 | 42.954 | 1.00 | 19.07 | O |
| ATOM | 2584 | CE  | VAL | A | 336 | 35.647 | 42.554 | 43.371 | 1.00 | 20.60 | C |
| ATOM | 2585 | CG1 | VAL | A | 336 | 35.785 | 42.841 | 41.883 | 1.00 | 21.06 | C |
| ATOM | 2586 | CG2 | VAL | A | 336 | 36.463 | 41.316 | 43.743 | 1.00 | 20.68 | C |
| ATOM | 2587 | N   | GLY | A | 337 | 34.260 | 45.275 | 43.842 | 1.00 | 19.61 | N |
| ATOM | 2588 | CA  | GLY | A | 337 | 33.593 | 46.437 | 43.317 | 1.00 | 19.45 | C |
| ATOM | 2589 | C   | GLY | A | 337 | 34.205 | 47.760 | 43.731 | 1.00 | 19.51 | C |
| ATOM | 2590 | O   | GLY | A | 337 | 34.522 | 48.576 | 42.871 | 1.00 | 18.93 | O |
| ATOM | 2591 | N   | PRO | A | 338 | 34.333 | 48.010 | 45.032 | 1.00 | 20.41 | N |
| ATOM | 2592 | CA  | PRO | A | 338 | 34.959 | 49.253 | 45.503 | 1.00 | 20.40 | C |
| ATOM | 2593 | C   | PRO | A | 338 | 36.368 | 49.500 | 44.923 | 1.00 | 20.13 | C |
| ATOM | 2594 | O   | PRO | A | 338 | 36.674 | 50.630 | 44.548 | 1.00 | 19.20 | O |
| ATOM | 2595 | CB  | PRO | A | 338 | 34.960 | 49.092 | 47.035 | 1.00 | 20.63 | C |
| ATOM | 2596 | CG  | PRO | A | 338 | 33.749 | 48.261 | 47.298 | 1.00 | 21.17 | C |
| ATOM | 2597 | CD  | PRO | A | 338 | 33.782 | 47.221 | 46.151 | 1.00 | 20.95 | C |
| ATOM | 2598 | N   | LEU | A | 339 | 37.199 | 48.470 | 44.831 | 1.00 | 20.34 | N |
| ATOM | 2599 | CA  | LEU | A | 339 | 38.518 | 48.655 | 44.234 | 1.00 | 20.55 | C |
| ATOM | 2600 | C   | LEU | A | 339 | 38.382 | 49.060 | 42.768 | 1.00 | 20.06 | C |
| ATOM | 2601 | O   | LEU | A | 339 | 39.020 | 50.019 | 42.330 | 1.00 | 19.61 | O |
| ATOM | 2602 | CB  | LEU | A | 339 | 39.383 | 47.408 | 44.358 | 1.00 | 20.81 | C |
| ATOM | 2603 | CG  | LEU | A | 339 | 40.855 | 47.618 | 43.943 | 1.00 | 22.54 | C |
| ATOM | 2604 | CD1 | LEU | A | 339 | 41.809 | 46.817 | 44.786 | 1.00 | 25.30 | C |
| ATOM | 2605 | CD2 | LEU | A | 339 | 41.035 | 47.209 | 42.496 | 1.00 | 23.17 | C |
| ATOM | 2606 | N   | LEU | A | 340 | 37.526 | 48.361 | 42.023 | 1.00 | 19.51 | N |
| ATOM | 2607 | CA  | LEU | A | 340 | 37.327 | 48.687 | 40.600 | 1.00 | 19.36 | C |
| ATOM | 2608 | C   | LEU | A | 340 | 36.827 | 50.120 | 40.427 | 1.00 | 19.30 | C |
| ATOM | 2609 | O   | LEU | A | 340 | 37.318 | 50.861 | 39.566 | 1.00 | 17.55 | O |
| ATOM | 2610 | CB  | LEU | A | 340 | 36.361 | 47.721 | 39.952 | 1.00 | 19.31 | C |
| ATOM | 2611 | CG  | LEU | A | 340 | 36.929 | 46.333 | 39.637 | 1.00 | 21.99 | C |
| ATOM | 2612 | CD1 | LEU | A | 340 | 35.842 | 45.506 | 39.069 | 1.00 | 22.03 | C |
| ATOM | 2613 | CD2 | LEU | A | 340 | 38.140 | 46.390 | 38.673 | 1.00 | 21.20 | C |
| ATOM | 2614 | N   | ASN | A | 341 | 35.879 | 50.521 | 41.270 | 1.00 | 19.17 | N |
| ATOM | 2615 | CA  | ASN | A | 341 | 35.369 | 51.887 | 41.232 | 1.00 | 20.20 | C |
| ATOM | 2616 | C   | ASN | A | 341 | 36.465 | 52.914 | 41.530 | 1.00 | 19.98 | C |
| ATOM | 2617 | O   | ASN | A | 341 | 36.598 | 53.920 | 40.848 | 1.00 | 19.61 | O |
| ATOM | 2618 | CB  | ASN | A | 341 | 34.181 | 52.043 | 42.196 | 1.00 | 20.66 | C |
| ATOM | 2619 | CG  | ASN | A | 341 | 32.898 | 51.459 | 41.619 | 1.00 | 24.17 | C |
| ATOM | 2620 | OD1 | ASN | A | 341 | 32.484 | 51.843 | 40.531 | 1.00 | 30.93 | O |
| ATOM | 2621 | ND2 | ASN | A | 341 | 32.294 | 50.499 | 42.317 | 1.00 | 26.37 | N |
| ATOM | 2622 | N   | THR | A | 342 | 37.245 | 52.633 | 42.558 | 1.00 | 20.07 | N |
| ATOM | 2623 | CA  | THR | A | 342 | 38.351 | 53.489 | 42.939 | 1.00 | 20.49 | C |
| ATOM | 2624 | C   | THR | A | 342 | 39.322 | 53.613 | 41.763 | 1.00 | 20.27 | C |
| ATOM | 2625 | O   | THR | A | 342 | 39.835 | 54.688 | 41.502 | 1.00 | 19.66 | O |
| ATOM | 2626 | CB  | THR | A | 342 | 39.001 | 52.909 | 44.189 | 1.00 | 20.82 | C |
| ATOM | 2627 | OG1 | THR | A | 342 | 38.123 | 53.124 | 45.320 | 1.00 | 22.13 | O |
| ATOM | 2628 | CG2 | THR | A | 342 | 40.308 | 53.625 | 44.545 | 1.00 | 21.01 | C |
| ATOM | 2629 | N   | MET | A | 343 | 39.517 | 52.525 | 41.024 | 1.00 | 20.30 | N |
| ATOM | 2630 | CA  | MET | A | 343 | 40.402 | 52.543 | 39.873 | 1.00 | 20.66 | C |
| ATOM | 2631 | C   | MET | A | 343 | 39.932 | 53.445 | 38.758 | 1.00 | 20.29 | C |
| ATOM | 2632 | O   | MET | A | 343 | 40.750 | 54.119 | 38.129 | 1.00 | 19.31 | O |
| ATOM | 2633 | CE  | MET | A | 343 | 40.560 | 51.157 | 39.270 | 1.00 | 20.76 | C |
| ATOM | 2634 | CG  | MET | A | 343 | 41.810 | 50.453 | 39.625 | 1.00 | 23.39 | C |
| ATOM | 2635 | SD  | MET | A | 343 | 42.247 | 49.059 | 38.524 | 1.00 | 25.69 | S |
| ATOM | 2636 | CE  | MET | A | 343 | 41.161 | 48.058 | 38.968 | 1.00 | 26.74 | C |
| ATOM | 2637 | N   | ILE | A | 344 | 38.631 | 53.438 | 38.466 | 1.00 | 20.76 | N |
| ATOM | 2638 | CA  | ILE | A | 344 | 38.167 | 54.187 | 37.312 | 1.00 | 21.23 | C |

TABLE 3-continued

Coordinates for structures 1 to 4

| ATOM | 2639 | C   | ILE | A | 344 | 37.648 | 55.577 | 37.565 | 1.00 | 20.71 | C |
| ---- | ---- | --- | --- | - | --- | ------ | ------ | ------ | ---- | ----- | - |
| ATOM | 2640 | O   | ILE | A | 344 | 37.763 | 56.403 | 36.666 | 1.00 | 20.65 | O |
| ATOM | 2641 | CB  | ILE | A | 344 | 37.109 | 53.400 | 36.458 | 1.00 | 22.07 | C |
| ATOM | 2642 | CG1 | ILE | A | 344 | 35.710 | 53.613 | 36.992 | 1.00 | 23.91 | C |
| ATOM | 2643 | CG2 | ILE | A | 344 | 37.482 | 51.943 | 36.352 | 1.00 | 24.35 | C |
| ATOM | 2644 | CD1 | ILE | A | 344 | 34.650 | 53.199 | 36.033 | 1.00 | 28.26 | C |
| ATOM | 2645 | N   | LYS | A | 345 | 37.069 | 55.886 | 38.726 | 1.00 | 20.84 | N |
| ATOM | 2646 | CA  | LYS | A | 345 | 36.482 | 57.231 | 38.817 | 1.00 | 21.15 | C |
| ATOM | 2647 | C   | LYS | A | 345 | 37.464 | 58.376 | 38.784 | 1.00 | 19.86 | C |
| ATOM | 2648 | O   | LYS | A | 345 | 38.459 | 58.429 | 39.517 | 1.00 | 19.23 | O |
| ATOM | 2649 | CB  | LYS | A | 345 | 35.438 | 57.451 | 39.922 | 1.00 | 22.66 | C |
| ATOM | 2650 | CG  | LYS | A | 345 | 35.562 | 56.714 | 41.190 | 1.00 | 27.82 | C |
| ATOM | 2651 | CD  | LYS | A | 345 | 34.214 | 56.021 | 41.489 | 1.00 | 30.51 | C |
| ATOM | 2652 | CE  | LYS | A | 345 | 33.398 | 56.782 | 42.502 | 1.00 | 32.51 | C |
| ATOM | 2653 | NZ  | LYS | A | 345 | 34.069 | 56.806 | 43.829 | 1.00 | 37.63 | N |
| ATOM | 2654 | N   | GLY | A | 346 | 37.143 | 59.307 | 37.899 | 1.00 | 18.18 | N |
| ATOM | 2655 | CA  | GLY | A | 346 | 37.978 | 60.453 | 37.644 | 1.00 | 17.22 | C |
| ATOM | 2656 | C   | GLY | A | 346 | 39.303 | 60.105 | 36.978 | 1.00 | 16.31 | C |
| ATOM | 2657 | O   | GLY | A | 346 | 40.172 | 60.949 | 36.889 | 1.00 | 16.63 | O |
| ATOM | 2658 | N   | ARG | A | 347 | 39.453 | 58.872 | 36.531 | 1.00 | 16.85 | N |
| ATOM | 2659 | CA  | ARG | A | 347 | 40.697 | 58.413 | 35.904 | 1.00 | 17.52 | C |
| ATOM | 2660 | C   | ARG | A | 347 | 40.469 | 57.811 | 34.502 | 1.00 | 17.57 | C |
| ATOM | 2661 | O   | ARG | A | 347 | 41.178 | 58.143 | 33.559 | 1.00 | 17.10 | O |
| ATOM | 2662 | CB  | ARG | A | 347 | 41.379 | 57.384 | 36.812 | 1.00 | 17.20 | C |
| ATOM | 2663 | CG  | ARG | A | 347 | 41.822 | 57.949 | 38.181 | 1.00 | 16.77 | C |
| ATOM | 2664 | CD  | ARG | A | 347 | 43.287 | 57.491 | 38.583 | 1.00 | 18.88 | C |
| ATOM | 2665 | NE  | ARG | A | 347 | 43.254 | 56.087 | 38.618 | 1.00 | 17.77 | N |
| ATOM | 2666 | CZ  | ARG | A | 347 | 44.115 | 55.220 | 38.149 | 1.00 | 16.11 | C |
| ATOM | 2667 | NH1 | ARG | A | 347 | 45.323 | 55.512 | 37.658 | 1.00 | 16.59 | N |
| ATOM | 2668 | NH2 | ARG | A | 347 | 43.734 | 53.978 | 38.276 | 1.00 | 13.22 | N |
| ATOM | 2669 | N   | TYR | A | 348 | 39.472 | 56.954 | 34.375 | 1.00 | 18.74 | N |
| ATOM | 2670 | CA  | TYR | A | 348 | 39.138 | 56.317 | 33.091 | 1.00 | 20.48 | C |
| ATOM | 2671 | C   | TYR | A | 348 | 37.674 | 56.499 | 32.671 | 1.00 | 21.75 | C |
| ATOM | 2672 | O   | TYR | A | 348 | 37.296 | 56.047 | 31.596 | 1.00 | 22.39 | O |
| ATOM | 2673 | CB  | TYR | A | 348 | 39.411 | 54.800 | 33.124 | 1.00 | 19.97 | C |
| ATOM | 2674 | CG  | TYR | A | 348 | 40.874 | 54.384 | 33.199 | 1.00 | 19.65 | C |
| ATOM | 2675 | CD1 | TYR | A | 348 | 41.661 | 54.310 | 32.054 | 1.00 | 18.48 | C |
| ATOM | 2676 | CD2 | TYR | A | 348 | 41.458 | 54.051 | 34.414 | 1.00 | 17.73 | C |
| ATOM | 2677 | CE1 | TYR | A | 348 | 42.986 | 53.921 | 32.122 | 1.00 | 19.00 | C |
| ATOM | 2678 | CE2 | TYR | A | 348 | 42.775 | 53.667 | 34.494 | 1.00 | 18.72 | C |
| ATOM | 2679 | CZ  | TYR | A | 348 | 43.543 | 53.600 | 33.339 | 1.00 | 18.96 | C |
| ATOM | 2680 | OH  | TYR | A | 348 | 44.856 | 53.203 | 33.419 | 1.00 | 17.77 | Q |
| ATOM | 2681 | N   | ASN | A | 349 | 36.837 | 57.123 | 33.488 | 1.00 | 23.99 | N |
| ATOM | 2682 | CA  | ASN | A | 349 | 35.429 | 57.244 | 33.089 | 1.00 | 26.57 | C |
| ATOM | 2683 | C   | ASN | A | 349 | 34.947 | 58.611 | 32.689 | 1.00 | 27.62 | C |
| ATOM | 2684 | O   | ASN | A | 349 | 35.646 | 59.606 | 32.655 | 1.00 | 28.49 | O |
| ATOM | 2685 | CE  | ASN | A | 349 | 34.496 | 56.720 | 34.150 | 1.00 | 26.11 | C |
| ATOM | 2686 | CG  | ASN | A | 349 | 34.511 | 57.552 | 35.386 | 1.00 | 28.01 | C |
| ATOM | 2687 | OD1 | ASN | A | 349 | 35.282 | 58.518 | 35.517 | 1.00 | 29.49 | O |
| ATOM | 2688 | ND2 | ASN | A | 349 | 33.658 | 57.173 | 36.342 | 1.00 | 31.84 | N |
| ATOM | 2689 | OXT | ASN | A | 349 | 33.761 | 58.686 | 32.399 | 1.00 | 31.04 | O |
| TER  | 2690 |     | ASN | A | 349 |        |        |        |      |       |   |
| ATOM | 2691 | N   | LEU | S | 795 | 45.837 | 35.555 | 30.600 | 1.00 | 35.49 | N |
| ATOM | 2692 | CA  | LEU | S | 795 | 44.757 | 36.539 | 30.946 | 1.00 | 35.77 | C |
| ATOM | 2693 | C   | LEU | S | 795 | 43.580 | 36.250 | 30.030 | 1.00 | 35.54 | C |
| ATOM | 2694 | O   | LEU | S | 795 | 42.418 | 36.338 | 30.412 | 1.00 | 34.79 | C |
| ATOM | 2695 | CB  | LEU | S | 795 | 45.257 | 37.967 | 30.787 | 1.00 | 36.01 | C |
| ATOM | 2696 | CG  | LEU | S | 795 | 44.695 | 38.978 | 31.791 | 1.00 | 37.16 | C |
| ATOM | 2697 | CE1 | LEU | S | 795 | 44.761 | 38.459 | 33.204 | 1.00 | 37.65 | C |
| ATOM | 2698 | CD2 | LEU | S | 795 | 45.450 | 40.289 | 31.718 | 1.00 | 38.07 | C |
| ATOM | 2699 | N   | THR | S | 796 | 43.936 | 35.940 | 28.796 | 1.00 | 35.47 | N |
| ATOM | 2700 | CA  | THR | S | 796 | 43.060 | 35.351 | 27.800 | 1.00 | 36.25 | C |
| ATOM | 2701 | C   | THR | S | 796 | 42.644 | 33.888 | 28.079 | 1.00 | 35.84 | C |
| ATOM | 2702 | O   | THR | S | 796 | 41.819 | 33.331 | 27.365 | 1.00 | 36.38 | C |
| ATOM | 2703 | CB  | THR | S | 796 | 43.817 | 35.429 | 26.457 | 1.00 | 36.63 | C |
| ATOM | 2704 | OG1 | THR | S | 796 | 43.251 | 34.528 | 25.524 | 1.00 | 38.48 | O |
| ATOM | 2705 | CG2 | THR | S | 796 | 45.257 | 34.907 | 26.593 | 1.00 | 37.07 | C |
| ATOM | 2706 | N   | SER | S | 797 | 43.197 | 33.251 | 29.101 | 1.00 | 35.44 | N |
| ATOM | 2707 | CA  | SER | S | 797 | 42.835 | 31.860 | 29.377 | 1.00 | 35.29 | C |
| ATOM | 2708 | C   | SER | S | 797 | 41.426 | 31.760 | 29.984 | 1.00 | 35.18 | C |
| ATOM | 2709 | O   | SER | S | 797 | 40.925 | 32.701 | 30.611 | 1.00 | 33.96 | O |
| ATOM | 2710 | CB  | SER | S | 797 | 43.856 | 31.189 | 30.291 | 1.00 | 35.17 | C |
| ATOM | 2711 | OG  | SER | S | 797 | 43.716 | 31.654 | 31.624 | 1.00 | 36.65 | O |
| ATOM | 2712 | N   | TYR | S | 798 | 40.789 | 30.611 | 29.790 | 1.00 | 35.36 | N |
| ATOM | 2713 | CA  | TYR | S | 798 | 39.427 | 30.430 | 30.256 | 1.00 | 35.94 | C |
| ATOM | 2714 | C   | TYR | S | 798 | 39.148 | 29.075 | 30.890 | 1.00 | 35.14 | C |
| ATOM | 2715 | O   | TYR | S | 798 | 39.845 | 28.095 | 30.657 | 1.00 | 35.54 | O |

TABLE 3-continued

| | | | | | Coordinates for structures 1 to 4 | | | | | | |
|---|---|---|---|---|---|---|---|---|---|---|---|
| ATOM | 2716 | CB | TYR | S | 798 | 38.440 | 30.707 | 29.120 | 1.00 | 36.37 | C |
| ATOM | 2717 | CG | TYR | S | 798 | 38.554 | 29.794 | 27.920 | 1.00 | 39.89 | C |
| ATOM | 2718 | CD1 | TYR | S | 798 | 39.587 | 29.934 | 26.996 | 1.00 | 42.41 | C |
| ATOM | 2719 | CD2 | TYR | S | 798 | 37.606 | 28.808 | 27.697 | 1.00 | 43.13 | C |
| ATOM | 2720 | CE1 | TYR | S | 798 | 39.681 | 29.095 | 25.893 | 1.00 | 43.97 | C |
| ATOM | 2721 | CE2 | TYR | S | 798 | 37.687 | 27.963 | 26.597 | 1.00 | 44.94 | C |
| ATOM | 2722 | CZ | TYR | S | 798 | 38.723 | 28.109 | 25.698 | 1.00 | 44.95 | C |
| ATOM | 2723 | OH | TYR | S | 798 | 38.781 | 27.270 | 24.613 | 1.00 | 44.37 | O |
| ATOM | 2724 | N | ASP | S | 799 | 38.108 | 29.046 | 31.709 | 1.00 | 34.54 | N |
| ATOM | 2725 | CA | ASP | S | 799 | 37.685 | 27.840 | 32.392 | 1.00 | 33.87 | C |
| ATOM | 2726 | C | ASP | S | 799 | 36.600 | 27.187 | 31.545 | 1.00 | 32.58 | C |
| ATOM | 2727 | O | ASP | S | 799 | 36.465 | 27.501 | 30.366 | 1.00 | 32.32 | O |
| ATOM | 2728 | CB | ASP | S | 799 | 37.140 | 28.208 | 33.770 | 1.00 | 34.50 | C |
| ATOM | 2729 | CG | ASP | S | 799 | 37.299 | 27.104 | 34.773 | 1.00 | 36.07 | C |
| ATOM | 2730 | OD1 | ASP | S | 799 | 36.790 | 25.986 | 34.551 | 1.00 | 37.15 | O |
| ATOM | 2731 | OD2 | ASP | S | 799 | 37.918 | 27.279 | 35.833 | 1.00 | 41.54 | O |
| ATOM | 2732 | N | CYS | S | 800 | 35.812 | 26.301 | 32.141 | 1.00 | 30.83 | N |
| ATOM | 2733 | CA | CYS | S | 800 | 34.798 | 25.586 | 31.392 | 1.00 | 29.83 | C |
| ATOM | 2734 | C | CYS | S | 800 | 33.490 | 25.511 | 32.161 | 1.00 | 29.15 | C |
| ATOM | 2735 | O | CYS | S | 800 | 32.794 | 24.502 | 32.092 | 1.00 | 28.68 | O |
| ATOM | 2736 | CB | CYS | S | 800 | 35.273 | 24.167 | 31.092 | 1.00 | 29.46 | C |
| ATOM | 2737 | SG | CYS | S | 800 | 35.576 | 23.194 | 32.601 | 1.00 | 30.36 | S |
| ATOM | 2738 | N | GLU | S | 801 | 33.152 | 26.578 | 32.874 | 1.00 | 28.36 | N |
| ATOM | 2739 | CA | GLU | S | 801 | 31.936 | 26.605 | 33.670 | 1.00 | 28.63 | C |
| ATOM | 2740 | C | GLU | S | 803. | 30.667 | 26.793 | 32.829 | 1.00 | 28.34 | C |
| ATOM | 2741 | O | GLU | S | 801 | 30.626 | 27.562 | 31.867 | 1.00 | 27.30 | O |
| ATOM | 2742 | CB | GLU | S | 801 | 32.038 | 27.688 | 34.751 | 1.00 | 28.61 | C |
| ATOM | 2743 | CG | GLU | S | 801 | 33.252 | 27.501 | 35.655 | 1.00 | 30.83 | C |
| ATOM | 2744 | CD | GLU | S | 801 | 33.188 | 28.346 | 36.907 | 1.00 | 32.58 | C |
| ATOM | 2745 | OE1 | GLU | S | 801 | 32.414 | 27.985 | 37.805 | 1.00 | 33.57 | O |
| ATOM | 2746 | OE2 | GLU | S | 801 | 33.910 | 29.362 | 36.989 | 1.00 | 33.97 | O |
| ATOM | 2747 | N | VAL | S | 802 | 29.627 | 26.062 | 33.212 | 1.00 | 28.85 | N |
| ATOM | 2748 | CA | VAL | S | 802 | 28.350 | 26.079 | 32.515 | 1.00 | 29.03 | C |
| ATOM | 2749 | C | VAL | S | 802 | 27.233 | 26.056 | 33.546 | 1.00 | 29.80 | C |
| ATOM | 2750 | O | VAL | S | 802 | 27.505 | 25.948 | 34.726 | 1.00 | 29.92 | O |
| ATOM | 2751 | CB | VAL | S | 802 | 28.221 | 24.834 | 31.606 | 1.00 | 28.44 | C |
| ATOM | 2752 | CG1 | VAL | S | 802 | 29.288 | 24.856 | 30.523 | 1.00 | 26.99 | C |
| ATOM | 2753 | CG2 | VAL | S | 802 | 28.333 | 23.551 | 32.428 | 1.00 | 29.08 | C |
| ATOM | 2754 | N | ASN | S | 803 | 25.978 | 26.135 | 33.111 | 1.00 | 31.09 | N |
| ATOM | 2755 | CA | ASN | S | 803 | 24.853 | 26.053 | 34.042 | 1.00 | 32.53 | C |
| ATOM | 2756 | C | ASN | S | 803 | 24.550 | 24.641 | 34.497 | 1.00 | 33.81 | C |
| ATOM | 2757 | O | ASN | S | 803 | 23.456 | 24.143 | 34.270 | 1.00 | 34.27 | O |
| ATOM | 2758 | CB | ASN | S | 803 | 23.575 | 26.659 | 33.463 | 1.00 | 32.29 | C |
| ATOM | 2759 | CG | ASN | S | 803 | 23.640 | 28.146 | 33.367 | 1.00 | 31.77 | C |
| ATOM | 2760 | OD1 | ASN | S | 803 | 24.688 | 28.741 | 33.616 | 1.00 | 33.47 | O |
| ATOM | 2761 | ND2 | ASN | S | 803 | 22.525 | 28.772 | 33.005 | 1.00 | 29.83 | N |
| ATOM | 2762 | N | ALA | S | 804 | 25.521 | 24.015 | 35.147 | 1.00 | 35.23 | N |
| ATOM | 2763 | CA | ALA | S | 804 | 25.365 | 22.689 | 35.740 | 1.00 | 36.86 | C |
| ATOM | 2764 | C | ALA | S | 804 | 26.577 | 22.452 | 36.638 | 1.00 | 37.98 | C |
| ATOM | 2765 | O | ALA | S | 804 | 27.660 | 22.949 | 36.360 | 1.00 | 37.44 | O |
| ATOM | 2766 | CB | ALA | S | 804 | 25.285 | 21.610 | 34.676 | 1.00 | 36.63 | C |
| ATOM | 2767 | N | PRO | S | 805 | 26.394 | 21.694 | 37.711 | 1.00 | 40.20 | N |
| ATOM | 2768 | CA | PRO | S | 805 | 27.495 | 21.381 | 38.635 | 1.00 | 41.46 | C |
| ATOM | 2769 | C | PRO | S | 805 | 28.572 | 20.511 | 37.983 | 1.00 | 42.51 | C |
| ATOM | 2770 | O | PRO | S | 805 | 28.342 | 19.931 | 36.938 | 1.00 | 43.07 | O |
| ATOM | 2771 | CB | PRO | S | 805 | 26.799 | 20.615 | 39.774 | 1.00 | 41.54 | C |
| ATOM | 2772 | CG | PRO | S | 805 | 25.506 | 20.116 | 39.185 | 1.00 | 41.29 | C |
| ATOM | 2773 | CD | PRO | S | 805 | 25.117 | 21.076 | 38.115 | 1.00 | 40.40 | C |
| ATOM | 2774 | N | ILE | S | 806 | 29.728 | 20.406 | 38.622 | 1.00 | 44.25 | H |
| ATOM | 2775 | CA | ILE | S | 806 | 30.854 | 19.627 | 38.099 | 1.00 | 44.96 | C |
| ATOM | 2776 | C | ILE | S | 806 | 30.770 | 18.169 | 38.532 | 1.00 | 45.18 | C |
| ATOM | 2777 | O | ILE | S | 806 | 29.902 | 17.801 | 39.323 | 1.00 | 45.78 | O |
| ATOM | 2778 | CB | ILE | S | 806 | 32.197 | 20.246 | 38.569 | 1.00 | 45.19 | C |
| ATOM | 2779 | CG1 | ILE | S | 806 | 32.412 | 20.018 | 40.070 | 1.00 | 46.10 | C |
| ATOM | 2780 | CG2 | ILE | S | 806 | 32.230 | 21.743 | 38.246 | 1.00 | 46.08 | C |
| ATOM | 2781 | CD1 | ILE | S | 806 | 33.740 | 20.574 | 40.597 | 1.00 | 46.98 | C |
| ATOM | 2782 | N | LEU | S | 812 | 29.934 | 8.629 | 39.561 | 1.00 | 43.80 | N |
| ATOM | 2783 | CA | LEU | S | 812 | 29.027 | 8.736 | 38.425 | 1.00 | 43.90 | C |
| ATOM | 2784 | C | LEU | S | 812 | 29.761 | 9.243 | 37.182 | 1.00 | 43.45 | C |
| ATOM | 2785 | O | LEU | S | 812 | 30.160 | 10.410 | 37.114 | 1.00 | 43.36 | O |
| ATOM | 2786 | CE | LEU | S | 812 | 27.862 | 9.678 | 38.757 | 1.00 | 44.22 | C |
| ATOM | 2787 | CG | LEU | S | 812 | 26.979 | 9.292 | 39.951 | 1.00 | 45.50 | C |
| ATOM | 2788 | CD1 | LEU | S | 812 | 25.871 | 10.341 | 40.144 | 1.00 | 46.20 | C |
| ATOM | 2789 | CD2 | LEU | S | 812 | 26.385 | 7.894 | 39.793 | 1.00 | 45.08 | C |
| ATOM | 2790 | N | LEU | S | 813 | 29.928 | 8.375 | 36.190 | 1.00 | 42.70 | N |
| ATOM | 2791 | CA | LEU | S | 813 | 30.620 | 8.776 | 34.969 | 1.00 | 42.21 | C |
| ATOM | 2792 | C | LEU | S | 813 | 29.711 | 9.604 | 34.057 | 1.00 | 41.46 | C |

TABLE 3-continued

| | | | | | | | | | | | |
|---|---|---|---|---|---|---|---|---|---|---|---|
| ATOM | 2793 | O | LEU | S | 813 | 28.492 | 9.438 | 34.062 | 1.00 | 41.23 | O |
| ATOM | 2794 | CB | LEU | S | 813 | 31.167 | 7.554 | 34.225 | 1.00 | 42.30 | C |
| ATOM | 2795 | CG | LEU | S | 813 | 32.093 | 6.644 | 35.046 | 1.00 | 42.35 | C |
| ATOM | 2796 | CD1 | LEU | S | 813 | 32.494 | 5.419 | 34.233 | 1.00 | 42.48 | C |
| ATOM | 2797 | CD2 | LEU | S | 813 | 33.322 | 7.398 | 35.527 | 1.00 | 41.80 | C |
| ATOM | 2798 | N | GLN | S | 814 | 30.326 | 10.492 | 33.283 | 1.00 | 40.74 | N |
| ATOM | 2799 | CA | GLN | S | 814 | 29.603 | 11.385 | 32.378 | 1.00 | 40.26 | C |
| ATOM | 2800 | C | GLN | S | 814 | 30.475 | 11.775 | 31.190 | 1.00 | 39.82 | C |
| ATOM | 2801 | O | GLN | S | 814 | 31.674 | 11.514 | 31.176 | 1.00 | 39.19 | O |
| ATOM | 2802 | CE | GLN | S | 814 | 29.173 | 12.649 | 33.122 | 1.00 | 40.24 | C |
| ATOM | 2803 | CG | GLN | S | 814 | 30.336 | 13.501 | 33.615 | 1.00 | 40.51 | C |
| ATOM | 2804 | CD | GLN | S | 814 | 29.879 | 14.725 | 34.406 | 1.00 | 41.88 | C |
| ATOM | 2805 | OE1 | GLN | S | 814 | 29.200 | 14.590 | 35.419 | 1.00 | 41.86 | O |
| ATOM | 2806 | NE2 | GLN | S | 814 | 30.253 | 15.919 | 33.940 | 1.00 | 40.63 | H |
| ATOM | 2807 | H | GLY | S | 815 | 29.864 | 12.416 | 30.200 | 1.00 | 39.81 | H |
| ATOM | 2808 | CA | GLY | S | 815 | 30.568 | 12.851 | 29.012 | 1.00 | 39.53 | C |
| ATOM | 2809 | C | GLY | S | 815 | 31.402 | 11.755 | 28.365 | 1.00 | 39.85 | C |
| ATOM | 2810 | O | GLY | S | 815 | 30.962 | 10.609 | 28.210 | 1.00 | 38.55 | O |
| ATOM | 2811 | N | GLU | S | 816 | 32.624 | 12.123 | 27.995 | 1.00 | 40.44 | H |
| ATOM | 2812 | CA | GLU | S | 816 | 33.553 | 11.208 | 27.352 | 1.00 | 41.24 | C |
| ATOM | 2813 | C | GLU | S | 816 | 33.744 | 9.926 | 28.154 | 1.00 | 41.73 | C |
| ATOM | 2814 | O | GLU | S | 816 | 33.895 | 8.852 | 27.577 | 1.00 | 41.11 | O |
| ATOM | 2815 | CE | GLU | S | 816 | 34.909 | 11.884 | 27.148 | 1.00 | 41.24 | C |
| ATOM | 2816 | CG | GLU | S | 816 | 35.752 | 11.238 | 26.063 | 1.00 | 42.19 | C |
| ATOM | 2817 | CD | GLU | S | 816 | 37.161 | 11.790 | 26.019 | 1.00 | 43.70 | C |
| ATOM | 2818 | OE1 | GLU | S | 816 | 37.985 | 11.311 | 26.814 | 1.00 | 45.25 | O |
| ATOM | 2819 | OE2 | GLU | S | 816 | 37.447 | 12.696 | 25.201 | 1.00 | 44.50 | O |
| ATOM | 2820 | N | GLU | S | 817 | 33.724 | 10.039 | 29.479 | 1.00 | 42.66 | N |
| ATOM | 2821 | CA | GLU | S | 817 | 33.925 | 8.877 | 30.340 | 1.00 | 43.73 | C |
| ATOM | 2822 | C | GLU | S | 817 | 32.744 | 7.917 | 30.268 | 1.00 | 44.19 | C |
| ATOM | 2823 | O | GLU | S | 817 | 32.930 | 6.699 | 30.252 | 1.00 | 43.99 | O |
| ATOM | 2824 | CB | GLU | S | 817 | 34.167 | 9.308 | 31.788 | 1.00 | 43.81 | C |
| ATOM | 2825 | CG | GLU | S | 817 | 35.463 | 10.077 | 31.989 | 1.00 | 44.98 | C |
| ATOM | 2826 | CD | GLU | S | 817 | 35.337 | 11.569 | 31.688 | 1.00 | 46.95 | C |
| ATOM | 2827 | OE1 | GLU | S | 817 | 34.221 | 12.052 | 31.394 | 1.00 | 48.87 | O |
| ATOM | 2828 | OE2 | GLU | S | 817 | 36.362 | 12.277 | 31.748 | 1.00 | 49.02 | O |
| ATOM | 2829 | N | LEU | S | 818 | 31.536 | 8.470 | 30.231 | 1.00 | 44.93 | N |
| ATOM | 2830 | CA | LEU | S | 818 | 30.335 | 7.663 | 30.149 | 1.00 | 45.78 | C |
| ATOM | 2831 | C | LEU | S | 818 | 30.359 | 6.882 | 28.846 | 1.00 | 46.89 | C |
| ATOM | 2832 | O | LEU | S | 818 | 30.163 | 5.663 | 28.833 | 1.00 | 46.50 | O |
| ATOM | 2833 | CB | LEU | S | 818 | 29.077 | 8.537 | 30.219 | 1.00 | 45.65 | C |
| ATOM | 2834 | CG | LEU | S | 818 | 27.741 | 7.788 | 30.147 | 1.00 | 45.58 | C |
| ATOM | 2835 | CD1 | LEU | S | 818 | 27.612 | 6.809 | 31.318 | 1.00 | 45.36 | C |
| ATOM | 2836 | CD2 | LEU | S | 818 | 26.551 | 8.719 | 30.133 | 1.00 | 43.95 | C |
| ATOM | 2837 | N | LEU | S | 819 | 30.654 | 7.588 | 27.760 | 1.00 | 48.01 | N |
| ATOM | 2838 | CA | LEU | S | 819 | 30.607 | 7.014 | 26.420 | 1.00 | 49.24 | C |
| ATOM | 2839 | C | LEU | S | 819 | 31.559 | 5.829 | 26.247 | 1.00 | 50.32 | C |
| ATOM | 2840 | O | LEU | S | 819 | 31.169 | 4.777 | 25.731 | 1.00 | 50.11 | O |
| ATOM | 2841 | CB | LEU | S | 819 | 30.903 | 8.105 | 25.380 | 1.00 | 49.22 | C |
| ATOM | 2842 | CG | LEU | S | 819 | 30.848 | 7.724 | 23.901 | 1.00 | 49.32 | C |
| ATOM | 2843 | CD1 | LEU | S | 819 | 29.495 | 7.178 | 23.497 | 1.00 | 48.73 | C |
| ATOM | 2844 | CD2 | LEU | S | 819 | 31.205 | 8.944 | 23.058 | 1.00 | 49.85 | C |
| ATOM | 2845 | N | ARG | S | 820 | 32.801 | 6.005 | 26.684 | 1.00 | 51.33 | N |
| ATOM | 2846 | CA | ARG | S | 820 | 33.807 | 4.966 | 26.550 | 1.00 | 52.53 | C |
| ATOM | 2847 | C | ARG | S | 820 | 33.471 | 3.748 | 27.414 | 1.00 | 52.95 | C |
| ATOM | 2848 | O | ARG | S | 820 | 33.534 | 2.606 | 26.942 | 1.00 | 53.06 | O |
| ATOM | 2849 | CB | ARG | S | 820 | 35.185 | 5.529 | 26.898 | 1.00 | 52.91 | C |
| ATOM | 2850 | CG | ARG | S | 820 | 35.620 | 6.583 | 25.904 | 1.00 | 54.20 | C |
| ATOM | 2851 | CD | ARG | S | 820 | 37.044 | 7.046 | 26.040 | 1.00 | 55.94 | C |
| ATOM | 2852 | NE | ARG | S | 820 | 37.320 | 8.113 | 25.081 | 1.00 | 58.09 | N |
| ATOM | 2853 | CZ | ARG | S | 820 | 38.453 | 8.808 | 25.022 | 1.00 | 59.82 | C |
| ATOM | 2854 | NH1 | ARG | S | 820 | 39.448 | 8.555 | 25.867 | 1.00 | 60.28 | N |
| ATOM | 2855 | NH2 | ARG | S | 820 | 38.590 | 9.765 | 24.108 | 1.00 | 60.61 | N |
| ATOM | 2856 | N | ALA | S | 821 | 33.106 | 3.994 | 28.670 | 1.00 | 53.36 | N |
| ATOM | 2857 | CA | ALA | S | 821 | 32.698 | 2.920 | 29.561 | 1.00 | 53.67 | C |
| ATOM | 2858 | C | ALA | S | 821 | 31.598 | 2.094 | 28.892 | 1.00 | 54.08 | C |
| ATOM | 2859 | O | ALA | S | 821 | 31.648 | 0.862 | 28.897 | 1.00 | 54.01 | O |
| ATOM | 2860 | CB | ALA | S | 821 | 32.215 | 3.479 | 30.883 | 1.00 | 53.55 | C |
| ATOM | 2861 | N | LEU | S | 822 | 30.616 | 2.777 | 28.308 | 1.00 | 54.44 | N |
| ATOM | 2862 | CA | LEU | S | 822 | 29.516 | 2.110 | 27.622 | 1.00 | 54.93 | C |
| ATOM | 2863 | C | LEU | S | 822 | 30.007 | 1.342 | 26.398 | 1.00 | 55.41 | C |
| ATOM | 2864 | O | LEU | S | 822 | 29.557 | 0.230 | 26.143 | 1.00 | 55.60 | O |
| ATOM | 2865 | CB | LEU | S | 822 | 28.445 | 3.117 | 27.212 | 1.00 | 54.90 | C |
| ATOM | 2866 | CG | LEU | S | 822 | 27.667 | 3.756 | 28.361 | 1.00 | 54.80 | C |
| ATOM | 2867 | CD1 | LEU | S | 822 | 26.531 | 4.601 | 27.801 | 1.00 | 54.39 | C |
| ATOM | 2868 | CD2 | LEU | S | 822 | 27.139 | 2.702 | 29.335 | 1.00 | 54.48 | C |
| ATOM | 2869 | N | ASP | S | 823 | 30.911 | 1.949 | 25.634 | 1.00 | 55.82 | N |

TABLE 3-continued

Coordinates for structures 1 to 4

| ATOM   | 2870 | CA  | ASP | S | 823  | 31.525 | 1.282  | 24.492 | 1.00 | 56.04 | C  |
|--------|------|-----|-----|---|------|--------|--------|--------|------|-------|----|
| ATOM   | 2871 | C   | ASP | S | 823  | 32.893 | 0.735  | 24.901 | 1.00 | 56.10 | C  |
| ATOM   | 2872 | O   | ASP | S | 823  | 33.186 | 0.451  | 24.731 | 1.00 | 56.09 | O  |
| ATOM   | 2873 | CB  | ASP | S | 823  | 31.688 | 2.252  | 23.320 | 1.00 | 56.21 | C  |
| ATOM   | 2874 | CG  | ASP | S | 823  | 31.858 | 1.535  | 21.997 | 1.00 | 56.45 | C  |
| ATOM   | 2875 | OD1 | ASP | S | 823  | 32.245 | 0.351  | 22.028 | 1.00 | 58.65 | O  |
| ATOM   | 2876 | OD2 | ASP | S | 823  | 31.628 | 2.056  | 20.885 | 1.00 | 56.19 | O  |
| TER    | 2877 |     | ASP | S | 823  |        |        |        |      |       |    |
| HETATM | 2878 | FE  | FE2 | A | 1350 | 23.294 | 27.501 | 28.594 | 1.00 | 20.46 | FE |
| HETATM | 2879 | C1  | OGA | A | 1351 | 22.091 | 25.173 | 27.594 | 1.00 | 24.79 | C  |
| HETATM | 2880 | C2  | OGA | A | 1351 | 21.066 | 25.829 | 28.202 | 1.00 | 24.27 | C  |
| HETATM | 2881 | C4  | OGA | A | 1351 | 18.756 | 25.714 | 29.004 | 1.00 | 23.09 | C  |
| HETATM | 2882 | C5  | OGA | A | 1351 | 17.415 | 25.241 | 28.495 | 1.00 | 23.17 | C  |
| HETATM | 2883 | O1  | OGA | A | 1351 | 21.909 | 24.061 | 27.090 | 1.00 | 25.24 | O  |
| HETATM | 2884 | O2  | OGA | A | 1351 | 23.219 | 25.658 | 27.531 | 1.00 | 24.40 | O  |
| HETATM | 2885 | O2  | OGA | A | 1351 | 21.192 | 26.959 | 28.711 | 1.00 | 21.19 | O  |
| HETATM | 2886 | O3  | OGA | A | 1351 | 16.416 | 25.662 | 29.055 | 1.00 | 23.03 | O  |
| HETATM | 2887 | M1  | OGA | A | 1351 | 19.886 | 25.203 | 28.228 | 1.00 | 21.70 | N  |
| HETATM | 2888 | O4  | OGA | A | 1351 | 17.332 | 24.475 | 27.537 | 1.00 | 23.98 | O  |
| HETATM | 2889 | S   | SO4 | A | 1352 | 0.316  | 25.182 | 43.602 | 1.00 | 77.77 | S  |
| HETATM | 2890 | O1  | SO4 | A | 1352 | 1.239  | 25.980 | 44.403 | 1.00 | 77.64 | O  |
| HETATM | 2891 | O2  | SO4 | A | 1352 | 1.075  | 24.260 | 42.760 | 1.00 | 77.88 | O  |
| HETATM | 2892 | O3  | SO4 | A | 1352 | 0.525  | 24.416 | 44.514 | 1.00 | 78.38 | O  |
| HETATM | 2893 | O4  | SO4 | A | 1352 | 0.507  | 26.042 | 42.757 | 1.00 | 76.90 | O  |
| HETATM | 2894 | S   | SO4 | A | 1353 | 1.990  | 28.487 | 29.834 | 1.00 | 69.20 | s  |
| HETATM | 2895 | O1  | SO4 | A | 1353 | 3.243  | 29.065 | 30.309 | 1.00 | 68.34 | O  |
| HETATM | 2896 | O2  | SO4 | A | 1353 | 2.236  | 27.438 | 28.847 | 1.00 | 67.90 | O  |
| HETATM | 2897 | O3  | SO4 | A | 1353 | 1.298  | 27.948 | 31.009 | 1.00 | 70.32 | O  |
| HETATM | 2898 | O4  | SO4 | A | 1353 | 1.162  | 29.517 | 29.203 | 1.00 | 69.63 | O  |
| HETATM | 2899 | O   | HOH | H | 1    | 35.955 | 31.618 | 40.285 | 1.00 | 80.01 | O  |
| HETATM | 2900 | O   | HOH | H | 2    | 38.513 | 33.804 | 31.613 | 1.00 | 33.04 | O  |
| HETATM | 2901 | O   | HOH | H | 3    | 36.648 | 25.786 | 38.779 | 1.00 | 76.96 | O  |
| HETATM | 2902 | O   | HOH | H | 4    | 38.106 | 25.337 | 29.179 | 1.00 | 54.79 | O  |
| HETATM | 2903 | O   | HOH | H | 5    | 34.990 | 30.561 | 34.967 | 1.00 | 30.13 | O  |
| HETATM | 2904 | O   | HOH | H | 6    | 33.934 | 31.237 | 38.711 | 1.00 | 40.66 | O  |
| HETATM | 2905 | O   | HOH | H | 7    | 30.766 | 25.787 | 37.613 | 1.00 | 54.75 | O  |
| HETATM | 2906 | O   | HOH | H | 8    | 33.667 | 28.867 | 40.196 | 1.00 | 59.66 | O  |
| HETATM | 2907 | O   | HOH | H | 9    | 28.622 | 27.043 | 37.556 | 1.00 | 57.58 | O  |
| HETATM | 2908 | O   | HOH | H | 10   | 19.894 | 26.655 | 33.706 | 1.00 | 54.88 | O  |
| HETATM | 2909 | O   | HOH | H | 11   | 30.052 | 24.213 | 35.628 | 1.00 | 41.23 | O  |
| HETATM | 2910 | O   | HOH | H | 12   | 28.737 | 12.960 | 37.083 | 1.00 | 59.80 | O  |
| HETATM | 2911 | O   | HOH | H | 13   | 35.568 | 13.822 | 23.888 | 1.00 | 38.00 | O  |
| HETATM | 2912 | O   | HOH | H | 14   | 30.722 | 1.323  | 21.296 | 1.00 | 48.92 | O  |
| HETATM | 2913 | O   | HOH | H | 15   | 32.110 | 2.136  | 17.673 | 1.00 | 69.92 | O  |
| HETATM | 2914 | O   | HOH | Z | 1    | 9.466  | 21.720 | 12.039 | 1.00 | 63.79 | O  |
| HETATM | 2915 | O   | HOH | Z | 2    | 1.367  | 21.270 | 7.724  | 1.00 | 60.01 | O  |
| HETATM | 2916 | O   | HOH | Z | 3    | 3.426  | 13.325 | 8.811  | 1.00 | 43.04 | O  |
| HETATM | 2917 | O   | HOH | Z | 4    | 0.760  | 13.029 | 7.574  | 1.00 | 47.08 | O  |
| HETATM | 2918 | O   | HOH | Z | 5    | 2.515  | 19.304 | 5.195  | 1.00 | 46.76 | O  |
| HETATM | 2919 | O   | HOH | Z | 6    | 4.861  | 33.534 | 13.331 | 1.00 | 75.60 | O  |
| HETATM | 2920 | O   | HOH | Z | 7    | 1.403  | 29.250 | 13.007 | 1.00 | 46.80 | O  |
| HETATM | 2921 | O   | HOH | Z | 8    | 1.614  | 32.100 | 13.758 | 1.00 | 66.18 | O  |
| HETATM | 2922 | O   | HOH | Z | 9    | 12.671 | 34.540 | 13.968 | 1.00 | 43.83 | O  |
| HETATM | 2923 | O   | HOH | Z | 10   | 11.399 | 2.867  | 17.750 | 1.00 | 68.06 | O  |
| HETATM | 2924 | O   | HOH | Z | 11   | 1.220  | 30.205 | 22.820 | 1.00 | 80.54 | O  |
| HETATM | 2925 | O   | HOH | Z | 12   | 6.576  | 36.529 | 29.511 | 1.00 | 43.88 | O  |
| HETATM | 2926 | O   | HOH | Z | 13   | 3.525  | 32.513 | 31.866 | 1.00 | 65.87 | O  |
| HETATM | 2927 | O   | HOH | Z | 14   | 5.033  | 37.447 | 27.566 | 1.00 | 54.03 | O  |
| HETATM | 2928 | O   | HOH | Z | 15   | 10.981 | 35.615 | 30.196 | 1.00 | 36.24 | O  |
| HETATM | 2929 | O   | HOH | Z | 16   | 12.816 | 42.461 | 26.787 | 1.00 | 37.83 | O  |
| HETATM | 2930 | O   | HOH | Z | 17   | 13.508 | 37.138 | 13.905 | 1.00 | 50.79 | O  |
| HETATM | 2931 | O   | HOH | Z | 18   | 16.409 | 3.305  | 16.425 | 1.00 | 59.87 | O  |
| HETATM | 2932 | O   | HOH | Z | 19   | 14.424 | 4.598  | 17.530 | 1.00 | 54.39 | O  |
| HETATM | 2933 | O   | HOH | Z | 20   | 11.439 | 7.927  | 15.708 | 1.00 | 63.10 | O  |
| HETATM | 2934 | O   | HOH | Z | 21   | 15.821 | 30.360 | 12.573 | 1.00 | 43.61 | O  |
| HETATM | 2935 | O   | HOH | Z | 22   | 13.496 | 22.189 | 7.246  | 1.00 | 57.93 | O  |
| HETATM | 2936 | O   | HOH | Z | 23   | 17.591 | 29.863 | 7.160  | 1.00 | 49.97 | O  |
| HETATM | 2937 | O   | HOH | Z | 24   | 14.617 | 26.200 | 13.898 | 1.00 | 48.56 | O  |
| HETATM | 2938 | O   | HOH | Z | 25   | 20.840 | 23.785 | 3.695  | 1.00 | 38.79 | O  |
| HETATM | 2939 | O   | HOH | Z | 26   | 27.946 | 19.151 | 9.101  | 1.00 | 43.14 | O  |
| HETATM | 2940 | O   | HOH | Z | 27   | 23.279 | 21.788 | 0.672  | 1.00 | 62.23 | O  |
| HETATM | 2941 | O   | HOH | Z | 28   | 27.443 | 22.009 | 43.177 | 1.00 | 68.81 | O  |
| HETATM | 2942 | O   | HOH | Z | 29   | 27.326 | 30.900 | 5.769  | 1.00 | 84.31 | O  |
| HETATM | 2943 | O   | HOH | Z | 30   | 16.938 | 35.662 | 41.749 | 1.00 | 51.88 | O  |
| HETATM | 2944 | O   | HOH | Z | 31   | 36.792 | 29.262 | 21.033 | 1.00 | 42.38 | O  |
| HETATM | 2945 | O   | HOH | Z | 32   | 26.719 | 37.403 | 13.167 | 1.00 | 60.20 | .0 |
| HETATM | 2946 | O   | HOH | Z | 33   | 29.797 | 37.021 | 10.379 | 1.00 | 60.24 | O  |

TABLE 3-continued

Coordinates for structures 1 to 4

| | | | | | | | | | | | |
|---|---|---|---|---|---|---|---|---|---|---|---|
| HETATM | 2947 | O | HOH | Z | 34 | 28.365 | 37.713 | 15.023 | 1.00 | 68.08 | O |
| HETATM | 2948 | O | HOH | Z | 35 | 27.471 | 34.815 | 9.298 | 1.00 | 63.90 | O |
| HETATM | 2949 | O | HOH | Z | 36 | 24.262 | 32.919 | 12.792 | 1.00 | 45.02 | O |
| HETATM | 2950 | O | HOH | Z | 37 | 19.704 | 17.909 | 13.178 | 1.00 | 28.78 | O |
| HETATM | 2951 | O | HOH | Z | 38 | 22.022 | 12.870 | 8.792 | 1.00 | 48.37 | O |
| HETATM | 2952 | O | HOH | Z | 39 | 18.151 | 14.971 | 12.982 | 1.00 | 36.76 | O |
| HETATM | 2953 | O | HOH | Z | 40 | 29.160 | 5.439 | 16.977 | 1.00 | 44.05 | O |
| HETATM | 2954 | O | HOH | Z | 41 | 18.863 | 14.590 | 16.204 | 1.00 | 30.84 | O |
| HETATM | 2955 | O | HOH | Z | 42 | 12.149 | 5.293 | 13.385 | 1.00 | 72.13 | O |
| HETATM | 2956 | O | HOH | Z | 43 | 15.651 | 2.782 | 13.845 | 1.00 | 41.52 | O |
| HETATM | 2957 | O | HOH | Z | 44 | 14.014 | 7.467 | 18.234 | 1.00 | 52.22 | O |
| HETATM | 2958 | O | HOH | Z | 45 | 5.548 | 12.548 | 27.846 | 1.00 | 38.03 | O |
| HETATM | 2959 | O | HOH | Z | 46 | 12.742 | 5.782 | 36.187 | 1.00 | 51.07 | O |
| HETATM | 2960 | O | HOH | Z | 47 | 19.063 | 6.567 | 36.600 | 1.00 | 49.16 | O |
| HETATM | 2961 | O | HOH | Z | 48 | 19.545 | 2.633 | 38.104 | 1.00 | 67.28 | O |
| HETATM | 2962 | O | HOH | Z | 49 | 7.710 | 14.276 | 19.473 | 1.00 | 48.41 | O |
| HETATM | 2963 | O | HOH | Z | 50 | 15.732 | 7.234 | 38.833 | 1.00 | 54.12 | O |
| HETATM | 2964 | O | HOH | Z | 51 | 21.932 | 13.291 | 44.351 | 1.00 | 62.49 | O |
| HETATM | 2965 | O | HOH | Z | 52 | 33.998 | 44.086 | 25.334 | 1.00 | 53.56 | O |
| HETATM | 2966 | O | HOH | Z | 53 | 12.673 | 21.178 | 43.612 | 1.00 | 63.01 | O |
| HETATM | 2967 | O | HOH | Z | 54 | 8.172 | 26.738 | 44.107 | 1.00 | 61.46 | 0. |
| HETATM | 2968 | O | HOH | Z | 55 | 9.613 | 30.854 | 42.520 | 1.00 | 54.56 | O |
| HETATM | 2969 | O | HOH | Z | 56 | 13.563 | 35.806 | 31.131 | 1.00 | 39.09 | O |
| HETATM | 2970 | O | HOH | Z | 57 | 15.688 | 37.473 | 35.304 | 1.00 | 47.58 | O |
| HETATM | 2971 | O | HOH | Z | 58 | 7.422 | 43.868 | 25.982 | 1.00 | 75.57 | O |
| HETATM | 2972 | O | HOH | Z | 59 | 7.978 | 38.223 | 34.865 | 1.00 | 59.51 | O |
| HETATM | 2973 | O | HOH | Z | 60 | 16.338 | 30.836 | 40.223 | 1.00 | 38.80 | O |
| HETATM | 2974 | O | HOH | Z | 61 | 17.035 | 27.760 | 38.288 | 1.00 | 52.22 | O |
| HETATM | 2975 | O | HOH | Z | 62 | 22.131 | 25.023 | 41.390 | 1.00 | 55.16 | O |
| HETATM | 2976 | O | HOH | Z | 63 | 29.869 | 29.910 | 39.122 | 1.00 | 47.28 | O |
| HETATM | 2977 | O | HOH | Z | 64 | 28.353 | 24.399 | 41.766 | 1.00 | 60.35 | O |
| HETATM | 2978 | O | HOH | Z | 65 | 31.794 | 27.570 | 41.962 | 1.00 | 48.59 | O |
| HETATM | 2979 | O | HOH | Z | 66 | 28.058 | 28.695 | 48.927 | 1.00 | 65.95 | O |
| HETATM | 2980 | O | HOH | Z | 67 | 24.838 | 24.783 | 42.190 | 1.00 | 52.90 | O |
| HETATM | 2981 | O | HOH | Z | 68 | 11.541 | 32.183 | 15.082 | 1.00 | 63.99 | O |
| HETATM | 2982 | O | HOH | Z | 69 | 31.599 | 33.767 | 45.823 | 1.00 | 44.28 | O |
| EETATM | 2983 | O | HOH | Z | 70 | 24.728 | 38.721 | 49.282 | 1.00 | 48.25 | O |
| HETATM | 2984 | O | HOH | Z | 71 | 16.271 | 36.399 | 44.087 | 1.00 | 58.46 | O |
| HETATM | 2985 | O | HOH | Z | 72 | 17.845 | 37.716 | 46.244 | 1.00 | 57.93 | O |
| HETATM | 2986 | O | HOH | Z | 73 | 16.480 | 33.117 | 41.520 | 1.00 | 59.15 | O |
| HETATM | 2987 | O | HOH | Z | 74 | 40.791 | 21.415 | 26.920 | 1.00 | 58.98 | O |
| HETATM | 2988 | O | HOH | Z | 75 | 21.842 | 17.819 | 48.106 | 1.00 | 67.11 | O |
| HETATM | 2989 | O | HOH | Z | 76 | 8.791 | 17.468 | 46.626 | 1.00 | 63.28 | O |
| HETATM | 2990 | O | HOH | Z | 77 | 17.141 | 16.914 | 47.607 | 1.00 | 52.87 | O |
| HETATM | 2991 | O | HOH | Z | 78 | 21.626 | 14.804 | 40.702 | 1.00 | 53.91 | O |
| HETATM | 2992 | O | HOH | Z | 79 | 39.117 | 50.091 | 47.735 | 1.00 | 57.17 | O |
| HETATM | 2993 | O | HOH | Z | 80 | 10.617 | 19.257 | 44.587 | 1.00 | 69.00 | O |
| HETATM | 2994 | O | HOH | Z | 81 | 1.682 | 24.435 | 36.842 | 1.00 | 55.40 | O |
| HETATM | 2995 | O | HOH | Z | 82 | 4.627 | 30.781 | 36.487 | 1.00 | 53.38 | O |
| HETATM | 2996 | O | HOH | Z | 83 | 17.463 | 26.906 | 33.818 | 1.00 | 38.64 | O |
| HETATM | 2997 | O | HOH | Z | 84 | 18.429 | 25.785 | 36.464 | 1.00 | 54.65 | O |
| HETATM | 2998 | O | HOH | Z | 85 | 23.466 | 17.336 | 36.578 | 1.00 | 41.94 | O |
| HETATM | 2999 | O | HOH | Z | 86 | 26.890 | 12.949 | 30.365 | 1.00 | 49.34 | O |
| HETATM | 3000 | O | HOH | Z | 87 | 21.694 | 10.405 | 34.333 | 1.00 | 45.95 | O |
| HETATM | 30D1 | O | HOH | Z | 88 | 20.030 | 9.589 | 36.847 | 1.00 | 52.33 | O |
| HETATM | 3002 | O | HOH | Z | 89 | 18.447 | 1.706 | 32.981 | 1.00 | 66.29 | O |
| HETATM | 3003 | O | HOH | Z | 90 | 16.300 | 0.205 | 30.017 | 1.00 | 50.70 | O |
| HETATM | 3004 | O | HOH | Z | 91 | 17.950 | 1.645 | 20.589 | 1.00 | 51.55 | O |
| HETATM | 3005 | O | HOH | Z | 92 | 26.301 | 5.439 | 16.918 | 1.00 | 36.67 | O |
| HETATH | 3006 | O | HOH | Z | 93 | 33.944 | 10.218 | 13.383 | 1.00 | 51.60 | O |
| HETATM | 3007 | O | HOH | Z | 94 | 30.893 | 16.371 | 11.174 | 1.00 | 40.00 | O |
| HETATM | 3008 | O | HOH | Z | 95 | 32.606 | 13.689 | 20.709 | 1.00 | 45.01 | O |
| HETATM | 3009 | O | HOH | Z | 96 | 31.860 | 10.158 | 7.765 | 1.00 | 58.55 | O |
| HETATM | 3010 | O | HOH | Z | 97 | 36.957 | 10.422 | 7.614 | 1.00 | 76.91 | O |
| HETATM | 3011 | O | HOH | Z | 98 | 35.951 | 16.836 | 31.735 | 1.00 | 59.28 | O |
| HETATM | 3012 | O | HOH | Z | 99 | 39.867 | 18.412 | 27.150 | 1.00 | 50.38 | O |
| HETATM | 3013 | O | HOH | Z | 100 | 13.436 | 20.952 | 28.355 | 1.00 | 27.89 | O |
| HETATM | 3014 | O | HOH | Z | 101 | 3.992 | 21.265 | 30.540 | 1.00 | 43.76 | O |
| HETATM | 3015 | O | HOH | Z | 102 | 30.735 | 37.910 | 33.103 | 1.00 | 30.45 | O |
| HETATM | 3016 | O | HOH | Z | 103 | 25.986 | 26.303 | 26.047 | 1.00 | 26.08 | O |
| HETATM | 3017 | O | HOH | Z | 104 | 36.837 | 32.025 | 33.001 | 1.00 | 37.86 | O |
| HETATM | 3018 | O | HOH | Z | 105 | 35.845 | 25.360 | 27.653 | 1.00 | 33.53 | O |
| HETATM | 3019 | O | HOH | Z | 106 | 31.874 | 20.474 | 33.040 | 1.00 | 55.47 | O |
| HETATH | 3020 | O | HOH | Z | 107 | 36.793 | 26.619 | 20.918 | 1.00 | 34.57 | O |
| HETATM | 3021 | O | HOH | Z | 108 | 17.114 | 16.909 | 17.862 | 1.00 | 35.83 | O |
| HETATM | 3022 | O | HOH | Z | 109 | 9.968 | 13.510 | 19.464 | 1.00 | 37.10 | O |
| HETATM | 3023 | O | HOH | Z | 110 | 5.274 | 16.717 | 22.023 | 1.00 | 44.26 | O |

TABLE 3-continued

Coordinates for structures 1 to 4

| | | | | | | | | | | | |
|---|---|---|---|---|---|---|---|---|---|---|---|
| HETATM | 3024 | O | HOH | Z | 111 | 7.041 | 16.862 | 20.149 | 1.00 | 37.71 | O |
| HETATH | 3025 | O | HOH | Z | 112 | 6.517 | 22.763 | 22.963 | 1.00 | 38.94 | O |
| HETATM | 3026 | O | HOH | Z | 113 | 29.471 | 38.812 | 26.249 | 1.00 | 22.19 | O |
| HETATM | 3027 | O | HOH | Z | 114 | 32.253 | 43.121 | 24.229 | 1.00 | 53.95 | O |
| HETATM | 3028 | O | HOH | Z | 115 | 28.797 | 40.227 | 16.136 | 1.00 | 64.15 | O |
| HETATM | 3029 | O | HOH | Z | 116 | 30.645 | 39.042 | 18.925 | 1.00 | 33.21 | O |
| HETATM | 3030 | O | HOH | Z | 117 | 25.466 | 42.302 | 17.883 | 1.00 | 64.00 | O |
| HETATM | 3031 | O | HOH | Z | 118 | 27.698 | 44.486 | 31.068 | 1.00 | 26.13 | O |
| HETATM | 3032 | O | HOH | Z | 119 | 30.274 | 44.879 | 25.031 | 1.00 | 38.32 | O |
| HETATM | 3033 | O | HOH | Z | 120 | 27.635 | 48.525 | 29.776 | 1.00 | 35.59 | O |
| HETATM | 3034 | O | HOH | Z | 121 | 25.933 | 50.527 | 30.463 | 1.00 | 35.79 | O |
| HETATM | 3035 | O | HOH | Z | 122 | 26.614 | 31.094 | 38.158 | 1.00 | 32.11 | O |
| HETATM | 3036 | O | HOH | Z | 123 | 29.486 | 36.934 | 35.226 | 1.00 | 27.40 | O |
| HETATM | 3037 | O | HOH | Z | 124 | 30.510 | 30.229 | 36.300 | 1.00 | 31.99 | O |
| HETATM | 3038 | O | HOH | Z | 125 | 19.859 | 31.575 | 33.786 | 1.00 | 31.77 | O |
| HETATM | 3039 | O | HOH | Z | 126 | 18.490 | 38.301 | 36.415 | 1.00 | 43.54 | O |
| HETATM | 3040 | O | HOH | Z | 127 | 19.538 | 36.155 | 33.217 | 1.00 | 30.91 | O |
| HETATM | 3041 | O | HOH | Z | 128 | 25.386 | 44.358 | 40.124 | 1.00 | 54.33 | O |
| HETATM | 3042 | O | HOH | Z | 129 | 21.227 | 42.704 | 39.938 | 1.00 | 38.88 | O |
| HETATM | 3043 | O | HOH | Z | 130 | 17.603 | 37.763 | 31.961 | 1.00 | 35.39 | O |
| HETATH | 3044 | O | HOH | Z | 131 | 9.290 | 41.007 | 35.589 | 1.00 | 51.53 | O |
| HETATM | 3045 | O | HOH | Z | 132 | 9.348 | 43.374 | 27.752 | 1.00 | 61.17 | O |
| HETATM | 3046 | O | HOH | Z | 133 | 15.089 | 37.816 | 32.481 | 1.00 | 32.05 | O |
| HETATM | 3047 | O | HOH | Z | 134 | 10.824 | 48.278 | 31.295 | 1.00 | 52.52 | O |
| HETATM | 3048 | O | HOH | Z | 135 | 15.691 | 44.668 | 34.824 | 1.00 | 31.47 | O |
| HETATM | 3049 | O | HOH | Z | 136 | 15.962 | 46.870 | 38.981 | 1.00 | 51.42 | O |
| HETATM | 3050 | O | HOH | Z | 137 | 13.481 | 51.613 | 32.894 | 1.00 | 45.77 | O |
| HETATM | 3051 | O | HOH | Z | 138 | 14.202 | 48.658 | 24.558 | 1.00 | 43.59 | O |
| HETATH | 3052 | O | HOH | Z | 139 | 16.193 | 44.497 | 37.574 | 1.00 | 58.87 | O |
| HETATM | 3053 | O | HOH | Z | 140 | 15.573 | 46.265 | 24.419 | 1.00 | 39.51 | O |
| HETATM | 3054 | O | HOH | Z | 141 | 18.684 | 55.873 | 28.304 | 1.00 | 58.28 | O |
| HETATM | 3055 | O | HOH | Z | 142 | 14.817 | 55.477 | 27.388 | 1.00 | 52.87 | O |
| HETATM | 3056 | O | HOH | Z | 143 | 15.284 | 50.258 | 22.000 | 1.00 | 32.96 | O |
| HETATM | 3057 | O | HOH | Z | 144 | 23.651 | 46.151 | 19.718 | 1.00 | 33.04 | O |
| HETATM | 3058 | O | HOH | Z | 145 | 16.751 | 46.565 | 21.800 | 1.00 | 33.97 | O |
| HETATM | 3059 | O | HOH | Z | 146 | 12.595 | 29.171 | 13.536 | 1.00 | 39.79 | O |
| HETATM | 3060 | O | HOH | Z | 147 | 10.812 | 19.188 | 14.084 | 1.00 | 50.88 | O |
| HETATM | 3061 | O | HOH | Z | 148 | 11.495 | 21.508 | 13.792 | 1.00 | 44.23 | O |
| HETATM | 3062 | O | HOH | Z | 149 | 14.521 | 18.471 | 12.156 | 1.00 | 37.16 | O |
| HETATM | 3063 | O | HOH | Z | 150 | 33.566 | 26.082 | 16.801 | 1.00 | 38.34 | O |
| HETATM | 3064 | O | HOH | Z | 151 | 27.798 | 27.494 | 24.390 | 1.00 | 25.11 | O |
| HETATM | 3065 | O | HOH | Z | 152 | 30.253 | 36.176 | 26.688 | 1.00 | 27.79 | O |
| HETATM | 3066 | O | HOH | Z | 153 | 32.762 | 34.069 | 19.065 | 1.00 | 47.61 | O |
| HETATM | 3067 | O | HOH | Z | 154 | 27.363 | 30.094 | 25.612 | 1.00 | 23.74 | O |
| HETATM | 3068 | O | HOH | Z | 155 | 16.282 | 36.168 | 29.566 | 1.00 | 33.13 | O |
| HETATM | 3069 | O | HOH | Z | 156 | 13.289 | 26.522 | 28.472 | 1.00 | 47.17 | O |
| HETATM | 3070 | O | HOH | Z | 157 | 7.556 | 30.888 | 24.716 | 1.00 | 44.35 | O |
| HETATM | 3071 | O | HOH | Z | 158 | 7.790 | 30.392 | 27.265 | 1.00 | 37.71 | O |
| HETATM | 3072 | O | HOH | Z | 159 | 3.910 | 21.360 | 21.198 | 1.00 | 60.23 | O |
| HETATM | 3073 | O | HOH | Z | 160 | 6.411 | 23.837 | 25.422 | 1.00 | 40.51 | O |
| HETATM | 3074 | O | HOH | Z | 161 | 3.001 | 17.561 | 27.759 | 1.00 | 55.61 | O |
| HETATM | 3075 | O | HOH | Z | 162 | 5.352 | 18.754 | 24.064 | 1.00 | 42.17 | O |
| HETATM | 3076 | O | HOH | Z | 163 | 40.897 | 21.985 | 24.633 | 1.00 | 54.83 | O |
| HETATM | 3077 | O | HOH | Z | 164 | 42.626 | 37.977 | 17.732 | 1.00 | 71.69 | O |
| HETATM | 3078 | O | HOH | Z | 165 | 42.463 | 44.114 | 19.559 | 1.00 | 54.59 | O |
| HETATM | 3079 | O | HOH | Z | 166 | 33.754 | 36.855 | 19.984 | 1.00 | 36.17 | O |
| HETATM | 3080 | O | HOH | Z | 167 | 33.194 | 39.271 | 33.406 | 1.00 | 28.26 | O |
| HETATM | 3081 | O | HOH | Z | 168 | 37.482 | 29.751 | 37.743 | 1.00 | 57.74 | O |
| HETATM | 3082 | O | HOH | Z | 169 | 38.789 | 34.566 | 42.752 | 1.00 | 40.46 | O |
| HETATM | 3083 | O | HOH | Z | 170 | 32.020 | 40.390 | 44.008 | 1.00 | 38.46 | O |
| HETATM | 3084 | O | HOH | Z | 171 | 31.865 | 44.151 | 45.174 | 1.00 | 45.64 | O |
| HETATM | 3085 | O | HOH | Z | 172 | 41.427 | 43.475 | 51.164 | 1.00 | 50.64 | O |
| HETATM | 3086 | O | HOH | Z | 173 | 38.498 | 47.344 | 48.085 | 1.00 | 60.19 | O |
| HETATM | 3087 | O | HOH | Z | 174 | 35.239 | 52.784 | 45.826 | 1.00 | 54.63 | O |
| HETATM | 3088 | O | HOH | Z | 175 | 32.343 | 51.933 | 45.286 | 1.00 | 58.03 | O |
| HETATM | 3089 | O | HOH | Z | 176 | 39.267 | 57.239 | 41.745 | 1.00 | 26.45 | O |
| HETATM | 3090 | O | HOH | Z | 177 | 32.755 | 59.287 | 44.804 | 1.00 | 60.46 | O |
| HETATM | 3091 | O | HOH | Z | 178 | 46.839 | 53.182 | 31.757 | 1.00 | 31.38 | O |
| HETATM | 3092 | O | HOH | Z | 179 | 37.840 | 55.111 | 29.241 | 1.00 | 44.20 | O |
| CONECT | 1478 | 2878 | | | | | | | | | |
| CONECT | 1498 | 2878 | | | | | | | | | |
| CONECT | 2167 | 2878 | | | | | | | | | |
| CONECT | 2878 | 2885 | 2884 | 1478 | 2167 | 1498 | | | | | |
| CONECT | 2879 | 2880 | 2883 | 2884 | | | | | | | |
| CONECT | 2880 | 2879 | 2885 | 2887 | | | | | | | |
| CONECT | 2881 | 2882 | 2887 | | | | | | | | |
| CONECT | 2882 | 2881 | 2886 | 2888 | | | | | | | |

TABLE 3-continued

Coordinates for structures 1 to 4

| | | | | | | | | | | |
|---|---|---|---|---|---|---|---|---|---|---|
| CONECT | 2883 | 2879 | | | | | | | | |
| CONECT | 2884 | 2879 | 2878 | | | | | | | |
| CONECT | 2885 | 2880 | 2878 | | | | | | | |
| CONECT | 2886 | 2882 | | | | | | | | |
| CONECT | 2887 | 2880 | 2881 | | | | | | | |
| CONECT | 2888 | 2882 | | | | | | | | |
| CONECT | 2889 | 2890 | 2891 | 2892 | 2893 | | | | | |
| CONECT | 2890 | 2889 | | | | | | | | |
| CONECT | 2891 | 2889 | | | | | | | | |
| CONECT | 2892 | 2889 | | | | | | | | |
| CONECT | 2893 | 2889 | | | | | | | | |
| CONECT | 2894 | 2895 | 2896 | 2897 | 2898 | | | | | |
| CONECT | 2895 | 2894 | | | | | | | | |
| CONECT | 2896 | 2894 | | | | | | | | |
| CONECT | 2897 | 2894 | | | | | | | | |
| CONECT | 2898 | 2894 | | | | | | | | |
| MASTER | 455 | 0 | 4 | 15 | 20 | 0 | 7 | 63090 | 2 | 24 | 31 |
| END | | | | | | | | | | | |

Structure 2
Below are the coordinates for structure 2 (the 2.25 Å structure of
FIH:Fe(II):2OG:CAD)

| | |
|---|---|
| HEADER | TRANSCRIPTION ACTIVATOR/INHIBITOR     12-AUG-02     1H2L |
| TITLE | FACTOR INHIBITING HIF-1 ALPHA IN COMPLEX WITH HIF-1 ALPHA |
| TITLE | 2 FRAGMENT PEPTIDE |
| COMPND | MOL_ID: 1; |
| COMPND | 2 MOLECULE: FACTOR INHIBITING HIF1; |
| COMPND | 3 CHAIN: A; |
| COMPND | 4 ENGINEERED: YES; |
| COMPND | 5 MOL_ID: 2; |
| COMPND | 6 MOLECULE: HYPOXIAINDUCIBLE FACTOR 1 ALPHA; |
| COMPND | 7 SYNONYM: HIF-1 ALPHA, ARNT IN THRACTING PROTEIN, |
| COMPND | 8 MEMBER OF PAS PROTEIN 1; |
| COMPND | 9 CHAIN: 5; |
| COMPND | 10 FRAGMENT: C-THRMINAL TRANSACTIVATION DOMAIN FRAGMENT |
| COMPND | 11 RESIDUES 786-826 |
| SOURCE | MOL_ID: 1; |
| SOURCE | 2 ORGANISM_SCIENTIFIC: *HOMO SAPIENS*; |
| SOURCE | 3 ORGANISM COMMON: HUMAN; |
| SOURCE | 4 EXPRESSION_SYSTEM: *ESCHERICHIA COLI*; |
| SOURCE | 5 EXPRESSION_SYSTEM STRAIN: BL21(DE3); |
| SOURCE | 6 EXPRESSION_SYSTEM_PLASMID: PET28A(+); |
| SOURCE | 7 MOL_ID: 2; |
| SOURCE | 8 ORGANISM_SCIENTIFIC: *HOMO SAPIENS*; |
| SOURCE | 9 ORGANISM_COMMON: HUMAN; |
| SOURCE | 10 EXPRESSION SYSTEM: *ESCHERICHIA COLI*; |
| SOURCE | 11 EXPRESSION SYSTEM STRAIN: BL21(DE3); |
| SOURCE | 12 EXPRESSION_SYSTEM_PLASMID: PGEXGP1 |
| KEYWDS | FIH, HIF, DSBH, OXYGENASE, TRANSCRIPTION, HYPOXIA, |
| KEYWDS | 2 2-OXOGLUTARATE, ASPARAGINYL HYDROXYLASE, HYDROXYLASE |
| EXPDTA | X-RAY DIFFRACTION |
| AUTHOR | J. M. ELKINS, K. S. HEWITSON, L. A. MCNEILL, I. SCHLEMMINGER |
| AUTHOR | 2 J. F. SEIBEL, C. J. SCHOFIELD |
| REVDAT | 1 04-SEP-02 1H2L 0 |
| JRNL | AUTH     J. M. ELKINS, K. S. HEWITSON, L. A. MCNEILL, |
| JRNL | AUTH    2 I. SCHLEMMINGER, J. F. SEIBEL, C. J. SCHOFIELD |
| JRNL | TITL     FIH:HIF-FRAGMENT COMPLEXES |
| JRNL | REF      TO BE PUBLISHED |
| JRNL | REFN |
| REMARK | 2 |
| REMARK | 2 RESOLUTION. 2.25 ANGSTROMS. |
| REMARK | 3 |
| REMARK | 3 REFINEMENT. |
| REMARK | 3 PROGRAM:    REFMAC 5.0 |
| REMARK | 3 AUTHORS:    MURSHUDOV, VAGIN, DODSON |
| REMARK | 3 |
| REMARK | 3 REFINEMENT TARGET: MAXIMUM LIKELIHOOD |
| REMARK | 3 |
| REMARK | 3 DATA USED IN REFINEMENT. |
| REMARK | 3 RESOLUTION RANGE HIGH (ANGSTROMS):       2.25 |
| REMARK | 3 RESOLUTION RANGE LOW (ANGSTROMS):        38.00 |
| REMARK | 3 DATA CUTOFF (SIGMA(F)):                  NONE |
| REMARK | 3 COMPLETENESS FOR RANGE (%):              99.98 |
| REMARK | 3 NUMBER OF REFLECTIONS:                   25127 |
| REMARK | 3 |
| REMARK | 3 FIT TO DATA USED IN REFINEMENT. |

TABLE 3-continued

Coordinates for structures 1 to 4

| | | | | | |
|---|---|---|---|---|---|
| REMARK | 3 CROSSVALIDATION METHOD: | THROUGHOUT | | | |
| REMARK | 3 FREE R VALUE TEST SET SELECTION: | RANDOM | | | |
| REMARK | 3 R VALUE (WORKING + TEST SET): | 0.18514 | | | |
| REMARK | 3 R VALUE (WORKING SET): | 0.1825 | | | |
| REMARK | 3 FREE R VALUE: | 0.21 | | | |
| REMARK | 3 FREE R VALUE TEST SET SIZE (%): | 7.7 | | | |
| REMARK | 3 FREE R VALUE TEST SET COUNT: | 2104 | | | |
| REMARK | 3 | | | | |
| REMARK | 3 FIT IN THE HIGHEST RESOLUTION BIN. | | | | |
| REMARK | 3 TOTAL NUMBER OF BINS USED: | 20 | | | |
| REMARK | 3 BIN RESOLUTION RANGE HIGH: | 2.250 | | | |
| REMARK | 3 BIN RESOLUTION RANGE LOW: | 2.308 | | | |
| REMARK | 3 REFLECTION IN BIN (WORKING SET): | 1783 | | | |
| REMARK | 3 BIN R VALUE (WORKING SET): | 0.194 | | | |
| REMARK | 3 BIN FREE R VALUE SET COUNT: | 170 | | | |
| REMARK | 3 BIN FREE R VALUE: | 0.228 | | | |
| REMARK | 3 | | | | |
| REMARK | 3 NUMBER OF NON-HYDROGEN ATOMS USED IN REFINEMENT. | | | | |
| REMARK | 3 PROTEIN ATOMS: | 2863 | | | |
| REMARK | 3 NUCLEIC ACID ATOMS: | 0 | | | |
| REMARK | 3 HETHROGEN ATOMS: | 21 | | | |
| REMARK | 3 SOLVENT ATOMS: | 139 | | | |
| REMARK | 3 | | | | |
| REMARK | 3 B VALUES. | | | | |
| REMARK | 3 FROM WILSON PLOT (A**2): | NULL | | | |
| REMARK | 3 MEAN B VALUE (OVERALL, A**2): | 27.234 | | | |
| REMARK | 3 OVERALL ANISOTROPIC B VALUE. | | | | |
| REMARK | 3 B11 (A**2): 0.40 | | | | |
| REMARK | 3 B22 (A**2): 0.40 | | | | |
| REMARK | 3 B33 (A**2): 0.80 | | | | |
| REMARK | 3 B12 (A**2): 0.00 | | | | |
| REMARK | 3 B13 (A**2): 0.00 | | | | |
| REMARK | 3 B23 (A**2): 0.00 | | | | |
| REMARK | 3 | | | | |
| REMARK | 3 ESTIMATED OVERALL COORDINATE ERROR. | | | | |
| REMARK | 3 ESU BASED ON R VALUE (A): | | 0.203 | | |
| REMARK | 3 ESU BASED ON FREE R VALUE (A): | | 0.174 | | |
| REMARK | 3 ESU BASED ON MAXIMUM LIKELIHOOD (A): | | 0.165 | | |
| REMARK | 3 ESU FOR B VALUES BASED ON MAXIMUM LIKELIHOOD (A**2): | | 6.444 | | |
| REMARK | 3 | | | | |
| REMARK | 3 CORRELATION COEFFICIENTS. | | | | |
| REMARK | 3 CORRELATION COEFFICIENT FO-FC: | 0.956 | | | |
| REMARK | 3 CORRELATION COEFFICIENT FO-FC FREE: | 0.939 | | | |
| REMARK | 3 | | | | |
| REMARK | 3 RMS DEVIATIONS FROM IDEAL VALUES | | COUNT | RMS | WEIGHT |
| REMARK | 3 BOND LENGTHS REFINED (A): | | 2961; | 0.013; | 0.021 |
| REMARK | 3 BOND LENGTHS REFINED (A): | | 2961; | 0.013; | 0.021 |
| REMARK | 3 BOND LENGTHS OTHERS (A): | | 2554; | 0.001; | 0.020 |
| REMARK | 3 BOND ANGLES REFINED (DEGREES): | | 4026; | 1.404; | 1.949 |
| REMARK | 3 BOND ANGLES OTHERS (DEGREES): | | 5966; | 0.727; | 3.000 |
| REMARK | 3 TORSION ANGLES, PERIOD 1 (DEGREES): | | 350; | 4.037; | 3.000 |
| REMARK | 3 TORSION ANGLES, PERIOD 3 (DEGREES): | | 515; | 18.189; | 15.000 |
| REMARK | 3 CHIRAL-CENTER RESTRAINTS (A**3): | | 413; | 0.085; | 0.200 |
| REMARK | 3 GENERAL PLANES REFINED (A): | | 3315; | 0.005; | 0.020 |
| REMARK | 3 GENERAL PLANES OTHERS (A): | | 602; | 0.002; | 0.020 |
| REMARK | 3 NON-BONDED CONTACTS REFINED (A): | | 693; | 0.221; | 0.300 |
| REMARK | 3 NON-BONDED CONTACTS OTHERS (A): | | 2483; | 0.204; | 0.300 |
| REMARK | 3 HBOND (X...Y) REFINED (A): | | 208; | 0.156; | 0.500 |
| REMARK | 3 SYMMETRY VDW REFINED (A): | | 16; | 0.256; | 0.300 |
| REMARK | 3 SYMMETRY VDW OTHERS (A): | | 63; | 0.259; | 0.300 |
| REMARK | 3 SYMMETRY H-BOND REFINED (A): | | 10; | 0.200; | 0.500 |
| REMARK | 3 | | | | |
| REMARK | 3 ISOTROPIC THERMAL FACTOR RESTRAINTS. | | COUNT | RMS | WEIGHT |
| REMARK | 3 MAINCHAIN BOND REFINED (A**2): | | 1767; | 0.649; | 1.500 |
| REMARK | 3 MAINCHAIN ANGLE REFINED (A**2): | | 2847; | 1.227; | 2.000 |
| REMARK | 3 SIDECHAIN BOND REFINED (A**2): | | 1194; | 1.887; | 3.000 |
| REMARK | 3 SIDECHAIN ANGLE REFINED (A**2): | | 1179; | 3.111; | 4.500 |
| REMARK | 3 | | | | |
| REMARK | 3 NCS RESTRAINTS STATISTICS | | | | |
| REMARK | 3 NUMBER OF NCS GROUPS: NULL | | | | |
| REMARK | 3 | | | | |
| REMARK | 3 TLS DETAILS | | | | |
| REMARK | 3 NUMBER OF TLS GROUPS: 1 | | | | |
| REMARK | 3 | | | | |
| REMARK | 3 TLS GROUP: 1 | | | | |
| REMARK | 3 NUMBER OF COMPONENTS GROUP: 2 | | | | |
| REMARK | 3 COMPONENTS     C     SSSEQI     TO     2 C     SSSEQI | | | | |

TABLE 3-continued

| | | Coordinates for structures 1 to 4 | | | | | | |
|---|---|---|---|---|---|---|---|---|
| REMARK | 3 | RESIDUE | RANGE | A | 15 | | A | 451 |
| REMARK | 3 | RESIDUE | RANGE | S | 795 | | A | 822 |
| REMARK | 3 | ORIGIN FOR THE GROUP (A): | | 22.2240 | 27.6230 | 28.5830 | | |
| REMARK | 3 | T TENSOR | | | | | | |
| REMARK | 3 | T11: | 0.1744 | T22: | 0.0216 | | | |
| REMARK | 3 | T33: | 0.0949 | T12: | 0.0059 | | | |
| REMARK | 3 | T13: | 0.0546 | T23: | 0.0427 | | | |
| REMARK | 3 | L TENSOR | | | | | | |
| REMARK | 3 | L11: | 1.1183 | L22: | 2.4664 | | | |
| REMARK | 3 | L33: | 1.3415 | L12: | 0.7934 | | | |
| REMARK | 3 | L13: | 0.5409 | L23: | 1.2249 | | | |
| REMARK | 3 | S TENSOR | | | | | | |
| REMARK | 3 | S11: | 0.0358 | S12: | 0.1772 | S13: | 0.0521 | |
| REMARK | 3 | S21: | 0.1763 | S22: | 0.0025 | S23: | 0.1089 | |
| REMARK | 3 | S31: | 0.2114 | S32: | 0.0339 | S33: | 0.0383 | |
| REMARK | 3 | | | | | | | |
| REMARK | 3 | BULK SOLVENT MODELLING. | | | | | | |
| REMARK | 3 | METHOD USED: BABINET MODEL WITH MASK | | | | | | |
| REMARK | 3 | PARAMETHRS FOR MASK CALCULATION | | | | | | |
| REMARK | 3 | VDW PROBE RADIUS: | | 1.40 | | | | |
| REMARK | 3 | ION PROBE RADIUS: | | 0.80 | | | | |
| REMARK | 3 | SHRINKAGE RADIUS: | | 0.80 | | | | |
| REMARK | 3 | | | | | | | |
| REMARK | 3 | OTHER REFINEMENT REMARKS: HYDROGENS HAVE BEEN ADDED IN THE | | | | | | |
| REMARK | 3 | RIDING POSITIONS | | | | | | |
| REMARK | 4 | | | | | | | |
| REMARK | 4 | 1H2L COMPLIES WITH FORMAT V. 2.3, 09-JULY-1998 | | | | | | |
| REMARK | 100 | | | | | | | |
| REMARK | 100 | THIS ENTRY HAS BEEN PROCESSED BY EBI ON 12-AUG-2002. | | | | | | |
| REMARK | 100 | THE EBI ID CODE IS EBI-11172. | | | | | | |
| REMARK | 200 | | | | | | | |
| REMARK | 200 | EXPERIMENTAL DETAILS | | | | | | |
| REMARK | 200 | EXPERIMENT TYPE: | | X-RAY DIFFRACTION | | | | |
| REMARK | 200 | DATE OF DATA COLLECTION: | | 15-MAY-2002 | | | | |
| REMARK | 200 | TEMPERATURE (KELVIN): | | 100 | | | | |
| REMARK | 200 | PH: | | 7.5 | | | | |
| REMARK | 200 | NUMBER OF CRYSTALS USED: | | 1 | | | | |
| REMARK | 200 | | | | | | | |
| REMARK | 200 | SYNCHROTRON (Y/N): | | Y | | | | |
| REMARK | 200 | RADIATION SOURCE: | | SRS BEAMLINE PX14.2 | | | | |
| REMARK | 200 | BEAMLINE: | | PX14.2 | | | | |
| REMARK | 200 | X-RAY GENERATOR MODEL: | | NULL | | | | |
| REMARK | 200 | MONOCHROMATIC OR LAUE(M/L): | | M | | | | |
| REMARK | 200 | WAVELENGTH OR RANGE (A): | | 0.983 | | | | |
| REMARK | 200 | MONOCHROMATOR: | | NULL | | | | |
| REMARK | 200 | OPTICS: | | NULL | | | | |
| REMARK | 200 | | | | | | | |
| REMARK | 200 | DETECTOR TYPE: | | CCD | | | | |
| REMARK | 200 | DETECTOR MANUFACTURER: | | ADSC | | | | |
| REMARK | 200 | INTENSITY-INTEGRATION SOFTWARE: | | MOSFLM | | | | |
| REMARX | 200 | DATA SCALING SOFTWARE: | | SCALA | | | | |
| REMARK | 200 | | | | | | | |
| REMARK | 200 | NUMBER OF UNIQUE REFLECTIONS: | | 27294 | | | | |
| REMARK | 200 | RESOLUTION RANGE HIGH (A): | | 2.25 | | | | |
| REMARK | 200 | RESOLUTION RANGE LOW (A) | | 38.63 | | | | |
| REMARK | 200 | REJECTION CRITERIA (SIGMA(I)): | | NONE | | | | |
| REMARK | 200 | | | | | | | |
| REMARK | 200 | OVERALL. | | | | | | |
| REMARK | 200 | COMPLETENESS FOR RANGE (%): | | 100.0 | | | | |
| REMARK | 200 | DATA REDUNDANCY: | | 7.0 | | | | |
| REMARK | 200 | R MERGE (I): | | 0.058 | | | | |
| REMARK | 200 | R SYM (I): | | NULL | | | | |
| REMARK | 200 | <I/SIGMA(I)> FOR THE DATA SET: | | 9.7 | | | | |
| REMARK | 200 | | | | | | | |
| REMARK | 200 | IN THE HIGHEST RESOLUTION SHELL. | | | | | | |
| REMARK | 200 | HIGHEST RESOLUTION SHELL, RANGE HIGH (A): | | | 2.25 | | | |
| REMARK | 200 | HIGHEST RESOLUTION SHELL, RANGE LOW (A): | | | 2.37 | | | |
| REMARK | 200 | COMPLETENESS FOR SHELL (%): | | 100.0 | | | | |
| REMARK | 200 | DATA REDUNDANCY IN SHELL: | | 7.2 | | | | |
| REMARK | 200 | R MERGE FOR SHELL (I): | | 0.307 | | | | |
| REMARK | 200 | R SYM FOR SHELL (I): | | NULL | | | | |
| REMARK | 200 | <I/SIGMA(I)> FOR SHELL: | | 2.5 | | | | |
| REMARK | 200 | | | | | | | |
| REMARK | 200 | DIFFRACTION PROTOCOL: SINGLE WAVELENGTH | | | | | | |
| REMARK | 200 | METHOD USED TO DETERMINE THE STRUCTURE: MOLECULAR REPLACEMENT | | | | | | |
| REMARK | 200 | SOFTWARE USED: NULL | | | | | | |
| REMARK | 200 | STARTING MODEL: NULL | | | | | | |

TABLE 3-continued

Coordinates for structures 1 to 4

| REMARK | 200 | | | | | |
|---|---|---|---|---|---|---|
| REMARK | 200 | REMARK: NULL | | | | |
| REMARK | 280 | | | | | |
| REMARK | 280 | CRYSTAL | | | | |
| REMARK | 280 | SOLVENT CONTENT, VS (%): 63 | | | | |
| REMARK | 280 | MATTHEWS COEFFICIENT, VM (ANGSTROMS**3/DA): 3.4 | | | | |
| REMARK | 280 | | | | | |
| REMARK | 280 | CRYSTALLIZATION CONDITIONS: 1.2 M AMMONIUM SULPHATE, 4% PEG400, | | | | |
| REMARK | 280 | 0.1 M HEPES PH 7.5, ARGON ATMOSPHERE, 11 MG/ML PROTEIN WITH | | | | |
| REMARK | 280 | 1 MM FE(II), 2.5 MM AKG AND 2.5 MM PEPTIDE | | | | |
| REMARK | 290 | | | | | |
| REMARK | 290 | CRYSTALLOGRAPHIC SYMMETRY | | | | |
| REMARK | 290 | SYMMETRY OPERATORS FOR SPACE GROUP: P 41 21 2 | | | | |
| REMARK | 290 | | | | | |
| REMARK | 290 | SYMOP | SYMMETRY | | | |
| REMARK | 290 | NNNMMM | OPERATOR | | | |
| REMARK | 290 | 1555 | X,Y,Z | | | |
| REMARK | 290 | 2555 | −X,−Y,1/2+Z | | | |
| REMARK | 290 | 3555 | 1/2−Y,1/2+X,1/4+Z | | | |
| REMARK | 290 | 4555 | 1/2+Y,1/2−X,3/4+Z | | | |
| REMARK | 290 | 5555 | 1/2−X,1/2+Y,1/4−Z | | | |
| REMARK | 290 | 6555 | 1/2+X,1/2−Y,3/4−Z | | | |
| REMARK | 290 | 7555 | Y,X,−Z | | | |
| REMARK | 290 | 8555 | −Y,−X,1/2−Z | | | |
| REMARK | 290 | | | | | |
| REMARK | 290 | WHERE NNN -> OPERATOR NUMBER | | | | |
| REMARK | 290 | MMM -> TRANSLATION VECTOR | | | | |
| REMARK | 290 | | | | | |
| REMARK | 290 | CRYSTALLOGRAPHIC SYMMETRY TRANSFORMATIONS | | | | |
| REMARK | 290 | THE FOLLOWING TRANSFORMATIONS OPERATE ON THE ATOM/HETATM | | | | |
| REMARK | 290 | RECORDS IN THIS ENTRY TO PRODUCE CRYSTALLOGRAPHICALLY | | | | |
| REMARK | 290 | RELATED MOLECULES. | | | | |
| REMARK | 290 | SMTRY1 | 1 | 1.000000 | 0.000000 | 0.000000 | 0.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | 1.000000 | 0.000000 | 0.000000 | 0.00000 |
| REMARK | 290 | SMTRY2 | 2 | 0.000000 | 1.000000 | 0.000000 | 0.00000 |
| REMARK | 290 | SMTRY3 | 2 | 0.000000 | 0.000000 | 1.000000 | 73.95700 |
| REMARK | 290 | SMTRY1 | 3 | 0.000000 | 1.000000 | 0.000000 | 43.13200 |
| REMARK | 290 | SMTRY2 | 3 | 1.000000 | 0.000000 | 0.000000 | 43.13200 |
| REMARK | 290 | SMTRY3 | 3 | 0.000000 | 0.000000 | 1.000000 | 36.97850 |
| REMARK | 290 | SMTRY1 | 4 | 0.000000 | 1.000000 | 0.000000 | 43.13200 |
| REMARK | 290 | SMTRY2 | 4 | 1.000000 | 0.000000 | 0.000000 | 43.13200 |
| REMARK | 290 | SMTRY3 | 4 | 0.000000 | 0.000000 | 1.000000 | 110.93550 |
| REMARK | 290 | SMTRY1 | 5 | 1.000000 | 0.000000 | 0.000000 | 43.13200 |
| REMARK | 290 | SMTRY2 | 5 | 0.000000 | 1.000000 | 0.000000 | 43.13200 |
| REMARK | 290 | SMTRY3 | 5 | 0.000000 | 0.000000 | 1.000000 | 36.97850 |
| REMARK | 290 | SMTRY1 | 6 | 1.000000 | 0.000000 | 0.000000 | 43.13200 |
| REMARK | 290 | SMTRY2 | 6 | 0.000000 | 1.000000 | 0.000000 | 43.13200 |
| REMARK | 290 | SMTRY3 | 6 | 0.000000 | 0.000000 | 1.000000 | 110.93550 |
| REMARK | 290 | SMTRY1 | 7 | 0.000000 | 1.000000 | 0.000000 | 0.00000 |
| REMARK | 290 | SMTRY2 | 7 | 1.000000 | 0.000000 | 0.000000 | 0.00000 |
| REMARK | 290 | SMTRY3 | 7 | 0.000000 | 0.000000 | 1.000000 | 0.00000 |
| REMARK | 290 | SMTRY1 | 8 | 0.000000 | 1.000000 | 0.000000 | 0.00000 |
| REMARK | 290 | SMTRY2 | 8 | 1.000000 | 0.000000 | 0.000000 | 0.00000 |
| REMARK | 290 | SMTRY3 | 8 | 0.000000 | 0.000000 | 1.000000 | 73.95700 |
| REMARK | 290 | | | | | |
| REMARK | 290 | REMARK: NULL | | | | |
| REMARK | 300 | | | | | |
| REMARK | 300 | BIOMOLECULE: 1 | | | | |
| REMARK | 300 | THIS ENTRY CONTAINS THE CRYSTALLOGRAPHIC ASYMMETRIC UNIT | | | | |
| REMARK | 300 | WHICH CONSISTS OF 2 CHAIN(S). SEE REMARK 350 FOR | | | | |
| REMARK | 300 | INFORMATION ON GENERATING THE BIOLOGICAL MOLECULE(S). | | | | |
| REMARK | 300 | | | | | |
| REMARK | 300 | QUATERNARY STRUCTURE FOR THIS ENTRY: TETRAMERIC | | | | |
| REMARK | 300 | | | | | |
| REMARK | 300 | THE PROTEIN IS A HOMODIMER FORMED BY CHAIN A. | | | | |
| REMARK | 300 | A HETHRODIMERIC ASSOCIATION OF CHAIN A WITH CHAIN S | | | | |
| REMARK | 300 | PRODUCES A TETRAMER. | | | | |
| REMARK | 300 | | | | | |
| REMARK | 300 | THE BURIED SURFACE AREA SHOWN BELOW IS AN AVERAGE | | | | |
| REMARK | 300 | CALCULATED FOR THE HETEROTETRAMER AND DOES NOT | | | | |
| REMARK | 300 | CORRESPOND TO THE BURIED SURFACE AREA FOR THE | | | | |
| REMARK | 300 | HOMODIMER OF CHAIN A | | | | |
| REMARK | 300 | | | | | |
| REMARK | 300 | THE HETERO-ASSEMBLY DESCRIBED BY REMARK 350 APPEARS | | | | |
| REMARK | 300 | TO BE A CASE OF STRONG CRYSTAL PACKING WITH | | | | |

TABLE 3-continued

Coordinates for structures 1 to 4

| REMARK | 300 | THE MEAN DIFFERENCE IN ACCESSIBLE SURFACE AREA PER |
|---|---|---|
| REMARK | 300 | CHAIN BETWEEN THE ISOLATED CHAIN AND THAT FOR |
| REMARK | 300 | THE CHAIN IN THE COMPLEX IS 2141.3 ANGSTROM**2 |
| REMARK | 350 | |
| REMARK | 350 | GENERATING THE BIOMOLECULE |
| REMARK | 350 | COORDINATES FOR A COMPLETE MULTIMER REPRESENTING THE KNOWN |
| REMARK | 350 | BIOLOGICALLY SIGNIFICANT OLIGOMERIZATION STATE OF THE |
| REMARK | 350 | MOLECULE CAN BE GENERATED BY APPLYING BIOMT TRANSFORMATIONS |
| REMARK | 350 | GIVEN BELOW. BOTH NON-CRYSTALLOGRAPHIC AND |
| REMARK | 350 | CRYSTALLOGRAPHIC OPERATIONS ARE GIVEN. |
| REMARK | 350 | |
| REMARK | 350 | BIOMOLECULE: 1 |
| REMARK | 350 | APPLY THE FOLLOWING TO CHAINS: A, S |
| REMARK | 350 | BIOMT1    1  1.000000  0.000000  0.000000  0.00000 |
| REMARK | 350 | BIOMT2    1  0.000000  1.000000  0.000000  0.00000 |
| REMARK | 350 | BIOMT3    1  0.000000  0.000000  1.000000  0.00000 |
| REMARK | 350 | BIOMT1    2  0.000000  1.000000  0.000000  86.26400 |
| REMARK | 350 | BIOMT2    2  1.000000  0.000000  0.000000  86.26400 |
| REMARK | 350 | BIOMT3    2  0.000000  0.000000  1.000000  73.95700 |
| REMARK | 465 | |
| REMARK | 465 | MISSING RESIDUES |
| REMARK | 465 | THE FOLLOWING RESIDUES WERE NOT LOCATED IN THE |
| REMARK | 465 | EXPERIMENT. (M=MODEL NUMBER; RES=RESIDUE NAME; C=CHAIN |
| REMARK | 465 | IDENTIFIER; SSSEQ=SEQUENCE NUMBER; I=INSERTION CODE.) |
| REMARK | 465 | |
| REMARK | 465 | M   RES  C   SSSEQI |
| REMARK | 465 |     MET  A   1 |
| REMARK | 465 |     ALA  A   2 |
| REMARK | 465 |     ALA  A   3 |
| REMARK | 465 |     THR  A   4 |
| REMARK | 465 |     ALA  A   5 |
| REMARK | 465 |     ALA  A   6 |
| REMARK | 465 |     GLU  A   7 |
| REMARK | 465 |     ALA  A   8 |
| REMARK | 465 |     VAL  A   9 |
| REMARK | 465 |     ALA  A   10 |
| REMARK | 465 |     SER  A   11 |
| REMARK | 465 |     GLY  A   12 |
| REMARK | 465 |     SER  A   13 |
| REMARK | 465 |     GLY  A   14 |
| REMARK | 465 |     LYS  A   304 |
| REMARK | 465 |     ARG  A   305 |
| REMARK | 465 |     ILE  A   306 |
| REMARK | 465 |     SER  5   786 |
| REMARK | 465 |     MET  5   787 |
| REMARK | 465 |     ASP  5   788 |
| REMARK | 465 |     GLU  5   789 |
| REMARK | 465 |     SER  5   790 |
| REMARK | 465 |     GLY  S   791 |
| REMARK | 465 |     LEU  S   792 |
| REMARK | 465 |     PRO  5   793 |
| REMARK | 465 |     GLN  5   794 |
| REMARK | 465 |     GLN  5   807 |
| REMARK | 465 |     GLY  5   808 |
| REMARK | 465 |     SER  5   809 |
| REMARK | 465 |     ARG  5   810 |
| REMARK | 465 |     ASN  5   811 |
| REMARK | 465 |     LEU  5   812 |
| REMARK | 465 |     ASP  5   823 |
| REMARK | 465 |     GLN  5   824 |
| REMARK | 465 |     VAL  5   825 |
| REMARK | 465 |     ASN  5   826 |
| REMARK | 470 | |
| REMARK | 470 | MISSING ATOM |
| REMARK | 470 | THE FOLLOWING RESIDUES HAVE MISSING ATOMS (M=MODEL NUMBER; |
| REMARK | 470 | RES=RESIDUE NAME; C=CHAIN IDENTIFIER; SSEQ=SEQUENCE NUMBER; |
| REMARK | 470 | I=INSERTION CODE): |
| REMARK | 470 | M   RES  CSSEQI    ATOMS |
| REMARK | 470 |     GLU  A   15    CG   CD   OE1  OE2 |
| REMARK | 470 |     GLU  A   29    CG   CD   OE1  OE2 |
| REMARK | 470 |     ASN  A   87    CG   OD1  ND2 |
| REMARK | 470 |     LYS  A   106   CD   CE   MZ |
| REMARK | 470 |     ARG  A   117   CG   CD   NE   CZ   NH1  NH2 |
| REMARK | 470 |     GLN  A   133   CG   CD   OE1  NE2 |
| REMARK | 470 |     GLN  A   136   CG   CD   OE1  NE2 |
| REMARK | 470 |     GLN  A   137   CG   CD   OE1  NE2 |
| REMARK | 470 |     ARG  A   156   CG   CD   NE   CZ   NH1  NH2 |

TABLE 3-continued

| | | | | | | | | | | |
|---|---|---|---|---|---|---|---|---|---|---|
| | | | Coordinates for structures 1 to 4 | | | | | | | |
| REMARK | 470 | | LYS | A | 157 | CD | CE | NZ | | |
| REMARK | 470 | | LYS | A | 311 | CG | CD | CE | NZ | |
| REMARK | 500 | | | | | | | | | |
| REMARK | 500 | GEOMETRY AND STEREOCHEMISTRY | | | | | | | | |
| REMARK | 500 | SUBTOPIC: COVALENT BOND LENGTHS | | | | | | | | |
| REMARK | 500 | | | | | | | | | |
| REMARK | 500 | THE STEREOCHEMICAL PARAMETERS OF THE FOLLOWING RESIDUES | | | | | | | | |
| REMARK | 500 | HAVE VALUES WHICH DEVIATE FROM EXPECTED VALUES BY MORE | | | | | | | | |
| REMARK | 500 | THAN 6*RMSD AND BY MORE THAN 0.150 ANGSTROMS (M=MODEL | | | | | | | | |
| REMARK | 500 | NUMBER; RES=RESIDUE NAME; C=CHAIN IDENTIFIER; SSEQ=SEQUENCE | | | | | | | | |
| REMARK | 500 | NUMBER; I=INSERTION CODE). | | | | | | | | |
| REMARK | 500 | | | | | | | | | |
| REMARK | 500 | STANDARD TABLE: | | | | | | | | |
| REMARK | 500 | FORMAT: (10X,13,1X,A3,1X,A1,14,A1,1X,2(A4,A1,3X),12X,F5.3) | | | | | | | | |
| REMARK | 500 | | | | | | | | | |
| REMARK | 500 | EXPECTED VALUESS: ENGH AND HUBER, 1991 | | | | | | | | |
| REMARK | 500 | | | | | | | | | |
| REMARK | 500 | M | RES | CSSEQI | ATM1 | RES | CSSEQI | ATM2 | DEVIATION | |
| REMARK | 500 | | MET | A 343 | SD | MET | A 343 | CE | −0.243 | |
| REMARK | 500 | | | | | | | | | |
| REMARK | 500 | REMARK: NULL | | | | | | | | |
| REMARK | 500 | | | | | | | | | |
| REMARK | 500 | GEOMETRY AND STEREOCHEMISTRY | | | | | | | | |
| REMARK | 500 | SUBTOPIC: CLOSE CONTACTS IN SAME ASYMMETRIC UNIT | | | | | | | | |
| REMARK | 500 | | | | | | | | | |
| REMARK | 500 | THE FOLLOWING ATOMS ARE IN CLOSE CONTACT. | | | | | | | | |
| REMARK | 500 | | | | | | | | | |
| REMARK | 500 | ATM1 | RES | C | SSEQ IATM2 | RES | C | SSEQI | DISTANCE | |
| REMARK | 500 | | | | | | | | | |
| REMARK | 500 | O | ALA | A 300 | OH | TYR | S 798 | 2.18 | | |
| REMARK | 525 | | | | | | | | | |
| REMARK | 525 | SOLVENT | | | | | | | | |
| REMARK | 525 | | | | | | | | | |
| REMARK | 525 | THE SOLVENT MOLECULES ARE GIVEN CHAIN IDENTIFIERS TO | | | | | | | | |
| REMARK | 525 | INDICATE THE PROTEIN CHAIN TO WHICH THEY ARE MOST CLOSELY | | | | | | | | |
| REMARK | 525 | ASSOCIATED WITH: | | | | | | | | |
| REMARK | 525 | PROTEIN CHAIN | | SOLVENT CHAIN | | | | | | |
| REMARK | 525 | A | | Z | | | | | | |
| REMARK | 525 | 5 | | H | | | | | | |
| REMARK | 600 | | | | | | | | | |
| REMARK | 600 | HETEROGEN | | | | | | | | |
| REMARK | 600 | | | | | | | | | |
| REMARK | 600 | FOR METAL ATOM FE FE2 A1350 THE COORDINATION ANGLES ARE: | | | | | | | | |
| REMARK | 600 | 1 | HIS | 199A | NE2 | | | | | |
| REMARK | 600 | 2 | ASP | 201A | OD2 | | 103.4 | | | |
| REMARK | 600 | 3 | HIS | 279A | NE2 | | 83.1 | 86.0 | | |
| REMARK | 600 | 4 | AKG | 1351A | O1 | | 168.9 | 87.6 | 98.2 | |
| REMARK | 600 | 5 | AKG | 1351A | O5 | | 87.0 | 169.4 | 97.2 | 81.9 |
| REMARK | 600 | | | | | | 1 | 2 | 3 | 4 | |
| REMARK | 700 | | | | | | | | | |
| REMARK | 700 | SHEET | | | | | | | | |
| REMARK | 700 | THE SHEET STRUCTURE OF THIS MOLECULE IS BIFURCATED. IN | | | | | | | | |
| REMARK | 700 | ORDER TO REPRESENT THIS FEATURE IN THE SHEET RECORDS BELOW, | | | | | | | | |
| REMARK | 700 | TWO SHEETS ARE DEFINED. | | | | | | | | |
| REMARK | 800 | | | | | | | | | |
| REMARK | 800 | SITE | | | | | | | | |
| REMARK | 800 | SITE_IDENTIFIER: FE1 | | | | | | | | |
| REMARK | 800 | SITE_DESCRIPTION: FE BINDING SITE FOR CHAIN A | | | | | | | | |
| REMARK | 800 | | | | | | | | | |
| REMARK | 800 | SITE_IDENTIFIER: AKG | | | | | | | | |
| REMARK | 800 | SITE_DESCRIPTION: AKG BINDING SITE FOR CHAIN A | | | | | | | | |
| REMARK | 800 | | | | | | | | | |
| REMARK | 800 | SITE_IDENTIFIER: SO1 | | | | | | | | |
| REMARK | 800 | SITE_DESCRIPTION: SO4 BINDING SITE FOR CHAIN A | | | | | | | | |
| REMARK | 800 | | | | | | | | | |
| REMARK | 800 | SITE_IDENTIFIER: SO2 | | | | | | | | |
| REMARK | 800 | SITE_DESCRIPTION: SO4 BINDING SITE FOR CHAIN A | | | | | | | | |
| REMARK | 900 | | | | | | | | | |
| REMARK | 900 | RELATED ENTRIES | | | | | | | | |
| REMARK | 900 | RELATED ID: 1D7G RELATED DB: PDB | | | | | | | | |
| REMARK | 900 | A MODEL FOR THE COMPLEX BETWEEN THE | | | | | | | | |
| REMARK | 900 | HYPOXIA-INDUCIBLE FACTOR-1 (HIF-1) AND ITS | | | | | | | | |
| REMARK | 900 | CONSENSUS DEOXYRIBONUCLEIC ACID SEQUENCE | | | | | | | | |
| REMARK | 900 | RELATED ID: 1H2K RELATED DB: PDB | | | | | | | | |
| REMARK | 900 | FACTOR INHIBITING HIF-1 ALPHA IN COMPLEX | | | | | | | | |
| REMARK | 900 | WITH HIF-1 ALPHA FRAGMENT PEPTIDE | | | | | | | | |
| REMARK | 900 | RELATED ID: 1H2M RELATED DB: PDB | | | | | | | | |

TABLE 3-continued

Coordinates for structures 1 to 4

| | | | | | | | | | | | | | | |
|---|---|---|---|---|---|---|---|---|---|---|---|---|---|---|
| REMARK | 900 FACTOR INHIBITING HIF-1 ALPHA IN COMPLEX | | | | | | | | | | | | | |
| REMARK | 900 WITH HIF-1 ALPHA FRAGMENT PEPTIDE | | | | | | | | | | | | | |
| REMARK | 900 RELATED ID: 1H2N RELATED DB: PDB | | | | | | | | | | | | | |
| REMARK | 900 FACTOR INHIBITING HIF3. ALPHA IN COMPLEX | | | | | | | | | | | | | |
| REMARK | 900 WITH HIF-1 ALPHA FRAGMENT PEPTIDE | | | | | | | | | | | | | |
| REMARK | 900 RELATED ID: 1L8C RELATED DB: 2DB | | | | | | | | | | | | | |
| REMARK | 900 STRUCTURAj, BASIS FOR HIF-1ALPHA/CBP | | | | | | | | | | | | | |
| REMARK | 900 RECOGNITION IN THECELLULAR HYPOXIC RESPONSE | | | | | | | | | | | | | |
| REMARK | 900 RELATED ID: 1LM8 RELATED DB: PUB | | | | | | | | | | | | | |
| REMARK | 900 STRUCTURE OF A HIF-1A-PVHL-ELONGINB- | | | | | | | | | | | | | |
| REMARK | 900 ELONGINC COMPLEX | | | | | | | | | | | | | |
| REMARK | 900 RELATED ID: 1LQB RELATED UB: PDB | | | | | | | | | | | | | |
| REMARK | 900 CRYSTAL STRUCTURE OF A HYDROXYLATED HIF1 | | | | | | | | | | | | | |
| REMARK | 900 ALPHA PEPTIDEBOUND TO THE PVHL/ELONGIN-C/ | | | | | | | | | | | | | |
| REMARK | 900 ELONGIN-B COMPLEX | | | | | | | | | | | | | |
| DBREF | 1H2L A | | 1 349 | SWS | Q969Q7 | | Q969Q7 | | 1 349 | | | | | |
| DBREF | 1H2L S | | 786 826 | SWS | Q16665 | | HIFA_ HUMAN | | 786 826 | | | | | |
| SEQRES | 1 A 349 | MET | ALA | ALA | THR | ALA | ALA | GLU | ALA | VAL | ALA | SER | GLY | SER |
| SEQRES | 2 A 349 | GLY | GLU | PRO | ARG | GLU | GLU | ALA | GLY | ALA | LEU | GLY | PRO | ALA |
| SEQRES | 3 A 349 | TRP | ASP | GLU | SER | GLN | LEU | ARG | SER | TYR | SER | PHE | PRO | THR |
| SEQRES | 4 A 349 | ARG | PRO | ILE | PRO | ARG | LEU | SER | GLN | SER | ASP | PRO | ARG | ALA |
| SEQRES | 5 A 349 | GLU | GLU | LEU | ILE | GLU | ASN | GLU | GLU | PRO | VAL | VAL | LEU | THR |
| SEQRES | 6 A 349 | ASP | THR | ASN | LEU | VAL | TYR | PRO | ALA | LEU | LYS | TRP | ASP | LEU |
| SEQRES | 7 A 349 | GLU | TYR | LEU | GLN | GLU | ASN | ILE | GLY | ASN | GLY | ASP | PHE | SER |
| SEQRES | 8 A 349 | VAL | TYR | SER | ALA | SER | THR | HIS | LYS | PHE | LEU | TYR | TYR | ASP |
| SEQRES | 9 A 349 | GLU | LYS | LYS | MET | ALA | ASN | PHE | GLN | ASN | PHE | LYS | PRO | ARO |
| SEQRES | 10 A 349 | SER | ASN | ARG | GLU | GLU | MET | LYS | PHE | HIS | GLU | PHE | VAL | GLU |
| SEQRES | 11 A 349 | LYS | LEU | GLN | ASP | ILE | GLN | GLN | ARO | GLY | GLY | GLU | GLU | ARO |
| SEQRES | 12 A 349 | LEU | TYR | LEU | GLN | GLN | THR | LEU | ASN | ASP | THR | VAL | GLY | ARG |
| SEQRES | 13 A 349 | LYS | ILE | VAL | MET | ASP | PHE | LEU | GLY | PHE | ASN | TRP | ASN | TRP |
| SEQRES | 14 A 349 | ILE | ASN | LYS | GLN | GLN | GLY | LYS | ARG | GLY | TRP | GLY | GLN | LEU |
| SEQRES | 15 A 349 | THR | SER | ASN | LEU | LEU | LEU | ILE | GLY | MET | GLU | GLY | ASN | VAL |
| SEQRES | 16 A 349 | THR | PRO | ALA | HIS | TYR | ASP | GLU | GLN | GLN | ASN | PHE | PHE | ALA |
| SEQRES | 17 A 349 | GLN | ILE | LYS | GLY | TYR | LYS | ARO | CYS | ILE | LEU | PHE | PRO | PRO |
| SEQRES | 18 A 349 | ASP | GLN | PHE | GLU | CYS | LEU | TYR | PRO | TYR | PRO | VAL | HIS | HIS |
| SEQRES | 19 A 349 | PRO | CYS | ASP | ARO | GLN | SER | GLN | VAL | ASP | PHE | ASP | ASN | PRO |
| SEORES | 20 A 349 | ASP | TYR | GLU | ARO | PHE | PRO | ASN | PHE | GLN | ASN | VAL | VAL | GLY |
| SEQRES | 21 A 349 | TYR | GLU | THR | VAL | VAL | GLY | PRO | GLY | ASP | VAL | LEU | TYR | ILE |
| SEQRES | 22 A 349 | PRO | MET | TYR | TRP | TRP | HIS | HIS | ILE | GLU | SER | LEU | LEU | ASN |
| SEQRES | 23 A 349 | GLY | GLY | ILE | THR | ILE | THR | VAL | ASN | PHE | TRP | TYR | LYS | GLY |
| SEQRES | 24 A 349 | ALA | PRO | THR | PRO | LYS | ARO | ILE | GLU | TYR | PRO | LEU | LYS | ALA |
| SEQRES | 25 A 349 | HIS | GLN | LYS | VAL | ALA | ILE | MET | ARO | ASN | ILE | GLU | LYS | MET |
| SEQRES | 26 A 349 | LEU | GLY | GLU | ALA | LEU | GLY | ASN | PRO | GLN | GLU | VAL | GLY | PRO |
| SEQRES | 27 A 349 | LEU | LEU | ASN | THR | MET | ILE | LYS | GLY | ARG | TYR | ASN | | |
| SEQRES | 1 S 41 | SER | MET | ASP | GLU | SER | GLY | LEU | PRO | GLN | LEU | THR | SER | TYR |
| SEQRES | 2 S 41 | ASP | CYS | GLU | VAL | ASN | ALA | PRO | ILE | GLN | GLY | SER | ARG | ASN |
| SEQRES | 3 S 41 | LEU | LEU | GLN | GLY | GLU | GLU | LEU | LEU | ARG | ALA | LEU | ASP | GLN |
| SEQRES | 4 S 41 | VAL | ASN | | | | | | | | | | | |
| HET | FE2 A1350 | | 1 | | | | | | | | | | | |
| HET | AKG A1351 | | 10 | | | | | | | | | | | |
| HET | SO4 A1352 | | 5 | | | | | | | | | | | |
| HET | SO4 A1353 | | 5 | | | | | | | | | | | |
| HETNAM | FE2 FE (II) ION | | | | | | | | | | | | | |
| HETNAM | AKG 2-OXYGLUTARIC ACID | | | | | | | | | | | | | |
| HETNAM | SO4 SULFATE ION | | | | | | | | | | | | | |
| FORMUL | 3 FE2 | FE1 | 2+ | | | | | | | | | | | |
| FORMUL | 4 AKG | C5 | H6 | O5 | | | | | | | | | | |
| FORMUL | 5 SO4 | 2(O4 | Si | 2-) | | | | | | | | | | |
| FORMUL | 6 HOH | *139(H2 | O1) | | | | | | | | | | | |
| HELIX | 1 1 | 1 | ASP | A | 28 LEU | A | 32 5 | | | | | | | 5 |
| HELIX | 2 2 | ASP | A | 49 | ASN A | 58 | 1 10 | | | | | | | |
| HELIX | 3 3 | VAL | A | 70 | TRP A | 76 | 5 7 | | | | | | | |
| HELIX | 4 4 | ASP | A | 77 | ILE A | 85 | 1 9 | | | | | | | |
| HELIX | 5 5 | ASP | A | 104 | PHE A | 111 | 5 8 | | | | | | | |
| HELIX | 6 6 | LYS | A | 124 | ARG A | 138 | 1 | | | | | | | |
| HELIX | 7 7 | GLY | A | 155 | GLY A | 164 | 1 10 | | | | | | | |
| HELIX | 8 8 | ASN | A | 166 | GLY A | 178 | 1 13 | | | | | | | |
| HELIX | 9 9 | PRO | A | 220 | ASP A | 222 | 5 3 | | | | | | | |
| HELIX | 10 10 | GLN | A | 223 | TYR A | 228 | 1 6 | | | | | | | |
| HELIX | 11 11 | PHE | A | 252 | VAL A | 258 | 5 7 | | | | | | | |
| HELIX | 12 12 | LYS | A | 311 | GLY A | 331 | 1 21 | | | | | | | |
| HELIX | 13 13 | ASN | A | 332 | GLN A | 334 | 5 3 | | | | | | | |
| HELIX | 14 14 | GLU | A | 335 | LYS A | 345 | 1 11 | | | | | | | |
| HELIX | 15 15 | GLN | S | 814 | LEU S | 822 | 1 9 | | | | | | | |
| SHEET | 1 AA | 5 | THR | A | 39 | PRO | A | 41 | 0 | | | | | |
| SHEET | 2 AA | 5 | GLY | A | 260 | VAL | A | 265 | 1 O | GLY A | 260 | N | ARG A | 40 |

TABLE 3-continued

Coordinates for structures 1 to 4

| | | | | | | | | | | | | | | | | | |
|---|---|---|---|---|---|---|---|---|---|---|---|---|---|---|---|---|---|
| SHEET | 3 | AA | 5 | LYS | A | 214 | PHE | A | 219 | −1 | O | LYS | A | 214 | N | VAL | A | 265 |
| SHEET | 4 | AA | 5 | TRP | A | 278 | SER | A | 283 | −1 | O | TRP | A | 278 | N | PHE | A | 219 |
| SHEET | 5 | AA | 5 | VAL | A | 195 | HIS | A | 199 | 1 | O | THR | A | 196 | N | ILE | A | 281 |
| SHEET | 1 | AB | 6 | ARG | A | 44 | LEU | A | 450 | | | | | | | | | |
| SHEET | 2 | AB | 6 | VAL | A | 62 | LEU | A | 64 | 1 | O | VAL | A | 63 | N | LEU | A | 45 |
| SHEET | 3 | AB | 6 | VAL | A | 270 | ILE | A | 273 | −1 | O | VAL | A | 270 | N | LEU | A | 64 |
| SHEET | 4 | AB | 6 | GLN | A | 204 | LYS | A | 211 | 1 | O | ASN | A | 205 | N | ILE | A | 273 |
| SHEET | 5 | AB | 6 | THR | A | 290 | TYR | A | 297 | −1 | O | ILE | A | 291 | N | ILE | A | 210 |
| SHEET | 6 | AB | 6 | LEU | A | 182 | SER | A | 184 | −1 | N | THR | A | 183 | O | TRP | A | 296 |
| SHEET | 1 | AC | 9 | ARG | A | 44 | LEU | A | 450 | | | | | | | | | |
| SHEET | 2 | AC | 9 | VAL | A | 62 | LEU | A | 64 | 1 | O | VAL | A | 63 | N | LEU | A | 45 |
| SHEET | 3 | AC | 9 | VAL | A | 270 | ILE | A | 273 | −1 | O | VAL | A | 270 | N | LEU | A | 64 |
| SHEET | 4 | AC | 9 | GLN | A | 204 | LYS | A | 211 | 1 | O | ASN | A | 205 | N | ILE | A | 273 |
| SHEET | 5 | AC | 9 | THR | A | 290 | TYR | A | 297 | −1 | O | ILE | A | 291 | N | ILE | A | 210 |
| SHEET | 6 | AC | 9 | LEU | A | 186 | GLY | A | 190 | −1 | O | LEU | A | 186 | N | ASN | A | 294 |
| SHEET | 7 | AC | 9 | ARG | A | 143 | THR | A | 149 | 1 | O | LEU | A | 146 | N | ILE | A | 189 |
| SHEET | 8 | AC | 9 | PHE | A | 90 | ALA | A | 95 | −1 | O | SER | A | 91 | N | GLN | A | 147 |
| SHEET | 9 | AC | 9 | SER | A | 118 | MET | A | 123 | 1 | O | ASN | A | 119 | N | SER | A | 94 |
| LINK | | FE | | FE2 | A | 1350 | | | | | | NE2 | HIS | A | 199 | 1555 | 1555 |
| LINK | | FE | | FE2 | A | 1350 | | | | | | OD2 | ASP | A | 201 | 1555 | 1555 |
| LINK | | FE | | FE2 | A | 1350 | | | | | | NE2 | HIS | A | 279 | 1555 | 1555 |
| LINK | | FE | | FE2 | A | 1350 | | | | | | O1 | AKG | A | 1351 | 1555 | 1555 |
| LINK | | FE | | FE2 | A | 1350 | | | | | | O5 | AKG | A | 1351 | 1555 | 1555 |
| CISPEP | 1 | TYR | A | 308 | | PRO | A | 309 | | | | O | | 1.27 | | | | |
| SITE | 1 | FE1 | 3 | HIS | A | 199 | ASP | A | 201 | HIS | A | 279 | | | | | | |
| SITE | 1 | AKG | 12 | TYR | A | 145 | THR | A | 196 | HIS | A | 199 | ASP | A | 201 | | |
| SITE | 2 | AKG | 12 | ASN | A | 205 | PHE | A | 207 | LYS | A | 214 | HIS | A | 279 | | |
| SITE | 3 | AKG | 12 | ILE | A | 281 | ASN | A | 294 | TRPA | 296 | HOHZ | | 65 | | |
| SITE | 1 | SO1 | 4 | ARG | A | 138 | GLY | A | 140 | GLU | A | 141 | GLU | A | 142 | | |
| SITE | 1 | SO2 | 5 | ARG | A | 143 | GLU | A | 192 | GLY | A | 193 | LEU | A | 285 | | |
| SITE | 2 | SO2 | 5 | ASN | A | 286 | | | | | | | | | | | | |
| CRYST1 | 86.264 | 86.264 | 147.914 | 90.00 | 90.00 | 90.00 | P | 41 | 21 | 2 | 8 | | | | | | | |
| ORIGX1 | | 1.000000 | | 0.000000 | | 0.000000 | | 0.00000 | | | | | | | | | | |
| ORIGX2 | | 0.000000 | | 1.000000 | | 0.000000 | | 0.00000 | | | | | | | | | | |
| ORIGX3 | | 0.000000 | | 0.000000 | | 1.000000 | | 0.00000 | | | | | | | | | | |
| SCALE1 | | 0.011592 | | 0.000000 | | 0.000000 | | 0.00000 | | | | | | | | | | |
| SCALE2 | | 0.000000 | | 0.011592 | | 0.000000 | | 0.00000 | | | | | | | | | | |
| SCALE3 | | 0.000000 | | 0.000000 | | 0.006761 | | 0.00000 | | | | | | | | | | |
| ATOM | 1 | N | GLU | A | 15 | 8.505 | 32.866 | 9.893 | 1.00 | 61.72 | N | | | | | | | |
| ATOM | 2 | CA | GLU | A | 15 | 7.173 | 32.223 | 9.682 | 1.00 | 61.95 | C | | | | | | | |
| ATOM | 3 | C | GLU | A | 15 | 7.251 | 30.749 | 10.070 | 1.00 | 61.54 | C | | | | | | | |
| ATOM | 4 | O | GLU | A | 15 | 8.109 | 30.026 | 9.581 | 1.00 | 61.66 | O | | | | | | | |
| ATOM | 5 | CB | GLU | A | 15 | 6.724 | 32.375 | 8.234 | 1.00 | 62.08 | C | | | | | | | |
| ATOM | 6 | N | PRO | A | 16 | 6.353 | 30.305 | 10.941 | 1.00 | 61.24 | N | | | | | | | |
| ATOM | 7 | CA | PRO | A | 16 | 6.386 | 28.928 | 11.455 | 1.00 | 60.97 | C | | | | | | | |
| ATOM | 8 | C | PRO | A | 16 | 6.342 | 27.853 | 10.368 | 1.00 | 60.27 | C | | | | | | | |
| ATOM | 9 | O | PRO | A | 16 | 5.494 | 27.879 | 9.479 | 1.00 | 60.01 | O | | | | | | | |
| ATOM | 10 | CB | PRO | A | 16 | 5.134 | 28.849 | 12.333 | 1.00 | 61.10 | C | | | | | | | |
| ATOM | 11 | CG | PRO | A | 16 | 4.790 | 30.262 | 12.653 | 1.00 | 61.53 | C | | | | | | | |
| ATOM | 12 | CD | PRO | A | 16 | 5.228 | 31.079 | 11.488 | 1.00 | 61.35 | C | | | | | | | |
| ATOM | 13 | N | ARG | A | 17 | 7.256 | 26.900 | 10.464 | 1.00 | 59.45 | N | | | | | | | |
| ATOM | 14 | CA | ARG | A | 17 | 7.348 | 25.820 | 9.494 | 1.00 | 59.05 | C | | | | | | | |
| ATOM | 15 | C | ARG | A | 17 | 6.083 | 24.971 | 9.478 | 1.00 | 57.86 | C | | | | | | | |
| ATOM | 16 | O | ARG | A | 17 | 5.312 | 24.963 | 10.437 | 1.00 | 57.86 | O | | | | | | | |
| ATOM | 17 | CB | ARG | A | 17 | 8.541 | 24.913 | 9.827 | 1.00 | 59.53 | C | | | | | | | |
| ATOM | 18 | CG | ARG | A | 17 | 9.906 | 25.621 | 9.859 | 1.00 | 60.69 | C | | | | | | | |
| ATOM | 19 | CD | ARG | A | 17 | 11.080 | 24.696 | 10.194 | 1.00 | 62.32 | C | | | | | | | |
| ATOM | 20 | NE | ARG | A | 17 | 11.040 | 24.185 | 11.567 | 1.00 | 63.73 | N | | | | | | | |
| ATOM | 21 | CZ | ARG | A | 17 | 11.464 | 24.852 | 12.649 | 1.00 | 65.28 | C | | | | | | | |
| ATOM | 22 | NH1 | ARG | A | 17 | 11.962 | 26.085 | 12.544 | 1.00 | 65.01 | N | | | | | | | |
| ATOM | 23 | NH2 | ARG | A | 17 | 11.385 | 24.282 | 13.848 | 1.00 | 65.09 | N | | | | | | | |
| ATOM | 24 | N | GLU | A | 18 | 5.878 | 24.254 | 8.382 | 1.00 | 56.26 | N | | | | | | | |
| ATOM | 25 | CA | GLU | A | 18 | 4.749 | 23.351 | 8.273 | 1.00 | 55.12 | C | | | | | | | |
| ATOM | 26 | C | GLU | A | 18 | 5.222 | 21.931 | 8.587 | 1.00 | 53.54 | C | | | | | | | |
| ATOM | 27 | O | GLU | A | 18 | 6.214 | 21.468 | 8.031 | 3..00 | 52.86 | O | | | | | | | |
| ATOM | 28 | CB | GLU | A | 18 | 4.150 | 23.406 | 6.867 | 1.00 | 55.33 | C | | | | | | | |
| ATOM | 29 | CG | GLU | A | 18 | 3.482 | 24.731 | 6.519 | 1.00 | 56.39 | C | | | | | | | |
| ATOM | 30 | CD | GLU | A | 18 | 2.100 | 24.904 | 7.139 | 1.00 | 57.19 | C | | | | | | | |
| ATOM | 31 | OE1 | GLU | A | 18 | 1.559 | 23.935 | 7.718 | 1.00 | 56.35 | O | | | | | | | |
| ATOM | 32 | OE2 | GLU | A | 18 | 1.548 | 26.023 | 7.028 | 1.00 | 58.12 | O | | | | | | | |
| ATOM | 33 | N | GLU | A | 19 | 4.526 | 21.260 | 9.501 | 1.00 | 51.73 | N | | | | | | | |
| ATOM | 34 | CA | GLU | A | 19 | 4.823 | 19.867 | 9.816 | 1.00 | 50.56 | C | | | | | | | |
| ATOM | 35 | C | GLU | A | 19 | 4.409 | 18.944 | 8.663 | 1.00 | 48.36 | C | | | | | | | |
| ATOM | 36 | O | GLU | A | 19 | 3.312 | 19.066 | 8.102 | 1.00 | 47.54 | O | | | | | | | |
| ATOM | 37 | CB | GLU | A | 19 | 4.115 | 19.422 | 11.100 | 1.00 | 51.05 | C | | | | | | | |
| ATOM | 38 | CG | GLU | A | 19 | 4.577 | 20.139 | 12.360 | 1.00 | 53.53 | C | | | | | | | |
| ATOM | 39 | CD | GLU | A | 19 | 4.363 | 19.323 | 13.638 | 1.00 | 57.67 | C | | | | | | | |

TABLE 3-continued

| | | | | | | | | | | | |
|---|---|---|---|---|---|---|---|---|---|---|---|
| ATOM | 40 | OE1 | GLU | A | 19 | 3.906 | 18.146 | 13.561 | 1.00 | 59.24 | O |
| ATOM | 41 | OE2 | GLU | A | 19 | 4.663 | 19.864 | 14.735 | 1.00 | 59.50 | O |
| ATOM | 42 | N | ALA | A | 20 | 5.314 | 18.035 | 8.320 | 1.00 | 46.04 | N |
| ATOM | 43 | CA | ALA | A | 20 | 5.100 | 17.030 | 7.283 | 1.00 | 44.66 | C |
| ATOM | 44 | C | ALA | A | 20 | 3.741 | 16.365 | 7.394 | 1.00 | 42.92 | C |
| ATOM | 45 | O | ALA | A | 20 | 3.230 | 16.154 | 8.491 | 1.00 | 42.14 | O |
| ATOM | 46 | CB | ALA | A | 20 | 6.182 | 15.965 | 7.360 | 1.00 | 44.46 | C |
| ATOM | 47 | N | GLY | A | 21 | 3.173 | 16.025 | 6.247 | 1.00 | 41.16 | N |
| ATOM | 48 | CA | GLY | A | 21 | 1.897 | 15.341 | 6.215 | 1.00 | 40.22 | C |
| ATOM | 49 | C | GLY | A | 21 | 0.757 | 16.300 | 6.480 | 1.00 | 39.27 | C |
| ATOM | 50 | O | GLY | A | 21 | 0.309 | 15.895 | 6.908 | 1.00 | 38.03 | O |
| ATOM | 51 | N | ALA | A | 22 | 1.005 | 17.584 | 6.240 | 1.00 | 38.86 | N |
| ATOM | 52 | CA | ALA | A | 22 | 0.018 | 18.611 | 6.371 | 1.00 | 38.79 | C |
| ATOM | 53 | C | ALA | A | 22 | 0.618 | 18.613 | 7.758 | 1.00 | 38.64 | C |
| ATOM | 54 | O | ALA | A | 22 | 1.820 | 18.759 | 7.924 | 1.00 | 38.07 | O |
| ATOM | 55 | CB | ALA | A | 22 | 1.102 | 18.409 | 5.324 | 1.00 | 38.68 | C |
| ATOM | 56 | N | LEU | A | 23 | 0.231 | 18.451 | 8.760 | 1.00 | 39.07 | N |
| ATOM | 57 | CA | LEU | A | 23 | 0.233 | 18.473 | 10.135 | 1.00 | 39.72 | C |
| ATOM | 58 | C | LEU | A | 23 | 0.290 | 19.886 | 10.692 | 1.00 | 39.39 | C |
| ATOM | 59 | O | LEU | A | 23 | 0.464 | 20.075 | 11.880 | 1.00 | 39.41 | O |
| ATOM | 60 | CB | LEU | A | 23 | 0.642 | 17.574 | 11.003 | 1.00 | 40.11 | C |
| ATOM | 61 | CG | LEU | A | 23 | 0.528 | 16.118 | 10.558 | 1.00 | 41.82 | C |
| ATOM | 62 | CD1 | LEU | A | 23 | 1.414 | 15.185 | 11.384 | 1.00 | 43.18 | C |
| ATOM | 63 | CD2 | LEU | A | 23 | 0.916 | 15.673 | 10.633 | 1.00 | 43.43 | C |
| ATOM | 64 | N | GLY | A | 24 | 0.156 | 20.879 | 9.823 | 1.00 | 39.21 | N |
| ATOM | 65 | CA | GLY | A | 24 | 0.290 | 22.258 | 10.237 | 1.00 | 39.16 | C |
| ATOM | 66 | C | GLY | A | 24 | 0.964 | 22.862 | 10.820 | 1.00 | 39.21 | C |
| ATOM | 67 | O | GLY | A | 24 | 2.011 | 22.219 | 10.916 | 1.00 | 39.16 | O |
| ATOM | 68 | N | PRO | A | 25 | 0.854 | 24.118 | 11.223 | 1.00 | 39.08 | N |
| ATOM | 69 | CA | PRO | A | 25 | 1.997 | 24.830 | 11.775 | 1.00 | 38.84 | C |
| ATOM | 70 | C | PRO | A | 25 | 2.410 | 24.197 | 13.086 | 1.00 | 38.68 | C |
| ATOM | 71 | O | PRO | A | 25 | 1.572 | 23.842 | 13.914 | 1.00 | 38.08 | O |
| ATOM | 72 | CB | PRO | A | 25 | 1.477 | 26.259 | 12.001 | 1.00 | 38.76 | C |
| ATOM | 73 | CG | PRO | A | 25 | 0.004 | 26.197 | 11.895 | 1.00 | 39.12 | C |
| ATOM | 74 | CD | PRO | A | 25 | 0.375 | 24.930 | 11.210 | 1.00 | 39.17 | C |
| ATOM | 75 | N | ALA | A | 26 | 3.713 | 24.037 | 13.246 | 1.00 | 38.92 | N |
| ATOM | 76 | CA | ALA | A | 26 | 4.269 | 23.489 | 14.467 | 1.00 | 39.38 | C |
| ATOM | 77 | C | ALA | A | 26 | 3.924 | 24.381 | 15.676 | 1.00 | 38.73 | C |
| ATOM | 78 | O | ALA | A | 26 | 3.677 | 23.882 | 16.772 | 1.00 | 39.39 | O |
| ATOM | 79 | CE | ALA | A | 26 | 5.762 | 23.347 | 14.319 | 1.00 | 39.60 | C |
| ATOM | 80 | N | TRP | A | 27 | 3.871 | 25.687 | 15.468 | 1.00 | 37.43 | N |
| ATOM | 81 | CA | TRP | A | 27 | 3.516 | 26.602 | 16.543 | 1.00 | 36.82 | C |
| ATOM | 82 | C | TRP | A | 27 | 3.034 | 27.919 | 15.941 | 1.00 | 36.10 | C |
| ATOM | 83 | O | TRP | A | 27 | 3.013 | 28.074 | 14.731 | 1.00 | 35.54 | O |
| ATOM | 84 | CE | TRP | A | 27 | 4.746 | 26.835 | 17.424 | 1.00 | 36.91 | C |
| ATOM | 85 | CG | TRP | A | 27 | 5.949 | 27.019 | 16.596 | 1.00 | 36.01 | C |
| ATOM | 86 | CD1 | TRP | A | 27 | 6.770 | 26.041 | 16.089 | 1.00 | 36.29 | C |
| ATOM | 87 | CO2 | TRP | A | 27 | 6.450 | 28.249 | 16.107 | 1.00 | 34.41 | C |
| ATOM | 88 | NE1 | TRP | A | 27 | 7.761 | 26.610 | 15.324 | 1.00 | 36.06 | N |
| ATOM | 89 | CE2 | TRP | A | 27 | 7.592 | 27.966 | 15.332 | 1.00 | 34.97 | C |
| ATOM | 90 | CE3 | TRP | A | 27 | 6.066 | 29.568 | 16.263 | 1.00 | 34.24 | C |
| ATOM | 91 | CZ2 | TRP | A | 27 | 8.332 | 28.947 | 14.720 | 1.00 | 36.39 | C |
| ATOM | 92 | CZ3 | TRP | A | 27 | 6.808 | 30.539 | 15.664 | 1.00 | 36.24 | C |
| ATOM | 93 | CR2 | TRP | A | 27 | 7.927 | 30.225 | 14.890 | 1.00 | 36.25 | C |
| ATOM | 94 | N | ASP | A | 28 | 2.620 | 28.860 | 16.775 | 1.00 | 35.59 | N |
| ATOM | 95 | CA | ASP | A | 28 | 2.253 | 30.168 | 16.267 | 1.00 | 35.15 | C |
| ATOM | 96 | C | ASP | A | 28 | 2.816 | 31.224 | 17.160 | 1.00 | 33.93 | C |
| ATOM | 97 | O | ASP | A | 28 | 3.311 | 30.948 | 18.250 | 1.00 | 33.56 | O |
| ATOM | 98 | CB | ASP | A | 28 | 0.739 | 30.338 | 16.131 | 1.00 | 36.08 | C |
| ATOM | 99 | CG | ASP | A | 28 | 0.038 | 30.310 | 17.449 | 1.00 | 38.11 | C |
| ATOM | 100 | OD1 | ASP | A | 28 | 0.096 | 31.392 | 18.076 | 1.00 | 41.06 | O |
| ATOM | 101 | OD2 | ASP | A | 28 | 0.392 | 29.240 | 17.938 | 1.00 | 41.04 | O |
| ATOM | 102 | N | GLU | A | 29 | 2.737 | 32.448 | 16.665 | 1.00 | 32.84 | N |
| ATOM | 103 | CA | GLU | A | 29 | 3.288 | 33.615 | 17.330 | 1.00 | 31.31 | C |
| ATOM | 104 | C | GLU | A | 29 | 2.792 | 33.767 | 18.756 | 1.00 | 29.80 | C |
| ATOM | 105 | O | GLU | A | 29 | 3.547 | 34.124 | 19.639 | 1.00 | 29.03 | O |
| ATOM | 106 | CE | GLU | A | 29 | 2.938 | 34.841 | 16.537 | 1.00 | 31.81 | C |
| ATOM | 107 | N | SER | A | 30 | 1.524 | 33.478 | 18.989 | 1.00 | 28.55 | N |
| ATOM | 108 | CA | SER | A | 30 | 0.957 | 33.680 | 20.314 | 1.00 | 28.00 | C |
| ATOM | 109 | C | SER | A | 30 | 1.613 | 32.830 | 21.391 | 1.00 | 27.25 | C |
| ATOM | 110 | O | SER | A | 30 | 1.360 | 33.035 | 22.563 | 1.00 | 26.88 | O |
| ATOM | 111 | CE | SER | A | 30 | 0.546 | 33.404 | 20.302 | 1.00 | 27.71 | C |
| ATOM | 112 | OG | SER | A | 30 | 0.800 | 32.015 | 20.328 | 1.00 | 28.97 | O |
| ATOM | 113 | N | GLN | A | 31 | 2.434 | 31.864 | 20.994 | 1.00 | 26.92 | N |
| ATOM | 114 | CA | GLN | A | 31 | 3.089 | 30.988 | 21.950 | 1.00 | 26.85 | C |
| ATOM | 115 | C | GLN | A | 31 | 4.447 | 31.558 | 22.362 | 1.00 | 26.63 | C |
| ATOM | 116 | O | GLN | A | 31 | 5.115 | 30.995 | 23.220 | 1.00 | 25.89 | O |

TABLE 3-continued

| | | | | | | | | | | | |
|---|---|---|---|---|---|---|---|---|---|---|---|
| \multicolumn{12}{|c|}{Coordinates for structures 1 to 4} |
| ATOM | 117 | GB | GLN | A | 31 | 3.270 | 29.576 | 21.375 | 1.00 | 26.90 | C |
| ATOM | 118 | CG | GLN | A | 31 | 1.975 | 28.816 | 21.097 | 1.00 | 27.50 | C |
| ATOM | 119 | CD | GLN | A | 31 | 2.227 | 27.446 | 20.480 | 1.00 | 27.30 | C |
| ATOM | 120 | OE1 | GLN | A | 31 | 2.332 | 27.330 | 19.262 | 1.00 | 28.39 | O |
| ATOM | 121 | NE2 | GLN | A | 31 | 2.354 | 26.419 | 21.319 | 1.00 | 23.43 | N |
| ATOM | 122 | N | LEU | A | 32 | 4.835 | 32.682 | 21.757 | 1.00 | 26.56 | N |
| ATOM | 123 | CA | LEU | A | 32 | 6.094 | 33.351 | 22.078 | 1.00 | 26.88 | C |
| ATOM | 124 | C | LEU | A | 32 | 5.854 | 34.500 | 23.047 | 1.00 | 26.64 | C |
| ATOM | 125 | O | LEU | A | 32 | 4.875 | 35.214 | 22.913 | 1.00 | 26.22 | O |
| ATOM | 126 | GB | LEU | A | 32 | 6.743 | 33.906 | 20.807 | 1.00 | 26.71 | C |
| ATOM | 127 | CG | LEU | A | 32 | 7.054 | 32.866 | 19.724 | 1.00 | 29.00 | C |
| ATOM | 128 | CD1 | LEU | A | 32 | 7.704 | 33.537 | 18.535 | 1.00 | 31.11 | C |
| ATOM | 129 | CD2 | LEU | A | 32 | 7.942 | 31.773 | 20.245 | 1.00 | 28.07 | C |
| ATOM | 130 | N | ARG | A | 33 | 6.737 | 34.671 | 24.026 | 1.00 | 26.49 | N |
| ATOM | 131 | CA | ARG | A | 33 | 6.622 | 35.799 | 24.957 | 1.00 | 26.48 | C |
| ATOM | 132 | C | ARG | A | 33 | 7.070 | 37.071 | 24.252 | 1.00 | 26.68 | C |
| ATOM | 133 | O | ARG | A | 33 | 7.810 | 37.025 | 23.280 | 1.00 | 26.97 | O |
| ATOM | 134 | GB | ARG | A | 33 | 7.454 | 35.554 | 26.224 | 1.00 | 26.44 | C |
| ATOM | 135 | CG | ARG | A | 33 | 7.071 | 34.261 | 26.976 | 1.00 | 25.53 | C |
| ATOM | 136 | CD | ARG | A | 33 | 7.869 | 34.029 | 28.245 | 1.00 | 25.76 | C |
| ATOM | 137 | NE | ARG | A | 33 | 7.329 | 32.926 | 29.021 | 1.00 | 25.87 | N |
| ATOM | 138 | CZ | ARG | A | 33 | 6.418 | 33.033 | 29.969 | 1.00 | 25.35 | C |
| ATOM | 139 | NH1 | ARG | A | 33 | 5.916 | 34.198 | 30.309 | 1.00 | 24.02 | N |
| ATOM | 140 | NH2 | ARG | A | 33 | 6.003 | 31.941 | 30.587 | 1.00 | 28.18 | N |
| ATOM | 141 | N | SER | A | 34 | 6.643 | 38.214 | 24.751 | 1.00 | 26.73 | N |
| ATOM | 142 | CA | SER | A | 34 | 6.939 | 39.469 | 24.090 | 1.00 | 27.21 | C |
| ATOM | 143 | C | SER | A | 34 | 8.021 | 40.251 | 24.840 | 1.00 | 26.40 | C |
| ATOM | 144 | O | SER | A | 34 | 7.957 | 40.391 | 26.046 | 1.00 | 25.65 | O |
| ATOM | 145 | GB | SER | A | 34 | 5.657 | 40.278 | 24.028 | 1.00 | 27.92 | C |
| ATOM | 146 | OG | SER | A | 34 | 5.402 | 40.780 | 25.323 | 1.00 | 31.78 | O |
| ATOM | 147 | N | TYR | A | 35 | 9.009 | 40.750 | 24.110 | 1.00 | 26.09 | N |
| ATOM | 148 | CA | TYR | A | 35 | 10.169 | 41.390 | 24.711 | 1.00 | 26.44 | C |
| ATOM | 149 | C | TYR | A | 35 | 10.412 | 42.731 | 24.046 | 1.00 | 27.00 | C |
| ATOM | 150 | O | TYR | A | 35 | 9.815 | 43.009 | 23.028 | 1.00 | 27.14 | O |
| ATOM | 151 | GB | TYR | A | 35 | 11.386 | 40.479 | 24.577 | 1.00 | 25.83 | C |
| ATOM | 152 | CG | TYR | A | 35 | 11.217 | 39.198 | 25.357 | 1.00 | 25.49 | C |
| ATOM | 153 | CD1 | TYR | A | 35 | 11.041 | 39.226 | 26.739 | 1.00 | 23.65 | C |
| ATOM | 154 | CD2 | TYR | A | 35 | 11.219 | 37.963 | 24.723 | 1.00 | 23.87 | C |
| ATOM | 155 | GE1 | TYR | A | 35 | 10.869 | 38.063 | 27.459 | 1.00 | 23.41 | C |
| ATOM | 156 | CE2 | TYR | A | 35 | 11.061 | 36.795 | 25.445 | 1.00 | 24.37 | C |
| ATOM | 157 | CZ | TYR | A | 35 | 10.881 | 36.847 | 26.809 | 1.00 | 22.92 | C |
| ATOM | 158 | OH | TYR | A | 35 | 10.698 | 35.686 | 27.522 | 1.00 | 23.94 | O |
| ATOM | 159 | N | SER | A | 36 | 11.326 | 43.531 | 24.596 | 1.00 | 27.45 | N |
| ATOM | 160 | CA | SER | A | 36 | 11.555 | 44.905 | 24.127 | 1.00 | 27.58 | C |
| ATOM | 161 | C | SER | A | 36 | 12.553 | 45.092 | 22.987 | 1.00 | 27.13 | C |
| ATOM | 162 | O | SER | A | 36 | 12.764 | 46.211 | 22.533 | 1.00 | 27.71 | O |
| ATOM | 163 | CB | SER | A | 36 | 12.109 | 45.724 | 25.286 | 1.00 | 27.62 | C |
| ATOM | 164 | OG | SER | A | 36 | 13.365 | 45.201 | 25.697 | 1.00 | 27.53 | O |
| ATOM | 165 | N | PHE | A | 37 | 13.181 | 44.025 | 22.543 | 1.00 | 25.62 | N |
| ATOM | 166 | CA | PHE | A | 37 | 14.263 | 44.169 | 21.590 | 1.00 | 24.95 | C |
| ATOM | 167 | C | PHE | A | 37 | 13.949 | 43.447 | 20.301 | 1.00 | 25.32 | C |
| ATOM | 168 | O | PHE | A | 37 | 13.191 | 42.512 | 20.274 | 1.00 | 25.29 | O |
| ATOM | 169 | GB | PHE | A | 37 | 15.537 | 43.571 | 22.185 | 1.00 | 23.88 | C |
| ATOM | 170 | CG | PHE | A | 37 | 15.340 | 42.162 | 22.731 | 1.00 | 22.69 | C |
| ATOM | 171 | CD1 | PHE | A | 37 | 15.353 | 41.077 | 21.890 | 1.00 | 20.43 | C |
| ATOM | 172 | CD2 | PHE | A | 37 | 15.104 | 41.949 | 24.076 | 1.00 | 23.12 | C |
| ATOM | 173 | GE1 | PHE | A | 37 | 15.160 | 39.778 | 22.386 | 1.00 | 22.83 | C |
| ATOM | 174 | CE2 | PHE | A | 37 | 14.920 | 40.666 | 24.578 | 1.00 | 22.73 | C |
| ATOM | 175 | CZ | PHE | A | 37 | 14.944 | 39.585 | 23.737 | 1.00 | 22.04 | C |
| ATOM | 176 | N | PRO | A | 38 | 14.533 | 43.907 | 19.222 | 1.00 | 25.57 | N |
| ATOM | 177 | CA | PRO | A | 38 | 14.396 | 43.216 | 17.950 | 1.00 | 25.50 | C |
| ATOM | 178 | C | PRO | A | 38 | 15.321 | 42.002 | 17.861 | 1.00 | 25.35 | C |
| ATOM | 179 | O | PRO | A | 38 | 16.280 | 41.887 | 18.640 | 1.00 | 25.01 | O |
| ATOM | 180 | CB | PRO | A | 38 | 14.815 | 44.278 | 16.944 | 1.00 | 25.31 | C |
| ATOM | 181 | CG | PRO | A | 38 | 15.776 | 45.181 | 17.729 | 1.00 | 26.61 | C |
| ATOM | 182 | CD | PRO | A | 38 | 15.271 | 45.178 | 19.125 | 1.00 | 25.73 | C |
| ATOM | 183 | N | THR | A | 39 | 15.032 | 41.124 | 16.902 | 1.00 | 24.60 | N |
| ATOM | 184 | CA | THR | A | 39 | 15.876 | 39.979 | 16.607 | 1.00 | 24.58 | C |
| ATOM | 185 | C | THR | A | 39 | 15.881 | 39.686 | 15.112 | 1.00 | 25.39 | C |
| ATOM | 186 | O | THR | A | 39 | 15.004 | 40.121 | 14.383 | 1.00 | 24.72 | O |
| ATOM | 187 | CB | THR | A | 39 | 15.364 | 38.721 | 17.295 | 1.00 | 24.33 | C |
| ATOM | 188 | OG1 | THR | A | 39 | 14.023 | 38.453 | 16.860 | 1.00 | 21.36 | O |
| ATOM | 189 | CG2 | THR | A | 39 | 15.256 | 38.892 | 18.832 | 1.00 | 23.91 | C |
| ATOM | 190 | N | ARG | A | 40 | 16.875 | 38.912 | 14.692 | 1.00 | 26.09 | N |
| ATOM | 191 | CA | ARG | A | 40 | 17.000 | 38.399 | 13.337 | 1.00 | 26.92 | C |
| ATOM | 192 | C | ARG | A | 40 | 17.057 | 36.884 | 13.469 | 1.00 | 26.73 | C |
| ATOM | 193 | O | ARG | A | 40 | 17.407 | 36.366 | 14.517 | 1.00 | 26.53 | O |

TABLE 3-continued

Coordinates for structures 1 to 4

| ATOM | 194 | CB | ARG | A | 40 | 18.291 | 38.888 | 12.696 | 1.00 | 27.12 | C |
|---|---|---|---|---|---|---|---|---|---|---|---|
| ATOM | 195 | CG | ARG | A | 40 | 18.289 | 40.360 | 12.400 | 1.00 | 32.37 | C |
| ATOM | 196 | CD | ARG | A | 40 | 16.925 | 40.858 | 11.994 | 1.00 | 36.79 | C |
| ATOM | 197 | NE | ARG | A | 40 | 16.783 | 41.137 | 10.583 | 1.00 | 41.20 | N |
| ATOM | 198 | CZ | ARG | A | 40 | 15.617 | 41.408 | 10.023 | 1.00 | 46.28 | C |
| ATOM | 199 | NH1 | ARG | A | 40 | 14.512 | 41.388 | 10.768 | 1.00 | 47.83 | N |
| ATOM | 200 | NH2 | ARG | A | 40 | 15.548 | 41.708 | 8.731 | 1.00 | 48.02 | N |
| ATOM | 201 | N | PRO | A | 41 | 16.728 | 36.163 | 12.413 | 1.00 | 26.96 | N |
| ATOM | 202 | CA | PRO | A | 41 | 16.709 | 34.706 | 12.510 | 1.00 | 27.17 | C |
| ATOM | 203 | C | PRO | A | 41 | 18.085 | 34.054 | 12.469 | 1.00 | 26.50 | C |
| ATOM | 204 | O | PRO | A | 41 | 19.002 | 34.538 | 11.830 | 1.00 | 26.34 | O |
| ATOM | 205 | CB | PRO | A | 41 | 15.867 | 34.277 | 11.298 | 1.00 | 27.12 | C |
| ATOM | 206 | CG | PRO | A | 41 | 16.027 | 35.434 | 10.296 | 1.00 | 27.66 | C |
| ATOM | 207 | CD | PRO | A | 41 | 16.337 | 36.661 | 11.077 | 1.00 | 26.70 | C |
| ATOM | 208 | N | ILE | A | 42 | 18.214 | 32.951 | 13.185 | 1.00 | 25.35 | N |
| ATOM | 209 | CA | ILE | A | 42 | 19.400 | 32.143 | 13.070 | 1.00 | 24.29 | C |
| ATOM | 210 | C | ILE | A | 42 | 19.161 | 31.290 | 11.832 | 1.00 | 23.98 | C |
| ATOM | 211 | O | ILE | A | 42 | 18.050 | 30.793 | 11.632 | 1.00 | 24.20 | O |
| ATOM | 212 | CB | ILE | A | 42 | 19.530 | 31.283 | 14.302 | 1.00 | 24.58 | C |
| ATOM | 213 | CG1 | ILE | A | 42 | 19.779 | 32.181 | 15.518 | 1.00 | 22.71 | C |
| ATOM | 214 | CG2 | ILE | A | 42 | 20.644 | 30.233 | 14.113 | 1.00 | 24.95 | C |
| ATOM | 215 | CD1 | ILE | A | 42 | 19.466 | 31.516 | 16.837 | 1.00 | 22.70 | C |
| ATOM | 216 | N | PRO | A | 43 | 20.168 | 31.122 | 10.989 | 1.00 | 23.44 | N |
| ATOM | 217 | CA | PRO | A | 43 | 20.016 | 30.276 | 9.807 | 1.00 | 23.74 | C |
| ATOM | 218 | C | PRO | A | 43 | 19.709 | 28.802 | 10.154 | 1.00 | 24.82 | C |
| ATOM | 219 | O | PRO | A | 43 | 20.281 | 28.292 | 11.130 | 1.00 | 24.03 | O |
| ATOM | 220 | OB | PRO | A | 43 | 21.372 | 30.397 | 9.107 | 1.00 | 24.23 | C |
| ATOM | 221 | CG | PRO | A | 43 | 22.071 | 31.602 | 9.740 | 1.00 | 23.91 | C |
| ATOM | 222 | CD | PRO | A | 43 | 21.504 | 31.737 | 11.092 | 1.00 | 23.12 | C |
| ATOM | 223 | N | ARG | A | 44 | 18.784 | 28.178 | 9.406 | 1.00 | 25.20 | N |
| ATOM | 224 | CA | ARG | A | 44 | 18.439 | 26.767 | 9.520 | 1.00 | 26.19 | C |
| ATOM | 225 | C | ARG | A | 44 | 18.977 | 26.125 | 8.269 | 1.00 | 25.69 | C |
| ATOM | 226 | O | ARG | A | 44 | 18.563 | 26.468 | 7.159 | 1.00 | 25.67 | O |
| ATOM | 227 | CB | ARG | A | 44 | 16.934 | 26.504 | 9.513 | 1.00 | 27.16 | C |
| ATOM | 228 | CG | ARG | A | 44 | 16.140 | 27.062 | 10.678 | 1.00 | 31.24 | C |
| ATOM | 229 | CD | ARG | A | 44 | 14.653 | 26.529 | 10.769 | 1.00 | 32.98 | C |
| ATOM | 230 | NE | ARG | A | 44 | 14.400 | 25.143 | 10.311 | 1.00 | 34.09 | N |
| ATOM | 231 | CZ | ARG | A | 44 | 14.258 | 24.070 | 11.128 | 1.00 | 33.28 | C |
| ATOM | 232 | NH1 | ARG | A | 44 | 14.384 | 24.177 | 12.453 | 1.00 | 29.63 | N |
| ATOM | 233 | NH2 | ARG | A | 44 | 13.995 | 22.873 | 10.617 | 1.00 | 34.28 | N |
| ATOM | 234 | N | LEU | A | 45 | 19.870 | 25.174 | 8.433 | 1.00 | 24.68 | N |
| ATOM | 235 | CA | LEU | A | 45 | 20.551 | 24.608 | 7.302 | 1.00 | 24.30 | C |
| ATOM | 236 | C | LEU | A | 45 | 20.768 | 23.134 | 7.471 | 1.00 | 24.39 | C |
| ATOM | 237 | O | LEU | A | 45 | 20.711 | 22.623 | 8.588 | 1.00 | 23.97 | O |
| ATOM | 238 | CB | LEU | A | 45 | 21.934 | 25.233 | 7.205 | 1.00 | 23.42 | C |
| ATOM | 239 | CG | LEU | A | 45 | 21.929 | 26.724 | 6.941 | 1.00 | 24.95 | C |
| ATOM | 240 | CD1 | LEU | A | 45 | 23.339 | 27.284 | 7.080 | 1.00 | 26.26 | C |
| ATOM | 241 | CD2 | LEU | A | 45 | 21.375 | 26.953 | 5.533 | 1.00 | 24.54 | C |
| ATOM | 242 | N | SER | A | 46 | 21.092 | 22.494 | 6.352 | 1.00 | 24.71 | N |
| ATOM | 243 | CA | SER | A | 46 | 21.498 | 21.119 | 6.345 | 1.00 | 25.24 | C |
| ATOM | 244 | C | SER | A | 46 | 22.930 | 21.043 | 6.804 | 1.00 | 25.58 | C |
| ATOM | 245 | O | SER | A | 46 | 23.741 | 21.908 | 6.522 | 1.00 | 24.65 | O |
| ATOM | 246 | CB | SER | A | 46 | 21.401 | 20.505 | 4.950 | 1.00 | 25.11 | C |
| ATOM | 247 | OG | SER | A | 46 | 21.863 | 19.150 | 4.965 | 1.00 | 24.50 | O |
| ATOM | 248 | N | GLN | A | 47 | 23.208 | 19.970 | 7.517 | 1.00 | 26.68 | N |
| ATOM | 249 | CA | GLN | A | 47 | 24.524 | 19.626 | 8.011 | 1.00 | 27.63 | C |
| ATOM | 250 | C | GLN | A | 47 | 25.510 | 19.442 | 6.853 | 1.00 | 28.01 | C |
| ATOM | 251 | O | GLN | A | 47 | 26.704 | 19.613 | 7.026 | 1.00 | 28.15 | O |
| ATOM | 252 | CB | GLN | A | 47 | 24.368 | 18.317 | 8.803 | 1.00 | 28.89 | C |
| ATOM | 253 | CG | GLN | A | 47 | 25.580 | 17.447 | 8.920 | 1.00 | 31.28 | C |
| ATOM | 254 | CD | GLN | A | 47 | 25.826 | 16.556 | 7.765 | 1.00 | 32.33 | C |
| ATOM | 255 | OE1 | GLN | A | 47 | 24.906 | 16.149 | 7.048 | 1.00 | 37.08 | O |
| ATOM | 256 | NE2 | GLN | A | 47 | 27.089 | 16.213 | 7.576 | 1.00 | 35.81 | N |
| ATOM | 257 | N | SER | A | 48 | 25.026 | 19.086 | 5.667 | 1.00 | 28.11 | N |
| ATOM | 258 | CA | SER | A | 48 | 25.930 | 18.925 | 4.524 | 1.00 | 28.72 | C |
| ATOM | 259 | C | SER | A | 48 | 26.222 | 20.262 | 3.828 | 1.00 | 29.21 | C |
| ATOM | 260 | O | SER | A | 48 | 27.068 | 20.339 | 2.936 | 1.00 | 29.21 | O |
| ATOM | 261 | CB | SER | A | 48 | 25.343 | 17.952 | 3.508 | 1.00 | 28.66 | C |
| ATOM | 262 | OG | SER | A | 48 | 24.111 | 18.440 | 2.993 | 1.00 | 29.43 | O |
| ATOM | 263 | N | ASP | A | 49 | 25.525 | 21.314 | 4.236 | 1.00 | 29.60 | N |
| ATOM | 264 | CA | ASP | A | 49 | 25.683 | 22.610 | 3.596 | 1.00 | 30.12 | C |
| ATOM | 265 | C | ASP | A | 49 | 26.949 | 23.307 | 4.087 | 1.00 | 30.43 | C |
| ATOM | 266 | O | ASP | A | 49 | 27.100 | 23.565 | 5.272 | 1.00 | 29.60 | O |
| ATOM | 267 | CB | ASP | A | 49 | 24.450 | 23.458 | 3.858 | 1.00 | 30.26 | C |
| ATOM | 268 | CG | ASP | A | 49 | 24.491 | 24.792 | 3.151 | 1.00 | 31.74 | C |
| ATOM | 269 | OD1 | ASP | A | 49 | 25.589 | 25.306 | 2.859 | 1.00 | 31.79 | O |
| ATOM | 270 | OD2 | ASP | A | 49 | 23.454 | 25.418 | 2.878 | 1.00 | 34.13 | O |

TABLE 3-continued

Coordinates for structures 1 to 4

| | | | | | | | | | | | |
|---|---|---|---|---|---|---|---|---|---|---|---|
| ATOM | 271 | N | PRO | A | 50 | 27.829 | 23.668 | 3.155 | 1.00 | 31.31 | N |
| ATOM | 272 | CA | PRO | A | 50 | 29.123 | 24.273 | 3.499 | 1.00 | 31.63 | C |
| ATOM | 273 | C | PRO | A. | 50 | 28.965 | 25.514 | 4.355 | 1.00 | 31.72 | C |
| ATOM | 274 | O | PRO | A | 50 | 29.849 | 25.807 | 5.164 | 1.00 | 31.85 | O |
| ATOM | 275 | CB | PRO | A | 50 | 29.726 | 24.643 | 2.124 | 1.00 | 31.53 | C |
| ATOM | 276 | CG | PRO | A | 50 | 29.036 | 23.738 | 1.168 | 1.00 | 32.13 | C |
| ATOM | 277 | CD | PRO | A | 50 | 27.624 | 23.620 | 1.697 | 1.00 | 31.55 | C |
| ATOM | 278 | N | ARG | A | 51 | 27.875 | 26.246 | 4.171 | 1.00 | 32.04 | N |
| ATOM | 279 | CA | ARG | A | 51 | 27.648 | 27.443 | 4.962 | 1.00 | 32.56 | C |
| ATOM | 280 | C | ARG | A | 51 | 27.478 | 27.078 | 6.439 | 1.00 | 32.09 | C |
| ATOM | 281 | O | ARG | A | 51 | 27.853 | 27.855 | 7.322 | 1.00 | 31.87 | O |
| ATOM | 282 | CB | ARG | A | 51 | 26.420 | 28.221 | 4.464 | 1.00 | 32.95 | C |
| ATOM | 283 | CG | ARG | A | 51 | 26.568 | 28.810 | 3.064 | 1.00 | 34.79 | C |
| ATOM | 284 | CD | ARG | A | 51 | 25.273 | 29.372 | 2.480 | 1.00 | 35.89 | C |
| ATOM | 285 | NE | ARG | A | 51 | 24.276 | 28.325 | 2.228 | 1.00 | 37.56 | N |
| ATOM | 286 | CZ | ARG | A | 51 | 22.982 | 28.564 | 2.061 | 1.00 | 39.54 | C |
| ATOM | 287 | NH1 | ARG | A | 51 | 22.531 | 29.814 | 2.124 | 1.00 | 40.85 | N |
| ATOM | 288 | NH2 | ARG | A | 51 | 22.135 | 27.573 | 1.823 | 1.00 | 38.55 | N |
| ATOM | 289 | N | ALA | A | 52 | 26.932 | 25.903 | 6.721 | 1.00 | 31.50 | N |
| ATOM | 290 | CA | ALA | A | 52 | 26.769 | 25.513 | 8.117 | 1.00 | 31.34 | C |
| ATOM | 291 | C | ALA | A | 52 | 28.135 | 25.310 | 8.744 | 1.00 | 31.24 | C |
| ATOM | 292 | O | ALA | A | 52 | 28.409 | 25.763 | 9.865 | 1.00 | 30.91 | O |
| ATOM | 293 | CB | ALA | A | 52 | 25.953 | 24.284 | 8.236 | 1.00 | 31.35 | C |
| ATOM | 294 | N | GLU | A | 53 | 29.005 | 24.652 | 8.005 | 1.00 | 30.92 | N |
| ATOM | 295 | CA | GLU | A | 53 | 30.332 | 24.404 | 8.501 | 1.00 | 31.92 | C |
| ATOM | 296 | C | GLU | A | 53 | 31.059 | 25.730 | 8.728 | 1.00 | 31.52 | C |
| ATOM | 297 | O | GLU | A | 53 | 31.766 | 25.898 | 9.717 | 1.00 | 30.52 | O |
| ATOM | 298 | CB | GLU | A | 53 | 31.119 | 23.554 | 7.525 | 1.00 | 32.10 | C |
| ATOM | 299 | CG | GLU | A | 53 | 32.216 | 22.795 | 8.229 | 1.00 | 36.08 | C |
| ATOM | 300 | CD | GLU | A | 53 | 31.776 | 21.411 | 8.717 | 1.00 | 39.44 | C |
| ATOM | 301 | OE1 | GLU | A | 53 | 30.629 | 21.234 | 9.167 | 1.00 | 40.34 | O |
| ATOM | 302 | OE2 | GLU | A | 53 | 32.606 | 20.487 | 8.652 | 1.00 | 43.45 | O |
| ATOM | 303 | N | GLU | A | 54 | 30.870 | 26.665 | 7.808 | 1.00 | 31.32 | N |
| ATOM | 304 | CA | GLU | A | 54 | 31.507 | 27.968 | 7.919 | 1.00 | 32.09 | C |
| ATOM | 305 | C | GLU | A | 54 | 31.039 | 28.685 | 9.193 | 1.00 | 31.07 | C |
| ATOM | 306 | O | GLU | A | 54 | 31.833 | 29.295 | 9.881 | 1.00 | 31.27 | O |
| ATOM | 307 | CB | GLU | A | 54 | 31.218 | 28.812 | 6.681 | 1.00 | 32.42 | C |
| ATOM | 308 | CG | GLU | A | 54 | 31.939 | 30.146 | 6.669 | 1.00 | 37.01 | C |
| ATOM | 309 | CD | GLU | A | 54 | 31.662 | 30.966 | 5.410 | 1.00 | 40.45 | C |
| ATOM | 310 | OE1 | GLU | A | 54 | 30.843 | 30.528 | 4.558 | 1.00 | 41.94 | O |
| ATOM | 311 | OE2 | GLU | A | 54 | 32.268 | 32.051 | 5.285 | 1.00 | 43.43 | O |
| ATOM | 312 | N | LEU | A | 55 | 29.761 | 28.567 | 9.534 | 1.00 | 29.85 | N |
| ATOM | 313 | CA | LEU | A | 55 | 29.251 | 29.240 | 10.708 | 1.00 | 28.58 | C |
| ATOM | 314 | C | LEU | A | 55 | 29.848 | 28.667 | 11.983 | 1.00 | 27.91 | C |
| ATOM | 315 | O | LEU | A | 55 | 30.304 | 29.419 | 12.841 | 1.00 | 26.43 | O |
| ATOM | 316 | CB | LEU | A | 55 | 27.734 | 29.179 | 10.733 | 1.00 | 28.61 | C |
| ATOM | 317 | CG | LEU | A | 55 | 27.097 | 30.041 | 9.652 | 1.00 | 28.69 | C |
| ATOM | 318 | CD1 | LEU | A | 55 | 25.647 | 29.633 | 9.423 | 1.00 | 29.69 | C |
| ATOM | 319 | CD2 | LEU | A | 55 | 27.193 | 31.507 | 10.005 | 1.00 | 27.60 | C |
| ATOM | 320 | N | ILE | A | 56 | 29.889 | 27.334 | 12.086 | 1.00 | 27.51 | N |
| ATOM | 321 | CA | ILE | A | 56 | 30.432 | 26.679 | 13.278 | 1.00 | 27.49 | C |
| ATOM | 322 | C | ILE | A | 56 | 31.910 | 27.014 | 13.457 | 1.00 | 28.32 | C |
| ATOM | 323 | O | ILE | A | 56 | 32.359 | 27.353 | 14.549 | 1.00 | 28.51 | O |
| ATOM | 324 | CB | ILE | A | 56 | 30.260 | 25.174 | 13.192 | 1.00 | 27.21 | C |
| ATOM | 325 | CG1 | ILE | A | 56 | 28.771 | 24.787 | 13.218 | 1.00 | 25.69 | C |
| ATOM | 326 | CG2 | ILE | A | 56 | 30.982 | 24.505 | 14.354 | 1.00 | 27.65 | C |
| ATOM | 327 | CD1 | ILE | A | 56 | 28.484 | 23.341 | 12.760 | 1.00 | 23.98 | C |
| ATOM | 328 | N | GLU | A | 57 | 32.645 | 26.935 | 12.357 | 1.00 | 28.85 | N |
| ATOM | 329 | CA | GLU | A | 57 | 34.068 | 27.230 | 12.308 | 1.00 | 29.98 | C |
| ATOM | 330 | C | GLU | A | 57 | 34.319 | 28.623 | 12.837 | 1.00 | 30.12 | C |
| ATOM | 331 | O | GLU | A | 57 | 35.306 | 28.869 | 13.524 | 1.00 | 31.00 | O |
| ATOM | 332 | CB | GLU | A | 57 | 34.557 | 27.137 | 10.850 | 1.00 | 30.52 | C |
| ATOM | 333 | CG | GLU | A | 57 | 36.003 | 27.518 | 10.610 | 1.00 | 33.37 | C |
| ATOM | 334 | CD | GLU | A | 57 | 36.968 | 26.742 | 11.482 | 1.00 | 38.19 | C |
| ATOM | 335 | OE1 | GLU | A | 57 | 36.689 | 25.558 | 11.810 | 1.00 | 41.02 | O |
| ATOM | 336 | OE2 | GLU | A | 57 | 38.015 | 27.329 | 11.847 | 1.00 | 42.74 | O |
| ATOM | 337 | N | ASN | A | 58 | 33.409 | 29.527 | 12.516 | 1.00 | 29.57 | N |
| ATOM | 338 | CA | ASN | A | 58 | 33.516 | 30.911 | 12.929 | 1.00 | 29.62 | C |
| ATOM | 339 | C | ASN | A | 58 | 32.852 | 31.222 | 14.230 | 1.00 | 27.88 | C |
| ATOM | 340 | O | ASN | A | 58 | 32.690 | 32.364 | 14.566 | 1.00 | 26.74 | O |
| ATOM | 341 | CB | ASN | A | 58 | 32.805 | 31.769 | 11.918 | 1.00 | 30.43 | C |
| ATOM | 342 | CG | ASN | A | 58 | 33.719 | 32.439 | 11.040 | 1.00 | 33.87 | C |
| ATOM | 343 | OD1 | ASN | A | 58 | 34.040 | 31.918 | 9.965 | 1.00 | 36.67 | O |
| ATOM | 344 | ND2 | ASN | A | 58 | 34.189 | 33.629 | 11.467 | 1.00 | 38.66 | N |
| ATOM | 345 | N | GLU | A | 59 | 32.396 | 30.205 | 14.922 | 1.00 | 27.73 | N |
| ATOM | 346 | CA | GLU | A | 59 | 31.753 | 30.411 | 16.205 | 1.00 | 27.50 | C |
| ATOM | 347 | C | GLU | A | 59 | 30.545 | 31.320 | 16.104 | 1.00 | 26.07 | C |

TABLE 3-continued

Coordinates for structures 1 to 4

| | | | | | | | | | | | |
|---|---|---|---|---|---|---|---|---|---|---|---|
| ATOM | 348 | O | GLU | A | 59 | 30.366 | 32.255 | 16.861 | 1.00 | 25.28 | O |
| ATOM | 349 | CB | GLU | A | 59 | 32.795 | 30.867 | 17.224 | 1.00 | 28.12 | C |
| ATOM | 350 | CG | GLU | A | 59 | 33.720 | 29.688 | 17.531 | 1.00 | 31.06 | C |
| ATOM | 351 | CD | GLU | A | 59 | 34.739 | 29.965 | 18.604 | 1.00 | 35.24 | C |
| ATOM | 352 | OE1 | GLU | A | 59 | 35.826 | 30.432 | 18.239 | 1.00 | 39.24 | O |
| ATOM | 353 | OE2 | GLU | A | 59 | 34.469 | 29.698 | 19.795 | 1.00 | 37.54 | O |
| ATOM | 354 | N | GLU | A | 60 | 29.691 | 30.982 | 15.155 | 1.00 | 25.70 | N |
| ATOM | 355 | CA | GLU | A | 60 | 28.417 | 31.643 | 14.971 | 1.00 | 25.50 | C |
| ATOM | 356 | C | GLU | A | 60 | 27.345 | 30.576 | 14.998 | 1.00 | 24.10 | C |
| ATOM | 357 | O | GLU | A | 60 | 27.527 | 29.479 | 14.487 | 1.00 | 22.92 | O |
| ATOM | 358 | CB | GLU | A | 60 | 28.402 | 32.404 | 13.664 | 1.00 | 25.96 | C |
| ATOM | 359 | CG | GLU | A | 60 | 29.454 | 33.497 | 13.697 | 1.00 | 30.39 | C |
| ATOM | 360 | CD | GLU | A | 60 | 29.218 | 34.599 | 12.703 | 1.00 | 35.90 | C |
| ATOM | 361 | OE1 | GLU | A | 60 | 29.281 | 34.349 | 11.478 | 1.00 | 38.45 | O |
| ATOM | 362 | OE2 | GLU | A | 60 | 28.998 | 35.732 | 13.165 | 1.00 | 43.84 | O |
| ATOM | 363 | N | PRO | A | 61 | 26.203 | 30.933 | 15.546 | 1.00 | 22.92 | N |
| ATOM | 364 | CA | PRO | A | 61 | 25.112 | 29.983 | 15.735 | 1.00 | 22.31 | C |
| ATOM | 365 | C | PRO | A | 61 | 24.482 | 29.519 | 14.445 | 1.00 | 21.76 | C |
| ATOM | 366 | O | PRO | A | 61 | 24.394 | 30.252 | 13.474 | 1.00 | 21.59 | O |
| ATOM | 367 | CB | PRO | A | 61 | 24.079 | 30.775 | 16.525 | 1.00 | 22.55 | C |
| ATOM | 368 | CG | PRO | A | 61 | 24.450 | 32.218 | 16.380 | 1.00 | 21.42 | C |
| ATOM | 369 | CD | PRO | A | 61 | 25.863 | 32.295 | 15.967 | 1.00 | 22.38 | C |
| ATOM | 370 | N | VAL | A | 62 | 24.032 | 28.279 | 14.444 | 1.00 | 21.55 | N |
| ATOM | 371 | CA | VAL | A | 62 | 23.306 | 27.739 | 13.317 | 1.00 | 21.90 | C |
| ATOM | 372 | C | VAL | A | 62 | 22.415 | 26.622 | 13.817 | 1.00 | 22.38 | C |
| ATOM | 373 | O | VAL | A | 62 | 22.771 | 25.886 | 14.757 | 1.00 | 22.77 | O |
| ATOM | 374 | CE | VAL | A | 62 | 24.262 | 27.217 | 12.218 | 1.00 | 22.10 | C |
| ATOM | 375 | CG1 | VAL | A | 62 | 25.134 | 26.112 | 12.738 | 1.00 | 22.89 | C |
| ATOM | 376 | CG2 | VAL | A | 62 | 23.486 | 26.748 | 11.000 | 1.00 | 21.98 | C |
| ATOM | 377 | N | VAL | A | 63 | 21.234 | 26.517 | 13.226 | 1.00 | 22.90 | N |
| ATOM | 378 | CA | VAL | A | 63 | 20.373 | 25.398 | 13.499 | 1.00 | 23.20 | C |
| ATOM | 379 | C | VAL | A | 63 | 20.586 | 24.373 | 12.378 | 1.00 | 23.18 | C |
| ATOM | 380 | O | VAL | A | 63 | 20.395 | 24.682 | 11.208 | 1.00 | 23.38 | O |
| ATOM | 381 | CB | VAL | A | 63 | 18.880 | 25.768 | 13.561 | 1.00 | 23.27 | C |
| ATOM | 382 | CG1 | VAL | A | 63 | 18.046 | 24.483 | 13.754 | 1.00 | 24.19 | C |
| ATOM | 383 | CG2 | VAL | A | 63 | 18.620 | 26.695 | 14.692 | 1.00 | 22.51 | C |
| ATOM | 384 | N | LEU | A | 64 | 21.007 | 23.181 | 12.756 | 1.00 | 23.15 | N |
| ATOM | 385 | CA | LEU | A | 64 | 21.158 | 22.060 | 11.835 | 1.00 | 24.29 | C |
| ATOM | 386 | C | LEU | A | 64 | 19.904 | 21.203 | 11.906 | 1.00 | 23.48 | C |
| ATOM | 387 | O | LEU | A | 64 | 19.488 | 20.816 | 12.988 | 1.00 | 23.20 | O |
| ATOM | 388 | CB | LEU | A | 64 | 22.383 | 21.235 | 12.206 | 1.00 | 24.79 | C |
| ATOM | 389 | CG | LEU | A | 64 | 23.649 | 22.089 | 12.141 | 1.00 | 28.22 | C |
| ATOM | 390 | CD1 | LEU | A | 64 | 24.810 | 21.338 | 12.699 | 1.00 | 32.80 | C |
| ATOM | 391 | CD2 | LEU | A | 64 | 23.946 | 22.478 | 10.719 | 1.00 | 30.04 | C |
| ATOM | 392 | N | THR | A | 65 | 19.308 | 20.910 | 10.759 | 1.00 | 22.79 | N |
| ATOM | 393 | CA | THR | A | 65 | 18.019 | 20.218 | 10.740 | 1.00 | 23.27 | C |
| ATOM | 394 | C | THR | A | 65 | 18.088 | 18.730 | 10.534 | 1.00 | 23.05 | C |
| ATOM | 395 | O | THR | A | 65 | 17.102 | 18.050 | 10.765 | 1.00 | 22.85 | O |
| ATOM | 396 | CE | THR | A | 65 | 17.150 | 20.724 | 9.571 | 1.00 | 23.53 | C |
| ATOM | 397 | OG1 | THR | A | 65 | 17.855 | 20.496 | 8.352 | 1.00 | 22.75 | O |
| ATOM | 398 | CG2 | THR | A | 65 | 16.966 | 22.226 | 9.609 | 1.00 | 24.78 | C |
| ATOM | 399 | N | ASP | A | 66 | 19.231 | 18.227 | 10.093 | 1.00 | 23.33 | N |
| ATOM | 400 | CA | ASP | A | 66 | 19.330 | 16.828 | 9.731 | 1.00 | 23.76 | C |
| ATOM | 401 | C | ASP | A | 66 | 20.581 | 16.076 | 10.209 | 1.00 | 23.41 | C |
| ATOM | 402 | O | ASP | A | 66 | 21.117 | 15.265 | 9.457 | 1.00 | 23.64 | O |
| ATOM | 403 | CE | ASP | A | 66 | 19.245 | 16.732 | 8.199 | 1.00 | 23.97 | C |
| ATOM | 404 | CG | ASP | A | 66 | 20.326 | 17.517 | 7.514 | 1.00 | 24.64 | C |
| ATOM | 405 | OD1 | ASP | A | 66 | 21.175 | 18.099 | 8.223 | 1.00 | 23.06 | O |
| ATOM | 406 | OD2 | ASP | A | 66 | 20.417 | 17.612 | 6.268 | 1.00 | 26.54 | O |
| ATOM | 407 | N | THR | A | 67 | 21.050 | 16.336 | 11.428 | 1.00 | 22.72 | N |
| ATOM | 408 | CA | THR | A | 67 | 22.235 | 15.655 | 11.912 | 1.00 | 21.85 | C |
| ATOM | 409 | C | THR | A | 67 | 21.928 | 14.246 | 12.349 | 1.00 | 21.26 | C |
| ATOM | 410 | O | THR | A | 67 | 22.813 | 13.429 | 12.353 | 1.00 | 20.41 | O |
| ATOM | 411 | CE | THR | A | 67 | 22.836 | 16.345 | 13.138 | 1.00 | 21.92 | C |
| ATOM | 412 | OG1 | THR | A | 67 | 21.884 | 16.347 | 14.200 | 1.00 | 20.59 | O |
| ATOM | 413 | CG2 | THR | A | 67 | 23.161 | 17.822 | 12.873 | 1.00 | 23.29 | C |
| ATOM | 414 | N | ASN | A | 68 | 20.684 | 13.993 | 12.752 | 1.00 | 20.82 | N |
| ATOM | 415 | CA | ASN | A | 68 | 20.321 | 12.741 | 13.386 | 1.00 | 21.01 | C |
| ATOM | 416 | C | ASN | A | 68 | 21.146 | 12.525 | 14.652 | 1.00 | 20.47 | C |
| ATOM | 417 | O | ASN | A | 68 | 21.370 | 11.377 | 15.069 | 1.00 | 20.06 | O |
| ATOM | 418 | GB | ASN | A | 68 | 20.516 | 11.546 | 12.444 | 1.00 | 21.63 | C |
| ATOM | 419 | CG | ASN | A | 68 | 19.476 | 11.493 | 11.340 | 1.00 | 22.28 | C |
| ATOM | 420 | OD1 | ASN | A | 68 | 18.276 | 11.429 | 11.601 | 1.00 | 23.83 | O |
| ATOM | 421 | ND2 | ASN | A | 68 | 19.936 | 11.492 | 10.108 | 1.00 | 22.82 | N |
| ATOM | 422 | N | LEU | A | 69 | 21.613 | 13.617 | 15.248 | 1.00 | 19.86 | N |
| ATOM | 423 | CA | LEU | A | 69 | 22.442 | 13.533 | 16.464 | 1.00 | 19.68 | C. |
| ATOM | 424 | C | LEU | A | 69 | 21.814 | 12.707 | 17.571 | 1.00 | 19.03 | C |

TABLE 3-continued

| | | | | | | | | | | | |
|---|---|---|---|---|---|---|---|---|---|---|---|
| \multicolumn{12}{l}{Coordinates for structures 1 to 4} |
| ATOM | 425 | O | LEU | A | 69 | 22.492 | 11.878 | 18.169 | 1.00 | 18.33 | O |
| ATOM | 426 | GB | LEU | A | 69 | 22.770 | 14.907 | 17.009 | 1.00 | 19.89 | C |
| ATOM | 427 | CG | LEU | A | 69 | 23.654 | 14.999 | 18.239 | 1.00 | 19.87 | C |
| ATOM | 428 | CD1 | LEU | A | 69 | 24.970 | 14.289 | 18.035 | 1.00 | 20.74 | C |
| ATOM | 429 | CD2 | LEU | A | 69 | 23.911 | 16.459 | 18.577 | 1.00 | 20.41 | C |
| ATOM | 430 | N | VAL | A | 70 | 20.538 | 12.940 | 17.860 | 1.00 | 18.84 | N |
| ATOM | 431 | CA | VAL | A | 70 | 19.843 | 12.177 | 18.894 | 1.00 | 18.85 | C |
| ATOM | 432 | C | VAL | A | 70 | 18.634 | 11.447 | 18.339 | 1.00 | 19.17 | C |
| ATOM | 433 | O | VAL | A | 70 | 17.604 | 11.325 | 19.000 | 1.00 | 18.71 | O |
| ATOM | 434 | GB | VAL | A | 70 | 19.418 | 13.038 | 20.097 | 1.00 | 18.97 | C |
| ATOM | 435 | CG1 | VAL | A | 70 | 20.645 | 13.557 | 20.812 | 1.00 | 20.41 | C |
| ATOM | 436 | CG2 | VAL | A | 70 | 18.513 | 14.185 | 19.686 | 1.00 | 18.87 | C |
| ATOM | 437 | N | TYR | A | 71 | 18.796 | 10.916 | 17.133 | 1.00 | 20.12 | N |
| ATOM | 438 | CA | TYR | A | 71 | 17.711 | 10.224 | 16.454 | 1.00 | 20.64 | C |
| ATOM | 439 | C | TYR | A | 71 | 17.003 | 9.218 | 17.377 | 1.00 | 20.76 | C |
| ATOM | 440 | O | TYR | A | 71 | 15.804 | 9.275 | 17.507 | 1.00 | 20.54 | O |
| ATOM | 441 | GB | TYR | A | 71 | 18.186 | 9.591 | 15.136 | 1.00 | 20.75 | C |
| ATOM | 442 | CG | TYR | A | 71 | 17.243 | 8.517 | 14.628 | 1.00 | 23.02 | C |
| ATOM | 443 | CD1 | TYR | A | 71 | 16.012 | 8.837 | 14.046 | 1.00 | 24.62 | C |
| ATOM | 444 | CD2 | TYR | A | 71 | 17.572 | 7.182 | 14.754 | 1.00 | 22.94 | C |
| ATOM | 445 | GE1 | TYR | A | 71 | 15.132 | 7.800 | 13.595 | 1.00 | 23.64 | C |
| ATOM | 446 | CE2 | TYR | A | 71 | 16.730 | 6.174 | 14.312 | 1.00 | 23.48 | C |
| ATOM | 447 | CZ | TYR | A | 71 | 15.524 | 6.478 | 13.730 | 1.00 | 24.03 | C |
| ATOM | 448 | OH | TYR | A | 71 | 14.697 | 5.422 | 13.349 | 1.00 | 29.55 | O |
| ATOM | 449 | N | PRO | A | 72 | 17.728 | 8.356 | 18.068 | 1.00 | 21.35 | N |
| ATOM | 450 | CA | PRO | A | 72 | 17.080 | 7.363 | 18.945 | 1.00 | 21.89 | C |
| ATOM | 451 | C | PRO | A | 72 | 16.296 | 7.955 | 20.106 | 1.00 | 22.22 | C |
| ATOM | 452 | O | PRO | A | 72 | 15.432 | 7.269 | 20.628 | 1.00 | 21.25 | O |
| ATOM | 453 | GB | PRO | A | 72 | 18.248 | 6.538 | 19.493 | 1.00 | 21.83 | C |
| ATOM | 454 | CG | PRO | A | 72 | 19.420 | 6.849 | 18.606 | 1.00 | 22.53 | C |
| ATOM | 455 | CD | PRO | A | 72 | 19.192 | 8.240 | 18.080 | 1.00 | 21.81 | C |
| ATOM | 456 | N | ALA | A | 73 | 16.568 | 9.206 | 20.484 | 1.00 | 22.77 | N |
| ATOM | 457 | CA | ALA | A | 73 | 15.859 | 9.836 | 21.605 | 1.00 | 23.23 | C |
| ATOM | 458 | C | ALA | A | 73 | 14.542 | 10.487 | 21.178 | 1.00 | 23.64 | C |
| ATOM | 459 | O | ALA | A | 73 | 13.764 | 10.966 | 22.014 | 1.00 | 23.47 | O |
| ATOM | 460 | GB | ALA | A | 73 | 16.750 | 10.860 | 22.284 | 1.00 | 22.77 | C |
| ATOM | 461 | N | LEU | A | 74 | 14.275 | 10.507 | 19.881 | 1.00 | 24.25 | N |
| ATOM | 462 | GA | LEU | A | 74 | 13.057 | 11.148 | 19.405 | 1.00 | 24.86 | C |
| ATOM | 463 | C | LEU | A | 74 | 11.792 | 10.466 | 19.920 | 1.00 | 25.46 | C |
| ATOM | 464 | O | LEU | A | 74 | 10.729 | 11.070 | 19.967 | 1.00 | 25.11 | O |
| ATOM | 465 | GB | LEU | A | 74 | 13.055 | 11.240 | 17.881 | 1.00 | 24.77 | C |
| ATOM | 466 | CG | LEU | A | 74 | 14.160 | 12.161 | 17.338 | 1.00 | 26.74 | C |
| ATOM | 467 | CD1 | LEU | A | 74 | 13.915 | 12.478 | 15.867 | 1.00 | 28.86 | C |
| ATOM | 468 | CD2 | LEU | A | 74 | 14.288 | 13.447 | 18.135 | 1.00 | 26.86 | C |
| ATOM | 469 | N | LYS | A | 75 | 11.908 | 9.204 | 20.306 | 1.00 | 26.12 | N |
| ATOM | 470 | GA | LYS | A | 75 | 10.756 | 8.460 | 20.814 | 1.00 | 26.39 | C |
| ATOM | 471 | C | LYS | A | 75 | 10.585 | 8.687 | 22.309 | 1.00 | 26.71 | C |
| ATOM | 472 | O | LYS | A | 75 | 9.584 | 8.284 | 22.875 | 1.00 | 26.80 | O |
| ATOM | 473 | GB | LYS | A | 75 | 10.918 | 6.963 | 20.534 | 1.00 | 26.36 | C |
| ATOM | 474 | CG | LYS | A | 75 | 12.141 | 6.322 | 21.185 | 1.00 | 26.49 | C |
| ATOM | 475 | CD | LYS | A | 75 | 12.254 | 4.813 | 20.838 | 1.00 | 27.59 | C |
| ATOM | 476 | CE | LYS | A | 75 | 13.732 | 4.367 | 20.671 | 1.00 | 27.21 | C |
| ATOM | 477 | NZ | LYS | A | 75 | 14.475 | 4.226 | 21.912 | 1.00 | 24.71 | N |
| ATOM | 478 | N | TRP | A | 76 | 11.561 | 9.327 | 22.950 | 1.00 | 26.64 | N |
| ATOM | 479 | CA | TRP | A | 76 | 11.484 | 9.557 | 24.383 | 1.00 | 26.78 | C |
| ATOM | 480 | C | TRP | A | 76 | 10.253 | 10.368 | 24.770 | 1.00 | 27.48 | C |
| ATOM | 481 | O | TRP | A | 76 | 9.889 | 11.317 | 24.095 | 1.00 | 27.93 | O |
| ATOM | 482 | CB | TRP | A | 76 | 12.717 | 10.311 | 24.888 | 1.00 | 26.57 | C |
| ATOM | 483 | CG | TRP | A. | 76 | 13.963 | 9.500 | 24.895 | 1.00 | 25.80 | C |
| ATOM | 484 | CD1 | TRP | A | 76 | 14.101 | 8.219 | 24.486 | 1.00 | 24.26 | C |
| ATOM | 485 | CD2 | TRP | A | 76 | 15.255 | 9.917 | 25.347 | 1.00 | 22.71 | C |
| ATOM | 486 | NE1 | TRP | A | 76 | 15.399 | 7.804 | 24.647 | 1.00 | 23.20 | N |
| ATOM | 487 | CE2 | TRP | A | 76 | 16.128 | 8.829 | 25.178 | 1.00 | 22.53 | C |
| ATOM | 488 | CE3 | TRP | A | 76 | 15.767 | 11.107 | 25.867 | 1.00 | 21.96 | C |
| ATOM | 489 | CZ2 | TRP | A | 76 | 17.468 | 8.890 | 25.520 | 1.00 | 22.50 | C |
| ATOM | 490 | CZ3 | TRP | A | 76 | 17.090 | 11.172 | 26.202 | 1.00 | 20.53 | C |
| ATOM | 491 | CR2 | TRP | A | 76 | 17.931 | 10.076 | 26.029 | 1.00 | 22.36 | C |
| ATOM | 492 | N | ASP | A | 77 | 9.639 | 9.976 | 25.880 | 1.00 | 27.85 | N |
| ATOM | 493 | CA | ASP | A | 77 | 8.532 | 10.684 | 26.484 | 1.00 | 27.74 | C |
| ATOM | 494 | C | ASP | A | 77 | 8.560 | 10.277 | 27.957 | 1.00 | 27.45 | C |
| ATOM | 495 | O | ASP | A | 77 | 9.373 | 9.460 | 28.336 | 1.00 | 27.22 | O |
| ATOM | 496 | CB | ASP | A | 77 | 7.208 | 10.368 | 25.800 | 1.00 | 27.89 | C |
| ATOM | 497 | CG | ASP | A | 77 | 6.802 | 8.913 | 25.903 | 1.00 | 29.06 | C |
| ATOM | 498 | OD1 | ASP | A | 77 | 7.354 | 8.108 | 26.708 | 1.00 | 30.51 | O |
| ATOM | 499 | OD2 | ASP | A | 77 | 5.894 | 8.489 | 25.179 | 1.00 | 31.13 | O |
| ATOM | 500 | N | LEU | A | 78 | 7.710 | 10.847 | 28.796 | 1.00 | 27.47 | N |
| ATOM | 501 | CA | LEU | A | 78 | 7.819 | 10.578 | 30.229 | 1.00 | 27.63 | C |

TABLE 3-continued

| | | | | | Coordinates for structures 1 to 4 | | | | | |
|---|---|---|---|---|---|---|---|---|---|---|
| ATOM | 502 | C | LEU | A | 78 | 7.655 | 9.101 | 30.542 | 1.00 | 27.81 | C |
| ATOM | 503 | O | LEU | A | 78 | 8.386 | 8.548 | 31.367 | 1.00 | 27.16 | O |
| ATOM | 504 | CB | LEU | A | 78 | 6.818 | 11.409 | 31.011 | 1.00 | 27.59 | C |
| ATOM | 505 | CG | LEU | A | 78 | 7.007 | 12.916 | 30.880 | 1.00 | 28.68 | C |
| ATOM | 506 | CD1 | LEU | A | 78 | 5.906 | 13.677 | 31.612 | 1.00 | 28.95 | C |
| ATOM | 507 | CD2 | LEU | A | 78 | 8.369 | 13.328 | 31.412 | 1.00 | 29.32 | C |
| ATOM | 508 | N | GLU | A | 79 | 6.721 | 8.450 | 29.860 | 1.00 | 28.17 | N |
| ATOM | 509 | CA | GLU | A | 79 | 6.480 | 7.035 | 30.102 | 1.00 | 28.56 | C |
| ATOM | 510 | C | GLU | A | 79 | 7.715 | 6.185 | 29.781 | 1.00 | 28.22 | C |
| ATOM | 511 | O | GLU | A | 79 | 8.167 | 5.388 | 30.600 | 1.00 | 27.73 | O |
| ATOM | 512 | CB | GLU | A | 79 | 5.267 | 6.540 | 29.298 | 1.00 | 28.87 | C |
| ATOM | 513 | CG | GLU | A | 79 | 5.051 | 5.049 | 29.467 | 1.00 | 31.45 | C |
| ATOM | 514 | CD | GLU | A | 79 | 3.849 | 4.516 | 28.716 | 1.00 | 34.79 | C |
| ATOM | 515 | OE1 | GLU | A | 79 | 3.422 | 5.129 | 27.709 | 1.00 | 35.78 | O |
| ATOM | 516 | OE2 | GLU | A | 79 | 3.343 | 3.457 | 29.144 | 1.00 | 37.92 | O |
| ATOM | 517 | N | TYR | A | 80 | 8.260 | 6.346 | 28.582 | 1.00 | 28.27 | N |
| ATOM | 518 | CA | TYR | A | 80 | 9.452 | 5.597 | 28.200 | 1.00 | 28.00 | C |
| ATOM | 519 | C | TYR | A | 80 | 10.628 | 5.873 | 29.142 | 1.00 | 27.64 | C |
| ATOM | 520 | O | TYR | A | 80 | 11.330 | 4.958 | 29.563 | 1.00 | 27.16 | O |
| ATOM | 521 | CB | TYR | A | 80 | 9.838 | 5.964 | 26.787 | 1.00 | 28.13 | C |
| ATOM | 522 | CG | TYR | A | 80 | 11.054 | 5.250 | 26.246 | 1.00 | 27.95 | C |
| ATOM | 523 | CD1 | TYR | A | 80 | 10.952 | 3.991 | 25.644 | 1.00 | 27.39 | C |
| ATOM | 524 | CD2 | TYR | A | 80 | 12.300 | 5.846 | 26.306 | 1.00 | 25.55 | C |
| ATOM | 525 | CE1 | TYR | A | 80 | 12.089 | 3.352 | 25.128 | 1.00 | 26.82 | C |
| ATOM | 526 | CE2 | TYR | A | 80 | 13.417 | 5.224 | 25.808 | 1.00 | 25.50 | C |
| ATOM | 527 | CZ | TYR | A | 80 | 13.320 | 3.992 | 25.213 | 1.00 | 25.64 | C |
| ATOM | 528 | OH | TYR | A | 80 | 14.467 | 3.426 | 24.703 | 1.00 | 23.50 | O |
| ATOM | 529 | N | LEU | A | 81 | 10.839 | 7.135 | 29.482 | 1.00 | 27.51 | N |
| ATOM | 530 | CA | LEU | A | 81 | 11.952 | 7.477 | 30.371 | 1.00 | 27.75 | C |
| ATOM | 531 | C | LEU | A | 81 | 11.741 | 6.943 | 31.801 | 1.00 | 27.76 | C |
| ATOM | 532 | O | LEU | A | 81 | 12.682 | 6.459 | 32.437 | 1.00 | 27.35 | O |
| ATOM | 533 | CB | LEU | A | 81 | 12.194 | 8.990 | 30.399 | 1.00 | 27.35 | C |
| ATOM | 534 | CG | LEU | A | 81 | 12.659 | 9.656 | 29.096 | 1.00 | 28.06 | C |
| ATOM | 535 | CD1 | LEU | A | 81 | 12.664 | 11.170 | 29.269 | 1.00 | 28.55 | C |
| ATOM | 536 | CD2 | LEU | A | 81 | 14.036 | 9.192 | 28.655 | 1.00 | 27.65 | C |
| ATOM | 537 | N | GLN | A | 82 | 10.521 | 7.049 | 32.313 | 1.00 | 28.10 | N |
| ATOM | 538 | CA | GLN | A | 82 | 10.234 | 6.557 | 33.656 | 1.00 | 28.61 | C |
| ATOM | 539 | C | GLN | A | 82 | 10.525 | 5.066 | 33.689 | 1.00 | 28.32 | C |
| ATOM | 540 | O | GLN | A | 82 | 11.070 | 4.550 | 34.643 | 1.00 | 28.25 | O |
| ATOM | 541 | CB | GLN | A | 82 | 8.774 | 6.805 | 34.032 | 1.00 | 29.04 | C |
| ATOM | 542 | CG | GLN | A | 82 | 8.325 | 6.063 | 35.293 | 1.00 | 30.18 | C |
| ATOM | 543 | CD | GLN | A | 82 | 7.184 | 6.754 | 36.042 | 1.00 | 32.25 | C |
| ATOM | 544 | OE1 | GLN | A | 82 | 6.642 | 7.758 | 35.594 | 1.00 | 34.51 | O |
| ATOM | 545 | NE2 | GLN | A | 82 | 6.822 | 6.204 | 37.189 | 1.00 | 36.79 | N |
| ATOM | 546 | N | GLU | A | 83 | 10.193 | 4.397 | 32.601 | 1.00 | 28.58 | N |
| ATOM | 547 | CA | GLU | A | 83 | 10.349 | 2.950 | 32.492 | 1.00 | 28.70 | C |
| ATOM | 548 | C | GLU | A | 83 | 11.801 | 2.515 | 32.314 | 1.00 | 28.14 | C |
| ATOM | 549 | O | GLU | A | 83 | 12.166 | 1.424 | 32.713 | 1.00 | 27.54 | O |
| ATOM | 550 | CB | GLU | A | 83 | 9.506 | 2.438 | 31.319 | 1.00 | 28.53 | C |
| ATOM | 551 | CG | GLU | A | 83 | 9.562 | 0.937 | 31.101 | 1.00 | 30.76 | C |
| ATOM | 552 | CD | GLU | A | 83 | 8.985 | 0.150 | 32.265 | 1.00 | 33.31 | C |
| ATOM | 553 | OE1 | LU | A | 83 | 8.172 | 0.713 | 33.030 | 1.00 | 35.22 | O |
| ATOM | 554 | OE2 | GLU | A | 83 | 9.352 | 1.033 | 32.428 | 1.00 | 35.98 | O |
| ATOM | 555 | N | ASN | A | 84 | 12.644 | 3.374 | 31.753 | 1.00 | 27.44 | N |
| ATOM | 556 | CA | ASN | A | 84 | 13.985 | 2.938 | 31.400 | 1.00 | 27.09 | C |
| ATOM | 557 | C | ASN | A | 84 | 15.168 | 3.729 | 31.913 | 1.00 | 27.31 | C |
| ATOM | 558 | O | ASN | A | 84 | 16.291 | 3.276 | 31.759 | 1.00 | 27.17 | O |
| ATOM | 559 | CE | ASN | A | 84 | 14.099 | 2.917 | 29.879 | 1.00 | 27.17 | C |
| ATOM | 560 | CG | ASN | A | 84 | 13.226 | 1.890 | 29.254 | 1.00 | 26.24 | C |
| ATOM | 561 | OD1 | ASN | A | 84 | 13.361 | 0.696 | 29.532 | 1.00 | 27.49 | O |
| ATOM | 562 | ND2 | ASN | A | 84 | 12.312 | 2.333 | 28.413 | 1.00 | 23.37 | N |
| ATOM | 563 | N | ILE | A | 85 | 14.952 | 4.893 | 32.511 | 1.00 | 27.52 | N |
| ATOM | 564 | CA | ILE | A | 85 | 16.088 | 5.734 | 32.861 | 1.00 | 28.25 | C |
| ATOM | 565 | C | ILE | A | 85 | 16.788 | 5.390 | 34.185 | 1.00 | 28.03 | C |
| ATOM | 566 | O | ILE | A | 85 | 17.700 | 6.094 | 34.610 | 1.00 | 28.40 | O |
| ATOM | 567 | CE | ILE | A | 85 | 15.684 | 7.221 | 32.801 | 1.00 | 28.23 | C |
| ATOM | 568 | CG1 | ILE | A | 85 | 16.872 | 8.069 | 32.342 | 1.00 | 29.61 | C |
| ATOM | 569 | CG2 | ILE | A | 85 | 15.143 | 7.694 | 34.139 | 1.00 | 29.11 | C |
| ATOM | 570 | CD1 | ILE | A | 85 | 16.520 | 9.535 | 31.996 | 1.00 | 28.97 | C |
| ATOM | 571 | N | GLY | A | 86 | 16.368 | 4.317 | 34.833 | 1.00 | 28.14 | N |
| ATOM | 572 | CA | GLY | A | 86 | 17.014 | 3.874 | 36.061 | 1.00 | 28.15 | C |
| ATOM | 573 | C | GLY | A | 86 | 16.478 | 4.504 | 37.335 | 1.00 | 28.11 | C |
| ATOM | 574 | O | GLY | A | 86 | 15.494 | 5.251 | 37.308 | 1.00 | 27.93 | O |
| ATOM | 575 | N | ASN | A | 87 | 17.162 | 4.220 | 38.444 | 1.00 | 27.96 | N |
| ATOM | 576 | CA | ASN | A | 87 | 16.754 | 4.672 | 39.767 | 1.00 | 27.88 | C |
| ATOM | 577 | C | ASN | A | 87 | 17.736 | 5.677 | 40.373 | 1.00 | 27.82 | C |
| ATOM | 578 | O | ASN | A | 87 | 17.751 | 5.886 | 41.585 | 1.00 | 27.63 | O |

TABLE 3-continued

Coordinates for structures 1 to 4

| ATOM | 579 | CE  | ASN | A | 87 | 16.571 | 3.447  | 40.713 | 1.00 | 27.89 | C |
|------|-----|-----|-----|---|----|--------|--------|--------|------|-------|---|
| ATOM | 580 | N   | GLY | A | 88 | 18.559 | 6.301  | 39.538 | 1.00 | 28.21 | N |
| ATOM | 581 | CA  | GLY | A | 88 | 19.478 | 7.336  | 40.006 | 1.00 | 28.18 | C |
| ATOM | 582 | C   | GLY | A | 88 | 18.706 | 8.584  | 40.396 | 1.00 | 28.19 | C |
| ATOM | 583 | O   | GLY | A | 88 | 17.520 | 8.676  | 40.097 | 1.00 | 28.62 | O |
| ATOM | 584 | N   | ASP | A | 89 | 19.357 | 9.530  | 41.068 | 1.00 | 27.99 | N |
| ATOM | 585 | CA  | ASP | A | 89 | 18.707 | 10.781 | 41.468 | 1.00 | 28.09 | C |
| ATOM | 586 | C   | ASP | A | 89 | 18.655 | 11.806 | 40.335 | 1.00 | 28.00 | C |
| ATOM | 587 | O   | ASP | A | 89 | 19.557 | 11.866 | 39.507 | 1.00 | 28.07 | O |
| ATOM | 588 | CE  | ASP | A | 89 | 19.467 | 11.433 | 42.613 | 1.00 | 28.24 | C |
| ATOM | 589 | CG  | ASP | A | 89 | 19.249 | 10.747 | 43.935 | 1.00 | 28.53 | C |
| ATOM | 590 | OD1 | ASP | A | 89 | 18.398 | 9.843  | 44.024 | 1.00 | 30.26 | O |
| ATOM | 591 | OD2 | ASP | A | 89 | 19.884 | 11.070 | 44.955 | 1.00 | 29.31 | O |
| ATOM | 592 | N   | PHE | A | 90 | 17.620 | 12.637 | 40.330 | 1.00 | 27.56 | C |
| ATOM | 593 | CA  | PHE | A | 90 | 17.510 | 13.687 | 39.332 | 1.00 | 27.37 | C |
| ATOM | 594 | C   | PHE | A | 90 | 17.291 | 15.037 | 39.993 | 1.00 | 27.78 | C |
| ATOM | 595 | O   | PHE | A | 90 | 16.453 | 15.171 | 40.884 | 1.00 | 27.69 | O |
| ATOM | 596 | CB  | PHE | A | 90 | 16.378 | 13.388 | 38.351 | 1.00 | 27.05 | C |
| ATOM | 597 | CG  | PHE | A | 90 | 16.678 | 12.262 | 37.408 | 1.00 | 25.85 | C |
| ATOM | 598 | CD1 | PHE | A | 90 | 16.525 | 10.943 | 37.806 | 1.00 | 25.70 | C |
| ATOM | 599 | CD2 | PHE | A | 90 | 17.119 | 12.521 | 36.121 | 1.00 | 26.20 | C |
| ATOM | 600 | CE1 | PHE | A | 90 | 16.797 | 9.908  | 36.943 | 1.00 | 24.06 | C |
| ATOM | 601 | CE2 | PHE | A | 90 | 17.395 | 21.489 | 35.248 | 1.00 | 25.49 | C |
| ATOM | 602 | CZ  | PHE | A | 90 | 17.235 | 10.176 | 35.666 | 1.00 | 25.33 | C |
| ATOM | 603 | N   | SER | A | 91 | 18.062 | 16.033 | 39.560 | 1.00 | 27.85 | N |
| ATOM | 604 | CA  | SER | A | 91 | 17.902 | 17.384 | 40.075 | 1.00 | 28.17 | C |
| ATOM | 605 | C   | SER | A | 91 | 16.695 | 18.023 | 39.419 | 1.00 | 28.48 | C |
| ATOM | 606 | O   | SER | A | 91 | 16.589 | 18.085 | 38.192 | 1.00 | 28.35 | O |
| ATOM | 607 | GB  | SER | A | 91 | 19.149 | 18.236 | 39.838 | 1.00 | 27.86 | C |
| ATOM | 608 | OG  | SER | A | 91 | 20.260 | 17.652 | 40.485 | 1.00 | 27.15 | O |
| ATOM | 609 | N   | VAL | A | 92 | 15.784 | 18.482 | 40.261 | 1.00 | 29.05 | N |
| ATOM | 610 | CA  | VAL | A | 92 | 14.585 | 19.141 | 39.812 | 1.00 | 29.67 | C |
| ATOM | 611 | C   | VAL | A | 92 | 14.437 | 20.465 | 40.529 | 1.00 | 30.31 | C |
| ATOM | 612 | O   | VAL | A | 92 | 14.442 | 20.537 | 41.763 | 1.00 | 30.37 | O |
| ATOM | 613 | GB  | VAL | A | 92 | 13.352 | 18.313 | 40.106 | 1.00 | 29.81 | C |
| ATOM | 614 | CO1 | VAL | A | 92 | 12.106 | 19.026 | 39.582 | 1.00 | 29.93 | C |
| ATOM | 615 | CG2 | VAL | A | 92 | 13.490 | 16.930 | 39.507 | 1.00 | 29.60 | C |
| ATOM | 616 | N   | TYR | A | 93 | 14.329 | 21.516 | 39.732 | 1.00 | 31.00 | N |
| ATOM | 617 | CA  | TYR | A | 93 | 14.135 | 22.845 | 40.241 | 1.00 | 31.29 | C |
| ATOM | 618 | C   | TYR | A | 93 | 12.662 | 23.113 | 40.298 | 1.00 | 31.54 | C |
| ATOM | 619 | O   | TYR | A | 93 | 11.892 | 22.701 | 39.423 | 1.00 | 31.35 | O |
| ATOM | 620 | GB  | TYR | A | 93 | 14.829 | 23.853 | 39.345 | 1.00 | 31.87 | C |
| ATOM | 621 | CG  | TYR | A | 93 | 16.310 | 23.711 | 39.436 | 1.00 | 33.05 | C |
| ATOM | 622 | CD1 | TYR | A | 93 | 17.012 | 24.283 | 40.482 | 1.00 | 34.67 | C |
| ATOM | 623 | CD2 | TYR | A | 93 | 16.998 | 22.954 | 38.525 | 1.00 | 34.24 | G |
| ATOM | 624 | GE1 | TYR | A | 93 | 18.357 | 24.125 | 40.593 | 1.00 | 35.09 | C |
| ATOM | 625 | CE2 | TYR | A | 93 | 18.338 | 22.789 | 38.634 | 1.00 | 36.36 | C |
| ATOM | 626 | CZ  | TYR | A | 93 | 19.011 | 23.379 | 39.670 | 1.00 | 36.33 | C |
| ATOM | 627 | OH  | TYR | A | 93 | 20.357 | 23.204 | 39.772 | 1.00 | 40.81 | O |
| ATOM | 628 | N   | SER | A | 94 | 12.286 | 23.813 | 41.351 | 1.00 | 32.03 | N |
| ATOM | 629 | CA  | SER | A | 94 | 10.919 | 24.182 | 41.599 | 1.00 | 32.31 | C |
| ATOM | 630 | C   | SER | A | 94 | 10.884 | 25.692 | 41.704 | 1.00 | 32.42 | C |
| ATOM | 631 | O   | SER | A | 94 | 11.743 | 26.286 | 42.350 | 1.00 | 32.48 | O |
| ATOM | 632 | GB  | SER | A | 94 | 10.464 | 23.566 | 42.914 | 1.00 | 32.38 | G |
| ATOM | 633 | OG  | SER | A | 94 | 9.062  | 23.691 | 43.052 | 1.00 | 33.53 | O |
| ATOM | 634 | N   | ALA | A | 95 | 9.902  | 26.314 | 41.070 | 1.00 | 32.58 | N |
| ATOM | 635 | CA  | ALA | A | 95 | 9.766  | 27.757 | 41.135 | 1.00 | 32.90 | C |
| ATOM | 636 | C   | ALA | A | 95 | 8.312  | 28.172 | 41.076 | 1.00 | 33.48 | C |
| ATOM | 637 | O   | ALA | A | 95 | 7.446  | 27.429 | 40.620 | 1.00 | 33.62 | O |
| ATOM | 638 | GB  | ALA | A | 95 | 10.528 | 28.413 | 39.996 | 1.00 | 32.80 | C |
| ATOM | 639 | N   | SER | A | 96 | 8.053  | 29.382 | 41.539 | 1.00 | 34.08 | N |
| ATOM | 640 | CA  | SER | A | 96 | 6.721  | 29.932 | 41.482 | 1.00 | 34.75 | C |
| ATOM | 641 | C   | SER | A | 96 | 6.616  | 30.974 | 40.382 | 1.00 | 34.55 | C |
| ATOM | 642 | O   | SER | A | 96 | 5.603  | 31.659 | 40.275 | 1.00 | 35.29 | O |
| ATOM | 643 | GB  | SER | A | 96 | 6.363  | 30.592 | 42.801 | 1.00 | 35.05 | C |
| ATOM | 644 | OG  | SER | A | 96 | 5.165  | 31.311 | 42.627 | 1.00 | 36.18 | O |
| ATOM | 645 | N   | THR | A | 97 | 7.673  | 31.107 | 39.593 | 1.00 | 33.88 | N |
| ATOM | 646 | CA  | THR | A | 97 | 7.716  | 32.046 | 38.477 | 1.00 | 33.41 | C |
| ATOM | 647 | C   | THR | A | 97 | 8.084  | 31.238 | 37.265 | 1.00 | 32.32 | C |
| ATOM | 648 | O   | THR | A | 97 | 8.590  | 30.143 | 37.411 | 1.00 | 32.10 | O |
| ATOM | 649 | GB  | THR | A | 97 | 8.797  | 33.144 | 38.695 | 1.00 | 33.64 | C |
| ATOM | 650 | OG1 | THR | A | 97 | 9.067  | 33.810 | 37.460 | 1.00 | 33.76 | C |
| ATOM | 651 | CG2 | THR | A | 97 | 10.190 | 32.559 | 39.058 | 1.00 | 34.25 | C |
| ATOM | 652 | N   | HIS | A | 98 | 7.840  | 31.762 | 36.073 | 1.00 | 31.47 | N |
| ATOM | 653 | CA  | HIS | A | 98 | 8.278  | 31.071 | 34.863 | 1.00 | 30.97 | C |
| ATOM | 654 | C   | HIS | A | 98 | 9.804  | 31.134 | 34.707 | 1.00 | 30.53 | C |
| ATOM | 655 | O   | HIS | A | 98 | 10.378 | 30.379 | 33.940 | 1.00 | 29.14 | O |

TABLE 3-continued

| | | | | | | | | | | | |
|---|---|---|---|---|---|---|---|---|---|---|---|
| | Coordinates for structures 1 to 4 |

| ATOM | 656 | GB | HIS | A | 98 | 7.613 | 31.666 | 33.621 | 1.00 | 31.14 | C |
|---|---|---|---|---|---|---|---|---|---|---|---|
| ATOM | 657 | CG | HIS | A | 98 | 7.878 | 33.125 | 33.415 | 1.00 | 30.86 | C |
| ATOM | 658 | ND1 | HIS | A | 98 | 7.121 | 34.112 | 34.011 | 1.00 | 31.51 | N |
| ATOM | 659 | CD2 | HIS | A | 98 | 8.795 | 33.767 | 32.651 | 1.00 | 31.48 | C |
| ATOM | 660 | GE1 | HIS | A | 98 | 7.566 | 35.298 | 33.634 | 1.00 | 31.14 | C |
| ATOM | 661 | ND2 | HIS | A | 98 | 8.581 | 35.118 | 32.805 | 1.00 | 30.50 | N |
| ATOM | 662 | N | LYS | A | 99 | 10.459 | 32.025 | 35.449 | 1.00 | 30.36 | N |
| ATOM | 663 | CA | LYS | A | 99 | 11.895 | 32.198 | 35.298 | 1.00 | 31.07 | C |
| ATOM | 664 | C | LYS | A | 99 | 12.761 | 31.288 | 36.166 | 1.00 | 31.00 | C |
| ATOM | 665 | O | LYS | A | 99 | 12.693 | 31.337 | 37.396 | 1.00 | 31.91 | O |
| ATOM | 666 | CB | LYS | A | 99 | 12.265 | 33.643 | 35.544 | 1.00 | 31.15 | C |
| ATOM | 667 | CG | LYS | A | 99 | 11.887 | 34.551 | 34.391 | 1.00 | 33.39 | C |
| ATOM | 668 | CD | LYS | A | 99 | 12.486 | 35.945 | 34.556 | 1.00 | 36.16 | C |
| ATOM | 669 | CE | LYS | A | 99 | 11.763 | 36.771 | 35.607 | 1.00 | 37.52 | C |
| ATOM | 670 | NZ | LYS | A | 99 | 10.620 | 37.507 | 35.006 | 1.00 | 38.84 | N |
| ATOM | 671 | N | PHE | A | 100 | 13.572 | 30.453 | 35.518 | 1.00 | 30.20 | N |
| ATOM | 672 | CA | PHE | A | 100 | 14.517 | 29.606 | 36.232 | 1.00 | 30.03 | C |
| ATOM | 673 | C | PHE | A | 100 | 15.952 | 30.123 | 36.138 | 1.00 | 29.72 | C |
| ATOM | 674 | O | PHE | A | 100 | 16.826 | 29.544 | 35.481 | 1.00 | 29.39 | O |
| ATOM | 675 | CB | PHE | A | 100 | 14.441 | 28.168 | 35.744 | 1.00 | 29.93 | C |
| ATOM | 676 | CG | PHE | A | 100 | 13.223 | 27.452 | 36.206 | 1.00 | 29.72 | C |
| ATOM | 677 | CD1 | PHE | A | 100 | 12.014 | 27.637 | 35.566 | 1.00 | 28.98 | C |
| ATOM | 678 | CD2 | PHE | A | 100 | 13.283 | 26.596 | 37.289 | 1.00 | 30.77 | C |
| ATOM | 679 | CE1 | PHE | A | 100 | 10.896 | 26.969 | 35.983 | 1.00 | 30.22 | C |
| ATOM | 680 | CE2 | PHE | A | 100 | 12.158 | 25.919 | 37.719 | 1.00 | 30.51 | C |
| ATOM | 681 | CZ | PHE | A | 100 | 10.967 | 26.105 | 37.069 | 1.00 | 30.63 | C |
| ATOM | 682 | N | LEU | A | 101 | 16.178 | 31.235 | 36.809 | 1.00 | 29.87 | N |
| ATOM | 683 | CA | LEU | A | 101 | 17.495 | 31.812 | 36.919 | 1.00 | 29.57 | C |
| ATOM | 684 | C | LEU | A | 101 | 18.451 | 30.814 | 37.555 | 1.00 | 29.61 | C |
| ATOM | 685 | O | LEU | A | 101 | 18.249 | 30.380 | 38.679 | 1.00 | 28.35 | O |
| ATOM | 686 | CB | LEU | A | 101 | 17.412 | 33.057 | 37.787 | 1.00 | 29.68 | C |
| ATOM | 687 | CG | LEU | A | 101 | 18.707 | 33.845 | 37.954 | 1.00 | 29.68 | C |
| ATOM | 688 | CD1 | LEU | A | 101 | 19.184 | 34.337 | 36.620 | 1.00 | 28.70 | C |
| ATOM | 689 | CD2 | LEU | A | 101 | 18.474 | 35.014 | 38.909 | 1.00 | 31.41 | C |
| ATOM | 690 | N | TYR | A | 102 | 19.490 | 30.440 | 36.816 | 1.00 | 30.36 | N |
| ATOM | 691 | CA | TYR | A | 102 | 20.516 | 29.535 | 37.338 | 1.00 | 30.64 | C |
| ATOM | 692 | C | TYR | A | 102 | 21.332 | 30.228 | 38.440 | 1.00 | 30.93 | C |
| ATOM | 693 | O | TYR | A | 102 | 21.623 | 31.425 | 38.339 | 1.00 | 30.67 | O |
| ATOM | 694 | CB | TYR | A | 102 | 21.480 | 29.101 | 36.224 | 1.00 | 30.45 | C |
| ATOM | 695 | CG | TYR | A | 102 | 22.609 | 28.271 | 36.774 | 1.00 | 31.25 | C |
| ATOM | 696 | CD1 | TYR | A | 102 | 22.430 | 26.916 | 37.062 | 1.00 | 31.33 | C |
| ATOM | 697 | CD2 | TYR | A | 102 | 23.842 | 28.844 | 37.054 | 1.00 | 31.29 | C |
| ATOM | 698 | CE1 | TYR | A | 102 | 23.456 | 26.163 | 37.612 | 1.00 | 32.81 | C |
| ATOM | 699 | CE2 | TYR | A | 102 | 24.869 | 28.098 | 37.601 | 1.00 | 32.24 | C |
| ATOM | 700 | CZ | TYR | A | 102 | 24.676 | 26.764 | 37.876 | 1.00 | 34.18 | C |
| ATOM | 701 | OH | TYR | A | 102 | 25.720 | 26.030 | 38.418 | 1.00 | 39.06 | O |
| ATOM | 702 | N | TYR | A | 103 | 21.684 | 29.478 | 39.488 | 1.00 | 31.28 | N |
| ATOM | 703 | CA | TYR | A | 103 | 22.569 | 29.983 | 40.539 | 1.00 | 31.56 | C |
| ATOM | 704 | C | TYR | A | 103 | 23.524 | 28.911 | 41.058 | 1.00 | 31.11 | C |
| ATOM | 705 | O | TYR | A | 103 | 23.190 | 27.732 | 41.165 | 1.00 | 30.75 | O |
| ATOM | 706 | CB | TYR | A | 103 | 21.796 | 30.599 | 41.706 | 1.00 | 31.98 | C |
| ATOM | 707 | CG | TYR | A | 103 | 20.846 | 29.663 | 42.385 | 1.00 | 33.92 | C |
| ATOM | 708 | CO1 | TYR | A | 103 | 19.577 | 29.445 | 41.868 | 1.00 | 36.08 | C |
| ATOM | 709 | CD2 | TYR | A | 103 | 21.203 | 29.010 | 43.553 | 1.00 | 36.91 | C |
| ATOM | 710 | CE1 | TYR | A | 103 | 18.696 | 28.587 | 42.483 | 1.00 | 37.42 | C |
| ATOM | 711 | CE2 | TYR | A | 103 | 20.325 | 28.153 | 44.189 | 1.00 | 37.63 | C |
| ATOM | 712 | CZ | TYR | A | 103 | 19.070 | 27.947 | 43.647 | 1.00 | 38.74 | C |
| ATOM | 713 | OH | TYR | A | 103 | 18.183 | 27.099 | 44.264 | 1.00 | 40.90 | O |
| ATOM | 714 | N | ASP | A | 104 | 24.725 | 29.345 | 41.391 | 1.00 | 30.34 | N |
| ATOM | 715 | CA | ASP | A | 104 | 25.752 | 28.444 | 41.873 | 1.00 | 30.04 | C |
| ATOM | 716 | C | ASP | A | 104 | 25.735 | 28.408 | 43.394 | 1.00 | 29.73 | C |
| ATOM | 717 | O | ASP | A | 104 | 26.079 | 29.388 | 44.062 | 1.00 | 28.53 | O |
| ATOM | 718 | CB | ASP | A | 104 | 27.089 | 28.931 | 41.350 | 1.00 | 30.07 | C |
| ATOM | 719 | CG | ASP | A | 104 | 28.233 | 28.037 | 41.731 | 1.00 | 30.02 | C |
| ATOM | 720 | OD1 | ASP | A | 104 | 28.069 | 27.137 | 42.605 | 1.00 | 28.92 | O |
| ATOM | 721 | OD2 | ASP | A | 104 | 29.339 | 28.183 | 41.168 | 1.00 | 29.24 | O |
| ATOM | 722 | N | GLU | A | 105 | 25.327 | 27.263 | 43.931 | 1.00 | 29.74 | N |
| ATOM | 723 | CA | GLU | A | 105 | 25.169 | 27.095 | 45.371 | 1.00 | 29.91 | C |
| ATOM | 724 | C | GLU | A | 105 | 26.461 | 27.343 | 46.155 | 1.00 | 29.29 | C |
| ATOM | 725 | O | GLU | A | 105 | 26.412 | 27.872 | 47.263 | 1.00 | 28.37 | O |
| ATOM | 726 | CB | GLU | A | 105 | 24.601 | 25.699 | 45.672 | 1.00 | 30.40 | C |
| ATOM | 727 | CG | GLU | A | 105 | 23.097 | 25.621 | 45.410 | 1.00 | 32.58 | C |
| ATOM | 728 | CD | GLU | A | 105 | 22.546 | 24.210 | 45.287 | 1.00 | 34.72 | C |
| ATOM | 729 | OE1 | GLU | A | 105 | 22.945 | 23.320 | 46.072 | 1.00 | 35.38 | O |
| ATOM | 730 | OE2 | GLU | A | 105 | 21.683 | 24.001 | 44.402 | 1.00 | 35.93 | O |
| ATOM | 731 | N | LYS | A | 106 | 27.607 | 27.000 | 45.565 | 1.00 | 29.02 | N |
| ATOM | 732 | CA | LYS | A | 106 | 28.897 | 27.156 | 46.243 | 1.00 | 29.26 | C |

TABLE 3-continued

| | | | | | | | | | | |
|---|---|---|---|---|---|---|---|---|---|---|
| | | | | | Coordinates for structures 1 to 4 | | | | | |
| ATOM | 733 | C | LYS | A | 106 | 29.245 | 28.608 | 46.493 | 1.00 | 29.31 | C |
| ATOM | 734 | O | LYS | A | 106 | 30.051 | 28.903 | 47.363 | 1.00 | 28.83 | O |
| ATOM | 735 | CB | LYS | A | 106 | 30.036 | 26.530 | 45.433 | 1.00 | 29.60 | C |
| ATOM | 736 | CG | LYS | A | 106 | 29.864 | 25.036 | 45.094 | 1.00 | 30.18 | C |
| ATOM | 737 | N | LYS | A | 107 | 28.646 | 29.516 | 45.724 | 1.00 | 29.27 | N |
| ATOM | 738 | CA | LYS | A | 107 | 28.925 | 30.933 | 45.876 | 1.00 | 29.61 | C |
| ATOM | 739 | C | LYS | A | 107 | 27.933 | 31.605 | 46.820 | 1.00 | 30.29 | C |
| ATOM | 740 | O | LYS | A | 107 | 28.062 | 32.785 | 47.100 | 1.00 | 30.16 | O |
| ATOM | 741 | CB | LYS | A | 107 | 28.924 | 31.636 | 44.504 | 1.00 | 29.35 | C |
| ATOM | 742 | CG | LYS | A | 107 | 30.222 | 31.411 | 43.697 | 1.00 | 28.97 | C |
| ATOM | 743 | CD | LYS | A | 107 | 30.142 | 31.864 | 42.230 | 1.00 | 26.18 | C |
| ATOM | 744 | CE | LYS | A | 107 | 31.459 | 31.534 | 41.498 | 1.00 | 26.51 | C |
| ATOM | 745 | NZ | LYS | A | 107 | 31.578 | 32.052 | 40.083 | 1.00 | 24.21 | N |
| ATOM | 746 | N | MET | A | 108 | 26.950 | 30.869 | 47.320 | 1.00 | 31.39 | N |
| ATOM | 747 | CA | MET | A | 108 | 25.939 | 31.482 | 48.186 | 1.00 | 32.74 | C |
| ATOM | 748 | C | MET | A | 108 | 26.468 | 32.050 | 49.514 | 1.00 | 33.50 | C |
| ATOM | 749 | O | MET | A | 108 | 25.987 | 33.082 | 49.988 | 1.00 | 33.27 | O |
| ATOM | 750 | CB | MET | A | 108 | 24.787 | 30.509 | 48.417 | 1.00 | 33.11 | C |
| ATOM | 751 | CG | MET | A | 108 | 23.976 | 30.300 | 47.127 | 1.00 | 34.43 | C |
| ATOM | 752 | SD | MET | A | 108 | 22.458 | 29.330 | 47.263 | 1.00 | 37.47 | S |
| ATOM | 753 | CE | MET | A | 108 | 21.487 | 30.326 | 48.417 | 1.00 | 37.24 | C |
| ATOM | 754 | N | ALA | A | 109 | 27.484 | 31.427 | 50.090 | 1.00 | 34.73 | N |
| ATOM | 755 | CA | ALA | A | 109 | 28.039 | 31.922 | 51.359 | 1.00 | 36.13 | C |
| ATOM | 756 | C | ALA | A | 109 | 28.555 | 33.361 | 51.266 | 1.00 | 37.12 | C |
| ATOM | 757 | O | ALA | A | 109 | 28.455 | 34.127 | 52.213 | 1.00 | 37.35 | O |
| ATOM | 758 | CB | ALA | A | 109 | 29.147 | 30.991 | 51.860 | 1.00 | 35.96 | C |
| ATOM | 759 | N | ASN | A | 110 | 29.076 | 33.745 | 50.112 | 1.00 | 38.70 | N |
| ATOM | 760 | CA | ASN | A | 110 | 29.631 | 35.090 | 49.949 | 1.00 | 39.61 | C |
| ATOM | 761 | C | ASN | A | 110 | 28.605 | 36.188 | 49.621 | 1.00 | 39.61 | C |
| ATOM | 762 | O | ASN | A | 110 | 28.950 | 37.359 | 49.500 | 1.00 | 39.50 | O |
| ATOM | 763 | CB | ASN | A | 110 | 30.730 | 35.036 | 48.888 | 1.00 | 39.94 | C |
| ATOM | 764 | CG | ASN | A | 110 | 31.916 | 34.186 | 49.329 | 1.00 | 41.54 | C |
| ATOM | 765 | OD1 | ASN | A | 110 | 32.341 | 34.223 | 50.503 | 1.00 | 41.36 | O |
| ATOM | 766 | ND2 | ASN | A | 110 | 32.451 | 33.406 | 48.399 | 1.00 | 43.06 | N |
| ATOM | 767 | N | PHE | A | 111 | 27.349 | 35.802 | 49.465 | 1.00 | 40.12 | N |
| ATOM | 768 | CA | PHE | A | 111 | 26.278 | 36.753 | 49.208 | 1.00 | 40.43 | C |
| ATOM | 769 | C | PHE | A | 111 | 25.064 | 36.292 | 50.016 | 1.00 | 41.38 | C |
| ATOM | 770 | O | PHE | A | 111 | 24.068 | 35.811 | 49.471 | 1.00 | 40.89 | O |
| ATOM | 771 | CB | PHE | A | 111 | 25.954 | 36.839 | 47.710 | 1.00 | 40.30 | C |
| ATOM | 772 | CG | PHE | A | 111 | 26.973 | 37.597 | 46.910 | 1.00 | 38.60 | C |
| ATOM | 773 | CD1 | PHE | A | 111 | 28.199 | 37.033 | 46.618 | 1.00 | 37.50 | C |
| ATOM | 774 | CD2 | PHE | A | 111 | 26.705 | 38.867 | 46.445 | 1.00 | 38.02 | C |
| ATOM | 775 | CE1 | PHE | A | 111 | 29.140 | 37.725 | 45.890 | 1.00 | 36.74 | C |
| ATOM | 776 | CE2 | PHE | A | 111 | 27.649 | 39.560 | 45.705 | 1.00 | 36.60 | C |
| ATOM | 777 | CZ | PHE | A | 111 | 28.863 | 38.986 | 45.433 | 1.00 | 35.45 | C |
| ATOM | 778 | N | GLN | A | 112 | 25.175 | 36.457 | 51.329 | 1.00 | 42.72 | N |
| ATOM | 779 | CA | GLN | A | 112 | 24.154 | 36.022 | 52.276 | 1.00 | 43.86 | C |
| ATOM | 780 | C | GLN | A | 112 | 22.790 | 36.598 | 51.948 | 1.00 | 44.00 | C |
| ATOM | 781 | O | GLN | A | 112 | 21.774 | 35.994 | 52.280 | 1.00 | 44.39 | O |
| ATOM | 782 | CB | GLN | A | 112 | 24.535 | 36.428 | 53.706 | 1.00 | 44.29 | C |
| ATOM | 783 | CG | GLN | A | 112 | 25.923 | 35.985 | 54.166 | 1.00 | 46.45 | C |
| ATOM | 784 | CD | GLN | A | 112 | 26.050 | 34.477 | 54.296 | 1.00 | 49.14 | C |
| ATOM | 785 | OE1 | GLN | A | 112 | 25.523 | 33.733 | 53.466 | 1.00 | 50.83 | O |
| ATOM | 786 | NE2 | GLN | A | 112 | 26.756 | 34.022 | 55.332 | 1.00 | 50.52 | N |
| ATOM | 787 | N | ASN | A | 113 | 22.765 | 37.759 | 51.299 | 1.00 | 43.96 | N |
| ATOM | 788 | CA | ASN | A | 113 | 21.504 | 38.416 | 50.971 | 1.00 | 44.15 | C |
| ATOM | 789 | C | ASN | A | 113 | 20.827 | 37.921 | 49.679 | 1.00 | 44.12 | C |
| ATOM | 790 | O | ASN | A | 113 | 19.768 | 38.431 | 49.309 | 1.00 | 44.11 | O |
| ATOM | 791 | CB | ASN | A | 113 | 21.696 | 39.941 | 50.918 | 1.00 | 44.21 | C |
| ATOM | 792 | CG | ASN | A | 113 | 22.084 | 40.541 | 52.283 | 1.00 | 44.80 | C |
| ATOM | 793 | OD1 | ASN | A | 113 | 21.759 | 39.991 | 53.349 | 1.00 | 43.65 | O |
| ATOM | 794 | ND2 | ASN | A | 113 | 22.778 | 41.675 | 52.246 | 1.00 | 44.92 | N |
| ATOM | 795 | N | PHE | A | 114 | 21.415 | 36.939 | 48.995 | 1.00 | 43.98 | N |
| ATOM | 796 | CA | PHE | A | 114 | 20.793 | 36.411 | 47.787 | 1.00 | 43.71 | C |
| ATOM | 797 | C | PHE | A | 114 | 19.778 | 35.345 | 48.150 | 1.00 | 43.76 | C |
| ATOM | 798 | O | PHE | A | 114 | 20.111 | 34.362 | 48.815 | 1.00 | 43.32 | O |
| ATOM | 799 | CB | PHE | A | 114 | 21.813 | 35.808 | 46.833 | 1.00 | 43.82 | C |
| ATOM | 800 | CG | PHE | A | 114 | 21.184 | 35.128 | 45.650 | 1.00 | 43.80 | C |
| ATOM | 801 | CD1 | PHE | A | 114 | 20.567 | 35.881 | 44.661 | 1.00 | 43.54 | C |
| ATOM | 802 | CD2 | PRE | A | 114 | 21.170 | 33.745 | 45.541 | 1.00 | 43.65 | C |
| ATOM | 803 | CE1 | PHE | A | 114 | 19.963 | 35.276 | 43.587 | 1.00 | 43.55 | C |
| ATOM | 804 | CE2 | PHE | A | 114 | 20.566 | 33.129 | 44.451 | 1.00 | 43.21 | C |
| ATOM | 805 | CZ | PRE | A | 114 | 19.961 | 33.897 | 43.476 | 1.00 | 42.89 | C |
| ATOM | 806 | N | LYS | A | 115 | 18.543 | 35.543 | 47.705 | 1.00 | 43.96 | N |
| ATOM | 807 | CA | LYS | A | 115 | 17.459 | 34.613 | 47.999 | 1.00 | 44.38 | C |
| ATOM | 808 | C | LYS | A | 115 | 16.933 | 34.026 | 46.693 | 1.00 | 44.04 | C |
| ATOM | 809 | O | LYS | A | 115 | 16.213 | 34.687 | 45.945 | 1.00 | 43.97 | O |

TABLE 3-continued

Coordinates for structures 1 to 4

| ATOM | 810 | CE  | LYS | A | 115 | 16.342 | 35.329 | 48.761 | 1.00 | 44.79 | C |
| ---- | --- | --- | --- | - | --- | ------ | ------ | ------ | ---- | ----- | - |
| ATOM | 811 | CG  | LYS | A | 115 | 16.763 | 35.866 | 50.129 | 1.00 | 46.74 | C |
| ATOM | 812 | CD  | LYS | A | 115 | 17.021 | 34.744 | 51.130 | 1.00 | 48.83 | C |
| ATOM | 813 | CE  | LYS | A | 115 | 17.461 | 35.288 | 52.484 | 1.00 | 50.18 | C |
| ATOM | 814 | NZ  | LYS | A | 115 | 17.498 | 34.224 | 53.539 | 1.00 | 51.05 | N |
| ATOM | 815 | N   | PRO | A | 116 | 17.270 | 32.771 | 46.433 | 1.00 | 43.65 | N |
| ATOM | 816 | CA  | PRO | A | 116 | 16.918 | 32.133 | 45.160 | 1.00 | 43.43 | C |
| ATOM | 817 | C   | PRO | A | 116 | 15.415 | 32.034 | 44.969 | 1.00 | 42.76 | C |
| ATOM | 818 | O   | PRO | A | 116 | 14.711 | 31.724 | 45.915 | 1.00 | 42.78 | O |
| ATOM | 819 | CB  | PRO | A | 116 | 17.525 | 30.732 | 45.273 | 1.00 | 43.57 | C |
| ATOM | 820 | CG  | PRO | A | 116 | 18.385 | 30.743 | 46.496 | 1.00 | 43.88 | C |
| ATOM | 821 | CD  | PRO | A | 116 | 17.948 | 31.855 | 47.359 | 1.00 | 43.68 | C |
| ATOM | 822 | N   | ARG | A | 117 | 14.940 | 32.306 | 43.761 | 1.00 | 42.20 | N |
| ATOM | 823 | CA  | ARG | A | 117 | 13.518 | 32.214 | 43.451 | 1.00 | 41.56 | C |
| ATOM | 824 | C   | ARG | A | 117 | 13.140 | 30.780 | 43.104 | 1.00 | 41.00 | C |
| ATOM | 825 | O   | ARG | A | 117 | 11.957 | 30.461 | 43.007 | 1.00 | 41.15 | O |
| ATOM | 826 | CB  | ARG | A | 117 | 13.164 | 33.132 | 42.311 | 1.00 | 41.47 | C |
| ATOM | 827 | N   | SER | A | 118 | 14.139 | 29.925 | 42.904 | 1.00 | 40.00 | N |
| ATOM | 828 | CA  | SER | A | 118 | 13.882 | 28.517 | 42.654 | 1.00 | 39.60 | C |
| ATOM | 829 | C   | SER | A | 118 | 14.700 | 27.655 | 43.621 | 1.00 | 39.30 | C |
| ATOM | 830 | O   | SER | A | 118 | 15.756 | 28.078 | 44.087 | 1.00 | 39.24 | O |
| ATOM | 831 | CB  | SER | A | 118 | 14.184 | 28.158 | 41.196 | 1.00 | 39.30 | C |
| ATOM | 832 | OG  | SER | A | 118 | 15.560 | 28.228 | 40.942 | 1.00 | 38.53 | O |
| ATOM | 833 | N   | ASN | A | 119 | 14.180 | 26.471 | 43.943 | 1.00 | 38.96 | N |
| ATOM | 834 | CA  | ASN | A | 119 | 14.838 | 25.537 | 44.854 | 1.00 | 38.95 | C |
| ATOM | 835 | C   | ASN | A | 119 | 15.115 | 24.215 | 44.160 | 1.00 | 37.99 | C |
| ATOM | 836 | O   | ASN | A | 119 | 14.314 | 23.751 | 43.359 | 1.00 | 37.35 | O |
| ATOM | 837 | CB  | ASN | A | 119 | 13.958 | 25.220 | 46.068 | 1.00 | 39.54 | C |
| ATOM | 838 | CG  | ASN | A | 119 | 13.466 | 26.456 | 46.797 | 1.00 | 41.82 | C |
| ATOM | 839 | OD1 | ASN | A | 119 | 14.255 | 27.279 | 47.289 | 1.00 | 44.50 | O |
| ATOM | 840 | ND2 | ASN | A | 119 | 12.145 | 26.574 | 46.906 | 1.00 | 44.99 | N |
| ATOM | 841 | N   | ARG | A | 120 | 16.243 | 23.607 | 44.492 | 1.00 | 37.46 | N |
| ATOM | 842 | CA  | ARG | A | 120 | 16.627 | 22.325 | 43.927 | 1.00 | 37.15 | C |
| ATOM | 843 | C   | ARG | A | 120 | 16.209 | 21.193 | 44.844 | 1.00 | 37.03 | C |
| ATOM | 844 | O   | ARG | A | 120 | 16.359 | 21.272 | 46.069 | 1.00 | 37.28 | O |
| ATOM | 845 | CB  | ARG | A | 120 | 18.144 | 22.264 | 43.730 | 1.00 | 37.07 | C |
| ATOM | 846 | CG  | ARG | A | 120 | 18.632 | 21.020 | 42.993 | 1.00 | 36.32 | C |
| ATOM | 847 | CD  | ARG | A | 120 | 20.152 | 20.886 | 42.938 | 1.00 | 35.46 | C |
| ATOM | 848 | NE  | ARG | A | 120 | 20.777 | 21.277 | 44.198 | 1.00 | 34.29 | N |
| ATOM | 849 | CZ  | ARG | A | 120 | 21.049 | 20.445 | 45.202 | 1.00 | 36.66 | C |
| ATOM | 850 | NH1 | ARG | A | 120 | 20.753 | 19.147 | 45.122 | 1.00 | 35.60 | N |
| ATOM | 851 | NH2 | ARG | A | 120 | 21.614 | 20.915 | 46.305 | 1.00 | 37.13 | N |
| ATOM | 852 | N   | GLU | A | 121 | 15.665 | 20.141 | 44.250 | 1.00 | 36.76 | N |
| ATOM | 853 | CA  | GLU | A | 121 | 15.326 | 18.944 | 44.993 | 1.00 | 36.29 | C |
| ATOM | 854 | C   | GLU | A | 121 | 15.810 | 17.746 | 44.187 | 1.00 | 35.35 | C |
| ATOM | 855 | O   | GLU | A | 121 | 15.709 | 17.726 | 42.953 | 1.00 | 35.38 | O |
| ATOM | 856 | CB  | GLU | A | 121 | 13.820 | 18.863 | 45.262 | 1.00 | 36.78 | C |
| ATOM | 857 | CG  | GLU | A | 121 | 13.398 | 17.585 | 45.971 | 1.00 | 39.29 | C |
| ATOM | 858 | CD  | GLU | A | 121 | 12.126 | 17.732 | 46.795 | 1.00 | 42.09 | C |
| ATOM | 859 | OE1 | GLU | A | 121 | 12.200 | 18.310 | 47.904 | 1.00 | 45.56 | O |
| ATOM | 860 | OE2 | GLU | A | 121 | 11.059 | 17.254 | 46.350 | 1.00 | 43.04 | O |
| ATOM | 861 | N   | GLU | A | 122 | 16.366 | 16.764 | 44.886 | 1.00 | 34.04 | N |
| ATOM | 862 | CA  | GLU | A | 122 | 16.840 | 15.547 | 44.266 | 1.00 | 33.04 | C |
| ATOM | 863 | C   | GLU | A | 122 | 15.748 | 14.518 | 44.415 | 1.00 | 32.55 | C |
| ATOM | 864 | O   | GLU | A | 122 | 15.253 | 14.306 | 45.511 | 1.00 | 32.52 | O |
| ATOM | 865 | CB  | GLU | A | 122 | 18.103 | 15.052 | 44.961 | 1.00 | 32.71 | C |
| ATOM | 866 | CG  | GLU | A | 122 | 19.265 | 16.018 | 44.885 | 1.00 | 31.86 | C |
| ATOM | 867 | CD  | GLU | A | 122 | 19.705 | 16.296 | 43.454 | 1.00 | 31.04 | C |
| ATOM | 868 | OE1 | GLU | A | 122 | 20.065 | 15.331 | 42.757 | 1.00 | 29.68 | O |
| ATOM | 869 | OE2 | GLU | A | 122 | 19.694 | 17.479 | 43.025 | 1.00 | 29.20 | O |
| ATOM | 870 | N   | MET | A | 123 | 15.349 | 13.885 | 43.321 | 1.00 | 31.83 | N |
| ATOM | 871 | CA  | MET | A | 123 | 14.329 | 12.858 | 43.415 | 1.00 | 31.40 | C |
| ATOM | 872 | C   | MET | A | 123 | 14.532 | 11.820 | 42.343 | 1.00 | 30.68 | C |
| ATOM | 873 | O   | MET | A | 123 | 15.380 | 11.982 | 41.457 | 1.00 | 30.07 | O |
| ATOM | 874 | CB  | MET | A | 123 | 12.931 | 13.466 | 43.309 | 1.00 | 31.52 | C |
| ATOM | 875 | CG  | MET | A | 123 | 12.667 | 14.205 | 42.032 | 1.00 | 32.93 | C |
| ATOM | 876 | SD  | MET | A | 123 | 11.115 | 15.145 | 42.034 | 1.00 | 35.27 | S |
| ATOM | 877 | CE  | MET | A | 123 | 11.554 | 16.565 | 42.966 | 1.00 | 35.33 | C |
| ATOM | 878 | N   | LYS | A | 124 | 13.766 | 10.738 | 42.464 | 1.00 | 29.85 | N |
| ATOM | 879 | CA  | LYS | A | 124 | 13.752 |  9.671 | 41.483 | 1.00 | 29.22 | C |
| ATOM | 880 | C   | LYS | A | 124 | 12.891 | 10.140 | 40.307 | 1.00 | 28.45 | C |
| ATOM | 881 | O   | LYS | A | 124 | 12.066 | 11.039 | 40.466 | 1.00 | 27.39 | O |
| ATOM | 882 | CB  | LYS | A | 124 | 13.183 |  8.389 | 42.100 | 1.00 | 29.57 | C |
| ATOM | 883 | CG  | LYS | A | 124 | 13.954 |  7.857 | 43.321 | 1.00 | 29.88 | C |
| ATOM | 884 | CD  | LYS | A | 124 | 15.392 |  7.501 | 42.950 | 1.00 | 30.48 | C |
| ATOM | 885 | CE  | LYS | A | 124 | 16.231 |  7.129 | 44.167 | 1.00 | 30.33 | C |
| ATOM | 886 | NZ  | LYS | A | 124 | 17.691 |  7.276 | 43.872 | 1.00 | 30.47 | N |

TABLE 3-continued

Coordinates for structures 1 to 4

| ATOM | 887 | N | PHE | A | 125 | 13.075 | 9.536 | 39.133 | 1.00 | 27.71 | N |
| --- | --- | --- | --- | --- | --- | --- | --- | --- | --- | --- | --- |
| ATOM | 888 | CA | PHE | A | 125 | 12.364 | 10.000 | 37.949 | 1.00 | 27.22 | C |
| ATOM | 889 | C | PHE | A | 125 | 10.869 | 9.891 | 38.114 | 1.00 | 27.29 | C |
| ATOM | 890 | O | PHE | A | 125 | 10.138 | 10.825 | 37.801 | 1.00 | 26.75 | O |
| ATOM | 891 | CB | PHE | A | 125 | 12.794 | 9.270 | 36.681 | 1.00 | 26.90 | C |
| ATOM | 892 | CG | PHE | A | 125 | 12.494 | 10.051 | 35.433 | 1.00 | 27.63 | C |
| ATOM | 893 | CD1 | PHE | A | 125 | 13.330 | 11.083 | 35.032 | 1.00 | 27.70 | C |
| ATOM | 894 | CD2 | PHE | A | 125 | 11.351 | 9.802 | 34.702 | 1.00 | 28.29 | C |
| ATOM | 895 | CE1 | PHE | A | 125 | 13.059 | 11.828 | 33.905 | 1.00 | 27.96 | C |
| ATOM | 896 | CE2 | PHE | A | 125 | 11.065 | 10.540 | 33.563 | 1.00 | 29.16 | C |
| ATOM | 897 | CZ | PHE | A | 125 | 11.924 | 11.568 | 33.167 | 1.00 | 28.71 | C |
| ATOM | 898 | N | HIS | A | 126 | 10.426 | 8.743 | 38.620 | 1.00 | 27.46 | N |
| ATOM | 899 | CA | HIS | A | 126 | 9.013 | 8.499 | 38.832 | 1.00 | 27.77 | C |
| ATOM | 900 | C | HIS | A | 126 | 8.430 | 9.522 | 39.794 | 1.00 | 27.71 | C |
| ATOM | 901 | O | HIS | A | 126 | 7.245 | 9.821 | 39.731 | 1.00 | 27.27 | O |
| ATOM | 902 | CB | HIS | A | 126 | 8.770 | 7.056 | 39.329 | 1.00 | 27.96 | C |
| ATOM | 903 | CG | HIS | A | 126 | 8.897 | 6.880 | 40.812 | 1.00 | 28.47 | C |
| ATOM | 904 | ND1 | HIS | A | 126 | 7.831 | 7.026 | 41.672 | 1.00 | 29.29 | N |
| ATOM | 905 | CD2 | HIS | A | 126 | 9.961 | 6.552 | 41.585 | 1.00 | 29.43 | C |
| ATOM | 906 | CE1 | HIS | A | 126 | 8.236 | 6.812 | 42.912 | 1.00 | 30.26 | C |
| ATOM | 907 | NE2 | HIS | A | 126 | 9.525 | 6.524 | 42.887 | 1.00 | 29.64 | N |
| ATOM | 908 | N | GLU | A | 127 | 9.262 | 10.059 | 40.679 | 1.00 | 28.09 | N |
| ATOM | 909 | CA | GLU | A | 127 | 8.803 | 11.078 | 41.615 | 1.00 | 28.68 | C |
| ATOM | 910 | C | GLU | A | 127 | 8.585 | 12.400 | 40.865 | 1.00 | 28.99 | C |
| ATOM | 911 | O | GLU | A | 127 | 7.626 | 13.129 | 41.123 | 1.00 | 29.15 | O |
| ATOM | 912 | CB | GLU | A | 127 | 9.795 | 11.233 | 42.775 | 1.00 | 28.52 | C |
| ATOM | 913 | CG | GLU | A | 127 | 9.931 | 9.968 | 43.626 | 1.00 | 29.84 | C |
| ATOM | 914 | CD | GLU | A | 127 | 10.873 | 10.121 | 44.810 | 1.00 | 30.26 | C |
| ATOM | 915 | OE1 | GLU | A | 127 | 12.069 | 10.398 | 44.603 | 1.00 | 29.68 | O |
| ATOM | 916 | OE2 | GLU | A | 127 | 10.410 | 9.943 | 45.962 | 1.00 | 32.95 | O |
| ATOM | 917 | N | PHE | A | 128 | 9.471 | 12.696 | 39.927 | 1.00 | 29.39 | N |
| ATOM | 918 | CA | PHE | A | 128 | 9.354 | 13.914 | 39.119 | 1.00 | 29.64 | C |
| ATOM | 919 | C | PHE | A | 128 | 8.047 | 13.859 | 38.333 | 1.00 | 30.31 | C |
| ATOM | 920 | O | PHE | A | 128 | 7.274 | 14.817 | 38.294 | 1.00 | 29.97 | O |
| ATOM | 921 | CB | PHE | A | 128 | 10.551 | 14.017 | 38.167 | 1.00 | 29.10 | C |
| ATOM | 922 | CG | PHE | A | 128 | 10.337 | 14.950 | 36.991 | 1.00 | 28.33 | C |
| ATOM | 923 | CD1 | PHE | A | 128 | 10.106 | 16.301 | 37.188 | 1.00 | 26.53 | C |
| ATOM | 924 | CD2 | PHE | A | 128 | 10.397 | 14.475 | 35.696 | 1.00 | 26.99 | C |
| ATOM | 925 | CE1 | PHE | A | 128 | 9.920 | 17.149 | 36.120 | 1.00 | 27.50 | C |
| ATOM | 926 | CE2 | PHE | A | 128 | 10.217 | 15.341 | 34.610 | 1.00 | 28.49 | C |
| ATOM | 927 | CZ | PHE | A | 128 | 9.976 | 16.668 | 34.823 | 1.00 | 26.78 | C |
| ATOM | 928 | N | VAL | A | 129 | 7.797 | 12.705 | 37.736 | 1.00 | 31.32 | N |
| ATOM | 929 | CA | VAL | A | 129 | 6.603 | 12.499 | 36.930 | 1.00 | 32.38 | C |
| ATOM | 930 | C | VAL | A | 129 | 5.338 | 12.658 | 37.775 | 1.00 | 32.96 | C |
| ATOM | 931 | O | VAL | A | 129 | 4.398 | 13.362 | 37.388 | 1.00 | 32.79 | O |
| ATOM | 932 | CB | VAL | A | 129 | 6.606 | 11.094 | 36.313 | 1.00 | 32.48 | C |
| ATOM | 933 | CG1 | VAL | A | 129 | 5.313 | 10.840 | 35.551 | 1.00 | 32.96 | C |
| ATOM | 934 | CG2 | VAL | A | 129 | 7.828 | 10.901 | 35.417 | 1.00 | 31.98 | C |
| ATOM | 935 | N | GLU | A | 130 | 5.329 | 11.993 | 38.925 | 1.00 | 33.61 | N |
| ATOM | 936 | CA | GLU | A | 130 | 4.205 | 12.067 | 39.853 | 1.00 | 34.29 | C |
| ATOM | 937 | C | GLU | A | 130 | 3.963 | 13.515 | 40.246 | 1.00 | 34.51 | C |
| ATOM | 938 | O | GLU | A | 130 | 2.832 | 13.986 | 40.220 | 1.00 | 33.80 | O |
| ATOM | 939 | CB | GLU | A | 130 | 4.481 | 11.206 | 41.087 | 1.00 | 34.35 | C |
| ATOM | 940 | CG | GLU | A | 130 | 4.372 | 9.711 | 40.815 | 1.00 | 34.92 | C |
| ATOM | 941 | CD | GLU | A | 130 | 5.204 | 8.858 | 41.761 | 1.00 | 35..66 | C |
| ATOM | 942 | OE1 | GLU | A | 130 | 5.595 | 9.345 | 42.845 | 1.00 | 36.55 | O |
| ATOM | 943 | OE2 | GLU | A | 130 | 5.477 | 7.692 | 41.407 | 1.00 | 36.06 | O |
| ATOM | 944 | N | LYS | A | 131 | 5.033 | 14.223 | 40.587 | 1.00 | 35.27 | N |
| ATOM | 945 | CA | LYS | A | 131 | 4.912 | 15.632 | 40.920 | 1.00 | 36.15 | C |
| ATOM | 946 | C | LYS | A | 131 | 4.286 | 16.408 | 39.758 | 1.00 | 36.63 | C |
| ATOM | 947 | O | LYS | A | 131 | 3.420 | 17.253 | 39.972 | 1.00 | 36.42 | O |
| ATOM | 948 | CB | LYS | A | 131 | 6.269 | 16.240 | 41.261 | 1.00 | 36.51 | C |
| ATOM | 949 | CG | LYS | A | 131 | 6.467 | 16.623 | 42.712 | 1.00 | 37.67 | C |
| ATOM | 950 | CD | LYS | A | 131 | 7.125 | 18.001 | 42.822 | 1.00 | 38.95 | C |
| ATOM | 951 | CE | LYS | A | 131 | 7.581 | 18.324 | 44.252 | 1.00 | 40.39 | C |
| ATOM | 952 | NZ | LYS | A | 131 | 8.073 | 19.747 | 44.404 | 1.00 | 40.82 | N |
| ATOM | 953 | N | LEU | A | 132 | 4.725 | 16.142 | 38.532 | 1.00 | 37.30 | N |
| ATOM | 954 | CA | LEU | A | 132 | 4.156 | 16.845 | 37.383 | 1.00 | 38.29 | C |
| ATOM | 955 | C | LEU | A | 132 | 2.669 | 16.557 | 37.280 | 1.00 | 38.83 | C |
| ATOM | 956 | O | LEU | A | 132 | 1.875 | 17.449 | 36.976 | 1.00 | 38.56 | O |
| ATOM | 957 | CB | LEU | A | 132 | 4.819 | 16.424 | 36.081 | 1.00 | 38.42 | C |
| ATOM | 958 | CG | LEU | A | 132 | 6.224 | 16.916 | 35.791 | 1.00 | 39.15 | C |
| ATOM | 959 | CE1 | LEU | A | 132 | 6.671 | 16.296 | 34.485 | 1.00 | 39.76 | C |
| ATOM | 960 | CD2 | LEU | A | 132 | 6.281 | 18.433 | 35.712 | 1.00 | 39.81 | C |
| ATOM | 961 | N | GLN | A | 133 | 2.311 | 15.300 | 37.529 | 1.00 | 39.68 | N |
| ATOM | 962 | CA | GLN | A | 133 | 0.920 | 14.863 | 37.495 | 1.00 | 40.45 | C |
| ATOM | 963 | C | GLN | A | 133 | 0.057 | 15.580 | 38.541 | 1.00 | 41.05 | C |

TABLE 3-continued

Coordinates for structures 1 to 4

| ATOM | 964 | O | GLN | A | 133 | 1.035 | 16.040 | 38.222 | 1.00 | 41.20 | O |
|---|---|---|---|---|---|---|---|---|---|---|---|
| ATOM | 965 | CB | GLN | A | 133 | 0.835 | 13.344 | 37.681 | 1.00 | 40.31 | C |
| ATOM | 966 | N | ASP | A | 134 | 0.542 | 15.682 | 39.777 | 1.00 | 41.89 | N |
| ATOM | 967 | CA | ASP | A | 134 | 0.232 | 16.313 | 40.854 | 1.00 | 42.72 | C |
| ATOM | 968 | C | ASP | A | 134 | 0.506 | 17.792 | 40.576 | 1.00 | 42.60 | C |
| ATOM | 969 | O | ASP | A | 134 | 1.570 | 18.316 | 40.900 | 1.00 | 42.25 | O |
| ATOM | 970 | CB | ASP | A | 134 | 0.491 | 16.169 | 42.200 | 1.00 | 43.21 | C |
| ATOM | 971 | CG | ASP | A | 134 | 0.429 | 16.419 | 43.396 | 1.00 | 45.71 | C |
| ATOM | 972 | OD1 | ASP | A | 134 | 1.566 | 16.916 | 43.213 | 1.00 | 48.39 | O |
| ATOM | 973 | OD2 | ASP | A | 134 | 0.104 | 16.131 | 44.571 | 1.00 | 49.60 | O |
| ATOM | 974 | N | ILE | A | 135 | 0.467 | 18.467 | 39.981 | 1.00 | 42.77 | N |
| ATOM | 975 | CA | ILE | A | 135 | 0.306 | 19.872 | 39.660 | 1.00 | 42.91 | C |
| ATOM | 976 | C | ILE | A | 135 | 0.793 | 20.050 | 38.626 | 1.00 | 43.15 | C |
| ATOM | 977 | O | ILE | A | 135 | 1.690 | 20.871 | 38.800 | 1.00 | 43.03 | O |
| ATOM | 978 | CB | ILE | A | 135 | 1.623 | 20.443 | 39.155 | 1.00 | 42.94 | C |
| ATOM | 979 | CG1 | ILE | A | 135 | 2.586 | 20.607 | 40.330 | 1.00 | 43.10 | C |
| ATOM | 980 | CG2 | ILE | A | 135 | 1.396 | 21.778 | 38.473 | 1.00 | 42.80 | C |
| ATOM | 981 | CD1 | ILE | A | 135 | 4.040 | 20.621 | 39.934 | 1.00 | 43.49 | C |
| ATOM | 982 | N | GLN | A | 136 | 0.716 | 19.272 | 37.554 | 1.00 | 43.64 | N |
| ATOM | 983 | CA | GLN | A | 136 | 1.712 | 19.321 | 36.496 | 1.00 | 44.17 | C |
| ATOM | 984 | C | GLN | A | 136 | 3.103 | 19.129 | 37.081 | 1.00 | 44.65 | C |
| ATOM | 985 | O | GLN | A | 136 | 3.976 | 19.984 | 36.936 | 1.00 | 44.71 | O |
| ATOM | 986 | CE | GLN | A | 136 | 1.431 | 18.240 | 35.466 | 1.00 | 44.19 | C |
| ATOM | 987 | N | GLN | A | 137 | 3.289 | 18.014 | 37.776 | 1.00 | 45.23 | N |
| ATOM | 988 | CA | GLN | A | 137 | 4.596 | 17.654 | 38.314 | 1.00 | 45.66 | C |
| ATOM | 989 | C | GLN | A | 137 | 5.146 | 18.696 | 39.277 | 1.00 | 45.88 | C |
| ATOM | 990 | O | GLN | A | 137 | 6.337 | 19.005 | 39.238 | 1.00 | 46.33 | O |
| ATOM | 991 | CB | GLN | A | 137 | 4.535 | 16.277 | 38.991 | 1.00 | 45.74 | C |
| ATOM | 992 | N | ARG | A | 138 | 4.288 | 19.246 | 40.131 | 1.00 | 45.93 | N |
| ATOM | 993 | CA | ARG | A | 138 | 4.740 | 20.211 | 41.132 | 1.00 | 45.84 | C |
| ATOM | 994 | C | ARG | A | 138 | 4.720 | 21.640 | 40.592 | 1.00 | 45.53 | C |
| ATOM | 995 | O | ARG | A | 138 | 4.911 | 22.598 | 41.344 | 1.00 | 45.72 | O |
| ATOM | 996 | CB | ARG | A | 138 | 3.880 | 20.108 | 42.398 | 1.00 | 45.92 | C |
| ATOM | 997 | CG | ARG | A | 138 | 2.551 | 20.866 | 42.340 | 1.00 | 46.84 | C |
| ATOM | 998 | CD | ARG | A | 138 | 1.589 | 20.458 | 43.437 | 1.00 | 47.70 | C |
| ATOM | 999 | NE | ARG | A | 138 | 0.509 | 21.418 | 43.652 | 1.00 | 47.78 | N |
| ATOM | 1000 | CZ | ARG | A | 138 | 0.788 | 21.125 | 43.578 | 1.00 | 49.17 | C |
| ATOM | 1001 | NH1 | ARG | A | 138 | 1.186 | 19.897 | 43.274 | 1.00 | 50.12 | N |
| ATOM | 1002 | NH2 | ARG | A | 138 | 1.702 | 22.064 | 43.798 | 1.00 | 49.52 | N |
| ATOM | 1003 | N | GLY | A | 139 | 4.492 | 21.783 | 39.290 | 1.00 | 44.99 | N |
| ATOM | 1004 | CA | GLY | A | 139 | 4.419 | 23.094 | 38.669 | 1.00 | 44.52 | C |
| ATOM | 1005 | C | GLY | A | 139 | 3.412 | 24.041 | 39.310 | 1.00 | 44.06 | C |
| ATOM | 1006 | O | GLY | A | 139 | 3.551 | 25.259 | 39.203 | 1.00 | 44.28 | O |
| ATOM | 1007 | N | GLY | A | 140 | 2.382 | 23.495 | 39.953 | 1.00 | 43.28 | N |
| ATOM | 1008 | CA | GLY | A | 140 | 1.388 | 24.309 | 40.629 | 1.00 | 42.49 | C |
| ATOM | 1009 | C | GLY | A | 140 | 0.609 | 25.218 | 39.694 | 1.00 | 41.92 | C |
| ATOM | 1010 | O | GLY | A | 140 | 0.556 | 24.989 | 38.480 | 1.00 | 41.85 | O |
| ATOM | 1011 | N | GLU | A | 141 | 0.004 | 26.264 | 40.250 | 1.00 | 40.90 | N |
| ATOM | 1012 | CA | GLU | A | 141 | 0.789 | 27.186 | 39.444 | 1.00 | 40.07 | C |
| ATOM | 1013 | C | GLU | A | 141 | 2.286 | 26.884 | 39.549 | 1.00 | 38.68 | C |
| ATOM | 1014 | O | GLU | A | 141 | 3.096 | 27.503 | 38.867 | 1.00 | 38.67 | O |
| ATOM | 1015 | CB | GLU | A | 141 | 0.513 | 28.644 | 39.839 | 1.00 | 40.36 | C |
| ATOM | 1016 | CG | GLU | A | 141 | 0.799 | 29.224 | 39.309 | 1.00 | 41.91 | C |
| ATOM | 1017 | CD | GLU | A | 141 | 1.001 | 29.042 | 37.805 | 1.00 | 44.25 | C |
| ATOM | 1018 | OE1 | GLU | A | 141 | 0.004 | 29.008 | 37.043 | 1.00 | 45.69 | O |
| ATOM | 1019 | OE2 | GLU | A | 141 | 2.181 | 28.940 | 37.380 | 1.00 | 44.55 | O |
| ATOM | 1020 | N | GLU | A | 142 | 2.648 | 25.944 | 40.413 | 1.00 | 37.02 | N |
| ATOM | 1021 | CA | GLU | A | 142 | 4.040 | 25.573 | 40.596 | 1.00 | 35.61 | C |
| ATOM | 1022 | C | GLU | A | 142 | 4.629 | 25.120 | 39.265 | 1.00 | 34.41 | C |
| ATOM | 1023 | O | GLU | A | 142 | 3.923 | 24.594 | 38.408 | 1.00 | 34.25 | O |
| ATOM | 1024 | CB | GLU | A | 142 | 4.150 | 24.443 | 41.627 | 1.00 | 35.49 | C |
| ATOM | 1025 | CG | GLU | A | 142 | 5.571 | 24.173 | 42.095 | 1.00 | 35.47 | C |
| ATOM | 1026 | CD | GLU | A | 142 | 5.710 | 22.944 | 42.978 | 1.00 | 36.48 | C |
| ATOM | 1027 | GE1 | GLU | A | 142 | 4.733 | 22.174 | 43.142 | 1.00 | 37.45 | O |
| ATOM | 1028 | OE2 | GLU | A | 142 | 6.821 | 22.739 | 43.511 | 1.00 | 36.76 | O |
| ATOM | 1029 | N | ARG | A | 143 | 5.926 | 25.323 | 39.096 | 1.00 | 32.91 | N |
| ATOM | 1030 | CA | ARG | A | 143 | 6.596 | 24.893 | 37.884 | 1.00 | 31.95 | C |
| ATOM | 1031 | C | ARG | A | 143 | 7.803 | 24.058 | 38.214 | 1.00 | 30.62 | C |
| ATOM | 1032 | O | ARG | A | 143 | 8.514 | 24.354 | 39.166 | 1.00 | 30.75 | O |
| ATOM | 1033 | CB | ARG | A | 143 | 7.072 | 26.097 | 37.082 | 1.00 | 32.19 | C |
| ATOM | 1034 | CG | ARG | A | 143 | 5.968 | 26.912 | 36.447 | 1.00 | 32.57 | C |
| ATOM | 1035 | CD | ARG | A | 143 | 6.507 | 28.170 | 35.801 | 1.00 | 32.53 | C |
| ATOM | 1036 | NE | ARG | A | 143 | 5.492 | 28.885 | 35.037 | 1.00 | 32.25 | N |
| ATOM | 1037 | CZ | ARG | A | 143 | 5.158 | 28.617 | 33.790 | 1.00 | 31.80 | C |
| ATOM | 1038 | NH1 | ARG | A | 143 | 5.757 | 27.637 | 33.105 | 1.00 | 31.28 | N |
| ATOM | 1039 | NH2 | ARG | A | 143 | 4.214 | 29.345 | 33.221 | 1.00 | 32.77 | N |
| ATOM | 1040 | N | LEU | A | 144 | 8.054 | 23.028 | 37.417 | 1.00 | 28.97 | N |

TABLE 3-continued

| | | | | | Coordinates for structures 1 to 4 | | | | | |
|---|---|---|---|---|---|---|---|---|---|---|
| ATOM | 1041 | CA | LEU | A | 144 | 9.235 | 22.219 | 37.617 | 1.00 | 28.09 | C |
| ATOM | 1042 | C | LEU | A | 144 | 10.150 | 22.257 | 36.398 | 1.00 | 27.14 | C |
| ATOM | 1043 | O | LEU | A | 144 | 9.690 | 22.418 | 35.272 | 1.00 | 26.74 | O |
| ATOM | 1044 | CB | LEU | A | 144 | 8.834 | 20.783 | 37.887 | 1.00 | 28.28 | C |
| ATOM | 1045 | CG | LEU | A | 144 | 7.839 | 20.606 | 39.038 | 1.00 | 28.89 | C |
| ATOM | 1046 | CD1 | LEU | A | 144 | 7.515 | 19.123 | 39.216 | 1.00 | 29.62 | C |
| ATOM | 1047 | CD2 | LEU | A | 144 | 8.364 | 21.212 | 40.333 | 1.00 | 27.84 | C |
| ATOM | 1048 | N | TYR | A | 145 | 11.447 | 22.102 | 36.636 | 1.00 | 25.69 | N |
| ATOM | 1049 | CA | TYR | A | 145 | 12.395 | 21.976 | 35.548 | 1.00 | 25.05 | C |
| ATOM | 1050 | C | TYR | A | 145 | 13.459 | 20.957 | 35.968 | 1.00 | 25.00 | C |
| ATOM | 1051 | O | TYR | A | 145 | 14.239 | 21.193 | 36.881 | 1.00 | 25.01 | O |
| ATOM | 1052 | CB | TYR | A | 145 | 13.022 | 23.327 | 35.183 | 1.00 | 24.76 | C |
| ATOM | 1053 | CG | TYR | A | 145 | 13.471 | 23.485 | 33.728 | 1.00 | 23.25 | C |
| ATOM | 1054 | CD1 | TYR | A | 145 | 13.739 | 22.385 | 32.931 | 1.00 | 21.70 | C |
| ATOM | 1055 | CD2 | TYR | A | 145 | 13.667 | 24.746 | 33.175 | 1.00 | 22.16 | C |
| ATOM | 1056 | CE1 | TYR | A | 145 | 14.154 | 22.526 | 31.620 | 1.00 | 20.98 | C |
| ATOM | 1057 | CE2 | TYR | A | 145 | 14.097 | 24.904 | 31.846 | 1.00 | 21.30 | C |
| ATOM | 1058 | CZ | TYR | A | 145 | 14.332 | 23.799 | 31.071 | 1.00 | 20.66 | C |
| ATOM | 1059 | OH | TYR | A | 145 | 14.737 | 23.933 | 29.740 | 1.00 | 18.41 | O |
| ATOM | 1060 | N | LEU | A | 146 | 13.446 | 19.808 | 35.318 | 1.00 | 24.95 | N |
| ATOM | 1061 | CA | LEU | A | 146 | 14.453 | 18.787 | 35.547 | 1.00 | 25.43 | C |
| ATOM | 1062 | C | LEU | A | 146 | 15.678 | 19.100 | 34.694 | 1.00 | 24.91 | C |
| ATOM | 1063 | O | LEU | A | 146 | 15.555 | 19.313 | 33.493 | 1.00 | 24.10 | O |
| ATOM | 1064 | CB | LEU | A | 146 | 13.907 | 17.419 | 35.162 | 1.00 | 25.59 | C |
| ATOM | 1065 | CG | LEU | A | 146 | 14.875 | 16.238 | 35.334 | 1.00 | 27.52 | C |
| ATOM | 1066 | CD1 | LEU | A | 146 | 14.111 | 14.966 | 35.672 | 1.00 | 26.95 | C |
| ATOM | 1067 | CD2 | LEU | A | 146 | 15.742 | 16.023 | 34.084 | 1.00 | 29.46 | C |
| ATOM | 1068 | N | GLN | A | 147 | 16.845 | 19.097 | 35.330 | 1.00 | 24.91 | N |
| ATOM | 1069 | CA | GLN | A | 147 | 18.115 | 19.394 | 34.685 | 1.00 | 25.27 | C |
| ATOM | 1070 | C | GLN | A | 147 | 19.146 | 18.490 | 35.317 | 1.00 | 25.28 | C |
| ATOM | 1071 | O | GLN | A | 147 | 19.610 | 18.740 | 36.419 | 1.00 | 27.14 | O |
| ATOM | 1072 | CB | GLN | A | 147 | 18.475 | 20.876 | 34.863 | 1.00 | 25.02 | C |
| ATOM | 1073 | CG | GLN | A | 147 | 17.321 | 21.804 | 34.485 | 1.00 | 24.97 | C |
| ATOM | 1074 | CD | GLN | A | 147 | 17.682 | 23.283 | 34.560 | 1.00 | 27.08 | C |
| ATOM | 1075 | OE1 | GLN | A | 147 | 16.891 | 24.149 | 34.141 | 1.00 | 27.93 | O |
| ATOM | 1076 | NE2 | GLN | A | 147 | 18.860 | 23.575 | 35.064 | 1.00 | 23.50 | N |
| ATOM | 1077 | N | GLN | A | 148 | 19.487 | 17.428 | 34.611 | 1.00 | 25.47 | N |
| ATOM | 1078 | CA | GLN | A | 148 | 20.319 | 16.365 | 35.146 | 1.00 | 25.45 | C |
| ATOM | 1079 | C | GLN | A | 148 | 21.254 | 15.816 | 34.105 | 1.00 | 25.50 | C |
| ATOM | 1080 | O | GLN | A | 148 | 20.862 | 15.485 | 32.992 | 1.00 | 25.04 | O |
| ATOM | 1081 | CB | GLN | A | 148 | 19.436 | 15.231 | 35.640 | 1.00 | 25.37 | C |
| ATOM | 1082 | CG | GLN | A | 148 | 20.201 | 14.021 | 36.167 | 1.00 | 26.15 | C |
| ATOM | 1083 | CD | GLN | A | 148 | 21.129 | 14.383 | 37.314 | 1.00 | 26.56 | C |
| ATOM | 1084 | OE1 | GLN | A | 148 | 20.718 | 15.093 | 38.240 | 1.00 | 23.94 | O |
| ATOM | 1085 | NE2 | GLN | A | 148 | 22.383 | 13.916 | 37.248 | 1.00 | 25.29 | N |
| ATOM | 1086 | N | THR | A | 149 | 22.510 | 15.769 | 34.482 | 1.00 | 25.86 | N |
| ATOM | 1087 | CA | THR | A | 149 | 23.552 | 15.219 | 33.667 | 1.00 | 27.04 | C |
| ATOM | 1088 | C | THR | A | 149 | 23.298 | 13.720 | 33.527 | 1.00 | 27.25 | C |
| ATOM | 1089 | O | THR | A | 149 | 23.012 | 13.044 | 34.508 | 1.00 | 26.86 | O |
| ATOM | 1090 | GB | THR | A | 149 | 24.903 | 15.540 | 34.375 | 1.00 | 27.42 | C |
| ATOM | 1091 | OG1 | THR | A | 149 | 25.300 | 16.882 | 34.020 | 1.00 | 29.80 | O |
| ATOM | 1092 | CG2 | THR | A | 149 | 26.034 | 14.702 | 33.873 | 1.00 | 28.98 | C |
| ATOM | 1093 | H | LEU | A | 150 | 23.338 | 13.224 | 32.298 | 1.00 | 27.70 | H |
| ATOM | 1094 | CA | LEU | A | 150 | 23.195 | 11.812 | 32.027 | 1.00 | 28.46 | C |
| ATOM | 1095 | C | LEU | A | 150 | 24.429 | 11.076 | 32.573 | 1.00 | 28.97 | C |
| ATOM | 1096 | O | LEU | A | 150 | 25.548 | 11.468 | 32.268 | 1.00 | 29.00 | O |
| ATOM | 1097 | GB | LEU | A | 150 | 23.084 | 11.580 | 30.524 | 1.00 | 28.34 | C |
| ATOM | 1098 | CG | LEU | A | 150 | 21.780 | 11.981 | 29.837 | 1.00 | 29.63 | C |
| ATOM | 1099 | CD1 | LEU | A | 150 | 21.944 | 11.862 | 28.328 | 1.00 | 30.03 | C |
| ATOM | 1100 | CD2 | LEU | A | 150 | 20.619 | 11.140 | 30.310 | 1.00 | 31.15 | C |
| ATOM | 1101 | N | ASN | A | 151 | 24.230 | 10.030 | 33.378 | 1.00 | 29.35 | N |
| ATOM | 1102 | CA | ASN | A | 151 | 25.348 | 9.258 | 33.949 | 1.00 | 29.51 | C |
| ATOM | 1103 | C | ASN | A | 151 | 25.137 | 7.732 | 33.934 | 1.00 | 29.92 | C |
| ATOM | 1104 | O | ASN | A | 151 | 24.162 | 7.241 | 33.348 | 1.00 | 29.73 | O |
| ATOM | 1105 | GB | ASN | A | 151 | 25.590 | 9.710 | 35.385 | 1.00 | 29.78 | C |
| ATOM | 1106 | CG | ASN | A | 151 | 24.362 | 9.553 | 36.241 | 1.00 | 29.19 | C |
| ATOM | 1107 | OD1 | ASN | A | 151 | 23.735 | 8.497 | 36.260 | 1.00 | 30.09 | O |
| ATOM | 1108 | ND2 | ASN | A | 151 | 23.991 | 10.611 | 36.930 | 1.00 | 29.31 | N |
| ATOM | 1109 | N | ASP | A | 152 | 26.020 | 6.999 | 34.627 | 1.00 | 30.27 | N |
| ATOM | 1110 | CA | ASP | A | 152 | 26.034 | 5.514 | 34.649 | 1.00 | 30.85 | C |
| ATOM | 1111 | C | ASP | A | 152 | 24.830 | 4.797 | 35.212 | 1.00 | 30.51 | C |
| ATOM | 1112 | O | ASP | A | 152 | 24.779 | 3.562 | 35.137 | 1.00 | 30.29 | O |
| ATOM | 1113 | GB | ASP | A | 152 | 27.178 | 4.965 | 35.519 | 1.00 | 31.48 | C |
| ATOM | 1114 | CG | ASP | A | 152 | 28.384 | 5.812 | 35.493 | 1.00 | 34.64 | C |
| ATOM | 1115 | OD1 | ASP | A | 152 | 28.588 | 6.523 | 34.482 | 1.00 | 41.71 | O |
| ATOM | 1116 | OD2 | ASP | A | 152 | 29.177 | 5.857 | 36.437 | 1.00 | 37.31 | O |
| ATOM | 1117 | N | THR | A | 153 | 23.894 | 5.501 | 35.833 | 1.00 | 30.21 | N |

TABLE 3-continued

Coordinates for structures 1 to 4

| | | | | | | | | | | | |
|---|---|---|---|---|---|---|---|---|---|---|---|
| ATOM | 1118 | CA | THR | A | 153 | 22.767 | 4.785 | 36.432 | 1.00 | 30.13 | C |
| ATOM | 1119 | C | THR | A | 153 | 21.612 | 4.626 | 35.463 | 1.00 | 29.54 | C |
| ATOM | 1120 | O | THR | A | 153 | 20.639 | 3.970 | 35.778 | 1.00 | 29.38 | O |
| ATOM | 1121 | GB | THR | A | 153 | 22.277 | 5.481 | 37.704 | 1.00 | 30.37 | C |
| ATOM | 1122 | OG1 | THR | A | 153 | 21.735 | 6.770 | 37.373 | 1.00 | 31.06 | O |
| ATOM | 1123 | CG2 | THR | A | 153 | 23.452 | 5.763 | 38.658 | 1.00 | 30.56 | C |
| ATOM | 1124 | N | VAL | A | 154 | 21.703 | 5.213 | 34.280 | 1.00 | 29.07 | N |
| ATOM | 1125 | CA | VAL | A | 154 | 20.596 | 5.082 | 33.346 | 1.00 | 28.90 | C |
| ATOM | 1126 | C | VAL | A | 154 | 20.488 | 3.613 | 32.968 | 1.00 | 28.83 | C |
| ATOM | 1127 | O | VAL | A | 154 | 21.486 | 2.898 | 33.002 | 1.00 | 28.78 | O |
| ATOM | 1128 | GB | VAL | A | 154 | 20.762 | 5.952 | 32.088 | 1.00 | 28.61 | C |
| ATOM | 1129 | CG1 | VAL | A | 154 | 20.808 | 7.410 | 32.462 | 1.00 | 29.14 | C |
| ATOM | 1130 | CG2 | VAL | A | 154 | 21.999 | 5.547 | 31.305 | 1.00 | 28.52 | C |
| ATOM | 1131 | H | GLY | A | 155 | 19.283 | 3.170 | 32.615 | 1.00 | 28.74 | H |
| ATOM | 1132 | CA | GLY | A | 155 | 19.043 | 1.780 | 32.263 | 1.00 | 28.33 | C |
| ATOM | 1133 | C | GLY | A | 155 | 19.484 | 1.387 | 30.860 | 1.00 | 28.70 | C |
| ATOM | 1134 | O | GLY | A | 155 | 19.862 | 2.235 | 30.031 | 1.00 | 28.27 | O |
| ATOM | 1135 | N | ARG | A | 156 | 19.384 | 0.088 | 30.591 | 1.00 | 28.47 | N |
| ATOM | 1136 | CA | ARG | A | 156 | 19.857 | 0.519 | 29.349 | 1.00 | 28.54 | C |
| ATOM | 1137 | C | ARG | A | 156 | 19.291 | 0.096 | 28.084 | 1.00 | 28.18 | C |
| ATOM | 1138 | O | ARG | A | 156 | 20.029 | 0.346 | 27.143 | 1.00 | 28.69 | O |
| ATOM | 1139 | GB | ARG | A | 156 | 19.582 | 2.019 | 29.362 | 1.00 | 28.58 | C |
| ATOM | 1140 | N | LYS | A | 157 | 17.986 | 0.304 | 28.042 | 1.00 | 27.53 | N |
| ATOM | 1141 | CA | LYS | A | 157 | 17.390 | 0.888 | 26.860 | 1.00 | 27.32 | C |
| ATOM | 1142 | C | LYS | A | 157 | 17.947 | 2.306 | 26.625 | 1.00 | 27.10 | C |
| ATOM | 1143 | O | LYS | A | 157 | 18.213 | 2.672 | 25.490 | 1.00 | 26.76 | O |
| ATOM | 1144 | CE | LYS | A | 157 | 15.858 | 0.902 | 26.960 | 1.00 | 27.68 | C |
| ATOM | 1145 | CG | LYS | A | 157 | 15.171 | 0.451 | 26.656 | 1.00 | 26.26 | C |
| ATOM | 1146 | H | ILE | A | 158 | 18.138 | 3.086 | 27.688 | 1.00 | 26.68 | H |
| ATOM | 1147 | CA | ILE | A | 158 | 18.665 | 4.450 | 27.543 | 1.00 | 26.67 | C |
| ATOM | 1148 | C | ILE | A | 158 | 20.107 | 4.368 | 27.100 | 1.00 | 26.53 | C |
| ATOM | 1149 | O | ILE | A | 158 | 20.558 | 5.170 | 26.285 | 1.00 | 25.74 | O |
| ATOM | 1150 | CB | ILE | A | 158 | 18.570 | 5.245 | 28.837 | 1.00 | 26.51 | C |
| ATOM | 1151 | CG1 | ILE | A | 158 | 17.114 | 5.399 | 29.269 | 1.00 | 27.11 | C |
| ATOM | 1152 | CG2 | ILE | A | 158 | 19.208 | 6.618 | 28.667 | 1.00 | 27.55 | C |
| ATOM | 1153 | CD1 | ILE | A | 158 | 16.232 | 6.028 | 28.260 | 1.00 | 28.98 | C |
| ATOM | 1154 | N | VAL | A | 159 | 20.817 | 3.378 | 27.629 | 1.00 | 26.46 | N |
| ATOM | 1155 | CA | VAL | A | 159 | 22.187 | 3.125 | 27.226 | 1.00 | 26.70 | C |
| ATOM | 1156 | C | VAL | A | 159 | 22.191 | 2.813 | 25.728 | 1.00 | 26.30 | C |
| ATOM | 1157 | O | VAL | A | 159 | 23.022 | 3.332 | 24.999 | 1.00 | 25.90 | O |
| ATOM | 1158 | CB | VAL | A | 159 | 22.819 | 1.963 | 28.018 | 1.00 | 27.18 | C |
| ATOM | 1159 | CG1 | VAL | A | 159 | 24.045 | 1.436 | 27.311 | 1.00 | 28.12 | C |
| ATOM | 1160 | CG2 | VAL | A | 159 | 23.180 | 2.410 | 29.427 | 1.00 | 27.44 | C |
| ATOM | 1161 | N | MET | A | 160 | 21.255 | 1.984 | 25.269 | 1.00 | 26.08 | N |
| ATOM | 1162 | CA | MET | A | 160 | 21.175 | 1.652 | 23.840 | 1.00 | 26.30 | C |
| ATOM | 1163 | C | MET | A | 160 | 20.906 | 2.929 | 23.005 | 1.00 | 24.71 | C |
| ATOM | 1164 | O | MET | A | 160 | 21.559 | 3.164 | 22.000 | 1.00 | 23.40 | O |
| ATOM | 1165 | CB | MET | A | 160 | 20.081 | 0.617 | 23.565 | 1.00 | 26.71 | C |
| ATOM | 1166 | CG | MET | A | 160 | 20.401 | 0.790 | 24.070 | 1.00 | 30.23 | C |
| ATOM | 1167 | SD | MET | A | 160 | 21.721 | 1.628 | 23.154 | 1.00 | 35.73 | S |
| ATOM | 1168 | CE | MET | A | 160 | 20.883 | 1.823 | 21.524 | 1.00 | 36.68 | C |
| ATOM | 1169 | N | ASP | A | 161 | 19.948 | 3.739 | 23.439 | 1.00 | 23.86 | N |
| ATOM | 1170 | CA | ASP | A | 161 | 19.636 | 5.000 | 22.756 | 1.00 | 23.67 | C |
| ATOM | 1171 | C | ASP | A | 161 | 20.840 | 5.943 | 22.664 | 1.00 | 22.65 | C |
| ATOM | 1172 | O | ASP | A | 161 | 21.148 | 6.478 | 21.593 | 1.00 | 23.02 | O |
| ATOM | 1173 | CB | ASP | A | 161 | 18.472 | 5.699 | 23.455 | 1.00 | 23.42 | C |
| ATOM | 1174 | CG | ASP | A | 161 | 17.178 | 4.898 | 23.369 | 1.00 | 24.19 | C |
| ATOM | 1175 | OD1 | ASP | A | 161 | 17.095 | 3.941 | 22.552 | 1.00 | 19.47 | O |
| ATOM | 1176 | OD2 | ASP | A | 161 | 16.197 | 5.164 | 24.087 | 1.00 | 24.90 | O |
| ATOM | 1177 | N | PHE | A | 162 | 21.513 | 6.132 | 23.791 | 1.00 | 21.70 | N |
| ATOM | 1178 | CA | PHE | A | 162 | 22.667 | 7.003 | 23.903 | 1.00 | 21.16 | C |
| ATOM | 1179 | C | PHE | A | 162 | 23.777 | 6.557 | 22.964 | 1.00 | 20.02 | C |
| ATOM | 1180 | O | PHE | A | 162 | 24.393 | 7.362 | 22.310 | 1.00 | 20.22 | O |
| ATOM | 1181 | CB | PHE | A | 162 | 23.144 | 7.010 | 25.364 | 1.00 | 21.38 | C |
| ATOM | 1182 | CG | PHE | A | 162 | 24.286 | 7.936 | 25.650 | 1.00 | 22.82 | C |
| ATOM | 1183 | CD1 | PHE | A | 162 | 24.072 | 9.290 | 25.882 | 1.00 | 26.05 | C |
| ATOM | 1184 | CD2 | PHE | A | 162 | 25.579 | 7.450 | 25.738 | 1.00 | 24.99 | C |
| ATOM | 1185 | CE1 | PHE | A | 162 | 25.144 | 10.136 | 26.181 | 1.00 | 25.32 | C |
| ATOM | 1186 | CE2 | PHE | A | 162 | 26.654 | 8.301 | 26.026 | 1.00 | 24.73 | C |
| ATOM | 1187 | CZ | PHE | A | 162 | 26.438 | 9.622 | 26.250 | 1.00 | 24.82 | C |
| ATOM | 1188 | N | LEU | A | 163 | 24.029 | 5.271 | 22.894 | 1.00 | 19.74 | N |
| ATOM | 1189 | CA | LEU | A | 163 | 25.064 | 4.767 | 21.998 | 1.00 | 19.88 | C |
| ATOM | 1190 | C | LEU | A | 163 | 24.688 | 4.965 | 20.533 | 1.00 | 18.90 | C |
| ATOM | 1191 | O | LEU | A | 163 | 25.554 | 5.020 | 19.675 | 1.00 | 18.20 | O |
| ATOM | 1192 | CB | LEU | A | 163 | 25.320 | 3.287 | 22.256 | 1.00 | 19.78 | C |
| ATOM | 1193 | CG | LEU | A | 163 | 26.078 | 3.019 | 23.546 | 1.00 | 20.79 | C |
| ATOM | 1194 | CD1 | LEU | A | 163 | 26.069 | 1.534 | 23.811 | 1.00 | 21.16 | C |

TABLE 3-continued

| | | | | | Coordinates for structures 1 to 4 | | | | | |
|---|---|---|---|---|---|---|---|---|---|---|
| ATOM | 1195 | CD2 | LEU | A | 163 | 27.498 | 3.567 | 23.456 | 1.00 | 21.66 | C |
| ATOM | 1196 | N | GLY | A | 164 | 23.395 | 5.055 | 20.272 | 1.00 | 18.33 | N |
| ATOM | 1197 | CA | GLY | A | 164 | 22.883 | 5.296 | 18.941 | 1.00 | 19.05 | C |
| ATOM | 1198 | C | GLY | A | 164 | 22.879 | 6.764 | 18.519 | 1.00 | 19.33 | C |
| ATOM | 1199 | O | GLY | A | 164 | 22.347 | 7.079 | 17.451 | 1.00 | 20.16 | O |
| ATOM | 1200 | N | PHE | A | 165 | 23.424 | 7.651 | 19.350 | 1.00 | 18.45 | N |
| ATOM | 1201 | CA | PHE | A | 165 | 23.516 | 9.048 | 18.974 | 1.00 | 19.26 | C |
| ATOM | 1202 | C | PHE | A | 165 | 24.548 | 9.102 | 17.850 | 1.00 | 19.34 | C |
| ATOM | 1203 | O | PHE | A | 165 | 25.363 | 8.177 | 17.720 | 1.00 | 18.77 | O |
| ATOM | 1204 | CB | PHE | A | 165 | 23.947 | 9.915 | 20.158 | 1.00 | 19.09 | C |
| ATOM | 1205 | CG | PHE | A | 165 | 22.862 | 10.139 | 21.208 | 1.00 | 20.44 | C |
| ATOM | 1206 | CD1 | PHE | A | 165 | 21.572 | 9.632 | 21.047 | 1.00 | 21.56 | C |
| ATOM | 1207 | CD2 | PHE | A | 165 | 23.143 | 10.878 | 22.357 | 1.00 | 20.27 | C |
| ATOM | 1208 | CE1 | PHE | A | 165 | 20.604 | 9.840 | 22.010 | 1.00 | 21.01 | C |
| ATOM | 1209 | CE2 | PHE | A | 165 | 22.174 | 11.096 | 23.326 | 1.00 | 20.14 | C |
| ATOM | 1210 | CZ | PHE | A | 165 | 20.913 | 10.567 | 23.163 | 1.00 | 22.00 | C |
| ATOM | 1211 | N | ASN | A | 166 | 24.508 | 10.157 | 17.040 | 1.00 | 19.48 | N |
| ATOM | 1212 | CA | ASN | A | 166 | 25.428 | 10.290 | 15.897 | 1.00 | 20.08 | C |
| ATOM | 1213 | C | ASN | A | 166 | 26.827 | 10.792 | 16.305 | 1.00 | 20.53 | C |
| ATOM | 1214 | O | ASN | A | 166 | 27.193 | 11.975 | 16.076 | 1.00 | 20.34 | O |
| ATOM | 1215 | CB | ASN | A | 166 | 24.836 | 11.183 | 14.790 | 1.00 | 19.52 | C |
| ATOM | 1216 | CG | ASN | A | 166 | 25.572 | 11.003 | 13.451 | 1.00 | 19.82 | C |
| ATOM | 1217 | OD1 | ASN | A | 166 | 26.652 | 10.376 | 13.412 | 1.00 | 18.39 | O |
| ATOM | 1218 | ND2 | ASN | A | 166 | 24.987 | 11.528 | 12.350 | 1.00 | 15.25 | N |
| ATOM | 1219 | N | TRP | A | 167 | 27.564 | 9.892 | 16.955 | 1.00 | 20.69 | N |
| ATOM | 1220 | CA | TRP | A | 167 | 28.911 | 10.161 | 17.441 | 1.00 | 21.20 | C |
| ATOM | 1221 | C | TRP | A | 167 | 29.858 | 10.404 | 16.270 | 1.00 | 21.35 | C |
| ATOM | 1222 | O | TRP | A | 167 | 30.806 | 11.171 | 16.371 | 1.00 | 21.36 | O |
| ATOM | 1223 | CB | TRP | A | 167 | 29.402 | 8.977 | 18.316 | 1.00 | 21.31 | C |
| ATOM | 1224 | CG | TRP | A | 167 | 28.550 | 8.849 | 19.539 | 1.00 | 21.63 | C |
| ATOM | 1225 | CD1 | TRP | A | 167 | 27.673 | 7.841 | 19.844 | 1.00 | 22.35 | C |
| ATOM | 1226 | CD2 | TRP | A | 167 | 28.433 | 9.808 | 20.591 | 1.00 | 20.88 | C |
| ATOM | 1227 | NE1 | TRP | A | 167 | 27.030 | 8.119 | 21.028 | 1.00 | 22.98 | N |
| ATOM | 1228 | CE2 | TRP | A | 167 | 27.486 | 9.315 | 21.511 | 1.00 | 21.22 | C |
| ATOM | 1229 | CE3 | TRP | A | 167 | 29.054 | 11.036 | 20.863 | 1.00 | 20.14 | C |
| ATOM | 1230 | CZ2 | TRP | A | 167 | 27.143 | 9.999 | 22.670 | 1.00 | 22.17 | C |
| ATOM | 1231 | CZ3 | TRP | A | 167 | 28.693 | 11.724 | 21.990 | 1.00 | 19.81 | C |
| ATOM | 1232 | CH2 | TRP | A | 167 | 27.742 | 11.206 | 22.889 | 1.00 | 21.02 | C |
| ATOM | 1233 | N | ASN | A | 168 | 29.610 | 9.743 | 15.153 | 1.00 | 21.50 | N |
| ATOM | 1234 | CA | ASN | A | 168 | 30.464 | 9.927 | 13.991 | 1.00 | 21.77 | C |
| ATOM | 1235 | C | ASN | A | 168 | 30.488 | 11.406 | 13.605 | 1.00 | 21.48 | C |
| ATOM | 1236 | O | ASN | A | 168 | 31.549 | 11.992 | 13.428 | 1.00 | 20.55 | O |
| ATOM | 1237 | CB | ASN | A | 168 | 29.964 | 9.101 | 12.814 | 1.00 | 22.00 | C |
| ATOM | 1238 | CG | ASN | A | 168 | 30.856 | 9.236 | 11.584 | 1.00 | 23.99 | C |
| ATOM | 1239 | OD1 | ASN | A | 168 | 32.052 | 8.974 | 11.661 | 1.00 | 26.79 | O |
| ATOM | 1240 | ND2 | ASN | A | 168 | 30.277 | 9.652 | 10.448 | 1.00 | 24.40 | N |
| ATOM | 1241 | N | TRP | A | 169 | 29.302 | 11.995 | 13.484 | 1.00 | 21.28 | N |
| ATOM | 1242 | CA | TRP | A | 169 | 29.183 | 13.372 | 13.071 | 1.00 | 21.23 | C |
| ATOM | 1243 | C | TRP | A | 169 | 29.708 | 14.331 | 14.133 | 1.00 | 21.44 | C |
| ATOM | 1244 | O | TRP | A | 169 | 30.450 | 15.258 | 13.822 | 1.00 | 20.50 | O |
| ATOM | 1245 | CB | TRP | A | 169 | 27.736 | 13.741 | 12.740 | 1.00 | 21.29 | C |
| ATOM | 1246 | CG | TRP | A | 169 | 27.611 | 15.186 | 12.397 | 1.00 | 20.56 | C |
| ATOM | 1247 | CD1 | TRP | A | 169 | 27.840 | 15.766 | 11.173 | 1.00 | 19.81 | C |
| ATOM | 1248 | CD2 | TRP | A | 169 | 27.293 | 16.256 | 13.290 | 1.00 | 20.58 | C |
| ATOM | 1249 | NE1 | TRP | A | 169 | 27.641 | 17.124 | 11.253 | 1.00 | 20.45 | N |
| ATOM | 1250 | CE2 | TRP | A | 169 | 27.313 | 17.453 | 12.540 | 1.00 | 21.52 | C |
| ATOM | 1251 | CE3 | TRP | A | 169 | 26.951 | 16.324 | 14.636 | 1.00 | 22.34 | C |
| ATOM | 1252 | CZ2 | TRP | A | 169 | 27.036 | 18.705 | 13.102 | 1.00 | 24.24 | C |
| ATOM | 1253 | CZ3 | TRP | A | 169 | 26.690 | 17.558 | 15.195 | 1.00 | 24.93 | C |
| ATOM | 1254 | CH2 | TRP | A | 169 | 26.728 | 18.736 | 14.423 | 1.00 | 25.53 | C |
| ATOM | 1255 | N | ILE | A | 170 | 29.318 | 14.124 | 15.381 | 1.00 | 21.81 | N |
| ATOM | 1256 | CA | ILE | A | 170 | 29.742 | 15.056 | 16.412 | 1.00 | 22.51 | C |
| ATOM | 1257 | C | ILE | A | 170 | 31.245 | 14.894 | 16.755 | 1.00 | 23.07 | C |
| ATOM | 1258 | O | ILE | A | 170 | 31.917 | 15.872 | 17.067 | 1.00 | 23.88 | O |
| ATOM | 1259 | CB | ILE | A | 170 | 28.837 | 14.988 | 17.662 | 1.00 | 21.97 | C |
| ATOM | 1260 | CG1 | ILE | A | 170 | 28.878 | 16.326 | 18.396 | 1.00 | 21.44 | C |
| ATOM | 1261 | CG2 | ILE | A | 170 | 29.262 | 13.894 | 18.581 | 1.00 | 21.76 | C |
| ATOM | 1262 | CD1 | ILE | A | 170 | 27.794 | 16.472 | 19.409 | 1.00 | 21.59 | C |
| ATOM | 1263 | N | ASN | A | 171 | 31.781 | 13.692 | 16.674 | 1.00 | 23.52 | N |
| ATOM | 1264 | CA | ASN | A | 171 | 33.209 | 13.516 | 16.934 | 1.00 | 24.55 | C |
| ATOM | 1265 | C | ASN | A | 171 | 34.021 | 14.254 | 15.874 | 1.00 | 25.23 | C |
| ATOM | 1266 | O | ASN | A | 171 | 35.067 | 14.828 | 16.171 | 1.00 | 25.14 | O |
| ATOM | 1267 | CB | ASN | A | 171 | 33.626 | 12.031 | 16.949 | 1.00 | 24.52 | C |
| ATOM | 1268 | CG | ASN | A | 171 | 33.095 | 11.271 | 18.171 | 1.00 | 24.45 | C |
| ATOM | 1269 | OD1 | ASN | A | 171 | 32.625 | 11.855 | 19.154 | 1.00 | 23.01 | O |
| ATOM | 1270 | ND2 | ASN | A | 171 | 33.169 | 9.969 | 18.099 | 1.00 | 22.49 | N |
| ATOM | 1271 | N | LYS | A | 172 | 33.560 | 14.219 | 14.630 | 1.00 | 25.46 | N |

TABLE 3-continued

Coordinates for structures 1 to 4

| | | | | | | | | | | |
|---|---|---|---|---|---|---|---|---|---|---|
| ATOM | 1272 | CA | LYS | A | 172 | 34.255 | 14.963 | 13.592 | 1.00 | 26.46 | C |
| ATOM | 1273 | C | LYS | A | 172 | 34.221 | 16.478 | 13.873 | 1.00 | 25.77 | C |
| ATOM | 1274 | O | LYS | A | 172 | 35.224 | 17.169 | 13.681 | 1.00 | 25.85 | O |
| ATOM | 1275 | CB | LYS | A | 172 | 33.705 | 14.634 | 12.205 | 1.00 | 26.90 | C |
| ATOM | 1276 | CG | LYS | A | 172 | 34.262 | 13.351 | 11.668 | 1.00 | 29.88 | C |
| ATOM | 1277 | CD | LYS | A | 172 | 33.752 | 13.033 | 10.240 | 1.00 | 34.20 | C |
| ATOM | 1278 | CE | LYS | A | 172 | 34.458 | 11.810 | 9.690 | 1.00 | 36.15 | C |
| ATOM | 1279 | NZ | LYS | A | 172 | 34.556 | 11.800 | 8.188 | 1.00 | 40.56 | N |
| ATOM | 1280 | N | GLN | A | 173 | 33.088 | 16.986 | 14.338 | 1.00 | 25.37 | N |
| ATOM | 1281 | CA | GLN | A | 173 | 32.981 | 18.400 | 14.690 | 1.00 | 25.52 | C |
| ATOM | 1282 | C | GLN | A | 173 | 34.002 | 18.741 | 15.774 | 1.00 | 25.71 | C |
| ATOM | 1283 | O | GLN | A | 173 | 34.780 | 19.669 | 15.618 | 1.00 | 26.05 | O |
| ATOM | 1284 | CB | GLN | A | 173 | 31.589 | 18.740 | 15.200 | 1.00 | 25.30 | C |
| ATOM | 1285 | CG | GLN | A | 173 | 30.522 | 18.729 | 14.138 | 1.00 | 25.28 | C |
| ATOM | 1286 | CD | GLN | A | 173 | 30.783 | 19.753 | 13.061 | 1.00 | 26.34 | C |
| ATOM | 1287 | OE1 | GLN | A | 173 | 31.252 | 20.872 | 13.345 | 1.00 | 26.57 | O |
| ATOM | 1288 | NE2 | GLN | A | 173 | 30.492 | 19.386 | 11.822 | 1.00 | 23.68 | N |
| ATOM | 1289 | N | GLN | A | 174 | 33.972 | 17.985 | 16.867 | 1.00 | 25.20 | N |
| ATOM | 1290 | CA | GLN | A | 174 | 34.931 | 18.124 | 17.944 | 1.00 | 25.45 | C |
| ATOM | 1291 | C | GLN | A | 174 | 36.380 | 18.182 | 17.392 | 1.00 | 25.74 | C |
| ATOM | 1292 | O | GLN | A | 174 | 37.152 | 19.066 | 17.767 | 1.00 | 24.76 | O |
| ATOM | 1293 | CB | GLN | A | 174 | 34.770 | 16.951 | 18.923 | 1.00 | 25.13 | C |
| ATOM | 1294 | CG | GLN | A | 174 | 35.771 | 16.925 | 20.048 | 1.00 | 26.00 | C |
| ATOM | 1295 | CD | GLN | A | 174 | 35.636 | 15.697 | 20.929 | 1.00 | 26.76 | C |
| ATOM | 1296 | OE1 | GLN | A | 174 | 35.278 | 14.629 | 20.450 | 1.00 | 28.02 | O |
| ATOM | 1297 | NE2 | GLN | A | 174 | 35.917 | 15.851 | 22.222 | 1.00 | 26.75 | N |
| ATOM | 1298 | N | GLY | A | 175 | 36.724 | 17.249 | 16.505 | 1.00 | 25.61 | N |
| ATOM | 1299 | CA | GLY | A | 175 | 38.040 | 17.201 | 15.887 | 1.00 | 26.56 | C |
| ATOM | 1300 | C | GLY | A | 175 | 38.333 | 18.393 | 14.980 | 1.00 | 27.62 | C |
| ATOM | 1301 | O | GLY | A | 175 | 39.371 | 19.051 | 15.111 | 1.00 | 28.21 | O |
| ATOM | 1302 | N | LYS | A | 176 | 37.415 | 18.695 | 14.074 | 1.00 | 28.41 | N |
| ATOM | 1303 | CA | LYS | A | 176 | 37.583 | 19.834 | 13.173 | 1.00 | 29.52 | C |
| ATOM | 1304 | C | LYS | A | 176 | 37.778 | 21.177 | 13.895 | 1.00 | 29.38 | C |
| ATOM | 1305 | O | LYS | A | 176 | 38.557 | 22.009 | 13.443 | 1.00 | 29.30 | O |
| ATOM | 1306 | CB | LYS | A | 176 | 36.371 | 19.977 | 12.257 | 1.00 | 29.90 | C |
| ATOM | 1307 | CG | LYS | A | 176 | 36.212 | 18.895 | 11.227 | 1.00 | 32.69 | C |
| ATOM | 1308 | CD | LYS | A | 176 | 35.023 | 19.242 | 10.336 | 1.00 | 36.10 | C |
| ATOM | 1309 | CE | LYS | A | 176 | 34.114 | 18.065 | 10.148 | 1.00 | 37.89 | C |
| ATOM | 1310 | NZ | LYS | A | 176 | 32.736 | 18.469 | 9.746 | 1.00 | 40.12 | N |
| ATOM | 1311 | N | ARG | A | 177 | 37.060 | 21.397 | 14.993 | 1.00 | 29.00 | N |
| ATOM | 1312 | CA | ARG | A | 177 | 37.164 | 22.671 | 15.710 | 1.00 | 29.17 | C |
| ATOM | 1313 | C | ARG | A | 177 | 38.260 | 22.741 | 16.781 | 1.00 | 28.13 | C |
| ATOM | 1314 | O | ARG | A | 177 | 38.433 | 23.788 | 17.394 | 1.00 | 27.46 | O |
| ATOM | 1315 | CB | ARG | A | 177 | 35.831 | 23.025 | 16.391 | 1.00 | 29.67 | C |
| ATOM | 1316 | CG | ARG | A | 177 | 34.606 | 22.876 | 15.536 | 1.00 | 31.86 | C |
| ATOM | 1317 | CD | ARG | A | 177 | 34.629 | 23.648 | 14.243 | 1.00 | 35.68 | C |
| ATOM | 1318 | NE | ARG | A | 177 | 33.691 | 23.034 | 13.313 | 1.00 | 38.08 | N |
| ATOM | 1319 | CZ | ARG | A | 177 | 33.865 | 22.938 | 12.015 | 1.00 | 40.57 | C |
| ATOM | 1320 | NH1 | ARG | A | 177 | 34.958 | 23.420 | 11.436 | 1.00 | 41.44 | N |
| ATOM | 1321 | NH2 | ARG | A | 177 | 32.927 | 22.362 | 11.283 | 1.00 | 42.98 | N |
| ATOM | 1322 | N | GLY | A | 178 | 38.972 | 21.640 | 17.014 | 1.00 | 27.36 | N |
| ATOM | 1323 | CA | GLY | A | 178 | 40.013 | 21.589 | 18.028 | 1.00 | 26.75 | C |
| ATOM | 1324 | C | GLY | A | 178 | 39.460 | 21.655 | 19.444 | 1.00 | 26.55 | C |
| ATOM | 1325 | O | GLY | A | 178 | 40.175 | 21.999 | 20.394 | 1.00 | 27.31 | O |
| ATOM | 1326 | N | TRP | A | 179 | 38.195 | 21.308 | 19.620 | 1.00 | 25.19 | N |
| ATOM | 1327 | CA | TRP | A | 179 | 37.626 | 21.379 | 20.947 | 1.00 | 25.17 | C |
| ATOM | 1328 | C | TRP | A | 179 | 38.257 | 20.404 | 21.926 | 1.00 | 25.28 | C |
| ATOM | 1329 | O | TRP | A | 179 | 38.909 | 19.454 | 21.541 | 1.00 | 24.67 | O |
| ATOM | 1330 | CB | TRP | A | 179 | 36.127 | 21.139 | 20.901 | 1.00 | 24.78 | C |
| ATOM | 1331 | CG | TRP | A | 179 | 35.364 | 22.197 | 20.201 | 1.00 | 24.55 | C |
| ATOM | 1332 | CD1 | TRP | A | 179 | 35.830 | 23.425 | 19.776 | 1.00 | 23.00 | C |
| ATOM | 1394 | CE | LEU | A | 187 | 18.525 | 14.883 | 30.604 | 1.00 | 21.36 | C |
| ATOM | 1395 | CG | LEU | A | 187 | 17.037 | 14.555 | 30.489 | 1.00 | 22.46 | C |
| ATOM | 1396 | CD1 | LEU | A | 187 | 16.550 | 14.530 | 29.038 | 1.00 | 22.25 | C |
| ATOM | 1397 | CD2 | LEU | A | 187 | 16.783 | 13.200 | 31.154 | 1.00 | 22.25 | C |
| ATOM | 1398 | N | LEU | A | 188 | 17.301 | 18.028 | 29.826 | 1.00 | 21.68 | N |
| ATOM | 1399 | CA | LEU | A | 188 | 16.400 | 19.052 | 30.329 | 1.00 | 22.46 | C |
| ATOM | 1400 | C | LEU | A | 188 | 14.925 | 18.743 | 30.021 | 1.00 | 22.70 | C |
| ATOM | 1401 | O | LEU | A | 188 | 14.511 | 18.622 | 28.864 | 1.00 | 23.01 | O |
| ATOM | 1402 | CB | LEU | A | 188 | 16.747 | 20.432 | 29.769 | 1.00 | 22.51 | C |
| ATOM | 1403 | CG | LEU | A | 188 | 18.166 | 20.932 | 29.998 | 1.00 | 24.09 | C |
| ATOM | 1404 | CD1 | LEU | A | 188 | 18.916 | 20.996 | 28.697 | 1.00 | 26.99 | C |
| ATOM | 1405 | CD2 | LEU | A | 188 | 18.135 | 22.308 | 30.564 | 1.00 | 25.94 | C |
| ATOM | 1406 | N | ILE | A | 189 | 14.117 | 18.652 | 31.061 | 1.00 | 22.31 | N |
| ATOM | 1407 | CA | ILE | A | 189 | 12.721 | 18.383 | 30.851 | 1.00 | 22.23 | C |
| ATOM | 1408 | C | ILE | A | 189 | 11.959 | 19.459 | 31.554 | 1.00 | 22.43 | C |
| ATOM | 1409 | O | ILE | A | 189 | 12.045 | 19.599 | 32.773 | 1.00 | 22.44 | O |

TABLE 3-continued

| | | | | | Coordinates for structures 1 to 4 | | | | | |
|---|---|---|---|---|---|---|---|---|---|---|
| ATOM | 1410 | CE | ILE | A | 189 | 12.328 | 17.009 | 31.369 | 1.00 | 21.56 | C |
| ATOM | 1411 | CG1 | ILE | A | 189 | 13.178 | 15.944 | 30.695 | 1.00 | 21.26 | C |
| ATOM | 1412 | CG2 | ILE | A | 189 | 10.873 | 16.794 | 31.078 | 1.00 | 21.74 | C |
| ATOM | 1413 | CD1 | ILE | A | 189 | 12.851 | 14.481 | 31.136 | 1.00 | 22.52 | C |
| ATOM | 1414 | N | GLY | A | 190 | 11.226 | 20.239 | 30.770 | 1.00 | 23.11 | N |
| ATOM | 1415 | CA | GLY | A | 190 | 10.545 | 21.396 | 31.294 | 1.00 | 23.06 | C |
| ATOM | 1416 | C | GLY | A | 190 | 9.084 | 21.395 | 30.988 | 1.00 | 23.56 | C |
| ATOM | 1417 | O | GLY | A | 190 | 8.594 | 20.646 | 30.117 | 1.00 | 23.29 | O |
| ATOM | 1418 | N | MET | A | 191 | 8.385 | 22.224 | 31.755 | 1.00 | 24.04 | N |
| ATOM | 1419 | CA | MET | A | 191 | 6.980 | 22.468 | 31.542 | 1.00 | 24.73 | C |
| ATOM | 1420 | C | MET | A | 191 | 6.837 | 23.623 | 30.576 | 1.00 | 24.58 | C |
| ATOM | 1421 | O | MET | A | 191 | 7.747 | 24.464 | 30.443 | 1.00 | 24.72 | O |
| ATOM | 1422 | CB | MET | A | 191 | 6.301 | 22.821 | 32.860 | 1.00 | 25.52 | C |
| ATOM | 1423 | CG | MET | A | 191 | 6.212 | 21.649 | 33.806 | 1.00 | 26.99 | C |
| ATOM | 1424 | SD | MET | A | 191 | 5.710 | 22.122 | 35.447 | 1.00 | 30.62 | S |
| ATOM | 1425 | CE | MET | A | 191 | 4.076 | 22.639 | 35.135 | 1.00 | 32.05 | C |
| ATOM | 1426 | N | GLU | A | 192 | 5.701 | 23.659 | 29.893 | 1.00 | 24.37 | N |
| ATOM | 1427 | CA | GLU | A | 192 | 5.407 | 24.718 | 28.940 | 1.00 | 24.51 | C |
| ATOM | 1428 | C | GLU | A | 192 | 5.468 | 26.072 | 29.628 | 1.00 | 24.20 | C |
| ATOM | 1429 | O | GLU | A | 192 | 5.013 | 26.237 | 30.745 | 1.00 | 24.12 | O |
| ATOM | 1430 | CB | GLU | A | 192 | 4.029 | 24.514 | 28.342 | 1.00 | 24.59 | C |
| ATOM | 1431 | CG | GLU | A | 192 | 2.930 | 24.487 | 29.384 | 1.00 | 26.08 | C |
| ATOM | 1432 | CD | GLU | A | 192 | 1.590 | 24.051 | 28.830 | 1.00 | 26.38 | C |
| ATOM | 1433 | OE1 | GLU | A | 192 | 1.530 | 23.568 | 27.676 | 1.00 | 27.04 | O |
| ATOM | 1434 | OE2 | GLU | A | 192 | 0.599 | 24.219 | 29.562 | 1.00 | 25.46 | O |
| ATOM | 1435 | N | GLY | A | 193 | 6.045 | 27.051 | 28.962 | 1.00 | 24.44 | N |
| ATOM | 1436 | CA | GLY | A | 193 | 6.153 | 28.364 | 29.562 | 1.00 | 24.21 | C |
| ATOM | 1437 | C | GLY | A | 193 | 7.428 | 28.565 | 30.358 | 1.00 | 23.71 | C |
| ATOM | 1438 | O | GLY | A | 193 | 7.728 | 29.691 | 30.697 | 1.00 | 24.97 | O |
| ATOM | 1439 | N | ASN | A | 194 | 8.181 | 27.507 | 30.663 | 1.00 | 23.27 | N |
| ATOM | 1440 | CA | ASN | A | 194 | 9.445 | 27.656 | 31.413 | 1.00 | 22.47 | C |
| ATOM | 1441 | C | ASN | A | 194 | 10.465 | 28.476 | 30.636 | 1.00 | 22.35 | C |
| ATOM | 1442 | O | ASN | A | 194 | 10.594 | 28.317 | 29.416 | 1.00 | 22.38 | O |
| ATOM | 1443 | CB | ASN | A | 194 | 10.108 | 26.299 | 31.708 | 1.00 | 22.17 | C |
| ATOM | 1444 | CG | ASN | A | 194 | 9.476 | 25.555 | 32.882 | 1.00 | 22.24 | C |
| ATOM | 1445 | OD1 | ASN | A | 194 | 8.477 | 25.992 | 33.453 | 1.00 | 23.81 | O |
| ATOM | 1446 | ND2 | ASN | A | 194 | 10.075 | 24.429 | 33.253 | 1.00 | 18.58 | N |
| ATOM | 1447 | N | VAL | A | 195 | 11.226 | 29.295 | 31.362 | 1.00 | 21.64 | N |
| ATOM | 1448 | CA | VAL | A | 195 | 12.263 | 30.114 | 30.789 | 1.00 | 21.41 | C |
| ATOM | 1449 | C | VAL | A | 195 | 13.569 | 29.988 | 31.556 | 1.00 | 20.40 | C |
| ATOM | 1450 | O | VAL | A | 195 | 13.603 | 30.014 | 32.790 | 1.00 | 20.03 | O |
| ATOM | 1451 | CB | VAL | A | 195 | 11.889 | 31.621 | 30.828 | 1.00 | 21.72 | C |
| ATOM | 1452 | CG1 | VAL | A | 195 | 13.038 | 32.476 | 30.327 | 1.00 | 21.84 | C |
| ATOM | 1453 | CG2 | VAL | A | 195 | 10.628 | 31.904 | 30.043 | 1.00 | 23.61 | C |
| ATOM | 1454 | N | THR | A | 196 | 14.644 | 29.834 | 30.813 | 1.00 | 19.77 | N |
| ATOM | 1455 | CA | THR | A | 196 | 15.980 | 29.917 | 31.376 | 1.00 | 20.37 | C |
| ATOM | 1456 | C | THR | A | 196 | 16.467 | 31.291 | 30.933 | 1.00 | 20.92 | C |
| ATbM | 1457 | O | THR | A | 196 | 16.649 | 31.505 | 29.724 | 1.00 | 20.45 | O |
| ATOM | 1458 | GB | THR | A | 196 | 16.882 | 28.865 | 30.793 | 1.00 | 19.87 | C |
| ATOM | 1459 | OG1 | THR | A | 196 | 16.457 | 27.564 | 31.227 | 1.00 | 21.07 | O |
| ATOM | 1460 | CG2 | THR | A | 196 | 18.273 | 29.043 | 31.340 | 1.00 | 20.00 | C |
| ATOM | 1461 | N | PRO | A | 197 | 16.602 | 32.225 | 31.879 | 1.00 | 21.53 | N |
| ATOM | 1462 | CA | PRO | A | 197 | 16.997 | 33.609 | 31.572 | 1.00 | 22.24 | C |
| ATOM | 1463 | C | PRO | A | 197 | 18.375 | 33.688 | 30.952 | 1.00 | 22.26 | C |
| ATOM | 1464 | O | PRO | A | 197 | 19.195 | 32.773 | 31.130 | 1.00 | 22.66 | O |
| ATOM | 1465 | GB | PRO | A | 197 | 16.998 | 34.305 | 32.934 | 1.00 | 22.51 | C |
| ATOM | 1466 | CG | PRO | A | 197 | 16.282 | 33.411 | 33.839 | 1.00 | 22.92 | C |
| ATOM | 1467 | CD | PRO | A | 197 | 16.367 | 32.028 | 33.312 | 1.00 | 21.85 | C |
| ATOM | 1468 | N | ALA | A | 198 | 18.606 | 34.776 | 30.234 | 1.00 | 21.54 | N |
| ATOM | 1469 | CA | ALA | A | 198 | 19.821 | 34.976 | 29.486 | 1.00 | 21.47 | C |
| ATOM | 1470 | C | ALA | A | 198 | 21.110 | 34.764 | 30.282 | 1.00 | 21.22 | C |
| ATOM | 1471 | O | ALA | A | 198 | 21.298 | 35.310 | 31.386 | 1.00 | 20.56 | O |
| ATOM | 1472 | CE | ALA | A | 198 | 19.809 | 36.397 | 28.891 | 1.00 | 21.92 | C |
| ATOM | 1473 | N | HIS | A | 199 | 22.023 | 34.020 | 29.683 | 1.00 | 21.01 | N |
| ATOM | 1474 | CA | HIS | A | 199 | 23.321 | 33.764 | 30.288 | 1.00 | 21.40 | C |
| ATOM | 1475 | C | HIS | A | 199 | 24.250 | 33.279 | 29.213 | 1.00 | 21.61 | C |
| ATOM | 1476 | O | HIS | A | 199 | 23.811 | 33.017 | 28.089 | 1.00 | 21.18 | O |
| ATOM | 1477 | GB | HIS | A | 199 | 23.217 | 32.669 | 31.338 | 1.00 | 21.05 | C |
| ATOM | 1478 | CG | HIS | A | 199 | 22.864 | 31.354 | 30.746 | 1.00 | 22.98 | C |
| ATOM | 1479 | ND1 | HIS | A | 199 | 21.576 | 31.048 | 30.370 | 1.00 | 21.97 | N |
| ATOM | 1480 | CD2 | HIS | A | 199 | 23.630 | 30.287 | 30.399 | 1.00 | 21.48 | C |
| ATOM | 1481 | GE1 | HIS | A | 199 | 21.558 | 29.838 | 29.838 | 1.00 | 22.85 | C |
| ATOM | 1482 | ND2 | HIS | A | 199 | 22.791 | 29.368 | 29.821 | 1.00 | 24.36 | N |
| ATOM | 1483 | N | TYR | A | 200 | 25.538 | 33.177 | 29.555 | 1.00 | 22.22 | N |
| ATOM | 1484 | GA | TYR | A | 200 | 26.531 | 32.597 | 28.654 | 1.00 | 22.56 | C |
| ATOM | 1485 | C | TYR | A | 200 | 27.234 | 31.448 | 29.380 | 1.00 | 22.96 | C |
| ATOM | 1486 | O | TYR | A | 200 | 27.293 | 31.430 | 30.612 | 1.00 | 22.90 | O |

TABLE 3-continued

| | | | | | | | | | | |
|---|---|---|---|---|---|---|---|---|---|---|
| | | | | Coordinates for structures 1 to 4 | | | | | | |
| ATOM | 1487 | CE | TYR | A | 200 | 27.528 | 33.610 | 28.129 | 1.00 | 22.56 | C |
| ATOM | 1488 | CG | TYR | A | 200 | 28.492 | 34.228 | 29.145 | 1.00 | 23.02 | C |
| ATOM | 1489 | CD1 | TYR | A | 200 | 29.731 | 33.671 | 29.385 | 1.00 | 22.79 | C |
| ATOM | 1490 | GD2 | TYR | A | 200 | 28.180 | 35.419 | 29.799 | 1.00 | 23.89 | C |
| ATOM | 1491 | GE1 | TYR | A | 200 | 30.612 | 34.229 | 30.283 | 1.00 | 22.32 | C |
| ATOM | 1492 | GE2 | TYR | A | 200 | 29.062 | 35.991 | 30.722 | 1.00 | 22.06 | C |
| ATOM | 1493 | CZ | TYR | A | 200 | 30.277 | 35.402 | 30.947 | 1.00 | 22.13 | C |
| ATOM | 1494 | OH | TYR | A | 200 | 31.163 | 35.957 | 31.843 | 1.00 | 20.46 | O |
| ATOM | 1495 | N | ASP | A | 201 | 27.723 | 30.467 | 28.619 | 1.00 | 23.11 | N |
| ATOM | 1496 | CA | ASP | A | 201 | 28.433 | 29.326 | 29.213 | 1.00 | 23.02 | C |
| ATOM | 1497 | C | ASP | A | 201 | 29.833 | 29.338 | 28.687 | 1.00 | 23.38 | C |
| ATOM | 1498 | O | ASP | A | 201 | 30.038 | 29.811 | 27.597 | 1.00 | 24.05 | O |
| ATOM | 1499 | GB | ASP | A | 201 | 27.776 | 28.012 | 28.829 | 1.00 | 22.85 | C |
| ATOM | 1500 | CG | ASP | A | 201 | 26.365 | 27.898 | 29.338 | 1.00 | 21.12 | C |
| ATOM | 1501 | OD1 | ASP | A | 201 | 26.176 | 27.802 | 30.568 | 1.00 | 23.22 | O |
| ATOM | 1502 | OD2 | ASP | A | 201 | 25.387 | 27.845 | 28.574 | 1.00 | 20.55 | O |
| ATOM | 1503 | N | GLU | A | 202 | 30.799 | 28.820 | 29.437 | 1.00 | 23.78 | N |
| ATOM | 1504 | CA | GLU | A | 202 | 32.184 | 28.782 | 28.950 | 1.00 | 25.14 | C |
| ATOM | 1505 | C | GLU | A | 202 | 32.524 | 27.467 | 28.269 | 1.00 | 24.96 | C |
| ATOM | 1506 | O | GLU | A | 202 | 33.657 | 27.001 | 28.394 | 1.00 | 26.76 | O |
| ATOM | 1507 | GB | GLU | A | 202 | 33.218 | 28.965 | 30.091 | 1.00 | 24.67 | C |
| ATOM | 1508 | GG | GLU | A | 202 | 33.017 | 30.199 | 30.941 | 1.00 | 27.79 | C |
| ATOM | 1509 | CD | GLU | A | 202 | 34.089 | 30.312 | 32.025 | 1.00 | 30.13 | C |
| ATOM | 1510 | OE1 | GLU | A | 202 | 34.018 | 29.584 | 33.030 | 1.00 | 32.67 | O |
| ATOM | 1511 | OE2 | GLU | A | 202 | 35.010 | 31.114 | 31.844 | 1.00 | 29.05 | O |
| ATOM | 1512 | N | GLN | A | 203 | 31.547 | 26.818 | 27.653 | 1.00 | 24.30 | N |
| ATOM | 1513 | CA | GLU | A | 203 | 31.804 | 25.624 | 26.874 | 1.00 | 23.24 | C |
| ATOM | 1514 | C | GLN | A | 203 | 31.036 | 25.764 | 25.572 | 1.00 | 22.84 | C |
| ATOM | 1515 | O | GLN | A | 203 | 30.122 | 26.560 | 25.468 | 1.00 | 23.00 | O |
| ATOM | 1516 | CB | GLN | A | 203 | 31.373 | 24.363 | 27.618 | 1.00 | 23.43 | C |
| ATOM | 1517 | CG | GLN | A | 203 | 32.256 | 24.031 | 28.826 | 1.00 | 23.66 | C |
| ATOM | 1518 | CD | GLN | A | 203 | 32.061 | 22.612 | 29.354 | 1.00 | 25.58 | C |
| ATOM | 1519 | OE1 | GLN | A | 203 | 31.915 | 21.661 | 28.582 | 1.00 | 27.85 | O |
| ATOM | 1520 | NE2 | GLN | A | 203 | 32.084 | 22.468 | 30.670 | 1.00 | 25.67 | N |
| ATOM | 1521 | N | GLN | A | 204 | 31.465 | 25.013 | 24.575 | 1.00 | 22.51 | N |
| ATOM | 1522 | CA | GLN | A | 204 | 30.791 | 24.910 | 23.299 | 1.00 | 22.51 | C |
| ATOM | 1523 | C | GLN | A | 204 | 29.626 | 23.980 | 23.504 | 1.00 | 21.70 | C |
| ATOM | 1524 | O | GLN | A | 204 | 29.737 | 23.026 | 24.255 | 1.00 | 21.24 | O |
| ATOM | 1525 | CE | GLN | A | 204 | 31.718 | 24.307 | 22.255 | 1.00 | 22.29 | C |
| ATOM | 1526 | CG | GLN | A | 204 | 33.001 | 25.081 | 22.072 | 1.00 | 22.69 | C |
| ATOM | 1527 | CD | GLN | A | 204 | 32.820 | 26.346 | 21.259 | 1.00 | 22.39 | C |
| ATOM | 1528 | OE1 | GLN | A | 204 | 31.699 | 26.736 | 20.932 | 1.00 | 19.22 | O |
| ATOM | 1529 | NE2 | GLN | A | 204 | 33.937 | 26.970 | 20.906 | 1.00 | 19.77 | N |
| ATOM | 1530 | N | ASN | A | 205 | 28.523 | 24.241 | 22.810 | 1.00 | 21.48 | N |
| ATOM | 1531 | CA | ASN | A | 205 | 27.309 | 23.471 | 23.017 | 1.00 | 21.04 | C |
| ATOM | 1532 | C | ASN | A | 205 | 26.558 | 23.136 | 21.730 | 1.00 | 21.10 | C |
| ATOM | 1533 | O | ASN | A | 205 | 26.188 | 24.043 | 20.949 | 1.00 | 20.02 | O |
| ATOM | 1534 | CE | ASN | A | 205 | 26.401 | 24.322 | 23.920 | 1.00 | 21.70 | C |
| ATOM | 1535 | CG | ASN | A | 205 | 25.084 | 23.654 | 24.269 | 1.00 | 21.87 | C |
| ATOM | 1536 | OD1 | ASN | A | 205 | 24.732 | 22.577 | 23.775 | 1.00 | 22.07 | O |
| ATOM | 1537 | ND2 | ASN | A | 205 | 24.332 | 24.320 | 25.118 | 1.00 | 19.37 | N |
| ATOM | 1538 | N | PHE | A | 206 | 26.350 | 21.835 | 21.497 | 1.00 | 20.28 | N |
| ATOM | 1539 | CA | PHE | A | 206 | 25.372 | 21.414 | 20.523 | 1.00 | 20.14 | C |
| ATOM | 1540 | C | PHE | A | 206 | 24.141 | 21.030 | 21.323 | 1.00 | 19.94 | C |
| ATOM | 1541 | O | PHE | A | 206 | 24.164 | 20.052 | 22.065 | 1.00 | 20.71 | O |
| ATOM | 1542 | CB | PHE | A | 206 | 25.851 | 20.238 | 19.693 | 1.00 | 20.65 | C |
| ATOM | 1543 | CG | PHE | A | 206 | 26.799 | 20.618 | 18.620 | 1.00 | 20.30 | C |
| ATOM | 1544 | CD1 | PHE | A | 206 | 26.394 | 21.438 | 17.600 | 1.00 | 20.89 | C |
| ATOM | 1545 | CD2 | PHE | A | 206 | 28.101 | 20.168 | 18.642 | 1.00 | 21.26 | C |
| ATOM | 1546 | CE1 | PHE | A | 206 | 27.254 | 21.783 | 16.605 | 1.00 | 22.17 | C |
| ATOM | 1547 | CE2 | PHE | A | 206 | 28.980 | 20.523 | 17.641 | 1.00 | 21.31 | C |
| ATOM | 1548 | CZ | PHE | A | 206 | 28.558 | 21.336 | 16.632 | 1.00 | 21.79 | C |
| ATOM | 1549 | N | PHE | A | 207 | 23.058 | 21.764 | 21.081 | 1.00 | 19.87 | N |
| ATOM | 1550 | CA | PHE | A | 207 | 21.790 | 21.723 | 21.824 | 1.00 | 20.08 | C |
| ATOM | 1551 | C | PHE | A | 207 | 20.766 | 20.988 | 20.975 | 1.00 | 20.29 | C |
| ATOM | 1552 | O | PHE | A | 207 | 20.276 | 21.519 | 20.011 | 1.00 | 19.94 | O |
| ATOM | 1553 | CE | PHE | A | 207 | 21.385 | 23.190 | 22.083 | 1.00 | 20.46 | C |
| ATOM | 1554 | CG | PHE | A | 207 | 20.129 | 23.404 | 22.890 | 1.00 | 19.14 | C |
| ATOM | 1555 | CD1 | PHE | A | 207 | 18.947 | 23.708 | 22.267 | 1.00 | 19.77 | C |
| ATOM | 1556 | CD2 | PHE | A | 207 | 20.169 | 23.428 | 24.259 | 1.00 | 19.99 | C |
| ATOM | 1557 | CE1 | PHE | A | 207 | 17.818 | 23.980 | 22.984 | 1.00 | 21.67 | C |
| ATOM | 1558 | CE2 | PHE | A | 207 | 19.037 | 23.683 | 24.992 | 1.00 | 22.36 | C |
| ATOM | 1559 | CZ | PHE | A | 207 | 17.854 | 23.975 | 24.351 | 1.00 | 22.30 | C |
| ATOM | 1560 | N | ALA | A | 208 | 20.480 | 19.746 | 21.352 | 1.00 | 21.01 | N |
| ATOM | 1561 | CA | ALA | A | 208 | 19.688 | 18.827 | 20.541 | 1.00 | 21.26 | C |
| ATOM | 1562 | C | ALA | A | 208 | 18.260 | 18.669 | 21.030 | 1.00 | 21.74 | C |
| ATOM | 1563 | O | ALA | A | 208 | 18.000 | 17.983 | 22.049 | 1.00 | 21.21 | O |

TABLE 3-continued

Coordinates for structures 1 to 4

| ATOM | 1564 | CE  | ALA | A | 208 | 20.365 | 17.464 | 20.557 | 1.00 | 20.94 | C |
| ATOM | 1565 | N   | GLN | A | 209 | 17.329 | 19.245 | 20.276 | 1.00 | 21.56 | N |
| ATOM | 1566 | CA  | GLN | A | 209 | 15.940 | 19.219 | 20.697 | 1.00 | 21.78 | C |
| ATOM | 1567 | C   | GLN | A | 209 | 15.289 | 17.864 | 20.393 | 1.00 | 21.84 | C |
| ATOM | 1568 | O   | GLN | A | 209 | 15.506 | 17.245 | 19.323 | 1.00 | 20.40 | O |
| ATOM | 1569 | CB  | GLN | A | 209 | 15.203 | 20.391 | 20.068 | 1.00 | 22.08 | C |
| ATOM | 1570 | CG  | GLN | A | 209 | 13.790 | 20.597 | 20.542 | 1.00 | 22.02 | C |
| ATOM | 1571 | CD  | GLN | A | 209 | 13.688 | 20.986 | 22.013 | 1.00 | 22.84 | C |
| ATOM | 1572 | OE1 | GLN | A | 209 | 14.700 | 21.240 | 22.678 | 1.00 | 22.55 | O |
| ATOM | 1573 | NE2 | GLN | A | 209 | 12.448 | 21.034 | 22.524 | 1.00 | 21.97 | N |
| ATOM | 1574 | N   | ILE | A | 210 | 14.480 | 17.418 | 21.351 | 1.00 | 22.17 | N |
| ATOM | 1575 | CA  | ILE | A | 210 | 13.904 | 16.084 | 21.329 | 1.00 | 22.53 | C |
| ATOM | 1576 | C   | ILE | A | 210 | 12.397 | 16.074 | 21.316 | 1.00 | 23.45 | C |
| ATOM | 1577 | O   | ILE | A | 210 | 11.813 | 15.429 | 20.467 | 1.00 | 24.08 | O |
| ATOM | 1578 | CB  | ILE | A | 210 | 14.411 | 15.306 | 22.541 | 1.00 | 22.81 | C |
| ATOM | 1579 | CG1 | ILE | A | 210 | 15.857 | 14.886 | 22.284 | 1.00 | 23.77 | C |
| ATOM | 1580 | CG2 | ILE | A | 210 | 13.573 | 14.064 | 22.785 | 1.00 | 23.17 | C |
| ATOM | 1581 | CD1 | ILE | A | 210 | 16.631 | 14.512 | 23.519 | 1.00 | 24.86 | C |
| ATOM | 1582 | N   | LYS | A | 211 | 11.772 | 16.778 | 22.258 | 1.00 | 23.73 | N |
| ATOM | 1583 | CA  | LYS | A | 211 | 10.318 | 16.829 | 22.351 | 1.00 | 22.99 | C |
| ATOM | 1584 | C   | LYS | A | 211 | 9.873  | 18.253 | 22.566 | 1.00 | 22.73 | C |
| ATOM | 1585 | O   | LYS | A | 211 | 10.436 | 18.969 | 23.391 | 1.00 | 22.34 | O |
| ATOM | 1586 | CB  | LYS | A | 211 | 9.818  | 16.014 | 23.527 | 1.00 | 23.40 | C |
| ATOM | 1587 | CG  | LYS | A | 211 | 8.285  | 15.757 | 23.509 | 1.00 | 24.55 | C |
| ATOM | 1588 | CD  | LYS | A | 211 | 7.794  | 15.232 | 24.870 | 1.00 | 25.75 | C |
| ATOM | 1589 | CE  | LYS | A | 211 | 6.389  | 14.579 | 24.861 | 1.00 | 25.61 | C |
| ATOM | 1590 | NZ  | LYS | A | 211 | 5.580  | 14.641 | 23.613 | 1.00 | 25.29 | N |
| ATOM | 1591 | N   | GLY | A | 212 | 8.832  | 18.655 | 21.847 | 1.00 | 22.34 | N |
| ATOM | 1592 | CA  | GLY | A | 212 | 8.292  | 19.989 | 21.983 | 1.00 | 22.46 | C |
| ATOM | 1593 | C   | GLN | A | 212 | 9.188  | 21.026 | 21.338 | 1.00 | 22.40 | C |
| ATOM | 1594 | O   | GLY | A | 212 | 10.172 | 20.705 | 20.650 | 1.00 | 21.93 | O |
| ATOM | 1595 | N   | TYR | A | 213 | 8.859  | 22.281 | 21.592 | 1.00 | 22.95 | N |
| ATOM | 1596 | CA  | TYR | A | 213 | 9.530  | 23.400 | 20.944 | 1.00 | 23.32 | C |
| ATOM | 1597 | C   | TYR | A | 213 | 10.079 | 24.412 | 21.926 | 1.00 | 23.27 | C |
| ATOM | 1598 | O   | TYR | A | 213 | 9.434  | 24.740 | 22.918 | 1.00 | 23.34 | O |
| ATOM | 1599 | CB  | TYR | A | 213 | 8.547  | 24.092 | 20.012 | 1.00 | 23.77 | C |
| ATOM | 1600 | CG  | TYR | A | 213 | 8.133  | 23.198 | 18.887 | 1.00 | 25.58 | C |
| ATOM | 1601 | CD1 | TYR | A | 213 | 7.110  | 22.261 | 19.041 | 1.00 | 28.74 | C |
| ATOM | 1602 | CD2 | TYR | A | 213 | 8.798  | 23.253 | 17.687 | 1.00 | 28.55 | C |
| ATOM | 1603 | CE1 | TYR | A | 213 | 6.764  | 21.410 | 17.995 | 1.00 | 30.77 | C |
| ATOM | 1604 | CE2 | TYR | A | 213 | 8.465  | 22.429 | 16.651 | 1.00 | 30.41 | C |
| ATOM | 1605 | CZ  | TYR | A | 213 | 7.461  | 21.516 | 16.795 | 1.00 | 31.44 | C |
| ATOM | 1606 | OH  | TYR | A | 213 | 7.188  | 20.720 | 15.708 | 1.00 | 35.50 | O |
| ATOM | 1607 | N   | LYS | A | 214 | 11.270 | 24.911 | 21.620 | 1.00 | 22.60 | N |
| ATOM | 1608 | CA  | LYS | A | 214 | 11.916 | 25.911 | 22.431 | 1.00 | 22.58 | C |
| ATOM | 1609 | C   | LYS | A | 214 | 12.353 | 27.077 | 21.576 | 1.00 | 22.52 | C |
| ATOM | 1610 | O   | LYS | A | 214 | 12.937 | 26.898 | 20.493 | 1.00 | 23.74 | O |
| ATOM | 1611 | CB  | LYS | A | 214 | 13.132 | 25.345 | 23.169 | 1.00 | 22.31 | C |
| ATOM | 1612 | CG  | LYS | A | 214 | 12.784 | 24.539 | 24.392 | 1.00 | 22.79 | C |
| ATOM | 1613 | CD  | LYS | A | 214 | 14.053 | 24.007 | 25.077 | 1.00 | 22.96 | C |
| ATOM | 1614 | CE  | LYS | A | 214 | 13.821 | 23.675 | 26.530 | 1.00 | 20.69 | C |
| ATOM | 1615 | NZ  | LYS | A | 214 | 15.076 | 23.085 | 27.149 | 1.00 | 19.14 | N |
| ATOM | 1616 | N   | ARG | A | 215 | 12.037 | 28.277 | 22.047 | 1.00 | 21.95 | N |
| ATOM | 1617 | CA  | ARG | A | 215 | 12.480 | 29.482 | 21.378 | 1.00 | 21.48 | C |
| ATOM | 1618 | C   | ARG | A | 215 | 13.790 | 29.864 | 22.018 | 1.00 | 21.06 | C |
| ATOM | 1619 | O   | ARG | A | 215 | 13.890 | 29.954 | 23.230 | 1.00 | 20.53 | O |
| ATOM | 1620 | CB  | ARG | A | 215 | 11.466 | 30.582 | 21.576 | 1.00 | 22.15 | C |
| ATOM | 1621 | CG  | ARG | A | 215 | 11.843 | 31.913 | 20.969 | 1.00 | 22.00 | C |
| ATOM | 1622 | CD  | ARG | A | 215 | 11.231 | 33.041 | 21.727 | 1.00 | 23.87 | C |
| ATOM | 1623 | NE  | ARG | A | 215 | 11.224 | 34.272 | 20.959 | 1.00 | 25.87 | N |
| ATOM | 1624 | CZ  | ARG | A | 215 | 10.566 | 35.364 | 21.297 | 1.00 | 25.54 | C |
| ATOM | 1625 | NH1 | ARG | A | 215 | 9.873  | 35.425 | 22.423 | 1.00 | 24.05 | N |
| ATOM | 1626 | NH2 | ARG | A | 215 | 10.634 | 36.420 | 20.505 | 1.00 | 29.37 | N |
| ATOM | 1627 | N   | CYS | A | 216 | 14.794 | 30.090 | 21.193 | 1.00 | 21.48 | N |
| ATOM | 1628 | CA  | CYS | A | 216 | 16.123 | 30.355 | 21.668 | 1.00 | 21.40 | C |
| ATOM | 1629 | C   | CYS | A | 216 | 16.533 | 31.723 | 21.146 | 1.00 | 21.86 | C |
| ATOM | 1630 | O   | CYS | A | 216 | 16.532 | 31.952 | 19.948 | 1.00 | 22.82 | O |
| ATOM | 1631 | CB  | CYS | A | 216 | 17.079 | 29.309 | 21.127 | 1.00 | 21.46 | C |
| ATOM | 1632 | SG  | CYS | A | 216 | 16.689 | 27.562 | 21.469 | 1.00 | 22.63 | S |
| ATOM | 1633 | N   | ILE | A | 217 | 16.878 | 32.630 | 22.045 | 1.00 | 21.29 | N |
| ATOM | 1634 | CA  | ILE | A | 217 | 17.331 | 33.960 | 21.663 | 1.00 | 21.28 | C |
| ATOM | 1635 | C   | ILE | A | 217 | 18.782 | 34.114 | 22.102 | 1.00 | 20.86 | C |
| ATOM | 1636 | O   | ILE | A | 217 | 19.085 | 34.007 | 23.310 | 1.00 | 21.04 | O |
| ATOM | 1637 | CB  | ILE | A | 217 | 16.456 | 35.025 | 22.327 | 1.00 | 21.80 | C |
| ATOM | 1638 | CG1 | ILE | A | 217 | 14.978 | 34.807 | 21.955 | 1.00 | 22.90 | C |
| ATOM | 1639 | CG2 | ILE | A | 217 | 16.874 | 36.414 | 21.861 | 1.00 | 22.72 | C |
| ATOM | 1640 | CD1 | ILE | A | 217 | 14.031 | 35.695 | 22.693 | 1.00 | 24.99 | C |

TABLE 3-continued

| | | | | | Coordinates for structures 1 to 4 | | | | | |
|---|---|---|---|---|---|---|---|---|---|---|
| ATOM | 1641 | N | LEU | A | 218 | 19.666 | 34.346 | 21.128 | 1.00 | 20.25 | N |
| ATOM | 1642 | CA | LEU | A | 218 | 21.094 | 34.451 | 21.373 | 1.00 | 20.55 | C |
| ATOM | 1643 | C | LEU | A | 218 | 21.630 | 35.853 | 21.128 | 1.00 | 21.19 | C |
| ATOM | 1644 | O | LEU | A | 218 | 21.141 | 36.560 | 20.253 | 1.00 | 21.62 | O |
| ATOM | 1645 | CE | LEU | A | 218 | 21.874 | 33.493 | 20.467 | 1.00 | 20.31 | C |
| ATOM | 1646 | CG | LEU | A | 218 | 21.964 | 32.019 | 20.906 | 1.00 | 20.46 | C |
| ATOM | 1647 | CE1 | LEU | A | 218 | 20.628 | 31.415 | 21.054 | 1.00 | 20.19 | C |
| ATOM | 1648 | CD2 | LEU | A | 218 | 22.732 | 31.229 | 19.907 | 1.00 | 22.84 | C |
| ATOM | 1649 | N | PHE | A | 219 | 22.658 | 36.231 | 21.886 | 1.00 | 21.06 | N |
| ATOM | 1650 | CA | PHE | A | 219 | 23.331 | 37.498 | 21.682 | 1.00 | 21.62 | C |
| ATOM | 1651 | C | PHE | A | 219 | 24.842 | 37.244 | 21.611 | 1.00 | 21.87 | C |
| ATOM | 1652 | O | PHE | A | 219 | 25.390 | 36.490 | 22.416 | 1.00 | 21.88 | O |
| ATOM | 1653 | CB | PHE | A | 219 | 23.005 | 38.484 | 22.820 | 1.00 | 20.94 | C |
| ATOM | 1654 | CG | PHE | A | 219 | 21.541 | 38.617 | 23.106 | 1.00 | 21.13 | C |
| ATOM | 1655 | CD1 | PHE | A | 219 | 20.907 | 37.779 | 23.995 | 1.00 | 21.92 | C |
| ATOM | 1656 | CD2 | PHE | A | 219 | 20.785 | 39.589 | 22.476 | 1.00 | 24.21 | C. |
| ATOM | 1657 | CE1 | PHE | A | 219 | 19.563 | 37.915 | 24.250 | 1.00 | 21.95. | C |
| ATOM | 1658 | CE2 | PHE | A | 219 | 19.442 | 39.724 | 22.735 | 1.00 | 22.06 | C |
| ATOM | 1659 | CZ | PHE | A | 219 | 18.840 | 38.904 | 23.621 | 1.00 | 23.11 | C |
| ATOM | 1660 | N | PRO | A | 220 | 25.512 | 37.877 | 20.662 | 1.00 | 22.38 | N |
| ATOM | 1661 | CA | PRO | A | 220 | 26.962 | 37.744 | 20.557 | 1.00 | 22.81 | C |
| ATOM | 1662 | C | PRO | A | 220 | 27.683 | 38.287 | 21.793 | 1.00 | 22.78 | C |
| ATOM | 1663 | O | PRO | A | 220 | 27.173 | 39.123 | 22.564 | 1.00 | 22.88 | O |
| ATOM | 1664 | CB | PRO | A | 220 | 27.335 | 38.561 | 19.317 | 1.00 | 22.81 | C |
| ATOM | 1665 | CG | PRO | A | 220 | 2.6.005 | 39.005 | 18.685 | 1.00 | 23.68 | C |
| ATOM | 1666 | CD | PRO | A | 220 | 24.940 | 38.792 | 19.663 | 1.00 | 22.86 | C |
| ATOM | 1667 | N | PRO | A | 221 | 28.885 | 37.774 | 21.999 | 1.00 | 22.84 | N |
| ATOM | 1668 | CA | PRO | A | 221 | 29.724 | 38.204 | 23.124 | 1.00 | 22.73 | C |
| ATOM | 1669 | C | PRO | A | 221 | 29.976 | 39.714 | 23.143 | 1.00 | 22.28. | C |
| ATOM | 1670 | O | PRO | A | 221 | 30.192 | 40.279 | 24.212 | 1.00 | 21.03 | O |
| ATOM | 1671 | CB | PRO | A | 221 | 31.030 | 37.455 | 22.892 | 1.00 | 22.78 | C |
| ATOM | 1672 | CG | PRO | A | 221 | 30.644 | 36.296 | 22.026 | 1.00 | 23.22 | C |
| ATOM | 1673 | CD | PRO | A | 221 | 29.521 | 36.733 | 21.174 | 1.00 | 22.58 | C |
| ATOM | 1674 | N | ASP | A | 222 | 29.897 | 40.378 | 21.993 | 1.00 | 22.60 | N |
| ATOM | 1675 | CA | ASP | A | 222 | 30.172 | 41.821 | 21.965 | 1.00 | 22.84 | C |
| ATOM | 1676 | C | ASP | A | 222 | 28.996 | 42.623 | 22.493 | 1.00 | 23.36 | C |
| ATOM | 1677 | O | ASP | A | 222 | 29.031 | 43.847 | 22.500 | 1.00 | 24.43 | O |
| ATOM | 1678 | CE | ASP | A | 222 | 30.638 | 42.308 | 20.579 | 1.00 | 22.47 | C |
| ATOM | 1679 | CG | ASP | A | 222 | 29.502 | 42.389 | 19.537 | 1.00 | 25.07 | C |
| ATOM | 1680 | OD1 | ASP | A | 222 | 28.355 | 41.942 | 19.764 | 1.00 | 25.24 | O |
| ATOM | 1681 | OD2 | ASP | A | 222 | 29.690 | 42.876 | 18.410 | 1.00 | 29.46 | O |
| ATOM | 1682 | N | GLN | A | 223 | 27.940 | 41.940 | 22.926 | 1.00 | 23.79 | N |
| ATOM | 1683 | CA | GLN | A | 223 | 26.826 | 42.624 | 23.565 | 1.00 | 23.85 | C |
| ATOM | 1684 | C | GLN | A | 223 | 26.942 | 42.570 | 25.114 | 1.00 | 23.37 | C |
| ATOM | 1685 | O | GLN | A | 223 | 25.986 | 42.875 | 25.850 | 1.00 | 23.78 | O |
| ATOM | 1686 | CE | GLN | A | 223 | 25.510 | 42.084 | 23.007 | 1.00 | 24.80 | C |
| ATOM | 1687 | CG | GLN | A | 223 | 25.217 | 42.672 | 21.550 | 1.00 | 28.46 | C |
| ATOM | 1688 | CD | GLN | A | 223 | 23.786 | 42.471 | 21.094 | 1.00 | 32.35 | C |
| ATOM | 1689 | OE1 | GLN | A | 223 | 22.861 | 42.619 | 21.893 | 1.00 | 36.73 | O |
| ATOM | 1690 | NE2 | GLN | A | 223 | 23.592 | 42.105 | 19.815 | 1.00 | 33.48 | N |
| ATOM | 1691 | N | PHE | A | 224 | 28.111 | 42.167 | 25.601 | 1.00 | 21.59 | N |
| ATOM | 1692 | CA | PHE | A | 224 | 28.394 | 42.195 | 27.035 | 1.00 | 21.84 | C |
| ATOM | 1693 | C | PHE | A | 224 | 27.888 | 43.509 | 27.706 | 1.00 | 21.56 | C |
| ATOM | 1694 | O | PHE | A | 224 | 27.233 | 43.455 | 28.738 | 1.00 | 20.27 | O |
| ATOM | 1695 | CE | PHE | A | 224 | 29.917 | 42.068 | 27.271 | 1.00 | 21.34 | C |
| ATOM | 1696 | CG | PHE | A | 224 | 30.309 | 41.943 | 28.732 | 1.00 | 22.22 | C |
| ATOM | 1697 | CO1 | PHE | A | 224 | 30.449 | 43.071 | 29.540 | 1.00 | 21.80 | C |
| ATOM | 1698 | CD2 | PHE | A | 224 | 30.583 | 40.723 | 29.279 | 1.00 | 20.92 | C |
| ATOM | 1699 | CE1 | PHE | A | 224 | 30.842 | 42.945 | 30.868 | 1.00 | 22.58 | C |
| ATOM | 1700 | CE2 | PHE | A | 224 | 30.979 | 40.593 | 30.587 | 1.00 | 22.14 | C |
| ATOM | 1701 | CZ | PHE | A | 224 | 31.087 | 41.725 | 31.394 | 1.00 | 22.16. | C |
| ATOM | 1702 | N | GLU | A | 225 | 28.190 | 44.665 | 27.106 | 1.00 | 22.03 | N |
| ATOM | 1703 | CA | GLU | A | 225 | 27.813 | 45.963 | 27.677 | 1.00 | 23.55 | C |
| ATOM | 1704 | C | GLU | A | 225 | 26.322 | 46.216 | 27.764 | 1.00 | 23.06 | C |
| ATOM | 1705 | O | GLU | A | 225 | 25.907 | 47.129 | 28.483 | 1.00 | 22.10 | O |
| ATOM | 1706 | CB | GLU | A | 225 | 28.396 | 47.111 | 26.856 | 1.00 | 24.92 | C |
| ATOM | 1707 | CG | GLU | A | 225 | 29.897 | 47.228 | 27.013 | 1.00 | 30.17 | C |
| ATOM | 1708 | CD | GLU | A | 225 | 30.386 | 48.632 | 27.280 | 1.00 | 36.52 | C |
| ATOM | 1709 | OE1 | GLU | A | 225 | 29.901 | 49.319 | 28.242 | 1.00 | 40.52 | O |
| ATOM | 1710 | OE2 | GLU | A | 225 | 31.310 | 49.028 | 26.532 | 1.00 | 41.63 | O |
| ATOM | 1711 | N | CYS | A | 226 | 25.532 | 45.456 | 27.003 | 1.00 | 22.07 | N |
| ATOM | 1712 | CA | CYS | A | 226 | 24.087 | 45.619 | 27.027 | 1.00 | 22.09 | C |
| ATOM | 1713 | C | CYS | A | 226 | 23.372 | 44.631 | 27.935 | 1.00 | 21.89 | C |
| ATOM | 1714 | O | CYS | A | 226 | 22.170 | 44.781 | 28.162 | 1.00 | 20.73 | O |
| ATOM | 1715 | CS | CYS | A | 226 | 23.523 | 45.416 | 25.630 | 1.00 | 22.22 | C |
| ATOM | 1716 | SG | CYS | A | 226 | 24.206 | 46.488 | 24.368 | 1.00 | 22.59 | S |
| ATOM | 1717 | N | LEU | A | 227 | 24.102 | 43.633 | 28.451 | 1.00 | 22.08 | N |

TABLE 3-continued

Coordinates for structures 1 to 4

| ATOM | 1718 | CA | LEU | A | 227 | 23.467 | 42.529 | 29.169 | 1.00 | 22.08 | C |
|---|---|---|---|---|---|---|---|---|---|---|---|
| ATOM | 1719 | C | LEU | A | 227 | 23.771 | 42.393 | 30.657 | 1.00 | 21.99 | C |
| ATOM | 1720 | O | LEU | A | 227 | 23.118 | 41.611 | 31.373 | 1.00 | 22.28 | O |
| ATOM | 1721 | CB | LEU | A | 227 | 23.751 | 41.244 | 28.418 | 1.00 | 22.29 | C |
| ATOM | 1722 | CG | LEU | A | 227 | 22.874 | 41.185 | 27.158 | 1.00 | 23.54 | C |
| ATOM | 1723 | CE1 | LEU | A | 227 | 23.428 | 40.186 | 26.144 | 1.00 | 23.51 | C |
| ATOM | 1724 | CD2 | LEU | A | 227 | 21.423 | 40.819 | 27.544 | 1.00 | 24.49 | C |
| ATOM | 1725 | N | TYR | A | 228 | 24.763 | 43.140 | 31.109 | 1.00 | 20.87 | N |
| ATOM | 1726 | CA | TYR | A | 228 | 24.996 | 43.320 | 32.521 | 1.00 | 21.33 | C |
| ATOM | 1727 | C | TYR | A | 228 | 25.018 | 42.057 | 33.382 | 1.00 | 21.27 | C |
| ATOM | 1728 | O | TYR | A | 228 | 24.205 | 41.920 | 34.301 | 1.00 | 21.72 | O |
| ATOM | 1729 | CB | TYR | A | 228 | 23.957 | 44.311 | 33.077 | 1.00 | 20.92 | C |
| ATOM | 1730 | CG | TYR | A | 228 | 23.949 | 45.649 | 32.339 | 1.00 | 20.91 | C |
| ATOM | 1731 | CD1 | TYR | A | 228 | 24.768 | 46.677 | 32.739 | 1.00 | 18.87 | C |
| ATOM | 1732 | CD2 | TYR | A | 228 | 23.122 | 45.862 | 31.232 | 1.00 | 20.51 | C |
| ATOM | 1733 | CE1 | TYR | A | 228 | 24.780 | 47.912 | 32.076 | 1.00 | 20.36 | C |
| ATOM | 1734 | CE2 | TYR | A | 228 | 23.117 | 47.074 | 30.561 | 1.00 | 21.07 | C |
| ATOM | 1735 | CZ | TYR | A | 228 | 23.931 | 48.113 | 31.000 | 1.00 | 20.84 | C |
| ATOM | 1736 | OH | TYR | A | 228 | 23.947 | 49.325 | 30.336 | 1.00 | 19.16 | O |
| ATOM | 1737 | N | PRO | A | 229 | 25.985 | 41.175 | 33.141 | 1.00 | 20.77 | N |
| ATOM | 1738 | CA | PRO | A | 229 | 26.128 | 39.971 | 33.966 | 1.00 | 21.05 | C |
| ATOM | 1739 | C | PRO | A | 229 | 26.428 | 40.332 | 35.408 | 1.00 | 20.08 | C |
| ATOM | 1740 | O | PRO | A | 229 | 27.021 | 41.379 | 35.675 | 1.00 | 20.20 | O |
| ATOM | 1741 | CB | PRO | A | 229 | 27.360 | 39.271 | 33.363 | 1.00 | 20.51 | C |
| ATOM | 1742 | CG | PRO | A | 229 | 28.084 | 40.340 | 32.651 | 1.00 | 21.64 | C |
| ATOM | 1743 | CD | PRO | A | 229 | 27.025 | 41.241 | 32.105 | 1.00 | 20.97 | C |
| ATOM | 1744 | N | TYR | A | 230 | 25.988 | 39.490 | 36.326 | 1.00 | 19.73 | N |
| ATOM | 1745 | CA | TYR | A | 230 | 26.282 | 39.656 | 37.724 | 1.00 | 18.80 | C |
| ATOM | 1746 | C | TYR | A | 230 | 27.809 | 39.657 | 37.947 | 1.00 | 18.61 | C |
| ATOM | 1747 | O | TYR | A | 230 | 28.575 | 39.250 | 37.094 | 1.00 | 18.26 | O |
| ATOM | 1748 | CB | TYR | A | 230 | 25.669 | 38.507 | 38.520 | 1.00 | 18.86 | C |
| ATOM | 1749 | CG | TYR | A | 230 | 24.172 | 38.597 | 38.725 | 1.00 | 19.28 | C |
| ATOM | 1750 | CD1 | TYR | A | 230 | 23.297 | 38.110 | 37.760 | 1.00 | 18.53 | C |
| ATOM | 1751 | CD2 | TYR | A | 230 | 23.629 | 39.172 | 39.885 | 1.00 | 19.38 | C |
| ATOM | 1752 | CE1 | TYR | A | 230 | 21.932 | 38.161 | 37.935 | 1.00 | 18.86 | C |
| ATOM | 1753 | CE2 | TYR | A | 230 | 22.234 | 39.222 | 40.076 | 1.00 | 19.53 | C |
| ATOM | 1754 | CZ | TYR | A | 230 | 21.404 | 38.719 | 39.073 | 1.00 | 20.93 | C |
| ATOM | 1755 | OH | TYR | A | 230 | 20.034 | 38.771 | 39.176 | 1.00 | 23.69 | O |
| ATOM | 1756 | N | PRO | A | 231 | 28.251 | 40.137 | 39.098 | 1.00 | 18.40 | N |
| ATOM | 1757 | CA | PRO | A | 231 | 29.651 | 39.983 | 39.476 | 1.00 | 18.58 | C |
| ATOM | 1758 | C | PRO | A | 231 | 30.070 | 38.507 | 39.399 | 1.00 | 19.41 | C |
| ATOM | 1759 | O | PRO | A | 231 | 29.240 | 37.624 | 39.654 | 1.00 | 18.89 | O |
| ATOM | 1760 | CB | PRO | A | 231 | 29.675 | 40.477 | 40.933 | 1.00 | 18.95 | C |
| ATOM | 1761 | CG | PRO | A | 231 | 28.542 | 41.507 | 41.001 | 1.00 | 19.0.2 | C |
| ATOM | 1762 | CD | PRO | A | 231 | 27.460 | 40.868 | 40.105 | 1.00 | 18.02 | C |
| ATOM | 1763 | N | VAL | A | 232 | 31.335 | 38.248 | 39.071 | 1.00 | 19.55 | N |
| ATOM | 1764 | CA | VAL | A | 232 | 31.826 | 36.884 | 38.969 | 1.00 | 20.65 | C |
| ATOM | 1765 | C | VAL | A | 232 | 31.640 | 36.034 | 40.236 | 1.00 | 20.79 | C |
| ATOM | 1766 | O | VAL | A | 232 | 31.379 | 34.838 | 40.145 | 1.00 | 21.82 | O |
| ATOM | 1767 | CE | VAL | A | 232 | 33.318 | 36.869 | 38.545 | 1.00 | 20.71 | C |
| ATOM | 1768 | CG1 | VAL | A | 232 | 33.945 | 35.524 | 38.807 | 1.00 | 21.96 | C |
| ATOM | 1769 | CG2 | VAL | A | 232 | 33.452 | 37.225 | 37.075 | 1.00 | 20.83 | C |
| ATOM | 1770 | N | HIS | A | 233 | 31.770 | 36.639 | 41.409 | 1.00 | 20.87 | N |
| ATOM | 1771 | CA | HIS | A | 233 | 31.643 | 35.907 | 42.661 | 1.00 | 20.70 | C |
| ATOM | 1772 | C | HIS | A | 233 | 30.203 | 35.739 | 43.168 | 1.00 | 20.59 | C |
| ATOM | 1773 | O | HIS | A | 233 | 29.940 | 35.010 | 44.119 | 1.00 | 20.49 | O |
| ATOM | 1774 | CE | HIS | A | 233 | 32.482 | 36.593 | 43.706 | 1.00 | 20.63 | C |
| ATOM | 1775 | CG | HIS | A | 233 | 33.948 | 36.529 | 43.426 | 1.00 | 21.92 | C |
| ATOM | 1776 | ND1 | HIS | A | 233 | 34.659 | 37.595 | 42.913 | 1.00 | 22.17 | N |
| ATOM | 1777 | CD2 | HIS | A | 233 | 34.843 | 35.527 | 43.610 | 1.00 | 22.03 | C |
| ATOM | 1778 | CE1 | HIS | A | 233 | 35.929 | 37.249 | 42.793 | 1.00 | 23.69 | C |
| ATOM | 1779 | ND2 | HIS | A | 233 | 36.066 | 35.998 | 43.203 | 1.00 | 23.04 | N |
| ATOM | 1780 | N | HIS | A | 234 | 29.273 | 36.433 | 42.543 | 1.00 | 20.53 | N |
| ATOM | 1781 | CA | HIS | A | 234 | 27.869 | 36.251 | 42.857 | 1.00 | 20.60 | C |
| ATOM | 1782 | C | HIS | A | 234 | 27.388 | 34.895 | 42.306 | 1.00 | 20.45 | C |
| ATOM | 1783 | O | HIS | A | 234 | 27.873 | 34.428 | 41.291 | 1.00 | 19.86 | O |
| ATOM | 1784 | CB | HIS | A | 234 | 27.088 | 37.359 | 42.206 | 1.00 | 20.65 | C |
| ATOM | 1785 | CG | HIS | A | 234 | 25.661 | 37.441 | 42.625 | 1.00 | 20.68 | C |
| ATOM | 1786 | ND1 | HIS | A | 234 | 24.667 | 36.700 | 42.021 | 1.00 | 21.46 | N |
| ATOM | 1787 | CD2 | HIS | A | 234 | 25.044 | 38.249 | 43.518 | 1.00 | 20.20 | C |
| ATOM | 1788 | CE1 | HIS | A | 234 | 23.504 | 37.013 | 42.563 | 1.00 | 21.99 | C |
| ATOM | 1789 | ND2 | HIS | A | 234 | 23.707 | 37.951 | 43.473 | 1.00 | 21.29 | N |
| ATOM | 1790 | N | PRO | A | 235 | 26.463 | 34.261 | 43.007 | 1.00 | 20.40 | N |
| ATOM | 1791 | CA | PRO | A | 235 | 25.888 | 32.993 | 42.572 | 1.00 | 20.85 | C |
| ATOM | 1792 | C | PRO | A | 235 | 25.360 | 33.021 | 41.152 | 1.00 | 21.20 | C |
| ATOM | 1793 | O | PRO | A | 235 | 25.437 | 31.984 | 40.502 | 1.00 | 20.43 | O |
| ATOM | 1794 | CB | PRO | A | 235 | 24.756 | 32.771 | 43.575 | 1.00 | 21.58 | C |

TABLE 3-continued

Coordinates for structures 1 to 4

| ATOM | 1795 | CG  | PRO | A | 235 | 25.273 | 33.452 | 44.826 | 1.00 | 20.78 | C |
|------|------|-----|-----|---|-----|--------|--------|--------|------|-------|---|
| ATOM | 1796 | CD  | PRO | A | 235 | 25.941 | 34.685 | 44.317 | 1.00 | 20.56 | C |
| ATOM | 1797 | N   | CYS | A | 236 | 24.905 | 34.173 | 40.663 | 1.00 | 20.46 | N |
| ATOM | 1798 | CA  | CYS | A | 236 | 24.379 | 34.235 | 39.308 | 1.00 | 20.63 | C |
| ATOM | 1799 | C   | CYS | A | 236 | 25.430 | 34.707 | 38.301 | 1.00 | 20.58 | C |
| ATOM | 1800 | O   | CYS | A | 236 | 25.110 | 35.283 | 37.258 | 1.00 | 21.60 | O |
| ATOM | 1801 | CB  | CYS | A | 236 | 23.114 | 35.084 | 39.268 | 1.00 | 20.06 | C |
| ATOM | 1802 | SG  | CYS | A | 236 | 21.824 | 34.377 | 40.326 | 1.00 | 21.70 | S |
| ATOM | 1803 | N   | ASP | A | 237 | 26.693 | 34.474 | 38.629 | 1.00 | 20.17 | N |
| ATOM | 1804 | CA  | ASP | A | 237 | 27.785 | 34.632 | 37.679 | 1.00 | 19.98 | C |
| ATOM | 1805 | C   | ASP | A | 237 | 27.381 | 34.050 | 36.313 | 1.00 | 19.79 | C |
| ATOM | 1806 | O   | ASP | A | 237 | 26.830 | 32.950 | 36.234 | 1.00 | 19.19 | O |
| ATOM | 1807 | CE  | ASP | A | 237 | 28.997 | 33.872 | 38.200 | 1.00 | 19.91 | C |
| ATOM | 1808 | CG  | ASP | A | 237 | 30.209 | 33.968 | 37.290 | 1.00 | 21.43 | C |
| ATOM | 1809 | OD1 | ASP | A | 237 | 30.407 | 35.010 | 36.546 | 1.00 | 18.96 | O |
| ATOM | 1810 | OD2 | ASP | A | 237 | 31.039 | 33.017 | 37.288 | 1.00 | 18.57 | O |
| ATOM | 1811 | N   | ARG | A | 238 | 27.664 | 34.812 | 35.263 | 1.00 | 20.18 | N |
| ATOM | 1812 | CA  | ARG | A | 238 | 27.365 | 34.473 | 33.865 | 1.00 | 21.48 | C |
| ATOM | 1813 | C   | ARG | A | 238 | 25.905 | 34.713 | 33.444 | 1.00 | 20.90 | C |
| ATOM | 1814 | O   | ARG | A | 238 | 25.600 | 34.619 | 32.269 | 1.00 | 21.92 | O |
| ATOM | 1815 | CE  | ARG | A | 238 | 27.765 | 33.024 | 33.531 | 1.00 | 21.70 | C |
| ATOM | 1816 | CG  | ARG | A | 238 | 29.245 | 32.739 | 33.699 | 1.00 | 22.10 | C |
| ATOM | 1817 | CD  | ARG | A | 238 | 29.612 | 31.313 | 33.329 | 1.00 | 23.08 | C |
| ATOM | 1818 | NE  | ARG | A | 238 | 28.988 | 30.409 | 34.278 | 1.00 | 25.97 | N |
| ATOM | 1819 | CZ  | ARG | A | 238 | 27.863 | 29.725 | 34.066 | 1.00 | 27.01 | C |
| ATOM | 1820 | NH1 | ARG | A | 238 | 27.208 | 29.799 | 32.904 | 1.00 | 24.08 | N |
| ATOM | 1821 | NH2 | ARG | A | 238 | 27.399 | 28.949 | 35.036 | 1.00 | 27.47 | N |
| ATOM | 1822 | N   | GLN | A | 239 | 25.021 | 35.028 | 34.375 | 1.00 | 20.56 | N |
| ATOM | 1823 | CA  | GLN | A | 239 | 23.641 | 35.334 | 34.014 | 1.00 | 21.11 | C |
| ATOM | 1824 | C   | GLN | A | 239 | 23.459 | 36.865 | 33.920 | 1.00 | 20.84 | C |
| ATOM | 1825 | O   | GLN | A | 239 | 24.145 | 37.624 | 34.610 | 1.00 | 21.25 | O |
| ATOM | 1826 | CB  | GLN | A | 239 | 22.646 | 34.776 | 35.027 | 1.00 | 20.14 | C |
| ATOM | 1827 | CG  | GLN | A | 239 | 23.052 | 33.505 | 35.726 | 1.00 | 22.87 | C |
| ATOM | 1828 | CD  | GLN | A | 239 | 23.281 | 32.320 | 34.807 | 1.00 | 23.97 | C |
| ATOM | 1829 | OE1 | GLN | A | 239 | 22.367 | 31.842 | 34.132 | 1.00 | 23.63 | O |
| ATOM | 1830 | NE2 | GLN | A | 239 | 24.502 | 31.834 | 34.796 | 1.00 | 24.34 | N |
| ATOM | 1831 | N   | SER | A | 240 | 22.541 | 37.307 | 33.071 | 1.00 | 20.31 | N |
| ATOM | 1832 | CA  | SER | A | 240 | 22.246 | 38.725 | 32.926 | 1.00 | 19.92 | C |
| ATOM | 1833 | C   | SER | A | 240 | 21.448 | 39.218 | 34.119 | 1.00 | 20.07 | C |
| ATOM | 1834 | O   | SER | A | 240 | 20.538 | 38.533 | 34.564 | 1.00 | 19.79 | O |
| ATOM | 1835 | CB  | SER | A | 240 | 21.384 | 38.953 | 31.700 | 1.00 | 19.45 | C |
| ATOM | 1836 | OG  | SER | A | 240 | 21.018 | 40.312 | 31.564 | 1.00 | 20.53 | O |
| ATOM | 1837 | N   | GLN | A | 241 | 21.763 | 40.408 | 34.623 | 1.00 | 19.46 | N |
| ATOM | 1838 | CA  | GLN | A | 241 | 20.962 | 40.988 | 35.701 | 1.00 | 20.32 | C |
| ATOM | 1839 | C   | GLN | A | 241 | 19.657 | 41.569 | 35.175 | 1.00 | 20.51 | C |
| ATOM | 1840 | O   | GLN | A | 241 | 18.808 | 41.956 | 35.959 | 1.00 | 21.06 | .0 |
| ATOM | 1841 | CB  | GLN | A | 241 | 21.697 | 42.141 | 36.417 | 1.00 | 20.15 | C |
| ATOM | 1842 | CG  | GLN | A | 241 | 22.910 | 41.749 | 37.230 | 1.00 | 21.41 | C |
| ATOM | 1843 | CD  | GLN | A | 241 | 23.690 | 42.980 | 37.695 | 1.00 | 22.76 | C |
| ATOM | 1844 | OE1 | GLN | A | 241 | 23.455 | 43.481 | 38.775 | 1.00 | 24.42 | O |
| ATOM | 1845 | NE2 | GLN | A | 241 | 24.585 | 43.465 | 36.871 | 1.00 | 21.93 | N |
| ATOM | 1846 | N   | VAL | A | 242 | 19.489 | 41.678 | 33.862 | 1.00 | 20.66 | N |
| ATOM | 1847 | CA  | VAL | A | 242 | 18.309 | 42.355 | 33.372 | 1.00 | 20.76 | C |
| ATOM | 1848 | C   | VAL | A | 242 | 17.089 | 41.465 | 33.391 | 1.00 | 21.26 | C |
| ATOM | 1849 | O   | VAL | A | 242 | 17.119 | 40.352 | 32.871 | 1.00 | 21.01 | O |
| ATOM | 1850 | CB  | VAL | A | 242 | 18.476 | 42.813 | 31.909 | 1.00 | 20.97 | C |
| ATOM | 1851 | CG1 | VAL | A | 242 | 17.194 | 43.502 | 31.431 | 1.00 | 21.21 | C |
| ATOM | 1852 | CG2 | VAL | A | 242 | 19.687 | 43.704 | 31.716 | 1.00 | 18.95 | C |
| ATOM | 1853 | N   | ASP | A | 243 | 16.001 | 41.960 | 33.958 | 1.00 | 21.16 | N |
| ATOM | 1854 | CA  | ASP | A | 243 | 14.730 | 41.223 | 33.907 | 1.00 | 21.36 | C |
| ATOM | 1855 | C   | ASP | A | 243 | 14.091 | 41.523 | 32.552 | 1.00 | 21.20 | C |
| ATOM | 1856 | O   | ASP | A | 243 | 13.566 | 42.631 | 32.310 | 1.00 | 19.97 | O |
| ATOM | 1857 | CB  | ASP | A | 243 | 13.840 | 41.682 | 35.054 | 1.00 | 21.65 | C |
| ATOM | 1858 | CG  | ASP | A | 243 | 12.474 | 41.051 | 35.037 | 1.00 | 22.45 | C |
| ATOM | 1859 | OD1 | ASP | A | 243 | 12.122 | 40.338 | 34.070 | 1.00 | 25.16 | O |
| ATOM | 1860 | OD2 | ASP | A | 243 | 11.671 | 41.232 | 35.978 | 1.00 | 25.29 | O |
| ATOM | 1861 | N   | PHE | A | 244 | 14.182 | 40.554 | 31.650 | 1.00 | 21.28 | N |
| ATOM | 1862 | CA  | PHE | A | 244 | 13.687 | 40.733 | 30.291 | 1.00 | 21.65 | C |
| ATOM | 1863 | C   | PHE | A | 244 | 12.202 | 41.074 | 30.274 | 1.00 | 22.36 | C |
| ATOM | 1864 | O   | PHE | A | 244 | 11.733 | 41.653 | 29.304 | 1.00 | 22.09 | O |
| ATOM | 1865 | CB  | PHE | A | 244 | 13.915 | 39.478 | 29.442 | 1.00 | 22.22 | C |
| ATOM | 1866 | CG  | PHE | A | 244 | 15.284 | 39.370 | 28.815 | 1.00 | 21.43 | C |
| ATOM | 1867 | CD1 | PHE | A | 244 | 16.414 | 39.800 | 29.465 | 1.00 | 20.12 | C |
| ATOM | 1868 | CD2 | PHE | A | 244 | 15.422 | 38.778 | 27.575 | 1.00 | 21.05 | C |
| ATOM | 1869 | CE1 | PHE | A | 244 | 17.655 | 39.671 | 28.873 | 1.00 | 20.83 | C |
| ATOM | 1870 | CE2 | PHE | A | 244 | 16.645 | 38.643 | 26.993 | 1.00 | 21.47 | C |
| ATOM | 1871 | CZ  | PHE | A | 244 | 17.767 | 39.104 | 27.633 | 1.00 | 20.74 | C |

TABLE 3-continued

| | | | | | | | | | | | |
|---|---|---|---|---|---|---|---|---|---|---|---|
| | | | | | Coordinates for structures 1 to 4 | | | | | | |
| ATOM | 1872 | N | ASP | A | 245 | 11.464 | 40.696 | 31.322 | 1.00 | 23.26 | N |
| ATOM | 1873 | CA | ASP | A | 245 | 10.035 | 40.973 | 31.393 | 1.00 | 24.31 | C |
| ATOM | 1874 | C | ASP | A | 245 | 9.756 | 42.401 | 31.877 | 1.00 | 25.05 | C |
| ATOM | 1875 | O | ASP | A | 245 | 8.679 | 42.916 | 31.646 | 1.00 | 24.27 | O |
| ATOM | 1876 | CB | ASP | A | 245 | 9.333 | 40.004 | 32.348 | 1.00 | 24.79 | C |
| ATOM | 1877 | CG | ASP | A | 245 | 9.397 | 38.571 | 31.887 | 1.00 | 25.46 | C |
| ATOM | 1878 | OD1 | ASP | A | 245 | 9.409 | 38.342 | 30.663 | 1.00 | 27.47 | O |
| ATOM | 1879 | OD2 | ASP | A | 245 | 9.445 | 37.610 | 32.678 | 1.00 | 25.22 | O |
| ATOM | 1880 | N | ASN | A | 246 | 10.702 | 43.006 | 32.589 | 1.00 | 25.30 | N |
| ATOM | 1881 | CA | ASN | A | 246 | 10.531 | 44.365 | 33.099 | 1.00 | 26.37 | C |
| ATOM | 1882 | C | ASN | A | 246 | 11.876 | 45.054 | 33.204 | 1.00 | 25.61 | C |
| ATOM | 1883 | O | ASN | A | 246 | 12.436 | 45.192 | 34.282 | 1.00 | 26.05 | O |
| ATOM | 1884 | CB | ASN | A | 246 | 9.871 | 44.360 | 34.472 | 1.00 | 26.89 | C |
| ATOM | 1885 | CG | ASN | A | 246 | 9.545 | 45.770 | 34.958 | 1.00 | 30.93 | C |
| ATOM | 1886 | CD1 | ASN | A | 246 | 9.353 | 46.701 | 34.150 | 1.00 | 35.10 | O |
| ATOM | 1887 | ND2 | ASN | A | 246 | 9.493 | 45.943 | 36.2B1 | 1.00 | 35.04 | N |
| ATOM | 1888 | N | PRO | A | 247 | 12.415 | 45.450 | 32.068 | 1.00 | 24.71 | N |
| ATOM | 1889 | CA | PRO | A | 247 | 13.775 | 45.979 | 32.026 | 1.00 | 24.24 | C |
| ATOM | 1890 | C | PRO | A | 247 | 13.909 | 47.352 | 32.684 | 1.00 | 24.48 | C |
| ATOM | 1891 | O | PRO | A | 247 | 13.189 | 48.296 | 32.374 | 1.00 | 23.54 | O |
| ATOM | 1892 | CB | PRO | A | 247 | 14.109 | 46.036 | 30.538 | 1.00 | 24.23 | C |
| ATOM | 1893 | CG | PRO | A | 247 | 12.900 | 45.524 | 29.803 | 1.00 | 25.13 | C |
| ATOM | 1894 | CD | PRO | A | 247 | 11.769 | 45.385 | 30.752 | 1.00 | 24.61 | C |
| ATOM | 1895 | N | ASP | A | 248 | 14.867 | 47.437 | 33.593 | 1.00 | 24.04 | N |
| ATOM | 1896 | CA | ASP | A | 248 | 15.140 | 48.656 | 34.285 | 1.00 | 24.53 | C |
| ATOM | 1897 | C | ASP | A | 248 | 16.206 | 49.440 | 33.496 | 1.00 | 24.15 | C |
| ATOM | 1898 | O | ASP | A | 248 | 17.410 | 49.221 | 33.629 | 1.00 | 23.11 | O |
| ATOM | 1899 | CE | ASP | A | 248 | 15.609 | 48.312 | 35.689 | 1.00 | 24.75 | C |
| ATOM | 1900 | CG | ASP | A | 248 | 15.731 | 49.512 | 36.554 | 1.00 | 26.08 | C |
| ATOM | 1901 | OD1 | ASP | A | 248 | 15.956 | 50.616 | 36.009 | 1.00 | 27.08 | O |
| ATOM | 1902 | OD2 | ASP | A | 248 | 15.623 | 49.439 | 37.797 | 1.00 | 30.33 | O |
| ATOM | 1903 | N | TYR | A | 249 | 15.735 | 50.329 | 32.642 | 1.00 | 24.42 | N |
| ATOM | 1904 | CA | TYR | A | 249 | 16.612 | 51.129 | 31.807 | 1.00 | 25.30 | C |
| ATOM | 1905 | C | TYR | A | 249 | 17.462 | 52.136 | 32.589 | 1.00 | 26.13 | C |
| ATOM | 1906 | O | TYR | A | 249 | 18.495 | 52.584 | 32.083 | 1.00 | 26.46 | O |
| ATOM | 1907 | CB | TYR | A | 249 | 15.796 | 51.826 | 30.713 | 1.00 | 25.41 | C |
| ATOM | 1908 | CG | TYR | A | 249 | 15.119 | 50.853 | 29.768 | 1.00 | 22.90 | C |
| ATOM | 1909 | CO1 | TYR | A | 249 | 15.844 | 49.873 | 29.130 | 1.00 | 22.91 | C |
| ATOM | 1910 | CD2 | TYR | A | 249 | 13.760 | 50.923 | 29.519 | 1.00 | 22.21 | C |
| ATOM | 1911 | CE1 | TYR | A | 249 | 15.238 | 48.964 | 28.271 | 1.00 | 22.19 | C |
| ATOM | 1912 | CE2 | TYR | A | 249 | 13.144 | 50.023 | 28.660 | 1.00 | 21.56 | C |
| ATOM | 1913 | CZ | TYR | A | 249 | 13.895 | 49.044 | 28.046 | 1.00 | 21.23 | C |
| ATOM | 1914 | OH | TYR | A | 249 | 13.304 | 48.163 | 27.173 | 1.00 | 23.38 | O |
| ATOM | 1915 | N | GLU | A | 250 | 17.071 | 52.465 | 33.822 | 1.00 | 26.65 | N |
| ATOM | 1916 | CA | GLU | A | 250 | 17.894 | 53.365 | 34.640 | 1.00 | 27.47 | C |
| ATOM | 1917 | C | GLU | A | 250 | 19.161 | 52.651 | 35.086 | 1.00 | 26.52 | C |
| ATOM | 1918 | O | GLU | A | 250 | 20.238 | 53.224 | 35.086 | 1.00 | 27.17 | O |
| ATOM | 1919 | CB | GLU | A | 250 | 17.133 | 53.908 | 35.866 | 1.00 | 27.89 | C |
| ATOM | 1920 | CG | GLU | A | 250 | 15.880 | 54.684 | 35.485 | 1.00 | 32.57 | C |
| ATOM | 1921 | CD | GLU | A | 250 | 15.258 | 55.459 | 36.631 | 1.00 | 37.09 | C |
| ATOM | 1922 | OE1 | GLU | A | 250 | 15.809 | 55.491 | 37.753 | 1.00 | 42.28 | O |
| ATOM | 1923 | OE2 | GLU | A | 250 | 14.198 | 56.055 | 36.399 | 1.00 | 42.29 | O |
| ATOM | 1924 | N | ARG | A | 251 | 19.042 | 51.399 | 35.490 | 1.00 | 25.57 | N |
| ATOM | 1925 | CA | ARG | A | 251 | 20.224 | 50.657 | 35.900 | 1.00 | 24.72 | C |
| ATOM | 1926 | C | ARG | A | 251 | 20.955 | 50.069 | 34.718 | 1.00 | 23.56 | C |
| ATOM | 1927 | O | ARG | A | 251 | 22.150 | 49.919 | 34.769 | 1.00 | 22.92 | O |
| ATOM | 1928 | CE | ARG | A | 251 | 19.845 | 49.520 | 36.845 | 1.00 | 25.64 | C |
| ATOM | 1929 | CG | ARG | A | 251 | 19.435 | 49.957 | 38.255 | 1.00 | 26.79 | C |
| ATOM | 1930 | CD | ARG | A | 251 | 18.858 | 48.815 | 39.123 | 1.00 | 30.01 | C |
| ATOM | 1931 | NE | ARG | A | 251 | 19.900 | 47.875 | 39.540 | 1.00 | 31.06 | N |
| ATOM | 1932 | CZ | ARG | A | 251 | 19.709 | 46.579 | 39.766 | 1.00 | 32.72 | C |
| ATOM | 1933 | NH1 | ARG | A | 251 | 18.508 | 46.029 | 39.628 | 1.00 | 33.10 | N |
| ATOM | 1934 | NH2 | ARG | A | 251 | 20.734 | 45.828 | 40.135 | 1.00 | 33.44 | N |
| ATOM | 1935 | N | PHE | A | 252 | 20.234 | 49.725 | 33.652 | 1.00 | 22.66 | N |
| ATOM | 1936 | CA | PHE | A | 252 | 20.826 | 49.019 | 32.532 | 1.00 | 21.99 | C |
| ATOM | 1937 | C | PHE | A | 252 | 20.521 | 49.719 | 31.198 | 1.00 | 21.71 | C |
| ATOM | 1938 | O | PHE | A | 252 | 19.900 | 49.160 | 30.289 | 1.00 | 21.32 | O |
| ATOM | 1939 | CE | PHE | A | 252 | 20.261 | 47.610 | 32.519 | 1.00 | 22.03 | C |
| ATOM | 1940 | CG | PHE | A | 252 | 20.292 | 46.915 | 33.868 | 1.00 | 21.75 | C |
| ATOM | 1941 | CO1 | PHE | A | 252 | 21.484 | 46.729 | 34.556 | 1.00 | 20.90 | C |
| ATOM | 1942 | CD2 | PHE | A | 252 | 19.124 | 46.402 | 34.423 | 1.00 | 21.94 | C |
| ATOM | 1943 | CE1 | PHE | A | 252 | 21.506 | 46.040 | 35.785 | 1.00 | 20.51 | C |
| ATOM | 1944 | CE2 | PHE | A | 252 | 19.136 | 45.730 | 35.662 | 1.00 | 21.77 | C |
| ATOM | 1945 | CZ | PHE | A | 252 | 20.320 | 45.553 | 36.333 | 1.00 | 21.41 | C |
| ATOM | 1946 | N | PRO | A | 253 | 20.989 | 50.944 | 31.071 | 1.00 | 20.88 | N |
| ATOM | 1947 | CA | PRO | A | 253 | 20.615 | 51.754 | 29.909 | 1.00 | 20.51 | C |
| ATOM | 1948 | C | PRO | A | 253 | 20.956 | 51.077 | 28.578 | 1.00 | 20.47 | C |

TABLE 3-continued

| | | | | | | | | | | |
|---|---|---|---|---|---|---|---|---|---|---|
| ATOM | 1949 | O | PRO | A | 253 | 20.153 | 51.159 | 27.656 | 1.00 | 20.01 | O |
| ATOM | 1950 | CB | PRO | A | 253 | 21.371 | 53.077 | 30.130 | 1.00 | 20.00 | C |
| ATOM | 1951 | CG | PRO | A | 253 | 22.538 | 52.697 | 31.136 | 1.00 | 20.46 | C |
| ATOM | 1952 | CD | PRO | A | 253 | 21.921 | 51.641 | 31.994 | 1.00 | 20.89 | C |
| ATOM | 1953 | N | ASN | A | 254 | 22.088 | 50.393 | 28.455 | 1.00 | 20.68 | N |
| ATOM | 1954 | CA | ASN | A | 254 | 22.401 | 49.805 | 27.160 | 1.00 | 20.72 | C |
| ATOM | 1955 | C | ASN | A | 254 | 21.537 | 48.601 | 26.790 | 1.00 | 20.29 | C |
| ATOM | 1956 | O | ASN | A | 254 | 21.644 | 48.068 | 25.688 | 1.00 | 20.03 | O |
| ATOM | 1957 | CB | ASN | A | 254 | 23.882 | 49.463 | 27.033 | 1.00 | 20.89 | C |
| ATOM | 1958 | CG | ASN | A | 254 | 24.736 | 50.698 | 26.899 | 1.00 | 22.24 | C |
| ATOM | 1959 | OD1 | ASN | A | 254 | 25.532 | 50.999 | 27.785 | 1.00 | 24.48 | O |
| ATOM | 1960 | ND2 | ASN | A | 254 | 24.557 | 51.446 | 25.791 | 1.00 | 22.23 | N |
| ATOM | 1961 | N | PHE | A | 255 | 20.678 | 48.160 | 27.690 | 1.00 | 20.01 | N |
| ATOM | 1962 | CA | PHE | A | 255 | 19.781 | 47.086 | 27.305 | 1.00 | 20.02 | C |
| ATOM | 1963 | C | PHE | A | 255 | 18.855 | 47.599 | 26.185 | 1.00 | 20.33 | C |
| ATOM | 1964 | O | PHE | A | 255 | 18.224 | 46.818 | 25.472 | 1.00 | 19.82 | O |
| ATOM | 1965 | CB | PHE | A | 255 | 18.970 | 46.552 | 28.484 | 1.00 | 19.63 | C |
| ATOM | 1966 | CG | PHE | A | 255 | 18.239 | 45.318 | 28.145 | 1.00 | 18.96 | C |
| ATOM | 1967 | CD1 | PHE | A | 255 | 18.928 | 44.149 | 27.930 | 1.00 | 19.50 | C |
| ATOM | 1968 | CD2 | PHE | A | 255 | 16.889 | 45.335 | 27.942 | 1.00 | 17.83 | C |
| ATOM | 1969 | CE1 | PHE | A | 255 | 18.267 | 42.997 | 27.575 | 1.00 | 20.08 | C |
| ATOM | 1970 | CE2 | PHE | A | 255 | 16.230 | 44.206 | 27.561 | 1.00 | 17.77 | C |
| ATOM | 1971 | CZ | PHE | A | 255 | 16.912 | 43.036 | 27.381 | 1.00 | 21.57 | C |
| ATOM | 1972 | N | GLN | A | 256 | 18.788 | 48.919 | 26.035 | 1.00 | 20.15 | N |
| ATOM | 1973 | CA | GLN | A | 256 | 17.973 | 49.533 | 24.986 | 1.00 | 20.63 | C |
| ATOM | 1974 | C | GLN | A | 256 | 18.594 | 49.343 | 23.591 | 1.00 | 20.12 | C |
| ATOM | 1975 | O | GLN | A | 256 | 17.955 | 49.612 | 22.592 | 1.00 | 19.87 | O |
| ATOM | 1976 | CB | GLN | A | 256 | 17.787 | 51.036 | 25.272 | 1.00 | 20.67 | C |
| ATOM | 1977 | CG | GLN | A | 256 | 16.744 | 51.306 | 26.362 | 1.00 | 22.56 | C |
| ATOM | 1978 | CD | GLN | A | 256 | 16.747 | 52.732 | 26.888 | 1.00 | 22.75 | C |
| ATOM | 1979 | OE1 | GLN | A | 256 | 15.727 | 53.420 | 26.816 | 1.00 | 24.69 | O |
| ATOM | 1980 | NE2 | GLN | A | 256 | 17.873 | 53.172 | 27.419 | 1.00 | 23.90 | N |
| ATOM | 1981 | N | ASN | A | 257 | 19.850 | 48.915 | 23.553 | 1.00 | 20.07 | N |
| ATOM | 1982 | CA | ASN | A | 257 | 20.583 | 48.700 | 22.310 | 1.00 | 20.66 | C |
| ATOM | 1983 | C | ASN | A | 257 | 20.778 | 47.233 | 21.963 | 1.00 | 21.21 | C |
| ATOM | 1984 | O | ASN | A | 257 | 21.446 | 46.921 | 20.979 | 1.00 | 21.28 | O |
| ATOM | 1985 | CB | ASN | A | 257 | 21.975 | 49.300 | 22.420 | 1.00 | 20.31 | C |
| ATOM | 1986 | CG | ASN | A | 257 | 21.937 | 50.757 | 22.776 | 1.00 | 20.83 | C |
| ATOM | 1987 | OD1 | ASN | A | 257 | 22.395 | 51.141 | 23.850 | 1.00 | 20.15 | O |
| ATOM | 1988 | ND2 | ASN | A | 257 | 21.366 | 51.577 | 21.889 | 1.00 | 16.99 | N |
| ATOM | 1989 | N | VAL | A | 258 | 20.218 | 46.333 | 22.758 | 1.00 | 21.91 | N |
| ATOM | 1990 | CA | VAL | A | 258 | 20.440 | 44.908 | 22.532 | 1.00 | 23.55 | C |
| ATOM | 1991 | C | VAL | A | 258 | 19.720 | 44.400 | 21.284 | 1.00 | 24.29 | C |
| ATOM | 1992 | O | VAL | A | 258 | 18.600 | 44.845 | 20.947 | 1.00 | 24.28 | O |
| ATOM | 1993 | CB | VAL | A | 258 | 20.026 | 44.110 | 23.772 | 1.00 | 24.18 | C |
| ATOM | 1994 | CG1 | VAL | A | 258 | 18.529 | 43.868 | 23.785 | 1.00 | 23.69 | C |
| ATOM | 1995 | CG2 | VAL | A | 258 | 20.761 | 42.851 | 23.826 | 1.00 | 28.07 | C |
| ATOM | 1996 | N | VAL | A | 259 | 20.381 | 43.506 | 20.562 | 1.00 | 24.48 | N |
| ATOM | 1997 | CA | VAL | A | 259 | 19.787 | 42.922 | 19.364 | 1.00 | 25.21 | C |
| ATOM | 1998 | C | VAL | A | 259 | 20.104 | 41.427 | 19.331 | 1.00 | 25.19 | C |
| ATOM | 1999 | O | VAL | A | 259 | 21.260 | 41.046 | 19.333 | 1.00 | 25.58 | O |
| ATOM | 2000 | CB | VAL | A | 259 | 20.345 | 43.551 | 18.094 | 1.00 | 25.37 | C |
| ATOM | 2001 | CG1 | VAL | A | 259 | 19.726 | 42.893 | 16.882 | 1.00 | 27.15 | C |
| ATOM | 2002 | CG2 | VAL | A | 259 | 20.074 | 45.059 | 18.066 | 1.00 | 25.97 | C |
| ATOM | 2003 | N | GLY | A | 260 | 19.068 | 40.603 | 19.308 | 1.00 | 25.20 | N |
| ATOM | 2004 | CA | GLY | A | 260 | 19.214 | 39.161 | 19.312 | 1.00 | 25.52 | C |
| ATOM | 2005 | C | GLY | A | 260 | 19.108 | 38.433 | 17.961 | 1.00 | 25.26 | C |
| ATOM | 2006 | O | GLY | A | 260 | 18.762 | 39.016 | 16.914 | 1.00 | 24.66 | O |
| ATOM | 2007 | N | TYR | A | 261 | 19.484 | 37.160 | 18.015 | 1.00 | 24.49 | N |
| ATOM | 2008 | CA | TYR | A | 261 | 19.379 | 36.217 | 16.925 | 1.00 | 25.05 | C |
| ATOM | 2009 | C | TYR | A | 261 | 18.435 | 35.145 | 17.475 | 1.00 | 24.39 | C |
| ATOM | 2010 | O | TYR | A | 261 | 18.671 | 34.620 | 18.552 | 1.00 | 23.82 | O |
| ATOM | 2011 | CB | TYR | A | 261 | 20.730 | 35.574 | 16.627 | 1.00 | 25.82 | C |
| ATOM | 2012 | CG | TYR | A | 261 | 21.748 | 36.476 | 15.965 | 1.00 | 28.98 | C |
| ATOM | 2013 | CD1 | TYR | A | 261 | 21.804 | 36.598 | 14.585 | 1.00 | 35.41 | C |
| ATOM | 2014 | CD2 | TYR | A | 261 | 22.649 | 37.194 | 16.712 | 1.00 | 29.78 | C |
| ATOM | 2015 | CE1 | TYR | A | 261 | 22.737 | 37.429 | 13.976 | 1.00 | 35.73 | C |
| ATOM | 2016 | CE2 | TYR | A | 261 | 23.592 | 37.994 | 16.126 | 1.00 | 32.54 | C |
| ATOM | 2017 | CZ | TYR | A | 261 | 23.643 | 38.116 | 14.768 | 1.00 | 35.98 | C |
| ATOM | 2018 | OH | TYR | A | 261 | 24.580 | 38.959 | 14.202 | 1.00 | 38.02 | O |
| ATOM | 2019 | N | GLU | A | 262 | 17.353 | 34.823 | 16.790 | 1.00 | 24.04 | N |
| ATOM | 2020 | CA | GLU | A | 262 | 16.432 | 33.860 | 17.387 | 1.00 | 23.96 | C |
| ATOM | 2021 | C | GLU | A | 262 | 15.992 | 32.773 | 16.435 | 1.00 | 23.90 | C |
| ATOM | 2022 | O | GLU | A | 262 | 16.116 | 32.890 | 15.213 | 1.00 | 23.56 | O |
| ATOM | 2023 | CB | GLU | A | 262 | 15.224 | 34.553 | 18.020 | 1.00 | 23.70 | C |
| ATOM | 2024 | CG | GLU | A | 262 | 14.029 | 34.782 | 17.127 | 1.00 | 24.33 | C |
| ATOM | 2025 | CD | GLU | A | 262 | 12.829 | 35.382 | 17.870 | 1.00 | 26.49 | C |

TABLE 3-continued

Coordinates for structures 1 to 4

| ATOM | 2026 | OE1 | GLU | A | 262 | 12.753 | 36.611 | 18.029 | 1.00 | 27.38 | O |
|---|---|---|---|---|---|---|---|---|---|---|---|
| ATOM | 2027 | OE2 | GLU | A | 262 | 11.946 | 34.631 | 18.306 | 1.00 | 28.26 | O |
| ATOM | 2028 | N | THR | A | 263 | 15.485 | 31.713 | 17.034 | 1.00 | 23.68 | N |
| ATOM | 2029 | CA | THR | A | 263 | 14.974 | 30.605 | 16.279 | 1.00 | 24.40 | C |
| ATOM | 2030 | C | THR | A | 263 | 14.091 | 29.786 | 17.193 | 1.00 | 24.29 | C |
| ATOM | 2031 | O | THR | A | 263 | 14.131 | 29.936 | 18.423 | 1.00 | 24.53 | O |
| ATOM | 2032 | CE | THR | A | 263 | 16.148 | 29.762 | 15.751 | 1.00 | 24.52 | C |
| ATOM | 2033 | OG1 | THR | A | 263 | 15.684 | 28.839 | 14.762 | 1.00 | 24.43 | O |
| ATOM | 2034 | CG2 | THR | A | 263 | 16.737 | 28.876 | 16.854 | 1.00 | 24.33 | C |
| ATOM | 2035 | N | VAL | A | 264 | 13.263 | 28.954 | 16.593 | 1.00 | 23.62 | N |
| ATOM | 2036 | CA | VAL | A | 264 | 12.500 | 28.019 | 17.370 | 1.00 | 24.01 | C |
| ATOM | 2037 | C | VAL | A | 264 | 12.936 | 26.627 | 16.935 | 1.00 | 24.53 | C |
| ATOM | 2038 | O | VAL | A | 264 | 12.879 | 26.291 | 15.768 | 1.00 | 24.27 | O |
| ATOM | 2039 | CE | VAL | A | 264 | 11.008 | 28.194 | 17.177 | 1.00 | 24.69 | C |
| ATOM | 2040 | CG1 | VAL | A | 264 | 10.256 | 26.958 | 17.712 | 1.00 | 23.69 | C |
| ATOM | 2041 | CG2 | VAL | A | 264 | 10.520 | 29.526 | 17.857 | 1.00 | 23.81 | C |
| ATOM | 2042 | N | VAL | A | 265 | 13.450 | 25.844 | 17.872 | 1.00 | 24.91 | N |
| ATOM | 2043 | CA | VAL | A | 265 | 13.833 | 24.484 | 17.540 | 1.00 | 24.93 | C |
| ATOM | 2044 | C | VAL | A | 265 | 12.792 | 23.470 | 17.967 | 1.00 | 24.20 | C |
| ATOM | 2045 | O | VAL | A | 265 | 12.167 | 23.617 | 19.018 | 1.00 | 24.01 | O |
| ATOM | 2046 | CE | VAL | A | 265 | 15.196 | 24.072 | 18.173 | 1.00 | 25.05 | C |
| ATOM | 2047 | CG1 | VAL | A | 265 | 16.291 | 24.884 | 17.557 | 1.00 | 26.38 | C |
| ATOM | 2048 | CG2 | VAL | A | 265 | 15.190 | 24.164 | 19.702 | 1.00 | 23.59 | C |
| ATOM | 2049 | N | GLY | A | 266 | 12.641 | 22.439 | 17.144 | 1.00 | 23.26 | N |
| ATOM | 2050 | CA | GLY | A | 266 | 11.776 | 21.316 | 17.451 | 1.00 | 23.22 | C |
| ATOM | 2051 | C | GLY | A | 266 | 12.467 | 19.961 | 17.359 | 1.00 | 22.26 | C |
| ATOM | 2052 | O | GLY | A | 266 | 13.661 | 19.872 | 17.131 | 1.00 | 22.37 | O |
| ATOM | 2053 | N | PRO | A | 267 | 11.712 | 18.884 | 17.524 | 1.00 | 21.90 | N |
| ATOM | 2054 | CA | PRO | A | 267 | 12.305 | 17.544 | 17.479 | 1.00 | 21.60 | C |
| ATOM | 2055 | C | PRO | A | 267 | 13.206 | 17.355 | 16.280 | 1.00 | 20.82 | C |
| ATOM | 2056 | O | PRO | A | 267 | 12.768 | 17.588 | 15.169 | 1.00 | 20.29 | C |
| ATOM | 2057 | CE | PRO | A | 267 | 11.086 | 16.622 | 17.364 | 1.00 | 21.36 | C |
| ATOM | 2058 | CG | PRO | A | 267 | 10.023 | 17.330 | 18.028 | 1.00 | 23.23 | C |
| ATOM | 2059 | CD | PRO | A | 267 | 10.254 | 18.831 | 17.753 | 1.00 | 21.99 | C |
| ATOM | 2060 | N | GLY | A | 268 | 14.445 | 16.938 | 16.496 | 1.00 | 20.81 | N |
| ATOM | 2061 | CA | GLY | A | 268 | 15.340 | 16.674 | 15.383 | 1.00 | 20.31 | C |
| ATOM | 2062 | C | GLY | A | 268 | 16.296 | 17.806 | 15.111 | 1.00 | 20.37 | C |
| ATOM | 2063 | O | GLY | A | 268 | 17.333 | 17.605 | 14.476 | 1.00 | 21.79 | O |
| ATOM | 2064 | N | ASP | A | 269 | 15.975 | 19.002 | 15.582 | 1.00 | 19.89 | N |
| ATOM | 2065 | CA | ASP | A | 269 | 16.849 | 20.141 | 15.364 | 1.00 | 19.78 | C |
| ATOM | 2066 | C | ASP | A | 269 | 17.991 | 20.162 | 16.395 | 1.00 | 19.63 | C |
| ATOM | 2067 | O | ASP | A | 269 | 17.829 | 19.729 | 17.551 | 1.00 | 18.28 | O |
| ATOM | 2068 | CE | ASP | A | 269 | 16.069 | 21.436 | 15.532 | 1.00 | 20.34 | C |
| ATOM | 2069 | CG | ASP | A | 269 | 14.976 | 21.636 | 14.500 | 1.00 | 20.66 | C |
| ATOM | 2070 | OD1 | ASP | A | 269 | 14.977 | 21.015 | 13.419 | 1.00 | 22.15 | O |
| ATOM | 2071 | OD2 | ASP | A | 269 | 14.072 | 22.454 | 14.703 | 1.00 | 23.30 | O |
| ATOM | 2072 | N | VAL | A | 270 | 19.129 | 20.681 | 15.953 | 1.00 | 19.76 | N |
| ATOM | 2073 | CA | VAL | A | 270 | 20.304 | 20.879 | 16.782 | 1.00 | 20.24 | C |
| ATOM | 2074 | C | VAL | A | 270 | 20.793 | 22.318 | 16.601 | 1.00 | 19.84 | C |
| ATOM | 2075 | O | VAL | A | 270 | 21.052 | 22.754 | 15.487 | 1.00 | 19.90 | O |
| ATOM | 2076 | CB | VAL | A | 270 | 21.421 | 19.942 | 16.377 | 1.00 | 20.08 | C |
| ATOM | 2077 | CG1 | VAL | A | 270 | 22.676 | 20.288 | 17.121 | 1.00 | 21.38 | C |
| ATOM | 2078 | CG2 | VAL | A | 270 | 21.017 | 18.521 | 16.671 | 1.00 | 21.15 | C |
| ATOM | 2079 | N | LEU | A | 271 | 20.885 | 23.056 | 17.699 | 1.00 | 19.86 | N |
| ATOM | 2080 | CA | LEU | A | 271 | 21.341 | 24.427 | 17.656 | 1.00 | 20.03 | C |
| ATOM | 2081 | C | LEU | A | 271 | 22.757 | 24.465 | 18.202 | 1.00 | 20.23 | C |
| ATOM | 2082 | O | LEU | A | 271 | 23.032 | 23.946 | 19.276 | 1.00 | 19.73 | O |
| ATOM | 2083 | CB | LEU | A | 271 | 20.429 | 25.328 | 18.465 | 1.00 | 20.59 | C |
| ATOM | 2084 | CG | LEU | A | 271 | 20.934 | 26.742 | 18.724 | 1.00 | 20.93 | C |
| ATOM | 2085 | CD1 | LEU | A | 271 | 21.011 | 27.562 | 17.431 | 1.00 | 20.35 | C |
| ATOM | 2086 | CD2 | LEU | A | 271 | 20.039 | 27.428 | 19.728 | 1.00 | 22.31 | C |
| ATOM | 2087 | N | TYR | A | 272 | 23.669 | 25.024 | 17.416 | 1.00 | 20.58 | N |
| ATOM | 2088 | CA | TYR | A | 272 | 25.010 | 25.229 | 17.883 | 1.00 | 20.58 | C |
| ATOM | 2089 | C | TYR | A | 272 | 24.985 | 26.535 | 18.653 | 1.00 | 20.69 | C |
| ATOM | 2090 | O | TYR | A | 272 | 24.692 | 27.576 | 18.089 | 1.00 | 21.54 | O |
| ATOM | 2091 | CB | TYR | A | 272 | 26.004 | 25.312 | 16.728 | 1.00 | 20.30 | C |
| ATOM | 2092 | CG | TYR | A | 272 | 27.381 | 25.776 | 17.158 | 1.00 | 21.24 | C |
| ATOM | 2093 | CD1 | TYR | A | 272 | 27.997 | 25.250 | 18.275 | 1.00 | 21.70 | C |
| ATOM | 2094 | CD2 | TYR | A | 272 | 28.039 | 26.788 | 16.472 | 1.00 | 22.21 | C |
| ATOM | 2095 | CE1 | TYR | A | 272 | 29.232 | 25.692 | 18.674 | 1.00 | 21.69 | C |
| ATOM | 2096 | CE2 | TYR | A | 272 | 29.275 | 27.215 | 16.857 | 1.00 | 22.99 | C |
| ATOM | 2097 | CZ | TYR | A | 272 | 29.868 | 26.672 | 17.961 | 1.00 | 22.01 | C |
| ATOM | 2098 | OH | TYR | A | 272 | 31.109 | 27.111 | 18.352 | 1.00 | 22.77 | O |
| ATOM | 2099 | N | ILE | A | 273 | 25.216 | 26.454 | 19.951 | 1.00 | 21.22 | N |
| ATOM | 2100 | CA | ILE | A | 273 | 25.362 | 27.629 | 20.805 | 1.00 | 21.49 | C |
| ATOM | 2101 | C | ILE | A | 273 | 26.852 | 27.809 | 21.117 | 1.00 | 22.00 | C |
| ATOM | 2102 | O | ILE | A | 273 | 27.413 | 27.112 | 21.962 | 1.00 | 22.55 | O |

TABLE 3-continued

Coordinates for structures 1 to 4

| ATOM | 2103 | CB | ILE | A | 273 | 24.607 | 27.471 | 22.073 | 1.00 | 21.14 | C |
|---|---|---|---|---|---|---|---|---|---|---|---|
| ATOM | 2104 | CG1 | ILE | A | 273 | 23.148 | 27.132 | 21.776 | 1.00 | 21.68 | C |
| ATOM | 2105 | CG2 | ILE | A | 273 | 24.661 | 28.791 | 22.854 | 1.00 | 21.75 | C |
| ATOM | 2106 | CD1 | ILE | A | 273 | 22.318 | 26.972 | 23.026 | 1.00 | 21.44 | C |
| ATOM | 2107 | N | PRO | A | 274 | 27.493 | 28.723 | 20.413 | 1.00 | 21.86 | N |
| ATOM | 2108 | CA | PRO | A | 274 | 28.929 | 28.916 | 20.557 | 1.00 | 22.49 | C |
| ATOM | 2109 | C | PRO | A | 274 | 29.278 | 29.462 | 21.926 | 1.00 | 22.77 | C |
| ATOM | 2110 | O | PRO | A | 274 | 28.510 | 30.231 | 22.521 | 1.00 | 21.72 | O |
| ATOM | 2111 | CB | PRO | A | 274 | 29.305 | 29.908 | 19.429 | 1.00 | 23.00 | C |
| ATOM | 2112 | CG | PRO | A | 274 | 28.022 | 30.225 | 18.658 | 1.00 | 23.03 | C |
| ATOM | 2113 | CD | PRO | A | 274 | 26.889 | 29.582 | 19.398 | 1.00 | 22.21 | C |
| ATOM | 2114 | N | MET | A | 275 | 30.441 | 29.028 | 22.404 | 1.00 | 22.72 | N |
| ATOM | 2115 | CA | MET | A | 275 | 30.962 | 29.403 | 23.702 | 1.00 | 23.40 | C |
| ATOM | 2116 | C | MET | A | 275 | 30.949 | 30.921 | 23.864 | 1.00 | 22.42 | C |
| ATOM | 2117 | O | MET | A | 275 | 31.282 | 31.636 | 22.937 | 1.00 | 20.73 | O |
| ATOM | 2118 | CB | MET | A | 275 | 32.373 | 28.856 | 23.826 | 1.00 | 23.99 | C |
| ATOM | 2119 | CG | MET | A | 275 | 32.933 | 28.944 | 25.203 | 1.00 | 28.99 | C |
| ATOM | 2120 | SD | MET | A | 275 | 34.517 | 28.083 | 25.337 | 1.00 | 35.05 | S |
| ATOM | 2121 | CE | MET | A | 275 | 35.287 | 28.525 | 23.832 | 1.00 | 31.30 | C |
| ATOM | 2122 | N | TYR | A | 276 | 30.509 | 31.388 | 25.030 | 1.00 | 22.30 | N |
| ATOM | 2123 | CA | TYR | A | 276 | 30.419 | 32.831 | 25.349 | 1.00 | 23.06 | C |
| ATOM | 2124 | C | TYR | A | 276 | 29.221 | 33.543 | 24.752 | 1.00 | 22.11 | C |
| ATOM | 2125 | O | TYR | A | 276 | 29.012 | 34.705 | 25.041 | 1.00 | 21.84 | O |
| ATOM | 2126 | CB | TYR | A | 276 | 31.673 | 33.594 | 24.934 | 1.00 | 23.42 | C |
| ATOM | 2127 | CG | TYR | A | 276 | 32.857 | 33.283 | 25.796 | 1.00 | 28.51 | C |
| ATOM | 2128 | CD1 | TYR | A | 276 | 32.969 | 33.799 | 27.072 | 1.00 | 33.00 | C |
| ATOM | 2129 | CD2 | TYR | A | 276 | 33.876 | 32.460 | 25.321 | 1.00 | 34.41 | C |
| ATOM | 2130 | CE1 | TYR | A | 276 | 34.066 | 33.490 | 27.877 | 1.00 | 36.36 | C |
| ATOM | 2131 | CE2 | TYR | A | 276 | 34.968 | 32.151 | 26.102 | 1.00 | 36.45 | C |
| ATOM | 2132 | CZ | TYR | A | 276 | 35.059 | 32.651 | 27.371 | 1.00 | 37.63 | C |
| ATOM | 2133 | OH | TYR | A | 276 | 36.192 | 32.314 | 28.077 | 1.00 | 40.88 | O |
| ATOM | 2134 | N | TRP | A | 277 | 28.455 | 32.878 | 23.906 | 1.00 | 20.75 | N |
| ATOM | 2135 | CA | TRP | A | 277 | 27.272 | 33.528 | 23.360 | 1.00 | 20.85 | C |
| ATOM | 2136 | C | TRP | A | 277 | 26.173 | 33.482 | 24.372 | 1.00 | 20.33 | C |
| ATOM | 2137 | O | TRP | A | 277 | 25.907 | 32.431 | 24.949 | 1.00 | 20.72 | O |
| ATOM | 2138 | CB | TRP | A | 277 | 26.791 | 32.874 | 22.068 | 1.00 | 20.13 | C |
| ATOM | 2139 | CG | TRP | A | 277 | 27.552 | 33.323 | 20.879 | 1.00 | 19.28 | C |
| ATOM | 2140 | CD1 | TRP | A | 277 | 28.887 | 33.175 | 20.673 | 1.00 | 21.27 | C |
| ATOM | 2141 | CD2 | TRP | A | 277 | 27.042 | 33.995 | 19.730 | 1.00 | 20.60 | C |
| ATOM | 2142 | ME1 | TRP | A | 277 | 29.246 | 33.721 | 19.467 | 1.00 | 21.05 | N |
| ATOM | 2143 | CE2 | TRP | A | 277 | 28.128 | 34.232 | 18.864 | 1.00 | 21.04 | C |
| ATOM | 2144 | CE3 | TRP | A | 277 | 25.780 | 34.456 | 19.352 | 1.00 | 21.08 | C |
| ATOM | 2145 | CZ2 | TRP | A | 277 | 27.989 | 34.893 | 17.643 | 1.00 | 20.38 | C |
| ATOM | 2146 | CZ3 | TRP | A | 277 | 25.641 | 35.110 | 18.122 | 1.00 | 20.48 | C |
| ATOM | 2147 | CH2 | TRP | A | 277 | 26.736 | 35.306 | 17.288 | 1.00 | 21.03 | C |
| ATOM | 2148 | N | TRP | A | 278 | 25.572 | 34.632 | 24.629 | 1.00 | 19.39 | N |
| ATOM | 2149 | CA | TRP | A | 278 | 24.430 | 34.711 | 25.521 | 1.00 | 19.80 | C |
| ATOM | 2150 | C | TRP | A | 278 | 23.243 | 33.927 | 24.927 | 1.00 | 20.18 | C |
| ATOM | 2151 | O | TRP | A | 278 | 23.019 | 33.939 | 23.732 | 1.00 | 21.04 | O |
| ATOM | 2152 | CB | TRP | A | 278 | 23.989 | 36.168 | 25.646 | 1.00 | 20.39 | C |
| ATOM | 2153 | CG | TRP | A | 278 | 24.979 | 37.031 | 26.300 | 1.00 | 21.20 | C |
| ATOM | 2154 | OD1 | TRP | A | 278 | 26.022 | 37.672 | 25.720 | 1.00 | 21.06 | C |
| ATOM | 2155 | CD2 | TRP | A | 278 | 25.056 | 37.301 | 27.691 | 1.00 | 20.38 | C |
| ATOM | 2156 | ME1 | TRP | A | 278 | 26.725 | 38.369 | 26.668 | 1.00 | 22.44 | N |
| ATOM | 2157 | CE2 | TRP | A | 278 | 26.139 | 38.155 | 27.891 | 1.00 | 21.86 | C |
| ATOM | 2158 | CE3 | TRP | A | 278 | 24.282 | 36.937 | 28.789 | 1.00 | 21.09 | C |
| ATOM | 2159 | CZ2 | TRP | A | 278 | 26.480 | 38.640 | 29.147 | 1.00 | 21.13 | C |
| ATOM | 2160 | CZ3 | TRP | A | 278 | 24.623 | 37.412 | 30.019 | 1.00 | 23.38 | C |
| ATOM | 2161 | CR2 | TRP | A | 278 | 25.704 | 38.258 | 30.194 | 1.00 | 21.06 | C |
| ATOM | 2162 | N | HIS | A | 279 | 22.465 | 33.278 | 25.761 | 1.00 | 20.76 | N |
| ATOM | 2163 | CA | HIS | A | 279 | 21.262 | 32.646 | 25.294 | 1.00 | 21.56 | C |
| ATOM | 2164 | C | HIS | A | 279 | 20.198 | 32.659 | 26.361 | 1.00 | 21.24 | C |
| ATOM | 2165 | O | HIS | A | 279 | 20.475 | 32.456 | 27.540 | 1.00 | 21.63 | O |
| ATOM | 2166 | CB | HIS | A | 279 | 21.501 | 31.203 | 24.819 | 1.00 | 21.83 | C |
| ATOM | 2167 | CG | HIS | A | 279 | 22.342 | 30.379 | 25.738 | 1.00 | 23.50 | C |
| ATOM | 2168 | ND1 | HIS | A | 279 | 23.713 | 30.494 | 25.785 | 1.00 | 24.98 | N |
| ATOM | 2169 | CD2 | HIS | A | 279 | 22.017 | 29.385 | 26.602 | 1.00 | 26.21 | C |
| ATOM | 2170 | CE1 | HIS | A | 279 | 24.200 | 29.599 | 26.628 | 1.00 | 26.46 | C |
| ATOM | 2171 | ND2 | HIS | A | 279 | 23.192 | 28.927 | 27.158 | 1.00 | 25.14 | N |
| ATOM | 2172 | N | HIS | A | 280 | 18.994 | 32.900 | 25.874 | 1.00 | 21.71 | N |
| ATOM | 2173 | CA | HIS | A | 280 | 17.736 | 32.956 | 26.602 | 1.00 | 21.78 | C |
| ATOM | 2174 | C | HIS | A | 280 | 16.890 | 31.860 | 25.951 | 1.00 | 21.70 | C |
| ATOM | 2175 | O | HIS | A | 280 | 16.722 | 31.846 | 24.736 | 1.00 | 21.40 | O |
| ATOM | 2176 | CB | HIS | A | 280 | 17.104 | 34.322 | 26.374 | 1.00 | 21.20 | C |
| ATOM | 2177 | CG | HIS | A | 280 | 15.642 | 34.367 | 26.626 | 1.00 | 21.64 | C |
| ATOM | 2178 | ND1 | HIS | A | 280 | 15.100 | 35.028 | 27.705 | 1.00 | 22.67 | N |
| ATOM | 2179 | CD2 | HIS | A | 280 | 14.600 | 33.826 | 25.951 | 1.00 | 23.33 | C |

TABLE 3-continued

| | | | | | | | | | | |
|---|---|---|---|---|---|---|---|---|---|---|
| | | | | Coordinates for structures 1 to 4 | | | | | | |
| ATOM | 2180 | CE1 | HIS | A | 280 | 13.786 | 34.891 | 27.684 | 1.00 | 23.20 | C |
| ATOM | 2181 | ND2 | HIS | A | 280 | 13.457 | 34.158 | 26.635 | 1.00 | 23.30 | N |
| ATOM | 2182 | N | ILE | A | 281 | 16.368 | 30.934 | 26.733 | 1.00 | 22.98 | N |
| ATOM | 2183 | CA | ILE | A | 281 | 15.658 | 29.779 | 26.158 | 1.00 | 23.36 | C |
| ATOM | 2184 | C | ILE | A | 281 | 14.313 | 29.606 | 26.800 | 1.00 | 23.58 | C |
| ATOM | 2185 | O | ILE | A | 281 | 14.209 | 29.592 | 28.014 | 1.00 | 23.63 | O |
| ATOM | 2186 | CB | ILE | A | 281 | 16.512 | 28.525 | 26.301 | 1.00 | 23.87 | C |
| ATOM | 2187 | CG1 | ILE | A | 281 | 17.771 | 28.675 | 25.435 | 1.00 | 25.77 | C |
| ATOM | 2188 | CG2 | ILE | A | 281 | 15.748 | 27.261 | 25.863 | 1.00 | 23.54 | C |
| ATOM | 2189 | CD1 | ILE | A | 281 | 18.752 | 27.659 | 25.690 | 1.00 | 29.36 | C |
| ATOM | 2190 | N | GLU | A | 282 | 13.268 | 29.510 | 25.982 | 1.00 | 23.92 | N |
| ATOM | 2191 | CA | GLU | A | 282 | 11.923 | 29.337 | 26.525 | 1.00 | 24.26 | C |
| ATOM | 2192 | C | GLU | A | 282 | 11.113 | 28.234 | 25.834 | 1.00 | 23.82 | C |
| ATOM | 2193 | O | GLU | A | 282 | 11.115 | 28.107 | 24.606 | 1.00 | 24.00 | O |
| ATOM | 2194 | CB | GLU | A | 282 | 11.166 | 30.681 | 26.490 | 1.00 | 24.35 | C |
| ATOM | 2195 | CG | GLU | A | 282 | 10.887 | 31.249 | 25.112 | 1.00 | 25.59 | C |
| ATOM | 2196 | CD | GLU | A | 282 | 10.320 | 32.668 | 25.168 | 1.00 | 25.45 | C |
| ATOM | 2197 | OE1 | GLU | A | 282 | 10.861 | 33.494 | 25.929 | 1.00 | 26.04 | O |
| ATOM | 2198 | OE2 | GLU | A | 282 | 9.332 | 32.954 | 24.451 | 1.00 | 25.08 | O |
| ATOM | 2199 | N | SER | A | 283 | 10.460 | 27.419 | 26.648 | 1.00 | 23.28 | N |
| ATOM | 2200 | CA | SER | A | 283 | 9.573 | 26.373 | 26.166 | 1.00 | 23.66 | C |
| ATOM | 2201 | C | SER | A | 283 | 8.257 | 27.054 | 25.787 | 1.00 | 23.86 | C |
| ATOM | 2202 | O | SER | A | 283 | 7.678 | 27.780 | 26.593 | 1.00 | 23.20 | O |
| ATOM | 2203 | CB | SER | A | 283 | 9.341 | 25.321 | 27.247 | 1.00 | 23.36 | C |
| ATOM | 2204 | OG | SER | A | 283 | 10.473 | 24.497 | 27.401 | 1.00 | 23.30 | O |
| ATOM | 2205 | N | LEU | A | 284 | 7.792 | 26.837 | 24.564 | 1.00 | 24.56 | N |
| ATOM | 2206 | CA | LEU | A | 284 | 6.626 | 27.583 | 24.084 | 1.00 | 25.62 | C |
| ATOM | 2207 | C | LEU | A | 284 | 5.401 | 27.487 | 25.004 | 1.00 | 25.52 | C |
| ATOM | 2208 | O | LEU | A | 284 | 5.114 | 26.431 | 25.589 | 1.00 | 24.71 | O |
| ATOM | 2209 | CB | LEU | A | 284 | 6.237 | 27.157 | 22.680 | 1.00 | 25.64 | C |
| ATOM | 2210 | CG | LEU | A | 284 | 7.274 | 27.308 | 21.576 | 1.00 | 27.12 | C |
| ATOM | 2211 | CD1 | LEU | A | 284 | 6.591 | 27.546 | 20.242 | 1.00 | 28.93 | C |
| ATOM | 2212 | CD2 | LEU | A | 284 | 8.248 | 28.364 | 21.851 | 1.00 | 27.08 | C |
| ATOM | 2213 | N | LEU | A | 285 | 4.713 | 28.615 | 25.144 | 1.00 | 25.85 | N |
| ATOM | 2214 | CA | LEU | A | 285 | 3.490 | 28.676 | 25.942 | 1.00 | 26.84 | C |
| ATOM | 2215 | C | LEU | A | 285 | 2.507 | 27.691 | 25.345 | 1.00 | 27.10 | C |
| ATOM | 2216 | O | LEU | A | 285 | 2.424 | 27.565 | 24.139 | 1.00 | 27.10 | O |
| ATOM | 2217 | CB | LEU | A | 285 | 2.875 | 30.071 | 25.906 | 1.00 | 26.48 | C |
| ATOM | 2218 | CG | LEU | A | 285 | 3.709 | 31.225 | 26.438 | 1.00 | 27.70 | C |
| ATOM | 2219 | CD1 | LEU | A | 285 | 3.075 | 32.554 | 26.026 | 1.00 | 28.22 | C |
| ATOM | 2220 | CD2 | LEU | A | 285 | 3.845 | 31.125 | 27.928 | 1.00 | 28.39 | C |
| ATOM | 2221 | N | ASN | A | 286 | 1.779 | 26.987 | 26.196 | 1.00 | 27.81 | N |
| ATOM | 2222 | CA | ASN | A | 286 | 0.790 | 26.007 | 25.753 | 1.00 | 28.27 | C |
| ATOM | 2223 | C | ASN | A | 286 | 1.313 | 24.977 | 24.744 | 1.00 | 27.42 | C |
| ATOM | 2224 | O | ASN | A | 286 | 0.555 | 24.481 | 23.922 | 1.00 | 26.50 | O |
| ATOM | 2225 | CB | ASN | A | 286 | 0.417 | 26.741 | 25.160 | 1.00 | 29.08 | C |
| ATOM | 2226 | CG | ASN | A | 286 | 0.931 | 27.846 | 26.078 | 1.00 | 32.15 | C |
| ATOM | 2227 | OD1 | ASN | A | 286 | 1.484 | 27.577 | 27.154 | 1.00 | 34.93 | O |
| ATOM | 2228 | ND2 | ASN | A | 286 | 0.725 | 29.099 | 25.670 | 1.00 | 35.91 | N |
| ATOM | 2229 | N | GLY | A | 287 | 2.608 | 24.672 | 24.799 | 1.00 | 26.54 | N |
| ATOM | 2230 | CA | GLY | A | 287 | 3.201 | 23.727 | 23.879 | 1.00 | 25.64 | C |
| ATOM | 2231 | C | GLY | A | 287 | 3.474 | 22.371 | 24.497 | 1.00 | 25.01 | C |
| ATOM | 2232 | O | GLY | A | 287 | 4.031 | 21.502 | 23.829 | 1.00 | 24.77 | O |
| ATOM | 2233 | N | GLY | A | 288 | 3.110 | 22.187 | 25.766 | 1.00 | 24.43 | N |
| ATOM | 2234 | CA | GLY | A | 288 | 3.357 | 20.922 | 26.455 | 1.00 | 23.99 | C |
| ATOM | 2235 | C | GLY | A | 288 | 4.804 | 20.844 | 26.935 | 1.00 | 24.11 | C |
| ATOM | 2236 | O | GLY | A | 288 | 5.546 | 21.810 | 26.786 | 1.00 | 22.82 | O |
| ATOM | 2237 | N | ILE | A | 289 | 5.211 | 19.695 | 27.472 | 1.00 | 23.99 | N |
| ATOM | 2238 | CA | ILE | A | 289 | 6.550 | 19.522 | 28.000 | 1.00 | 24.69 | C |
| ATOM | 2239 | C | ILE | A | 289 | 7.605 | 19.496 | 26.900 | 1.00 | 24.25 | C |
| ATOM | 2240 | O | ILE | A | 289 | 7.350 | 19.092 | 25.774 | 1.00 | 25.20 | O |
| ATOM | 2241 | CB | ILE | A | 289 | 6.691 | 18.234 | 28.836 | 1.00 | 25.39 | C |
| ATOM | 2242 | CG1 | ILE | A | 289 | 6.702 | 17.006 | 27.941 | 1.00 | 27.43 | C |
| ATOM | 2243 | CG2 | ILE | A | 289 | 5.613 | 18.151 | 29.921 | 1.00 | 26.30 | C |
| ATOM | 2244 | CD1 | ILE | A | 289 | 7.255 | 15.752 | 28.650 | 1.00 | 30.57 | C |
| ATOM | 2245 | N | THR | A | 290 | 8.808 | 19.912 | 27.267 | 1.00 | 23.28 | N |
| ATOM | 2246 | CA | THR | A | 290 | 9.908 | 19.908 | 26.334 | 1.00 | 22.12 | C |
| ATOM | 2247 | C | THR | A | 290 | 11.008 | 18.984 | 26.824 | 1.00 | 21.52 | C |
| ATOM | 2248 | O | THR | A | 290 | 11.193 | 18.789 | 28.029 | 1.00 | 20.85 | O |
| ATOM | 2249 | CB | THR | A | 290 | 10.473 | 21.318 | 26.168 | 1.00 | 22.19 | C |
| ATOM | 2250 | OG1 | THR | A | 290 | 10.758 | 21.885 | 27.444 | 1.00 | 21.69 | O |
| ATOM | 2251 | CG2 | THR | A | 290 | 9.436 | 22.268 | 25.557 | 1.00 | 23.05 | C |
| ATOM | 2252 | N | ILE | A | 291 | 11.746 | 18.421 | 25.880 | 1.00 | 20.44 | N |
| ATOM | 2253 | CA | ILE | A | 291 | 12.880 | 17.616 | 26.234 | 1.00 | 21.24 | C |
| ATOM | 2254 | C | ILE | A | 291 | 14.033 | 17.981 | 25.347 | 1.00 | 20.47 | C |
| ATOM | 2255 | O | ThE | A | 291 | 13.869 | 18.064 | 24.137 | 1.00 | 21.04 | O |
| ATOM | 2256 | CB | ILE | A | 291 | 12.559 | 16.118 | 26.078 | 1.00 | 21.40 | C |

TABLE 3-continued

| | | | | | | | | | | | |
|---|---|---|---|---|---|---|---|---|---|---|---|
| | | | | | Coordinates for structures 1 to 4 | | | | | | |
| ATOM | 2257 | CG1 | ILE | A | 291 | 11.405 | 15.724 | 27.004 | 1.00 | 22.31 | C |
| ATOM | 2258 | CG2 | ILE | A | 291 | 13.798 | 15.310 | 26.383 | 1.00 | 22.63 | C |
| ATOM | 2259 | CD1 | ILE | A | 291 | 10.969 | 14.262 | 26.867 | 1.00 | 23.92 | C |
| ATOM | 2260 | N | THR | A | 292 | 15.194 | 18.188 | 25.953 | 1.00 | 20.24 | N |
| ATOM | 2261 | CA | THR | A | 292 | 16.395 | 18.517 | 25.236 | 1.00 | 20.13 | C |
| ATOM | 2262 | C | THR | A | 292 | 17.560 | 17.794 | 25.831 | 1.00 | 20.29 | C |
| ATOM | 2263 | O | THR | A | 292 | 17.605 | 17.557 | 27.021 | 1.00 | 20.94 | O |
| ATOM | 2264 | CB | THR | A | 292 | 16.688 | 20.044 | 25.365 | 1.00 | 20.34 | C |
| ATOM | 2265 | OG1 | THR | A | 292 | 15.524 | 20.799 | 25.022 | 1.00 | 19.08 | O |
| ATOM | 2266 | CG2 | THR | A | 292 | 17.730 | 20.487 | 24.355 | 1.00 | 20.32 | C |
| ATOM | 2267 | N | VAL | A | 293 | 18.530 | 17.454 | 25.003 | 1.00 | 20.52 | N |
| ATOM | 2268 | CA | VAL | A | 293 | 19.784 | 16.939 | 25.516 | 1.00 | 20.48 | C |
| ATOM | 2269 | C | VAL | A | 293 | 20.892 | 17.803 | 24.918 | 1.00 | 20.80 | C |
| ATOM | 2270 | O | VAL | A | 293 | 20.936 | 17.954 | 23.709 | 1.00 | 19.58 | O |
| ATOM | 2271 | CB | VAL | A | 293 | 19.995 | 15.483 | 25.129 | 1.00 | 20.78 | C |
| ATOM | 2272 | CG1 | VAL | A | 293 | 21.436 | 15.068 | 25.385 | 1.00 | 20.33 | C |
| ATOM | 2273 | CG2 | VAL | A | 293 | 19.047 | 14.597 | 25.919 | 1.00 | 20.95 | C |
| ATOM | 2274 | N | ASN | A | 294 | 21.749 | 18.412 | 25.752 | 1.00 | 21.34 | N |
| ATOM | 2275 | CA | ASN | A | 294 | 22.855 | 19.192 | 25.205 | 1.00 | 22.04 | C |
| ATOM | 2276 | C | ASN | A | 294 | 24.144 | 18.362 | 25.204 | 1.00 | 22.29 | C |
| ATOM | 2277 | O | ASN | A | 294 | 24.182 | 17.241 | 25.720 | 1.00 | 23.22 | O |
| ATOM | 2278 | CB | ASN | A | 294 | 23.012 | 20.581 | 25.883 | 1.00 | 22.35 | C |
| ATOM | 2279 | CG | ASN | A | 294 | 23.703 | 20.520 | 27.259 | 1.00 | 23.08 | C. |
| ATOM | 2280 | OD1 | ASN | A | 294 | 24.240 | 19.493 | 27.628 | 1.00 | 22.91 | O |
| ATOM | 2281 | ND2 | ASN | A | 294 | 23.657 | 21.640 | 28.027 | 1.00 | 21.75 | N |
| ATOM | 2282 | N | PHE | A | 295 | 25.168 | 18.903 | 24.565 | 1.00 | 22.27 | N |
| ATOM | 2283 | CA | PHE | A | 295 | 26.467 | 18.269 | 24.452 | 1.00 | 22.31 | C |
| ATOM | 2284 | C | PHE | A | 295 | 27.444 | 19.408 | 24.704 | 1.00 | 22.66 | C |
| ATOM | 2285 | O | PHE | A | 295 | 27.602 | 20.299 | 23.865 | 1.00 | 23.12 | O |
| ATOM | 228~ | CB | PHE | A | 295 | 26.709 | 17.748 | 23.040 | 1.00 | 22.32 | C |
| ATOM | 2287 | CG | PHE | A | 295 | 25.871 | 16.568 | 22.653 | 1.00 | 22.18 | C |
| ATOM | 2288 | CD1 | PHE | A | 295 | 24.494 | 16.689 | 22.477 | 1.00 | 22.38 | C |
| ATOM | 2289 | CD2 | PHE | A | 295 | 26.465 | 15.336 | 22.441 | 1.00 | 21.44 | C |
| ATOM | 2290 | CE1 | PHE | A | 295 | 23.757 | 15.604 | 22.111 | 1.00 | 24.06 | C |
| ATOM | 2291 | CE2 | PHE | A | 295 | 25.718 | 14.248 | 22.064 | 1.00 | 19.77 | C |
| ATOM | 2292 | CZ | PHE | A | 295 | 24.380 | 14.366 | 21.911 | 1.00 | 21.39 | C |
| ATOM | 2293 | N | TRP | A | 296 | 28.062 | 19.403 | 25.869 | 1.00 | 22.66 | N |
| ATOM | 2294 | CA | TRP | A | 296 | 28.998 | 20.450 | 26.256 | 1.00 | 23.09 | C |
| ATOM | 2295 | C | TRP | A | 296 | 30.454 | 19.991 | 26.081 | 1.00 | 23.22 | C |
| ATOM | 2296 | O | TRP | A | 296 | 30.865 | 18.932 | 26.595 | 1.00 | 22.78 | O |
| ATOM | 2297 | CB | TRP | A | 296 | 28.734 | 20.834 | 27.707 | 1.00 | 22.89 | C |
| ATOM | 2298 | CG | TRP | A | 296 | 27.830 | 22.013 | 27.906 | 1.00 | 23.61 | C |
| ATOM | 2299 | CD1 | TRP | A | 296 | 27.783 | 23.129 | 27.149 | 1.00 | 25.47 | C |
| ATOM | 2300 | CD2 | TRP | A | 296 | 26.894 | 22.219 | 28.975 | 1.00 | 24.55 | C |
| ATOM | 2301 | NE1 | TRP | A | 296 | 26.874 | 24.018 | 27.667 | 1.00 | 25.25 | N |
| ATOM | 2302 | CE2 | TRP | A | 296 | 26.308 | 23.478 | 28.783 | 1.00 | 24.33 | C |
| ATOM | 2303 | CE3 | TRP | A | 296 | 26.464 | 21.444 | 30.061 | 1.00 | 27.49 | C |
| ATOM | 2304 | CZ2 | TRP | A | 296 | 25.335 | 23.994 | 29.631 | 1.00 | 25.91 | C |
| ATOM | 2305 | CZ3 | TRP | A | 296 | 25.474 | 21.952 | 30.899 | 1.00 | 27.19 | C |
| ATOM | 2306 | CH2 | TRP | A | 296 | 24.935 | 23.224 | 30.682 | 1.00 | 26.96 | C |
| ATOM | 2307 | N | TYR | A | 297 | 31.216 | 20.783 | 25.337 | 1.00 | 23.29 | N |
| ATOM | 2308 | CA | TYR | A | 297 | 32.627 | 20.510 | 25.100 | 1.00 | 23.80 | C |
| ATOM | 2309 | C | TYR | A | 297 | 33.506 | 21.660 | 25.554 | 1.00 | 24.51 | C |
| ATOM | 2310 | O | TYR | A | 297 | 33.188 | 22.825 | 25.323 | 1.00 | 23.73 | O |
| ATOM | 2311 | GB | TYR | A | 297 | 32.882 | 20.332 | 23.610 | 1.00 | 23.38 | C |
| ATOM | 2312 | CG | TYR | A | 297 | 32.284 | 19.092 | 23.021 | 1.00 | 23.42 | C |
| ATOM | 2313 | CD1 | TYR | A | 297 | 30.940 | 19.053 | 22.641 | 1.00 | 23.90 | C |
| ATOM | 2314 | CD2 | TYR | A | 297 | 33.056 | 17.971 | 22.808 | 1.00 | 21.43 | C |
| ATOM | 2315 | CE1 | TYR | A | 297 | 30.394 | 17.920 | 22.089 | 1.00 | 23.32 | C |
| ATOM | 2316 | CE2 | TYR | A | 297 | 32.515 | 16.826 | 22.250 | 1.00 | 22.05 | C |
| ATOM | 2317 | CZ | TYR | A | 297 | 31.186 | 16.806 | 21.905 | 1.00 | 21.88 | C |
| ATOM | 2318 | OH | TYR | A | 297 | 30.644 | 15.669 | 21.365 | 1.00 | 21.30 | O |
| ATOM | 2319 | N | LYS | A | 298 | 34.637 | 21.334 | 26.160 | 1.00 | 25.35 | N |
| ATOM | 2320 | CA | LYS | A | 298 | 35.589 | 22.362 | 26.536 | 1.00 | 26.48 | C |
| ATOM | 2321 | C | LYS | A | 298 | 36.070 | 23.017 | 25.268 | 1.00 | 26.23 | C |
| ATOM | 2322 | O | LYS | A | 298 | 36.224 | 22.364 | 24.249 | 1.00 | 24.85 | O |
| ATOM | 2323 | GB | LYS | A | 298 | 36.783 | 21.771 | 27.308 | 1.00 | 27.15 | C |
| ATOM | 2324 | CG | LYS | A | 298 | 36.474 | 21.471 | 28.777 | 1.00 | 30.00 | C |
| ATOM | 2325 | CD | LYS | A | 298 | 37.666 | 20.901 | 29.550 | 1.00 | 33.20 | C |
| ATOM | 2326 | CE | LYS | A | 298 | 37.232 | 20.493 | 30.969 | 1.00 | 36.09 | C |
| ATOM | 2327 | NZ | LYS | A | 298 | 38.299 | 19.766 | 31.764 | 1.00 | 39.03 | N |
| ATOM | 2328 | N | GLY | A | 299 | 36.321 | 24.313 | 25.329 | 1.00 | 27.13 | N |
| ATOM | 2329 | CA | GLY | A | 299 | 36.798 | 25.014 | 24.159 | 1.00 | 28.27 | C |
| ATOM | 2330 | C | GLY | A | 299 | 38.229 | 24.649 | 23.837 | 1.00 | 29.23 | C |
| ATOM | 2331 | O | GLY | A | 299 | 38.892 | 24.005 | 24.613 | 1.00 | 28.19 | O |
| ATOM | 2332 | N | ALA | A | 300 | 38.674 | 25.046 | 22.660 | 1.00 | 31.78 | N |
| ATOM | 2333 | CA | ALA | A | 300 | 40.046 | 24.852 | 22.233 | 1.00 | 34.32 | C |

TABLE 3-continued

Coordinates for structures 1 to 4

| ATOM | 2334 | C | ALA | A | 300 | 40.992 | 25.610 | 23.155 | 1.00 | 36.37 | C |
| ATOM | 2335 | O | ALA | A | 300 | 40.573 | 26.430 | 23.956 | 1.00 | 35.96 | O |
| ATOM | 2336 | CB | ALA | A | 300 | 40.210 | 25.355 | 20.806 | 1.00 | 34.38 | C |
| ATOM | 2337 | N | PRO | A | 301 | 42.280 | 25.349 | 23.025 | 1.00 | 39.70 | N |
| ATOM | 2338 | CA | PRO | A | 301 | 43.278 | 26.051 | 23.845 | 1.00 | 41.64 | C |
| ATOM | 2339 | C | PRO | A | 301 | 43.465 | 27.482 | 23.386 | 1.00 | 43.35 | C |
| ATOM | 2340 | O | PRO | A | 301 | 43.220 | 27.803 | 22.228 | 1.00 | 43.86 | O |
| ATOM | 2341 | GB | PRO | A | 301 | 44.566 | 25.275 | 23.572 | 1.00 | 41.46 | C |
| ATOM | 2342 | CG | PRO | A | 301 | 44.382 | 24.736 | 22.199 | 1.00 | 41.25 | C |
| ATOM | 2343 | CD | PRO | A | 301 | 42.906 | 24.416 | 22.068 | 1.00 | 40.04 | C |
| ATOM | 2344 | N | THR | A | 302 | 43.900 | 28.328 | 24.300 | 1.00 | 45.97 | N |
| ATOM | 2345 | CA | THR | A | 302 | 44.214 | 29.715 | 24.001 | 1.00 | 47.77 | C |
| ATOM | 2346 | C | THR | A | 302 | 45.593 | 29.713 | 23.362 | 1.00 | 48.92 | C |
| ATOM | 2347 | O | THR | A | 302 | 46.532 | 29.251 | 24.006 | 1.00 | 49.23 | O |
| ATOM | 2348 | GB | THR | A | 302 | 44.282 | 30.469 | 25.322 | 1.00 | 48.10 | C |
| ATOM | 2349 | OG1 | TRR | A | 302 | 43.006 | 30.416 | 25.976 | 1.00 | 49.37 | O |
| ATOM | 2350 | CG2 | THR | A | 302 | 44.520 | 31.924 | 25.100 | 1.00 | 48.91 | C |
| ATOM | 2351 | N | PRO | A | 303 | 45.761 | 30.248 | 22.148 | 1.00 | 50.22 | N |
| ATOM | 2352 | CA | PRO | A | 303 | 47.064 | 30.150 | 21.474 | 1.00 | 50.62 | C |
| ATOM | 2353 | C | PRO | A | 303 | 48.191 | 30.728 | 22.316 | 1.00 | 50.64 | C |
| ATOM | 2354 | O | PRO | A | 303 | 47.883 | 31.390 | 23.307 | 1.00 | 50.98 | O |
| ATOM | 2355 | GB | PRO | A | 303 | 46.877 | 30.986 | 20.202 | 1.00 | 50.93 | C |
| ATOM | 2356 | CG | PRO | A | 303 | 45.407 | 30.999 | 19.968 | 1.00 | 50.70 | C |
| ATOM | 2357 | CD | PRO | A | 303 | 44.814 | 31.064 | 21.360 | 1.00 | 50.45 | C |
| ATOM | 2358 | N | GLU | A | 307 | 46.978 | 37.074 | 18.830 | 1.00 | 53.59 | N |
| ATOM | 2359 | CA | GLU | A | 307 | 46.946 | 38.016 | 17.714 | 1.00 | 53.82 | C |
| ATOM | 2360 | C | GLU | A | 307 | 45.902 | 39.090 | 17.922 | 1.00 | 52.97 | C |
| ATOM | 2361 | O | GLU | A | 307 | 44.792 | 38.810 | 18.358 | 1.00 | 53.64 | O |
| ATOM | 2362 | CB | GLU | A | 307 | 46.672 | 37.308 | 16.371 | 1.00 | 54.37 | C |
| ATOM | 2363 | CG | GLU | A | 307 | 46.875 | 38.231 | 15.159 | 1.00 | 56.16 | C |
| ATOM | 2364 | CD | GLU | A | 307 | 46.966 | 37.504 | 13.822 | 1.00 | 57.96 | C |
| ATOM | 2365 | OE1 | GLU | A | 307 | 46.621 | 36.303 | 13.738 | 1.00 | 59.31 | O |
| ATOM | 2366 | OE2 | GLU | A | 307 | 47.388 | 38.150 | 12.839 | 1.00 | 59.69 | O |
| ATOM | 2367 | N | TYR | A | 308 | 46.267 | 40.324 | 17.610 | 1.00 | 51.95 | N |
| ATOM | 2368 | CA | TYR | A | 308 | 45.343 | 41.436 | 17.702 | 1.00 | 51.19 | C |
| ATOM | 2369 | C | TYR | A | 308 | 44.693 | 41.603 | 16.337 | 1.00 | 50.27 | C |
| ATOM | 2370 | O | TYR | A | 308 | 45.246 | 41.146 | 15.331 | 1.00 | 50.45 | O |
| ATOM | 2371 | CB | TYR | A | 308 | 46.083 | 42.684 | 18.162 | 1.00 | 51.43 | C |
| ATOM | 2372 | CG | TYR | A | 308 | 46.675 | 42.460 | 19.532 | 1.00 | 52.65 | C |
| ATOM | 2373 | CO1 | TYR | A | 308 | 45.925 | 42.712 | 20.674 | 1.00 | 52.95 | C |
| ATOM | 2374 | CD2 | TYR | A | 308 | 47.948 | 41.912 | 19.685 | 1.00 | 53.42 | C |
| ATOM | 2375 | CE1 | TYR | A | 308 | 46.435 | 42.472 | 21.925 | 1.00 | 54.01 | C |
| ATOM | 2376 | CE2 | TYR | A | 308 | 48.467 | 41.662 | 20.937 | 1.00 | 54.33 | C |
| ATOM | 2377 | CZ | TYR | A | 308 | 47.703 | 41.949 | 22.058 | 1.00 | 54.84 | C |
| ATOM | 2378 | OH | TYR | A | 308 | 48.189 | 41.714 | 23.323 | 1.00 | 56.45 | O |
| ATOM | 2379 | N | PRO | A | 309 | 43.496 | 42.186 | 16.290 | 1.00 | 48.69 | N |
| ATOM | 2380 | CA | PRO | A | 309 | 42.789 | 42.696 | 17.474 | 1.00 | 47.07 | C |
| ATOM | 2381 | C | PRO | A | 309 | 42.127 | 41.586 | 18.280 | 1.00 | 44.55 | C |
| ATOM | 2382 | O | PRO | A | 309 | 41.782 | 40.555 | 17.728 | 1.00 | 45.01 | O |
| ATOM | 2383 | CB | PRO | A | 309 | 41.720 | 43.606 | 16.869 | 1.00 | 47.45 | C |
| ATOM | 2384 | CG | PRO | A | 309 | 41.420 | 42.978 | 15.508 | 1.00 | 48.43 | C |
| ATOM | 2385 | CD | PRO | A | 309 | 42.701 | 42.336 | 15.056 | 1.00 | 48.78 | C |
| ATOM | 2386 | N | LEU | A | 310 | 41.967 | 41.790 | 19.577 | 1.00 | 41.78 | N |
| ATOM | 2387 | CA | LEU | A | 310 | 41.344 | 40.781 | 20.427 | 1.00 | 39.59 | C |
| ATOM | 2388 | C | LEU | A | 310 | 39.858 | 40.652 | 20.133 | 1.00 | 37.52 | C |
| ATOM | 2389 | O | LEU | A | 310 | 39.171 | 41.655 | 19.923 | 1.00 | 38.11 | O |
| ATOM | 2390 | CB | LEU | A | 310 | 41.499 | 41.174 | 21.893 | 1.00 | 39.43 | C |
| ATOM | 2391 | CG | LEU | A | 310 | 42.527 | 40.468 | 22.784 | 1.00 | 38.86 | C |
| ATOM | 2392 | CD1 | LEU | A | 310 | 43.799 | 40.123 | 22.092 | 1.00 | 37.07 | C |
| ATOM | 2393 | CD2 | LEU | A | 310 | 42.799 | 41.326 | 24.000 | 1.00 | 38.37 | C |
| ATOM | 2394 | N | LYS | A | 311 | 39.361 | 39.425 | 20.141 | 1.00 | 34.45 | N |
| ATOM | 2395 | CA | LYS | A | 311 | 37.932 | 39.180 | 20.001 | 1.00 | 32.51 | C |
| ATOM | 2396 | C | LYS | A | 311 | 37.144 | 39.537 | 21.257 | 1.00 | 30.59 | C |
| ATOM | 2397 | O | LYS | A | 311 | 37.675 | 39.546 | 22.375 | 1.00 | 28.88 | O |
| ATOM | 2398 | CB | LYS | A | 311 | 37.674 | 37.736 | 19.652 | 1.00 | 32.87 | C |
| ATOM | 2399 | N | ALA | A | 312 | 35.853 | 39.786 | 21.057 | 1.00 | 28.39 | N |
| ATOM | 2400 | CA | ALA | A | 312 | 34.991 | 40.141 | 22.155 | 1.00 | 27.14 | C |
| ATOM | 2401 | C | ALA | A | 312 | 35.110 | 39.121 | 23.260 | 1.00 | 26.12 | C |
| ATOM | 2402 | O | ALA | A | 312 | 35.274 | 39.509 | 24.411 | 1.00 | 24.47 | O |
| ATOM | 2403 | CB | ALA | A | 312 | 33.552 | 40.323 | 21.710 | 1.00 | 26.63 | C |
| ATOM | 2404 | N | HIS | A | 313 | 35.126 | 37.830 | 22.910 | 1.00 | 25.90 | N |
| ATOM | 2405 | CA | HIS | A | 313 | 35.106 | 36.796 | 23.932 | 1.00 | 25.82 | C |
| ATOM | 2406 | C | HIS | A | 313 | 36.411 | 36.749 | 24.690 | 1.00 | 25.03 | C |
| ATOM | 2407 | O | HIS | A | 313 | 36.447 | 36.323 | 25.825 | 1.00 | 24.89 | O |
| ATOM | 2408 | CB | HIS | A | 313 | 34.724 | 35.406 | 23.368 | 1.00 | 27.19 | C |
| ATOM | 2409 | CG | HIS | A | 313 | 35.788 | 34.773 | 22.535 | 1.00 | 29.47 | C |
| ATOM | 2410 | ND1 | HIS | A | 313 | 35.963 | 35.078 | 21.198 | 1.00 | 34.94 | N |

TABLE 3-continued

Coordinates for structures 1 to 4

| | | | | | | | | | | | |
|---|---|---|---|---|---|---|---|---|---|---|---|
| ATOM | 2411 | CD2 | HIS | A | 313 | 36.753 | 33.880 | 22.847 | 1.00 | 33.69 | C |
| ATOM | 2412 | CE1 | HIS | A | 313 | 37.006 | 34.411 | 20.730 | 1.00 | 35.11 | C |
| ATOM | 2413 | ND2 | HIS | A | 313 | 37.495 | 33.665 | 21.705 | 1.00 | 35.57 | N |
| ATOM | 2414 | N | GLN | A | 314 | 37.491 | 37.185 | 24.072 | 1.00 | 24.60 | N |
| ATOM | 2415 | CA | GLN | A | 314 | 38.764 | 37.226 | 24.753 | 1.00 | 24.57 | C |
| ATOM | 2416 | C | GLN | A | 314 | 38.776 | 38.352 | 25.813 | 1.00 | 24.74 | C |
| ATOM | 2417 | O | GLN | A | 314 | 39.371 | 38.201 | 26.881 | 1.00 | 24.48 | O |
| ATOM | 2418 | CB | GLN | A | 314 | 39.898 | 37.420 | 23.745 | 1.00 | 24.79 | C |
| ATOM | 2419 | CG | GLN | A | 314 | 40.067 | 36.241 | 22.794 | 1.00 | 26.08 | C |
| ATOM | 2420 | CD | GLN | A | 314 | 41.109 | 36.488 | 21.730 | 1.00 | 27.10 | C |
| ATOM | 2421 | OE1 | GLN | A | 314 | 41.013 | 37.450 | 20.949 | 1.00 | 27.68 | O |
| ATOM | 2422 | NE2 | GLN | A | 314 | 42.123 | 35.629 | 21.699 | 1.00 | 29.52 | N |
| ATOM | 2423 | N | LYS | A | 315 | 38.115 | 39.462 | 25.506 | 1.00 | 23.99 | N |
| ATOM | 2424 | CA | LYS | A | 315 | 37.983 | 40.545 | 26.454 | 1.00 | 24.95 | C |
| ATOM | 2425 | C | LYS | A | 315 | 37.099 | 40.114 | 27.622 | 1.00 | 24.32 | C |
| ATOM | 2426 | O | LYS | A | 315 | 37.345 | 40.491 | 28.765 | 1.00 | 22.87 | O |
| ATOM | 2427 | CB | LYS | A | 315 | 37.408 | 41.783 | 25.785 | 1.00 | 25.11 | C |
| ATOM | 2428 | CG | LYS | A | 315 | 38.403 | 42.449 | 24.874 | 1.00 | 29.28 | C |
| ATOM | 2429 | CD | LYS | A | 315 | 37.821 | 43.693 | 24.226 | 1.00 | 34.17 | C |
| ATOM | 2430 | CE | LYS | A | 315 | 38.844 | 44.360 | 23.332 | 1.00 | 37.47 | C |
| ATOM | 2431 | NZ | LYS | A | 315 | 38.206 | 45.270 | 22.318 | 1.00 | 41.38 | N |
| ATOM | 2432 | N | VAL | A | 316 | 36.079 | 39.314 | 27.330 | 1.00 | 23.78 | N |
| ATOM | 2433 | CA | VAL | A | 316 | 35.258 | 38.796 | 28.396 | 1.00 | 23.67 | C |
| ATOM | 2434 | C | VAL | A | 316 | 36.138 | 37.937 | 29.329 | 1.00 | 23.61 | C |
| ATOM | 2435 | O | VAL | A | 316 | 36.094 | 38.075 | 30.558 | 1.00 | 22.63 | O |
| ATOM | 2436 | CE | VAL | A | 316 | 34.092 | 37.961 | 27.873 | 1.00 | 23.67 | C |
| ATOM | 2437 | CG1 | VAL | A | 316 | 33.315 | 37.370 | 29.037 | 1.00 | 23.53 | C |
| ATOM | 2438 | CG2 | VAL | A | 316 | 33.159 | 38.816 | 27.005 | 1.00 | 23.69 | C |
| ATOM | 2439 | N | ALA | A | 317 | 36.940 | 37.065 | 28.732 | 1.00 | 22.51 | N |
| ATOM | 2440 | CA | ALA | A | 317 | 37.834 | 36.207 | 29.507 | 1.00 | 22.28 | C |
| ATOM | 2441 | C | ALA | A | 317 | 38.730 | 37.067 | 30.391 | 1.00 | 21.32 | C |
| ATOM | 2442 | O | ALA | A | 317 | 38.926 | 36.783 | 31.556 | 1.00 | 21.45 | O |
| ATOM | 2443 | CB | ALA | A | 317 | 38.680 | 35.325 | 28.574 | 1.00 | 21.87 | C |
| ATOM | 2444 | N | ILE | A | 318 | 39.220 | 38.153 | 29.834 | 1.00 | 20.92 | N |
| ATOM | 2445 | CA | ILE | A | 318 | 40.091 | 39.053 | 30.574 | 1.00 | 21.36 | C |
| ATOM | 2446 | C | ILE | A | 318 | 39.375 | 39.662 | 31.784 | 1.00 | 21.54 | C |
| ATOM | 2447 | O | ILE | A | 318 | 39.930 | 39.697 | 32.895 | 1.00 | 20.69 | O |
| ATOM | 2448 | CB | ILE | A | 318 | 40.650 | 40.153 | 29.646 | 1.00 | 21.19 | C |
| ATOM | 2449 | CG1 | ILE | A | 318 | 41.664 | 39.560 | 28.670 | 1.00 | 21.41 | C |
| ATOM | 2450 | CG2 | ILE | A | 318 | 41.315 | 41.267 | 30.461 | 1.00 | 21.05 | C |
| ATOM | 2451 | CD1 | ILE | A | 318 | 42.217 | 40.569 | 27.663 | 1.00 | 21.73 | C |
| ATOM | 2452 | N | MET | A | 319 | 38.146 | 40.122 | 31.569 | 1.00 | 21.31 | N |
| ATOM | 2453 | CA | MET | A | 319 | 37.400 | 40.774 | 32.632 | 1.00 | 21.99 | C |
| ATOM | 2454 | C | MET | A | 319 | 37.094 | 39.787 | 33.748 | 1.00 | 22.21 | C |
| ATOM | 2455 | O | MET | A | 319 | 37.219 | 40.114 | 34.937 | 1.00 | 23.25 | O |
| ATOM | 2456 | CE | MET | A | 319 | 36.133 | 41.446 | 32.108 | 1.00 | 21.66 | C |
| ATOM | 2457 | CG | MET | A | 319 | 36.369 | 42.703 | 31.233 | 1.00 | 21.49 | C |
| ATOM | 2458 | SD | MET | A | 319 | 34.787 | 43.525 | 30.787 | 1.00 | 23.05 | S |
| ATOM | 2459 | CE | MET | A | 319 | 34.192 | 42.395 | 29.453 | 1.00 | 22.63 | C |
| ATOM | 2460 | N | ARG | A | 320 | 36.736 | 38.568 | 33.379 | 1.00 | 21.99 | N |
| ATOM | 2461 | CA | ARG | A | 320 | 36.492 | 37.544 | 34.383 | 1.00 | 21.57 | C |
| ATOM | 2462 | C | ARG | A | 320 | 37.750 | 37.319 | 35.223 | 1.00 | 21.22 | C |
| ATOM | 2463 | O | ARG | A | 320 | 37.669 | 37.210 | 36.439 | 1.00 | 21.65 | O |
| ATOM | 2464 | CE | ARG | A | 320 | 36.083 | 36.237 | 33.726 | 1.00 | 20.79 | C |
| ATOM | 2465 | CG | ARG | A | 320 | 34.702 | 36.243 | 33.014 | 1.00 | 22.36 | C |
| ATOM | 2466 | CD | ARG | A | 320 | 34.300 | 34.857 | 32.452 | 1.00 | 21.24 | C |
| ATOM | 2467 | NE | ARG | A | 320 | 34.147 | 33.910 | 33.558 | 1.00 | 21.37 | N |
| ATOM | 2468 | CZ | ARG | A | 320 | 33.148 | 33.957 | 34.423 | 1.00 | 21.73 | C |
| ATOM | 2469 | NH1 | ARG | A | 320 | 32.196 | 34.869 | 34.308 | 1.00 | 22.69 | N |
| ATOM | 2470 | NH2 | ARG | A | 320 | 33.100 | 33.109 | 35.425 | 1.00 | 23.33 | N |
| ATOM | 2471 | N | ASN | A | 321 | 38.908 | 37.216 | 34.571 | 1.00 | 21.35 | N |
| ATOM | 2472 | CA | ASN | A | 321 | 40.159 | 36.947 | 35.282 | 1.00 | 21.20 | C |
| ATOM | 2473 | C | ASN | A | 321 | 40.510 | 38.078 | 36.239 | 1.00 | 21.02 | C |
| ATOM | 2474 | O | ASN | A | 321 | 40.958 | 37.828 | 37.364 | 1.00 | 21.80 | O |
| ATOM | 2475 | CE | ASN | A | 321 | 41.314 | 36.648 | 34.311 | 1.00 | 21.07 | C |
| ATOM | 2476 | CG | ASN | A | 321 | 41.263 | 35.209 | 33.752 | 1.00 | 22.81 | C |
| ATOM | 2477 | OD1 | ASN | A | 321 | 40.821 | 34.306 | 34.431 | 1.00 | 23.88 | O |
| ATOM | 2478 | ND2 | ASN | A | 321 | 41.713 | 35.018 | 32.521 | 1.00 | 20.59 | N |
| ATOM | 2479 | N | ILE | A | 322 | 40.336 | 39.320 | 35.802 | 1.00 | 20.31 | N |
| ATOM | 2480 | CA | ILE | A | 322 | 40.611 | 40.447 | 36.683 | 1.00 | 19.83 | C |
| ATOM | 2481 | C | ILE | A | 322 | 39.721 | 40.344 | 37.918 | 1.00 | 19.45 | C |
| ATOM | 2482 | O | ILE | A | 322 | 40.178 | 40.531 | 39.037 | 1.00 | 18.04 | O |
| ATOM | 2483 | CE | ILE | A | 322 | 40.327 | 41.775 | 35.980 | 1.00 | 20.01 | C |
| ATOM | 2484 | CG1 | ILE | A | 322 | 41.320 | 42.009 | 34.849 | 1.00 | 21.62 | C |
| ATOM | 2485 | CG2 | ILE | A | 322 | 40.351 | 42.930 | 36.989 | 1.00 | 20.64 | C |
| ATOM | 2486 | CD1 | ILE | A | 322 | 42.782 | 41.987 | 35.278 | 1.00 | 23.99 | C |
| ATOM | 2487 | N | GLU | A | 323 | 38.444 | 40.035 | 37.716 | 1.00 | 18.87 | N |

TABLE 3-continued

Coordinates for structures 1 to 4

| | | | | | | | | | | | |
|---|---|---|---|---|---|---|---|---|---|---|---|
| ATOM | 2488 | CA | GLU | A | 323 | 37.533 | 39.940 | 38.841 | 1.00 | 19.15 | C |
| ATOM | 2489 | C | GLU | A | 323 | 37.964 | 38.845 | 39.781 | 1.00 | 19.09 | C |
| ATOM | 2490 | O | GLU | A | 323 | 37.997 | 39.044 | 40.980 | 1.00 | 19.36 | O |
| ATOM | 2491 | CB | GLU | A | 323 | 36.095 | 39.721 | 38.366 | 1.00 | 19.19 | C |
| ATOM | 2492 | CG | GLU | A | 323 | 35.478 | 40.987 | 37.787 | 1.00 | 19.24 | C |
| ATOM | 2493 | CD | GLU | A | 323 | 34.096 | 40.764 | 37.189 | 1.00 | 17.51 | C |
| ATOM | 2494 | OE1 | GLU | A | 323 | 33.140 | 40.470 | 37.922 | 1.00 | 17.44 | O |
| ATOM | 2495 | OE2 | GLU | A | 323 | 33.982 | 40.901 | 35.974 | 1.00 | 16.60 | O |
| ATOM | 2496 | N | LYS | A | 324 | 38.357 | 37.711 | 39.227 | 1.00 | 19.47 | N |
| ATOM | 2497 | CA | LYS | A | 324 | 38.781 | 36.570 | 40.037 | 1.00 | 20.33 | C |
| ATOM | 2498 | C | LYS | A | 324 | 40.040 | 36.869 | 40.839 | 1.00 | 20.67 | C |
| ATOM | 2499 | O | LYS | A | 324 | 40.090 | 36.562 | 42.023 | 1.00 | 20.56 | O |
| ATOM | 2500 | CB | LYS | A | 324 | 39.040 | 35.334 | 39.172 | 1.00 | 20.11 | C |
| ATOM | 2501 | CG | LYS | A | 324 | 37.803 | 34.678 | 38.572 | 1.00 | 20.73 | C |
| ATOM | 2502 | CD | LYS | A | 324 | 38.238 | 33.413 | 37.761 | 1.00 | 21.68 | C |
| ATOM | 2503 | CE | LYS | A | 324 | 37.117 | 32.866 | 36.857 | 1.00 | 22.30 | C |
| ATOM | 2504 | NZ | LYS | A | 324 | 37.534 | 31.609 | 36.153 | 1.00 | 19.72 | N |
| ATOM | 2505 | N | MET | A | 325 | 41.045 | 37.456 | 40.194 | 1.00 | 21.37 | N |
| ATOM | 2506 | CA | MET | A | 325 | 42.305 | 37.782 | 40.860 | 1.00 | 22.78 | C |
| ATOM | 2507 | C | MET | A | 325 | 42.106 | 38.789 | 41.990 | 1.00 | 22.78 | C |
| ATOM | 2508 | O | MET | A | 325 | 42.734 | 38.694 | 43.047 | 1.00 | 22.48 | O |
| ATOM | 2509 | CB | MET | A | 325 | 43.308 | 38.369 | 39.865 | 1.00 | 23.14 | C |
| ATOM | 2510 | CG | MET | A | 325 | 43.964 | 37.359 | 38.978 | 1.00 | 27.30 | C |
| ATOM | 2511 | SD | MET | A | 325 | 44.699 | 38.147 | 37.511 | 1.00 | 35.72 | S |
| ATOM | 2512 | CE | MET | A | 325 | 45.804 | 39.221 | 38.338 | 1.00 | 36.16 | C |
| ATOM | 2513 | N | LEU | A | 326 | 41.248 | 39.765 | 41.752 | 1.00 | 23.21 | N |
| ATOM | 2514 | CA | LEU | A | 326 | 40.977 | 40.795 | 42.751 | 1.00 | 24.47 | C |
| ATOM | 2515 | C | LEU | A | 326 | 40.307 | 40.195 | 43.969 | 1.00 | 24.48 | C |
| ATOM | 2516 | O | LEU | A | 326 | 40.659 | 40.500 | 45.083 | 1.00 | 24.21 | O |
| ATOM | 2517 | CB | LEU | A | 326 | 40.087 | 41.863 | 42.159 | 1.00 | 24.63 | C |
| ATOM | 2518 | CG | LEU | A | 326 | 40.618 | 43.282 | 41.988 | 1.00 | 27.80 | C |
| ATOM | 2519 | CD1 | LEU | A | 326 | 42.135 | 43.441 | 42.036 | 1.00 | 28.29 | C |
| ATOM | 2520 | CD2 | LEU | A | 326 | 40.038 | 43.820 | 40.682 | 1.00 | 28.01 | C |
| ATOM | 2521 | N | GLN | A | 327 | 39.350 | 39.314 | 43.726 | 1.00 | 25.29 | N |
| ATOM | 2522 | CA | GLY | A | 327 | 38.663 | 38.608 | 44.782 | 1.00 | 25.73 | C |
| ATOM | 2523 | C | GLY | A | 327 | 39.644 | 37.854 | 45.638 | 1.00 | 25.86 | C |
| ATOM | 2524 | O | GLY | A | 327 | 39.597 | 37.931 | 46.863 | 1.00 | 25.83 | O |
| ATOM | 2525 | N | GLU | A | 328 | 40.556 | 37.137 | 45.002 | 1.00 | 26.02 | N |
| ATOM | 2526 | CA | GLU | A | 328 | 41.558 | 36.397 | 45.762 | 1.00 | 26.93 | C |
| ATOM | 2527 | C | GLU | A | 328 | 42.557 | 37.306 | 46.480 | 1.00 | 25.70 | C |
| ATOM | 2528 | O | GLU | A | 328 | 42.883 | 37.070 | 47.635 | 1.00 | 24.67 | O |
| ATOM | 2529 | CB | GLU | A | 328 | 42.293 | 35.423 | 44.853 | 1.00 | 27.76 | C |
| ATOM | 2530 | CG | GLU | A | 328 | 41.403 | 34.282 | 44.375 | 1.00 | 31.57 | C |
| ATOM | 2531 | CD | GLU | A | 328 | 41.635 | 32.992 | 45.146 | 1.00 | 37.39 | C |
| ATOM | 2532 | OE1 | GLU | A | 328 | 42.048 | 33.058 | 46.335 | 1.00 | 41.34 | O |
| ATOM | 2533 | OE2 | GLU | A | 328 | 41.430 | 31.902 | 44.552 | 1.00 | 42.69 | O |
| ATOM | 2534 | N | ALA | A | 329 | 43.024 | 38.356 | 45.816 | 1.00 | 25.20 | N |
| ATOM | 2535 | CA | ALA | A | 329 | 44.031 | 39.219 | 46.433 | 1.00 | 25.42 | C |
| ATOM | 2536 | C | ALA | A | 329 | 43.475 | 40.039 | 47.582 | 1.00 | 25.67 | C |
| ATOM | 2537 | O | ALA | A | 329 | 44.141 | 40.247 | 48.570 | 1.00 | 25.92 | O |
| ATOM | 2538 | CB | ALA | A | 329 | 44.670 | 40.109 | 45.409 | 1.00 | 25.31 | C |
| ATOM | 2539 | N | LEU | A | 330 | 42.241 | 40.496 | 47.467 | 1.00 | 26.51 | N |
| ATOM | 2540 | CA | LEU | A | 330 | 41.656 | 41.306 | 48.529 | 1.00 | 27.12 | C |
| ATOM | 2541 | C | LEU | A | 330 | 41.156 | 40.453 | 49.677 | 1.00 | 27.74 | C |
| ATOM | 2542 | O | LEU | A | 330 | 40.845 | 40.959 | 50.748 | 1.00 | 27.62 | |
| ATOM | 2543 | CB | LEU | A | 330 | 40.517 | 42.138 | 47.984 | 1.00 | 27.19 | C |
| ATOM | 2544 | CG | LEU | A | 330 | 40.966 | 43.131 | 46.915 | 1.00 | 27.69 | C |
| ATOM | 2545 | CD1 | LEU | A | 330 | 39.747 | 43.661 | 46.211 | 1.00 | 28.15 | C |
| ATOM | 2546 | CD2 | LEU | A | 330 | 41.774 | 44.271 | 47.525 | 1.00 | 27.60 | C |
| ATOM | 2547 | N | GLY | A | 331 | 41.054 | 39.154 | 49.434 | 1.00 | 28.45 | N |
| ATOM | 2548 | CA | GLY | A | 331 | 40.637 | 38.222 | 50.457 | 1.00 | 29.04 | C |
| ATOM | 2549 | C | GLY | A | 331 | 39.154 | 38.239 | 50.748 | 1.00 | 29.16 | C |
| ATOM | 2550 | O | GLY | A | 331 | 38.698 | 37.505 | 51.615 | 1.00 | 29.67 | O |
| ATOM | 2551 | N | ASN | A | 332 | 38.409 | 39.088 | 50.052 | 1.00 | 29.16 | N |
| ATOM | 2552 | CA | ASN | A | 332 | 36.973 | 39.190 | 50.243 | 1.00 | 29.38 | C |
| ATOM | 2553 | C | ASN | A | 332 | 36.342 | 39.718 | 48.958 | 1.00 | 28.80 | C |
| ATOM | 2554 | O | ASN | A | 332 | 36.579 | 40.847 | 48.570 | 1.00 | 28.58 | O |
| ATOM | 2555 | GB | ASN | A | 332 | 36.662 | 40.123 | 51.413 | 1.00 | 29.68 | C |
| ATOM | 2556 | CG | ASN | A | 332 | 35.181 | 40.214 | 51.702 | 1.00 | 31.38 | C |
| ATOM | 2557 | OD1 | ASN | A | 332 | 34.368 | 39.630 | 50.991 | 1.00 | 35.54 | O |
| ATOM | 2558 | ND2 | ASN | A | 332 | 34.820 | 40.944 | 52.751 | 1.00 | 33.23 | N |
| ATOM | 2559 | N | PRO | A | 333 | 35.504 | 38.922 | 48.325 | 1.00 | 28.45 | N |
| ATOM | 2560 | CA | PRO | A | 333 | 34.944 | 39.288 | 47.025 | 1.00 | 28.38 | C |
| ATOM | 2561 | C | PRO | A | 333 | 34.094 | 40.534 | 47.093 | 1.00 | 28.04 | C |
| ATOM | 2562 | O | PRO | A | 333 | 33.913 | 41.187 | 46.073 | 1.00 | 28.11 | O |
| ATOM | 2563 | GB | PRO | A | 333 | 34.071 | 38.093 | 46.640 | 1.00 | 28.23 | C |
| ATOM | 2564 | CG | PRO | A | 333 | 34.203 | 37.097 | 47.701 | 1.00 | 29.36 | C |

TABLE 3-continued

| | | | | | | | | | | | |
|---|---|---|---|---|---|---|---|---|---|---|---|
| \multicolumn{12}{|c|}{Coordinates for structures 1 to 4} |
| ATOM | 2565 | CD | PRO | A | 333 | 34.999 | 37.641 | 48.822 | 1.00 | 28.91 | C |
| ATOM | 2566 | N | GLN | A | 334 | 33.556 | 40.844 | 48.262 | 1.00 | 27.75 | N |
| ATOM | 2567 | CA | GLN | A | 334 | 32.727 | 42.033 | 48.400 | 1.00 | 28.08 | C |
| ATOM | 2568 | C | GLN | A | 334 | 33.582 | 43.282 | 48.300 | 1.00 | 26.62 | C |
| ATOM | 2569 | O | GLN | A | 334 | 33.064 | 44.365 | 48.086 | 1.00 | 26.31 | O |
| ATOM | 2570 | GB | GLN | A | 334 | 31.857 | 41.989 | 49.686 | 1.00 | 28.89 | C |
| ATOM | 2571 | CG | GLN | A | 334 | 30.594 | 41.090 | 49.459 | 1.00 | 32.52 | C |
| ATOM | 2572 | CD | GLN | A | 334 | 29.523 | 41.114 | 50.556 | 1.00 | 36.22 | C |
| ATOM | 2573 | OE1 | GLN | A | 334 | 29.500 | 42.004 | 51.421 | 1.00 | 39.82 | O |
| ATOM | 2574 | NE2 | GLN | A | 334 | 28.612 | 40.127 | 50.503 | 1.00 | 38.24 | N |
| ATOM | 2575 | N | GLU | A | 335 | 34.894 | 43.138 | 48.414 | 1.00 | 25.23 | N |
| ATOM | 2576 | CA | GLU | A | 335 | 35.763 | 44.290 | 48.269 | 1.00 | 24.55 | C |
| ATOM | 2577 | C | GLU | A | 335 | 36.090 | 44.584 | 46.790 | 1.00 | 22.95 | C |
| ATOM | 2578 | O | GLU | A | 335 | 36.691 | 45.597 | 46.475 | 1.00 | 21.47 | O |
| ATOM | 2579 | GB | GLU | A | 335 | 37.038 | 44.091 | 49.088 | 1.00 | 25.61 | C |
| ATOM | 2580 | CG | GLU | A | 335 | 36.820 | 44.189 | 50.599 | 1.00 | 29.47 | C |
| ATOM | 2581 | CD | GLU | A | 335 | 38.115 | 44.280 | 51.369 | 1.00 | 34.49 | C |
| ATOM | 2582 | OE1 | GLU | A | 335 | 38.964 | 45.124 | 51.004 | 1.00 | 39.50 | O |
| ATOM | 2583 | OE2 | GLU | A | 335 | 38.288 | 43.521 | 52.350 | 1.00 | 40.05 | O |
| ATOM | 2584 | N | VAL | A | 336 | 35.654 | 43.722 | 45.877 | 1.00 | 21.52 | N |
| ATOM | 2585 | CA | VAL | A | 336 | 35.993 | 43.898 | 44.458 | 1.00 | 20.69 | C |
| ATOM | 2586 | C | VAL | A | 336 | 35.422 | 45.176 | 43.855 | 1.00 | 19.97 | C |
| ATOM | 2587 | O | VAL | A | 336 | 36.134 | 45.949 | 43.239 | 1.00 | 19.57 | O |
| ATOM | 2588 | GB | VAL | A | 336 | 35.594 | 42.683 | 43.653 | 1.00 | 20.59 | C |
| ATOM | 2589 | CG1 | VAL | A | 336 | 35.746 | 42.933 | 42.179 | 1.00 | 21.20 | C |
| ATOM | 2590 | CG2 | VAL | A | 336 | 36.467 | 41.513 | 44.067 | 1.00 | 21.28 | C |
| ATOM | 2591 | N | GLY | A | 337 | 34.146 | 45.421 | 44.080 | 1.00 | 19.82 | N |
| ATOM | 2592 | CA | GLY | A | 337 | 33.492 | 46.598 | 43.568 | 1.00 | 19.66 | C |
| ATOM | 2593 | C | GLY | A | 337 | 34.130 | 47.906 | 43.981 | 1.00 | 19.56 | C |
| ATOM | 2594 | O | GLY | A | 337 | 34.510 | 48.693 | 43.131 | 1.00 | 19.35 | O |
| ATOM | 2595 | N | PRO | A | 338 | 34.202 | 48.162 | 45.278 | 1.00 | 19.93 | N |
| ATOM | 2596 | CA | PRO | A | 338 | 34.846 | 49.383 | 45.790 | 1.00 | 19.88 | C |
| ATOM | 2597 | C | PRO | A | 338 | 36.272 | 49.631 | 45.254 | 1.00 | 19.22 | C |
| ATOM | 2598 | O | PRO | A | 338 | 36.591 | 50.758 | 44.908 | 1.00 | 18.43 | O |
| ATOM | 2599 | GB | PRO | A | 338 | 34.830 | 49.191 | 47.316 | 1.00 | 19.61 | C |
| ATOM | 2600 | CG | PRO | A | 338 | 33.625 | 48.380 | 47.555 | 1.00 | 20.33 | C |
| ATOM | 2601 | CD | PRO | A | 338 | 33.579 | 47.367 | 46.359 | 1.00 | 20.75 | C |
| ATOM | 2602 | N | LEU | A | 339 | 37.107 | 48.612 | 45.171 | 1.00 | 19.21 | N |
| ATOM | 2603 | CA | LEU | A | 339 | 38.416 | 48.814 | 44.566 | 1.00 | 19.65 | C |
| ATOM | 2604 | C | LEU | A | 339 | 38.283 | 49.219 | 43.081 | 1.00 | 19.35 | C |
| ATOM | 2605 | O | LEU | A | 339 | 38.927 | 50.188 | 42.621 | 1.00 | 17.91 | O |
| ATOM | 2606 | GB | LEU | A | 339 | 39.279 | 47.570 | 44.693 | 1.00 | 20.38 | C |
| ATOM | 2607 | CG | LEU | A | 339 | 40.745 | 47.814 | 44.291 | 1.00 | 21.96 | C |
| ATOM | 2608 | CD1 | LEU | A | 339 | 41.681 | 47.151 | 45.220 | 1.00 | 25.12 | C |
| ATOM | 2609 | CD2 | LEU | A | 339 | 40.991 | 47.293 | 42.899 | 1.00 | 22.54 | C |
| ATOM | 2610 | N | LEU | A | 340 | 37.420 | 48.512 | 42.345 | 1.00 | 19.18 | N |
| ATOM | 2611 | CA | LEU | A | 340 | 37.231 | 48.821 | 40.928 | 1.00 | 19.26 | C |
| ATOM | 2612 | C | LEU | A | 340 | 36.764 | 50.260 | 40.746 | 1.00 | 19.52 | C |
| ATOM | 2613 | O | LEU | A | 340 | 37.306 | 50.989 | 39.893 | 1.00 | 18.71 | O |
| ATOM | 2614 | CB | LEU | A | 340 | 36.260 | 47.857 | 40.273 | 1.00 | 19.85 | C |
| ATOM | 2615 | CG | LEU | A | 340 | 36.823 | 46.470 | 39.960 | 1.00 | 21.77 | C |
| ATOM | 2616 | CD1 | LEU | A | 340 | 35.745 | 45.671 | 39.299 | 1.00 | 22.81 | C |
| ATOM | 2617 | CD2 | LEU | A | 340 | 38.088 | 46.539 | 39.072 | 1.00 | 21.14 | C |
| ATOM | 2618 | N | ASN | A | 341 | 35.798 | 50.676 | 41.570 | 1.00 | 19.12 | N |
| ATOM | 2619 | CA | ASN | A | 341 | 35.296 | 52.052 | 41.536 | 1.00 | 20.43 | C |
| ATOM | 2620 | C | ASN | A | 341 | 36.367 | 53.086 | 41.865 | 1.00 | 19.90 | C |
| ATOM | 2621 | O | ASN | A | 341 | 36.474 | 54.110 | 41.206 | 1.00 | 19.81 | O |
| ATOM | 2622 | CE | ASN | A | 341 | 34.090 | 52.232 | 42.485 | 1.00 | 20.40 | C |
| ATOM | 2623 | CG | ASN | A | 341 | 32.814 | 51.659 | 41.898 | 1.00 | 24.06 | C |
| ATOM | 2624 | CD1 | ASN | A | 341 | 32.390 | 52.073 | 40.829 | 1.00 | 31.36 | O |
| ATOM | 2625 | ND2 | ASN | A | 341 | 32.229 | 50.666 | 42.561 | 1.00 | 25.82 | N |
| ATOM | 2626 | N | THR | A | 342 | 37.129 | 52.812 | 42.912 | 1.00 | 19.43 | N |
| ATOM | 2627 | CA | THR | A | 342 | 38.227 | 53.664 | 43.305 | 1.00 | 19.71 | C |
| ATOM | 2628 | C | THR | A | 342 | 39.230 | 53.781 | 42.154 | 1.00 | 19.45 | C |
| ATOM | 2629 | O | THR | A | 342 | 39.739 | 54.859 | 41.893 | 1.00 | 19.23 | O |
| ATOM | 2630 | CE | THR | A | 342 | 38.873 | 53.073 | 44.555 | 1.00 | 20.44 | C |
| ATOM | 2631 | OG1 | THR | A | 342 | 38.030 | 53.322 | 45.700 | 1.00 | 21.13 | O |
| ATOM | 2632 | CG2 | THR | A | 342 | 40.208 | 53.756 | 44.874 | 1.00 | 20.71 | C |
| ATOM | 2633 | N | MET | A | 343 | 39.464 | 52.691 | 41.427 | 1.00 | 19.49 | N |
| ATOM | 2634 | CA | MET | A | 343 | 40.381 | 52.723 | 40.287 | 1.00 | 19.90 | C |
| ATOM | 2635 | C | MET | A | 343 | 39.932 | 53.649 | 39.164 | 1.00 | 19.94 | C |
| ATOM | 2636 | O | MET | A | 343 | 40.775 | 54.344 | 38.567 | 1.00 | 18.43 | O |
| ATOM | 2637 | CE | MET | A | 343 | 40.543 | 51.347 | 39.664 | 1.00 | 19.92 | C |
| ATOM | 2638 | CG | MET | A | 343 | 41.701 | 50.556 | 40.115 | 1.00 | 23.07 | C |
| ATOM | 2639 | SD | MET | A | 343 | 42.163 | 49.194 | 38.959 | 1.00 | 24.93 | S |
| ATOM | 2640 | CE | MET | A | 343 | 41.013 | 48.220 | 39.315 | 1.00 | 27.48 | C |
| ATOM | 2641 | N | ILE | A | 344 | 38.629 | 53.643 | 38.837 | 1.00 | 20.84 | N |

TABLE 3-continued

Coordinates for structures 1 to 4

| ATOM | 2642 | CA | ILE | A | 344 | 38.159 | 54.412 | 37.679 | 1.00 | 21.51 | C |
|------|------|----|----|---|-----|--------|--------|--------|------|-------|---|
| ATOM | 2643 | C | ILE | A | 344 | 37.624 | 55.800 | 37.918 | 1.00 | 21.46 | C |
| ATOM | 2644 | O | ILE | A | 344 | 37.751 | 56.639 | 37.018 | 1.00 | 21.65 | O |
| ATOM | 2645 | CE | ILE | A | 344 | 37.089 | 53.641 | 36.805 | 1.00 | 22.58 | C |
| ATOM | 2646 | CG1 | ILE | A | 344 | 35.714 | 53.723 | 37.435 | 1.00 | 24.65 | C |
| ATOM | 2647 | CG2 | ILE | A | 344 | 37.506 | 52.220 | 36.555 | 1.00 | 23.63 | C |
| ATOM | 2648 | CD1 | ILE | A | 344 | 34.635 | 53.407 | 36.511 | 1.00 | 28.35 | C |
| ATOM | 2649 | N | LYS | A | 345 | 37.009 | 56.092 | 39.062 | 1.00 | 21.48 | N |
| ATOM | 2650 | CA | LYS | A | 345 | 36.410 | 57.433 | 39.154 | 1.00 | 22.11 | C |
| ATOM | 2651 | C | LYS | A | 345 | 37.382 | 58.569 | 39.127 | 1.00 | 20.79 | C |
| ATOM | 2652 | O | LYS | A | 345 | 38.380 | 58.614 | 39.863 | 1.00 | 20.06 | O |
| ATOM | 2653 | CE | LYS | A | 345 | 35.405 | 57.656 | 40.279 | 1.00 | 23.49 | C |
| ATOM | 2654 | CG | LYS | A | 345 | 35.497 | 56.838 | 41.473 | 1.00 | 28.03 | C |
| ATOM | 2655 | CD | LYS | A | 345 | 34.120 | 56.183 | 41.683 | 1.00 | 30.07 | C |
| ATOM | 2656 | CE | LYS | A | 345 | 33.282 | 56.986 | 42.624 | 1.00 | 32.44 | C |
| ATOM | 2657 | NZ | LYS | A | 345 | 33.859 | 56.977 | 43.982 | 1.00 | 36.32 | H |
| ATOM | 2658 | N | GLY | A | 346 | 37.062 | 59.501 | 38.243 | 1.00 | 19.28 | N |
| ATOM | 2659 | CA | GLY | A | 346 | 37.911 | 60.636 | 38.013 | 1.00 | 18.60 | C |
| ATOM | 2660 | C | GLY | A | 346 | 39.222 | 60.254 | 37.350 | 1.00 | 17.41 | C |
| ATOM | 2661 | O | GLY | A | 346 | 40.090 | 61.079 | 37.229 | 1.00 | 18.04 | O |
| ATOM | 2662 | H | ARG | A | 347 | 39.353 | 59.024 | 36.898 | 1.00 | 17.62 | N |
| ATOM | 2663 | CA | ARG | A | 347 | 40.616 | 58.563 | 36.297 | 1.00 | 17.91 | C |
| ATOM | 2664 | C | ARG | A | 347 | 40.415 | 57.992 | 34.874 | 1.00 | 18.08 | C |
| ATOM | 2665 | O | ARG | A | 347 | 41.108 | 58.395 | 33.938 | 1.00 | 17.06 | O |
| ATOM | 2666 | CE | ARG | A | 347 | 41.284 | 57.532 | 37.213 | 1.00 | 17.51 | C |
| ATOM | 2667 | CG | ARG | A | 347 | 41.719 | 58.081 | 38.592 | 1.00 | 15.94 | C |
| ATOM | 2668 | CD | ARG | A | 347 | 43.179 | 57.649 | 38.985 | 1.00 | 19.49 | C |
| ATOM | 2669 | NE | ARG | A | 347 | 43.165 | 56.242 | 38.980 | 1.00 | 18.58 | H |
| ATOM | 2670 | CZ | ARG | A | 347 | 44.048 | 55.405 | 38.518 | 1.00 | 14.88 | C |
| ATOM | 2671 | NH1 | ARG | A | 347 | 45.271 | 55.726 | 38.085 | 1.00 | 17.47 | N |
| ATOM | 2672 | NH2 | ARG | A | 347 | 43.678 | 54.158 | 38.611 | 1.00 | 11.18 | N |
| ATOM | 2673 | N | TYR | A | 348 | 39.450 | 57.091 | 34.732 | 1.00 | 18.81 | N |
| ATOM | 2674 | CA | TYR | A | 348 | 39.098 | 56.480 | 33.444 | 1.00 | 20.50 | C |
| ATOM | 2675 | C | TYR | A | 348 | 37.637 | 56.691 | 33.036 | 1.00 | 22.07 | C |
| ATOM | 2676 | O | TYR | A | 348 | 37.233 | 56.236 | 31.978 | 1.00 | 22.11 | O |
| ATOM | 2677 | CB | TYR | A | 348 | 39.311 | 54.963 | 33.478 | 1.00 | 19.77 | C |
| ATOM | 2678 | CG | TYR | A | 348 | 40.753 | 54.545 | 33.561 | 1.00 | 20.36 | C |
| ATOM | 2679 | CD1 | TYR | A | 348 | 41.540 | 54.483 | 32.422 | 1.00 | 19.91 | C |
| ATOM | 2680 | CD2 | TYR | A | 348 | 41.335 | 54.225 | 34.780 | 1.00 | 18.20 | C |
| ATOM | 2681 | CE1 | TYR | A | 348 | 42.859 | 54.099 | 32.489 | 1.00 | 19.81 | C |
| ATOM | 2682 | CE2 | TYR | A | 348 | 42.662 | 53.841 | 34.863 | 1.00 | 19.47 | C |
| ATOM | 2683 | CZ | TYR | A | 348 | 43.425 | 53.785 | 33.711 | 1.00 | 19.43 | C |
| ATOM | 2684 | OH | TYR | A | 348 | 44.742 | 53.414 | 33.773 | 1.00 | 15.61 | O |
| ATOM | 2685 | N | ASN | A | 349 | 36.820 | 57.344 | 33.850 | 1.00 | 24.37 | N |
| ATOM | 2686 | CA | ASN | A | 349 | 35.414 | 57.472 | 33.456 | 1.00 | 26.66 | C |
| ATOM | 2687 | C | ASN | A | 349 | 34.941 | 58.854 | 33.092 | 1.00 | 28.03 | C |
| ATOM | 2688 | O | ASN | A | 349 | 35.663 | 59.847 | 32.992 | 1.00 | 27.79 | O |
| ATOM | 2689 | CS | ASN | A | 349 | 34.498 | 56.919 | 34.518 | 1.00 | 26.23 | C |
| ATOM | 2690 | CG | ASN | A | 349 | 34.463 | 57.764 | 35.748 | 1.00 | 27.89 | C |
| ATOM | 2691 | OD1 | ASN | A | 349 | 35.247 | 58.718 | 35.927 | 1.00 | 27.38 | O |
| ATOM | 2692 | ND2 | ASN | A | 349 | 33.545 | 57.409 | 36.645 | 1.00 | 32.46 | H |
| ATOM | 2693 | OXT | ASN | A | 349 | 33.736 | 58.963 | 32.900 | 1.00 | 32.44 | O |
| TER | 2694 | | ASN | A | 349 | | | | | | |
| ATOM | 2695 | H | LEU | S | 795 | 45.819 | 35.786 | 30.984 | 1.00 | 36.91 | H |
| ATOM | 2696 | CA | LEU | S | 795 | 44.711 | 36.756 | 31.250 | 1.00 | 37.26 | C |
| ATOM | 2697 | C | LEU | S | 795 | 43.553 | 36.418 | 30.323 | 1.00 | 37.49 | C |
| ATOM | 2698 | O | LEU | S | 795 | 42.391 | 36.451 | 30.712 | 1.00 | 36.90 | O |
| ATOM | 2699 | CB | LEU | S | 795 | 45.183 | 38.186 | 31.044 | 1.00 | 37.26 | C |
| ATOM | 2700 | CG | LEU | S | 795 | 44.683 | 39.204 | 32.074 | 1.00 | 37.32 | C |
| ATOM | 2701 | CD1 | LEU | S | 795 | 44.775 | 38.671 | 33.479 | 1.00 | 37.34 | C |
| ATOM | 2702 | CD2 | LEU | S | 795 | 45.479 | 40.493 | 32.006 | 1.00 | 37.95 | C |
| ATOM | 2703 | H | THR | S | 796 | 43.907 | 36.155 | 29.076 | 1.00 | 38.07 | N |
| ATOM | 2704 | CA | THR | S | 796 | 43.029 | 35.548 | 28.076 | 1.00 | 39.17 | C |
| ATOM | 2705 | C | THR | S | 796 | 42.608 | 34.088 | 28.347 | 1.00 | 38.93 | C |
| ATOM | 2706 | O | THR | S | 796 | 41.784 | 33.533 | 27.622 | 1.00 | 39.51 | O |
| ATOM | 2707 | CB | THR | S | 796 | 43.750 | 35.628 | 26.705 | 1.00 | 39.45 | C |
| ATOM | 2708 | OG1 | THR | S | 796 | 43.287 | 34.597 | 25.850 | 1.00 | 41.87 | O |
| ATOM | 2709 | CG2 | THR | S | 796 | 45.232 | 35.275 | 26.824 | 1.00 | 40.14 | C |
| ATOM | 2710 | N | SER | S | 797 | 43.154 | 33.451 | 29.369 | 1.00 | 38.98 | H |
| ATOM | 2711 | CA | SER | S | 797 | 42.770 | 32.067 | 29.654 | 1.00 | 39.24 | C |
| ATOM | 2712 | C | SER | S | 797 | 41.370 | 31.981 | 30.274 | 1.00 | 39.32 | C |
| ATOM | 2713 | O | SER | S | 797 | 40.901 | 32.905 | 30.939 | 1.00 | 38.28 | C |
| ATOM | 2714 | CB | SER | S | 797 | 43.775 | 31.398 | 30.574 | 1.00 | 38.98 | C |
| ATOM | 2715 | OG | SER | S | 797 | 43.613 | 31.884 | 31.891 | 1.00 | 40.40 | O |
| ATOM | 2716 | N | TYR | S | 798 | 40.713 | 30.851 | 30.059 | 1.00 | 39.93 | H |
| ATOM | 2717 | CA | TYR | S | 798 | 39.345 | 30.682 | 30.515 | 1.00 | 40.53 | C |
| ATOM | 2718 | C | TYR | S | 798 | 39.088 | 29.350 | 31.183 | 1.00 | 39.72 | C |

TABLE 3-continued

| | | | | | Coordinates for structures 1 to 4 | | | | | |
|---|---|---|---|---|---|---|---|---|---|---|
| ATOM | 2719 | O | TYR | S | 798 | 39.797 | 28.383 | 30.958 | 1.00 | 39.72 | O |
| ATOM | 2720 | CB | TYR | S | 798 | 38.377 | 30.881 | 29.351 | 1.00 | 41.28 | C |
| ATOM | 2721 | CG | TYR | S | 798 | 38.524 | 29.939 | 28.171 | 1.00 | 44.57 | C |
| ATOM | 2722 | CD1 | TYR | S | 798 | 39.574 | 30.071 | 27.261 | 1.00 | 47.13 | C |
| ATOM | 2723 | CD2 | TYR | S | 798 | 37.574 | 28.953 | 27.932 | 1.00 | 47.85 | C |
| ATOM | 2724 | CE1 | TYR | S | 798 | 39.692 | 29.219 | 26.163 | 1.00 | 48.81 | C |
| ATOM | 2725 | CE2 | TYR | S | 798 | 37.680 | 28.094 | 26.833 | 1.00 | 50.32 | C |
| ATOM | 2726 | CZ | TYR | S | 798 | 38.744 | 28.229 | 25.955 | 1.00 | 49.97 | C |
| ATOM | 2727 | OH | TYR | S | 798 | 38.835 | 27.387 | 24.866 | 1.00 | 49.58 | O |
| ATOM | 2728 | H | ASP | S | 799 | 38.051 | 29.306 | 32.005 | 1.00 | 39.16 | N |
| ATOM | 2729 | CA | ASP | S | 799 | 37.676 | 28.076 | 32.690 | 1.00 | 38.61 | C |
| ATOM | 2730 | C | ASP | S | 799 | 36.588 | 27.391 | 31.868 | 1.00 | 37.26 | C |
| ATOM | 2731 | O | ASP | S | 799 | 36.468 | 27.657 | 30.671 | 1.00 | 36.81 | O |
| ATOM | 2732 | CB | ASP | S | 799 | 37.186 | 28.399 | 34.105 | 1.00 | 39.29 | C |
| ATOM | 2733 | CG | ASP | S | 799 | 37.303 | 27.223 | 35.048 | 1.00 | 40.55 | C |
| ATOM | 2734 | OD1 | ASP | S | 799 | 36.767 | 26.128 | 34.756 | 1.00 | 41.68 | O |
| ATOM | 2735 | OD2 | ASP | S | 799 | 37.913 | 27.319 | 36.121 | 1.00 | 45.38 | O |
| ATOM | 2736 | N | CYS | S | 800 | 35.795 | 26.517 | 32.486 | 1.00 | 35.61 | N |
| ATOM | 2737 | CA | CYS | S | 800 | 34.781 | 25.787 | 31.732 | 1.00 | 34.66 | C |
| ATOM | 2738 | C | CYS | S | 800 | 33.439 | 25.714 | 32.450 | 1.00 | 34.03 | C |
| ATOM | 2739 | O | CYS | S | 800 | 32.749 | 24.708 | 32.388 | 1.00 | 33.81 | O |
| ATOM | 2740 | CB | CYS | S | 800 | 35.274 | 24.380 | 31.423 | 1.00 | 34.32 | C |
| ATOM | 2741 | SG | CYS | S | 800 | 35.538 | 23.392 | 32.911 | 1.00 | 33.88 | S |
| ATOM | 2742 | N | GLU | S | 801 | 33.051 | 26.792 | 33.101 | 1.00 | 33.69 | N |
| ATOM | 2743 | CA | GLU | S | 801 | 31.808 | 26.803 | 33.859 | 1.00 | 33.94 | C |
| ATOM | 2744 | C | GLU | S | 801 | 30.551 | 26.980 | 32.991 | 1.00 | 33.69 | C |
| ATOM | 2745 | O | GLU | S | 801 | 30.520 | 27.739 | 32.012 | 1.00 | 32.67 | O |
| ATOM | 2746 | CB | GLU | S | 801 | 31.886 | 27.877 | 34.942 | 1.00 | 34.03 | C |
| ATOM | 2747 | CG | GLU | S | 801 | 33.128 | 27.703 | 35.818 | 1.00 | 36.03 | C |
| ATOM | 2748 | CD | GLU | S | 801 | 33.095 | 28.557 | 37.065 | 1.00 | 36.15 | C |
| ATOM | 2749 | OE1 | GLU | S | 801 | 32.408 | 28.163 | 38.010 | 1.00 | 35.62 | O |
| ATOM | 2750 | OE2 | GLU | S | 801 | 33.751 | 29.619 | 37.090 | 1.00 | 38.69 | O |
| ATOM | 2751 | N | VAL | S | 802 | 29.519 | 26.242 | 33.377 | 1.00 | 33.95 | N |
| ATOM | 2752 | CA | VAL | S | 802 | 28.244 | 26.223 | 32.691 | 1.00 | 33.82 | C |
| ATOM | 2753 | C | VAL | S | 802 | 27.137 | 26.148 | 33.735 | 1.00 | 34.17 | C |
| ATOM | 2754 | O | VAL | S | 802 | 27.408 | 25.928 | 34.908 | 1.00 | 33.56 | O |
| ATOM | 2755 | CB | VAL | S | 802 | 28.139 | 24.972 | 31.781 | 1.00 | 33.63 | C |
| ATOM | 2756 | CG1 | VAL | S | 802 | 29.263 | 24.948 | 30.753 | 1.00 | 32.61 | C |
| ATOM | 2757 | CG2 | VAL | S | 802 | 28.165 | 23.682 | 32.624 | 1.00 | 33.77 | C |
| ATOM | 2758 | N | ASN | S | 803 | 25.887 | 26.304 | 33.300 | 1.00 | 35.05 | N |
| ATOM | 2759 | CA | ASN | S | 803 | 24.745 | 26.222 | 34.204 | 1.00 | 35.82 | C |
| ATOM | 2760 | C | ASN | S | 803 | 24.457 | 24.784 | 34.642 | 1.00 | 37.45 | C |
| ATOM | 2761 | O | ASN | S | 803 | 23.379 | 24.241 | 34.642 | 1.00 | 37.12 | O |
| ATOM | 2762 | CB | ASN | S | 803 | 23.490 | 26.836 | 33.573 | 1.00 | 35.36 | C |
| ATOM | 2763 | CG | ASN | S | 803 | 23.548 | 28.344 | 33.506 | 1.00 | 33.54 | C |
| ATOM | 2764 | OD1 | ASN | S | 803 | 24.605 | 28.941 | 33.685 | 1.00 | 32.05 | O |
| ATOM | 2765 | ND2 | ASN | S | 803 | 22.414 | 28.967 | 33.230 | 1.00 | 29.41 | N |
| ATOM | 2766 | N | ALA | S | 804 | 25.442 | 24.187 | 35.298 | 1.00 | 39.28 | N |
| ATOM | 2767 | CA | ALA | S | 804 | 25.340 | 22.846 | 35.855 | 1.00 | 41.13 | C |
| ATOM | 2768 | C | ALA | S | 804 | 26.566 | 22.620 | 36.734 | 1.00 | 42.43 | C |
| ATOM | 2769 | O | ALA | S | 804 | 27.638 | 23.153 | 36.464 | 1.00 | 42.47 | O |
| ATOM | 2770 | CB | ALA | S | 804 | 25.277 | 21.791 | 34.762 | 1.00 | 41.08 | C |
| ATOM | 2771 | N | PRO | S | 805 | 26.410 | 21.830 | 37.786 | 1.00 | 44.47 | N |
| ATOM | 2772 | CA | PRO | S | 805 | 27.527 | 21.527 | 38.697 | 1.00 | 45.68 | C |
| ATOM | 2773 | C | PRO | S | 805 | 28.568 | 20.620 | 38.053 | 1.00 | 46.82 | C |
| ATOM | 2774 | O | PRO | S | 805 | 28.273 | 19.918 | 37.092 | 1.00 | 47.40 | O |
| ATOM | 2775 | CB | PRO | S | 805 | 26.847 | 20.783 | 39.854 | 1.00 | 45.66 | C |
| ATOM | 2776 | CG | PRO | S | 805 | 25.588 | 20.206 | 39.261 | 1.00 | 45.01 | C |
| ATOM | 2777 | CD | PRO | S | 805 | 25.161 | 21.146 | 38.177 | 1.00 | 44.63 | C |
| ATOM | 2778 | N | ILE | S | 806 | 29.770 | 20.613 | 38.605 | 1.00 | 48.31 | N |
| ATOM | 2779 | CA | ILE | S | 806 | 30.847 | 19.766 | 38.098 | 1.00 | 49.34 | C |
| ATOM | 2780 | C | ILE | S | 806 | 30.661 | 18.323 | 38.555 | 1.00 | 49.57 | C |
| ATOM | 2781 | O | ILE | S | 806 | 29.992 | 18.063 | 39.560 | 1.00 | 50.13 | O |
| ATOM | 2782 | CB | ILE | S | 806 | 32.215 | 20.311 | 38.574 | 1.00 | 49.85 | C |
| ATOM | 2783 | CG1 | ILE | S | 806 | 32.410 | 20.058 | 40.074 | 1.00 | 50.64 | C |
| ATOM | 2784 | CG2 | ILE | S | 806 | 32.327 | 21.816 | 38.250 | 1.00 | 50.45 | C |
| ATOM | 2785 | CO1 | ILE | S | 806 | 33.724 | 20.605 | 40.624 | 1.00 | 51.43 | C |
| ATOM | 2786 | N | LEU | S | 813 | 29.871 | 8.315 | 36.218 | 1.00 | 46.23 | N |
| ATOM | 2787 | CA | LEU | S | 813 | 30.588 | 8.788 | 35.034 | 1.00 | 46.32 | C |
| ATOM | 2788 | C | LEU | S | 813 | 29.685 | 9.635 | 34.140 | 1.00 | 45.87 | C |
| ATOM | 2789 | O | LEU | S | 813 | 28.463 | 9.511 | 34.185 | 1.00 | 45.43 | O |
| ATOM | 2790 | CB | LEU | S | 813 | 31.166 | 7.606 | 34.243 | 1.00 | 46.25 | C |
| ATOM | 2791 | CG | LEU | S | 813 | 32.057 | 6.663 | 35.059 | 1.00 | 46.61 | C |
| ATOM | 2792 | CE1 | LEU | S | 813 | 32.444 | 5.423 | 34.230 | 1.00 | 46.51 | C |
| ATOM | 2793 | CE2 | LEU | S | 813 | 33.292 | 7.406 | 35.579 | 1.00 | 45.98 | c |
| ATOM | 2794 | N | GLN | S | 814 | 30.309 | 10.503 | 33.351 | 1.00 | 45.81 | N |
| ATOM | 2795 | CA | GLN | S | 814 | 29.595 | 11.400 | 32.446 | 1.00 | 45.92 | c |

TABLE 3-continued

Coordinates for structures 1 to 4

| | | | | | | | | | | | |
|---|---|---|---|---|---|---|---|---|---|---|---|
| ATOM | 2796 | C | GLN | S | 814 | 30.497 | 11.838 | 31.296 | 1.00 | 45.66 | C |
| ATOM | 2797 | O | GLN | S | 814 | 31.706 | 11.626 | 31.329 | 1.00 | 45.05 | O |
| ATOM | 2798 | CB | GLN | S | 814 | 29.123 | 12.643 | 33.198 | 1.00 | 46.09 | C |
| ATOM | 2799 | OG | GLN | S | 814 | 30.265 | 13.531 | 33.696 | 1.00 | 47.32 | C |
| ATOM | 2800 | CD | GLN | S | 814 | 29.781 | 14.722 | 34.520 | 1.00 | 49.22 | C |
| ATOM | 2801 | OE1 | GLN | S | 814 | 29.165 | 14.541 | 35.569 | 1.00 | 50.40 | O |
| ATOM | 2802 | NE2 | GLN | S | 814 | 30.070 | 15.937 | 34.053 | 1.00 | 49.45 | N |
| ATOM | 2803 | N | GLY | S | 815 | 29.898 | 12.476 | 30.294 | 1.00 | 45.88 | N |
| ATOM | 2804 | CA | GLY | S | 815 | 30.621 | 12.956 | 29.135 | 1.00 | 45.84 | C |
| ATOM | 2805 | C | GLY | S | 815 | 31.426 | 11.863 | 28.462 | 1.00 | 46.13 | C |
| ATOM | 2806 | O | GLY | S | 815 | 30.968 | 10.732 | 28.339 | 1.00 | 45.49 | O |
| ATOM | 2807 | N | GLU | S | 816 | 32.633 | 12.216 | 28.035 | 1.00 | 46.94 | N |
| ATOM | 2808 | CA | GLU | S | 816 | 33.548 | 11.285 | 27.382 | 1.00 | 48.03 | C |
| ATOM | 2809 | C | GLU | S | 816 | 33.721 | 9.994 | 28.186 | 1.00 | 48.62 | C |
| ATOM | 2810 | O | GLU | S | 816 | 33.823 | 8.910 | 27.614 | 1.00 | 48.54 | O |
| ATOM | 2811 | CB | GLU | S | 816 | 34.920 | 11.948 | 27.184 | 1.00 | 48.06 | C |
| ATOM | 2812 | CG | GLU | S | 816 | 35.783 | 11.312 | 26.102 | 1.00 | 48.93 | C |
| ATOM | 2813 | CD | GLU | S | 816 | 37.189 | 11.887 | 26.062 | 1.00 | 49.77 | C |
| ATOM | 2814 | OE1 | GLU | S | 816 | 38.031 | 11.413 | 26.848 | 1.00 | 50.86 | O |
| ATOM | 2815 | OE2 | GLU | S | 816 | 37.457 | 12.802 | 25.247 | 1.00 | 49.55 | O |
| ATOM | 2816 | N | GLU | S | 817 | 33.737 | 10.112 | 29.509 | 1.00 | 49.67 | N |
| ATOM | 2817 | CA | GLU | S | 817 | 33.947 | 8.957 | 30.373 | 1.00 | 50.75 | C |
| ATOM | 2818 | C | GLU | S | 817 | 32.786 | 7.982 | 30.309 | 1.00 | 51.10 | C |
| ATOM | 2819 | O | GLU | S | 817 | 32.989 | 6.771 | 30.278 | 1.00 | 51.12 | O |
| ATOM | 2820 | CB | GLU | S | 817 | 34.164 | 9.406 | 31.815 | 1.00 | 50.97 | C |
| ATOM | 2821 | CG | GLU | S | 817 | 35.476 | 10.140 | 32.032 | 1.00 | 52.22 | C |
| ATOM | 2822 | CD | GLU | S | 817 | 35.395 | 11.637 | 31.764 | 1.00 | 54.47 | C |
| ATOM | 2823 | OE1 | GLU | S | 817 | 34.289 | 12.166 | 31.489 | 1.00 | 55.57 | O |
| ATOM | 2824 | OE2 | GLU | S | 817 | 36.456 | 12.296 | 31.833 | 1.00 | 56.41 | O |
| ATOM | 2825 | N | LEU | S | 818 | 31.572 | 8.521 | 30.295 | 1.00 | 51.81 | N |
| ATOM | 2826 | CA | LEU | S | 818 | 30.376 | 7.706 | 30.204 | 1.00 | 52.37 | C |
| ATOM | 2827 | C | LEU | S | 818 | 30.399 | 6.929 | 28.901 | 1.00 | 53.14 | C |
| ATOM | 2828 | O | LEU | S | 818 | 30.216 | 5.714 | 28.894 | 1.00 | 53.00 | O |
| ATOM | 2829 | CB | LEU | S | 818 | 29.116 | 8.575 | 30.258 | 1.00 | 52.25 | C |
| ATOM | 2830 | CG | LEU | S | 818 | 27.786 | 7.814 | 30.176 | 1.00 | 52.17 | C |
| ATOM | 2831 | CD1 | LEU | S | 818 | 27.661 | 6.836 | 31.335 | 1.00 | 52.37 | C |
| ATOM | 2832 | CD2 | LEU | S | 818 | 26.596 | 8.749 | 30.173 | 1.00 | 51.16 | C |
| ATOM | 2833 | N | LEU | S | 819 | 30.660 | 7.643 | 27.809 | 1.00 | 54.00 | N |
| ATOM | 2834 | CA | LEU | S | 819 | 30.623 | 7.068 | 26.465 | 1.00 | 54.73 | C |
| ATOM | 2835 | C | LEU | S | 819 | 31.573 | 5.874 | 26.295 | 1.00 | 55.32 | C |
| ATOM | 2836 | O | LEU | S | 819 | 31.171 | 4.823 | 25.794 | 1.00 | 55.08 | O |
| ATOM | 2837 | CB | LEU | S | 819 | 30.929 | 8.162 | 25.426 | 1.00 | 54.66 | C |
| ATOM | 2838 | CG | LEU | S | 819 | 30.838 | 7.789 | 23.942 | 1.00 | 54.90 | C |
| ATOM | 2839 | OD1 | LEU | S | 819 | 29.480 | 7.239 | 23.559 | 1.00 | 54.56 | C |
| ATOM | 2840 | CD2 | LEU | S | 819 | 31.170 | 8.997 | 23.088 | 1.00 | 55.68 | C |
| ATOM | 2841 | N | ARG | S | 820 | 32.821 | 6.036 | 26.725 | 1.00 | 55.92 | N |
| ATOM | 2842 | CA | ARG | S | 820 | 33.817 | 4.987 | 26.576 | 1.00 | 56.75 | C |
| ATOM | 2843 | C | ARG | S | 820 | 33.488 | 3.762 | 27.428 | 1.00 | 56.92 | C |
| ATOM | 2844 | O | ARG | S | 820 | 33.578 | 2.617 | 26.951 | 1.00 | 56.86 | O |
| ATOM | 2845 | CB | ARG | S | 820 | 35.207 | 5.530 | 26.915 | 1.00 | 57.13 | C |
| ATOM | 2846 | CG | ARG | S | 820 | 35.638 | 6.596 | 25.927 | 1.00 | 58.55 | C |
| ATOM | 2847 | CD | ARG | S | 820 | 37.073 | 7.038 | 26.036 | 1.00 | 60.19 | C |
| ATOM | 2848 | NE | ARG | S | 820 | 37.336 | 8.126 | 25.096 | 1.00 | 62.23 | O |
| ATOM | 2849 | CZ | ARG | S | 820 | 38.465 | 8.831 | 25.039 | 1.00 | 64.08 | C |
| ATOM | 2850 | NH1 | ARG | S | 820 | 39.475 | 8.567 | 25.865 | 1.00 | 64.81 | N |
| ATOM | 2851 | NH2 | ARG | S | 820 | 38.586 | 9.805 | 24.142 | 1.00 | 64.58 | N |
| ATOM | 2852 | N | ALA | S | 821 | 33.109 | 4.003 | 28.682 | 1.00 | 56.90 | N |
| ATOM | 2853 | CA | ALA | S | 821 | 32.713 | 2.919 | 29.567 | 1.00 | 56.79 | C |
| ATOM | 2854 | C | ALA | S | 821 | 31.611 | 2.106 | 28.880 | 1.00 | 56.74 | C |
| ATOM | 2855 | O | ALA | S | 821 | 31.665 | 0.873 | 28.843 | 1.00 | 56.66 | O |
| ATOM | 2856 | CB | ALA | S | 821 | 32.236 | 3.463 | 30.899 | 1.00 | 56.66 | C |
| ATOM | 2857 | N | LEU | S | 822 | 30.629 | 2.806 | 28.317 | 1.00 | 56.51 | N |
| ATOM | 2858 | CA | LEU | S | 822 | 29.537 | 2.155 | 27.607 | 1.00 | 56.58 | C |
| ATOM | 2859 | C | LEU | S | 822 | 30.031 | 1.473 | 26.338 | 1.00 | 56.66 | C |
| ATOM | 2860 | O | LEU | S | 822 | 29.482 | 0.451 | 25.931 | 1.00 | 57.09 | O |
| ATOM | 2861 | CB | LEU | S | 822 | 28.451 | 3.167 | 27.250 | 1.00 | 56.48 | C |
| ATOM | 2862 | CG | LEU | S | 822 | 27.681 | 3.779 | 28.417 | 1.00 | 56.11 | C |
| ATOM | 2863 | CD1 | LEU | S | 822 | 26.543 | 4.612 | 27.870 | 1.00 | 55.96 | C |
| ATOM | 2864 | CD2 | LEU | S | 822 | 27.156 | 2.717 | 29.379 | 1.00 | 55.80 | C |
| THR | 2865 | | LEU | S | 822 | | | | | | |
| HETATM | 2866 | FE | FE2 | A | 1350 | 23.313 | 27.671 | 28.779 | 1.00 | 22.12 | FE |
| HETATM | 2867 | C1 | AKG | A | 1351 | 22.355 | 25.315 | 27.747 | 1.00 | 25.61 | C |
| HETATM | 2868 | O1 | AKG | A | 1351 | 23.449 | 25.880 | 27.756 | 1.00 | 27.58 | O |
| HETATM | 2869 | O2 | AKG | A | 1351 | 22.172 | 24.103 | 27.197 | 1.00 | 27.99 | O |
| HETATM | 2870 | C2 | AKG | A | 1351 | 21.128 | 25.999 | 28.365 | 1.00 | 24.14 | C |
| HETATM | 2871 | O5 | AKG | A | 1351 | 21.211 | 27.117 | 28.854 | 1.00 | 23.66 | O |
| HETATM | 2872 | C3 | AKG | A | 1351 | 19.829 | 25.231 | 28.280 | 1.00 | 23.46 | C |

TABLE 3-continued

| | | | | | | | | | | |
|---|---|---|---|---|---|---|---|---|---|---|
| | | | | Coordinates for structures 1 to 4 | | | | | | |
| HETATM | 2873 | C4 | AKG | A | 1351 | 18.717 | 25.967 | 29.008 | 1.00 | 22.15 | C |
| HETATM | 2874 | C5 | AKG | A | 1351 | 17.351 | 25.435 | 28.649 | 1.00 | 23.90 | C |
| HETATM | 2875 | O3 | AKG | A | 1351 | 17.136 | 24.674 | 27.706 | 1.00 | 23.27 | O |
| HETATM | 2876 | O4 | AKG | A | 1351 | 16.353 | 25.844 | 29.406 | 1.00 | 25.34 | O |
| HETATM | 2877 | S | SO4 | A | 1352 | 0.196 | 25.255 | 43.681 | 1.00 | 83.69 | S |
| HETATM | 2878 | O1 | SO4 | A | 1352 | 1.049 | 26.078 | 44.531 | 1.00 | 83.03 | O |
| HETATM | 2879 | O2 | SO4 | A | 1352 | 1.028 | 24.391 | 42.840 | 1.00 | 82.84 | O |
| HETATM | 2880 | O3 | SO4 | A | 1352 | −0.643 | 24.431 | 44.542 | 1.00 | 83.90 | O |
| HETATM | 2881 | O4 | SO4 | A | 1352 | −0.630 | 26.114 | 42.830 | 1.00 | 82.82 | O |
| HETATM | 2882 | S | SO4 | A | 1353 | 1.937 | 28.607 | 29.759 | 1.00 | 80.69 | S |
| HETATM | 2883 | O1 | SO4 | A | 1353 | 3.164 | 29.179 | 30.298 | 1.00 | 79.82 | O |
| HETATM | 2884 | O2 | SO4 | A | 1353 | 2.228 | 27.552 | 28.793 | 1.00 | 79.89 | O |
| HETATM | 2885 | O3 | SO4 | A | 1353 | 1.188 | 28.079 | 30.902 | 1.00 | 82.14 | O |
| HETATM | 2886 | O4 | SO4 | A | 1353 | 1.145 | 29.630 | 29.081 | 1.00 | 81.49 | O |
| HETATM | 2887 | O | HOH | H | 1 | 38.423 | 33.864 | 31.899 | 1.00 | 39.52 | O |
| HETATM | 2888 | O | HOH | H | 2 | 38.025 | 25.366 | 29.554 | 1.00 | 64.59 | O |
| HETATM | 2889 | O | HOH | H | 3 | 34.915 | 30.689 | 35.190 | 1.00 | 34.36 | O |
| HETATM | 2890 | O | HOH | H | 4 | 20.482 | 27.037 | 33.306 | 1.00 | 55.20 | O |
| HETATM | 2891 | O | HOH | H | 5 | 21.066 | 24.447 | 32.916 | 1.00 | 43.55 | O |
| HETATM | 2892 | O | HOH | H | 6 | 29.978 | 24.394 | 35.721 | 1.00 | 43.81 | O |
| HETATM | 2893 | O | HOH | H | 7 | 29.346 | 18.985 | 42.744 | 1.00 | 86.25 | O |
| HETATM | 2894 | O | HOH | H | 8 | 35.530 | 13.904 | 24.157 | 1.00 | 42.65 | O |
| HETATM | 2895 | O | HOH | H | 9 | 33.804 | −1.383 | 26.877 | 1.00 | 65.05 | O |
| HETATM | 2896 | O | HOH | Z | 1 | 11.560 | 21.626 | 13.846 | 1.00 | 41.47 | O |
| HETATM | 2897 | O | HOH | Z | 2 | 9.590 | 21.877 | 12.314 | 1.00 | 61.59 | O |
| HETATM | 2898 | O | HOH | Z | 3 | 1.321 | 21.339 | 7.657 | 1.00 | 58.53 | O |
| HETATM | 2899 | O | HOH | Z | 4 | 3.579 | 13.365 | 8.778 | 1.00 | 47.77 | O |
| HETATM | 2900 | O | HOH | Z | 5 | 4.515 | 16.855 | 3.766 | 1.00 | 51.50 | O |
| HETATM | 2901 | O | HOH | Z | 6 | 2.462 | 19.552 | 5.161 | 1.00 | 56.40 | O |
| HETATM | 2902 | O | HOH | Z | 7 | 1.251 | 29.413 | 13.184 | 1.00 | 52.18 | O |
| HETATM | 2903 | O | HOH | Z | 8 | 2.053 | 32.304 | 13.875 | 1.00 | 71.43 | O |
| HETATM | 2904 | O | HOH | Z | 9 | 11.574 | 44.907 | 14.867 | 1.00 | 67.18 | O |
| HETATM | 2905 | O | HOH | Z | 10 | 11.615 | 3.238 | 17.221 | 1.00 | 63.99 | O |
| HETATM | 2906 | O | HOH | Z | 11 | 3.752 | 32.951 | 32.37S | 1.00 | 72.66 | O |
| HETATM | 2907 | O | HOH | Z | 12 | 4.803 | 37.611 | 27.421 | 1.00 | 63.47 | O |
| HETATM | 2908 | O | HOH | Z | 13 | 11.007 | 35.734 | 30.393 | 1.00 | 34.95 | O |
| HETATM | 2909 | O | HOH | Z | 14 | 15.551 | 46.392 | 24.481 | 1.00 | 43.01 | O |
| HETATM | 2910 | O | HOH | Z | 15 | 12.231 | 41.979 | 15.720 | 1.00 | 53.94 | O |
| HETATM | 2911 | O | HOH | Z | 16 | 13.868 | 4.815 | 17.661 | 1.00 | 48.46 | O |
| HETATM | 2912 | O | HOH | Z | 17 | 15.860 | 30.606 | 12.755 | 1.00 | 44.45 | O |
| HETATM | 2913 | O | HOH | Z | 18 | 13.462 | 22.030 | 7.390 | 1.00 | 59.18 | O |
| HETATM | 2914 | O | HOH | Z | 19 | 14.706 | 26.336 | 13.845 | 1.00 | 51.42 | O |
| HETATM | 2915 | O | HOH | Z | 20 | 17.028 | 29.994 | 7.603 | 1.00 | 64.07 | O |
| HETATM | 2916 | O | HOH | Z | 21 | 21.13S | 23.988 | 3.773 | 1.00 | 46.32 | O |
| HETATM | 2917 | O | HOH | Z | 22 | 27.581 | 31.130 | 6.026 | 1.00 | 64.13 | O |
| HETATM | 2918 | O | HOH | Z | 23 | 27.341 | 22.242 | 43.414 | 1.00 | 79.43 | O |
| HETATM | 2919 | O | HOH | Z | 24 | 36.742 | 29.331 | 21.279 | 1.00 | 50.70 | O |
| HETATM | 2920 | O | HOH | Z | 25 | 30.029 | 33.533 | 9.206 | 1.00 | 50.33 | O |
| HETATM | 2921 | O | HOH | Z | 26 | 29.955 | 37.104 | 10.551 | 1.00 | 70.40 | O |
| HETATM | 2922 | O | HOH | Z | 27 | 18.215 | 15.129 | 13.036 | 1.00 | 37.33 | O |
| HETATM | 2923 | O | HOH | Z | 28 | 29.069 | 5.533 | 17.355 | 1.00 | 44.84 | O |
| HETATM | 2924 | O | HOH | Z | 29 | 18.941 | 14.771 | 16.383 | 1.00 | 31.41 | O |
| HETATM | 2925 | O | HOH | Z | 30 | 13.624 | 7.655 | 18.343 | 1.00 | 46.45 | O |
| HETATM | 2926 | O | HOH | Z | 31 | 5.649 | 12.667 | 27.758 | 1.00 | 44.15 | O |
| HETATM | 2927 | O | HOH | Z | 32 | 18.818 | 6.772 | 36.717 | 1.00 | 51.59 | O |
| HETATM | 2928 | O | HOH | Z | 33 | 7.620 | 14.589 | 19.463 | 1.00 | 50.93 | O |
| HETATM | 2929 | O | HOH | Z | 34 | 20.087 | 9.746 | 36.974 | 1.00 | 52.81 | O |
| HETATM | 2930 | O | HOH | Z | 35 | 21.912 | 13.173 | 44.511 | 1.00 | 59.64 | O |
| HETATM | 2931 | O | HOH | Z | 36 | 29.233 | 39.992 | 16.108 | 1.00 | 75.75 | O |
| HETATM | 2932 | O | HOH | Z | 37 | 33.785 | 44.067 | 25.671 | 1.00 | 62.06 | O |
| HETATM | 2933 | O | HOH | Z | 38 | 15.613 | 37.779 | 35.493 | 1.00 | 52.50 | O |
| HETATM | 2934 | O | HOH | Z | 39 | 8.070 | 38.292 | 35.056 | 1.00 | 60.61 | O |
| HETATM | 2935 | O | HOH | Z | 40 | 16.339 | 30.957 | 40.378 | 1.00 | 43.15 | O |
| HETATM | 2936 | O | HOH | Z | 41 | 28.116 | 27.147 | 37.617 | 1.00 | 59.20 | O |
| HETATM | 2937 | O | HOH | Z | 42 | 29.707 | 30.087 | 39.279 | 1.00 | 54.89 | O |
| HETATM | 2938 | O | HOH | Z | 43 | 28.116 | 24.509 | 42.048 | 1.00 | 63.13 | O |
| HETATM | 2939 | O | HOH | Z | 44 | 25.074 | 24.801 | 42.258 | 1.00 | 54.81 | O |
| HETATM | 2940 | O | HOH | Z | 45 | 33.873 | 31.493 | 39.077 | 1.00 | 45.97 | O |
| HETATM | 2941 | O | HOH | Z | 46 | 31.533 | 33.860 | 46.118 | 1.00 | 50.65 | O |
| HETATM | 2942 | O | HOH | Z | 47 | 13.319 | 35.957 | 31.390 | 1.00 | 44.72 | O |
| HETATM | 2943 | O | HOH | Z | 48 | 27.155 | 38.119 | 52.311 | 1.00 | 64.05 | O |
| HETATM | 2944 | O | HOH | Z | 49 | 24.587 | 38.767 | 49.612 | 1.00 | 50.58 | O |
| HETATM | 2945 | O | HOH | Z | 50 | 21.687 | 17.630 | 48.071 | 1.00 | 77.36 | O |
| HETATM | 2946 | O | HOH | Z | 51 | 21.437 | 14.872 | 40.880 | 1.00 | 60.20 | O |
| HETATM | 2947 | O | HOH | Z | 52 | 24.790 | 15.406 | 39.359 | 1.00 | 78.81 | O |
| HETATM | 2948 | O | HOH | Z | 53 | 23.347 | 17.356 | 36.625 | 1.00 | 52.48 | O |
| HETATM | 2949 | O | HOH | Z | 54 | 21.628 | 10.475 | 34.469 | 1.00 | 47.30 | O |

TABLE 3-continued

Coordinates for structures 1 to 4

| | | | | | | | | | | |
|---|---|---|---|---|---|---|---|---|---|---|
| HETATM | 2950 | O | HOH | Z | 55 | 18.013 | −1.527 | 33.036 | 1.00 | 61.93 | O |
| HETATM | 2951 | O | HOH | Z | 56 | 16.101 | −0.104 | 30.078 | 1.00 | 59.33 | O |
| HETATM | 2952 | O | HOH | Z | 57 | 26.268 | 5.539 | 16.988 | 1.00 | 38.42 | O |
| HETATM | 2953 | O | HOH | Z | 58 | 30.916 | 16.527 | 11.437 | 1.00 | 44.01 | O |
| HETATM | 2954 | O | HOH | Z | 59 | 32.683 | 13.953 | 20.664 | 1.00 | 50.04 | O |
| HETATM | 2955 | O | HOH | Z | 60 | 36.797 | 10.766 | 7.771 | 1.00 | 80.75 | O |
| HETATM | 2956 | O | HOH | Z | 61 | 33.878 | 26.222 | 17.133 | 1.00 | 45.23 | O |
| HETATM | 2957 | O | HOH | Z | 62 | 13.442 | 21.089 | 28.459 | 1.00 | 36.04 | O |
| HETATM | 2958 | O | HOH | Z | 63 | 3.999 | 21.370 | 30.471 | 1.00 | 47.33 | O |
| HETATM | 2959 | O | HOH | Z | 64 | 30.697 | 38.141 | 33.290 | 1.00 | 31.70 | O |
| HETATM | 2960 | O | HOH | Z | 65 | 26.005 | 26.456 | 26.227 | 1.00 | 28.76 | O |
| HETATM | 2961 | O | HOH | Z | 66 | 36.729 | 32.146 | 33.280 | 1.00 | 42.61 | O |
| HETATM | 2962 | O | HOH | Z | 67 | 35.846 | 25.574 | 27.896 | 1.00 | 34.95 | O |
| HETATM | 2963 | O | HOH | Z | 68 | 36.793 | 26.712 | 21.173 | 1.00 | 33.97 | O |
| HETATM | 2964 | O | HOH | Z | 69 | 17.427 | 17.022 | 18.148 | 1.00 | 31.28 | O |
| HETATM | 2965 | O | HOH | Z | 70 | 9.904 | 13.694 | 19.533 | 1.00 | 41.70 | O |
| HETATM | 2966 | O | HOH | Z | 71 | 5.361 | 16.931 | 22.051 | 1.00 | 43.04 | O |
| HETATM | 2967 | O | HOH | Z | 72 | 7.094 | 16.984 | 20.250 | 1.00 | 43.57 | O |
| HETATM | 2968 | O | HOH | Z | 73 | 6.562 | 22.961 | 22.902 | 1.00 | 42.74 | O |
| HETATM | 2969 | O | HOH | Z | 74 | 29.508 | 38.942 | 26.471 | 1.00 | 26.72 | O |
| HETATM | 2970 | O | HOH | Z | 75 | 30.732 | 39.209 | 19.135 | 1.00 | 37.64 | O |
| HETATM | 2971 | O | HOH | Z | 76 | 26.368 | 42.318 | 17.836 | 1.00 | 57.14 | O |
| HETATM | 2972 | O | HOH | Z | 77 | 27.688 | 44.616 | 31.257 | 1.00 | 30.61 | O |
| HETATM | 2973 | O | HOH | Z | 78 | 30.230 | 44.988 | 25.170 | 1.00 | 39.14 | O |
| HETATM | 2974 | O | NON | Z | 79 | 27.780 | 48.720 | 30.030 | 1.00 | 38.89 | O |
| HETATM | 2975 | O | HOH | Z | 80 | 25.931 | 50.741 | 30.611 | 1.00 | 40.27 | O |
| HETATM | 2976 | O | HOH | Z | 81 | 18.521 | 38.529 | 36.775 | 1.00 | 43.87 | O |
| HETATM | 2977 | O | HOH | Z | 82 | 26.678 | 31.402 | 38.482 | 1.00 | 36.08 | O |
| HETATM | 2978 | O | HOH | Z | 83 | 30.586 | 30.409 | 36.592 | 1.00 | 32.57 | O |
| HETATM | 2979 | O | HOH | Z | 84 | 29.411 | 37.141 | 35.473 | 1.00 | 26.16 | O |
| HETATM | 2980 | O | HOH | Z | 85 | 19.821 | 31.713 | 33.874 | 1.00 | 34.80 | O |
| HETATM | 2981 | O | HOH | Z | 86 | 19.420 | 36.322 | 33.379 | 1.00 | 32.92 | O |
| HETATM | 2982 | O | HOH | Z | 87 | 21.063 | 42.853 | 40.110 | 1.00 | 41.23 | O |
| HETATM | 2983 | O | HOH | Z | 88 | 17.544 | 37.859 | 32.276 | 1.00 | 35.87 | O |
| HETATM | 2984 | O | HOH | Z | 89 | 9.230 | 41.082 | 35.833 | 1.00 | 51.41 | O |
| HETATM | 2985 | O | HOH | Z | 90 | 9.313 | 43.744 | 27.890 | 1.00 | 70.60 | O |
| HETATM | 2986 | O | HOH | Z | 91 | 12.728 | 42.598 | 26.938 | 1.00 | 40.87 | O |
| HETATM | 2987 | O | HOH | Z | 92 | 15.113 | 37.993 | 32.591 | 1.00 | 35.5.5 | O |
| HETATM | 2988 | O | HOH | Z | 93 | 10.676 | 48.283 | 31.613 | 1.00 | 62.24 | O |
| HETATM | 2989 | O | HOH | Z | 94 | 15.611 | 44.853 | 34.883 | 1.00 | 32.72 | O |
| HETATM | 2990 | O | HOH | Z | 95 | 15.874 | 51.836 | 39.217 | 1.00 | 66.58 | O |
| HETATM | 2991 | O | HOH | Z | 96 | 15.796 | 47.224 | 39.264 | 1.00 | 52.95 | O |
| HETATM | 2992 | O | HOH | Z | 97 | 26.624 | 53.557 | 28.816 | 1.00 | 69.05 | O |
| HETATM | 2993 | O | HOH | Z | 98 | 15.381 | 50.418 | 22.170 | 1.00 | 36.68 | O |
| HETATM | 2994 | O | HOH | Z | 99 | 15.121 | 55.730 | 27.489 | 1.00 | 51.35 | O |
| HETATM | 2995 | O | HOH | Z | 100 | 18.542 | 56.170 | 28.175 | 1.00 | 58.02 | O |
| HETATM | 2996 | O | HOH | Z | 101 | 23.731 | 46.355 | 19.907 | 1.00 | 39.06 | O |
| HETATM | 2997 | O | HOH | Z | 102 | 16.618 | 46.781 | 22.039 | 1.00 | 33.91 | O |
| HETATM | 2998 | O | HOH | Z | 103 | 26.585 | 40.624 | 15.634 | 1.00 | 69.17 | O |
| HETATM | 2999 | O | HQH | Z | 104 | 12.758 | 29.333 | 13.489 | 1.00 | 35.42 | O |
| HETATM | 3000 | O | HOH | Z | 105 | 10.886 | 19.245 | 14.132 | 1.00 | 51.89 | O |
| HETATM | 3001 | O | HOH | Z | 106 | 19.776 | 18.049 | 13.245 | 1.00 | 33.88 | O |
| HETATM | 3002 | O | HOH | Z | 107 | 14.725 | 18.642 | 12.190 | 1.00 | 40.50 | O |
| HETATM | 3003 | O | HOH | Z | 108 | 27.783 | 27.681 | 24.556 | 1.00 | 27.24 | O |
| HETATM | 3004 | O | HOH | Z | 109 | 35.999 | 32.896 | 30.270 | 1.00 | 41.19 | O |
| HETATM | 3005 | O | HOH | Z | 110 | 30.237 | 36.282 | 26.881 | 1.00 | 28.77 | O |
| HETATM | 3006 | O | HOH | Z | 111 | 32.759 | 34.258 | 19.346 | 1.00 | 47.40 | O |
| HETATM | 3007 | O | HOH | Z | 112 | 27.418 | 30.315 | 25.756 | 1.00 | 27.70 | O |
| HETATM | 3008 | O | HOH | Z | 113 | 16.248 | 36.360 | 29.657 | 1.00 | 34.03 | O |
| HETATM | 3009 | O | HOH | Z | 114 | 7.438 | 31.072 | 24.792 | 1.00 | 43.13 | O |
| HETATM | 3010 | O | HOH | Z | 115 | 7.743 | 30.565 | 27.379 | 1.00 | 39.83 | O |
| HETATM | 3011 | O | HOH | Z | 116 | 5.158 | 19.080 | 24.012 | 1.00 | 45.77 | O |
| HETATM | 3012 | O | HOH | Z | 117 | 6.366 | 24.013 | 25.459 | 1.00 | 41.84 | O |
| HETATM | 3013 | O | HOH | Z | 118 | 42.594 | 37.813 | 18.527 | 1.00 | 64.57 | O |
| HETATM | 3014 | O | HOH | Z | 119 | 42.361 | 44.340 | 19.742 | 1.00 | 59.24 | O |
| HETATM | 3015 | O | HOH | Z | 120 | 34.674 | 39.749 | 17.782 | 1.00 | 53.99 | O |
| HETATM | 3016 | O | HOH | Z | 121 | 33.762 | 37.015 | 20.310 | 1.00 | 39.85 | O |
| HETATM | 3017 | O | HOH | Z | 122 | 33.121 | 39.446 | 33.667 | 1.00 | 30.35 | O |
| HETATM | 3018 | O | HOH | Z | 123 | 37.674 | 29.865 | 38.229 | 1.00 | 64.32 | O |
| HETATM | 3019 | O | HOH | Z | 124 | 38.677 | 34.824 | 42.977 | 1.00 | 44.37 | O |
| HETATM | 3020 | O | HOH | Z | 125 | 41.375 | 43.570 | 51.489 | 1.00 | 52.41 | O |
| HETATM | 3021 | O | HOH | Z | 126 | 31.947 | 40.559 | 44.192 | 1.00 | 38.39 | O |
| HETATM | 3022 | O | HOH | Z | 127 | 39.124 | 57.396 | 42.134 | 1.00 | 27.12 | O |
| HETATM | 3023 | O | HOH | Z | 128 | 41.949 | 60.812 | 33.590 | 1.00 | 49.78 | O |
| HETATM | 3024 | O | HOH | Z | 129 | 46.835 | 53.394 | 32.063 | 1.00 | 33.50 | O |
| HETATM | 3025 | O | HOH | Z | 130 | 37.841 | 55.408 | 29.621 | 1.00 | 45.14 | O |
| CONECT | 1482 | 2866 | | | | | | | | | |

TABLE 3-continued

Coordinates for structures 1 to 4

| CONECT | 1502 | 2866 | | | | |
|---|---|---|---|---|---|---|
| CONECT | 2171 | 2866 | | | | |
| CONECT | 2866 | 2871 | 2868 | 1482 | 2171 | 1502 |
| CONECT | 2867 | 2868 | 2869 | 2870 | | |
| CONECT | 2868 | 2867 | 2866 | | | |
| CONECT | 2869 | 2867 | | | | |
| CONECT | 2870 | 2867 | 2871 | 2872 | | |
| CONECT | 2871 | 2866 | 2870 | | | |
| CONECT | 2872 | 2870 | 2873 | | | |
| CONECT | 2873 | 2872 | 2874 | | | |
| CONECT | 2874 | 2873 | 2875 | 2876 | | |
| CONECT | 2875 | 2874 | | | | |
| CONECT | 2876 | 2874 | | | | |
| CONECT | 2877 | 2878 | 2879 | 2880 | 2881 | |
| CONECT | 2878 | 2877 | | | | |
| CONECT | 2879 | 2877 | | | | |
| CONECT | 2880 | 2877 | | | | |
| CONECT | 2881 | 2877 | | | | |
| CONECT | 2882 | 2883 | 2884 | 2885 | 2886 | |
| CONECT | 2883 | 2882 | | | | |
| CONECT | 2884 | 2882 | | | | |
| CONECT | 2885 | 2882 | | | | |
| CONECT | 2886 | 2882 | | | | |
| MASTER | 437 0 | 4 | 15 | 20 | 0 | 7 | 6 3023 | 2 | 24 | 31 |
| END | | | | | | |

Structure 3
Below are the coordinates for structure 3 (the 2.5 Å structure of
FIH:Zn(II):NOG:CAD):

| HEADER | TRANSCRIPTION ACTIVATOR/INHIBITOR 12-AUG-02 1H2M |
|---|---|
| TITLE | FACTOR INHIBITING HIF-1 ALPHA IN COMPLEX WITH HIF-1 ALPHA |
| TITLE | 2 FRAGMENT PEPTIDE |
| COMPND | MOL_ID: 1; |
| COMPND | 2 MOLECULE: FACTOR INHIBITING HIF1; |
| COMPND | 3 SYNONYM: FIH1; |
| COMPND | 4 CHAIN: A; |
| COMPND | 5 ENGINEERED: YES; |
| COMPND | 6 MOL_ID: 2; |
| COMPND | 7 MOLECULE: HYPOXIA-INDUCIBLE FACTOR 1 ALPHA; |
| COMPND | 8 SYNONYM: HIF-1 ALPHA, ARNT INTERACTING PROTEIN, |
| COMPND | 9 MEMBER OF PAS PROTEIN 1, MOP1, HIF1 ALPHA, HIF1A. |
| COMPND | 10 CHAIN: S; |
| COMPND | 11 FRAGMENT: C-TERMINAL TRANSACTIVATION DOMAIN FRAGMENT |
| COMPND | 12 RESIDUES 775-826 |
| SOURCE | MOL_ID: 1; |
| SOURCE | 2 ORGANISM_SCIENTIFIC: *HOMO SAPIENS*; |
| SOURCE | 3 ORGANISM_COMMON: HUMAN; |
| SOURCE | 4 EXPRESSION_SYSTEM: *ESCHERICHIA COLI*; |
| SOURCE | 5 EXPRESSION_SYSTEM_STRAIN: BL21(DE3); |
| SOURCE | 6 EXPRESSION_SYSTEM_PLASMID: PET28A(+); |
| SOURCE | 7 MOL_ID: 2; |
| SOURCE | 8 ORGANISM_SCIENTIFIC: *HOMO SAPIENS*; |
| SOURCE | 9 ORGANISM_COMMON: HUMAN; |
| SOURCE | 10 EXPRESSION_SYSTEM: *ESCHERICHIA COLI*; |
| SOURCE | 11 EXPRESSION_SYSTEM_STRAIN: BL21(DE3); |
| SOURCE | 12 EXPRESSION_SYSTEM_PLASMID: PGEX-GP-1 |
| KEYWDS | FIH, HIF, DSBH, DSBH, OXYGENASE, TRANSCRIPTION, HYPOXIA, |
| KEYWDS | 2 2-OXOGLUTARATE, ASPARAGINYL HYDROXYLASE, HYDROXYLASE |
| EXPDTA | X-RAY DIFFRACTION |
| AUTHOR | J. M. ELKINS, K. S. HEWITSON, L. A. MCNEILL, I. SCHLEMMINGER, |
| AUTHOR | 2 J. F. SEIBEL, C. J. SCHOFIELD |
| REVDAT | 1 04-SEP-02 1H2M 0 |
| JRNL | AUTH J. M. ELKINS, K. S. HEWITSON, L. A. MCNEILL, |
| JRNL | AUTH 2 I. SCHLEMMINGER, J. F. SEIBEL, C. J. SCHOFIELD |
| JRNL | TITL FIH:HIF-FRAGMENT COMPLEXES |
| JRNL | REF TO BE PUBLISHED |
| JRNL | REFN |
| REMARK | 2 |
| REMARK | 2 RESOLUTION. 2.5 ANGSTROMS. |
| REMARK | 3 |
| REMARK | 3 REFINEMENT. |
| REMARK | 3 PROGRAM: REFMAC 5.0 |
| REMARK | 3 AUTHORS: MURSHUDOV,VAGIN,DODSON |
| REMARK | 3 |
| REMARK | 3 REFINEMENT TARGET: MAXIMUM LIKELIHOOD |
| REMARK | 3 |

TABLE 3-continued

Coordinates for structures 1 to 4

| REMARK | 3 DATA USED IN REFINEMENT. | | | |
|---|---|---|---|---|
| REMARK | 3 RESOLUTION RANGE HIGH (ANGSTROMS): | 2.50 | | |
| REMARK | 3 RESOLUTION RANGE LOW (ANGSTROMS): | 18.00 | | |
| REMARK | 3 DATA CUTOFF (SIGMA(F)): | NONE | | |
| REMARK | 3 COMPLETENESS FOR RANGE (%): | 99.68 | | |
| REMARK | 3 NUMBER OF REFLECTIONS: | 18404 | | |
| REMARK | 3 | | | |
| REMARK | 3 FIT TO DATA USED IN REFINEMENT. | | | |
| REMARK | 3 CROSS-VALIDATION METHOD: | THROUGHOUT | | |
| REMARK | 3 FREE R VALUE TEST SET SELECTION: | RANDOM | | |
| REMARK | 3 R VALUE (WORKING + TEST SET): | 0.19432 | | |
| REMARK | 3 R VALUE (WORKING SET): | 0.19185 | | |
| REMARK | 3 FREE R VALUE: | 0.22491 | | |
| REMARK | 3 FREE R VALUE TEST SET SIZE (%): | 7.6 | | |
| REMARK | 3 FREE R VALUE TEST SET COUNT: | 1516 | | |
| REMARK | 3 | | | |
| REMARK | 3 FIT IN THE HIGHEST RESOLUTION BIN. | | | |
| REMARK | 3 TOTAL NUMBER OF BINS USED: | 20 | | |
| REMARK | 3 BIN RESOLUTION RANGE HIGH: | 2.500 | | |
| REMARK | 3 BIN RESOLUTION RANGE LOW: | 2.564 | | |
| REMARK | 3 REFLECTION IN BIN (WORKING SET): | 1267 | | |
| REMARK | 3 BIN R VALUE (WORKING SET): | 0.227 | | |
| REMARK | 3 BIN FREE R VALUE SET COUNT: | 106 | | |
| REMARK | 3 BIN FREE R VALUE: | 0.297 | | |
| REMARK | 3 | | | |
| REMARK | 3 NUMBER OF NON-HYDROGEN ATOMS USED IN REFINEMENT. | | | |
| REMARK | 3 ALL ATOMS: 2979 | | | |
| REMARK | 3 | | | |
| REMARK | 3 B VALUES. | | | |
| REMARK | 3 FROM WILSON PLOT (A**2): | NULL | | |
| REMARK | 3 MEAN B VALUE (OVERALL, A**2): | 35.778 | | |
| REMARK | 3 OVERALL ANISOTROPIC B VALUE. | | | |
| REMARK | 3 B11 (A**2): 0.68 | | | |
| REMARK | 3 B22 (A**2): 0.68 | | | |
| REMARK | 3 B33 (A**2): 1.35 | | | |
| REMARK | 3 B12 (A**2): 0.00 | | | |
| REMARK | 3 B13 (A**2): 0.00 | | | |
| REMARK | 3 B23 (A**2): 0.00 | | | |
| REMARK | 3 | | | |
| REMARK | 3 ESTIMATED OVERALL COORDINATE ERROR. | | | |
| REMARK | 3 ESU BASED ON R VALUE (A): | | 0.334 | |
| REMARK | 3 ESU BASED ON FREE R VALUE (A): | | 0.233 | |
| REMARK | 3 ESU BASED ON MAXIMUM LIKELIHOOD (a**2): | | 0.244 | |
| REMARK | 3 ESU FOR B VALUES BASED ON MAXIMUM LIKELIHOOD (A**2): | | 9.825 | |
| REMARK | 3 | | | |
| REMARK | 3 CORRELATION COEFFICIENTS. | | | |
| REMARK | 3 CORRELATION COEFFICIENT FO-FC: | 0.948 | | |
| REMARK | 3 CORRELATION COEFFICIENT FO-FC FREE: | 0.935 | | |
| REMARK | 3 | | | |
| REMARK | 3 RMS DEVIATIONS FROM IDEAL VALUES | COUNT | RMS | WEIGHT |
| REMARK | 3 BOND LENGTHS REFINED ATOMS (A): | 2957; | 0.017; | 0.021 |
| REMARK | 3 BOND LENGTHS OTHERS (A): | 2546; | 0.001; | 0.020 |
| REMARK | 3 BOND ANGLES REFINED ATOMS (DEGREES): | 4022; | 1.612; | 11.948 |
| REMARK | 3 BOND ANGLES OTHERS (DEGREES): | 5944; | 0.832; | 3.000 |
| REMARK | 3 TORSION ANGLES, PERIOD 1 (DEGREES): | 350; | 4.024; | 3.000 |
| REMARK | 3 TORSION ANGLES, PERIOD 3 (DEGREES): | 512; | 18.015; | 15.000 |
| REMARK | 3 CHIRAL-CENTER RESTRAINTS (A**3): | 413; | 0.097; | 0.200 |
| REMARK | 3 GENERAL PLANES REFINED ATOMS (A): | 3315; | 0.006; | 0.020 |
| REMARK | 3 GENERAL PLANES OTHERS (A): | 602; | 0.002; | .020 |
| REMARK | 3 NON-BONDED CONTACTS REFINED ATOMS (A): | 731; | 0.232; | 0.300 |
| REMARK | 3 NON-BONDED CONTACTS OTHERS (A): | 2492; | 0.214; | 0.300 |
| REMARK | 3 H-BOND (X . . . Y) REFINED ATOMS (A): | 193; | 0.173; | 0.500 |
| REMARK | 3 HBOND (X . . . Y) OTHERS (A): | 6; | 0.126; | 0.500 |
| REMARK | 3 POTENTIAL METAL-ION REFINED ATOMS (A): | 2; | 0.054; | 0.500 |
| REMARK | 3 SYMMETRY VDW REFINED ATOMS (A): | 15; | 0.194; | 0.300 |
| REMARK | 3 SYMMETRY VDW OTHERS (A): | 54; 0.255; | 0.300 | |
| REMARK | 3 SYMMETRY H-BOND REFINED ATOMS (A): | 7; | 0.244; | 0.500 |
| REMARK | 3 SYMMETRY H-BOND OTHERS (A): | 1; | 0.053; | 0.500 |
| REMARK | 3 | | | |
| REMARK | 3 ISOTROPIC THERMAL FACTOR RESTRAINTS. | COUNT | RMS | WEIGHT |
| REMARK | 3 MAINCHAIN BOND REFINED ATOMS (A**2): | 1767; | 0.761; | 1.500 |
| REMARK | 3 MAIN-CHAIN ANGLE REFINED ATOMS (A**2): | 2846; | 1.421; | 2.000 |
| REMARK | 3 SIDE-CHAIN BOND REFINED ATOMS (A**2): | 1190; | 2.220; | 3.000 |
| REMARK | 3 SIDE-CHAIN ANGLE REFINED ATOMS (A**2): | 1176; | 3.678; | 4.500 |
| REMARK | 3 | | | |
| REMARK | 3 NCS RESTRAINTS STATISTICS | | | |
| REMARK | 3 NUMBER OF NCS GROUPS: NULL | | | |

TABLE 3-continued

Coordinates for structures 1 to 4

| REMARK | 3 |  |  |  |  |  |  |
|---|---|---|---|---|---|---|---|
| REMARK | 3 TLS DETAILS |  |  |  |  |  |  |
| REMARK | 3 NUMBER OF TLS GROUPS: 1 |  |  |  |  |  |  |
| REMARK | 3 |  |  |  |  |  |  |
| REMARK | 3 TLS GROUPS: 1 |  |  |  |  |  |  |
| REMARK | 3 NUMBER OF COMPONENT GROUP: 2 |  |  |  |  |  |  |
| REMARK | 3 COMPONENTS | C | SSSEQI | TO | C | SSSEQI |  |
| REMARK | 3 RESIDUE RANGE: | A | 15 |  | A | 451 |  |
| REMARK | 3 RESIDUE RANGE: | S | 795 |  | S | 822 |  |
| REMARK | 3 ORIGIN FOR THE GROUP (A): 22.5990 | | | 26.9200 | | 28.6340 |  |
| REMARK | 3 T TENSOR |  |  |  |  |  |  |
| REMARK | 3  T11: | 0.1903 | T22: | 0.0302 |  |  |  |
| REMARK | 3  T33: | 0.0452 | T12: | −0.0025 |  |  |  |
| REMARK | 3  T13: | −0.0536 | T23: | 0.0309 |  |  |  |
| REMARK | 3 L TENSOR |  |  |  |  |  |  |
| REMARK | 3  L11: | 0.7638 | L22: | 2.2674 |  |  |  |
| REMARK | 3  L33: | 1.0629 | L12: | 0.7977 |  |  |  |
| REMARK | 3  L13: | 0.4200 | L23: | 1.0769 |  |  |  |
| REMARK | 3 S TENSOR |  |  |  |  |  |  |
| REMARK | 3  S11: | 0.0306 | S12: | −0.1225 | S13: | −0.0490 |  |
| REMARK | 3  S21: | 0.1656 | S22: | 0.0303 | S23: | 0.0478 |  |
| REMARK | 3  S31: | 0.2046 | S32: | 0.0231 | S33: | −0.0609 |  |
| REMARK | 3 |  |  |  |  |  |  |
| REMARK | 3 BULK SOLVENT MODELLING. |  |  |  |  |  |  |
| REMARK | 3 METHOD USED: BABINET MODEL WITH MASK |  |  |  |  |  |  |
| REMARK | 3 PARAMETERS FOR MASK CALCULATION |  |  |  |  |  |  |
| REMARK | 3 VDW PROBE RADIUS: 1.40 |  |  |  |  |  |  |
| REMARK | 3 ION PROBE RADIUS: 0.80 |  |  |  |  |  |  |
| REMARK | 3 SHRINKAGE RADIUS: 0.80 |  |  |  |  |  |  |
| REMARK | 3 |  |  |  |  |  |  |
| REMARK | 3 OTHER REFINEMENT REMARKS: |  |  |  |  |  |  |
| REMARK | 3 HYDROGENS HAVE BEEN ADDED IN THE RIDING POSITIONS |  |  |  |  |  |  |
| REMARK | 4 |  |  |  |  |  |  |
| REMARK | 4 1H2M COMPLIES WITH FORMAT V. 2.3, 09-JULY-1998 |  |  |  |  |  |  |
| REMARK | 100 |  |  |  |  |  |  |
| REMARK | 100 THIS ENTRY HAS BEEN PROCESSED BY EBI ON 12-AUG-2002. |  |  |  |  |  |  |
| REMARK | 100 THE EBI ID CODE IS EBI-11173. |  |  |  |  |  |  |
| REMARK | 200 |  |  |  |  |  |  |
| REMARK | 200 EXPERIMENTAL DETAILS |  |  |  |  |  |  |
| REMARK | 200 EXPERIMENT TYPE: | | | | X-RAY DIFFRACTION | | |
| REMARK | 200 DATE OF DATA COLLECTION: | | | | 15-MAY-2002 | | |
| REMARK | 200 TEMPERATURE (KELVIN): | | | | 100 | | |
| REMARK | 200 PH: | | | | 7.5 | | |
| REMARK | 200 NUMBER OF CRYSTALS USED: | | | | 1 | | |
| REMARK | 200 |  |  |  |  |  |  |
| REMARK | 200 SYNCHROTRON (Y/N): | | | | Y | | |
| REMARK | 200 RADIATION SOURCE: | | | | SRS BEAMLINE PX9.6 | | |
| REMARK | 200 BEAMLINE: | | | | PX9.6 | | |
| REMARK | 200 X-RAY GENERATOR MODEL: | | | | NULL | | |
| REMARK | 200 MONOCHROMATIC OR LAUE (M/L): | | | | M | | |
| REMARK | 200 WAVELENGTH OR RANGE (A): | | | | 0.87 | | |
| REMARK | 200 MONOCHROMATOR: | | | | NULL | | |
| REMARK | 200 OPTICS: | | | | NULL | | |
| REMARK | 200 |  |  |  |  |  |  |
| REMARK | 200 DETECTOR TYPE: | | | | ADSC QUANTUM 4 | | |
| REMARK | 200 DETECTOR MANUFACTURER: | | | | ADSC | | |
| REMARK | 200 INTENSITY-INTEGRATION SOFTWARE: | | | | MOSFLM | | |
| REMARK | 200 DATA SCALING SOFTWARE: | | | | SCALA | | |
| REMARK | 200 |  |  |  |  |  |  |
| REMARK | 200 NUMBER OF UNIQUE REFLECTIONS: | | | | 20058 | | |
| REMARK | 260 RESOLUTION RANGE HIGH (A): | | | | 2.50 | | |
| REMARK | 200 RESOLUTION RANGE LOW (A): | | | | 87.71 | | |
| REMARK | 200 REJECTION CRITERIA(SIGMA(I)): | | | | NONE | | |
| REMARK | 200 |  |  |  |  |  |  |
| REMARK | 200 OVERALL. |  |  |  |  |  |  |
| REMARK | 200 COMPLETENESS FOR RANGE (%): | | | | 99.7 | | |
| REMARK | 200 DATA REDUNDANCY: | | | | 6.5 | | |
| REMARK | 200 R MERGE (I): | | | | 0.050 | | |
| REMARK | 200 R SYM (I): | | | | NULL | | |
| REMARK | 200 <I/SIGMA(I)> FOR THE DATA SET: | | | | 10.7 | | |
| REMARK | 200 |  |  |  |  |  |  |
| REMARK | 200 IN THE HIGHEST RESOLUTION SHELL. |  |  |  |  |  |  |
| REMARK | 200 HIGHEST RESOLUTION SHELL, RANGE HIGH (A): | | | | 2.50 | | |
| REMARK | 200 HIGHEST RESOLUTION SHELL, RANGE LOW (A): | | | | 2.64 | | |
| REMARK | 200 COMPLETENESS FOR SHELL (%): | | | | 97.9 | | |
| REMARK | 200 DATA REDUNDANCY IN SHELL: | | | | 4.4 | | |
| REMARK | 200 R MERGE FOR SHELL (I): | | | | 0.289 | | |

TABLE 3-continued

| | | Coordinates for structures 1 to 4 | | | | |
|---|---|---|---|---|---|---|
| REMARK | 200 | R SYM FOR SHELL (I): | | | NULL | |
| REMARK | 200 | <I/SIGMA(I)> FOR SHELL: | | | 2.6 | |
| REMARK | 200 | | | | | |
| REMARK | 200 | DIFFRACTION PROTOCOL: SINGLE WAVELENGTH | | | | |
| REMARK | 200 | METHOD USED TO DETHRMINE THE STRUCTURE: MOLECULAR REPLACEMENT | | | | |
| REMARK | 200 | SOFTWARE USED: NULL | | | | |
| REMARK | 200 | STARTING MODEL: NULL | | | | |
| REMARK | 200 | | | | | |
| REMARK | 200 | REMARK: NULL | | | | |
| REMARK | 280 | | | | | |
| REMARK | 280 | CRYSTAL | | | | |
| REMARK | 280 | SOLVENT CONTENT, VS (%): 63 | | | | |
| REMARK | 280 | MATTHEWS COEFFICIENT, VM (ANGSTROMS**3/DA): 3.4 | | | | |
| REMARK | 280 | | | | | |
| REMARK | 280 | CRYSTALLIZATION CONDITIONS: 1.2 M AMMONIUM SULPHATE, | | | | |
| REMARK | 280 | 4% PEG400, 0.1 M HEPES PH 7.5, 11 MG/ML PROTEIN WITH | | | | |
| REMARK | 280 | 1 MM FE(II), 2.5 MM NOG AND 2.5 MM PEPTIDE | | | | |
| REMARK | 290 | | | | | |
| REMARK | 290 | CRYSTALLOGRAPHIC SYMMETRY | | | | |
| REMARK | 290 | SYMMETRY OPERATORS FOR SPACE GROUP: P 41 21 2 | | | | |
| REMARK | 290 | | | | | |
| REMARK | 290 | SYMOP | SYMMETRY | | | |
| REMARK | 290 | NNNMNM | OPERATOR | | | |
| REMARK | 290 | 1555 | X,Y,Z | | | |
| REMARK | 290 | 2555 | −X,Y,1/2+Z | | | |
| REMARK | 290 | 3555 | 1/2−Y,1/2+X,1/4+Z | | | |
| REMARK | 290 | 4555 | 1/2+Y,1/2−X,3/4+Z | | | |
| REMARK | 290 | 5555 | 1/2−X,1/2+Y,1/4−Z | | | |
| REMARK | 290 | 6555 | 1/2+X,1/2−Y,3/4−Z | | | |
| REMARK | 290 | 7555 | Y,X,−Z | | | |
| REMARK | 290 | 8555 | −Y,−X,1/2−Z | | | |
| REMARK | 290 | | | | | |
| REMARK | 290 | WHERE NNN −> | OPERATOR NUMBER | | | |
| REMARK | 290 | MMM −> | TRANSLATION VECTOR | | | |
| REMARK | 290 | | | | | |
| REMARK | 290 | CRYSTALLOGRAPHIC SYMMETRY TRANSFORMATIONS | | | | |
| REMARK | 290 | THE FOLLOWING TRANSFORMATIONS OPERATE ON THE ATOM/HETATM | | | | |
| REMARK | 290 | RECORDS IN THIS ENTRY TO PRODUCE CRYSTALLOGHAPHICALLY | | | | |
| REMARK | 290 | RELATED MOLECULES. | | | | |
| REMARK | 290 | SMTRY1 | 1 0.000000 | 0.000000 | 0.000000 | 0.00000 |
| REMARK | 290 | SMTRY2 | 1 0.000000 | 1.000000 | 0.000000 | 0.00000 |
| REMARK | 290 | SMTRY3 | 1 0.000000 | 0.000000 | 1.000000 | 0.00000 |
| REMARK | 290 | SMTRY1 | 2 −1.000000 | 0.000000 | 0.000000 | 0.00000 |
| REMARK | 290 | SMTRY2 | 2 0.000000 | −1.000000 | 0.000000 | 0.00000 |
| REMARK | 290 | SMTRY3 | 2 0.000000 | 0.000000 | 1.000000 | 74.13000 |
| REMARK | 290 | SMTRY1 | 3 0.000000 | −1.000000 | 0.000000 | 43.12450 |
| REMARK | 290 | SMTRY2 | 3 1.000000 | 0.000000 | 0.000000 | 43.12450 |
| REMARK | 290 | SMTRY3 | 3 0.000000 | 0.000000 | 1.000000 | 37.06500 |
| REMARK | 290 | SMTRY1 | 4 0.000000 | 1.000000 | 0.000000 | 43.12450 |
| REMARK | 290 | SMTRY2 | 4 −1.000000 | 0.000000 | 0.000000 | 43.12450 |
| REMARK | 290 | SMTRY3 | 4 0.000000 | 0.000000 | 1.000000 | 111.19500 |
| REMARK | 290 | SMTRY1 | 5 −1.000000 | 0.000000 | 0.000000 | 43.12450 |
| REMARK | 290 | SMTRY2 | 5 0.000000 | 1.000000 | 0.000000 | 43.12450 |
| REMARK | 290 | SMTRY3 | 5 0.000000 | 0.000000 | −1.000000 | 37.06500 |
| REMARK | 290 | SMTRY1 | 6 1.000000 | 0.000000 | 0.000000 | 43.12450 |
| REMARK | 290 | SMTRY2 | 6 0.000000 | −1.000000 | 0.000000 | 43.12450 |
| REMARK | 290 | SMTRY3 | 6 0.000000 | 0.000000 | −1.000000 | 111.19500 |
| REMARK | 290 | SMTRY1 | 7 0.000000 | 1.000000 | 0.000000 | 0.00000 |
| REMARK | 290 | SMTRY2 | 7 1.000000 | 0.000000 | 0.000000 | 0.00000 |
| REMARK | 290 | SMTRY3 | 7 0.000000 | 0.000000 | −1.000000 | 0.00000 |
| REMARK | 290 | SMTRY1 | 8 0.000000 | −1.000000 | 0.000000 | 0.00000 |
| REMARK | 290 | SMTRY2 | 8 −1.000000 | 0.000000 | 0.000000 | 0.00000 |
| REMARK | 290 | SMTRY3 | 8 0.000000 | 0.000000 | −1.000000 | 74.13000 |
| REMARK | 290 | | | | | |
| REMARK | 290 | REMARK: NULL | | | | |
| REMARK | 300 | | | | | |
| REMARK | 300 | BIOMOLECULE: 1 | | | | |
| REMARK | 300 | THIS ENTRY CONTAINS THE CRYSTALLOGRAPHIC ASYMMETRIC UNIT | | | | |
| REMARK | 300 | WHICH CONSISTS OF 2 CHAIN(S). SEE REMARK 350 FOR | | | | |
| REMARK | 300 | INFORMATION ON GENERATING THE BIOLOGICAL MOLECULE(S). | | | | |
| REMARK | 300 | | | | | |
| REMARK | 300 | QUATERNARY STRUCTURE FOR THIS ENTRY: TETRAMERIC | | | | |
| REMARK | 300 | | | | | |
| REMARK | 300 | THE PROTEIN IS A HOMODIMER FORMED BY CHAIN A. | | | | |
| REMARK | 300 | A HETERODIMERIC ASSOCIATION OF CHAIN A WITH CHAIN S | | | | |
| REMARK | 300 | PRODUCES A TETRAMER. | | | | |
| REMARK | 300 | | | | | |

TABLE 3-continued

Coordinates for structures 1 to 4

| | | | | | | | |
|---|---|---|---|---|---|---|---|
| REMARK | 300 | THE BURIED SURFACE AREA SHOWN BELOW IS AN AVERAGE | | | | | |
| REMARK | 300 | CALCULATED FOR THE HETEROTETRAMER AND DOES NOT | | | | | |
| REMARK | 300 | CORRESPOND TO THE BURIED SURFACE AREA FOR THE | | | | | |
| REMARK | 300 | HOMODIMER OF CHAIN A | | | | | |
| REMARK | 300 | | | | | | |
| REMARK | 300 | THE HETEROASSEMBLY DESCRIBED BY REMARK 350 APPEARS | | | | | |
| REMARK | 300 | TO BE A CASE OF STRONG CRYSTAL PACKING WITH | | | | | |
| REMARK | 300 | THE MEAN DIFFERENCE IN ACCESSIBLE SURFACE AREA PER | | | | | |
| REMARK | 300 | CHAIN BETWEEN THE ISOLATED CHAIN AND THAT FOR | | | | | |
| REMARK | 300 | THE CHAIN IN THE COMPLEX IS 2149.4 ANGSTROM**2 | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE:1 | | | | | |
| REMARK | 350 | APPLY THE FOLLOWING TO CHAINS: A, S | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | 0.000000 | −1.000000 | 0.000000 | 86.24900 |
| REMARK | 350 | BIOMT2 | 2 | −1.000000 | 0.000000 | 0.000000 | 86.24900 |
| REMARK | 350 | BIOMT3 | 2 | 0.000000 | 0.000000 | −1.000000 | 74.13000 |
| REMARK | 465 | | | | | | |
| REMARK | 465 | MISSING RESIDUES | | | | | |
| REMARK | 465 | THE FOLLOWING RESIDUES WERE NOT LOCATED IN THE | | | | | |
| REMARK | 465 | EXPERIMENT. (M=MODEL NUMBER; RES=RESIDUE NAME; C=CHAIN | | | | | |
| REMARK | 465 | IDENTIFIER; SSSEQ=SEQUENCE NUMBER; I=INSERTION CODE.) | | | | | |
| REMARK | 465 | | | | | | |
| REMARK | 465 | M | RES | C | SSSEQI | | |
| REMARK | 465 | | MET | A | 1 | | |
| REMARK | 465 | | ALA | A | 2 | | |
| REMARK | 465 | | ALA | A | 3 | | |
| REMARK | 465 | | THR | A | 4 | | |
| REMARK | 465 | | ALA | A | 5 | | |
| REMARK | 465 | | ALA | A | 6 | | |
| REMARK | 465 | | GLU | A | 7 | | |
| REMARK | 465 | | ALA | A | 8 | | |
| REMARK | 465 | | VAL | A | 9 | | |
| REMARK | 465 | | ALA | A | 10 | | |
| REMARK | 465 | | SER | A | 11 | | |
| REMARK | 465 | | GLY | A | 12 | | |
| REMARK | 465 | | SER | A | 13 | | |
| REMARK | 465 | | GLY | A | 14 | | |
| REMARK | 465 | | LYS | A | 304 | | |
| REMARK | 465 | | ARG | A | 305 | | |
| REMARK | 465 | | ILE | A | 306 | | |
| REMARK | 465 | | PRO | S | 775 | | |
| REMARK | 465 | | SER | S | 776 | | |
| REMARK | 465 | | ASP | S | 777 | | |
| REMARK | 465 | | LEU | S | 778 | | |
| REMARK | 465 | | ALA | S | 779 | | |
| REMARK | 465 | | CYS | S | 780 | | |
| REMARK | 465 | | ARG | S | 781 | | |
| REMARK | 465 | | LEU | S | 782 | | |
| REMARK | 465 | | LEU | S | 783 | | |
| REMARK | 465 | | GLY | S | 784 | | |
| REMARK | 465 | | GLN | S | 785 | | |
| REMARK | 465 | | SER | S | 786 | | |
| REMARK | 465 | | MET | S | 787 | | |
| REMARK | 465 | | ASP | S | 788 | | |
| REMARK | 465 | | GLU | S | 789 | | |
| REMARK | 465 | | SER | S | 790 | | |
| REMARK | 465 | | GLY | S | 791 | | |
| REMARK | 465 | | LEU | S | 792 | | |
| REMARK | 465 | | PRO | S | 793 | | |
| REMARK | 465 | | GLN | S | 794 | | |
| REMARK | 465 | | GLN | S | 807 | | |
| REMARK | 465 | | GLY | S | 808 | | |
| REMARK | 465 | | SER | S | 809 | | |
| REMARK | 465 | | ARG | S | 810 | | |
| REMARK | 465 | | ASN | S | 811 | | |
| REMARK | 465 | | LEU | S | 812 | | |
| REMARK | 465 | | ASP | S | 823 | | |

TABLE 3-continued

Coordinates for structures 1 to 4

| REMARK | 465 | | GLN | S | 824 | | | | | | |
|---|---|---|---|---|---|---|---|---|---|---|---|
| REMARK | 465 | | VAL | S | 825 | | | | | | |
| REMARK | 465 | | ASN | S | 826 | | | | | | |
| REMARK | 470 | | | | | | | | | | |
| REMARK | 470 | MISSING ATOM | | | | | | | | | |
| REMARK | 470 | THE FOLLOWING RESIDUES HAVE MISSING ATOMS (M=MODEL NUMBER; | | | | | | | | | |
| REMARK | 470 | RES=RESIDUE NAME; C=CHAIN IDENTIFIER; SSEQ=SEQUENCE NUMBER; | | | | | | | | | |
| REMARK | 470 | I=INSERTION CODE): | | | | | | | | | |
| REMARK | 470 | M | RES | CSSEQI | | ATOMS | | | | | |
| REMARK | 470 | | GLU | A | 15 | | CG | CD | OE1 | OE2 | |
| REMARK | 470 | | GLU | A | 29 | | CG | CD | OE1 | OE2 | |
| REMARK | 470 | | ASN | A | 87 | | CG | OD1 | ND2 | | |
| REMARK | 470 | | LYS | A | 106 | | CD | CE | NZ | | |
| REMARK | 470 | | LYS | A | 115 | | CG | CD | CE | NZ | |
| REMARK | 470 | | ARG | A | 117 | | CG | CD | NE | CZ | NH1 NH2 |
| REMARK | 470 | | GLN | A | 133 | | CG | CD | OE1 | NE2 | |
| REMARK | 470 | | GLN | A | 136 | | CG | CD | OE1 | NE2 | |
| REMARK | 470 | | GLN | A | 137 | | CG | CD | OE1 | NE2 | |
| REMARK | 470 | | ARG | A | 156 | | CG | CD | NE | CZ | NH1 NH2 |
| REMARK | 470 | | LYS | A | 157 | | CD | CE | NZ | | |
| REMARK | 470 | | LYS | A | 311 | | CG | CD | CE | NZ | |
| REMARK | 500 | | | | | | | | | | |
| REMARK | 500 | GEOMETRY AND STEREOCHEMISTRY | | | | | | | | | |
| REMARK | 500 | SUBTOPIC: COVALENT BOND ANGLES | | | | | | | | | |
| REMARK | 500 | | | | | | | | | | |
| REMARK | 500 | THE STEREOCHEMICAL PARAMETERS OF THE FOLLOWING RESIDUES | | | | | | | | | |
| REMARK | 500 | HAVE VALUES WHICH DEVIATE FROM EXPECTED VALUES BY MORE | | | | | | | | | |
| REMARK | 500 | THAN 6*RMSD AND BY MORE THAN 0.150 ANGSTROMS (M=MODEL | | | | | | | | | |
| REMARK | 500 | NUMBER; RES=RESIDUE NAME; C=CHAIN IDENTIFIER; SSEQ=SEQUENCE | | | | | | | | | |
| REMARK | 500 | NUMBER; I=INSERTION CODE). | | | | | | | | | |
| REMARK | 500 | | | | | | | | | | |
| REMARK | 500 | STANDARD TABLE: | | | | | | | | | |
| REMARK | 500 | FORMAT: (10X,I3,1X,A3,1X,A1,I4,A1,3(1X,A4,2X),12X,F5.1) | | | | | | | | | |
| REMARK | 500 | | | | | | | | | | |
| REMARK | 500 | EXPECTED VALUES: ENGH AND HUBER, 1991 | | | | | | | | | |
| REMARK | 500 | | | | | | | | | | |
| REMARK | 500 | M | RES | CSSEQI | ATM1 | | ATM2 | | ATM3 | | |
| REMARK | 500 | | LEU | A 227 | CA | - | CB | - | CG | ANGL. DEV. = −11.0 DEGREES | |
| REMARK | 500 | | | | | | | | | | |
| REMARK | 500 | REMARK: NULL | | | | | | | | | |
| REMARK | 500 | | | | | | | | | | |
| REMARK | 500 | GEOMETRY AND STEREOCHEMISTRY | | | | | | | | | |
| REMARK | 500 | SUBTOPIC: COVALENT BOND LENGTHS | | | | | | | | | |
| REMARK | 500 | | | | | | | | | | |
| REMARK | 500 | THE STEREOCHEMICAL PARAMETERS OF THE FOLLOWING RESIDUES | | | | | | | | | |
| REMARK | 500 | HAVE VALUES WHICH DEVIATE FROM EXPECTED VALUES BY MORE | | | | | | | | | |
| REMARK | 500 | THAN 6*RMSD AND BY MORE THAN 0.150 ANGSTROMS (M=MODEL | | | | | | | | | |
| REMARK | 500 | NUMBER; RES=RESIDUE NAME; C=CHAIN IDENTIFIER; SSEQ=SEQUENCE | | | | | | | | | |
| REMARK | 500 | NUMBER; I=INSERTION CODE). | | | | | | | | | |
| REMARK | 500 | | | | | | | | | | |
| REMARK | 500 | STANDARD TABLE: | | | | | | | | | |
| REMARK | 500 | FORMAT: (10X,I3,1X,A3,1X,A1,I4,A1,1X,2(A4,A1,3X),12X,F5.3) | | | | | | | | | |
| REMARK | 500 | | | | | | | | | | |
| REMARK | 500 | EXPECTED VALUESS: ENGH AND HUBER, 1991 | | | | | | | | | |
| REMARK | 500 | | | | | | | | | | |
| REMARK | 500 | M | RES | CSSEQI | ATM1 | RES | CSSEQI | | ATM2 | DEVIATION | |
| REMARK | 500 | | MET | A 343 | SD | MET | A 343 | | CE | −0.209 | |
| REMARK | 500 | | | | | | | | | | |
| REMARK | 500 | REMARK: NULL | | | | | | | | | |
| REMARK | 500 | | | | | | | | | | |
| REMARK | 500 | GEOMETRY AND STEREOCHEMISTRY | | | | | | | | | |
| REMARK | 500 | SUBTOPIC: CLOSE CONTACTS IN SAME ASYMMETRIC UNIT | | | | | | | | | |
| REMARK | 500 | | | | | | | | | | |
| REMARK | 500 | THE FOLLOWING ATOMS ARE IN CLOSE CONTACT. | | | | | | | | | |
| REMARK | 500 | | | | | | | | | | |
| REMARK | 500 | ATM1 | RES | C | SSEQI | ATM2 | RES | C | SSEQI | DISTANCE | |
| REMARK | 500 | | | | | | | | | | |
| REMARK | 500 | O | ALA | A | 300 | OH | TYR | S | 798 | 2.09 | |
| REMARK | 525 | | | | | | | | | | |
| REMARK | 525 | SOLVENT | | | | | | | | | |
| REMARK | 525 | | | | | | | | | | |
| REMARK | 525 | THE SOLVENT MOLECULES ARE GIVEN CHAIN IDENTIFIERS TO | | | | | | | | | |
| REMARK | 525 | INDICATE THE PROTEIN CHAIN TO WHICH THEY ARE MOST CLOSELY | | | | | | | | | |
| REMARK | 525 | ASSOCIATED WITH: | | | | | | | | | |
| REMARK | 525 | PROTEIN CHAIN | | SOLVENT CHAIN | | | | | | | |
| REMARK | 525 | A | | | Z | | | | | | |
| REMARK | 525 | S | | | H | | | | | | |

TABLE 3-continued

Coordinates for structures 1 to 4

| | | | | | | | | | | | | | | |
|---|---|---|---|---|---|---|---|---|---|---|---|---|---|---|
| REMARK | 600 | | | | | | | | | | | | | |
| REMARK | 600 | HETEROGEN | | | | | | | | | | | | |
| REMARK | 600 | | | | | | | | | | | | | |
| REMARK | 600 | FOR METAL ATOM ZN ZN A1350 THE COORDINATION ANGLES ARE: | | | | | | | | | | | | |
| REMARK | 600 | 1 | HIS | 199A | NE2 | | | | | | | | | |
| REMARK | 600 | 2 | ASP | 201A | OD2 | | 103.4 | | | | | | | |
| REMARK | 600 | 3 | HIS | 279A | NE2 | | 84.2 | 88.5 | | | | | | |
| REMARK | 600 | 4 | OGA | 1351A | O2 | | 169.0 | 87.2 | 99.0 | | | | | |
| REMARK | 600 | 5 | OGA | 1351A | O2' | | 86.3 | 169.1 | 97.3 | 82.8 | | | | |
| REMARK | 600 | | | | | | 1 | 2 | 3 | 4 | | | | |
| REMARK | 700 | | | | | | | | | | | | | |
| REMARK | 700 | SHEET | | | | | | | | | | | | |
| REMARK | 700 | THE SHEET STRUCTURE OF THIS MOLECULE IS BIFURCATED. IN | | | | | | | | | | | | |
| REMARK | 700 | ORDER TO REPRESENT THIS FEATURE IN THE SHEET RECORDS BELOW, | | | | | | | | | | | | |
| REMARK | 700 | TWO SHEETS ARE DEFINED. | | | | | | | | | | | | |
| REMARK | 800 | | | | | | | | | | | | | |
| REMARK | 800 | SITE | | | | | | | | | | | | |
| REMARK | 800 | SITE_IDENTIFIER: ZNA | | | | | | | | | | | | |
| REMARK | 800 | SITE_DESCRIPTION: ZN BINDING SITE FOR CHAIN A | | | | | | | | | | | | |
| REMARK | 800 | | | | | | | | | | | | | |
| REMARK | 800 | SITE_IDENTIFIER: OGA | | | | | | | | | | | | |
| REMARK | 800 | SITE_DESCRIPTION: OGA BINDING SITE FOR CHAIN A | | | | | | | | | | | | |
| REMARK | 800 | | | | | | | | | | | | | |
| REMARK | 800 | SITE_IDENTIFIER: SA1 | | | | | | | | | | | | |
| REMARK | 800 | SITE_DESCRIPTION: SO4 BINDING SITE FOR CHAIN A | | | | | | | | | | | | |
| REMARK | 800 | | | | | | | | | | | | | |
| REMARK | 800 | SITE_IDENTIFIER: SA2 | | | | | | | | | | | | |
| REMARK | 800 | SITE_DESCRIPTION: SO4 BINDING SITE FOR CHAIN A | | | | | | | | | | | | |
| REMARK | 900 | | | | | | | | | | | | | |
| REMARK | 900 | RELATED ENTRIES | | | | | | | | | | | | |
| REMARK | 900 | RELATED ID: 1D7G RELATED DB: PDB | | | | | | | | | | | | |
| REMARK | 900 | A MODEL FOR THE COMPLEX BETWEEN THE | | | | | | | | | | | | |
| REMARK | 900 | HYPOXIA-INDUCIBLE FACTOR-1 (HIF-1) AND ITS | | | | | | | | | | | | |
| REMARK | 900 | CONSENSUS DEOXYRIBONUCLEIC ACID SEQUENCE | | | | | | | | | | | | |
| REMARK | 900 | RELATED ID: 1H2K RELATED DB: PDB | | | | | | | | | | | | |
| REMARK | 900 | FACTOR INHIBITING HIF-1 ALPHA IN COMPLEX | | | | | | | | | | | | |
| REMARK | 900 | WITH HIOF1 ALPHA FRAGMENT PEPTIDE | | | | | | | | | | | | |
| REMARK | 900 | RELATED ID: 1H2L RELATED DB: PDB | | | | | | | | | | | | |
| REMARK | 900 | FACTOR INHIBITING HIF1 ALPHA IN COMPLEX | | | | | | | | | | | | |
| REMARK | 900 | WITH HIF-1 ALPHA FRAGMENT PEPTIDE | | | | | | | | | | | | |
| REMARK | 900 | RELATED ID: 1H2N RELATED DB: PDB | | | | | | | | | | | | |
| REMARK | 900 | FACTOR INHIBITING HIF-1 ALPHA IN COMPLEX | | | | | | | | | | | | |
| REMARK | 900 | WITH HIF1 ALPHA FRAGMENT PEPTIDE | | | | | | | | | | | | |
| REMARK | 900 | RELATED ID: 1L8C RELATED DB: POB | | | | | | | | | | | | |
| REMARK | 900 | STRUCTURAL BASIS FOR HIF-1ALPHA/CBP | | | | | | | | | | | | |
| REMARK | 900 | RECOGNITION IN THE CELLULAR HYPOXIC RESPONSE | | | | | | | | | | | | |
| REMARK | 900 | RELATED ID: 1LM8 RELATED DB: PDB | | | | | | | | | | | | |
| REMARK | 900 | STRUCTURE OF A HIF-1A-PVHL-ELONGINB- | | | | | | | | | | | | |
| REMARK | 900 | ELONGINC COMPLEX | | | | | | | | | | | | |
| REMARK | 900 | RELATED ID: 1LQB RELATED DB:PDB | | | | | | | | | | | | |
| REMARK | 900 | CRYSTAL STRUCTURE OF A HYDROXYLATED HIF-1 | | | | | | | | | | | | |
| REMARK | 900 | ALPHA PEPTIDEBOUND TO THE PVHL/ELONGIN-C/ | | | | | | | | | | | | |
| REMARK | 900 | ELONGIN-B COMPLEX | | | | | | | | | | | | |
| DBREF | 1H2M A | | 1 349 | SWS | Q969Q7 | Q969Q7 | | | 1 49 | | | | | |
| DBREF | 1H2M S | | 775 826 | SWS | Q16665 | HIFA_HUMAN | | | 775 826 | | | | | |
| SEQRES | 1 A | 349 | MET | ALA | ALA | THR | ALA | ALA | GLU | ALA | VAL | ALA | SER | GLY | SER |
| SEQRES | 2 A | 349 | GLY | GLU | PRO | ARG | GLU | GLU | ALA | GLY | ALA | LEU | GLY | PRO | ALA |
| SEQRES | 3 A | 349 | TRP | ASP | GLU | SER | GLN | LEU | ARG | SER | TYR | SER | PHE | PRO | THR |
| SEQRES | 4 A | 349 | ARG | PRO | ILE | PRO | ARG | LEU | SER | GLN | SER | ASP | PRO | ARG | ALA |
| SEQRES | 5 A | 349 | GLU | GLU | LEU | ILE | GLU | ASN | GLU | GLU | PRO | VAL | VAL | LEU | THR |
| SEQRES | 6 A | 349 | ASP | THR | ASN | LEU | VAL | TYR | PRO | ALA | LEU | LYS | TRP | ASP | LEU |
| SEQRES | 7 A | 349 | GLU | TYR | LEU | GLN | GLU | ASN | ILE | GLY | ASN | GLY | ASP | PHE | SER |
| SEQRES | 8 A | 349 | VAL | TYR | SER | ALA | SER | THR | HIS | LYS | PHE | LEU | TYR | TYR | ASP |
| SEQRES | 9 A | 349 | GLU | LYS | LYS | MET | ALA | ASN | PilE | GLN | ASN | PHE | LYS | PRO | ARG |
| SEQRES | 10 A | 349 | SER | ASN | ARG | GLU | GLU | MET | LYS | PHE | HIS | GLU | PHE | VAL | GLU |
| SEQRES | 11 A | 349 | LYS | LEU | GLN | ASP | ILE | GLN | GLN | ARG | GLY | GLY | GLU | GLU | ARG |
| SEQRES | 12 A | 349 | LEU | TYR | LEU | GLN | GLN | THR | LEU | ASN | ASP | THR | VAL | GLY | ARG |
| SEQRES | 13 A | 349 | LYS | ILE | VAL | MET | ASP | PHE | LEU | GLY | PHE | ASN | TRP | ASN | TRP |
| SEQRES | 14 A | 349 | ILE | ASN | LYS | GLN | GLN | GLY | LYS | ARG | GLY | TRP | GLY | GLN | LEU |
| SEQRES | 15 A | 349 | THR | SER | ASN | LEU | LEU | LEU | ILE | GLY | MET | GLU | GLY | ASN | VAL |
| SEQRES | 16 A | 349 | THR | PRO | ALA | HIS | TYR | ASP | GLU | GLN | GLN | ASN | PHE | PHE | ALA |
| SEQRES | 17 A | 349 | GLN | ILE | LYS | GLY | TYR | LYS | ARG | CYS | ILE | LEU | PHE | PRO | PRO |
| SEQRES | 18 A | 349 | ASP | GLN | PHE | GLU | CYS | LEU | TYR | PRO | TYR | PRO | VAL | HIS | HIS |
| SEQRES | 19 A | 349 | PRO | CYS | ASP | ARG | GLN | SER | GLN | VAL | ASP | PHE | ASP | ASN | PRO |
| SEQRES | 20 A | 349 | ASP | TYR | GLU | ARG | PHE | PRO | ASN | PHE | GLN | ASN | VAL | VAL | GLY |
| SEQRES | 21 A | 349 | TYR | GLU | THR | VAL | VAL | GLY | PRO | GLY | ASP | VAL | LEU | TYR | ILE |
| SEQRES | 22 A | 349 | PRO | MET | TYR | TRP | TRP | HIS | HIS | ILE | GLU | SER | LEU | LEU | ASN |

TABLE 3-continued

Coordinates for structures 1 to 4

| | | | | | | | | | | | | | | | | | | |
|---|---|---|---|---|---|---|---|---|---|---|---|---|---|---|---|---|---|---|
| SEQRES | 23 | A | 349 | GLY | GLY | ILE | THR | ILE | THR | VAL | ASN | PHE | TRP | TYR | LYS | GLY | | |
| SEQRES | 24 | A | 349 | ALA | PRO | THR | PRO | LYS | ARG | ILE | GLU | TYR | PRO | LEU | LYS | ALA | | |
| SEQRES | 25 | A | 349 | HIS | GLN | LYS | VAL | ALA | ILE | MET | ARG | ASN | ILE | GLU | LYS | MET | | |
| SEQRES | 26 | A | 349 | LEU | GLY | GLU | ALA | LEU | GLY | ASN | PRO | GLN | GLU | VAL | GLY | PRO | | |
| SEQRES | 27 | A | 349 | LEU | LEU | ASN | THR | MET | ILE | LYS | GLY | ARG | TYR | ASN | | | | |
| SEQRES | 1 | S | 52 | PRO | SER | ASP | LEU | ALA | CYS | ARG | LEU | LEU | GLY | GLN | SER | MET | | |
| SEQRES | 2 | 5 | 52 | ASP | GLU | SER | GLY | LEU | PRO | GLN | LEU | THR | SER | TYR | ASP | CYS | | |
| SEQRES | 3 | S | 52 | GLU | VAL | ASN | ALA | PRO | ILE | GLN | GLY | SER | ARG | ASN | LEU | LEU | | |
| SEQRES | 4 | 5 | 52 | GLN | GLY | GLU | GLU | LEU | LEU | ARG | ALA | LEU | ASP | GLN | VAL | ASN | | |
| HET | ZN | A | 1350 | 1 | | | | | | | | | | | | | | |
| HET | OGA | A | 1351 | 10 | | | | | | | | | | | | | | |
| HET | SO4 | A | 1352 | 5 | | | | | | | | | | | | | | |
| HET | SO4 | A | 1353 | 5 | | | | | | | | | | | | | | |
| HETNAM | | ZN | ZINC ION | | | | | | | | | | | | | | | |
| HETNAM | | OGA | N-OXALYOLGLYCIHE | | | | | | | | | | | | | | | |
| HETNAM | | SO4 | SULFATE ION | | | | | | | | | | | | | | | |
| FORMUL | | 3 | ZN | ZN1 2+ | | | | | | | | | | | | | | |
| FORMUL | | 4 | OGA | C4 H5 N1 O5 | | | | | | | | | | | | | | |
| FORMUL | | 5 | SO4 | 2(O4 S1 2) | | | | | | | | | | | | | | |
| FORMUL | | 6 | HOH | *99(H2 O1) | | | | | | | | | | | | | | |
| HELIX | 1 | 1 | ASP | A | 28 | LEU | A | 32 | 5 | | | | | | | | | 5 |
| HELIX | 2 | 2 | ASP | A | 49 | ASN | A | 58 | 1 | | | | | | | | | 10 |
| HELIX | 3 | 3 | VAL | A | 70 | TRP | A | 76 | 5 | | | | | | | | | 7 |
| HELIX | 4 | 4 | ASP | A | 77 | ILE | A | 85 | 1 | | | | | | | | | 9 |
| HELIX | 5 | S | ASP | A | 104 | GLN | A | 112 | 5 | | | | | | | | | 9 |
| HELIX | 6 | 6 | LYS | A | 124 | ARG | A | 138 | 1 | | | | | | | | | 15 |
| HELIX | 7 | 7 | GLY | A | 155 | GLY | A | 164 | 1 | | | | | | | | | 10 |
| HELIX | 8 | 8 | ASN | A | 166 | ARG | A | 177 | 1 | | | | | | | | | 12 |
| HELIX | 9 | 9 | PRO | A | 220 | ASP | A | 222 | 5 | | | | | | | | | 3 |
| HELIX | 10 | 10 | GLN | A | 223 | TYR | A | 228 | 1 | | | | | | | | | 6 |
| HELIX | 11 | 11 | PHE | A | 252 | VAL | A | 258 | 5 | | | | | | | | | 7 |
| HELIX | 12 | 12 | LYS | A | 311 | GLY | A | 331 | 1 | | | | | | | | | 21 |
| HELIX | 13 | 13 | ASN | A | 332 | GLN | A | 334 | 5 | | | | | | | | | 3 |
| HELIX | 14 | 14 | GLU | A | 335 | LYS | A | 345 | 1 | | | | | | | | | 11 |
| HELIX | 15 | 15 | GLN | 5 | 814 | LEU | 5 | 822 | 1 | | | | | | | | | 9 |
| SHEET | 1 | AA | 5 | THR | A | 39 | PRO | A | 41 | 0 | | | | | | | | |
| SHEET | 2 | AA | 5 | GLY | A | 26O | VAL | A | 265 | 1 | O | GLY | A | 26O | N | ARG | A | 40 |
| SHEET | 3 | AA | 5 | LYS | A | 214 | PHE | A | 219 | -1 | O | LYS | A | 214 | N | VAL | A | 265 |
| SHEET | 4 | AA | 5 | TRP | A | 278 | SER | A | 283 | -1 | O | TRP | A | 278 | N | PHE | A | 219 |
| SHEET | 5 | AA | 5 | VAL | A | 195 | HIS | A | 199 | -1 | O | THR | A | 196 | N | ILE | A | 281 |
| SHEET | 1 | AB | 6 | ARG | A | 44 | LEU | A | 45 | 0 | | | | | | | | |
| SHEET | 2 | AB | 6 | VAL | A | 62 | LEU | A | 64 | 1 | O | VAL | A | 63 | N | LEU | A | 45 |
| SHEET | 3 | AB | 6 | VAL | A | 270 | ILE | A | 273 | -1 | O | VAL | A | 270 | N | LEU | A | 64 |
| SHEET | 4 | AB | 6 | GLN | A | 203 | LYS | A | 211 | -1 | O | ASN | A | 205 | N | ILE | A | 273 |
| SHEET | 5 | AB | 6 | THR | A | 290 | LYS | A | 298 | -1 | O | ILE | A | 291 | N | ILE | A | 210 |
| SHEET | 6 | AB | 6 | LEU | A | 182 | SER | A | 184 | 1 | N | THR | A | 183 | O | TRP | A | 296 |
| SHEET | 1 | AC | 9 | ARG | A | 44 | LEU | A | 45 | 0 | | | | | | | | |
| SHEET | 2 | AC | 9 | VAL | A | 62 | LEU | A | 64 | 1 | O | VAL | A | 63 | N | LEU | A | 45 |
| SHEET | 3 | AC | 9 | VAL | A | 270 | ILE | A | 273 | -1 | O | VAL | A | 270 | N | LEU | A | 64 |
| SHEET | 4 | AC | 9 | GLN | A | 203 | LYS | A | 211 | -1 | O | ASN | A | 205 | N | ILE | A | 273 |
| SHEET | 5 | AC | 9 | THR | A | 290 | LYS | A | 298 | -1 | O | ILE | A | 291 | N | ILE | A | 210 |
| SHEET | 6 | AC | 9 | LEU | A | 186 | GLY | A | 190 | -1 | O | LEU | A | 186 | N | ASN | A | 294 |
| SHEET | 7 | AC | 9 | ARG | A | 143 | THR | A | 149 | -1 | O | LEU | A | 146 | N | ILE | A | 189 |
| SHEET | 8 | AC | 9 | PHE | A | 90 | ALA | A | 95 | -1 | O | SER | A | 91 | N | GLN | A | 147 |
| SHEET | 9 | AC | 9 | SER | A | 118 | MET | A | 123 | -1 | O | ASN | A | 119 | N | SER | A | 94 |
| LINK | | ZN | | ZN | A1350 | | | | | NE2 | HIS | A199 | | 1555 | 1555 | | | |
| LINK | | ZN | | ZN | A1350 | | | | | OD2 | ASP | A201 | | 1555 | 1555 | | | |
| LINK | | ZN | | ZN | A1350 | | | | | NE2 | HIS | A279 | | 1555 | 1555 | | | |
| LINK | | ZN | | ZN | A1350 | | | | | O2 | OGA | A1351 | | 1555 | 1555 | | | |
| LINK | | ZN | | ZN | A1350 | | | | | O2' | OGA | A1351 | | 1555 | 1555 | | | |
| CISPEP | 1 | TYR | A | 308 | PRO | A | 309 | 0 | 1.05 | | | | | | | | | |
| SITE | 1 | ZNA | 3 | HIS | A | 199 | ASP | A | 201 | HIS | A | 279 | | | | | | |
| SITE | 1 | OGA | 13 | TYR | A | 145 | LEU | A | 188 | THR | A | 196 | HIS | A | 199 | | | |
| SITE | 2 | OGA | 13 | ASP | A | 201 | ASN | A | 205 | PHE | A | 207 | LYS | A | 214 | | | |
| SITE | 3 | OGA | 13 | HIS | A | 279 | ILE | A | 281 | ASN | A | 294 | TRP | A | 296 | | | |
| SITE | 4 | OGA | 13 | HOH | Z | 47 | | | | | | | | | | | | |
| SITE | 1 | SA1 | 4 | ARG | A | 138 | GLY | A | 140 | GLU | A | 141 | GLU | A | 142 | | | |
| SITE | 1 | SA2 | 5 | ARG | A | 143 | GLU | A | 192 | GLY | A | 193 | LEU | A | 285 | | | |
| SITE | 2 | SA2 | 5 | ASN | A | 286 | | | | | | | | | | | | |
| CRYST1 | 86.249 | 86.249 | | 148.260 | 90.00 | | 90.00 | | 90.00 | | P | 41 | 21 | 2 | | 8 | | |
| ORIGX1 | | 1.000000 | | 0.000000 | | 0.000000 | | 0.00000 | | | | | | | | | | |
| ORIGX2 | | 0.000000 | | 1.000000 | | 0.000000 | | 0.00000 | | | | | | | | | | |
| ORIGX3 | | 0.000000 | | 0.000000 | | 1.000000 | | 0.00000 | | | | | | | | | | |
| SCALE1 | | 0.011594 | | 0.000000 | | 0.000000 | | 0.00000 | | | | | | | | | | |
| SCALE2 | | 0.000000 | | 0.011594 | | 0.000000 | | 0.00000 | | | | | | | | | | |
| SCALE3 | | 0.000000 | | 0.000000 | | 0.006745 | | 0.00000 | | | | | | | | | | |
| ATOM | 1 | N | GLU | A | | 15 | 8.462 | | 32.732 | | 9.880 | | 1.00 | | 78.57 | N | | |

TABLE 3-continued

Coordinates for structures 1 to 4

| ATOM | 2 | CA | GLU | A | 15 | 7.114 | 32.108 | 9.773 | 1.00 | 78.75 | C |
| --- | --- | --- | --- | --- | --- | --- | --- | --- | --- | --- | --- |
| ATOM | 3 | C | GLU | A | 15 | 7.207 | 30.654 | 10.192 | 1.00 | 78.42 | C |
| ATOM | 4 | O | GLU | A | 15 | 8.067 | 29.928 | 9.714 | 1.00 | 78.63 | O |
| ATOM | 5 | CB | GLU | A | 15 | 6.580 | 32.219 | 8.345 | 1.00 | 78.95 | C |
| ATOM | 6 | N | PRO | A | 16 | 6.316 | 30.214 | 11.067 | 1.00 | 78.20 | N |
| ATOM | 7 | CA | PRO | A | 16 | 6.376 | 28.840 | 11.584 | 1.00 | 77.89 | C |
| ATOM | 8 | C | PRO | A | 16 | 6.328 | 27.796 | 10.467 | 1.00 | 77.35 | C |
| ATOM | 9 | O | PRO | A | 16 | 5.541 | 27.888 | 9.527 | 1.00 | 76.95 | O |
| ATOM | 10 | CB | PRO | A | 16 | 5.146 | 28.746 | 12.493 | 1.00 | 78.00 | C |
| ATOM | 11 | CG | PRO | A | 16 | 4.763 | 30.167 | 12.790 | 1.00 | 78.28 | C |
| ATOM | 12 | CD | PRO | A | 16 | 5.173 | 30.969 | 11.605 | 1.00 | 78.24 | C |
| ATOM | 13 | N | ARG | A | 17 | 7.184 | 26.796 | 10.580 | 1.00 | 76.88 | N |
| ATOM | 14 | CA | ARG | A | 17 | 7.264 | 25.749 | 9.575 | 1.00 | 76.63 | C |
| ATOM | 15 | C | ARG | A | 17 | 6.005 | 24.891 | 9.539 | 1.00 | 75.45 | C |
| ATOM | 16 | O | ARG | A | 17 | 5.247 | 24.836 | 10.505 | 1.00 | 75.40 | O |
| ATOM | 17 | CB | ARG | A | 17 | 8.444 | 24.820 | 9.875 | 1.00 | 77.06 | C |
| ATOM | 18 | CG | ARG | A | 17 | 9.816 | 25.481 | 9.900 | 1.00 | 78.68 | C |
| ATOM | 19 | CD | ARG | A | 17 | 10.954 | 24.522 | 10.293 | 1.00 | 80.53 | C |
| ATOM | 20 | NE | ARG | A | 17 | 10.908 | 24.086 | 11.699 | 1.00 | 82.60 | N |
| ATOM | 21 | CZ | ARG | A | 17 | 11.401 | 24.776 | 12.744 | 1.00 | 84.27 | C |
| ATOM | 22 | NH1 | ARG | A | 17 | 11.980 | 25.968 | 12.584 | 1.00 | 83.33 | N |
| ATOM | 23 | NH2 | ARG | A | 17 | 11.311 | 24.268 | 13.967 | 1.00 | 85.10 | N |
| ATOM | 24 | N | GLU | A | 18 | 5.796 | 24.209 | 8.421 | 1.00 | 74.01 | N |
| ATOM | 25 | CA | GLU | A | 18 | 4.692 | 23.274 | 8.319 | 1.00 | 72.99 | C |
| ATOM | 26 | C | GLU | A | 18 | 5.193 | 21.855 | 8.607 | 1.00 | 71.43 | C |
| ATOM | 27 | O | GLU | A | 18 | 6.210 | 21.421 | 8.061 | 1.00 | 70.71 | O |
| ATOM | 28 | CB | GLU | A | 18 | 4.033 | 23.352 | 6.938 | 1.00 | 73.29 | C |
| ATOM | 29 | CG | GLU | A | 18 | 3.333 | 24.677 | 6.659 | 1.00 | 73.91 | C |
| ATOM | 30 | CD | GLU | A | 18 | 1.949 | 24.794 | 7.283 | 1.00 | 74.30 | C |
| ATOM | 31 | OE1 | GLU | A | 18 | 1.355 | 23.776 | 7.692 | 1.00 | 74.07 | O |
| ATOM | 32 | OE2 | GLU | A | 18 | 1.444 | 25.929 | 7.356 | 1.00 | 75.76 | O |
| ATOM | 33 | N | GLU | A | 19 | 4.482 | 21.157 | 9.491 | 1.00 | 69.89 | N |
| ATOM | 34 | CA | GLU | A | 19 | 4.786 | 19.764 | 9.818 | 1.00 | 68.89 | C |
| ATOM | 35 | C | GLU | A | 19 | 4.393 | 18.854 | 8.661 | 1.00 | 66.65 | C |
| ATOM | 36 | O | GLU | A | 19 | 3.324 | 19.011 | 8.065 | 1.00 | 65.9Z | O |
| ATOM | 37 | CB | GLU | A | 19 | 4.058 | 19.311 | 11.096 | 1.00 | 69.41 | C |
| ATOM | 38 | CG | GLU | A | 19 | 4.544 | 19.996 | 12.370 | 1.00 | 72.06 | C |
| ATOM | 39 | CD | GLU | A | 19 | 4.308 | 19.194 | 13.657 | 1.00 | 76.41 | C |
| ATOM | 40 | OE1 | GLU | A | 19 | 3.855 | 18.016 | 13.609 | 1.00 | 78.21 | O |
| ATOM | 41 | OE2 | GLU | A | 19 | 4.590 | 19.758 | 14.746 | 1.00 | 79.64 | O |
| ATOM | 42 | N | ALA | A | 20 | 5.283 | 17.919 | 8.349 | 1.00 | 64.54 | N |
| ATOM | 43 | CA | ALA | A | 20 | 5.067 | 16.921 | 7.303 | 1.00 | 63.03 | C |
| ATOM | 44 | C | ALA | A | 20 | 3.735 | 16.225 | 7.449 | 1.00 | 61.23 | C |
| ATOM | 45 | O | ALA | A | 20 | 3.303 | 15.903 | 8.556 | 1.00 | 60.61 | O |
| ATOM | 46 | CB | ALA | A | 20 | 6.177 | 15.889 | 7.312 | 1.00 | 62.82 | C |
| ATOM | 47 | N | GLY | A | 21 | 3.087 | 16.002 | 6.316 | 1.00 | 59.29 | N |
| ATOM | 48 | CA | GLY | A | 21 | 1.833 | 15.289 | 6.304 | 1.00 | 58.26 | C |
| ATOM | 49 | C | GLY | A | 21 | 0.651 | 16.200 | 6.530 | 1.00 | 57.44 | C |
| ATOM | 50 | O | GLY | A | 21 | 0.416 | 15.739 | 6.873 | 1.00 | 56.42 | O |
| ATOM | 51 | N | ALA | A | 22 | 0.858 | 17.500 | 6.341 | 1.00 | 57.28 | N |
| ATOM | 52 | CA | ALA | A | 22 | 0.182 | 18.509 | 6.492 | 1.00 | 56.92 | C |
| ATOM | 53 | C | ALA | A | 22 | 0.737 | 18.544 | 7.909 | 1.00 | 56.53 | C |
| ATOM | 54 | O | ALA | A | 22 | 1.926 | 18.737 | 8.108 | 1.00 | 56.32 | O |
| ATOM | 55 | CB | ALA | A | 22 | 1.285 | 18.277 | 5.488 | 1.00 | 57.10 | C |
| ATOM | 56 | N | LEU | A | 23 | 0.133 | 18.369 | 8.898 | 1.00 | 56.25 | N |
| ATOM | 57 | CA | LEU | A | 23 | 0.306 | 18.397 | 10.289 | 1.00 | 56.07 | C |
| ATOM | 58 | C | LEU | A | 23 | 0.385 | 19.811 | 10.827 | 1.00 | 55.03 | C |
| ATOM | 59 | O | LEU | A | 23 | 0.638 | 20.037 | 11.998 | 1.00 | 54.89 | O |
| ATOM | 60 | CB | LEU | A | 23 | 0.583 | 17.519 | 11.149 | 1.00 | 56.05 | C |
| ATOM | 61 | CG | LEU | A | 23 | 0.445 | 16.067 | 10.678 | 1.00 | 58.06 | C |
| ATOM | 62 | CD1 | LEU | A | 23 | 1.307 | 15.080 | 11.478 | 1.00 | 59.22 | C |
| ATOM | 63 | CD2 | LEU | A | 23 | 1.030 | 15.653 | 10.735 | 1.00 | 59.53 | C |
| ATOM | 64 | N | GLY | A | 24 | 0.202 | 20.768 | 9.941 | 1.00 | 54.17 | N |
| ATOM | 65 | CA | GLY | A | 24 | 0.337 | 22.151 | 10.305 | 1.00 | 53.43 | C |
| ATOM | 66 | C | GLY | A | 24 | 0.932 | 22.758 | 10.834 | 1.00 | 52.71 | C |
| ATOM | 67 | O | GLY | A | 24 | 2.025 | 22.189 | 10.807 | 1.00 | 52.28 | O |
| ATOM | 68 | N | PRO | A | 25 | 0.775 | 23.965 | 11.324 | 1.00 | 51.60 | N |
| ATOM | 69 | CA | PRO | A | 25 | 1.908 | 24.695 | 11.858 | 1.00 | 50.67 | C |
| ATOM | 70 | C | PRO | A | 25 | 2.310 | 24.047 | 13.168 | 1.00 | 49.52 | C |
| ATOM | 71 | O | PRO | A | 25 | 1.481 | 23.648 | 13.982 | 1.00 | 47.61 | O |
| ATOM | 72 | CB | PRO | A | 25 | 1.366 | 26.110 | 12.065 | 1.00 | 50.61 | C |
| ATOM | 73 | CG | PRO | A | 25 | 0.109 | 26.034 | 11.931 | 1.00 | 50.61 | C |
| ATOM | 74 | CD | PRO | A | 25 | 0.493 | 24.689 | 11.463 | 1.00 | 51.58 | C |
| ATOM | 75 | N | ALA | A | 26 | 3.616 | 23.922 | 13.321 | 1.00 | 49.47 | N |
| ATOM | 76 | CA | ALA | A | 26 | 4.218 | 23.390 | 14.526 | 1.00 | 49.29 | C |
| ATOM | 77 | C | ALA | A | 26 | 3.894 | 24.266 | 15.759 | 1.00 | 47.94 | C |
| ATOM | 78 | O | ALA | A | 26 | 3.646 | 23.735 | 16.836 | 1.00 | 48.27 | O |

TABLE 3-continued

Coordinates for structures 1 to 4

| ATOM | 79 | CB | ALA | A | 26 | 5.712 | 23.288 | 14.328 | 1.00 | 49.68 | C |
|---|---|---|---|---|---|---|---|---|---|---|---|
| ATOM | 80 | N | TRP | A | 27 | 3.864 | 25.581 | 15.592 | 1.00 | 45.91 | N |
| ATOM | 81 | CA | TRP | A | 27 | 3.494 | 26.487 | 16.683 | 1.00 | 45.16 | C |
| ATOM | 82 | C | TRP | A | 27 | 3.003 | 27.818 | 16.107 | 1.00 | 44.47 | C |
| ATOM | 83 | O | TRP | A | 27 | 2.985 | 27.981 | 14.901 | 1.00 | 44.30 | O |
| ATOM | 84 | CB | TRP | A | 27 | 4.719 | 26.727 | 17.568 | 1.00 | 44.91 | C |
| ATOM | 85 | CG | TRP | A | 27 | 5.916 | 26.910 | 16.737 | 1.00 | 42.67 | C |
| ATOM | 86 | CD1 | TRP | A | 27 | 6.702 | 25.934 | 16.197 | 1.00 | 43.38 | C |
| ATOM | 87 | CD2 | TRP | A | 27 | 6.411 | 28.129 | 16.255 | 1.00 | 38.70 | C |
| ATOM | 88 | NE1 | TRP | A | 27 | 7.690 | 26.494 | 15.425 | 1.00 | 41.56 | N |
| ATOM | 89 | CE2 | TRP | A | 27 | 7.532 | 27.847 | 15.452 | 1.00 | 39.59 | C |
| ATOM | 90 | CE3 | TRP | A | 27 | 6.039 | 29.442 | 16.431 | 1.00 | 38.28 | C |
| ATOM | 91 | CZ2 | TRP | A | 27 | 8.284 | 28.827 | 14.861 | 1.00 | 39.74 | C |
| ATOM | 92 | CZ3 | TRP | A | 27 | 6.781 | 30.409 | 15.849 | 1.00 | 39.48 | C |
| ATOM | 93 | CH2 | TRP | A | 27 | 7.884 | 30.104 | 15.057 | 1.00 | 40.17 | C |
| ATOM | 94 | N | ASP | A | 28 | 2.580 | 28.760 | 16.941 | 1.00 | 43.91 | N |
| ATOM | 95 | CA | ASP | A | 28 | 2.230 | 30.079 | 16.417 | 1.00 | 43.87 | C |
| ATOM | 96 | C | ASP | A | 28 | 2.750 | 31.161 | 17.305 | 1.00 | 42.33 | C |
| ATOM | 97 | O | ASP | A | 28 | 3.191 | 30.901 | 18.409 | 1.00 | 42.11 | O |
| ATOM | 98 | CB | ASP | A | 28 | 0.722 | 30.251 | 16.199 | 1.00 | 44.82 | C |
| ATOM | 99 | CG | ASP | A | 28 | 0.052 | 30.162 | 17.462 | 1.00 | 47.87 | C |
| ATOM | 100 | OD1 | ASP | A | 28 | 0.240 | 31.236 | 18.108 | 1.00 | 50.91 | O |
| ATOM | 101 | OD2 | ASP | A | 28 | 0.501 | 29.054 | 17.877 | 1.00 | 49.06 | O |
| ATOM | 102 | N | GLU | A | 29 | 2.713 | 32.385 | 16.790 | 1.00 | 41.29 | N |
| ATOM | 103 | CA | GLU | A | 29 | 3.208 | 33.586 | 17.499 | 1.00 | 39.69 | C |
| ATOM | 104 | C | GLU | A | 29 | 2.685 | 33.711 | 18.917 | 1.00 | 37.94 | C |
| ATOM | 105 | O | GLU | A | 29 | 3.415 | 34.069 | 19.801 | 1.00 | 37.26 | O |
| ATOM | 106 | CB | GLU | A | 29 | 2.840 | 34.812 | 16.735 | 1.00 | 39.59 | C |
| ATOM | 107 | N | SER | A | 30 | 1.427 | 33.371 | 19.135 | 1.00 | 36.78 | N |
| ATOM | 108 | CA | SER | A | 30 | 0.810 | 33.558 | 20.443 | 1.00 | 36.13 | C |
| ATOM | 109 | C | SER | A | 30 | 1.501 | 32.756 | 21.517 | 1.00 | 35.30 | C |
| ATOM | 110 | O | SER | A | 30 | 1.252 | 32.968 | 22.678 | 1.00 | 35.21 | O |
| ATOM | 111 | CB | SER | A | 30 | 0.686 | 33.180 | 20.406 | 1.00 | 35.84 | C |
| ATOM | 112 | OD | SER | A | 30 | 0.901 | 31.762 | 20.450 | 1.00 | 36.93 | O |
| ATOM | 113 | N | GLN | A | 31 | 2.326 | 31.795 | 21.116 | 1.00 | 35.24 | N |
| ATOM | 114 | CA | GLN | A | 31 | 3.021 | 30.918 | 22.060 | 1.00 | 34.89 | C |
| ATOM | 115 | C | GLN | A | 31 | 4.366 | 31.506 | 22.487 | 1.00 | 34.60 | C |
| ATOM | 116 | O | GLN | A | 31 | 5.010 | 30.969 | 23.365 | 1.00 | 34.18 | O |
| ATOM | 117 | CB | GLN | A | 31 | 3.224 | 29.513 | 21.473 | 1.00 | 34.65 | C |
| ATOM | 118 | CG | GLN | A | 31 | 1.969 | 28.649 | 21.402 | 1.00 | 34.74 | C |
| ATOM | 119 | CD | GLN | A | 31 | 2.212 | 27.322 | 20.707 | 1.00 | 33.47 | C |
| ATOM | 120 | OE1 | GLN | A | 31 | 2.215 | 27.249 | 19.476 | 1.00 | 32.57 | O |
| ATOM | 121 | NE2 | GLN | A | 31 | 2.442 | 26.278 | 21.492 | 1.00 | 32.95 | N |
| ATOM | 122 | N | LEU | A | 32 | 4.753 | 32.632 | 21.895 | 1.00 | 34.85 | N |
| ATOM | 123 | CA | LEU | A | 32 | 6.016 | 33.293 | 22.212 | 1.00 | 35.01 | C |
| ATOM | 124 | C | LEU | A | 32 | 5.798 | 34.391 | 23.223 | 1.00 | 34.91 | C |
| ATOM | 125 | O | LEU | A | 32 | 4.834 | 35.134 | 23.125 | 1.00 | 35.83 | O |
| ATOM | 126 | CB | LEU | A | 32 | 6.631 | 33.885 | 20.945 | 1.00 | 34.96 | C |
| ATOM | 127 | CG | LEU | A | 32 | 6.995 | 32.860 | 19.849 | 1.00 | 36.03 | C |
| ATOM | 128 | CD1 | LEU | A | 32 | 7.691 | 33.525 | 18.701 | 1.00 | 36.15 | C |
| ATOM | 129 | CD2 | LEU | A | 32 | 7.855 | 31.780 | 20.377 | 1.00 | 35.18 | C |
| ATOM | 130 | N | ARG | A | 33 | 6.675 | 34.500 | 24.209 | 1.00 | 34.49 | N |
| ATOM | 131 | CA | ARG | A | 33 | 6.564 | 35.591 | 25.170 | 1.00 | 34.33 | C |
| ATOM | 132 | C | ARG | A | 33 | 7.005 | 36.867 | 24.460 | 1.00 | 34.37 | C |
| ATOM | 133 | O | ARG | A | 33 | 7.733 | 36.815 | 23.498 | 1.00 | 34.87 | O |
| ATOM | 134 | CB | ARG | A | 33 | 7.442 | 35.338 | 26.394 | 1.00 | 34.16 | C |
| ATOM | 135 | CG | ARG | A | 33 | 7.056 | 34.124 | 27.212 | 1.00 | 32.83 | C |
| ATOM | 136 | CD | ARG | A | 33 | 7.951 | 33.894 | 28.428 | 1.00 | 33.34 | C |
| ATOM | 137 | NE | ARO | A | 33 | 7.413 | 32.820 | 29.252 | 1.00 | 34.91 | N |
| ATOM | 138 | CZ | ARG | A | 33 | 6.445 | 32.963 | 30.137 | 1.00 | 36.51 | C |
| ATOM | 139 | NH1 | ARG | A | 33 | 5.900 | 34.144 | 30.382 | 1.00 | 34.89 | N |
| ATOM | 140 | NH2 | ARG | A | 33 | 6.027 | 31.905 | 30.795 | 1.00 | 39.39 | N |
| ATOM | 141 | N | SER | A | 34 | 6.608 | 38.022 | 24.947 | 1.00 | 34.36 | N |
| ATOM | 142 | CA | SER | A | 34 | 6.944 | 39.247 | 24.244 | 1.00 | 34.69 | C |
| ATOM | 143 | C | SER | A | 34 | 8.002 | 40.055 | 24.987 | 1.00 | 33.26 | C |
| ATOM | 144 | O | SER | A | 34 | 7.958 | 40.142 | 26.200 | 1.00 | 33.50 | O |
| ATOM | 145 | GB | SER | A | 34 | 5.698 | 40.096 | 24.143 | 1.00 | 35.23 | C |
| ATOM | 146 | OG | SER | A | 34 | 5.586 | 40.744 | 25.393 | 1.00 | 39.99 | O |
| ATOM | 147 | N | TYR | A | 35 | 8.911 | 40.682 | 24.252 | 1.00 | 32.38 | N |
| ATOM | 148 | CA | TYR | A | 35 | 10.080 | 41.329 | 24.843 | 1.00 | 32.03 | C |
| ATOM | 149 | C | TYR | A | 35 | 10.339 | 42.675 | 24.193 | 1.00 | 32.52 | C |
| ATOM | 150 | O | TYR | A | 35 | 9.763 | 42.979 | 23.172 | 1.00 | 32.78 | O |
| ATOM | 151 | CE | TYR | A | 35 | 11.290 | 40.422 | 24.686 | 1.00 | 31.20 | C |
| ATOM | 152 | CG | TYR | A | 35 | 11.139 | 39.161 | 25.482 | 1.00 | 30.69 | C |
| ATOM | 153 | CD1 | TYR | A | 35 | 10.935 | 39.215 | 26.853 | 1.00 | 30.40 | C |
| ATOM | 154 | CD2 | TYR | A | 35 | 11.186 | 37.915 | 24.875 | 1.00 | 30.34 | C |
| ATOM | 155 | GE1 | TYR | A | 35 | 10.804 | 38.054 | 27.609 | 1.00 | 31.74 | C |

TABLE 3-continued

| | | | | | | Coordinates for structures 1 to 4 | | | | |
|---|---|---|---|---|---|---|---|---|---|---|
| ATOM | 156 | CE2 | TYR | A | 35 | 11.050 | 36.741 | 25.617 | 1.00 | 32.05 | C |
| ATOM | 157 | CZ | TYR | A | 35 | 10.858 | 36.812 | 26.991 | 1.00 | 31.98 | C |
| ATOM | 158 | OH | TYR | A | 35 | 10.687 | 35.658 | 27.742 | 1.00 | 30.13 | O |
| ATOM | 159 | N | SER | A | 36 | 11.240 | 43.463 | 24.761 | 1.00 | 33.06 | N |
| ATOM | 160 | CA | SER | A | 36 | 11.469 | 44.838 | 24.289 | 1.00 | 32.95 | C |
| ATOM | 161 | C | SER | A | 36 | 12.469 | 44.977 | 23.159 | 1.00 | 32.65 | C |
| ATOM | 162 | O | SER | A | 36 | 12.705 | 46.084 | 22.674 | 1.00 | 33.04 | O |
| ATOM | 163 | CB | SER | A | 36 | 11.979 | 45.698 | 25.438 | 1.00 | 32.92 | C |
| ATOM | 164 | OG | SER | A | 36 | 13.272 | 45.325 | 25.844 | 1.00 | 33.05 | O |
| ATOM | 165 | N | PHE | A | 37 | 13.041 | 43.880 | 22.711 | 1.00 | 31.44 | N |
| ATOM | 166 | CA | PHE | A | 37 | 14.100 | 43.988 | 21.740 | 1.00 | 31.55 | C |
| ATOM | 167 | C | PHE | A | 37 | 13.784 | 43.269 | 20.444 | 1.00 | 31.69 | C |
| ATOM | 168 | O | PHE | A | 37 | 13.020 | 42.326 | 20.386 | 1.00 | 32.65 | O |
| ATOM | 169 | CE | PHE | A | 37 | 15.421 | 43.431 | 22.339 | 1.00 | 30.68 | C |
| ATOM | 170 | CG | PHE | A | 37 | 15.275 | 42.054 | 22.890 | 1.00 | 30.10 | C |
| ATOM | 171 | CD1 | PHE | A | 37 | 15.329 | 40.967 | 22.060 | 1.00 | 28.43 | C |
| ATOM | 172 | CD2 | PHE | A | 37 | 15.022 | 41.852 | 24.231 | 1.00 | 29.43 | C |
| ATOM | 173 | GE1 | PHE | A | 37 | 15.168 | 39.679 | 22.564 | 1.00 | 31.59 | C |
| ATOM | 174 | CE2 | PHE | A | 37 | 14.852 | 40.580 | 24.733 | 1.00 | 30.52 | C |
| ATOM | 175 | CZ | PHE | A | 37 | 14.927 | 39.495 | 23.915 | 1.00 | 31.81 | C |
| ATOM | 176 | N | PRO | A | 38 | 14.403 | 43.721 | 19.384 | 1.00 | 31.70 | N |
| ATOM | 177 | CA | PRO | A | 38 | 14.268 | 43.036 | 18.106 | 1.00 | 31.23 | C |
| ATOM | 178 | C | PRO | A | 38 | 15.231 | 41.895 | 17.984 | 1.00 | 31.71 | C |
| ATOM | 179 | O | PRO | A | 38 | 16.205 | 41.880 | 18.743 | 1.00 | 31.59 | O |
| ATOM | 189 | GB | PRO | A | 38 | 14.652 | 44.118 | 17.117 | 1.00 | 31.44 | C |
| ATOM | 181 | CG | PRO | A | 38 | 15.636 | 45.005 | 17.922 | 1.00 | 32.43 | C |
| ATOM | 182 | CD | PRO | A | 38 | 15.186 | 44.973 | 19.320 | 1.00 | 30.26 | C |
| ATOM | 183 | N | THR | A | 39 | 14.996 | 41.008 | 17.003 | 1.00 | 31.90 | N |
| ATOM | 184 | CA | THR | A | 39 | 15.868 | 39.891 | 16.702 | 1.00 | 32.00 | C |
| ATOM | 185 | C | THR | A | 39 | 15.865 | 39.606 | 15.203 | 1.00 | 32.89 | C |
| ATOM | 186 | O | THR | A | 39 | 14.998 | 40.048 | 14.476 | 1.00 | 32.28 | O |
| ATOM | 187 | GB | THR | A | 39 | 15.370 | 38.647 | 17.377 | 1.00 | 32.26 | C |
| ATOM | 188 | OG1 | THR | A | 39 | 14.024 | 38.389 | 16.949 | 1.00 | 30.59 | O |
| ATOM | 189 | GG2 | THR | A | 39 | 15.235 | 38.832 | 18.905 | 1.00 | 32.99 | C |
| ATOM | 190 | N | ARG | A | 40 | 16.855 | 38.844 | 14.770 | 1.00 | 33.28 | N |
| ATOM | 191 | GA | ARG | A | 40 | 16.980 | 38.372 | 13.421 | 1.00 | 34.30 | C |
| ATOM | 192 | C | ARG | A | 40 | 17.023 | 36.853 | 13.562 | 1.00 | 33.77 | C |
| ATOM | 193 | O | ARG | A | 40 | 17.288 | 36.324 | 14.614 | 1.00 | 34.68 | O |
| ATOM | 194 | GB | ARG | A | 40 | 18.267 | 38.847 | 12.795 | 1.00 | 34.73 | C |
| ATOM | 195 | GG | ARG | A | 40 | 18.273 | 40.306 | 12.451 | 1.00 | 41.24 | C |
| ATOM | 196 | CD | ARG | A | 40 | 16.909 | 40.799 | 12.022 | 1.00 | 48.38 | C |
| ATOM | 197 | NE | ARG | A | 40 | 16.728 | 41.025 | 10.597 | 1.00 | 51.83 | N |
| ATOM | 198 | GZ | ARG | A | 40 | 15.553 | 41.291 | 10.092 | 1.00 | 56.70 | C |
| ATOM | 199 | NE1 | ARG | A | 40 | 14.501 | 41.300 | 10.908 | 1.00 | 57.84 | N |
| ATOM | 200 | NE2 | ARG | A | 40 | 15.415 | 41.549 | 8.795 | 1.00 | 60.30 | |
| ATOM | 201 | N | PRO | A | 41 | 16.663 | 36.147 | 12.533 | 1.00 | 33.50 | N |
| ATOM | 202 | GA | PRO | A | 41 | 16.646 | 34.681 | 12.569 | 1.00 | 33.48 | C |
| ATOM | 203 | C | PRO | A | 41 | 18.002 | 34.010 | 12.475 | 1.00 | 32.72 | C |
| ATOM | 204 | O | PRO | A | 41 | 18.907 | 34.475 | 11.801 | 1.00 | 34.64 | O |
| ATOM | 205 | GB | PRO | A | 41 | 15.800 | 34.299 | 11.340 | 1.00 | 33.22 | C |
| ATOM | 206 | CG | PRO | A | 41 | 15.409 | 35.563 | 10.675 | 1.00 | 33.55 | C |
| ATOM | 207 | CD | PRO | A | 41 | 16.038 | 36.717 | 11.343 | 1.00 | 32.95 | C |
| ATOM | 208 | N | ILE | A | 42 | 18.154 | 32.925 | 13.192 | 1.00 | 30.97 | N |
| ATOM | 209 | CA | ILE | A | 42 | 19.337 | 32.144 | 13.049 | 1.00 | 29.87 | C |
| ATOM | 210 | C | ILE | A | 42 | 19.077 | 31.289 | 11.814 | 1.00 | 30.07 | C |
| ATOM | 211 | O | ILE | A | 42 | 17.946 | 30.857 | 11.587 | 1.00 | 30.17 | O |
| ATOM | 212 | GB | ILE | A | 42 | 19.477 | 31.306 | 14.273 | 1.00 | 29.85 | C |
| ATOM | 213 | CG1 | ILE | A | 42 | 19.721 | 32.215 | 15.478 | 1.00 | 27.79 | C |
| ATOM | 214 | CG2 | ILE | A | 42 | 20.582 | 30.264 | 14.105 | 1.00 | 30.60 | C |
| ATOM | 215 | CD1 | ILE | A | 42 | 19.565 | 31.503 | 16.788 | 1.00 | 25.35 | C |
| ATOM | 216 | N | PRO | A | 43 | 20.085 | 31.075 | 10.985 | 1.00 | 29.34 | N |
| ATOM | 217 | CA | PRO | A | 43 | 19.922 | 30.219 | 9.823 | 1.00 | 29.60 | C |
| ATOM | 218 | C | PRO | A | 43 | 19.623 | 28.751 | 10.176 | 1.00 | 30.65 | C |
| ATOM | 219 | O | PRO | A | 43 | 20.207 | 28.265 | 11.160 | 1.00 | 31.73 | O |
| ATOM | 220 | GB | PRO | A | 43 | 21.288 | 30.310 | 9.139 | 1.00 | 30.00 | C |
| ATOM | 221 | CG | PRO | A | 43 | 21.933 | 31.491 | 9.665 | 1.00 | 28.87 | C |
| ATOM | 222 | CD | PRO | A | 43 | 21.420 | 31.676 | 11.047 | 1.00 | 28.76 | C |
| ATOM | 223 | N | ARG | A | 44 | 18.725 | 28.103 | 9.419 | 1.00 | 30.34 | N |
| ATOM | 224 | CA | ARG | A | 44 | 18.415 | 26.693 | 9.507 | 1.00 | 31.59 | C |
| ATOM | 225 | C | ARG | A | 44 | 18.965 | 26.050 | 8.267 | 1.00 | 31.44 | C |
| ATOM | 226 | O | ARG | A | 44 | 18.540 | 26.359 | 7.169 | 1.00 | 32.24 | O |
| ATOM | 227 | GB | ARG | A | 44 | 16.923 | 26.399 | 9.502 | 1.00 | 32.07 | C |
| ATOM | 228 | CG | ARG | A | 44 | 16.105 | 27.115 | 10.563 | 1.00 | 36.61 | C |
| ATOM | 229 | CD | ARG | A | 44 | 14.638 | 26.534 | 10.809 | 1.00 | 39.09 | C |
| ATOM | 230 | NE | ARG | A | 44 | 14.350 | 25.140 | 10.395 | 1.00 | 41.98 | N |
| ATOM | 231 | CZ | ARG | A | 44 | 14.179 | 24.099 | 11.246 | 1.00 | 43.25 | C |
| ATOM | 232 | NH1 | ARG | A | 44 | 14.332 | 24.244 | 12.561 | 1.00 | 40.76 | N |

TABLE 3-continued

Coordinates for structures 1 to 4

| ATOM | 233 | NH2 | ARG | A | 44 | 13.864 | 22.892 | 10.777 | 1.00 | 44.70 | N |
|------|-----|-----|-----|---|----|--------|--------|--------|------|-------|---|
| ATOM | 234 | N   | LEU | A | 45 | 19.878 | 25.118 | 8.428  | 1.00 | 31.29 | N |
| ATOM | 235 | CA  | LEU | A | 45 | 20.544 | 24.560 | 7.294  | 1.00 | 30.82 | C |
| ATOM | 236 | C   | LEU | A | 45 | 20.744 | 23.083 | 7.470  | 1.00 | 31.52 | C |
| ATOM | 237 | O   | LEU | A | 45 | 20.690 | 22.550 | 8.597  | 1.00 | 31.99 | O |
| ATOM | 238 | GB  | LEU | A | 45 | 21.909 | 25.221 | 7.134  | 1.00 | 29.63 | C |
| ATOM | 239 | CG  | LEU | A | 45 | 21.873 | 26.697 | 6.813  | 1.00 | 31.00 | C |
| ATOM | 240 | CD1 | LEU | A | 45 | 23.279 | 27.338 | 7.030  | 1.00 | 31.79 | C |
| ATOM | 241 | CD2 | LEU | A | 45 | 21.403 | 26.918 | 5.378  | 1.00 | 31.14 | C |
| ATOM | 242 | N   | SER | A | 46 | 21.004 | 22.437 | 6.338  | 1.00 | 31.72 | N |
| ATOM | 243 | CA  | SER | A | 46 | 21.345 | 21.057 | 6.327  | 1.00 | 32.17 | C |
| ATOM | 244 | C   | SER | A | 46 | 22.771 | 20.978 | 6.767  | 1.00 | 32.55 | C |
| ATOM | 245 | O   | SER | A | 46 | 23.568 | 21.871 | 6.562  | 1.00 | 31.31 | O |
| ATOM | 246 | GB  | SER | A | 46 | 21.255 | 20.447 | 4.936  | 1.00 | 32.06 | C |
| ATOM | 247 | OG  | SER | A | 46 | 21.909 | 19.187 | 4.931  | 1.00 | 31.15 | O |
| ATOM | 248 | N   | GLN | A | 47 | 23.068 | 19.849 | 7.358  | 1.00 | 33.60 | N |
| ATOM | 249 | CA  | GLN | A | 47 | 24.370 | 19.546 | 7.878  | 1.00 | 34.42 | C |
| ATOM | 250 | C   | GLN | A | 47 | 25.385 | 19.453 | 6.754  | 1.00 | 34.74 | C |
| ATOM | 251 | O   | GLN | A | 47 | 26.554 | 19.685 | 6.971  | 1.00 | 35.40 | O |
| ATOM | 252 | GB  | GLN | A | 47 | 24.232 | 18.194 | 8.593  | 1.00 | 35.09 | C |
| ATOM | 253 | GG  | GLN | A | 47 | 25.465 | 17.417 | 8.733  | 1.00 | 36.19 | C |
| ATOM | 254 | CD  | GLN | A | 47 | 25.670 | 16.422 | 7.678  | 1.00 | 36.93 | C |
| ATOM | 255 | OE1 | GLN | A | 47 | 24.757 | 16.093 | 6.902  | 1.00 | 38.75 | O |
| ATOM | 256 | NE2 | GLN | A | 47 | 26.894 | 15.903 | 7.630  | 1.00 | 40.53 | N |
| ATOM | 257 | N   | SER | A | 48 | 24.933 | 19.095 | 5.556  | 1.00 | 34.63 | N |
| ATOM | 258 | CA  | SER | A | 48 | 25.821 | 18.922 | 4.415  | 1.00 | 34.93 | C |
| ATOM | 259 | C   | SER | A | 48 | 26.128 | 20.249 | 3.735  | 1.00 | 35.90 | C |
| ATOM | 260 | O   | SER | A | 48 | 26.990 | 20.315 | 2.862  | 1.00 | 36.31 | O |
| ATOM | 261 | GB  | SER | A | 48 | 25.182 | 17.991 | 3.381  | 1.00 | 34.59 | C |
| ATOM | 262 | OG  | SER | A | 48 | 23.912 | 18.483 | 2.955  | 1.00 | 33.48 | O |
| ATOM | 263 | N   | ASP | A | 49 | 25.415 | 21.302 | 4.124  | 1.00 | 36.41 | N |
| ATOM | 264 | CA  | ASP | A | 49 | 25.583 | 22.606 | 3.512  | 1.00 | 37.09 | C |
| ATOM | 265 | C   | ASP | A | 49 | 26.855 | 23.291 | 3.989  | 1.00 | 37.81 | C |
| ATOM | 266 | O   | ASP | A | 49 | 27.020 | 23.523 | 5.182  | 1.00 | 36.99 | O |
| ATOM | 267 | CB  | ASP | A | 49 | 24.383 | 23.451 | 3.877  | 1.00 | 37.42 | C |
| ATOM | 268 | CG  | ASP | A | 49 | 24.323 | 24.733 | 3.117  | 1.00 | 38.29 | C |
| ATOM | 269 | OD1 | ASP | A | 49 | 25.383 | 25.351 | 2.849  | 1.00 | 37.80 | O |
| ATOM | 270 | OD2 | ASP | A | 49 | 23.223 | 25.191 | 2.760  | 1.00 | 40.61 | O |
| ATOM | 271 | N   | PRO | A | 50 | 27.740 | 23.649 | 3.056  | 1.00 | 38.39 | N |
| ATOM | 272 | CA  | PRO | A | 50 | 29.005 | 24.291 | 3.409  | 1.00 | 38.24 | C |
| ATOM | 273 | C   | PRO | A | 50 | 28.802 | 25.502 | 4.285  | 1.00 | 38.16 | C |
| ATOM | 274 | O   | PRO | A | 50 | 29.671 | 25.797 | 5.088  | 1.00 | 37.37 | O |
| ATOM | 275 | CB  | PRO | A | 50 | 29.577 | 24.738 | 2.051  | 1.00 | 38.14 | C |
| ATOM | 276 | CG  | PRO | A | 50 | 28.978 | 23.915 | 1.070  | 1.00 | 38.31 | C |
| ATOM | 277 | CD  | PRO | A | 50 | 27.620 | 23.473 | 1.601  | 1.00 | 38.85 | C |
| ATOM | 278 | N   | ARG | A | 51 | 27.686 | 26.199 | 4.125  | 1.00 | 38.66 | N |
| ATOM | 279 | CA  | ARG | A | 51 | 27.448 | 27.403 | 4.912  | 1.00 | 39.05 | C |
| ATOM | 280 | C   | ARG | A | 51 | 27.332 | 27.077 | 6.391  | 1.00 | 38.94 | C |
| ATOM | 281 | O   | ARG | A | 51 | 27.668 | 27.908 | 7.259  | 1.00 | 38.35 | O |
| ATOM | 282 | CB  | ARG | A | 51 | 26.199 | 28.120 | 4.438  | 1.00 | 39.34 | C |
| ATOM | 283 | CG  | ARG | A | 51 | 26.372 | 28.781 | 3.067  | 1.00 | 41.10 | C |
| ATOM | 284 | CD  | ARG | A | 51 | 25.099 | 29.355 | 2.486  | 1.00 | 42.20 | C |
| ATOM | 285 | NE  | ARG | A | 51 | 24.111 | 28.314 | 2.192  | 1.00 | 44.96 | N |
| ATOM | 286 | CZ  | ARG | A | 51 | 22.815 | 28.551 | 2.043  | 1.00 | 46.68 | C |
| ATOM | 287 | NH1 | ARG | A | 51 | 22.348 | 29.795 | 2.162  | 1.00 | 47.61 | N |
| ATOM | 288 | NH2 | ARG | A | 51 | 21.980 | 27.563 | 1.774  | 1.00 | 46.08 | N |
| ATOM | 289 | N   | ALA | A | 52 | 26.882 | 25.867 | 6.688  | 1.00 | 38.31 | N |
| ATOM | 290 | CA  | ALA | A | 52 | 26.729 | 25.498 | 8.082  | 1.00 | 38.63 | C |
| ATOM | 291 | C   | ALA | A | 52 | 28.093 | 25.311 | 8.677  | 1.00 | 38.81 | C |
| ATOM | 292 | O   | ALA | A | 52 | 28.341 | 25.682 | 9.816  | 1.00 | 39.03 | O |
| ATOM | 293 | CB  | ALA | A | 52 | 25.907 | 24.233 | 8.235  | 1.00 | 38.36 | C |
| ATOM | 294 | N   | GLU | A | 53 | 28.988 | 24.733 | 7.899  | 1.00 | 39.48 | N |
| ATOM | 295 | CA  | GLU | A | 53 | 30.316 | 24.484 | 8.388  | 1.00 | 40.51 | C |
| ATOM | 296 | C   | GLU | A | 53 | 31.038 | 25.802 | 8.621  | 1.00 | 40.41 | C |
| ATOM | 297 | O   | GLU | A | 53 | 31.740 | 25.954 | 9.618  | 1.00 | 39.82 | O |
| ATOM | 298 | CB  | GLU | A | 53 | 31.093 | 23.614 | 7.436  | 1.00 | 40.70 | C |
| ATOM | 299 | CG  | GLU | A | 53 | 32.129 | 22.790 | 8.171  | 1.00 | 44.79 | C |
| ATOM | 300 | CD  | GLU | A | 53 | 31.596 | 21.435 | 8.633  | 1.00 | 48.98 | C |
| ATOM | 301 | OE1 | GLU | A | 53 | 30.427 | 21.329 | 9.017  | 1.00 | 51.56 | O |
| ATOM | 302 | OE2 | GLU | A | 53 | 32.354 | 20.454 | 8.620  | 1.00 | 54.44 | O |
| ATOM | 303 | N   | GLU | A | 54 | 30.851 | 26.752 | 7.713  | 1.00 | 40.45 | N |
| ATOM | 304 | CA  | GLU | A | 54 | 31.465 | 28.060 | 7.853  | 1.00 | 41.40 | C |
| ATOM | 305 | C   | GLU | A | 54 | 30.991 | 28.731 | 9.162  | 1.00 | 40.32 | C |
| ATOM | 306 | O   | GLU | A | 54 | 31.760 | 29.374 | 9.836  | 1.00 | 39.89 | O |
| ATOM | 307 | CB  | GLU | A | 54 | 31.119 | 28.974 | 6.679  | 1.00 | 42.12 | C |
| ATOM | 308 | CG  | GLU | A | 54 | 31.697 | 28.557 | 5.333  | 1.00 | 47.25 | C |
| ATOM | 309 | CD  | GLU | A | 54 | 30.953 | 29.191 | 4.129  | 1.00 | 53.54 | C |

TABLE 3-continued

| | | | | | | | | | | | |
|---|---|---|---|---|---|---|---|---|---|---|---|
| ATOM | 310 | OE1 | GLU | A | 54 | 30.459 | 30.366 | 4.276 | 1.00 | 57.47 | O |
| ATOM | 311 | OE2 | GLU | A | 54 | 30.882 | 28.527 | 3.036 | 1.00 | 53.82 | O |
| ATOM | 312 | N | LEU | A | 55 | 29.735 | 28.534 | 9.533 | 1.00 | 39.03 | N |
| ATOM | 313 | CA | LEU | A | 55 | 29.223 | 29.198 | 10.687 | 1.00 | 37.80 | C |
| ATOM | 314 | C | LEU | A | 55 | 29.840 | 28.673 | 11.956 | 1.00 | 36.83 | C |
| ATOM | 315 | O | LEU | A | 55 | 30.293 | 29.464 | 12.795 | 1.00 | 35.66 | O |
| ATOM | 316 | CB | LEU | A | 55 | 27.715 | 29.081 | 10.725 | 1.00 | 38.06 | C |
| ATOM | 317 | CG | LEU | A | 55 | 27.072 | 29.921 | 9.621 | 1.00 | 37.63 | C |
| ATOM | 318 | CD1 | LEU | A | 55 | 25.620 | 29.569 | 9.449 | 1.00 | 39.63 | C |
| ATOM | 319 | CD2 | LEU | A | 55 | 27.174 | 31.356 | 9.928 | 1.00 | 36.27 | C |
| ATOM | 320 | N | ILE | A | 56 | 29.876 | 27.346 | 12.079 | 1.00 | 35.87 | N |
| ATOM | 321 | CA | ILE | A | 56 | 30.436 | 26.684 | 13.257 | 1.00 | 35.35 | c |
| ATOM | 322 | C | ILE | A | 56 | 31.916 | 27.001 | 13.410 | 1.00 | 35.82 | C |
| ATOM | 323 | O | ILE | A | 56 | 32.377 | 27.299 | 14.499 | 1.00 | 36.59 | O |
| ATOM | 324 | CB | ILE | A | 56 | 30.281 | 25.198 | 13.139 | 1.00 | 34.84 | C |
| ATOM | 325 | CG1 | ILE | A | 56 | 28.790 | 24.810 | 13.132 | 1.00 | 34.00 | C |
| ATOM | 326 | CG2 | ILE | A | 56 | 31.022 | 24.535 | 14.280 | 1.00 | 34.89 | C |
| ATOM | 327 | CD1 | ILE | A | 56 | 28.502 | 23.361 | 12.684 | 1.00 | 30.65 | C |
| ATOM | 328 | N | GLU | A | 57 | 32.636 | 26.964 | 12.301 | 1.00 | 36.28 | N |
| ATOM | 329 | CA | GLU | A | 57 | 34.056 | 27.244 | 12.255 | 1.00 | 37.26 | C |
| ATOM | 330 | C | GLU | A | 57 | 34.295 | 28.634 | 12.809 | 1.00 | 37.41 | C |
| ATOM | 331 | O | GLU | A | 57 | 35.278 | 28.879 | 13.516 | 1.00 | 38.73 | C |
| ATOM | 332 | CB | GLU | A | 57 | 34.562 | 27.167 | 10.795 | 1.00 | 37.54 | C |
| ATOM | 333 | CG | GLU | A | 57 | 36.035 | 27.462 | 10.572 | 1.00 | 39.41 | C |
| ATOM | 334 | CD | GLU | A | 57 | 36.948 | 26.668 | 11.493 | 1.00 | 44.86 | C |
| ATOM | 335 | OE1 | GLU | A | 57 | 36.666 | 25.458 | 11.741 | 1.00 | 48.72 | O |
| ATOM | 336 | OE2 | GLU | A | 57 | 37.961 | 27.260 | 11.965 | 1.00 | 46.32 | O |
| ATOM | 337 | N | ASN | A | 58 | 33.386 | 29.537 | 12.485 | 1.00 | 36.64 | N |
| ATOM | 338 | CA | ASN | A | 58 | 33.456 | 30.907 | 12.926 | 1.00 | 36.26 | C |
| ATOM | 339 | C | ASN | A | 58 | 32.768 | 31.226 | 14.219 | 1.00 | 35.28 | C |
| ATOM | 340 | O | ASN | A | 58 | 32.569 | 32.376 | 14.531 | 1.00 | 33.45 | C |
| ATOM | 341 | CB | ASN | A | 58 | 32.798 | 31.758 | 11.898 | 1.00 | 36.88 | C |
| ATOM | 342 | CO | ASN | A | 58 | 33.763 | 32.461 | 11.107 | 1.00 | 39.77 | C |
| ATOM | 343 | OD1 | ASN | A | 58 | 34.140 | 31.983 | 10.018 | 1.00 | 41.34 | O |
| ATOM | 344 | ND2 | ASN | A | 58 | 34.241 | 33.617 | 11.639 | 1.00 | 41.14 | N |
| ATOM | 345 | N | GLU | A | 59 | 32.366 | 30.205 | 14.945 | 1.00 | 35.05 | N |
| ATOM | 346 | CA | GLU | A | 59 | 31.706 | 30.415 | 16.226 | 1.00 | 35.00 | C |
| ATOM | 347 | C | GLU | A | 59 | 30.481 | 31.314 | 16.133 | 1.00 | 33.86 | C |
| ATOM | 348 | O | GLU | A | 59 | 30.293 | 32.238 | 16.904 | 1.00 | 33.16 | O |
| ATOM | 349 | CB | GLU | A | 59 | 32.729 | 30.855 | 17.244 | 1.00 | 34.95 | C |
| ATOM | 350 | CO | GLU | A | 59 | 33.708 | 29.700 | 17.423 | 1.00 | 37.79 | C |
| ATOM | 351 | CD | GLU | A | 59 | 34.652 | 29.820 | 18.586 | 1.00 | 39.57 | C |
| ATOM | 352 | OE1 | GLU | A | 59 | 35.809 | 30.145 | 18.349 | 1.00 | 43.67 | O |
| ATOM | 353 | OE2 | GLU | A | 59 | 34.254 | 29.545 | 19.723 | 1.00 | 45.29 | O |
| ATOM | 354 | N | GLU | A | 60 | 29.644 | 30.995 | 15.157 | 1.00 | 32.92 | N |
| ATOM | 355 | CA | GLU | A | 60 | 28.359 | 31.641 | 14.983 | 1.00 | 32.66 | C |
| ATOM | 356 | C | GLU | A | 60 | 27.284 | 30.576 | 14.993 | 1.00 | 30.59 | C |
| ATOM | 357 | O | GLU | A | 60 | 27.456 | 29.485 | 14.461 | 1.00 | 30.47 | O |
| ATOM | 358 | CB | GLU | A | 60 | 28.312 | 32.400 | 13.685 | 1.00 | 33.20 | C |
| ATOM | 359 | CO | GLU | A | 60 | 29.384 | 33.454 | 13.615 | 1.00 | 38.62 | C |
| ATOM | 360 | CD | GLU | A | 60 | 28.955 | 34.617 | 12.762 | 1.00 | 45.73 | C |
| ATOM | 361 | OE1 | GLU | A | 60 | 29.075 | 34.553 | 11.519 | 1.00 | 48.47 | O |
| ATOM | 362 | OE2 | GLU | A | 60 | 28.466 | 35.587 | 13.367 | 1.00 | 53.89 | O |
| ATOM | 36~ | N | PRO | A | 61 | 26.152 | 30.915 | 15.560 | 1.00 | 28.63 | N |
| ATOM | 364 | CA | PRO | A | 61 | 25.073 | 29.954 | 15.735 | 1.00 | 28.05 | C |
| ATOM | 365 | C | PRO | A | 61 | 24.462 | 29.451 | 14.443 | 1.00 | 27.61 | C |
| ATOM | 366 | O | PRO | A | 61 | 24.475 | 30.120 | 13.426 | 1.00 | 27.23 | O |
| ATOM | 367 | CB | PRO | A | 61 | 24.021 | 30.754 | 16.492 | 1.00 | 28.67 | C |
| ATOM | 368 | CO | PRO | A | 61 | 24.385 | 32.140 | 16.400 | 1.00 | 27.46 | C |
| ATOM | 369 | CD | PRO | A | 61 | 25.811 | 32.253 | 16.038 | 1.00 | 27.71 | C |
| ATOM | 370 | N | VAL | A | 62 | 23.936 | 28.237 | 14.475 | 1.00 | 27.43 | |
| ATOM | 371 | CA | VAL | A | 62 | 23.254 | 27.685 | 13.317 | 1.00 | 27.09 | C |
| ATOM | 372 | C | VAL | A | 62 | 22.372 | 26.569 | 13.802 | 1.00 | 27.40 | C |
| ATOM | 373 | 0. | VAL | A | 62 | 22.707 | 25.893 | 14.780 | 1.00 | 27.79 | O |
| ATOM | 374 | CB | VAL | A | 62 | 24.219 | 27.181 | 12.270 | 1.00 | 27.04 | C |
| ATOM | 375 | CG1 | VAL | A | 62 | 25.106 | 26.166 | 12.829 | 1.00 | 27.34 | C |
| ATOM | 376 | CG2 | VAL | A | 62 | 23.473 | 26.659 | 11.037 | 1.00 | 27.58 | C |
| ATOM | 377 | N | VAL | A | 63 | 21.195 | 26.440 | 13.199 | 1.00 | 27.19 | N |
| ATOM | 378 | CA | VAL | A | 63 | 20.339 | 25.338 | 13.526 | 1.00 | 27.37 | C |
| ATOM | 379 | C | VAL | A | 63 | 20.540 | 24.324 | 12.383 | 1.00 | 27.33 | C |
| ATOM | 380 | O | VAL | A | 63 | 20.360 | 24.672 | 11.208 | 1.00 | 27.05 | O |
| ATOM | 381 | CB | VAL | A | 63 | 18.857 | 25.737 | 13.611 | 1.00 | 27.47 | C |
| ATOM | 382 | CG1 | VAL | A | 63 | 17.976 | 24.446 | 13.695 | 1.00 | 28.55 | C |
| ATOM | 383 | CG2 | VAL | A | 63 | 18.616 | 26.603 | 14.793 | 1.00 | 25.77 | C |
| ATOM | 384 | N | LEU | A | 64 | 20.933 | 23.114 | 12.743 | 1.00 | 27.26 | N |
| ATOM | 385 | CA | LEU | A | 64 | 21.119 | 22.001 | 11.820 | 1.00 | 28.51 | C |
| ATOM | 386 | C | LEU | A | 64 | 19.897 | 21.128 | 11.894 | 1.00 | 28.40 | C |

TABLE 3-continued

| | | | | | | | | | | | |
|---|---|---|---|---|---|---|---|---|---|---|---|
| \multicolumn{12}{c}{Coordinates for structures 1 to 4} |
| ATOM | 387 | O | LEU | A | 64 | 19.517 | 20.692 | 12.982 | 1.00 | 28.69 | O |
| ATOM | 388 | CB | LEU | A | 64 | 22.352 | 21.187 | 12.204 | 1.00 | 28.92 | C |
| ATOM | 389 | CG | LEU | A | 64 | 23.624 | 22.016 | 12.142 | 1.00 | 31.65 | C |
| ATOM | 390 | CD1 | LEU | A | 64 | 24.800 | 21.273 | 12.534 | 1.00 | 34.84 | C |
| ATOM | 391 | CD2 | LEU | A | 64 | 23.843 | 22.490 | 10.722 | 1.00 | 35.77 | C |
| ATOM | 392 | N | THR | A | 65 | 19.284 | 20.868 | 10.752 | 1.00 | 28.44 | N |
| ATOM | 393 | CA | THR | A | 65 | 18.003 | 20.164 | 10.721 | 1.00 | 29.54 | C |
| ATOM | 394 | C | TRR | A | 65 | 18.054 | 18.659 | 10.534 | 1.00 | 29.40 | C |
| ATOM | 395 | O | THR | A | 65 | 17.046 | 17.985 | 10.799 | 1.00 | 29.20 | O |
| ATOM | 396 | CB | THR | A | 65 | 17.139 | 20.679 | 9.552 | 1.00 | 30.07 | C |
| ATOM | 397 | OG1 | THR | A | 65 | 17.879 | 20.569 | 8.318 | 1.00 | 30.75 | O |
| ATOM | 398 | CG2 | THR | A | 65 | 16.878 | 22.137 | 9.665 | 1.00 | 31.86 | C |
| ATOM | 399 | N | ASP | A | 66 | 19.183 | 18.150 | 10.059 | 1.00 | 29.30 | N |
| ATOM | 400 | CA | ASP | A | 66 | 19.323 | 16.722 | 9.719 | 1.00 | 29.78 | C |
| ATOM | 401 | C | ASP | A | 66 | 20.573 | 15.970 | 10.196 | 1.00 | 29.12 | C |
| ATOM | 402 | O | ASP | A | 66 | 21.081 | 15.141 | 9.432 | 1.00 | 29.09 | O |
| ATOM | 403 | CB | ASP | A | 66 | 19.301 | 16.582 | 8.195 | 1.00 | 29.41 | C |
| ATOM | 404 | CG | ASP | A | 66 | 20.274 | 17.507 | 7.525 | 1.00 | 32.36 | C |
| ATOM | 405 | OD1 | ASP | A | 66 | 20.924 | 18.319 | 8.230 | 1.00 | 34.87 | O |
| ATOM | 406 | OD2 | ASP | A | 66 | 20.447 | 17.534 | 6.287 | 1.00 | 35.70 | O |
| ATOM | 407 | N | THR | A | 67 | 21.078 | 16.254 | 11.404 | 1.00 | 28.05 | N |
| ATOM | 408 | CA | THR | A | 67 | 22.266 | 15.565 | 11.897 | 1.00 | 27.24 | C |
| ATOM | 409 | C | THR | A | 67 | 21.943 | 14.171 | 12.355 | 1.00 | 26.92 | C |
| ATOM | 410 | O | THR | A | 67 | 22.807 | 13.297 | 12.367 | 1.00 | 25.98 | O |
| ATOM | 411 | CB | THR | A | 67 | 22.856 | 16.258 | 13.134 | 1.00 | 27.78 | C |
| ATOM | 412 | OG1 | THR | A | 67 | 21.874 | 16.338 | 14.186 | 1.00 | 25.71 | O |
| ATOM | 413 | CG2 | THR | A | 67 | 23.268 | 17.664 | 12.820 | 1.00 | 29.22 | C |
| ATOM | 414 | N | ASN | A | 68 | 20.704 | 13.979 | 12.777 | 1.00 | 26.53 | N |
| ATOM | 415 | CA | ASN | A | 68 | 20.307 | 12.711 | 13.355 | 1.00 | 27.10 | C |
| ATOM | 416 | C | ASN | A | 68 | 21.075 | 12.499 | 14.647 | 1.00 | 26.46 | C |
| ATOM | 417 | O | ASN | A | 68 | 21.223 | 11.399 | 15.092 | 1.00 | 26.90 | O |
| ATOM | 418 | CB | ASN | A | 68 | 20.583 | 11.547 | 12.401 | 1.00 | 27.41 | C |
| ATOM | 419 | CG | ASN | A | 68 | 19.546 | 11.415 | 11.308 | 1.00 | 28.18 | C |
| ATOM | 420 | OD1 | ASN | A | 68 | 18.345 | 11.286 | 11.566 | 1.00 | 29.22 | O |
| ATOM | 421 | ND2 | ASN | A | 68 | 20.006 | 11.445 | 10.077 | 1.00 | 29.40 | N |
| ATOM | 422 | N | LEU | A | 69 | 21.585 | 13.569 | 15.227 | 1.00 | 26.58 | N |
| ATOM | 423 | CA | LEU | A | 69 | 22.429 | 13.481 | 16.427 | 1.00 | 26.67 | C |
| ATOM | 424 | C | LEU | A | 69 | 21.832 | 12.639 | 17.558 | 1.00 | 26.73 | C |
| ATOM | 425 | O | LEU | A | 69 | 22.550 | 11.822 | 18.166 | 1.00 | 27.74 | O |
| ATOM | 426 | CB | LEU | A | 69 | 22.739 | 14.870 | 16.968 | 1.00 | 26.04 | C |
| ATOM | 427 | CG | LEU | A | 69 | 23.677 | 14.904 | 18.157 | 1.00 | 26.23 | C |
| ATOM | 428 | CD1 | LEU | A | 69 | 24.986 | 14.168 | 17.894 | 1.00 | 27.92 | C |
| ATOM | 429 | CD2 | LEU | A | 69 | 23.976 | 16.343 | 18.556 | 1.00 | 24.74 | C |
| ATOM | 430 | N | VAL | A | 70 | 20.557 | 12.857 | 17.861 | 1.00 | 26.02 | N |
| ATOM | 431 | CA | VAL | A | 70 | 19.882 | 12.091 | 18.898 | 1.00 | 26.50 | C |
| ATOM | 432 | C | VAL | A | 70 | 18.673 | 11.364 | 18.345 | 1.00 | 26.71 | C |
| ATOM | 433 | O | VAL | A | 70 | 17.650 | 11.183 | 19.015 | 1.00 | 25.59 | O |
| ATOM | 434 | CB | VAL | A | 70 | 19.479 | 12.943 | 20.098 | 1.00 | 26.46 | C |
| ATOM | 435 | CG1 | VAL | A | 70 | 20.717 | 13.505 | 20.764 | 1.00 | 28.17 | C |
| ATOM | 436 | CG2 | VAL | A | 70 | 18.517 | 14.016 | 19.716 | 1.00 | 23.88 | C |
| ATOM | 437 | N | TYR | A | 71 | 18.832 | 10.920 | 17.113 | 1.00 | 27.86 | N |
| ATOM | 438 | CA | TYR | A | 71 | 17.791 | 10.159 | 16.451 | 1.00 | 29.60 | C |
| ATOM | 439 | C | TYR | A | 71 | 17.093 | 9.167 | 17.388 | 1.00 | 29.76 | C |
| ATOM | 440 | O | TYR | A | 71 | 15.905 | 9.202 | 17.478 | 1.00 | 30.54 | O |
| ATOM | 441 | CB | TYR | A | 71 | 18.326 | 9.459 | 15.208 | 1.00 | 29.31 | C |
| ATOM | 442 | CG | TYR | A | 71 | 17.347 | 8.479 | 14.686 | 1.00 | 31.42 | C |
| ATOM | 443 | CD1 | TYR | A | 71 | 16.136 | 8.884 | 14.120 | 1.00 | 31.39 | C |
| ATOM | 444 | CD2 | TYR | A | 71 | 17.610 | 7.107 | 14.779 | 1.00 | 32.30 | C |
| ATOM | 445 | CE1 | TYR | A | 71 | 15.223 | 7.905 | 13.641 | 1.00 | 31.86 | C |
| ATOM | 446 | CE2 | TYR | A | 71 | 16.736 | 6.181 | 14.317 | 1.00 | 29.75 | C |
| ATOM | 447 | CZ | TYR | A | 71 | 15.556 | 6.558 | 13.755 | 1.00 | 31.10 | C |
| ATOM | 448 | OH | TYR | A | 71 | 14.698 | 5.530 | 13.342 | 1.00 | 39.44 | O |
| ATOM | 449 | N | PRO | A | 72 | 17.807 | 8.317 | 18.108 | 1.00 | 30.56 | N |
| ATOM | 450 | CA | PRO | A | 72 | 17.150 | 7.336 | 18.991 | 1.00 | 30.85 | C |
| ATOM | 451 | C | PRO | A | 72 | 16.389 | 7.914 | 20.158 | 1.00 | 30.85 | C |
| ATOM | 452 | O | PRO | A | 72 | 15.549 | 7.233 | 20.750 | 1.00 | 30.12 | O |
| ATOM | 453 | CB | PRO | A | 72 | 18.310 | 6.468 | 19.507 | 1.00 | 30.71 | C |
| ATOM | 454 | CG | PRO | A | 72 | 19.420 | 6.692 | 18.515 | 1.00 | 31.79 | C |
| ATOM | 455 | CD | PRO | A | 72 | 19.268 | 8.158 | 18.096 | 1.00 | 30.88 | C |
| ATOM | 456 | N | ALA | A | 73 | 16.650 | 9.166 | 20.508 | 1.00 | 31.72 | N |
| ATOM | 457 | CA | ALA | A | 73 | 15.918 | 9.743 | 21.627 | 1.00 | 31.71 | C |
| ATOM | 458 | C | ALA | A | 73 | 14.596 | 10.371 | 21.172 | 1.00 | 31.83 | C |
| ATOM | 459 | O | ALA | A | 73 | 13.786 | 10.808 | 22.000 | 1.00 | 31.52 | O |
| ATOM | 460 | CB | ALA | A | 73 | 16.762 | 10.742 | 22.340 | 1.00 | 32.17 | C |
| ATOM | 461 | N | LEU | A | 74 | 14.345 | 10.408 | 19.868 | 1.00 | 31.19 | N |
| ATOM | 462 | CA | LEU | A | 74 | 13.108 | 11.028 | 19.439 | 1.00 | 32.01 | C |
| ATOM | 463 | C | LEU | A | 74 | 11.856 | 10.343 | 19.965 | 1.00 | 32.30 | C |

TABLE 3-continued

| | | | | | Coordinates for structures 1 to 4 | | | | | |
|---|---|---|---|---|---|---|---|---|---|---|
| ATOM | 464 | O | LEU | A | 74 | 10.807 | 10.914 | 19.963 | 1.00 | 31.90 | O |
| ATOM | 465 | CB | LEU | A | 74 | 13.050 | 11.191 | 17.931 | 1.00 | 31.25 | C |
| ATOM | 466 | CG | LEU | A | 74 | 14.140 | 12.103 | 17.400 | 1.00 | 34.53 | C |
| ATOM | 467 | CD1 | LEU | A | 74 | 13.904 | 12.418 | 15.965 | 1.00 | 37.35 | C |
| ATOM | 468 | CD2 | LEU | A | 74 | 14.264 | 13.436 | 18.200 | 1.00 | 34.44 | C |
| ATOM | 469 | N | LYS | A | 75 | 11.963 | 9.100 | 20.396 | 1.00 | 34.18 | N |
| ATOM | 470 | CA | LYS | A | 75 | 10.802 | 8.376 | 20.910 | 1.00 | 34.36 | C |
| ATOM | 471 | C | LYS | A | 75 | 10.618 | 8.616 | 22.403 | 1.00 | 35.18 | C |
| ATOM | 472 | O | LYS | A | 75 | 9.575 | 8.304 | 22.945 | 1.00 | 35.70 | O |
| ATOM | 473 | CB | LYS | A | 75 | 10.950 | 6.876 | 20.631 | 1.00 | 34.51 | C |
| ATOM | 474 | CG | LYS | A | 75 | 12.138 | 6.219 | 21.294 | 1.00 | 33.19 | C |
| ATOM | 475 | CD | LYS | A | 75 | 12.302 | 4.754 | 20.834 | 1.00 | 31.54 | C |
| ATOM | 476 | CE | LYS | A | 75 | 13.796 | 4.304 | 20.744 | 1.00 | 29.70 | C |
| ATOM | 477 | NZ | LYS | A | 75 | 14.460 | 4.158 | 22.026 | 1.00 | 28.79 | N |
| ATOM | 478 | N | TRP | A | 76 | 11.619 | 9.181 | 23.071 | 1.00 | 35.44 | N |
| ATOM | 479 | CA | TRP | A | 76 | 11.517 | 9.426 | 24.495 | 1.00 | 36.05 | C |
| ATOM | 480 | C | TRP | A | 76 | 10.307 | 10.264 | 24.893 | 1.00 | 37.47 | C |
| ATOM | 481 | O | TRP | A | 76 | 9.958 | 11.222 | 24.212 | 1.00 | 38.43 | O |
| ATOM | 482 | CB | TRP | A | 76 | 12.742 | 10.179 | 24.994 | 1.00 | 35.67 | C |
| ATOM | 483 | CG | TRP | A | 76 | 13.980 | 9.395 | 24.963 | 1.00 | 33.87 | C |
| ATOM | 484 | CD1 | TRP | A | 76 | 14.136 | 8.116 | 24.520 | 1.00 | 32.29 | C |
| ATOM | 485 | CD2 | TRP | A | 76 | 15.252 | 9.821 | 25.409 | 1.00 | 30.36 | C |
| ATOM | 486 | NE1 | TRP | A | 76 | 15.440 | 7.723 | 24.673 | 1.00 | 30.42 | N |
| ATOM | 487 | CE2 | TRP | A | 76 | 16.143 | 8.754 | 25.221 | 1.00 | 28.82 | C |
| ATOM | 488 | CE3 | TRP | A | 76 | 15.739 | 11.013 | 25.954 | 1.00 | 29.45 | C |
| ATOM | 489 | CZ2 | TRP | A | 76 | 17.471 | 8.833 | 25.560 | 1.00 | 30.56 | C |
| ATOM | 490 | CZ3 | TRP | A | 76 | 17.056 | 11.091 | 26.291 | 1.00 | 29.56 | C |
| ATOM | 491 | CH2 | TRP | A | 76 | 17.917 | 10.017 | 26.092 | 1.00 | 30.20 | C |
| ATOM | 492 | N | ASP | A | 77 | 9.698 | 9.894 | 26.014 | 1.00 | 38.14 | N |
| ATOM | 493 | CA | ASP | A | 77 | 8.620 | 10.640 | 26.635 | 1.00 | 38.33 | C |
| ATOM | 494 | C | ASP | A | 77 | 8.653 | 10.223 | 28.094 | 1.00 | 37.89 | C |
| ATOM | 495 | O | ASP | A | 77 | 9.443 | 9.390 | 28.447 | 1.00 | 37.97 | O |
| ATOM | 496 | CB | ASP | A | 77 | 7.283 | 10.353 | 25.974 | 1.00 | 38.71 | C |
| ATOM | 497 | CG | ASP | A | 77 | 6.882 | 8.904 | 26.049 | 1.00 | 39.50 | C |
| ATOM | 498 | OD1 | ASP | A | 77 | 7.414 | 8.107 | 26.867 | 1.00 | 41.50 | O |
| ATOM | 499 | OD2 | ASP | A | 77 | 6.006 | 8.472 | 25.299 | 1.00 | 41.98 | O |
| ATOM | 500 | N | LEU | A | 78 | 7.838 | 10.800 | 28.955 | 1.00 | 38.47 | N |
| ATOM | 501 | CA | LEU | A | 78 | 7.941 | 10.481 | 30.375 | 1.00 | 39.09 | C |
| ATOM | 502 | C | LEU | A | 78 | 7.734 | 9.002 | 30.662 | 1.00 | 39.89 | C |
| ATOM | 503 | O | LEU | A | 78 | 8.421 | 8.423 | 31.507 | 1.00 | 40.19 | O |
| ATOM | 504 | CB | LEU | A | 78 | 6.966 | 11.310 | 31.171 | 1.00 | 39.02 | C |
| ATOM | 505 | CG | LEU | A | 78 | 7.169 | 12.815 | 31.042 | 1.00 | 41.51 | C |
| ATOM | 506 | CD1 | LEU | A | 78 | 6.058 | 13.567 | 31.764 | 1.00 | 42.72 | C |
| ATOM | 507 | CD2 | LEU | A | 78 | 8.522 | 13.216 | 31.618 | 1.00 | 42.31 | C |
| ATOM | 508 | N | GLU | A | 79 | 6.795 | 8.369 | 29.971 | 1.00 | 40.66 | N |
| ATOM | 509 | CA | GLU | A | 79 | 6.557 | 6.948 | 30.212 | 1.00 | 41.43 | C |
| ATOM | 510 | C | GLU | A | 79 | 7.794 | 6.086 | 29.909 | 1.00 | 40.84 | C |
| ATOM | 511 | O | GLU | A | 79 | 8.228 | 5.283 | 30.742 | 1.00 | 40.45 | O |
| ATOM | 512 | CB | GLU | A | 79 | 5.343 | 6.458 | 29.418 | 1.00 | 42.10 | C |
| ATOM | 513 | CG | GLU | A | 79 | 5.023 | 4.998 | 29.658 | 1.00 | 45.06 | C |
| ATOM | 514 | CD | GLU | A | 79 | 3.840 | 4.525 | 28.846 | 1.00 | 49.74 | C |
| ATOM | 515 | OE1 | GLU | A | 79 | 3.436 | 5.254 | 27.914 | 1.00 | 52.37 | O |
| ATOM | 516 | OE2 | GLU | A | 79 | 3.316 | 3.426 | 29.150 | 1.00 | 53.21 | O |
| ATOM | 517 | N | TYR | A | 80 | 8.361 | 6.248 | 28.718 | 1.00 | 40.43 | N |
| ATOM | 518 | CA | TYR | A | 80 | 9.559 | 5.495 | 28.362 | 1.00 | 40.14 | C |
| ATOM | 519 | C | TYR | A | 80 | 10.750 | 5.765 | 29.297 | 1.00 | 40.06 | C |
| ATOM | 520 | O | TYR | A | 80 | 11.485 | 4.844 | 29.664 | 1.00 | 39.72 | O |
| ATOM | 521 | CB | TYR | A | 80 | 9.946 | 5.832 | 26.946 | 1.00 | 39.96 | C |
| ATOM | 522 | CG | TYR | A | 80 | 11.193 | 5.147 | 26.420 | 1.00 | 39.51 | C |
| ATOM | 523 | CD1 | TYR | A | 80 | 11.118 | 3.897 | 25.804 | 1.00 | 38.93 | C |
| ATOM | 524 | CD2 | TYR | A | 80 | 12.433 | 5.768 | 26.490 | 1.00 | 36.89 | C |
| ATOM | 525 | CE1 | TYR | A | 80 | 12.253 | 3.277 | 25.290 | 1.00 | 38.08 | C |
| ATOM | 526 | CE2 | TYR | A | 80 | 13.562 | 5.154 | 25.993 | 1.00 | 38.15 | C |
| ATOM | 527 | CZ | TYR | A | 80 | 13.468 | 3.915 | 25.379 | 1.00 | 39.06 | C |
| ATOM | 528 | OH | TYR | A | 80 | 14.604 | 3.319 | 24.863 | 1.00 | 38.99 | O |
| ATOM | 529 | N | LEU | A | 81 | 10.935 | 7.017 | 29.688 | 1.00 | 39.68 | N |
| ATOM | 530 | CA | LEU | A | 81 | 12.061 | 7.362 | 30.565 | 1.00 | 40.01 | C |
| ATOM | 531 | C | LEU | A | 81 | 11.858 | 6.806 | 31.978 | 1.00 | 39.86 | C |
| ATOM | 532 | O | LEU | A | 81 | 12.792 | 6.284 | 32.608 | 1.00 | 39.47 | O |
| ATOM | 533 | CB | LEU | A | 81 | 12.314 | 8.889 | 30.604 | 1.00 | 39.50 | C |
| ATOM | 534 | CG | LEU | A | 81 | 12.765 | 9.532 | 29.287 | 1.00 | 39.76 | C |
| ATOM | 535 | CO1 | LEU | A | 81 | 12.805 | 11.045 | 29.402 | 1.00 | 39.84 | C |
| ATOM | 536 | CD2 | LEU | A | 81 | 14.117 | 9.018 | 28.840 | 1.00 | 39.32 | C |
| ATOM | 537 | N | GLN | A | 82 | 10.645 | 6.932 | 32.482 | 1.00 | 40.38 | N |
| ATOM | 538 | CA | GLN | A | 82 | 10.346 | 6.415 | 33.804 | 1.00 | 41.02 | C |
| ATOM | 539 | C | GLN | A | 82 | 10.612 | 4.920 | 33.799 | 1.00 | 40.84 | C |
| ATOM | 540 | O | GLN | A | 82 | 11.193 | 4.379 | 34.711 | 1.00 | 40.35 | O |

TABLE 3-continued

Coordinates for structures 1 to 4

| ATOM | 541 | CB | GLN | A | 82 | 8.900 | 6.688 | 34.164 | 1.00 | 41.40 | C |
|---|---|---|---|---|---|---|---|---|---|---|---|
| ATOM | 542 | CG | GLN | A | 82 | 8.447 | 5.906 | 35.351 | 1.00 | 42.97 | C |
| ATOM | 543 | CD | GLN | A | 82 | 7.291 | 6.560 | 36.099 | 1.00 | 45.14 | C |
| ATOM | 544 | OE1 | GLN | A | 82 | 6.662 | 7.502 | 35.616 | 1.00 | 44.10 | O |
| ATOM | 545 | NE2 | GLN | A | 82 | 7.003 | 6.039 | 37.287 | 1.00 | 48.04 | N |
| ATOM | 546 | N | GLU | A | 83 | 10.222 | 4.256 | 32.728 | 1.00 | 41.35 | N |
| ATOM | 547 | CA | GLU | A | 83 | 10.442 | 2.816 | 32.620 | 1.00 | 41.46 | C |
| ATOM | 548 | C | GLU | A | 83 | 11.926 | 2.444 | 32.465 | 1.00 | 40.81 | C |
| ATOM | 549 | O | GLU | A | 83 | 12.350 | 1.407 | 32.958 | 1.00 | 41.13 | O |
| ATOM | 550 | CB | GLU | A | 83 | 9.610 | 2.243 | 31.472 | 1.00 | 41.27 | |
| ATOM | 551 | CG | GLU | A | 83 | 9.609 | 0.728 | 31.366 | 1.00 | 44.77 | C |
| ATOM | 552 | CD | GLU | A | 83 | 8.878 | 0.018 | 32.514 | 1.00 | 49.16 | C |
| ATOM | 553 | OE1 | GLU | A | 83 | 8.219 | 0.672 | 33.347 | 1.00 | 52.26 | O |
| ATOM | 554 | OE2 | GLU | A | 83 | 8.978 | 1.220 | 32.606 | 1.00 | 53.23 | O |
| ATOM | 555 | N | ASN | A | 84 | 12.743 | 3.298 | 31.854 | 1.00 | 39.81 | N |
| ATOM | 556 | CA | ASN | A | 84 | 14.099 | 2.859 | 31.515 | 1.00 | 38.82 | C |
| ATOM | 557 | C | ASN | A | 84 | 15.290 | 3.611 | 32.048 | 1.00 | 38.20 | C |
| ATOM | 558 | O | ASN | A | 84 | 16.402 | 3.117 | 31.919 | 1.00 | 36.98 | O |
| ATOM | 559 | CB | ASN | A | 84 | 14.244 | 2.828 | 29.995 | 1.00 | 38.83 | C |
| ATOM | 560 | CG | ASN | A | 84 | 13.301 | 1.865 | 29.349 | 1.00 | 38.45 | C |
| ATOM | 561 | OD1 | ASN | A | 84 | 13.307 | 0.670 | 29.664 | 1.00 | 40.40 | O |
| ATOM | 562 | ND2 | ASN | A | 84 | 12.480 | 2.365 | 28.441 | 1.00 | 35.77 | N |
| ATOM | 563 | N | ILE | A | 85 | 15.088 | 4.781 | 32.645 | 1.00 | 38.08 | N |
| ATOM | 564 | CA | ILE | A | 85 | 16.226 | 5.598 | 32.998 | 1.00 | 38.57 | C |
| ATOM | 565 | C | ILE | A | 85 | 16.929 | 5.280 | 34.307 | 1.00 | 38.70 | C |
| ATOM | 566 | O | ILE | A | 85 | 17.849 | 5.993 | 34.702 | 1.00 | 39.78 | O |
| ATOM | 567 | CB | ILE | A | 85 | 15.827 | 7.056 | 32.932 | 1.00 | 39.02 | C |
| ATOM | 568 | CG1 | ILE | A | 85 | 17.001 | 7.891 | 32.418 | 1.00 | 39.43 | C |
| ATOM | 569 | CG2 | ILE | A | 85 | 15.291 | 7.544 | 34.266 | 1.00 | 39.22 | C |
| ATOM | 570 | CD1 | ILE | A | 85 | 16.618 | 9.347 | 32.148 | 1.00 | 40.41 | C |
| ATOM | 571 | N | GLY | A | 86 | 16.513 | 4.227 | 34.993 | 1.00 | 38.59 | N |
| ATOM | 572 | CA | GLY | A | 86 | 17.208 | 3.801 | 36.199 | 1.00 | 38.15 | C |
| ATOM | 573 | C | GLY | A | 86 | 16.658 | 4.386 | 37.476 | 1.00 | 37.92 | C |
| ATOM | 574 | O | GLY | A | 86 | 15.652 | 5.097 | 37.461 | 1.00 | 37.90 | O |
| ATOM | 575 | N | ASN | A | 87 | 17.359 | 4.113 | 38.574 | 1.00 | 37.70 | N |
| ATOM | 576 | CA | ASN | A | 87 | 26.941 | 4.542 | 39.899 | 1.00 | 37.34 | C |
| ATOM | 577 | C | ASN | A | 87 | 17.898 | 5.576 | 40.487 | 1.00 | 36.99 | C |
| ATOM | 578 | O | ASN | A | 87 | 17.920 | 5.807 | 41.710 | 1.00 | 36.36 | O |
| ATOM | 579 | CB | ASN | A | 87 | 16.786 | 3.306 | 40.840 | 1.00 | 37.40 | C |
| ATOM | 580 | N | GLY | A | 88 | 18.676 | 6.224 | 39.618 | 1.00 | 37.00 | N |
| ATOM | 581 | CA | GLY | A | 88 | 19.593 | 7.272 | 40.056 | 1.00 | 36.90 | C |
| ATOM | 582 | C | GLY | A | 88 | 18.855 | 8.506 | 40.541 | 1.00 | 36.61 | C |
| ATOM | 583 | O | GLY | A | 88 | 17.673 | 8.648 | 40.298 | 1.00 | 36.55 | O |
| ATOM | 584 | N | ASP | A | 89 | 19.532 | 9.392 | 41.250 | 1.00 | 37.05 | N |
| ATOM | 585 | CA | ASP | A | 89 | 18.882 | 10.640 | 41.687 | 1.00 | 37.92 | C |
| ATOM | 586 | C | ASP | A | 89 | 18.812 | 11.654 | 40.548 | 1.00 | 37.52 | C |
| ATOM | 587 | O | ASP | A | 89 | 19.724 | 11.713 | 39.730 | 1.00 | 37.73 | O |
| ATOM | 588 | CB | ASP | A | 89 | 19.639 | 11.281 | 42.840 | 1.00 | 38.02 | C |
| ATOM | 589 | CG | ASP | A | 89 | 19.342 | 10.639 | 44.165 | 1.00 | 40.19 | C |
| ATOM | 590 | OD1 | ASP | A | 89 | 18.398 | 9.813 | 44.252 | 1.00 | 44.15 | O |
| ATOM | 591 | OD2 | ASP | A | 89 | 20.002 | 10.918 | 45.186 | 1.00 | 42.25 | O |
| ATOM | 592 | N | PHE | A | 90 | 17.734 | 12.438 | 40.491 | 1.00 | 37.19 | N |
| ATOM | 593 | CA | PHE | A | 90 | 17.638 | 13.546 | 39.520 | 1.00 | 36.65 | C |
| ATOM | 594 | C | PHE | A | 90 | 17.435 | 14.912 | 40.182 | 1.00 | 36.57 | C |
| ATOM | 595 | O | PHE | A | 90 | 16.551 | 15.078 | 41.015 | 1.00 | 36.80 | O |
| ATOM | 596 | CB | PHE | A | 90 | 16.512 | 13.310 | 38.551 | 1.00 | 35.79 | C |
| ATOM | 597 | CG | PHE | A | 90 | 16.793 | 12.200 | 37.551 | 1.00 | 35.34 | C |
| ATOM | 598 | CD1 | PHE | A | 90 | 16.627 | 10.870 | 37.931 | 1.00 | 34.10 | C |
| ATOM | 599 | CD2 | PHE | A | 90 | 17.235 | 12.472 | 36.275 | 1.00 | 34.19 | C |
| ATOM | 600 | CE1 | PHE | A | 90 | 16.875 | 9.854 | 37.061 | 1.00 | 31.47 | C |
| ATOM | 601 | CE2 | PHE | A | 90 | 17.488 | 11.452 | 35.404 | 1.00 | 35.32 | C |
| ATOM | 602 | CZ | PHE | A | 90 | 17.315 | 10.123 | 35.813 | 1.00 | 34.26 | C |
| ATOM | 603 | N | SER | A | 91 | 18.257 | 15.886 | 39.803 | 1.00 | 36.85 | N |
| ATOM | 604 | CA | SER | A | 91 | 18.077 | 17.264 | 40.278 | 1.00 | 37.16 | C |
| ATOM | 605 | C | SER | A | 91 | 16.856 | 17.884 | 39.612 | 1.00 | 37.28 | C |
| ATOM | 606 | O | SER | A | 91 | 16.761 | 17.912 | 38.392 | 1.00 | 36.72 | O |
| ATOM | 607 | CB | SER | A | 91 | 19.278 | 18.146 | 39.971 | 1.00 | 36.75 | C |
| ATOM | 608 | OG | SER | A | 91 | 20.470 | 17.600 | 40.456 | 1.00 | 35.79 | O |
| ATOM | 609 | N | VAL | A | 92 | 15.938 | 18.374 | 40.434 | 1.00 | 37.83 | N |
| ATOM | 610 | CA | VAL | A | 92 | 14.740 | 19.022 | 39.963 | 1.00 | 38.40 | C |
| ATOM | 611 | C | VAL | A | 92 | 14.549 | 20.334 | 40.690 | 1.00 | 39.41 | C |
| ATOM | 612 | O | VAL | A | 92 | 14.465 | 20.394 | 41.941 | 1.00 | 39.08 | O |
| ATOM | 613 | CB | VAL | A | 92 | 13.507 | 18.227 | 40.298 | 1.00 | 38.96 | C |
| ATOM | 614 | CG1 | VAL | A | 92 | 12.270 | 19.005 | 39.893 | 1.00 | 38.57 | C |
| ATOM | 615 | CG2 | VAL | A | 92 | 13.556 | 16.837 | 39.651 | 1.00 | 39.45 | C |
| ATOM | 616 | N | TYR | A | 93 | 14.426 | 21.386 | 39.895 | 1.00 | 39.95 | N |
| ATOM | 617 | CA | TYR | A | 93 | 14.214 | 22.701 | 40.419 | 1.00 | 40.34 | C |

TABLE 3-continued

| | | | | | | | | | | | |
|---|---|---|---|---|---|---|---|---|---|---|---|
| ATOM | 618 | C | TYR | A | 93 | 12.756 | 22.950 | 40.459 | 1.00 | 40.76 | C |
| ATOM | 619 | O | TYR | A | 93 | 11.999 | 22.493 | 39.583 | 1.00 | 40.39 | O |
| ATOM | 620 | CB | TYR | A | 93 | 14.897 | 23.729 | 39.529 | 1.00 | 40.89 | C |
| ATOM | 621 | CG | TYR | A | 93 | 16.369 | 23.580 | 39.627 | 1.00 | 40.80 | C |
| ATOM | 622 | CD1 | TYR | A | 93 | 17.067 | 24.135 | 40.681 | 1.00 | 40.79 | C |
| ATOM | 623 | CD2 | TYR | A | 93 | 17.042 | 22.801 | 38.743 | 1.00 | 41.05 | C |
| ATOM | 624 | CE1 | TYR | A | 93 | 18.395 | 23.953 | 40.802 | 1.00 | 41.05 | C |
| ATOM | 625 | CE2 | TYR | A | 93 | 18.363 | 22.629 | 38.852 | 1.00 | 42.75 | C |
| ATOM | 626 | CZ | TYR | A | 93 | 19.037 | 23.204 | 39.881 | 1.00 | 42.45 | C |
| ATOM | 627 | OS | TYR | A | 93 | 20.372 | 22.965 | 39.971 | 1.00 | 47.63 | O |
| ATOM | 628 | N | SER | A | 94 | 12.385 | 23.699 | 41.482 | 1.00 | 41.70 | N |
| ATOM | 629 | CA | SER | A | 94 | 11.014 | 24.053 | 41.743 | 1.00 | 42.70 | C |
| ATOM | 630 | C | SER | A | 94 | 10.965 | 25.565 | 41.855 | 1.00 | 43.09 | C |
| ATOM | 631 | O | SER | A | 94 | 11.851 | 26.181 | 42.441 | 1.00 | 43.63 | O |
| ATOM | 632 | CB | SER | A | 94 | 10.570 | 23.415 | 43.051 | 1.00 | 42.76 | C |
| ATOM | 633 | OG | SER | A | 94 | 9.258 | 23.841 | 43.395 | 1.00 | 45.05 | O |
| ATOM | 634 | N | ALA | A | 95 | 9.929 | 26.171 | 41.308 | 1.00 | 43.42 | N |
| ATOM | 635 | CA | ALA | A | 95 | 9.839 | 27.607 | 41.323 | 1.00 | 43.49 | C |
| ATOM | 636 | C | ALA | A | 95 | 8.416 | 28.083 | 41.281 | 1.00 | 43.87 | C |
| ATOM | 637 | O | ALA | A | 95 | 7.520 | 27.416 | 40.789 | 1.00 | 43.95 | O |
| ATOM | 638 | CB | ALA | A | 95 | 10.572 | 28.164 | 40.145 | 1.00 | 43.70 | C |
| ATOM | 639 | N | SER | A | 96 | 8.219 | 29.287 | 41.770 | 1.00 | 44.66 | N |
| ATOM | 640 | CA | SER | A | 96 | 6.901 | 29.866 | 41.757 | 1.00 | 45.08 | C |
| ATOM | 641 | C | SER | A | 96 | 6.767 | 30.914 | 40.668 | 1.00 | 44.27 | C |
| ATOM | 642 | O | SER | A | 96 | 5.783 | 31.636 | 40.637 | 1.00 | 45.20 | O |
| ATOM | 643 | CB | SER | A | 96 | 6.604 | 30.510 | 43.095 | 1.00 | 45.33 | C |
| ATOM | 644 | OG | SER | A | 96 | 5.384 | 31.199 | 42.973 | 1.00 | 47.96 | O |
| ATOM | 645 | N | THR | A | 97 | 7.776 | 31.034 | 39.819 | 1.00 | 42.95 | N |
| ATOM | 646 | CA | THR | A | 97 | 7.738 | 31.962 | 38.688 | 1.00 | 42.08 | C |
| ATOM | 647 | C | THR | A | 97 | 8.103 | 31.184 | 37.461 | 1.00 | 40.94 | C |
| ATOM | 648 | O | THR | A | 97 | 8.604 | 30.095 | 37.584 | 1.00 | 40.73 | O |
| ATOM | 649 | CB | THR | A | 97 | 8.779 | 33.088 | 38.826 | 1.00 | 42.48 | C |
| ATOM | 650 | OG1 | THR | A | 97 | 8.964 | 33.707 | 37.546 | 1.00 | 43.60 | O |
| ATOM | 651 | CG2 | THR | A | 97 | 10.209 | 32.544 | 39.156 | 1.00 | 42.12 | C |
| ATOM | 652 | N | HIS | A | 98 | 7.904 | 31.734 | 36.275 | 1.00 | 40.18 | N |
| ATOM | 653 | CA | HIS | A | 98 | 8.319 | 31.012 | 35.074 | 1.00 | 40.09 | C |
| ATOM | 654 | C | HIS | A | 98 | 9.840 | 31.036 | 34.883 | 1.00 | 39.78 | C |
| ATOM | 655 | O | HIS | A | 98 | 10.376 | 30.277 | 34.078 | 1.00 | 38.48 | O |
| ATOM | 656 | CB | HIS | A | 98 | 7.660 | 31.580 | 33.824 | 1.00 | 40.00 | C |
| ATOM | 657 | CG | HIS | A | 98 | 7.947 | 33.028 | 33.582 | 1.00 | 40.56 | C |
| ATOM | 658 | ND1 | HIS | A | 98 | 7.297 | 34.041 | 34.259 | 1.00 | 40.13 | N |
| ATOM | 659 | CD2 | HIS | A | 98 | 8.805 | 33.640 | 32.729 | 1.00 | 42.26 | C |
| ATOM | 660 | CE1 | HIS | A | 98 | 7.741 | 35.212 | 33.841 | 1.00 | 37.08 | C |
| ATOM | 661 | ND2 | HIS | A | 98 | 8.661 | 35.002 | 32.915 | 1.00 | 39.74 | N |
| ATOM | 662 | N | LYS | A | 99 | 10.526 | 31.883 | 35.652 | 1.00 | 39.73 | N |
| ATOM | 663 | CA | LYS | A | 99 | 11.948 | 32.082 | 35.476 | 1.00 | 40.45 | C |
| ATOM | 664 | C | LYS | A | 99 | 12.861 | 31.221 | 36.332 | 1.00 | 40.34 | C |
| ATOM | 665 | O | LYS | A | 99 | 12.904 | 31.376 | 37.554 | 1.00 | 41.93 | O |
| ATOM | 666 | CB | LYS | A | 99 | 12.279 | 33.535 | 35.730 | 1.00 | 40.89 | C |
| ATOM | 667 | CG | LYS | A | 99 | 11.819 | 34.443 | 34.624 | 1.00 | 43.12 | C |
| ATOM | 668 | CD | LYS | A | 99 | 12.466 | 35.806 | 34.753 | 1.00 | 46.04 | C |
| ATOM | 669 | CE | LYS | A | 99 | 11.733 | 36.727 | 35.711 | 1.00 | 48.26 | C |
| ATOM | 670 | NZ | LYS | A | 99 | 10.662 | 37.495 | 35.003 | 1.00 | 49.55 | N |
| ATOM | 671 | N | PHE | A | 100 | 13.622 | 30.335 | 35.700 | 1.00 | 39.70 | N |
| ATOM | 672 | CA | PHE | A | 100 | 14.554 | 29.487 | 36.447 | 1.00 | 39.48 | C |
| ATOM | 673 | C | PHE | A | 100 | 16.001 | 30.011 | 36.390 | 1.00 | 39.52 | C |
| ATOM | 674 | O | PHE | A | 100 | 16.874 | 29.435 | 35.718 | 1.00 | 38.87 | O |
| ATOM | 675 | CB | PHE | A | 100 | 14.485 | 28.056 | 35.939 | 1.00 | 39.33 | C |
| ATOM | 676 | CG | PHE | A | 100 | 13.266 | 27.328 | 36.377 | 1.00 | 38.47 | C |
| ATOM | 677 | CD1 | PHE | A | 100 | 12.059 | 27.519 | 35.725 | 1.00 | 36.20 | C |
| ATOM | 678 | CD2 | PHE | A | 100 | 13.327 | 26.441 | 37.443 | 1.00 | 37.31 | C |
| ATOM | 679 | CE1 | PHE | A | 100 | 10.960 | 26.846 | 36.125 | 1.00 | 36.52 | C |
| ATOM | 680 | CE2 | PHE | A | 100 | 12.212 | 25.751 | 37.849 | 1.00 | 36.40 | C |
| ATOM | 681 | CZ | PHE | A | 100 | 11.037 | 25.946 | 37.206 | 1.00 | 36.52 | C |
| ATOM | 682 | N | LEU | A | 101 | 16.244 | 31.130 | 37.066 | 1.00 | 39.53 | N |
| ATOM | 683 | CA | LEU | A | 101 | 17.592 | 31.667 | 37.170 | 1.00 | 39.36 | C |
| ATOM | 684 | C | LEU | A | 101 | 18.548 | 30.642 | 37.787 | 1.00 | 39.88 | C |
| ATOM | 685 | O | LEU | A | 101 | 18.345 | 30.152 | 38.899 | 1.00 | 39.47 | O |
| ATOM | 686 | CB | LEU | A | 101 | 17.574 | 32.912 | 38.036 | 1.00 | 39.37 | C |
| ATOM | 687 | CG | LEU | A | 101 | 18.828 | 33.777 | 38.071 | 1.00 | 39.44 | C |
| ATOM | 688 | CD1 | LEU | A | 101 | 19.258 | 34.290 | 36.693 | 1.00 | 37.56 | C |
| ATOM | 689 | CD2 | LEU | A | 101 | 18.546 | 34.926 | 39.008 | 1.00 | 39.90 | C |
| ATOM | 690 | N | TYR | A | 102 | 19.578 | 30.297 | 37.032 | 1.00 | 41.10 | N |
| ATOM | 691 | CA | TYR | A | 102 | 20.623 | 29.415 | 37.507 | 1.00 | 41.59 | C |
| ATOM | 692 | C | TYR | A | 102 | 21.439 | 30.097 | 38.611 | 1.00 | 42.23 | C |
| ATOM | 693 | O | TYR | A | 102 | 21.778 | 31.296 | 38.500 | 1.00 | 42.28 | O |
| ATOM | 694 | CB | TYR | A | 102 | 21.580 | 29.048 | 36.370 | 1.00 | 41.49 | C |

TABLE 3-continued

Coordinates for structures 1 to 4

| | | | | | | | | | | | |
|---|---|---|---|---|---|---|---|---|---|---|---|
| ATOM | 695 | CG | TYR | A | 102 | 22.706 | 28.209 | 36.894 | 1.00 | 43.02 | C |
| ATOM | 696 | CD1 | TYR | A | 102 | 22.507 | 26.864 | 37.200 | 1.00 | 42.85 | C |
| ATOM | 697 | CD2 | TYR | A | 102 | 23.941 | 28.761 | 37.150 | 1.00 | 43.85 | C |
| ATOM | 698 | GE1 | TYR | A | 102 | 23.504 | 26.110 | 37.725 | 1.00 | 45.04 | C |
| ATOM | 699 | CE2 | TYR | A | 102 | 24.942 | 28.005 | 37.696 | 1.00 | 46.05 | C |
| ATOM | 700 | CZ | TYR | A | 102 | 24.725 | 26.681 | 37.984 | 1.00 | 46.73 | C |
| ATOM | 701 | OH | TYR | A | 102 | 25.752 | 25.915 | 38.544 | 1.00 | 52.49 | O |
| ATOM | 702 | N | TYR | A | 103 | 21.759 | 29.340 | 39.657 | 1.00 | 42.12 | N |
| ATOM | 703 | CA | TYR | A | 103 | 22.665 | 29.832 | 40.690 | 1.00 | 42.58 | C |
| ATOM | 704 | C | TYR | A | 103 | 23.632 | 28.750 | 41.207 | 1.00 | 41.98 | C |
| ATOM | 705 | O | TYR | A | 103 | 23.333 | 27.560 | 41.237 | 1.00 | 42.05 | O |
| ATOM | 706 | CB | TYR | A | 103 | 21.901 | 30.435 | 41.843 | 1.00 | 43.03 | C |
| ATOM | 707 | CG | TYR | A | 103 | 20.964 | 29.493 | 42.477 | 1.00 | 44.79 | C |
| ATOM | 708 | CD1 | TYR | A | 103 | 19.691 | 29.333 | 41.971 | 1.00 | 47.69 | C |
| ATOM | 709 | CD2 | TYR | A | 103 | 21.338 | 28.769 | 43.590 | 1.00 | 49.51 | C |
| ATOM | 710 | CE1 | TYR | A | 103 | 18.798 | 28.456 | 42.544 | 1.00 | 50.63 | C |
| ATOM | 711 | CE2 | TYR | A | 103 | 20.449 | 27.890 | 44.202 | 1.00 | 52.43 | C |
| ATOM | 712 | CZ | TYR | A | 103 | 19.181 | 27.736 | 43.658 | 1.00 | 52.68 | C |
| ATOM | 713 | OH | TYR | A | 103 | 18.297 | 26.875 | 44.234 | 1.00 | 56.40 | O |
| ATOM | 714 | N | ASP | A | 104 | 24.809 | 29.190 | 41.603 | 1.00 | 41.00 | N |
| ATOM | 715 | CA | ASP | A | 104 | 25.844 | 28.288 | 42.026 | 1.00 | 40.33 | C |
| ATOM | 716 | C | ASP | A | 104 | 25.842 | 28.250 | 43.530 | 1.00 | 39.98 | C |
| ATOM | 717 | O | ASP | A | 104 | 26.177 | 29.224 | 44.219 | 1.00 | 38.58 | O |
| ATOM | 718 | CB | ASP | A | 104 | 27.169 | 28.768 | 41.492 | 1.00 | 40.13 | C |
| ATOM | 719 | CG | ASP | A | 104 | 28.310 | 27.929 | 41.958 | 1.00 | 42.26 | C |
| ATOM | 720 | OD1 | ASP | A | 104 | 28.117 | 27.151 | 42.942 | 1.00 | 44.33 | O |
| ATOM | 721 | OD2 | ASP | A | 104 | 29.429 | 27.989 | 41.393 | 1.00 | 42.30 | O |
| ATOM | 722 | N | GLU | A | 105 | 25.425 | 27.110 | 44.041 | 1.00 | 40.20 | N |
| ATOM | 723 | CA | GLU | A | 105 | 25.294 | 26.950 | 45.472 | 1.00 | 40.26 | C |
| ATOM | 724 | C | GLU | A | 105 | 26.605 | 27.213 | 46.228 | 1.00 | 39.92 | C |
| ATOM | 725 | O | GLU | A | 105 | 26.577 | 27.824 | 47.293 | 1.00 | 40.11 | O |
| ATOM | 726 | CB | GLU | A | 105 | 24.747 | 25.570 | 45.744 | 1.00 | 40.54 | C |
| ATOM | 727 | CG | GLU | A | 105 | 23.245 | 25.502 | 45.533 | 1.00 | 42.55 | C |
| ATOM | 728 | CD | GLU | A | 105 | 22.709 | 24.086 | 45.506 | 1.00 | 44.11 | C |
| ATOM | 729 | OE1 | GLU | A | 105 | 23.178 | 23.251 | 46.323 | 1.00 | 46.78 | O |
| ATOM | 730 | OE2 | GLU | A | 105 | 21.801 | 23.815 | 44.684 | 1.00 | 42.74 | O |
| ATOM | 731 | N | LYS | A | 106 | 27.748 | 26.819 | 45.661 | 1.00 | 39.52 | N |
| ATOM | 732 | CA | LYS | A | 106 | 29.041 | 26.991 | 46.336 | 1.00 | 39.53 | C |
| ATOM | 733 | C | LYS | A | 106 | 29.370 | 28.419 | 46.623 | 1.00 | 39.68 | C |
| ATOM | 734 | O | LYS | A | 106 | 30.199 | 28.697 | 47.471 | 1.00 | 40.24 | O |
| ATOM | 735 | GB | LYS | A | 106 | 30.221 | 26.479 | 45.504 | 1.00 | 39.89 | C |
| ATOM | 736 | CG | LYS | A | 106 | 30.257 | 24.976 | 45.143 | 1.00 | 40.25 | C |
| ATOM | 737 | N | LYS | A | 107 | 28.747 | 29.333 | 45.894 | 1.00 | 40.07 | N |
| ATOM | 738 | CA | LYS | A | 107 | 29.043 | 30.740 | 46.031 | 1.00 | 39.35 | C |
| ATOM | 739 | C | LYS | A | 107 | 28.061 | 31.421 | 46.937 | 1.00 | 39.82 | C |
| ATOM | 740 | O | LYS | A | 107 | 28.208 | 32.586 | 47.188 | 1.00 | 39.28 | O |
| ATOM | 741 | CB | LYS | A | 107 | 29.050 | 31.410 | 44.645 | 1.00 | 39.29 | C |
| ATOM | 742 | CG | LYS | A | 107 | 30.329 | 31.155 | 43.827 | 1.00 | 37.47 | C |
| ATOM | 743 | CD | LYS | A | 107 | 30.286 | 31.702 | 42.406 | 1.00 | 34.55 | C |
| ATOM | 744 | CE | LYS | A | 107 | 31.606 | 31.470 | 41.651 | 1.00 | 33.57 | C |
| ATOM | 745 | NZ | LYS | A | 107 | 31.607 | 31.880 | 40.178 | 1.00 | 30.95 | N |
| ATOM | 746 | N | MET | A | 108 | 27.071 | 30.707 | 47.458 | 1.00 | 41.78 | N |
| ATOM | 747 | CA | MET | A | 108 | 26.079 | 31.341 | 48.341 | 1.00 | 43.69 | C |
| ATOM | 748 | C | MET | A | 108 | 26.621 | 31.950 | 49.646 | 1.00 | 44.68 | C |
| ATOM | 749 | O | MET | A | 108 | 26.154 | 33.004 | 50.061 | 1.00 | 44.99 | O |
| ATOM | 750 | CB | MET | A | 108 | 24.923 | 30.396 | 48.594 | 1.00 | 44.05 | C |
| ATOM | 751 | CG | MET | A | 108 | 24.195 | 30.105 | 47.282 | 1.00 | 46.49 | C |
| ATOM | 752 | SD | MET | A | 108 | 22.723 | 29.125 | 47.315 | 1.00 | 51.54 | S |
| ATOM | 753 | CE | MET | A | 108 | 21.653 | 30.080 | 48.484 | 1.00 | 51.43 | C |
| ATOM | 754 | N | ALA | A | 109 | 27.630 | 31.341 | 50.254 | 1.00 | 46.34 | N |
| ATOM | 755 | CA | ALA | A | 109 | 28.211 | 31.855 | 51.510 | 1.00 | 47.87 | C |
| ATOM | 756 | C | ALA | A | 109 | 28.697 | 33.308 | 51.406 | 1.00 | 49.27 | C |
| ATOM | 757 | O | ALA | A | 109 | 28.533 | 34.114 | 52.323 | 1.00 | 49.44 | O |
| ATOM | 758 | CB | ALA | A | 109 | 29.355 | 30.958 | 51.960 | 1.00 | 47.63 | C |
| ATOM | 759 | N | ASN | A | 110 | 29.276 | 33.651 | 50.269 | 1.00 | 50.88 | N |
| ATOM | 760 | CA | ASN | A | 110 | 29.792 | 35.004 | 50.069 | 1.00 | 51.99 | C |
| ATOM | 761 | C | ASN | A | 110 | 28.732 | 36.070 | 49.736 | 1.00 | 51.88 | C |
| ATOM | 762 | O | ASN | A | 110 | 29.038 | 37.252 | 49.562 | 1.00 | 51.14 | O |
| ATOM | 763 | CB | ASN | A | 110 | 30.876 | 34.939 | 48.994 | 1.00 | 52.43 | C |
| ATOM | 764 | CG | ASN | A | 110 | 32.077 | 34.080 | 49.433 | 1.00 | 54.41 | C |
| ATOM | 765 | OD1 | ASN | A | 110 | 32.460 | 34.050 | 50.624 | 1.00 | 54.72 | O |
| ATOM | 766 | ND2 | ASN | A | 110 | 32.663 | 33.373 | 48.478 | 1.00 | 56.75 | N |
| ATOM | 767 | N | PHE | A | 111 | 27.484 | 35.651 | 49.632 | 1.00 | 52.59 | N |
| ATOM | 768 | CA | PHE | A | 111 | 26.404 | 36.598 | 49.409 | 1.00 | 53.32 | |
| ATOM | 769 | C | PHE | A | 111 | 25.202 | 36.180 | 50.261 | 1.00 | 54.75 | C |
| ATOM | 770 | O | PHE | A | 111 | 24.149 | 35.801 | 49.749 | 1.00 | 54.37 | O |
| ATOM | 771 | CB | PHE | A | 111 | 26.053 | 36.693 | 47.923 | 1.00 | 52.83 | C |

TABLE 3-continued

| | | | | | | | | | | | |
|---|---|---|---|---|---|---|---|---|---|---|---|
| | Coordinates for structures 1 to 4 |
| ATOM | 772 | CG | PHE | A | 111 | 27.058 | 37.461 | 47.107 | 1.00 | 50.42 | C |
| ATOM | 773 | CD1 | PHE | A | 111 | 28.283 | 36.907 | 46.791 | 1.00 | 49.93 | C |
| ATOM | 774 | CD2 | PHE | A | 111 | 26.781 | 38.729 | 46.658 | 1.00 | 48.60 | C |
| ATOM | 775 | CE1 | PHE | A | 111 | 29.205 | 37.609 | 46.044 | 1.00 | 49.18 | C |
| ATOM | 776 | CE2 | PHE | A | 111 | 27.701 | 39.429 | 45.904 | 1.00 | 47.91 | C |
| ATOM | 777 | CZ | PHE | A | 111 | 28.910 | 38.869 | 45.601 | 1.00 | 47.42 | C |
| ATOM | 778 | N | GLN | A | 112 | 25.376 | 36.279 | 51.576 | 1.00 | 56.74 | N |
| ATOM | 779 | CA | GLN | A | 112 | 24.353 | 35.855 | 52.536 | 1.00 | 58.14 | C |
| ATOM | 780 | C | GLN | A | 112 | 22.970 | 36.399 | 52.192 | 1.00 | 58.29 | C |
| ATOM | 781 | O | GLN | A | 112 | 21.972 | 35.742 | 52.468 | 1.00 | 58.53 | O |
| ATOM | 782 | CB | GLN | A | 112 | 24.730 | 36.282 | 53.961 | 1.00 | 58.65 | C |
| ATOM | 783 | CG | GLN | A | 112 | 26.100 | 35.815 | 54.441 | 1.00 | 61.33 | C |
| ATOM | 784 | CD | GLN | A | 112 | 26.213 | 34.307 | 54.467 | 1.00 | 64.34 | C |
| ATOM | 785 | DE1 | GLN | A | 112 | 25.483 | 33.622 | 53.750 | 1.00 | 66.46 | O |
| ATOM | 786 | NE2 | GLN | A | 112 | 27.133 | 33.784 | 55.281 | 1.00 | 66.00 | N |
| ATOM | 787 | N | ASN | A | 113 | 22.919 | 37.581 | 51.580 | 1.00 | 58.45 | N |
| ATOM | 788 | CA | ASN | A | 113 | 21.653 | 38.222 | 51.240 | 1.00 | 58.79 | C |
| ATOM | 789 | C | ASN | A | 113 | 21.000 | 37.740 | 49.936 | 1.00 | 58.82 | C |
| ATOM | 790 | O | ASN | A | 113 | 19.971 | 38.284 | 49.536 | 1.00 | 59.69 | O |
| ATOM | 791 | CB | ASN | A | 113 | 21.813 | 39.759 | 51.171 | 1.00 | 58.81 | C |
| ATOM | 792 | CG | ASN | A | 113 | 22.160 | 40.387 | 52.525 | 1.00 | 59.17 | C |
| ATOM | 793 | OD1 | ASN | A | 113 | 21.863 | 39.824 | 53.593 | 1.00 | 57.49 | O |
| ATOM | 794 | ND2 | ASN | A | 113 | 22.786 | 41.567 | 52.482 | 1.00 | 58.34 | N |
| ATOM | 795 | N | PHE | A | 114 | 21.570 | 36.760 | 49.245 | 1.00 | 58.33 | N |
| ATOM | 796 | CA | PHE | A | 114 | 20.930 | 36.306 | 48.015 | 1.00 | 57.84 | C |
| ATOM | 797 | C | PHE | A | 114 | 19.922 | 35.220 | 48.334 | 1.00 | 57.57 | C |
| ATOM | 798 | O | PHE | A | 114 | 20.264 | 34.208 | 48.953 | 1.00 | 57.24 | O |
| ATOM | 799 | CB | PHE | A | 114 | 21.933 | 35.774 | 47.013 | 1.00 | 57.99 | C |
| ATOM | 800 | CG | PHE | A | 114 | 21.289 | 35.126 | 45.822 | 1.00 | 58.28 | C |
| ATOM | 801 | CD1 | PHE | A | 114 | 20.642 | 35.897 | 44.867 | 1.00 | 58.11 | C |
| ATOM | 802 | CD2 | PHE | A | 114 | 21.300 | 33.744 | 45.674 | 1.00 | 58.56 | C |
| ATOM | 803 | CE1 | PHE | A | 114 | 20.028 | 35.312 | 43.781 | 1.00 | 58.29 | C |
| ATOM | 804 | CE2 | PHE | A | 114 | 20.687 | 33.149 | 44.580 | 1.00 | 59.09 | C |
| ATOM | 805 | CZ | PHE | A | 114 | 20.050 | 33.937 | 43.630 | 1.00 | 58.80 | C |
| ATOM | 806 | N | LYS | A | 115 | 16.686 | 35.429 | 47.899 | 1.00 | 57.18 | N |
| ATOM | 807 | CA | LYS | A | 115 | 17.604 | 34.511 | 48.204 | 1.00 | 57.19 | C |
| ATOM | 808 | C | LYS | A | 115 | 17.037 | 33.942 | 46.903 | 1.00 | 57.17 | C |
| ATOM | 809 | O | LYS | A | 115 | 16.268 | 34.598 | 46.193 | 1.00 | 57.12 | O |
| ATOM | 810 | CB | LYS | A | 115 | 16.524 | 35.234 | 49.016 | 1.00 | 57.33 | C |
| ATOM | 811 | N | PRO | A | 116 | 17.384 | 32.699 | 46.610 | 1.00 | 56.97 | N |
| ATOM | 812 | CA | PRO | A | 116 | 17.042 | 32.097 | 45.319 | 1.00 | 57.01 | C |
| ATOM | 813 | C | PRO | A | 116 | 15.554 | 31.979 | 45.151 | 1.00 | 56.69 | C |
| ATOM | 814 | O | PRO | A | 116 | 14.864 | 31.676 | 46.103 | 1.00 | 57.03 | O |
| ATOM | 815 | CE | PRO | A | 116 | 17.672 | 30.701 | 45.378 | 1.00 | 57.15 | C |
| ATOM | 816 | CG | PRO | A | 116 | 18.474 | 30.658 | 46.662 | 1.00 | 57.53 | C |
| ATOM | 817 | CD | PRO | A | 116 | 18.045 | 31.763 | 47.522 | 1.00 | 57.03 | C |
| ATOM | 818 | N | ARG | A | 117 | 15.073 | 32.212 | 43.945 | 1.00 | 56.65 | N |
| ATOM | 819 | CA | ARG | A | 117 | 13.663 | 32.087 | 43.656 | 1.00 | 56.39 | C |
| ATOM | 820 | C | ARG | A | 117 | 13.335 | 30.639 | 43.332 | 1.00 | 56.16 | C |
| ATOM | 821 | O | ARG | A | 117 | 12.160 | 30.272 | 43.279 | 1.00 | 56.65 | O |
| ATOM | 822 | CE | ARG | A | 117 | 13.280 | 32.971 | 42.508 | 1.00 | 56.56 | C |
| ATOM | 823 | N | SER | A | 118 | 14.350 | 29.810 | 43.110 | 1.00 | 55.25 | N |
| ATOM | 824 | CA | SER | A | 118 | 14.083 | 28.393 | 42.878 | 1.00 | 55.12 | C |
| ATOM | 825 | C | SER | A | 118 | 14.924 | 27.511 | 43.809 | 1.00 | 54.45 | C |
| ATOM | 826 | O | SER | A | 118 | 16.022 | 27.895 | 44.174 | 1.00 | 54.64 | O |
| ATOM | 827 | CB | SER | A | 118 | 14.322 | 28.029 | 41.415 | 1.00 | 54.89 | C |
| ATOM | 828 | OG | SER | A | 118 | 15.672 | 28.196 | 41.087 | 1.00 | 55.13 | O |
| ATOM | 829 | N | ASN | A | 119 | 14.381 | 26.362 | 44.211 | 1.00 | 53.66 | N |
| ATOM | 830 | CA | ASN | A | 119 | 15.089 | 25.412 | 45.060 | 1.00 | 53.43 | C |
| ATOM | 831 | C | ASN | A | 119 | 15.307 | 24.118 | 44.326 | 1.00 | 51.73 | C |
| ATOM | 832 | O | ASN | A | 119 | 14.472 | 23.705 | 43.552 | 1.00 | 51.23 | O |
| ATOM | 833 | CE | ASN | A | 119 | 14.277 | 25.063 | 46.311 | 1.00 | 54.32 | C |
| ATOM | 834 | CG | ASN | A | 119 | 13.711 | 26.272 | 46.994 | 1.00 | 57.18 | C |
| ATOM | 835 | OD1 | ASN | A | 119 | 14.448 | 27.099 | 47.563 | 1.00 | 60.84 | O |
| ATOM | 836 | ND2 | ASN | A | 119 | 12.384 | 26.384 | 46.964 | 1.00 | 61.01 | N |
| ATOM | 837 | N | ARG | A | 120 | 16.418 | 23.470 | 44.621 | 1.00 | 50.77 | N |
| ATOM | 838 | CA | ARG | A | 120 | 16.772 | 22.182 | 44.049 | 1.00 | 49.89 | C |
| ATOM | 839 | C | ARG | A | 120 | 16.388 | 21.062 | 44.999 | 1.00 | 49.87 | C |
| ATOM | 840 | O | ARG | A | 120 | 16.620 | 21.150 | 46.206 | 1.00 | 50.40 | O |
| ATOM | 841 | CB | ARG | A | 120 | 18.283 | 22.133 | 43.843 | 1.00 | 49.75 | C |
| ATOM | 842 | CG | ARG | A | 120 | 18.799 | 20.901 | 43.144 | 1.00 | 47.86 | C |
| ATOM | 843 | CD | ARG | A | 120 | 20.318 | 20.812 | 43.074 | 1.00 | 45.29 | C |
| ATOM | 844 | NE | ARG | A | 120 | 20.972 | 21.240 | 44.301 | 1.00 | 43.79 | N |
| ATOM | 845 | CZ | ARG | A | 120 | 21.316 | 20.432 | 45.314 | 1.00 | 43.05 | C |
| ATOM | 846 | NH1 | ARG | A | 120 | 21.053 | 19.126 | 45.277 | 1.00 | 40.07 | N |
| ATOM | 847 | NH2 | ARG | A | 120 | 21.921 | 20.942 | 46.379 | 1.00 | 41.03 | N |
| ATOM | 848 | N | GLU | A | 121 | 15.801 | 20.010 | 44.451 | 1.00 | 49.51 | N |

TABLE 3-continued

Coordinates for structures 1 to 4

| ATOM | 849 | CA | GLU | A | 121 | 15.435 | 18.830 | 45.206 | 1.00 | 48.90 | C |
| ATOM | 850 | C | GLU | A | 121 | 15.905 | 17.609 | 44.411 | 1.00 | 47.95 | C |
| ATOM | 851 | O | GLU | A | 121 | 15.793 | 17.564 | 43.192 | 1.00 | 48.02 | O |
| ATOM | 852 | CE | GLU | A | 121 | 13.922 | 18.782 | 45.461 | 1.00 | 49.38 | C |
| ATOM | 853 | CG | GLU | A | 121 | 13.444 | 17.500 | 46.141 | 1.00 | 51.77 | C |
| ATOM | 854 | CD | GLU | A | 121 | 12.185 | 17.695 | 46.961 | 1.00 | 54.65 | C |
| ATOM | 855 | OE1 | GLU | A | 121 | 12.312 | 18.258 | 48.073 | 1.00 | 58.68 | O |
| ATOM | 856 | OE2 | GLU | A | 121 | 11.087 | 17.284 | 46.512 | 1.00 | 55.59 | O |
| ATOM | 857 | N | GLU | A | 122 | 16.455 | 16.622 | 45.104 | 1.00 | 47.05 | N |
| ATOM | 858 | CA | GLU | A | 122 | 16.938 | 15.423 | 44.463 | 1.00 | 46.05 | C |
| ATOM | 859 | C | GLU | A | 122 | 15.848 | 14.400 | 44.594 | 1.00 | 45.48 | C |
| ATOM | 860 | O | GLU | A | 122 | 15.313 | 14.220 | 45.666 | 1.00 | 45.63 | O |
| ATOM | 861 | CE | GLU | A | 122 | 18.200 | 14.940 | 45.158 | 1.00 | 45.67 | C |
| ATOM | 862 | CG | GLU | A | 122 | 19.346 | 15.921 | 45.063 | 1.00 | 44.97 | C |
| ATOM | 863 | CD | GLU | A | 122 | 19.789 | 16.154 | 43.623 | 1.00 | 45.49 | C |
| ATOM | 864 | OE1 | GLU | A | 122 | 19.985 | 15.144 | 42.902 | 1.00 | 44.79 | O |
| ATOM | 865 | OE2 | GLU | A | 122 | 19.925 | 17.337 | 43.207 | 1.00 | 42.47 | O |
| ATOM | 866 | N | MET | A | 123 | 15.481 | 13.751 | 43.503 | 1.00 | 44.95 | N |
| ATOM | 867 | CA | MET | A | 123 | 14.462 | 12.731 | 43.589 | 1.00 | 44.35 | C |
| ATOM | 868 | C | MET | A | 123 | 14.657 | 11.712 | 42.503 | 1.00 | 43.59 | C |
| ATOM | 869 | O | MET | A | 123 | 15.495 | 11.891 | 41.613 | 1.00 | 43.44 | O |
| ATOM | 870 | CB | MET | A | 123 | 13.078 | 13.358 | 43.490 | 1.00 | 44.59 | C |
| ATOM | 871 | CG | MET | A | 123 | 12.831 | 14.092 | 42.205 | 1.00 | 45.95 | C |
| ATOM | 872 | SD | MET | A | 123 | 11.244 | 14.946 | 42.206 | 1.00 | 47.99 | S |
| ATOM | 873 | CE | MET | A | 123 | 11.648 | 16.411 | 43.089 | 1.00 | 47.81 | C |
| ATOM | 874 | N | LYS | A | 124 | 13.880 | 10.638 | 42.603 | 1.00 | 42.37 | N |
| ATOM | 875 | CA | LYS | A | 124 | 13.869 | 9.575 | 41.623 | 1.00 | 41.47 | C |
| ATOM | 876 | C | LYS | A | 124 | 12.958 | 10.026 | 40.469 | 1.00 | 40.66 | C |
| ATOM | 877 | O | LYS | A | 124 | 12.066 | 10.862 | 40.654 | 1.00 | 39.80 | O |
| ATOM | 878 | CB | LYS | A | 124 | 13.354 | 8.267 | 42.250 | 1.00 | 41.45 | C |
| ATOM | 879 | CG | LYS | A | 124 | 14.160 | 7.756 | 43.470 | 1.00 | 41.70 | C |
| ATOM | 880 | CD | LYS | A | 124 | 15.574 | 7.301 | 43.076 | 1.00 | 42.20 | C |
| ATOM | 881 | CE | LYS | A | 124 | 16.451 | 6.989 | 44.273 | 1.00 | 41.37 | C |
| ATOM | 882 | NZ | LYS | A | 124 | 17.894 | 7.201 | 43.966 | 1.00 | 41.63 | N |
| ATOM | 883 | N | PHE | A | 125 | 13.178 | 9.460 | 39.284 | 1.00 | 39.69 | N |
| ATOM | 884 | CA | PHE | A | 125 | 12.463 | 9.889 | 38.101 | 1.00 | 38.95 | C |
| ATOM | 885 | C | PHE | A | 125 | 10.981 | 9.729 | 38.257 | 1.00 | 38.85 | C |
| ATOM | 886 | O | PHE | A | 125 | 10.217 | 10.613 | 37.890 | 1.00 | 37.81 | O |
| ATOM | 887 | CB | PHE | A | 125 | 12.942 | 9.154 | 36.862 | 1.00 | 38.45 | C |
| ATOM | 888 | CG | PHE | A | 125 | 12.618 | 9.871 | 35.610 | 1.00 | 39.49 | C |
| ATOM | 889 | CD1 | PHE | A | 125 | 13.471 | 10.840 | 35.118 | 1.00 | 40.78 | C |
| ATOM | 890 | CD2 | PHE | A | 125 | 11.428 | 9.655 | 34.967 | 1.00 | 40.81 | C |
| ATOM | 891 | CE1 | PHE | A | 125 | 13.181 | 11.530 | 33.992 | 1.00 | 40.48 | C |
| ATOM | 892 | CE2 | PHE | A | 125 | 11.123 | 10.353 | 33.825 | 1.00 | 41.39 | C |
| ATOM | 893 | CZ | PHE | A | 125 | 12.008 | 11.300 | 33.335 | 1.00 | 41.11 | C |
| ATOM | 894 | N | HIS | A | 126 | 10.575 | 8.602 | 38.835 | 1.00 | 39.49 | N |
| ATOM | 895 | CA | HIS | A | 126 | 9.161 | 8.342 | 39.044 | 1.00 | 39.91 | C |
| ATOM | 896 | C | HIS | A | 126 | 8.599 | 9.408 | 39.976 | 1.00 | 39.98 | C |
| ATOM | 897 | O | HIS | A | 126 | 7.455 | 9.821 | 39.830 | 1.00 | 39.26 | O |
| ATOM | 898 | CB | HIS | A | 126 | 8.906 | 6.899 | 39.552 | 1.00 | 40.45 | C |
| ATOM | 899 | CG | HIS | A | 126 | 9.034 | 6.727 | 41.033 | 1.00 | 41.06 | C |
| ATOM | 900 | ND1 | HIS | A | 126 | 7.987 | 6.950 | 41.899 | 1.00 | 40.98 | N |
| ATOM | 901 | CD2 | HIS | A | 126 | 10.092 | 6.367 | 41.801 | 1.00 | 41.92 | C |
| ATOM | 902 | CE1 | HIS | A | 126 | 8.403 | 6.759 | 43.140 | 1.00 | 43.22 | C |
| ATOM | 903 | ND2 | HIS | A | 126 | 9.676 | 6.405 | 43.108 | 1.00 | 42.45 | N |
| ATOM | 904 | N | GLU | A | 127 | 9.428 | 9.898 | 40.890 | 1.00 | 40.59 | N |
| ATOM | 905 | CA | GLU | A | 127 | 8.975 | 10.919 | 41.824 | 1.00 | 41.56 | C |
| ATOM | 906 | C | GLU | A | 127 | 8.749 | 12.213 | 41.062 | 1.00 | 41.66 | C |
| ATOM | 907 | O | GLU | A | 127 | 7.774 | 12.941 | 41.294 | 1.00 | 41.64 | O |
| ATOM | 908 | CB | GLU | A | 127 | 9.968 | 11.102 | 42.972 | 1.00 | 41.64 | C |
| ATOM | 909 | CG | GLU | A | 127 | 10.149 | 9.839 | 43.811 | 1.00 | 43.10 | C |
| ATOM | 910 | CD | GLU | A | 127 | 11.116 | 10.017 | 44.958 | 1.00 | 44.79 | C |
| ATOM | 911 | OE1 | GLU | A | 127 | 12.326 | 10.217 | 44.712 | 1.00 | 43.71 | O |
| ATOM | 912 | OE2 | GLU | A | 127 | 10.649 | 9.938 | 46.122 | 1.00 | 49.43 | O |
| ATOM | 913 | N | PHE | A | 128 | 9.636 | 12.491 | 40.124 | 1.00 | 41.96 | N |
| ATOM | 914 | CA | PHE | A | 128 | 9.504 | 13.705 | 39.337 | 1.00 | 41.99 | C |
| ATOM | 915 | C | PHE | A | 128 | 8.213 | 13.612 | 38.538 | 1.00 | 42.56 | C |
| ATOM | 916 | O | PHE | A | 128 | 7.400 | 14.537 | 38.507 | 1.00 | 41.93 | O |
| ATOM | 917 | CB | PHE | A | 128 | 10.708 | 13.864 | 38.416 | 1.00 | 41.57 | |
| ATOM | 918 | CG | PHE | A | 128 | 10.470 | 14.795 | 37.244 | 1.00 | 41.38 | C |
| ATOM | 919 | CD1 | PHE | A | 128 | 10.199 | 16.136 | 37.449 | 1.00 | 39.65 | C |
| ATOM | 920 | CD2 | PHE | A | 128 | 10.537 | 14.330 | 35.950 | 1.00 | 39.22 | C |
| ATOM | 921 | CE1 | PHE | A | 128 | 9.980 | 16.975 | 36.399 | 1.00 | 40.36 | C |
| ATOM | 922 | CE2 | PHE | A | 128 | 10.329 | 15.191 | 34.888 | 1.00 | 41.57 | C |
| ATOM | 923 | CZ | PHE | A | 128 | 10.044 | 16.510 | 35.112 | 1.00 | 40.14 | C |
| ATOM | 924 | N | VAL | A | 129 | 7.999 | 12.463 | 37.921 | 1.00 | 43.85 | N |
| ATOM | 925 | CA | VAL | A | 129 | 6.813 | 12.288 | 37.095 | 1.00 | 44.87 | C |

TABLE 3-continued

Coordinates for structures 1 to 4

| ATOM | 926 | C | VAL | A | 129 | 5.536 | 12.443 | 37.932 | 1.00 | 46.07 | C |
|------|-----|------|-----|---|-----|-------|--------|--------|------|-------|---|
| ATOM | 927 | O | VAL | A | 129 | 4.574 | 13.093 | 37.505 | 1.00 | 45.32 | O |
| ATOM | 928 | CB | VAL | A | 129 | 6.798 | 10.920 | 36.425 | 1.00 | 44.99 | C |
| ATOM | 929 | CG1 | VAL | A | 129 | 5.496 | 10.725 | 35.631 | 1.00 | 44.81 | C |
| ATOM | 930 | CG2 | VAL | A | 129 | 8.030 | 10.718 | 35.550 | 1.00 | 43.96 | C |
| ATOM | 931 | N | GLU | A | 130 | 5.553 | 11.854 | 39.128 | 1.00 | 47.64 | N |
| ATOM | 932 | CA | GLU | A | 130 | 4.415 | 11.932 | 40.037 | 1.00 | 49.12 | C |
| ATOM | 933 | C | GLU | A | 130 | 4.136 | 13.390 | 40.384 | 1.00 | 49.48 | C |
| ATOM | 934 | O | GLU | A | 130 | 3.003 | 13.846 | 40.250 | 1.00 | 48.66 | O |
| ATOM | 935 | CB | GLU | A | 130 | 4.654 | 11.079 | 41.296 | 1.00 | 49.63 | C |
| ATOM | 936 | CG | GLU | A | 130 | 4.534 | 9.576 | 41.062 | 1.00 | 50.81 | C |
| ATOM | 937 | CD | GLU | A | 130 | 5.257 | 8.747 | 42.117 | 1.00 | 53.77 | C |
| ATOM | 938 | OE1 | GLU | A | 130 | 5.566 | 9.295 | 43.204 | 1.00 | 55.27 | O |
| ATOM | 939 | OE2 | GLU | A | 130 | 5.518 | 7.543 | 41.856 | 1.00 | 54.73 | O |
| ATOM | 940 | N | LYS | A | 131 | 5.170 | 14.121 | 40.798 | 1.00 | 50.56 | N |
| ATOM | 941 | CA | LYS | A | 131 | 5.010 | 15.547 | 41.082 | 1.00 | 51.84 | C |
| ATOM | 942 | C | LYS | A | 131 | 4.385 | 16.276 | 39.886 | 1.00 | 52.55 | C |
| ATOM | 943 | O | LYS | A | 131 | 3.482 | 17.070 | 40.061 | 1.00 | 52.15 | O |
| ATOM | 944 | CE | LYS | A | 131 | 6.340 | 16.209 | 41.438 | 1.00 | 52.23 | C |
| ATOM | 945 | CG | LYS | A | 131 | 6.554 | 16.568 | 42.907 | 1.00 | 53.75 | C |
| ATOM | 946 | CD | LYS | A | 131 | 7.249 | 17.944 | 43.054 | 1.00 | 56.27 | C |
| ATOM | 947 | CE | LYS | A | 131 | 7.879 | 18.168 | 44.448 | 1.00 | 58.66 | C |
| ATOM | 948 | NZ | LYS | A | 131 | 8.247 | 19.628 | 44.725 | 1.00 | 59.31 | N |
| ATOM | 949 | N | LEU | A | 132 | 4.845 | 16.014 | 38.667 | 1.00 | 53.84 | N |
| ATOM | 950 | CA | LEU | A | 132 | 4.247 | 16.691 | 37.513 | 1.00 | 55.23 | C |
| ATOM | 951 | C | LEU | A | 132 | 2.762 | 16.408 | 37.407 | 1.00 | 55.96 | C |
| ATOM | 952 | O | LEU | A | 132 | 1.973 | 17.292 | 37.063 | 1.00 | 55.69 | O |
| ATOM | 953 | CB | LEU | A | 132 | 4.906 | 16.278 | 36.206 | 1.00 | 55.45 | C |
| ATOM | 954 | CG | LEU | A | 132 | 6.301 | 16.811 | 35.966 | 1.00 | 56.60 | C |
| ATOM | 955 | CD1 | LEU | A | 132 | 6.785 | 16.291 | 34.646 | 1.00 | 57.60 | C |
| ATOM | 956 | CD2 | LEU | A | 132 | 6.303 | 18.327 | 35.966 | 1.00 | 57.89 | C |
| ATOM | 957 | N | GLN | A | 133 | 2.397 | 15.157 | 37.669 | 1.00 | 57.19 | N |
| ATOM | 958 | CA | GLN | A | 133 | 0.998 | 14.739 | 37.663 | 1.00 | 58.15 | C |
| ATOM | 959 | C | GLN | A | 133 | 0.172 | 15.450 | 38.751 | 1.00 | 58.99 | C |
| ATOM | 960 | O | GLN | A | 133 | 0.915 | 15.950 | 38.470 | 1.00 | 58.73 | O |
| ATOM | 961 | CB | GLN | A | 133 | 0.897 | 13.230 | 37.824 | 1.00 | 58.03 | C |
| ATOM | 962 | N | ASP | A | 134 | 0.678 | 15.510 | 39.981 | 1.00 | 60.11 | N |
| ATOM | 963 | CA | ASP | A | 134 | 0.081 | 16.145 | 41.063 | 1.00 | 61.49 | C |
| ATOM | 964 | C | ASP | A | 134 | 0.362 | 17.629 | 40.783 | 1.00 | 61.55 | C |
| ATOM | 965 | O | ASP | A | 134 | 1.427 | 18.149 | 41.104 | 1.00 | 61.55 | O |
| ATOM | 966 | CE | ASP | A | 134 | 0.621 | 15.985 | 42.417 | 1.00 | 61.99 | C |
| ATOM | 967 | CG | ASP | A | 134 | 0.253 | 16.454 | 43.587 | 1.00 | 64.74 | C |
| ATOM | 968 | OD1 | ASP | A | 134 | 1.310 | 17.082 | 43.346 | 1.00 | 67.52 | O |
| ATOM | 969 | OD2 | ASP | A | 134 | 0.022 | 16.237 | 44.791 | 1.00 | 69.05 | O |
| ATOM | 970 | N | ILE | A | 135 | 0.594 | 18.312 | 40.179 | 1.00 | 61.80 | N |
| ATOM | 971 | CA | ILE | A | 135 | 0.402 | 19.706 | 39.860 | 1.00 | 62.08 | C |
| ATOM | 972 | C | ILE | A | 135 | 0.700 | 19.856 | 38.823 | 1.00 | 62.29 | C |
| ATOM | 973 | O | ILE | A | 135 | 1.639 | 20.620 | 39.013 | 1.00 | 61.91 | O |
| ATOM | 974 | CB | ILE | A | 135 | 1.711 | 20.301 | 39.366 | 1.00 | 62.21 | C |
| ATOM | 975 | CG1 | ILE | A | 135 | 2.705 | 20.391 | 40.528 | 1.00 | 62.47 | C |
| ATOM | 976 | CG2 | ILE | A | 135 | 1.478 | 21.670 | 38.783 | 1.00 | 62.19 | C |
| ATOM | 977 | CD1 | ILE | A | 135 | 4.157 | 20.437 | 40.100 | 1.00 | 62.96 | C |
| ATOM | 978 | N | GLN | A | 136 | 0.593 | 19.112 | 37.733 | 1.00 | 62.99 | N |
| ATOM | 979 | CA | GLN | A | 136 | 1.585 | 19.184 | 36.674 | 1.00 | 63.71 | C |
| ATOM | 980 | C | GLN | A | 136 | 2.977 | 18.992 | 37.259 | 1.00 | 64.44 | C |
| ATOM | 981 | O | GLN | A | 136 | 3.844 | 19.856 | 37.123 | 1.00 | 64.73 | O |
| ATOM | 982 | CB | GLN | A | 136 | 1.305 | 18.136 | 35.619 | 1.00 | 63.77 | C |
| ATOM | 983 | N | GLN | A | 137 | 3.170 | 17.871 | 37.948 | 1.00 | 65.12 | N |
| ATOM | 984 | CA | GLN | A | 137 | 4.472 | 17.509 | 38.497 | 1.00 | 65.60 | C |
| ATOM | 985 | C | GLN | A | 137 | 4.989 | 18.540 | 39.477 | 1.00 | 65.70 | C |
| ATOM | 986 | O | GLN | A | 137 | 6.175 | 18.871 | 39.447 | 1.00 | 66.17 | O |
| ATOM | 987 | CB | GLN | A | 137 | 4.421 | 16.117 | 39.161 | 1.00 | 65.72 | C |
| ATOM | 988 | N | ARG | A | 138 | 4.115 | 19.056 | 40.336 | 1.00 | 65.61 | N |
| ATOM | 989 | CA | ARG | A | 138 | 4.549 | 20.011 | 41.358 | 1.00 | 65.53 | C |
| ATOM | 990 | C | ARG | A | 138 | 4.578 | 21.441 | 40.823 | 1.00 | 64.96 | C |
| ATOM | 991 | O | ARG | A | 138 | 4.748 | 22.392 | 41.589 | 1.00 | 64.93 | O |
| ATOM | 992 | CB | ARG | A | 138 | 3.670 | 19.912 | 42.613 | 1.00 | 65.65 | C |
| ATOM | 993 | CG | ARG | A | 138 | 2.375 | 20.712 | 42.588 | 1.00 | 67.10 | C |
| ATOM | 994 | CD | ARG | A | 138 | 1.482 | 20.352 | 43.745 | 1.00 | 68.96 | C |
| ATOM | 995 | NE | ARG | A | 138 | 0.372 | 21.270 | 43.957 | 1.00 | 69.79 | N |
| ATOM | 996 | CZ | ARG | A | 138 | 0.905 | 20.919 | 43.880 | 1.00 | 71.69 | C |
| ATOM | 997 | NH1 | ARG | A | 138 | 1.238 | 19.674 | 43.569 | 1.00 | 72.88 | N |
| ATOM | 998 | NH2 | ARG | A | 138 | 1.862 | 21.811 | 44.106 | 1.00 | 72.52 | N |
| ATOM | 999 | N | GLY | A | 139 | 4.426 | 21.593 | 39.508 | 1.00 | 64.31 | N |
| ATOM | 1000 | CA | GLY | A | 139 | 4.370 | 22.912 | 38.897 | 1.00 | 63.53 | C |
| ATOM | 1001 | C | GLY | A | 139 | 3.401 | 23.874 | 39.578 | 1.00 | 62.69 | C |
| ATOM | 1002 | O | GLY | A | 139 | 3.631 | 25.080 | 39.570 | 1.00 | 62.92 | O |

TABLE 3-continued

| | | | | | | | | | | |
|---|---|---|---|---|---|---|---|---|---|---|
| | Coordinates for structures 1 to 4 |
| ATOM | 1003 | N | GLY | A | 140 | 2.312 | 23.357 | 40.148 | 1.00 | 61.58 | N |
| ATOM | 1004 | CA | GLY | A | 140 | 1.345 | 24.183 | 40.861 | 1.00 | 60.52 | C |
| ATOM | 1005 | C | GLY | A | 140 | 0.539 | 25.103 | 39.958 | 1.00 | 59.56 | C |
| ATOM | 1006 | O | GLY | A | 140 | 0.449 | 24.867 | 38.748 | 1.00 | 59.45 | O |
| ATOM | 1007 | N | GLU | A | 141 | 0.041 | 26.159 | 40.530 | 1.00 | 58.05 | N |
| ATOM | 1008 | CA | GLU | A | 141 | 0.859 | 27.090 | 39.748 | 1.00 | 56.92 | C |
| ATOM | 1009 | C | GLU | A | 141 | 2.366 | 26.751 | 39.832 | 1.00 | 54.97 | C |
| ATOM | 1010 | O | GLU | A | 141 | 3.189 | 27.326 | 39.113 | 1.00 | 54.51 | O |
| ATOM | 1011 | CB | GLU | A | 141 | 0.602 | 28.547 | 40.177 | 1.00 | 57.45 | C |
| ATOM | 1012 | CG | GLU | A | 141 | 0.707 | 29.171 | 39.680 | 1.00 | 59.67 | C |
| ATOM | 1013 | CD | GLU | A | 141 | 0.851 | 29.193 | 38.154 | 1.00 | 63.48 | C |
| ATOM | 1014 | OE1 | GLU | A | 141 | 0.179 | 29.107 | 37.436 | 1.00 | 65.30 | O |
| ATOM | 1015 | OE2 | GLU | A | 141 | 2.007 | 29.298 | 37.664 | 1.00 | 66.13 | O |
| ATOM | 1016 | N | GLU | A | 142 | 2.720 | 25.814 | 40.708 | 1.00 | 52.62 | N |
| ATOM | 1017 | CA | GLU | A | 142 | 4.106 | 25.398 | 40.862 | 1.00 | 50.91 | C |
| ATOM | 1018 | C | GLU | A | 142 | 4.679 | 24.958 | 39.516 | 1.00 | 48.93 | C |
| ATOM | 1019 | O | GLU | A | 142 | 3.960 | 24.477 | 38.641 | 1.00 | 48.64 | O |
| ATOM | 1020 | CB | GLU | A | 142 | 4.225 | 24.263 | 41.886 | 1.00 | 51.00 | C |
| ATOM | 1021 | CG | GLU | A | 142 | 5.656 | 24.005 | 42.352 | 1.00 | 51.76 | C |
| ATOM | 1022 | CD | GLU | A | 142 | 5.814 | 22.811 | 43.282 | 1.00 | 52.64 | C |
| ATOM | 1023 | OE1 | GLU | A | 142 | 4.871 | 22.009 | 43.447 | 1.00 | 55.52 | O |
| ATOM | 1024 | OE2 | GLU | A | 142 | 6.911 | 22.667 | 43.855 | 1.00 | 53.97 | O |
| ATOM | 1025 | N | ARG | A | 143 | 5.979 | 25.139 | 39.356 | 1.00 | 46.58 | N |
| ATOM | 1026 | CA | ARG | A | 143 | 6.652 | 24.751 | 38.133 | 1.00 | 45.12 | C |
| ATOM | 1027 | C | ARG | A | 143 | 7.900 | 23.960 | 38.425 | 1.00 | 43.39 | C |
| ATOM | 1028 | O | ARG | A | 143 | 8.616 | 24.242 | 39.387 | 1.00 | 43.58 | O |
| ATOM | 1029 | CB | ARG | A | 143 | 7.069 | 25.983 | 37.360 | 1.00 | 45.52 | C |
| ATOM | 1030 | CG | ARG | A | 143 | 5.943 | 26.747 | 36.729 | 1.00 | 45.38 | C |
| ATOM | 1031 | CD | ARG | A | 143 | 6.488 | 27.899 | 35.969 | 1.00 | 46.06 | C |
| ATOM | 1032 | NE | ARG | A | 143 | 5.473 | 28.649 | 35.252 | 1.00 | 45.33 | N |
| ATOM | 1033 | CZ | ARG | A | 143 | 5.194 | 28.491 | 33.984 | 1.00 | 42.93 | C |
| ATOM | 1034 | NH1 | ARG | A | 143 | 5.836 | 27.573 | 33.253 | 1.00 | 41.86 | N |
| ATOM | 1035 | NH2 | ARG | A | 143 | 4.257 | 29.252 | 33.452 | 1.00 | 43.53 | N |
| ATOM | 1036 | N | LEU | A | 144 | 8.182 | 22.991 | 37.578 | 1.00 | 41.08 | N |
| ATOM | 1037 | CA | LEU | A | 144 | 9.337 | 22.163 | 37.784 | 1.00 | 39.63 | C |
| ATOM | 1038 | C | LEU | A | 144 | 10.213 | 22.166 | 36.568 | 1.00 | 37.88 | C |
| ATOM | 1039 | O | LEU | A | 144 | 9.734 | 22.249 | 35.444 | 1.00 | 36.26 | O |
| ATOM | 1040 | CB | LEU | A | 144 | 8.889 | 20.727 | 38.018 | 1.00 | 40.26 | C |
| ATOM | 1041 | CG | LEU | A | 144 | 7.974 | 20.529 | 39.223 | 1.00 | 41.73 | C |
| ATOM | 1042 | CD1 | LEU | A | 144 | 7.639 | 19.036 | 39.392 | 1.00 | 42.57 | C |
| ATOM | 1043 | CD2 | LEU | A | 144 | 8.585 | 21.102 | 40.503 | 1.00 | 41.42 | C |
| ATOM | 1044 | N | TYR | A | 145 | 11.507 | 22.033 | 36.800 | 1.00 | 36.36 | N |
| ATOM | 1045 | CA | TYR | A | 145 | 12.434 | 21.892 | 35.703 | 1.00 | 35.24 | C |
| ATOM | 1046 | C | TYR | A | 145 | 13.485 | 20.862 | 36.107 | 1.00 | 34.89 | C |
| ATOM | 1047 | O | TYR | A | 145 | 14.264 | 21.098 | 37.013 | 1.00 | 33.74 | O |
| ATOM | 1048 | CB | TYR | A | 145 | 13.071 | 23.243 | 35.352 | 1.00 | 35.01 | C |
| ATOM | 1049 | CG | TYR | A | 145 | 13.524 | 23.408 | 33.901 | 1.00 | 32.68 | C |
| ATOM | 1050 | CD1 | TYR | A | 145 | 13.817 | 22.324 | 33.099 | 1.00 | 30.20 | C |
| ATOM | 1051 | CD2 | TYR | A | 145 | 13.689 | 24.666 | 33.355 | 1.00 | 31.53 | C |
| ATOM | 1052 | CE1 | TYR | A | 145 | 14.237 | 22.493 | 31.762 | 1.00 | 29.87 | C |
| ATOM | 1053 | CE2 | TYR | A | 145 | 14.110 | 24.852 | 32.031 | 1.00 | 29.82 | C |
| ATOM | 1054 | CZ | TYR | A | 145 | 14.373 | 23.765 | 31.228 | 1.00 | 30.06 | C |
| ATOM | 1055 | OH | TYR | A | 145 | 14.789 | 23.953 | 29.897 | 1.00 | 28.17 | O |
| ATOM | 1056 | N | LEU | A | 146 | 13.479 | 19.708 | 35.446 | 1.00 | 34.87 | N |
| ATOM | 1057 | CA | LEU | A | 146 | 14.511 | 18.703 | 35.690 | 1.00 | 35.40 | C |
| ATOM | 1058 | C | LEU | A | 146 | 15.753 | 18.977 | 34.864 | 1.00 | 35.24 | C |
| ATOM | 1059 | O | LEU | A | 146 | 15.665 | 19.211 | 33.653 | 1.00 | 34.63 | O |
| ATOM | 1060 | GB | LEU | A | 146 | 14.008 | 17.312 | 35.358 | 1.00 | 35.79 | C |
| ATOM | 1061 | CG | LEU | A | 146 | 14.998 | 16.157 | 35.614 | 1.00 | 37.21 | C |
| ATOM | 1062 | CE1 | LEU | A | 146 | 14.221 | 14.918 | 35.969 | 1.00 | 36.28 | C |
| ATOM | 1063 | CD2 | LEU | A | 146 | 15.907 | 15.872 | 34.399 | 1.00 | 38.78 | C |
| ATOM | 1064 | N | GLN | A | 147 | 16.907 | 18.883 | 35.515 | 1.00 | 34.82 | N |
| ATOM | 1065 | CA | GLN | A | 147 | 18.179 | 19.206 | 34.884 | 1.00 | 35.00 | C |
| ATOM | 1066 | C | GLN | A | 147 | 19.222 | 18.341 | 35.525 | 1.00 | 34.90 | C |
| ATOM | 1067 | O | GLN | A | 147 | 19.626 | 18.568 | 36.664 | 1.00 | 35.65 | O |
| ATOM | 1068 | CB | GLN | A | 147 | 18.526 | 20.679 | 35.078 | 1.00 | 35.09 | C |
| ATOM | 1069 | CG | GLN | A | 147 | 17.392 | 21.636 | 34.720 | 1.00 | 35.83 | C |
| ATOM | 1070 | CD | GLN | A | 147 | 17.848 | 23.085 | 34.706 | 1.00 | 36.90 | C |
| ATOM | 1071 | OE1 | GLN | A | 147 | 17.091 | 23.961 | 34.302 | 1.00 | 39.61 | O |
| ATOM | 1072 | NE2 | GLN | A | 147 | 19.088 | 23.336 | 35.126 | 1.00 | 35.05 | N |
| ATOM | 1073 | N | GLN | A | 148 | 19.673 | 17.358 | 34.773 | 1.00 | 35.00 | N |
| ATOM | 1074 | CA | GLN | A | 148 | 20.492 | 16.300 | 35.294 | 1.00 | 34.89 | C |
| ATOM | 1075 | C | GLN | A | 148 | 21.376 | 15.709 | 34.255 | 1.00 | 35.35 | C |
| ATOM | 1076 | O | GLN | A | 148 | 20.941 | 15.318 | 33.181 | 1.00 | 35.25 | O |
| ATOM | 1077 | CB | GLN | A | 148 | 19.580 | 15.186 | 35.791 | 1.00 | 35.27 | C |
| ATOM | 1078 | CG | GLN | A | 148 | 20.335 | 13.914 | 36.269 | 1.00 | 35.11 | C |
| ATOM | 1079 | CD | GLN | A | 148 | 21.317 | 14.230 | 37.389 | 1.00 | 34.12 | C |

TABLE 3-continued

| | | | | | Coordinates for structures 1 to 4 | | | | | |
|---|---|---|---|---|---|---|---|---|---|---|
| ATOM | 1080 | OE1 | GLN | A | 148 | 20.998 | 15.033 | 38.277 | 1.00 | 33.18 | O |
| ATOM | 1081 | NE2 | GLN | A | 148 | 22.521 | 13.652 | 37.324 | 1.00 | 30.47 | N |
| ATOM | 1082 | N | THR | A | 149 | 22.631 | 15.641 | 34.600 | 1.00 | 36.56 | N |
| ATOM | 1083 | CA | THR | A | 149 | 23.648 | 15.088 | 33.754 | 1.00 | 38.26 | C |
| ATOM | 1084 | C | THR | A | 149 | 23.394 | 13.609 | 33.615 | 1.00 | 38.31 | C |
| ATOM | 1085 | O | THR | A | 149 | 23.068 | 12.956 | 34.597 | 1.00 | 38.70 | O |
| ATOM | 1086 | CE | THR | A | 149 | 24.992 | 15.362 | 34.463 | 1.00 | 38.76 | C |
| ATOM | 1087 | OG1 | THR | A | 149 | 25.290 | 16.747 | 34.277 | 1.00 | 41.68 | O |
| ATOM | 1088 | CG2 | THR | A | 149 | 26.139 | 14.710 | 33.797 | 1.00 | 40.77 | C |
| ATOM | 1089 | N | LEU | A | 150 | 23.516 | 13.087 | 32.399 | 1.00 | 38.77 | N |
| ATOM | 1090 | CA | LEU | A | 150 | 23.373 | 11.664 | 32.149 | 1.00 | 39.27 | C |
| ATOM | 1091 | C | LEU | A | 150 | 24.604 | 10.898 | 32.679 | 1.00 | 39.85 | C |
| ATOM | 1092 | O | LEU | A | 150 | 25.733 | 11.207 | 32.321 | 1.00 | 39.99 | O |
| ATOM | 1093 | GB | LEU | A | 150 | 23.220 | 11.402 | 30.660 | 1.00 | 39.15 | C |
| ATOM | 1094 | CG | LEU | A | 150 | 21.943 | 11.860 | 29.962 | 1.00 | 40.72 | C |
| ATOM | 1095 | CD1 | LEU | A | 150 | 22.058 | 11.673 | 28.459 | 1.00 | 41.91 | C |
| ATOM | 1096 | CD2 | LEU | A | 150 | 20.764 | 11.106 | 30.458 | 1.00 | 41.30 | C |
| ATOM | 1097 | N | ASN | A | 151 | 24.392 | 9.898 | 33.526 | 1.00 | 40.26 | N |
| ATOM | 1098 | CA | ASN | A | 151 | 25.510 | 9.124 | 34.062 | 1.00 | 40.90 | C |
| ATOM | 1099 | C | ASN | A | 151 | 25.291 | 7.607 | 34.041 | 1.00 | 41.95 | C |
| ATOM | 1100 | O | ASN | A | 151 | 24.327 | 7.098 | 33.441 | 1.00 | 41.72 | O |
| ATOM | 1101 | CB | ASN | A | 151 | 25.778 | 9.575 | 35.489 | 1.00 | 40.77 | C |
| ATOM | 1102 | CG | ASN | A | 151 | 24.564 | 9.439 | 36.349 | 1.00 | 39.85 | C |
| ATOM | 1103 | OD1 | ASN | A | 151 | 24.002 | 8.340 | 36.483 | 1.00 | 37.92 | O |
| ATOM | 1104 | ND2 | ASN | A | 151 | 24.107 | 10.558 | 36.897 | 1.00 | 36.89 | N |
| ATOM | 1105 | N | ASP | A | 152 | 26.176 | 6.894 | 34.735 | 1.00 | 42.89 | N |
| ATOM | 1106 | CA | ASP | A | 152 | 26.175 | 5.431 | 34.756 | 1.00 | 43.75 | C |
| ATOM | 1107 | C | ASP | A | 152 | 24.950 | 4.768 | 35.272 | 1.00 | 43.37 | C |
| ATOM | 1108 | O | ASP | A | 152 | 24.787 | 3.581 | 35.052 | 1.00 | 43.66 | O |
| ATOM | 1109 | CB | ASP | A | 152 | 27.256 | 4.895 | 35.695 | 1.00 | 44.77 | C |
| ATOM | 1110 | CG | ASP | A | 152 | 28.539 | 5.555 | 35.500 | 1.00 | 48.22 | C |
| ATOM | 1111 | OD1 | ASP | A | 152 | 28.835 | 5.881 | 34.325 | 1.00 | 57.47 | O |
| ATOM | 1112 | OD2 | ASP | A | 152 | 29.291 | 5.826 | 36.437 | 1.00 | 51.28 | O |
| ATOM | 1113 | N | THR | A | 153 | 24.119 | 5.466 | 36.025 | 1.00 | 43.41 | N |
| ATOM | 1114 | CA | THR | A | 153 | 22.983 | 4.783 | 36.631 | 1.00 | 43.38 | C |
| ATOM | 1115 | C | THR | A | 153 | 21.820 | 4.605 | 35.676 | 1.00 | 42.99 | C |
| ATOM | 1116 | O | THR | A | 153 | 20.866 | 3.945 | 36.012 | 1.00 | 43.44 | O |
| ATOM | 1117 | GB | THR | A | 153 | 22.489 | 5.507 | 37.875 | 1.00 | 43.44 | C |
| ATOM | 1118 | OG1 | TUR | A | 153 | 21.749 | 6.678 | 37.499 | 1.00 | 46.09 | O |
| ATOM | 1119 | CG2 | THR | A | 153 | 23.651 | 6.008 | 38.725 | 1.00 | 42.99 | C |
| ATOM | 1120 | N | VAL | A | 154 | 21.874 | 5.185 | 34.491 | 1.00 | 42.88 | N |
| ATOM | 1121 | CA | VAL | A | 154 | 20.757 | 5.015 | 33.572 | 1.00 | 42.71 | C |
| ATOM | 1122 | C | VAL | A | 154 | 20.700 | 3.563 | 33.177 | 1.00 | 42.42 | C |
| ATOM | 1123 | O | VAL | A | 154 | 21.729 | 2.892 | 33.193 | 1.00 | 42.39 | O |
| ATOM | 1124 | CB | VAL | A | 154 | 20.889 | 5.875 | 32.300 | 1.00 | 42.67 | C |
| ATOM | 1125 | CG1 | VAL | A | 154 | 20.857 | 7.347 | 32.660 | 1.00 | 43.04 | C |
| ATOM | 1126 | CG2 | VAL | A | 154 | 22.159 | 5.516 | 31.538 | 1.00 | 42.56 | C |
| ATOM | 1127 | N | GLY | A | 155 | 19.502 | 3.097 | 32.814 | 1.00 | 42.11 | N |
| ATOM | 1128 | CA | GLY | A | 155 | 19.261 | 1.725 | 32.411 | 1.00 | 41.52 | C |
| ATOM | 1129 | C | GLY | A | 155 | 19.642 | 1.317 | 30.992 | 1.00 | 41.85 | C |
| ATOM | 1130 | O | GLY | A | 155 | 19.977 | 2.140 | 30.123 | 1.00 | 41.87 | O |
| ATOM | 1131 | N | ARG | A | 156 | 19.512 | 0.012 | 30.750 | 1.00 | 41.36 | N |
| ATOM | 1132 | CA | ARG | A | 156 | 19.961 | 0.623 | 29.511 | 1.00 | 40.88 | C |
| ATOM | 1133 | C | ARG | A | 156 | 19.397 | 0.005 | 28.247 | 1.00 | 40.03 | C |
| ATOM | 1134 | O | ARG | A | 156 | 20.135 | 0.304 | 27.339 | 1.00 | 40.36 | O |
| ATOM | 1135 | CB | ARG | A | 156 | 19.670 | 2.148 | 29.555 | 1.00 | 40.77 | C |
| ATOM | 1136 | N | LYS | A | 157 | 18.090 | 0.146 | 28.181 | 1.00 | 39.16 | N |
| ATOM | 1137 | CA | LYS | A | 157 | 17.503 | 0.697 | 26.990 | 1.00 | 38.81 | C |
| ATOM | 1138 | C | LYS | A | 157 | 18.078 | 2.114 | 26.738 | 1.00 | 38.38 | C |
| ATOM | 1139 | O | LYS | A | 157 | 18.363 | 2.464 | 25.594 | 1.00 | 37.97 | O |
| ATOM | 1140 | CB | LYS | A | 157 | 15.968 | 0.714 | 27.090 | 1.00 | 39.20 | C |
| ATOM | 1141 | CG | LYS | A | 157 | 15.266 | 0.575 | 26.642 | 1.00 | 36.80 | C |
| ATOM | 1142 | N | ILE | A | 158 | 18.268 | 2.909 | 27.791 | 1.00 | 37.56 | N |
| ATOM | 1143 | CA | ILE | A | 158 | 18.759 | 4.287 | 27.606 | 1.00 | 37.28 | C |
| ATOM | 1144 | C | ILE | A | 158 | 20.180 | 4.281 | 27.126 | 1.00 | 37.22 | C |
| ATOM | 1145 | O | ILE | A | 158 | 20.582 | 5.120 | 26.302 | 1.00 | 37.08 | O |
| ATOM | 1146 | CB | ILE | A | 158 | 18.692 | 5.101 | 28.882 | 1.00 | 36.72 | C |
| ATOM | 1147 | CG1 | ILE | A | 158 | 17.257 | 5.220 | 29.356 | 1.00 | 37.17 | C |
| ATOM | 1148 | CG2 | ILE | A | 158 | 19.254 | 6.465 | 28.646 | 1.00 | 36.48 | C |
| ATOM | 1149 | CD1 | ILE | A | 158 | 16.359 | 5.900 | 28.409 | 1.00 | 38.28 | C |
| ATOM | 1150 | N | VAL | A | 159 | 20.934 | 3.335 | 27.655 | 1.00 | 36.85 | N |
| ATOM | 1151 | CA | VAL | A | 159 | 22.319 | 3.177 | 27.284 | 1.00 | 37.05 | C |
| ATOM | 1152 | C | VAL | A | 159 | 22.349 | 2.864 | 25.785 | 1.00 | 36.45 | C |
| ATOM | 1153 | O | VAL | A | 159 | 23.165 | 3.410 | 25.057 | 1.00 | 35.81 | O |
| ATOM | 1154 | CE | VAL | A | 159 | 22.988 | 2.042 | 28.096 | 1.00 | 37.36 | C |
| ATOM | 1155 | CG1 | VAL | A | 159 | 24.248 | 1.567 | 27.427 | 1.00 | 38.43 | C |
| ATOM | 1156 | CG2 | VAL | A | 159 | 23.302 | 2.499 | 29.494 | 1.00 | 37.81 | C |

TABLE 3-continued

Coordinates for structures 1 to 4

| ATOM | 1157 | N | MET | A | 160 | 21.453 | 1.990 | 25.339 | 1.00 | 35.84 | N |
| ATOM | 1158 | CA | MET | A | 160 | 21.369 | 1.637 | 23.910 | 1.00 | 36.30 | C |
| ATOM | 1159 | C | MET | A | 160 | 21.064 | 2.883 | 23.074 | 1.00 | 34.46 | C |
| ATOM | 1160 | O | MET | A | 160 | 21.715 | 3.142 | 22.083 | 1.00 | 33.88 | O |
| ATOM | 1161 | CB | MET | A | 160 | 20.294 | 0.576 | 23.656 | 1.00 | 36.83 | C |
| ATOM | 1162 | CG | MET | A | 160 | 20.654 | 0.763 | 24.225 | 1.00 | 39.89 | C |
| ATOM | 1163 | SD | MET | A | 160 | 21.916 | 1.579 | 23.249 | 1.00 | 46.87 | S |
| ATOM | 1164 | CE | MET | A | 160 | 21.005 | 1.940 | 21.669 | 1.00 | 47.08 | C |
| ATOM | 1165 | N | ASP | A | 161 | 20.078 | 3.648 | 23.505 | 1.00 | 33.13 | N |
| ATOM | 1166 | CA | ASP | A | 161 | 19.732 | 4.901 | 22.857 | 1.00 | 32.80 | C |
| ATOM | 1167 | C | ASP | A | 161 | 20.931 | 5.877 | 22.747 | 1.00 | 31.75 | C |
| ATOM | 1168 | O | ASP | A | 161 | 21.209 | 6.425 | 21.691 | 1.00 | 31.06 | O |
| ATOM | 1169 | CB | ASP | A | 161 | 18.598 | 5.553 | 23.631 | 1.00 | 32.93 | C |
| ATOM | 1170 | CG | ASP | A | 161 | 17.278 | 4.822 | 23.473 | 1.00 | 33.90 | C |
| ATOM | 1171 | OD1 | ASP | A | 161 | 17.148 | 3.961 | 22.568 | 1.00 | 28.71 | O |
| ATOM | 1172 | OD2 | ASP | A | 161 | 16.301 | 5.064 | 24.226 | 1.00 | 38.17 | O |
| ATOM | 1173 | N | PHE | A | 162 | 21.646 | 6.052 | 23.849 | 1.00 | 31.05 | N |
| ATOM | 1174 | CA | PHE | A | 162 | 22.763 | 6.968 | 23.930 | 1.00 | 30.52 | C |
| ATOM | 1175 | C | PHE | A | 162 | 23.835 | 6.553 | 22.979 | 1.00 | 28.89 | C |
| ATOM | 1176 | O | PHE | A | 162 | 24.477 | 7.369 | 22.371 | 1.00 | 29.43 | O |
| ATOM | 1177 | CB | PHE | A | 162 | 23.311 | 6.948 | 25.375 | 1.00 | 30.80 | C |
| ATOM | 1178 | CG | PHE | A | 162 | 24.493 | 7.839 | 25.617 | 1.00 | 31.81 | C |
| ATOM | 1179 | CD1 | PHE | A | 162 | 24.325 | 9.179 | 25.904 | 1.00 | 35.81 | C |
| ATOM | 1180 | CD2 | PHE | A | 162 | 25.770 | 7.322 | 25.653 | 1.00 | 35.00 | C |
| ATOM | 1181 | GE1 | PHE | A | 162 | 25.430 | 10.000 | 26.197 | 1.00 | 35.94 | C |
| ATOM | 1182 | CE2 | PHE | A | 162 | 26.887 | 8.143 | 25.941 | 1.00 | 35.90 | C |
| ATOM | 1183 | CZ | PHE | A | 162 | 26.711 | 9.467 | 26.202 | 1.00 | 35.61 | C |
| ATOM | 1184 | N | LEU | A | 163 | 24.067 | 5.271 | 22.914 | 1.00 | 28.19 | N |
| ATOM | 1185 | CA | LEU | A | 163 | 25.103 | 4.728 | 22.065 | 1.00 | 28.08 | C |
| ATOM | 1186 | C | LEU | A | 163 | 24.735 | 4.923 | 20.590 | 1.00 | 27.13 | C |
| ATOM | 1187 | O | LEU | A | 163 | 25.603 | 4.973 | 19.751 | 1.00 | 26.83 | O |
| ATOM | 1188 | GB | LEU | A | 163 | 25.306 | 3.244 | 22.368 | 1.00 | 27.86 | C |
| ATOM | 1189 | CG | LEU | A | 163 | 26.137 | 2.987 | 23.604 | 1.00 | 28.73 | C |
| ATOM | 1190 | CD1 | LEU | A | 163 | 26.180 | 1.512 | 23.849 | 1.00 | 29.77 | C |
| ATOM | 1191 | CD2 | LEU | A | 163 | 27.559 | 3.522 | 23.464 | 1.00 | 29.70 | C |
| ATOM | 1192 | N | GLY | A | 164 | 23.448 | 4.998 | 20.303 | 1.00 | 26.50 | N |
| ATOM | 1193 | CA | GLY | A | 164 | 22.956 | 5.244 | 18.959 | 1.00 | 27.37 | C |
| ATOM | 1194 | C | GLY | A | 164 | 22.949 | 6.712 | 18.493 | 1.00 | 27.88 | C |
| ATOM | 1195 | O | GLY | A | 164 | 22.483 | 6.988 | 17.365 | 1.00 | 28.42 | O |
| ATOM | 1196 | N | PHE | A | 165 | 23.420 | 7.635 | 19.344 | 1.00 | 26.36 | N |
| ATOM | 1197 | GA | PHE | A | 165 | 23.530 | 9.011 | 18.958 | 1.00 | 26.57 | C |
| ATOM | 1198 | C | PHE | A | 165 | 24.540 | 9.052 | 17.820 | 1.00 | 26.12 | C |
| ATOM | 1199 | O | PHE | A | 165 | 25.381 | 8.202 | 17.756 | 1.00 | 24.23 | O |
| ATOM | 1200 | CB | PHE | A | 165 | 24.024 | 9.867 | 20.153 | 1.00 | 26.86 | C |
| ATOM | 1201 | CG | PHE | A | 165 | 22.979 | 10.070 | 21.252 | 1.00 | 27.80 | C |
| ATOM | 1202 | GD1 | PHE | A | 165 | 21.701 | 9.533 | 21.144 | 1.00 | 27.80 | C |
| ATOM | 1203 | CD2 | PHE | A | 165 | 23.274 | 10.820 | 22.367 | 1.00 | 28.58 | C |
| ATOM | 1204 | GE1 | PHE | A | 165 | 20.765 | 9.744 | 22.117 | 1.00 | 26.89 | C |
| ATOM | 1205 | CE2 | PHE | A | 165 | 22.329 | 11.042 | 23.364 | 1.00 | 28.45 | C |
| ATOM | 1206 | CZ | PHE | A | 165 | 21.086 | 10.504 | 23.243 | 1.00 | 28.78 | C |
| ATOM | 1207 | N | ASN | A | 166 | 24.496 | 10.077 | 16.963 | 1.00 | 26.15 | N |
| ATOM | 1208 | CA | ASN | A | 166 | 25.441 | 10.165 | 15.837 | 1.00 | 25.91 | C |
| ATOM | 1209 | C | ASN | A | 166 | 26.861 | 10.675 | 16.226 | 1.00 | 26.12 | C |
| ATOM | 1210 | O | ASN | A | 166 | 27.288 | 11.793 | 15.894 | 1.00 | 25.48 | O |
| ATOM | 1211 | CE | ASN | A | 166 | 24.834 | 11.004 | 14.705 | 1.00 | 25.51 | C |
| ATOM | 1212 | CG | ASN | A | 166 | 25.634 | 10.916 | 13.431 | 1.00 | 24.43 | C |
| ATOM | 1213 | OD1 | ASN | A | 166 | 26.751 | 10.323 | 13.429 | 1.00 | 23.40 | O |
| ATOM | 1214 | ND2 | ASN | A | 166 | 25.078 | 11.479 | 12.318 | 1.00 | 17.22 | N |
| ATOM | 1215 | N | TRP | A | 167 | 27.566 | 9.817 | 16.940 | 1.00 | 26.11 | N |
| ATOM | 1216 | CA | TRP | A | 167 | 28.907 | 10.080 | 17.401 | 1.00 | 26.58 | C |
| ATOM | 1217 | C | TRP | A | 167 | 29.817 | 10.336 | 16.206 | 1.00 | 27.07 | C |
| ATOM | 1218 | O | TRP | A | 167 | 30.737 | 11.139 | 16.252 | 1.00 | 26.92 | O |
| ATOM | 1219 | GB | TRP | A | 167 | 29.389 | 8.860 | 18.249 | 1.00 | 26.02 | C |
| ATOM | 1220 | CG | TRP | A | 167 | 28.537 | 8.750 | 19.498 | 1.00 | 27.18 | C |
| ATOM | 1221 | GD1 | TRP | A | 167 | 27.620 | 7.784 | 19.809 | 1.00 | 28.08 | C |
| ATOM | 1222 | CD2 | TRP | A | 167 | 28.452 | 9.719 | 20.550 | 1.00 | 27.33 | C |
| ATOM | 1223 | NE1 | TRP | A | 167 | 27.013 | 8.071 | 21.013 | 1.00 | 27.87 | N |
| ATOM | 1224 | CE2 | TRP | A | 167 | 27.503 | 9.254 | 21.481 | 1.00 | 26.46 | C |
| ATOM | 1225 | CE3 | TRP | A | 167 | 29.103 | 10.929 | 20.804 | 1.00 | 26.22 | C |
| ATOM | 1226 | CZ2 | TRP | A | 167 | 27.180 | 9.951 | 22.622 | 1.00 | 28.27 | C |
| ATOM | 1227 | CZ3 | TRP | A | 167 | 28.784 | 11.615 | 21.920 | 1.00 | 27.56 | C |
| ATOM | 1228 | CH2 | TRP | A | 167 | 27.821 | 11.128 | 22.833 | 1.00 | 28.04 | C |
| ATOM | 1229 | N | ASN | A | 168 | 29.585 | 9.632 | 15.114 | 1.00 | 27.98 | N |
| ATOM | 1230 | CA | ASN | A | 168 | 30.430 | 9.833 | 13.959 | 1.00 | 28.32 | C |
| ATOM | 1231 | C | ASN | A | 168 | 30.470 | 11.319 | 13.573 | 1.00 | 29.00 | C |
| ATOM | 1232 | O | ASN | A | 168 | 31.547 | 11.894 | 13.390 | 1.00 | 30.41 | O |
| ATOM | 1233 | GB | ASN | A | 168 | 29.909 | 9.018 | 12.812 | 1.00 | 28.58 | C |

TABLE 3-continued

Coordinates for structures 1 to 4

| ATOM | 1234 | CG  | ASN | A | 168 | 30.758 | 9.145  | 11.570 | 1.00 | 29.28 | C |
|------|------|-----|-----|---|-----|--------|--------|--------|------|-------|---|
| ATOM | 1235 | OD1 | ASN | A | 168 | 31.899 | 8.739  | 11.579 | 1.00 | 30.27 | O |
| ATOM | 1236 | ND2 | ASN | A | 168 | 30.186 | 9.677  | 10.487 | 1.00 | 28.46 | N |
| ATOM | 1237 | N   | TRP | A | 169 | 29.301 | 11.942 | 13.462 | 1.00 | 27.93 | N |
| ATOM | 1238 | GA  | TRP | A | 169 | 29.228 | 13.343 | 13.074 | 1.00 | 27.25 | C |
| ATOM | 1239 | C   | TRP | A | 169 | 29.726 | 14.266 | 14.179 | 1.00 | 27.20 | C |
| ATOM | 1240 | O   | TRP | A | 169 | 30.444 | 15.224 | 13.925 | 1.00 | 26.30 | O |
| ATOM | 1241 | CE  | TRP | A | 169 | 27.777 | 13.734 | 12.691 | 1.00 | 26.63 | C |
| ATOM | 1242 | CG  | TRP | A | 169 | 27.615 | 15.168 | 12.355 | 1.00 | 25.15 | C |
| ATOM | 1243 | CD1 | TRP | A | 169 | 27.804 | 15.745 | 11.130 | 1.00 | 24.89 | C |
| ATOM | 1244 | CD2 | TRP | A | 169 | 27.261 | 16.229 | 13.237 | 1.00 | 23.66 | C |
| ATOM | 1245 | HE1 | TRP | A | 169 | 27.591 | 17.095 | 11.195 | 1.00 | 22.98 | N |
| ATOM | 1246 | CE2 | TRP | A | 169 | 27.257 | 17.427 | 12.476 | 1.00 | 25.81 | C |
| ATOM | 1247 | CE3 | TRP | A | 169 | 26.927 | 16.292 | 14.576 | 1.00 | 24.44 | C |
| ATOM | 1248 | CZ2 | TRP | A | 169 | 26.933 | 18.680 | 13.018 | 1.00 | 26.96 | C |
| ATOM | 1249 | CZ3 | TRP | A | 169 | 26.624 | 17.525 | 15.127 | 1.00 | 28.68 | C |
| ATOM | 1250 | CH2 | TRP | A | 169 | 26.611 | 18.710 | 14.336 | 1.00 | 28.73 | C |
| ATOM | 1251 | N   | ILE | A | 170 | 29.323 | 14.026 | 15.409 | 1.00 | 27.29 | N |
| ATOM | 1252 | CA  | ILE | A | 170 | 29.725 | 14.985 | 16.406 | 1.00 | 28.36 | C |
| ATOM | 1253 | C   | ILE | A | 170 | 31.252 | 14.874 | 16.686 | 1.00 | 29.15 | C |
| ATOM | 1254 | O   | ILE | A | 170 | 31.920 | 15.875 | 16.866 | 1.00 | 29.81 | O |
| ATOM | 1255 | CE  | ILE | A | 170 | 28.814 | 14.947 | 17.672 | 1.00 | 28.10 | C |
| ATOM | 1256 | CG1 | ILE | A | 170 | 28.882 | 16.277 | 18.386 | 1.00 | 26.98 | C |
| ATOM | 1257 | CG2 | ILE | A | 170 | 29.198 | 13.838 | 18.593 | 1.00 | 27.15 | C |
| ATOM | 1258 | CD1 | ILE | A | 170 | 27.855 | 16.400 | 19.530 | 1.00 | 28.88 | C |
| ATOM | 1259 | N   | ASN | A | 171 | 31.809 | 13.679 | 16.653 | 1.00 | 29.35 | N |
| ATOM | 1260 | CA  | ASN | A | 171 | 33.261 | 13.535 | 16.843 | 1.00 | 30.18 | C |
| ATOM | 1261 | C   | ASN | A | 171 | 34.060 | 14.259 | 15.752 | 1.00 | 30.67 | C |
| ATOM | 1262 | O   | ASN | A | 171 | 35.117 | 14.823 | 16.036 | 1.00 | 31.32 | O |
| ATOM | 1263 | CB  | ASN | A | 171 | 33.705 | 12.058 | 16.861 | 1.00 | 29.80 | C |
| ATOM | 1264 | CG  | ASN | A | 171 | 33.210 | 11.274 | 18.094 | 1.00 | 30.17 | C |
| ATOM | 1265 | OD1 | ASN | A | 171 | 32.682 | 11.821 | 19.051 | 1.00 | 30.65 | O |
| ATOM | 1266 | ND2 | ASN | A | 171 | 33.372 | 9.968  | 18.036 | 1.00 | 31.44 | N |
| ATOM | 1267 | N   | LYS | A | 172 | 33.591 | 14.231 | 14.509 | 1.00 | 30.94 | N |
| ATOM | 1268 | CA  | LYS | A | 172 | 34.297 | 14.960 | 13.461 | 1.00 | 32.29 | C |
| ATOM | 1269 | C   | LYS | A | 172 | 34.211 | 16.473 | 13.755 | 1.00 | 31.79 | C |
| ATOM | 1270 | O   | LYS | A | 172 | 35.128 | 17.234 | 13.482 | 1.00 | 32.06 | O |
| ATOM | 1271 | CE  | LYS | A | 172 | 33.754 | 14.646 | 12.055 | 1.00 | 32.47 | C |
| ATOM | 1272 | CG  | LYS | A | 172 | 34.168 | 13.298 | 11.539 | 1.00 | 36.36 | C |
| ATOM | 1273 | CD  | LYS | A | 172 | 33.697 | 13.012 | 10.072 | 1.00 | 41.05 | C |
| ATOM | 1274 | CE  | LYS | A | 172 | 34.338 | 11.721 | 9.543  | 1.00 | 44.14 | C |
| ATOM | 1275 | NZ  | LYS | A | 172 | 34.321 | 11.571 | 8.024  | 1.00 | 49.11 | H |
| ATOM | 1276 | H   | GLN | A | 173 | 33.099 | 16.900 | 14.316 | 1.00 | 31.59 | N |
| ATOM | 1277 | CA  | GLN | A | 173 | 32.931 | 18.299 | 14.616 | 1.00 | 31.80 | C |
| ATOM | 1278 | C   | GLN | A | 173 | 33.965 | 18.680 | 15.681 | 1.00 | 32.04 | C |
| ATOM | 1279 | O   | GLN | A | 173 | 34.670 | 19.687 | 15.534 | 1.00 | 32.67 | O |
| ATOM | 1280 | CE  | GLN | A | 173 | 31.522 | 18.581 | 15.117 | 1.00 | 31.45 | C |
| ATOM | 1281 | CG  | GLN | A | 173 | 30.477 | 18.685 | 14.067 | 1.00 | 31.68 | C |
| ATOM | 1282 | CD  | GLN | A | 173 | 30.782 | 19.751 | 13.050 | 1.00 | 32.76 | C |
| ATOM | 1283 | OE1 | GLN | A | 173 | 31.198 | 20.852 | 13.405 | 1.00 | 36.55 | O |
| ATOM | 1284 | NE2 | GLN | A | 173 | 30.583 | 19.440 | 11.790 | 1.00 | 32.28 | H |
| ATOM | 1285 | H   | GLN | A | 174 | 34.044 | 17.871 | 16.735 | 1.00 | 31.40 | H |
| ATOM | 1286 | CA  | GLN | A | 174 | 34.999 | 18.074 | 17.811 | 1.00 | 31.28 | C |
| ATOM | 1287 | C   | GLN | A | 174 | 36.437 | 18.098 | 17.244 | 1.00 | 30.94 | C |
| ATOM | 1288 | O   | GLN | A | 174 | 37.253 | 18.939 | 17.602 | 1.00 | 30.50 | O |
| ATOM | 1289 | CE  | GLN | A | 174 | 34.808 | 16.971 | 18.861 | 1.00 | 31.20 | C |
| ATOM | 1290 | CG  | GLN | A | 174 | 35.859 | 16.917 | 19.935 | 1.00 | 31.64 | C |
| ATOM | 1291 | CD  | GLN | A | 174 | 35.704 | 15.717 | 20.836 | 1.00 | 31.52 | C |
| ATOM | 1292 | OE1 | GLN | A | 174 | 35.313 | 14.661 | 20.382 | 1.00 | 35.10 | O |
| ATOM | 1293 | HE2 | GLN | A | 174 | 36.007 | 15.880 | 22.121 | 1.00 | 32.92 | N |
| ATOM | 1294 | N   | GLY | A | 175 | 36.732 | 17.202 | 16.317 | 1.00 | 30.54 | N |
| ATOM | 1295 | CA  | GLY | A | 175 | 38.048 | 17.169 | 15.721 | 1.00 | 30.38 | C |
| ATOM | 1296 | C   | GLY | A | 175 | 38.288 | 18.339 | 14.783 | 1.00 | 31.21 | C |
| ATOM | 1297 | O   | GLY | A | 175 | 39.339 | 18.974 | 14.812 | 1.00 | 31.31 | O |
| ATOM | 1298 | N   | LYS | A | 176 | 37.317 | 18.661 | 13.946 | 1.00 | 31.67 | N |
| ATOM | 1299 | CA  | LYS | A | 176 | 37.524 | 19.767 | 13.029 | 1.00 | 32.84 | C |
| ATOM | 1300 | C   | LYS | A | 176 | 37.758 | 21.127 | 13.749 | 1.00 | 32.90 | C |
| ATOM | 1301 | O   | LYS | A | 176 | 38.563 | 21.906 | 13.291 | 1.00 | 32.85 | O |
| ATOM | 1302 | GB  | LYS | A | 176 | 36.351 | 19.915 | 12.074 | 1.00 | 33.80 | C |
| ATOM | 1303 | CG  | LYS | A | 176 | 36.187 | 18.832 | 11.037 | 1.00 | 35.93 | C |
| ATOM | 1304 | CD  | LYS | A | 176 | 34.982 | 19.185 | 10.168 | 1.00 | 39.44 | C |
| ATOM | 1305 | CE  | LYS | A | 176 | 34.055 | 18.032 | 9.961  | 1.00 | 40.94 | C |
| ATOM | 1306 | NZ  | LYS | A | 176 | 32.686 | 18.495 | 9.578  | 1.00 | 45.01 | N |
| ATOM | 1307 | N   | ARG | A | 177 | 37.074 | 21.398 | 14.859 | 1.00 | 32.98 | N |
| ATOM | 1308 | CA  | ARG | A | 177 | 37.242 | 22.677 | 15.571 | 1.00 | 33.61 | C |
| ATOM | 1309 | C   | ARG | A | 177 | 38.313 | 22.713 | 16.678 | 1.00 | 33.16 | C |
| ATOM | 1310 | O   | ARG | A | 177 | 38.453 | 23.717 | 17.370 | 1.00 | 33.01 | O |

TABLE 3-continued

| | | | | | | | | | | | |
|---|---|---|---|---|---|---|---|---|---|---|---|
| | | | | | Coordinates for structures 1 to 4 | | | | | | |
| ATOM | 1311 | CB | ARG | A | 177 | 35.920 | 23.101 | 16.220 | 1.00 | 33.86 | C |
| ATOM | 1312 | CG | ARG | A | 177 | 34.716 | 22.947 | 15.353 | 1.00 | 35.87 | C |
| ATOM | 1313 | CD | ARG | A | 177 | 34.728 | 23.721 | 14.062 | 1.00 | 37.56 | C |
| ATOM | 1314 | NE | ARG | A | 177 | 33.704 | 23.135 | 13.222 | 1.00 | 42.96 | N |
| ATOM | 1315 | CZ | ARG | A | 177 | 33.803 | 22.893 | 11.928 | 1.00 | 45.93 | C |
| ATOM | 1316 | NH1 | ARG | A | 177 | 34.897 | 23.218 | 11.247 | 1.00 | 46.65 | N |
| ATOM | 1317 | NH2 | ARG | A | 177 | 32.770 | 22.349 | 11.304 | 1.00 | 47.47 | N |
| ATOM | 1318 | N | GLY | A | 178 | 39.038 | 21.624 | 16.887 | 1.00 | 32.79 | N |
| ATOM | 1319 | CA | GLY | A | 178 | 40.068 | 21.629 | 17.907 | 1.00 | 31.78 | C |
| ATOM | 1320 | C | GLY | A | 178 | 39.511 | 21.614 | 19.313 | 1.00 | 31.64 | C |
| ATOM | 1321 | O | GLY | A | 178 | 40.251 | 21.782 | 20.292 | 1.00 | 33.25 | O |
| ATOM | 1322 | N | TRP | A | 179 | 38.223 | 21.380 | 19.468 | 1.00 | 30.56 | N |
| ATOM | 1323 | CA | TRP | A | 179 | 37.690 | 21.361 | 20.821 | 1.00 | 30.44 | C |
| ATOM | 1324 | C | TRP | A | 179 | 38.328 | 20.385 | 21.789 | 1.00 | 30.36 | C |
| ATOM | 1325 | O | TRP | A | 179 | 39.008 | 19.446 | 21.416 | 1.00 | 29.60 | O |
| ATOM | 1326 | GB | TRP | A | 179 | 36.200 | 21.115 | 20.806 | 1.00 | 30.43 | C |
| ATOM | 1327 | CG | TRP | A | 179 | 35.426 | 22.183 | 20.136 | 1.00 | 29.86 | C |
| ATOM | 1328 | CO1 | TRP | A | 179 | 35.882 | 23.409 | 19.721 | 1.00 | 27.42 | C |
| ATOM | 1329 | CD2 | TRP | A | 179 | 34.054 | 22.115 | 19.769 | 1.00 | 29.51 | C |
| ATOM | 1330 | NE1 | TRP | A | 179 | 34.870 | 24.102 | 19.104 | 1.00 | 30.05 | N |
| ATOM | 1331 | CE2 | TRP | A | 179 | 33.728 | 23.338 | 19.130 | 1.00 | 30.70 | C |
| ATOM | 1332 | CE3 | TRP | A | 179 | 33.067 | 21.145 | 19.902 | 1.00 | 27.24 | C |
| ATOM | 1333 | CZ2 | TRP | A | 179 | 32.470 | 23.602 | 18.626 | 1.00 | 27.82 | C |
| ATOM | 1334 | CZ3 | TRP | A | 179 | 31.829 | 21.397 | 19.389 | 1.00 | 28.43 | C |
| ATOM | 1335 | CH2 | TRP | A | 179 | 31.532 | 22.630 | 18.759 | 1.00 | 29.15 | C |
| ATOM | 1336 | N | GLY | A | 180 | 38.087 | 20.634 | 23.065 | 1.00 | 30.98 | N |
| ATOM | 1337 | CA | GLY | A | 180 | 38.515 | 19.723 | 24.104 | 1.00 | 30.78 | C |
| ATOM | 1338 | C | GLY | A | 180 | 37.468 | 18.637 | 24.246 | 1.00 | 31.74 | C |
| ATOM | 1339 | O | GLY | A | 180 | 36.621 | 18.448 | 23.343 | 1.00 | 31.97 | O |
| ATOM | 1340 | N | GLN | A | 181 | 37.498 | 17.941 | 25.378 | 1.00 | 32.16 | N |
| ATOM | 1341 | CA | GLN | A | 181 | 36.628 | 16.798 | 25.608 | 1.00 | 33.12 | C |
| ATOM | 1342 | C | GLN | A | 181 | 35.161 | 17.108 | 25.885 | 1.00 | 32.52 | C |
| ATOM | 1343 | O | GLN | A | 181 | 34.813 | 18.181 | 26.348 | 1.00 | 32.55 | O |
| ATOM | 1344 | CB | GLN | A | 181 | 37.161 | 15.962 | 26.773 | 1.00 | 33.24 | C |
| ATOM | 1345 | CG | GLN | A | 181 | 36.780 | 16.496 | 28.155 | 1.00 | 37.52 | C |
| ATOM | 1346 | CD | GLN | A | 181 | 37.066 | 15.488 | 29.282 | 1.00 | 42.63 | C |
| ATOM | 1347 | OE1 | GLN | A | 181 | 38.200 | 15.034 | 29.442 | 1.00 | 46.67 | O |
| ATOM | 1348 | NE2 | GLN | A | 181 | 36.037 | 15.131 | 30.043 | 1.00 | 45.13 | N |
| ATOM | 1349 | N | LEU | A | 182 | 34.310 | 16.134 | 25.588 | 1.00 | 32.12 | N |
| ATOM | 1350 | CA | LEU | A | 182 | 32.907 | 16.155 | 26.001 | 1.00 | 31.88 | C |
| ATOM | 1351 | C | LEU | A | 182 | 32.928 | 16.114 | 27.528 | 1.00 | 30.66 | C |
| ATOM | 1352 | O | LEU | A | 182 | 33.481 | 15.190 | 28.087 | 1.00 | 30.31 | O |
| ATOM | 1353 | GB | LEU | A | 182 | 32.228 | 14.880 | 25.512 | 1.00 | 31.80 | C |
| ATOM | 1354 | CG | LEU | A | 182 | 30.715 | 14.723 | 25.454 | 1.00 | 33.59 | C |
| ATOM | 1355 | CD1 | LEU | A | 182 | 30.319 | 13.250 | 25.572 | 1.00 | 32.15 | C |
| ATOM | 1356 | CD2 | LEU | A | 182 | 30.059 | 15.454 | 26.520 | 1.00 | 36.60 | C |
| ATOM | 1357 | N | THR | A | 183 | 32.373 | 17.112 | 28.207 | 1.00 | 29.62 | N |
| ATOM | 1358 | CA | THR | A | 183 | 32.383 | 17.088 | 29.657 | 1.00 | 28.62 | C |
| ATOM | 1359 | C | THR | A | 183 | 31.088 | 16.509 | 30.123 | 1.00 | 28.48 | C |
| ATOM | 1360 | O | THR | A | 183 | 31.034 | 15.991 | 31.207 | 1.00 | 28.46 | O |
| ATOM | 1361 | GB | THR | A | 183 | 32.504 | 18.509 | 30.276 | 1.00 | 28.82 | C |
| ATOM | 1362 | OG1 | THR | A | 183 | 31.441 | 19.364 | 29.795 | 1.00 | 28.93 | O |
| ATOM | 1363 | CG2 | THR | A | 183 | 33.764 | 19.178 | 29.846 | 1.00 | 28.28 | C |
| ATOM | 1364 | N | SER | A | 184 | 30.005 | 16.673 | 29.355 | 1.00 | 28.14 | N |
| ATOM | 1365 | CA | SER | A | 184 | 28.734 | 16.144 | 29.805 | 1.00 | 28.16 | C |
| ATOM | 1366 | C | SER | A | 184 | 27.602 | 16.374 | 28.878 | 1.00 | 28.07 | C |
| ATOM | 1367 | O | SER | A | 184 | 27.703 | 17.120 | 27.931 | 1.00 | 29.72 | O |
| ATOM | 1368 | CB | SER | A | 184 | 28.357 | 16.750 | 31.149 | 1.00 | 27.81 | C |
| ATOM | 1369 | OG | SER | A | 184 | 28.166 | 18.132 | 31.017 | 1.00 | 30.35 | O |
| ATOM | 1370 | N | ASN | A | 185 | 26.505 | 15.721 | 29.116 | 1.00 | 27.93 | N |
| ATOM | 1371 | CA | ASN | A | 185 | 25.288 | 15.850 | 28.434 | 1.00 | 28.66 | C |
| ATOM | 1372 | C | ASN | A | 185 | 24.235 | 16.086 | 29.476 | 1.00 | 28.67 | C |
| ATOM | 1373 | O | ASN | A | 185 | 23.974 | 15.226 | 30.291 | 1.00 | 27.67 | O |
| ATOM | 1374 | CB | ASN | A | 185 | 24.927 | 14.543 | 27.683 | 1.00 | 28.53 | C |
| ATOM | 1375 | CG | ASN | A | 185 | 25.914 | 14.191 | 26.589 | 1.00 | 29.19 | C |
| ATOM | 1376 | OD1 | ASN | A | 185 | 26.684 | 13.278 | 26.766 | 1.00 | 30.93 | O |
| ATOM | 1377 | ND2 | ASN | A | 185 | 25.891 | 14.910 | 25.451 | 1.00 | 29.67 | N |
| ATOM | 1378 | N | LEU | A | 186 | 23.583 | 17.221 | 29.415 | 1.00 | 29.39 | N |
| ATOM | 1379 | CA | LEU | A | 186 | 22.557 | 17.526 | 30.388 | 1.00 | 30.47 | C |
| ATOM | 1380 | C | LEU | A | 186 | 21.179 | 17.177 | 29.835 | 1.00 | 30.85 | C |
| ATOM | 1381 | O | LEU | A | 186 | 20.796 | 17.566 | 28.714 | 1.00 | 30.64 | O |
| ATOM | 1382 | CB | LEU | A | 186 | 22.617 | 18.998 | 30.730 | 1.00 | 30.48 | C |
| ATOM | 1383 | CG | LEU | A | 186 | 21.779 | 19.484 | 31.917 | 1.00 | 32.51 | C |
| ATOM | 1384 | CD1 | LEU | A | 186 | 22.330 | 18.952 | 33.238 | 1.00 | 31.55 | C |
| ATOM | 1385 | CD2 | LEU | A | 186 | 21.678 | 21.072 | 31.954 | 1.00 | 29.96 | C |
| ATOM | 1386 | N | LEU | A | 187 | 20.409 | 16.439 | 30.613 | 1.00 | 31.21 | N |
| ATOM | 1387 | CA | LEU | A | 187 | 19.042 | 16.155 | 30.188 | 1.00 | 30.60 | C |

TABLE 3-continued

Coordinates for structures 1 to 4

| ATOM | 1388 | C | LEU | A | 187 | 18.162 | 17.256 | 30.787 | 1.00 | 30.79 | C |
|---|---|---|---|---|---|---|---|---|---|---|---|
| ATOM | 1389 | O | LEU | A | 187 | 18.257 | 17.557 | 31.991 | 1.00 | 29.69 | O |
| ATOM | 1390 | CB | LEU | A | 187 | 18.626 | 14.781 | 30.644 | 1.00 | 30.50 | C |
| ATOM | 1391 | CG | LEU | A | 187 | 17.130 | 14.465 | 30.590 | 1.00 | 32.29 | C |
| ATOM | 1392 | CD1 | LEU | A | 187 | 16.592 | 14.409 | 29.164 | 1.00 | 33.95 | C |
| ATOM | 1393 | CD2 | LEU | A | 187 | 16.864 | 13.137 | 31.270 | 1.00 | 32.62 | C |
| ATOM | 1394 | N | LEU | A | 188 | 17.390 | 17.933 | 29.939 | 1.00 | 30.75 | N |
| ATOM | 1395 | CA | LEU | A | 188 | 16.513 | 18.973 | 30.426 | 1.00 | 31.42 | C |
| ATOM | 1396 | C | LEU | A | 188 | 15.053 | 18.646 | 30.107 | 1.00 | 32.02 | C |
| ATOM | 1397 | O | LEU | A | 188 | 14.676 | 18.481 | 28.941 | 1.00 | 31.44 | O |
| ATOM | 1398 | CB | LEU | A | 188 | 16.856 | 20.323 | 29.821 | 1.00 | 31.69 | C |
| ATOM | 1399 | CG | LEU | A | 188 | 18.253 | 20.823 | 30.131 | 1.00 | 32.24 | C |
| ATOM | 14Q0 | CO1 | LEU | A | 188 | 19.094 | 20.883 | 28.904 | 1.00 | 32.79 | C |
| ATOM | 1401 | CD2 | LEU | A | 188 | 18.121 | 22.200 | 30.658 | 1.00 | 32.69 | C |
| ATOM | 1402 | N | ILE | A | 189 | 14.228 | 18.568 | 31.146 | 1.00 | 32.26 | N |
| ATOM | 1403 | CA | ILE | A | 189 | 12.816 | 18.305 | 30.944 | 1.00 | 32.23 | C |
| ATOM | 1404 | C | ILE | A | 189 | 12.067 | 19.386 | 31.664 | 1.00 | 32.02 | C |
| ATOM | 1405 | O | ILE | A | 189 | 12.194 | 19.520 | 32.895 | 1.00 | 31.42 | O |
| ATOM | 1406 | CB | ILE | A | 189 | 12.427 | 16.966 | 31.479 | 1.00 | 32.05 | C |
| ATOM | 1407 | CG1 | ILE | A | 189 | 13.256 | 15.894 | 30.793 | 1.00 | 33.02 | C |
| ATOM | 1408 | CG2 | ILE | A | 189 | 10.957 | 16.764 | 31.232 | 1.00 | 32.90 | C |
| ATOM | 1409 | CD1 | ILE | A | 189 | 13.006 | 14.466 | 31.277 | 1.00 | 34.20 | C |
| ATOM | 1410 | N | GLY | A | 190 | 11.279 | 20.145 | 30.898 | 1.00 | 31.94 | N |
| ATOM | 1411 | CA | GLY | A | 190 | 10.623 | 21.334 | 31.414 | 1.00 | 31.49 | C |
| ATOM | 1412 | C | GLY | A | 190 | 9.147 | 21.362 | 31.125 | 1.00 | 31.41 | C |
| ATOM | 1413 | O | GLY | A | 190 | 8.671 | 20.649 | 30.245 | 1.00 | 30.40 | O |
| ATOM | 1414 | N | MET | A | 191 | 8.433 | 22.154 | 31.914 | 1.00 | 31.55 | N |
| ATOM | 1415 | CA | MET | A | 191 | 7.027 | 22.378 | 31.697 | 1.00 | 32.41 | C |
| ATOM | 1416 | C | MET | A | 191 | 6.863 | 23.547 | 30.751 | 1.00 | 32.03 | C |
| ATOM | 1417 | O | MET | A | 191 | 7.722 | 24.435 | 30.658 | 1.00 | 32.29 | O |
| ATOM | 1418 | CB | MET | A | 191 | 6.313 | 22.672 | 33.008 | 1.00 | 33.21 | C |
| ATOM | 1419 | CG | MET | A | 191 | 6.294 | 21.499 | 33.957 | 1.00 | 35.09 | C |
| ATOM | 1420 | SD | MET | A | 191 | 5.828 | 21.953 | 35.652 | 1.00 | 39.51 | S |
| ATOM | 1421 | CE | MET | A | 191 | 4.213 | 22.512 | 35.350 | 1.00 | 39.52 | C |
| ATOM | 1422 | N | GLU | A | 192 | 5.755 | 23.539 | 30.033 | 1.00 | 31.96 | N |
| ATOM | 1423 | CA | GLU | A | 192 | 5.459 | 24.588 | 29.081 | 1.00 | 32.31 | C |
| ATOM | 1424 | C | GLU | A | 192 | 5.511 | 25.919 | 29.776 | 1.00 | 31.73 | C |
| ATOM | 1425 | O | GLU | A | 192 | 5.096 | 26.041 | 30.913 | 1.00 | 31.73 | O |
| ATOM | 1426 | CB | GLU | A | 192 | 4.087 | 24.375 | 28.508 | 1.00 | 33.09 | C |
| ATOM | 1427 | CG | GLU | A | 192 | 2.995 | 24.434 | 29.552 | 1.00 | 34.74 | C |
| ATOM | 1428 | CD | GLU | A | 192 | 1.679 | 23.940 | 29.019 | 1.00 | 36.73 | C |
| ATOM | 1429 | OE1 | GLU | A | 192 | 1.630 | 23.515 | 27.832 | 1.00 | 37.30 | O |
| ATOM | 1430 | OE2 | GLU | A | 192 | 0.698 | 24.001 | 29.791 | 1.00 | 38.64 | O |
| ATOM | 1431 | N | GLY | A | 193 | 6.049 | 26.926 | 29.103 | 1.00 | 31.79 | N |
| ATOM | 1432 | CA | GLY | A | 193 | 6.201 | 28.242 | 29.714 | 1.00 | 30.87 | C |
| ATOM | 1433 | C | GLY | A | 193 | 7.480 | 28.432 | 30.521 | 1.00 | 30.28 | C |
| ATOM | 1434 | O | GLY | A | 193 | 7.777 | 29.534 | 30.901 | 1.00 | 30.29 | O |
| ATOM | 1435 | N | ASN | A | 194 | 8.223 | 27.375 | 30.825 | 1.00 | 29.85 | N |
| ATOM | 1436 | CA | ASN | A | 194 | 9.460 | 27.536 | 31.604 | 1.00 | 29.38 | C |
| ATOM | 1437 | C | ASN | A | 194 | 10.473 | 28.371 | 30.840 | 1.00 | 28.61 | C |
| ATOM | 1438 | O | ASN | A | 194 | 10.606 | 28.216 | 29.615 | 1.00 | 28.58 | O |
| ATOM | 1439 | CB | ASN | A | 194 | 10.136 | 26.186 | 31.866 | 1.00 | 29.15 | C |
| ATOM | 1440 | CG | ASN | A | 194 | 9.565 | 25.445 | 33.049 | 1.00 | 29.50 | C |
| ATOM | 1441 | OD1 | ASN | A | 194 | 8.632 | 25.896 | 33.714 | 1.00 | 32.61 | O |
| ATOM | 1442 | ND2 | ASN | A | 194 | 10.146 | 24.305 | 33.334 | 1.00 | 28.53 | N |
| ATOM | 1443 | N | VAL | A | 195 | 11.221 | 29.194 | 31.561 | 1.00 | 27.70 | N |
| ATOM | 1444 | CA | VAL | A | 195 | 12.272 | 29.998 | 30.962 | 1.00 | 27.80 | C |
| ATOM | 1445 | C | VAL | A | 195 | 13.586 | 29.858 | 31.701 | 1.00 | 27.07 | C |
| ATOM | 1446 | O | VAL | A | 195 | 13.636 | 29.898 | 32.939 | 1.00 | 27.43 | O |
| ATOM | 1447 | CB | VAL | A | 195 | 11.904 | 31.520 | 31.018 | 1.00 | 28.18 | C |
| ATOM | 1448 | CG1 | VAL | A | 195 | 13.056 | 32.371 | 30.560 | 1.00 | 26.78 | C |
| ATOM | 1449 | CG2 | VAL | A | 195 | 10.662 | 31.789 | 30.187 | 1.00 | 29.06 | C |
| ATOM | 1450 | N | THR | A | 196 | 14.659 | 29.712 | 30.953 | 1.00 | 26.48 | N |
| ATOM | 1451 | CA | THR | A | 196 | 15.994 | 29.811 | 31.530 | 1.00 | 26.08 | C |
| ATOM | 1452 | C | THR | A | 196 | 16.462 | 31.184 | 31.084 | 1.00 | 27.03 | C |
| ATOM | 1453 | O | THR | A | 196 | 16.614 | 31.425 | 29.876 | 1.00 | 26.51 | O |
| ATOM | 1454 | CE | THR | A | 196 | 16.915 | 28.811 | 30.934 | 1.00 | 25.96 | C |
| ATOM | 1455 | OG1 | THR | A | 196 | 16.525 | 27.478 | 31.309 | 1.00 | 26.20 | O |
| ATOM | 1456 | CG2 | THR | A | 196 | 18.340 | 29.012 | 31.457 | 1.00 | 23.99 | C |
| ATOM | 1457 | N | PRO | A | 197 | 16.647 | 32.090 | 32.036 | 1.00 | 27.21 | N |
| ATOM | 1458 | CA | PRO | A | 197 | 17.053 | 33.451 | 31.725 | 1.00 | 27.46 | C |
| ATOM | 1459 | C | PRO | A | 197 | 18.432 | 33.512 | 31.113 | 1.00 | 27.48 | C |
| ATOM | 1460 | O | PRO | A | 197 | 19.248 | 32.588 | 31.293 | 1.00 | 27.52 | O |
| ATOM | 1461 | CB | PRO | A | 197 | 17.007 | 34.166 | 33.075 | 1.00 | 27.56 | C |
| ATOM | 1462 | CG | PRO | A | 197 | 16.226 | 33.344 | 33.924 | 1.00 | 28.15 | C |
| ATOM | 1463 | CD | PRO | A | 197 | 16.384 | 31.914 | 33.470 | 1.00 | 27.92 | C |
| ATOM | 1464 | N | ALA | A | 198 | 18.668 | 34.616 | 30.413 | 1.00 | 26.77 | N |

TABLE 3-continued

Coordinates for structures 1 to 4

| ATOM | 1465 | CA | ALA | A | 198 | 19.877 | 34.830 | 29.647 | 1.00 | 26.92 | C |
|---|---|---|---|---|---|---|---|---|---|---|---|
| ATOM | 1466 | C | ALA | A | 198 | 21.172 | 34.681 | 30.438 | 1.00 | 27.14 | C |
| ATOM | 1467 | O | ALA | A | 198 | 21.354 | 35.278 | 31.520 | 1.00 | 25.53 | O |
| ATOM | 1468 | CB | ALA | A | 198 | 19.828 | 36.235 | 29.021 | 1.00 | 27.07 | C |
| ATOM | 1469 | N | HIS | A | 199 | 22.091 | 33.929 | 29.839 | 1.00 | 27.28 | N |
| ATOM | 1470 | CA | HIS | A | 199 | 23.399 | 33.673 | 30.424 | 1.00 | 27.81 | C |
| ATOM | 1471 | C | HIS | A | 199 | 24.319 | 33.208 | 29.333 | 1.00 | 28.09 | C |
| ATOM | 1472 | O | HIS | A | 199 | 23.857 | 32.933 | 28.197 | 1.00 | 28.34 | O |
| ATOM | 1473 | CB | HIS | A | 199 | 23.323 | 32.549 | 31.461 | 1.00 | 27.10 | C |
| ATOM | 1474 | CG | HIS | A | 199 | 22.963 | 31.221 | 30.864 | 1.00 | 29.70 | C |
| ATOM | 1475 | ND1 | HIS | A | 199 | 21.668 | 30.891 | 30.525 | 1.00 | 30.01 | N |
| ATOM | 1476 | CD2 | HIS | A | 199 | 23.728 | 30.180 | 30.463 | 1.00 | 29.60 | C |
| ATOM | 1477 | CE1 | HIS | A | 199 | 21.647 | 29.684 | 29.993 | 1.00 | 29.66 | C |
| ATOM | 1478 | ND2 | HIS | A | 199 | 22.881 | 29.236 | 29.926 | 1.00 | 30.43 | N |
| ATOM | 1479 | N | TYR | A | 200 | 25.612 | 33.104 | 29.671 | 1.00 | 28.30 | N |
| ATOM | 1480 | CA | TYR | A | 200 | 26.607 | 32.518 | 28.769 | 1.00 | 28.15 | C |
| ATOM | 1481 | C | TYR | A | 200 | 27.298 | 31.351 | 29.482 | 1.00 | 27.91 | C |
| ATOM | 1482 | O | TYR | A | 200 | 27.335 | 31.333 | 30.690 | 1.00 | 27.87 | O |
| ATOM | 1483 | CB | TYR | A | 200 | 27.585 | 33.534 | 28.217 | 1.00 | 28.02 | C |
| ATOM | 1484 | CG | TYR | A | 200 | 28.540 | 34.142 | 29.226 | 1.00 | 29.58 | C |
| ATOM | 1485 | CD1 | TYR | A | 200 | 29.784 | 33.571 | 29.462 | 1.00 | 28.14 | C |
| ATOM | 1486 | CD2 | TYR | A | 200 | 28.231 | 35.342 | 29.871 | 1.00 | 29.32 | C |
| ATOM | 1487 | CE1 | TYR | A | 200 | 30.660 | 34.128 | 30.367 | 1.00 | 30.20 | C |
| ATOM | 1488 | CE2 | TYR | A | 200 | 29.107 | 35.919 | 30.777 | 1.00 | 29.61 | C |
| ATOM | 1489 | CZ | TYR | A | 200 | 30.319 | 35.315 | 31.031 | 1.00 | 29.78 | C |
| ATOM | 1490 | OH | TYR | A | 200 | 31.180 | 35.864 | 31.940 | 1.00 | 24.43 | O |
| ATOM | 1491 | N | ASP | A | 201 | 27.797 | 30.363 | 28.727 | 1.00 | 27.73 | N |
| ATOM | 1492 | CA | ASP | A | 201 | 28.461 | 29.180 | 29.302 | 1.00 | 27.65 | C |
| ATOM | 1493 | C | ASP | A | 201 | 29.873 | 29.220 | 28.799 | 1.00 | 27.87 | C |
| ATOM | 1494 | O | ASP | A | 201 | 30.080 | 29.765 | 27.768 | 1.00 | 27.68 | O |
| ATOM | 1495 | CB | ASP | A | 201 | 27.775 | 27.884 | 28.855 | 1.00 | 26.32 | C |
| ATOM | 1496 | CG | ASP | A | 201 | 26.356 | 27.768 | 29.363 | 1.00 | 25.12 | C |
| ATOM | 1497 | OD1 | ASP | A | 201 | 26.156 | 27.722 | 30.605 | 1.00 | 23.49 | O |
| ATOM | 1498 | OD2 | ASP | A | 201 | 25.360 | 27.687 | 28.589 | 1.00 | 27.18 | O |
| ATOM | 1499 | N | GLU | A | 202 | 30.843 | 28.682 | 29.520 | 1.00 | 29.28 | N |
| ATOM | 1500 | CA | GLU | A | 202 | 32.228 | 28.672 | 29.013 | 1.00 | 31.18 | C |
| ATOM | 1501 | C | GLU | A | 202 | 32.571 | 27.435 | 28.190 | 1.00 | 31.54 | C |
| ATOM | 1502 | O | GLU | A | 202 | 33.734 | 27.060 | 28.139 | 1.00 | 33.48 | O |
| ATOM | 1503 | CB | GLU | A | 202 | 33.250 | 28.741 | 30.155 | 1.00 | 30.78 | C |
| ATOM | 1504 | CG | GLU | A | 202 | 33.122 | 29.981 | 31.003 | 1.00 | 33.61 | C |
| ATOM | 1505 | CD | GLU | A | 202 | 34.194 | 30.081 | 32.062 | 1.00 | 35.96 | C |
| ATOM | 1506 | OE1 | GLU | A | 202 | 34.036 | 29.531 | 33.166 | 1.00 | 41.25 | O |
| ATOM | 1507 | OE2 | GLU | A | 202 | 35.199 | 30.718 | 31.788 | 1.00 | 39.13 | O |
| ATOM | 1508 | N | GLN | A | 203 | 31.582 | 26.747 | 27.641 | 1.00 | 31.19 | N |
| ATOM | 1509 | CA | GLN | A | 203 | 31.844 | 25.589 | 26.833 | 1.00 | 30.78 | C |
| ATOM | 1510 | C | GLN | A | 203 | 31.078 | 25.743 | 25.556 | 1.00 | 29.96 | C |
| ATOM | 1511 | O | GLN | A | 203 | 30.213 | 26.581 | 25.462 | 1.00 | 30.22 | O |
| ATOM | 1512 | CB | GLN | A | 203 | 31.427 | 24.315 | 27.546 | 1.00 | 31.32 | C |
| ATOM | 1513 | CG | GLN | A | 203 | 32.364 | 23.971 | 28.725 | 1.00 | 34.97 | C |
| ATOM | 1514 | CD | GLN | A | 203 | 32.204 | 22.548 | 29.288 | 1.00 | 35.23 | C |
| ATOM | 1515 | OE1 | GLN | A | 203 | 32.161 | 21.559 | 28.551 | 1.00 | 36.82 | O |
| ATOM | 1516 | NE2 | GLN | A | 203 | 32.160 | 22.456 | 30.600 | 1.00 | 35.56 | N |
| ATOM | 1517 | N | GLN | A | 204 | 31.461 | 24.961 | 24.555 | 1.00 | 29.46 | N |
| ATOM | 1518 | CA | GLN | A | 204 | 30.791 | 24.911 | 23.292 | 1.00 | 28.65 | C |
| ATOM | 1519 | C | GLN | A | 204 | 29.641 | 23.941 | 23.494 | 1.00 | 28.27 | C |
| ATOM | 1520 | O | GLN | A | 204 | 29.797 | 22.941 | 24.194 | 1.00 | 27.65 | O |
| ATOM | 1521 | CB | GLN | A | 204 | 31.717 | 24.381 | 22.214 | 1.00 | 29.02 | C |
| ATOM | 1522 | CG | GLN | A | 204 | 33.006 | 25.154 | 22.028 | 1.00 | 28.50 | C |
| ATOM | 1523 | CD | GLN | A | 204 | 32.818 | 26.366 | 21.150 | 1.00 | 27.16 | C |
| ATOM | 1524 | OE1 | GLN | A | 204 | 31.690 | 26.742 | 20.846 | 1.00 | 22.90 | O |
| ATOM | 1525 | NE2 | GLN | A | 204 | 33.921 | 26.952 | 20.714 | 1.00 | 23.20 | N |
| ATOM | 1526 | N | ASN | A | 205 | 28.497 | 24.219 | 22.864 | 1.00 | 27.36 | N |
| ATOM | 1527 | CA | ASN | A | 205 | 27.302 | 23.424 | 23.058 | 1.00 | 27.13 | C |
| ATOM | 1528 | C | ASN | A | 205 | 26.552 | 23.052 | 21.777 | 1.00 | 27.39 | C |
| ATOM | 1529 | O | ASN | A | 205 | 26.151 | 23.930 | 20.999 | 1.00 | 27.36 | O |
| ATOM | 1530 | CB | ASN | A | 205 | 26.378 | 24.229 | 23.967 | 1.00 | 26.95 | C |
| ATOM | 1531 | CG | ASN | A | 205 | 25.083 | 23.525 | 24.327 | 1.00 | 27.30 | C |
| ATOM | 1532 | OD1 | ASN | A | 205 | 24.726 | 22.453 | 23.818 | 1.00 | 27.11 | O |
| ATOM | 1533 | ND2 | ASN | A | 205 | 24.319 | 24.190 | 25.171 | 1.00 | 24.64 | N |
| ATOM | 1534 | N | PHE | A | 206 | 26.383 | 21.749 | 21.542 | 1.00 | 26.46 | N |
| ATOM | 1535 | CA | PHE | A | 206 | 25.417 | 21.334 | 20.554 | 1.00 | 25.88 | C |
| ATOM | 1536 | C | PHE | A | 206 | 24.181 | 20.946 | 21.373 | 1.00 | 25.65 | C |
| ATOM | 1537 | O | PHE | A | 206 | 24.230 | 19.988 | 22.178 | 1.00 | 25.16 | O |
| ATOM | 1538 | CB | PHE | A | 206 | 25.909 | 20.170 | 19.717 | 1.00 | 26.28 | C |
| ATOM | 1539 | CG | PHE | A | 206 | 26.837 | 20.566 | 18.636 | 1.00 | 24.81 | C |
| ATOM | 1540 | CD | PHE | A | 206 | 26.416 | 21.374 | 17.633 | 1.00 | 26.27 | C |
| ATOM | 1541 | CD2 | PHE | A | 206 | 28.122 | 20.098 | 18.616 | 1.00 | 25.53 | C |

TABLE 3-continued

Coordinates for structures 1 to 4

| ATOM | 1542 | CE1 | PHE | A | 206 | 27.248 | 21.736 | 16.634 | 1.00 | 27.05 | C |
|---|---|---|---|---|---|---|---|---|---|---|---|
| ATOM | 1543 | CE2 | PHE | A | 206 | 28.991 | 20.469 | 17.617 | 1.00 | 26.80 | C |
| ATOM | 1544 | CZ | PHE | A | 206 | 28.549 | 21.274 | 16.619 | 1.00 | 28.34 | C |
| ATOM | 1545 | N | PHE | A | 207 | 23.084 | 21.648 | 21.086 | 1.00 | 25.08 | C |
| ATOM | 1546 | CA | PHE | A | 207 | 21.809 | 21.625 | 21.827 | 1.00 | 25.52 | C |
| ATOM | 1547 | C | PHE | A | 207 | 20.775 | 20.885 | 21.011 | 1.00 | 25.55 | C |
| ATOM | 1548 | O | PHE | A | 207 | 20.261 | 21.410 | 20.058 | 1.00 | 25.61 | O |
| ATOM | 1549 | CB | PHE | A | 207 | 21.408 | 23.107 | 22.074 | 1.00 | 25.37 | C |
| ATOM | 1550 | CG | PHE | A | 207 | 20.146 | 23.346 | 22.872 | 1.00 | 23.70 | C |
| ATOM | 1551 | CD1 | PHE | A | 207 | 18.938 | 23.547 | 22.234 | 1.00 | 24.08 | C |
| ATOM | 1552 | CD2 | PHE | A | 207 | 20.199 | 23.551 | 24.220 | 1.00 | 25.24 | C |
| ATOM | 1553 | CE1 | PHE | A | 207 | 17.800 | 23.864 | 22.927 | 1.00 | 24.50 | C |
| ATOM | 1554 | CE2 | PHE | A | 207 | 19.035 | 23.883 | 24.959 | 1.00 | 26.04 | C |
| ATOM | 1555 | CZ | PHE | A | 207 | 17.836 | 24.021 | 24.298 | 1.00 | 26.68 | C |
| ATOM | 1556 | N | ALA | A | 208 | 20.490 | 19.657 | 21.422 | 1.00 | 26.60 | N |
| ATOM | 1557 | CA | ALA | A | 208 | 19.667 | 18.710 | 20.689 | 1.00 | 26.45 | C |
| ATOM | 1558 | C | ALA | A | 208 | 18.231 | 18.594 | 21.210 | 1.00 | 27.10 | C |
| ATOM | 1559 | O | ALA | A | 208 | 17.966 | 17.987 | 22.273 | 1.00 | 26.47 | O |
| ATOM | 1560 | CB | ALA | A | 208 | 20.303 | 17.363 | 20.766 | 1.00 | 25.67 | C |
| ATOM | 1561 | N | GLN | A | 209 | 17.306 | 19.121 | 20.419 | 1.00 | 27.02 | N |
| ATOM | 1562 | CA | GLN | A | 209 | 15.918 | 19.125 | 20.833 | 1.00 | 27.37 | C |
| ATOM | 1563 | C | GLN | A | 209 | 15.276 | 17.781 | 20.519 | 1.00 | 27.55 | C |
| ATOM | 1564 | O | GLN | A | 209 | 15.489 | 17.190 | 19.427 | 1.00 | 26.51 | O |
| ATOM | 1565 | CE | GLN | A | 209 | 15.195 | 20.301 | 20.179 | 1.00 | 27.15 | C |
| ATOM | 1566 | CG | GLN | A | 209 | 13.806 | 20.508 | 20.662 | 1.00 | 27.77 | C |
| ATOM | 1567 | CD | GLN | A | 209 | 13.740 | 20.959 | 22.126 | 1.00 | 29.40 | C |
| ATOM | 1568 | OE1 | GLN | A | 209 | 14.773 | 21.166 | 22.774 | 1.00 | 27.27 | O |
| ATOM | 1569 | NE2 | GLN | A | 209 | 12.517 | 21.118 | 22.636 | 1.00 | 27.15 | N |
| ATOM | 1570 | N | ILE | A | 210 | 14.461 | 17.327 | 21.473 | 1.00 | 28.32 | N |
| ATOM | 1571 | CA | ILE | A | 210 | 13.897 | 15.998 | 21.429 | 1.00 | 29.37 | C |
| ATOM | 1572 | C | ILE | A | 210 | 12.403 | 15.966 | 21.435 | 1.00 | 30.37 | C |
| ATOM | 1573 | O | ILE | A | 210 | 11.849 | 15.275 | 20.619 | 1.00 | 31.58 | O |
| ATOM | 1574 | CB | ILE | A | 210 | 14.413 | 15.204 | 22.605 | 1.00 | 29.80 | C |
| ATOM | 1575 | CG1 | ILE | A | 210 | 15.830 | 14.734 | 22.302 | 1.00 | 30.27 | C |
| ATOM | 1576 | CG2 | ILE | A | 210 | 13.525 | 14.005 | 22.864 | 1.00 | 30.25 | C |
| ATOM | 1577 | CD1 | ILE | A | 210 | 16.624 | 14.421 | 23.516 | 1.00 | 32.28 | C |
| ATOM | 1578 | N | LYS | A | 211 | 11.757 | 16.664 | 22.374 | 1.00 | 31.18 | N |
| ATOM | 1579 | CA | LYS | A | 211 | 10.300 | 16.723 | 22.438 | 1.00 | 31.16 | C |
| ATOM | 1580 | C | LYS | A | 211 | 9.887 | 18.137 | 22.706 | 1.00 | 31.19 | C |
| ATOM | 1581 | O | LYS | A | 211 | 10.495 | 18.800 | 23.523 | 1.00 | 31.21 | O |
| ATOM | 1582 | CE | LYS | A | 211 | 9.767 | 15.891 | 23.591 | 1.00 | 32.00 | C |
| ATOM | 1583 | CG | LYS | A | 211 | 8.240 | 15.758 | 23.629 | 1.00 | 32.36 | C |
| ATOM | 1584 | CD | LYS | A | 211 | 7.787 | 15.177 | 24.970 | 1.00 | 33.23 | C |
| ATOM | 1585 | CE | LYS | A | 211 | 6.497 | 14.368 | 24.883 | 1.00 | 35.14 | C |
| ATOM | 1586 | NZ | LYS | A | 211 | 5.506 | 14.755 | 23.835 | 1.00 | 35.43 | N |
| ATOM | 1587 | N | GLY | A | 212 | 8.844 | 18.592 | 22.018 | 1.00 | 31.20 | N |
| ATOM | 1588 | CA | GLY | A | 212 | 8.337 | 19.934 | 22.174 | 1.00 | 30.96 | C |
| ATOM | 1589 | C | GLY | A | 212 | 9.209 | 20.975 | 21.495 | 1.00 | 31.42 | C |
| ATOM | 1590 | O | GLY | A | 212 | 10.167 | 20.670 | 20.771 | 1.00 | 31.06 | O |
| ATOM | 1591 | N | TYR | A | 213 | 8.857 | 22.224 | 21.734 | 1.00 | 31.43 | N |
| ATOM | 1592 | CA | TYR | A | 213 | 9.507 | 23.319 | 21.057 | 1.00 | 31.80 | C |
| ATOM | 1593 | C | TYR | A | 213 | 10.046 | 24.332 | 22.043 | 1.00 | 31.00 | C |
| ATOM | 1594 | O | TYR | A | 213 | 9.411 | 24.649 | 23.038 | 1.00 | 29.31 | O |
| ATOM | 1595 | CE | TYR | A | 213 | 8.502 | 23.959 | 20.127 | 1.00 | 32.64 | C |
| ATOM | 1596 | CG | TYR | A | 213 | 8.103 | 23.039 | 19.015 | 1.00 | 35.60 | C |
| ATOM | 1597 | CD1 | TYR | A | 213 | 7.089 | 22.071 | 19.174 | 1.00 | 38.37 | C |
| ATOM | 1598 | CD2 | TYR | A | 213 | 8.758 | 23.110 | 17.813 | 1.00 | 37.73 | C |
| ATOM | 1599 | CE1 | TYR | A | 213 | 6.765 | 21.223 | 18.137 | 1.00 | 39.37 | C |
| ATOM | 1600 | CE2 | TYR | A | 213 | 8.443 | 22.292 | 16.792 | 1.00 | 39.75 | C |
| ATOM | 1601 | CZ | TYR | A | 213 | 7.460 | 21.364 | 16.924 | 1.00 | 41.66 | C |
| ATOM | 1602 | OH | TYR | A | 213 | 7.232 | 20.603 | 15.782 | 1.00 | 46.53 | O |
| ATOM | 1603 | N | LYS | A | 214 | 11.260 | 24.787 | 21.777 | 1.00 | 30.99 | N |
| ATOM | 1604 | CA | LYS | A | 214 | 11.886 | 25.804 | 22.594 | 1.00 | 31.15 | C |
| ATOM | 1605 | C | LYS | A | 214 | 12.305 | 26.993 | 21.762 | 1.00 | 31.00 | C |
| ATOM | 1606 | O | LYS | A | 214 | 12.914 | 26.838 | 20.695 | 1.00 | 31.84 | O |
| ATOM | 1607 | CB | LYS | A | 214 | 13.112 | 25.244 | 23.311 | 1.00 | 31.08 | C |
| ATOM | 1608 | CG | LYS | A | 214 | 12.806 | 24.432 | 24.557 | 1.00 | 30.96 | C |
| ATOM | 1609 | CD | LYS | A | 214 | 14.106 | 23.949 | 25.159 | 1.00 | 30.84 | C |
| ATOM | 1610 | CE | LYS | A | 214 | 13.982 | 23.555 | 26.584 | 1.00 | 29.59 | C |
| ATOM | 1611 | NZ | LYS | A | 214 | 15.278 | 23.118 | 27.162 | 1.00 | 28.16 | N |
| ATOM | 1612 | N | ARG | A | 215 | 11.992 | 28.193 | 22.241 | 1.00 | 30.59 | N |
| ATOM | 1613 | CA | ARG | A | 215 | 12.445 | 29.385 | 21.549 | 1.00 | 29.98 | C |
| ATOM | 1614 | C | ARG | A | 215 | 13.764 | 29.790 | 22.154 | 1.00 | 29.65 | C |
| ATOM | 1615 | O | ARG | A | 215 | 13.850 | 29.982 | 23.349 | 1.00 | 29.61 | O |
| ATOM | 1616 | CB | ARG | A | 215 | 11.431 | 30.502 | 21.690 | 1.00 | 30.08 | C |
| ATOM | 1617 | CG | ARG | A | 215 | 11.835 | 31.810 | 21.004 | 1.00 | 29.82 | C |
| ATOM | 1618 | CD | ARG | A | 215 | 11.221 | 32.960 | 21.731 | 1.00 | 32.78 | C |

TABLE 3-continued

| | | | | | | | | | | |
|---|---|---|---|---|---|---|---|---|---|---|
| | | | | | Coordinates for structures 1 to 4 | | | | | |
| ATOM | 1619 | NE | ARG | A | 215 | 11.211 | 34.189 | 20.975 | 1.00 | 33.81 | N |
| ATOM | 1620 | CZ | ARG | A | 215 | 10.540 | 35.259 | 21.336 | 1.00 | 35.12 | C |
| ATOM | 1621 | NE1 | ARG | A | 215 | 9.828 | 35.262 | 22.441 | 1.00 | 35.28 | N |
| ATOM | 1622 | NH2 | ARG | A | 215 | 10.586 | 36.338 | 20.581 | 1.00 | 39.28 | N |
| ATOM | 1623 | N | CYS | A | 216 | 14.791 | 29.909 | 21.327 | 1.00 | 29.86 | N |
| ATOM | 1624 | CA | CYS | A | 216 | 16.129 | 30.237 | 21.797 | 1.00 | 29.64 | C |
| ATOM | 1625 | C | CYS | A | 216 | 16.533 | 31.603 | 21.274 | 1.00 | 30.06 | C |
| ATOM | 1626 | O | CYS | A | 216 | 16.516 | 31.807 | 20.092 | 1.00 | 31.32 | O |
| ATOM | 1627 | CB | CYS | A | 216 | 17.113 | 29.183 | 21.275 | 1.00 | 29.78 | C |
| ATOM | 1628 | SG | CYS | A | 216 | 16.658 | 27.438 | 21.641 | 1.00 | 30.35 | S |
| ATOM | 1629 | N | ILE | A | 217 | 16.849 | 32.556 | 22.149 | 1.00 | 30.28 | N |
| ATOM | 1630 | CA | ILE | A | 217 | 17.303 | 33.876 | 21.744 | 1.00 | 29.78 | C |
| ATOM | 1631 | C | ILE | A | 217 | 18.758 | 34.017 | 22.203 | 1.00 | 29.42 | C |
| ATOM | 1632 | O | ILE | A | 217 | 19.050 | 33.852 | 23.385 | 1.00 | 28.77 | O |
| ATOM | 1633 | CB | ILE | A | 217 | 16.427 | 34.969 | 22.391 | 1.00 | 30.51 | C |
| ATOM | 1634 | CG1 | ILE | A | 217 | 14.934 | 34.705 | 22.111 | 1.00 | 31.29 | C |
| ATOM | 1635 | CG2 | ILE | A | 217 | 16.785 | 36.313 | 21.843 | 1.00 | 30.11 | C |
| ATOM | 1636 | CD1 | ILE | A | 217 | 14.009 | 35.655 | 22.847 | 1.00 | 33.08 | C |
| ATOM | 1637 | N | LEU | A | 218 | 19.647 | 34.326 | 21.257 | 1.00 | 28.60 | N |
| ATOM | 1638 | CA | LEU | A | 218 | 21.059 | 34.392 | 21.501 | 1.00 | 28.59 | C |
| ATOM | 1639 | C | LEU | A | 218 | 21.606 | 35.781 | 21.257 | 1.00 | 28.74 | C |
| ATOM | 1640 | O | LEU | A | 218 | 21.102 | 36.522 | 20.412 | 1.00 | 29.64 | O |
| ATOM | 1641 | CB | LEU | A | 218 | 21.788 | 33.422 | 20.574 | 1.00 | 28.52 | C |
| ATOM | 1642 | CG | LEU | A | 218 | 21.927 | 31.980 | 21.028 | 1.00 | 28.46 | C |
| ATOM | 1643 | CD1 | LEU | A | 218 | 20.569 | 31.318 | 21.233 | 1.00 | 28.95 | C |
| ATOM | 1644 | CD2 | LEU | A | 218 | 22.707 | 31.196 | 20.026 | 1.00 | 27.94 | C |
| ATOM | 1645 | N | PHE | A | 219 | 22.659 | 36.145 | 21.986 | 1.00 | 28.61 | N |
| ATOM | 1646 | CA | PHE | A | 219 | 23.309 | 37.458 | 21.774 | 1.00 | 28.07 | C |
| ATOM | 1647 | C | PHE | A | 219 | 24.811 | 37.221 | 21.710 | 1.00 | 28.25 | C |
| ATOM | 1648 | O | PHE | A | 219 | 25.352 | 36.468 | 22.517 | 1.00 | 28.82 | O |
| ATOM | 1649 | CB | PHE | A | 219 | 22.987 | 38.415 | 22.908 | 1.00 | 26.73 | C |
| ATOM | 1650 | CG | PHE | A | 219 | 21.522 | 38.553 | 23.199 | 1.00 | 27.28 | C |
| ATOM | 1651 | CD1 | PHE | A | 219 | 20.874 | 37.658 | 24.029 | 1.00 | 25.73 | C |
| ATOM | 1652 | CD2 | PHE | A | 219 | 20.782 | 39.598 | 22.648 | 1.00 | 28.57 | C |
| ATOM | 1653 | CE1 | PHE | A | 219 | 19.536 | 37.811 | 24.311 | 1.00 | 26.59 | C |
| ATOM | 1654 | CE2 | PHE | A | 219 | 19.443 | 39.722 | 22.898 | 1.00 | 27.78 | C |
| ATOM | 1655 | CZ | PHE | A | 219 | 18.816 | 38.828 | 23.725 | 1.00 | 28.22 | C |
| ATOM | 1656 | N | PRO | A | 220 | 25.501 | 37.840 | 20.776 | 1.00 | 28.30 | N |
| ATOM | 1657 | CA | PRO | A | 220 | 26.946 | 37.641 | 20.675 | 1.00 | 28.76 | C |
| ATOM | 1658 | C | PRO | A | 220 | 27.688 | 38.195 | 21.881 | 1.00 | 29.07 | C |
| ATOM | 1659 | O | PRO | A | 220 | 27.172 | 39.019 | 22.661 | 1.00 | 29.11 | O |
| ATOM | 1660 | CB | PRO | A | 220 | 27.336 | 38.413 | 19.426 | 1.00 | 28.79 | C |
| ATOM | 1661 | CG | PRO | A | 220 | 26.016 | 38.847 | 18.795 | 1.00 | 29.65 | C |
| ATOM | 1662 | CD | PRO | A | 220 | 24.987 | 38.794 | 19.790 | 1.00 | 28.85 | C |
| ATOM | 1663 | N | PRO | A | 221 | 28.914 | 37.727 | 22.057 | 1.00 | 29.09 | N |
| ATOM | 1664 | CA | PRO | A | 221 | 29.725 | 38.147 | 23.188 | 1.00 | 28.85 | C |
| ATOM | 1665 | C | PRO | A | 221 | 29.979 | 39.656 | 23.199 | 1.00 | 28.60 | C |
| ATOM | 1666 | O | PRO | A | 221 | 30.223 | 40.182 | 24.270 | 1.00 | 26.85 | O |
| ATOM | 1667 | CB | PRO | A | 221 | 31.018 | 37.412 | 22.975 | 1.00 | 29.01 | C |
| ATOM | 1668 | CG | PRO | A | 221 | 30.665 | 36.286 | 22.114 | 1.00 | 30.46 | C |
| ATOM | 1669 | CD | PRO | A | 221 | 29.580 | 36.722 | 21.232 | 1.00 | 29.52 | C |
| ATOM | 1670 | N | ASP | A | 222 | 29.853 | 40.335 | 22.062 | 1.00 | 28.17 | N |
| ATOM | 1671 | CA | ASP | A | 222 | 30.155 | 41.763 | 22.044 | 1.00 | 28.79 | C |
| ATOM | 1672 | C | ASP | A | 222 | 28.976 | 42.554 | 22.533 | 1.00 | 28.84 | C |
| ATOM | 1673 | O | ASP | A | 222 | 28.948 | 43.767 | 22.432 | 1.00 | 30.46 | O |
| ATOM | 1674 | CB | ASP | A | 222 | 30.631 | 42.287 | 20.693 | 1.00 | 27.27 | C |
| ATOM | 1675 | CG | ASP | A | 222 | 29.541 | 42.288 | 19.655 | 1.00 | 30.76 | C |
| ATOM | 1676 | OD1 | ASP | A | 222 | 28.368 | 41.926 | 19.920 | 1.00 | 30.56 | O |
| ATOM | 1677 | OD2 | ASP | A | 222 | 29.785 | 42.609 | 18.495 | 1.00 | 39.36 | O |
| ATOM | 1678 | N | GLN | A | 223 | 28.000 | 41.885 | 23.083 | 1.00 | 29.33 | N |
| ATOM | 1679 | CA | GLN | A | 223 | 26.902 | 42.614 | 23.676 | 1.00 | 29.61 | C |
| ATOM | 1680 | C | GLN | A | 223 | 27.012 | 42.533 | 25.194 | 1.00 | 28.97 | C |
| ATOM | 1681 | O | GLN | A | 223 | 26.065 | 42.825 | 25.919 | 1.00 | 29.82 | O |
| ATOM | 1682 | CB | GLN | A | 223 | 25.575 | 42.131 | 23.110 | 1.00 | 30.22 | C |
| ATOM | 1683 | CG | GLN | A | 223 | 25.244 | 42.854 | 21.762 | 1.00 | 33.01 | C |
| ATOM | 1684 | CD | GLN | A | 223 | 23.866 | 42.562 | 21.241 | 1.00 | 37.71 | C |
| ATOM | 1685 | OE1 | GLN | A | 223 | 22.899 | 42.573 | 22.005 | 1.00 | 43.11 | O |
| ATOM | 1686 | NE2 | GLN | A | 223 | 23.760 | 42.285 | 19.943 | 1.00 | 38.91 | N |
| ATOM | 1687 | N | PHE | A | 224 | 28.181 | 42.148 | 25.672 | 1.00 | 27.69 | N |
| ATOM | 1688 | CA | PHE | A | 224 | 28.452 | 42.168 | 27.115 | 1.00 | 28.30 | C |
| ATOM | 1689 | C | PHE | A | 224 | 27.932 | 43.497 | 27.771 | 1.00 | 29.27 | C |
| ATOM | 1690 | O | PHE | A | 224 | 27.248 | 43.448 | 28.786 | 1.00 | 29.24 | O |
| ATOM | 1691 | CB | PHE | A | 224 | 29.968 | 42.025 | 27.373 | 1.00 | 26.64 | C |
| ATOM | 1692 | CG | PHE | A | 224 | 30.338 | 41.881 | 28.810 | 1.00 | 27.05 | C |
| ATOM | 1693 | CD1 | PHE | A | 224 | 30.526 | 42.992 | 29.619 | 1.00 | 26.91 | C |
| ATOM | 1694 | CD2 | PHE | A | 224 | 30.560 | 40.649 | 29.365 | 1.00 | 25.77 | C |
| ATOM | 1695 | CE1 | PHE | A | 224 | 30.878 | 42.864 | 30.930 | 1.00 | 24.95 | C |

TABLE 3-continued

| | | | | | | | | | | |
|---|---|---|---|---|---|---|---|---|---|---|
| | Coordinates for structures 1 to 4 |

| ATOM | 1696 | CE2 | PHE | A | 224 | 30.928 | 40.522 | 30.675 | 1.00 | 25.92 | C |
| ATOM | 1697 | CZ | PHE | A | 224 | 31.056 | 41.641 | 31.467 | 1.00 | 27.45 | C |
| ATOM | 1698 | N | GLU | A | 225 | 28.253 | 44.658 | 27.177 | 1.00 | 30.23 | N |
| ATOM | 1699 | CA | GLU | A | 225 | 27.873 | 45.951 | 27.753 | 1.00 | 31.35 | C |
| ATOM | 1700 | C | GLU | A | 225 | 26.362 | 46.120 | 27.909 | 1.00 | 30.48 | C |
| ATOM | 1701 | O | GLU | A | 225 | 25.925 | 46.920 | 28.738 | 1.00 | 28.49 | O |
| ATOM | 1702 | CB | GLU | A | 225 | 28.401 | 47.130 | 26.927 | 1.00 | 32.35 | C |
| ATOM | 1703 | CG | GLU | A | 225 | 29.894 | 47.356 | 27.083 | 1.00 | 37.72 | C |
| ATOM | 1704 | CD | GLU | A | 225 | 30.327 | 48.801 | 27.406 | 1.00 | 45.22 | C |
| ATOM | 1705 | OE1 | GLU | A | 225 | 29.848 | 49.472 | 28.389 | 1.00 | 44.87 | O |
| ATOM | 1706 | OE2 | GLU | A | 225 | 31.230 | 49.248 | 26.665 | 1.00 | 54.04 | O |
| ATOM | 1707 | N | CYS | A | 226 | 25.579 | 45.375 | 27.116 | 1.00 | 29.44 | N |
| ATOM | 1708 | CA | CYS | A | 226 | 24.132 | 45.532 | 27.155 | 1.00 | 28.60 | C |
| ATOM | 1709 | C | CYS | A | 226 | 23.429 | 44.524 | 28.056 | 1.00 | 28.86 | C |
| ATOM | 1710 | O | CYS | A | 226 | 22.236 | 44.716 | 28.352 | 1.00 | 27.16 | O |
| ATOM | 1711 | CB | CYS | A | 226 | 23.541 | 45.373 | 25.767 | 1.00 | 29.07 | C |
| ATOM | 1712 | SG | CYS | A | 226 | 24.193 | 46.391 | 24.441 | 1.00 | 29.66 | S |
| ATOM | 1713 | N | LEU | A | 227 | 24.133 | 43.455 | 28.483 | 1.00 | 28.37 | N |
| ATOM | 1714 | CA | LEU | A | 227 | 23.469 | 42.390 | 29.242 | 1.00 | 28.53 | C |
| ATOM | 1715 | C | LEU | A | 227 | 23.760 | 42.287 | 30.737 | 1.00 | 27.80 | C |
| ATOM | 1716 | O | LEU | A | 227 | 23.117 | 41.540 | 31.465 | 1.00 | 26.98 | O |
| ATOM | 1717 | CE | LEU | A | 227 | 23.701 | 41.062 | 28.531 | 1.00 | 28.86 | C |
| ATOM | 1718 | CG | LEU | A | 227 | 22.853 | 41.135 | 27.246 | 1.00 | 30.66 | C |
| ATOM | 1719 | CD1 | LEU | A | 227 | 23.335 | 40.152 | 26.186 | 1.00 | 32.05 | C |
| ATOM | 1720 | CD2 | LEU | A | 227 | 21.389 | 40.812 | 27.590 | 1.00 | 30.73 | C |
| ATOM | 1721 | N | TYR | A | 228 | 24.760 | 43.016 | 31.170 | 1.00 | 28.05 | N |
| ATOM | 1722 | CA | TYR | A | 228 | 25.034 | 43.219 | 32.596 | 1.00 | 28.59 | C |
| ATOM | 1723 | C | TYR | A | 228 | 25.051 | 41.978 | 33.504 | 1.00 | 29.27 | C |
| ATOM | 1724 | O | TYR | A | 228 | 24.253 | 41.863 | 34.483 | 1.00 | 29.59 | O |
| ATOM | 1725 | CE | TYR | A | 228 | 24.026 | 44.213 | 33.157 | 1.00 | 28.04 | C |
| ATOM | 1726 | CG | TYR | A | 228 | 24.019 | 45.556 | 32.464 | 1.00 | 28.00 | C |
| ATOM | 1727 | CD1 | TYR | A | 228 | 24.839 | 46.584 | 32.881 | 1.00 | 27.54 | C |
| ATOM | 1728 | CD2 | TYR | A | 228 | 23.177 | 45.799 | 31.389 | 1.00 | 28.83 | C |
| ATOM | 1729 | GE1 | TYR | A | 228 | 24.826 | 47.828 | 32.248 | 1.00 | 27.44 | C |
| ATOM | 1730 | CE2 | TYR | A | 228 | 23.160 | 47.018 | 30.745 | 1.00 | 27.63 | C |
| ATOM | 1731 | CZ | TYR | A | 228 | 23.964 | 48.040 | 31.186 | 1.00 | 29.01 | C |
| ATOM | 1732 | OH | TYR | A | 228 | 23.924 | 49.260 | 30.536 | 1.00 | 28.98 | O |
| ATOM | 1733 | N | PRO | A | 229 | 26.009 | 41.101 | 33.261 | 1.00 | 28.11 | N |
| ATOM | 1734 | CA | PRO | A | 229 | 26.146 | 39.900 | 34.082 | 1.00 | 28.54 | C |
| ATOM | 1735 | C | PRO | A | 229 | 26.424 | 40.223 | 35.534 | 1.00 | 27.88 | C |
| ATOM | 1736 | O | PRO | A | 229 | 27.085 | 41.212 | 35.786 | 1.00 | 28.01 | O |
| ATOM | 1737 | GB | PRO | A | 229 | 27.396 | 39.214 | 33.494 | 1.00 | 28.67 | C |
| ATOM | 1738 | CG | PRO | A | 229 | 28.116 | 40.314 | 32.802 | 1.00 | 28.96 | C |
| ATOM | 1739 | CD | PRO | A | 229 | 27.046 | 41.191 | 32.231 | 1.00 | 28.25 | C |
| ATOM | 1740 | N | TYR | A | 230 | 25.981 | 39.372 | 36.453 | 1.00 | 26.80 | N |
| ATOM | 1741 | CA | TYR | A | 230 | 26.296 | 39.542 | 37.840 | 1.00 | 25.91 | C |
| ATOM | 1742 | C | TYR | A | 230 | 27.838 | 39.508 | 38.028 | 1.00 | 25.72 | C |
| ATOM | 1743 | O | TYR | A | 230 | 28.582 | 39.094 | 37.167 | 1.00 | 25.79 | O |
| ATOM | 1744 | GB | TYR | A | 230 | 25.673 | 38.431 | 38.677 | 1.00 | 25.13 | C |
| ATOM | 1745 | CG | TYR | A | 230 | 24.193 | 38.523 | 38.900 | 1.00 | 24.95 | C |
| ATOM | 1746 | CD1 | TYR | A | 230 | 23.289 | 38.036 | 37.933 | 1.00 | 24.25 | C |
| ATOM | 1747 | CD2 | TYR | A | 230 | 23.675 | 39.063 | 40.090 | 1.00 | 25.16 | C |
| ATOM | 1748 | GE1 | TYR | A | 230 | 21.944 | 38.105 | 38.139 | 1.00 | 24.40 | C |
| ATOM | 1749 | CE2 | TYR | A | 230 | 22.311 | 39.114 | 40.320 | 1.00 | 23.86 | C |
| ATOM | 1750 | CZ | TYR | A | 230 | 21.464 | 38.647 | 39.336 | 1.00 | 26.74 | C |
| ATOM | 1751 | OH | TYR | A | 230 | 20.122 | 38.713 | 39.501 | 1.00 | 34.04 | O |
| ATOM | 1752 | N | PRO | A | 231 | 28.309 | 39.966 | 39.167 | 1.00 | 25.05 | N |
| ATOM | 1753 | CA | PRO | A | 231 | 29.711 | 39.806 | 39.517 | 1.00 | 24.73 | C |
| ATOM | 1754 | C | PRO | A | 231 | 30.151 | 38.318 | 39.500 | 1.00 | 24.94 | C |
| ATOM | 1755 | O | PRO | A | 231 | 29.359 | 37.410 | 39.817 | 1.00 | 24.30 | O |
| ATOM | 1756 | GB | PRO | A | 231 | 29.760 | 40.353 | 40.957 | 1.00 | 25.28 | C |
| ATOM | 1757 | CG | PRO | A | 231 | 28.613 | 41.331 | 41.016 | 1.00 | 25.28 | C |
| ATOM | 1758 | CD | PRO | A | 231 | 27.535 | 40.687 | 40.198 | 1.00 | 24.73 | C |
| ATOM | 1759 | N | VAL | A | 232 | 31.419 | 38.086 | 39.173 | 1.00 | 23.75 | N |
| ATOM | 1760 | CA | VAL | A | 232 | 31.898 | 36.766 | 39.055 | 1.00 | 24.45 | C |
| ATOM | 1761 | C | VAL | A | 232 | 31.725 | 35.935 | 40.351 | 1.00 | 24.83 | C |
| ATOM | 1762 | O | VAL | A | 232 | 31.402 | 34.754 | 40.263 | 1.00 | 24.83 | O |
| ATOM | 1763 | CB | VAL | A | 232 | 33.375 | 36.761 | 38.582 | 1.00 | 25.13 | C |
| ATOM | 1764 | CG1 | VAL | A | 232 | 33.974 | 35.405 | 38.828 | 1.00 | 23.91 | C |
| ATOM | 1765 | CG2 | VAL | A | 232 | 33.481 | 37.091 | 37.092 | 1.00 | 23.86 | C |
| ATOM | 1766 | N | HIS | A | 233 | 31.886 | 36.540 | 41.525 | 1.00 | 25.24 | N |
| ATOM | 1767 | CA | HIS | A | 233 | 31.766 | 35.806 | 42.790 | 1.00 | 26.43 | C |
| ATOM | 1768 | C | HIS | A | 233 | 30.321 | 35.656 | 43.304 | 1.00 | 26.47 | C |
| ATOM | 1769 | O | HIS | A | 233 | 30.052 | 34.986 | 44.289 | 1.00 | 26.08 | O |
| ATOM | 1770 | CB | HIS | A | 233 | 32.617 | 36.475 | 43.855 | 1.00 | 26.65 | C |
| ATOM | 1771 | CG | HIS | A | 233 | 34.078 | 36.428 | 43.564 | 1.00 | 28.51 | C |
| ATOM | 1772 | ND1 | HIS | A | 233 | 34.764 | 37.493 | 43.013 | 1.00 | 30.95 | N |

TABLE 3-continued

Coordinates for structures 1 to 4

| ATOM | 1773 | CD2 | HIS | A | 233 | 34.987 | 35.435 | 43.730 | 1.00 | 29.75 | C |
|---|---|---|---|---|---|---|---|---|---|---|---|
| ATOM | 1774 | GEl | HIS | A | 233 | 36.043 | 37.169 | 42.888 | 1.00 | 31.18 | C |
| ATOM | 1775 | NE2 | HIS | A | 233 | 36.201 | 35.919 | 43.302 | 1.00 | 32.10 | N |
| ATOM | 1776 | N | HIS | A | 234 | 29.391 | 36.283 | 42.626 | 1.00 | 26.94 | N |
| ATOM | 1777 | CA | HIS | A | 234 | 27.999 | 36.141 | 42.983 | 1.00 | 27.89 | C |
| ATOM | 1778 | C | HIS | A | 234 | 27.456 | 34.838 | 42.411 | 1.00 | 27.85 | C |
| ATOM | 1779 | O | HIS | A | 234 | 27.871 | 34.403 | 41.384 | 1.00 | 27.14 | O |
| ATOM | 1780 | CB | HIS | A | 234 | 27.219 | 37.258 | 42.372 | 1.00 | 28.20 | C |
| ATOM | 1781 | GG | HIS | A | 234 | 25.782 | 37.279 | 42.748 | 1.00 | 27.95 | C |
| ATOM | 1782 | NO1 | HIS | A | 234 | 24.840 | 36.514 | 42.092 | 1.00 | 30.05 | N |
| ATOM | 1783 | GD2 | HIS | A | 234 | 25.105 | 38.057 | 43.624 | 1.00 | 26.43 | C |
| ATOM | 1784 | CE1 | HIS | A | 234 | 23.644 | 36.789 | 42.588 | 1.00 | 29.87 | C |
| ATOM | 1785 | ND2 | HIS | A | 234 | 23.781 | 37.714 | 43.524 | 1.00 | 27.85 | N |
| ATOM | 1786 | N | PRO | A | 235 | 26.561 | 34.197 | 43.120 | 1.00 | 28.44 | N |
| ATOM | 1787 | CA | PRO | A | 235 | 26.018 | 32.929 | 42.678 | 1.00 | 28.87 | C |
| ATOM | 1788 | C | PRO | A | 235 | 25.431 | 32.956 | 41.294 | 1.00 | 28.34 | C |
| ATOM | 1789 | O | PRO | A | 235 | 25.387 | 31.884 | 40.716 | 1.00 | 28.04 | O |
| ATOM | 1790 | CB | PRO | A | 235 | 24.931 | 32.636 | 43.713 | 1.00 | 29.59 | C |
| ATOM | 1791 | CG | PRO | A | 235 | 25.473 | 33.290 | 44.975 | 1.00 | 29.10 | C |
| ATOM | 1792 | CD | PRO | A | 235 | 26.059 | 34.571 | 44.466 | 1.00 | 28.17 | C |
| ATOM | 1793 | N | CYS | A | 236 | 25.021 | 34.112 | 40.770 | 1.00 | 27.29 | N |
| ATOM | 1794 | CA | CYS | A | 236 | 24.447 | 34.135 | 39.455 | 1.00 | 26.15 | C |
| ATOM | 1795 | C | CYS | A | 236 | 25.478 | 34.602 | 38.451 | 1.00 | 25.39 | C |
| ATOM | 1796 | O | CYS | A | 236 | 25.140 | 35.102 | 37.361 | 1.00 | 26.21 | O |
| ATOM | 1797 | CE | CYS | A | 236 | 23.158 | 34.923 | 39.436 | 1.00 | 26.36 | C |
| ATOM | 1798 | SG | CYS | A | 236 | 21.908 | 34.207 | 40.555 | 1.00 | 29.77 | 5 |
| ATOM | 1799 | N | ASP | A | 237 | 26.746 | 34.411 | 38.803 | 1.00 | 24.07 | N |
| ATOM | 1800 | CA | ASP | A | 237 | 27.830 | 34.528 | 37.855 | 1.00 | 24.53 | C |
| ATOM | 1801 | C | ASP | A | 237 | 27.441 | 33.977 | 36.467 | 1.00 | 24.31 | C |
| ATOM | 1802 | O | ASP | A | 237 | 26.966 | 32.865 | 36.344 | 1.00 | 23.00 | O |
| ATOM | 1803 | CB | ASP | A | 237 | 29.018 | 33.769 | 38.353 | 1.00 | 24.42 | C |
| ATOM | 1804 | CG | ASP | A | 237 | 30.233 | 33.850 | 37.414 | 1.00 | 28.30 | C |
| ATOM | 1805 | OD1 | ASP | A | 237 | 30.433 | 34.877 | 36.673 | 1.00 | 29.51 | O |
| ATOM | 1806 | OD2 | ASP | A | 237 | 31.071 | 32.900 | 37.386 | 1.00 | 29.51 | O |
| ATOM | 1807 | N | ARG | A | 238 | 27.633 | 34.803 | 35.445 | 1.00 | 24.85 | N |
| ATOM | 1808 | CA | ARG | A | 238 | 27.388 | 34.434 | 34.041 | 1.00 | 26.59 | C |
| ATOM | 1809 | C | ARG | A | 238 | 25.921 | 34.663 | 33.595 | 1.00 | 25.95 | C |
| ATOM | 1810 | O | ARG | A | 238 | 25.647 | 34.628 | 32.426 | 1.00 | 26.55 | O |
| ATOM | 1811 | CE | ARG | A | 238 | 27.834 | 32.994 | 33.737 | 1.00 | 26.57 | C |
| ATOM | 1812 | CG | ARG | A | 238 | 29.311 | 32.758 | 33.891 | 1.00 | 27.77 | C |
| ATOM | 1813 | CD | ARG | A | 238 | 29.727 | 31.360 | 33.399 | 1.00 | 28.78 | C |
| ATOM | 1814 | NE | ARG | A | 238 | 29.142 | 30.434 | 34.337 | 1.00 | 33.68 | N |
| ATOM | 1815 | CZ | ARG | A | 238 | 28.046 | 29.736 | 34.140 | 1.00 | 36.98 | C |
| ATOM | 1816 | NH1 | ARG | A | 238 | 27.383 | 29.782 | 32.980 | 1.00 | 38.06 | N |
| ATOM | 1817 | NH2 | ARG | A | 238 | 27.609 | 28.987 | 35.129 | 1.00 | 37.87 | N |
| ATOM | 1818 | N | GLN | A | 239 | 25.012 | 34.933 | 34.516 | 1.00 | 25.97 | N |
| ATOM | 1819 | CA | GLN | A | 239 | 23.634 | 35.245 | 34.152 | 1.00 | 26.05 | C |
| ATOM | 1820 | C | GLN | A | 239 | 23.478 | 36.776 | 34.037 | 1.00 | 26.67 | C |
| ATOM | 1821 | O | GLN | A | 239 | 24.196 | 37.531 | 34.699 | 1.00 | 27.33 | O |
| ATOM | 1822 | CB | GLN | A | 239 | 22.663 | 34.724 | 35.201 | 1.00 | 25.55 | C |
| ATOM | 1823 | CG | GLN | A | 239 | 23.027 | 33.417 | 35.843 | 1.00 | 27.73 | C |
| ATOM | 1824 | CD | GLN | A | 239 | 23.246 | 32.282 | 34.859 | 1.00 | 31.42 | C |
| ATOM | 1825 | OE1 | GLN | A | 239 | 22.332 | 31.881 | 34.133 | 1.00 | 34.43 | O |
| ATOM | 1826 | NE2 | GLN | A | 239 | 24.457 | 31.761 | 34.835 | 1.00 | 31.35 | N |
| ATOM | 1827 | N | SER | A | 240 | 22.569 | 37.233 | 33.185 | 1.00 | 26.94 | N |
| ATOM | 1828 | CA | SER | A | 240 | 22.293 | 38.653 | 33.034 | 1.00 | 26.93 | C |
| ATOM | 1829 | C | SER | A | 240 | 21.490 | 39.118 | 34.229 | 1.00 | 26.78 | C |
| ATOM | 1830 | O | SER | A | 240 | 20.642 | 38.389 | 34.703 | 1.00 | 27.00 | O |
| ATOM | 1831 | CB | SER | A | 240 | 21.414 | 38.891 | 31.818 | 1.00 | 26.95 | C |
| ATOM | 1832 | OG | SER | A | 240 | 20.916 | 40.234 | 31.804 | 1.00 | 27.75 | O |
| ATOM | 1833 | N | GLN | A | 241 | 21.733 | 40.331 | 34.696 | 1.00 | 26.90 | N |
| ATOM | 1834 | CA | GLN | A | 241 | 20.963 | 40.903 | 35.816 | 1.00 | 27.25 | C |
| ATOM | 1835 | C | GLN | A | 241 | 19.632 | 41.520 | 35.311 | 1.00 | 27.84 | C |
| ATOM | 1836 | O | GLN | A | 241 | 18.763 | 41.866 | 36.104 | 1.00 | 27.28 | O |
| ATOM | 1837 | CB | GLN | A | 241 | 21.734 | 42.009 | 36.546 | 1.00 | 26.21 | C |
| ATOM | 1838 | CG | GLN | A | 241 | 22.971 | 41.636 | 37.344 | 1.00 | 26.53 | C |
| ATOM | 1839 | CD | GLN | A | 241 | 23.740 | 42.877 | 37.817 | 1.00 | 26.65 | C |
| ATOM | 1840 | OE1 | GLN | A | 241 | 23.436 | 43.425 | 38.859 | 1.00 | 31.02 | O |
| ATOM | 1841 | NE2 | GLN | A | 241 | 24.714 | 43.318 | 37.048 | 1.00 | 28.00 | N |
| ATOM | 1842 | N | VAL | A | 242 | 19.464 | 41.657 | 34.004 | 1.00 | 28.19 | N |
| ATOM | 1843 | CA | VAL | A | 242 | 18.284 | 42.335 | 33.552 | 1.00 | 28.55 | C |
| ATOM | 1844 | C | VAL | A | 242 | 17.117 | 41.409 | 33.563 | 1.00 | 28.88 | C |
| ATOM | 1845 | O | VAL | A | 242 | 17.198 | 40.314 | 33.053 | 1.00 | 28.92 | O |
| ATOM | 1846 | CB | VAL | A | 242 | 18.422 | 42.770 | 32.093 | 1.00 | 29.31 | C |
| ATOM | 1847 | CG1 | VAL | A | 242 | 17.165 | 43.549 | 31.647 | 1.00 | 27.90 | C |
| ATOM | 1848 | CG2 | VAL | A | 242 | 19.711 | 43.530 | 31.866 | 1.00 | 28.67 | C |
| ATOM | 1849 | N | ASP | A | 243 | 16.009 | 41.862 | 34.113 | 1.00 | 28.55 | N |

TABLE 3-continued

| | | | | | Coordinates for structures 1 to 4 | | | | | |
|---|---|---|---|---|---|---|---|---|---|---|
| ATOM | 1850 | CA | ASP | A | 243 | 14.766 | 41.103 | 34.052 | 1.00 | 27.62 | C |
| ATOM | 1851 | C | ASP | A | 243 | 14.121 | 41.396 | 32.709 | 1.00 | 27.45 | C |
| ATOM | 1852 | O | ASP | A | 243 | 13.579 | 42.480 | 32.452 | 1.00 | 25.90 | O |
| ATOM | 1853 | GB | ASP | A | 243 | 13.876 | 41.560 | 35.193 | 1.00 | 27.99 | C |
| ATOM | 1854 | CG | ASP | A | 243 | 12.509 | 40.945 | 35.177 | 1.00 | 29.40 | C |
| ATOM | 1855 | OD1 | ASP | A | 243 | 12.096 | 40.291 | 34.179 | 1.00 | 31.46 | O |
| ATOM | 1856 | OD2 | ASP | A | 243 | 11.747 | 41.110 | 36.161 | 1.00 | 32.65 | O |
| ATOM | 1857 | N | PHE | A | 244 | 14.180 | 40.419 | 31.825 | 1.00 | 28.27 | N |
| ATOM | 1858 | CA | PHE | A | 244 | 13.656 | 40.603 | 30.496 | 1.00 | 28.92 | C |
| ATOM | 1859 | C | PHE | A | 244 | 12.172 | 40.975 | 30.481 | 1.00 | 30.32 | C |
| ATOM | 1860 | O | PHE | A | 244 | 11.728 | 41.643 | 29.561 | 1.00 | 31.01 | O |
| ATOM | 1861 | GB | PHE | A | 244 | 13.900 | 39.369 | 29.657 | 1.00 | 29.32 | C |
| ATOM | 1862 | CG | PHE | A | 244 | 15.255 | 39.298 | 29.053 | 1.00 | 28.51 | C |
| ATOM | 1863 | CD1 | PHE | A | 244 | 16.397 | 39.628 | 29.775 | 1.00 | 31.29 | C |
| ATOM | 1864 | CD2 | PHE | A | 244 | 15.399 | 38.853 | 27.793 | 1.00 | 28.23 | C |
| ATOM | 1865 | CE1 | PHE | A | 244 | 17.649 | 39.535 | 29.196 | 1.00 | 29.39 | C |
| ATOM | 1866 | CE2 | PHE | A | 244 | 16.654 | 38.736 | 27.229 | 1.00 | 30.79 | C |
| ATOM | 1867 | CZ | PHE | A | 244 | 17.759 | 39.107 | 27.919 | 1.00 | 29.44 | C |
| ATOM | 1868 | N | ASP | A | 245 | 11.401 | 40.551 | 31.482 | 1.00 | 31.22 | N |
| ATOM | 1869 | CA | ASP | A | 245 | 10.007 | 40.913 | 31.544 | 1.00 | 31.40 | C |
| ATOM | 1870 | C | ASP | A | 245 | 9.770 | 42.349 | 32.032 | 1.00 | 31.91 | C |
| ATOM | 1871 | O | ASP | A | 245 | 8.704 | 42.891 | 31.786 | 1.00 | 30.40 | C |
| ATOM | 1872 | CB | ASP | A | 245 | 9.263 | 39.968 | 32.467 | 1.00 | 32.57 | C |
| ATOM | 1873 | CG | ASP | A | 245 | 9.292 | 38.546 | 31.988 | 1.00 | 33.29 | C |
| ATOM | 1874 | OD1 | ASP | A | 245 | 9.289 | 38.333 | 30.768 | 1.00 | 35.51 | O |
| ATOM | 1875 | OD2 | ASP | A | 245 | 9.348 | 37.577 | 32.764 | 1.00 | 35.50 | O |
| ATOM | 1876 | N | ASN | A | 246 | 10.735 | 42.954 | 32.731 | 1.00 | 32.07 | N |
| ATOM | 1877 | CA | ASN | A | 246 | 10.562 | 44.310 | 33.244 | 1.00 | 33.10 | C |
| ATOM | 1878 | C | ASN | A | 246 | 11.884 | 45.016 | 33.384 | 1.00 | 32.49 | C |
| ATOM | 1879 | O | ASN | A | 246 | 12.400 | 45.179 | 34.476 | 1.00 | 33.20 | O |
| ATOM | 1880 | GB | ASN | A | 246 | 9.873 | 44.296 | 34.603 | 1.00 | 33.31 | C |
| ATOM | 1881 | CG | ASN | A | 246 | 9.555 | 45.716 | 35.110 | 1.00 | 39.27 | C |
| ATOM | 1882 | OD1 | ASN | A | 246 | 9.331 | 46.678 | 34.313 | 1.00 | 43.28 | O |
| ATOM | 1883 | ND2 | ASN | A | 246 | 9.551 | 45.867 | 36.445 | 1.00 | 44.32 | N |
| ATOM | 1884 | N | PRO | A | 247 | 12.472 | 45.374 | 32.265 | 1.00 | 31.66 | N |
| ATOM | 1885 | CA | PRO | A | 247 | 13.822 | 45.936 | 32.263 | 1.00 | 31.26 | C |
| ATOM | 1886 | C | PRO | A | 247 | 13.924 | 47.298 | 32.933 | 1.00 | 31.58 | C |
| ATOM | 1887 | O | PRO | A | 247 | 13.185 | 48.211 | 32.629 | 1.00 | 31.85 | O |
| ATOM | 1888 | GB | PRO | A | 247 | 14.161 | 46.082 | 30.782 | 1.00 | 31.22 | C |
| ATOM | 1889 | CG | PRO | A | 247 | 13.017 | 45.510 | 30.022 | 1.00 | 31.05 | C |
| ATOM | 1890 | CD | PRO | A | 247 | 11.894 | 45.216 | 30.928 | 1.00 | 31.01 | C |
| ATOM | 1891 | N | ASP | A | 248 | 14.893 | 47.422 | 33.815 | 1.00 | 31.35 | N |
| ATOM | 1892 | CA | ASP | A | 248 | 15.161 | 48.643 | 34.467 | 1.00 | 31.48 | C |
| ATOM | 1893 | C | ASP | A | 248 | 16.222 | 49.413 | 33.650 | 1.00 | 31.23 | C |
| ATOM | 1894 | O | ASP | A | 248 | 17.422 | 49.217 | 33.784 | 1.00 | 30.76 | O |
| ATOM | 1895 | GB | ASP | A | 248 | 15.646 | 48.310 | 35.850 | 1.00 | 31.60 | C |
| ATOM | 1896 | CG | ASP | A | 248 | 15.745 | 49.504 | 36.720 | 1.00 | 33.62 | C |
| ATOM | 1897 | OD1 | ASP | A | 248 | 16.020 | 50.619 | 36.201 | 1.00 | 34.39 | O |
| ATOM | 1898 | OD2 | ASP | A | 248 | 15.578 | 49.395 | 37.949 | 1.00 | 38.39 | O |
| ATOM | 1899 | N | TYR | A | 249 | 15.764 | 50.285 | 32.783 | 1.00 | 31.95 | N |
| ATOM | 1900 | CA | TYR | A | 249 | 16.676 | 51.053 | 31.942 | 1.00 | 32.80 | C |
| ATOM | 1901 | C | TYR | A | 249 | 17.534 | 52.052 | 32.714 | 1.00 | 33.92 | C |
| ATOM | 1902 | O | TYR | A | 249 | 18.558 | 52.490 | 32.203 | 1.00 | 34.33 | O |
| ATOM | 1903 | GB | TYR | A | 249 | 15.906 | 51.732 | 30.825 | 1.00 | 32.56 | C |
| ATOM | 1904 | CG | TYR | A | 249 | 15.183 | 50.751 | 29.928 | 1.00 | 31.41 | C |
| ATOM | 1905 | CO1 | TYR | A | 249 | 15.859 | 49.695 | 29.316 | 1.00 | 30.27 | C |
| ATOM | 1906 | CD2 | TYR | A | 249 | 13.845 | 50.868 | 29.704 | 1.00 | 29.24 | C |
| ATOM | 1907 | GE1 | TYR | A | 249 | 15.205 | 48.814 | 28.478 | 1.00 | 29.30 | C |
| ATOM | 1908 | CE2 | TYR | A | 249 | 13.178 | 49.968 | 28.894 | 1.00 | 29.24 | C |
| ATOM | 1909 | GZ | TYR | A | 249 | 13.858 | 48.947 | 28.285 | 1.00 | 29.20 | C |
| ATOM | 1910 | OH | TYR | A | 249 | 13.173 | 48.078 | 27.452 | 1.00 | 29.69 | O |
| ATOM | 1911 | N | GLU | A | 250 | 17.155 | 52.369 | 33.952 | 1.00 | 34.69 | N |
| ATOM | 1912 | CA | GLU | A | 250 | 17.994 | 53.202 | 34.789 | 1.00 | 35.66 | C |
| ATOM | 1913 | C | GLU | A | 250 | 19.249 | 52.494 | 35.235 | 1.00 | 34.69 | C |
| ATOM | 1914 | O | GLU | A | 250 | 20.313 | 53.077 | 35.207 | 1.00 | 34.29 | O |
| ATOM | 1915 | CB | GLU | A | 250 | 17.252 | 53.685 | 36.021 | 1.00 | 36.82 | C |
| ATOM | 1916 | CG | GLU | A | 250 | 16.115 | 54.609 | 35.650 | 1.00 | 41.99 | C |
| ATOM | 1917 | CD | GLU | A | 250 | 15.554 | 55.360 | 36.827 | 1.00 | 48.02 | C |
| ATOM | 1918 | OE1 | GLU | A | 250 | 16.114 | 55.275 | 37.949 | 1.00 | 53.95 | O |
| ATOM | 1919 | OE2 | GLU | A | 250 | 14.543 | 56.043 | 36.614 | 1.00 | 52.47 | O |
| ATOM | 1920 | N | ARG | A | 251 | 19.139 | 51.254 | 35.691 | 1.00 | 33.87 | N |
| ATOM | 1921 | CA | ARG | A | 251 | 20.335 | 50.550 | 36.088 | 1.00 | 33.26 | C |
| ATOM | 1922 | C | ARG | A | 251 | 21.013 | 49.992 | 34.873 | 1.00 | 32.36 | C |
| ATOM | 1923 | O | ARG | A | 251 | 22.210 | 49.914 | 34.849 | 1.00 | 32.79 | O |
| ATOM | 1924 | CB | ARG | A | 251 | 20.040 | 49.425 | 37.066 | 1.00 | 34.36 | C |
| ATOM | 1925 | CG | ARG | A | 251 | 19.476 | 49.895 | 38.425 | 1.00 | 36.13 | C |
| ATOM | 1926 | CD | ARG | A | 251 | 18.966 | 48.771 | 39.339 | 1.00 | 39.31 | C |

TABLE 3-continued

Coordinates for structures 1 to 4

| ATOM | 1927 | NE | ARG | A | 251 | 20.052 | 47.860 | 39.733 | 1.00 | 42.09 | N |
|------|------|------|-----|---|-----|--------|--------|--------|------|-------|---|
| ATOM | 1928 | CZ | ARG | A | 251 | 19.890 | 46.563 | 39.964 | 1.00 | 41.90 | C |
| ATOM | 1929 | NH1 | ARG | A | 251 | 18.696 | 46.006 | 39.843 | 1.00 | 41.62 | N |
| ATOM | 1930 | NH2 | ARG | A | 251 | 20.932 | 45.815 | 40.296 | 1.00 | 41.98 | N |
| ATOM | 1931 | N | PHE | A | 252 | 20.272 | 49.654 | 33.825 | 1.00 | 31.66 | N |
| ATOM | 1932 | CA | PHE | A | 252 | 20.879 | 48.977 | 32.677 | 1.00 | 30.28 | C |
| ATOM | 1933 | C | PHE | A | 252 | 20.528 | 49.651 | 31.347 | 1.00 | 29.72 | C |
| ATOM | 1934 | O | PHE | A | 252 | 19.882 | 49.096 | 30.483 | 1.00 | 29.84 | O |
| ATOM | 1935 | CB | PHE | A | 252 | 20.420 | 47.531 | 32.675 | 1.00 | 29.99 | C |
| ATOM | 1936 | CG | PHE | A | 252 | 20.405 | 46.864 | 34.050 | 1.00 | 29.63 | C |
| ATOM | 1937 | CD1 | PHE | A | 252 | 21.562 | 46.717 | 34.796 | 1.00 | 29.74 | C |
| ATOM | 1938 | CD2 | PHE | A | 252 | 19.238 | 46.317 | 34.554 | 1.00 | 31.30 | C |
| ATOM | 1939 | CE1 | PHE | A | 252 | 21.546 | 46.067 | 36.039 | 1.00 | 30.44 | C |
| ATOM | 1940 | CE2 | PHE | A | 252 | 19.199 | 45.668 | 35.805 | 1.00 | 31.42 | C |
| ATOM | 1941 | CZ | PHE | A | 252 | 20.356 | 45.551 | 36.550 | 1.00 | 32.04 | C |
| ATOM | 1942 | N | PRO | A | 253 | 21.034 | 50.844 | 31.155 | 1.00 | 29.72 | N |
| ATOM | 1943 | CA | PRO | A | 253 | 20.607 | 51.662 | 30.022 | 1.00 | 28.89 | C |
| ATOM | 1944 | C | PRO | A | 253 | 20.953 | 50.996 | 28.689 | 1.00 | 29.46 | C |
| ATOM | 1945 | O | PRO | A | 253 | 20.166 | 51.061 | 27.722 | 1.00 | 28.81 | O |
| ATOM | 1946 | CB | PRO | A | 253 | 21.361 | 52.975 | 30.240 | 1.00 | 28.37 | C |
| ATOM | 1947 | CG | PRO | A | 253 | 22.543 | 52.614 | 31.155 | 1.00 | 27.97 | C |
| ATOM | 1948 | CD | PRO | A | 253 | 22.136 | 51.463 | 31.942 | 1.00 | 29.24 | C |
| ATOM | 1949 | N | ASN | A | 254 | 22.093 | 50.323 | 28.590 | 1.00 | 29.37 | N |
| ATOM | 1950 | CA | ASN | A | 254 | 22.401 | 49.742 | 27.274 | 1.00 | 28.85 | C |
| ATOM | 1951 | C | ASN | A | 254 | 21.547 | 48.529 | 26.902 | 1.00 | 28.28 | C |
| ATOM | 1952 | O | ASN | A | 254 | 21.663 | 47.970 | 25.794 | 1.00 | 27.47 | O |
| ATOM | 1953 | CB | ASN | A | 254 | 23.874 | 49.407 | 27.122 | 1.00 | 28.84 | C |
| ATOM | 1954 | CG | ASN | A | 254 | 24.745 | 50.654 | 26.996 | 1.00 | 29.96 | C |
| ATOM | 1955 | OD1 | ASN | A | 254 | 25.622 | 50.882 | 27.834 | 1.00 | 31.21 | O |
| ATOM | 1956 | ND2 | ASN | A | 254 | 24.531 | 51.443 | 25.931 | 1.00 | 29.17 | N |
| ATOM | 1957 | N | PHE | A | 255 | 20.687 | 48.091 | 27.797 | 1.00 | 27.30 | N |
| ATOM | 1958 | CA | PHE | A | 255 | 19.801 | 47.006 | 27.368 | 1.00 | 27.53 | C |
| ATOM | 1959 | C | PHE | A | 255 | 18.844 | 47.512 | 26.283 | 1.00 | 26.80 | C |
| ATOM | 1960 | O | PHE | A | 255 | 18.193 | 46.750 | 25.603 | 1.00 | 27.22 | O |
| ATOM | 1961 | CB | PHE | A | 255 | 19.015 | 46.448 | 28.538 | 1.00 | 27.48 | C |
| ATOM | 1962 | CG | PHE | A | 255 | 18.282 | 45.250 | 28.198 | 1.00 | 26.63 | C |
| ATOM | 1963 | CD1 | PHE | A | 255 | 18.950 | 44.073 | 27.998 | 1.00 | 29.74 | C |
| ATOM | 1964 | CD2 | PHE | A | 255 | 16.935 | 45.288 | 28.039 | 1.00 | 26.29 | C |
| ATOM | 1965 | CE1 | PHE | A | 255 | 18.273 | 42.947 | 27.681 | 1.00 | 29.50 | C |
| ATOM | 1966 | CE2 | PHE | A | 255 | 16.261 | 44.192 | 27.692 | 1.00 | 26.21 | C |
| ATOM | 1967 | CZ | PHE | A | 255 | 16.917 | 43.012 | 27.518 | 1.00 | 30.10 | C |
| ATOM | 1968 | N | GLN | A | 256 | 18.776 | 48.818 | 26.125 | 1.00 | 26.57 | N |
| ATOM | 1969 | CA | GLN | A | 256 | 17.918 | 49.429 | 25.137 | 1.00 | 26.55 | C |
| ATOM | 1970 | C | GLN | A | 256 | 18.522 | 49.253 | 23.745 | 1.00 | 26.46 | C |
| ATOM | 1971 | O | GLN | A | 256 | 17.881 | 49.560 | 22.771 | 1.00 | 24.39 | O |
| ATOM | 1972 | CB | GLN | A | 256 | 17.756 | 50.933 | 25.423 | 1.00 | 26.18 | C |
| ATOM | 1973 | CG | GLN | A | 256 | 16.656 | 51.226 | 26.406 | 1.00 | 28.72 | C |
| ATOM | 1974 | CD | GLN | A | 256 | 16.721 | 52.636 | 27.028 | 1.00 | 29.64 | C |
| ATOM | 1975 | OE1 | GLN | A | 256 | 15.737 | 53.358 | 27.005 | 1.00 | 32.56 | O |
| ATOM | 1976 | NE2 | GLN | A | 256 | 17.861 | 52.999 | 27.590 | 1.00 | 26.88 | N |
| ATOM | 1977 | N | ASN | A | 257 | 19.774 | 48.809 | 23.694 | 1.00 | 27.86 | N |
| ATOM | 1978 | CA | ASN | A | 257 | 20.509 | 48.611 | 22.452 | 1.00 | 29.22 | C |
| ATOM | 1979 | C | ASN | A | 257 | 20.733 | 47.143 | 22.116 | 1.00 | 30.46 | C |
| ATOM | 1980 | O | ASN | A | 257 | 21.399 | 46.855 | 21.132 | 1.00 | 32.28 | O |
| ATOM | 1981 | CB | ASN | A | 257 | 21.897 | 49.232 | 22.510 | 1.00 | 28.50 | C |
| ATOM | 1982 | CG | ASN | A | 257 | 21.878 | 50.666 | 22.890 | 1.00 | 29.30 | C |
| ATOM | 1983 | OD1 | ASN | A | 257 | 22.329 | 51.025 | 23.989 | 1.00 | 27.33 | O |
| ATOM | 1984 | ND2 | ASN | A | 257 | 21.382 | 51.523 | 21.982 | 1.00 | 25.68 | N |
| ATOM | 1985 | N | VAL | A | 258 | 20.200 | 46.213 | 22.900 | 1.00 | 31.51 | N |
| ATOM | 1986 | CA | VAL | A | 258 | 20.432 | 44.791 | 22.623 | 1.00 | 32.54 | C |
| ATOM | 1987 | C | VAL | A | 258 | 19.674 | 44.295 | 21.386 | 1.00 | 32.39 | C |
| ATOM | 1988 | O | VAL | A | 258 | 18.543 | 44.766 | 21.081 | 1.00 | 32.29 | O |
| ATOM | 1989 | CB | VAL | A | 258 | 20.050 | 43.937 | 23.841 | 1.00 | 33.12 | C |
| ATOM | 1990 | CG1 | VAL | A | 258 | 18.546 | 43.818 | 23.986 | 1.00 | 32.40 | C |
| ATOM | 1991 | CG2 | VAL | A | 258 | 20.646 | 42.566 | 23.686 | 1.00 | 36.78 | C |
| ATOM | 1992 | N | VAL | A | 259 | 20.302 | 43.386 | 20.654 | 1.00 | 32.45 | N |
| ATOM | 1993 | CA | VAL | A | 259 | 19.682 | 42.796 | 19.448 | 1.00 | 32.96 | C |
| ATOM | 1994 | C | VAL | A | 259 | 19.943 | 41.301 | 19.391 | 1.00 | 33.08 | C |
| ATOM | 1995 | O | VAL | A | 259 | 21.074 | 40.878 | 19.351 | 1.00 | 33.50 | O |
| ATOM | 1996 | CB | VAL | A | 259 | 20.269 | 43.401 | 18.172 | 1.00 | 33.19 | C |
| ATOM | 1997 | CG1 | VAL | A | 259 | 19.625 | 42.771 | 16.962 | 1.00 | 34.73 | C |
| ATOM | 1998 | CG2 | VAL | A | 259 | 20.054 | 44.901 | 18.143 | 1.00 | 32.25 | C |
| ATOM | 1999 | N | GLY | A | 260 | 18.902 | 40.491 | 19.406 | 1.00 | 33.70 | N |
| ATOM | 2000 | CA | GLY | A | 260 | 19.091 | 39.052 | 19.368 | 1.00 | 34.16 | C |
| ATOM | 2001 | C | GLY | A | 260 | 19.036 | 38.327 | 18.014 | 1.00 | 33.92 | C |
| ATOM | 2002 | O | GLY | A | 260 | 18.655 | 38.891 | 16.975 | 1.00 | 33.59 | O |
| ATOM | 2003 | N | TYR | A | 261 | 19.469 | 37.071 | 18.052 | 1.00 | 33.14 | N |

TABLE 3-continued

| | | | | | | Coordinates for structures 1 to 4 | | | | |
|---|---|---|---|---|---|---|---|---|---|---|
| ATOM | 2004 | CA | TYR | A | 261 | 19.375 | 36.157 | 16.938 | 1.00 | 33.55 | C |
| ATOM | 2005 | C | TYR | A | 261 | 18.439 | 35.095 | 17.489 | 1.00 | 33.41 | C |
| ATOM | 2006 | O | TYR | A | 261 | 18.700 | 34.542 | 18.561 | 1.00 | 33.67 | O |
| ATOM | 2007 | CB | TYR | A | 261 | 20.715 | 35.508 | 16.657 | 1.00 | 33.81 | C |
| ATOM | 2008 | CG | TYR | A | 261 | 21.758 | 36.416 | 16.061 | 1.00 | 36.80 | C |
| ATOM | 2009 | CD1 | TYR | A | 261 | 21.886 | 36.545 | 14.694 | 1.00 | 42.37 | C |
| ATOM | 2010 | CD2 | TYR | A | 261 | 22.602 | 37.139 | 16.851 | 1.00 | 38.31 | C |
| ATOM | 2011 | CE1 | TYR | A | 261 | 22.823 | 37.378 | 14.139 | 1.00 | 43.02 | C |
| ATOM | 2012 | CE2 | TYR | A | 261 | 23.556 | 37.938 | 16.312 | 1.00 | 40.85 | C |
| ATOM | 2013 | CZ | TYR | A | 261 | 23.660 | 38.058 | 14.955 | 1.00 | 42.50 | C |
| ATOM | 2014 | OH | TYR | A | 261 | 24.617 | 38.865 | 14.414 | 1.00 | 45.43 | O |
| ATOM | 2015 | N | GLU | A | 262 | 17.322 | 34.832 | 16.834 | 1.00 | 32.71 | N |
| ATOM | 2016 | CA | GLU | A | 262 | 16.394 | 33.886 | 17.438 | 1.00 | 32.21 | C |
| ATOM | 2017 | C | GLU | A | 262 | 15.975 | 32.768 | 16.508 | 1.00 | 30.89 | C |
| ATOM | 2018 | O | GLU | A | 262 | 16.180 | 32.819 | 15.294 | 1.00 | 30.63 | O |
| ATOM | 2019 | CB | GLU | A | 262 | 15.196 | 34.613 | 18.049 | 1.00 | 32.16 | C |
| ATOM | 2020 | CG | GLU | A | 262 | 13.968 | 34.753 | 17.210 | 1.00 | 30.84 | C |
| ATOM | 2021 | CD | GLU | A | 262 | 12.818 | 35.380 | 17.992 | 1.00 | 31.21 | C |
| ATOM | 2022 | OE1 | GLU | A | 262 | 12.761 | 36.612 | 18.108 | 1.00 | 34.58 | O |
| ATOM | 2023 | OE2 | GLU | A | 262 | 11.962 | 34.663 | 18.504 | 1.00 | 29.56 | O |
| ATOM | 2024 | N | THR | A | 263 | 15.447 | 31.746 | 17.133 | 1.00 | 28.97 | N |
| ATOM | 2025 | CA | THR | A | 263 | 14.941 | 30.587 | 16.447 | 1.00 | 28.44 | C |
| ATOM | 2026 | C | THR | A | 263 | 14.080 | 29.743 | 17.387 | 1.00 | 27.24 | C |
| ATOM | 2027 | O | THR | A | 263 | 14.088 | 29.893 | 18.620 | 1.00 | 26.43 | O |
| ATOM | 2028 | CB | THR | A | 263 | 16.093 | 29.746 | 15.9d2 | 1.00 | 28.50 | C |
| ATOM | 2029 | OG1 | THR | A | 263 | 15.592 | 28.798 | 14.964 | 1.00 | 27.18 | O |
| ATOM | 2030 | CG2 | THR | A | 263 | 16.697 | 28.854 | 16.975 | 1.00 | 28.63 | C |
| ATOM | 2031 | N | VAL | A | 264 | 13.306 | 28.887 | 16.776 | 1.00 | 27.22 | N |
| ATOM | 2032 | CA | VAL | A | 264 | 12.509 | 27.942 | 17.497 | 1.00 | 28.49 | C |
| ATOM | 2033 | C | VAL | A | 264 | 12.925 | 26.576 | 17.022 | 1.00 | 29.10 | C |
| ATOM | 2034 | O | VAL | A | 264 | 12.876 | 26.279 | 15.828 | 1.00 | 28.47 | O |
| ATOM | 2035 | CB | VAL | A | 264 | 11.025 | 28.126 | 17.252 | 1.00 | 29.23 | C |
| ATOM | 2036 | OG1 | VAL | A | 264 | 10.259 | 26.871 | 17.767 | 1.00 | 29.07 | C |
| ATOM | 2037 | CG2 | VAL | A | 264 | 10.520 | 29.431 | 17.973 | 1.00 | 28.52 | C |
| ATOM | 2038 | N | VAL | A | 265 | 13.401 | 25.763 | 17.954 | 1.00 | 29.56 | N |
| ATOM | 2039 | CA | VAL | A | 265 | 13.806 | 24.413 | 17.594 | 1.00 | 29.83 | C |
| ATOM | 2040 | C | VAL | A | 265 | 12.785 | 23.404 | 18.039 | 1.00 | 29.63 | C |
| ATOM | 2041 | O | VAL | A | 265 | 12.188 | 23.544 | 19.105 | 1.00 | 29.93 | O |
| ATOM | 2042 | CB | VAL | A | 265 | 15.197 | 24.015 | 18.203 | 1.00 | 29.88 | C |
| ATOM | 2043 | CG1 | VAL | A | 265 | 16.281 | 24.883 | 17.589 | 1.00 | 32.24 | C |
| ATOM | 2044 | CG2 | VAL | A | 265 | 15.234 | 24.114 | 19.712 | 1.00 | 26.80 | C |
| ATOM | 2045 | N | GLY | A | 266 | 12.642 | 22.371 | 17.226 | 1.00 | 28.96 | N |
| ATOM | 2046 | CA | GLY | A | 266 | 11.770 | 21.268 | 17.513 | 1.00 | 28.86 | C |
| ATOM | 2047 | C | GLY | A | 266 | 12.463 | 19.909 | 17.428 | 1.00 | 28.32 | C |
| ATOM | 2048 | O | GLY | A | 266 | 13.656 | 19.804 | 17.215 | 1.00 | 28.58 | O |
| ATOM | 2049 | N | PRO | A | 267 | 11.696 | 18.852 | 17.581 | 1.00 | 28.06 | N |
| ATOM | 2050 | CA | PRO | A | 267 | 12.278 | 17.505 | 17.565 | 1.00 | 28.37 | C |
| ATOM | 2051 | C | PRO | A | 267 | 13.148 | 17.313 | 16.360 | 1.00 | 28.01 | C |
| ATOM | 2052 | O | PRO | A | 267 | 12.674 | 17.573 | 15.265 | 1.00 | 28.36 | O |
| ATOM | 2053 | CB | PRO | A | 267 | 11.047 | 16.582 | 17.482 | 1.00 | 27.55 | C |
| ATOM | 2054 | CG | PRO | A | 267 | 10.000 | 17.278 | 18.220 | 1.00 | 28.05 | C |
| ATOM | 2055 | CD | PRO | A | 267 | 10.237 | 18.817 | 17.827 | 1.00 | 28.2B | C |
| ATOM | 2056 | N | GLY | A | 268 | 14.392 | 16.878 | 16.562 | 1.00 | 27.37 | N |
| ATOM | 2057 | CA | GLY | A | 268 | 15.273 | 16.605 | 15.453 | 1.00 | 25.78 | C |
| ATOM | 2058 | C | GLY | A | 268 | 16.231 | 17.726 | 15.175 | 1.00 | 25.51 | C |
| ATOM | 2059 | O | GLY | A | 268 | 17.237 | 17.508 | 14.519 | 1.00 | 26.07 | O |
| ATOM | 2060 | N | ASP | A | 269 | 15.957 | 18.928 | 15.653 | 1.00 | 25.79 | N |
| ATOM | 2061 | CA | ASP | A | 269 | 16.835 | 20.044 | 15.354 | 1.00 | 25.78 | C |
| ATOM | 2062 | C | ASP | A | 269 | 17.996 | 20.091 | 16.377 | 1.00 | 26.28 | C |
| ATOM | 2063 | O | ASP | A | 269 | 17.848 | 19.689 | 17.549 | 1.00 | 26.27 | O |
| ATOM | 2064 | CB | ASP | A | 269 | 16.106 | 21.376 | 15.504 | 1.00 | 26.89 | C |
| ATOM | 2065 | CG | ASP | A | 269 | 14.898 | 21.583 | 14.603 | 1.00 | 25.99 | C |
| ATOM | 2066 | OD1 | ASP | A | 269 | 14.745 | 20.966 | 13.562 | 1.00 | 28.50 | O |
| ATOM | 2067 | OD2 | ASP | A | 269 | 14.065 | 22.495 | 14.853 | 1.00 | 29.93 | O |
| ATOM | 2068 | N | VAL | A | 270 | 19.128 | 20.632 | 15.937 | 1.00 | 26.28 | N |
| ATOM | 2069 | CA | VAL | A | 270 | 20.291 | 20.847 | 16.775 | 1.00 | 26.03 | C |
| ATOM | 2070 | C | VAL | A | 270 | 20.780 | 22.271 | 16.628 | 1.00 | 26.03 | C |
| ATOM | 2071 | O | VAL | A | 270 | 21.123 | 22.727 | 15.547 | 1.00 | 25.72 | O |
| ATOM | 2072 | CB | VAL | A | 270 | 21.414 | 19.938 | 16.381 | 1.00 | 25.76 | C |
| ATOM | 2073 | CG1 | VAL | A | 270 | 22.675 | 20.325 | 17.113 | 1.00 | 26.27 | C |
| ATOM | 2074 | CG2 | VAL | A | 270 | 21.060 | 18.546 | 16.735 | 1.00 | 25.93 | C |
| ATOM | 2075 | N | LEU | A | 271 | 20.809 | 22.987 | 17.730 | 1.00 | 26.47 | N |
| ATOM | 2076 | CA | LEU | A | 271 | 21.257 | 24.364 | 17.713 | 1.00 | 26.42 | C |
| ATOM | 2077 | C | LEU | A | 271 | 22.673 | 24.422 | 18.228 | 1.00 | 27.12 | C |
| ATOM | 2078 | O | LEU | A | 271 | 22.973 | 23.936 | 19.310 | 1.00 | 26.82 | O |
| ATOM | 2079 | CB | LEU | A | 271 | 20.372 | 25.235 | 18.570 | 1.00 | 26.20 | C |
| ATOM | 2080 | CG | LEU | A | 271 | 20.935 | 26.646 | 18.783 | 1.00 | 27.91 | C |

TABLE 3-continued

Coordinates for structures 1 to 4

| ATOM | 2081 | CD1 | LEU | A | 271 | 20.962 | 27.396 | 17.500 | 1.00 | 27.86 | C |
|------|------|-----|-----|---|-----|--------|--------|--------|------|-------|---|
| ATOM | 2082 | CD2 | LEU | A | 271 | 20.100 | 27.425 | 19.789 | 1.00 | 29.16 | C |
| ATOM | 2083 | N   | TYR | A | 272 | 23.563 | 24.980 | 17.423 | 1.00 | 27.82 | N |
| ATOM | 2084 | CA  | TYR | A | 272 | 24.913 | 25.201 | 17.873 | 1.00 | 27.79 | C |
| ATOM | 2085 | C   | TYR | A | 272 | 24.918 | 26.494 | 18.662 | 1.00 | 26.67 | C |
| ATOM | 2086 | O   | TYR | A | 272 | 24.660 | 27.528 | 18.117 | 1.00 | 27.22 | O |
| ATOM | 2087 | CB  | TYR | A | 272 | 25.898 | 25.325 | 16.693 | 1.00 | 27.26 | C |
| ATOM | 2088 | CG  | TYR | A | 272 | 27.296 | 25.785 | 17.124 | 1.00 | 28.18 | C |
| ATOM | 2089 | CD1 | TYR | A | 272 | 27.924 | 25.237 | 18.221 | 1.00 | 28.32 | C |
| ATOM | 2090 | CD2 | TYR | A | 272 | 27.973 | 26.784 | 16.435 | 1.00 | 29.06 | C |
| ATOM | 2091 | CE1 | TYR | A | 272 | 29.169 | 25.653 | 18.600 | 1.00 | 28.29 | C |
| ATOM | 2092 | CE2 | TYR | A | 272 | 29.232 | 27.188 | 16.805 | 1.00 | 27.19 | C |
| ATOM | 2093 | CZ  | TYR | A | 272 | 29.821 | 26.632 | 17.903 | 1.00 | 27.41 | C |
| ATOM | 2094 | OH  | TYR | A | 272 | 31.081 | 27.026 | 18.322 | 1.00 | 24.66 | O |
| ATOM | 2095 | N   | ILE | A | 273 | 25.237 | 26.418 | 19.934 | 1.00 | 26.87 | N |
| ATOM | 2096 | CA  | ILE | A | 273 | 25.381 | 27.591 | 20.810 | 1.00 | 26.89 | C |
| ATOM | 2097 | C   | ILE | A | 273 | 26.841 | 27.751 | 21.182 | 1.00 | 27.37 | C |
| ATOM | 2098 | O   | ILE | A | 273 | 27.359 | 27.049 | 22.056 | 1.00 | 27.62 | O |
| ATOM | 2099 | CE  | ILE | A | 273 | 24.647 | 27.422 | 22.085 | 1.00 | 26.74 | C |
| ATOM | 2100 | CG1 | ILE | A | 273 | 23.182 | 27.185 | 21.799 | 1.00 | 25.89 | C |
| ATOM | 2101 | CG2 | ILE | A | 273 | 24.852 | 28.675 | 22.941 | 1.00 | 26.79 | C |
| ATOM | 2102 | CD1 | ILE | A | 273 | 22.338 | 27.108 | 23.065 | 1.00 | 25.37 | C |
| ATOM | 2103 | N   | PRO | A | 274 | 27.491 | 28.681 | 20.515 | 1.00 | 27.39 | N |
| ATOM | 2104 | CA  | PRO | A | 274 | 28.923 | 28.871 | 20.601 | 1.00 | 27.76 | C |
| ATOM | 2105 | C   | PRO | A | 274 | 29.287 | 29.415 | 21.934 | 1.00 | 27.42 | C |
| ATOM | 2106 | O   | PRO | A | 274 | 28.483 | 30.135 | 22.518 | 1.00 | 26.71 | O |
| ATOM | 2107 | CB  | PRO | A | 274 | 29.250 | 29.840 | 19.426 | 1.00 | 27.60 | C |
| ATOM | 2108 | CG  | PRO | A | 274 | 27.980 | 30.107 | 18.741 | 1.00 | 28.16 | C |
| ATOM | 2109 | CD  | PRO | A | 274 | 26.876 | 29.504 | 19.497 | 1.00 | 28.21 | C |
| ATOM | 2110 | N   | MET | A | 275 | 30.467 | 29.017 | 22.394 | 1.00 | 27.88 | N |
| ATOM | 2111 | CA  | MET | A | 275 | 30.979 | 29.346 | 23.717 | 1.00 | 28.91 | C |
| ATOM | 2112 | C   | MET | A | 275 | 30.974 | 30.849 | 23.919 | 1.00 | 28.27 | C |
| ATOM | 2113 | O   | MET | A | 275 | 31.284 | 31.589 | 23.000 | 1.00 | 27.69 | O |
| ATOM | 2114 | CE  | MET | A | 275 | 32.365 | 28.808 | 23.869 | 1.00 | 29.00 | C |
| ATOM | 2115 | CG  | MET | A | 275 | 32.861 | 28.842 | 25.313 | 1.00 | 34.03 | C |
| ATOM | 2116 | SD  | MET | A | 275 | 34.499 | 28.084 | 25.455 | 1.00 | 39.22 | S |
| ATOM | 2117 | CE  | MET | A | 275 | 35.200 | 28.479 | 23.871 | 1.00 | 36.40 | C |
| ATOM | 2118 | N   | TYR | A | 276 | 30.531 | 31.294 | 25.086 | 1.00 | 27.79 | N |
| ATOM | 2119 | CA  | TYR | A | 276 | 30.472 | 32.746 | 25.389 | 1.00 | 29.16 | C |
| ATOM | 2120 | C   | TYR | A | 276 | 29.267 | 33.465 | 24.802 | 1.00 | 27.80 | C |
| ATOM | 2121 | O   | TYR | A | 276 | 29.076 | 34.609 | 25.107 | 1.00 | 28.35 | O |
| ATOM | 2122 | CE  | TYR | A | 276 | 31.779 | 33.506 | 24.974 | 1.00 | 29.63 | C |
| ATOM | 2123 | CG  | TYR | A | 276 | 32.918 | 33.207 | 25.897 | 1.00 | 34.37 | C |
| ATOM | 2124 | CD1 | TYR | A | 276 | 32.966 | 33.783 | 27.146 | 1.00 | 38.52 | C |
| ATOM | 2125 | CD2 | TYR | A | 276 | 33.934 | 32.306 | 25.547 | 1.00 | 39.45 | C |
| ATOM | 2126 | CE1 | TYR | A | 276 | 33.955 | 33.493 | 28.022 | 1.00 | 39.83 | C |
| ATOM | 2127 | CE2 | TYR | A | 276 | 34.965 | 32.015 | 26.449 | 1.00 | 42.05 | C |
| ATOM | 2128 | CZ  | TYR | A | 276 | 34.954 | 32.609 | 27.685 | 1.00 | 42.46 | C |
| ATOM | 2129 | OH  | TYR | A | 276 | 35.949 | 32.343 | 28.624 | 1.00 | 48.60 | O |
| ATOM | 2130 | N   | TRP | A | 277 | 28.468 | 32.830 | 23.951 | 1.00 | 27.45 | N |
| ATOM | 2131 | CA  | TRP | A | 277 | 27.271 | 33.485 | 23.419 | 1.00 | 26.19 | C |
| ATOM | 2132 | C   | TRP | A | 277 | 26.160 | 33.442 | 24.424 | 1.00 | 25.93 | C |
| ATOM | 2133 | O   | TRP | A | 277 | 25.882 | 32.409 | 24.973 | 1.00 | 26.84 | O |
| ATOM | 2134 | CE  | TRP | A | 277 | 26.796 | 32.826 | 22.130 | 1.00 | 26.07 | C |
| ATOM | 2135 | CG  | TRP | A | 277 | 27.525 | 33.276 | 20.957 | 1.00 | 24.33 | C |
| ATOM | 2136 | CD1 | TRP | A | 277 | 28.862 | 33.118 | 20.731 | 1.00 | 24.81 | C |
| ATOM | 2137 | CD2 | TRP | A | 277 | 26.995 | 33.935 | 19.821 | 1.00 | 23.88 | C |
| ATOM | 2138 | NE1 | TRP | A | 277 | 29.204 | 33.674 | 19.531 | 1.00 | 24.86 | N |
| ATOM | 2139 | CE2 | TRP | A | 277 | 28.073 | 34.182 | 18.944 | 1.00 | 24.16 | C |
| ATOM | 2140 | CE3 | TRP | A | 277 | 25.727 | 34.398 | 19.464 | 1.00 | 25.16 | C |
| ATOM | 2141 | CZ2 | TRP | A | 277 | 27.923 | 34.858 | 17.747 | 1.00 | 23.53 | C |
| ATOM | 2142 | CZ3 | TRP | A | 277 | 25.579 | 35.064 | 18.250 | 1.00 | 25.92 | C |
| ATOM | 2143 | CH2 | TRP | A | 277 | 26.679 | 35.292 | 17.414 | 1.00 | 24.81 | C |
| ATOM | 2144 | N   | TRP | A | 278 | 25.516 | 34.566 | 24.673 | 1.00 | 26.34 | N |
| ATOM | 2145 | CA  | TRP | A | 278 | 24.408 | 34.623 | 25.625 | 1.00 | 26.96 | C |
| ATOM | 2146 | C   | TRP | A | 278 | 23.229 | 33.847 | 25.050 | 1.00 | 27.33 | C |
| ATOM | 2147 | O   | TRP | A | 278 | 23.021 | 33.846 | 23.847 | 1.00 | 27.18 | O |
| ATOM | 2148 | CE  | TRP | A | 278 | 23.952 | 36.062 | 25.838 | 1.00 | 26.87 | C |
| ATOM | 2149 | CG  | TRP | A | 278 | 24.965 | 36.916 | 26.455 | 1.00 | 27.61 | C |
| ATOM | 2150 | CD1 | TRP | A | 278 | 25.997 | 37.558 | 25.833 | 1.00 | 28.27 | C |
| ATOM | 2151 | CD2 | TRP | A | 278 | 25.065 | 37.228 | 27.830 | 1.00 | 25.52 | C |
| ATOM | 2152 | NE1 | TRP | A | 278 | 26.731 | 38.261 | 26.753 | 1.00 | 28.77 | N |
| ATOM | 2153 | CE2 | TRP | A | 278 | 26.164 | 38.072 | 27.991 | 1.00 | 29.02 | C |
| ATOM | 2154 | CE3 | TRP | A | 278 | 24.303 | 36.915 | 28.942 | 1.00 | 26.86 | C |
| ATOM | 2155 | CZ2 | TRP | A | 278 | 26.541 | 38.563 | 29.224 | 1.00 | 28.96 | C |
| ATOM | 2156 | CZ3 | TRP | A | 278 | 24.676 | 37.402 | 30.157 | 1.00 | 29.86 | C |
| ATOM | 2157 | CH2 | TRP | A | 278 | 25.780 | 38.224 | 30.293 | 1.00 | 27.89 | C |

TABLE 3-continued

| | | | | | | | | | | |
|---|---|---|---|---|---|---|---|---|---|---|
| | Coordinates for structures 1 to 4 |
| ATOM | 2158 | N | HIS | A | 279 | 22.455 | 33.193 | 25.890 | 1.00 | 27.47 | N |
| ATOM | 2159 | CA | HIS | A | 279 | 21.263 | 32.554 | 25.380 | 1.00 | 28.50 | C |
| ATOM | 2160 | C | HIS | A | 279 | 20.158 | 32.574 | 26.403 | 1.00 | 28.09 | C |
| ATOM | 2161 | O | HIS | A | 279 | 20.420 | 32.445 | 27.584 | 1.00 | 29.26 | O |
| ATOM | 2162 | CB | HIS | A | 279 | 21.528 | 31.112 | 24.899 | 1.00 | 28.46 | C |
| ATOM | 2163 | CO | HIS | A | 279 | 22.339 | 30.278 | 25.838 | 1.00 | 30.29 | C |
| ATOM | 2164 | ND1 | HIS | A | 279 | 23.712 | 30.381 | 25.928 | 1.00 | 31.17 | N |
| ATOM | 2165 | CD2 | HIS | A | 279 | 21.984 | 29.270 | 26.673 | 1.00 | 31.89 | C |
| ATOM | 2166 | CE1 | HIS | A | 279 | 24.161 | 29.484 | 26.790 | 1.00 | 31.48 | C |
| ATOM | 2167 | ND2 | HIS | A | 279 | 23.136 | 28.810 | 27.271 | 1.00 | 30.92 | N |
| ATOM | 2168 | N | HIS | A | 280 | 18.942 | 32.764 | 25.916 | 1.00 | 28.12 | N |
| ATOM | 2169 | CA | HIS | A | 280 | 17.713 | 32.827 | 26.695 | 1.00 | 28.50 | C |
| ATOM | 2170 | C | HIS | A | 280 | 16.884 | 31.731 | 26.071 | 1.00 | 28.78 | C |
| ATOM | 2171 | O | HIS | A | 280 | 16.739 | 31.709 | 24.851 | 1.00 | 29.67 | O |
| ATOM | 2172 | CB | HIS | A | 280 | 17.069 | 34.196 | 26.498 | 1.00 | 27.71 | C |
| ATOM | 2173 | CG | HIS | A | 280 | 15.600 | 34.223 | 26.727 | 1.00 | 29.69 | C |
| ATOM | 2174 | NO1 | HIS | A | 280 | 15.021 | 34.905 | 27.782 | 1.00 | 31.66 | N |
| ATOM | 2175 | CD2 | HIS | A | 280 | 14.579 | 33.648 | 26.047 | 1.00 | 31.45 | C |
| ATOM | 2176 | CE1 | HIS | A | 280 | 13.710 | 34.743 | 27.738 | 1.00 | 30.66 | C |
| ATOM | 2177 | ND2 | HIS | A | 280 | 13.415 | 33.985 | 26.696 | 1.00 | 31.28 | N |
| ATOM | 2178 | N | ILE | A | 281 | 16.346 | 30.814 | 26.860 | 1.00 | 29.23 | N |
| ATOM | 2179 | CA | ILE | A | 281 | 15.651 | 29.652 | 26.294 | 1.00 | 29.56 | C |
| ATOM | 2180 | C | ILE | A | 281 | 14.311 | 29.497 | 26.922 | 1.00 | 30.16 | C |
| ATOM | 2181 | O | ILE | A | 281 | 14.190 | 29.517 | 28.135 | 1.00 | 30.14 | O |
| ATOM | 2182 | CB | ILE | A | 281 | 16.478 | 28.409 | 26.516 | 1.00 | 29.69 | C |
| ATOM | 2183 | CG1 | ILE | A | 281 | 17.707 | 28.491 | 25.628 | 1.00 | 30.69 | C |
| ATOM | 2184 | CG2 | ILE | A | 281 | 15.686 | 27.119 | 26.172 | 1.00 | 28.22 | C |
| ATOM | 2185 | CD1 | ILE | A | 281 | 18.689 | 27.534 | 25.980 | 1.00 | 33.11 | C |
| ATOM | 2186 | N | GLU | A | 282 | 13.280 | 29.380 | 26.103 | 1.00 | 31.22 | N |
| ATOM | 2187 | CA | GLU | A | 282 | 11.931 | 29.278 | 26.665 | 1.00 | 31.99 | C |
| ATOM | 2188 | C | GLU | A | 282 | 11.123 | 28.182 | 26.007 | 1.00 | 31.79 | C |
| ATOM | 2189 | O | GLU | A | 282 | 11.131 | 28.021 | 24.806 | 1.00 | 32.77 | O |
| ATOM | 2190 | CB | GLU | A | 282 | 11.200 | 30.638 | 26.618 | 1.00 | 32.16 | C |
| ATOM | 2191 | CO | GLU | A | 282 | 11.017 | 31.265 | 25.253 | 1.00 | 33.49 | C |
| ATOM | 2192 | CD | GLU | A | 282 | 10.378 | 32.663 | 25.313 | 1.00 | 36.22 | C |
| ATOM | 2193 | OE1 | GLU | A | 282 | 10.879 | 33.552 | 26.043 | 1.00 | 38.20 | O |
| ATOM | 2194 | OE2 | GLU | A | 282 | 9.380 | 32.898 | 24.603 | 1.00 | 38.15 | O |
| ATOM | 2195 | N | SER | A | 283 | 10.454 | 27.392 | 26.827 | 1.00 | 31.81 | N |
| ATOM | 2196 | CA | SER | A | 283 | 9.592 | 26.333 | 26.331 | 1.00 | 30.79 | C |
| ATOM | 2197 | C | SER | A | 283 | 8.245 | 26.975 | 25.950 | 1.00 | 30.98 | C |
| ATOM | 2198 | O | SER | A | 283 | 7.635 | 27.640 | 26.780 | 1.00 | 30.36 | O |
| ATOM | 2199 | CB | SER | A | 283 | 9.430 | 25.305 | 27.424 | 1.00 | 30.62 | C |
| ATOM | 2200 | OG | SER | A | 283 | 10.586 | 24.463 | 27.496 | 1.00 | 29.45 | O |
| ATOM | 2201 | N | LEU | A | 284 | 7.776 | 26.790 | 24.709 | 1.00 | 31.06 | N |
| ATOM | 2202 | CA | LEU | A | 284 | 6.587 | 27.504 | 24.270 | 1.00 | 31.43 | C |
| ATOM | 2203 | C | LEU | A | 284 | 5.398 | 27.390 | 25.204 | 1.00 | 31.82 | C |
| ATOM | 2204 | O | LEU | A | 284 | 5.137 | 26.333 | 25.776 | 1.00 | 31.15 | O |
| ATOM | 2205 | CB | LEU | A | 284 | 6.156 | 27.098 | 22.895 | 1.00 | 31.75 | C |
| ATOM | 2206 | CO | LEU | A | 284 | 7.223 | 27.187 | 21.829 | 1.00 | 33.11 | C |
| ATOM | 2207 | CD1 | LEU | A | 284 | 6.571 | 27.388 | 20.478 | 1.00 | 33.62 | C |
| ATOM | 2208 | CD2 | LEU | A | 284 | 8.170 | 28.270 | 22.142 | 1.00 | 32.91 | C |
| ATOM | 2209 | N | LEU | A | 285 | 4.701 | 28.512 | 25.355 | 1.00 | 32.74 | N |
| ATOM | 2210 | CA | LEU | A | 285 | 3.481 | 28.564 | 26.147 | 1.00 | 34.35 | C |
| ATOM | 2211 | C | LEU | A | 285 | 2.502 | 27.591 | 25.540 | 1.00 | 34.74 | C |
| ATOM | 2212 | O | LEU | A | 285 | 2.375 | 27.510 | 24.332 | 1.00 | 34.70 | O |
| ATOM | 2213 | CB | LEU | A | 285 | 2.863 | 29.946 | 26.094 | 1.00 | 34.26 | C |
| ATOM | 2214 | CO | LEU | A | 285 | 3.729 | 31.060 | 26.638 | 1.00 | 34.74 | C |
| ATOM | 2215 | CO1 | LEU | A | 285 | 3.183 | 32.369 | 26.160 | 1.00 | 34.14 | C |
| ATOM | 2216 | CD2 | LEU | A | 285 | 3.780 | 30.970 | 28.136 | 1.00 | 34.97 | C |
| ATOM | 2217 | N | ASN | A | 286 | 1.838 | 26.829 | 26.380 | 1.00 | 35.89 | N |
| ATOM | 2218 | CA | ASN | A | 286 | 0.841 | 25.863 | 25.896 | 1.00 | 37.12 | C |
| ATOM | 2219 | C | ASN | A | 286 | 1.363 | 24.809 | 24.909 | 1.00 | 36.14 | C |
| ATOM | 2220 | O | ASN | A | 286 | 0.600 | 24.306 | 24.108 | 1.00 | 35.85 | O |
| ATOM | 2221 | CB | ASN | A | 286 | 0.336 | 26.635 | 25.274 | 1.00 | 37.80 | C |
| ATOM | 2222 | CG | ASN | A | 286 | 0.882 | 27.690 | 26.219 | 1.00 | 42.02 | C |
| ATOM | 2223 | OD1 | ASN | A | 286 | 1.326 | 27.365 | 27.326 | 1.00 | 47.86 | O |
| ATOM | 2224 | ND2 | ASN | A | 286 | 0.809 | 28.965 | 25.817 | 1.00 | 46.67 | N |
| ATOM | 2225 | N | GLY | A | 287 | 2.653 | 24.478 | 24.974 | 1.00 | 35.43 | N |
| ATOM | 2226 | CA | GLY | A | 287 | 3.262 | 23.539 | 24.057 | 1.00 | 34.11 | C |
| ATOM | 2227 | C | GLY | A | 287 | 3.569 | 22.202 | 24.666 | 1.00 | 34.02 | C |
| ATOM | 2228 | O | GLY | A | 287 | 4.073 | 21.317 | 23.977 | 1.00 | 34.98 | O |
| ATOM | 2229 | N | GLY | A | 288 | 3.242 | 22.023 | 25.944 | 1.00 | 33.71 | N |
| ATOM | 2230 | CA | GLY | A | 288 | 3.476 | 20.759 | 26.616 | 1.00 | 33.00 | C |
| ATOM | 2231 | C | GLY | A | 288 | 4.908 | 20.692 | 27.107 | 1.00 | 33.19 | C |
| ATOM | 2232 | O | GLY | A | 288 | 5.625 | 21.681 | 26.989 | 1.00 | 33.40 | O |
| ATOM | 2233 | N | ILE | A | 289 | 5.337 | 19.540 | 27.621 | 1.00 | 32.87 | N |
| ATOM | 2234 | CA | ILE | A | 289 | 6.647 | 19.425 | 28.195 | 1.00 | 33.57 | C |

TABLE 3-continued

| | | | | | | | | | | |
|---|---|---|---|---|---|---|---|---|---|---|
| | Coordinates for structures 1 to 4 |

| ATOM | 2235 | C | ILE | A | 289 | 7.695 | 19.434 | 27.118 | 1.00 | 33.13 | C |
|---|---|---|---|---|---|---|---|---|---|---|---|
| ATOM | 2236 | O | ILE | A | 289 | 7.454 | 19.023 | 25.995 | 1.00 | 34.41 | O |
| ATOM | 2237 | CB | ILE | A | 289 | 6.809 | 18.137 | 29.006 | 1.00 | 34.25 | C |
| ATOM | 2238 | CG1 | ILE | A | 289 | 6.789 | 16.920 | 28.102 | 1.00 | 36.60 | C |
| ATOM | 2239 | CG2 | ILE | A | 289 | 5.746 | 18.005 | 30.113 | 1.00 | 34.91 | C |
| ATOM | 2240 | CD1 | ILE | A | 289 | 7.271 | 15.659 | 28.834 | 1.00 | 38.16 | C |
| ATOM | 2241 | N | THR | A | 290 | 8.891 | 19.868 | 27.465 | 1.00 | 31.68 | N |
| ATOM | 2242 | CA | THR | A | 290 | 9.956 | 19.853 | 26.498 | 1.00 | 29.79 | C |
| ATOM | 2243 | C | THR | A | 290 | 11.054 | 18.938 | 26.958 | 1.00 | 27.97 | C |
| ATOM | 2244 | O | THR | A | 290 | 11.256 | 18.739 | 28.133 | 1.00 | 26.58 | O |
| ATOM | 2245 | CE | THR | A | 290 | 10.526 | 21.278 | 26.305 | 1.00 | 30.77 | C |
| ATOM | 2246 | OG1 | THR | A | 290 | 10.957 | 21.827 | 27.554 | 1.00 | 27.89 | O |
| ATOM | 2247 | CG2 | TIIR | A | 290 | 9.458 | 22.243 | 25.789 | 1.00 | 30.82 | C |
| ATOM | 2248 | N | ILE | A | 291 | 11.787 | 18.395 | 26.021 | 1.00 | 26.96 | N |
| ATOM | 2249 | CA | ILE | A | 291 | 12.910 | 17.594 | 26.383 | 1.00 | 27.83 | C |
| ATOM | 2250 | C | ILE | A | 291 | 14.059 | 17.952 | 25.493 | 1.00 | 27.31 | C |
| ATOM | 2251 | O | ILE | A | 291 | 13.880 | 18.028 | 24.289 | 1.00 | 27.83 | O |
| ATOM | 2252 | CE | ILE | A | 291 | 12.596 | 16.104 | 26.195 | 1.00 | 28.72 | C |
| ATOM | 2253 | CG1 | ILE | A | 291 | 11.480 | 15.671 | 27.140 | 1.00 | 29.09 | C |
| ATOM | 2254 | CG2 | ILE | A | 291 | 13.865 | 15.278 | 26.438 | 1.00 | 28.55 | C |
| ATOM | 2255 | CD1 | ILE | A | 291 | 11.115 | 14.232 | 26.986 | 1.00 | 30.86 | C |
| ATOM | 2256 | N | THR | A | 292 | 15.240 | 18.093 | 26.074 | 1.00 | 26.63 | N |
| ATOM | 2257 | CA | THR | A | 292 | 16.415 | 18.444 | 25.333 | 1.00 | 26.88 | C. |
| ATOM | 2258 | C | THR | A | 292 | 17.587 | 17.724 | 25.915 | 1.00 | 26.52 | C |
| ATOM | 2259 | O | THR | A | 292 | 17.631 | 17.524 | 27.102 | 1.00 | 26.40 | O |
| ATOM | 2260 | CE | THR | A | 292 | 16.753 | 19.971 | 25.532 | 1.00 | 27.41 | C |
| ATOM | 2261 | OG1 | THR | A | 292 | 15.652 | 20.841 | 25.187 | 1.00 | 28.64 | O |
| ATOM | 2262 | CG2 | THR | A | 292 | 17.852 | 20.398 | 24.592 | 1.00 | 28.03 | C |
| ATOM | 2263 | N | VAL | A | 293 | 18.577 | 17.414 | 25.093 | 1.00 | 26.32 | N |
| ATOM | 2264 | CA | VAL | A | 293 | 19.834 | 16.896 | 25.585 | 1.00 | 26.86 | C |
| ATOM | 2265 | C | VAL | A | 293 | 20.964 | 17.718 | 24.978 | 1.00 | 27.24 | C |
| ATOM | 2266 | O | VAL | A | 293 | 21.011 | 17.892 | 23.757 | 1.00 | 26.60 | O |
| ATOM | 2267 | CE | VAL | A | 293 | 20.029 | 15.422 | 25.226 | 1.00 | 27.56 | C |
| ATOM | 2268 | CG1 | VAL | A | 293 | 21.472 | 15.004 | 25.411 | 1.00 | 27.42 | C |
| ATOM | 2269 | CG2 | VAL | A | 293 | 19.138 | 14.546 | 26.126 | 1.00 | 29.64 | C |
| ATOM | 2270 | N | ASN | A | 294 | 21.849 | 18.278 | 25.814 | 1.00 | 27.26 | N |
| ATOM | 2271 | CA | ASN | A | 294 | 22.960 | 19.055 | 25.258 | 1.00 | 27.81 | C |
| ATOM | 2272 | C | ASN | A | 294 | 24.253 | 18.268 | 25.281 | 1.00 | 27.79 | C |
| ATOM | 2273 | O | ASN | A | 294 | 24.338 | 17.177 | 25.883 | 1.00 | 28.63 | O |
| ATOM | 2274 | CE | ASN | A | 294 | 23.118 | 20.446 | 25.881 | 1.00 | 27.69 | C |
| ATOM | 2275 | CG | ASN | A | 294 | 23.703 | 20.405 | 27.287 | 1.00 | 30.08 | C |
| ATOM | 2276 | OD1 | ASN | A | 294 | 24.309 | 19.397 | 27.677 | 1.00 | 29.80 | O |
| ATOM | 2277 | ND2 | ASN | A | 294 | 23.513 | 21.506 | 28.064 | 1.00 | 28.15 | N |
| ATOM | 2278 | N | PHE | A | 295 | 25.235 | 18.816 | 24.576 | 1.00 | 27.46 | N |
| ATOM | 2279 | CA | PHE | A | 295 | 26.548 | 18.219 | 24.428 | 1.00 | 27.53 | C |
| ATOM | 2280 | C | PHE | A | 295 | 27.543 | 19.352 | 24.675 | 1.00 | 28.01 | C |
| ATOM | 2281 | O | PHE | A | 295 | 27.720 | 20.239 | 23.811 | 1.00 | 28.48 | O |
| ATOM | 2282 | CB | PHE | A | 295 | 26.756 | 17.703 | 23.009 | 1.00 | 27.33 | C |
| ATOM | 2283 | CG | PHE | A | 295 | 25.955 | 16.487 | 22.658 | 1.00 | 27.87 | C |
| ATOM | 2284 | CD1 | PHE | A | 295 | 24.586 | 16.560 | 22.496 | 1.00 | 27.75 | C |
| ATOM | 2285 | CD2 | PHE | A | 295 | 26.581 | 15.287 | 22.426 | 1.00 | 26.57 | C |
| ATOM | 2286 | CE1 | PHE | A | 295 | 23.892 | 15.466 | 22.147 | 1.00 | 28.45 | C |
| ATOM | 2287 | CE2 | PHE | A | 295 | 25.869 | 14.187 | 22.095 | 1.00 | 27.40 | C |
| ATOM | 2288 | CZ | PHE | A | 295 | 24.541 | 14.262 | 21.952 | 1.00 | 27.57 | C |
| ATOM | 2289 | N | TRP | A | 296 | 28.166 | 19.346 | 25.852 | 1.00 | 28.46 | N |
| ATOM | 2290 | CA | TRP | A | 296 | 29.097 | 20.402 | 26.249 | 1.00 | 29.05 | C |
| ATOM | 2291 | C | TRP | A | 296 | 30.545 | 19.950 | 26.077 | 1.00 | 29.39 | C |
| ATOM | 2292 | O | TRP | A | 296 | 30.981 | 18.942 | 26.663 | 1.00 | 29.90 | O |
| ATOM | 2293 | CB | TRP | A | 296 | 28.850 | 20.825 | 27.696 | 1.00 | 29.23 | C |
| ATOM | 2294 | CG | TRP | A | 296 | 27.917 | 21.982 | 27.908 | 1.00 | 31.21 | C |
| ATOM | 2295 | CD1 | TRP | A | 296 | 27.805 | 23.080 | 27.135 | 1.00 | 33.45 | C |
| ATOM | 2296 | CD2 | TRP | A | 296 | 26.995 | 22.171 | 28.996 | 1.00 | 33.70 | C |
| ATOM | 2297 | NE1 | TRP | A | 296 | 26.864 | 23.941 | 27.651 | 1.00 | 33.91 | N |
| ATOM | 2298 | CE2 | TRP | A | 296 | 26.344 | 23.403 | 28.787 | 1.00 | 33.49 | C |
| ATOM | 2299 | CE3 | TRP | A | 296 | 26.638 | 21.414 | 30.113 | 1.00 | 36.30 | C |
| ATOM | 2300 | CZ2 | TRP | A | 296 | 25.377 | 23.902 | 29.642 | 1.00 | 35.59 | C |
| ATOM | 2301 | CZ3 | TRP | A | 296 | 25.643 | 21.899 | 30.967 | 1.00 | 37.80 | C |
| ATOM | 2302 | CH2 | TRP | A | 296 | 25.034 | 23.141 | 30.727 | 1.00 | 37.39 | C |
| ATOM | 2303 | N | TYR | A | 297 | 31.288 | 20.720 | 25.292 | 1.00 | 29.87 | N |
| ATOM | 2304 | CA | TYR | A | 297 | 32.693 | 20.472 | 25.017 | 1.00 | 30.43 | C |
| ATOM | 2305 | C | TYR | A | 297 | 33.548 | 21.629 | 25.518 | 1.00 | 30.98 | C |
| ATOM | 2306 | O | TYR | A | 297 | 33.167 | 22.765 | 25.387 | 1.00 | 29.50 | O |
| ATOM | 2307 | CB | TYR | A | 297 | 32.909 | 20.334 | 23.502 | 1.00 | 30.36 | C |
| ATOM | 2308 | CG | TYR | A | 297 | 32.304 | 19.083 | 22.919 | 1.00 | 30.07 | C |
| ATOM | 2309 | CD1 | TYR | A | 297 | 30.946 | 19.012 | 22.627 | 1.00 | 29.74 | C |
| ATOM | 2310 | CD2 | TYR | A | 297 | 33.083 | 17.960 | 22.687 | 1.00 | 28.56 | C |
| ATOM | 2311 | CE1 | TYR | A | 297 | 30.397 | 17.859 | 22.105 | 1.00 | 28.46 | C |

TABLE 3-continued

| | | | | | | | | | | | |
|---|---|---|---|---|---|---|---|---|---|---|---|
| | Coordinates for structures 1 to 4 |
| ATOM | 2312 | CE2 | TYR | A | 297 | 32.546 | 16.800 | 22.213 | 1.00 | 27.77 | C |
| ATOM | 2313 | CZ | TYR | A | 297 | 31.202 | 16.758 | 21.913 | 1.00 | 28.10 | C |
| ATOM | 2314 | OH | TYR | A | 297 | 30.654 | 15.613 | 21.438 | 1.00 | 27.72 | O |
| ATOM | 2315 | N | LYS | A | 298 | 34.723 | 21.325 | 26.060 | 1.00 | 32.77 | N |
| ATOM | 2316 | CA | LYS | A | 298 | 35.671 | 22.349 | 26.470 | 1.00 | 34.43 | C |
| ATOM | 2317 | C | LYS | A | 298 | 36.126 | 23.014 | 25.216 | 1.00 | 34.91 | C |
| ATOM | 2318 | O | LYS | A | 298 | 36.236 | 22.373 | 24.194 | 1.00 | 35.28 | O |
| ATOM | 2319 | CB | LYS | A | 298 | 36.865 | 21.749 | 27.221 | 1.00 | 35.25 | C |
| ATOM | 2320 | CG | LYS | A | 298 | 36.595 | 22.446 | 28.725 | 1.00 | 38.48 | C |
| ATOM | 2321 | CD | LYS | A | 298 | 37.834 | 20.990 | 29.532 | 1.00 | 42.40 | C |
| ATOM | 2322 | CE | LYS | A | 298 | 37.429 | 20.600 | 30.991 | 1.00 | 45.34 | C |
| ATOM | 2323 | NZ | LYS | A | 298 | 38.515 | 19.883 | 31.770 | 1.00 | 49.07 | N |
| ATOM | 2324 | N | GLY | A | 299 | 36.384 | 24.305 | 25.267 | 1.00 | 36.67 | N |
| ATOM | 2325 | CA | GLY | A | 299 | 36.837 | 24.998 | 24.080 | 1.00 | 38.01 | C |
| ATOM | 2326 | C | GLY | A | 299 | 38.249 | 24.618 | 23.689 | 1.00 | 39.33 | C |
| ATOM | 2327 | O | GLY | A | 299 | 38.965 | 23.987 | 24.437 | 1.00 | 39.19 | O |
| ATOM | 2328 | N | ALA | A | 300 | 38.644 | 25.017 | 22.498 | 1.00 | 41.68 | N |
| ATOM | 2329 | CA | ALA | A | 300 | 40.014 | 24.844 | 22.048 | 1.00 | 43.93 | C |
| ATOM | 2330 | C | ALA | A | 300 | 40.964 | 25.618 | 22.940 | 1.00 | 45.88 | C |
| ATOM | 2331 | O | ALA | A | 300 | 40.558 | 26.437 | 23.741 | 1.00 | 46.12 | O |
| ATOM | 2332 | CB | ALA | A | 300 | 40.148 | 25.343 | 20.639 | 1.00 | 43.86 | C |
| ATOM | 2333 | N | PRO | A | 301 | 42.254 | 25.393 | 22.773 | 1.00 | 49.19 | N |
| ATOM | 2334 | CA | PRO | A | 301 | 43.251 | 26.084 | 23.605 | 1.00 | 50.79 | C |
| ATOM | 2335 | C | PRO | A | 301 | 43.465 | 27.525 | 23.204 | 1.00 | 52.01 | C |
| ATOM | 2336 | O | PRO | A | 301 | 43.302 | 27.869 | 22.041 | 1.00 | 52.73 | O |
| ATOM | 2337 | CB | PRO | A | 301 | 44.534 | 25.325 | 23.303 | 1.00 | 50.51 | C |
| ATOM | 2338 | CG | PRO | A | 303. | 44.357 | 24.908 | 21.884 | 1.00 | 50.75 | C |
| ATOM | 2339 | CD | PRO | A | 301 | 42.890 | 24.521 | 21.766 | 1.00 | 49.57 | C |
| ATOM | 2340 | N | THR | A | 302 | 43.831 | 28.346 | 24.169 | 1.00 | 53.76 | N |
| ATOM | 2341 | CA | THR | A | 302 | 44.173 | 29.736 | 23.928 | 1.00 | 55.20 | C |
| ATOM | 2342 | C | THR | A | 302 | 45.563 | 29.720 | 23.307 | 1.00 | 56.14 | C |
| ATOM | 2343 | O | THR | A | 302 | 46.504 | 29.273 | 23.980 | 1.00 | 56.50 | O |
| ATOM | 2344 | CB | THR | A | 302 | 44.249 | 30.449 | 25.274 | 1.00 | 55.30 | C |
| ATOM | 2345 | OG1 | THR | A | 302 | 42.959 | 30.448 | 25.909 | 1.00 | 57.92 | O |
| ATOM | 2346 | CG2 | THR | A | 302 | 44.552 | 31.886 | 25.090 | 1.00 | 56.33 | C |
| ATOM | 2347 | N | PRO | A | 303 | 45.743 | 30.239 | 22.086 | 1.00 | 56.60 | N |
| ATOM | 2348 | CA | PRO | A | 303 | 47.057 | 30.145 | 21.427 | 1.00 | 56.45 | C |
| ATOM | 2349 | C | PRO | A | 303 | 48.168 | 30.743 | 22.280 | 1.00 | 56.31 | C |
| ATOM | 2350 | O | PRO | A | 303 | 47.845 | 31.449 | 23.235 | 1.00 | 56.29 | O |
| ATOM | 2351 | CB | PRO | A | 303 | 46.883 | 30.989 | 20.168 | 1.00 | 56.55 | C |
| ATOM | 2352 | CG | PRO | A | 303 | 45.418 | 31.007 | 19.927 | 1.00 | 56.34 | C |
| ATOM | 2353 | CD | PRO | A | 303 | 44.812 | 31.082 | 21.309 | 1.00 | 56.48 | C |
| ATOM | 2354 | N | GLU | A | 307 | 46.896 | 37.001 | 18.664 | 1.00 | 61.01 | N |
| ATOM | 2355 | CA | GLU | A | 307 | 46.873 | 37.991 | 17.591 | 1.00 | 61.50 | C |
| ATOM | 2356 | C | GLU | A | 307 | 45.852 | 39.079 | 17.834 | 1.00 | 60.73 | C |
| ATOM | 2357 | O | GLU | A | 307 | 44.755 | 38.828 | 18.308 | 1.00 | 61.45 | O |
| ATOM | 2358 | CB | GLU | A | 307 | 46.614 | 37.356 | 16.205 | 1.00 | 62.21 | C |
| ATOM | 2359 | OG | GLU | A | 307 | 46.871 | 38.339 | 15.045 | 1.00 | 63.86 | C |
| ATOM | 2360 | CD | GLU | A | 307 | 46.898 | 37.697 | 13.665 | 1.00 | 65.26 | C |
| ATOM | 2361 | OE1 | GLU | A | 307 | 46.468 | 36.535 | 13.516 | 1.00 | 65.73 | O |
| ATOM | 2362 | OE2 | GLU | A | 307 | 47.342 | 38.382 | 12.718 | 1.00 | 67.94 | O |
| ATOM | 2363 | N | TYR | A | 308 | 46.237 | 40.302 | 17.513 | 1.00 | 59.88 | N |
| ATOM | 2364 | CA | TYR | A | 308 | 45.349 | 41.441 | 17.639 | 1.00 | 59.19 | C |
| ATOM | 2365 | C | TYR | A | 308 | 44.706 | 41.622 | 16.279 | 1.00 | 58.70 | C |
| ATOM | 2366 | O | TYR | A | 308 | 45.224 | 41.120 | 15.273 | 1.00 | 59.29 | O |
| ATOM | 2367 | CB | TYR | A | 306 | 46.133 | 42.665 | 18.095 | 1.00 | 59.18 | C |
| ATOM | 2368 | CG | TYR | A | 308 | 46.677 | 42.418 | 19.478 | 1.00 | 59.73 | C |
| ATOM | 2369 | CD1 | TYR | A | 308 | 45.904 | 42.708 | 20.605 | 1.00 | 59.74 | C |
| ATOM | 2370 | CD2 | TYR | A | 308 | 47.912 | 41.801 | 19.665 | 1.00 | 59.94 | C |
| ATOM | 2371 | CE1 | TYR | A | 308 | 46.357 | 42.438 | 21.869 | 1.00 | 59.94 | C |
| ATOM | 2372 | CE2 | TYR | A | 308 | 48.377 | 41.519 | 20.933 | 1.00 | 61.17 | C |
| ATOM | 2373 | CZ | TYR | A | 308 | 47.592 | 41.843 | 22.038 | 1.00 | 61.68 | C |
| ATOM | 2374 | OH | TYR | A | 308 | 48.032 | 41.579 | 23.316 | 1.00 | 63.29 | O |
| ATOM | 2375 | N | PRO | A | 309 | 43.541 | 42.258 | 16.233 | 1.00 | 57.37 | N |
| ATOM | 2376 | CA | PRO | A | 309 | 42.849 | 42.815 | 17.411 | 1.00 | 55.72 | C |
| ATOM | 2377 | C | PRO | A | 309 | 42.113 | 41.742 | 18.225 | 1.00 | 52.85 | C |
| ATOM | 2378 | O | PRO | A | 309 | 41.627 | 40.815 | 17.613 | 1.00 | 53.22 | O |
| ATOM | 2379 | CB | PRO | A | 309 | 42.823 | 43.755 | 16.777 | 1.00 | 56.31 | C |
| ATOM | 2380 | CG | PRO | A | 309 | 41.512 | 43.113 | 15.410 | 1.00 | 57.04 | C |
| ATOM | 2381 | CD | PRO | A | 309 | 42.774 | 42.431 | 14.984 | 1.00 | 57.43 | C |
| ATOM | 2382 | N | LEU | A | 310 | 41.998 | 41.879 | 19.544 | 1.00 | 49.67 | N |
| ATOM | 2383 | CA | LEU | A | 310 | 41.368 | 40.825 | 20.363 | 1.00 | 47.23 | C |
| ATOM | 2384 | C | LEU | A | 310 | 39.870 | 40.656 | 20.128 | 1.00 | 45.07 | C |
| ATOM | 2385 | O | LEU | A | 310 | 39.131 | 41.635 | 19.956 | 1.00 | 45.94 | O |
| ATOM | 2386 | CB | LEU | A | 310 | 41.568 | 41.109 | 21.837 | 1.00 | 46.99 | C |
| ATOM | 2387 | CG | LEU | A | 310 | 42.579 | 40.351 | 22.706 | 1.00 | 46.52 | C |
| ATOM | 2388 | CE1 | LEU | A | 310 | 43.856 | 40.028 | 22.048 | 1.00 | 45.64 | C |

TABLE 3-continued

| | | | | | | Coordinates for structures 1 to 4 | | | | | |
|---|---|---|---|---|---|---|---|---|---|---|---|
| ATOM | 2389 | C02 | LEU | A | 310 | 42.840 | 41.179 | 23.975 | 1.00 | 46.57 | C |
| ATOM | 2390 | N | LYS | A | 311 | 39.408 | 39.414 | 20.139 | 1.00 | 41.52 | N |
| ATOM | 2391 | CA | LYS | A | 321 | 37.987 | 39.155 | 20.003 | 1.00 | 38.55 | C |
| ATOM | 2392 | C | LYS | A | 311 | 37.179 | 39.463 | 21.276 | 1.00 | 35.80 | C |
| ATOM | 2393 | O | LYS | A | 311 | 37.664 | 39.425 | 22.400 | 1.00 | 34.43 | O |
| ATOM | 2394 | CB | LYS | A | 311 | 37.760 | 37.727 | 19.553 | 1.00 | 39.46 | C |
| ATOM | 2395 | N | ALA | A | 312 | 35.920 | 39.786 | 21.076 | 1.00 | 32.82 | N |
| ATOM | 2396 | CA | ALA | A | 312 | 35.055 | 40.081 | 22.185 | 1.00 | 30.91 | C |
| ATOM | 2397 | C | ALA | A | 312 | 35.152 | 39.033 | 23.279 | 1.00 | 30.00 | C |
| ATOM | 2398 | O | ALA | A | 312 | 35.231 | 39.382 | 24.442 | 1.00 | 28.68 | O |
| ATOM | 2399 | CB | ALA | A | 312 | 33.625 | 40.234 | 21.707 | 1.00 | 30.07 | C |
| ATOM | 2400 | N | HIS | A | 313 | 35.148 | 37.753 | 22.916 | 1.00 | 29.85 | N |
| ATOM | 2401 | CA | HIS | A | 313 | 35.125 | 36.727 | 23.931 | 1.00 | 30.47 | C |
| ATOM | 2402 | C | HIS | A | 313 | 36.410 | 36.710 | 24.689 | 1.00 | 29.99 | C |
| ATOM | 2403 | O | HIS | A | 313 | 36.439 | 36.320 | 25.846 | 1.00 | 29.25 | O |
| ATOM | 2404 | CE | HIS | A | 313 | 34.787 | 35.331 | 23.392 | 1.00 | 31.64 | C |
| ATOM | 2405 | CG | HIS | A | 313 | 35.860 | 34.714 | 22.566 | 1.00 | 35.54 | C |
| ATOM | 2406 | ND1 | HIS | A | 313 | 35.987 | 34.950 | 21.208 | 1.00 | 41.10 | N |
| ATOM | 2407 | CD2 | HIS | A | 313 | 36.844 | 33.846 | 22.891 | 1.00 | 40.77 | C |
| ATOM | 2408 | CE1 | HIS | A | 313 | 37.047 | 34.303 | 20.750 | 1.00 | 40.02 | C |
| ATOM | 2409 | ND2 | HIS | A | 313 | 37.567 | 33.603 | 21.743 | 1.00 | 41.82 | N |
| ATOM | 2410 | N | GLN | A | 314 | 37.482 | 37.137 | 24.056 | 1.00 | 29.68 | N |
| ATOM | 2411 | CA | GLN | A | 314 | 38.754 | 37.185 | 24.751 | 1.00 | 29.77 | C |
| ATOM | 2412 | C | GLN | A | 314 | 38.729 | 38.294 | 25.817 | 1.00 | 30.57 | C |
| ATOM | 2413 | O | GLN | A | 314 | 39.222 | 38.120 | 26.956 | 1.00 | 29.69 | O |
| ATOM | 2414 | CE | GLN | A | 314 | 39.893 | 37.401 | 23.743 | 1.00 | 30.02 | C |
| ATOM | 2415 | CG | GLN | A | 314 | 40.111 | 36.182 | 22.786 | 1.00 | 29.84 | C |
| ATOM | 2416 | CD | GLN | A | 314 | 41.126 | 36.437 | 21.687 | 1.00 | 31.76 | C |
| ATOM | 2417 | OE1 | GLN | A | 314 | 40.982 | 37.377 | 20.885 | 1.00 | 32.81 | O |
| ATOM | 2418 | NE2 | GLN | A | 314 | 42.160 | 35.594 | 21.637 | 1.00 | 34.23 | N |
| ATOM | 2419 | N | LYS | A | 315 | 38.111 | 39.421 | 25.471 | 1.00 | 30.44 | N |
| ATOM | 2420 | CA | LYS | A | 315 | 38.026 | 40.491 | 26.431 | 1.00 | 31.27 | C |
| ATOM | 2421 | C | LYS | A | 315 | 37.192 | 40.023 | 27.635 | 1.00 | 30.75 | C |
| ATOM | 2422 | O | LYS | A | 315 | 37.511 | 40.373 | 28.784 | 1.00 | 29.60 | O |
| ATOM | 2423 | CE | LYS | A | 315 | 37.461 | 41.752 | 25.808 | 1.00 | 31.76 | C |
| ATOM | 2424 | CG | LYS | A | 315 | 38.483 | 42.491 | 24.982 | 1.00 | 33.90 | C |
| ATOM | 2425 | CD | LYS | A | 315 | 37.902 | 43.711 | 24.329 | 1.00 | 37.97 | C |
| ATOM | 2426 | CE | LYS | A | 315 | 38.911 | 44.380 | 23.419 | 1.00 | 41.69 | C |
| ATOM | 2427 | NZ | LYS | A | 315 | 38.264 | 45.411 | 22.536 | 1.00 | 44.93 | N |
| ATOM | 2428 | N | VAL | A | 316 | 36.163 | 39.216 | 27.362 | 1.00 | 29.26 | N |
| ATOM | 2429 | CA | VAL | A | 316 | 35.318 | 38.731 | 28.422 | 1.00 | 29.23 | C |
| ATOM | 2430 | C | VAL | A | 316 | 36.152 | 37.841 | 29.339 | 1.00 | 29.87 | C |
| ATOM | 2431 | O | VAL | A | 316 | 36.075 | 37.926 | 30.584 | 1.00 | 30.33 | O |
| ATOM | 2432 | CE | VAL | A | 316 | 34.079 | 37.973 | 27.900 | 1.00 | 28.68 | C |
| ATOM | 2433 | CG1 | VAL | A | 316 | 33.306 | 37.376 | 29.037 | 1.00 | 28.32 | C |
| ATOM | 2434 | CG2 | VAL | A | 316 | 33.144 | 38.887 | 27.136 | 1.00 | 28.57 | C |
| ATOM | 2435 | N | ALA | A | 317 | 36.976 | 37.007 | 28.728 | 1.00 | 29.36 | N |
| ATOM | 2436 | CA | ALA | A | 317 | 37.878 | 36.136 | 29.487 | 1.00 | 29.26 | C |
| ATOM | 2437 | C | ALA | A | 317 | 38.776 | 36.941 | 30.389 | 1.00 | 28.08 | C |
| ATOM | 2438 | O | ALA | A | 317 | 39.052 | 36.564 | 31.519 | 1.00 | 27.65 | O |
| ATOM | 2439 | CB | ALA | A | 317 | 38.733 | 35.267 | 28.561 | 1.00 | 28.70 | C |
| ATOM | 2440 | N | ILE | A | 318 | 39.211 | 38.068 | 29.873 | 1.00 | 28.33 | N |
| ATOM | 2441 | CA | ILE | A | 318 | 40.083 | 38.945 | 30.628 | 1.00 | 28.40 | C |
| ATOM | 2442 | C | ILE | A | 318 | 39.338 | 39.526 | 31.825 | 1.00 | 28.94 | C |
| ATOM | 2443 | O | ILE | A | 318 | 39.880 | 39.503 | 32.924 | 1.00 | 29.70 | O |
| ATOM | 2444 | CE | ILE | A | 318 | 40.697 | 40.053 | 29.732 | 1.00 | 27.74 | C |
| ATOM | 2445 | CG1 | ILE | A | 318 | 41.683 | 39.443 | 28.743 | 1.00 | 28.14 | C |
| ATOM | 2446 | CG2 | ILE | A | 318 | 41.433 | 41.082 | 30.577 | 1.00 | 27.98 | C |
| ATOM | 2447 | CD1 | ILE | A | 318 | 42.271 | 40.447 | 27.759 | 1.00 | 29.17 | C |
| ATOM | 2448 | N | MET | A | 319 | 38.115 | 40.032 | 31.630 | 1.00 | 28.75 | N |
| ATOM | 2449 | CA | MET | A | 319 | 37.402 | 40.666 | 32.735 | 1.00 | 28.64 | C |
| ATOM | 2450 | C | MET | A | 319 | 37.140 | 39.669 | 33.877 | 1.00 | 29.22 | C |
| ATOM | 2451 | O | MET | A | 319 | 37.308 | 39.981 | 35.082 | 1.00 | 30.32 | O |
| ATOM | 2452 | CE | MET | A | 319 | 36.123 | 41.355 | 32.273 | 1.00 | 28.33 | C |
| ATOM | 2453 | CG | MET | A | 319 | 36.327 | 42.553 | 31.334 | 1.00 | 27.88 | C |
| ATOM | 2454 | SD | MET | A | 319 | 34.779 | 43.349 | 30.857 | 1.00 | 29.90 | 5 |
| ATOM | 2455 | CE | MET | A | 319 | 34.146 | 42.288 | 29.455 | 1.00 | 28.71 | C |
| ATOM | 2456 | N | ARG | A | 320 | 36.802 | 38.446 | 33.515 | 1.00 | 29.22 | N |
| ATOM | 2457 | CA | ARG | A | 320 | 36.543 | 37.429 | 34.520 | 1.00 | 28.75 | C |
| ATOM | 2458 | C | ARG | A | 320 | 37.806 | 37.221 | 35.325 | 1.00 | 28.81 | C |
| ATOM | 2459 | O | ARG | A | 320 | 37.782 | 37.132 | 36.569 | 1.00 | 28.76 | O |
| ATOM | 2460 | CB | ARG | A | 320 | 36.142 | 36.118 | 33.861 | 1.00 | 28.67 | C |
| ATOM | 2461 | CG | ARG | A | 320 | 34.810 | 36.125 | 33.120 | 1.00 | 29.62 | C |
| ATOM | 2462 | CD | ARG | A | 320 | 34.371 | 34.747 | 32.603 | 1.00 | 27.74 | C |
| ATOM | 2463 | NE | ARG | A | 320 | 34.193 | 33.843 | 33.716 | 1.00 | 24.81 | N |
| ATOM | 2464 | CZ | ARG | A | 320 | 33.161 | 33.887 | 34.526 | 1.00 | 27.65 | C |
| ATOM | 2465 | NH1 | ARG | A | 320 | 32.180 | 34.752 | 34.330 | 1.00 | 29.97 | N |

TABLE 3-continued

Coordinates for structures 1 to 4

| ATOM | 2466 | NH2 | ARG | A | 320 | 33.088 | 33.064 | 35.542 | 1.00 | 27.59 | N |
| --- | --- | --- | --- | --- | --- | --- | --- | --- | --- | --- | --- |
| ATOM | 2467 | N | ASN | A | 321 | 38.933 | 37.167 | 34.627 | 1.00 | 28.60 | N |
| ATOM | 2468 | CA | ASN | A | 321 | 40.185 | 36.884 | 35.320 | 1.00 | 28.16 | C |
| ATOM | 2469 | C | ASN | A | 321 | 40.526 | 38.003 | 36.291 | 1.00 | 28.13 | C |
| ATOM | 2470 | O | ASN | A | 321 | 40.945 | 37.742 | 37.423 | 1.00 | 29.13 | O |
| ATOM | 2471 | CB | ASN | A | 321 | 41.318 | 36.615 | 34.319 | 1.00 | 28.09 | C |
| ATOM | 2472 | CG | ASN | A | 321 | 41.317 | 35.177 | 33.817 | 1.00 | 27.94 | C |
| ATOM | 2473 | OD1 | ASN | A | 321 | 40.924 | 34.286 | 34.555 | 1.00 | 28.53 | O |
| ATOM | 2474 | ND2 | ASN | A | 321 | 41.751 | 34.946 | 32.560 | 1.00 | 23.58 | N |
| ATOM | 2475 | N | ILE | A | 322 | 40.337 | 39.250 | 35.876 | 1.00 | 27.49 | N |
| ATOM | 2476 | CA | ILE | A | 322 | 40.659 | 40.350 | 36.749 | 1.00 | 27.70 | C |
| ATOM | 2477 | C | ILE | A | 322 | 39.792 | 40.209 | 38.017 | 1.00 | 27.39 | C |
| ATOM | 2478 | O | ILE | A | 322 | 40.284 | 40.315 | 39.101 | 1.00 | 26.48 | O |
| ATOM | 2479 | CB | ILE | A | 322 | 40.353 | 41.680 | 36.059 | 1.00 | 28.04 | C |
| ATOM | 2480 | CG1 | ILE | A | 322 | 41.302 | 41.941 | 34.897 | 1.00 | 30.79 | C |
| ATOM | 2481 | CG2 | ILE | A | 322 | 40.426 | 42.832 | 37.038 | 1.00 | 28.09 | C |
| ATOM | 2482 | CD1 | ILE | A | 322 | 42.756 | 41.766 | 35.226 | 1.00 | 32.31 | C |
| ATOM | 2483 | N | GLU | A | 323 | 38.494 | 39.961 | 37.854 | 1.00 | 27.37 | N |
| ATOM | 2484 | CA | GLU | A | 323 | 37.618 | 39.868 | 38.985 | 1.00 | 27.48 | C |
| ATOM | 2485 | C | GLU | A | 323 | 38.060 | 38.784 | 39.881 | 1.00 | 27.52 | C |
| ATOM | 2486 | O | GLU | A | 323 | 38.096 | 38.956 | 41.079 | 1.00 | 26.90 | O |
| ATOM | 2487 | CE | GLU | A | 323 | 36.183 | 39.637 | 38.558 | 1.00 | 27.48 | C |
| ATOM | 2488 | CG | GLU | A | 323 | 35.592 | 40.849 | 37.910 | 1.00 | 27.65 | C |
| ATOM | 2489 | CD | GLU | A | 323 | 34.199 | 40.631 | 37.318 | 1.00 | 25.69 | C |
| ATOM | 2490 | OE1 | GLU | A | 323 | 33.236 | 40.358 | 38.050 | 1.00 | 24.42 | O |
| ATOM | 2491 | OE2 | GLU | A | 323 | 34.072 | 40.808 | 36.101 | 1.00 | 24.98 | O |
| ATOM | 2492 | N | LYS | A | 324 | 38.419 | 37.659 | 39.297 | 1.00 | 29.13 | N |
| ATOM | 2493 | CA | LYS | A | 324 | 38.845 | 36.508 | 40.097 | 1.00 | 30.35 | C |
| ATOM | 2494 | C | LYS | A | 324 | 40.099 | 36.825 | 40.912 | 1.00 | 31.16 | C |
| ATOM | 2495 | O | LYS | A | 324 | 40.123 | 36.547 | 42.111 | 1.00 | 32.01 | O |
| ATOM | 2496 | CB | LYS | A | 324 | 39.116 | 35.289 | 39.222 | 1.00 | 30.16 | C |
| ATOM | 2497 | CG | LYS | A | 324 | 37.887 | 34.625 | 38.648 | 1.00 | 30.63 | C |
| ATOM | 24~8 | CD | LYS | A | 324 | 38.344 | 33.454 | 37.765 | 1.00 | 30.70 | C |
| ATOM | 2499 | CE | LYS | A | 324 | 37.204 | 32.713 | 37.038 | 1.00 | 30.66 | C |
| ATOM | 2500 | NZ | LYS | A | 324 | 37.728 | 31.451 | 36.325 | 1.00 | 27.19 | N |
| ATOM | 2501 | N | MET | A | 325 | 41.119 | 37.401 | 40.270 | 1.00 | 31.84 | N |
| ATOM | 2502 | CA | MET | A | 325 | 42.392 | 37.735 | 40.939 | 1.00 | 32.71 | C |
| ATOM | 2503 | C | MET | A | 325 | 42.216 | 38.743 | 42.078 | 1.00 | 32.44 | C |
| ATOM | 2504 | O | MET | A | 325 | 42.840 | 38.637 | 43.141 | 1.00 | 30.36 | O |
| ATOM | 2505 | CE | MET | A | 325 | 43.417 | 38.276 | 39.923 | 1.00 | 32.98 | C |
| ATOM | 2506 | CG | MET | A | 325 | 43.978 | 37.216 | 39.032 | 1.00 | 36.70 | C |
| ATOM | 2507 | SD | MET | A | 325 | 44.734 | 37.879 | 37.532 | 1.00 | 46.02 | S |
| ATOM | 2508 | CE | MET | A | 325 | 45.616 | 39.197 | 38.250 | 1.00 | 46.11 | C |
| ATOM | 2509 | N | LEU | A | 326 | 41.376 | 39.738 | 41.837 | 1.00 | 33.01 | N |
| ATOM | 2510 | CA | LEU | A | 326 | 41.116 | 40.756 | 42.852 | 1.00 | 34.17 | C |
| ATOM | 2511 | C | LEU | A | 326 | 40.490 | 40.151 | 44.083 | 1.00 | 33.83 | C |
| ATOM | 2512 | O | LEU | A | 326 | 40.871 | 40.464 | 45.188 | 1.00 | 33.22 | O |
| ATOM | 2513 | CE | LEU | A | 326 | 40.185 | 41.818 | 42.305 | 1.00 | 34.61 | C |
| ATOM | 2514 | CG | LEU | A | 326 | 40.740 | 43.194 | 41.974 | 1.00 | 37.32 | C |
| ATOM | 2515 | CD1 | LEU | A | 326 | 42.251 | 43.297 | 41.924 | 1.00 | 39.32 | C |
| ATOM | 2516 | CD2 | LEU | A | 326 | 40.158 | 43.607 | 40.643 | 1.00 | 39.20 | C |
| ATOM | 2517 | N | GLY | A | 327 | 39.534 | 39.262 | 43.861 | 1.00 | 34.50 | N |
| ATOM | 2518 | CA | GLY | A | 327 | 38.842 | 38.569 | 44.930 | 1.00 | 34.87 | C |
| ATOM | 2519 | C | GLY | A | 327 | 39.796 | 37.776 | 45.779 | 1.00 | 35.34 | C |
| ATOM | 2520 | O | GLY | A | 327 | 39.728 | 37.810 | 47.016 | 1.00 | 35.51 | O |
| ATOM | 2521 | N | GLU | A | 328 | 40.725 | 37.081 | 45.139 | 1.00 | 35.88 | N |
| ATOM | 2522 | CA | GLU | A | 328 | 42.708 | 36.346 | 45.926 | 1.00 | 36.96 | C |
| ATOM | 2523 | C | GLU | A | 328 | 42.668 | 37.302 | 46.614 | 1.00 | 35.46 | C |
| ATOM | 2524 | O | GLU | A | 328 | 42.958 | 37.144 | 47.799 | 1.00 | 35.65 | O |
| ATOM | 2525 | CB | GLU | A | 328 | 42.465 | 35.340 | 45.074 | 1.00 | 37.89 | C |
| ATOM | 2526 | CG | GLU | A | 328 | 41.555 | 34.272 | 44.481 | 1.00 | 43.40 | C |
| ATOM | 2527 | CD | GLU | A | 328 | 41.694 | 32.905 | 45.135 | 1.00 | 50.39 | C |
| ATOM | 2528 | OE1 | GLU | A | 328 | 42.006 | 32.861 | 46.361 | 1.00 | 53.07 | O |
| ATOM | 2529 | OE2 | GLU | A | 328 | 41.503 | 31.876 | 44.396 | 1.00 | 53.24 | O |
| ATOM | 2530 | N | ALA | A | 329 | 43.110 | 38.331 | 45.906 | 1.00 | 34.23 | N |
| ATOM | 2531 | CA | ALA | A | 329 | 44.130 | 39.208 | 46.469 | 1.00 | 33.82 | C |
| ATOM | 2532 | C | ALA | A | 329 | 43.652 | 40.031 | 47.632 | 1.00 | 33.70 | C |
| ATOM | 2533 | O | ALA | A | 329 | 44.384 | 40.279 | 48.547 | 1.00 | 33.79 | O |
| ATOM | 2534 | CB | ALA | A | 329 | 44.711 | 40.079 | 45.428 | 1.00 | 33.36 | C |
| ATOM | 2535 | N | LEU | A | 330 | 42.410 | 40.451 | 47.602 | 1.00 | 34.57 | N |
| ATOM | 2536 | CA | LEU | A | 330 | 41.869 | 41.243 | 48.694 | 1.00 | 35.04 | C |
| ATOM | 2537 | C | LEU | A | 330 | 41.351 | 40.397 | 49.837 | 1.00 | 35.29 | C |
| ATOM | 2538 | O | LEU | A | 330 | 41.011 | 40.922 | 50.884 | 1.00 | 35.39 | O |
| ATOM | 2539 | CB | LEU | A | 330 | 40.721 | 42.096 | 48.182 | 1.00 | 34.85 | C |
| ATOM | 2540 | CG | LEU | A | 330 | 41.141 | 43.081 | 47.095 | 1.00 | 35.83 | C |
| ATOM | 2541 | CD1 | LEU | A | 330 | 39.907 | 43.564 | 46.304 | 1.00 | 37.05 | C |
| ATOM | 2542 | CD2 | LEU | A | 330 | 41.842 | 44.244 | 47.662 | 1.00 | 34.12 | C |

TABLE 3-continued

Coordinates for structures 1 to 4

| ATOM | 2543 | N | GLY | A | 331 | 41.223 | 39.098 | 49.619 | 1.00 | 36.20 | N |
| ATOM | 2544 | CA | GLY | A | 331 | 40.751 | 38.207 | 50.659 | 1.00 | 36.87 | C |
| ATOM | 2545 | C | GLY | A | 331 | 39.260 | 38.250 | 50.957 | 1.00 | 37.48 | C |
| ATOM | 2546 | O | GLY | A | 331 | 38.807 | 37.527 | 51.846 | 1.00 | 38.53 | O |
| ATOM | 2547 | N | ASN | A | 332 | 38.509 | 39.085 | 50.242 | 1.00 | 37.67 | N |
| ATOM | 2548 | CA | ASN | A | 332 | 37.069 | 39.175 | 50.399 | 1.00 | 38.06 | C |
| ATOM | 2549 | C | ASN | A | 332 | 36.446 | 39.652 | 49.088 | 1.00 | 37.75 | C |
| ATOM | 2550 | O | ASN | A | 332 | 36.688 | 40.760 | 48.661 | 1.00 | 37.42 | O |
| ATOM | 2551 | CB | ASN | A | 332 | 36.728 | 40.152 | 51.523 | 1.00 | 38.50 | C |
| ATOM | 2552 | CG | ASN | A | 332 | 35.272 | 40.103 | 51.896 | 1.00 | 40.34 | C |
| ATOM | 2553 | OD1 | ASN | A | 332 | 34.493 | 39.377 | 51.274 | 1.00 | 43.85 | O |
| ATOM | 2554 | ND2 | ASN | A | 332 | 34.894 | 40.841 | 52.937 | 1.00 | 41.75 | N |
| ATOM | 2555 | N | PRO | A | 333 | 35.628 | 38.839 | 48.451 | 1.00 | 37.92 | N |
| ATOM | 2556 | CA | PRO | A | 333 | 35.076 | 39.209 | 47.146 | 1.00 | 37.97 | C |
| ATOM | 2557 | C | PRO | A | 333 | 34.245 | 40.456 | 47.211 | 1.00 | 37.96 | C |
| ATOM | 2558 | O | PRO | A | 333 | 34.086 | 41.143 | 46.204 | 1.00 | 37.81 | O |
| ATOM | 2559 | CB | PRO | A | 333 | 34.182 | 38.024 | 46.770 | 1.00 | 37.85 | C |
| ATOM | 2560 | CG | PRO | A | 333 | 34.327 | 37.037 | 47.801 | 1.00 | 38.26 | C |
| ATOM | 2561 | CD | PRO | A | 333 | 35.161 | 37.530 | 48.908 | 1.00 | 37.98 | C |
| ATOM | 2562 | N | GLN | A | 334 | 33.702 | 40.741 | 48.381 | 1.00 | 38.23 | N |
| ATOM | 2563 | CA | GLN | A | 334 | 32.872 | 41.928 | 48.539 | 1.00 | 38.84 | C |
| ATOM | 2564 | C | GLN | A | 334 | 33.713 | 43.177 | 48.442 | 1.00 | 37.04 | C |
| ATOM | 2565 | O | GLN | A | 334 | 33.185 | 44.254 | 48.276 | 1.00 | 37.42 | O |
| ATOM | 2566 | CB | GLEU | A | 334 | 32.041 | 41.870 | 49.850 | 1.00 | 39.97 | C |
| ATOM | 2567 | CG | GLN | A | 334 | 30.696 | 41.057 | 49.612 | 1.00 | 44.72 | C |
| ATOM | 2568 | CD | GLN | A | 334 | 29.669 | 41.117 | 50.756 | 1.00 | 49.62 | C |
| ATOM | 2569 | OE1 | GLN | A | 334 | 29.666 | 42.067 | 51.566 | 1.00 | 53.65 | O |
| ATOM | 2570 | NE2 | GLN | A | 334 | 28.781 | 40.106 | 50.808 | 1.00 | 50.33 | N |
| ATOM | 2571 | N | GLU | A | 335 | 35.026 | 43.036 | 48.489 | 1.00 | 35.15 | N |
| ATOM | 2572 | CA | GLU | A | 335 | 35.872 | 44.193 | 48.385 | 1.00 | 34.55 | C |
| ATOM | 2573 | C | GLU | A | 335 | 36.197 | 44.510 | 46.927 | 1.00 | 33.05 | C |
| ATOM | 2574 | O | GLU | A | 335 | 36.760 | 45.564 | 46.640 | 1.00 | 32.79 | O |
| ATOM | 2575 | CB | GLU | A | 335 | 37.144 | 44.028 | 49.247 | 1.00 | 35.19 | C |
| ATOM | 2576 | CG | GLU | A | 335 | 36.927 | 44.326 | 50.727 | 1.00 | 37.92 | C |
| ATOM | 2577 | CD | GLU | A | 335 | 38.195 | 44.232 | 51.550 | 1.00 | 43.46 | C |
| ATOM | 2578 | OE1 | GLU | A | 335 | 39.179 | 44.916 | 51.179 | 1.00 | 46.92 | O |
| ATOM | 2579 | OE2 | GLU | A | 335 | 38.211 | 43.499 | 52.589 | 1.00 | 49.17 | O |
| ATOM | 2580 | N | VAL | A | 336 | 35.792 | 43.633 | 46.005 | 1.00 | 31.25 | N |
| ATOM | 2581 | CA | VAL | A | 336 | 36.081 | 43.810 | 44.579 | 1.00 | 29.91 | C |
| ATOM | 2582 | C | VAL | A | 336 | 35.505 | 45.076 | 43.957 | 1.00 | 29.08 | C |
| ATOM | 2583 | O | VAL | A | 336 | 36.177 | 45.816 | 43.246 | 1.00 | 29.08 | O |
| ATOM | 2584 | CB | VAL | A | 336 | 35.648 | 42.584 | 43.791 | 1.00 | 30.21 | C |
| ATOM | 2585 | CG1 | VAL | A | 336 | 35.743 | 42.805 | 42.325 | 1.00 | 29.11 | C |
| ATOM | 2586 | CG2 | VAL | A | 336 | 36.540 | 41.391 | 44.161 | 1.00 | 29.98 | C |
| ATOM | 2587 | N | GLY | A | 337 | 34.263 | 45.354 | 44.240 | 1.00 | 28.54 | N |
| ATOM | 2588 | CA | GLY | A | 337 | 33.644 | 46.546 | 43.722 | 1.00 | 27.74 | C |
| ATOM | 2589 | C | GLY | A | 337 | 34.285 | 47.848 | 44.130 | 1.00 | 27.24 | C |
| ATOM | 2590 | O | GLY | A | 337 | 34.599 | 48.687 | 43.281 | 1.00 | 26.81 | O |
| ATOM | 2591 | N | PRO | A | 338 | 34.365 | 48.094 | 45.428 | 1.00 | 27.19 | C |
| ATOM | 2592 | CA | PRO | A | 338 | 34.994 | 49.334 | 45.905 | 1.00 | 26.74 | C |
| ATOM | 2593 | C | PRO | A | 338 | 36.378 | 49.553 | 45.328 | 1.00 | 26.42 | C |
| ATOM | 2594 | O | PRO | A | 338 | 36.678 | 50.668 | 44.932 | 1.00 | 27.57 | O |
| ATOM | 2595 | CE | PRO | A | 338 | 35.008 | 49.173 | 47.426 | 1.00 | 25.92 | C |
| ATOM | 2596 | CG | PRO | A | 338 | 33.800 | 48.384 | 47.682 | 1.00 | 27.15 | C |
| ATOM | 2597 | CD | PRO | A | 338 | 33.750 | 47.326 | 46.531 | 1.00 | 27.09 | C |
| ATOM | 2598 | N | LEU | A | 339 | 37.199 | 48.533 | 45.225 | 1.00 | 25.95 | N |
| ATOM | 2599 | CA | LEU | A | 339 | 38.505 | 48.762 | 44.652 | 1.00 | 26.15 | C |
| ATOM | 2600 | C | LEU | A | 339 | 38.384 | 49.205 | 43.192 | 1.00 | 25.74 | C |
| ATOM | 2601 | O | LEU | A | 339 | 39.021 | 50.203 | 42.784 | 1.00 | 23.97 | O |
| ATOM | 2602 | CE | LEU | A | 339 | 39.375 | 47.521 | 44.763 | 1.00 | 27.19 | C |
| ATOM | 2603 | CG | LEU | A | 339 | 40.835 | 47.787 | 44.367 | 1.00 | 28.71 | C |
| ATOM | 2604 | CD1 | LEU | A | 339 | 41.805 | 47.124 | 45.241 | 1.00 | 31.14 | C |
| ATOM | 2605 | CD2 | LEU | A | 339 | 41.028 | 47.264 | 42.987 | 1.00 | 30.12 | C |
| ATOM | 2606 | N | LEU | A | 340 | 37.555 | 48.491 | 42.416 | 1.00 | 25.64 | N |
| ATOM | 2607 | CA | LEU | A | 340 | 37.364 | 48.841 | 40.991 | 1.00 | 25.90 | C |
| ATOM | 2608 | C | LEU | A | 340 | 36.860 | 50.261 | 40.871 | 1.00 | 26.04 | C |
| ATOM | 2609 | O | LEU | A | 340 | 37.324 | 51.044 | 40.034 | 1.00 | 25.93 | O |
| ATOM | 2610 | CB | LEU | A | 340 | 36.399 | 47.900 | 40.293 | 1.00 | 25.64 | C |
| ATOM | 2611 | CG | LEU | A | 340 | 36.996 | 46.521 | 40.072 | 1.00 | 27.50 | C |
| ATOM | 2612 | CD1 | LEU | A | 340 | 35.943 | 45.559 | 39.555 | 1.00 | 26.88 | C |
| ATOM | 2613 | CD2 | LEU | A | 340 | 38.221 | 46.587 | 39.138 | 1.00 | 26.63 | C |
| ATOM | 2614 | N | ASN | A | 341 | 35.914 | 50.610 | 41.720 | 1.00 | 26.45 | N |
| ATOM | 2615 | CA | ASN | A | 341 | 35.377 | 51.963 | 41.669 | 1.00 | 27.35 | C |
| ATOM | 2616 | C | ASN | A | 341 | 36.450 | 52.983 | 41.983 | 1.00 | 27.08 | C |
| ATOM | 2617 | O | ASN | A | 341 | 36.578 | 54.012 | 41.324 | 1.00 | 26.82 | O |
| ATOM | 2618 | CB | ASN | A | 341 | 34.183 | 52.117 | 42.619 | 1.00 | 27.50 | C |
| ATOM | 2619 | CG | ASN | A | 341 | 32.901 | 51.709 | 41.975 | 1.00 | 28.85 | C |

TABLE 3-continued

Coordinates for structures 1 to 4

| | | | | | | | | | | |
|---|---|---|---|---|---|---|---|---|---|---|
| ATOM | 262p | OD1 | ASN | A | 341 | 32.509 | 52.283 | 40.957 | 1.00 | 37.23 O |
| ATOM | 2621 | ND2 | ASN | A | 341 | 32.263 | 50.697 | 42.504 | 1.00 | 29.29 N |
| ATOM | 2622 | N | THR | A | 342 | 37.234 | 52.665 | 42.994 | 1.00 | 26.89 N |
| ATOM | 2623 | CA | THR | A | 342 | 38.321 | 53.509 | 43.355 | 1.00 | 27.22 C |
| ATOM | 2624 | C | THR | A | 342 | 39.301 | 53.629 | 42.191 | 1.00 | 27.16 C |
| ATOM | 2625 | O | THR | A | 342 | 39.861 | 54.686 | 42.003 | 1.00 | 26.86 O |
| ATOM | 2626 | CB | THR | A | 342 | 38.995 | 52.934 | 44.568 | 1.00 | 27.76 C |
| ATOM | 2627 | OG1 | THR | A | 342 | 38.212 | 53.248 | 45.734 | 1.00 | 29.14 O |
| ATOM | 2628 | CG2 | THR | A | 342 | 40.367 | 53.604 | 44.784 | 1.00 | 28.62 C |
| ATOM | 2629 | N | MET | A | 343 | 39.502 | 52.560 | 41.419 | 1.00 | 26.80 N |
| ATOM | 2630 | CA | MET | A | 343 | 40.401 | 52.623 | 40.282 | 1.00 | 27.48 C |
| ATOM | 2631 | C | MET | A | 343 | 39.927 | 53.552 | 39.174 | 1.00 | 27.78 C |
| ATOM | 2632 | O | MET | A | 343 | 40.762 | 54.229 | 38.554 | 1.00 | 26.44 O |
| ATOM | 2633 | CE | MET | A | 343 | 40.602 | 51.253 | 39.634 | 1.00 | 28.13 C |
| ATOM | 2634 | CG | MET | A | 343 | 41.758 | 50.440 | 40.125 | 1.00 | 30.19 C |
| ATOM | 2635 | SD | MET | A | 343 | 42.279 | 49.088 | 38.964 | 1.00 | 32.27 S |
| ATOM | 2636 | CE | MET | A | 343 | 41.049 | 48.127 | 39.221 | 1.00 | 34.83 C |
| ATOM | 2637 | N | ILE | A | 344 | 38.619 | 53.568 | 38.864 | 1.00 | 28.41 N |
| ATOM | 2638 | CA | ILE | A | 344 | 38.193 | 54.350 | 37.700 | 1.00 | 29.03 C |
| ATOM | 2639 | C | ILE | A | 344 | 37.712 | 55.748 | 37.957 | 1.00 | 28.17 C |
| ATOM | 2640 | O | ILE | A | 344 | 37.879 | 56.587 | 37.064 | 1.00 | 27.26 O |
| ATOM | 2641 | CE | ILE | A | 344 | 37.146 | 53.650 | 36.818 | 1.00 | 29.47 C |
| ATOM | 2642 | CG1 | ILE | A | 344 | 35.766 | 53.866 | 37.384 | 1.00 | 32.69 C |
| ATOM | 2643 | CG2 | ILE | A | 344 | 37.457 | 52.176 | 36.667 | 1.00 | 32.43 C |
| ATOM | 2644 | CD1 | ILE | A | 344 | 34.724 | 53.358 | 36.590 | 1.00 | 35.46 C |
| ATOM | 2645 | N | LYS | A | 345 | 37.107 | 56.032 | 39.108 | 1.00 | 27.79 N |
| ATOM | 2646 | CA | LYS | A | 345 | 36.518 | 57.364 | 39.218 | 1.00 | 28.48 C |
| ATOM | 2647 | C | LYS | A | 345 | 37.489 | 58.485 | 39.219 | 1.00 | 27.72 C |
| ATOM | 2648 | O | LYS | A | 345 | 38.428 | 58.555 | 40.000 | 1.00 | 27.37 O |
| ATOM | 2649 | GB | LYS | A | 345 | 35.542 | 57.611 | 40.343 | 1.00 | 29.78 C |
| ATOM | 2650 | CG | LYS | A | 345 | 35.537 | 56.758 | 41.491 | 1.00 | 34.49 C |
| ATOM | 2651 | CD | LYS | A | 345 | 34.075 | 56.352 | 41.692 | 1.00 | 37.43 C |
| ATOM | 2652 | CE | LYS | A | 345 | 33.508 | 57.036 | 42.904 | 1.00 | 40.47 C |
| ATOM | 2653 | NZ | LYS | A | 345 | 34.223 | 56.522 | 44.138 | 1.00 | 46.19 N |
| ATOM | 2654 | N | GLY | A | 346 | 37.218 | 59.386 | 38.297 | 1.00 | 26.82 N |
| ATOM | 2655 | CA | GLY | A | 346 | 38.044 | 60.538 | 38.108 | 1.00 | 25.95 C |
| ATOM | 2656 | C | GLY | A | 346 | 39.314 | 60.175 | 37.392 | 1.00 | 25.08 C |
| ATOM | 2657 | O | GLY | A | 346 | 40.172 | 61.022 | 37.244 | 1.00 | 24.91 O |
| ATOM | 2658 | N | ARG | A | 347 | 39.419 | 58.935 | 36.944 | 1.00 | 24.84 N |
| ATOM | 2659 | CA | ARG | A | 347 | 40.647 | 58.436 | 36.347 | 1.00 | 25.30 C |
| ATOM | 2660 | C | ARG | A | 347 | 40.431 | 57.848 | 34.937 | 1.00 | 26.05 C |
| ATOM | 2661 | O | ARG | A | 347 | 41.138 | 58.196 | 34.007 | 1.00 | 24.59 O |
| ATOM | 2662 | GB | ARG | A | 347 | 41.279 | 57.395 | 37.272 | 1.00 | 25.27 C |
| ATOM | 2663 | CG | ARG | A | 347 | 41.716 | 57.934 | 38.696 | 1.00 | 24.21 C |
| ATOM | 2664 | CD | ARG | A | 347 | 43.159 | 57.506 | 39.082 | 1.00 | 25.10 C |
| ATOM | 2665 | NE | ARG | A | 347 | 43.175 | 56.084 | 39.017 | 1.00 | 24.49 N |
| ATOM | 2666 | CZ | ARG | A | 347 | 44.102 | 55.293 | 38.566 | 1.00 | 19.51 C |
| ATOM | 2667 | NH1 | ARG | A | 347 | 45.299 | 55.692 | 38.195 | 1.00 | 21.86 N |
| ATOM | 2668 | NH2 | ARG | A | 347 | 43.802 | 54.011 | 38.579 | 1.00 | 18.94 N |
| ATOM | 2669 | N | TYR | A | 348 | 39.438 | 56.991 | 34.794 | 1.00 | 27.91 N |
| ATOM | 2670 | CA | TYR | A | 348 | 39.119 | 56.380 | 33.507 | 1.00 | 29.80 C |
| ATOM | 2671 | C | TYR | A | 348 | 37.671 | 56.590 | 33.065 | 1.00 | 32.00 C |
| ATOM | 2672 | O | TYR | A | 348 | 37.309 | 56.173 | 31.964 | 1.00 | 32.29 O |
| ATOM | 2673 | GB | TYR | A | 348 | 39.379 | 54.877 | 33.543 | 1.00 | 28.38 C |
| ATOM | 2674 | CG | TYR | A | 348 | 40.836 | 54.498 | 33.597 | 1.00 | 27.86 C |
| ATOM | 2675 | CD1 | TYR | A | 348 | 41.617 | 54.473 | 32.446 | 1.00 | 26.79 C |
| ATOM | 2676 | CD2 | TYR | A | 348 | 41.422 | 54.124 | 34.787 | 1.00 | 25.32 C |
| ATOM | 2677 | GE1 | TYR | A | 348 | 42.945 | 54.106 | 32.496 | 1.00 | 25.35 C |
| ATOM | 2678 | CE2 | TYR | A | 348 | 42.734 | 53.762 | 34.847 | 1.00 | 27.07 C |
| ATOM | 2679 | CZ | TYR | A | 348 | 43.507 | 53.759 | 33.700 | 1.00 | 26.40 C |
| ATOM | 2680 | OH | TYR | A | 348 | 44.827 | 53.378 | 33.789 | 1.00 | 22.93 O |
| ATOM | 2681 | N | ASN | A | 349 | 36.824 | 57.193 | 33.894 | 1.00 | 34.78 N |
| ATOM | 2682 | CA | ASN | A | 349 | 35.426 | 57.360 | 33.473 | 1.00 | 37.16 C |
| ATOM | 2683 | C | ASN | A | 349 | 34.997 | 58.760 | 33.104 | 1.00 | 38.90 C |
| ATOM | 2684 | O | ASN | A | 349 | 35.690 | 59.756 | 33.136 | 1.00 | 38.66 O |
| ATOM | 2685 | CB | ASN | A | 349 | 34.474 | 56.837 | 34.493 | 1.00 | 36.69 C |
| ATOM | 2686 | CG | ASN | A | 349 | 34.480 | 57.633 | 35.727 | 1.00 | 39.34 C |
| ATOM | 2687 | OD1 | ASN | A | 349 | 35.229 | 58.632 | 35.875 | 1.00 | 40.92 O |
| ATOM | 2688 | ND2 | ASN | A | 349 | 33.654 | 57.188 | 36.684 | 1.00 | 42.73 N |
| ATOM | 2689 | OXT | ASN | A | 349 | 33.854 | 58.954 | 32.689 | 1.00 | 44.16 O |
| THR | 2690 | | ASN | A | 349 | | | | | |
| ATOM | 2691 | N | LEU | S | 795 | 45.870 | 35.442 | 31.163 | 1.00 | 49.68 N |
| ATOM | 2692 | CA | LEU | S | 795 | 44.790 | 36.472 | 31.262 | 1.00 | 49.90 C |
| ATOM | 2693 | C | LEU | S | 795 | 43.668 | 36.155 | 30.294 | 1.00 | 50.12 C |
| ATOM | 2694 | O | LEU | S | 795 | 42.492 | 36.182 | 30.666 | 1.00 | 49.41 O |
| ATOM | 2695 | CB | LEU | S | 795 | 45.331 | 37.873 | 31.004 | 1.00 | 50.09 C |
| ATOM | 2696 | CG | LEU | S | 795 | 44.774 | 38.924 | 31.976 | 1.00 | 50.19 C |

TABLE 3-continued

| | | | | | Coordinates for structures 1 to 4 | | | | | |
|---|---|---|---|---|---|---|---|---|---|---|
| ATOM | 2697 | CD1 | LEU | S | 795 | 44.929 | 38.464 | 33.388 | 1.00 | 50.50 | C |
| ATOM | 2698 | CD2 | LEU | S | 795 | 45.436 | 40.280 | 31.876 | 1.00 | 51.23 | C |
| ATOM | 2699 | N | THR | S | 796 | 44.041 | 35.979 | 29.033 | 1.00 | 50.69 | N |
| ATOM | 2700 | GA | THR | S | 796 | 43.178 | 35.421 | 27.997 | 1.00 | 51.67 | C |
| ATOM | 2701 | C | THR | S | 796 | 42.734 | 33.983 | 28.241 | 1.00 | 51.11 | C |
| ATOM | 2702 | O | THR | S | 796 | 41.884 | 33.464 | 27.535 | 1.00 | 51.41 | O |
| ATOM | 2703 | GB | THR | S | 796 | 43.888 | 35.547 | 26.626 | 1.00 | 51.86 | C |
| ATOM | 2704 | OG1 | THR | S | 796 | 43.253 | 34.704 | 25.671 | 1.00 | 56.26 | O |
| ATOM | 2705 | CG2 | THR | S | 796 | 45.272 | 34.981 | 26.662 | 1.00 | 52.69 | C |
| ATOM | 2706 | N | SER | S | 797 | 43.261 | 33.330 | 29.248 | 1.00 | 51.51 | N |
| ATOM | 2707 | CA | SER | S | 797 | 42.838 | 31.965 | 29.497 | 1.00 | 52.74 | C |
| ATOM | 2708 | C | SER | S | 797 | 41.471 | 31.865 | 30.165 | 1.00 | 53.39 | C |
| ATOM | 2709 | O | SER | S | 797 | 41.070 | 32.733 | 30.934 | 1.00 | 52.91 | O |
| ATOM | 2710 | CB | SER | S | 797 | 43.850 | 31.247 | 30.351 | 1.00 | 52.86 | C |
| ATOM | 2711 | OG | SER | S | 797 | 43.687 | 31.623 | 31.697 | 1.00 | 55.21 | O |
| ATOM | 2712 | N | TYR | S | 798 | 40.783 | 30.761 | 29.904 | 1.00 | 54.79 | N |
| ATOM | 2713 | CA | TYR | S | 798 | 39.424 | 30.584 | 30.372 | 1.00 | 56.02 | C |
| ATOM | 2714 | C | TYR | S | 798 | 39.168 | 29.271 | 31.042 | 1.00 | 55.81 | C |
| ATOM | 2715 | O | TYR | S | 798 | 39.880 | 28.305 | 30.827 | 1.00 | 56.61 | O |
| ATOM | 2716 | CB | TYR | S | 798 | 38.437 | 30.747 | 29.214 | 1.00 | 56.97 | C |
| ATOM | 2717 | CG | TYR | S | 798 | 38.599 | 29.821 | 28.015 | 1.00 | 60.68 | C |
| ATOM | 2718 | CD1 | TYR | S | 798 | 39.595 | 30.035 | 27.059 | 1.00 | 62.78 | C |
| ATOM | 2719 | CD2 | TYR | S | 798 | 37.689 | 28.783 | 27.793 | 1.00 | 64.68 | C |
| ATOM | 2720 | CE1 | TYR | S | 798 | 39.708 | 29.207 | 25.943 | 1.00 | 65.08 | C |
| ATOM | 2721 | CE2 | TYR | S | 798 | 37.798 | 27.944 | 26.669 | 1.00 | 66.15 | C |
| ATOM | 2722 | CZ | TYR | S | 798 | 38.808 | 28.155 | 25.755 | 1.00 | 65.29 | C |
| ATOM | 2723 | OH | TYR | S | 798 | 38.902 | 27.335 | 24.652 | 1.00 | 64.08 | O |
| ATOM | 2724 | N | ASP | S | 799 | 38.117 | 29.240 | 31.843 | 1.00 | 55.66 | N |
| ATOM | 2725 | CA | ASP | S | 799 | 37.727 | 28.032 | 32.546 | 1.00 | 55.90 | C |
| ATOM | 2726 | C | ASP | S | 799 | 36.636 | 27.385 | 31.739 | 1.00 | 54.64 | C |
| ATOM | 2727 | O | ASP | S | 799 | 36.430 | 27.785 | 30.604 | 1.00 | 55.18 | O |
| ATOM | 2728 | CB | ASP | S | 799 | 37.212 | 28.367 | 33.948 | 1.00 | 56.52 | C |
| ATOM | 2729 | CG | ASP | S | 799 | 37.366 | 27.225 | 34.906 | 1.00 | 57.36 | C |
| ATOM | 2730 | OD1 | ASP | S | 799 | 36.749 | 26.147 | 34.720 | 1.00 | 57.64 | O |
| ATOM | 2731 | OD2 | ASP | S | 799 | 38.108 | 27.331 | 35.881 | 1.00 | 62.28 | O |
| ATOM | 2732 | N | CYS | S | 800 | 35.915 | 26.428 | 32.326 | 1.00 | 53.45 | N |
| ATOM | 2733 | CA | CYS | S | 800 | 34.887 | 25.693 | 31.594 | 1.00 | 52.63 | C |
| ATOM | 2734 | C | CYS | S | 800 | 33.564 | 25.644 | 32.359 | 1.00 | 51.79 | C |
| ATOM | 2735 | O | CYS | S | 800 | 32.871 | 24.632 | 32.357 | 1.00 | 51.30 | O |
| ATOM | 2736 | CB | CY. | S | 800 | 35.372 | 24.282 | 31.327 | 1.00 | 52.47 | C |
| ATOM | 2737 | SG | CYS | S | 800 | 35.703 | 23.408 | 32.872 | 1.00 | 52.72 | 5 |
| ATOM | 2738 | N | GLU | S | 801 | 33.187 | 26.742 | 32.996 | 1.00 | 50.91 | N |
| ATOM | 2739 | CA | GLU | S | 801 | 31.939 | 26.732 | 33.762 | 1.00 | 50.65 | C |
| ATOM | 2740 | C | GLU | S | 801 | 30.657 | 26.939 | 32.909 | 1.00 | 50.18 | C |
| ATOM | 2741 | O | GLU | S | 801 | 30.617 | 27.687 | 31.928 | 1.00 | 48.39 | O |
| ATOM | 2742 | CB | GLU | S | 801 | 32.008 | 27.713 | 34.929 | 1.00 | 50.49 | C |
| ATOM | 2743 | CG | GLU | S | 801 | 33.199 | 27.450 | 35.853 | 1.00 | 51.78 | C |
| ATOM | 2744 | CD | GLU | S | 801 | 33.234 | 28.359 | 37.092 | 1.00 | 51.24 | C |
| ATOM | 2745 | OE1 | GLU | S | 801 | 32.589 | 28.038 | 38.102 | 1.00 | 49.25 | O |
| ATOM | 2746 | OE2 | GLU | S | 801 | 33.919 | 29.395 | 37.063 | 1.00 | 51.89 | O |
| ATOM | 2747 | N | VAL | S | 802 | 29.624 | 26.213 | 33.320 | 1.00 | 50.54 | N |
| ATOM | 2748 | CA | VAL | S | 802 | 28.338 | 26.161 | 32.650 | 1.00 | 50.71 | C |
| ATOM | 2749 | C | VAL | S | 802 | 27.213 | 26.094 | 33.694 | 1.00 | 51.25 | C |
| ATOM | 2750 | O | VAL | S | 802 | 27.464 | 25.960 | 34.885 | 1.00 | 50.69 | O |
| ATOM | 2751 | CB | VAL | S | 802 | 28.286 | 24.902 | 31.746 | 1.00 | 50.61 | C |
| ATOM | 2752 | CG1 | VAL | S | 802 | 29.420 | 24.932 | 30.727 | 1.00 | 49.62 | C |
| ATOM | 2753 | CG2 | VAL | S | 802 | 28.376 | 23.601 | 32.585 | 1.00 | 49.78 | C |
| ATOM | 2754 | N | ASN | S | 803 | 25.967 | 26.165 | 33.239 | 1.00 | 52.55 | N |
| ATOM | 2755 | CA | ASN | S | 803 | 24.816 | 26.099 | 34.140 | 1.00 | 53.28 | C |
| ATOM | 2756 | C | ASN | S | 803 | 24.516 | 24.663 | 34.561 | 1.00 | 54.95 | C |
| ATOM | 2757 | O | ASN | S | 803 | 23.440 | 24.150 | 34.298 | 1.00 | 54.22 | O |
| ATOM | 2758 | CB | ASN | S | 803 | 23.560 | 26.724 | 33.511 | 1.00 | 53.04 | C |
| ATOM | 2759 | CG | ASN | S | 803 | 23.546 | 28.245 | 33.569 | 1.00 | 51.60 | C |
| ATOM | 2760 | OD1 | ASN | S | 803 | 24.576 | 28.895 | 33.755 | 1.00 | 51.13 | O |
| ATOM | 2761 | ND2 | AEN | S | 803 | 22.367 | 28.817 | 33.406 | 1.00 | 46.28 | N |
| ATOM | 2762 | N | ALA | S | 804 | 25.498 | 24.033 | 35.201 | 1.00 | 57.29 | N |
| ATOM | 2763 | CA | ALA | S | 804 | 25.373 | 22.697 | 35.784 | 1.00 | 59.38 | C |
| ATOM | 2764 | C | ALA | S | 804 | 26.596 | 22.490 | 36.676 | 1.00 | 61.01 | C |
| ATOM | 2765 | O | ALA | S | 804 | 27.667 | 23.026 | 36.407 | 1.00 | 61.45 | O |
| ATOM | 2766 | CE | ALA | S | 804 | 25.315 | 21.603 | 34.716 | 1.00 | 59.47 | C |
| ATOM | 2767 | N | PRO | S | 805 | 26.438 | 21.707 | 37.732 | 1.00 | 62.94 | N |
| ATOM | 2768 | CA | PRO | S | 805 | 27.547 | 21.398 | 38.652 | 1.00 | 63.79 | C |
| ATOM | 2769 | C | PRO | S | 805 | 28.616 | 20.498 | 38.003 | 1.00 | 64.48 | C |
| ATOM | 2770 | O | PRO | S | 805 | 28.368 | 19.875 | 36.970 | 1.00 | 65.26 | O |
| ATOM | 2771 | CB | PRO | S | 805 | 26.851 | 20.654 | 39.807 | 1.00 | 63.79 | C |
| ATOM | 2772 | CG | PRO | S | 805 | 25.582 | 20.066 | 39.187 | 1.00 | 63.48 | C |
| ATOM | 2773 | CD | PRO | S | 805 | 25.175 | 21.035 | 38.107 | 1.00 | 63.26 | C |

TABLE 3-continued

Coordinates for structures 1 to 4

| ATOM | 2774 | N | ILE | S | 806 | 29.779 | 20.405 | 38.630 | 1.00 | 65.18 | N |
|---|---|---|---|---|---|---|---|---|---|---|---|
| ATOM | 2775 | CA | ILE | S | 806 | 30.903 | 19.626 | 38.100 | 1.00 | 65.66 | C |
| ATOM | 2776 | C | ILE | S | 806 | 30.853 | 18.145 | 38.489 | 1.00 | 65.84 | C |
| ATOM | 2777 | O | ILE | S | 806 | 30.287 | 17.780 | 39.522 | 1.00 | 66.22 | O |
| ATOM | 2778 | CB | ILE | S | 806 | 32.239 | 20.255 | 38.582 | 1.00 | 65.91 | C |
| ATOM | 2779 | CG1 | ILE | S | 806 | 32.435 | 20.046 | 40.089 | 1.00 | 65.62 | C |
| ATOM | 2780 | CG2 | ILE | S | 806 | 32.267 | 21.765 | 38.255 | 1.00 | 66.46 | C |
| ATOM | 2781 | CD1 | ILE | S | 806 | 33.719 | 20.639 | 40.611 | 1.00 | 65.48 | C |
| ATOM | 2782 | N | LEU | S | 813 | 29.912 | 8.313 | 36.265 | 1.00 | 60.30 | N |
| ATOM | 2783 | CA | LEU | S | 813 | 30.605 | 8.781 | 35.059 | 1.00 | 60.57 | C |
| ATOM | 2784 | C | LEU | S | 813 | 29.707 | 9.617 | 34.157 | 1.00 | 60.31 | C |
| ATOM | 2785 | O | LEU | S | 813 | 28.484 | 9.496 | 34.194 | 1.00 | 60.27 | O |
| ATOM | 2786 | CB | LEU | S | 813 | 31.167 | 7.599 | 34.266 | 1.00 | 60.46 | C |
| ATOM | 2787 | CG | LEU | S | 813 | 32.067 | 6.674 | 35.092 | 1.00 | 60.30 | C |
| ATOM | 2788 | CE1 | LEU | S | 813 | 32.450 | 5.418 | 34.281 | 1.00 | 61.04 | C |
| ATOM | 2789 | CD2 | LEU | S | 813 | 33.301 | 7.421 | 35.602 | 1.00 | 59.11 | C |
| ATOM | 2790 | N | GLN | S | 814 | 30.344 | 10.465 | 33.355 | 1.00 | 60.31 | N |
| ATOM | 2791 | CA | GLN | S | 814 | 29.648 | 11.353 | 32.440 | 1.00 | 60.05 | C |
| ATOM | 2792 | C | GLN | S | 814 | 30.557 | 11.803 | 31.295 | 1.00 | 59.62 | C |
| ATOM | 2793 | O | GLN | S | 814 | 31.765 | 11.584, | 31.322 | 1.00 | 58.97 | O |
| ATOM | 2794 | CE | GLN | S | 814 | 29.176 | 12.583 | 33.194 | 1.00 | 60.41 | C |
| ATOM | 2795 | CG | GLN | S | 814 | 30.302 | 13.488 | 33.634 | 1.00 | 62.13 | C |
| ATOM | 2796 | CD | GLN | S | 814 | 29.826 | 14.603 | 34.559 | 1.00 | 64.43 | C |
| ATOM | 2797 | OE1 | GLN | S | 814 | 29.260 | 14.327 | 35.616 | 1.00 | 65.48 | O |
| ATOM | 2798 | NE2 | GLN | S | 814 | 30.058 | 15.859 | 34.167 | 1.00 | 65.06 | N |
| ATOM | 2799 | N | GLY | S | 815 | 29.960 | 12.456 | 30.302 | 1.00 | 59.55 | N |
| ATOM | 2800 | CA | GLY | S | 815 | 30.675 | 12.927 | 29.136 | 1.00 | 59.21 | C |
| ATOM | 2801 | C | GLY | S | 815 | 31.493 | 11.823 | 28.493 | 1.00 | 59.26 | C |
| ATOM | 2802 | O | GLY | S | 815 | 31.049 | 10.678 | 28.399 | 1.00 | 58.48 | O |
| ATOM | 2803 | N | GLU | S | 816 | 32.693 | 12.183 | 28.049 | 1.00 | 59.73 | N |
| ATOM | 2804 | CA | GLU | S | 816 | 33.604 | 11.254 | 27.392 | 1.00 | 60.76 | C |
| ATOM | 2805 | C | GLU | S | 816 | 33.768 | 9.941 | 28.168 | 1.00 | 61.61 | C |
| ATOM | 2806 | O | GLU | S | 816 | 33.861 | 8.866 | 27.567 | 1.00 | 61.64 | O |
| ATOM | 2807 | CE | GLU | S | 816 | 34.978 | 11.913 | 27.190 | 1.00 | 60.71 | C |
| ATOM | 2808 | CG | GLU | S | 816 | 35.802 | 11.304 | 26.064 | 1.00 | 61.12 | C |
| ATOM | 2809 | CD | GLU | S | 816 | 37.208 | 11.872 | 25.979 | 1.00 | 61.35 | C |
| ATOM | 2810 | OE1 | GLU | S | 816 | 38.066 | 11.370 | 26.730 | 1.00 | 61.67 | O |
| ATOM | 2811 | OE2 | GLU | S | 816 | 37.467 | 12.801 | 25.168 | 1.00 | 60.68 | O |
| ATOM | 2812 | N | GLU | S | 817 | 33.791 | 10.030 | 29.495 | 1.00 | 62.56 | N |
| ATOM | 2813 | CA | GLU | S | 817 | 33.962 | 8.851 | 30.332 | 1.00 | 63.66 | C |
| ATOM | 2814 | C | GLU | S | 817 | 32.748 | 7.929 | 30.260 | 1.00 | 63.92 | C |
| ATOM | 2815 | O | GLU | S | 817 | 32.887 | 6.709 | 30.187 | 1.00 | 63.68 | O |
| ATOM | 2816 | CE | GLU | S | 817 | 34.217 | 9.257 | 31.777 | 1.00 | 63.99 | C |
| ATOM | 2817 | CG | GLU | S | 817 | 35.518 | 10.012 | 31.974 | 1.00 | 65.72 | C |
| ATOM | 2818 | CD | GLU | S | 817 | 35.371 | 11.514 | 31.786 | 1.00 | 69.17 | C |
| ATOM | 2819 | OE1 | GLU | S | 817 | 34.253 | 11.990 | 31.452 | 1.00 | 70.86 | O |
| ATOM | 2820 | OE2 | GLU | S | 817 | 36.384 | 12.228 | 31.984 | 1.00 | 71.76 | O |
| ATOM | 2821 | N | LEU | S | 818 | 31.558 | 8.517 | 30.296 | 1.00 | 64.38 | N |
| ATOM | 2822 | CA | LEU | S | 818 | 30.344 | 7.733 | 30.191 | 1.00 | 65.00 | C |
| ATOM | 2823 | C | LEU | S | 818 | 30.367 | 6.935 | 28.890 | 1.00 | 65.31 | C |
| ATOM | 2824 | O | LEU | S | 818 | 30.166 | 5.723 | 28.901 | 1.00 | 65.41 | O |
| ATOM | 2825 | CE | LEU | S | 818 | 29.092 | 8.624 | 30.232 | 1.00 | 64.90 | C |
| ATOM | 2826 | CG | LEU | S | 818 | 27.770 | 7.844 | 30.163 | 1.00 | 64.94 | C |
| ATOM | 2827 | CD1 | LEU | S | 818 | 27.702 | 6.871 | 31.316 | 1.00 | 66.53 | C |
| ATOM | 2828 | CD2 | LEU | S | 818 | 26.551 | 8.718 | 30.205 | 1.00 | 63.99 | C |
| ATOM | 2829 | N | LEU | S | 819 | 30.647 | 7.627 | 27.787 | 1.00 | 65.71 | N |
| ATOM | 2830 | CA | LEU | S | 819 | 30.608 | 7.037 | 26.445 | 1.00 | 66.10 | C |
| ATOM | 2831 | C | LEU | S | 819 | 31.569 | 5.851 | 26.294 | 1.00 | 66.37 | C |
| ATOM | 2832 | O | LEU | S | 819 | 31.174 | 4.773 | 25.852 | 1.00 | 65.86 | O |
| ATOM | 2833 | CB | LEU | S | 819 | 30.901 | 8.122 | 25.392 | 1.00 | 66.04 | C |
| ATOM | 2834 | CG | LEU | S | 819 | 30.860 | 7.737 | 23.916 | 1.00 | 66.00 | C |
| ATOM | 2835 | CD1 | LEU | S | 819 | 29.537 | 7.149 | 23.501 | 1.00 | 66.14 | C |
| ATOM | 2836 | CD2 | LEU | S | 819 | 31.162 | 8.967 | 23.083 | 1.00 | 67.31 | C |
| ATOM | 2837 | N | ARG | S | 820 | 32.820 | 6.053 | 26.684 | 1.00 | 66.68 | N |
| ATOM | 2838 | CA | ARG | S | 820 | 33.824 | 5.013 | 26.561 | 1.00 | 67.34 | C |
| ATOM | 2839 | C | ARG | S | 820 | 33.492 | 3.801 | 27.432 | 1.00 | 67.41 | C |
| ATOM | 2840 | O | ARG | S | 820 | 33.573 | 2.643 | 26.969 | 1.00 | 67.19 | O |
| ATOM | 2841 | CB | ARG | S | 820 | 35.196 | 5.574 | 26.917 | 1.00 | 67.66 | C |
| ATOM | 2842 | CG | ARG | S | 820 | 35.628 | 6.605 | 25.907 | 1.00 | 69.12 | C |
| ATOM | 2843 | CD | ARG | S | 820 | 37.048 | 7.061 | 26.030 | 1.00 | 71.00 | C |
| ATOM | 2844 | NE | ARG | S | 820 | 37.309 | 8.138 | 25.079 | 1.00 | 73.46 | N |
| ATOM | 2845 | CZ | ARG | S | 820 | 38.442 | 8.839 | 25.014 | 1.00 | 75.31 | C |
| ATOM | 2846 | NH1 | ARG | S | 820 | 39.451 | 8.581 | 25.851 | 1.00 | 75.90 | N |
| ATOM | 2847 | NH2 | ARG | S | 820 | 38.566 | 9.806 | 24.104 | 1.00 | 75.55 | N |
| ATOM | 2848 | N | ALA | S | 821 | 33.118 | 4.067 | 28.684 | 1.00 | 67.11 | N |
| ATOM | 2849 | CA | ALA | S | 821 | 32.712 | 2.999 | 29.580 | 1.00 | 66.99 | C |
| ATOM | 2850 | C | ALA | S | 821 | 31.609 | 2.171 | 28.898 | 1.00 | 66.7& | C |

TABLE 3-continued

| | | | | | Coordinates for structures 1 to 4 | | | | | |
|---|---|---|---|---|---|---|---|---|---|---|
| ATOM | 2851 | O | ALA | S | 821 | 31.660 | 0.945 | 28.889 | 1.00 | 66.63 | O |
| ATOM | 2852 | CB | ALA | S | 821 | 32.234 | 3.562 | 30.901 | 1.00 | 66.88 | C |
| ATOM | 2853 | N | LEU | S | 822 | 30.625 | 2.851 | 28.313 | 1.00 | 66.58 | N |
| ATOM | 2854 | CA | LEU | S | 822 | 29.538 | 2.173 | 27.607 | 1.00 | 66.36 | C |
| ATOM | 2855 | C | LEU | S | 822 | 30.027 | 1.439 | 26.359 | 1.00 | 66.21 | C |
| ATOM | 2856 | O | LEU | S | 822 | 29.429 | 0.444 | 25.956 | 1.00 | 66.11 | O |
| ATOM | 2857 | CB | LEU | S | 822 | 28.451 | 3.172 | 27.223 | 1.00 | 66.06 | C |
| ATOM | 2858 | CG | LEU | S | 822 | 27.710 | 3.789 | 28.406 | 1.00 | 65.45 | C |
| ATOM | 2859 | CE1 | LEU | S | 822 | 26.559 | 4.613 | 27.885 | 1.00 | 6S.37 | C |
| ATOM | 2860 | CD2 | LEU | S | 822 | 27.213 | 2.732 | 29.396 | 1.00 | 6S.08 | C |
| THR | 2861 | | LEU | S | 822 | | | | | | |
| HETATM | 2862 | ZN | ZN | A | 1350 | 23.324 | 27.578 | 28.817 | 1.00 | 32.29 | ZN |
| HETATM | 2863 | C1 | OGA | A | 1351 | 22.262 | 25.308 | 27.891 | 1.00 | 34.79 | C |
| HETATM | 2864 | C2 | OGA | A | 1351 | 21.209 | 25.940 | 28.487 | 1.00 | 32.90 | C |
| HETATM | 2865 | C4 | OGA | A | 1351 | 18.882 | 25.730 | 29.253 | 1.00 | 32.24 | C |
| HETATM | 2866 | C5 | OGA | A | 1351 | 17.543 | 25.2S1 | 28.735 | 1.00 | 32.20 | C |
| HETATM | 2867 | O1 | OGA | A | 1351 | 22.091 | 24.207 | 27.399 | 1.00 | 33.47 | O |
| HETATM | 2868 | O2 | OGA | A | 1351 | 23.404 | 25.817 | 27.813 | 1.00 | 33.83 | O |
| HETATM | 2869 | O2' | OGA | A | 1351 | 21.299 | 27.077 | 29.004 | 1.00 | 31.02 | O |
| HETATM | 2870 | O3 | OGA | A | 1351 | 17.430 | 24.476 | 27.795 | 1.00 | 33.67 | O |
| HETATM | 2871 | N1 | OGA | A | 1351 | 20.067 | 25.271 | 28.520 | 1.00 | 29.83 | N |
| HETATM | 2872 | O4 | OGA | A | 1351 | 16.551 | 25.641 | 29.307 | 1.00 | 32.21 | O |
| HETATM | 2873 | S | SO4 | A | 1352 | 0.290 | 25.194 | 43.827 | 1.00 | 90.02 | S |
| HETATM | 2874 | O1 | SO4 | A | 1352 | 1.120 | 26.025 | 44.689 | 1.00 | 89.95 | O |
| HETATM | 2875 | O2 | SO4 | A | 1352 | 1.151 | 24.261 | 43.106 | 1.00 | 88.91 | O |
| HETATM | 2876 | O3 | SO4 | A | 1352 | 0.627 | 24.447 | 44.672 | 1.00 | 90.38 | O |
| HETATM | 2877 | O4 | SO4 | A | 1352 | 0.468 | 26.028 | 42.891 | 1.00 | 89.30 | O |
| HETATM | 2878 | S | SO4 | A | 1353 | 1.893 | 28.515 | 29.870 | 1.00 | 98.62 | S |
| HETATM | 2879 | O1 | SO4 | A | 1353 | 3.138 | 29.102 | 30.350 | 1.00 | 97.69 | O |
| HETATM | 2880 | O2 | SO4 | A | 1353 | 2.145 | 27.399 | 28.947 | 1.00 | 97.91 | O |
| HETATM | 2881 | O3 | SO4 | A | 1353 | 1.205 | 28.059 | 31.078 | 1.00 | 99.26 | O |
| HETATM | 2882 | O4 | SO4 | A | 1353 | 1.078 | 29.515 | 29.171 | 1.00 | 98.46 | O |
| HETATM | 2883 | O | HOH | H | 1 | 38.820 | 33.858 | 31.965 | 1.00 | 46.43 | O |
| HETATM | 2884 | O | HOH | H | 2 | 33.795 | 30.509 | 39.255 | 1.00 | 71.93 | O |
| HETATM | 2885 | O | HOH | H | 3 | 34.891 | 30.536 | 35.372 | 1.00 | 48.26 | O |
| HETATM | 2886 | O | HOH | H | 4 | 35.615 | 13.844 | 24.220 | 1.00 | 48.67 | O |
| HETATM | 2887 | O | HOH | Z | 1 | 11.592 | 21.463 | 13.878 | 1.00 | 49.06 | O |
| HETATM | 2888 | O | HOH | Z | 2 | 9.700 | 21.662 | 12.247 | 1.00 | 70.56 | O |
| HETATM | 2889 | O | HOH | Z | 3 | 1.136 | 21.407 | 7.962 | 1.00 | 66.59 | O |
| HETATM | 2890 | O | HOH | Z | 4 | 2.407 | 19.370 | 5.351 | 1.00 | 60.28 | O |
| HETATM | 2891 | O | HOH | Z | 5 | 1.014 | 29.292 | 13.196 | 1.00 | 61.25 | O |
| HETATM | 2892 | O | HOH | Z | 6 | 2.256 | 32.365 | 14.166 | 1.00 | 73.91 | O |
| HETATM | 2893 | O | HOH | Z | 7 | 11.526 | 44.954 | 15.330 | 1.00 | 68.94 | O |
| HETATM | 2894 | O | HOH | Z | 8 | 1.438 | 30.257 | 22.663 | 1.00 | 85.46 | O |
| HETATM | 2895 | O | HOH | Z | 9 | 7.738 | 30.579 | 27.736 | 1.00 | 46.83 | O |
| HETATM | 2896 | O | HOH | Z | 10 | 3.543 | 32.597 | 32.323 | 1.00 | 73.21 | O |
| HETATM | 2897 | O | HOH | Z | 11 | 6.618 | 43.722 | 26.114 | 1.00 | 79.20 | O |
| HETATM | 2898 | O | HOH | Z | 12 | 4.723 | 37.184 | 27.600 | 1.00 | 69.48 | O |
| HETATM | 2899 | O | HOH | Z | 13 | 10.942 | 35.610 | 30.382 | 1.00 | 48.93 | O |
| HETATM | 2900 | O | HOH | Z | 14 | 13.888 | 48.615 | 19.570 | 1.00 | 55.60 | O |
| HETATM | 2901 | O | HOH | Z | 15 | 12.153 | 41.664 | 15.818 | 1.00 | 61.09 | O |
| HETATM | 2902 | O | HOH | Z | 16 | 15.898 | 30.602 | 12.921 | 1.00 | 48.84 | O |
| HETATM | 2903 | O | HOH | Z | 17 | 13.629 | 22.042 | 7.314 | 1.00 | 56.45 | O |
| HETATM | 2904 | O | HOH | Z | 18 | 14.608 | 26.242 | 13.702 | 1.00 | 55.84 | O |
| HETATM | 2905 | O | HOH | Z | 19 | 21.110 | 23.978 | 3.732 | 1.00 | 49.91 | O |
| HETATM | 2906 | O | HOH | Z | 20 | 22.517 | 24.246 | 0.061 | 1.00 | 58.70 | O |
| HETATM | 2907 | O | HOH | Z | 21 | 27.322 | 30.745 | 5.813 | 1.00 | 71.25 | O |
| HETATM | 2908 | O | HOH | Z | 22 | 26.669 | 21.831 | 43.291 | 1.00 | 84.79 | O |
| HETATM | 2909 | O | HOH | Z | 23 | 36.928 | 29.423 | 21.116 | 1.00 | 60.53 | O |
| HETATM | 2910 | O | HOH | Z | 24 | 28.560 | 37.933 | 15.396 | 1.00 | 65.84 | O |
| HETATM | 2911 | O | HOH | Z | 25 | 29.717 | 37.018 | 10.091 | 1.00 | 70.57 | O |
| HETATM | 2912 | O | HOH | Z | 26 | 19.889 | 17.921 | 13.411 | 1.00 | 40.68 | O |
| HETATM | 2913 | O | HOH | Z | 27 | 18.190 | 15.068 | 13.047 | 1.00 | 45.64 | O |
| HETATM | 2914 | O | HOH | Z | 28 | 19.229 | 14.479 | 16.581 | 1.00 | 44.23 | O |
| HETATM | 2915 | O | HOH | Z | 29 | 5.509 | 12.781 | 28.209 | 1.00 | 48.58 | O |
| HETATM | 2916 | O | HOH | Z | 30 | 19.118 | 6.397 | 36.829 | 1.00 | 62.79 | O |
| HETATM | 2917 | O | HOH | Z | 31 | 33.446 | 44.026 | 25.377 | 1.00 | 68.72 | O |
| HETATM | 2918 | O | HOH | Z | 32 | 8.427 | 26.875 | 44.426 | 1.00 | 65.85 | O |
| HETATM | 2919 | O | HOH | Z | 33 | 9.122 | 31.413 | 42.815 | 1.00 | 79.14 | O |
| HETATM | 2920 | O | HOH | Z | 34 | 15.645 | 37.855 | 35.686 | 1.00 | 55.81 | O |
| HETATM | 2921 | O | HOH | Z | 35 | 16.264 | 30.912 | 40.283 | 1.00 | 52.67 | O |
| HETATM | 2922 | O | HOH | Z | 36 | 28.580 | 24.804 | 42.231 | 1.00 | 71.47 | O |
| HETATM | 2923 | O | HOH | Z | 37 | 25.125 | 24.702 | 42.513 | 1.00 | 61.76 | O |
| HETATM | 2924 | O | HOH | Z | 38 | 31.710 | 33.903 | 46.336 | 1.00 | 58.86 | O |
| HETATM | 2925 | O | HOH | Z | 39 | 24.430 | 38.695 | 49.842 | 1.00 | 64.87 | O |
| HETATM | 2926 | O | HOH | Z | 40 | 21.999 | 17.349 | 48.274 | 1.00 | 78.90 | O |
| HETATM | 2927 | O | HOH | Z | 41 | 22.174 | 10.277 | 34.700 | 1.00 | 61.90 | O |

TABLE 3-continued

Coordinates for structures 1 to 4

| | | | | | | | | | | | |
|---|---|---|---|---|---|---|---|---|---|---|---|
| HETATM | 2928 | O | HOH | Z | 42 | 17.917 | 1.798 | 33.038 | 1.00 | 69.51 | O |
| HETATM | 2929 | O | HOH | Z | 43 | 36.654 | 10.887 | 7.525 | 1.00 | 72.57 | O |
| HETATM | 2930 | O | HOH | Z | 44 | 13.628 | 20.833 | 28.536 | 1.00 | 46.20 | O |
| HETATM | 2931 | O | HOH | Z | 45 | 3.910 | 21.434 | 31.018 | 1.00 | 60.17 | O |
| HETATM | 2932 | O | HOH | Z | 46 | 30.778 | 38.131 | 33.414 | 1.00 | 33.59 | O |
| HETATM | 2933 | O | HOH | Z | 47 | 25.976 | 26.458 | 26.213 | 1.00 | 38.20 | O |
| HETATM | 2934 | O | HOH | Z | 48 | 35.876 | 25.491 | 27.760 | 1.00 | 47.36 | O |
| HETATM | 2935 | O | HOH | Z | 49 | 36.704 | 26.679 | 21.111 | 1.00 | 49.53 | O |
| HETATM | 2936 | O | HOH | Z | 50 | 17.375 | 16.970 | 18.001 | 1.00 | 37.06 | O |
| HETATM | 2937 | O | HOH | Z | 51 | 5.442 | 16.762 | 21.954 | 1.00 | 48.45 | O |
| HETATM | 2938 | O | HOH | Z | 52 | 6.786 | 12.615 | 22.641 | 1.00 | 71.97 | O |
| HETATM | 2939 | O | HOH | Z | 53 | 7.201 | 17.017 | 20.359 | 1.00 | 48.19 | O |
| HETATM | 2940 | O | HOH | Z | 54 | 6.512 | 22.748 | 23.330 | 1.00 | 52.43 | O |
| HETATM | 2941 | O | HOH | Z | 55 | 29.528 | 38.794 | 26.547 | 1.00 | 33.74 | O |
| HETATM | 2942 | O | HOH | Z | 56 | 30.683 | 39.271 | 19.412 | 1.00 | 42.04 | O |
| HETATM | 2943 | O | HOH | Z | 57 | 26.571 | 42.213 | 18.009 | 1.00 | 59.45 | O |
| HETATM | 2944 | O | HOH | Z | 58 | 29.038 | 40.259 | 16.007 | 1.00 | 65.33 | O |
| HETATM | 2945 | O | HOH | Z | 59 | 27.631 | 44.557 | 31.407 | 1.00 | 36.71 | O |
| HETATM | 2946 | O | HOH | Z | 60 | 27.654 | 48.738 | 30.067 | 1.00 | 46.82 | O |
| HETATM | 2947 | O | HOH | Z | 61 | 30.426 | 45.052 | 25.424 | 1.00 | 49.55 | O |
| HETATM | 2948 | O | HOH | Z | 62 | 25.946 | 50.745 | 30.903 | 1.00 | 51.76 | O |
| HETATM | 2949 | O | HOH | Z | 63 | 26.759 | 31.212 | 38.332 | 1.00 | 39.21 | O |
| HETATM | 2950 | O | HOH | Z | 64 | 29.563 | 36.988 | 35.538 | 1.00 | 36.58 | O |
| HETATM | 2951 | O | HOH | Z | 65 | 30.608 | 30.268 | 36.508 | 1.00 | 39.97 | O |
| HETATM | 2952 | O | HOH | Z | 66 | 19.823 | 31.620 | 33.966 | 1.00 | 44.64 | O |
| HETATM | 2953 | O | HOH | Z | 67 | 19.517 | 36.182 | 33.531 | 1.00 | 39.38 | O |
| HETATM | 2954 | O | HOH | Z | 68 | 18.255 | 38.678 | 36.813 | 1.00 | 57.99 | O |
| HETATM | 2955 | O | HOH | Z | 69 | 21.026 | 42.838 | 40.240 | 1.00 | 56.11 | O |
| HETATM | 2956 | O | HOH | Z | 70 | 17.610 | 37.832 | 32.310 | 1.00 | 47.08 | O |
| HETATM | 2957 | O | HOH | Z | 71 | 15.109 | 37.973 | 32.827 | 1.00 | 45.82 | O |
| HETATM | 2958 | O | HOH | Z | 72 | 16.418 | 47.375 | 39.219 | 1.00 | 67.81 | O |
| HETATM | 2959 | O | HOH | Z | 73 | 15.605 | 44.895 | 35.040 | 1.00 | 43.78 | O |
| HETATM | 2960 | O | HOH | Z | 74 | 15.286 | 55.715 | 27.660 | 1.00 | 67.46 | O |
| HETATM | 2961 | O | HOH | Z | 75 | 15.476 | 50.403 | 22.363 | 1.00 | 44.42 | O |
| HETATM | 2962 | O | HOH | Z | 76 | 16.645 | 46.682 | 22.198 | 1.00 | 39.25 | O |
| HETATM | 2963 | O | HOH | Z | 77 | 26.589 | 40.795 | 15.622 | 1.00 | 68.21 | O |
| HETATM | 2964 | O | NON | Z | 78 | 10.674 | 19.290 | 14.058 | 1.00 | 55.87 | O |
| HETATM | 2965 | O | HOH | Z | 79 | 27.773 | 27.556 | 24.476 | 1.00 | 37.12 | O |
| HETATM | 2966 | O | HOH | Z | 80 | 30.214 | 36.062 | 27.011 | 1.00 | 40.11 | O |
| HETATM | 2967 | O | HOH | Z | 81 | 32.661 | 34.179 | 19.369 | 1.00 | 54.04 | O |
| HETATM | 2968 | O | HOH | Z | 82 | 27.339 | 30.221 | 25.948 | 1.00 | 38.07 | O |
| HETATM | 2969 | O | HOH | Z | 83 | 16.261 | 36.239 | 29.815 | 1.00 | 43.65 | O |
| HETATM | 2970 | O | HOH | Z | 84 | 6.400 | 23.973 | 25.697 | 1.00 | 45.37 | O |
| HETATM | 2971 | O | HOH | Z | 85 | 4.061 | 20.777 | 20.758 | 1.00 | 74.60 | O |
| HETATM | 2972 | O | HOH | Z | 86 | 42.841 | 37.277 | 18.598 | 1.00 | 67.00 | O |
| HETATM | 2973 | O | HOH | Z | 87 | 42.456 | 44.259 | 19.547 | 1.00 | 64.85 | O |
| HETATM | 2974 | O | HOH | Z | 88 | 33.750 | 36.936 | 20.231 | 1.00 | 46.70 | O |
| HETATM | 2975 | O | HOH | Z | 89 | 33.208 | 39.305 | 33.829 | 1.00 | 37.00 | O |
| HETATM | 2976 | O | HOH | Z | 90 | 32.098 | 40.251 | 44.432 | 1.00 | 46.81 | O |
| HETATM | 2977 | O | HOH | Z | 91 | 32.904 | 43.762 | 45.581 | 1.00 | 58.90 | O |
| HETATM | 2978 | O | HOH | Z | 92 | 39.242 | 57.294 | 42.204 | 1.00 | 36.08 | O |
| HETATM | 2979 | O | HOH | Z | 93 | 46.926 | 53.378 | 32.000 | 1.00 | 42.91 | O |
| HETATM | 2980 | O | HOH | Z | 94 | 37.922 | 55.476 | 29.664 | 1.00 | 46.42 | O |
| HETATM | 2981 | O | HOH | Z | 95 | 38.489 | 59.800 | 33.014 | 1.00 | 55.47 | O |
| CONECT | 1478 | 2862 | | | | | | | | | |
| CONECT | 1498 | 2862 | | | | | | | | | |
| CONECT | 2167 | 2862 | | | | | | | | | |
| CONECT | 2862 | 2869 | 2868 | 1478 | 2167 | 1498 | | | | | |
| CONECT | 2863 | 2864 | 2867 | 2868 | | | | | | | |
| CONECT | 2864 | 2863 | 2869 | 2871 | | | | | | | |
| CONECT | 2865 | 2866 | 2871 | | | | | | | | |
| CONECT | 2866 | 2865 | 2870 | 2872 | | | | | | | |
| CONECT | 2867 | 2863 | | | | | | | | | |
| CONECT | 2868 | 2863 | 2862 | | | | | | | | |
| CONECT | 2869 | 2864 | 2862 | | | | | | | | |
| CONECT | 2870 | 2866 | | | | | | | | | |
| CONECT | 2871 | 2864 | 2865 | | | | | | | | |
| CONECT | 2872 | 2866 | | | | | | | | | |
| CONECT | 2873 | 2874 | 2875 | 2876 | 2877 | | | | | | |
| CONECT | 2874 | 2873 | | | | | | | | | |
| CONECT | 2875 | 2873 | | | | | | | | | |
| CONECT | 2876 | 2873 | | | | | | | | | |
| CONECT | 2877 | 2873 | | | | | | | | | |
| CONECT | 2878 | 2879 | 2880 | 2881 | 2882 | | | | | | |
| CONECT | 2879 | 2878 | | | | | | | | | |
| CONECT | 2880 | 2878 | | | | | | | | | |
| CONECT | 2881 | 2878 | | | | | | | | | |

TABLE 3-continued

| Coordinates for structures 1 to 4 | | | | | | | | | | | | |
|---|---|---|---|---|---|---|---|---|---|---|---|---|
| CONECT | 2882 2878 | | | | | | | | | | | |
| MASTER | 446 | 0 | 4 | 15 | 20 | 0 | 8 | 6 2979 | 2 | 24 | 31 | |
| END | | | | | | | | | | | | |

Structure 4
Below are the coordinates for structure 4 (the 2.85 A structure of FIH:Fe(II):2OG)

| | |
|---|---|
| HEADER | TRANSCRIPTION ACTIVATOR/INHIBITOR 12-AUG-02 1H2N |
| TITLE | FACTOR INHIBITING HIF-1 ALPHA IN COMPLEX WITH HIF-1 ALPHA |
| TITLE | 2 FRAGMENT PEPTIDE |
| COMPND | MOL_ID: 1; |
| COMPND | 2 MOLECULE: FACTOR INHIBITING HIF1; |
| COMPND | 3 SYNONYM: FIH1; |
| COMPND | 4 CHAIN: A; |
| COMPND | 5 ENGINEERED: YES |
| SOURCE | MOL_ID: 1; |
| SOURCE | 2 ORGANISM SCIENTIFIC: *HOMO SAPIENS;* |
| SOURCE | 3 ORGANISM_COMMON: HUMAN; |
| SOURCE | 4 EXPRESSION_SYSTEM: *ESCHERICHIA COLI;* |
| SOURCE | 5 EXPRESSION_SYSTEM_STRAIN: BL21(DE3); |
| SOURCE | 6 EXPRESSION_SYSTEM_PLASMID: PET28A(+) |
| KEYWDS | FIH, HIF, DSBH, OXYGENASE, TRANSCRIPTION, HYPOXIA, |
| KEYWDS | 2 2-OXOGLUTARATE, ASPARAGINYL HYDROXYLASE, HYDROXYLASE |
| EXPDTA | X-RAY DIFFRACTION |
| AUTHOR | J. M. ELKINS, K. S. HEWITSON, L. A. MCNEILL, I. SCHLEMMINGER, |
| AUTHOR | 2 J. F. SEIBEL, C. J. SCHOFIELD |
| REVDAT | 1 04-SEP-02 1H2N 0 |
| JRNL | AUTH        J. M. ELKINS, K. S. HEWITSON, L. A. MCNEILL |
| JRNL | AUTH 2     I. SCHLEMMINGER, J. F. SEIBEL, C. J. SCHOFIELD |
| JRNL | TITL        FIH:HIF-FRAGMENT COMPLEXES |
| JRNL | REF TO BE PUBLISHED |
| JRNL | REFN |
| REMARK | 2 |
| REMARK | 2 RESOLUTION. 2.84 ANGSTROMS. |
| REMARK | 3 |
| REMARK | 3 REFINEMENT. |
| REMARK | 3 PROGRAM: REFMAC 5.0 |
| REMARK | 3 AUTHORS: MURSHUDOV, VAGIN, DODSON |
| REMARK | 3 |
| REMARK | 3 REFINEMENT TARGET: MAXIMUM LIKELIHOOD |
| REMARK | 3 |
| REMARK | 3 DATA USED IN REFINEMENT. |
| REMARK | 3 RESOLUTION RANGE HIGH (ANGSTROMS):     2.4 |
| REMARK | 3 RESOLUTION RANGE LOW (ANGSTROMS):      30.00 |
| REMARK | 3 DATA CUTOFF (SIGMA(F)):                NONE |
| REMARK | 3 COMPLETENESS FOR RANGE (%):            99.51 |
| REMARK | 3 NUMBER OF REFLECTIONS.:                12577 |
| REMARK | 3 |
| REMARk | 3 FIT TO DATA USED IN REFINEMENT. |
| REMARK | 3 CROSS-VALIDATION METHOD:               THROUGHOUT |
| REMARK | 3 FREE R VALUE TEST SET SELECTION:       RANDOM |
| REMARK | 3 R VALUE (WORKING + TEST SET):          0.23287 |
| REMARK | 3 R VALUE (WORKING SET):                 0.23094 |
| REMARK | 3 FREE R VALUE:                          0.25695 |
| REMARK | 3 FREE R VALUE TEST SET SIZE (%):        7.7 |
| REMARK | 3 FREE R VALUE TEST SET COUNT:           1046 |
| REMARK | 3 |
| REMARK | 3 FIT IN THE HIGHEST RESOLUTION BIN. |
| REMARK | 3 TOTAL NUMBER OF BINS USED:             20 |
| REMARK | 3 BIN RESOLUTION RANGE HIGH:             2.840 |
| REMARK | 3 BIN RESOLUTION RANGE LOW:              2.913 |
| REMARK | 3 REFLECTION IN BIN (WORKING SET):       828 |
| REMARK | 3 BIN R VALUE (WORKING SET):             0.286 |
| REMARK | 3 BIN FREE R VALUE SET COUNT:            81 |
| REMARK | 3 BIN FREE R VALUE:                      0.315 |
| REMARK | 3 |
| REMARK | 3 NUMBER OF NON-HYDROGEN ATOMS USED IN REFINEMENT. |
| REMARK | 3 PROTEIN ATOMS:           2689 |
| REMARK | 3 NUCLEIC ACID ATOMS:      0 |
| REMARK | 3 HETEROGEN ATOMS:         26 |
| REMARK | 3 SOLVENT ATOMS:           3 |
| REMARK | 3 |
| REMARK | 3 B VALUES. |
| REMARK | 3 FROM WILSON PLOT (A**2):               NULL |
| REMARK | 3 MEAN B VALUE (OVERALL, A**2):          35.345 |
| REMARK | 3 OVERALL ANISOTROPIC B VALUE. |

TABLE 3-continued

Coordinates for structures 1 to 4

| | | | | |
|---|---|---|---|---|
| REMARK | 3 B11 (A**2): | 1.02 | | |
| REMARK | 3 B22 (A**2): | 1.02 | | |
| REMARK | 3 B33 (A**2): | 2.03 | | |
| REMARK | 3 B12 (A**2): | 0.00 | | |
| REMARK | 3 B13 (A**2): | 0.00 | | |
| REMARK | 3 B23 (A**2): | 0.00 | | |
| REMARK | 3 | | | |
| REMARK | 3 ESTIMATED OVERALL COORDINATE ERROR. | | | |
| REMARK | 3 ESU BASED ON R VALUE (A): | | | 0.852 |
| REMARK | 3 ESU BASED ON FREE R VALUE (A): | | | 0.349 |
| REMARK | 3 ESU BASED ON MAXIMUM LIKELIHOOD (A**2): | | | 19.679 |
| REMARK | 3 ESU FOR B VALUES BASED ON MAXIMUM LIKELIHOOD (A**2): | | | 19.679 |
| REMARK | 3 | | | |
| REMARK | 3 CORRELATION COEFFICIEMTS. | | | |
| REMARK | 3 CORRELATION COEFFICIENT FO-FC: | | 0.913 | |
| REMARK | 3 CORRELATION COEFFICIENT FO-FC FREE: | | 0.901 | |
| REMARK | 3 | | | |
| REMARK | 3 RMS DEVIATIONS FROM IDEAL VALUES | COUNT | RMS | WEIGHT |
| REMARK | 3 BOND LENGTHS REFINED ATOMS (A): | 2791; | 0.015; | 0.021 |
| REMARK | 3 BOND LENGTHS OTHERS (A): | 2388; | 0.001; | 0.020 |
| REMARK | 3 BOND ANGLES REFINED ATOMS (DEGREES): | 3799; | 1.628; | 1.945 |
| REMARK | 3 BOND ANGLES OTHERS (DEGREES): | 5576; | 0.823; | 3.000 |
| REMARK | 3 TORSION ANGLES, PERIOD 1 (DEGREES): | 330; | 4.268; | 3.000 |
| REMARK | 3 TORSION ANGLES, PERIOD 3 (DEGREES): | 479 | ;18.082; | 15.000 |
| REMARK | 3 CHIRALCEN THR RESTRAINTS (A**3): | 384; | 0.095; | 0.200 |
| REMARK | 3 GENERAL PLANES REFINED ATOMS (A): | 3137; | 0.005; | 0.020 |
| REMARK | 3 GENERAL PLANES OTHERS (A): | 575; | 0.002; | 0.020 |
| REMARK | 3 NON-BONDED CONTACTS REFINED ATOMS (A): | 717; | 0.255; | 0.300 |
| REMARK | 3 NON-BONDED CONTACTS OTHERS (A): | 2425; | 0.224; | 0.300 |
| REMARK | 3 H-BOND (X...Y) REFINED ATOMS (A): | 165; | 0.139; | 0.500 |
| REMARK | 3 H-BOND (X...Y) OTHERS (A): | 1; | 0.102; | 0.500 |
| REMARK | 3 POTENTIAL METAL-ION REFINED ATOMS (A): | 3; | 0.112; | 0.500 |
| REMARK | 3 SYMMETRY VDW REFINED ATOMS (A): | 14; | 0.256; | 0.300 |
| REMARK | 3 SYMMETRY VDW OTHERS (A): | 62; | 0.273; | 0.300 |
| REMARK | 3 SYMMETRY H-BOND REFINED ATOMS (A): | 4; | 0.214; | 0.500 |
| REMARK | 3 SYMMETRY H-BOND OTHERS (A): | 1; | 0.061; | 0.500 |
| REMARK | 3 | | | |
| REMARK | 3 ISOTROPIC THERMAL FACTOR RESTRAINTS. | COUNT | RMS | WEIGHT |
| REMARK | 3 MAIN-CHAIN BOND REFINED ATOMS (A**2): | 1659; | 0.312; | 1.500 |
| REMARK | 3 MAIN-CHAIN ANGLE REFINED ATOMS (A**2): | 2675; | 0.598; | 2.000 |
| REMARK | 3 SIDE-CHAIN BOND REFINED ATOMS (A**2): | 1132; | 1.058; | 3.000 |
| REMARK | 3 SIDE-CHAIN ANGLE REFINED ATOMS (A**2): | 1124; | 1.795; | 4.500 |
| REMARK | 3 | | | |
| REMARK | 3 NCS RESTRAINTS STATISTICS | | | |
| REMARK | 3 NUMBER OF NCS GROUPS: NULL | | | |
| REMARK | 3 | | | |
| REMARK | 3 TLS DETAILS | | | |
| REMARK | 3 NUMBER OF TLS GROUPS: 1 | | | |
| REMARK | 3 | | | |
| REMARK | 3 TLS GROUP: 1 | | | |
| REMARK | 3 NUMBER OF COMPONENTS GROUP: 1 | | | |
| REMARK | 3 COMPONENTS   C   SSSEQI   TO   C   SSSEQI | | | |
| REMARK | 3 RESIDUE RANGE: A   15      A   452 | | | |
| REMARK | 3 ORIGIN FOR THE GROUP (A):   21.4490   27.4200   27.7870 | | | |
| REMARK | 3 T TENSOR | | | |
| REMARK | 3   T11:   0.2230   T22:   0.0562 | | | |
| REMARK | 3   T33:   0.0967   T12:   0.0111 | | | |
| REMARK | 3   T13:  −0.0923   T23:   0.0525 | | | |
| REMARK | 3 L TENSOR | | | |
| REMARK | 3   L11:   1.6842   L22:   4.4489 | | | |
| REMARK | 3   L33:   2.0658   L12:   1.5597 | | | |
| REMARK | 3   L13:   1.1572   L23:   2.3523 | | | |
| REMARK | 3 S TENSOR | | | |
| REMARK | 3   S11:   0.1098  S12:  −0.2106 S13:  −0.0766 | | | |
| REMARK | 3   S21:   0.3449  522:  −0.0455 S23:   0.2455 | | | |
| REMARK | 3   S31:   0.3515  S32:  −0.1199 S33:  −0.0643 | | | |
| REMARK | 3 | | | |
| REMARK | 3 BULK SOLVENT MODELLING. | | | |
| REMARK | 3 METHOD USED: BABINET MODEL WITH MASK | | | |
| REMARK | 3 PARAMETERS FOR MASK CALCULATION | | | |
| REMARK | 3 VDW PROBE RADIUS: 1.40 | | | |
| REMARK | 3 ION PROBE RADIUS: 0.80 | | | |
| REMARK | 3 SHRINKAGE RADIUS: 0.80 | | | |
| REMARK | 3 | | | |
| REMARK | 3 OTHER REFINEMENT REMARKS: SEE REMARK 400 | | | |
| REMARK | 4 | | | |
| REMARK | 4 1H2N COMPLIES WITH FORMAT V. 2.3, 09-JULY-1998 | | | |

TABLE 3-continued

| | Coordinates for structures 1 to 4 | |
|---|---|---|
| REMARK | 100 | |
| REMARK | 100 THIS ENTRY HAS BEEN PROCESSED BY EBI ON 12-AUG-2002. | |
| REMARK | 100 THE EBI ID CODE IS EBI-11174. | |
| REMARK | 200 | |
| REMARK | 200 EXPERIMENTAL DETAILS | |
| REMARK | 200 EXPERIMENT TYPE: | X-RAY DIFFRACTION |
| REMARK | 200 DATE OF DATA COLLECTION: | 15-MAY-2002 |
| REMARK | 200 TEMPERATURE (KELVIN): | 100 |
| REMARK | 200 PH: | 7.5 |
| REMARK | 200 NUMBER OF CRYSTALS USED: | 1 |
| REMARK | 200 | |
| REMARK | 200 SYNCHROTROH (Y/N): | Y |
| REMARK | 200 RADIATION SOURCE: | SRS BEAMLINE PX9.5 |
| REMARK | 200 BEAMLINE: | PX9.5 |
| REMARK | 200 X-RAY GENERATOR MODEL: | NULL |
| REMARK | 200 MONOCHROMATIC OR LAUE (M/L): | M |
| REMARK | 200 WAVELENGTH OR RANGE (A): | 0.92 |
| REMARK | 200 MONOCHROMATOR: | NULL |
| REMARK | 200 OPTICS: | NULL |
| REMARK | 200 | |
| REMARK | 200 DETECTOR TYPE: | MARCCD |
| REMARK | 200 DETECTOR MANUFACTURER: | MARRESEARCH |
| REMARK | 200 INTENSITY-INTEGRATION SOFTWARE: | MOSFLM |
| REMARK | 200 DATA SCALING SOFTWARE: | SC ALA |
| REMARK | 200 | |
| REMARK | 200 NUMBER OF UNIQUE REFLECTIONS: | 13703 |
| REMARK | 200 RESOLUTION RANGE HIGH (A): | 2.84 |
| REMARK | 200 RESOLUTION RANGE LOW (A): | 34.1 |
| REMARK | 200 REJECTION CRITERIA (SIGMA(I)): | NONE |
| REMARK | 200 | |
| REMARK | 200 OVERALL. | |
| REMARK | 200 COMPLETENESS FOR RANGE (%): | 99.2 |
| REMARK | 200 DATA REDUNDANCY: | 6.7 |
| REMARK | 200 R MERGE (I): | 0.067 |
| REMARK | 200 R SYM (I): | NULL |
| REMARK | 200 <I/SIGMA(I)> FOR THE DATA SET: | 9.4 |
| REMARK | 200 | |
| REMARK | 200 IN THE HIGHEST RESOLUTION SHELL. | |
| REMARK | 200 HIGHEST RESOLUTION SHELL, RANGE HIGH (A): | 2.84 |
| REMARK | 200 HIGHEST RESOLUTION SHELL, RANGE LOW (A): | 2.99 |
| REMARK | 200 COMPLETENESS FOR SHELL (%): | 94.9 |
| REMARK | 200 DATA REDUNDANCY IN SHELL: | 5.2 |
| REMARK | 200 R MERGE FOR SHELL (I): | 0.309 |
| REMARK | 200 R SYM FOR SHELL (I): | NULL |
| REMARK | 200 <I/SIGMA(I)> FOR SHELL: | 2.4 |
| REMARK | 200 | |
| REMARK | 200 DIFFRACTION PROTOCOL: SINGLE WAVELENGTH | |
| REMARK | 200 METHOD USED TO DETHRMINE THE STRUCTURE: MOLECULAR REPLACEMENT | |
| REMARK | 200 SOFTWARE USED: NULL | |
| REMARK | 200 STARTING MODEL: NULL | |
| REMARK | 200 | |
| REMARK | 200 REMARK: SEE REMARK 400 | |
| REMARK | 280 | |
| REMARK | 280 CRYSTAL | |
| REMARK | 280 SOLVENT CONTENT, VS (%): 63 | |
| REMARK | 280 MATTHEWS COEFFICIENT, VM (ANGSTROMS**3/DA): 3.4 | |
| REMARK | 280 | |
| REMARK | 280 CRYSTALLIZATION CONDITIONS: 1.2 M AMMONIUM SULPHATE, | |
| REMARK | 280 4% PEG400, 0.1 M HEPES PH 7.5 ARGON ATMOSPHERE, | |
| REMARK | 280 11 MG/ML PROTEIN WITH 1 MM FE(II), 2.5 MM AKG AND 2.5 MM | |
| REMARK | 280 PEPTIDE (SEE REMARK 400) | |
| REMARK | 290 | |
| REMARK | 290 CRYSTALLOGRAPHIC SYMMETRY | |
| REMARK | 290 SYMMETRY OPERATORS FOR SPACE GROUP: P   41   21   2 | |
| REMARK | 290 | |
| REMARK | 290 SYMOP        SYMMETRY | |
| REMARK | 290 NNNMMM     OPERATOR | |
| REMARK | 290 1555          X,Y,Z | |
| REMARK | 290 2555          −X,Y,1/2+Z | |
| REMARK | 290 3555          1/2−Y,1/2+X,1/4+Z | |
| REMARK | 290 4555          1/2+Y,1/2−X,3/4+Z | |
| REMARK | 290 5555          1/2−X,1/2+Y,1/4−Z | |
| REMARK | 290 6555          1/2+X,1/2−Y,3/4−Z | |
| REMARK | 290 7555          Y,X,Z | |
| REMARK | 290 8555          −Y, −X,1/2−Z | |
| REMARK | 290 | |
| REMARK | 290 WHERE NNN ->   OPERATOR NUMBER | |

TABLE 3-continued

Coordinates for structures 1 to 4

| REMARK | | | | | | | |
|---|---|---|---|---|---|---|---|
| REMARK | 290 | MMM -> | | TRANSLATION VECTOR | | | |
| REMARK | 290 | | | | | | |
| REMARK | 290 | CRYSTALLOGRAPHIC SYMMETRY TRANSFORMATIONS | | | | | |
| REMARK | 290 | THE FOLLOWING TRANSFORMATIONS OPERATE ON THE ATOM/HETATM | | | | | |
| REMARK | 290 | RECORDS IN THIS ENTRY TO PRODUCE CRYSTALLOGRAPHICALLY | | | | | |
| REMARK | 290 | RELATED MOLECULES. | | | | | |
| REMARK | 290 | SMTRY1 | 1 | 1.000000 | 0.000000 | 0.000000 | 30.00000 |
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 0.00000 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 73.36600 |
| REMARK | 290 | SMTRY1 | 3 | 0.000000 | −1.000000 | 0.000000 | 43.17100 |
| REMARK | 290 | SMTRY2 | 3 | 1.000000 | 0.000000 | 0.000000 | 43.17100 |
| REMARK | 290 | SMTRY3 | 3 | 0.000000 | 0.000000 | 1.000000 | 36.68300 |
| REMARK | 290 | SMTRY1 | 4 | 0.000000 | 1.000000 | 0.000000 | 43.17100 |
| REMARK | 290 | SMTRY2 | 4 | −1.000000 | 0.000000 | 0.000000 | 43.17100 |
| REMARK | 290 | SMTRY3 | 4 | 0.000000 | 0.000000 | 1.000000 | 110.04900 |
| REMARK | 290 | SMTRY1 | 5 | −1.000000 | 0.000000 | 0.000000 | 43.17100 |
| REMARK | 290 | SMTRY2 | 5 | 0.000000 | 1.000000 | 0.000000 | 43.17100 |
| REMARK | 290 | SMTRY3 | 5 | 0.000000 | 0.000000 | −1.000000 | 36.68300 |
| REMARK | 290 | SMTRY1 | 6 | 1.000000 | 0.000000 | 0.000000 | 43.17100 |
| REMARK | 290 | SMTRY2 | 6 | 0.000000 | −1.000000 | 0.000000 | 43.17100 |
| REMARK | 290 | SMTRY3 | 6 | 0.000000 | 0.000000 | −1.000000 | 110.04900 |
| REMARK | 290 | SMTRY1 | 7 | 0.000000 | 1.000000 | 0.000000 | 0.00000 |
| REMARK | 290 | SMTRY2 | 7 | 1.000000 | 0.000000 | 0.000000 | 0.00000 |
| REMARK | 290 | SMTRY3 | 7 | 0.000000 | 0.000000 | −1.000000 | 0.00000 |
| REMARK | 290 | SMTRY1 | 8 | 0.000000 | −1.000000 | 0.000000 | 0.00000 |
| REMARK | 290 | SMTRY2 | 8 | −1.000000 | 0.000000 | 0.000000 | 0.00000 |
| REMARK | 290 | SMTRY3 | 8 | 0.000000 | 0.000000 | −1.000000 | 73.36600 |
| REMARK | 290 | | | | | | |
| REMARK | 290 | REMARK: NULL | | | | | |
| REMARK | 300 | | | | | | |
| REMARK | 300 | BIOMOLECULE: 1 | | | | | |
| REMARK | 300 | THIS ENTRY CONTAINS THE CRYSTALLOGRAPHIC ASYMMETRIC UNIT | | | | | |
| REMARK | 300 | WHICH CONSISTS OF 2 CHAIN(S). SEE REMARK 350 FOR | | | | | |
| REMARK | 300 | INFORMATION ON GENERATING THE BIOLOGICAL MOLECULE(S). | | | | | |
| REMARK | 300 | | | | | | |
| REMARK | 300 | QUATERNARY STRUCTURE FOR THIS ENTRY: DIMERIC | | | | | |
| REMARK | 300 | | | | | | |
| REMARK | 300 | THE PROTEIN IS A HOMODIMER FORMED BY CHAIN A. | | | | | |
| REMARK | 300 | | | | | | |
| REMARK | 300 | FOR THE HOMOASSEMBLY DESCRIBED BY REMARK 350 | | | | | |
| REMARK | 300 | THE DIFFERENCE IN ACCESSIBLE SURFACE AREA PER | | | | | |
| REMARK | 300 | CHAIN BETWEEN THE ISOLATED CHAIN AND THAT FOR | | | | | |
| REMARK | 300 | THE CHAIN IN THE COMPLEX IS 1600.4 ANGSTROM**2 | | | | | |
| REMARK | 350 | | | | | | |
| REMARK | 350 | GENERATING THE BIOMOLECULE | | | | | |
| REMARK | 350 | COORDINATES FOR A COMPLETE MULTIMER REPRESENTING THE KNOWN | | | | | |
| REMARK | 350 | BIOLOGICALLY SIGNIFICANT OLIGOMERIZATION STATE OF THE | | | | | |
| REMARK | 350 | MOLECULE CAN BE GENERATED BY APPLYING BIOMT TRANSFORMATIONS | | | | | |
| REMARK | 350 | GIVEN BELOW. BOTH NON-CRYSTALLOGRAPHIC AND | | | | | |
| REMARK | 350 | CRYSTALLOGRAPHIC OPERATIONS ARE GIVEN. | | | | | |
| REMARK | 350 | | | | | | |
| REMARK | 350 | BIOMOLECULE: 1 | | | | | |
| REMARK | 350 | APPLY THE FOLLOWING TO CHAINS: A | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 350 | BIOMT1 | 2 | 0.000000 | −1.000000 | 0.000000 | 86.34200 |
| REMARK | 350 | BIOMT2 | 2 | −1.000000 | 0.000000 | 0.000000 | 86.34200 |
| REMARK | 350 | BIOMT3 | 2 | 0.000000 | 0.000000 | −1.000000 | 73.36600 |
| REMARK | 400 | | | | | | |
| REMARK | 400 | COMPOUND | | | | | |
| REMARK | 400 | | | | | | |
| REMARK | 400 | THE PROTEIN (CHAIN A) WAS CRYSTALLIZED IN THE PRESENCE | | | | | |
| REMARK | 400 | OF A PEPTIDE FRAGMENT FROM ENDOTHELIAL PAS DOMAIN PROTEIN 1 | | | | | |
| REMARK | 400 | SWISS-PROT ID Q99814 (RESIDUES 846858) BUT NONE OF THE | | | | | |
| REMARK | 400 | RESIDUES CORRESPONDING TO THE PEPTIDE WERE VISIBLE IN THE | | | | | |
| REMARK | 400 | ELECTRON DENSITY MAPS. IT IS POSSIBLE THAT THE PEPTIDE DID | | | | | |
| REMARK | 400 | NOT BIND TO THE PROTEIN AND HENCE HAS NOT BEEN INCLUDED IN THE | | | | | |
| REMARK | 400 | COMPND, SOURCE AND SEQRES RECORDS. | | | | | |
| REMARK | 400 | | | | | | |
| REMARK | 400 | THE SEQUENCE OF THE FRAGMENT IS GIVEN BELOW. | | | | | |
| REMARK | 400 | | | | | | |
| REMARK | 400 | VAL ASN VAL PRO VAL LEU GLY SER SER THR LEU LEU GLN | | | | | |
| REMARK | 465 | | | | | | |

TABLE 3-continued

Coordinates for structures 1 to 4

| | | | | | | | | | |
|---|---|---|---|---|---|---|---|---|---|
| REMARK | 465 | MISSING RESIDUES | | | | | | | |
| REMARK | 465 | THE FOLLOWING RESIDUES WERE NOT LOCATED IN THE | | | | | | | |
| REMARK | 465 | EXPERIMENT. (M=MODEL NUMBER; RES=RESIDUE NAME; C=CHAIN | | | | | | | |
| REMARK | 465 | IDENTIFIER; SSSEQ=SEQUENCE NUMBER; I=INSERTION CODE.) | | | | | | | |
| REMARK | 465 | | | | | | | | |
| REMARK | 465 | M | RES | C | SSSEQI | | | | |
| REMARK | 465 | | MET | A | 1 | | | | |
| REMARK | 465 | | ALA | A | 2 | | | | |
| REMARK | 465 | | ALA | A | 3 | | | | |
| REMARK | 465 | | THR | A | 4 | | | | |
| REMARK | 465 | | ALA | A | 5 | | | | |
| REMARK | 465 | | ALA | A | 6 | | | | |
| REMARK | 465 | | GLU | A | 7 | | | | |
| REMARK | 465 | | ALA | A | 8 | | | | |
| REMARK | 465 | | VAL | A | 9 | | | | |
| REMARK | 465 | | ALA | A | 10 | | | | |
| REMARK | 465 | | SER | A | 11 | | | | |
| REMARK | 465 | | GLY | A | 12 | | | | |
| REMARK | 465 | | SER | A | 13 | | | | |
| REMARK | 465 | | GLY | A | 14 | | | | |
| REMARK | 465 | | LYS | A | 304 | | | | |
| REMARK | 465 | | ARG | A | 305 | | | | |
| REMARK | 465 | | ILE | A | 306 | | | | |
| REMARK | 470 | | | | | | | | |
| REMARK | 470 | MISSING ATOM | | | | | | | |
| REMARK | 470 | THE FOLLOWING RESIDUES HAVE MISSING ATOMS (M=MODEL NUMBER; | | | | | | | |
| REMARK | 470 | RES=RESIDUE NAME; C=CHAIN IDENTIFIER; SSEQ=SEQUENCE NUMBER; | | | | | | | |
| REMARK | 470 | I=INSERTION CODE): | | | | | | | |
| REMARK | 470 | M | RES | CSSEQI | ATOMS | | | | |
| REMARK | 470 | | GLU | A | 15 | CG | CD | OE1 | OE2 |
| REMARK | 470 | | GLU | A | 29 | CG | CD | OE1 | OE2 |
| REMARK | 470 | | ASN | A | 87 | CG | OD1 | ND2 | |
| REMARK | 470 | | LYS | A | 106 | CD | CE | NZ | |
| REMARK | 470 | | LYS | A | 115 | CG | CD | CE | NZ |
| REMARK | 470 | | ARG | A | 117 | CG | CD | NE | CZ NH1 NH2 |
| REMARK | 470 | | GLN | A | 133 | CG | CD | OE1 | NE2 |
| REMARK | 470 | | GLN | A | 136 | CG | CD | OE1 | NE2 |
| REMARK | 470 | | GLN | A | 137 | CG | CD | OE1 | NE2 |
| REMARK | 470 | | ARG | A | 156 | CG | CD | NE | CZ NH1 NH2 |
| REMARK | 470 | | LYS | A | 157 | CD | CE | NZ | |
| REMARK | 470 | | LYS | A | 311 | CG | CD | CE | NZ |
| REMARK | 500 | | | | | | | | |
| REMARK | 500 | GEOMETRY AND STEREOCHEMISTRY | | | | | | | |
| REMARK | 500 | SUBTOPIC: COVALENT BOND ANGLES | | | | | | | |
| REMARK | 500 | | | | | | | | |
| REMARK | 500 | THE STEREOCHEMICAL PARAMETERS OF THE FOLLOWING RESIDUES | | | | | | | |
| REMARK | 500 | HAVE VALUES WHICH DEVIATE FROM EXPECTED VALUES BY MORE | | | | | | | |
| REMARK | 500 | THAN 6*RMSD (M=MODEL NUMBER; RES=RESIDUE NAME; C=CHAIN | | | | | | | |
| REMARK | 500 | IDENTIFIER; SSEQ=SEQUENCE NUMBER; I=INSERTION CODE) | | | | | | | |
| REMARK | 500 | | | | | | | | |
| REMARK | 500 | STANDARD TABLE: | | | | | | | |
| REMARK | 500 | FORMAT: (10X,I3,1X,A3,1X,A1,I4,A1,3(1X,A4,2X)12X,F5.1) | | | | | | | |
| REMARK | 500 | | | | | | | | |
| REMARK | 500 | EXPECTED VALUES: ENGH AND HUBER, 1991 | | | | | | | |
| REMARK | 500 | | | | | | | | |
| REMARK | 500 | M | RES | CSSEQI | ATM1 | ATM2 | ATM3 | | |
| REMARK | 500 | TYR A | | | 261 | N - | CA - | C | ANGL. DEV. = −10.1 DEGREES |
| REMARK | 500 | | | | | | | | |
| REMARK | 500 | REMARK: NULL | | | | | | | |
| REMARK | 500 | | | | | | | | |
| REMARK | 500 | GEOMETRY AND STEREOCHEMISTRY | | | | | | | |
| REMARK | 500 | SUBTOPIC: COVALENT BOND LENGTHS | | | | | | | |
| REMARK | 500 | | | | | | | | |
| REMARK | 500 | THE STEREOCHEMICAL PARAMETERS OF THE FOLLOWING RESIDUES | | | | | | | |
| REMARK | 500 | HAVE VALUES WHICH DEVIATE FROM EXPECTED VALUES BY MORE | | | | | | | |
| REMARK | 500 | THAN 6*RMSD AND BY MORE THAN 0.150 ANGSTROMS (M=MODEL | | | | | | | |
| REMARK | 500 | NUMBER; RES=RESIDUE NAME; C=CHAIN IDENTIFIER; SSEQ=SEQUENCE | | | | | | | |
| REMARK | 500 | NUMBER; I=INSERTION CODE). | | | | | | | |
| REMARK | 500 | | | | | | | | |
| REMARK | 500 | STANDARD TABLE: | | | | | | | |
| REMARK | 500 | FORMAT: (10X,I3,1X,A3,1X,A1,I4,A1,1X,2(A4,A1,3X)12X,F5.3) | | | | | | | |
| REMARK | 500 | | | | | | | | |
| REMARK | 500 | EXPECTED VALUESS: ENGH AND HUBER, 1991 | | | | | | | |
| REMARK | 500 | | | | | | | | |
| REMARK | 500 | M | RES | CSSEQI | ATM1 | RES | CSSEQI | ATM2 | DEVIATION |
| REMARK | 500 | | MET | A 343 | SD | MET | A 343 | CE | 0.151 |
| REMARK | 500 | | | | | | | | |

TABLE 3-continued

Coordinates for structures 1 to 4

| REMARK | 500 | REMARK: NULL | | | | | | | | | | | | |
|---|---|---|---|---|---|---|---|---|---|---|---|---|---|---|
| REMARK | 500 | | | | | | | | | | | | | |
| REMARK | 500 | GEOMETRY AND STEREOCHEMISTRY | | | | | | | | | | | | |
| REMARK | 500 | SUBTOPIC: CLOSE CONTACTS IN SAME ASYMMETRIC UNIT | | | | | | | | | | | | |
| REMARK | 500 | | | | | | | | | | | | | |
| REMARK | 500 | THE FOLLOWING ATOMS ARE IN CLOSE CONTACT. | | | | | | | | | | | | |
| REMARK | 500 | | | | | | | | | | | | | |
| REMARK | 500 | ATM1 | RES | C | SSEQI | ATM2 | RES | C | SSEQI | DISTANCE | | | | |
| REMARK | 500 | | | | | | | | | | | | | |
| REMARK | 500 | OG1 | THR | A | 39 | OE1 | GLU | A | 262 | 2.16 | | | | |
| REMARK | 525 | | | | | | | | | | | | | |
| REMARK | 525 | SOLVENT | | | | | | | | | | | | |
| REMARK | 525 | | | | | | | | | | | | | |
| REMARK | 525 | THE SOLVENT MOLECULES ARE GIVEN CHAIN IDENTIFIERS TO | | | | | | | | | | | | |
| REMARK | 525 | INDICATE THE PROTEIN CHAIN TO WHICH THEY ARE MOST CLOSELY | | | | | | | | | | | | |
| REMARK | 525 | ASSOCIATED WITH: | | | | | | | | | | | | |
| REMARK | 525 | PROTEIN CHAIN | | | SOLVENT CHAIN | | | | | | | | | |
| REMARK | 525 | A | | | Z | | | | | | | | | |
| REMARK | 600 | | | | | | | | | | | | | |
| REMARK | 600 | HETEROGEN | | | | | | | | | | | | |
| REMARK | 600 | | | | | | | | | | | | | |
| REMARK | 600 | FOR METAL ATOM FE FE2 A 1350 THE COORDINATION ANGLES ARE: | | | | | | | | | | | | |
| REMARK | 600 | 1 | HIS | 199A | NE2 | | | | | | | | | |
| REMARK | 600 | 2 | ASP | 201A | OD2 | 106.1 | | | | | | | | |
| REMARK | 600 | 3 | HIS | 279A | NE2 | 77.8 | 85.5 | | | | | | | |
| REMARK | 600 | 4 | AKG | 1351A | O1 | 168.0 | 81.1 | 93.4 | | | | | | |
| REMARK | 600 | 5 | AKG | 1351A | O5 | 88.7 | 163.3 | 90.2 | 83.1 | | | | | |
| REMARK | 600 | | | | | 1 | 2 | 3 | 4 | | | | | |
| REMARK | 700 | | | | | | | | | | | | | |
| REMARK | 700 | SHEET | | | | | | | | | | | | |
| REMARK | 700 | THE SHEET STRUCTURE OF THIS MOLECULE IS BIFURCATED. IN | | | | | | | | | | | | |
| REMARK | 700 | ORDER TO REPRESENT THIS FEATURE IN THE SHEET RECORDS BELOW, | | | | | | | | | | | | |
| REMARK | 700 | TWO SHEETS ARE DEFINED. | | | | | | | | | | | | |
| REMARK | 800 | | | | | | | | | | | | | |
| REMARK | 800 | SITE | | | | | | | | | | | | |
| REMARK | 800 | SITE_IDENTIFIER: FEA | | | | | | | | | | | | |
| REMARK | 800 | SITE_DESCRIPTION: FE BINDING SITE FOR CHAIN A | | | | | | | | | | | | |
| REMARK | 800 | | | | | | | | | | | | | |
| REMARK | 800 | SITE_IDENTIFIER: AKG | | | | | | | | | | | | |
| REMARK | 800 | SITE_DESCRIPTION: AKG BINDING SITE FOR CHAIN A | | | | | | | | | | | | |
| REMARK | 800 | | | | | | | | | | | | | |
| REMARK | 800 | SITE_IDENTIFIER: SA1 | | | | | | | | | | | | |
| REMARK | 800 | SITE_DESCRIPTION: SO4 BINDING SITE FOR CHAIN A | | | | | | | | | | | | |
| REMARK | 800 | | | | | | | | | | | | | |
| REMARK | 800 | SITE_IDENTIFIER: SA2 | | | | | | | | | | | | |
| REMARK | 800 | SITE_DESCRIPTION: SO4 BINDING SITE FOR CHAIN A | | | | | | | | | | | | |
| REMARK | 800 | | | | | | | | | | | | | |
| REMARK | 800 | SITE_IDENTIFIER: SA3 | | | | | | | | | | | | |
| REMARK | 800 | SITE_DESCRIPTION: SO4 BINDING SITE FOR CHAIN A | | | | | | | | | | | | |
| REMARK | 900 | | | | | | | | | | | | | |
| REMARK | 900 | RELATED ENTRIES | | | | | | | | | | | | |
| REMARK | 900 | RELATED ID: 1H2K RELATED DB: PDB | | | | | | | | | | | | |
| REMARK | 900 | FACTOR INHIBITING HIF-1 ALPHA IN COMPLEX | | | | | | | | | | | | |
| REMARK | 900 | WITH HIF-1 ALPHA FRAGMENT PEPTIDE | | | | | | | | | | | | |
| REMARK | 900 | RELATED ID: 1H2L RELATED DE: PDB | | | | | | | | | | | | |
| REMARK | 900 | FACTOR INHIBITING HIF-1 ALPHA IN COMPLEX | | | | | | | | | | | | |
| REMARK | 900 | WITH HIF-1 ALPHA FRAGMENT PEPTIDE | | | | | | | | | | | | |
| REMARK | 900 | RELATED ID: 1H2M RELATED DB: PDB | | | | | | | | | | | | |
| REMARK | 900 | FACTOR INHIBITING HIF-1 ALPHA IN COMPLEX | | | | | | | | | | | | |
| REMARK | 900 | WITH HIF-1 ALPHA FRAGMENT PEPTIDE | | | | | | | | | | | | |
| DBREF | 1H2N A | 1 | 349 | SWS | Q969Q7 | Q969Q7 | 1 | 349 | | | | | | |
| SEQRES | 1 A | 349 | MET | ALA | ALA | THR | ALA | ALA | GLU | ALA | VAL | ALA | SER | GLY | SER |
| SEQRES | 2 A | 349 | GLY | GLU | PRO | ARG | GLU | GLU | ALA | GLY | ALA | LEU | GLY | PRO | ALA |
| SEQRES | 3 A | 349 | TRP | ASP | GLU | SER | GLN | LEU | ARG | SER | TYR | SER | PHE | PRO | THR |
| SEQRES | 4 A | 349 | ARG | PRO | ILE | PRO | ARG | LEU | SER | GLN | SER | ASP | PRO | ARG | ALA |
| SEQRES | 5 A | 349 | GLU | GLU | LEU | ILE | GLU | ASN | GLU | GLU | PRO | VAL | VAL | LEU | THR |
| SEQRES | 6 A | 349 | ASP | THR | ASN | LEU | VAL | TYR | PRO | ALA | LEU | LYS | TRP | ASP | LEU |
| SEQRES | 7 A | 349 | GLU | TYR | LEU | GLN | GLU | ASN | ILE | GLY | ASN | GLY | ASP | PHE | SER |
| SEQRES | 8 A | 349 | VAL | TYR | SER | ALA | SER | THR | HIS | LYS | PHE | LEU | TYR | TYR | ASP |
| SEQRES | 9 A | 349 | GLU | LYS | LYS | MET | ALA | ASN | PHE | GLN | ASN | PHE | LYS | PRO | ARG |
| SEQRES | 10 A | 349 | SER | ASN | ARG | GLU | GLU | MET | LYS | PHE | HIS | GLU | PHE | VAL | GLU |
| SEQRES | 11 A | 349 | LYS | LEU | GLN | ASP | ILE | GLN | ARG | GLY | GLY | GLU | GLU | ARG |
| SEQRES | 12 A | 349 | LEU | TYR | LEU | GLN | GLN | THR | LEU | ASN | ASP | THR | VAL | GLY | ARG |
| SEQRES | 13 A | 349 | LYS | ILE | VAL | MET | ASP | PHE | LEU | GLY | PHE | ASN | TRP | ASN | TRP |
| SEQRES | 14 A | 349 | ILE | ASN | LYS | GLN | GLN | GLY | LYS | ARG | GLY | TRP | GLY | GLN | LEU |
| SEQRES | 15 A | 349 | THR | SER | ASN | LEU | LEU | LEU | ILE | GLY | MET | GLU | GLY | ASN | VAL |
| SEQRES | 16 A | 349 | THR | PRO | ALA | HIS | TYR | ASP | GLU | GLN | GLN | ASN | PHE | PHE | ALA |

TABLE 3-continued

Coordinates for structures 1 to 4

| | | | | | | | | | | | | | | | | | | |
|---|---|---|---|---|---|---|---|---|---|---|---|---|---|---|---|---|---|---|
| SEQRES | 17 | A | 349 | GLN | ILE | LYS | GLY | TYR | LYS | ARG | CYS | ILE | LEU | PHE | PRO | PRO | | |
| SEQRES | 18 | A | 349 | ASP | GLN | PHE | GLU | CYS | LEU | TYR | PRO | TYR | PRO | VAL | HIS | HIS | | |
| SEQRES | 19 | A | 349 | PRO | CYS | ASP | ARG | GLN | SER | GLN | VAL | ASP | PHE | ASP | ASN | PRO | | |
| SEQRES | 20 | A | 349 | ASP | TYR | GM) | ARG | PHE | PRO | ASN | PHE | GLN | ASN | VAL | VAL | GLY | | |
| SEQRES | 21 | A | 349 | TYR | GLU | THR | VAL | VAL | GLY | PRO | GLY | ASP | VAL | LEU | TYR | ILE | | |
| SEQRES | 22 | A | 349 | PRO | MET | TYR | TRP | TRP | HIS | HIS | ILE | GLU | SER | LEU | LEU | ASN | | |
| SEQRES | 23 | A | 349 | GLY | GLY | ILE | THR | ILE | THR | VAL | ASN | PHE | TRP | TYR | LYS | GLY | | |
| SEQRES | 24 | A | 349 | ALA | PRO | THR | PRO | LYS | ARG | ILE | GLU | TYR | PRO | LEU | LYS | ALA | | |
| SEQRES | 25 | A | 349 | HIS | GLN | LYS | VAL | ALA | ILE | MET | ARG | ASN | ILE | GLU | LYS | MET | | |
| SEQRES | 26 | A | 349 | LEU | GLY | GLU | ALA | LEU | GLY | ASN | PRO | GLN | GLU | VAL | GLY | PRO | | |
| SEQRES | 27 | A | 349 | LEU | LEU | ASN | THR | MET | ILE | LYS | GLY | ARG | TYR | ASN | | | | |
| HET | FE2 | | A1350 | | 1 | | | | | | | | | | | | | |
| HET | AKG | | A1351 | | 10 | | | | | | | | | | | | | |
| HET | SO4 | | A1352 | | 5 | | | | | | | | | | | | | |
| HET | SO4 | | A1353 | | S | | | | | | | | | | | | | |
| HET | SO4 | | A1354 | | 5 | | | | | | | | | | | | | |
| HETNAM | FE2 | | FE (II) ION | | | | | | | | | | | | | | | |
| HETNAM | AKG | | 2-OXYGLUTARIC ACID | | | | | | | | | | | | | | | |
| HETNAM | SO4 | | SULFATE ION | | | | | | | | | | | | | | | |
| FORMUL | 3 | | FE2 FE1 2+ | | | | | | | | | | | | | | | |
| FORMUL | 4 | | AKG C5 H6 O5 | | | | | | | | | | | | | | | |
| FORMUL | 5 | | SO4 3(O4 S1 2−) | | | | | | | | | | | | | | | |
| FORMUL | 6 | | HOH *3(H2 O1) | | | | | | | | | | | | | | | |
| HELIX | 1 | 1 | ASP | A | 28 | LEU | A | 32 | 5 | | | | | | | | | 5 |
| HELIX | 2 | 2 | ASP | A | 49 | ASN | A | 58 | 1 | | | | | | | | | 10 |
| HELIX | 3 | 3 | VAL | A | 70 | TRP | A | 76 | 5 | | | | | | | | | 7 |
| HELIX | 4 | 4 | ASP | A | 77 | ILE | A | 85 | 1 | | | | | | | | | 9 |
| HELIX | 5 | 5 | ASP | A | 104 | GLN | A | 112 | 5 | | | | | | | | | 9 |
| HELIX | 6 | 6 | PHE | A | 125 | ARG | A | 138 | 1 | | | | | | | | | 14 |
| HELIX | 7 | 7 | GLY | A | 155 | GLY | A | 164 | 1 | | | | | | | | | 10 |
| HELIX | 8 | 8 | ASN | A | 166 | ARG | A | 177 | 1 | | | | | | | | | 12 |
| HELIX | 9 | 9 | PRO | A | 220 | ASP | A | 222 | 5 | | | | | | | | | 3 |
| HELIX | 10 | 10 | GLN | A | 223 | TYR | A | 228 | 1 | | | | | | | | | 6 |
| HELIX | 11 | 11 | PHE | A | 252 | VAL | A | 258 | 5 | | | | | | | | | 7 |
| HELIX | 12 | 12 | LYS | A | 311 | GLY | A | 331 | 1 | | | | | | | | | 21 |
| HELIX | 13 | 13 | ASN | A | 332 | GLN | A | 334 | 5 | | | | | | | | | 3 |
| HELIX | 14 | 14 | GLU | A | 335 | LYS | A | 345 | 1 | | | | | | | | | 11 |
| SHEET | 1 | AA | 5 | THR | A | 39 | | | PRO | A | 41 | 0 | | | | | | |
| SHEET | 2 | AA | 5 | GLY | A | 260 | | | VAL | A | 265 | 1 | O | GLY | A | 260 | N | ARG A 40 |
| SHEET | 3 | AA | 5 | LYS | A | 214 | | | PHE | A | 219 | −1 | O | LYS | A | 214 | N | VAL A 265 |
| SHEET | 4 | AA | 5 | TRP | A | 278 | | | SER | A | 283 | −1 | O | TRP | A | 278 | N | PHE A 219 |
| SHEET | S | AA | 5 | VAL | A | 195 | | | HIS | A | 199 | −1 | O | THR | A | 196 | N | ILE A 281 |
| SHEET | 1 | AB | 6 | ARG | A | 44 | | | LEU | A | 45 | 0 | | | | | | |
| SHEET | 2 | AB | 6 | VAL | A | 62 | | | LEU | A | 64 | 1 | O | VAL | A | 63 | N | LEU A 45 |
| SHEET | 3 | AB | 6 | VAL | A | 270 | | | ILE | A | 273 | −1 | O | VAL | A | 270 | N | LEU A 64 |
| SHEET | 4 | AB | 6 | GLN | A | 203 | | | LYS | A | 211 | −1 | O | ASN | A | 205 | N | ILE A 273 |
| SHEET | 5 | AB | 6 | THR | A | 290 | | | LYS | A | 298 | −1 | O | ILE | A | 291 | N | ILE A 210 |
| SHEET | 6 | AB | 6 | LEU | A | 182 | | | SER | A | 184 | −1 | N | THR | A | 183 | O | TRP A 296 |
| SHEET | 1 | AC | 9 | ARG | A | 44 | | | LEU | A | 45 | 0 | | | | | | |
| SHEET | 2 | AC | 9 | VAL | A | 62 | | | LEU | A | 64 | 1 | O | VAL | A | 63 | N | LEU A 45 |
| SHEET | 3 | AC | 9 | VAL | A | 270 | | | ILE | A | 273 | −1 | O | VAL | A | 270 | N | LEU A 64 |
| SHEET | 4 | AC | 9 | GLN | A | 203 | | | LYS | A | 211 | −1 | O | ASN | A | 205 | N | ILE A 273 |
| SHEET | 5 | AC | 9 | THR | A | 290 | | | LYS | A | 298 | −1 | O | ILE | A | 291 | N | ILE A 210 |
| SHEET | 6 | AC | 9 | LEU | A | 186 | | | GLY | A | 190 | −1 | O | LEU | A | 186 | N | ASN A 294 |
| SHEET | 7 | AC | 9 | ARG | A | 143 | | | THR | A | 149 | −1 | O | LEU | A | 146 | N | ILE A 189 |
| SHEET | 8 | AC | 9 | ASP | A | 89 | | | ALA | A | 95 | −1 | O | SER | A | 91 | N | GLN A 147 |
| SHEET | 9 | AC | 9 | SER | A | 118 | | | LYS | A | 124 | −1 | O | ASN | A | 119 | N | SER A 94 |
| LINK | | FE | | FE2 | A | 1350 | | | | NE2 | HIS | A | 199 | 1555 | 1555 | | | |
| LINK | | FE | | FE2 | A | 1350 | | | | OD2 | ASP | A | 201 | 1555 | 1555 | | | |
| LINK | | FE | | FE2 | A | 1350 | | | | NE2 | HIS | A | 279 | 1555 | 1555 | | | |
| LINK | | FE | | FE2 | A | 1350 | | | | O1 | AKG | A | 1351 | 1555 | 1555 | | | |
| LINK | | FE | | FE2 | A | 1350 | | | | O5 | AKG | A | 1351 | 1555 | 1555 | | | |
| CISPEP | 1 | TYR | A | 308 | PRO | A | 309 | 0 | | 2.48 | | | | | | | | |
| SITE | 1 | FEA | 3 | HIS | A | 199 | ASP | A | 201 | HIS | A | 279 | | | | | | |
| SITE | 1 | AKG | 13 | TYR | A | 145 | LEU | A | 188 | THR | A | 196 | HIS | A | 199 | | | |
| SITE | 2 | AKG | 13 | ASP | A | 203 | ASN | A | 205 | PHE | A | 207 | LYS | A | 214 | | | |
| SITE | 3 | AKG | 13 | HIS | A | 279 | ILE | A | 281 | ASN | A | 294 | TRP | A | 296 | | | |
| SITE | 4 | AKG | 13 | HON | Z | 1 | | | | | | | | | | | | |
| SITE | 1 | SA1 | 4 | ARG | A | 138 | GLY | A | 140 | GLU | A | 141 | GLU | A | 142 | | | |
| SITE | 1 | SA2 | 5 | ARG | A | 143 | GLU | A | 192 | GLY | A | 193 | LEUU | A | 28S | | | |
| SITE | 2 | SA2 | 5 | ASN | A | 286 | | | | | | | | | | | | |
| SITE | 1 | SA3 | 4 | LYS | A | 107 | GLU | A | 202 | ARG | A | 320 | LYS | A | 324 | | | |
| CRYST1 | | | | 86.342 | 86.342 | 146.732 | 90.00 | 90.00 | 90.00 | P | 41 | 21 | 2 | | | 8 | | |
| ORIGX1 | | 1.000000 | | 0.000000 | 0.000000 | 0.00000 | | | | | | | | | | | | |
| ORIGX2 | | 0.000000 | | 1.000000 | 0.000000 | 0.00000 | | | | | | | | | | | | |
| ORIGX3 | | 0.000000 | | 0.000000 | 1.000000 | 0.00000 | | | | | | | | | | | | |
| SCALE1 | | 0.011582 | | 0.000000 | 0.000000 | 0.00000 | | | | | | | | | | | | |

TABLE 3-continued

Coordinates for structures 1 to 4

| | | | | | | | | | | | |
|---|---|---|---|---|---|---|---|---|---|---|---|
| SCALE2 | | 0.000000 | | 0.011582 | 0.000000 | 0.00000 | | | | | |
| SCALE3 | | 0.000000 | | 0.000000 | 0.006815 | 0.00000 | | | | | |
| ATOM | 1 | N | GLU | A | 15 | 8.558 | 32.684 | 9.824 | 1.00 | 41.85 | N |
| ATOM | 2 | CA | GLU | A | 15 | 7.178 | 32.135 | 9.672 | 1.00 | 42.19 | C |
| ATOM | 3 | C | GLU | A | 15 | 7.180 | 30.645 | 9.998 | 1.00 | 42.19 | C |
| ATOM | 4 | O | GLU | A | 15 | 7.959 | 29.895 | 9.424 | 1.00 | 42.28 | O |
| ATOM | 5 | CB | GLU | A | 15 | 6.661 | 32.366 | 8.258 | 1.00 | 42.28 | C |
| ATOM | 6 | N | PRO | A | 16 | 6.281 | 30.198 | 10.866 | 1.00 | 42.29 | N |
| ATOM | 7 | CA | PRO | A | 16 | 6.376 | 28.826 | 11.391 | 1.00 | 42.53 | C |
| ATOM | 8 | C | PRO | A | 16 | 6.351 | 27.762 | 10.307 | 1.00 | 42.54 | C |
| ATOM | 9 | O | PRO | A | 16 | 5.571 | 27.819 | 9.369 | 1.00 | 42.92 | O |
| ATOM | 10 | CB | PRO | A | 16 | 5.172 | 28.713 | 12.337 | 1.00 | 42.63 | C |
| ATOM | 11 | CG | PRO | A | 16 | 4.749 | 30.155 | 12.612 | 1.00 | 42.41 | C |
| ATOM | 12 | CD | PRO | A | 16 | 5.103 | 30.916 | 11.382 | 1.00 | 42.22 | C |
| ATOM | 13 | N | ARG | A | 17 | 7.231 | 26.791 | 10.446 | 1.00 | 42.51 | N |
| ATOM | 14 | CA | ARG | A | 17 | 7.337 | 25.723 | 9.478 | 1.00 | 42.62 | C |
| ATOM | 15 | C | ARG | A | 17 | 6.095 | 24.856 | 9.527 | 1.00 | 42.85 | C |
| ATOM | 16 | O | ARG | A | 17 | 5.492 | 24.705 | 10.587 | 1.00 | 43.51 | O |
| ATOM | 17 | CB | ARG | A | 17 | 8.505 | 24.800 | 9.845 | 1.00 | 42.50 | C |
| ATOM | 18 | CG | ARG | A | 17 | 9.871 | 25.434 | 9.859 | 1.00 | 42.22 | C |
| ATOM | 19 | CD | ARG | A | 17 | 10.995 | 24.466 | 10.228 | 1.00 | 42.12 | C |
| ATOM | 20 | NE | ARG | A | 17 | 11.085 | 24.138 | 11.656 | 1.00 | 42.49 | N |
| ATOM | 21 | CZ | ARG | A | 17 | 11.588 | 24.943 | 12.607 | 1.00 | 42.43 | C |
| ATOM | 22 | NH1 | ARG | A | 17 | 12.033 | 26.158 | 12.316 | 1.00 | 42.11 | N |
| ATOM | 23 | NH2 | ARG | A | 17 | 11.649 | 24.529 | 13.869 | 1.00 | 42.25 | N |
| ATOM | 24 | N | GLU | A | 18 | 5.742 | 24.242 | 8.404 | 1.00 | 42.60 | N |
| ATOM | 25 | CA | GLU | A | 18 | 4.662 | 23.268 | 8.405 | 1.00 | 42.36 | C |
| ATOM | 26 | C | GLU | A | 18 | 5.203 | 21.870 | 8.728 | 1.00 | 41.90 | C |
| ATOM | 27 | O | GLU | A | 18 | 6.249 | 21.472 | 8.216 | 1.00 | 41.98 | O |
| ATOM | 28 | CB | GLU | A | 18 | 3.988 | 23.224 | 7.041 | 1.00 | 42.57 | C |
| ATOM | 29 | CG | GLU | A | 18 | 3.363 | 24.537 | 6.620 | 1.00 | 43.60 | C |
| ATOM | 30 | CD | GLU | A | 18 | 1.993 | 24.756 | 7.233 | 1.00 | 45.11 | C |
| ATOM | 31 | OE1 | GLU | A | 18 | 1.365 | 23.766 | 7.686 | 1.00 | 45.48 | O |
| ATOM | 32 | OE2 | GLU | A | 18 | 1.546 | 25.926 | 7.253 | 1.00 | 46.49 | O |
| ATOM | 33 | N | GLU | A | 19 | 4.487 | 21.133 | 9.578 | 1.00 | 41.27 | N |
| ATOM | 34 | CA | GLU | A | 19 | 4.806 | 19.737 | 9.894 | 1.00 | 40.61 | C |
| ATOM | 35 | C | GLU | A | 19 | 4.478 | 18.802 | 8.748 | 1.00 | 39.73 | C |
| ATOM | 36 | O | GLU | A | 19 | 3.424 | 18.915 | 8.137 | 1.00 | 39.76 | O |
| ATOM | 37 | CB | GLU | A | 19 | 4.024 | 19.299 | 11.128 | 1.00 | 40.72 | C |
| ATOM | 38 | CG | GLU | A | 19 | 4.507 | 20.034 | 12.361 | 1.00 | 42.24 | C |
| ATOM | 39 | CD | GLU | A | 19 | 4.358 | 19.278 | 13.668 | 1.00 | 44.37 | C |
| ATOM | 40 | OE1 | GLU | A | 19 | 3.852 | 18.127 | 13.680 | 1.00 | 46.17 | O |
| ATOM | 41 | OE2 | GLU | A | 19 | 4.769 | 19.863 | 14.700 | 1.00 | 45.44 | O |
| ATOM | 42 | N | ALA | A | 20 | 5.369 | 17.859 | 8.478 | 1.00 | 36.99 | N |
| ATOM | 43 | CA | ALA | A | 20 | 5.164 | 16.922 | 7.390 | 1.00 | 38.71 | C |
| ATOM | 44 | C | ALA | A | 20 | 3.831 | 16.232 | 7.542 | 1.00 | 38.51 | C |
| ATOM | 45 | O | ALA | A | 20 | 3.391 | 15.933 | 8.649 | 1.00 | 38.80 | O |
| ATOM | 46 | CB | ALA | A | 20 | 6.280 | 15.895 | 7.328 | 1.00 | 38.51 | C |
| ATOM | 47 | N | GLY | A | 21 | 3.180 | 15.991 | 6.419 | 1.00 | 38.03 | N |
| ATOM | 48 | CA | GLY | A | 21 | 1.924 | 15.290 | 6.449 | 1.00 | 38.11 | C |
| ATOM | 49 | C | GLY | A | 21 | 0.746 | 16.205 | 6.682 | 1.00 | 38.19 | C |
| ATOM | 50 | O | GLY | A | 21 | 0.328 | 15.743 | 7.049 | 1.00 | 38.25 | O |
| ATOM | 51 | N | ALA | A | 22 | 0.941 | 17.497 | 6.447 | 1.00 | 38.40 | N |
| ATOM | 52 | CA | ALA | A | 22 | 0.130 | 18.472 | 6.571 | 1.00 | 38.50 | C |
| ATOM | 53 | C | ALA | A | 22 | 0.725 | 18.413 | 7.960 | 1.00 | 38.60 | C |
| ATOM | 54 | O | ALA | A | 22 | 1.930 | 18.547 | 8.142 | 1.00 | 38.65 | O |
| ATOM | 55 | CB | ALA | A | 22 | 1.196 | 18.242 | 5.520 | 1.00 | 38.61 | C |
| ATOM | 56 | N | LEU | A | 23 | 0.135 | 18.206 | 8.946 | 1.00 | 38.75 | N |
| ATOM | 57 | CA | LEU | A | 23 | 0.297 | 18.257 | 10.330 | 1.00 | 38.82 | C |
| ATOM | 58 | C | LEU | A | 23 | 0.321 | 19.684 | 10.843 | 1.00 | 38.78 | C |
| ATOM | 59 | O | LEU | A | 23 | 0.525 | 19.919 | 12.030 | 1.00 | 38.74 | O |
| ATOM | 60 | CB | LEU | A | 23 | 0.597 | 17.392 | 11.193 | 1.00 | 38.77 | C |
| ATOM | 61 | CG | LEU | A | 23 | 0.421 | 15.952 | 10.736 | 1.00 | 39.03 | C |
| ATOM | 62 | CD1 | LEU | A | 23 | 1.203 | 14.958 | 11.579 | 1.00 | 39.08 | C |
| ATOM | 63 | CD2 | LEU | A | 23 | 1.070 | 15.636 | 10.750 | 1.00 | 39.43 | C |
| ATOM | 64 | N | GLY | A | 24 | 0.094 | 20.636 | 9.947 | 1.00 | 38.75 | N |
| ATOM | 65 | CA | GLY | A | 24 | 0.248 | 22.025 | 10.298 | 1.00 | 38.79 | C |
| ATOM | 66 | C | GLY | A | 24 | 0.972 | 22.669 | 10.861 | 1.00 | 38.90 | C |
| ATOM | 67 | O | GLY | A | 24 | 2.042 | 22.084 | 10.961 | 1.00 | 39.06 | O |
| ATOM | 68 | N | PRO | A | 25 | 0.791 | 23.906 | 11.267 | 1.00 | 39.19 | N |
| ATOM | 69 | CA | PRO | A | 25 | 1.903 | 24.682 | 11.778 | 1.00 | 39.35 | C |
| ATOM | 70 | C | PRO | A | 25 | 2.332 | 24.037 | 13.074 | 1.00 | 39.62 | C |
| ATOM | 71 | O | PRO | A | 25 | 1.492 | 23.633 | 13.871 | 1.00 | 39.48 | O |
| ATOM | 72 | CE | PRO | A | 25 | 1.299 | 26.062 | 12.019 | 1.00 | 39.24 | C |
| ATOM | 73 | CG | PRO | A | 25 | 0.142 | 25.920 | 11.961 | 1.00 | 38.71 | C |
| ATOM | 74 | CD | PRO | A | 25 | 0.490 | 24.616 | 11.365 | 1.00 | 39.17 | C |
| ATOM | 75 | N | ALA | A | 26 | 3.631 | 23.899 | 13.252 | 1.00 | 40.22 | N |

TABLE 3-continued

Coordinates for structures 1 to 4

| | | | | | | | | | | |
|---|---|---|---|---|---|---|---|---|---|---|
| ATOM | 76 | CA | ALA | A | 26 | 4.170 | 23.342 | 14.476 | 1.00 | 40.79 | C |
| ATOM | 77 | C | ALA | A | 26 | 3.930 | 24.294 | 15.666 | 1.00 | 41.07 | C |
| ATOM | 78 | O | ALA | A | 26 | 3.769 | 23.837 | 16.797 | 1.00 | 41.57 | O |
| ATOM | 79 | CE | ALA | A | 26 | 5.633 | 23.068 | 14.300 | 1.00 | 40.98 | C |
| ATOM | 80 | N | TRP | A | 27 | 3.931 | 25.605 | 15.429 | 1.00 | 40.80 | N |
| ATOM | 81 | CA | TRP | A | 27 | 3.543 | 26.552 | 16.477 | 1.00 | 40.67 | C |
| ATOM | 82 | C | TRP | A | 27 | 2.982 | 27.848 | 15.880 | 1.00 | 40.33 | C |
| ATOM | 83 | O | TRP | A | 27 | 2.777 | 27.940 | 14.675 | 1.00 | 40.13 | O |
| ATOM | 84 | CB | TRP | A | 27 | 4.742 | 26.860 | 17.358 | 1.00 | 40.70 | C |
| ATOM | 85 | CG | TRP | A | 27 | 5.942 | 27.014 | 16.558 | 1.00 | 41.36 | C |
| ATOM | 86 | CD1 | TRP | A | 27 | 6.762 | 26.023 | 16.074 | 1.00 | 43.03 | C |
| ATOM | 87 | CD2 | TRP | A | 27 | 6.466 | 28.233 | 16.084 | 1.00 | 40.41 | C |
| ATOM | 88 | NE1 | TRP | A | 27 | 7.788 | 26.579 | 15.344 | 1.00 | 42.65 | N |
| ATOM | 89 | CE2 | TRP | A | 27 | 7.618 | 27.938 | 15.331 | 1.00 | 41.20 | C |
| ATOM | 90 | CE3 | TRP | A | 27 | 6.081 | 29.555 | 16.223 | 1.00 | 40.47 | C |
| ATOM | 91 | CZ2 | TRP | A | 27 | 8.370 | 28.912 | 14.732 | 1.00 | 41.10 | C |
| ATOM | 92 | CZ3 | TRP | A | 27 | 6.827 | 30.514 | 15.640 | 1.00 | 41.11 | C |
| ATOM | 93 | CR2 | TRP | A | 27 | 7.962 | 30.198 | 14.900 | 1.00 | 41.57 | C |
| ATOM | 94 | N | ASP | A | 28 | 2.677 | 28.830 | 16.723 | 1.00 | 39.99 | N |
| ATOM | 95 | CA | ASP | A | 28 | 2.322 | 30.143 | 16.209 | 1.00 | 39.78 | C |
| ATOM | 96 | C | ASP | A | 28 | 2.802 | 31.257 | 17.121 | 1.00 | 39.17 | C |
| ATOM | 97 | O | ASP | A | 28 | 3.227 | 31.013 | 18.240 | 1.00 | 39.00 | O |
| ATOM | 98 | CE | ASP | A | 28 | 0.826 | 30.254 | 15.981 | 1.00 | 40.16 | C |
| ATOM | 99 | CG | ASP | A | 28 | 0.066 | 30.380 | 17.258 | 1.00 | 40.79 | C |
| ATOM | 100 | OD1 | ASP | A | 28 | 0.044 | 31.496 | 17.821 | 1.00 | 41.30 | O |
| ATOM | 101 | OD2 | ASP | A | 28 | 0.531 | 29.414 | 17.774 | 1.00 | 42.25 | O |
| ATOM | 102 | N | GLU | A | 29 | 2.720 | 32.486 | 16.624 | 1.00 | 38.73 | N |
| ATOM | 103 | CA | GLU | A | 29 | 3.223 | 33.663 | 17.341 | 1.00 | 38.23 | C |
| ATOM | 104 | C | GLU | A | 29 | 2.739 | 33.764 | 18.781 | 1.00 | 37.69 | C |
| ATOM | 105 | O | GLU | A | 29 | 3.492 | 34.131 | 19.664 | 1.00 | 37.34 | O |
| ATOM | 106 | CE | GLU | A | 29 | 2.834 | 34.924 | 16.594 | 1.00 | 38.20 | C |
| ATOM | 107 | N | SER | A | 30 | 1.482 | 33.418 | 19.012 | 1.00 | 37.46 | N |
| ATOM | 108 | CA | SER | A | 30 | 0.874 | 33.583 | 20.324 | 1.00 | 37.18 | C |
| ATOM | 109 | C | SER | A | 30 | 1.562 | 32.774 | 21.399 | 1.00 | 36.93 | C |
| ATOM | 110 | O | SER | A | 30 | 1.282 | 32.949 | 22.577 | 1.00 | 36.82 | O |
| ATOM | 111 | CE | SER | A | 30 | 0.595 | 33.164 | 20.284 | 1.00 | 37.23 | C |
| ATOM | 112 | OG | SER | A | 30 | 0.744 | 31.792 | 20.619 | 1.00 | 36.97 | O |
| ATOM | 113 | N | GLN | A | 31 | 2.441 | 31.867 | 20.999 | 1.00 | 36.85 | N |
| ATOM | 114 | CA | GLN | A | 31 | 3.128 | 31.021 | 21.961 | 1.00 | 36.77 | C |
| ATOM | 115 | C | GLN | A | 31 | 4.445 | 31.636 | 22.340 | 1.00 | 36.59 | C |
| ATOM | 116 | O | GLN | A | 31 | 5.141 | 31.127 | 23.220 | 1.00 | 36.74 | O |
| ATOM | 117 | CE | GLN | A | 31 | 3.366 | 29.621 | 21.395 | 1.00 | 36.71 | C |
| ATOM | 118 | CG | GLN | A | 31 | 2.084 | 28.828 | 21.234 | 1.00 | 36.97 | C |
| ATOM | 119 | CD | GLN | A | 31 | 2.282 | 27.497 | 20.560 | 1.00 | 36.68 | C |
| ATOM | 120 | OE1 | GLN | A | 31 | 2.133 | 27.386 | 19.346 | 1.00 | 36.62 | O |
| ATOM | 121 | NE2 | GLN | A | 31 | 2.601 | 26.478 | 21.343 | 1.00 | 36.85 | N |
| ATOM | 122 | N | LEU | A | 32 | 4.794 | 32.726 | 21.670 | 1.00 | 36.32 | N |
| ATOM | 123 | CA | LEU | A | 32 | 6.050 | 33.381 | 21.942 | 1.00 | 36.17 | C |
| ATOM | 124 | C | LEU | A | 32 | 5.817 | 34.498 | 22.921 | 1.00 | 36.09 | C |
| ATOM | 125 | O | LEU | A | 32 | 4.837 | 35.233 | 22.815 | 1.00 | 36.18 | O |
| ATOM | 126 | CE | LEU | A | 32 | 6.673 | 33.928 | 20.664 | 1.00 | 36.07 | C |
| ATOM | 127 | CG | LEU | A | 32 | 6.990 | 32.871 | 19.604 | 1.00 | 36.72 | C |
| ATOM | 128 | CD1 | LEU | A | 32 | 7.747 | 33.457 | 18.453 | 1.00 | 36.96 | C |
| ATOM | 129 | CD2 | LEU | A | 32 | 7.797 | 31.744 | 20.161 | 1.00 | 37.31 | C |
| ATOM | 130 | N | ARG | A | 33 | 6.700 | 34.576 | 23.908 | 1.00 | 35.99 | N |
| ATOM | 131 | CA | ARG | A | 33 | 6.713 | 35.671 | 24.851 | 1.00 | 36.15 | C |
| ATOM | 132 | C | ARG | A | 33 | 7.171 | 36.941 | 24.130 | 1.00 | 35.95 | C |
| ATOM | 133 | O | ARG | A | 33 | 7.950 | 36.888 | 23.188 | 1.00 | 35.75 | O |
| ATOM | 134 | CB | ARG | A | 33 | 7.671 | 35.350 | 25.991 | 1.00 | 36.41 | C |
| ATOM | 135 | CG | ARG | A | 33 | 7.210 | 34.204 | 26.854 | 1.00 | 36.76 | C |
| ATOM | 136 | CD | ARG | A | 33 | 8.082 | 33.948 | 28.070 | 1.00 | 36.81 | C |
| ATOM | 137 | NE | ARG | A | 33 | 7.479 | 32.927 | 28.923 | 1.00 | 37.39 | N |
| ATOM | 138 | CZ | ARG | A | 33 | 6.501 | 33.160 | 29.785 | 1.00 | 37.61 | C |
| ATOM | 139 | NH1 | ARG | A | 33 | 6.027 | 34.385 | 29.931 | 1.00 | 37.75 | N |
| ATOM | 140 | NH2 | ARG | A | 33 | 6.001 | 32.171 | 30.513 | 1.00 | 38.47 | N |
| ATOM | 141 | N | SER | A | 34 | 6.707 | 38.088 | 24.588 | 1.00 | 35.92 | N |
| ATOM | 142 | CA | SER | A | 34 | 7.017 | 39.331 | 23.902 | 1.00 | 36.05 | C |
| ATOM | 143 | C | SER | A | 34 | 8.044 | 40.146 | 24.671 | 1.00 | 35.47 | C |
| ATOM | 144 | O | SER | A | 34 | 7.940 | 40.311 | 25.884 | 1.00 | 35.41 | O |
| ATOM | 145 | CB | SER | A | 34 | 5.732 | 40.120 | 23.691 | 1.00 | 36.27 | C |
| ATOM | 146 | OG | SER | A | 34 | 5.046 | 40.253 | 24.920 | 1.00 | 37.99 | O |
| ATOM | 147 | N | TYR | A | 35 | 9.031 | 40.655 | 23.945 | 1.00 | 35.01 | N |
| ATOM | 148 | CA | TYR | A | 35 | 10.140 | 41.370 | 24.543 | 1.00 | 34.69 | C |
| ATOM | 149 | C | TYR | A | 35 | 10.400 | 42.693 | 23.853 | 1.00 | 34.59 | C |
| ATOM | 150 | O | TYR | A | 35 | 9.841 | 42.989 | 22.813 | 1.00 | 34.45 | O |
| ATOM | 151 | CB | TYR | A | 35 | 11.384 | 40.501 | 24.469 | 1.00 | 34.71 | C |
| ATOM | 152 | CG | TYR | A | 35 | 11.228 | 39.222 | 25.232 | 1.00 | 34.43 | C |

TABLE 3-continued

| | | | | | | | | | | |
|---|---|---|---|---|---|---|---|---|---|---|
| | Coordinates for structures 1 to 4 |
| ATOM | 153 | CD1 | TYR | A | 35 | 20.928 | 39.246 | 26.573 | 1.00 | 33.87 | C |
| ATOM | 154 | CD2 | TYR | A | 35 | 11.350 | 37.986 | 24.602 | 1.00 | 35.32 | C |
| ATOM | 155 | CE1 | TYR | A | 35 | 10.775 | 38.087 | 27.285 | 1.00 | 34.96 | C |
| ATOM | 156 | CE2 | TYR | A | 35 | 11.192 | 36.807 | 25.309 | 1.00 | 35.50 | C |
| ATOM | 157 | CZ | TYR | A | 35 | 10.904 | 36.865 | 26.653 | 1.00 | 35.16 | C |
| ATOM | 158 | OH | TYR | A | 35 | 10.742 | 35.709 | 27.376 | 1.00 | 34.77 | O |
| ATOM | 159 | N | SER | A | 36 | 11.290 | 43.481 | 24.429 | 1.00 | 34.77 | N |
| ATOM | 160 | CA | SER | A | 36 | 11.572 | 44.814 | 23.924 | 1.00 | 34.74 | C |
| ATOM | 161 | C | SER | A | 36 | 12.567 | 44.926 | 22.771 | 1.00 | 34.30 | C |
| ATOM | 162 | O | SER | A | 36 | 12.805 | 46.011 | 22.287 | 1.00 | 34.23 | O |
| ATOM | 163 | CB | SER | A | 36 | 12.127 | 45.627 | 25.077 | 1.00 | 34.91 | C |
| ATOM | 164 | OG | SER | A | 36 | 13.395 | 45.116 | 25.449 | 1.00 | 35.56 | O |
| ATOM | 165 | N | PHE | A | 37 | 13.155 | 43.838 | 22.318 | 1.00 | 34.15 | N |
| ATOM | 166 | CA | PHE | A | 37 | 14.193 | 43.963 | 21.306 | 1.00 | 34.11 | C |
| ATOM | 167 | C | PHE | A | 37 | 13.969 | 43.177 | 20.044 | 1.00 | 34.07 | C |
| ATOM | 168 | O | PHE | A | 37 | 13.356 | 42.109 | 20.017 | 1.00 | 33.98 | O |
| ATOM | 169 | CB | PHE | A | 37 | 15.514 | 43.479 | 21.867 | 1.00 | 34.08 | C |
| ATOM | 170 | CG | PHE | A | 37 | 15.417 | 42.147 | 22.438 | 1.00 | 34.33 | C |
| ATOM | 171 | CD1 | PHE | A | 37 | 15.445 | 41.034 | 21.621 | 1.00 | 35.66 | C |
| ATOM | 172 | CD2 | PHE | A | 37 | 15.208 | 41.990 | 23.777 | 1.00 | 35.42 | C |
| ATOM | 173 | CE1 | PHE | A | 37 | 15.320 | 39.782 | 22.143 | 1.00 | 35.73 | C |
| ATOM | 174 | CE2 | PHE | A | 37 | 15.084 | 40.736 | 24.317 | 1.00 | 36.14 | C |
| ATOM | 175 | CZ | PHE | A | 37 | 15.141 | 39.628 | 23.497 | 1.00 | 36.55 | C |
| ATOM | 176 | N | PRO | A | 38 | 14.565 | 43.682 | 18.991 | 1.00 | 33.95 | N |
| ATOM | 177 | CA | PRO | A | 38 | 14.474 | 43.028 | 17.704 | 1.00 | 33.91 | C |
| ATOM | 178 | C | PRO | A | 38 | 15.445 | 41.878 | 17.640 | 1.00 | 33.74 | C |
| ATOM | 179 | O | PRO | A | 38 | 16.366 | 41.803 | 18.441 | 1.00 | 33.82 | O |
| ATOM | 180 | CE | PRO | A | 38 | 14.887 | 44.133 | 16.751 | 1.00 | 34.03 | C |
| ATOM | 181 | CG | PRO | A | 38 | 15.874 | 44.935 | 17.548 | 1.00 | 33.99 | C |
| ATOM | 182 | CD | PRO | A | 38 | 15.385 | 44.903 | 18.945 | 1.00 | 33.80 | C |
| ATOM | 183 | N | THR | A | 39 | 15.233 | 40.996 | 16.678 | 1.00 | 34.02 | N |
| ATOM | 184 | CA | THR | A | 39 | 16.089 | 39.844 | 16.464 | 1.00 | 34.00 | C |
| ATOM | 185 | C | THR | A | 39 | 16.035 | 39.490 | 15.008 | 1.00 | 34.09 | C |
| ATOM | 186 | O | THR | A | 39 | 15.137 | 39.894 | 14.311 | 1.00 | 34.05 | O |
| ATOM | 187 | CB | THR | A | 39 | 15.563 | 38.637 | 17.201 | 1.00 | 33.94 | C |
| ATOM | 188 | OG1 | THR | A | 39 | 14.250 | 38.336 | 16.714 | 1.00 | 34.18 | O |
| ATOM | 189 | CG2 | THR | A | 39 | 15.338 | 38.915 | 18.642 | 1.00 | 34.09 | C |
| ATOM | 190 | N | ARG | A | 40 | 16.992 | 38.695 | 14.576 | 1.00 | 34.62 | N |
| ATOM | 191 | CA | ARG | A | 40 | 17.066 | 38.204 | 13.228 | 1.00 | 35.13 | C |
| ATOM | 192 | C | ARG | A | 40 | 17.100 | 36.721 | 13.361 | 1.00 | 35.17 | C |
| ATOM | 193 | O | ARG | A | 40 | 17.419 | 36.189 | 14.434 | 1.00 | 34.96 | O |
| ATOM | 194 | CB | ARG | A | 40 | 18.352 | 38.649 | 12.568 | 1.00 | 35.54 | C |
| ATOM | 195 | CG | ARG | A | 40 | 18.358 | 40.103 | 12.287 | 1.00 | 38.87 | C |
| ATOM | 196 | CD | ARG | A | 40 | 16.975 | 40.597 | 11.893 | 1.00 | 42.88 | C |
| ATOM | 197 | NE | ARG | A | 40 | 16.737 | 40.908 | 10.489 | 1.00 | 44.50 | N |
| ATOM | 198 | CZ | ARG | A | 40 | 15.554 | 41.298 | 10.076 | 1.00 | 46.73 | C |
| ATOM | 199 | NH1 | ARG | A | 40 | 14.574 | 41.350 | 10.974 | 1.00 | 46.73 | N |
| ATOM | 200 | NH2 | ARG | A | 40 | 15.334 | 41.636 | 8.802 | 1.00 | 48.87 | N |
| ATOM | 201 | N | PRO | A | 42. | 16.775 | 36.026 | 12.285 | 1.00 | 35.20 | N |
| ATOM | 202 | CA | PRO | A | 41 | 16.749 | 34.579 | 12.348 | 1.00 | 35.24 | C |
| ATOM | 203 | C | PRO | A | 41 | 18.114 | 33.973 | 12.275 | 1.00 | 35.10 | C |
| ATOM | 204 | O | PRO | A | 41 | 18.995 | 34.455 | 11.573 | 1.00 | 35.96 | O |
| ATOM | 205 | CB | PRO | A | 41 | 16.003 | 34.208 | 11.079 | 1.00 | 35.27 | C |
| ATOM | 206 | CG | PRO | A | 41 | 15.408 | 35.453 | 10.640 | 1.00 | 34.93 | C |
| ATOM | 207 | CD | PRO | A | 41 | 16.381 | 36.494 | 10.953 | 1.00 | 34.81 | C |
| ATOM | 208 | N | ILE | A | 42 | 18.277 | 32.910 | 13.022 | 1.00 | 34.55 | N |
| ATOM | 209 | CA | ILE | A | 42 | 19.435 | 32.099 | 12.909 | 1.00 | 34.29 | C |
| ATOM | 210 | C | ILE | A | 42 | 19.145 | 31.194 | 11.713 | 1.00 | 34.29 | C |
| ATOM | 211 | O | ILE | A | 42 | 18.035 | 30.654 | 11.598 | 1.00 | 34.38 | O |
| ATOM | 212 | CB | ILE | A | 42 | 19.545 | 31.258 | 14.150 | 1.00 | 34.14 | C |
| ATOM | 213 | CG1 | ILE | A | 42 | 19.742 | 32.152 | 15.368 | 1.00 | 34.83 | C |
| ATOM | 214 | CG2 | ILE | A | 42 | 20.679 | 30.297 | 14.016 | 1.00 | 34.41 | C |
| ATOM | 215 | CD1 | ILE | A | 42 | 19.479 | 31.467 | 16.678 | 1.00 | 35.37 | C |
| ATOM | 216 | N | PRO | A | 43 | 20.127 | 31.010 | 10.836 | 1.00 | 33.80 | N |
| ATOM | 217 | CA | PRO | A | 43 | 19.982 | 30.122 | 9.686 | 1.00 | 33.62 | C |
| ATOM | 218 | C | PRO | A | 43 | 19.714 | 28.676 | 10.066 | 1.00 | 33.65 | C |
| ATOM | 219 | O | PRO | A | 43 | 20.320 | 28.198 | 11.015 | 1.00 | 33.60 | O |
| ATOM | 220 | CE | PRO | A | 43 | 21.366 | 30.174 | 9.043 | 1.00 | 33.63 | C |
| ATOM | 221 | CG | PRO | A | 43 | 21.986 | 31.385 | 9.543 | 1.00 | 33.11 | C |
| ATOM | 222 | CD | PRO | A | 43 | 21.455 | 31.630 | 10.882 | 1.00 | 33.51 | C |
| ATOM | 223 | N | ARG | A | 44 | 18.820 | 28.007 | 9.341 | 1.00 | 33.86 | N |
| ATOM | 224 | CA | ARG | A | 44 | 18.597 | 26.572 | 9.486 | 1.00 | 34.00 | C |
| ATOM | 225 | C | ARG | A | 44 | 19.176 | 25.968 | 8.247 | 1.00 | 33.87 | C |
| ATOM | 226 | O | ARG | A | 44 | 18.783 | 26.319 | 7.152 | 1.00 | 33.76 | O |
| ATOM | 227 | CB | ARG | A | 44 | 17.125 | 26.185 | 9.520 | 1.00 | 34.10 | C |
| ATOM | 228 | CG | ARG | A | 44 | 16.301 | 26.879 | 10.577 | 1.00 | 35.44 | C |
| ATOM | 229 | CD | ARG | A | 44 | 14.781 | 26.505 | 10.583 | 1.00 | 37.36 | C |

TABLE 3-continued

| | | | | | | | | | | |
|---|---|---|---|---|---|---|---|---|---|---|
| ATOM | 230 | NE | ARG | A | 44 | 14.415 | 25.108 | 10.265 | 1.00 | 37.59 | N |
| ATOM | 231 | CZ | ARG | A | 44 | 14.237 | 24.144 | 11.187 | 1.00 | 39.71 | C |
| ATOM | 232 | NH1 | ARG | A | 44 | 14.429 | 24.396 | 12.487 | 1.00 | 39.94 | N |
| ATOM | 233 | NH2 | ARG | A | 44 | 13.876 | 22.915 | 10.821 | 1.00 | 40.07 | N |
| ATOM | 234 | N | LEU | A | 45 | 20.086 | 25.030 | 8.407 | 1.00 | 33.98 | N |
| ATOM | 235 | CA | LEU | A | 45 | 20.747 | 24.467 | 7.269 | 1.00 | 34.15 | C |
| ATOM | 236 | C | LEU | A | 45 | 20.950 | 22.995 | 7.389 | 1.00 | 34.37 | C |
| ATOM | 237 | O | LEU | A | 45 | 20.901 | 22.453 | 8.486 | 1.00 | 34.52 | O |
| ATOM | 238 | CB | LEU | A | 45 | 22.116 | 25.090 | 7.183 | 1.00 | 34.25 | C |
| ATOM | 239 | CG | LEU | A | 45 | 22.080 | 26.576 | 6.905 | 1.00 | 34.80 | C |
| ATOM | 240 | CD1 | LEU | A | 45 | 23.454 | 27.095 | 7.177 | 1.00 | 36.05 | C |
| ATOM | 241 | CD2 | LEU | A | 45 | 21.655 | 26.837 | 5.481 | 1.00 | 34.78 | C |
| ATOM | 242 | N | SER | A | 46 | 21.199 | 22.343 | 6.255 | 1.00 | 34.55 | N |
| ATOM | 243 | CA | SER | A | 46 | 21.549 | 20.949 | 6.306 | 1.00 | 34.60 | C |
| ATOM | 244 | C | SER | A | 46 | 22.985 | 20.838 | 6.681 | 1.00 | 34.89 | C |
| ATOM | 245 | O | SER | A | 46 | 23.826 | 21.671 | 6.383 | 1.00 | 34.54 | O |
| ATOM | 246 | CB | SER | A | 46 | 21.356 | 20.206 | 5.006 | 1.00 | 34.64 | C |
| ATOM | 247 | OG | SER | A | 46 | 22.231 | 19.090 | 4.989 | 1.00 | 33.61 | O |
| ATOM | 248 | N | GLN | A | 47 | 23.247 | 19.736 | 7.324 | 1.00 | 35.61 | N |
| ATOM | 249 | CA | GLN | A | 47 | 24.539 | 19.462 | 7.866 | 1.00 | 36.10 | C |
| ATOM | 250 | C | GLN | A | 47 | 25.565 | 19.368 | 6.746 | 1.00 | 35.96 | C |
| ATOM | 251 | O | GLN | A | 47 | 26.754 | 19.537 | 6.969 | 1.00 | 36.13 | O |
| ATOM | 252 | CB | GLN | A | 47 | 24.399 | 18.168 | 8.669 | 1.00 | 36.22 | C |
| ATOM | 253 | CG | GLN | A | 47 | 25.604 | 17.340 | 8.730 | 1.00 | 37.25 | C |
| ATOM | 254 | CD | GLN | A | 47 | 25.724 | 16.459 | 7.532 | 1.00 | 39.03 | C |
| ATOM | 255 | OE1 | GLN | A | 47 | 24.766 | 16.306 | 6.759 | 1.00 | 38.79 | O |
| ATOM | 256 | NE2 | GLN | A | 47 | 26.902 | 15.872 | 7.354 | 1.00 | 41.44 | N |
| ATOM | 257 | N | SER | A | 48 | 25.088 | 19.146 | 5.531 | 1.00 | 35.87 | N |
| ATOM | 258 | CA | SER | A | 48 | 25.958 | 18.938 | 4.391 | 1.00 | 35.90 | C |
| ATOM | 259 | C | SER | A | 48 | 26.301 | 20.244 | 3.715 | 1.00 | 36.06 | C |
| ATOM | 260 | O | SER | A | 48 | 27.215 | 20.334 | 2.897 | 1.00 | 35.95 | O |
| ATOM | 261 | CB | SER | A | 48 | 25.214 | 18.073 | 3.402 | 1.00 | 35.97 | C |
| ATOM | 262 | OG | SER | A | 48 | 23.933 | 18.635 | 3.158 | 1.00 | 36.62 | O |
| ATOM | 263 | N | ASP | A | 49 | 25.552 | 21.266 | 4.075 | 1.00 | 36.34 | N |
| ATOM | 264 | CA | ASP | A | 49 | 25.701 | 22.564 | 3.491 | 1.00 | 36.65 | C |
| ATOM | 265 | C | ASP | A | 49 | 26.963 | 23.236 | 3.952 | 1.00 | 37.06 | C |
| ATOM | 266 | O | ASP | A | 49 | 27.114 | 23.507 | 5.138 | 1.00 | 37.24 | O |
| ATOM | 267 | CB | ASP | A | 49 | 24.545 | 23.405 | 3.953 | 1.00 | 36.80. | C |
| ATOM | 268 | CG | ASP | A | 49 | 24.441 | 24.674 | 3.206 | 1.00 | 37.08 | C |
| ATOM | 269 | OD1 | ASP | A | 49 | 25.490 | 25.217 | 2.810 | 1.00 | 37.38 | O |
| ATOM | 270 | OD2 | ASP | A | 49 | 23.343 | 25.187 | 2.953 | 1.00 | 38.64 | O |
| ATOM | 271 | N | PRO | A | 50 | 27.857 | 23.565 | 3.029 | 1.00 | 37.42 | N |
| ATOM | 272 | CA | PRO | A | 50 | 29.113 | 24.196 | 3.430 | 1.00 | 37.32 | C |
| ATOM | 273 | C | PRO | A | 50 | 28.881 | 25.413 | 4.298 | 1.00 | 37.46 | C |
| ATOM | 274 | O | PRO | A | 50 | 29.742 | 25.727 | 5.113 | 1.00 | 37.85 | O |
| ATOM | 275 | CB | PRO | A | 50 | 29.750 | 24.604 | 2.108 | 1.00 | 37.21 | C |
| ATOM | 276 | CG | PRO | A | 50 | 29.134 | 23.726 | 1.086 | 1.00 | 37.39 | C |
| ATOM | 277 | CD | PRO | A | 50 | 27.755 | 23.395 | 1.568 | 1.00 | 37.34 | C |
| ATOM | 278 | N | ARG | A | 51 | 27.743 | 26.081 | 4.162 | 1.00 | 37.64 | N |
| ATOM | 279 | CA | ARG | A | 51 | 27.535 | 27.301 | 4.932 | 1.00 | 38.06 | C |
| ATOM | 280 | C | ARG | A | 51 | 27.470 | 27.000 | 6.421 | 1.00 | 38.26 | C |
| ATOM | 281 | O | ARG | A | 51 | 27.920 | 27.798 | 7.250 | 1.00 | 38.47 | O |
| ATOM | 282 | CB | ARG | A | 51 | 26.282 | 28.055 | 4.470 | 1.00 | 38.14 | C |
| ATOM | 283 | CG | ARG | A | 51 | 26.418 | 28.692 | 3.059 | 1.00 | 38.89 | C |
| ATOM | 284 | CD | ARG | A | 51 | 25.117 | 29.259 | 2.455 | 1.00 | 39.65 | C |
| ATOM | 285 | NE | ARG | A | 51 | 24.121 | 28.211 | 2.175 | 1.00 | 41.25 | N |
| ATOM | 286 | CZ | ARG | A | 51 | 22.798 | 28.404 | 2.078 | 1.00 | 41.86 | C |
| ATOM | 287 | NH1 | ARG | A | 51 | 22.264 | 29.605 | 2.225 | 1.00 | 43.70 | N |
| ATOM | 288 | NH2 | ARG | A | 51 | 21.994 | 27.393 | 1.818 | 1.00 | 41.90 | N |
| ATOM | 289 | N | ALA | A | 52 | 26.936 | 25.837 | 6.770 | 1.00 | 38.26 | N |
| ATOM | 290 | CA | ALA | A | 52 | 26.807 | 25.499 | 8.171 | 1.00 | 38.30 | C |
| ATOM | 291 | C | ALA | A | 52 | 28.206 | 25.374 | 8.683 | 1.00 | 38.45 | C |
| ATOM | 292 | O | ALA | A | 52 | 28.572 | 25.922 | 9.732 | 1.00 | 38.37 | O |
| ATOM | 293 | CB | ALA | A | 52 | 26.085 | 24.208 | 8.344 | 1.00 | 38.25 | C |
| ATOM | 294 | N | GLU | A | 53 | 29.003 | 24.665 | 7.901 | 1.00 | 38.56 | N |
| ATOM | 295 | CA | GLU | A | 53 | 30.361 | 24.420 | 8.291 | 1.00 | 38.94 | C |
| ATOM | 296 | C | GLU | A | 53 | 31.145 | 25.717 | 8.484 | 1.00 | 39.00 | C |
| ATOM | 297 | O | GLU | A | 53 | 31.970 | 25.793 | 9.386 | 1.00 | 38.49 | O |
| ATOM | 298 | CB | GLU | A | 53 | 31.060 | 23.507 | 7.314 | 1.00 | 38.91 | C |
| ATOM | 299 | CG | GLU | A | 53 | 32.139 | 22.738 | 8.035 | 1.00 | 40.55 | C |
| ATOM | 300 | CD | GLU | A | 53 | 31.662 | 21.403 | 8.579 | 1.00 | 42.38 | C |
| ATOM | 301 | OE1 | GLU | A | 53 | 30.475 | 21.274 | 8.957 | 1.00 | 43.42 | O |
| ATOM | 302 | OE2 | GLU | A | 53 | 32.498 | 20.478 | 8.639 | 1.00 | 44.15 | O |
| ATOM | 303 | N | GLU | A | 54 | 30.897 | 26.737 | 7.662 | 1.00 | 39.21 | N |
| ATOM | 304 | CA | GLU | A | 54 | 31.592 | 28.004 | 7.870 | 1.00 | 39.44 | C |
| ATOM | 305 | C | GLU | A | 54 | 31.092 | 28.625 | 9.144 | 1.00 | 39.05 | C |
| ATOM | 306 | O | GLU | A | 54 | 31.848 | 29.262 | 9.869 | 1.00 | 39.51 | O |

TABLE 3-continued

Coordinates for structures 1 to 4

| ATOM | 307 | CB | GLU | A | 54 | 31.337 | 29.023 | 6.772 | 1.00 | 39.59 | C |
|------|-----|-----|-----|---|----|--------|--------|--------|------|-------|---|
| ATOM | 308 | CG | GLU | A | 54 | 31.940 | 28.693 | 5.433 | 1.00 | 41.75 | C |
| ATOM | 309 | CD | GLU | A | 54 | 31.098 | 29.263 | 4.302 | 1.00 | 44.74 | C |
| ATOM | 310 | OE1 | GLU | A | 54 | 30.546 | 30.379 | 4.509 | 1.00 | 46.67 | O |
| ATOM | 311 | OE2 | GLU | A | 54 | 30.972 | 28.596 | 3.234 | 1.00 | 44.49 | O |
| ATOM | 312 | N | LEU | A | 55 | 29.812 | 28.468 | 9.424 | 1.00 | 38.37 | N |
| ATOM | 313 | CA | LEU | A | 55 | 29.291 | 29.137 | 10.583 | 1.00 | 38.08 | C |
| ATOM | 314 | C | LEU | A | 55 | 29.906 | 28.613 | 11.847 | 1.00 | 37.88 | C |
| ATOM | 315 | O | LEU | A | 55 | 30.359 | 29.397 | 12.693 | 1.00 | 37.59 | O |
| ATOM | 316 | GB | LEU | A | 55 | 27.789 | 29.006 | 10.648 | 1.00 | 38.28 | C |
| ATOM | 317 | CG | LEU | A | 55 | 27.142 | 29.846 | 9.564 | 1.00 | 37.79 | C |
| ATOM | 318 | GD1 | LEU | A | 55 | 25.722 | 29.443 | 9.409 | 1.00 | 38.31 | C |
| ATOM | 319 | CD2 | LEU | A | 55 | 27.233 | 31.279 | 9.951 | 1.00 | 37.31 | C |
| ATOM | 320 | N | ILE | A | 56 | 29.938 | 27.286 | 11.971 | 1.00 | 37.71 | N |
| ATOM | 321 | GA | ILE | A | 56 | 30.455 | 26.667 | 13.183 | 1.00 | 37.35 | C |
| ATOM | 322 | C | ILE | A | 56 | 31.912 | 26.988 | 13.321 | 1.00 | 37.30 | C |
| ATOM | 323 | O | ILE | A | 56 | 32.373 | 27.320 | 14.406 | 1.00 | 36.89 | O |
| ATOM | 324 | GB | ILE | A | 56 | 30.288 | 25.171 | 13.175 | 1.00 | 37.30 | C |
| ATOM | 325 | GG1 | ILE | A | 56 | 28.810 | 24.789 | 13.213 | 1.00 | 36.97 | C |
| ATOM | 326 | GG2 | ILE | A | 56 | 30.968 | 24.602 | 14.397 | 1.00 | 37.75 | C |
| ATOM | 327 | GD1 | ILE | A | 56 | 28.543 | 23.358 | 12.820 | 1.00 | 36.35 | C |
| ATOM | 328 | N | GLU | A | 57 | 32.627 | 26.899 | 12.204 | 1.00 | 37.67 | N |
| ATOM | 329 | CA | GLU | A | 57 | 34.045 | 27.204 | 12.166 | 1.00 | 38.21 | C |
| ATOM | 330 | C | GLU | A | 57 | 34.277 | 28.569 | 12.784 | 1.00 | 38.33 | C |
| ATOM | 331 | O | GLU | A | 57 | 35.210 | 28.758 | 13.566 | 1.00 | 38.33 | O |
| ATOM | 332 | GB | GLU | A | 57 | 34.547 | 27.214 | 10.725 | 1.00 | 38.49 | C |
| ATOM | 333 | CG | GLU | A | 57 | 36.038 | 27.461 | 10.559 | 1.00 | 40.09 | C |
| ATOM | 334 | GD | GLU | A | 57 | 36.870 | 26.539 | 11.424 | 1.00 | 42.96 | C |
| ATOM | 335 | OE1 | GLU | A | 57 | 36.527 | 25.329 | 11.487 | 1.00 | 43.20 | O |
| ATOM | 336 | OE2 | GLU | A | 57 | 37.852 | 27.032 | 12.044 | 1.00 | 44.14 | O |
| ATOM | 337 | N | ASN | A | 58 | 33.394 | 29.508 | 12.460 | 1.00 | 38.32 | N |
| ATOM | 338 | CA | ASN | A | 58 | 33.546 | 30.890 | 12.891 | 1.00 | 38.38 | C |
| ATOM | 339 | C | ASN | A | 58 | 32.849 | 31.221 | 14.167 | 1.00 | 38.06 | C |
| ATOM | 340 | O | ASN | A | 58 | 32.683 | 32.387 | 14.507 | 1.00 | 37.86 | O |
| ATOM | 341 | CB | ASN | A | 58 | 32.955 | 31.813 | 11.853 | 1.00 | 38.73 | C |
| ATOM | 342 | GG | ASN | A | 58 | 33.991 | 32.455 | 11.013 | 1.00 | 39.49 | C |
| ATOM | 343 | OD1 | ASN | A | 58 | 34.501 | 31.841 | 10.083 | 1.00 | 42.51 | O |
| ATOM | 344 | ND2 | ASN | A | 58 | 34.322 | 33.704 | 11.324 | 1.00 | 40.15 | N |
| ATOM | 345 | N | GLU | A | 59 | 32.399 | 30.196 | 14.856 | 1.00 | 37.88 | N |
| ATOM | 346 | CA | GLU | A | 59 | 31.683 | 30.396 | 16.092 | 1.00 | 37.68 | C |
| ATOM | 347 | C | GLU | A | 59 | 30.479 | 31.307 | 16.005 | 1.00 | 37.57 | C |
| ATOM | 348 | O | GLU | A | 59 | 30.305 | 32.203 | 16.813 | 1.00 | 36.94 | O |
| ATOM | 349 | GB | GLU | A | 59 | 32.663 | 30.857 | 17.118 | 1.00 | 37.60 | G |
| ATOM | 350 | CG | GLU | A | 59 | 33.710 | 29.785 | 17.212 | 1.00 | 38.25 | G |
| ATOM | 351 | GD | GLU | A | 59 | 34.545 | 29.886 | 18.435 | 1.00 | 38.10 | G |
| ATOM | 352 | OE1 | GLU | A | 59 | 35.654 | 30.430 | 18.303 | 1.00 | 40.30 | O |
| ATOM | 353 | OE2 | GLU | A | 59 | 34.089 | 29.420 | 19.498 | 1.00 | 37.62 | O |
| ATOM | 354 | N | GLU | A | 60 | 29.630 | 31.025 | 15.025 | 1.00 | 37.73 | N |
| ATOM | 355 | GA | GLU | A | 60 | 28.347 | 31.692 | 14.902 | 1.00 | 37.79 | G |
| ATOM | 356 | G | GLU | A | 60 | 27.290 | 30.620 | 14.923 | 1.00 | 37.12 | G |
| ATOM | 357 | O | GLU | A | 60 | 27.488 | 29.539 | 14.388 | 1.00 | 37.94 | O |
| ATOM | 358 | GB | GLU | A | 60 | 28.252 | 32.456 | 13.606 | 1.00 | 38.14 | G |
| ATOM | 359 | GG | GLU | A | 60 | 29.388 | 33.411 | 13.414 | 1.00 | 39.56 | G |
| ATOM | 360 | GD | GLU | A | 60 | 28.986 | 34.547 | 12.518 | 1.00 | 42.62 | C |
| ATOM | 361 | OE1 | GLU | A | 60 | 29.023 | 34.389 | 11.276 | 1.00 | 42.22 | O |
| ATOM | 362 | OE2 | GLU | A | 60 | 28.611 | 35.601 | 13.082 | 1.00 | 46.90 | O |
| ATOM | 363 | N | PRO | A | 61 | 26.158 | 30.917 | 15.517 | 1.00 | 36.25 | N |
| ATOM | 364 | GA | PRO | A | 61 | 25.111 | 29.919 | 15.680 | 1.00 | 36.11 | C |
| ATOM | 365 | G | PRO | A | 61 | 24.522 | 29.448 | 14.373 | 1.00 | 35.80 | G |
| ATOM | 366 | O | PRO | A | 61 | 24.534 | 30.159 | 13.386 | 1.00 | 36.29 | O |
| ATOM | 367 | GB | PRO | A | 61 | 24.021 | 30.672 | 16.442 | 1.00 | 36.35 | G |
| ATOM | 368 | GG | PRO | A | 61 | 24.367 | 32.117 | 16.353 | 1.00 | 36.05 | G |
| ATOM | 369 | CD | PRO | A | 61 | 25.790 | 32.228 | 16.061 | 1.00 | 36.10 | G |
| ATOM | 370 | N | VAL | A | 62 | 23.981 | 28.247 | 14.380 | 1.00 | 35.41 | N |
| ATOM | 371 | GA | VAL | A | 62 | 23.291 | 27.722 | 13.228 | 1.00 | 34.88 | G |
| ATOM | 372 | G | VAL | A | 62 | 22.438 | 26.584 | 13.720 | 1.00 | 34.68 | G |
| ATOM | 373 | O | VAL | A | 62 | 22.807 | 25.885 | 14.658 | 1.00 | 34.41 | O |
| ATOM | 374 | GB | VAL | A | 62 | 24.237 | 27.189 | 12.156 | 1.00 | 34.79 | G |
| ATOM | 375 | GG1 | VAL | A | 62 | 25.108 | 26.062 | 12.695 | 1.00 | 34.66 | G |
| ATOM | 376 | CG2 | VAL | A | 62 | 23.440 | 26.693 | 10.996 | 1.00 | 34.83 | C |
| ATOM | 377 | N | VAL | A | 63 | 21.271 | 26.418 | 13.118 | 1.00 | 34.54 | N |
| ATOM | 378 | CA | VAL | A | 63 | 20.454 | 25.273 | 13.447 | 1.00 | 34.18 | C |
| ATOM | 379 | C | VAL | A | 63 | 20.660 | 24.230 | 12.372 | 1.00 | 33.85 | C |
| ATOM | 380 | O | VAL | A | 63 | 20.486 | 24.512 | 11.203 | 1.00 | 33.36 | O |
| ATOM | 381 | CB | VAL | A | 63 | 18.980 | 25.622 | 13.523 | 1.00 | 34.05 | C |
| ATOM | 382 | CG1 | VAL | A | 63 | 18.167 | 24.349 | 13.626 | 1.00 | 34.14 | C |
| ATOM | 383 | CG2 | VAL | A | 63 | 18.717 | 26.502 | 14.710 | 1.00 | 33.51 | C |

TABLE 3-continued

Coordinates for structures 1 to 4

| | | | | | | | | | | | |
|---|---|---|---|---|---|---|---|---|---|---|---|
| ATOM | 384 | N | LEU | A | 64 | 21.048 | 23.028 | 12.769 | 1.00 | 33.87 | N |
| ATOM | 385 | CA | LEU | A | 64 | 21.204 | 21.942 | 11.814 | 1.00 | 34.03 | C |
| ATOM | 386 | C | LEU | A | 64 | 19.894 | 21.193 | 11.856 | 1.00 | 33.70 | C |
| ATOM | 387 | O | LEU | A | 64 | 19.368 | 20.956 | 12.932 | 1.00 | 34.18 | O |
| ATOM | 388 | CB | LEU | A | 64 | 22.417 | 21.071 | 12.164 | 1.00 | 33.90 | C |
| ATOM | 389 | CG | LEU | A | 64 | 23.667 | 21.978 | 12.155 | 1.00 | 34.85 | C |
| ATOM | 390 | CD1 | LEU | A | 64 | 24.975 | 21.303 | 12.485 | 1.00 | 35.82 | C |
| ATOM | 391 | CD2 | LEU | A | 64 | 23.821 | 22.629 | 10.798 | 1.00 | 35.39 | C |
| ATOM | 392 | N | THR | A | 65 | 19.314 | 20.887 | 10.704 | 1.00 | 33.36 | N |
| ATOM | 393 | CA | THR | A | 65 | 18.035 | 20.177 | 10.704 | 1.00 | 33.24 | C |
| ATOM | 394 | C | THR | A | 65 | 18.105 | 18.683 | 10.517 | 1.00 | 32.87 | C |
| ATOM | 395 | O | THR | A | 65 | 17.096 | 18.016 | 10.715 | 1.00 | 32.11 | O |
| ATOM | 396 | CB | THR | A | 65 | 17.149 | 20.657 | 9.562 | 1.00 | 33.35 | C |
| ATOM | 397 | OG1 | THR | A | 65 | 17.858 | 20.540 | 8.320 | 1.00 | 33.15 | O |
| ATOM | 398 | CG2 | THR | A | 65 | 16.843 | 22.093 | 9.693 | 1.00 | 33.51 | C |
| ATOM | 399 | N | ASP | A | 66 | 19.265 | 18.173 | 10.106 | 1.00 | 33.09 | N |
| ATOM | 400 | CA | ASP | A | 66 | 19.392 | 16.767 | 9.724 | 1.00 | 33.53 | C |
| ATOM | 401 | C | ASP | A | 66 | 20.629 | 16.019 | 10.189 | 1.00 | 33.55 | C |
| ATOM | 402 | O | ASP | A | 66 | 21.136 | 15.179 | 9.458 | 1.00 | 33.68 | O |
| ATOM | 403 | CB | ASP | A | 66 | 19.339 | 16.653 | 8.192 | 1.00 | 33.55 | C |
| ATOM | 404 | CG | ASP | A | 66 | 20.397 | 17.484 | 7.508 | 1.00 | 34.00 | C |
| ATOM | 405 | OD1 | ASP | A | 66 | 21.124 | 18.232 | 8.188 | 1.00 | 35.03 | O |
| ATOM | 406 | OD2 | ASP | A | 66 | 20.583 | 17.456 | 6.284 | 1.00 | 35.31 | O |
| ATOM | 407 | N | THR | A | 67 | 21.107 | 16.264 | 11.397 | 1.00 | 33.83 | N |
| ATOM | 408 | CA | THR | A | 67 | 22.286 | 15.540 | 11.845 | 1.00 | 33.70 | C |
| ATOM | 409 | C | THR | A | 67 | 21.937 | 14.177 | 12.340 | 1.00 | 33.84 | C |
| ATOM | 410 | O | THR | A | 67 | 22.808 | 13.340 | 12.431 | 1.00 | 34.42 | O |
| ATOM | 411 | CB | THR | A | 67 | 22.951 | 16.215 | 13.020 | 1.00 | 33.66 | C |
| ATOM | 412 | OG1 | THR | A | 67 | 21.981 | 16.451 | 14.046 | 1.00 | 33.90 | O |
| ATOM | 413 | CG2 | THR | A | 67 | 23.472 | 17.562 | 12.674 | 1.00 | 33.56 | C |
| ATOM | 414 | N | ASN | A | 68 | 20.686 | 13.954 | 12.719 | 1.00 | 34.00 | N |
| ATOM | 415 | CA | ASN | A | 68 | 20.320 | 12.676 | 13.312 | 1.00 | 34.15 | C |
| ATOM | 416 | C | ASN | A | 68 | 21.108 | 12.454 | 14.575 | 1.00 | 33.97 | C |
| ATOM | 417 | O | ASN | A | 68 | 21.281 | 11.330 | 15.008 | 1.00 | 33.83 | O |
| ATOM | 418 | CB | ASN | A | 68 | 20.653 | 11.531 | 12.375 | 1.00 | 34.26 | C |
| ATOM | 419 | CG | ASN | A | 68 | 19.685 | 11.411 | 11.239 | 1.00 | 35.12 | C |
| ATOM | 420 | OD1 | ASN | A | 68 | 18.512 | 11.104 | 11.434 | 1.00 | 35.89 | O |
| ATOM | 421 | ND2 | ASN | A | 68 | 20.168 | 11.649 | 10.033 | 1.00 | 36.88 | N |
| ATOM | 422 | N | LEU | A | 69 | 21.598 | 13.531 | 15.162 | 1.00 | 34.12 | N |
| ATOM | 423 | CA | LEU | A | 69 | 22.446 | 13.419 | 16.334 | 1.00 | 34.19 | C |
| ATOM | 424 | C | LEU | A | 69 | 21.836 | 12.562 | 17.440 | 1.00 | 34.16 | C |
| ATOM | 425 | O | LEU | A | 69 | 22.538 | 11.737 | 18.039 | 1.00 | 33.75 | O |
| ATOM | 426 | CB | LEU | A | 69 | 22.774 | 14.808 | 16.881 | 1.00 | 34.13 | C |
| ATOM | 427 | CG | LEU | A | 69 | 23.652 | 14.795 | 18.125 | 1.00 | 34.10 | C |
| ATOM | 428 | CD1 | LEU | A | 69 | 24.978 | 14.105 | 17.854 | 1.00 | 34.66 | C |
| ATOM | 429 | CD2 | LEU | A | 69 | 23.883 | 16.183 | 18.582 | 1.00 | 33.94 | C |
| ATOM | 430 | N | VAL | A | 70 | 20.555 | 12.783 | 17.732 | 1.00 | 34.15 | N |
| ATOM | 431 | CA | VAL | A | 70 | 19.877 | 12.023 | 18.777 | 1.00 | 34.48 | C |
| ATOM | 432 | C | VAL | A | 70 | 18.654 | 11.307 | 18.228 | 1.00 | 34.64 | C |
| ATOM | 433 | O | VAL | A | 70 | 17.600 | 11.223 | 18.865 | 1.00 | 34.46 | O |
| ATOM | 434 | CB | VAL | A | 70 | 19.540 | 12.899 | 20.003 | 1.00 | 34.61 | C |
| ATOM | 435 | CG1 | VAL | A | 70 | 20.808 | 13.555 | 20.519 | 1.00 | 35.04 | C |
| ATOM | 436 | CG2 | VAL | A | 70 | 18.493 | 13.939 | 19.706 | 1.00 | 34.21 | C |
| ATOM | 437 | N | TYR | A | 71 | 18.833 | 10.762 | 17.033 | 1.00 | 34.98 | N |
| ATOM | 438 | CA | TYR | A | 71 | 17.779 | 10.041 | 16.352 | 1.00 | 35.19 | C |
| ATOM | 439 | C | TYR | A | 71 | 17.051 | 9.086 | 17.305 | 1.00 | 35.24 | C |
| ATOM | 440 | O | TYR | A | 71 | 15.837 | 9.148 | 17.421 | 1.00 | 35.61 | O |
| ATOM | 441 | CB | TYR | A | 71 | 18.337 | 9.291 | 15.137 | 1.00 | 35.26 | C |
| ATOM | 442 | CG | TYR | A | 71 | 17.352 | 8.278 | 14.618 | 1.00 | 35.95 | C |
| ATOM | 443 | CD1 | TYR | A | 71 | 16.155 | 8.696 | 14.055 | 1.00 | 35.96 | C |
| ATOM | 444 | CD2 | TYR | A | 71 | 17.584 | 6.915 | 14.731 | 1.00 | 34.66 | C |
| ATOM | 445 | CE1 | TYR | A | 71 | 15.239 | 7.805 | 13.610 | 1.00 | 35.86 | C |
| ATOM | 446 | CE2 | TYR | A | 71 | 16.664 | 6.011 | 14.281 | 1.00 | 34.47 | C |
| ATOM | 447 | CZ | TYR | A | 71 | 15.485 | 6.463 | 13.724 | 1.00 | 36.06 | C |
| ATOM | 448 | OH | TYR | A | 71 | 14.518 | 5.589 | 13.248 | 1.00 | 38.92 | O |
| ATOM | 449 | N | PRO | A | 72 | 17.774 | 8.211 | 17.993 | 1.00 | 35.15 | N |
| ATOM | 450 | CA | PRO | A | 72 | 17.141 | 7.271 | 18.924 | 1.00 | 35.16 | C |
| ATOM | 451 | C | PRO | A | 72 | 16.357 | 7.923 | 20.068 | 1.00 | 35.14 | C |
| ATOM | 452 | O | PRO | A | 72 | 15.473 | 7.294 | 20.643 | 1.00 | 34.97 | O |
| ATOM | 453 | CB | PRO | A | 72 | 18.327 | 6.475 | 19.487 | 1.00 | 35.18 | C |
| ATOM | 454 | CG | PRO | A | 72 | 19.433 | 6.677 | 18.524 | 1.00 | 35.26 | C |
| ATOM | 455 | CD | PRO | A | 72 | 19.233 | 8.031 | 17.938 | 1.00 | 35.29 | C |
| ATOM | 456 | N | ALA | A | 73 | 16.657 | 9.169 | 20.401 | 1.00 | 35.18 | N |
| ATOM | 457 | CA | ALA | A | 73 | 15.967 | 9.803 | 21.512 | 1.00 | 35.21 | C |
| ATOM | 458 | C | ALA | A | 73 | 14.657 | 10.414 | 21.097 | 1.00 | 35.08 | C |
| ATOM | 459 | O | ALA | A | 73 | 13.890 | 10.862 | 21.934 | 1.00 | 34.86 | O |
| ATOM | 460 | CB | ALA | A | 73 | 16.829 | 10.864 | 22.135 | 1.00 | 35.37 | C |

TABLE 3-continued

Coordinates for structures 1 to 4

| ATOM | 461 | N   | LEU | A | 74 | 14.370 | 10.434 | 19.812 | 1.00 | 35.25 | N  |
|------|-----|-----|-----|---|----|--------|--------|--------|------|-------|----|
| ATOM | 462 | CA  | LEU | A | 74 | 13.142 | 11.090 | 19.399 | 1.00 | 35.54 | C  |
| ATOM | 463 | C   | LEU | A | 74 | 11.903 | 10.434 | 19.958 | 1.00 | 35.66 | C. |
| ATOM | 464 | O   | LEU | A | 74 | 10.893 | 11.088 | 20.118 | 1.00 | 35.64 | O  |
| ATOM | 465 | CB  | LEU | A | 74 | 13.044 | 11.190 | 17.894 | 1.00 | 35.31 | C  |
| ATOM | 466 | CG  | LEU | A | 74 | 14.161 | 12.046 | 17.333 | 1.00 | 36.48 | C  |
| ATOM | 467 | CD1 | LEU | A | 74 | 13.887 | 12.277 | 15.890 | 1.00 | 37.76 | C  |
| ATOM | 468 | CD2 | LEU | A | 74 | 14.300 | 13.394 | 18.076 | 1.00 | 37.06 | C  |
| ATOM | 469 | N   | LYS | A | 75 | 11.979 | 9.151  | 20.282 | 1.00 | 36.19 | N  |
| ATOM | 470 | CA  | LYS | A | 75 | 10.795 | 8.453  | 20.767 | 1.00 | 36.36 | C  |
| ATOM | 471 | C   | LYS | A | 75 | 10.566 | 8.710  | 22.246 | 1.00 | 36.85 | C  |
| ATOM | 472 | O   | LYS | A | 75 | 9.491  | 8.437  | 22.765 | 1.00 | 37.12 | O  |
| ATOM | 473 | CB  | LYS | A | 75 | 10.904 | 6.956  | 20.505 | 1.00 | 36.04 | C  |
| ATOM | 474 | CG  | LYS | A | 75 | 12.060 | 6.284  | 21.216 | 1.00 | 35.77 | C  |
| ATOM | 475 | CD  | LYS | A | 75 | 12.245 | 4.829  | 20.782 | 1.00 | 34.46 | C  |
| ATOM | 476 | CE  | LYS | A | 75 | 13.720 | 4.460  | 20.710 | 1.00 | 33.42 | C  |
| ATOM | 477 | NZ  | LYS | A | 75 | 14.375 | 4.536  | 22.036 | 1.00 | 32.34 | N  |
| ATOM | 478 | N   | TRP | A | 76 | 11.578 | 9.244  | 22.920 | 1.00 | 37.24 | N  |
| ATOM | 479 | CA  | TRP | A | 76 | 11.481 | 9.510  | 24.345 | 1.00 | 37.30 | C  |
| ATOM | 480 | C   | TRP | A | 76 | 10.274 | 10.369 | 24.700 | 1.00 | 37.42 | C  |
| ATOM | 481 | O   | TRP | A | 76 | 9.917  | 11.306 | 23.984 | 1.00 | 37.54 | O  |
| ATOM | 482 | CB  | TRP | A | 76 | 12.728 | 10.247 | 24.838 | 1.00 | 37.12 | C  |
| ATOM | 483 | CG  | TRP | A | 76 | 13.980 | 9.446  | 24.816 | 1.00 | 36.77 | C  |
| ATOM | 484 | CD1 | TRP | A | 76 | 14.142 | 8.176  | 24.359 | 1.00 | 37.03 | C  |
| ATOM | 485 | CD2 | TRP | A | 76 | 15.255 | 9.864  | 25.291 | 1.00 | 36.31 | C  |
| ATOM | 486 | NE1 | TRP | A | 76 | 15.445 | 7.776  | 24.527 | 1.00 | 36.52 | N  |
| ATOM | 487 | CE2 | TRP | A | 76 | 16.147 | 8.801  | 25.097 | 1.00 | 36.08 | C  |
| ATOM | 488 | CE3 | TRP | A | 76 | 15.737 | 11.040 | 25.864 | 1.00 | 36.23 | C  |
| ATOM | 489 | CZ2 | TRP | A | 76 | 17.480 | 8.881  | 25.443 | 1.00 | 36.27 | C  |
| ATOM | 490 | CZ3 | TRP | A | 76 | 17.055 | 11.113 | 26.209 | 1.00 | 36.35 | C  |
| ATOM | 491 | CR2 | TRP | A | 76 | 17.915 | 10.045 | 25.996 | 1.00 | 36.41 | C  |
| ATOM | 492 | N   | ASP | A | 77 | 9.662  | 10.015 | 25.820 | 1.00 | 37.42 | N  |
| ATOM | 493 | CA  | ASP | A | 77 | 8.591  | 10.768 | 26.435 | 1.00 | 37.36 | C  |
| ATOM | 494 | C   | ASP | A | 77 | 8.707  | 10.370 | 27.907 | 1.00 | 37.09 | C  |
| ATOM | 495 | O   | ASP | A | 77 | 9.628  | 9.647  | 28.260 | 1.00 | 37.04 | O  |
| ATOM | 496 | CB  | ASP | A | 77 | 7.245  | 10.377 | 25.834 | 1.00 | 37.48 | C  |
| ATOM | 497 | CG  | ASP | A | 77 | 6.990  | 8.888  | 25.903 | 1.00 | 38.01 | C  |
| ATOM | 498 | OD1 | ASP | A | 77 | 7.704  | 8.191  | 26.658 | 1.00 | 38.42 | O  |
| ATOM | 499 | OD2 | ASP | A | 77 | 6.093  | 8.319  | 25.244 | 1.00 | 39.67 | O  |
| ATOM | 500 | N   | LEU | A | 78 | 7.789  | 10.798 | 28.763 | 1.00 | 36.79 | N  |
| ATOM | 501 | CA  | LEU | A | 78 | 7.913  | 10.496 | 30.182 | 1.00 | 36.49 | C  |
| ATOM | SO2 | C   | LEU | A | 78 | 7.729  | 9.026  | 30.464 | 1.00 | 36.62 | C  |
| ATOM | 503 | O   | LEU | A | 78 | 8.456  | 8.426  | 31.260 | 1.00 | 36.50 | O  |
| ATOM | SO4 | CB  | LEU | A | 78 | 6.903  | 11.296 | 30.974 | 1.00 | 36.33 | C  |
| ATOM | 505 | CG  | LEU | A | 78 | 7.119  | 12.796 | 30.863 | 1.00 | 36.49 | C  |
| ATOM | 506 | CO1 | LEU | A | 78 | 6.008  | 13.510 | 31.594 | 1.00 | 36.63 | C  |
| ATOM | 507 | CD2 | LEU | A | 78 | 8.494  | 13.194 | 31.399 | 1.00 | 36.10 | C  |
| ATOM | 508 | N   | GLU | A | 79 | 6.748  | 8.433  | 29.815 | 1.00 | 36.81 | N  |
| ATOM | 509 | CA  | GLU | A | 79 | 6.505  | 7.030  | 30.041 | 1.00 | 36.97 | C  |
| ATOM | 510 | C   | GLU | A | 79 | 7.737  | 6.176  | 29.738 | 1.00 | 36.75 | C  |
| ATOM | 511 | O   | GLU | A | 79 | 8.151  | 5.373  | 30.572 | 1.00 | 36.84 | O  |
| ATOM | 512 | CB  | GLU | A | 79 | 5.323  | 6.560  | 29.214 | 1.00 | 37.25 | C  |
| ATOM | 513 | CG  | GLU | A | 79 | 4.937  | 5.137  | 29.540 | 1.00 | 37.93 | C  |
| ATOM | 514 | CD  | GLU | A | 79 | 3.729  | 4.681  | 28.768 | 1.00 | 38.61 | C  |
| ATOM | 515 | OE1 | LEU | A | 79 | 3.381  | 5.352  | 27.775 | 1.00 | 38.32 | O  |
| ATOM | 516 | OE2 | GLU | A | 79 | 3.131  | 3.654  | 29.166 | 1.00 | 40.10 | O  |
| ATOM | 517 | N   | TYR | A | 80 | 8.318  | 6.337  | 28.553 | 1.00 | 36.50 | N  |
| ATOM | 518 | CA  | TYR | A | 80 | 9.489  | 5.549  | 28.176 | 1.00 | 36.32 | C  |
| ATOM | 519 | C   | TYR | A | 80 | 10.644 | 5.804  | 29.123 | 1.00 | 36.27 | C  |
| ATOM | 520 | O   | TYR | A | 80 | 11.343 | 4.872  | 24.515 | 1.00 | 36.15 | O  |
| ATOM | 521 | CB  | TYR | A | 80 | 9.921  | 5.889  | 26.751 | 1.00 | 36.39 | C  |
| ATOM | 522 | CG  | TYR | A | 80 | 11.180 | 5.202  | 26.228 | 1.00 | 36.06 | C  |
| ATOM | 523 | CD1 | TYR | A | 80 | 11.100 | 4.000  | 25.557 | 1.00 | 36.22 | C  |
| ATOM | 524 | CD2 | TYR | A | 80 | 12.432 | 5.793  | 26.349 | 1.00 | 35.91 | C  |
| ATOM | 525 | CE1 | TYR | A | 80 | 12.225 | 3.380  | 25.051 | 1.00 | 36.52 | C  |
| ATOM | 526 | CE2 | TYR | A | 80 | 13.568 | 5.179  | 25.844 | 1.00 | 36.04 | C  |
| ATOM | 527 | CZ  | TYR | A | 80 | 13.454 | 3.967  | 25.190 | 1.00 | 36.46 | C  |
| ATOM | 528 | OH  | TYR | A | 80 | 14.561 | 3.321  | 24.673 | 1.00 | 35.81 | O  |
| ATOM | 529 | N   | LEU | A | 81 | 10.846 | 7.064  | 29.493 | 1.00 | 36.13 | N  |
| ATOM | 530 | CA  | LEU | A | 81 | 11.971 | 7.408  | 30.353 | 1.00 | 36.22 | C  |
| ATOM | 531 | C   | LEU | A | 81 | 11.777 | 6.827  | 31.747 | 1.00 | 36.13 | C  |
| ATOM | 532 | O   | LEU | A | 81 | 12.706 | 6.259  | 32.325 | 1.00 | 35.90 | O  |
| ATOM | 533 | CB  | LEU | A | 81 | 12.208 | 8.930  | 30.406 | 1.00 | 36.22 | C  |
| ATOM | 534 | CG  | LEU | A | 81 | 12.774 | 9.568  | 29.121 | 1.00 | 36.35 | C  |
| ATOM | 535 | CD1 | LEU | A | 81 | 12.880 | 11.055 | 29.274 | 1.00 | 36.49 | C  |
| ATOM | 536 | CD2 | LEU | A | 81 | 14.132 | 9.017  | 28.718 | 1.00 | 36.18 | C  |
| ATOM | 537 | N   | GLN | A | 82 | 10.569 | 6.956  | 32.280 | 1.00 | 36.15 | N  |

TABLE 3-continued

Coordinates for structures 1 to 4

| ATOM | 538 | CA  | GLN | A | 82 | 10.284 | 6.424  | 33.597 | 1.00 | 36.29 | C |
|------|-----|-----|-----|---|----|--------|--------|--------|------|-------|---|
| ATOM | 539 | C   | GLN | A | 82 | 10.575 | 4.927  | 33.605 | 1.00 | 36.25 | C |
| ATOM | 540 | O   | GLN | A | 82 | 11.210 | 4.408  | 34.515 | 1.00 | 35.96 | O |
| ATOM | 541 | CB  | GLN | A | 82 | 8.838  | 6.710  | 33.976 | 1.00 | 36.38 | C |
| ATOM | 542 | CG  | GLN | A | 82 | 8.418  | 6.080  | 35.279 | 1.00 | 37.00 | C |
| ATOM | 543 | CD  | GLN | A | 82 | 7.191  | 6.740  | 35.872 | 1.00 | 37.85 | C |
| ATOM | 544 | OE1 | GLN | A | 82 | 6.640  | 7.676  | 35.295 | 1.00 | 38.24 | O |
| ATOM | 545 | NE2 | GLN | A | 82 | 6.754  | 6.247  | 37.020 | 1.00 | 38.93 | N |
| ATOM | 546 | N   | GLU | A | 83 | 10.136 | 4.240  | 32.560 | 1.00 | 36.46 | N |
| ATOM | 547 | CA  | GLU | A | 83 | 10.366 | 2.807  | 32.451 | 1.00 | 36.59 | C |
| ATOM | 548 | C   | GLU | A | 83 | 11.843 | 2.424  | 32.307 | 1.00 | 36.50 | C |
| ATOM | 549 | O   | GLU | A | 83 | 12.228 | 1.321  | 32.677 | 1.00 | 36.55 | O |
| ATOM | 550 | CB  | GLU | A | 83 | 9.568  | 2.237  | 31.271 | 1.00 | 36.57 | C |
| ATOM | 551 | CG  | GLU | A | 83 | 9.497  | 0.714  | 31.239 | 1.00 | 36.95 | C |
| ATOM | 552 | CD  | GLU | A | 83 | 8.732  | 0.107  | 32.416 | 1.00 | 37.61 | C |
| ATOM | 553 | OE1 | LEU | A | 83 | 7.922  | 0.815  | 33.050 | 1.00 | 37.88 | O |
| ATOM | 554 | OE2 | GLU | A | 83 | 8.938  | 1.090  | 32.719 | 1.00 | 37.54 | O |
| ATOM | 555 | N   | ASN | A | 84 | 12.680 | 3.324  | 31.805 | 1.00 | 36.58 | N |
| ATOM | 556 | CA  | ASN | A | 84 | 14.049 | 2.936  | 31.476 | 1.00 | 36.62 | C |
| ATOM | 557 | C   | ASN | A | 84 | 15.210 | 3.749  | 32.001 | 1.00 | 36.66 | C |
| ATOM | 558 | O   | ASN | A | 84 | 16.349 | 3.310  | 31.900 | 1.00 | 36.62 | O |
| ATOM | 559 | CB  | ASN | A | 84 | 14.211 | 2.936  | 29.960 | 1.00 | 36.62 | C |
| ATOM | 560 | CG  | ASN | A | 84 | 13.362 | 1.902  | 29.286 | 1.00 | 36.37 | C |
| ATOM | 561 | OD1 | ASN | A | 84 | 13.352 | 0.733  | 29.683 | 1.00 | 36.46 | O |
| ATOM | 562 | ND2 | ASN | A | 84 | 12.644 | 2.317  | 28.247 | 1.00 | 35.65 | N |
| ATOM | 563 | N   | ILE | A | 85 | 14.975 | 4.920  | 32.557 | 1.00 | 36.80 | N |
| ATOM | 564 | CA  | ILE | A | 85 | 16.125 | 5.730  | 32.885 | 1.00 | 37.13 | C |
| ATOM | 565 | C   | ILE | A | 85 | 16.834 | 5.365  | 34.180 | 1.00 | 37.28 | C |
| ATOM | 566 | O   | ILE | A | 85 | 17.793 | 6.022  | 34.568 | 1.00 | 37.74 | O |
| ATOM | 567 | CE  | ILE | A | 85 | 15.752 | 7.184  | 32.874 | 1.00 | 37.21 | C |
| ATOM | 568 | CG1 | ILE | A | 85 | 16.958 | 8.009  | 32.445 | 1.00 | 37.55 | C |
| ATOM | 569 | CG2 | ILE | A | 85 | 15.241 | 7.593  | 34.222 | 1.00 | 37.38 | C |
| ATOM | 570 | CD1 | ILE | A | 85 | 16.623 | 9.467  | 32.195 | 1.00 | 37.68 | C |
| ATOM | 571 | N   | GLY | A | 86 | 16.383 | 4.326  | 34.855 | 1.00 | 37.29 | N |
| ATOM | 572 | CA  | GLY | A | 86 | 17.089 | 3.892  | 36.038 | 1.00 | 37.39 | C |
| ATOM | 573 | C   | GLY | A | 86 | 16.553 | 4.496  | 37.308 | 1.00 | 37.43 | C |
| ATOM | 574 | O   | GLY | A | 86 | 15.583 | 5.265  | 37.290 | 1.00 | 37.34 | O |
| ATOM | 575 | N   | ASN | A | 87 | 17.212 | 4.167  | 38.414 | 1.00 | 37.34 | N |
| ATOM | 576 | CA  | ASN | A | 87 | 16.750 | 4.602  | 39.716 | 1.00 | 37.42 | C |
| ATOM | 577 | C   | ASN | A | 87 | 17.701 | 5.603  | 40.357 | 1.00 | 37.39 | C |
| ATOM | 578 | O   | ASN | A | 87 | 17.740 | 5.742  | 41.578 | 1.00 | 37.39 | O |
| ATOM | 579 | CE  | ASN | A | 87 | 16.545 | 3.399  | 40.612 | 1.00 | 37.40 | C |
| ATOM | 580 | N   | GLY | A | 88 | 18.451 | 6.321  | 39.529 | 1.00 | 37.47 | N |
| ATOM | 581 | CA  | GLY | A | 88 | 19.405 | 7.296  | 40.028 | 1.00 | 37.41 | C |
| ATOM | 582 | C   | GLY | A | 88 | 18.686 | 8.554  | 40.450 | 1.00 | 37.30 | C |
| ATOM | 583 | O   | GLY | A | 88 | 17.500 | 8.709  | 40.171 | 1.00 | 37.36 | O |
| ATOM | 584 | N   | ASP | A | 89 | 19.390 | 9.453  | 41.125 | 1.00 | 37.26 | N |
| ATOM | 585 | CA  | ASP | A | 89 | 18.780 | 10.716 | 41.531 | 1.00 | 37.21 | C |
| ATOM | 586 | C   | ASP | A | 89 | 18.726 | 11.681 | 40.355 | 1.00 | 36.91 | C |
| ATOM | 587 | O   | ASP | A | 89 | 19.607 | 11.654 | 39.500 | 1.00 | 36.62 | O |
| ATOM | 588 | CE  | ASP | A | 89 | 19.563 | 11.346 | 42.680 | 1.00 | 37.24 | C |
| ATOM | 589 | CG  | ASP | A | 89 | 19.277 | 10.690 | 44.000 | 1.00 | 37.24 | C |
| ATOM | 590 | OD1 | ASP | A | 89 | 18.398 | 9.802  | 44.044 | 1.00 | 37.14 | O |
| ATOM | 591 | OD2 | ASP | A | 89 | 19.876 | 11.002 | 45.047 | 1.00 | 37.98 | O |
| ATOM | 592 | N   | PHE | A | 90 | 17.667 | 12.492 | 40.295 | 1.00 | 36.88 | N |
| ATOM | 593 | CA  | PHE | A | 90 | 17.554 | 13.570 | 39.298 | 1.00 | 36.87 | C |
| ATOM | 594 | C   | PHE | A | 90 | 17.327 | 14.926 | 39.942 | 1.00 | 36.79 | C |
| ATOM | 595 | O   | PHE | A | 90 | 16.455 | 15.080 | 40.795 | 1.00 | 36.69 | O |
| ATOM | 596 | CE  | PHE | A | 90 | 16.420 | 13.308 | 38.321 | 1.00 | 36.70 | C |
| ATOM | 597 | CG  | PHE | A | 90 | 16.712 | 12.210 | 37.371 | 1.00 | 36.83 | C |
| ATOM | 598 | CD1 | PHE | A | 90 | 16.551 | 10.901 | 37.757 | 1.00 | 36.07 | C |
| ATOM | 599 | CD2 | PHE | A | 90 | 17.191 | 12.479 | 36.102 | 1.00 | 37.27 | C |
| ATOM | 600 | CE1 | PHE | A | 90 | 16.827 | 9.885  | 36.899 | 1.00 | 35.81 | C |
| ATOM | 601 | CE2 | PHE | A | 90 | 17.475 | 11.449 | 35.238 | 1.00 | 36.82 | C |
| ATOM | 602 | CZ  | PHE | A | 90 | 17.291 | 10.150 | 35.642 | 1.00 | 36.06 | C |
| ATOM | 603 | N   | SER | A | 91 | 18.123 | 15.905 | 39.529 | 1.00 | 36.92 | N |
| ATOM | 604 | CA  | SER | A | 91 | 17.971 | 17.266 | 40.027 | 1.00 | 36.99 | C |
| ATOM | 605 | C   | SER | A | 91 | 16.738 | 17.923 | 39.428 | 1.00 | 37.10 | C |
| ATOM | 606 | O   | SER | A | 91 | 16.586 | 17.985 | 38.206 | 1.00 | 36.78 | O |
| ATOM | 607 | CE  | SER | A | 91 | 19.200 | 18.105 | 39.699 | 1.00 | 36.86 | C |
| ATOM | 608 | OG  | SER | A | 91 | 20.350 | 17.616 | 40.358 | 1.00 | 36.54 | O |
| ATOM | 609 | N   | VAL | A | 92 | 15.857 | 18.402 | 40.303 | 1.00 | 37.42 | N |
| ATOM | 610 | CA  | VAL | A | 92 | 14.660 | 19.106 | 39.876 | 1.00 | 37.75 | C |
| ATOM | 611 | C   | VAL | A | 92 | 14.509 | 20.468 | 40.545 | 1.00 | 38.10 | C |
| ATOM | 612 | O   | VAL | A | 92 | 14.472 | 20.589 | 41.768 | 1.00 | 38.08 | O |
| ATOM | 613 | CB  | VAL | A | 92 | 13.406 | 18.303 | 40.159 | 1.00 | 37.63 | C |
| ATOM | 614 | CG1 | VAL | A | 92 | 12.197 | 19.034 | 39.621 | 1.00 | 37.42 | C |

TABLE 3-continued

Coordinates for structures 1 to 4

| ATOM | 615 | CG2 | VAL | A | 92 | 13.515 | 16.946 | 39.527 | 1.00 | 37.78 | C |
|---|---|---|---|---|---|---|---|---|---|---|---|
| ATOM | 616 | N | TYR | A | 93 | 14.384 | 21.487 | 39.709 | 1.00 | 38.59 | N |
| ATOM | 617 | CA | TYR | A | 93 | 14.220 | 22.849 | 40.166 | 1.00 | 38.91 | C |
| ATOM | 618 | C | TYR | A | 93 | 12.784 | 23.173 | 40.219 | 1.00 | 39.41 | C |
| ATOM | 619 | O | TYR | A | 93 | 12.019 | 22.786 | 39.343 | 1.00 | 39.64 | O |
| ATOM | 620 | CE | TYR | A | 93 | 14.883 | 23.799 | 39.202 | 1.00 | 38.84 | C |
| ATOM | 621 | CG | TYR | A | 93 | 16.332 | 23.588 | 39.288 | 1.00 | 38.25 | C |
| ATOM | 622 | CD1 | TYR | A | 93 | 17.044 | 24.122 | 40.334 | 1.00 | 38.21 | C |
| ATOM | 623 | CD2 | TYR | A | 93 | 16.968 | 22.750 | 38.415 | 1.00 | 37.50 | C |
| ATOM | 624 | CE1 | TYR | A | 93 | 18.362 | 23.893 | 40.464 | 1.00 | 37.90 | C |
| ATOM | 625 | CE2 | TYR | A | 93 | 18.287 | 22.512 | 38.534 | 1.00 | 37.82 | C |
| ATOM | 626 | CZ | TYR | A | 93 | 18.987 | 23.090 | 39.557 | 1.00 | 37.78 | C |
| ATOM | 627 | OH | TYR | A | 93 | 20.322 | 22.836 | 39.677 | 1.00 | 39.39 | O |
| ATOM | 6~8 | N | SER | A | 94 | 12.422 | 23.935 | 41.228 | 1.00 | 40.00 | N |
| ATOM | 629 | CA | SER | A | 94 | 11.043 | 24.274 | 41.416 | 1.00 | 40.51 | C |
| ATOM | 630 | C | SER | A | 94 | 11.020 | 25.773 | 41.426 | 1.00 | 40.68 | C |
| ATOM | 631 | O | SER | A | 94 | 11.962 | 26.384 | 41.896 | 1.00 | 41.00 | O |
| ATOM | 632 | CB | SER | A | 94 | 10.539 | 23.693 | 42.730 | 1.00 | 40.58 | C |
| ATOM | 633 | OG | SER | A | 94 | 9.139 | 23.874 | 42.858 | 1.00 | 41.30 | O |
| ATOM | 634 | N | ALA | A | 95 | 9.974 | 26.374 | 40.878 | 1.00 | 40.87 | N |
| ATOM | 635 | CA | ALA | A | 95 | 9.899 | 27.824 | 40.856 | 1.00 | 40.91 | C |
| ATOM | 636 | C | ALA | A | 95 | 8.483 | 28.343 | 40.826 | 1.00 | 41.03 | C |
| ATOM | 637 | O | ALA | A | 95 | 7.573 | 27.699 | 40.309 | 1.00 | 41.09 | O |
| ATOM | 638 | CB | ALA | A | 95 | 10.630 | 28.350 | 39.668 | 1.00 | 40.93 | C |
| ATOM | 639 | N | SER | A | 96 | 8.328 | 29.549 | 41.350 | 1.00 | 41.12 | N |
| ATOM | 640 | CA | SER | A | 96 | 7.034 | 30.200 | 41.413 | 1.00 | 41.05 | C |
| ATOM | 641 | C | SER | A | 96 | 6.834 | 31.208 | 40.305 | 1.00 | 40.72 | C |
| ATOM | 642 | O | SER | A | 96 | 5.833 | 31.912 | 40.277 | 1.00 | 40.86 | O |
| ATOM | 643 | CB | SER | A | 96 | 6.902 | 30.938 | 42.731 | 1.00 | 41.16 | C |
| ATOM | 644 | OG | SER | A | 96 | 5.767 | 31.779 | 42.693 | 1.00 | 41.90 | O |
| ATOM | 645 | N | THR | A | 97 | 7.808 | 31.314 | 39.423 | 1.00 | 40.34 | N |
| ATOM | .646 | CA | THR | A | 97 | 7.710 | 32.209 | 38.292 | 1.00 | 40.18 | C |
| ATOM | 647 | C | THR | A | 97 | 8.073 | 31.368 | 37.113 | 1.00 | 39.72 | C |
| ATOM | 648 | O | THR | A | 97 | 8.582 | 30.274 | 37.279 | 1.00 | 39.83 | O |
| ATOM | 649 | CB | THR | A | 97 | 8.732 | 33.336 | 38.393 | 1.00 | 40.49 | C |
| ATOM | 650 | OG1 | THR | A | 97 | 8.905 | 33.946 | 37.105 | 1.00 | 41.00 | O |
| ATOM | 651 | CG2 | THR | A | 97 | 10.145 | 32.779 | 38.718 | 1.00 | 40.86 | C |
| ATOM | 652 | N | HIS | A | 98 | 7.862 | 31.874 | 35.915 | 1.00 | 39.32 | N |
| ATOM | 653 | CA | HIS | A | 98 | 8.257 | 31.112 | 34.754 | 1.00 | 39.12 | C |
| ATOM | 654 | C | HIS | A | 98 | 9.765 | 31.163 | 34.543 | 1.00 | 39.41 | C |
| ATOM | 655 | O | HIS | A | 98 | 10.299 | 30.423 | 33.711 | 1.00 | 39.15 | O |
| ATOM | 656 | CB | HIS | A | 98 | 7.576 | 31.646 | 33.516 | 1.00 | 38.95 | C |
| ATOM | 657 | CG | HIS | A | 98 | 7.807 | 33.104 | 33.290 | 1.00 | 38.64 | C |
| ATOM | 658 | ND1 | HIS | A | 98 | 7.095 | 34.081 | 33.950 | 1.00 | 37.36 | N |
| ATOM | 659 | CD2 | HIS | A | 98 | 8.672 | 33.753 | 32.477 | 1.00 | 38.57 | C |
| ATOM | 660 | CE1 | HIS | A | 98 | 7.509 | 35.268 | 33.550 | 1.00 | 37.33 | C |
| ATOM | 661 | ND2 | HIS | A | 98 | 8.463 | 35.098 | 32.654 | 1.00 | 37.37 | N |
| ATOM | 662 | N | LYS | A | 99 | 10.452 | 32.021 | 35.294 | 1.00 | 39.52 | N |
| ATOM | 663 | CA | LYS | A | 99 | 11.881 | 32.184 | 35.105 | 1.00 | 39.98 | C |
| ATOM | 664 | C | LYS | A | 99 | 12.749 | 31.364 | 36.029 | 1.00 | 40.38 | C |
| ATOM | 665 | O | LYS | A | 99 | 12.744 | 31.554 | 37.246 | 1.00 | 40.33 | O |
| ATOM | 666 | CB | LYS | A | 99 | 12.281 | 33.631 | 35.297 | 1.00 | 40.10 | C |
| ATOM | 667 | CG | LYS | A | 99 | 11.814 | 34.527 | 34.219 | 1.00 | 40.15 | C |
| ATOM | 668 | CD | LYS | A | 99 | 12.537 | 35.820 | 34.337 | 1.00 | 40.36 | C |
| ATOM | 669 | CE | LYS | A | 99 | 11.725 | 36.835 | 35.072 | 1.00 | 41.10 | C |
| ATOM | 670 | NZ | LYS | A | 99 | 10.975 | 37.655 | 34.074 | 1.00 | 41.52 | N |
| ATOM | 671 | N | PHE | A | 100 | 13.541 | 30.486 | 35.433 | 1.00 | 40.77 | N |
| ATOM | 672 | CA | PHE | A | 100 | 14.450 | 29.665 | 36.201 | 1.00 | 41.12 | C |
| ATOM | 673 | C | PHE | A | 100 | 15.893 | 30.159 | 36.218 | 1.00 | 41.78 | C |
| ATOM | 674 | O | PHE | A | 100 | 16.808 | 29.463 | 35.765 | 1.00 | 42.13 | O |
| ATOM | 675 | CB | PHE | A | 100 | 14.418 | 28.255 | 35.658 | 1.00 | 40.86 | C |
| ATOM | 676 | CG | PHE | A | 100 | 13.211 | 27.494 | 36.060 | 1.00 | 40.53 | C |
| ATOM | 677 | CD1 | PHE | A | 100 | 12.040 | 27.604 | 35.344 | 1.00 | 39.76 | C |
| ATOM | 678 | CD2 | PHE | A | 100 | 13.249 | 26.666 | 37.159 | 1.00 | 39.54 | C |
| ATOM | 679 | CE1 | PHE | A | 100 | 10.942 | 26.890 | 35.707 | 1.00 | 39.56 | C |
| ATOM | 680 | CE2 | PHE | A | 100 | 12.155 | 25.955 | 37.526 | 1.00 | 39.79 | C |
| ATOM | 681 | CZ | PHE | A | 100 | 10.995 | 26.064 | 36.802 | 1.00 | 39.91 | C |
| ATOM | 682 | N | LEU | A | 101 | 16.124 | 31.347 | 36.747 | 1.00 | 42.23 | N |
| ATOM | 683 | CA | LEU | A | 101 | 17.501 | 31.800 | 36.868 | 1.00 | 42.74 | C |
| ATOM | 684 | C | LEU | A | 101 | 18.429 | 30.780 | 37.567 | 1.00 | 43.27 | C |
| ATOM | 685 | O | LEU | A | 101 | 18.213 | 30.392 | 38.736 | 1.00 | 43.22 | O |
| ATOM | 686 | CB | LEU | A | 101 | 17.549 | 33.097 | 37.657 | 1.00 | 42.90 | C |
| ATOM | 687 | CG | LEU | A | 101 | 18.900 | 33.800 | 37.793 | 1.00 | 43.35 | C |
| ATOM | 688 | CE1 | LEU | A | 101 | 19.441 | 34.288 | 36.455 | 1.00 | 43.59 | C |
| ATOM | 689 | CD2 | LEU | A | 101 | 18.703 | 34.967 | 38.724 | 1.00 | 43.91 | C |
| ATOM | 690 | N | TYR | A | 102 | 19.470 | 30.379 | 36.836 | 1.00 | 43.59 | N |
| ATOM | 691 | CA | TYR | A | 102 | 20.547 | 29.522 | 37.340 | 1.00 | 43.71 | C |

TABLE 3-continued

Coordinates for structures 1 to 4

| ATOM | 692 | C | TYR | A | 102 | 21.380 | 30.186 | 38.460 | 1.00 | 43.57 | C |
| ATOM | 693 | O | TYR | A | 102 | 21.746 | 31.364 | 38.343 | 1.00 | 44.09 | O |
| ATOM | 694 | CB | TYR | A | 102 | 21.531 | 29.218 | 36.193 | 1.00 | 43.90 | C |
| ATOM | 695 | CG | TYR | A | 102 | 22.703 | 28.421 | 36.700 | 1.00 | 44.68 | C |
| ATOM | 696 | CD1 | TYR | A | 102 | 22.553 | 27.080 | 37.033 | 1.00 | 44.29 | C |
| ATOM | 697 | CD2 | TYR | A | 102 | 23.935 | 29.023 | 36.918 | 1.00 | 44.88 | C |
| ATOM | 698 | CE1 | TYR | A | 102 | 23.602 | 26.358 | 37.541 | 1.00 | 44.98 | C |
| ATOM | 699 | CE2 | TYR | A | 102 | 24.987 | 28.309 | 37.422 | 1.00 | 45.44 | C |
| ATOM | 700 | CZ | TYR | A | 102 | 24.826 | 26.984 | 37.735 | 1.00 | 45.86 | C |
| ATOM | 701 | OH | TYR | A | 102 | 25.922 | 26.313 | 38.237 | 1.00 | 47.07 | O |
| ATOM | 702 | N | TYR | A | 103 | 21.704 | 29.451 | 39.523 | 1.00 | 42.91 | N |
| ATOM | 703 | CA | TYR | A | 103 | 22.642 | 29.970 | 40.527 | 1.00 | 42.67 | C |
| ATOM | 704 | C | TYR | A | 103 | 23.561 | 28.895 | 41.102 | 1.00 | 41.98 | C |
| ATOM | 705 | O | TYR | A | 103 | 23.165 | 27.768 | 41.351 | 1.00 | 41.99 | O |
| ATOM | 706 | CB | TYR | A | 103 | 21.922 | 30.638 | 41.670 | 1.00 | 42.83 | C |
| ATOM | 707 | CG | TYR | A | 103 | 20.974 | 29.692 | 42.265 | 1.00 | 44.33 | C |
| ATOM | 708 | CD1 | TYR | A | 103 | 19.770 | 29.454 | 41.646 | 1.00 | 46.69 | C |
| ATOM | 709 | CD2 | TYR | A | 103 | 21.306 | 28.959 | 43.390 | 1.00 | 45.99 | C |
| ATOM | 710 | CE1 | TYR | A | 103 | 18.880 | 28.539 | 42.147 | 1.00 | 47.83 | C |
| ATOM | 711 | CE2 | TYR | A | 103 | 20.426 | 28.045 | 43.917 | 1.00 | 47.23 | C |
| ATOM | 712 | CZ | TYR | A | 103 | 19.203 | 27.836 | 43.284 | 1.00 | 48.65 | C |
| ATOM | 713 | OH | TYR | A | 103 | 18.287 | 26.921 | 43.774 | 1.00 | 51.36 | O |
| ATOM | 714 | N | ASP | A | 104 | 24.786 | 29.300 | 41.369 | 1.00 | 41.25 | N |
| ATOM | 715 | CA | ASP | A | 104 | 25.829 | 28.399 | 41.764 | 1.00 | 40.65 | C |
| ATOM | 716 | C | ASP | A | 104 | 25.924 | 28.335 | 43.267 | 1.00 | 40.45 | C |
| ATOM | 717 | O | ASP | A | 104 | 26.430 | 29.240 | 43.924 | 1.00 | 40.13 | O |
| ATOM | 718 | CB | ASP | A | 104 | 27.110 | 28.904 | 41.142 | 1.00 | 40.60 | C |
| ATOM | 719 | CG | ASP | A | 104 | 28.306 | 28.117 | 41.548 | 1.00 | 41.02 | C |
| ATOM | 720 | OD1 | ASP | A | 104 | 28.270 | 27.482 | 42.629 | 1.00 | 42.21 | O |
| ATOM | 721 | OD2 | ASP | A | 104 | 29.337 | 28.095 | 40.838 | 1.00 | 40.68 | O |
| ATOM | 722 | N | GLU | A | 105 | 25.446 | 27.222 | 43.801 | 1.00 | 40.41 | N |
| ATOM | 723 | CA | GLU | A | 105 | 25.368 | 27.029 | 45.231 | 1.00 | 40.21 | C |
| ATOM | 724 | C | GLU | A | 105 | 26.734 | 27.234 | 45.895 | 1.00 | 39.89 | C |
| ATOM | 725 | O | GLU | A | 105 | 26.803 | 27.738 | 47.021 | 1.00 | 39.65 | O |
| ATOM | 726 | CB | GLU | A | 105 | 24.769 | 25.643 | 45.528 | 1.00 | 40.44 | C |
| ATOM | 727 | CG | GLU | A | 105 | 23.247 | 25.572 | 45.351 | 1.00 | 41.43 | C |
| ATOM | 728 | CD | GLU | A | 105 | 22.708 | 24.150 | 45.207 | 1.00 | 42.48 | C |
| ATOM | 729 | OE1 | GLU | A | 105 | 23.138 | 23.269 | 45.986 | 1.00 | 43.10 | O |
| ATOM | 730 | OE2 | GLU | A | 105 | 21.842 | 23.914 | 44.322 | 1.00 | 42.00 | O |
| ATOM | 731 | N | LYS | A | 106 | 27.824 | 26.899 | 45.204 | 1.00 | 39.58 | N |
| ATOM | 732 | CA | LYS | A | 106 | 29.141 | 27.042 | 45.831 | 1.00 | 39.58 | C |
| ATOM | 733 | C | LYS | A | 106 | 29.427 | 28.469 | 46.190 | 1.00 | 39.64 | C |
| ATOM | 734 | O | LYS | A | 106 | 30.165 | 28.730 | 47.128 | 1.00 | 39.93 | O |
| ATOM | 735 | CB | LYS | A | 106 | 30.302 | 26.592 | 44.945 | 1.00 | 39.49 | C |
| ATOM | 736 | CG | LYS | A | 106 | 30.444 | 25.096 | 44.731 | 1.00 | 39.29 | C |
| ATOM | 737 | N | LYS | A | 107 | 28.856 | 29.397 | 45.438 | 1.00 | 39.68 | N |
| ATOM | 738 | CA | LYS | A | 107 | 29.140 | 30.794 | 45.663 | 1.00 | 39.58 | C |
| ATOM | 739 | C | LYS | A | 107 | 28.151 | 31.452 | 46.607 | 1.00 | 40.18 | C |
| ATOM | 740 | O | LYS | A | 107 | 28.279 | 32.637 | 46.883 | 1.00 | 40.30 | O |
| ATOM | 741 | CB | LYS | A | 107 | 29.161 | 31.531 | 44.325 | 1.00 | 39.46 | C |
| ATOM | 742 | CG | LYS | A | 107 | 30.390 | 31.199 | 43.455 | 1.00 | 38.46 | C |
| ATOM | 743 | CD | LYS | A | 107 | 30.299 | 31.737 | 42.029 | 1.00 | 36.98 | C |
| ATOM | 744 | CE | LYS | A | 107 | 31.643 | 31.632 | 41.292 | 1.00 | 36.36 | C |
| ATOM | 745 | NZ | LYS | A | 107 | 31.553 | 31.935 | 39.819 | 1.00 | 35.12 | N |
| ATOM | 746 | N | MET | A | 108 | 27.197 | 30.697 | 47.148 | 1.00 | 40.92 | N |
| ATOM | 747 | CA | MET | A | 108 | 26.165 | 31.316 | 47.978 | 1.00 | 41.42 | C |
| ATOM | 748 | C | MET | A | 108 | 26.675 | 31.937 | 49.258 | 1.00 | 42.03 | C |
| ATOM | 749 | O | MET | A | 108 | 26.142 | 32.952 | 49.704 | 1.00 | 42.33 | O |
| ATOM | 750 | CB | MET | A | 108 | 25.006 | 30.366 | 48.210 | 1.00 | 41.31 | C |
| ATOM | 751 | CG | MET | A | 108 | 24.285 | 30.179 | 46.892 | 1.00 | 41.95 | C |
| ATOM | 752 | SD | MET | A | 108 | 22.861 | 29.100 | 46.846 | 1.00 | 43.29 | S |
| ATOM | 753 | CE | MET | A | 108 | 21.737 | 30.010 | 48.064 | 1.00 | 43.04 | C |
| ATOM | 754 | N | ALA | A | 109 | 27.737 | 31.382 | 49.816 | 1.00 | 42.84 | N |
| ATOM | 755 | CA | ALA | A | 109 | 28.282 | 31.912 | 51.064 | 1.00 | 43.65 | C |
| ATOM | 756 | C | ALA | A | 109 | 28.655 | 33.387 | 50.963 | 1.00 | 44.40 | C |
| ATOM | 757 | O | ALA | A | 109 | 28.321 | 34.195 | 51.823 | 1.00 | 44.44 | O |
| ATOM | 758 | CB | ALA | A | 109 | 29.486 | 31.107 | 51.476 | 1.00 | 43.66 | C |
| ATOM | 759 | N | ASN | A | 110 | 29.332 | 33.729 | 49.882 | 1.00 | 45.46 | N |
| ATOM | 760 | CA | ASN | A | 110 | 29.817 | 35.084 | 49.665 | 1.00 | 46.25 | C |
| ATOM | 761 | C | ASN | A | 110 | 28.789 | 36.154 | 49.317 | 1.00 | 46.26 | C |
| ATOM | 762 | O | ASN | A | 110 | 29.163 | 37.304 | 49.066 | 1.00 | 46.51 | O |
| ATOM | 763 | CB | ASN | A | 110 | 30.841 | 35.036 | 48.543 | 1.00 | 46.62 | C |
| ATOM | 764 | CG | ASN | A | 110 | 32.024 | 34.145 | 48.886 | 1.00 | 47.94 | C |
| ATOM | 765 | OD1 | ASN | A | 110 | 32.474 | 34.093 | 50.045 | 1.00 | 48.12 | O |
| ATOM | 766 | ND2 | ASN | A | 110 | 32.530 | 33.432 | 47.883 | 1.00 | 48.75 | N |
| ATOM | 767 | N | PHE | A | 111 | 27.517 | 35.786 | 49.228 | 1.00 | 46.12 | N |
| ATOM | 768 | CA | PHE | A | 111 | 26.470 | 36.795 | 49.057 | 1.00 | 45.97 | C |

TABLE 3-continued

Coordinates for structures 1 to 4

| ATOM | 769 | C | PHE | A | 111 | 25.267 | 36.385 | 49.889 | 1.00 | 46.17 | C |
|---|---|---|---|---|---|---|---|---|---|---|---|
| ATOM | 770 | O | PHE | A | 111 | 24.217 | 36.002 | 49.361 | 1.00 | 46.25 | O |
| ATOM | 771 | CB | PHE | A | 111 | 26.072 | 36.978 | 47.599 | 1.00 | 45.55 | C |
| ATOM | 772 | CG | PHE | A | 111 | 27.076 | 37.718 | 46.777 | 1.00 | 44.32 | C |
| ATOM | 773 | CD1 | PHE | A | 111 | 28.269 | 37.123 | 46.419 | 1.00 | 43.65 | C |
| ATOM | 774 | CD2 | PHE | A | 111 | 26.808 | 39.000 | 46.320 | 1.00 | 44.04 | C |
| ATOM | 775 | CE1 | PHE | A | 111 | 29.187 | 37.794 | 45.620 | 1.00 | 43.19 | C |
| ATOM | 776 | CE2 | PHE | A | 111 | 27.715 | 39.673 | 45.522 | 1.00 | 43.22 | C |
| ATOM | 777 | CZ | PHE | A | 111 | 28.911 | 39.068 | 45.177 | 1.00 | 43.00 | C |
| ATOM | 778 | N | GLN | A | 112 | 25.434 | 36.479 | 51.200 | 1.00 | 46.35 | N |
| ATOM | 779 | CA | GLN | A | 112 | 24.401 | 36.052 | 52.130 | 1.00 | 46.52 | C |
| ATOM | 780 | C | GLN | A | 112 | 23.040 | 36.638 | 51.754 | 1.00 | 46.68 | C |
| ATOM | 781 | O | GLN | A | 112 | 22.019 | 35.995 | 51.968 | 1.00 | 46.87 | O |
| ATOM | 782 | CB | GLN | A | 112 | 24.774 | 36.438 | 53.567 | 1.00 | 46.62 | C |
| ATOM | 783 | CG | GLN | A | 112 | 26.201 | 36.060 | 53.998 | 1.00 | 46.96 | C |
| ATOM | 784 | CD | GLN | A | 112 | 26.418 | 34.554 | 54.125 | 1.00 | 48.05 | C |
| ATOM | 785 | OE1 | GLN | A | 112 | 25.834 | 33.762 | 53.372 | 1.00 | 47.89 | O |
| ATOM | 786 | NE2 | GLN | A | 112 | 27.271 | 34.158 | 55.075 | 1.00 | 48.55 | N |
| ATOM | 787 | N | ASN | A | 113 | 23.019 | 37.836 | 51.168 | 1.00 | 46.80 | N |
| ATOM | 788 | CA | ASN | A | 113 | 21.750 | 38.463 | 50.793 | 1.00 | 46.89 | C |
| ATOM | 789 | C | ASN | A | 113 | 21.104 | 37.951 | 49.517 | 1.00 | 47.08 | C |
| ATOM | 790 | O | ASN | A | 113 | 20.105 | 38.521 | 49.077 | 1.00 | 47.55 | O |
| ATOM | 791 | CB | ASN | A | 113 | 21.898 | 39.976 | 50.682 | 1.00 | 46.69 | C |
| ATOM | 792 | CG | ASN | A | 113 | 22.258 | 40.604 | 52.001 | 1.00 | 46.91 | C |
| ATOM | 793 | OD1 | ASN | A | 113 | 22.085 | 39.982 | 53.055 | 1.00 | 46.08 | O |
| ATOM | 794 | ND2 | ASN | A | 113 | 22.767 | 41.837 | 51.962 | 1.00 | 46.59 | N |
| ATOM | 795 | N | PHE | A | 114 | 21.651 | 36.908 | 48.903 | 1.00 | 47.08 | N |
| ATOM | 796 | CA | PHE | A | 114 | 21.012 | 36.379 | 47.706 | 1.00 | 47.01 | C |
| ATOM | 797 | C | PHE | A | 114 | 19.986 | 35.364 | 48.145 | 1.00 | 47.11 | C |
| ATOM | 798 | O | PHE | A | 114 | 20.293 | 34.449 | 48.916 | 1.00 | 47.34 | O |
| ATOM | 799 | CB | PHE | A | 114 | 21.995 | 35.713 | 46.764 | 1.00 | 46.83 | C |
| ATOM | 800 | CG | PHE | A | 114 | 21.342 | 35.132 | 45.555 | 1.00 | 47.03 | C |
| ATOM | 801 | CO1 | PHE | A | 114 | 20.674 | 35.953 | 44.655 | 1.00 | 47.22 | C |
| ATOM | 802 | CD2 | PHE | A | 114 | 21.376 | 33.761 | 45.318 | 1.00 | 47.97 | C |
| ATOM | 803 | CE1 | PHE | A | 114 | 20.060 | 35.422 | 43.522 | 1.00 | 47.53 | C |
| ATOM | 804 | CE2 | PHE | A | 114 | 20.763 | 33.212 | 44.177 | 1.00 | 47.83 | C |
| ATOM | 805 | CZ | PHE | A | 114 | 20.104 | 34.044 | 43.282 | 1.00 | 47.67 | C |
| ATOM | 806 | N | LYS | A | 115 | 18.763 | 35.530 | 47.662 | 1.00 | 46.94 | N |
| ATOM | 807 | CA | LYS | A | 115 | 17.683 | 34.628 | 48.029 | 1.00 | 46.64 | C |
| ATOM | 808 | C | LYS | A | 115 | 17.109 | 34.063 | 46.744 | 1.00 | 46.38 | C |
| ATOM | 809 | O | LYS | A | 115 | 16.351 | 34.744 | 46.046 | 1.00 | 46.75 | O |
| ATOM | 810 | CB | LYS | A | 115 | 16.613 | 35.372 | 48.835 | 1.00 | 46.60 | C |
| ATOM | 811 | N | PRO | A | 116 | 17.445 | 32.813 | 46.449 | 1.00 | 45.84 | N |
| ATOM | 812 | CA | PRO | A | 116 | 17.079 | 32.192 | 45.165 | 1.00 | 45.70 | C |
| ATOM | 813 | C | PRO | A | 116 | 15.576 | 32.139 | 44.937 | 1.00 | 45.44 | C |
| ATOM | 814 | O | PRO | A | 116 | 14.827 | 31.956 | 45.892 | 1.00 | 45.46 | O |
| ATOM | 815 | CB | PRO | A | 116 | 17.640 | 30.761 | 45.260 | 1.00 | 45.71 | C |
| ATOM | 816 | CG | PRO | A | 116 | 18.435 | 30.689 | 46.536 | 1.00 | 45.66 | C |
| ATOM | 817 | CD | PRO | A | 116 | 18.137 | 31.890 | 47.359 | 1.00 | 45.75 | C |
| ATOM | 818 | N | ARG | A | 117 | 15.154 | 32.307 | 43.688 | 1.00 | 45.27 | N |
| ATOM | 819 | CA | ARG | A | 117 | 13.742 | 32.232 | 43.332 | 1.00 | 45.16 | C |
| ATOM | 820 | C | ARG | A | 117 | 13.291 | 30.791 | 43.104 | 1.00 | 45.12 | C |
| ATOM | 821 | O | ARG | A | 117 | 12.096 | 30.500 | 43.207 | 1.00 | 45.48 | O |
| ATOM | 822 | CB | ARG | A | 117 | 13.467 | 33.059 | 42.097 | 1.00 | 45.26 | C |
| ATOM | 823 | N | SER | A | 118 | 14.238 | 29.902 | 42.796 | 1.00 | 44.78 | N |
| ATOM | 824 | CA | SER | A | 118 | 13.944 | 28.480 | 42.594 | 1.00 | 44.60 | C |
| ATOM | 825 | C | SER | A | 118 | 14.782 | 27.583 | 43.509 | 1.00 | 44.63 | C |
| ATOM | 826 | O | SER | A | 118 | 15.925 | 27.921 | 43.816 | 1.00 | 45.32 | O |
| ATOM | 827 | CB | SER | A | 118 | 14.303 | 28.072 | 41.184 | 1.00 | 44.44 | C |
| ATOM | 828 | OG | SER | A | 118 | 15.651 | 27.624 | 41.186 | 1.00 | 44.35 | O |
| ATOM | 829 | N | ASN | A | 119 | 14.241 | 26.428 | 43.899 | 1.00 | 44.11 | N |
| ATOM | 830 | CA | ASN | A | 119 | 14.969 | 25.472 | 44.728 | 1.00 | 43.72 | C |
| ATOM | 831 | C | ASN | A | 119 | 15.295 | 24.196 | 43.953 | 1.00 | 43.16 | C |
| ATOM | 832 | O | ASN | A | 119 | 14.576 | 23.821 | 43.030 | 1.00 | 43.23 | O |
| ATOM | 833 | CB | ASN | A | 119 | 14.147 | 25.078 | 45.955 | 1.00 | 44.03 | C |
| ATOM | 834 | CG | ASN | A | 119 | 13.514 | 26.264 | 46.646 | 1.00 | 44.80 | C |
| ATOM | 835 | OD1 | ASN | A | 119 | 14.207 | 27.129 | 47.197 | 1.00 | 46.56 | O |
| ATOM | 836 | ND2 | ASN | A | 119 | 12.184 | 26.303 | 46.640 | 1.00 | 45.18 | N |
| ATOM | 837 | N | ARG | A | 120 | 16.380 | 23.533 | 44.337 | 1.00 | 42.37 | N |
| ATOM | 838 | CA | ARG | A | 120 | 16.778 | 22.278 | 43.716 | 1.00 | 41.69 | C |
| ATOM | 839 | C | ARG | A | 120 | 16.368 | 21.162 | 44.656 | 1.00 | 41.20 | C |
| ATOM | 840 | O | ARG | A | 120 | 16.577 | 21.267 | 45.859 | 1.00 | 41.46 | O |
| ATOM | 841 | CB | ARG | A | 120 | 18.299 | 22.239 | 43.504 | 1.00 | 41.70 | C |
| ATOM | 842 | CG | ARG | A | 120 | 18.827 | 21.002 | 42.754 | 1.00 | 40.96 | C |
| ATOM | 843 | CD | ARG | A | 120 | 20.351 | 20.897 | 42.683 | 1.00 | 39.92 | C |
| ATOM | 844 | NE | ARG | A | 120 | 21.001 | 21.327 | 43.920 | 1.00 | 39.89 | N |
| ATOM | 845 | CZ | ARG | A | 120 | 21.337 | 20.523 | 44.921 | 1.00 | 39.57 | C |

TABLE 3-continued

| | | | | | | | | | | | |
|---|---|---|---|---|---|---|---|---|---|---|---|
| | | | Coordinates for structures 1 to 4 | | | | | | | | |
| ATOM | 846 | NH1 | ARG | A | 120 | 21.084 | 19.217 | 44.856 | 1.00 | 39.43 | N |
| ATOM | 847 | NH2 | ARG | A | 120 | 21.930 | 21.027 | 45.998 | 1.00 | 39.06 | N |
| ATOM | 848 | N | GLU | A | 121 | 15.769 | 20.109 | 44.115 | 1.00 | 40.44 | N |
| ATOM | 849 | CA | GLU | A | 121 | 15.380 | 18.956 | 44.908 | 1.00 | 39.92 | C |
| ATOM | 850 | C | GLU | A | 121 | 15.840 | 17.702 | 44.161 | 1.00 | 39.36 | C |
| ATOM | 851 | O | GLU | A | 121 | 15.716 | 17.617 | 42.942 | 1.00 | 39.20 | O |
| ATOM | 852 | CB | GLU | A | 121 | 13.866 | 18.950 | 45.170 | 1.00 | 39.97 | C |
| ATOM | 853 | CG | GLU | A | 121 | 13.369 | 17.698 | 45.876 | 1.00 | 40.42 | C |
| ATOM | 854 | CD | GLU | A | 121 | 12.136 | 17.928 | 46.731 | 1.00 | 41.22 | C |
| ATOM | 855 | OE1 | GLU | A | 121 | 12.291 | 18.365 | 47.890 | 1.00 | 41.90 | O |
| ATOM | 856 | OE2 | GLU | A | 121 | 11.016 | 17.645 | 46.259 | 1.00 | 42.21 | O |
| ATOM | 857 | N | GLU | A | 122 | 16.414 | 16.752 | 44.889 | 1.00 | 38.78 | N |
| ATOM | 858 | CA | GLU | A | 122 | 16.879 | 15.519 | 44.285 | 1.00 | 38.34 | C |
| ATOM | 859 | C | GLU | A | 122 | 15.760 | 14.523 | 44.374 | 1.00 | 38.13 | C |
| ATOM | 860 | O | GLU | A | 122 | 15.171 | 14.353 | 45.435 | 1.00 | 38.09 | O |
| ATOM | 861 | CB | GLU | A | 122 | 18.092 | 14.989 | 45.025 | 1.00 | 38.08 | C |
| ATOM | 862 | CG | GLU | A | 122 | 19.263 | 15.928 | 44.936 | 1.00 | 38.04 | C |
| ATOM | 863 | CD | GLU | A | 122 | 19.581 | 16.289 | 43.497 | 1.00 | 39.25 | C |
| ATOM | 864 | OE1 | GLU | A | 122 | 19.763 | 15.364 | 42.667 | 1.00 | 38.89 | O |
| ATOM | 865 | OE2 | GLU | A | 122 | 19.627 | 17.501 | 43.183 | 1.00 | 40.06 | O |
| ATOM | 866 | H | MET | A | 123 | 15.434 | 13.879 | 43.265 | 1.00 | 37.93 | N |
| ATOM | 867 | CA | MET | A | 123 | 14.384 | 12.885 | 43.312 | 1.00 | 37.84 | C |
| ATOM | 868 | C | MET | A | 123 | 14.536 | 11.819 | 42.242 | 1.00 | 37.41 | C |
| ATOM | 869 | O | MET | A | 123 | 15.418 | 11.876 | 41.387 | 1.00 | 37.04 | O |
| ATOM | 870 | CB | MET | A | 123 | 13.021 | 13.565 | 43.225 | 1.00 | 38.01 | C |
| ATOM | 871 | CG | MET | A | 123 | 12.798 | 14.318 | 41.946 | 1.00 | 39.05 | C |
| ATOM | 872 | SD | MET | A | 123 | 11.177 | 15.064 | 41.910 | 1.00 | 41.38 | S |
| ATOM | 873 | CE | MET | A | 123 | 11.489 | 16.589 | 42.818 | 1.00 | 41.39 | C |
| ATOM | 874 | N | LYS | A | 124 | 13.675 | 10.820 | 42.332 | 1.00 | 37.17 | N |
| ATOM | 875 | CA | LYS | A | 124 | 13.692 | 9.715 | 41.401 | 1.00 | 36.98 | C |
| ATOM | 876 | C | LYS | A | 124 | 12.802 | 10.098 | 40.238 | 1.00 | 36.81 | C |
| ATOM | 877 | O | LYS | A | 124 | 11.814 | 10.813 | 40.402 | 1.00 | 36.91 | O |
| ATOM | 878 | CB | LYS | A | 124 | 13.213 | 8.434 | 42.087 | 1.00 | 36.82 | C |
| ATOM | 879 | CG | LYS | A | 124 | 14.081 | 7.989 | 43.281 | 1.00 | 36.79 | C |
| ATOM | 880 | CD | LYS | A | 124 | 15.488 | 7.553 | 42.856 | 1.00 | 36.83 | C |
| ATOM | 881 | CE | LYS | A | 124 | 16.390 | 7.206 | 44.031 | 1.00 | 36.89 | C |
| ATOM | 882 | NZ | LYS | A | 124 | 17.822 | 7.412 | 43.680 | 1.00 | 36.99 | N |
| ATOM | 883 | N | PHE | A | 125 | 13.145 | 9.622 | 39.056 | 1.00 | 36.49 | N |
| ATOM | 884 | CA | PHE | A | 125 | 12.416 | 10.031 | 37.885 | 1.00 | 36.33 | C |
| ATOM | 885 | C | PHE | A | 125 | 10.926 | 9.861 | 38.074 | 1.00 | 36.45 | C |
| ATOM | 886 | O | PHE | A | 125 | 10.143 | 10.743 | 37.732 | 1.00 | 36.30 | O |
| ATOM | 887 | CB | PHE | A | 125 | 12.879 | 9.270 | 36.665 | 1.00 | 36.24 | C |
| ATOM | 888 | CG | PHE | A | 125 | 12.555 | 9.967 | 35.407 | 1.00 | 36.21 | C |
| ATOM | 889 | CD1 | PHE | A | 125 | 13.403 | 10.936 | 34.924 | 1.00 | 35.98 | C |
| ATOM | 890 | CD2 | PHE | A | 125 | 11.374 | 9.714 | 34.743 | 1.00 | 36.15 | C |
| ATOM | 891 | CE1 | PHE | A | 125 | 13.108 | 11.616 | 33.794 | 1.00 | 36.07 | C |
| ATOM | 892 | CE2 | PHE | A | 125 | 11.073 | 10.390 | 33.597 | 1.00 | 36.71 | C |
| ATOM | 893 | CZ | PHE | A | 125 | 11.943 | 11.350 | 33.120 | 1.00 | 36.73 | C |
| ATOM | 894 | N | HIS | A | 126 | 10.527 | 8.733 | 38.640 | 1.00 | 36.80 | N |
| ATOM | 895 | CA | HIS | A | 126 | 9.111 | 8.492 | 38.845 | 1.00 | 36.98 | C |
| ATOM | 896 | C | HIS | A | 126 | 8.547 | 9.560 | 39.772 | 1.00 | 37.20 | C |
| ATOM | 897 | O | HIS | A | 126 | 7.376 | 9.923 | 39.669 | 1.00 | 37.15 | O |
| ATOM | 898 | CB | HIS | A | 126 | 8.845 | 7.080 | 39.390 | 1.00 | 36.97 | C |
| ATOM | 899 | CG | HIS | A | 126 | 8.990 | 6.946 | 40.877 | 1.00 | 36.62 | C |
| ATOM | 900 | ND1 | HIS | A | 126 | 7.935 | 7.115 | 41.747 | 1.00 | 35.91 | N |
| ATOM | 901 | CD2 | HIS | A | 126 | 10.058 | 6.618 | 41.644 | 1.00 | 36.38 | C |
| ATOM | 902 | CE1 | HIS | A | 126 | 8.352 | 6.921 | 42.986 | 1.00 | 35.63 | C |
| ATOM | 903 | ND2 | HIS | A | 126 | 9.636 | 6.619 | 42.951 | 1.00 | 35.43 | N |
| ATOM | 904 | N | GLU | A | 127 | 9.383 | 10.082 | 40.663 | 1.00 | 37.34 | N |
| ATOM | 905 | CA | GLU | A | 127 | 8.912 | 11.087 | 41.599 | 1.00 | 37.55 | C |
| ATOM | 906 | C | GLU | A | 127 | 8.657 | 12.379 | 40.835 | 1.00 | 37.54 | C |
| ATOM | 907 | O | GLU | A | 127 | 7.657 | 13.061 | 41.049 | 1.00 | 37.36 | O |
| ATOM | 908 | CB | GLU | A | 127 | 9.914 | 11.308 | 42.736 | 1.00 | 37.65 | C |
| ATOM | 909 | CG | GLU | A | 127 | 10.155 | 10.091 | 43.617 | 1.00 | 37.89 | C |
| ATOM | 910 | CD | GLU | A | 127 | 11.113 | 10.383 | 44.764 | 1.00 | 38.14 | C |
| ATOM | 911 | OB1 | GLU | A | 127 | 12.330 | 10.531 | 44.520 | 1.00 | 37.77 | O |
| ATOM | 912 | OE2 | GLU | A | 127 | 10.649 | 10.471 | 45.917 | 1.00 | 38.86 | O |
| ATOM | 913 | N | PHE | A | 128 | 9.557 | 12.702 | 39.920 | 1.00 | 37.65 | N |
| ATOM | 914 | CA | PHE | A | 128 | 9.393 | 13.904 | 39.127 | 1.00 | 37.81 | C |
| ATOM | 915 | C | PHE | A | 128 | 8.090 | 13.798 | 38.350 | 1.00 | 37.95 | C |
| ATOM | 916 | O | PHE | A | 128 | 7.280 | 14.726 | 38.342 | 1.00 | 37.90 | O |
| ATOM | 917 | CB | PHE | A | 128 | 10.578 | 14.061 | 38.173 | 1.00 | 37.88 | C |
| ATOM | 918 | CG | PHE | A | 128 | 10.332 | 15.012 | 37.028 | 1.00 | 37.52 | C |
| ATOM | 919 | CD1 | PHE | A | 128 | 10.088 | 16.355 | 37.258 | 1.00 | 36.94 | C |
| ATOM | 920 | CD2 | PHE | A | 128 | 10.380 | 14.559 | 35.720 | 1.00 | 37.02 | C |
| ATOM | 921 | CE1 | PHE | A | 128 | 9.876 | 17.219 | 36.203 | 1.00 | 37.09 | C |
| ATOM | 922 | CE2 | PHE | A | 128 | 10.170 | 15.423 | 34.663 | 1.00 | 37.21 | C |

TABLE 3-continued

Coordinates for structures 1 to 4

| ATOM | 923 | CZ | PHE | A | 128 | 9.917 | 16.748 | 34.901 | 1.00 | 37.15 | C |
|---|---|---|---|---|---|---|---|---|---|---|---|
| ATOM | 924 | N | VAL | A | 129 | 7.878 | 12.646 | 37.726 | 1.00 | 38.00 | N |
| ATOM | 925 | CA | VAL | A | 129 | 6.716 | 12.454 | 36.876 | 1.00 | 38.16 | C |
| ATOM | 926 | C | VAL | A | 129 | 5.442 | 12.637 | 37.671 | 1.00 | 38.24 | C |
| ATOM | 927 | O | VAL | A | 129 | 4.494 | 13.286 | 37.224 | 1.00 | 38.04 | O |
| ATOM | 928 | CB | VAL | A | 129 | 6.705 | 11.050 | 36.268 | 1.00 | 38.36 | C |
| ATOM | 929 | CG1 | VAL | A | 129 | 5.398 | 10.810 | 35.508 | 1.00 | 38.41 | C |
| ATOM | 930 | CG2 | VAL | A | 129 | 7.935 | 10.841 | 35.372 | 1.00 | 38.22 | C |
| ATOM | 931 | N | GLU | A | 130 | 5.430 | 12.038 | 38.854 | 1.00 | 38.42 | N |
| ATOM | 932 | CA | GLU | A | 130 | 4.289 | 12.115 | 39.745 | 1.00 | 38.54 | C |
| ATOM | 933 | C | GLU | A | 130 | 4.025 | 13.578 | 40.083 | 1.00 | 38.43 | C |
| ATOM | 934 | O | GLU | A | 130 | 2.898 | 14.056 | 39.960 | 1.00 | 38.29 | O |
| ATOM | 935 | CB | GLU | A | 130 | 4.547 | 11.265 | 40.997 | 1.00 | 38.69 | C |
| ATOM | 936 | CG | GLU | A | 130 | 4.404 | 9.763 | 40.745 | 1.00 | 39.15 | C |
| ATOM | 937 | CD | GLU | A | 130 | 5.160 | 8.897 | 41.740 | 1.00 | 39.75 | C |
| ATOM | 938 | OE1 | GLU | A | 130 | 5.551 | 9.403 | 42.815 | 1.00 | 40.08 | O |
| ATOM | 939 | OE2 | GLU | A | 130 | 5.355 | 7.697 | 41.441 | 1.00 | 40.15 | O |
| ATOM | 940 | N | LYS | A | 131 | 5.070 | 14.299 | 40.471 | 1.00 | 38.39 | N |
| ATOM | 941 | CA | LYS | A | 131 | 4.908 | 15.707 | 40.787 | 1.00 | 38.52 | C |
| ATOM | 942 | C | LYS | A | 131 | 4.290 | 16.431 | 39.598 | 1.00 | 38.61 | C |
| ATOM | 943 | O | LYS | A | 131 | 3.393 | 17.252 | 39.769 | 1.00 | 38.51 | O |
| ATOM | 944 | CB | LYS | A | 131 | 6.240 | 16.356 | 41.149 | 1.00 | 38.58 | C |
| ATOM | 945 | CG | LYS | A | 131 | 6.440 | 16.666 | 42.625 | 1.00 | 38.76 | C |
| ATOM | 946 | CD | LYS | A | 131 | 7.045 | 18.060 | 42.753 | 1.00 | 39.73 | C |
| ATOM | 947 | CE | LYS | A | 131 | 7.756 | 18.316 | 44.070 | 1.00 | 40.49 | C |
| ATOM | 948 | NZ | LYS | A | 131 | 8.117 | 19.772 | 44.197 | 1.00 | 40.68 | N |
| ATOM | 949 | N | LEU | A | 132 | 4.764 | 16.136 | 38.391 | 1.00 | 38.84 | N |
| ATOM | 950 | CA | LEU | A | 132 | 4.196 | 16.771 | 37.208 | 1.00 | 39.00 | C |
| ATOM | 951 | C | LEU | A | 132 | 2.726 | 16.429 | 37.113 | 1.00 | 39.11 | C |
| ATOM | 952 | O | LEU | A | 132 | 1.903 | 17.287 | 36.810 | 1.00 | 39.20 | O |
| ATOM | 953 | CB | LEU | A | 132 | 4.894 | 16.328 | 35.932 | 1.00 | 38.96 | C |
| ATOM | 954 | CG | LEU | A | 132 | 6.287 | 16.899 | 35.723 | 1.00 | 39.44 | C |
| ATOM | 955 | CD1 | LEU | A | 132 | 6.870 | 16.389 | 34.429 | 1.00 | 39.81 | C |
| ATOM | 956 | CD2 | LEU | A | 132 | 6.261 | 18.421 | 35.709 | 1.00 | 40.07 | C |
| ATOM | 957 | N | GLN | A | 133 | 2.396 | 15.170 | 37.367 | 1.00 | 39.22 | N |
| ATOM | 958 | CA | GLN | A | 133 | 1.005 | 14.758 | 37.335 | 1.00 | 39.38 | C |
| ATOM | 959 | C | GLN | A | 133 | 0.172 | 15.523 | 38.370 | 1.00 | 39.57 | C |
| ATOM | 960 | O | GLN | A | 133 | 0.893 | 16.034 | 38.029 | 1.00 | 39.48 | O |
| ATOM | 961 | CB | GLN | A | 133 | 0.874 | 13.250 | 37.536 | 1.00 | 39.22 | C |
| ATOM | 962 | N | ASP | A | 134 | 0.656 | 15.631 | 39.611 | 1.00 | 39.91 | N |
| ATOM | 963 | CA | ASP | A | 134 | 0.129 | 16.279 | 40.677 | 1.00 | 40.29 | C |
| ATOM | 964 | C | ASP | A | 134 | 0.437 | 17.732 | 40.379 | 1.00 | 40.17 | C |
| ATOM | 965 | O | ASP | A | 134 | 1.543 | 18.211 | 40.623 | 1.00 | 40.02 | O |
| ATOM | 966 | CB | ASP | A | 134 | 0.564 | 16.198 | 42.041 | 1.00 | 40.57 | C |
| ATOM | 967 | CG | ASP | A | 134 | 0.348 | 16.660 | 43.182 | 1.00 | 41.99 | C |
| ATOM | 968 | OD1 | ASP | A | 134 | 1.301 | 17.421 | 42.910 | 1.00 | 43.76 | O |
| ATOM | 969 | OD2 | ASP | A | 134 | 0.212 | 16.312 | 44.378 | 1.00 | 44.05 | O |
| ATOM | 970 | N | ILE | A | 135 | 0.545 | 18.438 | 39.846 | 1.00 | 40.17 | N |
| ATOM | 971 | CA | ILE | A | 135 | 0.350 | 19.836 | 39.556 | 1.00 | 40.10 | C |
| ATOM | 972 | C | ILE | A | 135 | 0.719 | 19.973 | 38.500 | 1.00 | 40.10 | C |
| ATOM | 973 | O | ILE | A | 135 | 1.648 | 20.759 | 38.652 | 1.00 | 40.26 | O |
| ATOM | 974 | CB | ILE | A | 135 | 1.639 | 20.455 | 39.085 | 1.00 | 40.10 | C |
| ATOM | 975 | CG1 | ILE | A | 135 | 2.612 | 20.560 | 40.261 | 1.00 | 40.11 | C |
| ATOM | 976 | CG2 | ILE | A | 135 | 1.358 | 21.817 | 38.507 | 1.00 | 40.22 | C |
| ATOM | 977 | CD1 | ILE | A | 135 | 4.056 | 20.688 | 39.842 | 1.00 | 40.17 | C |
| ATOM | 978 | N | GLN | A | 136 | 0.596 | 19.198 | 37.431 | 1.00 | 40.02 | N |
| ATOM | 979 | CA | GLN | A | 136 | 1.586 | 19.248 | 36.376 | 1.00 | 39.96 | C |
| ATOM | 980 | C | GLN | A | 136 | 2.956 | 19.094 | 37.000 | 1.00 | 39.99 | C |
| ATOM | 981 | O | GLN | A | 136 | 3.795 | 19.991 | 36.921 | 1.00 | 39.86 | O |
| ATOM | 982 | CB | GLN | A | 136 | 1.350 | 18.144 | 35.361 | 1.00 | 40.00 | C |
| ATOM | 983 | N | GLN | A | 137 | 3.158 | 17.972 | 37.679 | 1.00 | 40.18 | N |
| ATOM | 984 | CA | GLN | A | 137 | 4.486 | 17.630 | 38.164 | 1.00 | 40.31 | C |
| ATOM | 985 | C | GLN | A | 137 | 4.995 | 18.683 | 39.114 | 1.00 | 40.45 | C |
| ATOM | 986 | O | GLN | A | 137 | 6.170 | 19.046 | 39.068 | 1.00 | 40.75 | O |
| ATOM | 987 | CB | GLN | A | 137 | 4.502 | 16.247 | 38.829 | 1.00 | 40.24 | C |
| ATOM | 988 | N | ARG | A | 138 | 4.116 | 19.200 | 39.959 | 1.00 | 40.45 | N |
| ATOM | 989 | CA | ARG | A | 138 | 4.560 | 20.159 | 40.956 | 1.00 | 40.45 | C |
| ATOM | 990 | C | ARG | A | 138 | 4.568 | 21.588 | 40.419 | 1.00 | 40.54 | C |
| ATOM | 991 | O | ARG | A | 138 | 4.678 | 22.541 | 41.188 | 1.00 | 40.67 | O |
| ATOM | 992 | CB | ARG | A | 138 | 3.692 | 20.069 | 42.207 | 1.00 | 40.43 | C |
| ATOM | 993 | CG | ARG | A | 138 | 2.399 | 20.868 | 42.161 | 1.00 | 40.03 | C |
| ATOM | 994 | CD | ARG | A | 138 | 1.541 | 20.546 | 43.346 | 1.00 | 39.94 | C |
| ATOM | 995 | NE | ARG | A | 138 | 0.431 | 21.458 | 43.580 | 1.00 | 39.71 | N |
| ATOM | 996 | CZ | ARG | A | 138 | 0.842 | 21.098 | 43.498 | 1.00 | 40.13 | C |
| ATOM | 997 | NH1 | ARG | A | 138 | 1.164 | 19.857 | 43.150 | 1.00 | 40.53 | N |
| ATOM | 998 | NH2 | ARG | A | 138 | 1.800 | 21.978 | 43.747 | 1.00 | 40.33 | N |
| ATOM | 999 | N | GLY | A | 139 | 4.471 | 21.742 | 39.102 | 1.00 | 40.47 | N |

TABLE 3-continued

| | | | | | Coordinates for structures 1 to 4 | | | | | |
|---|---|---|---|---|---|---|---|---|---|---|
| ATOM | 1000 | CA | GLY | A | 139 | 4.418 | 23.066 | 38.508 | 1.00 | 40.46 | C |
| ATOM | 1001 | C | GLY | A | 139 | 3.432 | 24.021 | 39.176 | 1.00 | 40.45 | C |
| ATOM | 1002 | O | GLY | A | 139 | 3.616 | 25.235 | 39.110 | 1.00 | 40.46 | O |
| ATOM | 1003 | N | GLY | A | 140 | 2.370 | 23.490 | 39.780 | 1.00 | 40.47 | N |
| ATOM | 1004 | CA | GLY | A | 140 | 1.425 | 24.314 | 40.519 | 1.00 | 40.45 | C |
| ATOM | 1005 | C | GLY | A | 140 | 0.695 | 25.272 | 39.602 | 1.00 | 40.40 | C |
| ATOM | 1006 | O | GLY | A | 140 | 0.784 | 25.116 | 38.383 | 1.00 | 40.79 | O |
| ATOM | 1007 | N | GLU | A | 141 | 0.015 | 26.273 | 40.167 | 1.00 | 40.10 | N |
| ATOM | 1008 | CA | GLU | A | 141 | 0.807 | 27.195 | 39.371 | 1.00 | 40.01 | C |
| ATOM | 1009 | C | GLU | A | 141 | 2.305 | 26.854 | 39.458 | 1.00 | 39.64 | C |
| ATOM | 1010 | O | GLU | A | 141 | 3.112 | 27.386 | 38.692 | 1.00 | 39.52 | O |
| ATOM | 1011 | CB | GLU | A | 141 | 0.589 | 28.660 | 39.796 | 1.00 | 40.20 | C |
| ATOM | 1012 | CG | GLU | A | 141 | 0.711 | 29.298 | 39.315 | 1.00 | 41.00 | C |
| ATOM | 1013 | CD | GLU | A | 141 | 0.845 | 29.307 | 37.800 | 1.00 | 42.10 | C |
| ATOM | 1014 | OE1 | GLU | A | 141 | 0.194 | 29.181 | 37.113 | 1.00 | 41.99 | O |
| ATOM | 1015 | OE2 | GLU | A | 141 | 1.990 | 29.437 | 37.300 | 1.00 | 43.15 | O |
| ATOM | 1016 | N | GLU | A | 142 | 2.676 | 25.977 | 40.392 | 1.00 | 39.25 | N |
| ATOM | 1017 | CA | GLU | A | 142 | 4.075 | 25.589 | 40.563 | 1.00 | 38.95 | C |
| ATOM | 1018 | C | GLU | A | 142 | 4.613 | 25.162 | 39.210 | 1.00 | 38.74 | C |
| ATOM | 1019 | O | GLU | A | 142 | 3.859 | 24.694 | 38.351 | 1.00 | 38.77 | O |
| ATOM | 1020 | CB | GLU | A | 142 | 4.220 | 24.433 | 41.577 | 1.00 | 38.95 | C |
| ATOM | 1021 | CG | GLU | A | 142 | 5.658 | 24.138 | 42.019 | 1.00 | 38.90 | C |
| ATOM | 1022 | CD | GLU | A | 142 | 5.797 | 22.950 | 42.971 | 1.00 | 38.93 | C |
| ATOM | 1023 | OE1 | GLU | A | 142 | 4.836 | 22.164 | 43.130 | 1.00 | 39.58 | O |
| ATOM | 1024 | OE2 | GLU | A | 142 | 6.888 | 22.799 | 43.565 | 1.00 | 38.74 | O |
| ATOM | 1025 | N | ARG | A | 143 | 5.914 | 25.332 | 39.020 | 1.00 | 38.39 | N |
| ATOM | 1026 | CA | ARG | A | 143 | 6.569 | 24.908 | 37.796 | 1.00 | 38.25 | C |
| ATOM | 1027 | C | ARG | A | 143 | 7.809 | 24.122 | 38.122 | 1.00 | 38.14 | C |
| ATOM | 1028 | O | ARG | A | 143 | 8.512 | 24.450 | 39.078 | 1.00 | 38.46 | O |
| ATOM | 1029 | CB | ARG | A | 143 | 7.046 | 26.107 | 37.003 | 1.00 | 38.26 | C |
| ATOM | 1030 | CG | ARG | A | 143 | 5.986 | 26.945 | 36.398 | 1.00 | 37.89 | C |
| ATOM | 1031 | CD | ARG | A | 143 | 6.602 | 28.026 | 35.555 | 1.00 | 37.35 | C |
| ATOM | 1032 | NE | ARG | A | 143 | 5.610 | 28.814 | 34.849 | 1.00 | 36.66 | N |
| ATOM | 1033 | CZ | ARG | A | 143 | 5.316 | 28.668 | 33.573 | 1.00 | 36.40 | C |
| ATOM | 1034 | NH1 | ARG | A | 143 | 5.933 | 27.755 | 32.831 | 1.00 | 36.41 | N |
| ATOM | 1035 | NH2 | ARG | A | 143 | 4.397 | 29.443 | 33.034 | 1.00 | 37.02 | N |
| ATOM | 1036 | N | LEU | A | 144 | 8.116 | 23.124 | 37.304 | 1.00 | 37.71 | N |
| ATOM | 1037 | CA | LEU | A | 144 | 9.319 | 22.349 | 37.517 | 1.00 | 37.57 | C |
| ATOM | 1038 | C | LEU | A | 144 | 10.181 | 22.319 | 36.294 | 1.00 | 37.33 | C |
| ATOM | 1039 | O | LEU | A | 144. | 9.710 | 22.466 | 35.165 | 1.00 | 37.31 | O |
| ATOM | 1040 | CB | LEU | A | 144 | 8.979 | 20.909 | 37.858 | 1.00 | 37.69 | C |
| ATOM | 1041 | CG | LEU | A | 144 | 7.981 | 20.736 | 38.993 | 1.00 | 38.31 | C |
| ATOM | 1042 | CD1 | LEU | A | 144 | 7.612 | 19.255 | 39.165 | 1.00 | 39.02 | C |
| ATOM | 1043 | CD2 | LEU | A | 144 | 8.551 | 21.327 | 40.263 | 1.00 | 37.91 | C |
| ATOM | 1044 | N | TYR | A | 145 | 11.460 | 22.098 | 36.528 | 1.00 | 37.01 | N |
| ATOM | 1045 | CA | TYR | A | 145 | 12.379 | 21.922 | 35.437 | 1.00 | 36.87 | C |
| ATOM | 1046 | C | TYR | A | 145 | 13.397 | 20.886 | 35.871 | 1.00 | 36.85 | C |
| ATOM | 1047 | O | TYR | A | 145 | 14.146 | 21.093 | 36.819 | 1.00 | 36.51 | O |
| ATOM | 1048 | GB | TYR | A | 145 | 13.043 | 23.255 | 35.110 | 1.00 | 36.92 | C |
| ATOM | 1049 | CG | TYR | A | 145 | 13.505 | 23.446 | 33.686 | 1.00 | 36.38 | C |
| ATOM | 1050 | CD2 | TYR | A | 145 | 13.845 | 22.383 | 32.875 | 1.00 | 36.31 | C |
| ATOM | 1051 | CD2 | TYR | A | 145 | 13.619 | 24.716 | 33.163 | 1.00 | 36.28 | C |
| ATOM | 1052 | GE1 | TYR | A | 145 | 14.278 | 22.590 | 31.582 | 1.00 | 36.21 | C |
| ATOM | 1053 | CE2 | TYR | A | 145 | 14.047 | 24.923 | 31.880 | 1.00 | 35.94 | C |
| ATOM | 1054 | CZ | TYR | A | 145 | 14.374 | 23.862 | 31.093 | 1.00 | 35.54 | C |
| ATOM | 1055 | OH | TYR | A | 145 | 14.789 | 24.081 | 29.799 | 1.00 | 36.13 | O |
| ATOM | 1056 | N | LEU | A | 146 | 13.378 | 19.736 | 35.218 | 1.00 | 37.06 | N |
| ATOM | 1057 | CA | LEU | A | 146 | 14.396 | 18.742 | 35.477 | 1.00 | 37.49 | C |
| ATOM | 1058 | C | LEU | A | 146 | 15.628 | 19.029 | 34.629 | 1.00 | 37.55 | C |
| ATOM | 1059 | O | LEU | A | 146 | 15.532 | 19.241 | 33.427 | 1.00 | 37.31 | O |
| ATOM | 1060 | GB | LEU | A | 146 | 13.877 | 17.341 | 35.173 | 1.00 | 37.69 | C |
| ATOM | 1061 | CG | LEU | A | 146 | 14.919 | 16.233 | 35.349 | 1.00 | 37.95 | C |
| ATOM | 1062 | GD1 | LEU | A | 146 | 14.234 | 14.916 | 35.567 | 1.00 | 37.66 | C |
| ATOM | 1063 | CD2 | LEU | A | 146 | 15.849 | 16.133 | 34.151 | 1.00 | 39.00 | C |
| ATOM | 1064 | N | GLN | A | 147 | 16.786 | 18.993 | 35.269 | 1.00 | 37.84 | N |
| ATOM | 1065 | CA | GLN | A | 147 | 18.053 | 19.259 | 34.617 | 1.00 | 38.09 | C |
| ATOM | 1066 | C | GLN | A | 147 | 19.088 | 18.397 | 35.306 | 1.00 | 37.92 | C |
| ATOM | 1067 | O | GLN | A | 147 | 19.453 | 18.661 | 36.443 | 1.00 | 37.87 | O |
| ATOM | 1068 | GB | GLN | A | 147 | 18.421 | 20.725 | 34.773 | 1.00 | 38.37 | C |
| ATOM | 1069 | CG | GLN | A | 147 | 17.331 | 21.686 | 34.362 | 1.00 | 39.01 | C |
| ATOM | 1070 | CD | GLN | A | 147 | 17.867 | 23.064 | 34.191 | 1.00 | 39.92 | C |
| ATOM | 1071 | OE1 | GLN | A | 147 | 17.149 | 23.955 | 33.772 | 1.00 | 42.51 | O |
| ATOM | 1072 | NE2 | GLN | A | 147 | 19.137 | 23.253 | 34.520 | 1.00 | 40.24 | N |
| ATOM | 1073 | N | GLN | A | 148 | 19.576 | 17.385 | 34.601 | 1.00 | 37.81 | N |
| ATOM | 1074 | CA | GLN | A | 148 | 20.433 | 16.377 | 35.196 | 1.00 | 37.57 | C |
| ATOM | 1075 | C | GLN | A | 148 | 21.325 | 15.744 | 34.176 | 1.00 | 37.68 | C |
| ATOM | 1076 | O | GLN | A | 148 | 20.876 | 15.266 | 33.146 | 1.00 | 37.30 | O |

TABLE 3-continued

| | | | | | | | | | | | |
|---|---|---|---|---|---|---|---|---|---|---|---|
| | | | | | Coordinates for structures 1 to 4 | | | | | | |
| ATOM | 1077 | GB | GLN | A | 148 | 19.576 | 15.261 | 35.773 | 1.00 | 37.61 | C |
| ATOM | 1078 | CG | GLN | A | 148 | 20.336 | 13.971 | 36.068 | 1.00 | 36.79 | C |
| ATOM | 1079 | CD | GLN | A | 148 | 21.398 | 14.159 | 37.117 | 1.00 | 35.97 | C |
| ATOM | 1080 | OE1 | GLN | A | 148 | 21.162 | 14.814 | 38.135 | 1.00 | 35.11 | O |
| ATOM | 1081 | NE2 | GLN | A | 148 | 22.577 | 13.593 | 36.875 | 1.00 | 35.03 | N |
| ATOM | 1082 | N | THR | A | 149 | 22.596 | 15.698 | 34.503 | 1.00 | 38.15 | N |
| ATOM | 1083 | GA | THR | A | 149 | 23.574 | 15.130 | 33.622 | 1.00 | 38.57 | C |
| ATOM | 1084 | C | THR | A | 149 | 23.354 | 13.647 | 33.506 | 1.00 | 38.68 | C |
| ATOM | 1085 | O | THR | A | 149 | 23.154 | 12.973 | 34.509 | 1.00 | 39.07 | O |
| ATOM | 1086 | GB | THR | A | 149 | 24.936 | 15.410 | 34.214 | 1.00 | 38.75 | C |
| ATOM | 1087 | OG1 | THR | A | 149 | 25.206 | 16.807 | 34.088 | 1.00 | 38.86 | O |
| ATOM | 1088 | CG2 | THR | A | 149 | 26.036 | 14.759 | 33.418 | 1.00 | 39.39 | C |
| ATOM | 1089 | N | LEU | A | 150 | 23.393 | 13.144 | 32.279 | 1.00 | 38.87 | N |
| ATOM | 1090 | GA | LEU | A | 150 | 23.259 | 11.722 | 32.021 | 1.00 | 39.24 | C |
| ATOM | 1091 | C | LEU | A | 150 | 24.498 | 10.979 | 32.507 | 1.00 | 39.20 | C |
| ATOM | 1092 | O | LEU | A | 150 | 25.602 | 11.317 | 32.101 | 1.00 | 39.20 | O |
| ATOM | 1093 | GB | LEU | A | 150 | 23.146 | 11.465 | 30.519 | 1.00 | 39.46 | C |
| ATOM | 1094 | CG | LEU | A | 150 | 21.938 | 11.942 | 29.722 | 1.00 | 40.52 | C |
| ATOM | 1095 | CD1 | LEU | A | 150 | 22.077 | 11.563 | 28.237 | 1.00 | 41.06 | C |
| ATOM | 1096 | CD2 | LEU | A | 150 | 20.712 | 11.308 | 30.303 | 1.00 | 41.66 | C |
| ATOM | 1097 | N | ASN | A | 151 | 24.315 | 9.960 | 33.343 | 1.00 | 39.19 | N |
| ATOM | 1098 | CA | ASN | A | 151 | 25.436 | 9.171 | 33.861 | 1.00 | 39.46 | C |
| ATOM | 1099 | C | ASN | A | 151 | 25.193 | 7.642 | 33.883 | 1.00 | 39.43 | C |
| ATOM | 1100 | O | ASN | A | 151 | 24.198 | 7.162 | 33.333 | 1.00 | 39.15 | O |
| ATOM | 1101 | GB | ASN | A | 151 | 25.731 | 9.652 | 35.265 | 1.00 | 39.54 | C |
| ATOM | 1102 | CG | ASN | A | 151 | 24.511 | 9.588 | 36.150 | 1.00 | 40.08 | C |
| ATOM | 1103 | CD1 | ASN | A | 151 | 23.874 | 8.533 | 36.283 | 1.00 | 39.68 | O |
| ATOM | 1104 | ND2 | ASN | A | 151 | 24.158 | 10.725 | 36.751 | 1.00 | 40.83 | N |
| ATOM | 1105 | N | ASP | A | 152 | 26.075 | 6.892 | 34.556 | 1.00 | 39.43 | N |
| ATOM | 1106 | CA | ASP | A | 152 | 26.025 | 5.413 | 34.543 | 1.00 | 39.58 | C |
| ATOM | 1107 | C | ASP | A | 152 | 24.761 | 4.787 | 35.083 | 1.00 | 39.17 | C |
| ATOM | 1108 | O | ASP | A | 152 | 24.477 | 3.634 | 34.776 | 1.00 | 39.29 | O |
| ATOM | 1109 | GB | ASP | A | 152 | 27.138 | 4.756 | 35.385 | 1.00 | 39.92 | C |
| ATOM | 1110 | CG | ASP | A | 152 | 28.489 | 5.382 | 35.198 | 1.00 | 41.53 | C |
| ATOM | 1111 | OD1 | ASP | A | 152 | 28.722 | 6.005 | 34.134 | 1.00 | 45.10 | O |
| ATOM | 1112 | OD2 | ASP | A | 152 | 29.378 | 5.294 | 36.076 | 1.00 | 42.02 | O |
| ATOM | 1113 | N | THR | A | 153 | 24.008 | 5.493 | 35.909 | 1.00 | 38.78 | N |
| ATOM | 1114 | CA | THR | A | 153 | 22.881 | 4.830 | 36.542 | 1.00 | 38.50 | C |
| ATOM | 1115 | C | THR | A | 153 | 21.757 | 4.573 | 35.573 | 1.00 | 38.26 | C |
| ATOM | 1116 | O | THR | A | 153 | 20.842 | 3.838 | 35.882 | 1.00 | 38.29 | O |
| ATOM | 1117 | CB | THR | A | 153 | 22.329 | 5.624 | 37.733 | 1.00 | 38.46 | C |
| ATOM | 1118 | OG1 | THR | A | 153 | 21.622 | 6.780 | 37.269 | 1.00 | 39.25 | O |
| ATOM | 1119 | CG2 | THR | A | 153 | 23.445 | 6.161 | 38.611 | 1.00 | 38.28 | C |
| ATOM | 1120 | N | VAL | A | 154 | 21.804 | 5.165 | 34.396 | 1.00 | 38.28 | N |
| ATOM | 1121 | CA | VAL | A | 154 | 20.687 | 4.977 | 33.491 | 1.00 | 38.29 | C |
| ATOM | 1122 | C | VAL | A | 154 | 20.602 | 3.530 | 33.067 | 1.00 | 38.17 | C |
| ATOM | 1123 | O | VAL | A | 154 | 21.597 | 2.805 | 33.092 | 1.00 | 38.10 | O |
| ATOM | 1124 | GB | VAL | A | 154 | 20.786 | 5.838 | 32.251 | 1.00 | 38.15 | C |
| ATOM | 1125 | CG1 | VAL | A | 154 | 20.815 | 7.291 | 32.649 | 1.00 | 38.22 | C |
| ATOM | 1126 | CG2 | VAL | A | 154 | 22.007 | 5.437 | 31.443 | 1.00 | 38.40 | C |
| ATOM | 1127 | N | GLY | A | 155 | 19.395 | 3.132 | 32.681 | 1.00 | 38.05 | N |
| ATOM | 1128 | CA | GLY | A | 155 | 19.114 | 1.779 | 32.258 | 1.00 | 38.07 | C |
| ATOM | 1129 | C | GLY | A | 155 | 19.609 | 1.358 | 30.894 | 1.00 | 38.17 | c |
| ATOM | 1130 | O | GLY | A | 155 | 20.092 | 2.153 | 30.081 | 1.00 | 38.44 | O |
| ATOM | 1131 | N | ARG | A | 156 | 19.417 | 0.073 | 30.642 | 1.00 | 38.16 | N |
| ATOM | 1132 | CA | ARG | A | 156 | 19.932 | 0.588 | 29.461 | 1.00 | 38.16 | C |
| ATOM | 1133 | C | ARG | A | 156 | 19.414 | 0.065 | 28.210 | 1.00 | 38.01 | C |
| ATOM | 1134 | O | ARG | A | 156 | 20.185 | 0.490 | 27.346 | 1.00 | 38.04 | O |
| ATOM | 1135 | GB | ARG | A | 156 | 19.554 | 2.080 | 29.489 | 1.00 | 38.18 | C |
| ATOM | 1136 | N | LYS | A | 157 | 18.102 | 0.178 | 28.118 | 1.00 | 37.83 | N |
| ATOM | 1137 | CA | LYS | A | 157 | 17.545 | 0.713 | 26.905 | 1.00 | 37.67 | C |
| ATOM | 1138 | C | LYS | A | 157 | 18.144 | 2.092 | 26.679 | 1.00 | 37.77 | C |
| ATOM | 1139 | O | LYS | A | 157 | 18.579 | 2.386 | 25.571 | 1.00 | 37.84 | O |
| ATOM | 1140 | GB | LYS | A | 157 | 16.014 | 0.725 | 26.936 | 1.00 | 37.62 | C |
| ATOM | 1141 | CG | LYS | A | 157 | 15.379 | 0.624 | 26.550 | 1.00 | 36.92 | C |
| ATOM | 1142 | N | ILE | A | 158 | 18.247 | 2.911 | 27.728 | 1.00 | 37.82 | N |
| ATOM | 1143 | CA | ILE | A | 158 | 18.699 | 4.287 | 27.526 | 1.00 | 37.81 | C |
| ATOM | 1144 | C | ILE | A | 158 | 20.096 | 4.252 | 27.008 | 1.00 | 37.78 | C |
| ATOM | 1145 | O | ILE | A | 158 | 20.440 | 4.942 | 26.058 | 1.00 | 37.52 | O |
| ATOM | 1146 | GB | ILE | A | 158 | 18.666 | 5.109 | 28.802 | 1.00 | 37.90 | C |
| ATOM | 1147 | CG1 | ILE | A | 158 | 17.233 | 5.283 | 29.280 | 1.00 | 37.87 | C |
| ATOM | 1148 | CG2 | ILE | A | 158 | 19.281 | 6.477 | 28.538 | 1.00 | 37.57 | C |
| ATOM | 1149 | CD1 | ILE | A | 158 | 16.383 | 6.034 | 28.318 | 1.00 | 37.95 | C |
| ATOM | 1150 | N | VAL | A | 159 | 20.899 | 3.418 | 27.637 | 1.00 | 37.89 | N |
| ATOM | 1151 | CA | VAL | A | 159 | 22.263 | 3.265 | 27.211 | 1.00 | 38.06 | C |
| ATOM | 1152 | C | VAL | A | 159 | 22.255 | 2.906 | 25.725 | 1.00 | 38.07 | C |
| ATOM | 1153 | O | VAL | A | 159 | 23.025 | 3.462 | 24.955 | 1.00 | 37.93 | O |

TABLE 3-continued

| | | | | | | | | | | |
|---|---|---|---|---|---|---|---|---|---|---|
| ATOM | 1154 | GB | VAL | A | 159 | 22.987 | 2.196 | 28.039 | 1.00 | 38.12 | C |
| ATOM | 1155 | CG1 | VAL | A | 159 | 24.208 | 1.740 | 27.315 | 1.00 | 38.65 | C |
| ATOM | 1156 | CG2 | VAL | A | 159 | 23.368 | 2.734 | 29.410 | 1.00 | 37.65 | C |
| ATOM | 1157 | N | MET | A | 160 | 21.385 | 1.984 | 25.318 | 1.00 | 38.30 | N |
| ATOM | 1158 | CA | MET | A | 160 | 21.264 | 1.658 | 23.894 | 1.00 | 38.71 | C |
| ATOM | 1159 | C | MET | A | 160 | 21.024 | 2.923 | 23.084 | 1.00 | 38.35 | C |
| ATOM | 1160 | O | MET | A | 160 | 21.742 | 3.219 | 22.137 | 1.00 | 38.42 | O |
| ATOM | 1161 | GB | MET | A | 160 | 20.115 | 0.682 | 23.636 | 1.00 | 38.93 | C |
| ATOM | 1162 | CG | MET | A | 160 | 20.431 | 0.690 | 24.087 | 1.00 | 40.64 | C |
| ATOM | 1163 | SD | MET | A | 160 | 21.840 | 1.293 | 23.180 | 1.00 | 44.02 | S |
| ATOM | 1164 | CE | MET | A | 160 | 20.982 | 1.709 | 21.617 | 1.00 | 44.00 | C |
| ATOM | 1165 | N | ASP | A | 161 | 19.997 | 3.665 | 23.458 | 1.00 | 37.94 | N |
| ATOM | 1166 | CA | ASP | A | 161 | 19.702 | 4.902 | 22.773 | 1.00 | 37.82 | C |
| ATOM | 1167 | C | ASP | A | 161 | 20.955 | 5.788 | 22.684 | 1.00 | 37.50 | C |
| ATOM | 1168 | O | ASP | A | 161 | 21.395 | 6.154 | 21.596 | 1.00 | 37.66 | O |
| ATOM | 1169 | GB | ASP | A | 161 | 18.591 | 5.650 | 23.511 | 1.00 | 37.84 | C |
| ATOM | 1170 | CG | ASP | A | 161 | 17.274 | 4.908 | 23.501 | 1.00 | 37.82 | C |
| ATOM | 1171 | OD1 | ASP | A | 161 | 17.082 | 4.020 | 22.646 | 1.00 | 37.72 | O |
| ATOM | 1172 | OD2 | ASP | A | 161 | 16.366 | 5.155 | 24.320 | 1.00 | 38.41 | O |
| ATOM | 1173 | N | PHE | A | 162 | 21.539 | 6.100 | 23.836 | 1.00 | 36.93 | N |
| ATOM | 1174 | CA | PHE | A | 162 | 22.672 | 7.020 | 23.919 | 1.00 | 36.54 | C |
| ATOM | 1175 | C | PHE | A | 162 | 23.760 | 6.604 | 22.960 | 1.00 | 36.03 | C |
| ATOM | 1176 | O | PHE | A | 162 | 24.375 | 7.446 | 22.304 | 1.00 | 36.06 | O |
| ATOM | 1177 | CB | PHE | A | 162 | 23.201 | 7.063 | 25.364 | 1.00 | 36.52 | C |
| ATOM | 1178 | CG | PHE | A | 162 | 24.386 | 7.974 | 25.576 | 1.00 | 36.64 | C |
| ATOM | 1179 | CD1 | PHE | A | 162 | 24.209 | 9.319 | 25.871 | 1.00 | 36.67 | C |
| ATOM | 1180 | CD2 | PHE | A | 162 | 25.682 | 7.467 | 25.540 | 1.00 | 37.81 | C |
| ATOM | 1181 | CE1 | PHE | A | 162 | 25.299 | 10.155 | 26.081 | 1.00 | 36.91 | C |
| ATOM | 1182 | CE2 | PHE | A | 162 | 26.787 | 8.300 | 25.764 | 1.00 | 37.75 | C |
| ATOM | 1183 | CZ | PHE | A | 162 | 26.592 | 9.640 | 26.029 | 1.00 | 37.82 | C |
| ATOM | 1184 | N | LEU | A | 163 | 23.976 | 5.297 | 22.878 | 1.00 | 35.38 | N |
| ATOM | 1185 | CA | LEU | A | 163 | 24.998 | 4.730 | 22.023 | 1.00 | 34.93 | C |
| ATOM | 1186 | C | LEU | A | 163 | 24.635 | 4.948 | 20.591 | 1.00 | 34.41 | C |
| ATOM | 1187 | O | LEU | A | 163 | 25.502 | 5.067 | 19.732 | 1.00 | 34.36 | O |
| ATOM | 1188 | CB | LEU | A | 163 | 25.111 | 3.239 | 22.272 | 1.00 | 35.05 | C |
| ATOM | 1189 | CG | LEU | A | 163 | 25.977 | 2.932 | 23.473 | 1.00 | 35.25 | C |
| ATOM | 1190 | CD1 | LEU | A | 163 | 25.944 | 1.471 | 23.684 | 1.00 | 36.00 | C |
| ATOM | 1191 | CD2 | LEU | A | 163 | 27.404 | 3.425 | 23.270 | 1.00 | 35.64 | C |
| ATOM | 1192 | N | GLY | A | 164 | 23.336 | 4.977 | 20.338 | 1.00 | 33.85 | N |
| ATOM | 1193 | CA | GLY | A | 164 | 22.832 | 5.230 | 19.009 | 1.00 | 33.55 | C |
| ATOM | 1194 | C | GLY | A | 164 | 22.874 | 6.682 | 18.548 | 1.00 | 33.11 | C |
| ATOM | 1195 | O | GLY | A | 164 | 22.361 | 6.977 | 17.471 | 1.00 | 33.36 | O |
| ATOM | 1196 | N | PHE | A | 165 | 23.443 | 7.589 | 19.341 | 1.00 | 32.16 | N |
| ATOM | 1197 | CA | PHE | A | 165 | 23.593 | 8.964 | 18.894 | 1.00 | 31.85 | C |
| ATOM | 1198 | C | PHE | A | 165 | 24.628 | 8.972 | 17.752 | 1.00 | 30.93 | C |
| ATOM | 1199 | O | PHE | A | 165 | 25.413 | 8.063 | 17.650 | 1.00 | 30.67 | O |
| ATOM | 1200 | CB | PHE | A | 165 | 24.028 | 9.883 | 20.055 | 1.00 | 32.06 | C |
| ATOM | 1201 | CG | PHE | A | 165 | 22.989 | 10.052 | 21.160 | 1.00 | 32.55 | C |
| ATOM | 1202 | CD1 | PHE | A | 165 | 21.734 | 9.478 | 21.081 | 1.00 | 33.69 | C |
| ATOM | 1203 | CD2 | PHE | A | 165 | 23.293 | 10.786 | 22.289 | 1.00 | 32.64 | C |
| ATOM | 1204 | CE1 | PHE | A | 165 | 20.817 | 9.646 | 22.106 | 1.00 | 33.39 | C |
| ATOM | 1205 | CE2 | PHE | A | 165 | 22.380 | 10.948 | 23.308 | 1.00 | 32.11 | C |
| ATOM | 1206 | CZ | PHE | A | 165 | 21.150 | 10.380 | 23.218 | 1.00 | 32.69 | C |
| ATOM | 1207 | N | ASN | A | 166 | 24.600 | 9.977 | 16.881 | 1.00 | 30.43 | N |
| ATOM | 1208 | CA | ASN | A | 166 | 25.552 | 10.106 | 15.761 | 1.00 | 30.00 | C |
| ATOM | 1209 | C | ASN | A | 166 | 26.932 | 10.623 | 16.177 | 1.00 | 29.91 | C |
| ATOM | 1210 | O | ASN | A | 166 | 27.370 | 11.721 | 15.812 | 1.00 | 28.90 | O |
| ATOM | 1211 | CB | ASN | A | 166 | 24.957 | 11.013 | 14.673 | 1.00 | 29.86 | C |
| ATOM | 1212 | CG | ASN | A | 166 | 25.720 | 10.957 | 13.363 | 1.00 | 28.91 | C |
| ATOM | 1213 | OD1 | ASN | A | 166 | 26.836 | 10.423 | 13.282 | 1.00 | 27.68 | O |
| ATOM | 1214 | ND2 | ASN | A | 166 | 25.119 | 11.528 | 12.320 | 1.00 | 26.76 | N |
| ATOM | 1215 | N | TRP | A | 167 | 27.604 | 9.785 | 16.943 | 1.00 | 30.04 | N |
| ATOM | 1216 | CA | TRP | A | 167 | 28.938 | 10.044 | 17.399 | 1.00 | 30.41 | C |
| ATOM | 1217 | C | TRP | A | 167 | 29.823 | 10.295 | 16.205 | 1.00 | 30.80 | C |
| ATOM | 1218 | O | TRP | A | 167 | 30.708 | 11.141 | 16.237 | 1.00 | 30.55 | O |
| ATOM | 1219 | CB | TRP | A | 167 | 29.390 | 8.847 | 18.232 | 1.00 | 30.31 | C |
| ATOM | 1220 | CG | TRP | A | 167 | 28.513 | 8.746 | 19.433 | 1.00 | 30.59 | C |
| ATOM | 1221 | CD1 | TRP | A | 167 | 27.594 | 7.792 | 19.699 | 1.00 | 30.51 | C |
| ATOM | 1222 | CD2 | TRP | A | 167 | 28.422 | 9.696 | 20.502 | 1.00 | 31.94 | C |
| ATOM | 1223 | NE1 | TRP | A | 167 | 26.947 | 8.067 | 20.881 | 1.00 | 30.98 | N |
| ATOM | 1224 | CE2 | TRP | A | 167 | 27.442 | 9.232 | 21.395 | 1.00 | 31.41 | C |
| ATOM | 1225 | CE3 | TRP | A | 167 | 29.087 | 10.885 | 20.801 | 1.00 | 31.71 | C |
| ATOM | 1226 | CZ2 | TRP | A | 167 | 27.112 | 9.904 | 22.554 | 1.00 | 32.59 | C |
| ATOM | 1227 | CZ3 | TRP | A | 167 | 28.750 | 11.560 | 21.944 | 1.00 | 32.92 | C |
| ATOM | 1228 | CE2 | TRP | A | 167 | 27.773 | 11.072 | 22.811 | 1.00 | 33.34 | C |
| ATOM | 1229 | N | ASN | A | 168 | 29.549 | 9.596 | 15.119 | 1.00 | 31.69 | N |
| ATOM | 1230 | CA | ASN | A | 168 | 30.352 | 9.771 | 13.936 | 1.00 | 32.37 | C |

TABLE 3-continued

Coordinates for structures 1 to 4

| ATOM | 1231 | C | ASN | A | 168 | 30.447 | 11.229 | 13.590 | 1.00 | 32.97 | C |
|------|------|------|-----|---|-----|--------|--------|--------|------|-------|---|
| ATOM | 1232 | O | ASN | A | 168 | 31.541 | 11.747 | 13.390 | 1.00 | 33.15 | O |
| ATOM | 1233 | CB | ASN | A | 168 | 29.729 | 9.064 | 12.749 | 1.00 | 32.68 | C |
| ATOM | 1234 | CG | ASN | A | 168 | 30.594 | 9.147 | 11.507 | 1.00 | 32.86 | C |
| ATOM | 1235 | OD1 | ASN | A | 168 | 31.797 | 8.914 | 11.574 | 1.00 | 35.02 | O |
| ATOM | 1236 | ND2 | ASN | A | 168 | 29.989 | 9.473 | 10.368 | 1.00 | 31.39 | N |
| ATOM | 1237 | N | TRP | A | 169 | 29.284 | 11.884 | 13.518 | 1.00 | 33.38 | N |
| ATOM | 1238 | CA | TRP | A | 169 | 29.200 | 13.279 | 13.107 | 1.00 | 33.28 | C |
| ATOM | 1239 | C | TRP | A | 169 | 29.711 | 14.237 | 14.149 | 1.00 | 33.33 | C |
| ATOM | 1240 | O | TRP | A | 169 | 30.406 | 15.188 | 13.834 | 1.00 | 33.43 | O |
| ATOM | 1241 | CB | TRP | A | 169 | 27.756 | 13.673 | 12.765 | 1.00 | 33.43 | C |
| ATOM | 1242 | CG | TRP | A | 169 | 27.618 | 15.134 | 12.412 | 1.00 | 33.11 | C |
| ATOM | 1243 | CD1 | TRP | A | 169 | 27.814 | 15.698 | 11.191 | 1.00 | 33.49 | C |
| ATOM | 1244 | CD2 | TRP | A | 169 | 27.293 | 16.205 | 13.294 | 1.00 | 32.94 | C |
| ATOM | 1245 | NE1 | TRP | A | 169 | 27.629 | 17.056 | 11.251 | 1.00 | 33.21 | N |
| ATOM | 1246 | CE2 | TRP | A | 169 | 27.306 | 17.397 | 12.533 | 1.00 | 33.42 | C |
| ATOM | 1247 | CE3 | TRP | A | 169 | 26.994 | 16.284 | 14.655 | 1.00 | 33.15 | C |
| ATOM | 1248 | CZ2 | TRP | A | 169 | 27.026 | 18.648 | 13.081 | 1.00 | 33.66 | C |
| ATOM | 1249 | CZ3 | TRP | A | 169 | 26.719 | 17.526 | 15.204 | 1.00 | 34.02 | C |
| ATOM | 1250 | CH2 | TRP | A | 169 | 26.733 | 18.695 | 14.413 | 1.00 | 34.21 | C |
| ATOM | 1251 | N | ILE | A | 170 | 29.369 | 14.021 | 15.398 | 1.00 | 33.54 | N |
| ATOM | 1252 | CA | ILE | A | 170 | 29.739 | 15.024 | 16.368 | 1.00 | 33.92 | C |
| ATOM | 1253 | C | ILE | A | 170 | 31.225 | 14.935 | 16.713 | 1.00 | 34.07 | C |
| ATOM | 1254 | O | ILE | A | 170 | 31.855 | 15.939 | 16.988 | 1.00 | 34.23 | O |
| ATOM | 1255 | CB | ILE | A | 170 | 28.832 | 14.947 | 17.591 | 1.00 | 33.84 | C |
| ATOM | 1256 | CG1 | ILE | A | 170 | 28.803 | 16.288 | 18.306 | 1.00 | 34.22 | C |
| ATOM | 1257 | CG2 | ILE | A | 170 | 29.295 | 13.858 | 18.499 | 1.00 | 34.45 | C |
| ATOM | 1258 | CD1 | ILE | A | 170 | 27.869 | 16.309 | 19.478 | 1.00 | 34.73 | C |
| ATOM | 1259 | N | ASN | A | 171 | 31.801 | 13.743 | 16.650 | 1.00 | 34.41 | N |
| ATOM | 1260 | CA | ASN | A | 171 | 33.222 | 13.593 | 16.950 | 1.00 | 34.46 | C |
| ATOM | 1261 | C | ASN | A | 171 | 34.055 | 14.322 | 15.918 | 1.00 | 34.56 | C |
| ATOM | 1262 | O | ASN | A | 171 | 35.055 | 14.949 | 16.260 | 1.00 | 34.66 | O |
| ATOM | 1263 | CB | ASN | A | 171 | 33.632 | 12.116 | 16.996 | 1.00 | 34.47 | C |
| ATOM | 1264 | CG | ASN | A | 171 | 32.969 | 11.356 | 18.128 | 1.00 | 33.99 | C |
| ATOM | 1265 | OD1 | ASN | A | 171 | 32.391 | 11.951 | 19.031 | 1.00 | 35.35 | O |
| ATOM | 1266 | ND2 | ASN | A | 171 | 33.040 | 10.036 | 18.077 | 1.00 | 32.53 | N |
| ATOM | 1267 | N | LYS | A | 172 | 33.652 | 14.217 | 14.654 | 1.00 | 34.75 | N |
| ATOM | 1268 | CA | LYS | A | 172 | 34.337 | 14.917 | 13.584 | 1.00 | 35.18 | C |
| ATOM | 1269 | C | LYS | A | 172 | 34.261 | 16.415 | 13.907 | 1.00 | 35.29 | C |
| ATOM | 1270 | O | LYS | A | 172 | 35.248 | 17.133 | 13.800 | 1.00 | 34.89 | O |
| ATOM | 1271 | CB | LYS | A | 172 | 33.711 | 14.600 | 12.216 | 1.00 | 35.26 | C |
| ATOM | 1272 | CG | LYS | A | 172 | 34.200 | 13.299 | 11.587 | 1.00 | 36.55 | C |
| ATOM | 1273 | CD | LYS | A | 172 | 33.873 | 13.158 | 10.090 | 1.00 | 38.20 | C |
| ATOM | 1274 | CE | LYS | A | 172 | 34.512 | 11.872 | 9.537 | 1.00 | 39.82 | C |
| ATOM | 1275 | NZ | LYS | A | 172 | 34.369 | 11.661 | 8.050 | 1.00 | 41.20 | N |
| ATOM | 1276 | N | GLN | A | 173 | 33.093 | 16.875 | 14.339 | 1.00 | 35.70 | N |
| ATOM | 1277 | CA | GLN | A | 173 | 32.931 | 18.272 | 14.699 | 1.00 | 36.20 | C |
| ATOM | 1278 | C | GLN | A | 173 | 33.929 | 18.633 | 15.771 | 1.00 | 36.47 | C |
| ATOM | 1279 | O | GLN | A | 173 | 34.605 | 19.656 | 15.686 | 1.00 | 36.97 | O |
| ATOM | 1280 | CB | GLN | A | 173 | 31.534 | 18.555 | 15.231 | 1.00 | 36.19 | C |
| ATOM | 1281 | CG | GLN | A | 173 | 30.473 | 18.637 | 14.167 | 1.00 | 36.97 | C |
| ATOM | 1282 | CD | GLN | A | 173 | 30.765 | 19.720 | 13.157 | 1.00 | 37.19 | C |
| ATOM | 1283 | OE1 | GLN | A | 173 | 31.198 | 20.808 | 13.531 | 1.00 | 38.68 | O |
| ATOM | 1284 | NE2 | GLN | A | 173 | 30.551 | 19.425 | 11.879 | 1.00 | 35.94 | N |
| ATOM | 1285 | N | GLN | A | 174 | 34.000 | 17.806 | 16.802 | 1.00 | 36.38 | N |
| ATOM | 1286 | CA | GLN | A | 174 | 34.945 | 18.041 | 17.866 | 1.00 | 36.42 | C |
| ATOM | 1287 | C | GLN | A | 174 | 36.360 | 18.102 | 17.283 | 1.00 | 36.56 | C |
| ATOM | 1288 | O | GLN | A | 174 | 37.161 | 18.945 | 17.672 | 1.00 | 36.42 | O |
| ATOM | 1289 | CB | GLN | A | 174 | 34.815 | 16.937 | 18.912 | 1.00 | 36.33 | C |
| ATOM | 1290 | CG | GLN | A | 174 | 35.896 | 16.908 | 19.963 | 1.00 | 36.13 | C |
| ATOM | 1291 | CD | GLN | A | 174 | 35.785 | 15.676 | 20.815 | 1.00 | 36.16 | C |
| ATOM | 1292 | OE1 | GLN | A | 174 | 35.415 | 14.613 | 20.314 | 1.00 | 37.84 | O |
| ATOM | 1293 | NE2 | GLN | A | 174 | 36.082 | 15.803 | 22.103 | 1.00 | 34.98 | N |
| ATOM | 1294 | N | GLY | A | 175 | 36.649 | 17.231 | 16.322 | 1.00 | 36.76 | N |
| ATOM | 1295 | CA | GLY | A | 175 | 37.976 | 17.158 | 15.750 | 1.00 | 36.97 | C |
| ATOM | 1296 | C | GLY | A | 175 | 38.302 | 18.356 | 14.892 | 1.00 | 37.21 | C |
| ATOM | 1297 | O | GLY | A | 175 | 39.336 | 18.993 | 15.070 | 1.00 | 37.38 | O |
| ATOM | 1298 | N | LYS | A | 176 | 37.406 | 18.682 | 13.971 | 1.00 | 37.44 | N |
| ATOM | 1299 | CA | LYS | A | 176 | 37.634 | 19.793 | 13.064 | 1.00 | 37.56 | C |
| ATOM | 1300 | C | LYS | A | 176 | 37.898 | 21.090 | 13.822 | 1.00 | 37.47 | C |
| ATOM | 1301 | O | LYS | A | 176 | 38.713 | 21.907 | 13.400 | 1.00 | 37.47 | O |
| ATOM | 1302 | CB | LYS | A | 176 | 36.423 | 20.014 | 12.161 | 1.00 | 37.71 | C |
| ATOM | 1303 | CG | LYS | A | 176 | 36.134 | 18.905 | 11.163 | 1.00 | 38.70 | C |
| ATOM | 1304 | CD | LYS | A | 176 | 34.960 | 19.284 | 10.279 | 1.00 | 39.76 | C |
| ATOM | 1305 | CE | LYS | A | 176 | 34.064 | 18.092 | 10.037 | 1.00 | 41.48 | C |
| ATOM | 1306 | NZ | LYS | A | 176 | 32.663 | 18.481 | 9.690 | 1.00 | 43.43 | N |
| ATOM | 1307 | N | ARG | A | 177 | 37.212 | 21.283 | 14.938 | 1.00 | 37.10 | N |

TABLE 3-continued

Coordinates for structures 1 to 4

| ATOM | 1308 | CA  | ARG | A | 177 | 37.325 | 22.544 | 15.643 | 1.00 | 37.08 | C |
| ---- | ---- | --- | --- | - | --- | ------ | ------ | ------ | ---- | ----- | - |
| ATOM | 1309 | C   | ARG | A | 177 | 38.352 | 22.495 | 16.763 | 1.00 | 36.85 | C |
| ATOM | 1310 | O   | ARG | A | 177 | 38.445 | 23.420 | 17.564 | 1.00 | 36.21 | O |
| ATOM | 1311 | CB  | ARG | A | 177 | 35.980 | 22.969 | 16.228 | 1.00 | 37.21 | C |
| ATOM | 1312 | CG  | ARG | A | 177 | 34.807 | 22.773 | 15.326 | 1.00 | 37.50 | C |
| ATOM | 1313 | CD  | ARG | A | 177 | 34.802 | 23.591 | 14.053 | 1.00 | 38.49 | C |
| ATOM | 1314 | NE  | ARG | A | 177 | 33.750 | 23.066 | 13.185 | 1.00 | 39.56 | N |
| ATOM | 1315 | CZ  | ARG | A | 177 | 33.884 | 22.803 | 11.891 | 1.00 | 41.17 | C |
| ATOM | 1316 | NH1 | ARG | A | 177 | 35.026 | 23.050 | 11.254 | 1.00 | 41.34 | N |
| ATOM | 1317 | NH2 | ARG | A | 177 | 32.855 | 22.304 | 11.219 | 1.00 | 41.89 | N |
| ATOM | 1318 | N   | GLY | A | 178 | 39.088 | 21.401 | 16.859 | 1.00 | 36.70 | N |
| ATOM | 1319 | CA  | GLY | A | 178 | 40.131 | 21.337 | 17.854 | 1.00 | 36.74 | C |
| ATOM | 1320 | C   | GLY | A | 178 | 39.592 | 21.509 | 19.249 | 1.00 | 36.76 | C |
| ATOM | 1321 | O   | GLY | A | 178 | 40.340 | 21.817 | 20.171 | 1.00 | 37.18 | O |
| ATOM | 1322 | N   | TRP | A | 179 | 38.293 | 21.331 | 19.420 | 1.00 | 36.75 | N |
| ATOM | 1323 | CA  | TRP | A | 179 | 37.722 | 21.439 | 20.745 | 1.00 | 36.66 | C |
| ATOM | 1324 | C   | TRP | A | 179 | 38.309 | 20.400 | 21.679 | 1.00 | 36.60 | C |
| ATOM | 1325 | O   | TRP | A | 179 | 38.980 | 19.451 | 21.260 | 1.00 | 35.99 | O |
| ATOM | 1326 | CB  | TRP | A | 179 | 36.222 | 21.216 | 20.708 | 1.00 | 36.79 | C |
| ATOM | 1327 | CG  | TRP | A | 179 | 35.454 | 22.258 | 20.038 | 1.00 | 36.51 | C |
| ATOM | 1328 | CD1 | TRP | A | 179 | 35.889 | 23.470 | 19.620 | 1.00 | 36.67 | C |
| ATOM | 1329 | CD2 | TRP | A | 179 | 34.081 | 22.180 | 19.692 | 1.00 | 37.40 | C |
| ATOM | 1330 | NE1 | TRP | A | 179 | 34.860 | 24.168 | 19.035 | 1.00 | 36.91 | N |
| ATOM | 1331 | CE2 | TRP | A | 179 | 33.735 | 23.390 | 19.062 | 1.00 | 37.43 | C |
| ATOM | 1332 | CE3 | TRP | A | 179 | 33.099 | 21.198 | 19.840 | 1.00 | 36.64 | C |
| ATOM | 1333 | CZ2 | TRP | A | 179 | 32.456 | 23.641 | 18.583 | 1.00 | 36.83 | C |
| ATOM | 1334 | CZ3 | TRP | A | 179 | 31.840 | 21.450 | 19.365 | 1.00 | 36.84 | C |
| ATOM | 1335 | CH2 | TRP | A | 179 | 31.524 | 22.661 | 18.744 | 1.00 | 36.02 | C |
| ATOM | 1336 | N   | GLY | A | 180 | 38.022 | 20.595 | 22.958 | 1.00 | 36.66 | N |
| ATOM | 1337 | CA  | GLY | A | 180 | 38.444 | 19.681 | 23.992 | 1.00 | 36.96 | C |
| ATOM | 1338 | C   | GLY | A | 180 | 37.456 | 18.548 | 24.131 | 1.00 | 37.25 | C |
| ATOM | 1339 | O   | GLY | A | 180 | 36.698 | 18.285 | 23.204 | 1.00 | 37.69 | O |
| ATOM | 1340 | N   | GLN | A | 181 | 37.445 | 17.891 | 25.288 | 1.00 | 37.46 | N |
| ATOM | 1341 | CA  | GLN | A | 181 | 36.581 | 16.734 | 25.507 | 1.00 | 37.81 | C |
| ATOM | 1342 | C   | GLN | A | 181 | 35.136 | 17.088 | 25.802 | 1.00 | 37.40 | C |
| ATOM | 1343 | O   | GLN | A | 181 | 34.825 | 18.177 | 26.273 | 1.00 | 37.59 | O |
| ATOM | 1344 | CB  | GLN | A | 181 | 37.082 | 15.881 | 26.680 | 1.00 | 38.18 | C |
| ATOM | 1345 | CG  | GLN | A | 181 | 36.684 | 16.433 | 28.065 | 1.00 | 40.32 | C |
| ATOM | 1346 | CD  | GLN | A | 181 | 36.956 | 15.470 | 29.231 | 1.00 | 43.44 | C |
| ATOM | 1347 | OE1 | LN  | A | 181 | 38.004 | 14.802 | 29.284 | 1.00 | 44.84 | O |
| ATOM | 1348 | NE2 | GLN | A | 181 | 36.007 | 15.406 | 30.173 | 1.00 | 44.80 | N |
| ATOM | 1349 | N   | LEU | A | 182 | 34.266 | 16.130 | 25.510 | 1.00 | 37.00 | N |
| ATOM | 1350 | CA  | LEU | A | 182 | 32.866 | 16.181 | 25.878 | 1.00 | 36.47 | C |
| ATOM | 1351 | C   | LEU | A | 182 | 32.856 | 16.224 | 27.385 | 1.00 | 35.97 | C |
| ATOM | 1352 | O   | LEU | A | 182 | 33.345 | 15.298 | 28.009 | 1.00 | 35.98 | O |
| ATOM | 1353 | GB  | LEU | A | 182 | 32.208 | 14.865 | 25.468 | 1.00 | 36.38 | C |
| ATOM | 1354 | CG  | LEU | A | 182 | 30.691 | 14.707 | 25.336 | 1.00 | 36.76 | C |
| ATOM | 1355 | CD1 | LEU | A | 182 | 30.339 | 13.254 | 25.433 | 1.00 | 36.70 | C |
| ATOM | 1356 | CD2 | LEU | A | 182 | 29.917 | 15.417 | 26.376 | 1.00 | 37.66 | C |
| ATOM | 1357 | N   | THR | A | 183 | 32.337 | 17.270 | 28.005 | 1.00 | 35.50 | N |
| ATOM | 1358 | CA  | THR | A | 183 | 32.310 | 17.230 | 29.457 | 1.00 | 35.07 | C |
| ATOM | 1359 | C   | THR | A | 183 | 31.008 | 16.669 | 29.929 | 1.00 | 34.39 | C |
| ATOM | 1360 | O   | THR | A | 183 | 30.944 | 16.097 | 31.000 | 1.00 | 34.13 | O |
| ATOM | 1361 | GB  | THR | A | 183 | 32.528 | 18.599 | 30.105 | 1.00 | 35.07 | C |
| ATOM | 1362 | OG1 | THR | A | 183 | 31.402 | 19.444 | 29.883 | 1.00 | 35.21 | O |
| ATOM | 1363 | CG2 | THR | A | 183 | 33.652 | 19.310 | 29.453 | 1.00 | 35.76 | C |
| ATOM | 1364 | N   | SER | A | 184 | 29.947 | 16.848 | 29.163 | 1.00 | 33.83 | N |
| ATOM | 1365 | CA  | SER | A | 184 | 28.710 | 16.288 | 29.626 | 1.00 | 33.19 | C |
| ATOM | 1366 | C   | SER | A | 184 | 27.563 | 16.459 | 28.684 | 1.00 | 32.72 | C |
| ATOM | 1367 | O   | SER | A | 184 | 27.643 | 17.172 | 27.699 | 1.00 | 32.59 | O |
| ATOM | 1368 | GB  | SER | A | 184 | 28.363 | 16.954 | 30.949 | 1.00 | 33.18 | C |
| ATOM | 1369 | OG  | SER | A | 184 | 28.349 | 18.347 | 30.788 | 1.00 | 31.82 | O |
| ATOM | 1370 | N   | ASN | A | 185 | 26.484 | 15.776 | 29.013 | 1.00 | 32.44 | N |
| ATOM | 1371 | CA  | ASN | A | 185 | 25.259 | 15.893 | 28.077 | 1.00 | 32.59 | C |
| ATOM | 1372 | C   | ASN | A | 185 | 24.218 | 16.117 | 29.319 | 1.00 | 33.00 | C |
| ATOM | 1373 | O   | ASN | A | 185 | 24.027 | 15.285 | 30.184 | 1.00 | 32.72 | O |
| ATOM | 1374 | CB  | ASN | A | 185 | 24.917 | 14.619 | 27.520 | 1.00 | 32.46 | C |
| ATOM | 1375 | CG  | ASN | A | 185 | 25.850 | 14.351 | 26.369 | 1.00 | 31.69 | C |
| ATOM | 1376 | OD1 | ASN | A | 185 | 26.661 | 13.436 | 26.434 | 1.00 | 32.60 | O |
| ATOM | 1377 | ND2 | ASN | A | 185 | 25.725 | 15.121 | 25.297 | 1.00 | 29.86 | N |
| ATOM | 1378 | N   | LEU | A | 186 | 23.549 | 17.252 | 29.258 | 1.00 | 33.80 | N |
| ATOM | 1379 | CA  | LEU | A | 186 | 22.537 | 17.536 | 30.241 | 1.00 | 34.36 | C |
| ATOM | 1380 | C   | LEU | A | 186 | 21.199 | 17.117 | 29.684 | 1.00 | 34.78 | C |
| ATOM | 1381 | O   | LEU | A | 186 | 20.903 | 17.380 | 28.512 | 1.00 | 35.02 | O |
| ATOM | 1382 | GB  | LEU | A | 186 | 22.500 | 19.029 | 30.539 | 1.00 | 34.34 | C |
| ATOM | 1383 | CG  | LEU | A | 186 | 21.564 | 19.433 | 31.677 | 1.00 | 35.25 | C |
| ATOM | 1384 | CD1 | LEU | A | 186 | 22.122 | 18.827 | 32.930 | 1.00 | 35.58 | C |

TABLE 3-continued

| | | | | | | | | | | | |
|---|---|---|---|---|---|---|---|---|---|---|---|
| \multicolumn{12}{|c|}{Coordinates for structures 1 to 4} |
| ATOM | 1385 | CD2 | LEU | A | 186 | 21.402 | 20.956 | 31.845 | 1.00 | 35.43 | C |
| ATOM | 1386 | N | LEU | A | 187 | 20.393 | 16.456 | 30.507 | 1.00 | 34.95 | N |
| ATOM | 1387 | CA | LEU | A | 187 | 19.022 | 16.189 | 30.120 | 1.00 | 35.27 | C |
| ATOM | 1388 | C | LEU | A | 187 | 18.117 | 17.260 | 30.735 | 1.00 | 35.48 | C |
| ATOM | 1389 | O | LEU | A | 187 | 18.105 | 17.449 | 31.951 | 1.00 | 35.40 | O |
| ATOM | 1390 | CE | LEU | A | 187 | 18.593 | 14.805 | 30.563 | 1.00 | 35.33 | C |
| ATOM | 1391 | CG | LEU | A | 187 | 17.105 | 14.481 | 30.399 | 1.00 | 36.09 | C |
| ATOM | 1392 | CD1 | LEU | A | 187 | 16.624 | 14.525 | 28.969 | 1.00 | 36.40 | C |
| ATOM | 1393 | CD2 | LEU | A | 187 | 16.850 | 13.114 | 30.940 | 1.00 | 36.96 | C |
| ATOM | 1394 | N | LEU | A | 188 | 17.380 | 17.977 | 29.889 | 1.00 | 35.70 | N |
| ATOM | 1395 | CA | LEU | A | 188 | 16.466 | 19.005 | 30.362 | 1.00 | 35.89 | C |
| ATOM | 1396 | C | LEU | A | 188 | 15.047 | 18.668 | 29.972 | 1.00 | 36.32 | C |
| ATOM | 1397 | O | LEU | A | 188 | 14.738 | 18.548 | 28.792 | 1.00 | 36.89 | O |
| ATOM | 1398 | GB | LEU | A | 188 | 16.795 | 20.362 | 29.771 | 1.00 | 35.79 | C |
| ATOM | 1399 | CG | LEU | A | 188 | 18.210 | 20.889 | 29.937 | 1.00 | 35.66 | C |
| ATOM | 1400 | CD1 | LEU | A | 188 | 18.976 | 20.745 | 28.668 | 1.00 | 36.04 | C |
| ATOM | 1401 | CD2 | LEU | A | 188 | 18.125 | 22.328 | 30.284 | 1.00 | 35.23 | C |
| ATOM | 1402 | N | ILE | A | 189 | 14.184 | 18.514 | 30.967 | 1.00 | 36.45 | N |
| ATOM | 1403 | CA | ILE | A | 189 | 12.782 | 18.254 | 30.720 | 1.00 | 36.25 | C |
| ATOM | 1404 | C | ILE | A | 189 | 12.105 | 19.353 | 31.472 | 1.00 | 35.88 | C |
| ATOM | 1405 | O | ILE | A | 189 | 12.388 | 19.542 | 32.651 | 1.00 | 35.75 | O |
| ATOM | 1406 | GB | ILE | A | 189 | 12.368 | 16.916 | 31.274 | 1.00 | 36.47 | C |
| ATOM | 1407 | CG1 | ILE | A | 189 | 13.126 | 15.813 | 30.549 | 1.00 | 36.63 | C |
| ATOM | 1408 | CG2 | ILE | A | 189 | 10.865 | 16.748 | 31.143 | 1.00 | 36.55 | C |
| ATOM | 1409 | CD1 | ILE | A | 189 | 12.884 | 14.440 | 31.129 | 1.00 | 36.11 | C |
| ATOM | 1410 | N | GLY | A | 190 | 11.221 | 20.071 | 30.789 | 1.00 | 35.53 | N |
| ATOM | 1411 | CA | GLY | A | 190 | 10.614 | 21.257 | 31.344 | 1.00 | 35.37 | C |
| ATOM | 1412 | C | GLY | A | 190 | 9.184 | 21.420 | 30.921 | 1.00 | 35.23 | C |
| ATOM | 1413 | O | GLY | A | 190 | 8.748 | 20.857 | 29.930 | 1.00 | 35.26 | O |
| ATOM | 1414 | N | MET | A | 192. | 8.458 | 22.208 | 31.696 | 1.00 | 35.18 | N |
| ATOM | 1415 | CA | MET | A | 191 | 7.063 | 22.463 | 31.447 | 1.00 | 35.16 | C |
| ATOM | 1416 | C | MET | A | 191 | 6.916 | 23.584 | 30.446 | 1.00 | 35.00 | C |
| ATOM | 1417 | O | MET | A | 191 | 7.795 | 24.426 | 30.316 | 1.00 | 35.17 | O |
| ATOM | 1418 | CB | MET | A | 191 | 6.379 | 22.849 | 32.750 | 1.00 | 35.13 | C |
| ATOM | 1419 | CG | MET | A | 191 | 6.277 | 21.691 | 33.710 | 1.00 | 35.63 | C |
| ATOM | 1420 | SD | MET | A | 191 | 5.756 | 22.150 | 35.360 | 1.00 | 35.65 | S |
| ATOM | 1421 | CE | MET | A | 191 | 4.222 | 22.827 | 35.017 | 1.00 | 36.16 | C |
| ATOM | 1422 | N | GLU | A | 192 | 5.804 | 23.573 | 29.727 | 1.00 | 34.83 | N |
| ATOM | 1423 | CA | GLU | A | 192 | 5.492 | 24.626 | 28.791 | 1.00 | 34.74 | C |
| ATOM | 1424 | C | GLtI | A | 192 | 5.585 | 25.955 | 29.511 | 1.00 | 34.72 | C |
| ATOM | 1425 | O | GLU | A | 192 | 5.184 | 26.067 | 30.674 | 1.00 | 34.67 | O |
| ATOM | 1426 | CB | GLU | A | 192 | 4.085 | 24.447 | 28.264 | 1.00 | 34.75 | C |
| ATOM | 1427 | CG | GLU | A | 192 | 3.029 | 24.525 | 29.348 | 1.00 | 35.09 | C |
| ATOM | 1428 | CD | GLU | A | 192 | 1.669 | 24.117 | 28.842 | 1.00 | 34.97 | C |
| ATOM | 1429 | OE1 | GLU | A | 192 | 1.609 | 23.503 | 27.756 | 1.00 | 33.58 | O |
| ATOM | 1430 | OE2 | GLU | A | 192 | 0.672 | 24.422 | 29.530 | 1.00 | 35.72 | O |
| ATOM | 1431 | N | GLY | A | 193 | 6.121 | 26.953 | 28.818 | 1.00 | 34.53 | N |
| ATOM | 1432 | CA | GLY | A | 193 | 6.265 | 28.279 | 29.378 | 1.00 | 34.63 | C |
| ATOM | 1433 | C | GLY | A | 193 | 7.528 | 28.542 | 30.180 | 1.00 | 34.49 | C |
| ATOM | 1434 | O | GLY | A | 193 | 7.864 | 29.694 | 30.434 | 1.00 | 34.57 | O |
| ATOM | 1435 | N | ASN | A | 194 | 8.224 | 27.493 | 30.594 | 1.00 | 34.27 | N |
| ATOM | 1436 | CA | ASN | A | 194 | 9.441 | 27.672 | 31.367 | 1.00 | 34.06 | C |
| ATOM | 1437 | C | ASN | A | 194 | 10.466 | 28.492 | 30.609 | 1.00 | 33.93 | C |
| ATOM | 1438 | O | ASN | A | 194 | 10.552 | 28.415 | 29.392 | 1.00 | 33.84 | O |
| ATOM | 1439 | CB | ASN | A | 194 | 10.051 | 26.316 | 31.721 | 1.00 | 33.99 | C |
| ATOM | 1440 | CG | ASN | A | 194 | 9.314 | 25.625 | 32.836 | 1.00 | 33.19 | C |
| ATOM | 1441 | OD1 | ASN | A | 194 | 8.257 | 26.081 | 33.265 | 1.00 | 33.07 | O |
| ATOM | 1442 | ND2 | ASN | A | 194 | 9.869 | 24.528 | 33.323 | 1.00 | 31.93 | N |
| ATOM | 1443 | N | VAL | A | 195 | 11.243 | 29.285 | 31.332 | 1.00 | 33.86 | N |
| ATOM | 1444 | CA | VAL | A | 195 | 12.288 | 30.069 | 30.707 | 1.00 | 33.70 | C |
| ATOM | 1445 | C | VAL | A | 195 | 13.621 | 29.969 | 31.396 | 1.00 | 33.38 | C |
| ATOM | 1446 | O | VAL | A | 195 | 13.721 | 30.115 | 32.601 | 1.00 | 33.75 | O |
| ATOM | 1447 | CB | VAL | A | 195 | 11.964 | 31.552 | 30.779 | 1.00 | 33.96 | C |
| ATOM | 1448 | CG1 | VAL | A | 195 | 13.151 | 32.389 | 30.253 | 1.00 | 34.32 | C |
| ATOM | 1449 | CG2 | VAL | A | 195 | 10.693 | 31.854 | 30.032 | 1.00 | 34.15 | C |
| ATOM | 1450 | N | THR | A | 196 | 14.666 | 29.764 | 30.621 | 1.00 | 33.04 | N |
| ATOM | 1451 | CA | THR | A | 196 | 15.991 | 29.883 | 31.161 | 1.00 | 32.60 | C |
| ATOM | 1452 | C | THR | A | 196 | 16.438 | 31.256 | 30.723 | 1.00 | 32.21 | C |
| ATOM | 1453 | O | THR | A | 196 | 16.584 | 31.500 | 29.530 | 1.00 | 31.64 | O |
| ATOM | 1454 | CB | THR | A | 196 | 16.887 | 28.836 | 30.586 | 1.00 | 32.68 | C |
| ATOM | 1455 | OG1 | THR | A | 196 | 16.466 | 27.543 | 31.048 | 1.00 | 33.09 | O |
| ATOM | 1456 | CG2 | THR | A | 196 | 18.281 | 29.003 | 31.124 | 1.00 | 32.63 | C |
| ATOM | 1457 | N | PRO | A | 197 | 16.585 | 32.177 | 31.672 | 1.00 | 31.97 | N |
| ATOM | 1458 | CA | PRO | A | 197 | 17.000 | 33.530 | 31.350 | 1.00 | 31.74 | C |
| ATOM | 1459 | C | PRO | A | 197 | 18.385 | 33.564 | 30.816 | 1.00 | 31.92 | C |
| ATOM | 1460 | O | PRO | A | 197 | 19.215 | 32.717 | 31.129 | 1.00 | 32.52 | O |
| ATOM | 1461 | CB | PRO | A | 197 | 16.950 | 34.234 | 32.682 | 1.00 | 31.38 | C |

TABLE 3-continued

| | | | | | | | | | | | |
|---|---|---|---|---|---|---|---|---|---|---|---|
| | Coordinates for structures 1 to 4 |

| ATOM | 1462 | CG | PRO | A | 197 | 16.056 | 33.508 | 33.418 | 1.00 | 31.84 | C |
| ATOM | 1463 | CD | PRO | A | 197 | 16.305 | 32.055 | 33.107 | 1.00 | 32.08 | C |
| ATOM | 1464 | N | ALA | A | 198 | 18.615 | 34.592 | 30.024 | 1.00 | 32.06 | N |
| ATOM | 1465 | CA | ALA | A | 198 | 19.846 | 34.787 | 29.311 | 1.00 | 32.28 | C |
| ATOM | 1466 | C | ALA | A | 198 | 21.101 | 34.690 | 30.162 | 1.00 | 32.42 | C |
| ATOM | 1467 | O | ALA | A | 198 | 21.213 | 35.305 | 31.220 | 1.00 | 32.03 | O |
| ATOM | 1468 | CB | ALA | A | 198 | 19.798 | 36.131 | 28.625 | 1.00 | 32.42 | C |
| ATOM | 1469 | N | HIS | A | 199 | 22.064 | 33.953 | 29.630 | 1.00 | 32.77 | N |
| ATOM | 1470 | CA | HIS | A | 199 | 23.339 | 33.737 | 30.271 | 1.00 | 33.31 | C |
| ATOM | 1471 | C | HIS | A | 199 | 24.308 | 33.252 | 29.220 | 1.00 | 33.76 | C |
| ATOM | 1472 | O | HIS | A | 199 | 23.902 | 33.013 | 28.084 | 1.00 | 34.10 | O |
| ATOM | 1473 | CB | HIS | A | 199 | 23.194 | 32.622 | 31.275 | 1.00 | 33.24 | C |
| ATOM | 1474 | CG | HIS | A | 199 | 22.879 | 31.311 | 30.639 | 1.00 | 32.59 | C |
| ATOM | 1475 | ND1 | HIS | A | 199 | 21.602 | 30.958 | 30.269 | 1.00 | 31.40 | N |
| ATOM | 1476 | CD2 | HIS | A | 199 | 23.679 | 30.292 | 30.253 | 1.00 | 32.85 | C |
| ATOM | 1477 | GE1 | HIS | A | 199 | 21.624 | 29.761 | 29.714 | 1.00 | 32.37 | C |
| ATOM | 1478 | ND2 | HIS | A | 199 | 22.871 | 29.330 | 29.698 | 1.00 | 32.78 | N |
| ATOM | 1479 | N | TYR | A | 200 | 25.575 | 33.093 | 29.601 | 1.00 | 34.35 | N |
| ATOM | 1480 | CA | TYR | A | 200 | 26.580 | 32.502 | 28.712 | 1.00 | 34.92 | C |
| ATOM | 1481 | C | TYR | A | 200 | 27.256 | 31.350 | 29.431 | 1.00 | 35.15 | C |
| ATOM | 1482 | O | TYR | A | 200 | 27.285 | 31.318 | 30.661 | 1.00 | 35.76 | O |
| ATOM | 1483 | CB | TYR | A | 200 | 27.599 | 33.510 | 28.175 | 1.00 | 34.90 | C |
| ATOM | 1484 | CG | TYR | A | 200 | 28.586 | 34.096 | 29.156 | 1.00 | 34.89 | C |
| ATOM | 1485 | CD1 | TYR | A | 200 | 29.825 | 33.519 | 29.359 | 1.00 | 33.02 | C |
| ATOM | 1486 | CD2 | TYR | A | 200 | 28.307 | 35.292 | 29.802 | 1.00 | 36.04 | C |
| ATOM | 1487 | CE1 | TYR | A | 200 | 30.731 | 34.079 | 30.224 | 1.00 | 33.25 | C |
| ATOM | 1488 | CE2 | TYR | A | 200 | 29.200 | 35.857 | 30.664 | 1.00 | 35.45 | C |
| ATOM | 1489 | CZ | TYR | A | 200 | 30.410 | 35.253 | 30.882 | 1.00 | 34.40 | C |
| ATOM | 1490 | OH | TYR | A | 200 | 31.301 | 35.855 | 31.739 | 1.00 | 32.62 | O |
| ATOM | 1491 | N | ASP | A | 201 | 27.747 | 30.387 | 28.654 | 1.00 | 35.04 | N |
| ATOM | 1492 | CA | ASP | A | 201 | 28.386 | 29.182 | 29.182 | 1.00 | 34.82 | C |
| ATOM | 1493 | C | ASP | A | 201 | 29.818 | 29.220 | 28.652 | 1.00 | 34.87 | C |
| ATOM | 1494 | O | ASP | A | 201 | 30.047 | 29.734 | 27.588 | 1.00 | 34.81 | O |
| ATOM | 1495 | CB | ASP | A | 201 | 27.636 | 27.925 | 28.727 | 1.00 | 34.49 | C |
| ATOM | 1496 | CG | ASP | A | 201 | 26.212 | 27.854 | 29.256 | 1.00 | 34.63 | C |
| ATOM | 1497 | OD1 | ASP | A | 201 | 26.046 | 27.953 | 30.480 | 1.00 | 33.52 | O |
| ATOM | 1498 | OD2 | ASP | A | 201 | 25.191 | 27.680 | 28.533 | 1.00 | 36.84 | O |
| ATOM | 1499 | N | GLU | A | 202 | 30.795 | 28.727 | 29.399 | 1.00 | 35.74 | N |
| ATOM | 1500 | CA | GLU | A | 202 | 32.176 | 28.699 | 28.899 | 1.00 | 36.38 | C |
| ATOM | 1501 | C | GLU | A | 202 | 32.528 | 27.441 | 28.126 | 1.00 | 36.30 | C |
| ATOM | 1502 | O | GLU | A | 202 | 33.679 | 27.019 | 28.126 | 1.00 | 37.04 | O |
| ATOM | 1503 | CB | GLU | A | 202 | 33.172 | 28.830 | 30.048 | 1.00 | 36.61 | C |
| ATOM | 1504 | CG | GLU | A | 202 | 33.100 | 30.185 | 30.725 | 1.00 | 37.81 | C |
| ATOM | 1505 | CD | GLU | A | 202 | 33.960 | 30.276 | 31.949 | 1.00 | 38.93 | c |
| ATOM | 1506 | OE1 | GLU | A | 202 | 33.525 | 29.783 | 33.020 | 1.00 | 39.85 | O |
| ATOM | 1507 | OE2 | GLU | A | 202 | 35.055 | 30.858 | 31.832 | 1.00 | 40.19 | O |
| ATOM | 1508 | N | GLN | A | 203 | 31.556 | 26.840 | 27.462 | 1.00 | 35.68 | N |
| ATOM | 1509 | CA | GLN | A | 203 | 31.815 | 25.643 | 26.718 | 1.00 | 35.24 | C |
| ATOM | 1510 | C | GLN | A | 203 | 31.107 | 25.754 | 25.406 | 1.00 | 34.57 | C |
| ATOM | 1511 | O | GLN | A | 203 | 30.218 | 26.586 | 25.256 | 1.00 | 34.62 | O |
| ATOM | 1512 | CB | GLN | A | 203 | 31.317 | 24.446 | 27.514 | 1.00 | 35.59 | C |
| ATOM | 1513 | CG | GLN | A | 203 | 32.184 | 24.236 | 28.734 | 1.00 | 37.42 | C |
| ATOM | 1514 | CD | GLN | A | 203 | 32.234 | 22.819 | 29.233 | 1.00 | 38.70 | C |
| ATOM | 1515 | OE1 | GLN | A | 203 | 32.228 | 21.860 | 28.458 | 1.00 | 39.80 | O |
| ATOM | 1516 | NE2 | GLN | A | 203 | 32.326 | 22.680 | 30.541 | 1.00 | 41.01 | N |
| ATOM | 1517 | N | GLN | A | 204 | 31.524 | 24.939 | 24.443 | 1.00 | 33.68 | N |
| ATOM | 1518 | CA | GLN | A | 204 | 30.873 | 24.899 | 23.165 | 1.00 | 32.97 | C |
| ATOM | 1519 | C | GLN | A | 204 | 29.714 | 23.959 | 23.373 | 1.00 | 32.67 | C |
| ATOM | 1520 | O | GLN | A | 204 | 29.838 | 22.982 | 24.082 | 1.00 | 32.33 | O |
| ATOM | 1521 | CB | GLN | A | 204 | 31.793 | 24.352 | 22.093 | 1.00 | 32.85 | C |
| ATOM | 1522 | CG | GLN | A | 204 | 33.042 | 25.165 | 21.819 | 1.00 | 32.50 | C |
| ATOM | 1523 | CD | GLN | A | 204 | 32.786 | 26.454 | 21.057 | 1.00 | 30.59 | C |
| ATOM | 1524 | OE1 | GLN | A | 204 | 31.656 | 26.830 | 20.848 | 1.00 | 31.27 | O |
| ATOM | 1525 | NE2 | GLN | A | 204 | 33.843 | 27.132 | 20.664 | 1.00 | 29.18 | N |
| ATOM | 1526 | N | ASN | A | 205 | 28.583 | 24.247 | 22.755 | 1.00 | 32.81 | N |
| ATOM | 1527 | CA | ASN | A | 205 | 27.393 | 23.446 | 22.980 | 1.00 | 32.85 | C |
| ATOM | 1528 | C | ASN | A | 205 | 26.594 | 23.059 | 21.733 | 1.00 | 32.80 | C |
| ATOM | 1529 | O | ASN | A | 205 | 26.147 | 23.921 | 20.968 | 1.00 | 32.72 | O |
| ATOM | 1530 | CB | ASN | A | 205 | 26.484 | 24.246 | 23.919 | 1.00 | 32.83 | C |
| ATOM | 1531 | CG | ASN | A | 205 | 25.178 | 23.566 | 24.205 | 1.00 | 32.43 | C |
| ATOM | 1532 | OD1 | ASN | A | 205 | 24.914 | 22.465 | 23.732 | 1.00 | 32.78 | O |
| ATOM | 1533 | ND2 | ASN | A | 205 | 24.339 | 24.228 | 24.993 | 1.00 | 31.52 | N |
| ATOM | 1534 | N | PHE | A | 206 | 26.427 | 21.763 | 21.515 | 1.00 | 32.36 | N |
| ATOM | 1535 | CA | PHE | A | 206 | 25.454 | 21.326 | 20.541 | 1.00 | 32.02 | C |
| ATOM | 1536 | C | PHE | A | 206 | 24.167 | 20.977 | 21.301 | 1.00 | 31.59 | C |
| ATOM | 1537 | O | PHE | A | 206 | 24.144 | 20.067 | 22.096 | 1.00 | 31.13 | O |
| ATOM | 1538 | GB | PHE | A | 206 | 25.972 | 20.159 | 19.754 | 1.00 | 32.17 | C |

TABLE 3-continued

| | | | | | Coordinates for structures 1 to 4 | | | | | |
|---|---|---|---|---|---|---|---|---|---|---|
| ATOM | 1539 | CG | PHE | A | 206 | 26.844 | 20.554 | 18.639 | 1.00 | 32.42 | C |
| ATOM | 1540 | CD1 | PHE | A | 206 | 26.364 | 21.354 | 17.630 | 1.00 | 33.16 | C |
| ATOM | 1541 | CD2 | PHE | A | 206 | 28.149 | 20.132 | 18.600 | 1.00 | 33.19 | C |
| ATOM | 1542 | GE1 | PHE | A | 206 | 27.174 | 21.721 | 16.600 | 1.00 | 33.34 | C |
| ATOM | 1543 | CE2 | PHE | A | 206 | 28.963 | 20.487 | 17.580 | 1.00 | 32.88 | C |
| ATOM | 1544 | CZ | PHE | A | 206 | 28.485 | 21.279 | 16.574 | 1.00 | 33.50 | C |
| ATOM | 1545 | N | PHE | A | 207 | 23.104 | 21.717 | 21.012 | 1.00 | 31.65 | N |
| ATOM | 1546 | GA | PHE | A | 207 | 21.829 | 21.671 | 21.726 | 1.00 | 31.71 | C |
| ATOM | 1547 | C | PHE | A | 207 | 20.822 | 20.825 | 20.924 | 1.00 | 31.35 | C |
| ATOM | 1548 | O | PHE | A | 207 | 20.289 | 21.292 | 19.930 | 1.00 | 30.81 | O |
| ATOM | 1549 | CB | PHE | A | 207 | 21.391 | 23.148 | 21.883 | 1.00 | 31.56 | C |
| ATOM | 1550 | CG | PHE | A | 207 | 20.118 | 23.404 | 22.683 | 1.00 | 31.43 | C |
| ATOM | 1551 | CD1 | PHE | A | 207 | 18.926 | 23.676 | 22.036 | 1.00 | 32.30 | C |
| ATOM | 1552 | CD2 | PHE | A | 207 | 20.150 | 23.519 | 24.058 | 1.00 | 31.29 | C |
| ATOM | 1553 | CE1 | PHE | A | 207 | 17.781 | 23.982 | 22.748 | 1.00 | 32.37 | C |
| ATOM | 1554 | CE2 | PHE | A | 207 | 19.006 | 23.832 | 24.776 | 1.00 | 31.14 | C |
| ATOM | 1555 | CZ | PHE | A | 207 | 17.828 | 24.062 | 24.122 | 1.00 | 32.27 | C |
| ATOM | 1556 | N | ALA | A | 208 | 20.554 | 19.593 | 21.368 | 1.00 | 31.31 | N |
| ATOM | 1557 | CA | ALA | A | 208 | 19.685 | 18.672 | 20.611 | 1.00 | 31.33 | C |
| ATOM | 1558 | C | ALA | A | 208 | 18.264 | 18.543 | 21.138 | 1.00 | 31.59 | C |
| ATOM | 1559 | O | ALA | A | 208 | 18.016 | 17.860 | 22.133 | 1.00 | 31.13 | O |
| ATOM | 1560 | GB | ALA | A | 208 | 20.293 | 17.334 | 20.537 | 1.00 | 30.98 | C |
| ATOM | 1561 | N | GLN | A | 209 | 17.340 | 19.169 | 20.409 | 1.00 | 32.00 | N |
| ATOM | 1562 | CA | GLN | A | 209 | 15.935 | 19.183 | 20.751 | 1.00 | 32.37 | C |
| ATOM | 1563 | C | GLN | A | 209 | 15.288 | 17.867 | 20.358 | 1.00 | 32.76 | C |
| ATOM | 1564 | O | GLN | A | 209 | 15.492 | 17.360 | 19.247 | 1.00 | 32.19 | O |
| ATOM | 1565 | GB | GLN | A | 209 | 15.245 | 20.332 | 20.031 | 1.00 | 32.55 | C |
| ATOM | 1566 | CG | GLN | A | 209 | 13.802 | 20.589 | 20.470 | 1.00 | 32.44 | C |
| ATOM | 1567 | CD | GLN | A | 209 | 13.689 | 20.978 | 21.925 | 1.00 | 32.27 | C |
| ATOM | 1568 | OE1 | GLN | A | 209 | 14.699 | 21.254 | 22.587 | 1.00 | 31.73 | O |
| ATOM | 1569 | NE2 | GLN | A | 209 | 12.457 | 21.000 | 22.436 | 1.00 | 32.63 | N |
| ATOM | 1570 | N | ILE | A | 210 | 14.467 | 17.360 | 21.272 | 1.00 | 33.20 | N |
| ATOM | 1571 | GA | ILE | A | 210 | 13.907 | 16.030 | 21.165 | 1.00 | 33.55 | C |
| ATOM | 1572 | C | ILE | A | 210 | 12.399 | 15.998 | 21.195 | 1.00 | 33.37 | C |
| ATOM | 1573 | O | ILE | A | 210 | 11.788 | 15.337 | 20.369 | 1.00 | 33.25 | O |
| ATOM | 1574 | GB | ILE | A | 210 | 14.456 | 15.210 | 22.302 | 1.00 | 33.79 | C |
| ATOM | 1575 | GG1 | ILE | A | 210 | 15.900 | 14.837 | 21.980 | 1.00 | 34.71 | C |
| ATOM | 1576 | CG2 | ILE | A | 210 | 13.604 | 13.982 | 22.528 | 1.00 | 33.99 | C |
| ATOM | 1577 | GD1 | ILE | A | 210 | 16.679 | 14.375 | 23.191 | 1.00 | 35.48 | C |
| ATOM | 1578 | N | LYS | A | 211 | 11.804 | 16.688 | 22.156 | 1.00 | 33.27 | N |
| ATOM | 1579 | CA | LYS | A | 211 | 10.365 | 16.739 | 22.263 | 1.00 | 33.48 | C |
| ATOM | 1580 | C | LYS | A | 211 | 9.960 | 18.146 | 22.559 | 1.00 | 33.68 | C |
| ATOM | 1581 | O | LYS | A | 211 | 10.545 | 18.789 | 23.407 | 1.00 | 34.10 | O |
| ATOM | 1582 | GB | LYS | A | 211 | 9.867 | 15.875 | 23.405 | 1.00 | 33.57 | C |
| ATOM | 1583 | CG | LYS | A | 211 | 8.355 | 15.708 | 23.409 | 1.00 | 34.06 | C |
| ATOM | 1584 | CD | LYS | A | 211 | 7.840 | 15.250 | 24.752 | 1.00 | 34.79 | C |
| ATOM | 1585 | CE | LYS | A | 211 | 6.635 | 14.324 | 24.635 | 1.00 | 35.65 | C |
| ATOM | 1586 | NZ | LYS | A | 211 | 5.876 | 14.398 | 23.369 | 1.00 | 36.67 | N |
| ATOM | 1587 | N | GLY | A | 212 | 8.938 | 18.626 | 21.876 | 1.00 | 34.06 | N |
| ATOM | 1588 | CA | GLY | A | 212 | 8.460 | 19.969 | 22.103 | 1.00 | 34.09 | C |
| ATOM | 1589 | C | GLY | A | 212 | 9.270 | 20.966 | 21.314 | 1.00 | 34.27 | C |
| ATOM | 1590 | O | GLY | A | 212 | 10.156 | 20.599 | 20.532 | 1.00 | 34.27 | O |
| ATOM | 1591 | N | TYR | A | 213 | 8.955 | 22.237 | 21.523 | 1.00 | 34.23 | N |
| ATOM | 1592 | GA | TYR | A | 213 | 9.640 | 23.311 | 20.843 | 1.00 | 34.12 | C |
| ATOM | 1593 | C | TYR | A | 213 | 10.216 | 24.318 | 21.824 | 1.00 | 33.81 | C |
| ATOM | 1594 | O | TYR | A | 213 | 9.602 | 24.652 | 22.835 | 1.00 | 33.09 | O |
| ATOM | 1595 | GB | TYR | A | 213 | 8.665 | 23.994 | 19.899 | 1.00 | 34.42 | C |
| ATOM | 1596 | CG | TYR | A | 213 | 8.257 | 23.091 | 18.789 | 1.00 | 35.40 | C |
| ATOM | 1597 | CD1 | TYR | A | 213 | 7.228 | 22.163 | 18.955 | 1.00 | 36.80 | C |
| ATOM | 1598 | CD2 | TYR | A | 213 | 8.929 | 23.122 | 17.586 | 1.00 | 36.00 | C |
| ATOM | 1599 | GE1 | TYR | A | 213 | 6.873 | 21.323 | 17.944 | 1.00 | 36.82 | C |
| ATOM | 1600 | CE2 | TYR | A | 213 | 8.579 | 22.292 | 16.567 | 1.00 | 37.06 | C |
| ATOM | 1601 | CZ | TYR | A | 213 | 7.560 | 21.390 | 16.743 | 1.00 | 37.82 | C |
| ATOM | 1602 | OH | TYR | A | 213 | 7.242 | 20.568 | 15.688 | 1.00 | 40.76 | O |
| ATOM | 1603 | N | LYS | A | 214 | 11.410 | 24.804 | 21.517 | 1.00 | 33.91 | N |
| ATOM | 1604 | CA | LYS | A | 214 | 12.046 | 25.809 | 22.359 | 1.00 | 33.87 | C |
| ATOM | 1605 | C | LYS | A | 214 | 12.479 | 27.033 | 21.551 | 1.00 | 33.71 | C |
| ATOM | 1606 | O | LYS | A | 214 | 13.173 | 26.918 | 20.538 | 1.00 | 33.58 | O |
| ATOM | 1607 | GB | LYS | A | 214 | 13.237 | 25.208 | 23.101 | 1.00 | 33.64 | C |
| ATOM | 1608 | CG | LYS | A | 214 | 12.881 | 24.443 | 24.364 | 1.00 | 33.56 | C |
| ATOM | 1609 | CD | LYS | A | 214 | 14.126 | 23.861 | 24.973 | 1.00 | 33.29 | C |
| ATOM | 1610 | CE | LYS | A | 214 | 14.001 | 23.615 | 26.458 | 1.00 | 33.54 | C |
| ATOM | 1611 | NZ | LYS | A | 214 | 15.346 | 23.419 | 27.130 | 1.00 | 32.27 | N |
| ATOM | 1612 | N | ARG | A | 215 | 12.043 | 28.205 | 21.986 | 1.00 | 33.56 | N |
| ATOM | 1613 | CA | ARG | A | 215 | 12.479 | 29.427 | 21.339 | 1.00 | 33.91 | C |
| ATOM | 1614 | C | ARG | A | 215 | 13.816 | 29.800 | 21.944 | 1.00 | 33.54 | C |
| ATOM | 1615 | O | ARG | A | 215 | 13.946 | 29.923 | 23.146 | 1.00 | 32.78 | O |

TABLE 3-continued

| | | | | | | | | | | | |
|---|---|---|---|---|---|---|---|---|---|---|---|
| | Coordinates for structures 1 to 4 |
| ATOM | 1616 | GB | ARG | A | 215 | 11.482 | 30.552 | 21.558 | 1.00 | 34.15 | C |
| ATOM | 1617 | GG | ARG | A | 215 | 11.865 | 31.844 | 20.885 | 1.00 | 34.51 | C |
| ATOM | 1618 | CD | ARG | A | 215 | 11.287 | 33.028 | 21.593 | 1.00 | 34.99 | C |
| ATOM | 1619 | NE | ARG | A | 215 | 11.381 | 34.255 | 20.823 | 1.00 | 35.43 | N |
| ATOM | 1620 | CZ | ARG | A | 215 | 10.688 | 35.346 | 21.103 | 1.00 | 35.27 | C |
| ATOM | 1621 | NH1 | ARG | A | 215 | 9.860 | 35.371 | 22.144 | 1.00 | 34.68 | N |
| ATOM | 1622 | NH2 | ARG | A | 215 | 10.829 | 36.415 | 20.344 | 1.00 | 35.16 | N |
| ATOM | 1623 | N | CYS | A | 216 | 14.810 | 29.962 | 21.092 | 1.00 | 33.76 | N |
| ATOM | 1624 | CA | CYS | A | 216 | 16.152 | 30.238 | 21.542 | 1.00 | 33.91 | C |
| ATOM | 1625 | C | CYS | A | 216 | 16.555 | 31.613 | 21.068 | 1.00 | 34.31 | C |
| ATOM | 1626 | O | CYS | A | 216 | 16.534 | 31.885 | 19.872 | 1.00 | 34.69 | O |
| ATOM | 1627 | GB | CYS | A | 216 | 17.099 | 29.189 | 20.968 | 1.00 | 33.84 | C |
| ATOM | 1628 | SG | CYS | A | 216 | 16.655 | 27.490 | 21.397 | 1.00 | 32.85 | S |
| ATOM | 1629 | N | ILE | A | 217 | 16.886 | 32.494 | 22.004 | 1.00 | 34.57 | N |
| ATOM | 1630 | GA | ILE | A | 217 | 17.335 | 33.830 | 21.648 | 1.00 | 34.82 | C |
| ATOM | 1631 | C | ILE | A | 217 | 18.785 | 33.999 | 22.046 | 1.00 | 34.50 | C |
| ATOM | 1632 | O | ILE | A | 217 | 19.136 | 33.839 | 23.213 | 1.00 | 34.30 | O |
| ATOM | 1633 | CB | ILE | A | 217 | 16.475 | 34.890 | 22.324 | 1.00 | 35.07 | C |
| ATOM | 1634 | CG1 | ILE | A | 217 | 15.003 | 34.652 | 22.001 | 1.00 | 35.20 | C |
| ATOM | 1635 | CG2 | ILE | A | 217 | 16.881 | 36.259 | 21.844 | 1.00 | 35.38 | C |
| ATOM | 1636 | CD1 | ILE | A | 217 | 14.086 | 35.585 | 22.722 | 1.00 | 36.16 | C |
| ATOM | 1637 | N | LEU | A | 218 | 19.620 | 34.315 | 21.060 | 1.00 | 34.32 | N |
| ATOM | 1638 | CA | LEU | A | 218 | 21.052 | 34.443 | 21.277 | 1.00 | 34.44 | C |
| ATOM | 1639 | C | LEU | A | 218 | 21.565 | 35.844 | 21.017 | 1.00 | 34.27 | C |
| ATOM | 1640 | O | LEU | A | 218 | 21.074 | 36.561 | 20.148 | 1.00 | 34.59 | O |
| ATOM | 1641 | CB | LEU | A | 218 | 21.818 | 33.476 | 20.365 | 1.00 | 34.57 | C |
| ATOM | 1642 | CG | LEU | A | 218 | 21.953 | 32.036 | 20.844 | 1.00 | 34.62 | C |
| ATOM | 1643 | CO1 | LEU | A | 218 | 20.614 | 31.435 | 21.124 | 1.00 | 34.96 | C |
| ATOM | 1644 | CD2 | LEU | A | 218 | 22.638 | 31.235 | 19.789 | 1.00 | 35.31 | C |
| ATOM | 1645 | N | PHE | A | 219 | 22.594 | 36.200 | 21.768 | 1.00 | 33.79 | N |
| ATOM | 1646 | CA | PHE | A | 219 | 23.258 | 37.462 | 21.632 | 1.00 | 33.40 | C |
| ATOM | 1647 | C | PHE | A | 219 | 24.730 | 37.155 | 21.617 | 1.00 | 33.29 | C |
| ATOM | 1648 | O | PHE | A | 219 | 25.222 | 36.434 | 22.463 | 1.00 | 33.45 | O |
| ATOM | 1649 | CB | PHE | A | 219 | 22.964 | 38.330 | 22.832 | 1.00 | 33.37 | C |
| ATOM | 1650 | CG | PHE | A | 219 | 21.509 | 38.586 | 23.051 | 1.00 | 33.91 | C |
| ATOM | 1651 | GD1 | PHE | A | 219 | 20.852 | 39.607 | 22.379 | 1.00 | 33.73 | C |
| ATOM | 1652 | GD2 | PHE | A | 219 | 20.794 | 37.812 | 23.942 | 1.00 | 33.70 | C |
| ATOM | 1653 | GE1 | PHE | A | 219 | 19.512 | 39.832 | 22.600 | 1.00 | 33.52 | C |
| ATOM | 1654 | CE2 | PHE | A | 219 | 19.460 | 38.038 | 24.156 | 1.00 | 33.47 | C |
| ATOM | 1655 | GZ | PHE | A | 219 | 18.818 | 39.045 | 23.486 | 1.00 | 33.23 | C |
| ATOM | 1656 | N | PRO | A | 220 | 25.438 | 37.683 | 20.642 | 1.00 | 33.46 | N |
| ATOM | 1657 | CA | PRO | A | 220 | 26.888 | 37.496 | 20.536 | 1.00 | 33.50 | C |
| ATOM | 1658 | C | PRO | A | 220 | 27.675 | 38.131 | 21.699 | 1.00 | 33.51 | C |
| ATOM | 1659 | O | PRO | A | 220 | 27.185 | 39.049 | 22.363 | 1.00 | 33.18 | O |
| ATOM | 1660 | GB | PRO | A | 220 | 27.246 | 38.169 | 19.211 | 1.00 | 33.51 | C |
| ATOM | 1661 | CG | PRO | A | 220 | 25.977 | 38.683 | 18.629 | 1.00 | 33.41 | C |
| ATOM | 1662 | CD | PRO | A | 220 | 24.869 | 38.462 | 19.544 | 1.00 | 33.33 | C |
| ATOM | 1663 | N | PRO | A | 221 | 28.886 | 37.627 | 21.942 | 1.00 | 33.38 | N |
| ATOM | 1664 | CA | PRO | A | 221 | 29.731 | 38.102 | 23.044 | 1.00 | 33.30 | C |
| ATOM | 1665 | C | PRO | A | 221 | 29.966 | 39.581 | 23.081 | 1.00 | 33.55 | C |
| ATOM | 1666 | O | PRO | A | 221 | 30.043 | 40.151 | 24.147 | 1.00 | 33.66 | O |
| ATOM | 1667 | GB | PRO | A | 221 | 31.033 | 37.375 | 22.799 | 1.00 | 33.11 | C |
| ATOM | 1668 | CG | PRO | A | 221 | 30.589 | 36.128 | 22.147 | 1.00 | 33.06 | C |
| ATOM | 1669 | CD | PRO | A | 221 | 29.523 | 36.522 | 21.207 | 1.00 | 32.91 | C |
| ATOM | 1670 | N | ASP | A | 222 | 30.009 | 40.217 | 21.933 | 1.00 | 34.30 | N |
| ATOM | 1671 | CA | ASP | A | 222 | 30.277 | 41.628 | 21.904 | 1.00 | 34.71 | C |
| ATOM | 1672 | C | ASP | A | 222 | 29.073 | 42.419 | 22.382 | 1.00 | 34.56 | C |
| ATOM | 1673 | O | ASP | A | 222 | 29.048 | 43.634 | 22.241 | 1.00 | 34.68 | O |
| ATOM | 1674 | GB | ASP | A | 222 | 30.679 | 42.055 | 20.502 | 1.00 | 34.79 | C |
| ATOM | 1675 | CG | ASP | A | 222 | 29.508 | 42.228 | 19.608 | 1.00 | 36.26 | C |
| ATOM | 1676 | OD1 | ASP | A | 222 | 28.387 | 41.897 | 20.028 | 1.00 | 38.21 | O |
| ATOM | 1677 | OD2 | ASP | A | 222 | 29.601 | 42.692 | 18.462 | 1.00 | 40.87 | O |
| ATOM | 1678 | N | GLN | A | 223 | 28.062 | 41.760 | 22.930 | 1.00 | 34.48 | N |
| ATOM | 1679 | CA | GLN | A | 223 | 26.965 | 42.532 | 23.497 | 1.00 | 34.78 | C |
| ATOM | 1680 | C | GLN | A | 223 | 27.031 | 42.541 | 25.011 | 1.00 | 34.33 | C |
| ATOM | 1681 | O | GLN | A | 223 | 26.077 | 42.878 | 25.686 | 1.00 | 34.70 | O |
| ATOM | 1682 | CB | GLN | A | 223 | 25.595 | 42.133 | 22.940 | 1.00 | 34.87 | C |
| ATOM | 1683 | CG | GLN | A | 223 | 25.364 | 42.825 | 21.599 | 1.00 | 36.55 | C |
| ATOM | 1684 | CD | GIJN | A | 223 | 23.990 | 42.635 | 21.020 | 1.00 | 39.56 | C |
| ATOM | 1685 | OE1 | GLN | A | 223 | 22.986 | 42.824 | 21.701 | 1.00 | 42.40 | O |
| ATOM | 1686 | NE2 | GLN | A | 223 | 23.936 | 42.294 | 19.742 | 1.00 | 41.89 | N |
| ATOM | 1687 | N | PHE | A | 224 | 28.198 | 42.219 | 25.534 | 1.00 | 34.13 | N |
| ATOM | 1688 | CA | PHE | A | 224 | 28.437 | 42.270 | 26.965 | 1.00 | 34.17 | C |
| ATOM | 1689 | C | PHE | A | 224 | 27.941 | 43.571 | 27.570 | 1.00 | 34.88 | C |
| ATOM | 1690 | O | PHE | A | 224 | 27.310 | 43.549 | 28.622 | 1.00 | 35.50 | O |
| ATOM | 1691 | GB | PHE | A | 224 | 29.932 | 42.159 | 27.224 | 1.00 | 33.66 | C |
| ATOM | 1692 | CG | PHE | A | 224 | 30.305 | 42.027 | 28.661 | 1.00 | 32.69 | C |

TABLE 3-continued

Coordinates for structures 1 to 4

| ATOM | 1693 | CD1 | PHE | A | 224 | 30.429 | 43.137 | 29.476 | 1.00 | 33.11 | C |
|---|---|---|---|---|---|---|---|---|---|---|---|
| ATOM | 1694 | CD2 | PHE | A | 224 | 30.609 | 40.790 | 29.191 | 1.00 | 31.85 | C |
| ATOM | 1695 | GE1 | PHE | A | 224 | 30.821 | 43.003 | 30.817 | 1.00 | 31.76 | C |
| ATOM | 1696 | CE2 | PHE | A | 224 | 30.993 | 40.661 | 30.498 | 1.00 | 31.29 | C |
| ATOM | 1697 | CZ | PHE | A | 224 | 31.098 | 41.775 | 31.316 | 1.00 | 30.73 | C |
| ATOM | 1698 | N | GLU | A | 225 | 28.235 | 44.706 | 26.930 | 1.00 | 35.46 | N |
| ATOM | 1699 | CA | GLU | A | 225 | 27.852 | 45.994 | 27.492 | 1.00 | 35.85 | C |
| ATOM | 1700 | C | GLU | A | 225 | 26.362 | 46.133 | 27.608 | 1.00 | 35.42 | C |
| ATOM | 1701 | O | GLU | A | 225 | 25.873 | 46.955 | 28.386 | 1.00 | 35.16 | O |
| ATOM | 1702 | CB | GLU | A | 225 | 28.401 | 47.175 | 26.688 | 1.00 | 36.59 | C |
| ATOM | 1703 | GG | GLU | A | 225 | 29.892 | 47.377 | 26.917 | 1.00 | 39.78 | C |
| ATOM | 1704 | CD | GLU | A | 225 | 30.357 | 48.822 | 27.125 | 1.00 | 43.65 | C |
| ATOM | 1705 | OE1 | GLU | A | 225 | 29.937 | 49.524 | 28.099 | 1.00 | 44.64 | O |
| ATOM | 1706 | OE2 | GLU | A | 225 | 31.224 | 49.234 | 26.319 | 1.00 | 47.74 | O |
| ATOM | 1707 | N | CYS | A | 226 | 25.633 | 45.329 | 26.851 | 1.00 | 35.07 | N |
| ATOM | 1708 | CA | CYS | A | 226 | 24.192 | 45.453 | 26.842 | 1.00 | 34.93 | C |
| ATOM | 1709 | C | CYS | A | 226 | 23.473 | 44.498 | 27.770 | 1.00 | 34.91 | C |
| ATOM | 1710 | O | GYS | A | 226 | 22.266 | 44.654 | 28.019 | 1.00 | 34.86 | O |
| ATOM | 1711 | GB | GYS | A | 226 | 23.681 | 45.196 | 25.448 | 1.00 | 34.80 | C |
| ATOM | 1712 | SG | CYS | A | 226 | 24.135 | 46.461 | 24.291 | 1.00 | 34.76 | S |
| ATOM | 1713 | N | LEU | A | 227 | 24.191 | 43.521 | 28.296 | 1.00 | 34.47 | N |
| ATOM | 1714 | CA | LEU | A | 227 | 23.509 | 42.483 | 29.025 | 1.00 | 34.57 | C |
| ATOM | 1715 | C | LEU | A | 227 | 23.815 | 42.408 | 30.503 | 1.00 | 34.08 | C |
| ATOM | 1716 | O | LEU | A | 227 | 23.122 | 41.725 | 31.235 | 1.00 | 33.57 | O |
| ATOM | 1717 | CS | LEU | A | 227 | 23.739 | 41.162 | 28.313 | 1.00 | 34.97 | C |
| ATOM | 1718 | CG | LEU | A | 227 | 22.883 | 41.127 | 27.047 | 1.00 | 36.04 | C |
| ATOM | 1719 | CD1 | LEU | A | 227 | 23.454 | 40.177 | 26.043 | 1.00 | 37.99 | C |
| ATOM | 1720 | CD2 | LEU | A | 227 | 21.474 | 40.719 | 27.394 | 1.00 | 36.66 | C |
| ATOM | 1721 | N | TYR | A | 228 | 24.866 | 43.104 | 30.917 | 1.00 | 34.23 | N |
| ATOM | 1722 | CA | TYR | A | 228 | 25.172 | 43.334 | 32.329 | 1.00 | 34.02 | C |
| ATOM | 1723 | C | TYR | A | 228 | 25.163 | 42.091 | 33.196 | 1.00 | 33.81 | C |
| ATOM | 1724 | O | TYR | A | 228 | 24.294 | 41.900 | 34.041 | 1.00 | 33.87 | O |
| ATOM | 1725 | CB | TYR | A | 228 | 24.183 | 44.345 | 32.897 | 1.00 | 33.73 | C |
| ATOM | 1726 | CG | TYR | A | 228 | 24.153 | 45.658 | 32.166 | 1.00 | 33.50 | C |
| ATOM | 1727 | CD1 | TYR | A | 228 | 24.947 | 46.712 | 32.568 | 1.00 | 33.63 | C |
| ATOM | 1728 | CD2 | TYR | A | 228 | 23.312 | 45.853 | 31.086 | 1.00 | 35.03 | C |
| ATOM | 1729 | CE1 | TYR | A | 228 | 24.903 | 47.932 | 31.924 | 1.00 | 34.25 | C |
| ATOM | 1730 | CE2 | TYR | A | 228 | 23.268 | 47.066 | 30.419 | 1.00 | 35.62 | C |
| ATOM | 1731 | CZ | TYR | A | 228 | 24.068 | 48.106 | 30.848 | 1.00 | 35.60 | C |
| ATOM | 1732 | OH | TYR | A | 228 | 24.027 | 49.324 | 30.203 | 1.00 | 36.79 | O |
| ATOM | 1733 | N | PRO | A | 229 | 26.170 | 41.263 | 33.027 | 1.00 | 33.75 | N |
| ATOM | 1734 | CA | PRO | A | 229 | 26.255 | 40.032 | 33.791 | 1.00 | 33.73 | C |
| ATOM | 1735 | C | PRO | A | 229 | 26.538 | 40.313 | 35.231 | 1.00 | 33.32 | C |
| ATOM | 1736 | O | PRO | A | 229 | 27.228 | 41.263 | 35.530 | 1.00 | 33.73 | O |
| ATOM | 1737 | CE | PRO | A | 229 | 27.449 | 39.319 | 33.169 | 1.00 | 33.87 | C |
| ATOM | 1738 | CG | PRO | A | 229 | 28.264 | 40.366 | 32.543 | 1.00 | 33.66 | C |
| ATOM | 1739 | CD | PRO | A | 229 | 27.334 | 41.457 | 32.156 | 1.00 | 34.15 | C |
| ATOM | 1740 | N | TYR | A | 230 | 25.992 | 39.509 | 36.122 | 1.00 | 32.95 | N |
| ATOM | 1741 | CA | TYR | A | 230 | 26.330 | 39.654 | 37.510 | 1.00 | 32.64 | C |
| ATOM | 1742 | C | TYR | A | 230 | 27.836 | 39.534 | 37.651 | 1.00 | 32.59 | C |
| ATOM | 1743 | O | TYR | A | 230 | 28.536 | 39.020 | 36.793 | 1.00 | 32.76 | O |
| ATOM | 1744 | CB | TYR | A | 230 | 25.713 | 38.547 | 38.351 | 1.00 | 32.25 | C |
| ATOM | 1745 | CG | TYR | A | 230 | 24.237 | 38.640 | 38.573 | 1.00 | 31.53 | C |
| ATOM | 1746 | CD1 | TYR | A | 230 | 23.346 | 38.125 | 37.641 | 1.00 | 31.07 | C |
| ATOM | 1747 | CD2 | TYR | A | 230 | 23.727 | 39.192 | 39.748 | 1.00 | 29.93 | C |
| ATOM | 1748 | CE1 | TYR | A | 230 | 21.996 | 38.185 | 37.859 | 1.00 | 31.19 | C |
| ATOM | 1749 | CE2 | TYR | A | 230 | 22.395 | 39.253 | 39.980 | 1.00 | 28.83 | C |
| ATOM | 1750 | CZ | TYR | A | 230 | 21.523 | 38.755 | 39.040 | 1.00 | 31.04 | C |
| ATOM | 1751 | OH | TYR | A | 230 | 20.165 | 38.816 | 39.272 | 1.00 | 32.40 | O |
| ATOM | 1752 | N | PRO | A | 231 | 28.328 | 40.016 | 38.764 | 1.00 | 32.69 | N |
| ATOM | 1753 | CA | PRO | A | 231 | 29.725 | 39.852 | 39.124 | 1.00 | 32.75 | C |
| ATOM | 1754 | C | PRO | A | 231 | 30.159 | 38.384 | 39.159 | 1.00 | 32.72 | C |
| ATOM | 1755 | O | PRO | A | 231 | 29.434 | 37.497 | 39.604 | 1.00 | 32.86 | O |
| ATOM | 1756 | CB | PRO | A | 231 | 29.768 | 40.423 | 40.533 | 1.00 | 32.82 | C |
| ATOM | 1757 | CG | PRO | A | 231 | 28.625 | 41.349 | 40.605 | 1.00 | 32.96 | C |
| ATOM | 1758 | CD | PRO | A | 231 | 27.576 | 40.802 | 39.751 | 1.00 | 32.88 | C |
| ATOM | 1759 | N | VAL | A | 232 | 31.387 | 38.151 | 38.740 | 1.00 | 32.40 | N |
| ATOM | 1760 | CA | VAL | A | 232 | 31.938 | 36.825 | 38.680 | 1.00 | 32.10 | C |
| ATOM | 1761 | C | VAL | A | 232 | 31.776 | 36.022 | 39.963 | 1.00 | 32.41 | C |
| ATOM | 1762 | O | VAL | A | 232 | 31.546 | 34.826 | 39.906 | 1.00 | 32.96 | O |
| ATOM | 1763 | CE | VAL | A | 232 | 33.422 | 36.918 | 38.332 | 1.00 | 32.04 | C |
| ATOM | 1764 | CG1 | VAL | A | 232 | 34.131 | 35.666 | 38.721 | 1.00 | 31.82 | C |
| ATOM | 1765 | CG2 | VAL | A | 232 | 33.601 | 37.221 | 36.851 | 1.00 | 31.85 | C |
| ATOM | 1766 | N | HIS | A | 233 | 31.918 | 36.650 | 41.124 | 1.00 | 32.61 | N |
| ATOM | 1767 | CA | HIS | A | 233 | 31.819 | 35.910 | 42.376 | 1.00 | 32.41 | C |
| ATOM | 1768 | C | HIS | A | 233 | 30.383 | 35.727 | 42.874 | 1.00 | 32.27 | C |
| ATOM | 1769 | O | HIS | A | 233 | 30.134 | 35.052 | 43.860 | 1.00 | 32.05 | O |

TABLE 3-continued

Coordinates for structures 1 to 4

| ATOM | 1770 | CB | HIS | A | 233 | 32.667 | 36.577 | 43.458 | 1.00 | 32.52 | C |
|---|---|---|---|---|---|---|---|---|---|---|---|
| ATOM | 1771 | CG | HIS | A | 233 | 34.135 | 36.579 | 43.164 | 1.00 | 33.14 | C |
| ATOM | 1772 | ND1 | HIS | A | 233 | 34.787 | 37.672 | 42.631 | 1.00 | 34.57 | N |
| ATOM | 1773 | CD2 | HIS | A | 233 | 35.083 | 35.629 | 43.342 | 1.00 | 34.15 | C |
| ATOM | 1774 | CE1 | HIS | A | 233 | 36.071 | 37.398 | 42.497 | 1.00 | 34.40 | C |
| ATOM | 1775 | ND2 | HIS | A | 233 | 36.278 | 36.164 | 42.922 | 1.00 | 35.34 | N |
| ATOM | 1776 | N | HIS | A | 234 | 29.423 | 36.314 | 42.194 | 1.00 | 32.53 | N |
| ATOM | 1777 | CA | HIS | A | 234 | 28.038 | 36.145 | 42.604 | 1.00 | 33.01 | C |
| ATOM | 1778 | C | HIS | A | 234 | 27.503 | 34.834 | 42.094 | 1.00 | 33.09 | C |
| ATOM | 1779 | O | HIS | A | 234 | 27.932 | 34.325 | 41.068 | 1.00 | 33.26 | O |
| ATOM | 1780 | CB | HIS | A | 234 | 27.221 | 37.276 | 42.024 | 1.00 | 33.15 | C |
| ATOM | 1781 | CG | HIS | A | 234 | 25.817 | 37.383 | 42.531 | 1.00 | 32.96 | C |
| ATOM | 1782 | ND1 | HIS | A | 234 | 24.767 | 36.704 | 41.951 | 1.00 | 32.53 | N |
| ATOM | 1783 | CD2 | HIS | A | 234 | 25.268 | 38.191 | 43.471 | 1.00 | 32.12 | C |
| ATOM | 1784 | CE1 | HIS | A | 234 | 23.639 | 37.056 | 42.540 | 1.00 | 32.45 | C |
| ATOM | 1785 | ND2 | HIS | A | 234 | 23.916 | 37.953 | 43.470 | 1.00 | 32.09 | N |
| ATOM | 1786 | N | PRO | A | 235 | 26.571 | 34.263 | 42.827 | 1.00 | 33.15 | N |
| ATOM | 1787 | CA | PRO | A | 235 | 25.985 | 32.996 | 42.410 | 1.00 | 32.79 | C |
| ATOM | 1788 | C | PRO | A | 235 | 25.386 | 33.045 | 41.026 | 1.00 | 32.62 | C |
| ATOM | 1789 | O | PRO | A | 235 | 25.210 | 31.990 | 40.440 | 1.00 | 32.65 | O |
| ATOM | 1790 | CB | PRO | A | 235 | 24.897 | 32.773 | 43.450 | 1.00 | 33.00 | C |
| ATOM | 1791 | CG | PRO | A | 235 | 25.412 | 33.500 | 44.672 | 1.00 | 32.79 | C |
| ATOM | 1792 | CD | PRO | A | 235 | 26.049 | 34.725 | 44.128 | 1.00 | 33.00 | C |
| ATOM | 1793 | N | CYS | A | 236 | 25.095 | 34.226 | 40.493 | 1.00 | 32.39 | N |
| ATOM | 1794 | CA | CYS | A | 236 | 24.487 | 34.286 | 39.185 | 1.00 | 32.11 | C |
| ATOM | 1795 | C | CYS | A | 236 | 25.529 | 34.640 | 38.139 | 1.00 | 32.34 | C |
| ATOM | 1796 | O | CYS | A | 236 | 25.217 | 35.034 | 37.018 | 1.00 | 32.23 | O |
| ATOM | 1797 | CB | CYS | A | 236 | 23.270 | 35.192 | 39.206 | 1.00 | 32.02 | C |
| ATOM | 1798 | SG | CYS | A | 236 | 21.990 | 34.545 | 40.326 | 1.00 | 32.09 | S |
| ATOM | 1799 | N | ASP | A | 237 | 26.789 | 34.456 | 38.511 | 1.00 | 32.71 | N |
| ATOM | 1800 | CA | ASP | A | 237 | 27.883 | 34.609 | 37.576 | 1.00 | 33.21 | C |
| ATOM | 1801 | C | ASP | A | 237 | 27.518 | 34.022 | 36.211 | 1.00 | 33.63 | C |
| ATOM | 1802 | O | ASP | A | 237 | 27.042 | 32.911 | 36.095 | 1.00 | 33.33 | O |
| ATOM | 1803 | CB | ASP | A | 237 | 29.139 | 33.964 | 38.132 | 1.00 | 33.01 | C |
| ATOM | 1804 | CG | ASP | A | 237 | 30.283 | 33.981 | 37.151 | 1.00 | 33.76 | C |
| ATOM | 1805 | OD1 | ASP | A | 237 | 30.340 | 34.874 | 36.279 | 1.00 | 34.52 | O |
| ATOM | 1806 | OD2 | ASP | A | 237 | 31.193 | 33.135 | 37.181 | 1.00 | 36.09 | O |
| ATOM | 1807 | N | ARG | A | 238 | 27.731 | 34.821 | 35.180 | 1.00 | 34.68 | N |
| ATOM | 1808 | CA | ARG | A | 238 | 27.414 | 34.451 | 33.810 | 1.00 | 35.15 | C |
| ATOM | 1809 | C | ARG | A | 238 | 25.962 | 34.690 | 33.375 | 1.00 | 34.98 | C |
| ATOM | 1810 | O | ARG | A | 238 | 25.664 | 34.543 | 32.197 | 1.00 | 34.26 | O |
| ATOM | 1811 | CB | ARG | A | 238 | 27.819 | 33.020 | 33.561 | 1.00 | 35.64 | C |
| ATOM | 1812 | CG | ARG | A | 238 | 29.286 | 32.847 | 33.620 | 1.00 | 36.86 | C |
| ATOM | 1813 | CD | ARG | A | 238 | 29.682 | 31.474 | 33.268 | 1.00 | 38.59 | C |
| ATOM | 1814 | NE | ARG | A | 238 | 29.321 | 30.549 | 34.338 | 1.00 | 41.64 | N |
| ATOM | 1815 | CZ | ARG | A | 238 | 28.265 | 29.755 | 34.286 | 1.00 | 43.17 | C |
| ATOM | 1816 | NH1 | ARG | A | 238 | 27.459 | 29.802 | 33.218 | 1.00 | 44.38 | N |
| ATOM | 1817 | NH2 | ARG | A | 238 | 28.006 | 28.923 | 35.291 | 1.00 | 42.18 | N |
| ATOM | 1818 | N | GLN | A | 239 | 25.067 | 35.044 | 34.303 | 1.00 | 35.13 | N |
| ATOM | 1819 | CA | GLN | A | 239 | 23.683 | 35.360 | 33.920 | 1.00 | 35.13 | C |
| ATOM | 1820 | C | GLN | A | 239 | 23.558 | 36.872 | 33.825 | 1.00 | 34.56 | C |
| ATOM | 1821 | O | GLN | A | 239 | 24.240 | 37.587 | 34.539 | 1.00 | 34.65 | O |
| ATOM | 1822 | CB | GLN | A | 239 | 22.646 | 34.839 | 34.921 | 1.00 | 35.27 | C |
| ATOM | 1823 | CG | GLN | A | 239 | 22.952 | 33.510 | 35.566 | 1.00 | 37.30 | C |
| ATOM | 1824 | CD | GLN | A | 239 | 23.270 | 32.431 | 34.552 | 1.00 | 41.59 | C |
| ATOM | 1825 | OE1 | GLN | A | 239 | 22.418 | 32.072 | 33.726 | 1.00 | 45.42 | O |
| ATOM | 1826 | NE2 | GLN | A | 239 | 24.491 | 31.899 | 34.609 | 1.00 | 42.92 | N |
| ATOM | 1827 | N | SER | A | 240 | 22.705 | 37.358 | 32.930 | 1.00 | 33.99 | N |
| ATOM | 1828 | CA | SER | A | 240 | 22.455 | 38.785 | 32.802 | 1.00 | 33.14 | C |
| ATOM | 1829 | C | SER | A | 240 | 21.613 | 39.254 | 33.957 | 1.00 | 32.53 | C |
| ATOM | 1830 | O | SER | A | 240 | 20.773 | 38.528 | 34.446 | 1.00 | 31.77 | O |
| ATOM | 1831 | CB | SER | A | 240 | 21.663 | 39.077 | 31.542 | 1.00 | 33.15 | C |
| ATOM | 1832 | OG | SER | A | 240 | 20.971 | 40.309 | 31.668 | 1.00 | 33.28 | O |
| ATOM | 1833 | N | GLN | A | 241 | 21.805 | 40.492 | 34.371 | 1.00 | 32.52 | N |
| ATOM | 1834 | CA | GLN | A | 241 | 21.022 | 41.025 | 35.476 | 1.00 | 32.54 | C |
| ATOM | 1835 | C | GLN | A | 241 | 19.711 | 41.629 | 35.001 | 1.00 | 32.44 | C |
| ATOM | 1836 | O | GLN | A | 241 | 18.872 | 42.019 | 35.804 | 1.00 | 32.16 | O |
| ATOM | 1837 | CB | GLN | A | 241 | 21.791 | 42.116 | 36.196 | 1.00 | 32.36 | C |
| ATOM | 1838 | CG | GLN | A | 241 | 22.995 | 41.669 | 36.917 | 1.00 | 32.74 | C |
| ATOM | 1839 | CD | GLN | A | 241 | 23.760 | 42.837 | 37.450 | 1.00 | 33.65 | C |
| ATOM | 1840 | OE1 | GLN | A | 241 | 23.353 | 43.442 | 38.428 | 1.00 | 34.26 | O |
| ATOM | 1841 | NE2 | GLN | A | 241 | 24.858 | 43.182 | 36.794 | 1.00 | 35.62 | N |
| ATOM | 1842 | N | VAL | A | 242 | 19.513 | 41.708 | 33.705 | 1.00 | 32.07 | N |
| ATOM | 1843 | CA | VAL | A | 242 | 18.357 | 42.412 | 33.255 | 1.00 | 32.29 | C |
| ATOM | 1844 | C | VAL | A | 242 | 17.162 | 41.521 | 33.265 | 1.00 | 31.93 | C |
| ATOM | 1845 | O | VAL | A | 242 | 17.221 | 40.442 | 32.734 | 1.00 | 32.93 | O |
| ATOM | 1846 | CB | VAL | A | 242 | 18.516 | 42.848 | 31.808 | 1.00 | 32.63 | C |

TABLE 3-continued

Coordinates for structures 1 to 4

| | | | | | | | | | | | |
|---|---|---|---|---|---|---|---|---|---|---|---|
| ATOM | 1847 | CG1 | VAL | A | 242 | 17.252 | 43.532 | 31.320 | 1.00 | 32.50 | C |
| ATOM | 1848 | CG2 | VAL | A | 242 | 19.717 | 43.714 | 31.655 | 1.00 | 33.06 | C |
| ATOM | 1849 | N | ASP | A | 243 | 16.067 | 41.977 | 33.838 | 1.00 | 31.76 | N |
| ATOM | 1850 | CA | ASP | A | 243 | 14.812 | 41.271 | 33.714 | 1.00 | 31.73 | C |
| ATOM | 1851 | C | ASP | A | 243 | 14.177 | 41.559 | 32.346 | 1.00 | 31.87 | C |
| ATOM | 1852 | O | ASP | A | 243 | 13.536 | 42.595 | 32.150 | 1.00 | 31.46 | O |
| ATOM | 1853 | CB | ASP | A | 243 | 13.861 | 41.689 | 34.830 | 1.00 | 31.61 | C |
| ATOM | 1854 | CG | ASP | A | 243 | 12.488 | 41.049 | 34.708 | 1.00 | 32.08 | C |
| ATOM | 1855 | OD1 | ASP | A | 243 | 12.164 | 40.448 | 33.655 | 1.00 | 30.69 | O |
| ATOM | 1856 | OD2 | ASP | A | 243 | 11.654 | 41.103 | 35.635 | 1.00 | 33.90 | O |
| ATOM | 1857 | N | PHE | A | 244 | 14.326 | 40.623 | 31.410 | 1.00 | 32.16 | N |
| ATOM | 1858 | CA | PHE | A | 244 | 13.746 | 40.787 | 30.075 | 1.00 | 32.29 | C |
| ATOM | 1859 | C | PHE | A | 244 | 12.252 | 41.087 | 30.092 | 1.00 | 32.74 | C |
| ATOM | 1860 | O | PHE | A | 244 | 11.741 | 41.694 | 29.162 | 1.00 | 32.51 | O |
| ATOM | 1861 | CB | PHE | A | 244 | 13.963 | 39.559 | 29.220 | 1.00 | 31.99 | C |
| ATOM | 1862 | CG | PHE | A | 244 | 15.327 | 39.446 | 28.650 | 1.00 | 31.29 | C |
| ATOM | 1863 | CD1 | PHE | A | 244 | 16.436 | 39.886 | 29.342 | 1.00 | 31.05 | C |
| ATOM | 1864 | CD2 | PHE | A | 244 | 15.500 | 38.861 | 27.421 | 1.00 | 31.04 | C |
| ATOM | 1865 | CE1 | PHE | A | 244 | 17.684 | 39.733 | 28.815 | 1.00 | 31.37 | C |
| ATOM | 1866 | CE2 | PHE | A | 244 | 16.742 | 38.709 | 26.888 | 1.00 | 31.39 | C |
| ATOM | 1867 | CZ | PHE | A | 244 | 17.839 | 39.141 | 27.584 | 1.00 | 31.77 | C |
| ATOM | 1868 | N | ASP | A | 245 | 11.547 | 40.646 | 31.124 | 1.00 | 33.52 | N |
| ATOM | 1869 | CA | ASP | A | 245 | 10.130 | 40.946 | 31.214 | 1.00 | 34.33 | C |
| ATOM | 1870 | C | ASP | A | 245 | 9.831 | 42.375 | 31.606 | 1.00 | 34.52 | C |
| ATOM | 1871 | O | ASP | A | 245 | 8.789 | 42.902 | 31.251 | 1.00 | 34.40 | O |
| ATOM | 1872 | CB | ASP | A | 245 | 9.448 | 40.015 | 32.188 | 1.00 | 34.59 | C |
| ATOM | 1873 | CG | ASP | A | 245 | 9.361 | 38.639 | 31.658 | 1.00 | 35.47 | C |
| ATOM | 1874 | OD1 | ASP | A | 245 | 9.282 | 38.519 | 30.420 | 1.00 | 36.40 | O |
| ATOM | 1875 | OD2 | ASP | A | 245 | 9.384 | 37.624 | 32.383 | 1.00 | 37.65 | O |
| ATOM | 1876 | N | ASN | A | 246 | 10.737 | 43.000 | 32.339 | 1.00 | 35.03 | N |
| ATOM | 1877 | CA | ASN | A | 246 | 10.531 | 44.364 | 32.776 | 1.00 | 35.38 | C |
| ATOM | 1878 | C | ASN | A | 246 | 11.873 | 45.003 | 32.896 | 1.00 | 34.97 | C |
| ATOM | 1879 | O | ASN | A | 246 | 12.370 | 45.160 | 33.994 | 1.00 | 35.01 | O |
| ATOM | 1880 | CB | ASN | A | 246 | 9.843 | 44.397 | 34.136 | 1.00 | 35.69 | C |
| ATOM | 1881 | OG | ASN | A | 246 | 9.395 | 45.800 | 34.533 | 1.00 | 37.41 | C |
| ATOM | 1882 | OD1 | ASN | A | 246 | 9.241 | 46.691 | 33.682 | 1.00 | 38.99 | O |
| ATOM | 1883 | ND2 | ASN | A | 246 | 9.186 | 46.006 | 35.836 | 1.00 | 38.90 | N |
| ATOM | 1884 | N | PRO | A | 247 | 12.468 | 45.357 | 31.766 | 1.00 | 34.87 | N |
| ATOM | 1885 | CA | PRO | A | 247 | 13.816 | 45.931 | 31.766 | 1.00 | 34.87 | C |
| ATOM | 1886 | C | PRO | A | 247 | 13.868 | 47.295 | 32.407 | 1.00 | 34.83 | C |
| ATOM | 1887 | O | PRO | A | 247 | 13.038 | 48.159 | 32.127 | 1.00 | 34.82 | O |
| ATOM | 1888 | CB | PRO | A | 247 | 14.184 | 46.046 | 30.288 | 1.00 | 34.75 | C |
| ATOM | 1889 | CG | PRO | A | 247 | 13.028 | 45.475 | 29.507 | 1.00 | 34.95 | C |
| ATOM | 1890 | CD | PRO | A | 247 | 11.892 | 45.241 | 30.419 | 1.00 | 34.75 | C |
| ATOM | 1891 | N | ASP | A | 248 | 14.861 | 47.448 | 33.270 | 1.00 | 34.67 | N |
| ATOM | 1892 | CA | ASP | A | 248 | 15.112 | 48.654 | 34.003 | 1.00 | 34.76 | C |
| ATOM | 1893 | C | ASP | A | 248 | 16.205 | 49.419 | 33.294 | 1.00 | 34.89 | C |
| ATOM | 1894 | O | ASP | A | 248 | 17.395 | 49.240 | 33.568 | 1.00 | 34.59 | O |
| ATOM | 1895 | CB | ASP | A | 248 | 15.583 | 48.265 | 35.387 | 1.00 | 34.87 | C |
| ATOM | 1896 | CG | ASP | A | 248 | 15.703 | 49.433 | 36.329 | 1.00 | 35.10 | C |
| ATOM | 1897 | OD1 | ASP | A | 248 | 15.958 | 50.583 | 35.902 | 1.00 | 34.24 | O |
| ATOM | 1898 | OD2 | ASP | A | 248 | 15.574 | 49.259 | 37.550 | 1.00 | 36.72 | O |
| ATOM | 1899 | N | TYR | A | 249 | 15.793 | 50.302 | 32.399 | 1.00 | 35.08 | N |
| ATOM | 1900 | CA | TYR | A | 249 | 16.743 | 51.063 | 31.615 | 1.00 | 35.24 | C |
| ATOM | 1901 | C | TYR | A | 249 | 17.578 | 52.071 | 32.400 | 1.00 | 35.48 | C |
| ATOM | 1902 | O | TYR | A | 249 | 18.570 | 52.567 | 31.880 | 1.00 | 35.44 | O |
| ATOM | 1903 | GB | TYR | A | 249 | 16.021 | 51.741 | 30.465 | 1.00 | 35.05 | C |
| ATOM | 1904 | CG | TYR | A | 249 | 15.304 | 50.761 | 29.586 | 1.00 | 34.41 | C |
| ATOM | 1905 | CD1 | TYR | A | 249 | 15.977 | 49.718 | 28.971 | 1.00 | 34.17 | C |
| ATOM | 1906 | CD2 | TYR | A | 249 | 13.955 | 50.865 | 29.383 | 1.00 | 34.14 | C |
| ATOM | 1907 | GE1 | TYR | A | 249 | 15.312 | 48.828 | 28.172 | 1.00 | 33.95 | C |
| ATOM | 1908 | CE2 | TYR | A | 249 | 13.287 | 49.983 | 28.595 | 1.00 | 33.71 | C |
| ATOM | 1909 | CZ | TYR | A | 249 | 13.954 | 48.974 | 27.989 | 1.00 | 34.19 | C |
| ATOM | 1910 | OH | TYR | A | 249 | 13.232 | 48.113 | 27.194 | 1.00 | 35.60 | O |
| ATOM | 1911 | N | GLU | A | 250 | 17.207 | 52.393 | 33.631 | 1.00 | 35.82 | N |
| ATOM | 1912 | CA | GLU | A | 250 | 18.072 | 53.273 | 34.399 | 1.00 | 36.69 | C |
| ATOM | 1913 | C | GLU | A | 250 | 19.331 | 52.562 | 34.834 | 1.00 | 36.69 | C |
| ATOM | 1914 | O | GLU | A | 250 | 20.424 | 53.102 | 34.715 | 1.00 | 36.84 | O |
| ATOM | 1915 | GB | GLU | A | 250 | 17.369 | 53.836 | 35.607 | 1.00 | 37.10 | C |
| ATOM | 1916 | CG | GLU | A | 250 | 16.173 | 54.653 | 35.195 | 1.00 | 39.48 | C |
| ATOM | 1917 | CD | GLU | A | 250 | 15.559 | 55.362 | 36.359 | 1.00 | 42.67 | C |
| ATOM | 1918 | OE1 | GLU | A | 250 | 16.128 | 55.258 | 37.469 | 1.00 | 45.95 | O |
| ATOM | 1919 | OE2 | GLU | A | 250 | 14.529 | 56.030 | 36.160 | 1.00 | 44.93 | O |
| ATOM | 1920 | N | ARG | A | 251 | 19.202 | 51.344 | 35.332 | 1.00 | 36.55 | N |
| ATOM | 1921 | CA | ARG | A | 251 | 20.389 | 50.666 | 35.773 | 1.00 | 36.36 | C |
| ATOM | 1922 | C | ARG | A | 251 | 21.124 | 50.162 | 34.584 | 1.00 | 35.91 | C |
| ATOM | 1923 | O | ARG | A | 251 | 22.347 | 50.117 | 34.588 | 1.00 | 36.89 | O |

TABLE 3-continued

| | | | | | | | | | | | |
|---|---|---|---|---|---|---|---|---|---|---|---|
| | Coordinates for structures 1 to 4 |

| ATOM | 1924 | GB | ARG | A | 251 | 20.062 | 49.495 | 36.697 | 1.00 | 36.66 | C |
| ATOM | 1925 | CG | ARG | A | 251 | 19.329 | 49.936 | 37.981 | 1.00 | 38.10 | C |
| ATOM | 1926 | CD | ARG | A | 251 | 18.848 | 48.824 | 38.916 | 1.00 | 39.00 | C |
| ATOM | 1927 | NE | ARG | A | 251 | 19.969 | 48.005 | 39.371 | 1.00 | 40.55 | N |
| ATOM | 1928 | CZ | ARG | A | 251 | 19.895 | 46.712 | 39.648 | 1.00 | 41.33 | C |
| ATOM | 1929 | NH1 | ARG | A | 251 | 18.742 | 46.068 | 39.542 | 1.00 | 42.58 | N |
| ATOM | 1930 | NH2 | ARG | A | 251 | 20.978 | 46.058 | 40.025 | 1.00 | 41.49 | N |
| ATOM | 1931 | N | PHE | A | 252 | 20.388 | 49.807 | 33.545 | 1.00 | 35.06 | N |
| ATOM | 1932 | CA | PHE | A | 252 | 20.988 | 49.065 | 32.455 | 1.00 | 34.37 | C |
| ATOM | 1933 | C | PHE | A | 252 | 20.653 | 49.675 | 31.138 | 1.00 | 33.82 | C |
| ATOM | 1934 | O | PHE | A | 252 | 20.048 | 49.042 | 30.218 | 1.00 | 33.57 | O |
| ATOM | 1935 | GB | PHE | A | 252 | 20.429 | 47.662 | 32.458 | 1.00 | 34.19 | C |
| ATOM | 1936 | CG | PHE | A | 252 | 20.404 | 47.019 | 33.803 | 1.00 | 33.98 | C |
| ATOM | 1937 | GD1 | PHE | A | 252 | 21.559 | 46.855 | 34.532 | 1.00 | 33.98 | C |
| ATOM | 1938 | CD2 | PHE | A | 252 | 19.220 | 46.560 | 34.337 | 1.00 | 32.84 | C |
| ATOM | 1939 | GE1 | PHE | A | 252 | 21.519 | 46.238 | 35.760 | 1.00 | 33.51 | C |
| ATOM | 1940 | CE2 | PHE | A | 252 | 19.189 | 45.953 | 35.560 | 1.00 | 32.14 | C |
| ATOM | 1941 | GZ | PHE | A | 252 | 20.327 | 45.789 | 36.269 | 1.00 | 31.96 | C |
| ATOM | 1942 | N | PRO | A | 253 | 21.087 | 50.903 | 30.959 | 1.00 | 33.27 | N |
| ATOM | 1943 | GA | PRO | A | 253 | 20.677 | 51.675 | 29.795 | 1.00 | 32.92 | C |
| ATOM | 1944 | C | PRO | A | 253 | 21.008 | 50.995 | 28.470 | 1.00 | 32.86 | C |
| ATOM | 1945 | O | PRO | A | 253 | 20.215 | 51.136 | 27.541 | 1.00 | 32.58 | O |
| ATOM | 1946 | GB | PRO | A | 253 | 21.464 | 52.957 | 29.962 | 1.00 | 32.58 | C |
| ATOM | 1947 | CG | PRO | A | 253 | 22.584 | 52.562 | 30.808 | 1.00 | 32.44 | C |
| ATOM | 1948 | CD | PRO | A | 253 | 22.038 | 51.640 | 31.802 | 1.00 | 32.67 | C |
| ATOM | 1949 | N | ASN | A | 254 | 22.108 | 50.253 | 28.359 | 1.00 | 32.60 | N |
| ATOM | 1950 | GA | ASN | A | 254 | 22.419 | 49.726 | 27.037 | 1.00 | 32.87 | C |
| ATOM | 1951 | C | ASN | A | 254 | 21.564 | 48.569 | 26.615 | 1.00 | 32.59 | C |
| ATOM | 1952 | O | ASN | A | 254 | 21.671 | 48.088 | 25.503 | 1.00 | 32.69 | O |
| ATOM | 1953 | CE | ASN | A | 254 | 23.892 | 49.414 | 26.852 | 1.00 | 32.72 | C |
| ATOM | 1954 | GG | ASN | A | 254 | 24.710 | 50.665 | 26.745 | 1.00 | 33.92 | C |
| ATOM | 1955 | OD1 | ASN | A | 254 | 25.428 | 51.022 | 27.672 | 1.00 | 37.05 | O |
| ATOM | 1956 | ND2 | ASN | A | 254 | 24.569 | 51.380 | 25.626 | 1.00 | 34.86 | N |
| ATOM | 1957 | N | PHE | A | 255 | 20.690 | 48.124 | 27.491 | 1.00 | 32.37 | N |
| ATOM | 1958 | CA | PHE | A | 255 | 19.834 | 47.057 | 27.101 | 1.00 | 32.19 | C |
| ATOM | 1959 | C | PHE | A | 255 | 18.932 | 47.578 | 26.006 | 1.00 | 32.36 | C |
| ATOM | 1960 | O | PHE | A | 255 | 18.267 | 46.819 | 25.326 | 1.00 | 32.64 | O |
| ATOM | 1961 | GB | PHE | A | 255 | 18.990 | 46.572 | 28.250 | 1.00 | 31.93 | C |
| ATOM | 1962 | CG | PHE | A | 255 | 18.249 | 45.354 | 27.918 | 1.00 | 31.43 | C |
| ATOM | 1963 | CD1 | PHE | A | 255 | 18.919 | 44.176 | 27.718 | 1.00 | 33.75 | C |
| ATOM | 1964 | CD2 | PHE | A | 255 | 16.909 | 45.392 | 27.718 | 1.00 | 31.23 | C |
| ATOM | 1965 | CE1 | PHE | A | 255 | 18.239 | 43.035 | 27.367 | 1.00 | 34.05 | C |
| ATOM | 1966 | CE2 | PHE | A | 255 | 16.230 | 44.275 | 27.380 | 1.00 | 32.00 | C |
| ATOM | 1967 | CZ | PHE | A | 255 | 16.890 | 43.088 | 27.203 | 1.00 | 32.84 | C |
| ATOM | 1968 | N | GLN | A | 256 | 18.890 | 48.888 | 25.844 | 1.00 | 32.46 | N |
| ATOM | 1969 | CA | GLN | A | 256 | 18.078 | 49.456 | 24.794 | 1.00 | 32.37 | C |
| ATOM | 1970 | C | GLN | A | 256 | 18.776 | 49.342 | 23.455 | 1.00 | 32.34 | C |
| ATOM | 1971 | O | GLN | A | 256 | 18.260 | 49.815 | 22.470 | 1.00 | 32.11 | O |
| ATOM | 1972 | CB | GLN | A | 256 | 17.777 | 50.924 | 25.061 | 1.00 | 32.28 | C |
| ATOM | 1973 | CG | GLN | A | 256 | 16.775 | 51.169 | 26.144 | 1.00 | 32.39 | C |
| ATOM | 1974 | CD | GLN | A | 256 | 16.823 | 52.594 | 26.645 | 1.00 | 32.91 | C |
| ATOM | 1975 | OE1 | GLN | A | 256 | 15.830 | 53.303 | 26.588 | 1.00 | 34.66 | O |
| ATOM | 1976 | NE2 | GLN | A | 256 | 17.982 | 53.021 | 27.125 | 1.00 | 32.30 | N |
| ATOM | 1977 | N | ASN | A | 257 | 19.956 | 48.744 | 23.404 | 1.00 | 32.78 | N |
| ATOM | 1978 | CA | ASN | A | 257 | 20.634 | 48.617 | 22.126 | 1.00 | 33.17 | C |
| ATOM | 1979 | C | ASN | A | 257 | 20.828 | 47.159 | 21.763 | 1.00 | 34.01 | C |
| ATOM | 1980 | O | ASN | A | 257 | 21.406 | 46.841 | 20.721 | 1.00 | 34.41 | O |
| ATOM | 1981 | CB | ASN | A | 257 | 21.998 | 49.310 | 22.140 | 1.00 | 32.88 | C |
| ATOM | 1982 | CG | ASN | A | 257 | 21.928 | 50.750 | 22.595 | 1.00 | 31.31 | C |
| ATOM | 1983 | OD1 | ASN | A | 257 | 22.471 | 51.105 | 23.639 | 1.00 | 27.26 | O |
| ATOM | 1984 | ND2 | ASN | A | 257 | 21.283 | 51.595 | 21.797 | 1.00 | 29.34 | N |
| ATOM | 1985 | N | VAL | A | 258 | 20.338 | 46.263 | 22.606 | 1.00 | 34.66 | N |
| ATOM | 1986 | CA | VAL | A | 258 | 20.565 | 44.855 | 22.370 | 1.00 | 35.33 | C |
| ATOM | 1987 | C | VAL | A | 258 | 19.832 | 44.361 | 21.130 | 1.00 | 35.37 | C |
| ATOM | 1988 | O | VAL | A | 258 | 18.751 | 44.832 | 20.813 | 1.00 | 34.96 | O |
| ATOM | 1989 | CB | VAL | A | 258 | 20.144 | 44.010 | 23.558 | 1.00 | 35.59 | C |
| ATOM | 1990 | CG1 | VAL | A | 258 | 18.632 | 43.851 | 23.604 | 1.00 | 35.73 | C |
| ATOM | 1991 | CG2 | VAL | A | 258 | 20.780 | 42.662 | 23.428 | 1.00 | 36.60 | C |
| ATOM | 1992 | N | VAL | A | 259 | 20.447 | 43.418 | 20.428 | 1.00 | 35.87 | N |
| ATOM | 1993 | CA | VAL | A | 259 | 39.853 | 42.844 | 19.230 | 1.00 | 36.40 | C |
| ATOM | 1994 | C | VAL | A | 259 | 20.125 | 41.355 | 19.148 | 1.00 | 36.66 | C |
| ATOM | 1995 | O | VAL | A | 259 | 21.282 | 40.943 | 19.102 | 1.00 | 36.47 | O |
| ATOM | 1996 | CB | VAL | A | 259 | 20.450 | 43.459 | 17.969 | 1.00 | 36.47 | C |
| ATOM | 1997 | CG1 | VAL | A | 259 | 19.830 | 42.822 | 16.764 | 1.00 | 36.75 | C |
| ATOM | 1998 | CG2 | VAL | A | 259 | 20.212 | 44.931 | 17.932 | 1.00 | 36.66 | C |
| ATOM | 1999 | N | GLY | A | 260 | 19.066 | 40.551 | 19.085 | 1.00 | 37.15 | N |
| ATOM | 2000 | CA | GLY | A | 260 | 19.215 | 39.096 | 19.067 | 1.00 | 37.50 | C |

TABLE 3-continued

Coordinates for structures 1 to 4

| ATOM | 2001 | C   | GLY | A | 260 | 19.132 | 38.328 | 17.745 | 1.00 | 37.55 | C |
|------|------|-----|-----|---|-----|--------|--------|--------|------|-------|---|
| ATOM | 2002 | O   | GLY | A | 260 | 18.716 | 38.839 | 16.704 | 1.00 | 37.45 | O |
| ATOM | 2003 | N   | TYR | A | 261 | 19.578 | 37.079 | 17.817 | 1.00 | 37.54 | N |
| ATOM | 2004 | CA  | TYR | A | 261 | 19.466 | 36.113 | 16.744 | 1.00 | 37.52 | C |
| ATOM | 2005 | C   | TYR | A | 261 | 18.530 | 35.107 | 17.358 | 1.00 | 37.09 | C |
| ATOM | 2006 | O   | TYR | A | 261 | 18.788 | 34.648 | 18.466 | 1.00 | 37.12 | O |
| ATOM | 2007 | CB  | TYR | A | 261 | 20.796 | 35.429 | 16.481 | 1.00 | 37.79 | C |
| ATOM | 2008 | CG  | TYR | A | 261 | 21.838 | 36.327 | 15.874 | 1.00 | 39.43 | C |
| ATOM | 2009 | CD1 | TYR | A | 261 | 22.005 | 36.380 | 14.507 | 1.00 | 41.03 | C |
| ATOM | 2010 | CD2 | TYR | A | 261 | 22.648 | 37.125 | 16.662 | 1.00 | 41.07 | C |
| ATOM | 2011 | CE1 | TYR | A | 261 | 22.937 | 37.193 | 13.940 | 1.00 | 41.71 | C |
| ATOM | 2012 | CE2 | TYR | A | 261 | 23.593 | 37.938 | 16.093 | 1.00 | 41.99 | C |
| ATOM | 2013 | CZ  | TYR | A | 261 | 23.725 | 37.960 | 14.728 | 1.00 | 42.45 | C |
| ATOM | 2014 | OH  | TYR | A | 261 | 24.650 | 38.762 | 14.121 | 1.00 | 46.29 | O |
| ATOM | 2015 | N   | GLU | A | 262 | 17.430 | 34.773 | 16.699 | 1.00 | 36.56 | N |
| ATOM | 2016 | CA  | GLU | A | 262 | 16.500 | 33.866 | 17.346 | 1.00 | 35.87 | C |
| ATOM | 2017 | C   | GLU | A | 262 | 16.064 | 32.737 | 16.447 | 1.00 | 35.41 | C |
| ATOM | 2018 | O   | GLU | A | 262 | 16.310 | 32.747 | 15.248 | 1.00 | 35.03 | O |
| ATOM | 2019 | CB  | GLU | A | 262 | 15.320 | 34.639 | 17.943 | 1.00 | 35.67 | C |
| ATOM | 2020 | CG  | GLU | A | 262 | 14.085 | 34.789 | 17.098 | 1.00 | 35.22 | C |
| ATOM | 2021 | CD  | GLU | A | 262 | 13.039 | 35.601 | 17.821 | 1.00 | 35.62 | C |
| ATOM | 2022 | OE1 | GLU | A | 262 | 13.201 | 36.833 | 17.866 | 1.00 | 38.15 | O |
| ATOM | 2023 | OE2 | GLU | A | 262 | 12.074 | 35.031 | 18.367 | 1.00 | 35.12 | O |
| ATOM | 2024 | N   | THR | A | 263 | 15.440 | 31.744 | 17.060 | 1.00 | 35.07 | N |
| ATOM | 2025 | CA  | THR | A | 263 | 15.004 | 30.565 | 16.351 | 1.00 | 34.84 | C |
| ATOM | 2026 | C   | THR | A | 263 | 14.138 | 29.670 | 17.224 | 1.00 | 34.38 | C |
| ATOM | 2027 | O   | THR | A | 263 | 14.152 | 29.745 | 18.452 | 1.00 | 34.07 | O |
| ATOM | 2028 | CB  | THR | A | 263 | 16.235 | 29.767 | 15.847 | 1.00 | 34.75 | C |
| ATOM | 2029 | OG1 | THR | A | 263 | 15.864 | 28.964 | 14.731 | 1.00 | 35.81 | O |
| ATOM | 2030 | CG2 | THR | A | 263 | 16.693 | 28.745 | 16.837 | 1.00 | 34.59 | C |
| ATOM | 2031 | N   | VAL | A | 264 | 13.368 | 28.820 | 16.573 | 1.00 | 34.02 | N |
| ATOM | 2032 | CA  | VAL | A | 264 | 12.597 | 27.854 | 17.306 | 1.00 | 33.95 | C |
| ATOM | 2033 | C   | VAL | A | 264 | 13.054 | 26.460 | 16.918 | 1.00 | 33.60 | C |
| ATOM | 2034 | O   | VAL | A | 264 | 12.957 | 26.065 | 15.762 | 1.00 | 33.27 | O |
| ATOM | 2035 | CB  | VAL | A | 264 | 11.112 | 28.019 | 17.075 | 1.00 | 33.95 | C |
| ATOM | 2036 | CG1 | VAL | A | 264 | 10.393 | 26.788 | 17.568 | 1.00 | 34.24 | C |
| ATOM | 2037 | CG2 | VAL | A | 264 | 10.615 | 29.247 | 17.823 | 1.00 | 33.85 | C |
| ATOM | 2038 | N   | VAL | A | 265 | 13.572 | 25.708 | 17.880 | 1.00 | 33.43 | N |
| ATOM | 2039 | CA  | VAL | A | 265 | 13.984 | 24.354 | 17.546 | 1.00 | 33.48 | C |
| ATOM | 2040 | C   | VAL | A | 265 | 12.949 | 23.321 | 17.907 | 1.00 | 32.85 | C |
| ATOM | 2041 | O   | VAL | A | 265 | 12.234 | 23.441 | 18.884 | 1.00 | 32.91 | O |
| ATOM | 2042 | CB  | VAL | A | 265 | 15.332 | 23.954 | 18.139 | 1.00 | 33.61 | C |
| ATOM | 2043 | CG1 | VAL | A | 265 | 16.408 | 24.721 | 17.432 | 1.00 | 34.56 | C |
| ATOM | 2044 | CG2 | VAL | A | 265 | 15.381 | 24.153 | 19.636 | 1.00 | 33.15 | C |
| ATOM | 2045 | N   | GLY | A | 266 | 12.848 | 22.321 | 17.064 | 1.00 | 32.32 | N |
| ATOM | 2046 | CA  | GLY | A | 266 | 11.938 | 21.240 | 17.331 | 1.00 | 32.27 | C |
| ATOM | 2047 | C   | GLY | A | 266 | 12.634 | 19.905 | 17.310 | 1.00 | 31.78 | C |
| ATOM | 2048 | O   | GLY | A | 266 | 13.852 | 19.799 | 17.124 | 1.00 | 31.15 | O |
| ATOM | 2049 | N   | PRO | A | 267 | 11.827 | 18.872 | 17.454 | 1.00 | 31.56 | N |
| ATOM | 2050 | CA  | PRO | A | 267 | 12.343 | 17.516 | 17.547 | 1.00 | 31.40 | C |
| ATOM | 2051 | C   | PRO | A | 267 | 13.203 | 17.314 | 16.336 | 1.00 | 31.22 | C |
| ATOM | 2052 | O   | PRO | A | 267 | 12.755 | 17.631 | 15.241 | 1.00 | 31.24 | O |
| ATOM | 2053 | CB  | PRO | A | 267 | 11.074 | 16.664 | 17.552 | 1.00 | 30.81 | C |
| ATOM | 2054 | CG  | PRO | A | 267 | 10.048 | 17.568 | 18.087 | 1.00 | 31.26 | C |
| ATOM | 2055 | CD  | PRO | A | 267 | 10.358 | 18.900 | 17.451 | 1.00 | 31.85 | C |
| ATOM | 2056 | N   | GLY | A | 268 | 14.445 | 16.891 | 16.536 | 1.00 | 31.06 | N |
| ATOM | 2057 | CA  | GLY | A | 268 | 15.334 | 16.620 | 15.426 | 1.00 | 31.07 | C |
| ATOM | 2058 | C   | GLY | A | 268 | 16.337 | 17.703 | 15.112 | 1.00 | 31.31 | C |
| ATOM | 2059 | O   | GLY | A | 268 | 17.352 | 17.425 | 14.493 | 1.00 | 31.12 | O |
| ATOM | 2060 | N   | ASP | A | 269 | 16.061 | 18.939 | 15.517 | 1.00 | 31.87 | N |
| ATOM | 2061 | CA  | ASP | A | 269 | 16.975 | 20.032 | 15.253 | 1.00 | 32.18 | C |
| ATOM | 2062 | C   | ASP | A | 269 | 18.117 | 20.099 | 16.282 | 1.00 | 32.69 | C |
| ATOM | 2063 | O   | ASP | A | 269 | 17.974 | 19.720 | 17.450 | 1.00 | 32.69 | O |
| ATOM | 2064 | CB  | ASP | A | 269 | 16.282 | 21.381 | 15.390 | 1.00 | 32.73 | C |
| ATOM | 2065 | CG  | ASP | A | 269 | 15.094 | 21.583 | 14.478 | 1.00 | 32.07 | C |
| ATOM | 2066 | OD1 | ASP | A | 269 | 15.023 | 21.039 | 13.367 | 1.00 | 33.96 | O |
| ATOM | 2067 | OD2 | ASP | A | 269 | 14.191 | 22.368 | 14.806 | 1.00 | 30.81 | O |
| ATOM | 2068 | N   | VAL | A | 270 | 19.234 | 20.667 | 15.854 | 1.00 | 32.97 | N |
| ATOM | 2069 | CA  | VAL | A | 270 | 20.376 | 20.839 | 16.715 | 1.00 | 32.97 | C |
| ATOM | 2070 | C   | VAL | A | 270 | 20.844 | 22.258 | 16.579 | 1.00 | 32.97 | C |
| ATOM | 2071 | O   | VAL | A | 270 | 21.130 | 22.716 | 15.488 | 1.00 | 33.40 | O |
| ATOM | 2072 | CB  | VAL | A | 270 | 21.485 | 19.896 | 16.323 | 1.00 | 32.94 | C |
| ATOM | 2073 | CG1 | VAL | A | 270 | 22.755 | 20.207 | 17.066 | 1.00 | 33.16 | C |
| ATOM | 2074 | CG2 | VAL | A | 270 | 21.069 | 18.519 | 16.646 | 1.00 | 33.14 | C |
| ATOM | 2075 | N   | LEU | A | 271 | 20.883 | 22.965 | 17.692 | 1.00 | 32.91 | N |
| ATOM | 2076 | CA  | LEU | A | 271 | 21.321 | 24.337 | 17.690 | 1.00 | 32.91 | C |
| ATOM | 2077 | C   | LEU | A | 271 | 22.770 | 24.395 | 18.129 | 1.00 | 32.95 | C |

TABLE 3-continued

Coordinates for structures 1 to 4

| ATOM | 2078 | O | LEU | A | 271 | 23.116 | 23.864 | 19.161 | 1.00 | 32.76 | O |
|---|---|---|---|---|---|---|---|---|---|---|---|
| ATOM | 2079 | CB | LEU | A | 271 | 20.468 | 25.159 | 18.656 | 1.00 | 32.64 | C |
| ATOM | 2080 | CG | LEU | A | 271 | 20.896 | 26.616 | 18.773 | 1.00 | 32.61 | C |
| ATOM | 2081 | CD1 | LEU | A | 271 | 20.989 | 27.276 | 17.405 | 1.00 | 32.23 | C |
| ATOM | 2082 | CD2 | LEU | A | 271 | 19.936 | 27.383 | 19.638 | 1.00 | 33.12 | C |
| ATOM | 2083 | N | TYR | A | 272 | 23.633 | 25.006 | 17.333 | 1.00 | 33.19 | N |
| ATOM | 2084 | CA | TYR | A | 272 | 24.989 | 25.215 | 17.791 | 1.00 | 33.39 | C |
| ATOM | 2085 | C | TYR | A | 272 | 25.004 | 26.517 | 18.554 | 1.00 | 33.40 | C |
| ATOM | 2086 | O | TYR | A | 272 | 24.834 | 27.560 | 17.950 | 1.00 | 33.42 | O |
| ATOM | 2087 | GB | TYR | A | 272 | 25.991 | 25.297 | 16.633 | 1.00 | 33.28 | C |
| ATOM | 2088 | GG | TYR | A | 272 | 27.376 | 25.802 | 17.039 | 1.00 | 32.43 | C |
| ATOM | 2089 | CD1 | TYR | A | 272 | 28.005 | 25.340 | 18.279 | 1.00 | 31.06 | C |
| ATOM | 2090 | CD2 | TYR | A | 272 | 28.047 | 26.746 | 16.267 | 1.00 | 32.28 | C |
| ATOM | 2091 | GE1 | TYR | A | 272 | 29.265 | 25.805 | 18.544 | 1.00 | 30.52 | C |
| ATOM | 2092 | CE2 | TYR | A | 272 | 29.300 | 27.213 | 16.622 | 1.00 | 30.88 | C |
| ATOM | 2093 | CZ | TYR | A | 272 | 29.906 | 26.737 | 17.759 | 1.00 | 29.92 | C |
| ATOM | 2094 | OH | TYR | A | 272 | 31.146 | 27.216 | 18.113 | 1.00 | 27.15 | O |
| ATOM | 2095 | N | ILE | A | 273 | 25.178 | 26.438 | 19.872 | 1.00 | 33.69 | N |
| ATOM | 2096 | GA | ILE | A | 273 | 25.350 | 27.609 | 20.734 | 1.00 | 33.97 | C |
| ATOM | 2097 | C | ILE | A | 273 | 26.830 | 27.759 | 21.068 | 1.00 | 34.43 | C |
| ATOM | 2098 | O | ILE | A | 273 | 27.332 | 27.113 | 21.998 | 1.00 | 34.76 | O |
| ATOM | 2099 | GB | ILE | A | 273 | 24.595 | 27.436 | 22.032 | 1.00 | 33.75 | C |
| ATOM | 2100 | GG1 | ILE | A | 273 | 23.122 | 27.219 | 21.749 | 1.00 | 33.59 | C |
| ATOM | 2101 | CG2 | ILE | A | 273 | 24.779 | 28.654 | 22.896 | 1.00 | 33.60 | C |
| ATOM | 2102 | CD1 | ILE | A | 273 | 22.306 | 26.986 | 22.984 | 1.00 | 33.23 | C |
| ATOM | 2103 | N | PRO | A | 274 | 27.519 | 28.630 | 20.345 | 1.00 | 34.61 | N |
| ATOM | 2104 | GA | PRO | A | 274 | 28.965 | 28.780 | 20.485 | 1.00 | 34.92 | C |
| ATOM | 2105 | C | PRO | A | 274 | 29.348 | 29.378 | 21.803 | 1.00 | 35.17 | C |
| ATOM | 2106 | O | PRO | A | 274 | 28.639 | 30.252 | 22.300 | 1.00 | 35.16 | O |
| ATOM | 2107 | GB | PRO | A | 274 | 29.333 | 29.771 | 19.382 | 1.00 | 35.09 | C |
| ATOM | 2108 | CG | PRO | A | 274 | 28.113 | 29.929 | 18.551 | 1.00 | 35.02 | C |
| ATOM | 2109 | CD | PRO | A | 274 | 26.957 | 29.584 | 19.388 | 1.00 | 34.69 | C |
| ATOM | 2110 | N | MET | A | 275 | 30.476 | 28.927 | 22.339 | 1.00 | 35.69 | N |
| ATOM | 2111 | GA | MET | A | 275 | 30.982 | 29.399 | 23.622 | 1.00 | 36.15 | C |
| ATOM | 2112 | C | MET | A | 275 | 30.981 | 30.917 | 23.754 | 1.00 | 36.09 | C |
| ATOM | 2113 | O | MET | A | 275 | 31.316 | 31.635 | 22.805 | 1.00 | 36.23 | O |
| ATOM | 2114 | GB | MET | A | 275 | 32.400 | 28.928 | 23.805 | 1.00 | 36.23 | C |
| ATOM | 2115 | GG | MET | A | 275 | 32.813 | 28.928 | 25.229 | 1.00 | 38.02 | C |
| ATOM | 2116 | SD | MET | A | 275 | 34.361 | 28.108 | 25.442 | 1.00 | 42.07 | S |
| ATOM | 2117 | GE | MET | A | 275 | 35.330 | 28.680 | 23.895 | 1.00 | 42.34 | C |
| ATOM | 2118 | N | TYR | A | 276 | 30.611 | 31.401 | 24.935 | 1.00 | 35.76 | N |
| ATOM | 2119 | GA | TYR | A | 276 | 30.574 | 32.833 | 25.191 | 1.00 | 35.62 | C |
| ATOM | 2120 | C | TYR | A | 276 | 29.339 | 33.513 | 24.555 | 1.00 | 35.32 | C |
| ATOM | 2121 | O | TYR | A | 276 | 29.048 | 34.653 | 24.866 | 1.00 | 35.15 | O |
| ATOM | 2122 | GB | TYR | A | 276 | 31.921 | 33.510 | 24.804 | 1.00 | 35.75 | C |
| ATOM | 2123 | GG | TYR | A | 276 | 33.049 | 33.221 | 25.822 | 1.00 | 35.70 | C |
| ATOM | 2124 | GD1 | TYR | A | 276 | 33.036 | 33.805 | 27.077 | 1.00 | 34.51 | C |
| ATOM | 2125 | CD2 | TYR | A | 276 | 34.103 | 32.356 | 25.521 | 1.00 | 35.30 | C |
| ATOM | 2126 | GE1 | TYR | A | 276 | 34.013 | 33.549 | 27.997 | 1.00 | 34.63 | C |
| ATOM | 2127 | CE2 | TYR | A | 276 | 35.100 | 32.085 | 26.446 | 1.00 | 35.01 | C |
| ATOM | 2128 | CZ | TYR | A | 276 | 35.055 | 32.685 | 27.695 | 1.00 | 35.73 | C |
| ATOM | 2129 | OH | TYR | A | 276 | 36.051 | 32.433 | 28.657 | 1.00 | 34.27 | O |
| ATOM | 2130 | N | TRP | A | 277 | 28.573 | 32.838 | 23.708 | 1.00 | 35.19 | N |
| ATOM | 2131 | GA | TRP | A | 277 | 27.353 | 33.491 | 23.224 | 1.00 | 35.20 | C |
| ATOM | 2132 | C | TRP | A | 277 | 26.245 | 33.424 | 24.245 | 1.00 | 35.16 | C |
| ATOM | 2133 | O | TRP | A | 277 | 25.947 | 32.369 | 24.797 | 1.00 | 35.08 | O |
| ATOM | 2134 | GB | TRP | A | 277 | 26.806 | 32.880 | 21.944 | 1.00 | 35.27 | C |
| ATOM | 2135 | CG | TRP | A | 277 | 27.538 | 33.286 | 20.784 | 1.00 | 34.70 | C |
| ATOM | 2136 | CD1 | TRP | A | 277 | 28.858 | 33.128 | 20.579 | 1.00 | 35.11 | C |
| ATOM | 2137 | CD2 | TRP | A | 277 | 27.020 | 33.945 | 19.639 | 1.00 | 35.27 | C |
| ATOM | 2138 | NE1 | TRP | A | 277 | 29.213 | 33.648 | 19.361 | 1.00 | 35.58 | N |
| ATOM | 2139 | GE2 | TRP | A | 277 | 28.094 | 34.156 | 18.761 | 1.00 | 34.89 | C |
| ATOM | 2140 | CE3 | TRP | A | 277 | 25.751 | 34.388 | 19.258 | 1.00 | 35.56 | C |
| ATOM | 2141 | GZ2 | TRP | A | 277 | 27.946 | 34.781 | 17.543 | 1.00 | 32.83 | C |
| ATOM | 2142 | GZ3 | TRP | A | 277 | 25.612 | 35.012 | 18.041 | 1.00 | 34.41 | C |
| ATOM | 2143 | CH2 | TRP | A | 277 | 26.704 | 35.199 | 17.201 | 1.00 | 33.11 | C |
| ATOM | 2144 | N | TRP | A | 278 | 25.597 | 34.555 | 24.457 | 1.00 | 35.11 | N |
| ATOM | 2145 | GA | TRP | A | 278 | 24.501 | 34.612 | 25.388 | 1.00 | 35.03 | C |
| ATOM | 2146 | C | TRP | A | 278 | 23.334 | 33.859 | 24.838 | 1.00 | 35.14 | C |
| ATOM | 2147 | O | TRP | A | 278 | 23.068 | 33.939 | 23.637 | 1.00 | 35.16 | O |
| ATOM | 2148 | CB | TRP | A | 278 | 24.047 | 36.030 | 25.553 | 1.00 | 34.94 | C |
| ATOM | 2149 | CG | TRP | A | 278 | 25.025 | 36.909 | 26.165 | 1.00 | 35.52 | C |
| ATOM | 2150 | CD1 | TRP | A | 278 | 26.030 | 37.597 | 25.584 | 1.00 | 35.77 | C |
| ATOM | 2151 | CD2 | TRP | A | 278 | 25.071 | 37.244 | 27.560 | 1.00 | 36.19 | C |
| ATOM | 2152 | NE1 | TRP | A | 278 | 26.713 | 38.336 | 26.518 | 1.00 | 36.09 | N |
| ATOM | 2153 | CE2 | TRP | A | 278 | 26.133 | 38.132 | 27.741 | 1.00 | 36.37 | C |
| ATOM | 2154 | CE3 | TRP | A | 278 | 24.312 | 36.876 | 28.668 | 1.00 | 36.48 | C |

TABLE 3-continued

| | | | | | | | | | | | |
|---|---|---|---|---|---|---|---|---|---|---|---|
| | | | | | Coordinates for structures 1 to 4 | | | | | | |
| ATOM | 2155 | CZ2 | TRP | A | 278 | 26.463 | 38.637 | 28.976 | 1.00 | 37.12 | C |
| ATOM | 2156 | CZ3 | TRP | A | 278 | 24.636 | 37.375 | 29.877 | 1.00 | 36.37 | C |
| ATOM | 2157 | CH2 | TRP | A | 278 | 25.701 | 38.246 | 30.032 | 1.00 | 36.92 | C |
| ATOM | 2158 | N | HIS | A | 279 | 22.620 | 33.133 | 25.692 | 1.00 | 35.10 | N |
| ATOM | 2159 | CA | HIS | A | 279 | 21.400 | 32.516 | 25.218 | 1.00 | 35.20 | C |
| ATOM | 2160 | C | HIS | A | 279 | 20.300 | 32.555 | 26.231 | 1.00 | 34.69 | C |
| ATOM | 2161 | O | HIS | A | 279 | 20.540 | 32.348 | 27.414 | 1.00 | 34.75 | O |
| ATOM | 2162 | CB | HIS | A | 279 | 21.624 | 31.079 | 24.764 | 1.00 | 35.73 | C |
| ATOM | 2163 | CG | HIS | A | 279 | 22.403 | 30.236 | 25.727 | 1.00 | 37.15 | C |
| ATOM | 2164 | ND1 | HIS | A | 279 | 23.775 | 30.295 | 25.819 | 1.00 | 39.54 | N |
| ATOM | 2165 | CD2 | HIS | A | 279 | 22.010 | 29.283 | 26.609 | 1.00 | 38.10 | C |
| ATOM | 2166 | CE1 | HIS | A | 279 | 24.194 | 29.425 | 26.726 | 1.00 | 39.33 | C |
| ATOM | 2167 | NE2 | HIS | A | 279 | 23.143 | 28.797 | 27.221 | 1.00 | 37.68 | N |
| ATOM | 2168 | N | HIS | A | 280 | 19.092 | 32.795 | 25.721 | 1.00 | 34.17 | N |
| ATOM | 2169 | CA | HIS | A | 280 | 17.850 | 32.854 | 26.483 | 1.00 | 33.72 | C |
| ATOM | 2170 | C | HIS | A | 280 | 16.960 | 31.779 | 25.901 | 1.00 | 33.50 | C |
| ATOM | 2171 | O | HIS | A | 280 | 16.730 | 31.765 | 24.705 | 1.00 | 33.21 | O |
| ATOM | 2172 | CE | HIS | A | 280 | 17.215 | 34.208 | 26.257 | 1.00 | 33.58 | C |
| ATOM | 2173 | CG | HIS | A | 280 | 15.733 | 34.247 | 26.468 | 1.00 | 33.92 | C |
| ATOM | 2174 | ND1 | HIS | A | 280 | 15.151 | 34.997 | 27.464 | 1.00 | 33.67 | N |
| ATOM | 2175 | CD2 | HIS | A | 280 | 14.711 | 33.680 | 25.779 | 1.00 | 34.05 | C |
| ATOM | 2176 | CE1 | HIS | A | 280 | 13.838 | 34.874 | 27.395 | 1.00 | 33.47 | C |
| ATOM | 2177 | NE2 | HIS | A | 280 | 13.545 | 34.078 | 26.384 | 1.00 | 33.19 | N |
| ATOM | 2178 | N | ILE | A | 281 | 16.425 | 30.892 | 26.723 | 1.00 | 33.62 | N |
| ATOM | 2179 | CA | ILE | A | 281 | 15.699 | 29.755 | 26.176 | 1.00 | 33.56 | C |
| ATOM | 2180 | C | ILE | A | 281 | 14.358 | 29.554 | 26.806 | 1.00 | 33.01 | C |
| ATOM | 2181 | O | ILE | A | 281 | 14.242 | 29.475 | 28.012 | 1.00 | 32.55 | O |
| ATOM | 2182 | CE | ILE | A | 281 | 16.554 | 28.501 | 26.300 | 1.00 | 33.91 | C |
| ATOM | 2183 | CG1 | ILE | A | 281 | 17.699 | 28.600 | 25.295 | 1.00 | 35.00 | C |
| ATOM | 2184 | CG2 | ILE | A | 281 | 15.752 | 27.277 | 25.988 | 1.00 | 34.05 | C |
| ATOM | 2185 | CD1 | ILE | A | 281 | 18.797 | 27.663 | 25.562 | 1.00 | 36.33 | C |
| ATOM | 2186 | N | GLU | A | 282 | 13.343 | 29.445 | 25.960 | 1.00 | 33.12 | N |
| ATOM | 2187 | CA | GLU | A | 282 | 11.977 | 29.342 | 26.441 | 1.00 | 33.13 | C |
| ATOM | 2188 | C | GLU | A | 282 | 11.168 | 28.219 | 25.777 | 1.00 | 32.96 | C |
| ATOM | 2189 | O | GLU | A | 282 | 11.252 | 27.988 | 24.577 | 1.00 | 32.94 | O |
| ATOM | 2190 | CE | GLU | A | 282 | 11.290 | 30.707 | 26.327 | 1.00 | 33.06 | C |
| ATOM | 2191 | CG | GLU | A | 282 | 11.065 | 31.250 | 24.925 | 1.00 | 33.43 | C |
| ATOM | 2192 | CD | GLU | A | 282 | 10.529 | 32.682 | 24.951 | 1.00 | 33.96 | C |
| ATOM | 2193 | OE1 | GLU | A | 282 | 11.071 | 33.500 | 25.703 | 1.00 | 34.61 | O |
| ATOM | 2194 | OE2 | GLU | A | 282 | 9.563 | 33.009 | 24.236 | 1.00 | 35.15 | O |
| ATOM | 2195 | N | SER | A | 283 | 10.431 | 27.497 | 26.607 | 1.00 | 32.96 | N |
| ATOM | 2196 | CA | SER | A | 283 | 9.571 | 26.420 | 26.169 | 1.00 | 33.51 | C |
| ATOM | 2197 | C | SER | A | 283 | 8.247 | 27.070 | 25.784 | 1.00 | 34.03 | C |
| ATOM | 2198 | O | SER | A | 283 | 7.654 | 27.772 | 26.597 | 1.00 | 34.19 | O |
| ATOM | 2199 | CE | SER | A | 283 | 9.375 | 25.408 | 27.303 | 1.00 | 33.43 | C |
| ATOM | 2200 | OG | SER | A | 283 | 10.371 | 24.393 | 27.280 | 1.00 | 32.99 | O |
| ATOM | 2201 | N | LEU | A | 284 | 7.769 | 26.828 | 24.565 | 1.00 | 34.36 | N |
| ATOM | 2202 | CA | LEU | A | 284 | 6.610 | 27.553 | 24.081 | 1.00 | 34.81 | C |
| ATOM | 2203 | C | LEU | A | 284 | 5.399 | 27.454 | 24.982 | 1.00 | 35.14 | C |
| ATOM | 2204 | O | LEU | A | 284 | 5.128 | 26.425 | 25.599 | 1.00 | 35.08 | O |
| ATOM | 2205 | CE | LEU | A | 284 | 6.226 | 27.131 | 22.670 | 1.00 | 35.02 | C |
| ATOM | 2206 | CG | LEU | A | 284 | 7.302 | 27.255 | 21.596 | 1.00 | 35.52 | C |
| ATOM | 2207 | CE1 | LEU | A | 284 | 6.675 | 27.427 | 20.231 | 1.00 | 36.06 | C |
| ATOM | 2208 | CD2 | LEU | A | 284 | 8.197 | 28.404 | 21.862 | 1.00 | 36.37 | C |
| ATOM | 2209 | N | LEU | A | 285 | 4.674 | 28.561 | 25.040 | 1.00 | 35.48 | N |
| ATOM | 2210 | CA | LEU | A | 285 | 3.481 | 28.641 | 25.832 | 1.00 | 35.85 | C |
| ATOM | 2211 | C | LEU | A | 285 | 2.509 | 27.670 | 25.255 | 1.00 | 36.11 | C |
| ATOM | 2212 | O | LEU | A | 285 | 2.314 | 27.623 | 24.041 | 1.00 | 36.34 | O |
| ATOM | 2213 | CB | LEU | A | 285 | 2.876 | 30.024 | 25.742 | 1.00 | 35.90 | C |
| ATOM | 2214 | CG | LEU | A | 285 | 3.740 | 31.116 | 26.343 | 1.00 | 36.22 | C |
| ATOM | 2215 | CE1 | LEU | A | 285 | 3.271 | 32.449 | 25.821 | 1.00 | 36.13 | C |
| ATOM | 2216 | CD2 | LEU | A | 285 | 3.701 | 31.034 | 27.861 | 1.00 | 36.27 | C |
| ATOM | 2217 | N | ASN | A | 286 | 1.909 | 26.879 | 26.128 | 1.00 | 36.14 | N |
| ATOM | 2218 | CA | ASN | A | 286 | 0.890 | 25.958 | 25.703 | 1.00 | 36.04 | C |
| ATOM | 2219 | C | ASN | A | 286 | 1.373 | 24.932 | 24.663 | 1.00 | 35.65 | C |
| ATOM | 2220 | O | ASN | A | 286 | 0.593 | 24.471 | 23.833 | 1.00 | 35.84 | O |
| ATOM | 2221 | CB | ASN | A | 286 | 0.283 | 26.792 | 25.191 | 1.00 | 36.33 | C |
| ATOM | 2222 | CG | ASN | A | 286 | 0.805 | 27.766 | 26.254 | 1.00 | 36.97 | C |
| ATOM | 2223 | OD1 | ASN | A | 286 | 1.266 | 27.346 | 27.316 | 1.00 | 37.84 | O |
| ATOM | 2224 | ND2 | ASN | A | 286 | 0.716 | 29.067 | 25.977 | 1.00 | 37.29 | N |
| ATOM | 2225 | N | GLY | A | 287 | 2.648 | 24.550 | 24.736 | 1.00 | 35.18 | N |
| ATOM | 2226 | CA | GLY | A | 287 | 3.220 | 23.588 | 23.806 | 1.00 | 34.71 | C |
| ATOM | 2227 | C | GLY | A | 287 | 3.556 | 22.252 | 24.428 | 1.00 | 34.44 | C |
| ATOM | 2228 | O | GLY | A | 287 | 4.071 | 21.349 | 23.764 | 1.00 | 34.53 | O |
| ATOM | 2229 | N | GLY | A | 288 | 3.255 | 22.106 | 25.706 | 1.00 | 34.18 | N |
| ATOM | 2230 | CA | GLY | A | 288 | 3.521 | 20.858 | 26.371 | 1.00 | 34.22 | C |
| ATOM | 2231 | C | GLY | A | 288 | 4.964 | 20.793 | 26.766 | 1.00 | 34.25 | C |

TABLE 3-continued

| | | | | | Coordinates for structures 1 to 4 | | | | | |
|---|---|---|---|---|---|---|---|---|---|---|
| ATOM | 2232 | O | GLY | A | 288 | 5.727 | 21.719 | 26.523 | 1.00 | 34.28 | O |
| ATOM | 2233 | N | ILE | A | 289 | 5.351 | 19.674 | 27.349 | 1.00 | 34.55 | N |
| ATOM | 2234 | CA | ILE | A | 289 | 6.671 | 19.572 | 27.918 | 1.00 | 34.83 | C |
| ATOM | 2235 | C | ILE | A | 289 | 7.702 | 19.529 | 26.837 | 1.00 | 34.87 | C |
| ATOM | 2236 | O | ILE | A | 289 | 7.417 | 19.196 | 25.687 | 1.00 | 35.21 | O |
| ATOM | 2237 | CB | ILE | A | 289 | 6.815 | 18.325 | 28.786 | 1.00 | 35.01 | C |
| ATOM | 2238 | CG1 | ILE | A | 289 | 7.018 | 17.091 | 27.924 | 1.00 | 35.30 | C |
| ATOM | 2239 | CG2 | ILE | A | 289 | 5.610 | 18.143 | 29.694 | 1.00 | 35.22 | C |
| ATOM | 2240 | CO1 | ILE | A | 289 | 7.654 | 15.972 | 28.698 | 1.00 | 35.70 | C |
| ATOM | 2241 | N | THR | A | 290 | 8.921 | 19.853 | 27.219 | 1.00 | 34.80 | N |
| ATOM | 2242 | CA | THR | A | 290 | 10.001 | 19.849 | 26.273 | 1.00 | 34.64 | C |
| ATOM | 2243 | C | THR | A | 290 | 11.103 | 18.951 | 26.740 | 1.00 | 34.30 | C |
| ATOM | 2244 | O | THR | A | 290 | 11.286 | 18.742 | 27.924 | 1.00 | 34.66 | O |
| ATOM | 2245 | CB | THR | A | 290 | 10.522 | 21.258 | 26.094 | 1.00 | 34.75 | C |
| ATOM | 2246 | OG1 | THR | A | 290 | 10.747 | 21.863 | 27.375 | 1.00 | 34.33 | O |
| ATOM | 2247 | CG2 | THR | A | 290 | 9.455 | 22.105 | 25.458 | 1.00 | 34.98 | C |
| ATOM | 2248 | N | ILE | A | 291 | 11.832 | 18.395 | 25.802 | 1.00 | 33.95 | N |
| ATOM | 2249 | CA | ILE | A | 291 | 12.940 | 17.576 | 26.176 | 1.00 | 34.07 | C |
| ATOM | 2250 | C | ILE | A | 291 | 14.091 | 17.963 | 25.310 | 1.00 | 33.73 | C |
| ATOM | 2251 | O | ILE | A | 291 | 13.933 | 18.203 | 24.125 | 1.00 | 33.83 | O |
| ATOM | 2252 | CB | ILE | A | 291 | 12.590 | 16.111 | 26.029 | 1.00 | 34.23 | C |
| ATOM | 2253 | CG1 | ILE | A | 291 | 11.439 | 15.793 | 26.967 | 1.00 | 34.84 | C |
| ATOM | 2254 | CG2 | ILE | A | 291 | 13.758 | 15.248 | 26.429 | 1.00 | 34.60 | C |
| ATOM | 2255 | CD1 | ILE | A | 291 | 11.021 | 14.384 | 26.946 | 1.00 | 35.22 | C |
| ATOM | 2256 | N | THR | A | 292 | 15.254 | 18.062 | 25.913 | 1.00 | 33.47 | N |
| ATOM | 2257 | CA | THR | A | 292 | 16.410 | 18.418 | 25.158 | 1.00 | 33.68 | C |
| ATOM | 2258 | C | THR | A | 292 | 17.579 | 17.741 | 25.748 | 1.00 | 33.73 | C |
| ATOM | 2259 | O | THR | A | 292 | 17.623 | 17.472 | 26.942 | 1.00 | 33.28 | O |
| ATOM | 2260 | CB | THR | A | 292 | 16.725 | 19.921 | 25.265 | 1.00 | 33.93 | C |
| ATOM | 2261 | OG1 | THR | A | 292 | 15.590 | 20.725 | 24.921 | 1.00 | 33.80 | O |
| ATOM | 2262 | CG2 | THR | A | 292 | 17.774 | 20.293 | 24.245 | 1.00 | 34.05 | C |
| ATOM | 2263 | N | VAL | A | 293 | 18.565 | 17.518 | 24.906 | 1.00 | 34.13 | N |
| ATOM | 2264 | CA | VAL | A | 293 | 19.821 | 17.030 | 25.391 | 1.00 | 34.56 | C |
| ATOM | 2265 | C | VAL | A | 293 | 20.935 | 17.867 | 24.813 | 1.00 | 34.79 | C |
| ATOM | 2266 | O | VAL | A | 293 | 21.039 | 18.017 | 23.600 | 1.00 | 34.88 | O |
| ATOM | 2267 | CB | VAL | A | 293 | 20.029 | 15.603 | 25.019 | 1.00 | 34.66 | C |
| ATOM | 2268 | CG1 | VAL | A | 293 | 21.473 | 15.238 | 25.222 | 1.00 | 35.24 | C |
| ATOM | 2269 | CG2 | VAL | A | 293 | 19.141 | 14.741 | 25.880 | 1.00 | 35.15 | C |
| ATOM | 2270 | N | ASN | A | 294 | 21.768 | 18.433 | 24.882 | 1.00 | 34.82 | N |
| ATOM | 2271 | CA | ASN | A | 294 | 22.890 | 19.187 | 25.174 | 1.00 | 34.61 | C |
| ATOM | 2272 | C | ASN | A | 294 | 24.159 | 18.372 | 25.251 | 1.00 | 34.68 | C |
| ATOM | 2273 | O | ASN | A | 294 | 24.220 | 17.350 | 25.934 | 1.00 | 34.28 | O |
| ATOM | 2274 | CE | ASN | A | 294 | 23.036 | 20.571 | 25.829 | 1.00 | 34.77 | C |
| ATOM | 2275 | CG | ASN | A | 294 | 23.676 | 20.533 | 27.197 | 1.00 | 33.90 | C |
| ATOM | 2276 | OD1 | ASN | A | 294 | 24.170 | 19.504 | 27.653 | 1.00 | 36.35 | O |
| ATOM | 2277 | OD2 | ASN | A | 294 | 23.658 | 21.670 | 27.868 | 1.00 | 30.46 | N |
| ATOM | 2278 | N | PHE | A | 295 | 25.141 | 18.870 | 24.510 | 1.00 | 34.93 | N |
| ATOM | 2279 | CA | PHE | A | 295 | 26.450 | 18.291 | 24.326 | 1.00 | 35.27 | C |
| ATOM | 2280 | C | PHE | A | 295 | 27.467 | 19.411 | 24.552 | 1.00 | 35.69 | C |
| ATOM | 2281 | O | PHE | A | 295 | 27.610 | 20.288 | 23.698 | 1.00 | 35.68 | O |
| ATOM | 2282 | CB | PHE | A | 295 | 26.581 | 17.832 | 22.875 | 1.00 | 35.33 | C |
| ATOM | 2283 | CG | PHE | A | 295 | 25.858 | 16.554 | 22.545 | 1.00 | 34.85 | C |
| ATOM | 2284 | CD1 | PHE | A | 295 | 24.492 | 16.549 | 22.332 | 1.00 | 35.36 | C |
| ATOM | 2285 | CD2 | PHE | A | 295 | 26.559 | 15.371 | 22.383 | 1.00 | 33.46 | C |
| ATOM | 2286 | CE1 | PHE | A | 295 | 23.841 | 15.378 | 21.996 | 1.00 | 35.19 | C |
| ATOM | 2287 | CE2 | PHE | A | 295 | 25.918 | 14.207 | 22.048 | 1.00 | 33.20 | C |
| ATOM | 2288 | CZ | PHE | A | 295 | 24.566 | 14.202 | 21.853 | 1.00 | 34.09 | C |
| ATOM | 2289 | N | TRP | A | 296 | 28.182 | 19.369 | 25.677 | 1.00 | 36.18 | N |
| ATOM | 2290 | CA | TRP | A | 296 | 29.113 | 20.433 | 26.073 | 1.00 | 36.34 | C |
| ATOM | 2291 | C | TRP | A | 296 | 30.534 | 19.963 | 25.938 | 1.00 | 36.50 | C |
| ATOM | 2292 | O | TRP | A | 296 | 30.932 | 18.969 | 26.563 | 1.00 | 36.32 | O |
| ATOM | 2293 | CE | TRP | A | 296 | 28.913 | 20.830 | 27.541 | 1.00 | 36.57 | C |
| ATOM | 2294 | CG | TRP | A | 296 | 27.934 | 21.912 | 27.776 | 1.00 | 37.38 | C |
| ATOM | 2295 | CD1 | TRP | A | 296 | 26.997 | 22.361 | 26.909 | 1.00 | 38.36 | C |
| ATOM | 2296 | CD2 | TRP | A | 296 | 27.787 | 22.693 | 28.965 | 1.00 | 39.42 | C |
| ATOM | 2297 | NE1 | TRP | A | 296 | 26.275 | 23.384 | 27.473 | 1.00 | 38.20 | N |
| ATOM | 2298 | CE2 | TRP | A | 296 | 26.737 | 23.605 | 28.736 | 1.00 | 38.86 | C |
| ATOM | 2299 | CE3 | TRP | A | 296 | 28.450 | 22.730 | 30.204 | 1.00 | 40.74 | C |
| ATOM | 2300 | CZ2 | TRP | A | 296 | 26.327 | 24.529 | 29.682 | 1.00 | 41.03 | C |
| ATOM | 2301 | CZ3 | TRP | A | 296 | 28.037 | 23.665 | 31.160 | 1.00 | 40.86 | C |
| ATOM | 2302 | CH2 | TRP | A | 296 | 26.989 | 24.544 | 30.891 | 1.00 | 41.52 | C |
| ATOM | 2303 | N | TYR | A | 297 | 31.303 | 20.719 | 25.162 | 1.00 | 36.60 | N |
| ATOM | 2304 | CA | TYR | A | 297 | 32.703 | 20.442 | 24.923 | 1.00 | 36.79 | C |
| ATOM | 2305 | C | TYR | A | 297 | 33.534 | 21.597 | 25.457 | 1.00 | 36.96 | C |
| ATOM | 2306 | O | TYR | A | 297 | 33.117 | 22.734 | 25.363 | 1.00 | 36.32 | O |
| ATOM | 2307 | CE | TYR | A | 297 | 32.923 | 20.291 | 23.423 | 1.00 | 36.93 | C |
| ATOM | 2308 | CG | TYR | A | 297 | 32.280 | 19.054 | 22.868 | 1.00 | 37.30 | C |

TABLE 3-continued

Coordinates for structures 1 to 4

| | | | | | | | | | | | |
|---|---|---|---|---|---|---|---|---|---|---|---|
| ATOM | 2309 | CD1 | TYR | A | 297 | 30.939 | 19.046 | 22.523 | 1.00 | 37.28 | C |
| ATOM | 2310 | CD2 | TYR | A | 297 | 33.008 | 17.880 | 22.716 | 1.00 | 36.72 | C |
| ATOM | 2311 | CE1 | TYR | A | 297 | 30.346 | 17.907 | 22.039 | 1.00 | 37.15 | C |
| ATOM | 2312 | CE2 | TYR | A | 297 | 32.423 | 16.747 | 22.226 | 1.00 | 35.89 | C |
| ATOM | 2313 | CZ | TYR | A | 297 | 31.088 | 16.764 | 21.893 | 1.00 | 36.57 | C |
| ATOM | 2314 | OH | TYR | A | 297 | 30.467 | 15.641 | 21.405 | 1.00 | 36.99 | O |
| ATOM | 2315 | N | LYS | A | 298 | 34.696 | 21.303 | 26.039 | 1.00 | 37.93 | N |
| ATOM | 2316 | CA | LYS | A | 298 | 35.615 | 22.347 | 26.495 | 1.00 | 38.45 | C |
| ATOM | 2317 | C | LYS | A | 298 | 36.090 | 22.994 | 25.236 | 1.00 | 38.43 | C |
| ATOM | 2318 | O | LYS | A | 298 | 36.245 | 22.320 | 24.229 | 1.00 | 38.55 | O |
| ATOM | 2319 | CE | LYS | A | 298 | 36.835 | 21.782 | 27.233 | 1.00 | 38.67 | C |
| ATOM | 2320 | CG | LYS | A | 298 | 36.634 | 21.550 | 28.737 | 1.00 | 40.58 | C |
| ATOM | 2321 | CD | LYS | A | 298 | 37.928 | 21.093 | 29.484 | 1.00 | 42.63 | C |
| ATOM | 2322 | CE | LYS | A | 298 | 37.631 | 20.622 | 30.951 | 1.00 | 44.00 | C |
| ATOM | 2323 | NZ | LYS | A | 298 | 38.841 | 20.251 | 31.812 | 1.00 | 43.61 | N |
| ATOM | 2324 | N | GLY | A | 299 | 36.347 | 24.286 | 25.277 | 1.00 | 38.82 | N |
| ATOM | 2325 | CA | GLY | A | 299 | 36.768 | 24.976 | 24.080 | 1.00 | 39.19 | C |
| ATOM | 2326 | C | GLY | A | 299 | 38.174 | 24.582 | 23.719 | 1.00 | 39.60 | C |
| ATOM | 2327 | O | GLY | A | 299 | 38.859 | 23.930 | 24.502 | 1.00 | 39.93 | O |
| ATOM | 2328 | N | ALA | A | 300 | 38.594 | 24.963 | 22.520 | 1.00 | 40.20 | N |
| ATOM | 2329 | CA | ALA | A | 300 | 39.963 | 24.751 | 22.072 | 1.00 | 40.70 | C |
| ATOM | 2330 | C | ALA | A | 300 | 40.917 | 25.588 | 22.929 | 1.00 | 41.18 | C |
| ATOM | 2331 | O | ALA | A | 300 | 40.483 | 26.417 | 23.722 | 1.00 | 41.25 | O |
| ATOM | 2332 | CB | ALA | A | 300 | 40.085 | 25.143 | 20.616 | 1.00 | 40.64 | C |
| ATOM | 2333 | N | PRO | A | 301 | 42.215 | 25.408 | 22.733 | 1.00 | 41.91 | N |
| ATOM | 2334 | CA | PRO | A | 301 | 43.213 | 26.102 | 23.542 | 1.00 | 42.49 | C |
| ATOM | 2335 | C | PRO | A | 301 | 43.448 | 27.541 | 23.128 | 1.00 | 43.14 | C |
| ATOM | 2336 | O | PRO | A | 301 | 43.323 | 27.899 | 21.962 | 1.00 | 43.31 | O |
| ATOM | 2337 | CB | PRO | A | 301 | 44.483 | 25.326 | 23.230 | 1.00 | 42.38 | C |
| ATOM | 2338 | CG | PRO | A | 301 | 44.300 | 24.924 | 21.833 | 1.00 | 42.16 | C |
| ATOM | 2339 | CD | PRO | A | 301 | 42.851 | 24.571 | 21.701 | 1.00 | 41.99 | C |
| ATOM | 2340 | N | THR | A | 302 | 43.823 | 28.343 | 24.112 | 1.00 | 43.86 | N |
| ATOM | 2341 | CA | THR | A | 302 | 44.199 | 29.726 | 23.915 | 1.00 | 44.26 | C |
| ATOM | 2342 | C | THR | A | 302 | 45.588 | 29.732 | 23.318 | 1.00 | 44.56 | C |
| ATOM | 2343 | O | THR | A | 302 | 46.524 | 29.337 | 24.011 | 1.00 | 44.82 | C |
| ATOM | 2344 | CB | THR | A | 302 | 44.284 | 30.383 | 25.277 | 1.00 | 44.20 | C |
| ATOM | 2345 | CG1 | THR | A | 302 | 43.030 | 30.253 | 25.956 | 1.00 | 45.23 | O |
| ATOM | 2346 | CG2 | THR | A | 302 | 44.512 | 31.858 | 25.138 | 1.00 | 44.53 | C |
| ATOM | 2347 | N | PRO | A | 303 | 45.770 | 30.229 | 22.091 | 1.00 | 44.72 | N |
| ATOM | 2348 | CA | PRO | A | 303 | 47.083 | 30.128 | 21.438 | 1.00 | 44.51 | C |
| ATOM | 2349 | C | PRO | A | 303 | 48.177 | 30.759 | 22.306 | 1.00 | 44.48 | C |
| ATOM | 2350 | O | PRO | A | 303 | 47.835 | 31.522 | 23.221 | 1.00 | 44.02 | O |
| ATOM | 2351 | CB | PRO | A | 303 | 46.897 | 30.929 | 20.145 | 1.00 | 44.55 | C |
| ATOM | 2352 | CG | PRO | A | 303 | 45.426 | 30.929 | 19.904 | 1.00 | 44.28 | C |
| ATOM | 2353 | CD | PRO | A | 303 | 44.834 | 31.040 | 21.288 | 1.00 | 44.71 | C |
| ATOM | 2354 | N | GLU | A | 307 | 46.829 | 36.983 | 18.732 | 1.00 | 42.48 | N |
| ATOM | 2355 | CA | GLU | A | 307 | 46.845 | 37.952 | 17.646 | 1.00 | 42.70 | C |
| ATOM | 2356 | C | GLU | A | 307 | 45.812 | 39.039 | 17.801 | 1.00 | 42.57 | C |
| ATOM | 2357 | O | GLU | A | 307 | 44.654 | 38..807 | 18.138 | 1.00 | 42.62 | O |
| ATOM | 2358 | CB | GLU | A | 307 | 46.624 | 37.296 | 16.284 | 1.00 | 43.00 | C |
| ATOM | 2359 | CG | GLU | A | 307 | 46.980 | 38.235 | 15.127 | 1.00 | 43.85 | C |
| ATOM | 2360 | CD | GLU | A | 307 | 47.091 | 37.541 | 13.779 | 1.00 | 44.71 | C |
| ATOM | 2361 | OE1 | GLU | A | 307 | 46.618 | 36.385 | 13.643 | 1.00 | 45.10 | O |
| ATOM | 2362 | OE2 | GLU | A | 307 | 47.649 | 38.170 | 12.851 | 1.00 | 45.60 | O |
| ATOM | 2363 | N | TYR | A | 308 | 46.249 | 40.243 | 17.503 | 1.00 | 42.66 | N |
| ATOM | 2364 | CA | TYR | A | 308 | 45.384 | 41.379 | 17.577 | 1.00 | 42.64 | C |
| ATOM | 2365 | C | TYR | A | 308 | 44.814 | 41.530 | 16.189 | 1.00 | 42.85 | C |
| ATOM | 2366 | O | TYR | A | 308 | 45.413 | 41.066 | 15.203 | 1.00 | 43.43 | O |
| ATOM | 2367 | CB | TYR | A | 308 | 46.184 | 42.565 | 18.034 | 1.00 | 42.47 | C |
| ATOM | 2368 | CG | TYR | A | 308 | 46.744 | 42.281 | 19.399 | 1.00 | 43.35 | C |
| ATOM | 2369 | CD1 | TYR | A | 308 | 45.996 | 42.552 | 20.534 | 1.00 | 44.58 | C |
| ATOM | 2370 | CD2 | TYR | A | 308 | 47.986 | 41.681 | 19.559 | 1.00 | 43.97 | C |
| ATOM | 2371 | CE1 | TYR | A | 308 | 46.482 | 42.284 | 21.790 | 1.00 | 45.23 | C |
| ATOM | 2372 | CE2 | TYR | A | 308 | 48.483 | 41.401 | 20.818 | 1.00 | 44.79 | C |
| ATOM | 2373 | CZ | TYR | A | 308 | 47.726 | 41.708 | 21.935 | 1.00 | 45.46 | C |
| ATOM | 2374 | OH | TYR | A | 308 | 48.200 | 41.453 | 23.207 | 1.00 | 45.86 | O |
| ATOM | 2375 | N | PRO | A | 309 | 43.631 | 42.119 | 16.111 | 1.00 | 42.47 | N |
| ATOM | 2376 | CA | PRO | A | 309 | 42.930 | 42.648 | 17.285 | 1.00 | 42.08 | C |
| ATOM | 2377 | C | PRO | A | 309 | 42.209 | 41.528 | 18.051 | 1.00 | 41.24 | C |
| ATOM | 2378 | O | PRO | A | 309 | 41.774 | 40.578 | 17.408 | 1.00 | 40.92 | O |
| ATOM | 2379 | CB | PRO | A | 309 | 41.910 | 43.583 | 16.652 | 1.00 | 42.39 | C |
| ATOM | 2380 | CG | PRO | A | 309 | 41.574 | 42.895 | 15.337 | 1.00 | 42.16 | C |
| ATOM | 2381 | CD | PRO | A | 309 | 42.843 | 42.260 | 14.874 | 1.00 | 42.28 | C |
| ATOM | 2382 | N | LEU | A | 310 | 42.059 | 41.654 | 19.372 | 1.00 | 40.25 | N |
| ATOM | 2383 | CA | LEU | A | 310 | 41.436 | 40.596 | 20.180 | 1.00 | 39.46 | C |
| ATOM | 2384 | C | LEU | A | 310 | 39.971 | 40.434 | 19.884 | 1.00 | 38.93 | C |
| ATOM | 2385 | O | LEU | A | 310 | 39.288 | 41.412 | 19.624 | 1.00 | 39.65 | O |

TABLE 3-continued

Coordinates for structures 1 to 4

| ATOM | 2386 | CB | LEU | A | 310 | 41.526 | 40.916 | 21.658 | 1.00 | 39.21 | C |
| ATOM | 2387 | CG | LEU | A | 310 | 42.486 | 40.099 | 22.508 | 1.00 | 38.87 | C |
| ATOM | 2388 | CD1 | LEU | A | 310 | 43.727 | 39.738 | 21.750 | 1.00 | 38.58 | C |
| ATOM | 2389 | CD2 | LEU | A | 310 | 42.817 | 40.926 | 23.735 | 1.00 | 39.01 | C |
| ATOM | 2390 | N | LYS | A | 311 | 39.462 | 39.217 | 19.957 | 1.00 | 37.90 | N |
| ATOM | 2391 | CA | LYS | A | 311 | 38.036 | 39.029 | 19.731 | 1.00 | 37.53 | C |
| ATOM | 2392 | C | LYS | A | 311 | 37.217 | 39.359 | 20.978 | 1.00 | 36.85 | C |
| ATOM | 2393 | O | LYS | A | 311 | 37.705 | 39.272 | 22.092 | 1.00 | 36.85 | O |
| ATOM | 2394 | CB | LYS | A | 311 | 37.746 | 37.609 | 19.274 | 1.00 | 37.54 | C |
| ATOM | 2395 | N | ALA | A | 312 | 35.965 | 39.736 | 20.793 | 1.00 | 36.18 | N |
| ATOM | 2396 | CA | ALA | A | 312 | 35.112 | 40.015 | 21.937 | 1.00 | 35.92 | C |
| ATOM | 2397 | C | ALA | A | 312 | 35.232 | 38.994 | 23.058 | 1.00 | 35.88 | C |
| ATOM | 2398 | O | ALA | A | 312 | 35.347 | 39.384 | 24.213 | 1.00 | 35.99 | O |
| ATOM | 2399 | CB | ALA | A | 312 | 33.665 | 40.115 | 21.526 | 1.00 | 35.50 | C |
| ATOM | 2400 | N | HIS | A | 313 | 35.221 | 37.700 | 22.739 | 1.00 | 35.71 | N |
| ATOM | 2401 | CA | HIS | A | 313 | 35.136 | 36.709 | 23.797 | 1.00 | 35.52 | C |
| ATOM | 2402 | C | HIS | A | 313 | 36.429 | 36.694 | 24.517 | 1.00 | 35.31 | C |
| ATOM | 2403 | O | HIS | A | 313 | 36.489 | 36.278 | 25.667 | 1.00 | 35.53 | O |
| ATOM | 2404 | CB | HIS | A | 313 | 34.768 | 35.291 | 23.313 | 1.00 | 35.89 | C |
| ATOM | 2405 | CG | HIS | A | 313 | 35.844 | 34.613 | 22.535 | 1.00 | 36.41 | C |
| ATOM | 2406 | ND1 | HIS | A | 313 | 36.097 | 34.905 | 21.214 | 1.00 | 38.71 | N |
| ATOM | 2407 | CD2 | HIS | A | 313 | 36.741 | 33.665 | 22.889 | 1.00 | 37.90 | C |
| ATOM | 2408 | CE1 | HIS | A | 313 | 37.111 | 34.175 | 20.789 | 1.00 | 38.65 | C |
| ATOM | 2409 | ND2 | HIS | A | 313 | 37.524 | 33.416 | 21.788 | 1.00 | 38.60 | N |
| ATOM | 2410 | N | GLN | A | 314 | 37.478 | 37.162 | 23.861 | 1.00 | 35.08 | N |
| ATOM | 2411 | CA | GLN | A | 314 | 38.760 | 37.203 | 24.535 | 1.00 | 35.00 | C |
| ATOM | 2412 | C | GLN | A | 314 | 38.706 | 38.301 | 25.576 | 1.00 | 34.62 | C |
| ATOM | 2413 | O | GLN | A | 314 | 39.145 | 38.109 | 26.703 | 1.00 | 34.28 | O |
| ATOM | 2414 | CB | GLN | A | 314 | 39.924 | 37.399 | 23.558 | 1.00 | 35.10 | C |
| ATOM | 2415 | CG | GLN | A | 314 | 40.091 | 36.229 | 22.597 | 1.00 | 35.42 | C |
| ATOM | 2416 | CD | GLN | A | 314 | 41.107 | 36.478 | 21.500 | 1.00 | 35.10 | C |
| ATOM | 2417 | OE1 | GLN | A | 314 | 40.938 | 37.377 | 20.671 | 1.00 | 35.86 | O |
| ATOM | 2418 | NE2 | GLN | A | 314 | 42.150 | 35.666 | 21.476 | 1.00 | 34.32 | N |
| ATOM | 2419 | N | LYS | A | 315 | 38.173 | 39.454 | 25.197 | 1.00 | 34.70 | N |
| ATOM | 2420 | CA | LYS | A | 315 | 38.009 | 40.539 | 26.152 | 1.00 | 35.01 | C |
| ATOM | 2421 | C | LYS | A | 315 | 37.164 | 40.063 | 27.320 | 1.00 | 34.67 | C |
| ATOM | 2422 | O | LYS | A | 315 | 37.485 | 40.325 | 28.467 | 1.00 | 34.81 | O |
| ATOM | 2423 | CB | LYS | A | 315 | 37.395 | 41.766 | 25.501 | 1.00 | 35.19 | C |
| ATOM | 2424 | CG | LYS | A | 315 | 38.344 | 42.447 | 24.563 | 1.00 | 35.85 | C |
| ATOM | 2425 | CD | LYS | A | 315 | 37.703 | 43.636 | 23.931 | 1.00 | 37.25 | C |
| ATOM | 2426 | CE | LYS | A | 315 | 38.657 | 44.348 | 23.001 | 1.00 | 39.28 | C |
| ATOM | 2427 | NZ | LYS | A | 315 | 37.969 | 45.430 | 22.222 | 1.00 | 40.34 | N |
| ATOM | 2428 | N | VAL | A | 316 | 36.117 | 39.314 | 27.040 | 1.00 | 34.30 | N |
| ATOM | 2429 | CA | VAL | A | 316 | 35.321 | 38.787 | 28.118 | 1.00 | 34.31 | C |
| ATOM | 2430 | C | VAL | A | 316 | 36.175 | 37.925 | 29.047 | 1.00 | 34.37 | C |
| ATOM | 2431 | O | VAL | A | 316 | 36.071 | 38.023 | 30.273 | 1.00 | 34.57 | O |
| ATOM | 2432 | CB | VAL | A | 316 | 34.138 | 37.992 | 27.606 | 1.00 | 34.39 | C |
| ATOM | 2433 | CG1 | VAL | A | 316 | 33.334 | 37.434 | 28.794 | 1.00 | 34.91 | C |
| ATOM | 2434 | CG2 | VAL | A | 316 | 33.258 | 38.873 | 26.719 | 1.00 | 33.60 | C |
| ATOM | 2435 | N | ALA | A | 317 | 37.011 | 37.072 | 28.475 | 1.00 | 34.24 | N |
| ATOM | 2436 | CA | ALA | A | 317 | 37.907 | 36.267 | 29.288 | 1.00 | 34.17 | C |
| ATOM | 2437 | C | ALA | A | 317 | 38.744 | 37.160 | 30.166 | 1.00 | 34.10 | C |
| ATOM | 2438 | O | ALA | A | 317 | 38.919 | 36.906 | 31.352 | 1.00 | 33.87 | O |
| ATOM | 2439 | CB | ALA | A | 317 | 38.813 | 35.459 | 28.431 | 1.00 | 34.02 | C |
| ATOM | 2440 | N | ILE | A | 318 | 39.274 | 38.216 | 29.574 | 1.00 | 34.29 | N |
| ATOM | 2441 | CA | ILE | A | 318 | 40.178 | 39.062 | 30.322 | 1.00 | 34.26 | C |
| ATOM | 2442 | C | ILE | A | 318 | 39.467 | 39.611 | 31.546 | 1.00 | 33.99 | C |
| ATOM | 2443 | O | ILE | A | 318 | 39.993 | 39.556 | 32.661 | 1.00 | 33.96 | O |
| ATOM | 2444 | CB | ILE | A | 318 | 40.755 | 40.171 | 29.447 | 1.00 | 33.98 | C |
| ATOM | 2445 | CG1 | ILE | A | 318 | 41.775 | 39.558 | 28.489 | 1.00 | 34.02 | C |
| ATOM | 2446 | CG2 | ILE | A | 318 | 41.429 | 41.188 | 30.323 | 1.00 | 33.92 | C |
| ATOM | 2447 | CD1 | ILE | A | 318 | 42.356 | 40.498 | 27.428 | 1.00 | 33.97 | C |
| ATOM | 2448 | N | MET | A | 319 | 38.241 | 40.068 | 31.337 | 1.00 | 33.55 | N |
| ATOM | 2449 | CA | MET | A | 319 | 37.499 | 40.741 | 32.383 | 1.00 | 33.41 | C |
| ATOM | 2450 | C | MET | A | 319 | 37.196 | 39.772 | 33.496 | 1.00 | 33.38 | C |
| ATOM | 2451 | O | MET | A | 319 | 37.238 | 40.101 | 34.669 | 1.00 | 33.32 | O |
| ATOM | 2452 | CB | MET | A | 319 | 36.193 | 41.308 | 31.827 | 1.00 | 33.31 | C |
| ATOM | 2453 | CG | MET | A | 319 | 36.361 | 42.521 | 30.951 | 1.00 | 32.96 | C |
| ATOM | 2454 | SD | MET | A | 319 | 34.812 | 43.355 | 30.617 | 1.00 | 33.05 | S |
| ATOM | 2455 | CE | MET | A | 319 | 34.119 | 42.299 | 29.410 | 1.00 | 33.43 | C |
| ATOM | 2456 | N | ARG | A | 320 | 36.873 | 38.558 | 33.121 | 1.00 | 33.68 | N |
| ATOM | 2457 | CA | ARG | A | 320 | 36.575 | 37.568 | 34.112 | 1.00 | 33.61 | C |
| ATOM | 2458 | C | ARG | A | 320 | 37.796 | 37.392 | 34.996 | 1.00 | 33.82 | C |
| ATOM | 2459 | O | ARG | A | 320 | 37.719 | 37.448 | 36.225 | 1.00 | 33.48 | O |
| ATOM | 2460 | CB | ARG | A | 320 | 36.211 | 36.292 | 33.402 | 1.00 | 33.39 | C |
| ATOM | 2461 | CG | ARG | A | 320 | 34.875 | 36.406 | 32.725 | 1.00 | 33.88 | C |
| ATOM | 2462 | CD | ARG | A | 320 | 34.268 | 35.080 | 32.340 | 1.00 | 34.20 | C |

TABLE 3-continued

| | | | | | | Coordinates for structures 1 to 4 | | | | | |
|---|---|---|---|---|---|---|---|---|---|---|---|
| ATOM | 2463 | NE | ARG | A | 320 | 34.217 | 34.215 | 33.507 | 1.00 | 33.14 | N |
| ATOM | 2464 | CZ | ARG | A | 320 | 33.159 | 34.103 | 34.260 | 1.00 | 33.15 | C |
| ATOM | 2465 | NH1 | ARG | A | 320 | 32.077 | 34.762 | 33.933 | 1.00 | 33.83 | N |
| ATOM | 2466 | NH2 | ARG | A | 320 | 33.170 | 33.338 | 35.331 | 1.00 | 34.46 | N |
| ATOM | 2467 | N | ASN | A | 321 | 38.941 | 37.232 | 34.355 | 1.00 | 33.92 | N |
| ATOM | 2468 | CA | ASN | A | 321 | 40.143 | 36.978 | 35.085 | 1.00 | 34.08 | C |
| ATOM | 2469 | C | ASN | A | 321 | 40.486 | 38.141 | 36.018 | 1.00 | 34.26 | C |
| ATOM | 2470 | O | ASN | A | 321 | 40.874 | 37.919 | 37.164 | 1.00 | 34.14 | O |
| ATOM | 2471 | CB | ASN | A | 321 | 41.271 | 36.616 | 34.119 | 1.00 | 34.30 | C |
| ATOM | 2472 | CG | ASN | A | 321 | 41.195 | 35.161 | 33.663 | 1.00 | 34.44 | C |
| ATOM | 2473 | OD1 | ASN | A | 321 | 40.829 | 34.273 | 34.434 | 1.00 | 34.16 | O |
| ATOM | 2474 | ND2 | ASN | A | 321 | 41.522 | 34.918 | 32.402 | 1.00 | 35.05 | N |
| ATOM | 2475 | N | ILE | A | 322 | 40.318 | 39.379 | 35.569 | 1.00 | 34.24 | N |
| ATOM | 2476 | CA | ILE | A | 322 | 40.634 | 40.488 | 36.448 | 1.00 | 34.25 | C |
| ATOM | 2477 | C | ILE | A | 322 | 39.781 | 40.408 | 37.701 | 1.00 | 33.85 | C |
| ATOM | 2478 | O | ILE | A | 322 | 40.250 | 40.711 | 38.789 | 1.00 | 34.16 | O |
| ATOM | 2479 | CE | ILE | A | 322 | 40.412 | 41.837 | 35.760 | 1.00 | 34.70 | C |
| ATOM | 2480 | CG1 | ILE | A | 322 | 41.338 | 41.993 | 34.558 | 1.00 | 35.34 | C |
| ATOM | 2481 | CG2 | ILE | A | 322 | 40.651 | 43.007 | 36.748 | 1.00 | 35.37 | C |
| ATOM | 2482 | CD1 | ILE | A | 322 | 42.778 | 41.928 | 34.895 | 1.00 | 36.17 | C |
| ATOM | 2483 | N | GLU | A | 323 | 38.525 | 40.013 | 37.558 | 1.00 | 33.42 | N |
| ATOM | 2484 | CA | GLU | A | 323 | 37.636 | 39.935 | 38.704 | 1.00 | 32.97 | C |
| ATOM | 2485 | C | GLU | A | 323 | 38.085 | 38.842 | 39.652 | 1.00 | 33.11 | C |
| ATOM | 2486 | O | GLU | A | 323 | 38.067 | 39.001 | 40.864 | 1.00 | 32.66 | O |
| ATOM | 2487 | CE | GLU | A | 323 | 36.199 | 39.673 | 38.256 | 1.00 | 32.73 | C |
| ATOM | 2488 | CG | GLU | A | 323 | 35.543 | 40.907 | 37.672 | 1.00 | 33.02 | C |
| ATOM | 2489 | CD | GLU | A | 323 | 34.166 | 40.693 | 37.057 | 1.00 | 32.91 | C |
| ATOM | 2490 | OE1 | GLU | A | 323 | 33.193 | 40.309 | 37.740 | 1.00 | 31.94 | O |
| ATOM | 2491 | OE2 | GLU | A | 323 | 34.048 | 40.961 | 35.856 | 1.00 | 33.81 | O |
| ATOM | 2492 | H | LYS | A | 324 | 38.497 | 37.720 | 39.088 | 1.00 | 33.56 | N |
| ATOM | 2493 | CA | LYS | A | 324 | 38.882 | 36.588 | 39.895 | 1.00 | 33.72 | C |
| ATOM | 2494 | C | LYS | A | 324 | 40.138 | 36.937 | 40.670 | 1.00 | 34.09 | C |
| ATOM | 2495 | O | LYS | A | 324 | 40.228 | 36.664 | 41.859 | 1.00 | 34.15 | O |
| ATOM | 2496 | CE | LYS | A | 324 | 39.119 | 35.368 | 39.012 | 1.00 | 33.73 | C |
| ATOM | 2497 | CG | LYS | A | 324 | 37.877 | 34.766 | 38.353 | 1.00 | 33.83 | C |
| ATOM | 2498 | CD | LYS | A | 324 | 38.355 | 33.673 | 37.440 | 1.00 | 33.70 | C |
| ATOM | 2499 | CE | LYS | A | 324 | 37.294 | 32.883 | 36.723 | 1.00 | 33.57 | C |
| ATOM | 2500 | NZ | LYS | A | 324 | 37.993 | 31.761 | 35.984 | 1.00 | 32.76 | N |
| ATOM | 2501 | H | MET | A | 325 | 41.098 | 37.558 | 39.995 | 1.00 | 34.73 | H |
| ATOM | 2502 | CA | MET | A | 325 | 42.380 | 37.915 | 40.609 | 1.00 | 35.32 | C |
| ATOM | 2503 | C | MET | A | 325 | 42.248 | 38.883 | 41.766 | 1.00 | 35.06 | C |
| ATOM | 2504 | O | MET | A | 325 | 42.888 | 38.729 | 42.808 | 1.00 | 34.50 | O |
| ATOM | 2505 | CE | MET | A | 325 | 43.328 | 38.501 | 39.563 | 1.00 | 35.57 | C |
| ATOM | 2506 | CG | MET | A | 325 | 43.962 | 37.419 | 38.724 | 1.00 | 36.96 | C |
| ATOM | 2507 | SD | MET | A | 325 | 44.984 | 37.973 | 37.360 | 1.00 | 40.43 | S |
| ATOM | 2508 | CE | MET | A | 325 | 45.710 | 39.363 | 38.037 | 1.00 | 41.05 | C |
| ATOM | 2509 | N | LEU | A | 326 | 41.427 | 39.891 | 41.555 | 1.00 | 35.32 | H |
| ATOM | 2510 | CA | LEU | A | 326 | 41.178 | 40.895 | 42.570 | 1.00 | 35.83 | C |
| ATOM | 2511 | C | LEU | A | 326 | 40.556 | 40.230 | 43.770 | 1.00 | 35.60 | C |
| ATOM | 2512 | O | LEU | A | 326 | 40.914 | 40.507 | 44.910 | 1.00 | 35.34 | O |
| ATOM | 2513 | CE | LEU | A | 326 | 40.216 | 41.929 | 42.026 | 1.00 | 36.07 | C |
| ATOM | 2514 | CG | LEU | A | 326 | 40.721 | 43.321 | 41.689 | 1.00 | 37.48 | C |
| ATOM | 2515 | CD1 | LEU | A | 326 | 42.221 | 43.442 | 41.537 | 1.00 | 38.59 | C |
| ATOM | 2516 | CD2 | LEU | A | 326 | 40.049 | 43.692 | 40.413 | 1.00 | 38.65 | C |
| ATOM | 2517 | N | GLY | A | 327 | 39.613 | 39.341 | 43.493 | 1.00 | 35.59 | N |
| ATOM | 2518 | CA | GLY | A | 327 | 38.947 | 38.604 | 44.538 | 1.00 | 35.54 | C |
| ATOM | 2519 | C | GLY | A | 327 | 39.983 | 37.998 | 45.443 | 1.00 | 35.62 | C |
| ATOM | 2520 | O | GLY | A | 327 | 40.023 | 38.258 | 46.641 | 1.00 | 35.52 | O |
| ATOM | 2521 | N | GLU | A | 328 | 40.863 | 37.209 | 44.851 | 1.00 | 35.84 | N |
| ATOM | 2522 | CA | GLU | A | 328 | 41.831 | 36.486 | 45.632 | 1.00 | 35.91 | C |
| ATOM | 2523 | C | GLU | A | 328 | 42.783 | 37.424 | 46.298 | 1.00 | 35.44 | C |
| ATOM | 2524 | O | GLU | A | 328 | 43.086 | 37.272 | 47.465 | 1.00 | 35.60 | O |
| ATOM | 2525 | CB | GLU | A | 328 | 42.584 | 35.513 | 44.750 | 1.00 | 36.21 | C |
| ATOM | 2526 | CG | GLU | A | 328 | 41.675 | 34.419 | 44.226 | 1.00 | 38.20 | C |
| ATOM | 2527 | CD | GLU | A | 328 | 41.854 | 33.088 | 44.941 | 1.00 | 41.33 | C |
| ATOM | 2528 | OE1 | GLU | A | 328 | 42.244 | 33.084 | 46.138 | 1.00 | 42.40 | O |
| ATOM | 2529 | OE2 | GLU | A | 328 | 41.608 | 32.034 | 44.292 | 1.00 | 43.59 | O |
| ATOM | 2530 | N | ALA | A | 329 | 43.220 | 38.435 | 45.577 | 1.00 | 35.11 | N |
| ATOM | 2531 | CA | ALA | A | 329 | 44.259 | 39.282 | 46.110 | 1.00 | 34.85 | C |
| ATOM | 2532 | C | ALA | A | 329 | 43.790 | 40.103 | 47.296 | 1.00 | 34.75 | C |
| ATOM | 2533 | O | ALA | A | 329 | 44.533 | 40.282 | 48.258 | 1.00 | 34.53 | O |
| ATOM | 2534 | CE | ALA | A | 329 | 44.778 | 40.163 | 45.046 | 1.00 | 34.85 | C |
| ATOM | 2535 | N | LEU | A | 330 | 42.567 | 40.613 | 47.214 | 1.00 | 34.62 | N |
| ATOM | 2536 | CA | LEU | A | 330 | 41.996 | 41.399 | 48.291 | 1.00 | 34.55 | C |
| ATOM | 2537 | C | LEU | A | 330 | 41.478 | 40.555 | 49.448 | 1.00 | 34.90 | C |
| ATOM | 2538 | O | LEU | A | 330 | 41.234 | 41.072 | 50.532 | 1.00 | 35.33 | O |
| ATOM | 2539 | CE | LEU | A | 330 | 40.851 | 42.245 | 47.766 | 1.00 | 34.31 | C |

TABLE 3-continued

| | | | | | Coordinates for structures 1 to 4 | | | | | |
|---|---|---|---|---|---|---|---|---|---|---|
| ATOM | 2540 | CG | LEU | A | 330 | 41.202 | 43.322 | 46.743 | 1.00 | 34.06 | C |
| ATOM | 2541 | CD1 | LEU | A | 330 | 39.942 | 43.965 | 46.258 | 1.00 | 34.23 | C |
| ATOM | 2542 | CD2 | LEU | A | 330 | 42.078 | 44.382 | 47.285 | 1.00 | 34.05 | C |
| ATOM | 2543 | N | GLY | A | 331 | 41.295 | 39.262 | 49.232 | 1.00 | 35.23 | N |
| ATOM | 2544 | CA | GLY | A | 331 | 40.794 | 38.401 | 50.285 | 1.00 | 35.49 | C |
| ATOM | 2545 | C | GLY | A | 331 | 39.306 | 38.471 | 50.584 | 1.00 | 35.66 | C |
| ATOM | 2546 | O | GLY | A | 331 | 38.849 | 37.859 | 51.544 | 1.00 | 35.61 | O |
| ATOM | 2547 | N | ASN | A | 332 | 38.547 | 39.213 | 49.790 | 1.00 | 36.04 | N |
| ATOM | 2548 | CA | ASN | A | 332 | 37.113 | 39.295 | 49.992 | 1.00 | 36.44 | C |
| ATOM | 2549 | C | ASN | A | 332 | 36.483 | 39.791 | 48.732 | 1.00 | 36.55 | C |
| ATOM | 2550 | O | ASN | A | 332 | 36.647 | 40.951 | 48.381 | 1.00 | 37.01 | O |
| ATOM | 2551 | CE | ASN | A | 332 | 36.775 | 40.275 | 51.094 | 1.00 | 36.54 | C |
| ATOM | 2552 | CG | ASN | A | 332 | 35.311 | 40.260 | 51.440 | 1.00 | 37.47 | C |
| ATOM | 2553 | OD1 | ASN | A | 332 | 34.519 | 39.541 | 50.828 | 1.00 | 37.83 | O |
| ATOM | 2554 | ND2 | ASN | A | 332 | 34.938 | 41.043 | 52.444 | 1.00 | 39.90 | N |
| ATOM | 2555 | N | PRO | A | 333 | 35.699 | 38.957 | 48.078 | 1.00 | 36.46 | N |
| ATOM | 2556 | CA | PRO | A | 333 | 35.178 | 39.338 | 46.775 | 1.00 | 36.43 | C |
| ATOM | 2557 | C | PRO | A | 333 | 34.368 | 40.590 | 46.908 | 1.00 | 36.32 | C |
| ATOM | 2558 | O | PRO | A | 333 | 34.318 | 41.384 | 45.988 | 1.00 | 36.36 | O |
| ATOM | 2559 | CE | PRO | A | 333 | 34.278 | 38.170 | 46.366 | 1.00 | 36.50 | C |
| ATOM | 2560 | CG | PRO | A | 333 | 34.247 | 37.229 | 47.489 | 1.00 | 36.58 | C |
| ATOM | 2561 | CD | PRO | A | 333 | 35.180 | 37.668 | 48.548 | 1.00 | 36.54 | C |
| ATOM | 2562 | N | GLN | A | 334 | 33.743 | 40.800 | 48.047 | 1.00 | 36.44 | N |
| ATOM | 2563 | CA | GLN | A | 334 | 32.906 | 41.969 | 48.130 | 1.00 | 36.85 | C |
| ATOM | 2564 | C | GLN | A | 334 | 33.748 | 43.222 | 48.057 | 1.00 | 36.57 | C |
| ATOM | 2565 | O | GLN | A | 334 | 33.218 | 44.3Q4 | 47.868 | 1.00 | 36.98 | O |
| ATOM | 2566 | CE | GLN | A | 334 | 31.987 | 41.940 | 49.348 | 1.00 | 37.31 | C |
| ATOM | 2567 | CG | GLN | A | 334 | 30.685 | 41.151 | 49.026 | 1.00 | 38.95 | C |
| ATOM | 2568 | CD | GLN | A | 334 | 29.669 | 41.097 | 50.171 | 1.00 | 40.33 | C |
| ATOM | 2569 | OE1 | GLN | A | 334 | 29.751 | 41.872 | 51.137 | 1.00 | 41.70 | O |
| ATOM | 2570 | NE2 | GLN | A | 334 | 28.712 | 40.178 | 50.061 | 1.00 | 39.80 | N |
| ATOM | 2571 | N | GLU | A | 335 | 35.064 | 43.088 | 48.159 | 1.00 | 35.99 | N |
| ATOM | 2572 | CA | GLU | A | 335 | 35.914 | 44.261 | 48.067 | 1.00 | 35.53 | C |
| ATOM | 2573 | C | GLU | A | 335 | 36.229 | 44.610 | 46.621 | 1.00 | 34.53 | C |
| ATOM | 2574 | O | GLU | A | 335 | 36.715 | 45.689 | 46.338 | 1.00 | 34.20 | O |
| ATOM | 2575 | CB | GLU | A | 335 | 37.201 | 44.083 | 48.894 | 1.00 | 35.99 | C |
| ATOM | 2576 | CG | GLU | A | 335 | 37.054 | 44.507 | 50.354 | 1.00 | 37.38 | C |
| ATOM | 2577 | CD | GLU | A | 335 | 38.382 | 44.592 | 51.076 | 1.00 | 40.16 | C |
| ATOM | 2578 | OE1 | GLU | A | 335 | 39.271 | 45.318 | 50.570 | 1.00 | 42.04 | O |
| ATOM | 2579 | OE2 | GLU | A | 335 | 38.535 | 43.952 | 52.153 | 1.00 | 41.52 | O |
| ATOM | 2580 | N | VAL | A | 336 | 35.922 | 43.701 | 45.706 | 1.00 | 33.97 | N |
| ATOM | 2581 | CA | VAL | A | 336 | 36.165 | 43.901 | 44.276 | 1.00 | 33.49 | C |
| ATOM | 2582 | C | VAL | A | 336 | 35.537 | 45.159 | 43.670 | 1.00 | 33.00 | C |
| ATOM | 2583 | O | VAL | A | 336 | 36.194 | 45.904 | 42.946 | 1.00 | 33.01 | O |
| ATOM | 2584 | CB | VAL | A | 336 | 35.696 | 42.678 | 43.473 | 1.00 | 33.36 | C |
| ATOM | 2585 | CG1 | VAL | A | 336 | 35.726 | 42.951 | 41.992 | 1.00 | 34.05 | C |
| ATOM | 2586 | CG2 | VAL | A | 336 | 36.582 | 41.509 | 43.755 | 1.00 | 33.01 | C |
| ATOM | 2587 | N | GLY | A | 337 | 34.270 | 45.406 | 43.926 | 1.00 | 32.41 | N |
| ATOM | 2588 | CA | GLY | A | 337 | 33.675 | 46.592 | 43.351 | 1.00 | 32.21 | C |
| ATOM | 2589 | C | GLY | A | 337 | 34.332 | 47.903 | 43.724 | 1.00 | 31.72 | C |
| ATOM | 2590 | O | GLY | A | 337 | 34.682 | 48.711 | 42.859 | 1.00 | 31.40 | O |
| ATOM | 2591 | N | PRO | A | 338 | 34.433 | 48.163 | 45.013 | 1.00 | 31.50 | N |
| ATOM | 2592 | CA | PRO | A | 338 | 35.025 | 49.415 | 45.470 | 1.00 | 31.47 | C |
| ATOM | 2593 | C | PRO | A | 338 | 36.387 | 49.648 | 44.846 | 1.00 | 31.60 | C |
| ATOM | 2594 | O | PRO | A | 338 | 36.655 | 50.756 | 44.386 | 1.00 | 31.51 | O |
| ATOM | 2595 | CB | PRO | A | 338 | 35.065 | 49.230 | 46.977 | 1.00 | 31.27 | C |
| ATOM | 2596 | CG | PRO | A | 338 | 33.883 | 48.376 | 47.218 | 1.00 | 31.08 | C |
| ATOM | 2597 | CD | PRO | A | 338 | 33.933 | 47.359 | 46.137 | 1.00 | 31.28 | C |
| ATOM | 2598 | N | LEU | A | 339 | 37.219 | 48.620 | 44.765 | 1.00 | 31.80 | N |
| ATOM | 2599 | CA | LEU | A | 339 | 38.531 | 48.825 | 44.182 | 1.00 | 32.25 | C |
| ATOM | 2600 | C | LEU | A | 339 | 38.431 | 49.269 | 42.740 | 1.00 | 32.12 | C |
| ATOM | 2601 | O | LEU | A | 339 | 39.130 | 50.188 | 42.320 | 1.00 | 32.25 | O |
| ATOM | 2602 | CB | LEU | A | 339 | 39.395 | 47.581 | 44.278 | 1.00 | 32.49 | C |
| ATOM | 2603 | CG | LEU | A | 339 | 40.853 | 47.920 | 43.962 | 1.00 | 33.78 | C |
| ATOM | 2604 | CD1 | LEU | A | 339 | 41.793 | 47.121 | 44.797 | 1.00 | 34.64 | C |
| ATOM | 2605 | CD2 | LEU | A | 339 | 41.146 | 47.681 | 42.516 | 1.00 | 34.50 | C |
| ATOM | 2606 | N | LEU | A | 340 | 37.567 | 48.607 | 41.978 | 1.00 | 32.12 | N |
| ATOM | 2607 | CA | LEU | A | 340 | 37.385 | 48.963 | 40.584 | 1.00 | 31.85 | C |
| ATOM | 2608 | C | LEU | A | 340 | 36.854 | 50.376 | 40.483 | 1.00 | 31.56 | C |
| ATOM | 2609 | O | LEU | A | 340 | 37.342 | 51.169 | 39.701 | 1.00 | 31.42 | O |
| ATOM | 2620 | CB | LEU | A | 340 | 36.468 | 47.975 | 39.888 | 1.00 | 31.90 | C |
| ATOM | 2611 | CG | LEU | A | 340 | 37.089 | 46.598 | 39.669 | 1.00 | 32.44 | C |
| ATOM | 2612 | CD1 | LEU | A | 340 | 36.028 | 45.636 | 39.132 | 1.00 | 33.11 | C |
| ATOM | 2613 | CD2 | LEU | A | 340 | 38.281 | 46.660 | 38.728 | 1.00 | 31.95 | C |
| ATOM | 2614 | N | ASN | A | 341 | 35.865 | 50.717 | 41.282 | 1.00 | 31.61 | N |
| ATOM | 2615 | CA | ASN | A | 341 | 35.384 | 52.083 | 41.231 | 1.00 | 31.82 | C |
| ATOM | 2616 | C | ASN | A | 341 | 36.484 | 53.109 | 41.525 | 1.00 | 31.45 | C |

TABLE 3-continued

Coordinates for structures 1 to 4

| | | | | | | | | | | | |
|---|---|---|---|---|---|---|---|---|---|---|---|
| ATOM | 2617 | O | ASN | A | 341 | 36.600 | 54.119 | 40.845 | 1.00 | 30.80 | O |
| ATOM | 2618 | CB | ASN | A | 341 | 34.212 | 52.260 | 42.177 | 1.00 | 31.97 | C |
| ATOM | 2619 | CG | ASN | A | 341 | 32.901 | 51.883 | 41.532 | 1.00 | 32.77 | C |
| ATOM | 2620 | OD1 | ASN | A | 341 | 32.426 | 52.568 | 40.614 | 1.00 | 34.75 | O |
| ATOM | 2621 | ND2 | ASN | A | 341 | 32.310 | 50.789 | 41.992 | 1.00 | 31.86 | N |
| ATOM | 2622 | N | THR | A | 342 | 37.301 | 52.835 | 42.530 | 1.00 | 31.40 | N |
| ATOM | 2623 | CA | THR | A | 342 | 38.380 | 53.739 | 42.880 | 1.00 | 31.27 | C |
| ATOM | 2624 | C | THR | A | 342 | 39.317 | 53.842 | 41.707 | 1.00 | 31.14 | C |
| ATOM | 2625 | O | THR | A | 342 | 39.837 | 54.908 | 41.402 | 1.00 | 30.66 | O |
| ATOM | 2626 | CB | THR | A | 342 | 39.146 | 53.217 | 44.097 | 1.00 | 31.43 | C |
| ATOM | 2627 | OG1 | THR | A | 342 | 38.448 | 53.565 | 45.299 | 1.00 | 30.95 | O |
| ATOM | 2628 | CG2 | THR | A | 342 | 40.500 | 53.913 | 44.228 | 1.00 | 31.17 | C |
| ATOM | 2629 | N | MET | A | 343 | 39.549 | 52.714 | 41.059 | 1.00 | 31.29 | N |
| ATOM | 2630 | CA | MET | A | 343 | 40.406 | 52.703 | 39.898 | 1.00 | 31.59 | C |
| ATOM | 2631 | C | MET | A | 343 | 39.970 | 53.639 | 38.785 | 1.00 | 31.49 | C |
| ATOM | 2632 | O | MET | A | 343 | 40.804 | 54.361 | 38.255 | 1.00 | 31.46 | O |
| ATOM | 2633 | CB | MET | A | 343 | 40.516 | 51.310 | 39.314 | 1.00 | 31.79 | C |
| ATOM | 2634 | CG | MET | A | 343 | 41.831 | 50.662 | 39.629 | 1.00 | 32.65 | C |
| ATOM | 2635 | SD | MET | A | 343 | 42.271 | 49.379 | 38.468 | 1.00 | 33.09 | S |
| ATOM | 2636 | CE | MET | A | 343 | 41.116 | 48.304 | 38.916 | 1.00 | 34.22 | C |
| ATOM | 2637 | N | ILE | A | 344 | 38.690 | 53.641 | 38.418 | 1.00 | 31.31 | N |
| ATOM | 2638 | CA | ILE | A | 344 | 38.293 | 54.432 | 37.265 | 1.00 | 31.42 | C |
| ATOM | 2639 | C | ILE | A | 344 | 37.708 | 55.787 | 37.533 | 1.00 | 31.14 | C |
| ATOM | 2640 | O | ILE | A | 344 | 37.752 | 56.630 | 36.640 | 1.00 | 31.01 | O |
| ATOM | 2641 | CB | ILE | A | 344 | 37.272 | 53.708 | 36.362 | 1.00 | 31.86 | C |
| ATOM | 2642 | CG1 | ILE | A | 344 | 35.870 | 53.866 | 36.928 | 1.00 | 33.16 | C |
| ATOM | 2643 | CG2 | ILE | A | 344 | 37.633 | 52.229 | 36.118 | 1.00 | 32.09 | C |
| ATOM | 2644 | CD1 | ILE | A | 344 | 34.876 | 53.232 | 36.072 | 1.00 | 35.18 | C |
| ATOM | 2645 | N | LYS | A | 345 | 37.131 | 56.050 | 38.698 | 1.00 | 30.88 | N |
| ATOM | 2646 | CA | LYS | A | 345 | 36.455 | 57.334 | 38.758 | 1.00 | 30.94 | C |
| ATOM | 2647 | C | LYS | A | 345 | 37.412 | 58.468 | 38.853 | 1.00 | 30.72 | C |
| ATOM | 2648 | O | LYS | A | 345 | 38.250 | 58.558 | 39.743 | 1.00 | 30.61 | O |
| ATOM | 2649 | CB | LYS | A | 345 | 35.315 | 57.475 | 39.765 | 1.00 | 31.14 | C |
| ATOM | 2650 | CG | LYS | A | 345 | 35.361 | 56.680 | 40.977 | 1.00 | 32.16 | C |
| ATOM | 2651 | CD | LYS | A | 345 | 33.970 | 56.273 | 41.340 | 1.00 | 33.62 | C |
| ATOM | 2652 | CE | LYS | A | 345 | 33.514 | 56.873 | 42.665 | 1.00 | 34.71 | C |
| ATOM | 2653 | NZ | LYS | A | 345 | 34.302 | 56.317 | 43.840 | 1.00 | 36.28 | N |
| ATOM | 2654 | N | GLY | A | 346 | 37.280 | 59.332 | 37.870 | 1.00 | 30.83 | N |
| ATOM | 2655 | CA | GLY | A | 346 | 38.114 | 60.504 | 37.789 | 1.00 | 30.66 | C |
| ATOM | 2656 | C | GLY | A | 346 | 39.345 | 60.195 | 37.001 | 1.00 | 30.25 | C |
| ATOM | 2657 | O | GLY | A | 346 | 40.147 | 61.066 | 36.745 | 1.00 | 30.00 | O |
| ATOM | 2658 | N | ARG | A | 347 | 39.454 | 58.953 | 36.564 | 1.00 | 30.42 | N |
| ATOM | 2659 | CA | ARG | A | 347 | 40.652 | 58.496 | 35.923 | 1.00 | 30.66 | C |
| ATOM | 2660 | C | ARG | A | 347 | 40.389 | 57.879 | 34.566 | 1.00 | 30.89 | C |
| ATOM | 2661 | O | ARG | A | 347 | 41.033 | 58.241 | 33.588 | 1.00 | 30.30 | O |
| ATOM | 2662 | CB | ARG | A | 347 | 41.350 | 57.526 | 36.860 | 1.00 | 30.88 | C |
| ATOM | 2663 | CG | ARG | A | 347 | 41.786 | 58.177 | 38.171 | 1.00 | 30.97 | C |
| ATOM | 2664 | CD | ARG | A | 347 | 43.129 | 57.701 | 38.636 | 1.00 | 31.35 | C |
| ATOM | 2665 | NE | ARG | A | 347 | 43.128 | 56.255 | 38.597 | 1.00 | 30.88 | N |
| ATOM | 2666 | CZ | ARG | A | 347 | 44.088 | 55.482 | 38.128 | 1.00 | 29.55 | C |
| ATOM | 2667 | NH1 | ARG | A | 347 | 45.237 | 55.962 | 37.667 | 1.00 | 28.44 | N |
| ATOM | 2668 | NH2 | ARG | A | 347 | 43.876 | 54.181 | 38.147 | 1.00 | 29.95 | N |
| ATOM | 2669 | N | TYR | A | 348 | 39.446 | 56.953 | 34.480 | 1.00 | 31.67 | N |
| ATOM | 2670 | CA | TYR | A | 348 | 39.143 | 56.377 | 33.176 | 1.00 | 32.27 | C |
| ATOM | 2671 | C | TYR | A | 348 | 37.726 | 56.574 | 32.689 | 1.00 | 33.10 | C |
| ATOM | 2672 | O | TYR | A | 348 | 37.425 | 56.212 | 31.557 | 1.00 | 33.12 | O |
| ATOM | 2673 | CB | TYR | A | 348 | 39.422 | 54.896 | 33.154 | 1.00 | 31.96 | C |
| ATOM | 2674 | CG | TYR | A | 348 | 40.860 | 54.527 | 33.253 | 1.00 | 32.06 | C |
| ATOM | 2675 | CD1 | TYR | A | 348 | 41.652 | 54.424 | 32.114 | 1.00 | 31.60 | C |
| ATOM | 2676 | CD2 | TYR | A | 348 | 41.435 | 54.256 | 34.483 | 1.00 | 31.75 | C |
| ATOM | 2677 | CE1 | TYR | A | 348 | 42.980 | 54.061 | 32.203 | 1.00 | 31.08 | C |
| ATOM | 2678 | CE2 | TYR | A | 348 | 42.761 | 53.897 | 34.580 | 1.00 | 32.11 | C |
| ATOM | 2679 | CZ | TYR | A | 348 | 43.530 | 53.800 | 33.438 | 1.00 | 31.05 | C |
| ATOM | 2680 | OH | TYR | A | 348 | 44.845 | 53.427 | 33.544 | 1.00 | 29.83 | O |
| ATOM | 2681 | N | ASN | A | 349 | 36.850 | 57.137 | 33.507 | 1.00 | 34.48 | N |
| ATOM | 2682 | CA | ASN | A | 349 | 35.465 | 57.275 | 33.083 | 1.00 | 35.73 | C |
| ATOM | 2683 | C | ASN | A | 349 | 35.037 | 58.643 | 32.595 | 1.00 | 36.60 | C |
| ATOM | 2684 | O | ASN | A | 349 | 35.757 | 59.640 | 32.508 | 1.00 | 37.31 | O |
| ATOM | 2685 | CS | ASN | A | 349 | 34.542 | 56.900 | 34.212 | 1.00 | 35.62 | C |
| ATOM | 2686 | CG | ASN | A | 349 | 34.635 | 57.864 | 35.353 | 1.00 | 37.08 | C |
| ATOM | 2687 | OD1 | ASN | A | 349 | 35.398 | 58.840 | 35.308 | 1.00 | 36.55 | O |
| ATOM | 2688 | ND2 | ASN | A | 349 | 33.861 | 57.604 | 36.403 | 1.00 | 39.78 | N |
| ATOM | 2689 | OXT | ASN | A | 349 | 33.861 | 58.757 | 32.276 | 1.00 | 38.11 | O |
| THR | 2690 | | ASN | A | 349 | | | | | | |
| HETATM | 2691 | FE | FE2 | A | 1350 | 23.364 | 27.586 | 28.889 | 1.00 | 32.45 | FE |
| HETATM | 2692 | C1 | AKG | A | 1351 | 22.523 | 25.412 | 27.792 | 1.00 | 37.04 | C |
| HETATM | 2693 | O1 | AKG | A | 1351 | 23.535 | 26.092 | 27.914 | 1.00 | 39.03 | O |

TABLE 3-continued

| | | | | | Coordinates for structures 1 to 4 | | | | | |
|---|---|---|---|---|---|---|---|---|---|---|
| HETATM | 2694 | O2 | AKG | A | 1351 | 22.557 | 24.216 | 27.226 | 1.00 | 37.33 | O |
| HETATM | 2695 | C2 | AKG | A | 1351 | 21.186 | 25.964 | 28.297 | 1.00 | 35.25 | C |
| HETATM | 2696 | O5 | AKG | A | 1351 | 21.175 | 27.063 | 28.807 | 1.00 | 33.44 | O |
| HETATM | 2697 | C3 | AKG | A | 1351 | 19.937 | 25.139 | 28.167 | 1.00 | 36.11 | C |
| HETATM | 2698 | C4 | AKG | A | 1351 | 18.848 | 25.738 | 29.055 | 1.00 | 36.50 | C |
| HETATM | 2699 | C5 | AKG | A | 1351 | 17.464 | 25.331 | 28.632 | 1.00 | 35.97 | C |
| RETATM | 2700 | O3 | AKG | A | 1351 | 17.276 | 24.627 | 27.656 | 1.00 | 36.64 | O |
| HETATM | 2701 | O4 | AKG | A | 1351 | 16.432 | 25.771 | 29.338 | 1.00 | 36.31 | O |
| HETATM | 2702 | S  | SO4 | A | 1352 | 0.300  | 25.196 | 43.477 | 1.00 | 80.75 | S |
| HETATM | 2703 | O1 | SO4 | A | 1352 | 1.094  | 26.117 | 44.306 | 1.00 | 78.50 | O |
| HETATM | 2704 | O2 | SO4 | A | 1352 | 1.221  | 24.413 | 42.644 | 1.00 | 78.51 | O |
| HETATM | 2705 | O3 | SO4 | A | 1352 | 0.470  | 24.282 | 44.334 | 1.00 | 79.54 | O |
| HETATM | 2706 | O4 | SO4 | A | 1352 | 0.640  | 25.951 | 42.633 | 1.00 | 78.07 | O |
| HETATM | 2707 | S  | SO4 | A | 1353 | 1.825  | 28.603 | 29.515 | 1.00 | 77.38 | S |
| HETATM | 2708 | O1 | SO4 | A | 1353 | 3.041  | 29.212 | 30.061 | 1.00 | 76.05 | O |
| HETATM | 2709 | O2 | SO4 | A | 1353 | 2.144  | 27.528 | 28.574 | 1.00 | 75.24 | O |
| HETATM | 2710 | O3 | SO4 | A | 1353 | 1.090  | 28.086 | 30.675 | 1.00 | 76.52 | O |
| HETATM | 2711 | O4 | SO4 | A | 1353 | 1.011  | 29.586 | 28.783 | 1.00 | 76.04 | O |
| HETATM | 2712 | S  | SO4 | A | 1354 | 34.403 | 30.284 | 38.043 | 1.00 | 78.17 | S |
| HETATM | 2713 | O1 | SO4 | A | 1354 | 34.921 | 31.567 | 38.516 | 1.00 | 75.93 | O |
| HETATM | 2714 | O2 | SO4 | A | 1354 | 35.240 | 29.158 | 38.450 | 1.00 | 77.42 | O |
| HETATM | 2715 | O3 | SO4 | A | 1354 | 33.112 | 30.084 | 38.686 | 1.00 | 75.59 | O |
| HETATM | 2716 | O4 | SO4 | A | 1354 | 34.303 | 30.307 | 36.581 | 1.00 | 74.60 | O |
| HETATM | 2717 | O  | HOH | Z | 1    | 25.824 | 26.442 | 26.175 | 1.00 | 46.43 | O |
| HETATM | 2718 | O  | HOH | Z | 2    | 27.811 | 27.709 | 24.637 | 1.00 | 41.32 | O |
| HETATM | 2719 | O  | HOH | Z | 3    | 27.367 | 30.233 | 25.742 | 1.00 | 38.18 | O |
| CONECT | 1478 | 2691 | | | | | | | | | |
| CONECT | 1498 | 2691 | | | | | | | | | |
| CONECT | 2167 | 2691 | | | | | | | | | |
| CONECT | 2691 | 2696 | 2693 | 1478 | 2167 | 1498 | | | | | |
| CONECT | 2692 | 2693 | 2694 | 2695 | | | | | | | |
| CONECT | 2693 | 2692 | 2691 | | | | | | | | |
| CONECT | 2694 | 2692 | | | | | | | | | |
| CONECT | 2695 | 2692 | 2696 | 2697 | | | | | | | |
| CONECT | 2696 | 2691 | 2695 | | | | | | | | |
| CONECT | 2697 | 2695 | 2698 | | | | | | | | |
| CONECT | 2698 | 2697 | 2699 | | | | | | | | |
| CONECT | 2699 | 2698 | 2700 | 2701 | | | | | | | |
| CONECT | 2700 | 2699 | | | | | | | | | |
| CONECT | 2701 | 2699 | | | | | | | | | |
| CONECT | 2702 | 2703 | 2704 | 2705 | 2706 | | | | | | |
| CONECT | 2703 | 2702 | | | | | | | | | |
| CONECT | 2704 | 2702 | | | | | | | | | |
| CONECT | 2705 | 2702 | | | | | | | | | |
| CONECT | 2706 | 2702 | | | | | | | | | |
| CONECT | 2707 | 2708 | 2709 | 2710 | 2711 | | | | | | |
| CONECT | 2708 | 2707 | | | | | | | | | |
| CONECT | 2709 | 2707 | | | | | | | | | |
| CONECT | 2710 | 2707 | | | | | | | | | |
| CONECT | 2711 | 2707 | | | | | | | | | |
| CONECT | 2712 | 2713 | 2714 | 2715 | 2716 | | | | | | |
| CONECT | 2713 | 2712 | | | | | | | | | |
| CONECT | 2714 | 2712 | | | | | | | | | |
| CONECT | 2715 | 2712 | | | | | | | | | |
| CONECT | 2716 | 2712 | | | | | | | | | |
| MASTER | 433  | 0    | 5    | 14   | 20   | 0    | 9 | 6 | 2718 | 1 | 29 | 27 |
| END | | | | | | | | | | | |

The invention claimed is:

1. A method of identifying, screening, characterizing or designing a chemical entity that potentially binds a FIH (Factor Inhibiting HIF (Hypoxia Inducible Factor)), comprising:
   (a) generating a three-dimensional model of FIH on a computer wherein the three-dimensional model has the x-ray structural coordinates as set forth in the structure 1, 2 or 3 in Table 3;
   (b) providing a structural model of a chemical entity on the computer;
   (c) identifying the amino acid residues forming a binding site of the FIH from the three-dimensional model in step (a) in order to generate a three-dimensional representation of the binding site of the FIH, wherein the binding site of the FIH comprises amino acids Tyr145, Leu186, Leu188, Thr196, Phe207, Lys214 and Ile281 as set forth in SEQ ID NO: 30, wherein the amino acids have the structural coordinates as shown in the structure 1, 2 or 3 in Table 3;
   (d) employing the structural model from step (b) and the three-dimensional representation from step (c) to identify a chemical entity that potentially binds with the binding site of the FIH; and
   (e) obtaining the chemical entity.

2. The method according to claim 1, wherein said chemical entity is predicted to form hydrophobic interactions with the side chain of one or more amino acid residues selected from Leu186, Leu188, Thr196, Phe207, and Ile281 according to SEQ ID NO: 30.

3. The method according to claim 1, further comprising:
   (f) contacting the chemical entity with a polypeptide comprising SEQ ID NO:33 and a polypeptide comprising SEQ ID NO:30; and
   (g) monitoring for hydroxylation of said polypeptide comprising SEQ ID NO: 33 to identify a potential inhibitor of hydroxylation.

4. The method according to claim 1, wherein said chemical entity is predicted to form electrostatic or hydrogen bonding interactions with one or more amino acid residues selected from Tyr145, Thr196, and Lys214 according to SEQ ID NO: 30.

5. A method of identifying, screening, characterizing or designing a chemical entity that is potentially capable of inhibiting hydroxylation of a β-carbon of an asparagine of an HIF polypeptide by a FIH polypeptide, comprising:
   (a) generating a three-dimensional model of FIH on a computer wherein the three-dimensional model has the x-ray structural coordinates as set forth in the structure 1, 2 or 3 in Table 3;
   (b) providing a structural model of a chemical entity on the computer;
   (c) identifying the amino acid residues forming a binding site of the FIH from the three-dimensional model in step (a) in order to generate a three-dimensional representation of the binding site of the FIH, wherein the binding site of the FIH comprises amino acids Tyr145, Leu186, Leu188, Thr196, Phe207, Lys214 and Ile281 as set forth in SEQ ID NO: 30, wherein the amino acids have the structural coordinates as shown in the structure 1, 2 or 3 in Table 3;

(d) employing the structural model from step (b) and the three-dimensional representation from step (c) to identify a chemical entity that is potentially capable of inhibiting hydroxylation by the FIH polypeptide of the β-carbon of the asparagine 18 according to SEQ ID NO: 31, or the asparagine 29 according to SEQ ID NO: 32; and (e) obtaining the chemical entity.

6. The method according to claim 5, wherein said chemical entity is predicted to form hydrophobic interactions with the side chain of one or more amino acid residues selected from Leu186, Leu188, Thr196, Phe207, and Ile281 as set forth in SEQ ID NO: 30.

7. The method according to claim 5, further comprising:

(f) contacting the chemical entity with a polypeptide comprising SEQ ID NO:33 and a polypeptide comprising SEQ ID NO:30; and (g) monitoring for hydroxylation of said polypeptide comprising SEQ ID NO: 33 to identify a potential inhibitor of hydroxylation.

8. The method according to claim 5, wherein said chemical entity is predicted to form electrostatic or hydrogen bonding interactions with one or more amino acid residues selected from Tyr145, Thr196, and Lys214 according to SEQ ID NO: 30.

* * * * *

SEQUENCE LISTING

<160> NUMBER OF SEQ ID NOS: 34

<210> SEQ ID NO 1
<211> LENGTH: 14
<212> TYPE: PRT
<213> ORGANISM: Artificial sequence
<220> FEATURE:
<223> OTHER INFORMATION: Synthetic peptide

<400> SEQUENCE: 1

```
Asp Glu Ser Gly Leu Pro Gln Leu Thr Ser Tyr Asp Cys Glu
1               5                   10
```

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

```
Gln Leu Thr Ser Tyr Asp Cys Glu
1               5
```

<210> SEQ ID NO 3
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (16)..(16)
<223> OTHER INFORMATION: Xaa can be any naturally occurring amino acid
      except asparagine

<400> SEQUENCE: 3

```
Asp Glu Ser Gly Leu Pro Gln Leu Thr Ser Tyr Asp Cys Glu Val Xaa
1               5                   10                  15

Ala
```

<210> SEQ ID NO 4
<211> LENGTH: 58
<212> TYPE: PRT
<213> ORGANISM: Homo sapiens

<400> SEQUENCE: 4

```
Phe Asn Trp Asn Trp Ile Asn Lys Gln Gln Gly Lys Arg Gly Trp Gly
1               5                   10                  15

Gln Leu Thr Ser Asn Leu Leu Leu Ile Gly Met Glu Gly Asn Val Thr
            20                  25                  30

Pro Ala His Tyr Asp Glu Gln Gln Asn Phe Phe Ala Gln Ile Lys Gly
        35                  40                  45

Tyr Lys Arg Cys Ile Leu Phe Pro Pro Asp
    50                  55
```

<210> SEQ ID NO 5
<211> LENGTH: 16
<212> TYPE: PRT
<213> ORGANISM: Drosophila melanogaster

<400> SEQUENCE: 5

```
Glu Leu Ala Ala Asp Leu Arg Val Ser Asp Leu Asp Phe Ala Gln Gln
1               5                   10                  15
```

<210> SEQ ID NO 6
<211> LENGTH: 42
<212> TYPE: PRT
<213> ORGANISM: Drosophila melanogaster

<400> SEQUENCE: 6

```
Pro Pro Asp Ala Val Asn Phe Trp Leu Gly Asp Glu Arg Ala Val Thr
1               5                   10                  15

Ser Met His Lys Asp Pro Tyr Glu Asn Val Tyr Cys Val Ile Ser Gly
```

```
                20                  25                  30
His Lys Asp Phe Val Leu Ile Pro Pro His
        35                  40

<210> SEQ ID NO 7
<211> LENGTH: 14
<212> TYPE: PRT
<213> ORGANISM: Drosophila melanogaster

<400> SEQUENCE: 7

Ala Leu Lys Glu Asp Ile Ser Ile Pro Asp Tyr Cys Thr Ile
1               5                   10

<210> SEQ ID NO 8
<211> LENGTH: 43
<212> TYPE: PRT
<213> ORGANISM: Drosophila melanogaster

<400> SEQUENCE: 8

Pro Gly Ala Val Asp Ile Lys Ala Trp Leu Gly Pro Ala Gly Thr Val
1               5                   10                  15

Ser Pro Met His Tyr Asp Pro Lys His Asn Leu Leu Cys Gln Val Phe
            20                  25                  30

Gly Ser Lys Arg Ile Ile Leu Ala Ala Pro Ala
        35                  40

<210> SEQ ID NO 9
<211> LENGTH: 17
<212> TYPE: PRT
<213> ORGANISM: Homo sapiens

<400> SEQUENCE: 9

Lys Ile Val Arg Lys Leu Ser Trp Val Glu Asn Leu Trp Pro Glu Glu
1               5                   10                  15

Cys

<210> SEQ ID NO 10
<211> LENGTH: 44
<212> TYPE: PRT
<213> ORGANISM: Homo sapiens

<400> SEQUENCE: 10

Pro Asn Val Gln Lys Tyr Cys Leu Met Ser Val Arg Asp Ser Tyr Thr
1               5                   10                  15

Asp Phe His Ile Asp Phe Gly Gly Thr Ser Val Trp Tyr His Val Leu
            20                  25                  30

Lys Gly Glu Lys Ile Phe Tyr Leu Ile Arg Pro Thr
        35                  40

<210> SEQ ID NO 11
<211> LENGTH: 16
<212> TYPE: PRT
<213> ORGANISM: Caenorhabditis elegans

<400> SEQUENCE: 11

Arg Phe Val Gln Glu Ile Ser Met Val Asn Arg Leu Trp Pro Asp Val
1               5                   10                  15

<210> SEQ ID NO 12
<211> LENGTH: 44
<212> TYPE: PRT
<213> ORGANISM: Caenorhabditis elegans
```

<400> SEQUENCE: 12

Pro Lys Val Glu Gln Phe Cys Leu Ala Gly Met Ala Gly Ser Tyr Thr
1               5                   10                  15

Asp Phe His Val Asp Phe Gly Gly Ser Ser Val Tyr Tyr His Ile Leu
            20                  25                  30

Lys Gly Glu Lys Ile Phe Tyr Ile Ala Ala Pro Thr
        35                  40

<210> SEQ ID NO 13
<211> LENGTH: 16
<212> TYPE: PRT
<213> ORGANISM: Caenorhabditis elegans

<400> SEQUENCE: 13

Arg Phe Val Gln Asp Ile Ser Met Ala Lys Arg Leu Trp Ser Asp Val
1               5                   10                  15

<210> SEQ ID NO 14
<211> LENGTH: 44
<212> TYPE: PRT
<213> ORGANISM: Caenorhabditis elegans

<400> SEQUENCE: 14

Pro Lys Ile Glu Gln Ile Cys Ala Ala Ala Met Ala Asn Ser Tyr Thr
1               5                   10                  15

Asp Phe His Val Asp Phe Gly Gly Thr Ser Val Tyr Phe His Val Phe
            20                  25                  30

Lys Gly Glu Lys Ile Phe Tyr Ile Ala Ala Pro Thr
        35                  40

<210> SEQ ID NO 15
<211> LENGTH: 9
<212> TYPE: PRT
<213> ORGANISM: Caenorhabditis elegans

<400> SEQUENCE: 15

Lys Ile Phe Tyr Ile Ala Ala Pro Thr
1               5

<210> SEQ ID NO 16
<211> LENGTH: 16
<212> TYPE: PRT
<213> ORGANISM: Drosophila melanogaster

<400> SEQUENCE: 16

Glu Ile Val Arg Gln Ile Asp Trp Val Asp Val Trp Pro Lys Gln
1               5                   10                  15

<210> SEQ ID NO 17
<211> LENGTH: 44
<212> TYPE: PRT
<213> ORGANISM: Drosophila melanogaster

<400> SEQUENCE: 17

Pro Lys Val Gln Lys Tyr Cys Leu Met Ser Val Lys Asn Cys Tyr Thr
1               5                   10                  15

Asp Phe His Ile Asp Phe Gly Gly Thr Ser Val Trp Tyr His Ile Leu
            20                  25                  30

Arg Gly Ser Lys Val Phe Trp Leu Ile Pro Pro Thr
        35                  40

<210> SEQ ID NO 18
<211> LENGTH: 9
<212> TYPE: PRT
<213> ORGANISM: Drosophila melanogaster

<400> SEQUENCE: 18

Lys Val Phe Trp Leu Ile Pro Pro Thr
1               5

<210> SEQ ID NO 19
<211> LENGTH: 18
<212> TYPE: PRT
<213> ORGANISM: Saccharomyces cerevisiae

<400> SEQUENCE: 19

Gln Asn Asp Leu Val Asp Lys Ile Trp Ser Phe Asn Gly His Leu Glu
1               5                   10                  15

Lys Val

<210> SEQ ID NO 20
<211> LENGTH: 44
<212> TYPE: PRT
<213> ORGANISM: Saccharomyces cerevisiae

<400> SEQUENCE: 20

Pro Lys Val Thr Lys Tyr Ile Leu Met Ser Val Lys Asp Ala Tyr Thr
1               5                   10                  15

Asp Phe His Leu Asp Phe Ala Gly Thr Ser Val Tyr Tyr Asn Val Ile
                20                  25                  30

Ser Gly Gln Lys Lys Phe Leu Leu Phe Pro Pro Thr
        35                  40

<210> SEQ ID NO 21
<211> LENGTH: 61
<212> TYPE: PRT
<213> ORGANISM: Rattus norvegicus

<400> SEQUENCE: 21

Lys Thr Asp Val Phe Gln Glu Val Met Trp Ser Asp Phe Gly Phe Pro
1               5                   10                  15

Gly Arg Asn Gly Gln Glu Ser Thr Leu Trp Ile Gly Ser Leu Gly Ala
                20                  25                  30

His Thr Pro Cys His Leu Asp Ser Tyr Gly Cys Asn Leu Val Phe Gln
        35                  40                  45

Val Gln Gly Arg Lys Arg Trp His Leu Phe Pro Pro Glu
    50                  55                  60

<210> SEQ ID NO 22
<211> LENGTH: 57
<212> TYPE: PRT
<213> ORGANISM: Caenorhabditis elegans

<400> SEQUENCE: 22

Phe Glu Asp Asp Leu Phe His Tyr Ala Asp Asp Lys Lys Arg Pro Pro
1               5                   10                  15

His Arg Trp Phe Val Met Gly Pro Ala Arg Ser Gly Thr Ala Ile His
                20                  25                  30

Ile Asp Pro Leu Gly Thr Ser Ala Trp Asn Ser Leu Leu Gln Gly His
        35                  40                  45

Lys Arg Trp Val Leu Ile Pro Pro Ile

```
                50                  55

<210> SEQ ID NO 23
<211> LENGTH: 60
<212> TYPE: PRT
<213> ORGANISM: Drosophila melanogaster

<400> SEQUENCE: 23

Thr Ile Leu Asp Tyr Val Asn Lys Asp Tyr Asn Ile Gln Ile Asp Gly
1               5                   10                  15

Val Asn Thr Ala Tyr Leu Tyr Phe Gly Met Trp Lys Thr Thr Phe Ala
            20                  25                  30

Trp His Thr Glu Asp Met Asp Leu Tyr Ser Ile Asn Tyr Leu His Phe
        35                  40                  45

Gly Ala Pro Lys Thr Trp Tyr Val Val Pro Pro Glu
    50                  55                  60

<210> SEQ ID NO 24
<211> LENGTH: 60
<212> TYPE: PRT
<213> ORGANISM: Homo sapiens

<400> SEQUENCE: 24

Thr Val Leu Asp Val Val Glu Glu Cys Gly Ile Ser Ile Glu Gly
1               5                   10                  15

Val Asn Thr Pro Tyr Leu Tyr Phe Gly Met Trp Lys Thr Thr Phe Ala
            20                  25                  30

Trp His Thr Glu Asp Met Asp Leu Tyr Ser Ile Asn Tyr Leu His Phe
        35                  40                  45

Gly Glu Pro Lys Ser Trp Tyr Ala Ile Pro Pro Glu
    50                  55                  60

<210> SEQ ID NO 25
<211> LENGTH: 56
<212> TYPE: PRT
<213> ORGANISM: Caenorhabditis elegans

<400> SEQUENCE: 25

Thr Ile Leu Glu Asp Thr Asn Tyr Glu Ile Lys Gly Val Asn Thr Val
1               5                   10                  15

Tyr Leu Tyr Phe Gly Met Tyr Lys Thr Thr Phe Pro Trp His Ala Glu
            20                  25                  30

Asp Met Asp Leu Tyr Ser Ile Asn Phe Leu His Phe Gly Ala Pro Lys
        35                  40                  45

Tyr Trp Phe Ala Ile Ser Ser Glu
    50                  55

<210> SEQ ID NO 26
<211> LENGTH: 60
<212> TYPE: PRT
<213> ORGANISM: Drosophila melanogaster

<400> SEQUENCE: 26

Thr Ile Leu Asn Leu Val Asn Thr Asp Tyr Asn Ile Ile Ile Asp Gly
1               5                   10                  15

Val Asn Thr Ala Tyr Leu Tyr Phe Gly Met Trp Lys Ser Ser Phe Ala
            20                  25                  30

Trp His Thr Glu Asp Met Asp Leu Tyr Ser Ile Asn Tyr Leu His Phe
        35                  40                  45
```

```
Gly Ala Pro Lys Thr Trp Tyr Ala Ile Pro Pro Ala
        50                  55                  60

<210> SEQ ID NO 27
<211> LENGTH: 60
<212> TYPE: PRT
<213> ORGANISM: Homo sapiens

<400> SEQUENCE: 27

Thr Ile Leu Asp Leu Val Glu Lys Glu Ser Gly Ile Thr Ile Glu Gly
  1               5                  10                  15

Val Asn Thr Pro Tyr Leu Tyr Phe Gly Met Trp Lys Thr Ser Phe Ala
                 20                  25                  30

Trp His Thr Glu Asp Met Asp Leu Tyr Ser Ile Asn Tyr Leu His Phe
             35                  40                  45

Gly Glu Pro Arg Ser Trp Tyr Ser Val Pro Pro Glu
        50                  55                  60

<210> SEQ ID NO 28
<211> LENGTH: 58
<212> TYPE: PRT
<213> ORGANISM: Drosophila melanogaster

<400> SEQUENCE: 28

Phe Ala Ser Asp Trp Leu Asn Glu Gln Leu Ile Gln Gln Gly Lys Asp
  1               5                  10                  15

Asp Tyr Arg Phe Val Tyr Met Gly Pro Lys Asn Ser Trp Thr Ser Tyr
                 20                  25                  30

His Ala Asp Val Phe Gly Ser Phe Ser Trp Ser Thr Asn Ile Val Gly
             35                  40                  45

Leu Lys Lys Trp Leu Ile Met Pro Pro Gly
        50                  55

<210> SEQ ID NO 29
<211> LENGTH: 57
<212> TYPE: PRT
<213> ORGANISM: Schizosaccharomyces pombe

<400> SEQUENCE: 29

Phe Ala Asp Asp Trp Leu Asn Ala Tyr Val Ile Asp Cys Glu Ser Asp
  1               5                  10                  15

Asp Phe Arg Phe Ala Tyr Leu Gly Ser His Leu Thr Thr Thr Gly Leu
                 20                  25                  30

His Thr Asp Tyr Ala Ser His Ser Phe Ser Val Asn Leu Cys Gly Val
             35                  40                  45

Lys Cys Trp Leu Phe Ile Asp Pro Lys
        50                  55

<210> SEQ ID NO 30
<211> LENGTH: 349
<212> TYPE: PRT
<213> ORGANISM: Homo sapiens

<400> SEQUENCE: 30

Met Ala Ala Thr Ala Ala Glu Ala Val Ala Ser Gly Ser Gly Glu Pro
  1               5                  10                  15

Arg Glu Glu Ala Gly Ala Leu Gly Pro Ala Trp Asp Glu Ser Gln Leu
                 20                  25                  30

Arg Ser Tyr Ser Phe Pro Thr Arg Pro Ile Pro Arg Leu Ser Gln Ser
             35                  40                  45
```

Asp Pro Arg Ala Glu Glu Leu Ile Glu Asn Glu Pro Val Val Leu
    50                  55                  60

Thr Asp Thr Asn Leu Val Tyr Pro Ala Leu Lys Trp Asp Leu Glu Tyr
 65                  70                  75                  80

Leu Gln Glu Asn Ile Gly Asn Gly Asp Phe Ser Val Tyr Ser Ala Ser
                85                  90                  95

Thr His Lys Phe Leu Tyr Asp Glu Lys Lys Met Ala Asn Phe Gln
            100                 105                 110

Asn Phe Lys Pro Arg Ser Asn Arg Glu Glu Met Lys Phe His Glu Phe
            115                 120                 125

Val Glu Lys Leu Gln Asp Ile Gln Gln Arg Gly Gly Glu Arg Leu
130                 135                 140

Tyr Leu Gln Gln Thr Leu Asn Asp Thr Val Arg Lys Ile Val Met
145                 150                 155                 160

Asp Phe Leu Gly Phe Asn Trp Asn Trp Ile Asn Lys Gln Gln Gly Lys
                165                 170                 175

Arg Gly Trp Gly Gln Leu Thr Ser Asn Leu Leu Ile Gly Met Glu
            180                 185                 190

Gly Asn Val Thr Pro Ala His Tyr Asp Glu Gln Gln Asn Phe Phe Ala
            195                 200                 205

Gln Ile Lys Gly Tyr Lys Arg Cys Ile Leu Phe Pro Pro Asp Gln Phe
    210                 215                 220

Glu Cys Leu Tyr Pro Tyr Pro Val His His Pro Cys Asp Arg Gln Ser
225                 230                 235                 240

Gln Val Asp Phe Asp Asn Pro Asp Tyr Glu Arg Phe Pro Asn Phe Gln
                245                 250                 255

Asn Val Val Gly Tyr Glu Thr Val Val Gly Pro Gly Asp Val Leu Tyr
            260                 265                 270

Ile Pro Met Tyr Trp Trp His His Ile Glu Ser Leu Leu Asn Gly Gly
    275                 280                 285

Ile Thr Ile Thr Val Asn Phe Trp Tyr Lys Gly Ala Pro Thr Pro Lys
    290                 295                 300

Arg Ile Glu Tyr Pro Leu Lys Ala His Gln Lys Val Ala Ile Met Arg
305                 310                 315                 320

Asn Ile Glu Lys Met Leu Gly Glu Ala Leu Gly Asn Pro Gln Glu Val
                325                 330                 335

Gly Pro Leu Leu Asn Thr Met Ile Lys Gly Arg Tyr Asn
            340                 345

<210> SEQ ID NO 31
<211> LENGTH: 41
<212> TYPE: PRT
<213> ORGANISM: Homo sapiens

<400> SEQUENCE: 31

Ser Met Asp Glu Ser Gly Leu Pro Gln Leu Thr Ser Tyr Asp Cys Glu
1               5                   10                  15

Val Asn Ala Pro Ile Gln Gly Ser Arg Asn Leu Leu Gln Gly Glu Glu
            20                  25                  30

Leu Leu Arg Ala Leu Asp Gln Val Asn
        35                  40

<210> SEQ ID NO 32
<211> LENGTH: 52
<212> TYPE: PRT

-continued

```
<213> ORGANISM: Homo sapiens

<400> SEQUENCE: 32

Pro Ser Asp Leu Ala Cys Arg Leu Leu Gly Gln Ser Met Asp Glu Ser
1               5                   10                  15

Gly Leu Pro Gln Leu Thr Ser Tyr Asp Cys Glu Val Asn Ala Pro Ile
            20                  25                  30

Gln Gly Ser Arg Asn Leu Leu Gln Gly Glu Glu Leu Leu Arg Ala Leu
        35                  40                  45

Asp Gln Val Asn
    50

<210> SEQ ID NO 33
<211> LENGTH: 12
<212> TYPE: PRT
<213> ORGANISM: Homo sapiens

<400> SEQUENCE: 33

Leu Thr Ser Tyr Asp Cys Glu Val Asn Ala Pro Ile
1               5                   10

<210> SEQ ID NO 34
<211> LENGTH: 12
<212> TYPE: PRT
<213> ORGANISM: Homo sapiens

<400> SEQUENCE: 34

Leu Leu Gln Gly Glu Glu Leu Leu Arg Ala Leu Asp
1               5                   10
```